US006821724B1

(12) United States Patent
Mittman et al.

(10) Patent No.: US 6,821,724 B1
(45) Date of Patent: Nov. 23, 2004

(54) METHODS OF GENETIC ANALYSIS USING NUCLEIC ACID ARRAYS

(75) Inventors: Michael Mittman, Palo Alto, CA (US); David J. Mack, Menlo Park, CA (US); David J. Lockhart, Del Mar, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/396,196

(22) Filed: Sep. 15, 1999

Related U.S. Application Data

(60) Provisional application No. 60/100,678, filed on Sep. 17, 1998.

(51) Int. Cl.[7] .......................... C12Q 1/68; C07H 21/02; C07H 21/04; G01N 15/06; G01N 33/00
(52) U.S. Cl. ........................ 435/6; 422/68.1; 536/23.1; 536/24.3; 536/24.31
(58) Field of Search ............................ 436/6; 422/68.1; 536/23.1, 24.3, 24.31

(56) References Cited

U.S. PATENT DOCUMENTS

| | | | |
|---|---|---|---|
| 5,143,854 A | 9/1992 | Pirrung et al. | |
| 5,800,992 A | 9/1998 | Fodor et al. | |
| 5,994,075 A | 11/1999 | Goodfellow | |

OTHER PUBLICATIONS

Roberts et al. "RNA–peptide fusions for the in vitro selection of peptides and proteins," PNAS vol. 94 pp. 12297–12302, Nov. 1997.
Cho et al. Parallel analysis of genetic selections using whole genome oligonucleotide arrays PNAS vol. 95, pp. 3752–3757, Mar. 1998.
Lipschultz R.J. Letter from Lipschutz to Dr. Carrano, Aug. 22, 1994 *Link*.
AFFYMETRIC GeneChip®Assays and Controls Price List, Nov., 1997 *Link*.
AFFYMETRIC GeneChip®Arrays and Assays Product List, Jan. 1998, *Link*.
AFFYMETRIX: GeneChip®Arrays and Assays Product List, Nov. 1998 *Link*.
AFFYMETRIX: GeneChip® Arrays and Reagents, Feb. 1999, *Link*.
AFFYMETRIX: GeneChip® Price Catalog (U.S. and Canada), Jul. 1999. Link.
AFFYMETRIX: Addendum (U.S. and Canada) GeneChip®Arrays and Reagents, Aug. 1999 *Link*.
AFFYMETRIX: GenChip® Price Catalog (U.S. and Canada) Jan. 2000 *Link*.
AFFYMETRIX: Affymetrix® Price Catalog Addendum GeneChip® Arrays and Reagents (U.S. and Canada). Feb. 2000 *Link*.
AFFYMETRIX: Affymetrix® Product Catalog (Global) Aug. 2000 *Link*.
AFFYMETRIX: Affymetrix® Product Catalog (Global), Jan. 2001, *Link*.
AFFYMETRIX: Affymetrix® Product Catalog (Global), Jan. 2002, Link.
AFFYMETRIX: Affymetrix® Product Catalog (Global, Jul. 2002 Link.
AFFYMETRIX: Product Information GeneChip® HuSNP Managing Assay, 1999, Link.
AFFYMETRIX: Product Information GeneChip® GenFlex TM Tag Array, 2000, Link.
AFFYMETRIX: Product Information GeneChip® Yeast Genome S98 Array 2000 Link.
AFFYMETRIX: Product Information GeneChip® HIV PRT Assay, 1997 Link.
AFFYMETRIX: Product Information GeneChip® HIV PRT Plus, 1998. Link.
AFFYMETRIX: Product Information GeneChip® p53 Assay, 1997 Link.
AFFYMETRIX: Product Information GeneChip® p53 Probe Array and Reagents, 1998 Link.
AFFYMETRIX: Product Information GeneChip® CYP450 Assay, 1997 Link.
AFFYMETRIX: Product Information GeneChip® CYP450 Probe Array and Reagents, 1998 Link.
AFFYMETRIX: Product Information GeneChip® HU6800 Array, 1998 Link.
AFFYMETRIX: Product Information Human Genome U95 Set, 2000 Link.
AFFYMETRIX: Product Information GeneChip® Human Genome U133 Set, 2000 Link.
AFFYMETRIX: Product Information GeneChip® Human Genome Focus Array 2002 Link.
AFFYMETRIX: Product Information GeneChip® Human Cancer G110 Array, 1999 Link.
AFFYMETRIX: Product Information Rat Neurobiology U34 Array, 2000 Link.
AFFYMETRIX: Product Information GeneChip® Rat Genome U34 Array Set, 1999, Link.
AFFYMETRIX: Product Information GeneChip® Test 1, 1998 Link
AFFYMETRIX: Product Information GeneChip® Test 2 Array, 1999 Link.
AFFYMETRIX: PRoduct Information GeneChip® Test 3 Array, 2001. Link.
AFFYMETRIX: PRoduct Information GeneChip® Yeast GEnome S96 Array, 1999, Link.

(List continued on next page.)

*Primary Examiner*—John Brusca
*Assistant Examiner*—Shubo Joe Zhou
(74) *Attorney, Agent, or Firm*—Parsons Behle & Latimer

(57) ABSTRACT

The invention provides nucleic acid sequences which are complementary, in one embodiment, to a wide variety of murine genes. The invention provides the sequences in such a way as to make them available for a variety of analyses. As such, the invention related to diverse fields impacted by the nature of molecular interaction, including chemistry, biology, medicine, and medical diagnostics.

1 Claim, No Drawings

OTHER PUBLICATIONS

Affymetrix: Product Information GeneChip® Mu6500 Set, 1998. Link.
Affymetrix: Product Information GeneChip® Murine Genome U74 Set, 2001. Link.
Affymetrix: Product Information GeneChip® Murine 11K Set, 1998. Link.
Affymetrix: Product Information GeneChip® Murine 11K Set. 2001. Link.
Affymetrix: Product Information GeneChip® Murine 19K Set, 1998. Link.
Affymetrix: Product Information Arabidopsis Genome Array, 2000. Link.
Affymetrix: Product Information GeneChip® Arabidopsis ATH1 Genome Array, 2002. Link.
Affymetrix: Product Information E. coli Genome Array, 2000. Link.
Affymetrix: Product Information GeneChip® P. aeruginosa Genome Array, 2001. LinK.
Affymetrix: Product Information P. aeruginosa Genome Array, 2001. Link.
Affymetrix: Product Information Drosophia Genome Array, 2000. Link.
Affymetrix:Product Information GeneChip® B. subtilis Genome Array, 2002. Link.
Affymetrix: Product Information GeneChip® C. elegans Genome Array, 2002. Link.
Affymetrix: Product Information GeneChip® Custom Arrays, 1998. Link.
Affymetrix: Product Information GeneChip® Custom Arrays, 2002. Link.
Affymetrix: Product Information GeneChip® Ye6100 Set, 1998. Link.
Affymetrix: Product Information GeneChip® Human 35K Set, 1998. Link.
Cronin MT. et al. "Cystic fibrosis mutation detection by hybridization to light–generated DNA probe arrays", Human Mutation, 1996, 7, 3, 244–55. Link.
Hacia JG, et al. "Detection of heterozygous mutations in BRCA 1 using high density oligonucleolide arrays and two–colour fluorescene analysis", Nature Genetics, 1996, 14, 4, 441–7. Link.
Kozal MJ, et al. "Extensive polymorphisms observed in HIV–1 clade B protease gene using high–density oligonucleotide arrays", Nature Medicine, 1996, 2, 7, 753–9. Link.
Lockhart DJ, et al. "Expression monitoring by hybridization to high–density oligonucleotide arrays", Nature Biotechnology, 1996, 14, 13, 1675–80. Link.
Shoemaker DD, et al. "Quantitative phenolypic analysis of yeast deletion mutants using a highly parallel molecular bar–coding strategy", Nature Genetics, 1996, 14, 4, 450–6. Link.
Wodicka L, et al. "Genome–wide expression monitoring in Saccharomyces cerevisiae", Nature Biotechnology, 1997, 15, 13, 1359–67. Link.
DE Saizieu A, et al. "Bacterial transcript imaging by hybridization of total RNA to oligoncleotide arrays", Nature Biotechnology, 1998, 16, 1, 45–8. Link.

Fan JB. et al. "Parallel genotyping of human SNPs using generic high–density oligonucleotide tag arrays", Genome Research, 2000, 10, 6, 853–60. Link.
Harmer SL, et al. "Orchestrated transcription of key pathways in Arabidopsis by the circadian clock", Science, 2000, 290, 5499, 2110–3. Link.
Rieneck K, et al. "Massive parallel gene expression profiling of RINm5F pancreatic islet beta–cells stimulated with interleukin–1beta", Apmis, 2000, 108, 12, 855–72. Link.
Rudd KE, "New tools for an old workhorse", Nature Biotechnology, 2000, 18, 12, 1241–2. Link.
Selinger DW, et al. "RNA expression analysis using a 30 base pair resolution *Esherichia coli*genome array", Nature Biotechnology, 2000, 18, 12, 1262–8. Link.
Travers KJ, et al. "Functional and genomic analyses reveal an essential coordination between the unfolded protein response and ER–associated degradation", Cell, 2000, 101, 3, 249–58. Link.
Hakak Y, et al. "Genome–wide expression analysis reveals dysregulation of myelination–related genes in chronic schizophrenia", Proceedings of the National Academy of Sciences, USA, 2001, 98, 8, 4746–51. Link.
LU SC, et al. "Methionine adenosyltransferase 1A knockout mice are predisposed to liver injury and exhibit increased expression of genes involved in Proliferation", Proceedings of the National Academy of Sciences, USA, 2001, 98, 10, 5560–5. Link .
MacDonald TJ. et al. "Expression profiling of meculloblastoma PDGFRA and the RAS/MAPK pathway as therapeutic targets for metastatic disease", Nature Genetics, 2001, 2, 143–52. Link.
Niculescu AB. 3RD, et al. "The Human genome genetic testing and animal models", American Journal of Psychiatry, 2001, 158, 10, 1587. Link.
Stamey TA. et al. "Molecular genetic profiling of Gleason grade 4/5 prostate cancers compared to benign prostatic hyperplasia", Journal of Urology, 2001, 166, 6, 2171–7. Link.
Welsh JB. et al. "Analysis of gene expression profiles in normal and neoplastic ovarian tissue samples identifies candidate molecular markers of epithelial ovarian cancer", Proceedings of the National Academy of Sciences, USA, 2001, 96, 3, 1176–81. Link.
Chee M. et al. "Accessing genetic information with high–density DNA arrays", Science, 1996, 274, 5287, 610–4 Link.
Cho RJ. et al. "Parallel analysis of genetic selections using whole genome oligonucleotide arrays", Proceedings of the National Academy of Sciences of the United States of America, 1998, 95, 7, 3752–7. Link.
Bakay, et al. "Sources of variability and effect of experimental approach on expression profiling data interpretation", 2002, 3:4 Link.
Carmel, et al. "Gene expression profiling of acute spinal cord injury reveals spreading inflammatory signals and neuron loss", Pyhysiol Genomics 2001, 7:201–213. Link.
Affymetrix, Inc. Securities and Exchange Commission Filing S–3 filed on Oct. 17, 1997, also available at http://www.sec.gov/Archives/edgar/data/913077/0001047469–97–001100.txt. Link.

METHODS OF GENETIC ANALYSIS USING NUCLEIC ACID ARRAYS

CROSS REFERENCE TO RELATED APPLICATIONS

The present application is a non-provisional application claiming priority from Provisional U.S. Patent Application Serial No. 60/100,678 filed Sep. 17, 1998.

REFERENCE TO SEQUENCE LISTING

The sequence listing, including SEQ ID NOS: 1–127811, is contained on compact disc in two copies, labeled Copy 1 and Copy 2. The computer readable form is on a compact disc labeled CRF. The file name on each of the three compact discs is seqlist.rtf, created Jul. 12, 2002. Each file is approximately 16.3 kilobytes. The sequence listing information recorded in the computer readable form is identical to the written compact disc sequence listing. The sequence listing is hereby incorporated in this application in its entirety and is to be considered part of the disclosure of this specification.

BACKGROUND OF THE INVENTION

The present invention provides a unique pool of nucleic acid sequences useful for analyzing molecular interactions of biological interest. The invention therefore relates to diverse fields impacted by the nature of molecular interaction, including chemistry, biology, medicine, and medical diagnostics.

FIELD OF THE INVENTION

Many biological functions are carried out by regulating the expression levels of various genes, either through changes in levels of transcription (e.g. through control of initiation, provision of RNA precursors, RNA processing, etc.) of particular genes, through changes in the copy number of the genetic DNA, or through changes in protein synthesis. For example, control of the cell cycle and cell differentiation, as well as diseases, are characterized by the variations in the transcription levels of a group of genes.

Gene expression is not only responsible for physiological functions, but also associated with pathogenesis. For example, the lack of sufficient functional tumor suppressor genes and/or the over expression of oncogene/protooncogenes leads to tumorgenesis. (See. e.g., Marshall, Cell, 64: 313–326 (1991) and Weinberg, Science, 254: 1138–1146 (1991).) Thus, changes in the expression levels of particular genes (e.g. oncogenes or tumor suppressors), serve as signposts for the presence and progression of various diseases.

As a consequence, novel techniques and apparatus are needed to study gene expression in specific biological systems.

All documents, i.e., publications and patent applications, cited in this disclosure, including the foregoing, are incorporated by reference herein in their entireties for all purposes to the same extent as if each of the individual documents were specifically and individually indicated to be so incorporated by reference herein in its entirety.

SUMMARY OF THE INVENTION

The invention provides nucleic acid sequences which are complementary to particular genes and makes them available for a variety of analyses, including, for example, gene expression analysis. For example, in one embodiment the invention comprises an array comprising of any 10 or more, 100 or more, 1000, or more, 10,000 or more or 100,000 or more nucleic acid probes containing 9 or more consecutive nucleotides from the sequences listed in SEQ ID NOS: 1–127811, or the perfect match, perfect mismatch, antisense match or antisense mismatch thereof. In a further embodiment, the invention comprises the use of any of the above arrays or fragments disclosed in SEQ ID NOS: 1–127811 to: monitor gene expression levels by hybridization of the array to a DNA library; monitor gene expression levels by hybridization to an mRNA protein fusion compound; identify polymorphisms; identify biallelic markers; produce genetic maps; analyze genetic variation; comparatively analyze gene expression between different species; analyze gene knockouts; or, to hybridize tag-labeled compounds. In a further embodiment the invention comprises a method of analysis comprising of hybridizing one or more pools of nucleic acids to two or more of the fragments disclosed in TABLE 1 and detecting said hybridization. In a further embodiment the invention comprises the use of any one or more of the fragments disclosed in SEQ ID NOS: 1–127811 as a primer for PCR. In a further embodiment the invention comprises the use of any one or more of the fragments disclosed in SEQ ID NOS: 1–127811 as a ligand.

DETAILED DESCRIPTION OF THE INVENTION

1. Definitions

Massive Parallel Screening: The phrase "massively parallel screening" refers to the simultaneous screening of at least about 100, preferably about 1000, more preferably about 10,000 and more preferably about 100,000 different nucleic acid hybridizations.

Nucleic Acid: The terms "nucleic acid" or "nucleic acid molecule" refer to a deoxyribonucleotide or ribonucleotide polymer in either single-or double-stranded form, and unless otherwise limited, would encompass analogs of natural nucleotides that can function in a similar manner as naturally occurring nucleotides. Nucleic acids may be derived from a variety or sources including, but not limited to, naturally occurring nucleic acids, clones, synthesis in solution or solid phase synthesis.

Probe: As used herein a "probe" is defined as a nucleic acid capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases (7-deazaguanosine, inosine, etc.). In addition, the bases in probes may be joined by a linkage other than a phosphodiester bond, so long as it does not interfere with hybridization. Thus. probes may be peptide nucleic acids in which the constituent bases are joined by peptide bonds rather than phosphodiester linkages.

Target nucleic acid: The term "target nucleic acid" or "target sequence" refers to a nucleic acid or nucleic acid sequence which is to be analyzed. A target can be a nucleic acid to which a probe will hybridize. The probe may or may not be specifically designed to hybridize to the target. It is either the presence or absence of the target nucleic acid that is to be detected, or the amount of the target nucleic acid that is to be quantified. The term target nucleic acid may refer to the specific subsequence of a larger nucleic acid to which the probe is directed or to the overall sequence (e.g., gene or mRNA) whose expression level it is desired to detect. The difference in usage will be apparent from context.

mRNA or transcript: The term "mRNA" refers to transcripts of a gene. Transcripts are RNA including, for example, mature messenger RNA ready for translation, products of various stages of transcript processing. Transcript processing may include splicing, editing and degradation.

Subsequence: "Subsequence" refers to a sequence of nucleic acids that comprise a part of a longer sequence of nucleic acids.

Perfect match: The term "match," "perfect match," "perfect match probe" or "perfect match control" refers to a nucleic acid that has a sequence that is perfectly complementary to a particular target sequence. The nucleic acid is typically perfectly complementary to a portion (subsequence) of the target sequence. A perfect match (PM) probe can be a "test probe", a "normalization control" probe, an expression level control probe and the like. A perfect match control or perfect match is, however, distinguished from a "mismatch" or "mismatch probe." Mismatch: The term "mismatch," "mismatch control" or "mismatch probe" refers to a nucleic acid whose sequence is deliberately selected not to be perfectly complementary to a particular target sequence. As a non-limiting example, for each mismatch (MM) control in a high-density probe array there typically exists a corresponding perfect match (PM) probe that is perfectly complementary to the same particular target sequence. The mismatch may comprise one or more bases. While the mismatch(es) may be located anywhere in the mismatch probe, terminal mismatches are less desirable because a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions. A homo-mismatch substitutes an adenine (A) for a thymine (T) and vice versa and a guanine (G) for a cytosine (C) and vice versa. For example, if the target sequence was: AGGTCCA, a probe designed with a single homo-mismatch at the central, or fourth position, would result in the following sequence TCCTGGT.

Array: An "array" is a solid support with at least a first surface having a plurality of different nucleic acid sequences attached to the first surface.

Gene Knockout: the term "gene knockout," as defined in Lodish et al. *Molecular Cell Biology 3rd Edition,* Scientific American Books pub., which is hereby incorporated in its entirety for all purposes is, is a technique for selectively inactivating a gene by replacing it with a mutant allele in an otherwise normal organism.

DNA Library—as used herein the term "genomic library" or "genomic DNA library" refers to a collection of cloned DNA molecules consisting of fragments of the entire genome (genomic library) or of DNA copies of all the mRNA produced by a cell type (cDNA library) inserted into a suitable cloning vector.

Polymorphism—"polymorphism" refers to the occurrence of two or more genetically determined alternative sequences or alleles in a population. A polymorphic marker or site is the locus at which divergence occurs. Preferred markers have at least two alleles, each occurring at a frequency of greater than 1%, and more preferably greater than 10% or 20% of the selected population. A polymorphic locus may be as small as one base pair. Polymorphic markers include restriction fragment length polymorphisms, variable number or tandem repeats (VNTR's), hypervariable regions, minisatellites, dinucleotide repeats, trinucleotide repeats, tetranucleotide repeats, simple sequence repeats, and insertion elements such as ALU. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic or biallelic polymorphism has two forms. A triallelic polymorphism has three forms.

Genetic map—a "genetic map" is a map which presents the order of specific sequences on a chromosome.

Genetic variation—"genetic variation" refers to variation in the sequence of the same region between two or more organisms.

Hybridization—the association of two complementary nucleic acid strands or their derivatives (such as PNA) to form double stranded molecules. Hybrids can contain two DNA strands, two RNA strands, or one DNA and one RNA strand.

mRNA-protein fusion—a compound whereby an mRNA is directly attached to the peptide or protein it incodes by a stable covalent linkage.

Ligand—any molecule, other than an enzyme substrate, that binds tightly and specifically to a macromolecule, for example, a protein, forming a macromolecule-ligand complex.

II. General

SEQ ID NOS: 1–127811, encompassed in Appendix I, present target sequences included in the invention. Each target sequence from columns 2, 5 and 8 corresponds to and represents at least four additional nucleic acid sequences included in the invention. As an example, if a central portion of a nucleic acid sequence listed in SEQ ID NOS: 1–127811 happened to be: 5'-agcgtgcca-3' the additional sequences included in the invention which are represented by this nucleic acid sequence would be, for example:

5'-tggcacgct-3'=(perfect) sense match
5'-tggctcgct-3'=sense mismatch
5'-agcgtgcca-3' =(perfect) antisense match
5'-agcgagcca-3' =antisense mismatch.

Accordingly, for each nucleic acid sequence listed in SEQ ID NOS: 1–127811, this disclosure includes the corresponding sense match, sense mismatch, antisense match and antisense mismatch. The position of the mismatch is not limited to near the center of the nucleic acid as in the above example, it may be located anywhere in the nucleic acid sequence and may comprise one or more bases.

Consequently, the present invention includes: a) the target sequences listed in SEQ ID NOS: 1–127811, columns 2, 5 and 8 or the sense match, sense mismatch, antisense match or antisense mismatch thereof; b) clones which comprise the target nucleic acid sequences listed in SEQ ID NOS: 1–1 27811, columns 2, 5 and 8 or the sense-match, sense mismatch, antisense match or antisense mismatch thereof; c) longer nucleotide sequences which include the nucleic acid sequences listed in SEQ ID NOS 1–127811, columns 2, 5, and 8 or the sense match, sense mismatch, antisense match or antisense mismatch thereof and d) subsequences greater than 9 nucleotides in length of the target nucleic acid sequences listed in SEQ ID NOS: 1–127811, columns 2, 5, and 8 or the sense match, sense mismatch, antisense match or antisense mismatch.

Target sequences were chosen from clusters of known murine genes available on the Unigene database as of Aug. 15, 1996. Target sequences were selected using the computer based methods described in U.S. Pat. No. 6,309,822 (issued Oct. 30, 2001), incorporated herein by reference for all purposes.

For each target sequence listed in SEQ ID NOS: 1–127811 is a corresponding Genbank database accession number. These accession numbers allow for the identification of sequences located in the Genbank sequence database through the use of computer programs such as BLAST. Access to BLAST is available to the public through the Internet at, for example, httl://www.ncbi.nim.nih.gov. One of skill in the art will be familiar with the use of the BLAST program to obtain information about particular sequences in order to, for example, determine the species from which the sequence is derived, determine the gene from which the sequence is derived, to determine other genes and species which contain similar sequences and to determine the degree of similarity between one sequence and another. All information relating to the target sequences available through the Genbank database is hereby incorporated by reference for all purposes.

The present invention provides a pool of unique nucleotide sequences complementary to murine genes and ESTs in particular embodiments which alone, or in combinations of 2 or more, 10 or more, 100 or more, 1,000 or more, 10,000 or more, or 100,000 or more, can be used for a variety of applications.

In one embodiment, the present invention provides for a pool of unique nucleotide sequences which are complementary to approximately 6500 murine genes formed into a high density array of probes suitable for array based massive parallel gene expression. Array based methods for monitoring gene expression arc disclosed and discussed in detail in U.S. Pat. No. 5,800,992 (issued Sep. 9, 1998), and U.S. Pat. No. 6,309,822 (issued Oct. 30, 2001) and PCT Application WO 92/10588 (published on Jun. 25, 1992), all of which are incorporated herein by reference for all purposes. Generally those methods of monitoring gene expression involve (1) providing a pool of target nucleic acids comprising RNA transcript(s) of one or more target gene(s), or nucleic acids derived from the RNA transcript(s); (2) hybridizing the nucleic acid sample to a high density array of probes and (3) detecting the hybridized nucleic acids and calculating a relative expression (transcription, RNA processing or degradation) level.

The development of Very Large Scale Immobilized Polymer Synthesis or VLSIPS™ technology has provided methods for making very large arrays of nucleic acid probes in very small arrays. See U.S. Pat. No. 5,143,854 and PCT patent publication Nos. WO 90/15070 and 92/10092, and Fodor et al., *Science*, 251, 767–77 (1991), each of which is incorporated herein by reference. U.S. patent application Ser. No. 08/670,118, describes methods for making arrays of nucleic acid probes that can be used to detect the presence of a nucleic acid containing a specific nucleotide sequence. Methods of forming high density arrays of nucleic acids, peptides and other polymer sequences with a minimal number of synthetic steps are known. The nucleic acid array can be synthesized on a solid substrate by a variety of methods, including, but not limited to, light-directed chemical coupling, and mechanically directed coupling.

In a preferred detection method, the array of immobilized nucleic acids, or probes, is contacted with a sample containing target nucleic acids, to which a flourescent label is attached. Target nucleic acids hybridize to the probes on the array and any non-hybridized nucleic acids are removed. The array containing the hybridized target nucleic acids are exposed to light which excites the flourescent label. The resulting flourescent intensity, or brightness, is detected. Relative brightness is used to determine which probe is the best candidate for the perfect match to the hybridized target nucleic acid because flourescent intensity (brightness) corresponds to binding affinity. Once the position of the perfect match probe is known, the sequence of the hybridized target nucleic is known because the sequence and position of the probe is known.

In the array of the present invention the probes are presented in pairs, one probe in each pair being a perfect match to the target sequence and the other probe being identical to the perfect match probe except that the central base is a homo-mismatch. Mismatch probes provide a control for non-specific binding or cross-hybridization to a nucleic acid in the sample other than the target to which the probe is directed. Thus, mismatch probes indicate whether a hybridization is or is not specific. For example, if the target is present, the perfect match probes should be consistently brighter than the mismatch probes because fluorescence intensity, or brightness, corresponds to binding affinity. (See, for example U.S. Pat. No. 5,324,633, which is incorporated herein for all purposes.) In addition, if all central mismatches are present, the mismatch probes can be used to detect a mutation. Finally the difference in intensity between the perfect match and the mismatch probe (I(PM)-I(MM)) provides a good measure of the concentration of the hybridized material. See pending PCT application No. 98/11223, which is incorporated herein by reference for all purposes. The probe pairs are presented in both sense and antisense orientation, thereby eliciting a total of four probes per target sequence: sense match, sense mismatch, antisense match and antisense mismatch.

In another embodiment, the current invention provides a pool of sequences which may be used as probes for their complementary genes listed in the Genbank database. Methods for making probes are well known. See for example Sambrook, Fritsche and Maniatis. "Molecular 15 Cloning A laboratory Manual" 2nd Ed. Cold Spring Harbor Press (1989) ("Maniatis et al.") which is hereby incorporated in its entirety by reference for all purposes. Maniatis et al. describes a number of uses for nucleic acid probes of defined sequence. Some of the uses described by Maniatis et al. include: to screen cDNA or genomic DNA libraries, or subclones derived from them, for additional clones containing segments of DNA that have been isolated and previously sequenced; in Southern, northern, or dot-blot hybridization to identify or detect the sequences of specific genes; in Southern, or dot-blot hybridization of genomic DNA to detect specific mutations in genes of known sequence; to detect specific mutations generated by site-directed mutagenesis of cloned genes; and to map the 5' termini of mRNA molecules by primer extensions. Maniatis et al. describes other uses for probes throughout. See also Alberts et al. *Molecular Biology of the Cell 3rd edition,* Garland Publishing Inc. (1994) p. 307 and Lodish et al. *Molecular Cell Biology, 3rd edition,* Scientific American Books (1995) p. 285–286, each of which is hereby incorporated by reference in its entirety for all purposes, for a brief discussion of the use of nucleic acid probes in in situ hybridization. Other uses for probes derived from the sequences disclosed in this invention will be readily apparent to those of skill in the art. See, for example, Lodish et al. *Molecular Cell Biology, 3rd edition,* Scientific American Books (1995) p.229–233, incorporated above, for a description of the construction of genomic libraries.

In another embodiment, the current invention may be combined with known methods to monitor expression levels of genes in a wide variety of contexts. For example, where the effects of a drug on gene expression are to be determined, the drug will be administered to an organism, a tissue sample, or a cell and the gene expression levels will be analyzed. For example, nucleic acids are isolated from the treated tissue sample, cell, or a biological sample from the organism and from an untreated organism tissue sample or cell, hybridized to a high density probe array containing probes directed to the gene of interest and the expression levels of that gene are determined. The types of drugs that may be used in these types of experiments include, but are not limited to, antibiotics, antivirals, narcotics, anti-cancer drugs, tumor suppressing drugs, and any chemical composition which may affect the expression of genes in vivo or in vitro. The current invention is particularly suited to be used in the types of analyses described by, for example, pending U.S. Pat. No. 6,309,822 and PCT Application No. 98/11223, each of which is incorporated by reference in its entirety for all purposes. As described in Wodicka et al., Nature Biotechnology 15 (1997), (hereby incorporated by reference in its entirety for all purposes), because mRNA hybridization correlates to gene expression level, hybridization patterns can be compared to determine differential gene expression. As non-limiting examples: hybridization patterns from samples treated with certain types of drugs may be compared to hybridization patterns from samples which have not been treated or which have been treated with a different drug; hybridization patterns for samples infected with a specific virus may be compared against hybridization patterns from non-infected samples; hybridization patterns for samples with cancer may be compared against hybridization patterns for samples without cancer; hybridization patterns of samples from cancerous cells which have been treated with a tumor suppressing drug may be compared against untreated cancerous cells, etc. Zhang et al., Science 276 1268–1272, (hereby incorporated by reference in its entirety for all purposes), provides an example of how gene expression data can provide a great deal of insight into cancer research. One skilled in the art will appreciate that a wide range of applications will be available using 2 or more, 10 or more, 100 or more, 1000 or more, 10,000 or more or 100,000 or more of the SEQ ID NOS: 1–127811 sequences as probes for gene expression analysis. The combination of the DNA array technology and the mouse specific probes in this disclosure is a powerful tool for studying gene expression.

In another embodiment, the invention may be used in conjunction with the techniques which link specific proteins to the mRNA which encodes the protein. (See for example Roberts and Szostak Proc. Natl. Acad. Sci. 94 12297–12302 (1997) which is incorporated herein in its entirety for all purposes.) Hybridization of these mRNA-protein fusion compounds to arrays comprised of 2 or more, 10 or more, 100 or more, 1000 or more, 10,000 or more, or 100,000 or more the sequences disclosed in the present invention provides a powerful tool for monitoring expression levels.

In one embodiment, the current invention provides a pool of unique nucleic acid sequences which can be used for parallel analysis of gene expression under selective conditions. Without wishing to be limited, genetic selection under selective conditions could include: variation in the temperature of the organism's environment; variation in pH levels in the organism's environment; variation in an organism's food (type, texture, amount etc.); variation in an organism's surroundings; etc. Arrays, such as those in the present invention, can be used to determine whether gene expression is altered when an organism is exposed to selective conditions.

Methods for using nucleic acid arrays to analyze genetic selections under selective conditions are known. (See for example, R. Cho et al., Proc. Natl. Acad. Sci. 95 3752–3757 (1998) incorporated herein in its entirety for all purposes.)

Cho et al. describes the use of a high-density array containing oligonucleotides complementary to every gene in the yeast *Saccharomyces cerevisiae* to perform two-hybrid protein-protein interaction screens for *S. cerevisiae* genes implicated in mRNA splicing and microtubule assembly. Cho et al. was able to characterize the results of a screen in a single experiment by hybridization of labeled DNA derived from positive clones. Briefly, as described by Cho et al., two proteins are expressed in yeast as fusions to either the DNA-binding domain or the activation domain of a transcription factor. Physical interaction of the two proteins reconstitutes transcriptional activity, turning on a gene essential for survival under selective conditions. In screening for novel protein-protein interactions, yeast cells arc first transformed with a plasmid encoding a specific DNA-binding fusion protein. A plasmid library of activation domain fusions derived from genomic DNA is then introduced into these cells. Transcriptional activation fusions found in cells that survive selective conditions are considered to encode peptide domains that may interact with the DNA binding domain fusion protein. Clones are then isolated from the two-hybrid screen and mixed into a single pool. Plasmid DNA is purified from the pooled clones and the gene inserts are amplified using PCR. The DNA products are then hybridized to yeast whole genome arrays for characterization. The methods employed by Cho et al. are applicable to the analysis of a range of genetic selections. High density arrays created using two or more, 10 or more, 100 or more, 1000 or more, 10,000 or more, or 100,000 or more of the sequences disclosed in the current invention can be used to analyze genetic selections in the mouse system using the methods described in Cho et al.

In another embodiment, the current invention provides a pool of unique nucleic acid sequences which can be used to identify biallelic markers, providing a novel and efficient approach to the study of genetic variation. For example, methods for using high density arrays comprised of probes which are complementary to the genomic DNA of a particular species to interrogate polymorphisms are well known. (See for example, U.S. Pat. No. 6,300,063 (issued Oct. 9, 2001) and U.S. patent application Ser. No. 08/965, 620 which are hereby incorporated herein for all purposes.) Pools of 2 or more, 10 or more, 100 or more, 1000 or more, 10,000 or more, or 100,000 or more of the sequences disclosed in this invention combined with the methods described in the above patent applications provides a tool for studying genetic variation in the mouse system.

In another embodiment of the invention, genetic variation can be used to produce genetic maps of various strains of mouse. Winzeler et al., "Direct Allelic Variation Scanning of the Yeast Genome" Science (in press) (1998), which is hereby incorporated for all purposes describe methods for conducting this type of screening with arrays containing probes complementary to the yeast genome. Briefly, genomic DNA from strains which are phenotypically different are isolated, fragmented, and labelled. Each strain is then hybridized to identical arrays comprised of the nucleic acid sequences complementary to the system being studied. Comparison of hybridization patterns between the various strains then serve as genetic markers. As described by Winzler et al, these markers can then be used for linkage analysis. High density arrays created from 2 or more, 10 or more, 100 or more, 1000 or more, 10,000 or more, or 100,000 or more of the sequences disclosed in this invention can be used to study genetic variation using the methods described by Winzler et al.

In another embodiment, the present invention may be used for cross-species comparisons. One skilled in the art will appreciate that it is often useful to determine whether a gene present in one species, for example the mouse, is present in a conserved format in another species, including, without limitation, mouse, human, chicken, zebrafish, drosophila, or yeast. See, for example, Andersson et al., Mamm Genome 7(10):717–734 (1996,) which is hereby incorporated by reference for all purposes, which describes the utility of cross-species comparisons. The use of 2 or more, 10 or more, 100 or more, 1000 or more, 10,000 or more or 100,000 or more of the sequences disclosed in this invention in an array can be used to determine whether any of the sequence from one or more of the murine genes represented by the sequences disclosed in this invention is conserved in another species by, for example, hybridizing genomic nucleic acid samples from another species to an array comprised of the sequences disclosed in this invention. Areas of hybridization will yield genomic regions where the nucleotide sequence is highly conserved between the interrogation species and the mouse.

In another embodiment, the present invention may be used to characterize the genotype of knockouts. Methods for using gene knockouts to identify a gene are well known. See for example, Lodish et al. *Molecular Cell Biology, 3rd Edition,* Scientific American Books pub pp. 292–296 and U.S. Pat. No. 5,679,523 which are hereby incorporated by reference for all purposes. By isolating genomic nucleic acid samples from knockout species with a known phenotype and hybridizing the samples to an array comprised of 2 or more, 10 or more, 100 or more, 1000 or more, 10,000 or more, or 100,000 or more of the sequences disclosed in this invention, candidates genes which contribute to the phenotype will be identified and made accessible for further characterization.

In another embodiment, the present invention may be used to identify new gene family members. Methods of screening libraries with probes are well known. (See, for example, Maniatis et al, incorporated by reference above.) Because the present invention is comprised of nucleic acid sequences from specific known genes, 2 or more, 10 or more, 100 or more, 1000 or more, 10,000 or more, or 100,000 or more of sequences disclosed in this invention may be used as probes to screen genomic libraries to look for additional family members of those genes from which the target sequences are derived.

In another embodiment, the present invention may be used to provide nucleic acid sequences to be used as tag sequences. Tag sequences are a type of genetic "bar code" which can be used to label compounds of interest. The analysis of deletion mutants using tag sequences is described in, for example, Shoemaker et al., Nature Genetics 14 450–456 (1996), which is hereby incorporated by reference in its entirety for all purposes. Shoemaker et al. describes the use of PCR to generate large numbers of deletion strains. Each deletion strain is labelled with a unique 20-base tag sequence that can be hybridized to a high-density oligonucleotide array. The tags serve as unique identifiers (molecular bar codes) that allow analysis of large numbers of deletion strains simultaneously through selective growth conditions. The use of tag sequences need not be limited to this example however. The utility of using unique known short oligonucleotide sequences capable of hybridizing to a nucleic acid array to label various compounds will be apparent to one skilled in the art. One or more, 10 or more, 100 or more, 1000 or more, 10,000 or more, or 100,000 or more of the SEQ ID NOS: 1–127811 sequences are excellent candidates to be used as tag sequences.

In another embodiment of the invention, the sequences of this invention may be used to generate primers directed to their corresponding genes as disclosed in the Genbank or any other public database. These primers may be used in such basic techniques as sequencing or PCR, see for example Maniatis et al., incorporated by reference above.

In another embodiment, the invention provides a pool of nucleic acid sequences to be used as ligands for specific genes. The sequences disclosed in this invention may be used as ligands to their corresponding genes as disclosed in the Genbank or any other public database. Compounds which specifically bind known genes are of interest for a variety of uses. One particular clinical use is to act as an antisense protein which specifically binds and disables a gene which has been, for example, linked to a disease. Methods and uses for ligands to specific genes are known. See for example. U.S. Pat. No. 5,723,594 which is hereby incorporated by reference in its entirety for all purposes.

In a preferred embodiment, the hybridized nucleic acids are detected by detecting one or more labels attached to the sample nucleic acids. The labels may be incorporated by any of a number of means well known to those of skill in the art. In one embodiment, the label is simultaneously incorporated during the amplification step in the preparation of the sample nucleic acids. Thus, for example, polymerase chain reaction (PCR) with labeled primers or labeled nucleotides will provide a labeled amplification product. In a another embodiment, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic, acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescenn, texas red, rhodamine, green fluorescent protein, and the like), radiolabels (e.g., $^{3}$H, $^{125}$I, $^{35}$S, $^{14}$C, or $^{32}$p), phosphorescent labels, enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241, each of which is hereby incorporated by reference in its entirety for all purposes.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of, the enzyme on the substrate, and colorimetric labels are detected by simply visualizing the colored label.

The label may be added to the target nucleic acid(s) prior to, or after the hybridization. So called "direct labels" are detectable labels that are directly attached to or incorporated into the target nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization; After hybridization, an aviden-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol. 24: Hybridization With Nucleic Acid Probes,* P. Tijssen, ed. Elsevier, N.Y., (1993) which is hereby incorporated by reference in its entirely for all purposes.

Fluorescent labels are preferred and easily added during an in vitro transcription reaction. In a preferred embodiment, fluorescein labeled UTP and CTP are incorporated into the RNA produced in an vitro transcription reaction as described above.

EXAMPLE

The following example serves to illustrate the type of experiment that could be conducted using the invention.

Expression Monitoring by Hybridization to High Density Oligonucleotide Arrays Arrays containing the desired number of probes can be synthesized using the method described in U.S. Pat. No. 5,143,854, incorporated by reference above. Extracted poly $(A)^+$RNA can then be coverted to cDNA using the methods described below. The cDNA is then transcribed in the presence of labeled ribonucleotide triphosphates. The label may be biotin or a dye such as fluorescein. RNA is then fragmented with heat in the presence of magnesium ions. Hybridizations are carried out in a flow cell that contains the two-dimensional DNA probe arrays. Following a brief washing step to remove unhybridized RNA, the arrays are scanned using a scanning confocal microscope.

1. A method of RNA preparation:

Labeled RNA is prepared from clones containing a T7 RNA polymerase promoter site by incorporating labeled nbonucleotides in an IVT reaction. Either biotin-labeled or fluorescein-labeled UTP and CTP (1:3 labeled to unlabeled) plus unlabeled ATP and GTP is used for the reaction with 2500 U of T7 RNA polymerase. Following the reaction unincorporated nucleotide triphosphates are removed using size-selective membrane such as Microcon-100, (Amicon, Beverly, Mass.). The total molar concentration of RNA is based on a measurement of the absorbance at 260 inn. Following quantitation of RNA amounts, RNA is fragmented randomly to an average length of approximately 50 bases by heating at 94° in 40 mM Tris-acetate pH 8.1, 100 mM potassium acetate, 30 mM magnesium acetate, for 30 to 40 min. Fragmentation reduces possible interference from RNA secondary structure, and minimizes the effects of multiple interactions with closely spaced probe molecules. For material made directly from cellular RNA, cytoplasmic RNA is extracted from cells by the method of Favaloro et al. Methods Enzymol. 65:718–749 (1980) hereby incorporated by reference for all purposes, and poly $(A)^+$ RNA is isolated with an oligo dT selection step using, for example, Poly Atract, (Promega, Madison, Wis.). RNA can be amplified using a modification of the procedure described by Eberwine et al. Proc. Natl. Acad. Sci. USA 89:3010–3014 (1992) hereby incorporated by reference for all purposes. Microgram amounts of poly $(A)^+$ RNA are converted into double stranded cDNA using a cDNA synthesis kit (kits may be obtained from Life Technologies, Gaithersburg, Md.) with an oligo dT primer incorporating a T7 RNA polymerase promoter site. After second-strand synthesis, the reaction mixture is extracted with phenol/chloroform, and the double-stranded, DNA isolated using a membrane filtration step using, for example, Microcon-100, (Amicon). Labeled cDNA can be made directly, from the cDNA pool with an IVT step as described above. The total molar concentration of labeled cRNA is determined from the absorbance at 260 nm and assuming an average RNA size of 1000 ribonucleotides. The commonly used convention is that 1 OD is equivalent to 40 ug of RNA, and that 1 ug of cellular mRNA consists of 3 pmol of RNA molecules. Cellular mRNA may also be labeled directly without any intermediate cDNA synthesis steps. In this case, Poly $(A)^+$ RNA is fragmented as described, and the 5' ends of the fragments are kinased and then incubated overnight with a biotinylated oligoribonucleotide (5'-biotin-AAAAAA-3') in the presence of T4 RNA ligase (available from Epicentre Technologies, Madison, Wis.). Alternatively, mRNA has been labeled directly by UV-induced cross-linking to a psoralen derivative linked to biotin (available from Schleicher & Schuell, Keene, N.H.).

2. Array hybridization and Scanning:

Array hybridization solutions can be made containing 0.9 M NaCl, 60 mM EDTA, and 0.005% of the product octylphenol ethylene oxide condensate sold under the trademark Triton® as described by Sigma Product number X-100, adjusted to pH 7.6 (referred to as 6×SSPE-T). In addition, the solutions should contain 0.5 mg/ml unlabeled, degraded herring sperm DNA (available from Sigma, St. Louis, Mo.). Prior to hybridization, RNA samples are heated in the hybridization solution to 99° C. for 10 min, placed on ice for 5 min, and allowed to equilibrate at room temperature before being placed in the hybridization flow cell. Following hybridization, the solutions are removed, the arrays washed with 6×SSPE-T at 22C for 7 min, and then washed with 0.5×SSPE-T at 40° C. for 15 min. When biotin labeled RNA is used the hybridized RNA should be stained with a streptavidin-phycoerythrin in 6×SSPE-T at 40° C. for 5 min. The arrays are read using a scanning confocal microscope made by Molecular Dynamics (commercially available through Affymetnx, Santa Clara, Calif.). The scanner uses an argon ion laser as the excitation source, with the emission detected by a photomultiplier tube through either a 530 nm bandpass filter (flourescein) or a 560 nm longpass filter (phycoerythrin). Nucleic acids of either sense or antisense orientations may be used in hybridization experiments. Arrays for probes with either orientation (reverse complements of each other) are made using the same set of photolithgraphic masks by reversing the order of the photochemical steps and incorporating the complementary nucleotide.

3. Quantitative analysis of hybridization patterns and intensities.

Following a quantitative scan of an array, a grid is aligned to the image using the known dimensions of the array and the corner control regions as markers. The image is then reduced to a simple text file containing position and intensity information using software developed at Affymetnx (available with the confocal scanner). This information is merged with another text file that contains information relating physical position on the array to probe sequence and the identity of the RNA (and the specific pan of the RNA) for which the oligonucleotide probe is designed. The quantitative analysis of the hybridization results involves a simple form of pattern recognition based on the assumption that, in the presence of a specific RNA, the perfect match (PM) probes will hybridize more strongly on average than their mismatch (MM) partners. The number of instances in which the PM hybridization is larger than the MM signal is computed along with the average of the logarithm of the PN1/MM ratios for each probe set. These values are used to make a decision (using a predefined decision matrix) concerning the presence or absence of an RNA. To determine the quantitative RNA abundance, the average of the difference (PM-MM) for each probe family is calculated. The advantage of the difference method is that signals from random cross-hybridization contribute equally, on average, to the PM and MM probes, while specific hybridization contributes more to the PM probes. By averaging the pairwise differences, the real signals add constructively while the contributions from cross-hybridization tend to cancel. When assessing the differences between two different RNA samples, the hybridization signals from side-by-side experiments on identically synthesized arrays are compared directly. The magnitude of the changes in the average of the difference (PM-MM) values is interpreted by comparison with the results of spiking experiments as well as the signals observed for the internal standard bacterial and phase RNAs spiked into each sample at a known amount. Data analysis programs, such as those described in U.S. patent Ser. No. 08/828,952 perform these operations automatically.

CONCLUSION

The inventions herein provide a pool of unique nucleic acid sequences which are complementary to approximately 6500 specific known murine genes. These sequences can be used for a variety of types of analyses.

The above description is illustrative and not restrictive. Many variations of the invention will become apparent to those of skill in the art upon review of this disclosure. The scope of the invention should, therefore, be determined not with reference to the above description, but instead be determined with reference to the appended claims along with their full scope of equivalents.

TABLE 1

| SEQ ID NO | sequence | DBAxnID | SEQ ID NO | sequence | DBAxnID | SEQ ID NO | sequence | DBAxnID |
|---|---|---|---|---|---|---|---|---|
| 1 | gacatgtcgcaagtcacagaatta | | 42605 | cagaaggagctttgcctgttctt | AA017966 | 85209 | tggctcttcagctgctaccagcag | D86948 |
| 2 | attgctgcaatgcacagaatattt | | 42606 | tggttcttcgggaacgtggcact | AA017966 | 85210 | ctgctaccagcaggcagagtcgag | D86948 |
| 3 | gttgctggatctgctgtttgaagcg | | 42607 | ttcttcctgggaacgtggcacttg | AA017966 | 85211 | gagataccaaggctaggccacata | D86948 |
| 4 | ggatctgctgtttgaagcgcagcag | | 42608 | tcttcctgggaacgtggcacttga | AA017966 | 85212 | ataccaaggctaggccacataagt | D86948 |
| 5 | ggcgcaggtgcatcgccagcatt | | 42609 | cctgggaacgtggcacttgatgaa | AA017966 | 85213 | cccaaggctaggccacataagtcac | D86948 |
| 6 | gcaggtgcatcgccagcatcgat | | 42610 | tgagcagacagcactccgcatggt | AA017966 | 85214 | cagctgacccactggaagtgccaacc | D86948 |
| 7 | gcatcgcagcatttcgatcctgt | | 42611 | agcagacagcactccgcatggttg | AA017966 | 85215 | cttggccacctgtaccaagtccag | D86948 |
| 8 | gcattgcatcctcgtcaggtcga | | 42612 | agacgcactccgcatggttggaa | AA017966 | 85216 | cctgcacgcaggccaattctat | D86948 |
| 9 | cgatctgtcaggtcaggtcagc | | 42613 | gacgcactccgcatggttggaag | AA017966 | 85217 | catgcaggccaattctatcgctgt | D86948 |
| 10 | tcgtcaggtgcaggtcagcacgtg | | 42614 | cagcactccgcatggttggaagaa | AA017966 | 85218 | ttcctatcgtgtgatgaaggt | D86948 |
| 11 | gcaggtgcacgtgctgcgtcagtt | | 42615 | actcgtgcatggttgggagaagcg | AA017966 | 85219 | ttcctgagccgcctcgtgcct | D86948 |
| 12 | cagcacgttgctgtgctgattaagacc | | 42616 | ggcactccaggagagagaggtccc | AA017966 | 85220 | gatacaggcgtgctgttctgc | D86948 |
| 13 | gctgtcgattaagaccggacgttgt | | 42617 | gcactccaggagagagaggtccca | AA017966 | 85221 | acagctgggcatgttctccagg | D86948 |
| 14 | agctgtccggaagatgcaatac | | 42618 | catcctatagagttgaataatgt | AA017966 | 85222 | tagatacaggggtcctcaacca | AA105976 |
| 15 | agattgcaaatactgcccgcaaacg | | 42619 | atctctatagagttgataatgt | AA017966 | 85223 | tgcccgatttgtgctgcatg | AA105976 |
| 16 | caaatactgcccgcaaacgtcgcgc | | 42620 | gttccttcaggttgctgtttctcctca | AA017966 | 85224 | gaccaagactgcctggcctggtcct | AA105976 |
| 17 | tgaacaggttcggagtgcgcgc | | 42621 | agttttgagctagtcagttagttg | AA017966 | 85225 | ccaagactgctggcctggttccta | AA105976 |
| 18 | gggagtcgcggcaaagcgaaagcg | | 42622 | gttagacactcctctgtctatgac | AA017966 | 85226 | gactcgtggcctggttcctcagagg | AA105976 |
| 19 | caaagcgaaagcgcaggatcgaag | | 42623 | ttagacactccttcgtctatgaca | AA017966 | 85227 | cctggcctggttcctcagaggatt | AA105976 |
| 20 | gcccgagtttacgcagggcttcctgtatg | | 42624 | tggcatcgtttgatcctctgtt | AA017966 | 85228 | cgtggcctggttcctcagaggta | AA105976 |
| 21 | gccagaggtttacgcagggcttcctgtg | | 42625 | ggcaactgttgatccctatagttc | AA017966 | 85229 | tggcctggttcctcagaggattg | AA105976 |
| 22 | gtttacgcaatatcatcaccaca | | 42626 | catcgtgttgatcctatagttcta | AA017966 | 85230 | gcctggttcctcagaggtatggc | AA105976 |
| 23 | caaatcatcaccacacgcacta | | 42627 | tttgatccctatagttctatttggg | AA017966 | 85231 | cgtggttcctcagaggtatggaa | AA105976 |
| 24 | atcaccacacgcacttatcatggaac | | 42628 | gatcctatagttctattgggtc | AA017966 | 85232 | ctgttcctcagaggtatgggtaaag | AA105976 |
| 25 | acgcactcaggaagaacgctcgat | | 42629 | atccctatagttctatttgggctcg | AA017966 | 85233 | ttcctcagaggtatttggcaaatg | AA105976 |
| 26 | atacgctgaaaaagtgcgcgatc | | 42630 | taattgtcatcagttgctccctt | AA017966 | 85234 | tctgatttgctgtcgtgccatgac | AA105976 |
| 27 | ggaaaagtgcgcgatgccggatc | | 42631 | attgctatcagtttgctcccctta | AA017966 | 85235 | ctgatgttgtgctgtcgtgccatgacct | AA105976 |
| 28 | agtcgcggatgccgggatcaaagtc | | 42632 | ttgctatcagttgctccccttac | AA017966 | 85236 | ttgttggtcgccatgacctgga | AA105976 |
| 29 | gccggatcaaagtcgtgttgctgg | | 42633 | gtcatcagttgctcccccttat | AA017966 | 85237 | gttggtcgccatgacttggaag | AA105976 |
| 30 | aagtcgtcgtggtgccatgtggg | | 42634 | tctatcagttgctcccctttacat | AA017966 | 85238 | tggtgtgccatgacttggaagggaa | AA105976 |
| 31 | aagatcgcgcggattatttgctgcaa | | 42635 | tatcagttgctcccctttacatct | AA017966 | 85239 | gtcgtgccatgacttgcaaggcc | AA105976 |
| 32 | gccggatcatttgcaactggcaa | | 42636 | atcagttgctcccctttacacatctg | AA017966 | 85240 | tttgaccaagactgctggcctggt | AA105976 |
| 33 | atttgctgcaactgcaaactgccg | | 42637 | agttgctcccctttacatctggct | AA017966 | 85241 | ttgaccaagactgcgggctggttc | AA105976 |
| 34 | cgccgaaagtgccaaatcaacat | | 42638 | agaatgagctgcagtcggggagta | AA017977 | 85242 | tggtcctcctcctggctggaag | AA105980 |
| 35 | aaggtgccaatcaacatgctggtg | | 42639 | aggctaccaggtcagcttgcaagg | X95226 | 85243 | gtcctcctcctggctggaagcat | AA105980 |
| 36 | caatcaacatgctgggtgaaggtgaa | | 42640 | ctctgtaacatggtcatccctgg | X95226 | 85244 | ctacaggccaatatcctgaatgac | AA105980 |
| 37 | tgggtgaaggtgaaagcgaagccgct | | 42641 | taacatgctcaccccgtgttcaa | X95226 | 85245 | aaggccaatatcctgaatgacagc | AA105980 |
| 38 | acgcctgcggataacgatgatg | | 42642 | caccacaggctgagcgctgt | X95226 | 85246 | aatatcctgaatgacagcgcggt | AA105980 |
| 39 | ttgcgataacgatgcatgcctgatgc | | 42643 | tgctcgttacacaggacaacga | X95226 | 85247 | tcctgaatgacagcgcggttat | AA105980 |
| 40 | acgatgatcgatgcttgatt | | 42644 | tgttacacaggacacagatac | X95226 | 85248 | ctgaatgacagcgcggttatc | AA105980 |
| 41 | ggtcgcgggatcatgatgccaacc | | 42645 | ccagcattaacttgcacacatga | X95226 | 85249 | atttaactgagatgtgttca | AA105980 |
| 42 | ggatcatgatgccaacctctacgt | | 42646 | ttaacttgcacatatgaccgtca | X95226 | 85250 | ttaactgagatgtgttca | AA105980 |
| 43 | tgcaacctctacgtgcgctttc | | 42647 | tgcacacatatgaccgcagttaca | X95226 | 85251 | gttcacagtgtcaattccgaaaag | AA105980 |
| 44 | gccctttcgccgacgcgagcag | | 42648 | catatgaccgtcagttacacgcaat | X95226 | 85252 | tcacagtgattctccgaaaaagcc | AA105980 |
| 45 | gccgacgcagatgacgatgaacgaac | | 42649 | acgtcagttgcaatatatac | X95226 | 85253 | tcacagtgtaattccgaagctcaa | AA105980 |
| 46 | cagacgaacgaacagactctag | | 42650 | accaggctagctgcaaggttgaat | X95226 | 85254 | ttcctcttggctgaagcactaa | AA105980 |
| 47 | gatgaacgaacagactccgtgatg | | 42651 | gaaagatacaatgctctcctgtgtg | X95226 | 85255 | cctcttggctgaagcactctaaga | AA105980 |
| 48 | aacagactccagggatgtgtttat | | 42652 | tgttctgacgcctgtatgcagcta | X95226 | 85256 | tggctgcgaagcatctaagatt | AA105980 |
| 49 | tcaggcgatgctgttatggcaggc | | 42653 | gacgctgtaggcgcagctagcttc | X95226 | 85257 | attaatactgagatgtgttca | AA105980 |

TABLE 1-continued

| SEQ ID NO | DBAxnID | sequence | SEQ ID NO | DBAxnID | sequence | SEQ ID NO | DBAxnID |
|---|---|---|---|---|---|---|---|
| 50 | | gtgctttatgcaggcgcaaactg | 42654 | X95226 | gcagctagcttctgttctaaattc | 85258 | AA105980 |
| 51 | | atgcaggcgcaaactgcgattct | 42655 | X95226 | taaattctgagttctcagggtgt | 85259 | AA105980 |
| 52 | | taaggtgcaaacgtctgaccacgc | 42656 | X95226 | tatcaactccatctctgtaacatg | 85260 | AA105980 |
| 53 | | caaactgtgaccacgccgaatccg | 42657 | X95226 | ctccatctctgtaacatggctcat | 85261 | AA105980 |
| 54 | | gacctgaactgcgtccgcaaactgg | 42658 | X95226 | gctcccacagttcttctggact | 85262 | AA020028 |
| 55 | | gggctaaatccgcagcaaactgccg | 42659 | AA020028 | agttctctgtactcctgtgaga | 85263 | AA106069 |
| 56 | | cgcagcaaactgccgtcggcagg | 42660 | AA020028 | agttcattggccagaatgccaacga | 85264 | AA106069 |
| 57 | | acagcaggcctgaacagccgctg | 42661 | AA020028 | ttggccagaatgccaacgattttgc | 85265 | AA106069 |
| 58 | | cgtctgaacaggcgctagatccc | 42662 | AA020028 | agaatgccaacgatttgctgaaac | 85266 | AA106069 |
| 59 | | acagggctgatgaccccggacacc | 42663 | AA020028 | atgccaaacgatttgctgaaacgg | 85267 | AA106069 |
| 60 | | atattacaacgcggcagcattatga | 42664 | AA020028 | atttgctgaaaccgcatctggat | 85268 | AA106069 |
| 61 | | cagcggcatttgatgtcggcagccgc | 42665 | AA020028 | actctcgaagttcttcctcatgtt | 85269 | AA106069 |
| 62 | | gtcgggcagccgcacactatgacccg | 42666 | AA020028 | tgttactgatctcctcctgtgaa | 85270 | AA106069 |
| 63 | | cgcacactatgagccgccagccagat | 42667 | AA020028 | tctcctcctctgtgaaatccacttt | 85271 | AA106069 |
| 64 | | aacatgcagactcacgccgcagag | 42668 | AA020028 | cctcgtgaaatccacttttcccag | 85272 | AA106069 |
| 65 | | tacaggccagagtgcgaccgcctt | 42669 | AA020028 | tgaaatccactttcccagcaaatc | 85273 | AA106069 |
| 66 | | gagtctgacgccttagctgcaatg | 42670 | AA020028 | tactcctgtgaggaggtgctgctcca | 85274 | AA106069 |
| 67 | | tactggcaagcttcacacgcgtaa | 42671 | AA020028 | ctgtgtccacacaagttaacactg | 85275 | AA106069 |
| 68 | | gggttggacctgctggatgagc | 42672 | AA020028 | tcgtcacacaagttaacactgcgt | 85276 | AA106069 |
| 69 | | tgagcgccactgcgggaaagtca | 42673 | AA020028 | ttttcaatagcctcattaatgcta | 85277 | AA106069 |
| 70 | | gccaggtgacgggctctagatctct | 42674 | AA020028 | actgcagcatgtagtgcagcttcgt | 85278 | AA106069 |
| 71 | | gccttagatctctgccgccatgc | 42675 | AA020028 | gcagttcgtccacagacgttcat | 85279 | AA106069 |
| 72 | | gccgccaatgttgttcaggccacgc | 42676 | AA020028 | tccacagttcattggccagaa | 85280 | AA106069 |
| 73 | | tgttcaggccacgccgaaggatgcc | 42677 | AA020028 | acagagcagttcattggccgaaatgc | 85281 | AA106069 |
| 74 | | agagaatgccgacgaccattact | 42678 | Z16078 | caagccagttcaggctttagggctgact | 85282 | X92523 |
| 75 | | gccgaccattatctggggag | 42679 | Z16078 | gccagttaggctgactgctggtgc | 85283 | X92523 |
| 76 | | cgttagcgactgcgactgcgatct | 42680 | Z16078 | tcctcctctagaaagtcaaagcatcc | 85284 | X92523 |
| 77 | | gacgtcgatctcatggagcaa | 42681 | Z16078 | aaagtcaaagcatccattccatgag | 85285 | X92523 |
| 78 | | gatcttgcaggagaatctgcag | 42682 | Z16078 | gtcaaagcatccatccatgagaac | 85286 | X92523 |
| 79 | | caatctccaggccaggtgcgt | 42683 | Z16078 | caagcatccatccatgagaactt | 85287 | X92523 |
| 80 | | attattccaccgcactccgtgagct | 42684 | Z16078 | aaagcatccatccatgagaacta | 85288 | X92523 |
| 81 | | taccgcgaacgtcatcaggcgtgca | 42685 | Z16078 | agcatccatccatgagaacttaaa | 85289 | X92523 |
| 82 | | ggtgacgagccgtccgcatgctaat | 42686 | Z16078 | gccatccatcatgagaacttaaaca | 85290 | X92523 |
| 83 | | cgtccgatgctaatcgcttttac | 42687 | Z16078 | atccatccatgagaacttaaacaa | 85291 | X92523 |
| 84 | | tttaccgccagatgaaatcgaacag | 42688 | Z16078 | acttaaacaattacctgcctgactg | 85292 | X92523 |
| 85 | | gatgaaatcgaacagtcgctgaacg | 42689 | Z16078 | taaacaattacctgcctgactgca | 85293 | X92523 |
| 86 | | aacagtcgctgaacagccgtgcatta | 42690 | Z16078 | ccaggttagggctgtgactgca | 85294 | X92523 |
| 87 | | acacatattcagccatcacgtg | 42691 | Z16078 | caattactgcctgactgcatttt | 85295 | X92523 |
| 88 | | ttcagccatcacgctgtggttga | 42692 | Z16078 | ggcttaggctgtgactgcaact | 85296 | X92523 |
| 89 | | atcacgctggttgatgctgcgc | 42693 | Z16078 | cttttaggctgactgcactcc | 85297 | X92523 |
| 90 | | ggtttgatgatgctgctcagtgcat | 42694 | Z16078 | taagtgacttattcctctagaa | 85298 | X92523 |
| 91 | | atgatgctcatgcgctcagtgtc | 42695 | Z16078 | aagtgactattcctctctagaaag | 85299 | X92523 |
| 92 | | ctcagtgcatgcgttccgctgaaag | 42696 | Z16078 | gtgacttatccctcctagaaagtc | 85300 | X92523 |
| 93 | | catgcgttccgcctgaaaggcatggt | 42697 | Z16078 | cttattcctctctagaaagtcaaag | 85301 | X92523 |
| 94 | | ctgaaaggcatccgtgcagctcatc | 42698 | Z16078 | attcctctctagaaagtcaaagcat | 85302 | X92523 |
| 95 | | ggcatccgtgccacgccatctctg | 42699 | Z16078 | attatcatgaaggcctgagaagtc | 85303 | X92523 |
| 96 | | tgccacgccatcttcatgaagggcg | 42700 | X04405 | agacattccgggactttggagcag | 85304 | AA106077 |
| 97 | | atctccatgaagggcgcgaccgcg | 42701 | X04405 | tgcagttgtaccttagcagaaga | 85305 | AA106077 |
| 98 | | attaacgcagttcagtcgcagcga | 42702 | X04405 | gtctcacctttgagagaacagaag | 85306 | AA106077 |
| 99 | | gttcgcagttcgtcagcgattgca | 42703 | X04405 | ccctcgcccagaggcaaagtg | 85307 | AA106077 |

TABLE 1-continued

| SEQ ID NO | DBAxnID | sequence | SEQ ID NO | DBAxnID | sequence | SEQ ID NO | DBAxnID | sequence |
|---|---|---|---|---|---|---|---|---|
| 100 | | agttgcagcgattgcaactggctg | 42704 | X04405 | ggcctttgctcagctgccgggtca | 85308 | AA106077 | gatgcgatcggttttccgtgaatc |
| 101 | | gggaaactgtgccagttgtgcac | 42705 | X04405 | ctctgccgggtcatgctcaggtctc | 85309 | AA106077 | atcgatcggttctccgtgaatca |
| 102 | | cgccagttgtgcactttacaagc | 42706 | X04405 | aatctcttttcactgtcacatttg | 85310 | AA106077 | gcgatcggttccgtgaatcagt |
| 103 | | cacttacaagcgcaaggcagc | 42707 | X04405 | tttccactgtcacatttgacccca | 85311 | AA106077 | tcggttttcccgtgaatcagttcgg |
| 104 | | caagccgcaaaggcagcaggctac | 42708 | X04405 | gacccaaatccaagtcactgacta | 85312 | AA106077 | ttctccgtgaatcagttcggacac |
| 105 | | gcaaaggcagcaggctaccggacgg | 42709 | X04405 | aaatcactgacagaccctgac | 85313 | AA106077 | tctccgtgaatcagttcggacacc |
| 106 | | aggttacgcaatagcacgcgctg | 42710 | X04405 | aagtcactgactgagacctgac | 85314 | AA106077 | tccgtgaatcagttgggacacccc |
| 107 | | cgcaatagcacgcggctggcttac | 42711 | X04405 | tccgggacttttgagcagatgctc | 85315 | AA106077 | gttgaactgggctcccgcgtgg |
| 108 | | ggacgcggctggcgttacagcgcaa | 42712 | X04405 | gcccctggagccttccggaatgaca | 85316 | AA106077 | acgattcgggactacaccgaggatg |
| 109 | | gcgctggcgttacagcgcaacagca | 42713 | X04405 | gagctctccggaatgacatttgccg | 85317 | AA106077 | cgattcgggactacaccgaggatga |
| 110 | | cgttacagcgcaacagcctga | 42714 | X04405 | ttccggaatgacatgccgcaagt | 85318 | AA106077 | gatcgggactacaccgaggatgaa |
| 111 | | agcgcaacagcagcctgattgga | 42715 | X04405 | aatgacattgccgcaagtacaagg | 85319 | AA106077 | ttcgggactacaccgaggatgaag |
| 112 | | cagcagccgcagtgattacgca | 42716 | X04405 | gagtaggcttccagggtgagcca | 85320 | AA106077 | tcgggactacaccgaggatgaacga |
| 113 | | ctgagctgaattacgcaacagtaa | 42717 | X04405 | ggcttccagggtgagccatgggt | 85321 | AA106077 | cgggactacaccgaggatgaacgat |
| 114 | | catcagcgcgcaagaggcagaacg | 42718 | X04405 | tgagccatgggtccccactgccag | 85322 | AA020066 | ggactcaacgagggatgaacgatct |
| 115 | | cgcaagagggcagaaccgatagaatc | 42719 | X04405 | caggcaccctgtcatgcagaacc | 85323 | AA020066 | aaccaaaaactcccaatgcagagat |
| 116 | | gggcagacgatgaatcatttggta | 42720 | X04405 | caccgtcatcgcaggcagaccactga | 85324 | AA020066 | aaatcccaatgcagatgagacgga |
| 117 | | gaccgatagaatcattggtaatggta | 42721 | X04405 | atctcaaggcacagtattacggtg | 85325 | AA020066 | tacactgaagaccaagccacctaat |
| 118 | | agaatcattggtaatgcgccgga | 42722 | X04405 | cggcacagtattacgtgcagta | 85326 | AA020066 | caagccacctcaattacaatctg |
| 119 | | ttgggtaatgagccggattacgcg | 42723 | X04405 | acgtccgtgcagtatcgtccagggtga | 85327 | AA020066 | tttcaaatgtcttttagtgcaatt |
| 120 | | atgagcgccgattaacgccgctg | 42724 | X04405 | atgctcagggtgacgtccgcctcg | 85328 | AA020066 | agctgaagacctgctcaaaatact |
| 121 | | gggtcggcgtttacggcgccgc | 42725 | X04405 | gcctcgttgctccggcttccgg | 85329 | AA020066 | agacctgctcaaaatacatctttg |
| 122 | | ctttcgaccttttcactttgcag | 42726 | X04405 | tcctgcctggacatcgcttccgcc | 85330 | AA020066 | gctcaaaatacattttggtcata |
| 123 | | tgacacttcactttgcagattgg | 42727 | X04405 | ccaccacgcttcctcagtaccgt | 85331 | AA020066 | aatacattttgtcataggttatg |
| 124 | | tttgcagattggtaacacaggaac | 42728 | X04405 | acatcgcctccagtaccgt | 85332 | X96585 | acatcttttgctcatatgttatgaaa |
| 125 | | gaaacgtcacgctgaatatatgac | 42729 | X04405 | cttcgctccagtacctgtggat | 85333 | X96585 | tgtgtacctatgctttaaataa |
| 126 | | aaacgtcacgctgaatatatgacca | 42730 | X04405 | taccgtgtggattccgcgacgact | 85334 | AA020066 | ttgtcatccatcactacatcccac |
| 127 | | cgtactgaatatatgaccaccgc | 42731 | X04405 | tcatcgcaggacccactgaggagat | 85335 | AA020066 | cccaatgcagagatgacggggc |
| 128 | | acgctgaatatatgaccaccgctcac | 42732 | X04405 | ccctgacagacccatggggaat | 85336 | AA020066 | ggcctcagctcatgtgttgtacc |
| 129 | | ctgaatatatgaccaccgctcagat | 42733 | X04405 | agtacatcatccggtgctcagcat | 85337 | AA020066 | ctctcagctcatgttgtacccg |
| 130 | | gaatatatgaccaccgctcaccga | 42734 | X04405 | tcatccggtcagacatcccaga | 85338 | AA020066 | tcagctcatgttgtacccggag |
| 131 | | cccgatgatttccgcgcgcgtgt | 42735 | X04405 | gggtcagacatcccagaatgct | 85339 | AA020066 | ggtttgtaccccgaggctgctgag |
| 132 | | catgatttccgcgcgcgctgcgga | 42736 | X04405 | cagacatcccagagatgctagtagt | 85340 | AA020066 | tgtaccccgaggctgctgaggcc |
| 133 | | gatttccgcgcgcgctgtcggagag | 42737 | X04405 | tagtagtctcactcatcatggggt | 85341 | AA020066 | ggctgctgaggcccactcttcaaa |
| 134 | | cgccgccgctgctggaagatccc | 42738 | X04405 | ggctaatctcacggcacagtatta | 85342 | AA020066 | actcttcatagtaagtacactg |
| 135 | | ccgctcgtggaagatccccggc | 42739 | AA020066 | tcatatgtctacctggtgagtaag | 85343 | AA106090 | acgaaacaacgtgtcgtgcaata |
| 136 | | ctgctgggaagatccccggctg | 42740 | AA020066 | atatgtctacctggtgagtaaggcc | 85344 | AA106090 | cgaaacaacgtgtcgtgcaataccc |
| 137 | | gctgggaagatcccccggctgca | 42741 | AA020066 | acccaaagagctcaggcaggtgtgg | 85345 | AA106090 | ctacattgaccacggggtgca |
| 138 | | gggaagatccccggctgcagaaa | 42742 | AA020066 | caaagagctcaggcagtgtgtgg | 85346 | AA106090 | tacattgaccacggggtgatgtact |
| 139 | | gatccccggctgcagaaaatc | 42743 | AA020066 | aaggtcctcaccagttgcagga | 85347 | AA106090 | cattgaccacggggtgatgtactta |
| 140 | | atccccggctgcagaaatccag | 42744 | AA020066 | ctcaccagagttgcaggaacctgc | 85348 | AA106090 | attgaccacggggtgatgtactta |
| 141 | | attgctgcattccggctgcatgc | 42745 | AA020066 | gggaaccttgcacaaccagccagc | 85349 | AA106090 | ttgaccacggggtgatgtacttag |
| 142 | | taccggtcgatcaacgagtgatga | 42746 | AA020066 | aggaacctgcacaaccagcagcatc | 85350 | AA106090 | tgaccacggggtgatgtactagt |
| 143 | | gagtgatgaggttcgcaagaacctg | 42747 | AA020066 | catccccctggctgcatcaagg | 85351 | AA106090 | acaggtgcgtgcaataccagaga |
| 144 | | gcagaacctcagggatcgcaggtcag | 42748 | AA020066 | cacccctctgatcaagtcagtatgg | 85352 | AA106090 | acgggtgcgtgcaataccagatat |
| 145 | | gacgtcagggatcggccaggggt | 42749 | AA020066 | gagcactcacaagcagtatgca | 85353 | AA106090 | gaggactcacattgaccacggggtg |
| 146 | | gccaggggttctgcataccgt | 42750 | AA020066 | cactctacaagcagtagtgggc | 85354 | AA106090 | agaatctacattgaccacggggtg |
| 147 | | gggcatgggctcaagttgaataacc | 42751 | AA020066 | taaggcacgtcacatccagaggcc | 85355 | AA106090 | attgaccacgggtgatgtacttga |
| 148 | | gaagtgtcgcgattatcttctat | 42752 | AA020066 | gccaggacctgcaaccagcgccat | 85356 | AA106090 | gaactacattgaccacgggtgat |
| 149 | | tctatatcttcagcgcgggtctg | 42753 | AA020066 | cagtcactccagaggccatage | 85357 | AA106090 | aatctacattgaccacgggtgatg |

| SEQ ID NO | sequence | DBAxnID | SEQ ID NO | sequence | DBAxnID | SEQ ID NO | sequence | DBAxnID |
|---|---|---|---|---|---|---|---|---|
| 150 | gcaacattgggccagctaaacatg | | 42754 | ctccagaggccatagcaccaggcct | AA106090 | 85358 | atctacattgaccacgggtgatgt | AA106090 |
| 151 | ccagctaaacatgcttcatcgtcgg | | 42755 | cagaggccatagcaccaggcctgag | AA106090 | 85359 | tctacatgaccacgggtgatgta | AA106090 |
| 152 | ccgggctgccaccaagtgctgctcag | | 42756 | ccatagcaccaggcctggggatcga | X64227 | 85360 | tttccttgtgtgctagcctcatg | X64227 |
| 153 | gaccaagtgacagcaatgctgtttc | | 42757 | gagtgtcaccccaaagagctccag | X64227 | 85361 | gctagcctcatgtcgttaagcgg | X64227 |
| 154 | aatgcgtttcactggttatgccgg | | 42758 | tgtgccaccccaaagagctccagga | X64227 | 85362 | ctaccgtcaatacccaagacgacgt | X64227 |
| 155 | atgccggtgaacgtgccaaacaggc | | 42759 | gtattgctgccatcacctgctgg | X64227 | 85363 | taacgacgcgcagtaatagagt | X64227 |
| 156 | acgtgcaaacaggctcctagcgttc | | 42760 | gctgccatcaccctgctgaagtgc | X64227 | 85364 | tgcaacaccaaagccaacacgaag | X64227 |
| 157 | ctctagcgttcgaacgcactgattt | | 42761 | tcagccacgtcaacgacctgtgt | X64227 | 85365 | gaagaccaaccaacaagaagctcact | X64227 |
| 158 | tcgttcactcatggtgaaaatagcat | | 42762 | acaagcacagacctgtgtggctca | X64227 | 85366 | caccaccaaagactcactgtctg | X64227 |
| 159 | atggaaaatagcgatcgctgccagg | | 42763 | tggctccttgtaccacttcagt | X64227 | 85367 | caagagctcactgtctgctggct | X64227 |
| 160 | tcaggtataagaatatctacagtac | | 42764 | ctttgtaccactttcagctggcgt | X64227 | 85368 | gctcactgtgtggtctgataca | X64227 |
| 161 | cgctgttagcaccgcaggtgaga | | 42765 | accaatttcagctggcgttaggcga | X64227 | 85369 | tgtctgtgtcatacaagagca | X64227 |
| 162 | cacccgcaggtgtagaaggcactt | | 42766 | caccaccgctgatgatctgagtaag | X64227 | 85370 | aacatgccccatctcttctctgttg | X64227 |
| 163 | tggctcgagcgatgaggattcgtc | | 42767 | gtgtctctgaccttacaaacat | X64227 | 85371 | agtctattggcgatgtgaaaaa | X64227 |
| 164 | atggattccgtcctcgtgtagct | | 42768 | ccttacaaacatgctagcgcac | X64227 | 85372 | cttcatggcgttaagcggatgatt | X64227 |
| 165 | gtctctgtgtagctgatgacgca | | 42769 | ctctgtacatgtacatgcacacac | X64227 | 85373 | tatctcaaaggccattggagcacaaa | X64227 |
| 166 | tgtagctgatgatcccgaataactac | | 42770 | tacatgcacacacagtattaa | X64227 | 85374 | agcattcaacagaggtccatgaac | X64227 |
| 167 | accagccagtcatcaactcgcgcc | | 42771 | atcaccctgctggaaatgccacatg | X64227 | 85375 | cgtggtccggtgcaacacagac | X64227 |
| 168 | ccaactcatcgatgattacggcg | | 42772 | ccacagtctgcaacaaggaaagtgg | X64227 | 85376 | caacagctactcatatcaggatgtt | X64227 |
| 169 | gattgattacggcgctcaaggatga | | 42773 | gagcacaacctgccagaagaagcca | X64227 | 85377 | atatcaggatgttcctactaccga | X64227 |
| 170 | taaggatctcggtccagagatac | | 42774 | aggagcaagctcagaactggggcatt | X64227 | 85378 | ggatgttccttactacgatcata | X64227 |
| 171 | tggtcagagatatccggtcctgtct | | 42775 | aagctcagagctggcatcttcaa | X64227 | 85379 | tccttactacgcaatacccagaa | X64227 |
| 172 | ctgtcggacacagtgccctgtgc | | 42776 | gggcattctcaagctcagagactg | X64227 | 85380 | gatcagctagaaacctgaagcgag | AA106126 |
| 173 | gtgcccgtcggagccgccgggaga | | 42777 | tctcaagtcagagactgtctgg | X64227 | 85381 | cagaaaacctgaagcgaggagaga | AA106126 |
| 174 | cagaatggcccgccgctgcagttt | | 42778 | gttgttccccaagacctagaagaa | X64227 | 85382 | gaacttcaggctgctctagaagaa | AA106126 |
| 175 | cgagttcaatacgcggatcatg | | 42779 | gagccgttgcatctggaggaaggc | X64227 | 85383 | cttcaggctgctctagaagaagc | AA106126 |
| 176 | ggagatatcgcaagctgtgtgctg | | 42780 | caggatcagtgcctttggctaccc | X64227 | 85384 | ggaaagatctgccgcatccagctgg | AA106126 |
| 177 | ctgtcattacacagatatccat | | 42781 | aggacctcatgctgccagttct | X64227 | 85385 | aagatcctcgcatccagctgagc | AA106126 |
| 178 | ccaagtaaaaatgtcatgaacta | | 42782 | aggacctcatgctgccagttct | X64227 | 85386 | atcctcgcatccagctgagctgagt | AA106126 |
| 179 | ttgtcatgaacatatcctataccct | | 42783 | ttctcccagagctgcatgagatt | X64227 | 85387 | ctgcgatccagctggcgtgaacc | AA106126 |
| 180 | tagtagaaaacagggcatggctggc | | 42784 | tctgccagagactgcatgagattgc | X64227 | 85388 | cgatccagtggagctgaaccaag | AA106126 |
| 181 | tggcagaacgaacaccacacttga | L38424 | 42785 | ccctgttcctgagacagggctcct | X80638 | 85389 | tgaaccaagctcaagtctgagatcg | AA106126 |
| 182 | tatctgatgctgtgtgagtc | L38424 | 42786 | tgccttcctgagacagggctcctc | X80638 | 85390 | aaccaagtcaagtctgagtgagaca | AA106126 |
| 183 | gtgatgctgtgtgcagatgctt | L38424 | 42787 | tgggctctagtccctctgcct | X80638 | 85391 | tcaagtgagatcgacagaagat | AA106126 |
| 184 | ttgagtcagatgctcagatgtt | L38424 | 42788 | cccatattacacaccagccactttat | X80638 | 85392 | ctagaaaccctgaagcgagagata | AA106126 |
| 185 | tgcttcatttacacagatatccat | L38424 | 42789 | catattacacaccagcacttata | X80638 | 85393 | gagattctgacctcacggaaccaga | AA106126 |
| 186 | tacacagatatccatgctgttta | L38424 | 42790 | tttggtcacaggaggggtctaggg | X80638 | 85394 | atttctgacctcacggaacagttg | AA106126 |
| 187 | gatatcatgctgtttacagaaa | L38424 | 42791 | ggatcacggccttgcttactacctga | X80638 | 85395 | tctgacctcacggaacagattgcag | AA106126 |
| 188 | aaaaatgcattagaccagaggc | L38424 | 42792 | cagtgcctttggctacctcgatgc | X80638 | 85396 | gacctcacggaacagattgcagaag | AA106126 |
| 189 | aggatgcgaggccatcatcgccgca | L38424 | 42793 | gtccattggctacctgcctcgatgctc | X80638 | 85397 | ggaaggccatccagaactggagaga | AA106126 |
| 190 | gagccatcgccgccaaatttgc | L38424 | 42794 | gccttcatgcctcggaagaataagcg | X80638 | 85398 | aaggccatcccagaacttggagaaata | AA106126 |
| 191 | tcatcgccaaatttgctctcccc | L38424 | 42795 | gtccattctgacttccccaag | X80638 | 85399 | cgcatccagaactggagaaaata | AA106126 |
| 192 | aaatttgctctcccgatactg | L38424 | 42796 | catttctgacttcccccaagctc | X80638 | 85400 | ccaaggacctggcgatccgggct | AA106126 |
| 193 | cgtcggtgatactgatgatgaa | L38424 | 42797 | cgcatccttgtaggactccagct | X80638 | 85401 | aaaggaactggcgcatccgcgggt | AA106126 |
| 194 | tgccaactatttgaggatgtgag | L38424 | 42798 | ccttgtagactccatgctgccgt | X80638 | 85402 | tatagacgcagttgaatatgaglggg | W35962 |
| 195 | gagatattgaggctttcatcatgacc | L38424 | 42799 | tatatatgaccatccatgctacgaa | X80638 | 85403 | acaatgtcgatgcattacctaccaat | W35962 |
| 196 | agcttcatcatgaccagaagctga | L38424 | 42800 | tacatgaccacgggcatgaggaag | AA020046 | 85404 | caattgtcgatgcatacctcaccaag | W35962 |
| 197 | catgaccagaagcttgacgcaccaa | L38424 | 42801 | gcacctgcctggaagaataagct | AA020046 | 85405 | attgcatgcataccatcacaaatgaa | W35962 |
| 198 | gaagttgacgaccaagctgggact | L38424 | 42802 | acctcggctggaggggtctcg | AA020046 | 85406 | ttgcgatgcatacctaccacaatgag | W35962 |
| 199 | caagctggacgaactgcgttaaacagc | L38424 | 42803 | atcaggtctaggtcatcctgagt | AA020046 | 85407 | tgccgatgcatacctaccacaatgaagg | W35962 |

TABLE 1-continued

| SEQ ID NO | DBAxnID | sequence | SEQ ID NO | DBAxnID | sequence | SEQ ID NO | DBAxnID | sequence |
|---|---|---|---|---|---|---|---|---|
| 200 | L38424 | agcagcaaggacatcggatgaaa | 42804 | L38424 | caggtctaggtcatcctgacgtcc | 85408 | W35962 | gatgcatactacaaatgaaggca |
| 201 | L38424 | catgtcagcgttaaactgcagtc | 42805 | L38424 | ggtctaggtcatcctgacgtccag | 85409 | W35962 | atgcatactacaaatgaaggcaa |
| 202 | L38424 | atgaagattgatcagcttgtgtag | 42806 | L38424 | tctaggtcatcctgacgtccagag | 85410 | W35962 | tgcatactacaaatgaaggcaac |
| 203 | L38424 | tgaaaatgcttgatcagccagga | 42807 | L38424 | taggtcatcctgacgtccagagtt | 85411 | W35962 | gcatactacaaatgaaggcaaca |
| 204 | L38424 | aggatatggttcaattacgactgc | 42808 | L38424 | ggtcatcctgacgtccagagttc | 85412 | W35962 | tgtttgctgtcgttagtcaaga |
| 205 | L38424 | tcaattacgactgcctatcggat | 42809 | L38424 | tcatcctgacgtccagagttcca | 85413 | W35962 | gtttgctgtcgttagtcaagac |
| 206 | L38424 | tcatgatctatacgcaaccggaacc | 42810 | L38424 | atcctgacgtccagagttccagg | 85414 | W35962 | ttgctgtcgttagtcaagacta |
| 207 | L38424 | ttcatgaggcacaggcttcaaat | 42811 | L38424 | catgacaccggccggcaatgaggtc | 85415 | W35962 | tgctgtcgttagtcaagacta t |
| 208 | L38424 | agcaacaggcactgatcgctgc | 42812 | L38424 | tgacgtccagagttccaggtcaa | 85416 | W35962 | gctgtcgttagtcaagactata |
| 209 | L38424 | tgcactgatcgctgccaatgcactc | 42813 | L38424 | tgaccacggccggcaatgaaggtct | 85417 | W35962 | caagactatagaccagttcgaatat |
| 210 | L38424 | gctgccaatgcactgatcgtca | 42814 | L38424 | tgcagaacagcgcgtccgggaga | 85418 | W35962 | actatagaccagttcgaatatgatg |
| 211 | L38424 | ccgctgcaccgcgcagccgccatgaa | 42815 | L38424 | atgtccgactggtagtcgccacgg | 85419 | U58105 | ctatagaccagttcgaatatgagg |
| 212 | L38424 | gatgtccggcattaatccatttat | 42816 | L38424 | gtagatccacaaggtccccgcacgt | 85420 | AA106116 | agcaccccggggcccccaggaaggagta |
| 213 | L38424 | cattaatcgtttatgtgatgtga | 42817 | L38424 | ggatccagctgccgctcagcctgt | 85421 | AA106116 | tagataaggccccaggcccaggaaggagta |
| 214 | L38424 | tgagtgtatccatccgtctgcc | 42818 | L38424 | ccagcagcacctctgcctgaggag | 85422 | AA106116 | tctccatccaatacaaggggccg |
| 215 | L38424 | gctccacaatatggggtactgcg | 42819 | L38424 | agcagcacctctgcctgaggag | 85423 | AA106116 | ctcatccaatacaaggggccg |
| 216 | L38424 | aaatctttgtcgcaaccactggtga | 42820 | L38424 | ggaacactgcacactgaaattgt | 85424 | AA106116 | tccatccaatacaaggggccgt |
| 217 | L38424 | gggcaactgtgatgaaggtgttttc | 42821 | L38424 | cttctagactcatcatgaggtaaaa | 85425 | AA106116 | catccaatacaaggggcccgtg |
| 218 | L38424 | atgctgacgttctgtcttggcgc | 42822 | L38424 | tgactgcgcgggctttctgttaccat | 85426 | AA106116 | atcccaatacaaggggccgttga |
| 219 | L38424 | gcttggcgccacagtgatgatg | 42823 | L38424 | cttctgtttacccatccaattcaggca | 85427 | AA106116 | tctccaatacaaggggccgcttgag |
| 220 | L38424 | cacagtgatgtgcgagatcggaa | 42824 | L38424 | ttacatccaattcaggcagaaggt | 85428 | AA106116 | ctccaatacaaggggccgcttgagt |
| 221 | L38424 | agagaagcagtgaagccgcccgc | 42825 | L38424 | tactctatatccccctcatgtta | 85429 | AA106116 | ttagccaatggccaagaaactcg |
| 222 | L38424 | gaagcagctgaagccgcccgcat | 42826 | L38424 | ccctacagttttatccattgtgac | 85430 | AA106116 | tagcccattggccaagaaactcgg |
| 223 | L38424 | gctgaagcagccggcatattaggcg | 42827 | L38424 | atgttatccattgtgaccactc | 85431 | AA106116 | tggccaagaaacctcggaagtcaag |
| 224 | L38424 | gcagcccgcatattaggggtgagcagata | 42828 | L38424 | ttgtgaccactccactgagctca | 85432 | AA106116 | gataagagccccgaataagagtacaa |
| 225 | L38424 | aagaattcagtgaagcttccagac | 42829 | L38424 | ccactgcactgactcattcaca | 85433 | AA106116 | taaagccccccagggaaggagtacaag |
| 226 | L38424 | aatgatgatcaggcaattcggtca | 42830 | L38424 | ccactgcactcattcacagaggca | 85434 | AA106116 | agtacaagatctccatcccaatac |
| 227 | L38424 | tgatcaggcaattgggcaattgc | 42831 | L38424 | attcacagaggcatgtttatacta | 85435 | AA106116 | gtacaagatctccatcccaataca |
| 228 | L38424 | atcggtcaattgctcactgtcatca | 42832 | L38424 | tcccatccaagttgtatgctattgc | 85436 | AA106116 | acaagatctccatcccaatacaag |
| 229 | L38424 | tccattgtcactgtcatcagatct | 42833 | L38424 | ttaaacagtaagcctctagactaaatc | 85437 | AA106116 | caagatctccatcccaatacaagg |
| 230 | L38424 | gtcactgtcatcagaatctgcggc | 42834 | L38424 | cagctaacagtgcctctagactaaattc | 85438 | AA106116 | agatctccatcccaatacaagggg |
| 231 | L38424 | catcagaatctgcggccaaagcg | 42835 | L38424 | attaatcttcatgtcttcatgaa | 85439 | AA106116 | atctccatcccaatacaagggc |
| 232 | L38424 | aggatcggccatccggatcacggcgca | 42837 | L38424 | cttcatgtcttgaaattcac | 85440 | U58105 | tgattcagttactgtaaagtgaa |
| 233 | L38424 | tccggatcacggcgatcaggtgtcga | 42838 | L38424 | tgctctcttttgaaatcccactaagt | 85441 | U58105 | tcatgttactgtaaagtgaaagt |
| 234 | L38424 | ggcaatgggctgcactgtgggaag | 42839 | L38424 | acacaaaggcacactgtgaagaa | 85442 | U58105 | cttatcacaatacatcgaaaact |
| 235 | L38424 | gcctccggcactgcaagtcagcaa | 42840 | L38424 | acccatggggatggggagcggaaga | 85443 | U58105 | ataccacaatacatcgaaaacttca |
| 236 | L38424 | gataaatggtttcatgccggat | 42841 | L38424 | accatggtcaaggagcggatc | 85444 | U58105 | cccaatacatcgaaactcagat |
| 237 | L38424 | ttttgttatgatatctggataca | 42842 | L38424 | gatacggtgctctctgacagtta | 85445 | U58105 | caatacatcgaaaactcagatca |
| 238 | L38424 | tgatatctggatacatagaggc | 42843 | L38424 | accggtgtctctgacacagttagag | 85446 | U58105 | aacttgcatgtgaaaaaca |
| 239 | L38424 | ctactctcgacgaatgggtatat | 42844 | L38424 | ggtgctctcgtgacagttagaaa | 85447 | U58105 | gtttaatatcctgtaaggcacgtgaa |
| 240 | L38424 | ggtatattgaaatgttgaagcgag | 42845 | L38424 | gctctcggacagttagaaaagt | 85448 | U58105 | taatatctgtaaggcacgtgaag |
| 241 | L38424 | gcagcaaaatcacaggtcatttt | 42846 | L38424 | acaactggcgtgggtttatatact | 85449 | U58105 | tatcctgtaaggcacggtgaggtac |
| 242 | X17013 | tagaaatcgggagtgggatcgctcct | 42847 | L38424 | tttataatcgcttgctcagaag | 85450 | U58105 | tatggaattctgggtttgattta |
| 243 | X17013 | aggggtgatgctctatttagcgc | 42848 | L38424 | atatactgcttgctcagaaggg | 85451 | U58105 | cctacctgtatgtgaattccat |
| 244 | X17013 | tggatgctctattagcggagaa | 42849 | L38424 | tactgcttgtcagaaggggctt | 85452 | U58105 | tttaagctgcaatttgaacact |
| 245 | X17013 | tggcacccttttaacatagat | 42850 | L38424 | tgctttgctcagaaggggctttt | 85453 | U58105 | tattgaccataactgtcaactccc |
| 246 | X17013 | cacctcttactagtatatgaatgtgc | 42851 | L38424 | tcagagccagccgctgtgagcatg | 85454 | U58105 | tgaccataactgtcaactccttt |
| 247 | X17013 | aggtgtgatgcctctatttagcgg | 42852 | L38424 | catttgcaaggagcgactcgga | 85455 | U58105 | cataaactgtcaactccctttgag |
| 248 | X17013 | tggcacccttttaacatagat | 42853 | L38424 | tgctccaaggagccgactcggagcc | 85456 | U58105 | taactgtcaactcccttttagctt |
| 249 | X17013 | gcaggttaattcgtcaggggctg |  |  |  | 85457 | U58105 | gcttcctccaagttgttattgtgt |

| SEQ ID NO | sequence | DBAxnID | SEQ ID NO | sequence | DBAxnID | SEQ ID NO | sequence | DBAxnID |
|---|---|---|---|---|---|---|---|---|
| 250 | tttattctgcaggcgtgaaagcac | X17013 | | ccacagctccgggctagaaaatg | D83144 | 85458 | aatgttgctctatacacacaataca | U58105 |
| 251 | gggctgaaagcacaggtggcatatg | X17013 | 42854 | gcggctgatccagttctggagata | D83144 | 85459 | gttgctctatacacacaatacatcg | U58105 |
| 252 | ggcatatgcgcacaaagcattcta | X17013 | 42855 | ggctgatccagttctggagataccg | D83144 | 85460 | ttccaggcactgaggaccgcagtc | AA106163 |
| 253 | atgcgagcaaagcattctcatcagt | X17013 | 42856 | tgatccagttctggagataccgtg | D83144 | 85461 | gaccgcagcccctaattcctgccag | AA106163 |
| 254 | gcaaagcattctcatcgtcgcaat | X17013 | 42857 | tccagttctggagataccggtgtc | D83144 | 85462 | agtactgtaacactagaaccatg | AA106163 |
| 255 | cattctcatcagtcgcaatgattca | X17013 | 42858 | ggagataccggtgctctggacag | D83144 | 85463 | gctaacactagaaacatggccagt | AA106163 |
| 256 | catcagtcgcaatgattcagctcgc | X17013 | 42859 | tgtccgaccacctcaagaagagcaa | D83144 | 85464 | aacactagaaacatggccagtgaa | AA106163 |
| 257 | tcgcaatgattcagctcgtgagga | X17013 | 42860 | agaacagctcagcctcagtgagat | U14135 | 85465 | actagaaaccatggccagtgaagaa | AA106163 |
| 258 | tcttagatgcgtatccggaggag | X17013 | 42861 | gatattgtcgactctcttatga | U14135 | 85466 | aaccatggccagtgaagaagaatat | AA106163 |
| 259 | atgtcgtatccgaggagagctata | X17013 | 42862 | taagacagcagcaccgagtcagca | U14135 | 85467 | agacggccacaggctatcattc | AA106163 |
| 260 | ggagagctataacggctgttgcag | X17013 | 42863 | caccgagtcagcactgttacatagca | U14135 | 85468 | cgggccacaggctatcattccac | AA106163 |
| 261 | gatgcggctlgagcaccgcatccgc | X17013 | 42864 | gtcagcagttacatacatagtac | U14135 | 85469 | cgcctgactgtgaggggctgcaag | AA106163 |
| 262 | cgctgagcaccgcatccggctgat | X17013 | 42865 | catagcatagtacctlccagttac | U14135 | 85470 | ctgcaaggctlcttcagtgatact | AA106163 |
| 263 | gcaccgcatccggctgcattggtg | X17013 | 42866 | cagttactgtcctaattgactgtg | U14135 | 85471 | gggcttcttcagtgatactgtcagc | AA106163 |
| 264 | gcatcgggctgcattgtlggtggatga | X17013 | 42867 | tagaacttagcatcagttaagttgc | U14135 | 85472 | agtcctaattcctggcagttcctg | AA106163 |
| 265 | ggataattctatgaaatcgcgctt | X17013 | 42868 | agtttgcacagcactagaacagg | U14135 | 85473 | ccctaattcctggcagttcctgaga | AA106163 |
| 266 | attctatgaaatcgcgttcttctcg | X17013 | 42869 | gtcaccaccgtgcggtgattc | U14135 | 85474 | taattcctggcagttcctgagatct | AA106163 |
| 267 | ctatgaaatcgcgttcttctgaagac | X17013 | 42870 | ccacgtgctgtgattccaactac | U14135 | 85475 | aggagcatcctacaccgatcctg | AA106166 |
| 268 | aatcgcgttcttgaagacctatgt | X17013 | 42871 | attacactacagttgacttcataag | U14135 | 85476 | cctacaccgatctlggcctgct | AA106166 |
| 269 | gtcactccatcgatgttcttctcg | X17013 | 42872 | ttcttaagttgcgccactctgtcg | U14135 | 85477 | acaccgatctlgggcctgctgcc | AA106166 |
| 270 | ttcggatcacgcgccgagtagaagc | X17013 | 42873 | agttcaccaccgtgcggtgattc | U14135 | 85478 | gatcttgcgtgattccaagg | AA106166 |
| 271 | gatcacgccgagtagaagcgcat | X17013 | 42874 | ccaccgtcgctgttgattccaactc | U14135 | 85479 | gacagttagtcaacactagaaacc | AA106166 |
| 272 | tagaagcgcatacgcatgactactat | X17013 | 42875 | tgatttcaacactctctgaagag | U14135 | 85480 | tgcgttccacgtatgcagagctcggt | AA106166 |
| 273 | agcgcatacgcatgactactaca | X17013 | 42876 | tcccagacttattgcgagaga | U14135 | 85481 | cgtgtccacgtatggagctcggag | AA106166 |
| 274 | atacgcatgactacatlaacagg | X17013 | 42877 | attgctgagagcaccgccgtgct | U14135 | 85482 | cagactcccagcagtcggaga | AA106166 |
| 275 | tcgatctcataacggacaaactga | X17013 | 42878 | gagagcaccgccgtccagtta | U14135 | 85483 | gacctccagcatcgtgggagaac | AA106166 |
| 276 | attacaatgggaacacattcagctg | X17013 | 42879 | cagtccagtttatccacaaaatg | U14135 | 85484 | cctlccagcatgtggaaggt | AA106166 |
| 277 | aatcggaacacattcagctgctggg | X17013 | 42880 | aaggcctctgtgtaatccaaggt | U14135 | 85485 | ttccagcatgtggaggaagtca | AA106166 |
| 278 | aacacattcagctgcgtgtcca | X17013 | 42881 | ctctgtgtaatccaaggcttggctg | U14135 | 85486 | agaagctgcaacgtlcatctctac | AA106166 |
| 279 | cattcagctgcgtggggtccaattgc | X17013 | 42882 | aatcggcgaaccctccgagcc | U27295 | 85487 | acgcaaagcatatctctact | AA106166 |
| 280 | agctgcgtgggtgccatat | X17013 | 42883 | acacaagcaataggaactcatctca | U27295 | 85488 | cgtcaagctcatcatctctact | AA106166 |
| 281 | tggagagtcatlcattlatccaagt | X17013 | 42884 | gactcatctcagggccctlcagc | U27295 | 85489 | aacgtcatcatctactacggcg | AA106166 |
| 282 | atlcatattcatttgtaltccaaggt | X17013 | 42885 | agggccctlcagccgaactgcatct | U27295 | 85490 | cgtcatcatctacctacgggcgag | AA106166 |
| 283 | catattcatttgatccaaggt | X17013 | 42886 | ctlcagccgaactgcatctttct | U27295 | 85491 | tcctggaccgtagcttggltctg | AA106166 |
| 284 | catltlgtatccaagglcgaatct | X17013 | 42887 | ccgaactgcatcltlcctgtatc | U27295 | 85492 | cagaaactgtgctgcgccaggccat | AA106166 |
| 285 | tttgtatccaaggtgcgaatctg | X17013 | 42888 | acatlttcattatgtlcatga | U27295 | 85493 | tgccaggccatcgtgaacgcat | AA106166 |
| 286 | tatccaaggtgcgaatctlggagg | X17013 | 42889 | catlgtlcagttaagtlgta | U27295 | 85494 | cgccaggccatcgtgaacgcatca | AA106166 |
| 287 | tatlcgtlatacggaactgaatgaa | X17013 | 42890 | gtcgtlatlgttgcttgaaccc | U27295 | 85495 | ccaggccatcgtgaacgcatcaag | AA106166 |
| 288 | aagatgatgaacggctlcatgccac | X17013 | 42891 | ttatgltcgtlatacgggaccttcat | U27295 | 85496 | gccatcgtgaacgcatcaagcccg | AA106166 |
| 289 | atgatgaacggctlcatgccactga | X17013 | 42892 | tcatltgggatgccagaccccgac | U27295 | 85497 | tcaagcccgtcgatgatgaacaa | AA106166 |
| 290 | tgaacggcttcactgaataaac | X17013 | 42893 | gacattltacatctlcagaggaaca | U27295 | 85498 | gccgctaccagacaccacgt | AA106166 |
| 291 | accgctlcatgccactgaatacgtt | X17013 | 42894 | tacatcttcagaggaacaccacgt | U27295 | 85499 | agctlaccagaccttccagcgat | AA106166 |
| 292 | tgggaccgcaggcacaactcltla | X17013 | 42895 | ttctcagaggacaccaacaagt | U27295 | 85500 | actgctccgaagccaagcaggagttggc | AA106166 |
| 293 | ggagacgcaggcacactcttatac | X17013 | 42896 | gaggacaccacgtacaagtgggact | U27295 | 85501 | gcaaggcaaggcaggcaggtga | AA106166 |
| 294 | gaacactcttlatacggttggctc | X17013 | 42897 | gattlgccacgctgctatcatg | U27295 | 85502 | gcataggacaccagcttctatgg | U76208 |
| 295 | ataagctgacacgltlcatcat | X17013 | 42898 | ccacagctgatcalgtggaaa | U27295 | 85503 | tagcggaccacagcltctatgcc | U76208 |
| 296 | agctgtacaatgttlcatcattg | X17013 | 42899 | tacaggtccaggaatcggacggaca | U27295 | 85504 | accacagttcggggtgccggagcc | U76208 |
| 297 | ctgtacaatcgttlcatccggc | X17013 | 42900 | tgglttcattlcggggatgccaga | AA020166 | 85505 | gctlcatgccgcggcccccgt | U76208 |
| 298 | tacaatcgltlcatlcattcggtg | X17013 | 42901 | tcatlcggggatgccagacccgac | AA020166 | 85506 | gctcaacgggactggggctctat | U76208 |
| 299 | aatcgtltcatlcatlcgggcgcga | X17013 | 42902 | atgcgcgtagacagaccagtgac | AA020166 | 85507 | cagtcccaaggctaacctgag | U76208 |
| | | | 42903 | tggcatagtccatagcccagtgac | AA020166 | | | |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 300 | cgttcatcattggcgtgcaatt | X17013 | 42904 | catagtccatagccagctgaccag | AA020166 | 85508 | gtaacctgagcccaaggcctcatt | U76208 |
| 301 | gacattactgtccgtgaagat | M24537 | 42905 | agtccatagcccagctgaccagtgc | AA020166 | 85509 | gcccacggcctcatgagggaatt | U76208 |
| 302 | actctgtccgtgaagatgtattgcc | M24537 | 42906 | tagccagtcgaccagtccatgag | AA020166 | 85510 | catcctactcgtcccgggagcact | U76208 |
| 303 | aagatgtatgccgtgcaatgag | M24537 | 42907 | cccagtcgaccagtccatgaggag | AA020166 | 85511 | cctatcgctcccgggagcactgt | U76208 |
| 304 | gtattgccgtgcaatgagaaaa | M24537 | 42908 | agctgaccagtgccatgagaggag | AA020166 | 85512 | acaggcccaagaggagttggcact | U76208 |
| 305 | agcagatcagtagcagatgccgtt | M24537 | 42909 | tgaccagtgccatgaggagcccaa | AA020166 | 85513 | actggtgtctcagacttctgtga | U76208 |
| 306 | cagtagcagatgccgtcaaaggt | M24537 | 42910 | tgaggccccaacagaaccaggaa | AA020166 | 85514 | tggcactcagcaaacagcgaagaag | U76208 |
| 307 | tacagagatgcgttttccattc | M24537 | 42911 | gggagcccaacagaaccaggaagat | AA020166 | 85515 | cactcagcaaaacgaagaagccg | U76208 |
| 308 | ggaggtatggtcaagtcgttatct | M24537 | 42912 | accgacgctgtggggccaggat | AA020166 | 85516 | atgacgccaaattaccaaagtcga | U76208 |
| 309 | taggtcaggtgcgttatctcagtt | M24537 | 42913 | gcccaacagaaccaggaagatcca | AA020166 | 85517 | acatctgggcactgactcagacgct | U76208 |
| 310 | gcgttatctcagtcttcaggcgg | M24537 | 42914 | cgacagcgtcaggtccaggatctg | AA020166 | 85518 | ggcacgtgactcagacgcgcgcat | U76208 |
| 311 | ctcagtctcaggcggtagctga | M24537 | 42915 | cccaagccaggtactggagtaagat | AA020166 | 85519 | tgactcagacctgcgcatagccgga | U76208 |
| 312 | tctcaggcggtagctgatctga | M24537 | 42916 | tgtttaagccccggacatccattg | AA020166 | 85520 | ctcagacgtcgcatagccgagaca | U76208 |
| 313 | ggcgtagctgattctgaagcaac | M24537 | 42917 | ttaagccccggacatccatgctg | AA020166 | 85521 | cgagcagtcagccccagaggaggaa | U34245 |
| 314 | ctgattctgaagcaaagtctttc | M24537 | 42918 | agcccggacatcatgctgagcc | AA020166 | 85522 | gatcagccagaggaagaaggtgc | U34245 |
| 315 | tctttccattcaccagaccattcg | M24537 | 42919 | cccggacatcatgctgagcctg | AA020166 | 85523 | gaaggaaccaggtggttctggagc | U34245 |
| 316 | accagaccattcgcttcaacgcag | M24537 | 42920 | acatccattgctgagcctgacta | AA020166 | 85524 | ggaaccaggtgtctggcagcacc | U34245 |
| 317 | ccattccgcttcaaggcagagcaaa | M24537 | 42921 | gaactggaagctgctgtcagaga | AA020166 | 85525 | agtgcctgcatctcccttcca | U34245 |
| 318 | cgcttcaaggcagagcaaatgac | M24537 | 42922 | ctggaagctgctgttcagaggactc | U27398 | 85526 | tgaacctgaagcactgcataccccc | U34245 |
| 319 | gcaaatgtgacactgtctatcagta | M24537 | 42923 | ctcctggccacagaaccgagaggat | U27398 | 85527 | tctgactcctttactccgagtctg | U34245 |
| 320 | cactgtctatcagtctgtggcaat | M24537 | 42924 | ctggccacagaaccgagaggatcca | U27398 | 85528 | tactccgagtctgttccacctat | U34245 |
| 321 | gaaatattaaggttcaggtcgataag | M24537 | 42925 | cctctttccgttgagaagctgtga | U27398 | 85529 | ggtttccactatctctagcacacca | U34245 |
| 322 | ttattaggtccagcagctacatt | M24537 | 42926 | aagccagtgtcctccagccagaa | U27398 | 85530 | tttccactatctctagcacacaga | U34245 |
| 323 | aggtccagcagtctacatttacat | M24537 | 42927 | ccagtctctccagccagaaagc | U27398 | 85531 | cccactccacgaaagatagcagc | U34245 |
| 324 | gctacatctacatttacatgccagtca | M24537 | 42928 | agtctgaccaaccccagcagtca | U27398 | 85532 | cactcaccgaaagagtagcagcage | U34245 |
| 325 | tacacactctacatcagtctgt | M24537 | 42929 | accagcgtgaatcccatctggg | U27398 | 85533 | caagctagcagctgtcgtcaagtgcag | U34245 |
| 326 | tcaaacgcgcgaacatgctgtgct | M24537 | 42930 | cagccagcgatccccatagccgtgc | U27398 | 85534 | gaaatcgggtgcgcgagagatt | U34245 |
| 327 | gaacatgtgctaccgcacat | M24537 | 42931 | gatcccataggtggctggtga | U27398 | 85535 | atcgggtgcagcgagagattgaa | U34245 |
| 328 | ccgcacatccggagtgtatagat | M24537 | 42932 | ccccataggtggctggtgagct | U27398 | 85536 | gaaggaagccttgactggtgctg | U34245 |
| 329 | gtgatagatgcagccgcgcaggc | M24537 | 42933 | aggactcctcatcagagaggctg | U27398 | 85537 | accgcctgagctggctggaagc | U34245 |
| 330 | gatgcagcgcgttgcaggcaagttg | M24537 | 42934 | actcctcatcagagaggctgaaa | U27398 | 85538 | ggaagccatccgcccatcgcaaa | U34245 |
| 331 | ctattaatacatgaacagccttg | M24537 | 42935 | gaaactccgctatggggccaagagc | U27398 | 85539 | cctcatctgcaaaatcccagaaga | U34245 |
| 332 | catgaacgccttgccaatcgtgg | M24537 | 42937 | ccgtatggggccaagagccaagag | U27398 | 85540 | tgtcaagaacctggagtgatacaa | AA106601 |
| 333 | gggtgaaatgacgttgccaatccac | M24537 | 42938 | cgaggcagcagtcccatgctgct | U27398 | 85541 | ctacatatctgaatgccaaactt | AA106601 |
| 334 | gacgttgccgatccaccagcactg | M24537 | 42939 | ggcagcagtccccatgctgctgga | U27398 | 85542 | ggactaccacttaggatacggcag | AA106601 |
| 335 | cactgctgtctcaccccaagag | M24537 | 42940 | cggcatctcttctgatgaaggaa | U27398 | 85543 | taccacttagggatacggacaa | AA106601 |
| 336 | ggcatctcttctgatgaaggaa | M24537 | 42941 | gcagtgtcttaaccgcagatct | U27398 | 85544 | atgatcataacatgccatgcatt | AA106601 |
| 337 | aattactacatctcacatcaacgcgat | M24537 | 42942 | ttaaccgcagaatctgctcttcta | AA161905 | 85545 | gattcataacatggccatgcattac | AA106601 |
| 338 | tccacatcacacgcagtgcgaat | M24537 | 42943 | aattgctccgttccgactgccca | AA161905 | 85546 | taacatggccatgcattacctgtt | AA106601 |
| 339 | acacgcagtgcaatgccaatgcataaa | M24537 | 42944 | gttcctgcagtgccaagatgtgaa | AA161905 | 85547 | atggccatgcattacctttcgag | AA106601 |
| 340 | attggccagtgccatcccgagc | M24537 | 42945 | agcatacactgctgctcatctactt | AA161905 | 85548 | ggccatgcattacctgttcgtgc | AA106601 |
| 341 | aagttgccgattcacccagactg | M24537 | 42946 | atacactgctgcatctactccaa | AA161905 | 85549 | atgcattacctgtttgagtcgaag | AA106601 |
| 342 | gtcagtgaccatccgagctgaata | M24537 | 42947 | cactgctgcatcacattactcacatt | AA161905 | 85550 | taccttggatacggacaa | AA106601 |
| 343 | ccatccgagctgaatacggggc | M24537 | 42948 | gcagtgcttaaccgcagatct | AA161905 | 85551 | atgatcataacatgccatgcatt | AA106601 |
| 344 | ggtgaataggtgcgccatgccac | M24537 | 42949 | ttaaccgcagaatctgctctta | AA161905 | 85552 | tacctgttttgagtcgaagatgt | AA106601 |
| 345 | tatcgggtcattgccaatgcatatag | M24537 | 42950 | aatgctccgttcctgcatgtcca | AA161905 | 85553 | tatctggaatgccaactgacaatg | AA106601 |
| 346 | gccaatgatatatgccgcttcacat | M24537 | 42951 | actgtctttataagagcagat | AA161905 | 85554 | gaatgccaaactgacaacttggg | AA106601 |
| 347 | atgccagctctacatacgaattaa | M24537 | 42952 | atgatgttcaattgcattggtg | AA161905 | 85555 | cttgacagccaactttggctgc | AA106601 |
| 348 | ctgtctccgatgaaacatatctt | M24537 | 42953 | ttccaatgatttctgtggcaataa | AA161905 | 85556 | cttgacagccaactttggctgcgt | AA106601 |
| 349 | gaattcaaaatgtgagctcaggccc | M24537 | | | | 85557 | tgacagcaacttggctgcgggtcc | AA106601 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 350 | ttaatgctatgctgccgcaggatg | M24537 | 42954 | gtcgactgtgctgatggagtaaa | AA161905 | 85558 | agcaacttggctgccggccgtca | AA106601 |
| 351 | catgtgccgcaggatgatcagtcc | M24537 | 42955 | gcgaagctgtcgctcttcagt | AA161905 | 85559 | tttggctgccggtcgctcaaagtga | AA106601 |
| 352 | ggatgatcagtccgggcgctgcat | M24537 | 42956 | tgtccgttcctcatgtacaggtccc | AA161905 | 85560 | tggctgccgccgtcaaagttaag | AA106601 |
| 353 | cgggcgcgtcatagagtgctgtct | M24537 | 42957 | ttcatgtacaggtccctccatggctg | AA161905 | 85561 | aaatggccaaggcattaaggaaatg | AA106624 |
| 354 | ctgatagggtgctgtcatttt | M24537 | 42958 | atgtacaggtccctccatggctgtga | AA161905 | 85562 | aatggccaaggcattaaggaaatgg | AA106624 |
| 355 | gtgctgtcgcattttctggagaa | M24537 | 42959 | tacaggtccctcatggctgtgaatt | AA161905 | 85563 | gctcgatttttcggcacatgctta | AA106624 |
| 356 | tgtctgcatgatttcaggagcc | M24537 | 42960 | tccctcatggctgtgaattgctccg | AA161905 | 85564 | tcgatttttcggcacatgcttat | AA106624 |
| 357 | gtatgattcaggggccatgcaggg | M24537 | 42961 | tagaattaggcctctcggagcaggg | AA161905 | 85565 | tcgatttttcggcacatgcttata | AA106624 |
| 358 | aggggccatgcaggaggcttgaagca | M24537 | 42962 | atcctaggcggttcattcctgagc | U33626 | 85566 | gattttcggcacatgcttataaa | AA106624 |
| 359 | agtgaggctctggggtgcataccag | M24537 | 42963 | gactgaactgctgttgctgtccaca | U33626 | 85567 | ttttttcggcacatgcttataaatg | AA106624 |
| 360 | cttcggggcatacactggttacc | M24537 | 42964 | tgcggccaggtgttttccagata | U33626 | 85568 | ttttcggcacatgcttataaatgc | AA106624 |
| 361 | ctgtaacagatcaaaacccgcgct | X04603 | 42965 | agcccagagtccagctttgacagc | U33626 | 85569 | ttttcggcacatgcttataaatgct | AA106624 |
| 362 | acacctctatctcaacctgcgaagc | X04603 | 42966 | tgacagctgatgacctccattc | U33626 | 85570 | ttcggcacatgcttataaatgctg | AA106624 |
| 363 | gaattgagctctcagtcaaaacgga | X04603 | 42967 | cctgatgacctccattttcatatga | U33626 | 85571 | tcggcacatgcttataaatgctga | AA106624 |
| 364 | sggatcattaaagatccggaatg | X04603 | 42968 | gacctccattcatatgaatggtg | U33626 | 85572 | tcggcacatgcttataaatgctgag | AA106624 |
| 365 | gaaggctcaatgacacgattatgtgcg | X04603 | 42969 | cacactctgactcatctcaggggt | U33626 | 85573 | aaggtctgtgccacaaaagagtg | AA106624 |
| 366 | acacgattatggtgcgctcaacacag | X04603 | 42970 | tcatcctatggtgtccaaggcac | U33626 | 85574 | aggtcgttgccacaaaaagagtgc | AA106624 |
| 367 | ggctcaacagtaaacactccgctg | X04603 | 42971 | tgttccaaggcacccaatgctccac | U33626 | 85575 | ggtcgttgccacaaaagagtgct | AA106624 |
| 368 | cacttccgctgctgccgcacatat | X04603 | 42972 | aaatcagttcttatggtggttgtg | U33626 | 85576 | gtctcgttgccacaaaagagtgctc | AA106624 |
| 369 | cggcagcatatgcagcccgtgctaa | X04603 | 42973 | ccggccatgcacattgagtatgat | U33626 | 85577 | ctcgtgccacaaaagagtgctcga | AA106624 |
| 370 | cagcccgtgcacatgaaatgcat | X04603 | 42974 | aaaggcagaactccagttgtcctgt | U33626 | 85578 | ttgccacaaagagtgctcgatttt | AA106624 |
| 371 | tgcattgtcatcatcccgaacgga | X04603 | 42975 | cagaactccagttgctctgtgaatt | U33626 | 85579 | agtgctcgattttttcggcacatgc | AA106624 |
| 372 | ggaaaactcgctcaagctgtcatgt | X04603 | 42976 | tccagttgctgtgagatggctga | U33626 | 85580 | gtgctcgatttttcggcacatgct | AA106624 |
| 373 | gtccgttccatcgtgcgagaatcac | X04603 | 42977 | tggctgacccgtgcgagcgaggattatc | U33626 | 85581 | catgatccttccagaaaaatgag | AA106624 |
| 374 | tgtgagaaatcaccgattgccctg | X04603 | 42978 | tattatctcgaccgtgcgctactgctg | U33626 | 85582 | gctcttccacgtcctcactacga | AA106625 |
| 375 | tcagtcaaacctaccgcattgaag | X04603 | 42979 | ggtccctgacccttatggccatctg | U33626 | 85583 | catgaaacctgttttgacttgtat | AA106625 |
| 376 | ctgctgcccttcgaagttgtgcgaaca | X04603 | 42980 | tgacctatggccatctcggaggtc | U33626 | 85584 | gactttgattccctgagctccctg | AA106625 |
| 377 | ctgctgccttcgaagttgtgcgaaca | X04603 | 42981 | ctgtactactgtcattggggatg | U33626 | 85585 | ttccctgacttcctgcactgaat | AA106625 |
| 378 | catgagaaacatcacgtactgga | X04603 | 42982 | ttactactgtacatggaatgatt | U33626 | 85586 | ggacttccctgactgcattgaatt | AA106625 |
| 379 | gcgcgggccaatcgtcgcgcaatgaag | X04603 | 42983 | ctatactgaatcctgcctcacaga | U33626 | 85587 | tgaagacactgcaactgctcctctac | AA106625 |
| 380 | gcaatcgtcgcgcaatgaagtgatg | X04603 | 42984 | atccttgcctcacagaaattgagtc | U33626 | 85588 | agacacgtcaacatcgtctacaat | AA106625 |
| 381 | gtaaaggcagcgcgaggaatccaaatg | X04603 | 42985 | catgccatgctaacctgtagctc | U33626 | 85589 | cagtcaacatcgtctacaatgcc | AA106625 |
| 382 | actgatgaatgaaatcctcacgcat | X04603 | 42986 | tgccatgctaacctgtaactctaa | U33626 | 85590 | aacactgctacaatgcctcagc | AA106625 |
| 383 | atcctcaegcatatcagtgatcg | X04603 | 42987 | aatctgctagctaactctatgaga | U33626 | 85591 | atctgctacaatgcctcagcagc | AA106625 |
| 384 | tatcagtctgatcgccgtagaag | X04603 | 42988 | ctgtagctctaatctatgagaaaa | U33626 | 85592 | tgctacaatgcctcagcagcctc | AA106625 |
| 385 | cagaaccaggttcgcgctctat | X04603 | 42989 | acctggtcgctgttttagcagta | U33626 | 85593 | tteacctgtctctactgcaagaatg | AA106625 |
| 386 | tgcgctctatcgcaggagtgctga | X04603 | 42990 | tggtctgtcgttttagcagtaaaa | U33626 | 85594 | caatgctccagccgcctctagtat | AA106625 |
| 387 | aaggcagcagcgtgacgtgtgt | X04603 | 42991 | atgtccgtatgtattgtaactgg | U33626 | 85595 | acctgtctactgaagagatgctg | AA106625 |
| 388 | aagatccgaacagaggcgtcgacat | X04603 | 42992 | tatgtcgggccaggccatatggtc | U33626 | 85596 | agagatgctctgaacctccaagc | AA106625 |
| 389 | gcgggctgacattcagaaatcaagc | X04603 | 42993 | ctacgtacattgggatgtattca | U33626 | 85597 | tcaactcgaagctctcggttcc | AA106625 |
| 390 | tcgaaatcaagctgtcacattgagc | X04603 | 42994 | atgagtctaccttcaccttttcgac | U33626 | 85598 | gaagctctcggttcagctccca | AA106625 |
| 391 | cctgtcacattgcgactgatgaag | X04603 | 42995 | agtctaccttcaccttctcacgt | U33626 | 85599 | cggttctagctcccattgagtatg | AA106625 |
| 392 | gacagcatcctgaatatgtaaaag | X04603 | 42996 | caccttctgcactgcatacacat | U33626 | 85600 | ttctagctcccattgagtatggt | AA106625 |
| 393 | acgaagcgacagtcgttctcgt | X04603 | 42997 | ctttccgcactgcatacacatttt | U33626 | 85601 | tagctcccattgagtatgcttta | AA106625 |
| 394 | tgcgttctctgtcctcccgg | X04603 | 42998 | ctgtcatacacattcacctttaa | U33626 | 85602 | gaacctgtccagtgcatccagaac | AA106625 |
| 395 | gctttgatttcagtcgggaatggcggt | X04603 | 42999 | tcatacacattcacctcacctttaatta | U33626 | 85603 | cctgaccagtcatccagaacaag | AA106625 |
| 396 | tcggaatgcgcgtcagcagatatt | X04603 | 43000 | cccagtccctactgaatcctg | U33626 | 85604 | ttagctgccctgcctgctttctc | AA106625 |
| 397 | cagatattgaagctgaccgctttt | X04603 | 43001 | cacaccaactgctttgagatcacgg | AA020222 | 85605 | gccttgcctgctgcttccctcatt | D10024 |
| 398 | tgaccgctttgaagctgacaaatg | X04603 | 43002 | gggagtccgtacacactctgcagc | AA020222 | 85606 | tctctcttatgccaaagaagtga | D10024 |
| 399 | cagtaaactgctgatctaccaaggcc | X04603 | 43003 | cggatcagtcagtcaaggccattgcc | AA020222 | 85607 | ctccttatgccaaagaagtgaaca | D10024 |

TABLE 1-continued

| SEQ ID NO | DBAxnID | sequence | SEQ ID NO | DBAxnID | sequence | SEQ ID NO | DBAxnID | sequence |
|---|---|---|---|---|---|---|---|---|
| 400 | X04603 | ctcctgtccatgtgaaggtgtgag | 43004 | AA020222 | atctcagtcaaaggcattgccacg | 85608 | D10024 | ggtcagtctgtgacatggagacact |
| 401 | X04603 | agaaggacaccgacaatgctggc | 43005 | AA020222 | tcagtcaaaggcattgccaagaca | 85609 | D10024 | gacatgagacattcctcttattgta |
| 402 | X04603 | cgcttctctgtcggcggacttgtg | 43006 | AA020222 | aaaggcattgccaagacatcacca | 85610 | D10024 | agacacttccttatgtactgtgt |
| 403 | X04603 | cggcggactgtgatcggcctgcat | 43007 | AA020222 | gccattgccacgacatcaccacag | 85611 | D10024 | cacttccttatgtactgtgtcgt |
| 404 | X04603 | cggcgcatgagggatgacgagacc | 43008 | AA020222 | acagcccaatggtggactactgga | 85612 | D10024 | ttcctttatgtactgtgtcgtgaa |
| 405 | X04603 | ccaaatgatccggccgaatgct | 43009 | AA020222 | ccaggatccacatgtcattgccc | 85613 | D10024 | ttagtactgtgtgaataaacc |
| 406 | X04603 | ccgaatgctgacatttgactagtc | 43010 | AA020222 | atccacatgtcattgcccaagcc | 85614 | D10024 | cagaacaaagcccctgacttcgt |
| 407 | X04603 | tgtcattcctttatgcaagtgctg | 43011 | AA020222 | attgtcattgcccaagcccctggct | 85615 | D10024 | tcagcacagtgactcacccagaagt |
| 408 | X04603 | tgaagtgtgacagagacgtccgaga | 43012 | AA020222 | gtcattgccaagcccctggctacg | 85616 | D10024 | gcacagtggatcacccagaagggc |
| 409 | X04603 | agacgcgagagacgtgctccgaag | 43013 | AA020222 | gccctgtacacactctggcagaca | 85617 | D10024 | tggatcacccagaagtgggctcacc |
| 410 | X04603 | gaaggagttccatatgccgatgcc | 43014 | AA020222 | caagccccctggctacgccaagtca | 85618 | D10024 | atcaccccagaagtggctctacctgt |
| 411 | X04603 | tgccgatgcgctaaaagcaagtgct | 43015 | AA020222 | ctgtacaacactggcagacacaca | 85619 | D10024 | accccagaagtgggctctactgtgcc |
| 412 | X04603 | tgctgtcagcaatatcctcatgct | 43016 | AA020222 | acactctggcagcacaacaaggagt | 85620 | D10024 | tctagagacttcgtctcctcactaa |
| 413 | X04603 | cctcatgctgcgatggccgctgtc | 43017 | AA020222 | ctctggcagcacaacaaggagtgac | 85621 | D10024 | atcttagctgccttgcctgcttgtt |
| 414 | X04603 | catgccaaggatggccgctgtc | 43018 | AA020222 | cacaacaaggagtcactcctgaatt | 85622 | J03928 | atgtccagactcagcctgtgtgat |
| 415 | X04603 | gttccatcagcgtaccggcgatg | 43019 | AA020222 | aaggagtcactcctgaatttcgtgg | 85623 | J03928 | cagactcgcctgtgtgatgcgcct |
| 416 | X04603 | gtaccgccgatgcttgtccgtag | 43020 | AA020222 | gtcaaaaacgccggatctcagtca | 85624 | J03928 | tggacgcgacacgccgcacctt |
| 417 | X04603 | agtagaggcacgtcgccgagatgaag | 43021 | AA020222 | aacgcccgatctcagtcaaggtca | 85625 | J03928 | cacgccgcacctgagcatagacaa |
| 418 | X04603 | atatggaacggctcagcgggagca | 43022 | U37351 | cctggcgtcagtggccttgtagca | 85626 | J03928 | geacttgagcatagacaaggtt |
| 419 | X04603 | cgggacaggccaacgattctcgtc | 43023 | U37351 | cgtcagtggccttgtagcatgatgt | 85627 | J03928 | ageggtttctgagcttactgtcacta |
| 420 | X04603 | gctccgctcattccctatgt | 43024 | U37351 | tcttcactccaaactgatatca | 85628 | J03928 | tctgagctcgtcactactgtc |
| 421 |  | ctttgatttacgattgccacgatgag | 43025 | U37351 | ctctaaactgatactcaattacgt | 85629 | J03928 | cttactgtcactactgttcctcgt |
| 422 |  | gattgcccacgatgagtgtaaaagaac | 43026 | U37351 | atttgcagttgcttcaacatgagaa | 85630 | J03928 | gctagccacagatcccagcaacgag |
| 423 |  | cggtgttgcatgcagacaggccggt | 43027 | U37351 | tagccccttgttctctattcagt | 85631 | J03928 | cacagatccacgaccgcgagggggaac |
| 424 |  | tacagcaaggtgccatggtgcc | 43028 | U37351 | tctcattcacgttgtaaataaaca | 85632 | J03928 | ggggtcgcctgctgctgggggt |
| 425 |  | cattgtccgattcgtcctgaa | 43029 | U37351 | ctgttagttacagtcttgtataga | 85633 | J03928 | ctttcagtcgaccccaatggctc |
| 426 |  | aagccgcgtgccgctgctgaaaacgat | 43030 | U37351 | ttttatcgcatgctgagttgc | 85634 | J03928 | cagcctgtgatcgatgcctgcggaa |
| 427 |  | gaaaacgaatttcatatgcagaagac | 43031 | U37351 | caatgcgaggcaggcccttaga | 85635 | J03928 | gtccggtcacagaactcaagaagaa |
| 428 |  | ctgatgaacagatttcacaattgt | 43032 | U37351 | tgagtgcagccccttagcacaga | 85636 | J03928 | atttgcacccagatccccgga |
| 429 |  | tactgccgtgaggctgaaacgctg | 43033 | U37351 | caggccttagtagcacactgggg | 85637 | J03928 | agcaccgcatgccccgggagagtg |
| 430 |  | tatgatgatgccgggaaatgact | 43034 | U37351 | tgtgcatctgcccggttaatggtc | 85638 | J03928 | cacactaccgcatcagcagcagcaga |
| 431 |  | gatatgtcaattcgtgtcatcg | 43035 | U37351 | aatggtccacctcaactgcagact | 85639 | J03928 | tcagcatcagatggcagactatgt |
| 432 |  | gttttcgtgaaggccaatgcgggcaca | 43036 | U37351 | caactgcagacctcaggtagtcgg | 85640 | J03928 | tcagcagactatgtcggggag |
| 433 |  | cgctaatgcggcaatgcgctttg | 43037 | U37351 | cagacctcaggtagctggatggaa | 85641 | J03928 | tggcagactatgtgctgggaggct |
| 434 |  | acacgctctacagtcgatggactt | 43038 | U37351 | acagcaaagcacacgtccccattg | 85642 | V00809 | ggtgattatgccaaagacaagt |
| 435 |  | tggactctgatattgataca | 43039 | U37351 | aagccacacgtcccattgcgtgg | 85643 | V00809 | tactgccaagacaagtccatct |
| 436 |  | tatctcaaaggcctggcaattgt | 43040 | U37351 | cccattgcgggtgtgtgctatt | 85644 | V00809 | gccaacaaccttcaaacttgcaga |
| 437 |  | ctcggcaatttgttgctggcagct | 43041 | U37351 | gctgtctcactcctaaactgt | 85645 | V00809 | aaattgttctgacatgcaggataa |
| 438 |  | gttgcctccgcagctgcctctggaggc | 43042 | AA020211 | gaaggtctatgcgctcctggaggcc | 85646 | V00809 | ttgttcgacatgcaggataatcc |
| 439 |  | cgcttactgtgaaggcaatggggcaca | 43043 | AA020211 | aaggtctatgcgctccttggaggct | 85647 | V00809 | tcgaggataatctctcttgtttacta |
| 440 |  | caatgcctcgtctcttcaaaag | 43044 | AA020211 | gctccttggaggctactgccaagc | 85648 | V00809 | aggtaatcctctcttactaata |
| 441 |  | gatttcggttcacaaaggccagac | 43045 | AA020211 | cgtcctggagcctactgccaagca | 85649 | V00809 | ataatcctcgttactaatagg |
| 442 |  | tttcacaaatggccactttgaagat | 43046 | AA020211 | tcctggaggctactgccaagcaca | 85650 | V00809 | atcctctcgttactaatatgggaa |
| 443 |  | tttacagttcgagctcaccgaaggag | 43047 | AA020211 | ccttggaggctactgccaagcacaa | 85651 | V00809 | atgctactggctccttccct |
| 444 |  | cacgaaaggagggccctatctctct | 43048 | AA020211 | ggtgaggctactgccaagcacaagtaccca | 85652 | V00809 | tctctccacaaacaggttagaaatt |
| 445 |  | aagagagcgctatctcattcagaa | 43049 | AA020211 | gaaggtcgtaagcttctgtccg | 85653 | V00809 | aatttcacgagattgccttgt |
| 446 |  | gagccgctatctcattcagaatt | 43050 | AA020211 | aaaggtctaagcttctgtcctcg | 85654 | V00809 | ctgcccaaagacaagtccatctgaagca |
| 447 |  | gcagcgttccgctttatctattac | 43051 | AA020211 | gctaagctctgtccgcctgccgg | 85655 | V00809 | cccaaagacaagtccatctgaagca |
| 448 |  | gctttaatgcgggagctgcgatt | 43052 | AA020211 | gctcaaatgcctggacatctct | 85656 | V00809 | gacaagtccatctgaagcaagaact |
| 449 |  | ttagagacgattacaaggcgaggcg | 43053 | AA020211 | gctcaaatgcctggaacatctctc | 85657 | V00809 | tccatctgaagcaagaactgactat |

TABLE 1-continued

| SEQ ID NO | DBAxnID | sequence | SEQ ID NO | DBAxnID | sequence | SEQ ID NO | DBAxnID |
|---|---|---|---|---|---|---|---|
| 450 | | agagattacaagcggaggcgctgc | 43054 | M12481 | aggtctatgctccttggaggccta | 85658 | V00809 |
| 451 | | gattacaagcggaggcgctgccgg | 43055 | M12481 | ggtctatgcgtccttggaggcctac | 85659 | V00809 |
| 452 | | ccggcagcttgaacgactaaaga | 43056 | M12481 | gctatgcgtccttggaggcctact | 85660 | V00809 |
| 453 | | gcagctgaacgactaaagacaaa | 43057 | M12481 | tctatgcgtccttggaggcctactg | 85661 | V00809 |
| 454 | | gagctgccttgcagaaacgtcat | 43058 | M12481 | ctatgcgtccttggaggcctactgc | 85662 | AA106634 |
| 455 | | gaggcgctgcaagccgaatcggt | 43059 | M12481 | tatgcgtccttggaggcctactgca | 85663 | AA106634 |
| 456 | | ttaaagagatttgtgcctgca | 43060 | M12481 | atgcgtccttggaggcctactgcaa | 85664 | AA106634 |
| 457 | | ttttgcctgcagattgcaata | 43061 | M12481 | tgcgtccttgaggcctactgcaag | 85665 | AA106634 |
| 458 | | gcagatgcaatagactatgaaggct | 43062 | M12481 | gctggcagcctcacattgggaa | 85666 | AA106634 |
| 459 | | atagactatgaaggctgcgaaggcag | 43063 | M12481 | gcagccttcacattgggaaggaga | 85667 | AA106634 |
| 460 | | actatgaaggctgcgaaggcagagc | 43064 | M12481 | aatgcttagccaagaacaatgagat | 85668 | AA106634 |
| 461 | | ttaacattgtcaatgaacatgggg | 43065 | M12481 | tcccaggatctatcagactgaaggc | 85669 | AA106634 |
| 462 | | gcgagctgtactatgcgtgaatca | 43066 | M12481 | agtgttacaatcaacagcaactgt | 85670 | AA106634 |
| 463 | | atgagacaaactctgcgtgaaag | 43067 | M12481 | tacaatacaggcaactgagctg | 85671 | AA106634 |
| 464 | | tctcagctaaagcaatccatgctt | 43068 | M12481 | cacaggcaactggactgagcact | 85672 | AA106634 |
| 465 | | gtcactaaaggatttgcagcttgcg | 43069 | M12481 | tggtgcagccatgctttctctgc | 85673 | AA106634 |
| 466 | | ttgcactgtgcgcgaaatcaacag | 43070 | M12481 | cagccagctttctctgctagact | 85674 | AA106634 |
| 467 | | gcggggaatcacaggctgattacc | 43071 | M12481 | ccatgtatagccaactttcctcca | 85675 | AA106634 |
| 468 | | atcaatagacgatgtcacgtatt | 43072 | M12481 | aactttctccatcgtagtgtgat | 85676 | AA106634 |
| 469 | | acgatgtcagtattgccaagagct | 43073 | M12481 | cttacaatactgcaatactgaatat | 85677 | AA106634 |
| 470 | | gtattgccaagcttgaagctga | 43074 | M12481 | acacaacttgaccgtggccaacctc | 85678 | AA106634 |
| 471 | | gagcttgaagctgcagctcattcag | 43075 | M12481 | agtgaaacaacccagacattggctc | 85679 | AA106634 |
| 472 | | ctcagcttcatcagcttcacggtg | 43076 | M12481 | cagacatggctccacaagcacaga | 85680 | AA106634 |
| 473 | | ttcagcttcaggtgatgaaaaac | 43077 | M12481 | ttggttcacactcaccaaccacca | 85681 | AA106634 |
| 474 | | gatagctgctctcgcaagctg | 43078 | M12481 | tccaccaagcatccattacagata | 85682 | AA106634 |
| 475 | | agctgcagagctgctgtgaaatatgaa | 43079 | M12481 | ccacaagcacagatcccagaaaag | 85683 | AA106634 |
| 476 | | gcgcttcaccatcagataacaca | 43080 | M12481 | cttggcaccagatacatgtgact | 85684 | AA106634 |
| 477 | | atgtgacggttgtgattgatc | 43081 | M12481 | tccctagcacaaatgcttagccaa | 85685 | AA106634 |
| 478 | | ttgattcatcgtaaagggctcag | 43082 | M12481 | atctgctacgaacaatgcagat | 85686 | U31758 |
| 479 | | tgggaatgtgtcgcggaatatcagc | 43083 | M12481 | aatggcagatgcctccactggtt | 85687 | U31758 |
| 480 | | tgccgaaatcagcaggcggctat | 43084 | M12481 | ctgtttcttctcggcctgaatat | 85688 | U31758 |
| 481 | | aatgggctcagaaggactcctatgg | 43085 | M12481 | ctccggtcctggaaatatagaagg | 85689 | U31758 |
| 482 | | gaaggactcctatgtgggtgagag | 43086 | M12481 | taaatactggttcacactccacca | 85690 | U31758 |
| 483 | | tgggtgacgaaggccagaagaag | 43087 | M12481 | ctggttcacactccaccaagatc | 85691 | U31758 |
| 484 | | gagaggtacctgacctgaagtac | 43088 | M12481 | tccaccaagcatccattacagata | 85692 | U31758 |
| 485 | | agtaccccattgaacatgcatgt | 43089 | M12481 | accaagcatccattacagatagaa | 85693 | U31758 |
| 486 | | ttgaacatggcattgtaccaactg | 43090 | M12481 | aagcatccattacagatagaagag | 85694 | U31758 |
| 487 | | tgttaccatggcgacgatggag | 43091 | M12481 | tcagcccatgaaaggctggag | 85695 | U31758 |
| 488 | | ggagaagatctgcaccacacctc | 43092 | M12481 | gccatcttagaggctggacaag | 85696 | U31758 |
| 489 | | accacaccttcacatgagctgcg | 43093 | M12481 | caaggacagctcaccaaaggatgac | 85697 | U31758 |
| 490 | | cctttcacaagactcctatgg | 43094 | M12481 | agatgcctccactgagctcgcaa | 85698 | U31758 |
| 491 | | acaatgacgtcgtgtgtcc | 43095 | M12481 | tgcctccactgagcttcagcaa | 85699 | U31758 |
| 492 | | ccccttgagagcgtgtgcctga | 43096 | M12481 | tgagcttcagcaagttcagcatc | 85700 | U31758 |
| 493 | | accctggtgcgctcaccgagtgcgt | 43097 | M12481 | gctcagcaagtcatccgatcc | 85701 | U31758 |
| 494 | | tgaccagatcagttgagacctt | 43098 | M12481 | agtcatccgatcctcgggaaca | 85702 | AA106256 |
| 495 | | agatcatgtttgagacctcaacac | 43099 | M12481 | catccgatcctcgggaacatt | 85703 | AA106256 |
| 496 | | cccagccatgtagtagccatccag | 43100 | M12481 | cctgatcctcgggaacatttcg | 85704 | AA106256 |
| 497 | | gtacttagccatccaggctgtgcg | 43101 | M12481 | aggagcctgtttcttcctggtctg | 85705 | AA106256 |
| 498 | | cctaaccaggctgctgccctga | 43102 | M12481 | ctctttaagcctccagtgttagttat | 85706 | AA106256 |
| 499 | | gctgccaggctgctgatgcctgt | 43103 | M12481 | tttaagcctccagtgttagttattg | 85707 | AA106256 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 500 | gtatgcctcggtgtaccacggc | M12481 | 43104 | atctatacattcgaagctgcaa | AA020264 | 85708 | agtggctcgtcaatgccaattgc | AA106256 |
| 501 | gtcgtaccacggcgcattgatgga | M12481 | 43105 | aggcctagacttgatcagtgtcagg | AA020264 | 85709 | tccgtcaatgccaattgcatgca | AA106256 |
| 502 | tgcccactacgagggctatgtct | M12481 | 43106 | gacttgatcagtgtcaggctggttg | AA020264 | 85710 | gtcaatgccaatttgcatggcagca | AA106256 |
| 503 | cctcacgccatccgcgtctggact | M12481 | 43107 | ctgatcagtgtcaggctggttgc | AA020264 | 85711 | aatgccaatttgcatggcagcagca | AA106256 |
| 504 | ccatccggtcggactggtcgg | M12481 | 43108 | ttgatcagtcaggctggttgtca | AA020264 | 85712 | aatttgcatggcagcaaggattct | AA106256 |
| 505 | ctgacggactacctcatgaagatcc | M12481 | 43109 | gatcagtcaggctggtgtgtcaat | AA020264 | 85713 | gaaacgactgtacctgggtgtacat | AA106256 |
| 506 | actacctgaagatcctgaccga | M12481 | 43110 | atcagtcaggctggttgtcaatt | AA020264 | 85714 | tcgcagatcatcatcctgacccta | AA106256 |
| 507 | tcatgaagatcctgaccgagctgtg | M12481 | 43111 | cagtcaggctgttgtcaattt | AA020264 | 85715 | cgagatcatcatcctgacctact | AA106256 |
| 508 | tcctgacgagctggctacagtt | M12481 | 43112 | agtgcaggctggttgtcaatttg | AA020264 | 85716 | acgtccgtgactaggtctacgg | AA106256 |
| 509 | gcttcaccaccagctgagaggga | M12481 | 43113 | tgtcaggctggtgtcaatttgat | AA020264 | 85717 | cgtgactatggtctacggctagtc | AA106256 |
| 510 | gaaactgtgcgtgacatcaaagaga | M12481 | 43114 | taagcctccagtgtagtattgtg | AA020264 | 85718 | tggtctacggctagtccaaactg | AA106256 |
| 511 | agctgtcgtatgtgctctagact | M12481 | 43115 | aagcctccagttgtagtattgtgg | AA020264 | 85719 | tctacggctagtccaaacctgtag | AA106256 |
| 512 | gctatgttgcctctagact | M12481 | 43116 | gcctccagtgtagtattgtggga | AA020264 | 85720 | agtcctgcctagcctagcctaaacctg | AA106256 |
| 513 | ctctagacttcgagcaggaggagc | M12481 | 43117 | tttgtggactgcaactgacaggagcag | AA020264 | 85721 | ctgcctgctagcctaaacctggca | AA106256 |
| 514 | caggatgcccactgccgcatcct | M12481 | 43118 | aaggcatactacatccattcgagaag | AA020264 | 85722 | tgcagtccccgtggaggagacagt | AA106256 |
| 515 | agaagagctatgaggctgcctgacgg | M12481 | 43119 | agcatatcatacattcggagaagt | AA020264 | 85723 | cagtcccgtggaggaacgttg | AA106256 |
| 516 | atgagctgcctgacgcccaagtcat | M12481 | 43120 | catatctatacattcggagagtcg | AA020264 | 85724 | aaggagctgcgtctgactctg | AA106256 |
| 517 | tgcctgacgcccaagtcatcactat | M12481 | 43121 | atatctatacattcggagaagtcgc | AA020264 | 85725 | gagctgctggctgctgactctgcc | AA106256 |
| 518 | gccaagtcatcactattggcaacga | M12481 | 43122 | cagatctccagttgagacttcatt | AA020264 | 85726 | ctggctgtcgactctgccctctagc | AA106256 |
| 519 | atcactattggcaacgagcggttcc | M12481 | 43123 | agacttcattccttgtccagtgga | AA020264 | 85727 | ctgctgacctgtcgggctccctcagaag | AA106256 |
| 520 | ggcaacgagcggttccgatgccctg | M12481 | 43124 | ggttccaaaatgcgcagcaaggat | AA020264 | 85728 | tgccctaagcggcctccaagtcagag | AA106256 |
| 521 | ttccatgccctgagctctttc | M12481 | 43125 | tccaaaatgcgcgagcaaagatgaa | AA020264 | 85729 | ctctagagggcctccaagaggcca | AA106256 |
| 522 | tgcctgaggctctttcagcct | M12481 | 43126 | cctcaaccagatctctgaaata | AA020264 | 85730 | ccacactgttcacaagccagtg | AA106256 |
| 523 | aactacattccaattcatcatgaag | M12481 | 43127 | accagatctctgaaatagtggaga | AA020264 | 85731 | tcacaagccagtgctcgtaggagt | AA106256 |
| 524 | ttccatcatgaagttggacttgac | M12481 | 43128 | gttgctctcctccagttgtgac | AA020264 | 85732 | acaagccagtcgtctgtagggttgg | AA106256 |
| 525 | tgaatccgtaaagaccctatgc | M12481 | 43129 | tctccagtttatagtacagaga | AA020264 | 85733 | aagccagtgctctgtagagggtggg | AA106256 |
| 526 | gacctatgccaacagtgttgt | M12481 | 43130 | aatgttacagtctctccctgtatct | AA020264 | 85734 | gtcctcgtgagagacagttgag | AA106256 |
| 527 | cacagtgtcgtggtaccaac | M12481 | 43131 | gtctcctcgtatctaatctagat | AA020264 | 85735 | aatgagctgtatttccagtgtgc | AA106256 |
| 528 | accatgtaccagccagtgctgca | M12481 | 43132 | ctctcgtatctaatctagattt | AA020264 | 85736 | tattcccagtgtcacagtggtt | AA106256 |
| 529 | aggcattgtgacaggatgcagaag | M12481 | 43133 | agattttgcattcttttctgaaat | AA020264 | 85737 | ccagttgcacgtgtcgtgggaggc | AA106256 |
| 530 | aagagattactgctctgcctccta | M12481 | 43134 | cattctgtccagtggatcaccc | AA020264 | 85738 | tgcacagtgctgtggagctgcatg | AA106256 |
| 531 | acgtcctgcctctagcaccatga | M12481 | 43135 | ctgtccagtggatcaccaaggcc | AA020264 | 85739 | cacagtcgtggaggctgatgg | AA106256 |
| 532 | tcctagcaccatgaagatcaagatc | M12481 | 43136 | tggatcaccaaggatcacagaaag | AA020264 | 85740 | ctgaatgccccgcgtgaagagact | AA106256 |
| 533 | gatcaagatcatgctcctctgg | M12481 | 43137 | cagcctcgaaaacacgtcttgaa | AA020264 | 85741 | tgaggcgtgtggcgcttgaact | AA106256 |
| 534 | tgctcctctgagcgcaagtactct | M12481 | 43138 | tcaccgaaccaggtcgaagtatt | AA020264 | 85742 | agcaaaaatgatccactgatgcca | AA106256 |
| 535 | cctgagcgcaagtactctgtgtga | M12481 | 43139 | gagtgaactgctacccgcaattga | AA020264 | 85743 | atggatccactgatgccaagtatc | AA106256 |
| 536 | gtactctgtgtgaggaccctcc | M12481 | 43140 | gctacccgcattgacatcagaga | AA020264 | 85744 | ttcttcactgtgctgctctcaca | U43076 |
| 537 | gtggatgcgtgggcctctggcc | M12481 | 43141 | acctgcatgacatcacagagga | AA020264 | 85745 | agcgctcatggaagactctgctctg | U43076 |
| 538 | ggctcatctggcctcactgcca | M12481 | 43142 | ctgactccaaaatcacacgctgc | AA020278 | 85746 | catgagactctgctctgggtta | U43076 |
| 539 | cttccagatgtggatacacaag | M12481 | 43143 | cacagcctgccacagcagattgt | AA020278 | 85747 | agatgccagttgccagggtcaccg | U43076 |
| 540 | tcctagcaacggcaggatacgatg | M12481 | 43144 | agtcctgcctgttgtgaat | AA020278 | 85748 | ggatacaaatgtcccatctaggca | U43076 |
| 541 | catctgcacgcagtgcttctag | M12481 | 43145 | cctcgcctgtggttctgaatcg | AA020278 | 85749 | aatgtcccatctaggcaaggtc | U43076 |
| 542 | cgcaagtgcttctaggggactctt | M12481 | 43146 | gcctgtgttcgtgaatctgact | AA020278 | 85750 | tgtctatggtattgtcactgt | U43076 |
| 543 | ggcgactgctacggcacgttt | M12481 | 43147 | cttgtttgctgaatctgacttg | AA020278 | 85751 | cctgaactggcaacactggccaat | U43076 |
| 544 | tgccgtatggaggcgctcaccc | M32599 | 43148 | tctgaatctgactttgctccggta | AA020278 | 85752 | gtcaataacaagtctcaatataacg | U43076 |
| 545 | tggctcaccagctgccattgcag | M32599 | 43149 | gaatctgactttgcttccggtacaa | AA020278 | 85753 | gtcaataacagtctcaggtctg | U43076 |
| 546 | ccatttgcagttgcaagtgggat | M32599 | 43150 | tctgactttgcttccggtacaaca | AA020278 | 85754 | cccactgcaagtatcaacag | U43076 |
| 547 | ccttcattgacctcaactacagt | M32599 | 43151 | gcttccgtacaaacaggccacctg | AA020278 | 85755 | aagtatcacatgcagcgttgcacg | U43076 |
| 548 | tgacctcaactacatggtcaacagt | M32599 | 43152 | tccggtacaaacaggccacctggag | AA020278 | 85756 | caggttgcatcgatctggctct | U43076 |
| 549 | actactaacatggttccagta | M32599 | 43153 | ggtacaacaggccacctgagact | AA020278 | 85757 | tgcagacttcggctctggggtcc | U43076 |

| SEQ ID NO | sequence | DBAxnID | SEQ ID NO | sequence | DBAxnID | SEQ ID NO | sequence | DBAxnID |
|---|---|---|---|---|---|---|---|---|
| 550 | ctacatgttccagtatgactccact | M32599 | 43154 | agcctgccacgcagcagattgctaaa | AA020278 | 85758 | tgggtcccaactccaagtctggtg | U43076 |
| 551 | tccagtatgactccactcacggcaa | M32599 | 43155 | ctgccacgcagcagattgctaaaag | AA020278 | 85759 | gtcagtgcgtgaccctctccggaa | U43076 |
| 552 | ctccactcacggcaaattcaacggc | M32599 | 43156 | gtccactcatgccctgtacccagg | AA020278 | 85760 | aacttagccaccatgccctagctc | U43076 |
| 553 | tcactcacggcaaattcaacggcagtc | M32599 | 43157 | atgccctgtacccaggcccctagcag | AA020278 | 85761 | cccaactcttcactgtgctgctc | U43076 |
| 554 | caacggcacagtcaaggccgagaat | M32599 | 43158 | ggtcagaggcctgagtccgcctg | AA020278 | 85762 | actgtctcatcaaggaaaaattgt | U43076 |
| 555 | tgggaagctgtcatcaacgggaag | M32599 | 43159 | cagagcctgagtccgcctgcctgtg | AA020278 | 85763 | catcagtttattctccgacacaa | U56650 |
| 556 | gctgtcatcaacgggaagccatc | M32599 | 43160 | agcctgagtccgcctgtggttct | AA020278 | 85764 | agagtcatggtccgttatgttc | U56650 |
| 557 | agccatcaacatcttccaggagccg | M32599 | 43161 | ctgagtccgcctgttggtctg | AA020278 | 85765 | tatgttccaaaccattaaggtcat | U56650 |
| 558 | ccatcaacatcttccaggagccgc | M32599 | 43162 | caggtcaccctagaatcagatctgctc | AA020278 | 85766 | tctgattccaattcaacaggtct | U56650 |
| 559 | gcgagaccccataacatcaaatgg | M32599 | 43163 | ggtcaccctagaatcagatctgct | AA020278 | 85767 | ttcacattatctttacagttga | U56650 |
| 560 | ctagtatgtgtggagtctactg | M32599 | 43164 | ctgctactttgatggccatgacgg | AA020278 | 85768 | actacaattaccalagtgagagacc | U56650 |
| 561 | tgtcgtggatcactggtgtctc | M32599 | 43165 | ctacttgatggccatgacgggct | AA020278 | 85769 | agagacatactatcttttggata | U56650 |
| 562 | agtctactggtctcttcaccacat | M32599 | 43166 | atggccatgacggggctgagcctgcc | AA020278 | 85770 | ttctccaatgtaatagaaatgaa | U56650 |
| 563 | gggggtagcaaggtgtcatc | M32599 | 43167 | gccatgacggggctgagcgctgcctg | AA020278 | 85771 | catgttacttacctaggaatgctc | U56650 |
| 564 | agccaaacgggtcatcatctccgcc | M32599 | 43168 | atgacggggctgagcgcctgtga | AA020278 | 85772 | acagtgccagattccatgcgcaaa | U56650 |
| 565 | ggtgtgaaccacgagaaaatatgaca | M32599 | 43169 | aggatcatcggctctggtgaagg | AA020278 | 85773 | gactgccaattccctgccagattc | U56650 |
| 566 | tatgcaacaatcaacagattgtca | M32599 | 43170 | atcatccgcctctggtgaggaa | AA020278 | 85774 | atttccgacaatccaacaggtct | U56650 |
| 567 | ctcactcaagattgtcagcaatga | M32599 | 43171 | atccgcctctggtgaaggagaagg | AA020278 | 85775 | gacacaatttcaacaggtctgggcaa | U56650 |
| 568 | aagatgtcagcaatgcatcctga | M32599 | 43172 | gtctgacaaggcctcggaccag | AA020278 | 85776 | atgtttcagtgagctggtacctcc | U56650 |
| 569 | ccctgccaaggtcatccatgaca | M32599 | 43173 | gacaaggcctcggaccagaattga | AA020278 | 85777 | aatctttaactgccatatgagta | U56650 |
| 570 | catccatgacacattggcattgg | M32599 | 43174 | cctagaatcagatcgtcctcccagc | AA020278 | 85778 | ctttgccaattgcgaccatccaa | U56650 |
| 571 | caacttgcattgggaaggcctc | M32599 | 43175 | gctcccagcatctctgttcctg | AA020278 | 85779 | gcaatttgaccccatccaaaatctg | U56650 |
| 572 | gaagggctcagccactgccatg | M32599 | 43176 | ccccagcatctctgttcctggtg | AA020278 | 85780 | tcgaccatccaaaatctgctacca | U56650 |
| 573 | catgaccacagtccatgccatcat | M32599 | 43177 | cagatctcgtttcctggagt | AA020278 | 85781 | ggtcacactgtgccggaatgtg | U56651 |
| 574 | atcacgccacagtccatgccatcatgg | M32599 | 43178 | catctctgtttcctggagtgat | AA020278 | 85782 | gaatgtgtcacctgctgctctg | U56651 |
| 575 | gactgggatgcccctctcaggtgg | M32599 | 43179 | ctgttcctggtgagtgattcctgc | AA020278 | 85783 | ataactccactgctcaaggggattgt | U56651 |
| 576 | ggcccctctcgaaggtgtgcgctg | M32599 | 43180 | tgatctctgctactttggatgccca | AA020278 | 85784 | tgtccggctctctcaagcctt | U56651 |
| 577 | ccgtggggctgccagaacatcatc | M32599 | 43181 | ttcctgctactttggatgcccatga | AA020278 | 85785 | gctctaagccctcaaggtgatctg | U56651 |
| 578 | gccagaacatcatcctcccgcatcca | M32599 | 43182 | gtaatcaaatcgcctcctccact | AA020278 | 85786 | tatgcctgcactaactatcacag | U56651 |
| 579 | tgcatccactgggtctgcaagct | M32599 | 43183 | tcaaaatcctctccactctg | AA020278 | 85787 | ctgactacaactatcaactgacaac | U56651 |
| 580 | ggcaaggtcatccagagcctgaacg | M32599 | 43184 | cccactggggaacgatcatcaat | AA020278 | 85788 | atcacagtgacaaccttactttcc | U56651 |
| 581 | cccagagcctgaacggaagctcact | M32599 | 43185 | ggatcatcaatgcctcttccaga | AA020278 | 85789 | ctgagactgaagccttgcggagttaa | U56651 |
| 582 | gaacggaagcctcactgccatggcc | M32599 | 43186 | catcaatgcctcttttccagagga | AA020278 | 85790 | ggtcacactgttgccctgaatgtg | U56651 |
| 583 | tggcatggcctccctgtctctacc | M32599 | 43187 | tcaatgcctcttttccagagggga | AA020278 | 85791 | gaatgtgtcacctgctgcttg | U56651 |
| 584 | tctgacgctgccgccgtgagaaactt | M32599 | 43188 | aggtaaacttcccgtcgattcatgcg | AA020278 | 85792 | gtctacctgctgctctgttgact | U56651 |
| 585 | gagaaacttcccgtcgattcatgacga | M32599 | 43189 | gtaaacttcccgtcgattcatgcgaa | AA020278 | 85793 | tggttgcacacactgctaggaaaac | U56651 |
| 586 | ggcaatctgagggccccagcagggc | M32599 | 43190 | aaactcccgtcgattcatgcgaact | AA020278 | 85794 | atttggcaacaaccgcgattga | U56651 |
| 587 | ggcccctgaagggcatctgggcc | M32599 | 43191 | ggatctcaggaactcgatggggct | AA020278 | 85795 | aagatcaagtcctccaactgg | U56651 |
| 588 | cactgaagggctctctgggctacac | M32599 | 43192 | tcagtgaactgtcattccg | AA020278 | 85796 | cctctaactgtcgcattgagtatga | U56651 |
| 589 | tggctacacgtgaggaccaggtgt | M32599 | 43193 | atgcgaactggtctcattcgcc | AA020278 | 85797 | tgtcgcattgagtatgagaaggt | U56651 |
| 590 | actggggaccaggtgtctctctg | M32599 | 43194 | aaatctgctccctccactccgag | AA020278 | 85798 | ttgacaaggccaacaagaacaacact | U56651 |
| 591 | ccaggtgtctctgtgctacctcac | M32599 | 43195 | atctgctccctccactctgagttg | AA020278 | 85799 | aggcaccaaggaacaacactctgcaa | U56651 |
| 592 | ttgctccttgggactcaacgaa | M32599 | 43196 | ccacttcctgagttgggtcaagaaac | AA020278 | 85800 | ccaagaacacactctcaactacga | U56651 |
| 593 | tgcgactcaaacgcaactcccat | M32599 | 43197 | gaaacactttccaagttcagttatt | AA020278 | 85801 | cctgtatccaggagagaccaaag | U56651 |
| 594 | cggagctccggaactttcaatgac | M32599 | 43198 | tataattgccacagaagtaaaatc | AA020278 | 85802 | agtcctttcaacttgttattcgg | U56651 |
| 595 | gcattgctccaatggtgt | M32599 | 43199 | taattgccacagaagtataaattc | AA020278 | 85803 | tgggtggtgctggaaagac | U76546 |
| 596 | caatgacaacttgtcaagcttcatt | M32599 | 43200 | taatttgccacagaagtaaaattcc | AA020278 | 85804 | tggactctgtgaltgtgagagat | U76546 |
| 597 | caacttgtcaagctcattcctg | M32599 | 43201 | attccagaactgcatcaaccaac | AA020278 | 85805 | atcaggaagtccctgctctatagt | U76546 |
| 598 | actgactcattcctgatgaccaatg | M32599 | 43202 | caccatccagtcagtcagtaagtcactgt | U50406 | 85806 | gagtcctgtggctacttatagtgctaa | U76546 |
| 599 | tgacaatgaatacggcacagcaac | M32599 | 43203 | ctcagttaaagtccgacagtcatt | U50406 | 85807 | actgcctgtctctctcagattga | U76546 |

| SEQ ID NO | sequence | DBAxnID | SEQ ID NO | sequence | DBAxnID | SEQ ID NO | sequence | DBAxnID |
|---|---|---|---|---|---|---|---|---|
| 600 | atacggctacagcaacaggggtg | M32599 | 43204 | agaagtgcctggcctactacatat | U50406 | 85808 | ctctcagagattgagaagtgtt | U76546 |
| 601 | ggtggacctcatggctacatggcc | M32599 | 43205 | gctggcctacctacatagtggc | U50406 | 85809 | aactggctcatcgactcctggca | U76546 |
| 602 | acctcatggcctacaggcctccaa | M32599 | 43206 | ctgaaatccagcacttgagagtg | U50406 | 85810 | tgagctcatcgactcctggcatct | U76546 |
| 603 | acccaccccagcagcaactgagc | M32599 | 43207 | tcctagcactgagagttgagaact | U50406 | 85811 | catcgactcctggcatcgcagcc | U76546 |
| 604 | cccagcaaggacactgagcaagag | M32599 | 43208 | tgcacttacagcagcctgagtac | U50406 | 85812 | tgcagccacctgcaatcatagg | U76546 |
| 605 | ggacactgagccaagagaggccctat | M32599 | 43209 | cagcctgagctacaaatgagatgtt | U50406 | 85813 | ccacctgcaatcatcaggagagtgg | U76546 |
| 606 | tccctcacaattccatccagacc | M32599 | 43210 | ttcccaaaacacacaaaagcaag | U50406 | 85814 | acaggctgcagttcaacgaattgt | U76546 |
| 607 | tcaaccagtcagcattcctcac | X57349 | 43211 | aagcaagtgccttaccgaggata | U50406 | 85815 | gcaattccaaaacagtcacttttca | U76546 |
| 608 | tttagctgtcggcaagtagalg | X57349 | 43212 | gtgcttacctggtcaagtaaatgt | U50406 | 85816 | ccaaaacagtcacttctacttctg | U76546 |
| 609 | agataacgtcatgtgagatgaaa | X57349 | 43213 | ttacagccctgggtgctagttgta | U50406 | 85817 | cagtcacttcacttcttgggatgt | U76546 |
| 610 | aatggaagactgcttgcagtca | X57349 | 43214 | taagtcacttggttcctacagtt | U50406 | 85818 | ctttcacttcgggatgtaggtgg | U76546 |
| 611 | actctgcttgcagaccatcagtg | X57349 | 43215 | ttgccttacagttggccaagaggac | U50406 | 85819 | ttcacttctgggattgtaggtggtca | U76546 |
| 612 | tctcttgattcatgagtgg | X57349 | 43216 | agagggacatctgttcacatcctg | U50406 | 85820 | ggaagtcataccaccgatgcaacaga | U76546 |
| 613 | ttcatggtgctacctgggctatt | X57349 | 43217 | atccttggaggccatcagacagcag | U50406 | 85821 | catacaccgatgcacagatggtat | U18372 |
| 614 | tggtacctgggctatgttaagcgt | X57349 | 43218 | caagacccctggaggactgtggt | U50406 | 85822 | ttacccctgggcatccctcattctac | U18372 |
| 615 | aaacagagatgttctacatcatc | X57349 | 43219 | ggtagcacctgctccatgggt | U50406 | 85823 | tcctcattctactcaggcggtccg | U18372 |
| 616 | cctacatcatccgctatatggg | X57349 | 43220 | acctgcctccatggtggtctgtaa | U50406 | 85824 | gcgctgcactccagaaggtggct | U18372 |
| 617 | atctcgtctatattgggcagacctc | X57349 | 43221 | cctccatgggtctgtaagaagtg | U50406 | 85825 | agagcctccagaaggtggctgcacaa | U18372 |
| 618 | agacctcaaaacactgttcagag | X57349 | 43222 | tcctctttggtctcagaacaggcct | AA020296 | 85826 | tgcacaacaatatcatctccatagt | U18372 |
| 619 | gaagttgaactcatagagttgct | X57349 | 43223 | ttggtctcgaacaggcctagagggc | AA020296 | 85827 | acaatatcatctccatagtgggaat | U18372 |
| 620 | catagagtttgtgacaccatcag | X57349 | 43224 | gtggcattgtgtgcccctttcctg | AA020296 | 85828 | tcatctccatagtgggaatcgtct | U18372 |
| 621 | tgacaccatcaagcagctgagcag | X57349 | 43225 | gctatttgtgccccttcctggg | AA020296 | 85829 | agtcggtcatgacgctcaat | U18372 |
| 622 | aagcagctgagccagaataacataca | X57349 | 43226 | tgccccttcctgcgctgatgatg | AA020296 | 85830 | gcttcatgacgctcaatatcct | U18372 |
| 623 | gaataacataactcctgtgaggt | X57349 | 43227 | ccctttctgcgctgatgggga | AA020296 | 85831 | tgacgctcaatattccgtgtag | U18372 |
| 624 | acactcctgtgaggctgatctca | X57349 | 43228 | gggacaggactgctctgatgctggga | AA020296 | 85832 | gaaatcgtcatacgtctatgacgg | U18372 |
| 625 | atgattaaatctcagcaaagtcg | X57349 | 43229 | accaggactgctctgatgggagcag | AA020296 | 85833 | tggatcacgtctatgacgctgag | U18372 |
| 626 | tcagcaaagtctgcgagatgaaca | X57349 | 43230 | actgctctgatcggcagtcgagga | AA020296 | 85834 | agagctaccgcacgaatccgatga | U18372 |
| 627 | gcagcatttgcaaaacatggtgac | X57349 | 43231 | gcagcattgtcaaaacatggtgac | AA020296 | 85835 | acccagcagaatccgatgatgacagc | U18372 |
| 628 | catgctcatctagagaactgtgat | X57349 | 43232 | agtcagttcagaatggcaagtg | AA020296 | 85836 | cacagtccaagtcgcacgatgtga | U18372 |
| 629 | ggtgatccatacacaccctggttc | X57349 | 43233 | catggtccaagatggcagtccag | AA020296 | 85837 | actgaacaaggcccagatgctgaa | U18372 |
| 630 | ttcctctttcatcatactagtgt | X57349 | 43234 | gggtccaagctctccggtctagagc | AA020296 | 85838 | acaaggccagatgcggaacgcgaa | U18372 |
| 631 | ctcatatcagttccgcccatcca | X57349 | 43235 | aagtccggctcagtgactc | AA020296 | 85839 | acaactccaccgtctttgataagct | U18372 |
| 632 | gttccgccatctcagtcatcagg | X57349 | 43236 | gctctagagctgactcctgccccga | AA020296 | 85840 | atgactccaccgtctttgataagct | U18372 |
| 633 | tctcagctcatcaggttgcctaata | X57349 | 43237 | ctagagtcgactctgcccgacaga | AA020296 | 85841 | tatgtgactccctgcaaagccca | U18372 |
| 634 | cctaatatacctgcaaacaatct | X57349 | 43238 | cagcacctccagtgtcttaccag | AA020296 | 85842 | gacaaggctagccgatgcgaga | AA106291 |
| 635 | ctgtcaaacaatctcaagagctgc | X57349 | 43239 | acaccttccagtgtcttaccag | AA020296 | 85843 | aggatgctagccgatgcgagagcc | AA106291 |
| 636 | aagagctgtcgaaaaagctatttt | X57349 | 43240 | agtgcttaccagtggctattgt | AA020296 | 85844 | tgccttgtgcacagatgtcga | AA106291 |
| 637 | ctgtcctagagaaaacatggctgt | X57349 | 43241 | gtcttaccagtggctattgtgt | AA020296 | 85845 | tcgttgaccacgatgtgaccaat | AA106291 |
| 638 | catagatttcatgtaagctgaa | X57349 | 43242 | gtatttcttgccacaccacccg | AA020296 | 85846 | acacgatgtgaccaagtcagca | AA106291 |
| 639 | gtaagctgaactttcacagaatca | X57349 | 43243 | tttcctaaacatagagaagtccac | AA020296 | 85847 | tgtgaccaagtccagcaataagt | AA106291 |
| 640 | tatgttgtagtaggcccagagag | X57349 | 43244 | ttacaaactgcttgcgtccagccgg | U05252 | 85848 | ctgaccaagtcagcaataagttgc | AA106291 |
| 641 | ggaggccagagagacgcttggtg | X57349 | 43245 | ttgtgtcaagggctgcaccaggt | U05252 | 85849 | accaagtcagcaataagttgcagg | AA106291 |
| 642 | gtgttgcgggaagtcagtgtggg | X57349 | 43246 | gctgcaccaggtgttaccctgt | U05252 | 85850 | ttgcaggtcccaagtcacacgagg | AA106291 |
| 643 | gaaactgcccaagtattccagat | X57349 | 43247 | gcaaccaggtgttgtacctgcag | U05252 | 85851 | caggtcccaagtcacacgaggact | AA106291 |
| 644 | agtattccagatgattcaaaa | X57349 | 43248 | tgttacccagtggctatgtgt | U05252 | 85852 | taaaggttaccaccgaggctgg | AA106291 |
| 645 | cagaagtataatctttgcaaga | X57349 | 43249 | accctggtccacacacacacggg | U05252 | 85853 | cttaccaccgaggctggagaact | AA106291 |
| 646 | ctttgccagtgactgccaggcgac | X57349 | 43250 | accgttcagcagatgatcacagtaaa | U05252 | 85854 | atgctagccgatgcggagcgga | AA106291 |
| 647 | ctgaggcggactttggagctgttgg | X57349 | 43251 | attattctggagctcaaaatagca | U05252 | 85855 | cagctcaaatgcaaaccaaaagcc | AA106291 |
| 648 | ttcatcttgcatttaaagttc | X57349 | 43252 | atttaaacttctgtgttattga | U05252 | 85856 | caaaccaaagccaggtgagcaggc | AA106291 |
| 649 | tcgaaagttcctcagtcaaccaa | X57349 | 43253 | ataacttctgtgtttatgattgc | U05252 | 85857 | ctctgaatcgctctggcattat | AA106291 |

TABLE 1-continued

| SEQ ID NO | DBAxnID | sequence | SEQ ID NO | DBAxnID | sequence | SEQ ID NO | DBAxnID |
|---|---|---|---|---|---|---|---|
| 650 | X57349 | aatggtcgtacagcagcggaagtg | 43254 | U05252 | atgagaagtcacccttgtgttcact | 85858 | AA106291 |
| 651 | X57349 | ggaagtggctgctcagctcattatt | 43255 | U05252 | ccacctgttcgttcactcagacaaac | 85859 | AA106291 |
| 652 | X57349 | tcagctcattattaaactttaccccat | 43256 | U05252 | tgtgttcactcagacaaacctttcat | 85860 | AA106291 |
| 653 | X57349 | tgaattgaacctgactactgagagatg | 43257 | U05252 | cactcagacaaacctttcattgttta | 85861 | AA106291 |
| 654 | X57349 | taacagaaactactgtcatttatg | 43258 | U05252 | tcagacaaacctttcattgttattg | 85862 | AA106291 |
| 655 | X57349 | gaaccagttcaaaaacagatatcagg | 43259 | U05252 | aatcttggaaactgcacaaacag | 85863 | D88577 |
| 656 | X57349 | tatgggtctaagttctacagtggctg | 43260 | U05252 | agcgccagcactcaaggttttact | 85864 | D88577 |
| 657 | X57349 | tctacagtgcgtgtattccgctcgt | 43261 | U05252 | agcccagcactcaaggttttactgg | 85865 | D88577 |
| 658 | X57349 | gtattccgctcgggagactactc | 43262 | U05252 | tggccagcagcaacagcagcactg | 85866 | D88577 |
| 659 | X57349 | tgctactctagataacaactgat | 43263 | U05252 | gcagcaaccagcagcactgagagca | 85867 | D88577 |
| 660 | X57349 | tgatttcataatgctgagaaaaca | 43264 | U05252 | gcctgctacgggaaggatggagact | 85868 | D88577 |
| 661 | X57349 | aggggatgtcacttcctgctcgccc | 43265 | U46854 | tttgtcctcacagcatgcacaatg | 85869 | D88577 |
| 662 | X57349 | cttcctgcctatgtatctca | 43266 | U46854 | gtctttgacagcatcagccacctca | 85870 | D88577 |
| 663 | X57349 | ctatgtatctccaagagagtctct | 43267 | U46854 | gacagcatcagccacctcatcaatt | 85871 | D88577 |
| 664 | X57349 | agagtctctttccgacatatctc | 43268 | U46854 | cacctcatcaattacacctcgaga | 85872 | D88577 |
| 665 | X57349 | ctgggctctggatctcacactctc | 43269 | U46854 | atcaattacacctcgagagcagcc | 85873 | D88577 |
| 666 | X57349 | tctccagcttagtgggagaactg | 43270 | U46854 | ctcgagagcagctgccactgtct | 85874 | D88577 |
| 667 | X57349 | tactggactattcaggagtcgca | 43271 | U46854 | atgtctctgcggagtgagttt | 85875 | D88577 |
| 668 | X57349 | gggagtcgcaaatgccctctggt | 43272 | U46854 | tgtctccagcaaccagtgagagga | 85876 | D88577 |
| 669 | X57349 | cctctcggtgacatttggaatatt | 43273 | U46854 | cttatgccaggtcaggaagactggc | 85877 | D88577 |
| 670 | L09192 | ctagttggctgactgaacaagatg | 43274 | U46854 | accagcagcactgagagcgccac | 85878 | D88577 |
| 671 | L09192 | gaggctccgagttgtcgcgatcc | 43275 | U46854 | actgtcgtgagcatcacattaaag | 85879 | D88577 |
| 672 | L09192 | agagtgagattgccatccgagtgt | 43276 | U46854 | agcactgagacgcccacggaaagg | 85880 | AA106010 |
| 673 | L09192 | catccgagtgtttcgctgcgtgca | 43277 | U46854 | ctggcccagttgagcaaagccg | 85881 | AA106010 |
| 674 | L09192 | gtgacagagctgggtatccgcaca | 43278 | U46854 | aaagccgctgtgtctggagtgatca | 85882 | AA106010 |
| 675 | L09192 | ccgcacagtcgcaggcgctactcggaa | 43279 | U46854 | tgcatccgccgtcacaccccagag | 85883 | AA106010 |
| 676 | L09192 | gctgtctactcggagcaggacacag | 43280 | U46854 | gatgccaggatgctggaggagctta | 85884 | AA106010 |
| 677 | L09192 | gagcaggacacagcgcgatgcaca | 43281 | U46854 | aacgctgagccctggtaccaaggag | 85885 | AA106010 |
| 678 | L09192 | gaggcagagatgacacagcgagaaagc | 43282 | U46854 | gagccctgccaaggagagaatga | 85886 | AA106010 |
| 679 | L09192 | ctgatgaagcctacctatggccg | 43283 | U46854 | tattctgcccaaggtcaacac | 85887 | AA106010 |
| 680 | L09192 | tattggccgtggccctgcaactgtg | 43284 | U46854 | tgtgcccaaggtcaacaccacatgc | 85888 | AA106010 |
| 681 | L09192 | gcacctgcaggcctactgcaca | 43285 | U46854 | cctacgagtcagagcagtgggtgt | 85889 | AA106010 |
| 682 | L09192 | atcccacatatcaagctggtgca | 43286 | U46854 | gtacagcgcaagctcaagctgtagta | 85890 | AA106010 |
| 683 | L09192 | ggtgtatccgctatggggttcctc | 43287 | U46854 | ggcactcaagctgtatgtagaaaca | 85891 | AA106010 |
| 684 | L09192 | ctctcgagagcgagcagactttgccc | 43288 | U46854 | agctctggtgtgtcagcagaagcac | 85892 | AA106010 |
| 685 | L09192 | ccgggccattgccatcgctgcggc | 43289 | U46854 | agaatgctagtcatttgtgtctaca | 85893 | AA106010 |
| 686 | L09192 | tcagctcccgccatcggccagga | 43290 | U46854 | atgctagtcatttgtctacaga | 85894 | AA106010 |
| 687 | L09192 | acgagcgcatgatggtctccaacaa | 43291 | U46854 | gctcatttgtgtctacagattg | 85895 | AA106010 |
| 688 | L09192 | gcttccctatatctttcaaggccgc | 43292 | U46854 | agtactcagagtactgccctacac | 85896 | AA106010 |
| 689 | L09192 | tgcgggtctgtcagctatgagga | 43293 | U46854 | ccagtagctcctactacagggct | 85897 | AA106010 |
| 690 | L09192 | gaatagctagaggggttgaagag | 43294 | U46854 | gactcctacatcgggctctcag | 85898 | AA106010 |
| 691 | L09192 | ccgcatcaatggctgccattcag | 43295 | U46854 | ccaagtcaacaactgccagtc | 85899 | AA106010 |
| 692 | L09192 | gccatcagtgtcgggtcacccacg | 43296 | U46854 | acacacatgcaacacatgcccggtcag | 85900 | AA106010 |
| 693 | L09192 | ccgcctgacaacgcctctgcatc | 43297 | U46854 | cacatgcccagtcctgggtcagtcc | 85901 | AA106010 |
| 694 | L09192 | gcctctgcatttccaggcgctgtc | 43298 | U46854 | ggtgttatcaaccggaaagcctct | 85902 | AA106010 |
| 695 | L09192 | ctctctgctcaaggtcattgca | 43299 | U46854 | atccaccgggaagctcttccactt | 85903 | AA106010 |
| 696 | L09192 | caaggtcattgcacacgcaaagat | 43300 | U46854 | ttcacctggggtacgaggggagag | 85904 | AA106010 |
| 697 | L09192 | ccaccaagatgagcagagcctggc | 43301 | U52433 | tccactcagcctacgagtcagagac | 85905 | U62297 |
| 698 | L09192 | atccctctcgagaagttctca | 43302 | U52433 | actgcctacagtcgtcagagacgt | 85906 | U62297 |
| 699 | L09192 | tctcaacaacagcgttcctgca | 43303 | X92591 | ggcttcaaacatccgttcgcatag | 85907 | U62297 |

| SEQ ID NO | DBAxnID | sequence | SEQ ID NO | DBAxnID | sequence | SEQ ID NO | DBAxnID |
|---|---|---|---|---|---|---|---|
| 700 | L09192 | ttcctgcaggcagcagtggacaccc | 43304 | L09192 | ttcaaacatccgttcgccatagaa | 85908 | X92591 | agatcacagacagaggtccagca | U62297 |
| 701 | L09192 | gacaccagtcatcgagatgagaacc | 43305 | L09192 | gtgccagtcaaggctcgtgccact | 85909 | X92591 | agcagctgtaccagatccagcaagt | U62297 |
| 702 | L09192 | atgagaacctgcgtgttccagct | 43306 | L09192 | aaggtctgtgccactcggcaaacc | 85910 | X92591 | tgtaccagatccagcaagtccacat | U62297 |
| 703 | L09192 | gttccagtccgcctgcacagaac | 43307 | L09192 | gctcgtgccactcggcaaaccaga | 85911 | X92591 | agatccgcaagtccaccatgcctgc | U62297 |
| 704 | L09192 | cctcggcagtcagtgggatcaggc | 43308 | L09192 | ctgtgccactcggcaaaccagagc | 85912 | X92591 | agcaagtccaccatgcctgcaggca | U62297 |
| 705 | L09192 | aatcctgtccaatgtgagcccagt | 43309 | L09192 | cactcggcaaaccagagctgccag | 85913 | X92591 | tcaccatgcctgcaggccaagacct | U62297 |
| 706 | L09192 | tgagcccagtcctgtggatcctgc | 43310 | L09192 | tcggcaaaccagagctgccagtcg | 85914 | X92591 | ttcagtcagccaatcagccctga | U62297 |
| 707 | L09192 | cctgtgttcctggtgtgccatag | 43311 | L09192 | agcctgccagtctaccggtgccca | 85915 | X92591 | cagccaatcagccctctgatgggca | U62297 |
| 708 | L09192 | gctggttcagggactccttctg | 43312 | L09192 | ctgccagtctaccggtcccatca | 85916 | X92591 | agcctggacagatcatttgcacaca | U62297 |
| 709 | L09192 | tcctctcgggagaaggccagagg | 43313 | L09192 | gggagctccctacactcgtgttgg | 85917 | X92591 | gacagatcattgcgcagtgcaata | U62297 |
| 710 | L09192 | tcccgagctgtgggaatcaccag | 43314 | L09192 | cactcggtgtggcattctagg | 85918 | X92591 | agctgccccagtcgcaata | U62297 |
| 711 | L09192 | aatcaccagggtctgctgtgatgg | 43315 | L09192 | ccgttcgccatagagaacatatcg | 85919 | X92591 | atgctgcccaatctgcaatatctcg | U62297 |
| 712 | L09192 | aaatactcacgtgatactacatg | 43316 | L09192 | gactacaaggggtcgtgcaggtg | 85920 | X92591 | cccagtccaatatacgattagc | U62297 |
| 713 | L09192 | tggagtactacatggggcctgtga | 43317 | L09192 | ttgccttggggtcggtcatgcacc | 85921 | X92591 | gatttagccaagtctgatcagggcac | U62297 |
| 714 | L09192 | tagctgaagaactgcgcgagctgg | 43318 | L09192 | cctttgcgtgggtcatgcaacac | 85922 | X92591 | ttgtcaaggacagatccagacact | U62297 |
| 715 | L09192 | gaactcacactcgtgcattaagga | 43319 | L09192 | gtcatgccaactgggctaccccg | 85923 | X92591 | ttgctaccaatgccaacagatcac | U62297 |
| 716 | L09192 | cattaaggacatggcggcctgctg | 43320 | L09192 | ccggcccgcaaatgctgccaatgtgtg | 85924 | X92591 | cactgcagccaccgaggctgtgg | AA106036 |
| 717 | L09192 | cctgtcgaagctgccgcctgcacc | 43321 | L09192 | ctcagcaatgtgtgcggtcgtgt | 85925 | X92591 | ctgctgcatcgggacacaggttc | AA106036 |
| 718 | L09192 | actgcactaccatccatgataca | 43322 | L09192 | ggctccgtggcctcatgttggcg | 85926 | X92591 | ttcccgtactgtaagtgcgtgcta | AA106036 |
| 719 | L09192 | tgtgggcagcatggcctgcctgcca | 43323 | L09192 | cagactgcccgcagcttctact | 85927 | X92591 | cccagtacgtaaggtcgtcatg | AA106036 |
| 720 | L09192 | gggctgatgttgggacgtggcagt | 43324 | L09192 | gactgagcccgcagcttctactta | 85928 | X92591 | tgtaagtgcgtgtatgcaggagag | AA106036 |
| 721 | L09192 | gactccatgtctggatgaccctac | 43325 | L09192 | gtcaggcccaaacagtgtccccag | 85929 | X92591 | taagtgcgtgtatgcaggagagcc | AA106036 |
| 722 | L09192 | gatgacctccacgccaagcatgggg | 43326 | L09192 | acaccaacaagttgagtgggatct | 85930 | X92591 | agtgcgtgtatgcaggagagagcga | AA106036 |
| 723 | L09192 | gtgtttgactacatgagtactggg | 43327 | L09192 | atagaatgtgggccctcgagcag | 85931 | X92591 | tgctatgcaggagagccgaggccca | AA106036 |
| 724 | L09192 | gaactccacgcttcagattgca | 43328 | L09192 | agagatgtggccctcagagcag | 85932 | X92591 | gagagcgagccaccctattcat | AA106036 |
| 725 | L09192 | gccttcgattgcaggctaccatg | 43329 | L09192 | ccctcagagcagaggtaggcatt | 85933 | X92591 | gagccgaggccacctattctct | AA106036 |
| 726 | L09192 | gcacgttaccatgaagtctggcaa | 43330 | L09192 | taggcattctgcattctgcagaga | 85934 | X92591 | agatggctgcgatgctggagacaa | AA106036 |
| 727 | L09192 | ggcgaactccgacgtgatgag | 43331 | L09192 | cattctgcagatgcacagatgcc | 85935 | X92591 | atggctgcgatgctggagacaact | AA106036 |
| 728 | L09192 | ggccagtccaactgcactcc | 43332 | L09192 | gcacagtgccagagagacaggatg | 85936 | X92591 | gctcatccggacacaggtccact | AA106036 |
| 729 | L09192 | caggccatagcatggccgttggt | 43333 | L09192 | agagcccagagagcagagccatgcttg | 85937 | X92591 | tggcatccggacacaggttccact | AA106036 |
| 730 | L09192 | gagggcaagaaggcctagtggagg | 43334 | L09192 | atgcccagagagcagcatgctgtg | 85938 | X92591 | ccggaacaggttccactcaactg | AA106036 |
| 731 | L09192 | aggtgacacacctccagattgt | 43335 | L09192 | ctgagcccagagagcttctactaa | 85939 | X92591 | gacacaggttccactcaactgaaga | AA106036 |
| 732 | L09192 | cagttcattaggtgcagaatggttga | 43336 | L09192 | ccagactttctacttactgccta | 85940 | X92591 | caggttccactcaactgaagacaaa | AA106036 |
| 733 | L09192 | ttcgatccattcggttaaagacac | 43337 | L09192 | agcagcttctacttacttaccta | 85941 | X92591 | atcaaggccgtggtcattgacctgg | AA106036 |
| 734 | L09192 | aagaaaccccaggccatgaagaagat | 43338 | L09192 | cagcttctacttacttacctaggt | 85942 | X92591 | gtcattgacctgggttccagctact | AA106036 |
| 735 | L09192 | gatgcactccatcccaaggctttg | 43339 | L09192 | tctacttacctactcaggtgcttg | 85943 | X92591 | tggttccagttactgaagtgcgt | AA106036 |
| 736 | L09192 | ggtcatagacactcaaggtggcagca | 43340 | L09192 | ctactaggtgcttggaggatgaac | 85944 | AA020304 | tgttcagcaaggtgcttctgcag | U66201 |
| 737 | L09192 | gccagccctgtgttggagagggc | 43341 | L09192 | acctaggtgcttgaggatgaactc | 85945 | AA020304 | tctgatccgcaagaggccagt | U66201 |
| 738 | L09192 | gtgctcagccgccatgaagatgaga | 43342 | L09192 | tctggtcaggtccaaacagtgtcc | 85946 | AA020304 | aaggctatctcactcgctccagat | U66201 |
| 739 | L09192 | aggtgactgggtgactcgcccatg | 43343 | L09192 | aaccattgactgggtagctttga | 85947 | AA020304 | atgtgatctatctccaaccctga | U66201 |
| 740 | L09192 | gacttcgccatgggaggccactatc | 43344 | L09192 | tgactgggtagcttttcagatc | 85948 | AA020325 | tctattcctcaacctgatccgca | U66201 |
| 741 | L09192 | catgttaccaaggacatgactctg | 43345 | L09192 | ctccaaggtggctgctttacctga | 85949 | AA020325 | cctcaacctgtatcgccagcagga | U66201 |
| 742 | L09192 | tgactctggaaggcgacgacctcat | 43346 | L09192 | caggttgcgtgctttacttact | 85950 | AA020325 | aatcaggccgtgcatggttctagg | U66201 |
| 743 | L09192 | aggcgacgacctcatcctagagatt | 43347 | L09192 | gttggctgcctgagaatcca | 85951 | AA020325 | gccgtgcatggttctcaggactcaa | U66201 |
| 744 | L09192 | ccaggtcagccactccataggagta | 43348 | L09192 | tgctttactgagaatccaccacagt | 85952 | AA020325 | ttgtaccaaactcattgaagtgtg | U66201 |
| 745 | L09192 | cttaggctcctgcctcaggagtga | 43349 | L09192 | ttactgagaatccaccagtctac | 85953 | AA020325 | acagaaccatcactaccagaaat | U66201 |
| 746 | L09192 | tccatggagacagcacactggc | 43350 | L09192 | acctgagaatccaccagtatgac | 85954 | AA020325 | aaccatcactacacgaaatttgaga | U66201 |
| 747 | L09192 | acacactacccatgcctgggccc | 43351 | L09192 | gaatccaccagctatgactggct | 85955 | AA020325 | catcactacgaaatttgagaaaa | U66201 |
| 748 | L09192 | tgccatccctcagtctatttgtc | 43352 | L09192 | tccaccagtatcgactgggttac | 85956 | AA020325 | gggaccgaaccccagtcgaaagg | U66201 |
| 749 | L09192 | tagttgctcacatattcatctctg | 43353 | L09192 | ttactcaaggccatgtggggcatag | 85957 | AA020325 | cagaacccccagtcgaaggattgt | U66201 |

| SEQ ID NO | sequence | DBAxnID | SEQ ID NO | sequence | DBAxnID | SEQ ID NO | sequence | DBAxnID |
|---|---|---|---|---|---|---|---|---|
| 750 | cacatattcatctctctgccaaataa | L09192 | 43354 | ggttccgtgcgcaggagatataat | AA020325 | 85958 | ggttattcagcgcagcaggataatt | U66201 |
| 751 | catctctgccaaataaggcctgc | L09192 | 43355 | tgcagagatcataccccagaaccaa | AA020325 | 85959 | gatattctcagatgcatccaga | U66201 |
| 752 | ttgccaaataaggcctgctcctcg | L09192 | 43356 | agggatcataccccagaaccaaaag | AA020325 | 85960 | tcctgcagatgcatccagatggtac | U66201 |
| 753 | tcacaggtcctcggaaattgctca | L09192 | 43357 | ccagaaccaaaaggccattgctagt | AA020325 | 85961 | acagcgactaccacccttccaatct | U66201 |
| 754 | agtagcatagctgtctccaaagt | X00686 | 43358 | ccaaaaggccattgctagttccctg | AA020325 | 85962 | tggccatccaagggttaaagccag | U66201 |
| 755 | atgctgtctcaaagattaagccat | X00686 | 43359 | ggccattgctagttccctgaaatcc | AA020325 | 85963 | gccttatgtggccatgaatggaga | U66201 |
| 756 | aagccatgcatgctaagtacgcac | X00686 | 43360 | tgcagttccctgaaatcctgaat | AA020325 | 85964 | ctatcttgatctacgtagccttct | U66201 |
| 757 | tgcatgctaagtacgcacggccgg | X00686 | 43361 | tagttcccgaaatcctggaatgag | AA020325 | 85965 | tgatctacgtagccttcttgagat | U11853 |
| 758 | aggaaactgcgaatggtcattaa | X00686 | 43362 | cctcacctccaggttggtcgtta | AA020325 | 85966 | tgaacaggacgtctcgaggct | U11853 |
| 759 | cgaatggtcattaaatcagttatg | X00686 | 43363 | tccaaatttacctgccaactgcaa | AA020325 | 85967 | gctctgagtgctgctatttctcacc | U11853 |
| 760 | ttatggtcctttggctgctgctc | X00686 | 43364 | gtgcgtcaccctggaatggggaag | AA020325 | 85968 | cactccatgaaactcagtcgcacc | U11853 |
| 761 | ggataactgtggtaatctagagct | X00686 | 43365 | gggagacccaactgccagatgta | AA020326 | 85969 | atgaaaactcagctgcaccaatgc | U11853 |
| 762 | tctagagctaatcatgccgacgag | X00686 | 43366 | gagacccaactgccagatgatt | AA020326 | 85970 | actcagtcgcaccaatgctggggt | U11853 |
| 763 | atacatgccgacgggcgctgacccc | X00686 | 43367 | agacccaactgccagatgtatttt | AA020326 | 85971 | ctgcacccaatgctgggggttgacca | U11853 |
| 764 | gcatttatcagatcaaaaccaacc | X00686 | 43368 | ataatgttctgcacgtgaaatatt | AA020326 | 85972 | ttgaccagatgccaatggcttta | U11853 |
| 765 | gcttggggactctagataacctgg | X00686 | 43369 | taatgttctgcacgtgaaatgtt | AA020326 | 85973 | accagatcgccaatggctttaagt | U11853 |
| 766 | tagatactctgggcgtcgatcgcacg | X00686 | 43370 | atttatactctagacatgcacatt | AA020326 | 85974 | agatcgccaatggctttaagtgtt | U11853 |
| 767 | ctatcaacttctgatgtagtcgcc | X00686 | 43371 | tttatactctagaacatgcacatt | AA020326 | 85975 | tgccaatggctttaagtgttga | U11853 |
| 768 | gtagtcgcctgctacaggtga | X00686 | 43372 | ttatactctagaacatgcacatta | AA020326 | 85976 | ccattgctgtggctgctgtgtaa | U11853 |
| 769 | tgcctaccatgggtgaccacgggga | X00686 | 43373 | atactctagaacatgcacatttata | AA020326 | 85977 | cctcaacttctgggtcggaagct | U11853 |
| 770 | cggctaccacatccaaggaaggcag | X00686 | 43374 | tactctagaacatgcacatttatat | AA020326 | 85978 | ctgcagcctactaggagccacgt | U11853 |
| 771 | acatccaaggaaggcagcagcaggcg | X00686 | 43375 | tggtctaccctggaatgggaaga | AA020326 | 85979 | cctacgttttatcactctcgctgc | U11853 |
| 772 | aagcagcaggcgcgcaaatacc | X00686 | 43376 | tctacccctggaatgggaagaggat | AA020326 | 85980 | tcatctctcgctcctcctcatct | U11853 |
| 773 | taacaataacggactctttgaggc | X00686 | 43377 | aagggatccctgggtctccagaga | AA020326 | 85981 | tcatctttctcctaatctctcacctt | U11853 |
| 774 | aggatccatgggggcaggctctgg | X00686 | 43378 | aggatccctgggtctccagatca | AA020326 | 85982 | ccctgcaacgctgagccgggag | U11853 |
| 775 | gctcgtagttggatcctgggggcg | X00686 | 43379 | tgggtctccagagatcagggagagc | AA020326 | 85983 | acctcatccagggatgaaccaggactg | U11853 |
| 776 | gccccctgatgcttagctgagt | X00686 | 43380 | gggtctccagagatcaggggaggagacc | AA020326 | 85984 | aactcttggctccaagaagaggcg | U11853 |
| 777 | gatgcttctgagtgtccgg | X00686 | 43381 | gtctccagagatcagggggagaccc | AA020326 | 85985 | ggagccagagcctcagcttaaggg | U66202 |
| 778 | ttagagttcaaggcaggccccgag | X00686 | 43382 | tctccagagatcagggggagacccca | AA020326 | 85986 | cggaacatttcacactgggtgcaa | U66202 |
| 779 | aggtgtcaaagcaggcccgacgcgc | X00686 | 43383 | agatgcctcgacagatcttct | AA020326 | 85987 | atttcacacctgcatgcaaatcaa | U66202 |
| 780 | caagcaggccgagccgcctggat | X00686 | 43384 | atgtcctcgacagatcttcgt | X92592 | 85988 | acgtgacatactcaatgatctacgtca | U66202 |
| 781 | ccgagccgcctggatacgcagcta | X00686 | 43385 | cctctgcacagattcgatcatggc | X92592 | 85989 | catactactcatcaatgatctca | U66202 |
| 782 | cgcctggatacgcagctaggaata | X00686 | 43386 | tctgcacagattgcatggatt | X92592 | 85990 | accgtcagcagcatccgccgcgagg | U66202 |
| 783 | tggatacgcagctaggaataatg | X00686 | 43387 | cacagaattcgcatgcatttaaa | X92592 | 85991 | ctgcagcacattctgccaacc | U66202 |
| 784 | cggaactgaggccatgattaagag | X00686 | 43388 | attgatgtcctgtctcagcatgc | X92592 | 85992 | ccaaaccactgaaagtggccatgta | U66202 |
| 785 | gggccattgctattcgccgctagag | X00686 | 43389 | tgatgtcctgtctcagcatgcc | X92592 | 85993 | agccatctcgcacgatctcacgga | U66202 |
| 786 | tcgtatgtcgcgcctagaggtgaa | X00686 | 43390 | gtctcagcatgcccatttaagac | X92592 | 85994 | agcgaaggtctcgtcggtgtactgaa | U66202 |
| 787 | attgcccgctagaaggtgaaattct | X00686 | 43391 | tctcagcatgcccatttaagacag | X92592 | 85995 | gcaaatcagcatgtcgcacacgaatc | U66202 |
| 788 | gggcaagacggacagagcgcctgaaagc | X00686 | 43392 | tcagcatgcccatttaagacacagaa | X92592 | 85996 | cagagcctcagtcttaaggctaagt | U66202 |
| 789 | agcattgccaagaatgtttcatt | X00686 | 43393 | agcatgcccatttaagacacagaagtt | X92592 | 85997 | catggccacacgaatcaacgtag | U66202 |
| 790 | cgcctgataccgcgtagttc | X00686 | 43394 | catgcccatttaagacagaagttt | X92592 | 85998 | ttaccaaactatacgcgcaagg | U66202 |
| 791 | tcgtagtccgaccataaacgatgc | X00686 | 43395 | cctcgacgatctttcgttaaa | X92592 | 85999 | actgcaactgcagcaatggaac | U66202 |
| 792 | gaccataaacgatgccgactgggga | X00686 | 43396 | tggtatgtcctttagcattcag | X92592 | 86000 | acagcactacactgtttaacct | U66202 |
| 793 | acgatgccgactgggcgatgcggggcgg | X00686 | 43397 | gtatgtcctttagcattcagt | X92592 | 86001 | ttaacctcatccctgtgggtctcg | U66202 |
| 794 | cgatgcgcggttatccatga | X00686 | 43398 | tctttttagcattctaggtaattga | X92592 | 86002 | tcatcccgggtctccgggtgt | U66202 |
| 795 | tgacgaaggcaccacccaggggtg | X00686 | 43399 | acaccaatagttgtccattgtg | X92592 | 86003 | gagttcaaaccaagctgtattggc | U66202 |
| 796 | acagattgtatgctcttctcgatt | X00686 | 43400 | cccaatagttctcattgtgact | X92592 | 86004 | acacctggaacatttcacacctga | U66202 |
| 797 | ggtggttggtgcatggcccgttcttag | X00686 | 43401 | tcttcctctgcacagaattcgca | X92592 | 86005 | ggatactcagctacctcccagcagc | AA106224 |
| 798 | tcatggccgtccttttagttggtgga | X00686 | 43402 | ttccttctgcacagattcgcatg | X92592 | 86006 | cagccccacagtactcaccatcaga | AA106224 |
| 799 | tggttgagcgattgtctggttaat | X00686 | 43403 | ctgtctttgcccgcccactgtgt | U46155 | 86007 | ctgcaggactgcgcgcactcgc | AA106224 |

| SEQ ID NO | sequence | DBAxnID | SEQ ID NO | sequence | DBAxnID | SEQ ID NO | sequence | DBAxnID |
|---|---|---|---|---|---|---|---|---|
| 800 | taacgaacgagagctctggcatgcta | X00686 | 43404 | tctttgcccgtccactgtgtcca | U46155 | 86008 | aatgtactgtacaaccacatcttca | AA106224 |
| 801 | gagactgtgcagctaactagtta | X00686 | 43405 | gcagctctgtgccagctacgcca | U46155 | 86009 | ctgtacaaccacatcttcacaatgt | AA106224 |
| 802 | tagaggacaagtgagggccgttcagcca | X00686 | 43406 | ccatcaccactgtgacggcttctgc | U46155 | 86010 | tacaaccacatcttcacaatgtcca | AA106224 |
| 803 | agtggcgttcagccaccgagattg | X00686 | 43407 | ctgtgacggcttctgctctgctgc | U46155 | 86011 | atcttcacaatgtccagtccagta | AA106224 |
| 804 | gttcagccaccgagattgtgcaat | X00686 | 43408 | cttcggtgactgtgtcgtgatcc | U46155 | 86012 | acaaagtccagtagccgagtccacc | AA106224 |
| 805 | ttgagcaataacaggtctgtgatgc | X00686 | 43409 | cctgtccaggtatgagagctaccc | U46155 | 86013 | agtagccagtccaccagtgtcac | AA106224 |
| 806 | taacaggtctgtgatgccctagat | X00686 | 43410 | gctatgagagctaccctgagactga | U46155 | 86014 | agccagtccaccagtgtcacagc | AA106224 |
| 807 | gtgatgccctagatgtcggggct | X00686 | 43411 | atgcagctaccctgagactgatca | U46155 | 86015 | agccagtccaccagtgtcacaga | AA106224 |
| 808 | ccctagatgtcggggctgcacgc | X00686 | 43412 | ctgatcacgggtgtattgaggatcc | U46155 | 86016 | gtcccagttgcacagatttgggg | AA106224 |
| 809 | gctgcacgcgcgctacactgactgg | X00686 | 43413 | tattttgaggatcctcatgtgccttt | U46155 | 86017 | cagtactccatcagacgacatccggt | AA106224 |
| 810 | cgggctcactgacgtgcctcagcgt | X00686 | 43414 | ttgaggatcctcatgtgcctttca | U46155 | 86018 | aagtgctagaacagttgtgtgttgtgg | AA106224 |
| 811 | actggctcagcgtgcctggggcaacc | X00686 | 43415 | ccadgtggtcatccgactccag | U46155 | 86019 | tcacatgacacatggttactgag | AA106224 |
| 812 | agcgtgtgcctaccctgcgcggca | X00686 | 43416 | tggccatccggactccagaactca | U46155 | 86020 | cagacacatcggactgagctgtgc | AA106224 |
| 813 | ccagtaagttgcgagtcataagctg | X00686 | 43417 | aaggccagcagcctcgaaggatcc | | 86021 | acacatcggactgagctgctgg | AA106224 |
| 814 | agtgcggtcataagcttgcgttga | X00686 | 43418 | cctacagacccgcgagagacgcttt | | 86022 | catcggtactgagctgctggagt | AA106224 |
| 815 | gcttcgtttgattaagtccctgccc | X00686 | 43419 | tttctactgaagggcattctggcc | | 86023 | gctgctgagtcgtcaagtgcac | AA106224 |
| 816 | tcgaactgactactctagagaagt | X00686 | 43420 | ctagaaatagggacgctcaggccc | | 86024 | tctgtagctcactgttgctatgc | AA106224 |
| 817 | gcgggagatggctctcgcccgtaag | | 43421 | gcaatagggaccgctcaggggcccg | | 86025 | ctcatgctgcaggactggctggc | AA106224 |
| 818 | gtgagatggctcgcccggtaagagc | | 43422 | ccgccatgggcagctcgtgtgccag | | 86026 | gactagcactgttgctagactgg | AA106783 |
| 819 | agatggctcgcccggtaagagcac | | 43423 | cttcacctggactgacagcaaaccc | | 86027 | tagcactgtttgctagacctggcat | AA106783 |
| 820 | cgggtaagagcacaaccaccatg | | 43424 | gactgacagcaaaccaaggcctgc | | 86028 | caccagttgcattgctcactggtac | AA106783 |
| 821 | tcaaaccccagcaaccacatgtagc | | 43425 | cagttctgccattccagctgtggg | | 86029 | cagtggcacgtcactgcttctg | AA106783 |
| 822 | ccagcaaccacatgtagcttcaac | | 43426 | tttctgccattccagctgcggggac | | 86030 | cactgttcactgcttctggggcagc | AA106783 |
| 823 | gcaaccacatggtagcttcaacaac | | 43427 | ctgccattccagctgtgtgggcacgtc | | 86031 | tgttcactgcttctcgggacagctc | AA106783 |
| 824 | accacatggtagcttcaacaacat | | 43428 | ccattccagctgtgggcacgtcag | | 86032 | tcactgcttctgggcagctctat | AA106783 |
| 825 | catggtagcttcaacaacactctcg | | 43429 | ctgtgggcacgtcaggcgaaggcaag | | 86033 | cttctgggcagcctcatcgttg | AA106783 |
| 826 | tggtagcttcaacaacactctcgta | | 43430 | caagccaggtcacctacgaccac | | 86034 | tctgggcagccctactcgctggg1g | AA106783 |
| 827 | tagcttcaacaacatctcgtaaca | | 43431 | cagtcacctgactgacacaaaccc | | 86035 | ctagacctgccattgctcctgtggggc | AA106783 |
| 828 | aaaatcgatgccctggtctgagt | | 43432 | gactgacagcaaaccacaggcctgc | | 86036 | ctatcgctgggcggttagtac | AA106783 |
| 829 | aatcgatgccctggtctgagtgt | | 43433 | gtcacctgaccacctgag | | 86037 | tcgctggggcctggtagtacag | AA106783 |
| 830 | ctgatgccctggtctgagtgtctg | | 43434 | cacctgaccacagctgctgagctgga | | 86038 | tgtttctagacctggcatttgctc | AA106783 |
| 831 | gatgcccctggtctgagtgtctgaa | | 43435 | ccagctgagctggaaggaaaatc | | 86039 | gtacagctacagttcatcaacctt | AA106783 |
| 832 | tgcccctggtctgagtgtctgaaga | | 43436 | tgcagcaaaccccaaggcctcgtc | | 86040 | ctagacctgcgattgctccggtaca | AA106783 |
| 833 | cctggtctgagtgtctgaagacag | | 43437 | caaaccaaggcctgctcaagatt | | 86041 | ctggcatttgctcggtacataaggt | AA106783 |
| 834 | ggagtgtcgaagagactagacagtg | | 43438 | acccaaggcctgctcaagattgacttgac | | 86042 | gcatttgctcggtacataaaggttca | AA106783 |
| 835 | ggtctgaagacagctacagtgct | | 43439 | ggcctgctcaagattgacttgaga | | 86043 | ttgctcggtacataaggttcaaag | AA106783 |
| 836 | gaagacagctacagtgtctaaataa | | 43440 | taaggtcggcgtctgatgtc | | 86044 | tatctgacgtgtccctgatcaat | AA106783 |
| 837 | gacagctacagtgtctaaataaata | | 43441 | cagaggcccagttctgccattcc | | 86045 | ctgtacgtgtccctgatcaatta | AA106783 |
| 838 | ttgggatttagctcagtggtagag | | 43442 | caggcccagtttctgccattccagct | | 86046 | gaaccaccagtggcactgtcactgc | AA106783 |
| 839 | tggggatttagctcagtggtagagc | | 43443 | gcccagttctgccattccagctgt | | 86047 | agtcacttgcccagaaacagtcct | AA106783 |
| 840 | gggattttagctcagtggtagagc | | 43444 | tcacttgcactgtctcgggtttca | | 86048 | gccccaagcctagcaagctcaaagg | U66203 |
| 841 | ttagctcagtggtagagcg | | 43445 | ttcgctctcatgtccagactgagc | | 86049 | ccatgaaccgtgaggggctatttgta | U66203 |
| 842 | gatttagctcagtggtagagcgt | | 43446 | tcggctcatgtccagactgagca | | 86050 | tattgtacagctgccacatttcac | U66203 |
| 843 | attttagctcagtggtagagcgctt | | 43447 | caaactgatgacaacagccatgtact | | 86051 | attactatgtcctgatcgctctgc | U66203 |
| 844 | ttagctcagtggtagagcggtttg | | 43448 | actgatgacaacagccatgtactact | | 86052 | ctgtaacgtggtccctgatcaat | U66203 |
| 845 | tagctcagtggtagagcggtgcct | | 43449 | cagccatgtactactgccagagc | | 86053 | atgtcctgatcgctctcga | U66203 |
| 846 | gctcagtggtagagcggtgcctag | | 43450 | gccatgtactactgccagagcgg | | 86054 | tgtatgcctctgctctcctacgca | U66203 |
| 847 | ctcagtggtagagcggtgcctagc | | 43451 | gattagactactgggccaggcgac | | 86055 | ctctcaccgcgctgtcttctgg | U66203 |
| 848 | tcagtggtagagcggtgcctagca | | 43452 | actctcacagtcctccagagtcg | | 86056 | ccaaggcagctgccacttgtgcc | U66203 |
| 849 | agtgggtagagcggctgcctagcaag | | 43453 | tctcacagtctccagtctgcg | | 86057 | cccacttgcccaagtcctcgga | U66203 |

| SEQ ID NO | DBAxnID | sequence | SEQ ID NO | sequence | DBAxnID | SEQ ID NO | sequence | DBAxnID |
|---|---|---|---|---|---|---|---|---|
| 850 | | gtggtagagcgctgcctagcaagc | 43454 | ctcacagtcctccagagtcgcga | X94418 | 86058 | ccatgtaccgggagcctctctcca | U66203 |
| 851 | | ggtagagcgctgcctagcaagcgc | 43455 | acttgcactgctctgggtttcat | X94418 | 86059 | cagagcctcagctcaaggcatcgt | U66203 |
| 852 | | cgcttgcctagcaagcgcaaggccc | 43456 | ttgcactgctctgggtttcatta | X94418 | 86060 | gcatcgtcaccaaactgttctgcg | U66203 |
| 853 | | gcttgcctagcaagcgcaaggccct | 43457 | gcactgctctgggtttcattaac | X94418 | 86061 | acctcaggcgaatccgatgggag | U66203 |
| 854 | | ttgcctagcaagcgcaaggccctgg | 43458 | tgctctgggtttcattaaccagc | X94418 | 86062 | aggcgaatccgatgggatatccca | U66203 |
| 855 | | tgcctagcaagcgcaaggccctggg | 43459 | gtaatagggctgtggaagcacaa | X94418 | 86063 | atccgatgggagtatccagggcac | U66203 |
| 856 | | ctagcaagcgcaaggccctgggttc | 43460 | tataattcggctctcatgtccagac | X94418 | 86064 | aggcaccccagggaccacagctc | U66203 |
| 857 | | tagcaagcgcaaggccctgggttcg | 43461 | ataattcggctctcatgtccagac | X94418 | 86065 | gactccgtgtggtcaccatccagag | U66203 |
| 858 | | gccctgggtcgctcagtctg | 43462 | attcggctctcatgtccagact | X94418 | 86066 | acatgccgtgaaccgtgaggggct | U66203 |
| 859 | | tgggagatgctcagtgggtaaga | 43463 | attcgaattcacaatgcagagctgc | X94418 | 86067 | acttgcagatgcacccgatggage | U66203 |
| 860 | | gagatggctcagtgggtaagagcac | 43464 | gaatcacacatgcagagctgcagcg | AA020368 | 86068 | agatgcacccgatggagctctcga | U66204 |
| 861 | | cagtgggtaagagcaccgactgct | 43465 | ctgcaaccttactaacagaggaatg | AA020368 | 86069 | atgtaatctactcatccatgctgta | U66204 |
| 862 | | tggggtaagagcaccgactgctctt | 43466 | atgtgaaaatgctccatctgct | AA020368 | 86070 | tctactcatcatgctgtacagga | U66204 |
| 863 | | cgactgctctccgaagtcagag | 43467 | gtgaaaatgctccatcctgtctcc | AA020368 | 86071 | cagcagctcattttctacccaagcc | U66204 |
| 864 | | ctgctctccgaagtccagagtc | 43468 | gctctccatctgctccaggctta | AA020368 | 86072 | ctcatttctacccaagccattgga | U66204 |
| 865 | | ggtccagagtccaacctcccagcaac | 43469 | tctcccatctgctccaggcttaga | AA020368 | 86073 | ttctaccaaggccattgaagttgc | U66204 |
| 866 | | tccagagttcaaatcccagcaacca | 43470 | ccatctgctccaggcttagatta | AA020368 | 86074 | aagttgcatgtaccgagaaccatc | U66204 |
| 867 | | cagagttcaaatcccagcaaccaca | 43471 | atctgctccaggcttagattatg | AA020368 | 86075 | ccatgtaccgagaaccatcctgca | U66204 |
| 868 | | agttcaaatcccagcaaccacatgg | 43472 | ctgctccaggcttagattatatgggg | AA020368 | 86076 | accgaaccatcctgcatgatgt | U66204 |
| 869 | | tcaaatcccagcaaccacatggg | 43473 | gctccaggcttagattatatggggga | AA020368 | 86077 | aaccatcctgcatgttggtga | U66204 |
| 870 | | aaatcccagcaaccacatggggct | 43474 | attgccttagggttagacagactga | AA020368 | 86078 | gcaaaccagtcaacaagtcaagac | U66204 |
| 871 | | cagcaaccacatggtggctcacaac | 43475 | attcacaatgcagagctgcagctt | AA020368 | 86079 | acccgatggagctctcgatggaac | U66204 |
| 872 | | gcaaccacatggtggctcacaacca | 43476 | tcacaatgcagagctgcagcgttat | AA020368 | 86080 | atgacagcaccaattccacactgt | U66204 |
| 873 | | acaccacatggtggctcacaaccatc | 43477 | acaatgcagagctgcagcgttat | AA020368 | 86081 | gccaattccacactgttcaacct | U66204 |
| 874 | | ctctcggtgtctgaagacagcgc | 43478 | tgcagagctgcagcgttatatctg | AA020368 | 86082 | tcaacctcatcccagtgggactgcg | U66204 |
| 875 | | ctctcggtgtctgaagacagcgca | 43479 | gctgcagcgttatatctggcaacc | AA020368 | 86083 | tcatcccagtgggactgcgcgtgt | U66204 |
| 876 | | gtgtctgaagacagctacagtgt | 43480 | cagcgttatatctggcaacctac | AA020368 | 86084 | cagtggagctgcgtgttgccat | U66204 |
| 877 | | tgtctgaagacagctacagtgtact | 43481 | gccgttatatctggcaacctacta | AA020368 | 86085 | ggttgtgccatccagggatggaa | U66204 |
| 878 | | acagctacagtgtactacatata | 43482 | tatatctgcaacctactaagg | AA020368 | 86086 | tgccatccagggatggaagagacagg | U66204 |
| 879 | | agctacagtgtactacatatata | 43483 | agcaaaactacgcacatagtcgagg | X79082 | 86087 | agagctgacttctccacctccg | U66204 |
| 880 | K02785 | catctccatatatctcatttaacc | 43484 | acgacatagtcgaggatgcactt | X79082 | 86088 | cacctcctgaccatcacaagcatatg | AA106190 |
| 881 | K02785 | tctccatatatctatttaaccgc | 43485 | agcgaagctctccagcttggctaa | X79082 | 86089 | agagaagctcactcacaaggaagtg | AA106190 |
| 882 | K02785 | ttaagctatcccggtttcagtggcca | 43486 | gctctccagcttggctaaccat | X79082 | 86090 | gaagctcacaaggaagtggat | AA106190 |
| 883 | K02785 | gctatcccgttcagtggccaaag | 43487 | cagcttggctaaccatccgagc | X79082 | 86091 | gctcactcacaggaagtggatgat | AA106190 |
| 884 | K02785 | tatcccgttcagtggccaaaagtg | 43488 | cttggctaaccaatccgagcaca | X79082 | 86092 | tgatcttttcaaggaagcaggcatt | AA106190 |
| 885 | K02785 | ccgttcagtggccaaaagtgtgca | 43489 | aaccaatccgagcacacaagaggt | X79082 | 86093 | tgaaccaacgcaagtagaaatat | AA106190 |
| 886 | K02785 | ttcctaggccgatctaccgggatg | 43490 | caatccgagcacacaagagttca | X79082 | 86094 | atatgacagttatccagaggatcc | AA106190 |
| 887 | K02785 | tcctaggccgatctaccgggatgt | 43491 | tccgagcacatcaagagttgtgacag | X79082 | 86095 | tgacagttatccagaggatcacc | AA106190 |
| 888 | K02785 | tagccgatctaccgggatggtgt | 43492 | atcaagagctcagtctgtgacag | X79082 | 86096 | cacgttatccagaggatccatt | AA106190 |
| 889 | K02785 | cgccatctaccgggatggtgtga | 43493 | aagaggctcagtctgtgacagtaa | X79082 | 86097 | gaggatcaccattcctgtgcga | AA106190 |
| 890 | K02785 | cgatctaccggggatgtgagat | 43494 | tatcttctgttgatgcagtcgc | X79082 | 86098 | cttccgaccatcatgtatgcaa | AA106190 |
| 891 | K02785 | gatctaccggggatgtgagatg | 43495 | gatcctgcttgcttcatggcttt | X79082 | 86099 | caccattcctgtgcgagactactaa | AA106190 |
| 892 | K02785 | catatatctattaaccgctg | 43496 | ggacttgtcctcaggcttggt | X79082 | 86100 | cctgaccatcatgcatatgcaaatc | AA106190 |
| 893 | K02785 | atctaccggggatgggtgagagc | 43497 | tgtcctcaggcttggtatctg | X79082 | 86101 | gaccatcatgcatatgcaaatcaag | AA106190 |
| 894 | K02785 | taacgcttgatccctttcatg | 43498 | tttcatattgttgctgcaggtagt | X79082 | 86102 | gaaagaaatcctggccatgctg | AA106190 |
| 895 | K02785 | tttatccattctatcctaag | 43499 | atgtttcgattggcaggtaagt | X79082 | 86103 | tctggccatgctgatggcagacaag | AA106190 |
| 896 | K02785 | ttatccattctatcctaagagg | 43500 | agtaacatactaactttcaatga | X79082 | 86104 | agttacatcatgcgctgagctg | AA106190 |
| 897 | K02785 | ttccatttctatcctaagagag | 43501 | gctcgtctgaagatcgtgtgaaa | X79082 | 86105 | agttacatcatgcgctgagctg | AA106190 |
| 898 | K02785 | catttctatcctaagagagagaga | 43502 | tcgctcgaagatgctgtggaaagca | X79082 | 86106 | ttacatcatgcgctgggctggg | AA106190 |
| 899 | K02785 | ttttctatcctaagaggaagact | 43503 | tgggtaaagccctgaacctgccctg | AA020403 | 86107 | catgctcgagctcgagctgagctcgaaa | AA106190 |

| SEQ ID NO | DBAxnID | sequence | SEQ ID NO | DBAxnID | sequence | SEQ ID NO | DBAxnID |
| --- | --- | --- | --- | --- | --- | --- | --- |
| 900 | K02785 | gaagagactatctctgaagaggaa | 43504 | L36135 | ttctttcccgctttggcatcgctg | 86108 | U66887 |
| 901 | L36135 | tctcagtgctcagactgacccttc | 43505 | L36135 | aggctccatggagcaccgaagcagt | 86109 | U66887 |
| 902 | L36135 | caccaccacatttaaacagctgcta | 43506 | L36135 | ggctccaaggagcaccgaagcagtg | 86110 | U66887 |
| 903 | L36135 | gggacacagcagctcattatccagagg | 43507 | L36135 | ctccatgagcaccgaagcagtt | 86111 | U66887 |
| 904 | L36135 | aagctgactcaactcactcctagc | 43508 | L36135 | tccatggagcaccgaagcagtgt | 86112 | U66887 |
| 905 | L36135 | gtattactccaatagtcacacagg | 43509 | L36135 | catggagcaccgaagcagtgttac | 86113 | U66887 |
| 906 | L36135 | actccaatagtcacacggagagt | 43510 | L36135 | tgttactgcgtcctgcagataa | 86114 | U66887 |
| 907 | L36135 | tttcctagtcagcactacggtgtgaa | 43511 | L36135 | gttactgcgtcgctgcagataag | 86115 | U66887 |
| 908 | L36135 | aactcacactggcttccttaatgc | 43512 | L36135 | tactgcgtcgctgcagataagaaa | 86116 | U66887 |
| 909 | L36135 | cactggcttccttaatgctctcca | 43513 | L36135 | ctgcgtcgcctgcagataagaaacg | 86117 | U66887 |
| 910 | L36135 | gcttcctaatgctctccaagcaga | 43514 | L36135 | tgcgctgcctgcagataagaaacga | 86118 | U66887 |
| 911 | L36135 | ctctccaagcagacaataagcttc | 43515 | L36135 | tttcccgcttggcatcgtcgtga | 86119 | U66887 |
| 912 | L36135 | aagctctaagatgcgatcaatta | 43516 | L36135 | ccgctttggcatgctgtgacgaa | 86120 | U66887 |
| 913 | L36135 | cacatttaaacagctgctaacaaaa | 43517 | L36135 | cgcttggcatgctgtgacgaaag | 86121 | U66887 |
| 914 | L36135 | taagatcgcatctaattatctcca | 43518 | L36135 | ctgtgacgaaagccctaggctcca | 86122 | U66887 |
| 915 | L36135 | taaacagctgctaacaaaccagct | 43519 | L36135 | acgaaagccttaggctcctaggag | 86123 | U66887 |
| 916 | L36135 | accagcttttctgacagcaacaa | 43520 | L36135 | cgaaagccctaggctcatggagc | 86124 | U66887 |
| 917 | L36135 | tttctgacagcaacagctag | 43521 | L36135 | aaagccctaggctccatgagcac | 86125 | U66887 |
| 918 | L36135 | gtgacagcaacagctagctaatc | 43522 | L36135 | ttaggctccatggagcaccgaagca | 86126 | U66887 |
| 919 | L36135 | agctagctaatctccagtctaga | 43523 | L36135 | agtatgcgagcccgagtgttcaa | 86127 | U66887 |
| 920 | L36135 | gctaatctccagtctagaagaaaa | 43524 | L36135 | gtgaagactcacgctttgtt | 86128 | AA106192 |
| 921 | L36135 | tcatttaccgaactcattaggaagtgg | 43525 | Y08640 | tgtctacgttaagagccctatgg | 86129 | AA106192 |
| 922 | L36135 | tgatctactggccatcatcaagtt | 43526 | Y08640 | aagcaaatataccagacattgcgg | 86130 | AA106192 |
| 923 | M12836 | ccatcatcaagttcttctgcttag | 43527 | Y08640 | tataccagacattgtgcgactcca | 86131 | AA106192 |
| 924 | M12836 | attctagaccatgcgaccatttttc | 43528 | Y08640 | cagacattgcgaccatttcc | 86132 | AA106192 |
| 925 | M12836 | atagcctacagctttaccatgg | 43529 | Y08640 | ctccattatacaaggaattgttcac | 86133 | AA106192 |
| 926 | M12836 | tacagctttaccatggccctgt | 43530 | Y08640 | tgttcacttcagtgagccagc | 86134 | AA106192 |
| 927 | M12836 | ccctgtgtctgtgaaccagctaa | 43531 | Y08640 | aatttgagccagccatgcaaatcga | 86135 | AA106192 |
| 928 | M12836 | ttgctcttgaaccagctaacccat | 43532 | Y08640 | agcagccatgcaaatcgatgggta | 86136 | AA106192 |
| 929 | M12836 | ttgaaccagctaacccatgaagac | 43533 | Y08640 | aaatgcgcgccgagcactctag | 86137 | AA106192 |
| 930 | M12836 | ctctagaacaactcgaagagcttct | 43534 | Y08640 | ctctagaacatctgagtacaaca | 86138 | AA106192 |
| 931 | M12836 | acaactggaaggcctcttactg | 43535 | Y08640 | tgtgttctatgcacctgaccgaaga | 86139 | AA106192 |
| 932 | M12836 | gcctgtatttcacatattgacaa | 43536 | Y08640 | ctatgcacctgaccgaagaggaacga | 86140 | AA106192 |
| 933 | M12836 | tatttcacatattgacaatatt | 43537 | Y08640 | tattttccattgcattcgattctgac | 86141 | AA106192 |
| 934 | M12836 | tcagcttctctgttctgaagaac | 43538 | Y08640 | ctgcattgcttactgatgtcagcgga | 86142 | AA106192 |
| 935 | M12836 | catctgtcgtggcaatgagaagaa | 43539 | Y08640 | cacgggatccgtcgtcgttctcagga | 86143 | AA106192 |
| 936 | M12836 | ttcatctcactgccataaaggtgc | 43540 | Y08640 | acatggcccttcagagttcctaca | 86144 | AA106192 |
| 937 | M12836 | ctctgtggcttcactctataa | 43541 | Y08640 | atggaattcaaccaagctaatatg | 86145 | AA106192 |
| 938 | M12836 | ttcactctataaagtccctcactc | 43542 | Y08640 | ttctaaccaagtcaatatgcaaggt | 86146 | AA106192 |
| 939 | M12836 | ctcactcatgttgcataaacatttt | 43543 | U16175 | cctgaccatgggcatggcgcgcgacatc | 86147 | AA106192 |
| 940 | M12836 | aaactgaactcactccttcctgat | 43544 | U16175 | ggtcctcctcggatgcgccgtcc | 86148 | AA106192 |
| 941 | M12836 | tcctgattccatccactccgat | 43545 | U16175 | caagtctgccatcagtttgtt | 86149 | AA106192 |
| 942 | M12836 | atagctcgaccattcgttctct | 43546 | U16175 | ccatacctgccaggcgtcttcc | 86150 | AA106192 |
| 943 | M12836 | ctcagaccattgtactccttac | 43547 | U16175 | tctgcttcctctggatgctccta | 86151 | AA106192 |
| 944 | M26053 | ctctgtggcttcacaatcct | 43548 | U16175 | tctgccttcatctctgtta | 86152 | U75506 |
| 945 | M26053 | tacttctgcacaatcctcgcac | 43549 | U16175 | tggatgcttcatctctgtta | 86153 | U75506 |
| 946 | M26053 | ccacttccgctccaaggtcagtc | 43550 | U16175 | attctctgtttactcgttggccta | 86154 | U75506 |
| 947 | M26053 | gcagttcatggggcttcagaggag | 43551 | U16175 | tgtgttacctgttggccttaggcggc | 86155 | U75506 |
| 948 | M26053 | agaggctcacccaaacctgtcaca | 43552 | U16175 | tggtcaggccgcaggtcatcatg | 86156 | U75506 |
| 949 | M26053 | tgtcacacagaacatgtgcgcag | 43553 | U16175 | aggccaggccgaggtcatcatgtctctg | 86157 | U75506 |

| SEQ ID NO | sequence | DBAxnID | SEQ ID NO | sequence | DBAxnID | SEQ ID NO | sequence | DBAxnID |
|---|---|---|---|---|---|---|---|---|
| 950 | acagaacatcagtgcagaggctgg | M26053 | 43554 | caggtcatcatgtctgtcgaccag | U16175 | 86158 | actggacatctgcgttcagcttg | U75506 |
| 951 | catcagtgcagaggcctgggccga | M26053 | 43555 | cttcctgatgccgtcctccgt | U16175 | 86159 | catctcgttcagcttgagtgta | U75506 |
| 952 | ataagcatcagtgctgtgccaagaa | M26053 | 43556 | cttccgtgggctgctgagtgccc | U16175 | 86160 | tgcgttcagcttgagtgatctgaa | U75506 |
| 953 | atcagtcgtcgtccaatgaaaaatg | M26053 | 43557 | tgttcagcgtcagaggccgcc | U16175 | 86161 | atgaaggcagcctgtcgagaag | U75506 |
| 954 | ggtcctgtttgagccatcaaa | M26053 | 43558 | cgtggtgaccaagcctgaggaaa | U16175 | 86162 | aggaactgcctgcaaagccctg | U75506 |
| 955 | gtgcttgccaggggcttcctcct | M26053 | 43559 | gggcttgccaaactgactgagcc | U16175 | 86163 | gccaaagccctgatgaggtgaaga | U75506 |
| 956 | ccacagtggggtcagcacgacct | M26053 | 43560 | tgccaactggactgagccgtcag | U16175 | 86164 | ttcccagaagacatggagaacgaca | U75506 |
| 957 | cagcagggaccctcaggcctacag | M26053 | 43561 | actggactgagccgttcagcgcc | U16175 | 86165 | aacgacaaggccatgctgataatga | U75506 |
| 958 | caattataagtactgcctgagcagc | M26053 | 43562 | gacctgagtctgctcccaagtct | U16175 | 86166 | cacgcaccatcttgctccgtgatg | U75506 |
| 959 | tagctactgctgagcgccgcgc | M26053 | 43563 | gctatctcccagctgggacttcctg | U16175 | 86167 | ccatcttgtccgtgatgtctcc | U75506 |
| 960 | ctgcctgagccagccgctgagggc | M26053 | 43564 | gtttctgctcccaggtcaactg | U16175 | 86168 | ttgctccgtgatgtcttccacacga | U75506 |
| 961 | ccgctgagggtctctgctcc | M26053 | 43565 | tagcttcatgacctcttccaaa | U16175 | 86169 | atcttattcactaaaagtctcatc | U75506 |
| 962 | ttctctggaacaacaacatgaag | M26053 | 43566 | catgacctcttccaaatgggc | U16175 | 86170 | tctattcactaaaagtctcatca | AA106406 |
| 963 | ggctgcagtccacccaagcccaaga | M26417 | 43567 | ctccaaatagggcctctgccagcta | U03715 | 86171 | aacttattcaccatatagtgct | AA106406 |
| 964 | agatatcctgatggatacaaggcc | M26417 | 43568 | agaggccatgcagaactttgacaca | U03715 | 86172 | acttattcaccatatagtgcta | AA106406 |
| 965 | caaggcctccagacaggccaagag | M26417 | 43569 | gaacttgacacaggcagggagca | U03715 | 86173 | cttattcaccatatagtgctaa | AA106406 |
| 966 | ggcctccagaccaagccaaggtctg | M26417 | 43570 | atcagtcagcaccagggctctgg | U03715 | 86174 | ttattcaccatatagtgctaat | AA106406 |
| 967 | ctccagaccaagccaagagaactc | M26417 | 43571 | tcagcacccagggtctggctggga | U03715 | 86175 | tattatcaccatatagtgctaatc | AA106406 |
| 968 | ccaagaaacttctccccatttg | M26417 | 43572 | ataccatctgtatagtccatt | U03715 | 86176 | attatcaccatatagtgctaatcc | AA106406 |
| 969 | ctccccattctgagttggctacc | M26417 | 43573 | catttaacacagacttcctgccctt | U03715 | 86177 | ttatcaccatatagtgctaatcca | AA106406 |
| 970 | tcagcaagtgtacttctgtgcc | M26417 | 43574 | cccactgaactggccagtcgtgt | U03715 | 86178 | tatcaccatatagtgctaatccac | AA106406 |
| 971 | gacatcagtgtacttctgtgccgc | M26417 | 43575 | tggctccagggtcaactgcaacc | U03715 | 86179 | atcaccatatagtgctaatccaca | AA106406 |
| 972 | atcagtgtacttctgtgccagcgt | M26417 | 43576 | agatgtcccgagacaccagcctgg | U03715 | 86180 | tcaccatatagtgctaatccacac | AA106406 |
| 973 | gtacttctgtgccagcggtaatcg | M26417 | 43577 | agcctggccgcagaaggcgtatgg | U03715 | 86181 | ctattcactaaaagtctcatcac | AA106406 |
| 974 | tcagctaataaccacaacatg | M26417 | 43578 | tactgagccagtcgcaggcctcc | U03715 | 86182 | caccatatagtgctaatccacacc | AA106406 |
| 975 | gactaataaccacaacatgtac | M26417 | 43579 | tcggagctccacaacagtactacac | U03715 | 86183 | ttatttcactaaaagtctcatca | AA106406 |
| 976 | taataaccacaacaacatgtactgg | M26417 | 43580 | ctgcaacacagctactacgtcctg | U03715 | 86184 | tatttcactaaaagtctcatcaca | AA106406 |
| 977 | ctccattctgagttggctacgg | M26417 | 43581 | caacactacatcgtctgtgcatt | U03715 | 86185 | gcacctccaccaaatcattaccac | AA106406 |
| 978 | caacagtggtatctgccaggac | M26417 | 43582 | ctacatctcctgcattgagaat | U03715 | 86186 | gttaaacttattatcaccccatatg | AA106406 |
| 979 | gctgatcattcatatggtgct | M26417 | 43583 | tgactcctgcatatctgccaaga | U03715 | 86187 | ttaaacttattatcaccccatatgc | AA106406 |
| 980 | gatccattattcatatggtgctggc | M26417 | 43584 | tatctgccaagacatcgtgacat | U03715 | 86188 | taaacttattatcaccccatatgtg | AA106406 |
| 981 | ccattattcatatggtgctggcagc | M26417 | 43585 | gtacgtgaacacgcagtggcttt | U03715 | 86189 | aaacttattatcaccccatatgtgc | AA106406 |
| 982 | ccgtctgtgactccaggaaatagc | M26417 | 43586 | tgaacacgcagtggcttttaaccctt | U51805 | 86190 | accgtgctcgtctgctttaga | U75530 |
| 983 | tcttcctgcagggccagccaaagt | M26417 | 43587 | tggcttaacctggctgctcgg | U51805 | 86191 | ggctctgtcgttttagagcagaa | U75530 |
| 984 | tctcatcaagtatgcctccagtcc | M26417 | 43588 | taaccttggctgtcggaactca | U51805 | 86192 | gacagtgtatctcccaggtctct | U75530 |
| 985 | caagtatgctccagtccatctct | M35667 | 43589 | accataagccaggagtgactgact | U51805 | 86193 | accggccatttccacactcgtgat | U75530 |
| 986 | gtagctccagtccatctctgggg | M35667 | 43590 | ttaaaccctaagtgactgaat | U51805 | 86194 | ccatttccacactgcatcagaag | U75530 |
| 987 | tgctcccagtcatctctgggat | M35667 | 43591 | tgccacatgaaaacccatctgggg | U51805 | 86195 | tccacatctgcatcaagaagatgc | U75530 |
| 988 | gacagattcactcagtatcaac | M35667 | 43592 | aaaccatctgggcatcacacagaaa | U51805 | 86196 | cctccatgctagtatctgataata | U75530 |
| 989 | agattcactcagtatcaacagt | M35667 | 43593 | gcatcacacagcaaagcaagacagaact | U51805 | 86197 | gataatatcagtctctcctatcag | U75530 |
| 990 | tttccatcagtatcaacagtg | M35667 | 43594 | cagaactgtcaccagacagagaa | U51805 | 86198 | atcactcctatcagaggagacett | U75530 |
| 991 | aatgtattctgcaacagtaac | M35667 | 43595 | acatcgtgacattggcttgcgaga | U51805 | 86199 | ctctccatcagaggagacactt | U75530 |
| 992 | gtattctgtcaacagagtaacagc | M35667 | 43596 | tgtacattggctgcgacgtaga | U51805 | 86200 | atgactacagaccctattttagata | U75530 |
| 993 | gagtaacgtgcagcctacacgttc | M35667 | 43597 | aaggacctctcagctacctgctggg | U51805 | 86201 | catctccagtattggaagttat | U75530 |
| 994 | ttctcaggcctcagcagcccaaagtatt | M35667 | 43598 | ggccgatccacctgagcttgtgt | U51805 | 86202 | agtgccaacacctgccgcacct | U75530 |
| 995 | tatttgcaacacactggtat | M35667 | 43599 | tgagcttgatgtgacggccagt | U51805 | 86203 | aacacctgccgcaccggtgag | U75530 |
| 996 | tggcaacaactacactggtatcaca | M35667 | 43600 | ttgatgtcgacggctgaccaagc | U51805 | 86204 | tggtagtccagcctgctccagg | U75530 |
| 997 | caacaacctacactggtatcacaa | M35667 | 43601 | acaagacagggtctctttcagact | U51805 | 86205 | ctagcggctgctgagaataca | U75530 |
| 998 | acatgagtctccaaggcttcatc | M35667 | 43602 | caggctccttcagacctagtat | U51805 | 86206 | aatacatcaggggcctgaagaag | U75530 |
| 999 | tgagtctccaaggctctcatcaag | M35667 | 43603 | atagccagctccaaaagtctcc | AA020447 | 86207 | gttgggtccgcaggttactata | U75530 |

TABLE 1-continued

| SEQ ID NO | DBAxnID | sequence | SEQ ID NO | sequence | DBAxnID | SEQ ID NO | sequence | DBAxnID |
|---|---|---|---|---|---|---|---|---|
| 1000 | M35667 | aaggtctcatcaagtatgcttcc | 43604 | agccagtctcaaagagtctccaa | AA020447 | 86208 | tgtcctgcaggttactatacctga | U75530 |
| 1001 | M35667 | gctctcatcaagtatgcctccag | 43605 | gccagtaccaacatgtgaagaaga | AA020447 | 86209 | ctttgatctgtcttgctggct | U75530 |
| 1002 | M60429 | agcacttccgctcagtcagtgaac | 43606 | accaaatacctgtaatcctagact | AA020447 | 86210 | tgtctgtatgtgtctgagaagg | D21099 |
| 1003 | M60429 | ttccgctcagtcagtgaacttcca | 43607 | ggattgcctgcactcagagattcaa | AA020447 | 86211 | gaaactatctagtccagttcta | D21099 |
| 1004 | M60429 | actacaagaacactcagcccatcat | 43608 | attgcctcactcaggagttcaga | AA020447 | 86212 | gaactcaattctagcactacatgt | D21099 |
| 1005 | M60429 | cagatggctcttacttcgtctacag | 43609 | tgcctgcactcaggagttcaagacc | AA020447 | 86213 | tgctcacggccactgctcgtaacac | D21099 |
| 1006 | M60429 | tctacagcaagtccaatgtgcagaa | 43610 | agtcaagaccagctgggcaacatg | AA020447 | 86214 | cggccactgctcgtaacaccccagc | D21099 |
| 1007 | M60429 | gaaatactttcacctgctcgtgtt | 43611 | ttcaagaccagctgggcaacatggt | AA020447 | 86215 | ttcgagcctcgcaggcactaggca | D21099 |
| 1008 | M60429 | ctttcacctgctcgtgtaacatga | 43612 | caagaccagctgggcaacatggtga | AA020447 | 86216 | ccctgcaggcactaggcatggatg | D21099 |
| 1009 | M60429 | ctgtgtacatgagggcctgcacaa | 43613 | agaccagctgggcaacatggtgaaa | AA020447 | 86217 | tatgcaggcaaaacaccatgcact | D21099 |
| 1010 | M60429 | cccactcctgtaaatgatcta | 43614 | accagctgggcaacatggtgaaac | AA020447 | 86218 | ggcaaaacaccatgcactgacttt | D21099 |
| 1011 | M60429 | gatctcaagtgtctggagccctct | 43615 | ccagctccaaagagtcccaata | AA020447 | 86219 | acaccactgacttttaagaa | D21099 |
| 1012 | M60429 | agtgtcctgagccctcggtcct | 43616 | agtctccaaaagagtctccaatag | AA020447 | 86220 | ctagtctgatctttcaattgtc | D21099 |
| 1013 | M60429 | tggctctacagactctgacaccta | 43617 | ctctcaaaagagtctccaataggaa | AA020447 | 86221 | atagctagtctgtctttaattcag | D21099 |
| 1014 | M60429 | cttcccatgtcaacaggactggc | 43618 | ctcaaaagagtctccaataggaaag | AA020447 | 86222 | agctccagttcagggatctgatc | D21099 |
| 1015 | M60429 | aaggccacaggaccagacgcgaa | 43619 | aatctgtatctagccagtaccaaca | AA020447 | 86223 | tctgatctcttctgacctctaca | D21099 |
| 1016 | M60429 | ggccacaggaccagacgaaggtcc | 43620 | tctgtatctagccagtaccaaca | AA020447 | 86224 | tctgatccacggcaaaattagg | D21099 |
| 1017 | M60429 | gaccgaaggtccacaggtgtacac | 43621 | tagccagtaccaacatgtgaaga | AA020447 | 86225 | gcaccctgggtgcacatatagc | D21099 |
| 1018 | M60429 | tgataacagacttccctgaaga | 43622 | tagccagtaccaacatgtgaagaaa | AA020447 | 86226 | tatatgcacgcaaacaatgaagt | D21099 |
| 1019 | M60429 | cagactctcctgaagacattac | 43623 | tcgaagccatgttctcttgggct | AA020447 | 86227 | cacgccaaacaacatgaagttacaaa | D21099 |
| 1020 | M60429 | tcttcccagaacattactgtgga | 43624 | gaagccatgttctcttgggctg | AA020447 | 86228 | gctctccaggaactagaactca | D21099 |
| 1021 | M60429 | acattactgtggagtgggcagtggaa | 43625 | ctccagcgagtgttcaccactgt | AA020447 | 86229 | aacctagaactcaattctagcacta | D21099 |
| 1022 | M60429 | taccgccatccgatggtctctttt | 43626 | cgagtggttcaccacctgttgctc | AA030302 | 86230 | ttactgttggtgatccggttcgcca | AA106486 |
| 1023 | M60429 | ccatccgatgtctctttcacct | 43627 | agtcggttcaccacctgtctcct | AA030302 | 86231 | tgtttggtcacctgtcgccagcc | AA106486 |
| 1024 | M60429 | gtctttgctccgctcctccagc | 43628 | tggttcaccacctgtctccttct | AA030302 | 86232 | gctcaaagtatctgcagtctgcta | AA106486 |
| 1025 | M60429 | cctcatagaggcccctgaagatgaga | 43629 | acaccgccacagggcctggtcagccag | AA030302 | 86233 | caacgtatctgcagtctcgctacta | AA106486 |
| 1026 | M96430 | gatgaacttaccctatgaaacat | 43630 | cagccgccacagggcctggtcagccag | AA030302 | 86234 | cgtatccgagtctgcactacag | AA106486 |
| 1027 | M96430 | tcctcccagtacacatcctaggc | 43631 | caggtgccagccagcatgggc | AA030302 | 86235 | atctgcagtctgcgctactacagag | AA106486 |
| 1028 | M96430 | gcttacctgccgatcctaccgcct | 43632 | gtggccagccagactatgggct | AA030302 | 86236 | ctcgcagtctacagagtgcagagat | AA106486 |
| 1029 | M96430 | tgtacaccgagaacatgaacttct | 43633 | gccagactatggtgctgccgcca | AA030302 | 86237 | gctactacagagtgcagagattat | AA106486 |
| 1030 | M96430 | gacatgaactctgttctttcac | 43634 | cagactatggtgctgccgccacg | AA030302 | 86238 | tgggtgtccgtttgtgaagccat | AA106486 |
| 1031 | M96430 | ctcctccaatcaaatttacatcct | 43635 | acacactccagtgtgtggacaggc | AA030302 | 86239 | ccatagacatgggtcactgggatg | AA106486 |
| 1032 | M96430 | aaatttacatcctccctgctcagct | 43636 | acactccagtgtgtggacaggcca | AA030302 | 86240 | tagacatggtcactgggatgcgt | AA106486 |
| 1033 | M96430 | tcctgctcagtccaataaatgg | 43637 | acagggccagcaccacctgggcct | AA030302 | 86241 | acatgggtcactgggatgcgtgt | AA106486 |
| 1034 | M96430 | gcctctcgacgttacctgcgga | 43638 | cccagtcgatgcctccagcgagt | AA030302 | 86242 | ttggtgatccggttgccagccgta | AA106486 |
| 1035 | M96430 | gcttacctgccgaactactacggcct | 43639 | gctcagtcctccagcgagtggtt | AA030302 | 86243 | gccagcgtacagggttaagtgat | AA106486 |
| 1036 | M96430 | ccagcctgcacctttaccatgct | 43640 | gatggcctccagcgagtggttcacc | AA030302 | 86244 | tagaactggatgggccagcatgt | AA106486 |
| 1037 | M96430 | tgtacactgcagagaactgcttacacaa | 43641 | tgccctccagcgagtggttcacc | AA030302 | 86245 | actgatcggccactcatgtatc | AA106486 |
| 1038 | M96430 | ctttaccattgctacacaaca | 43642 | gcctccagcgagtggttcaccact | AA030302 | 86246 | gtggaggccagtcatgtatcaaa | AA106486 |
| 1039 | M96430 | cattgctacacaacacagaggcac | 43643 | cttttgacaatgtcttcaatatgat | AA030302 | 86247 | agacgtgtccagtagtatcga | AA106486 |
| 1040 | M96430 | acacatgaggccaccgcacaagctg | 43644 | caatgtccttcaatatgatggttt | AA020468 | 86248 | agctgtgtcaacgatcgagtctg | AA106486 |
| 1041 | M96430 | ccgcacaacgtgtcttttgctcgg | 43645 | tcccagtgaagtttacactgccacat | AA020468 | 86249 | tgtgctcacgtactgcagtctcg | AA106486 |
| 1042 | M96430 | acacagctgtctctgctagagtt | 43646 | ttcacatgcactacatcaatagtca | AA020468 | 86250 | tgaagcagtccagacttagcctg | AA106486 |
| 1043 | D00659 | ctggtctcctgtcagtctcacag | 43647 | tgcacatcatcataagctcactgat | AA020468 | 86251 | cagtccagccactagcctggttgc | AA106486 |
| 1044 | D00659 | tgtgccaataatgcaagtctg | 43648 | tcatcataagtcactgctcatcctg | AA020468 | 86252 | tagaacaacgcagcagtctgcta | D88769 |
| 1045 | D00659 | gtactgtcagtgcagaatacata | 43649 | taagtcacctgccatcctggacagaa | AA020468 | 86253 | agcagcctgctaaccactgcagtg | D88769 |
| 1046 | D00659 | tctttcaccttaaaccagttgct | 43650 | acttgcatcctggacagaagcccca | AA020468 | 86254 | ctcgtaaccagtgtgactggc | D88769 |
| 1047 | D00659 | agttgcttacggtggatccacatgt | 43651 | tcctttgacacagaagccccaagtgg | AA020468 | 86255 | gtgtgtaggcctcactgactgc | D88769 |
| 1048 | D00659 | tggcccacatgtaaattgttggg | 43652 | ctcactgaactttggaacagacttca | AA020468 | 86256 | tgcctactgcattcaacggcc | D88769 |
| 1049 | D00659 | cgttttacttccaattgctcct | 43653 | tggaacagactcactgccagcact | AA020468 | 86257 | tggcactctagctaacggcccaaagg | D88769 |

| SEQ ID NO | sequence | DBAxnID | SEQ ID NO | sequence | DBAxnID | SEQ ID NO | sequence | DBAxnID |
|---|---|---|---|---|---|---|---|---|
| 1050 | ttactctcaatttgtgctcccagga | D00659 | 43654 | agactcactgccagcaactcaggt | AA020468 | 86258 | gaataccagtgtcacttcttatgtc | D88769 |
| 1051 | tcaattgtgctcccaggagtgtag | D00659 | 43655 | aggttccagtaggtctccagcatca | AA020468 | 86259 | caggtgcacttctatgtctggct | D88769 |
| 1052 | tgtgctcccaggagtgtagttagac | D00659 | 43656 | tggtgccaccttcctgagatgagg | AA020468 | 86260 | cactctttatgtcttggctacagta | D88769 |
| 1053 | agctaggagactctatgtgtgtag | D00659 | 43657 | cagtagtgtccagcatccacactt | AA020468 | 86261 | ttatgtcttggctacagtactggaa | D88769 |
| 1054 | tcctgctagagttctacagctgtg | D00659 | 43658 | gtctgagtcacacatctttgtaga | AA020468 | 86262 | ttcagacggtcaagcaagtgcaaag | D88769 |
| 1055 | tagagttctacagctgtgtcagca | D00659 | 43659 | agcatcacactttgtagagactct | AA020468 | 86263 | cctaataaacttcacttcagctcac | D88769 |
| 1056 | gctgtgtcagcacatccagaaatgac | D00659 | 43660 | ttgtagagactctgggaaggat | AA020468 | 86264 | attaccattctactccacgacat | D88769 |
| 1057 | acatcaagatgactctggcagaagt | D00659 | 43661 | agactctcgggaaggatccacga | AA020468 | 86265 | tactccacgaattgcatcgcagga | D88769 |
| 1058 | aaatgactctggcagaagtaacttaa | D00659 | 43662 | gaaggatccaagcaacttccactct | AA020468 | 86266 | acgacattgcatcgcaggaagatat | D88769 |
| 1059 | gtcaaactccagcatggggccagg | D00659 | 43663 | cactcttcccagtgaagttcacat | AA020468 | 86267 | ttcctgggcaaatgcaagtctggtg | D88769 |
| 1060 | atcccagcatggggccaggcataa | D00659 | 43664 | ggtatcatcacttcctgcgtgta | AA020468 | 86268 | tgcaagtctgggcatccacacgta | D88769 |
| 1061 | agggcgccccaaagcatgtgcca | D00659 | 43665 | atcacttttcctgcgggtgactctc | AA020468 | 86269 | tcctgggcatccacagtacggcac | D88769 |
| 1062 | aacacaagtctcacctcaaggacca | D00659 | 43666 | agcaattcctgcctttgtatttcagg | AA020468 | 86270 | aaccgtagcaaaccgtcagcatgc | D88769 |
| 1063 | agtcacctcaaggaccacgagag | L15325 | 43667 | gatacattatacggccatgtccc | AA020468 | 86271 | tgtccgtccacactgtcctgaaac | AA107038 |
| 1064 | acaccttgaccgtcttgtggcaat | L15325 | 43668 | ttttcctaaacactttaagatcatata | U49185 | 86272 | ccgctccacactgtctgaaactga | AA107038 |
| 1065 | tttacagctgtgtctggcggaac | L15325 | 43669 | cactgagccttccaattgtatcaga | U49185 | 86273 | aatcaggtgagcacaccgtgagag | AA107038 |
| 1066 | gcgttgtgctggaccttacagagta | L15325 | 43670 | tagaccttccattgtatcagagta | U49185 | 86274 | atcgggtgagcacaccgtgagagg | AA107038 |
| 1067 | cagtggcactccggttaggtgatt | L15325 | 43671 | accttccattgtatcagagtatcc | U49185 | 86275 | cggtgagcacaccgtgagaggtc | AA107038 |
| 1068 | gcactccggttaggtgattctcaa | L15325 | 43672 | agtatcaattacatttacaattat | U49185 | 86276 | ggtgagcacacacgtgagaggtca | AA107038 |
| 1069 | tctcaaattcaggcagtag | L15325 | 43673 | atccaattcattacaattagtac | U49185 | 86277 | gtagcacaccgtgagaggtcag | AA107038 |
| 1070 | attctcaaggacagttagttccta | L15325 | 43674 | tatttcaggaagtcaagttt | U49185 | 86278 | gagcacaccgtgagaggtcagag | AA107038 |
| 1071 | gtctagtattcatattcccatgaag | L15325 | 43675 | tattaaacctgatgttctcttcta | U49185 | 86279 | agcacaccgtgagaggtcagagg | AA107038 |
| 1072 | tattcatattcccatgaagctccca | L15325 | 43676 | tttcctgcggtgactctccaaact | U49185 | 86280 | gcacacactgagaggtcagaggc | AA107038 |
| 1073 | ttaatttgaaatctccttgtctgg | L15325 | 43677 | cctgcggtgacttctccaaactgaa | U49185 | 86281 | acacgtgagaggtcagaggctg | AA107038 |
| 1074 | acctccaaggacacagacagagaaga | L15325 | 43678 | gtgacttccaaactgaaactgcat | U49185 | 86282 | cacacgtgagaggtcagaggcgt | AA107038 |
| 1075 | ccaaggccttcgccaaaggcctcaga | L15325 | 43679 | actctccaaactgaaactgctag | U49185 | 86283 | cgctccacactgctcgaactgaa | AA107038 |
| 1076 | cctcagacctgaaggacgcatgagaa | L15325 | 43680 | ccaaactgaaactgctaaggcagtt | U49185 | 86284 | gctccacactgcctgaaactgaca | AA107038 |
| 1077 | acaatatgcacagtgaggaggaaaca | L15325 | 43681 | aactctaaggcagtttggctaag | U49185 | 86285 | actgctgaaactgacacctggg | AA107038 |
| 1078 | tggccgctgagcctgagcgcagt | L15325 | 43682 | aatgacagcattcctgcctttgat | U49185 | 86286 | ctgtcctgaaactgacaactgggc | AA107038 |
| 1079 | caattgcctgagctagaggtgatg | L15325 | 43683 | gacgcattcctgccttgtattc | U49185 | 86287 | tcctgaaactgacacctgggcata | AA107038 |
| 1080 | gattgcaaccttgtagtcagtgaa | L15325 | 43684 | ccgccatgaacatcttccggctgac | U49185 | 86288 | cctgaaactgacacctgggcata | AA107038 |
| 1081 | cagtgaaccttgtagtcagtgaa | L15325 | 43685 | tgaacatcttccggtgactgggga | U49185 | 86289 | agtccatttactgaatgtagaatc | AA107038 |
| 1082 | taaccaacaagtaggactcagc | L15325 | 43686 | agagtcagctctgtcgtctgcactggt | U49185 | 86290 | gtccatttactgaagtagaatcg | AA107038 |
| 1083 | acaccaagtatgactcagctgc | M21117 | 43687 | agctcctgtcgactgcttcac | AA028877 | 86291 | cacgaggctgtcgtagagctg | AA107038 |
| 1084 | aaccattccatgcatgtgatagta | M21117 | 43688 | acactctccggctgactggggacct | AA028877 | 86292 | agatgcttgacgtggcaagttc | Z75287 |
| 1085 | gacagagcaaacaaggccaaggctc | M21117 | 43689 | tctgtctcgcactggtcttcacgactg | AA028877 | 86293 | tcagctctacatacagatcatgag | Z75287 |
| 1086 | ctcatccgactgtttgtaggtc | M21117 | 43690 | cactgggtcttcacgactgctacct | AA028877 | 86294 | agaggcccccagatgatgatgagca | Z75287 |
| 1087 | ccttcatcagggtccttcatgta | M21117 | 43691 | tggtcttcacgactgctacctggac | AA028877 | 86295 | aatgtttgcaagtgctggagaca | Z75287 |
| 1088 | gtccttcatgtattgcaatgca | M21117 | 43692 | tcttcacgactgctacctggacct | AA028877 | 86296 | gtgctgcgagagctttgacgatctg | Z75287 |
| 1089 | atatgaaagcatcctcagctgtg | M21117 | 43693 | tcacttcctttattccatacaa | AA028877 | 86297 | ggagacctttgaagtctgtggagca | Z75287 |
| 1090 | aagcatcctttcagctgtgcgct | M21117 | 43694 | tcatttcctatatcaaacagtctat | AA028877 | 86298 | aataccagctagcatagagttatactg | Z75287 |
| 1091 | agctgtgctcaggcatgtatgaa | M21117 | 43695 | tttccttatacaacagtcatgaa | AA028877 | 86299 | tatactgccttgtcttcaagactc | Z75287 |
| 1092 | ttctttcatgtcttcagcaa | M21117 | 43696 | acactctccggctgactggggacct | AA028877 | 86300 | gccttgtcttcaagactcattgag | Z75287 |
| 1093 | tttgctttcagcaagacatcattca | M21117 | 43697 | cctttatacaacgctcatgaagct | AA028877 | 86301 | tcttcaagactcattgaagaaagc | Z75287 |
| 1094 | agatgaactcagcagctgcagacca | M21117 | 43698 | tcttcaggtctgactggggaccgtc | AA028877 | 86302 | ctgcttccaaaagcctttctgatgt | Z75287 |
| 1095 | actcagactcagcagcagtcctc | M21117 | 43699 | cggccagtcatcctactgctgaa | AA028877 | 86303 | tgaggcccagcatagtcaacatc | Z75287 |
| 1096 | cagaccagtcctctcaggcagcaga | M21117 | 43700 | ccatgtcatcctactgctgaagt | AA028877 | 86304 | ccagcatagtctaacatcacgct | Z75287 |
| 1097 | agtcctctaggcaggagagacaccac | M21117 | 43701 | tcatctactgctgaagatctgaa | AA028877 | 86305 | tatgtctaacatcagcgctatgtt | Z75287 |
| 1098 | aggcagacaccacatacaaccagca | M21117 | 43702 | tcctactgctgaagatctggggaa | AA028877 | 86306 | taacatcacgctagttgccacc | Z75287 |
| 1099 | catacaaccagcagcactagtccag | M21117 | 43703 | gctcctgctgaagatctctgggaa | AA028877 | 86307 | cagcgctatgtttgccactgcgaac | Z75287 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 1100 | atgaaagctgccatctagcctgag | M21117 | 43704 | gtgctgggatctgtgggaagagtca | AA028877 | 86308 | tatgttgccacctgcaactcagaa | Z75287 |
| 1101 | agctcaaccatgctagtaaggcaa | M21117 | 43705 | cgtacatagctcctatatggagc | U48797 | 86309 | tgccacctgcaactcagaaaatcca | Z75287 |
| 1102 | ctcagagtgctgatacagtgactt | W44034 | 43706 | tagtcctattggagcaagta | U48797 | 86310 | gaaatttcagctctacatcagatc | Z75287 |
| 1103 | taaccgctgtactctctcagcgat | W44034 | 43707 | ctctgtgccagctgagatcctat | U48797 | 86311 | gagatgaattcgccaagccgtgctt | AA107061 |
| 1104 | tcagtacttaacctgagacctccga | W44034 | 43708 | gtccagctgagatcctattgttc | U48797 | 86312 | agatgattcgccaggcgtcttc | AA107061 |
| 1105 | ctgagacctccgaaaaccaggatct | W44034 | 43709 | tgttcctctgaatgtccacgaa | U48797 | 86313 | ctagacatcagtggtgaatgtt | AA107061 |
| 1106 | ttagctatgcttacacaacaact | W44034 | 43710 | cctcttgaatgtccacgaaccactg | U48797 | 86314 | acatgggctcagcaagcaaaggcgtg | AA107061 |
| 1107 | atgctacactacaacactcgttac | W44034 | 43711 | accactgaatagcatcagaaccctt | U48797 | 86315 | catgggctcagcaagcaaaggcgtgg | AA107061 |
| 1108 | acacactgttacagctgttcttga | W44034 | 43712 | gtaatagcatcagaaccttaaatga | U48797 | 86316 | tggctcagcaaaggcgtggagt | AA107061 |
| 1109 | cagctgtctgaccgctgaatca | W44034 | 43713 | taactgcactcttgatattcaaat | U48797 | 86317 | tggagttctagcgtctcaagtaccc | AA107061 |
| 1110 | ttcctgacgctgaatcagtatga | W44034 | 43714 | tgtgaaaaacactccactactgtag | U48797 | 86318 | ggagttctagcgtctcaagtaccct | AA107061 |
| 1111 | agatcatcaatgttaagctgtcctt | W44034 | 43715 | atgtgaccaacttcaactacaacag | U48797 | 86319 | gagttctagcgtcaagtaccta | AA107061 |
| 1112 | ttaagctgtcctttgtatggctgat | W44034 | 43716 | ccaacttcaactacaacagtgtgt | U48797 | 86320 | tgtaggccgcactagacatcagtgg | AA107061 |
| 1113 | tgtccttgtatggctgattataca | W44034 | 43717 | gagttaaaaactccaacatgaatgg | U48797 | 86321 | gtaggccgcactagacatcagtggt | AA107061 |
| 1114 | tctgtacttctcagcgatctataa | W44034 | 43718 | gatggttcacatgtgctggagga | U48797 | 86322 | taggccgcactagacatcagtggtg | AA107061 |
| 1115 | cttcttcagcgatctataacattca | W44034 | 43719 | tctacatgttgctggaggactttta | U48797 | 86323 | aggccgcactagacatcagtgt | AA107061 |
| 1116 | acatcaatctcaagaaatgtttat | W44034 | 43720 | tcacacctgccaatgatcctcagt | U48797 | 86324 | ggccgcactagacatcagtggtgtg | AA107061 |
| 1117 | taacagacatcaaagcctttggtac | W44034 | 43721 | tttttgcctggaggaactgtctaga | U48797 | 86325 | gccgcactagacatcagtggtgtga | AA107061 |
| 1118 | acatcaaagcctttgtacagataa | W44034 | 43722 | attaaccacctcatttctaagctgc | U48797 | 86326 | ccgcactagacatcagtggtgtgaa | AA107061 |
| 1119 | atctgccattactcacatcgtac | W44034 | 43723 | cacctcatttctaagctgccaaaca | U48797 | 86327 | cgcactagacatcagtggtgtgaat | AA107061 |
| 1120 | ccattactcacatcagtacttaccc | W44034 | 43724 | atttctaagctgccaaacagtctt | U48797 | 86328 | gttacctcgaagctcccaagagc | AA107061 |
| 1121 | ctcacatcagtacttaccctgagac | W44034 | 43725 | tacaaagcctcttgtcatcaaaagc | U48797 | 86329 | tctgaagctcccaagaggcctggc | U40375 |
| 1122 | tcggatccatgccaggagatcagga | AA108947 | 43726 | aaagcctctcttgtcatcaaaagccgt | AA116706 | 86330 | tgagacaggccatcagaggcatgc | U40375 |
| 1123 | gatccatgccaggagatcaggagtg | AA108947 | 43727 | tgcatgctgacgcgacatgttggt | AA116706 | 86331 | ggcatgcagtcaattgctatgtc | U40375 |
| 1124 | atccatggccaggatgaccaccacag | AA108947 | 43728 | atgcatgcacgcgacatgttggtga | AA116706 | 86332 | cagctcaagttctatgtccccagc | U40375 |
| 1125 | atgaccaccagtgctgtataacg | AA108947 | 43729 | ctgacgcgacattgtgtcaggaa | AA116706 | 86333 | caccgatgctattattcagttgg | U40375 |
| 1126 | cccacagtgctgtagtacagg | AA108947 | 43730 | ggaatccagttcctggaatagcgca | AA116706 | 86334 | aagtagctcgatcctgatggcaag | U40375 |
| 1127 | gagatcctggcctcctcgtacccctg | AA108947 | 43731 | atccagttcctggaatagcgcaatt | AA116706 | 86335 | ctctgatccgatggcaagacctg | U40375 |
| 1128 | tctcgtaccctgaggagtccgtc | AA108947 | 43732 | ttcctgaatagccgcaattgaagt | AA116706 | 86336 | tcctgaagcaaggccttggctgc | U40375 |
| 1129 | cgtcgaatcaaccagaacatacccagc | AA108947 | 43733 | taacttggcttcctgagagactg | AA116706 | 86337 | tggcaagacctggcgtcaaagaa | U40375 |
| 1130 | cgaatcaaccagacataccagcagc | AA108947 | 43734 | ctttggcttcctgagagactgcag | AA116706 | 86338 | gaccttggctgtcaaagcaggactg | U40375 |
| 1131 | atcaacaccagacataccagcaat | AA108947 | 43735 | tggcttcctgagagactgcagttagg | AA116706 | 86339 | tctgccgtcattgaataaacag | U40375 |
| 1132 | aaccagacataccagcagcagcaatg | AA108947 | 43736 | cttcctgagagactgcagttatgg | AA116706 | 86340 | gctcccaagaggcctggccaccttat | U40375 |
| 1133 | cagacataccagcagcaatatggaa | AA108947 | 43737 | gcctcttgtcatcaaaaagccgtgac | AA116706 | 86341 | aagaggcctggccacttatggcctc | U40375 |
| 1134 | ccatgccaggagatgcagcaggatgct | AA108947 | 43738 | tcaattgagacttccactagcgta | AA116706 | 86342 | cttgtagctggtgtgcaccgagca | U40375 |
| 1135 | atcaggagtgcctacacagagcacca | AA108947 | 43739 | tctgtcatcaaaaagccgtgaccac | AA116706 | 86343 | ccgagagtagctgttccactcctcgg | U40375 |
| 1136 | gcctacaagaggccaccattggcagg | AA108947 | 43740 | tgtcatcaaaagccgtgaccactt | AA116706 | 86344 | agcagctgttccactccggctgt | U40375 |
| 1137 | tacaagaggcaccattggcaggggacc | AA108947 | 43741 | catcaaaagccgtgaccacttga | AA116706 | 86345 | actccgggctgtgtaaccactcg | U40375 |
| 1138 | agcaccattggcagggaccgattg | AA108947 | 43742 | ccgtgaccacttgaatgaaccag | AA116706 | 86346 | ggcttgctaaccaccctcttctg | U40375 |
| 1139 | accattgcagggaccgattgagg | AA108947 | 43743 | ccagttcattgcatgctgacgcgac | AA116706 | 86347 | tgctaaccactgtttcggggccag | U40375 |
| 1140 | agcagcaacttgagcaggtgacc | AA108947 | 43744 | gtcatgctgacgtgacgacatt | AA116706 | 86348 | gccgcgatcttgctgtca | U40375 |
| 1141 | gtgatctggggtgaatgacaccca | AA108947 | 43745 | cattgcatgctgacgcgacattgt | AA116706 | 86349 | gcccgtctgtaccctacctgg | U40375 |
| 1142 | agtggctttctatgtcagaag | AA124192 | 43746 | gagcccactgataagcatgacgtgcc | U52842 | 86350 | tcatgctttcatgaccattggcct | U40375 |
| 1143 | ctctatgtccagaagccatattg | AA124192 | 43747 | aagcatgacgccgagtctaccc | U52842 | 86351 | ttctatgaccattggccgtggt | U40375 |
| 1144 | tgacaatgcctgtcgaagctgcag | AA124192 | 43748 | tgggccatctaaaagtcggagcctgc | U52842 | 86352 | gaccatgggcgtcgtggtcacct | U40375 |
| 1145 | ctcgagctgcagtgccctcctcta | AA124192 | 43749 | atcaaatgcggagccgccattca | U52842 | 86353 | tctacctgcttagccgccaggaagc | D21207 |
| 1146 | gctgcagctgcgcctcaatgctgt | AA124192 | 43750 | atgcggagcctgccattcagagaaa | U52842 | 86354 | agtcctgcagacacagttataacc | D21207 |
| 1147 | gcagctgctgcccctaatgctcac | AA124192 | 43751 | tagaactactaggaacacaaaagtct | U52842 | 86355 | acacagttataacctgcctttctga | D21207 |
| 1148 | gctgcctcaatgctgtcacagt | AA124192 | 43752 | gaacaaagctctaactgtgtgcag | U52842 | 86356 | ttataacctgccttctgcactctc | D21207 |
| 1149 | gctctaatgctcacgtaagata | AA124192 | 43753 | taacgtgtgcagtcttaagcag | U52842 | 86357 | ttctgcactgctccaggcatgccct | D21207 |

| SEQ ID NO | sequence | DBAxnID | SEQ ID NO | sequence | DBAxnID | SEQ ID NO | sequence | DBAxnID |
|---|---|---|---|---|---|---|---|---|
| 1150 | tctaatgctcaacgtaagataac | AA124192 | 43754 | tgtcagcttcttaagcgaatgag | U52842 | 86358 | ccaggcatgccttaagcgatggtg | D21207 |
| 1151 | attcttatgtctatgccattcac | AA124192 | 43755 | ccatctccagctcagtgtcactc | U52842 | 86359 | gtaccggatctcgaatcgctggat | D21207 |
| 1152 | tcttattgctatgccattcacag | AA124192 | 43756 | tccagctcagtggtcactcctccag | U52842 | 86360 | taccttacctggcctggctggctt | D21207 |
| 1153 | tatgctcatgccattcacagatc | AA124192 | 43757 | acatgtcaagaatcaccagacattaa | U52842 | 86361 | tacctgccctggctgccttttgcca | D21207 |
| 1154 | tatgttccagaagccatattgatt | AA124192 | 43758 | acctctctcattctcggcgctgtc | U52842 | 86362 | ctggctttgtccacgtcgctcaact | D21207 |
| 1155 | tatgccattcacagatctgctgtg | AA124192 | 43759 | tgtcactgccctgctgccagagacc | U52842 | 86363 | accgtgctcaactactatgtatggc | D21207 |
| 1156 | tgtcgagggcctttgttttat | AA124192 | 43760 | tgccctgctgccagacctgggc | U52842 | 86364 | ctcaactactatgtatgcgtgata | D21207 |
| 1157 | tgcctgcccaagtcgtcagaca | AA124192 | 43761 | gctgccagagacctgggccagcg | U52842 | 86365 | tgaaggcaccccagccatcaggaatg | D21207 |
| 1158 | gccagtggcctgtcagacagtaggc | AA124192 | 43762 | tgatacagtgcaggaggaccgaagagc | U52842 | 86366 | gccagcaccatggggcagccatcgccat | D21207 |
| 1159 | cagtcgaagtccaccctgacaat | AA124192 | 43763 | acagcagtcgaacagcagaagcag | U52842 | 86367 | caccatgggggcagccatcatgct | D21207 |
| 1160 | tctgaagtccacactgacaatgc | AA124192 | 43764 | accactccaggtctcaacacaagag | U52842 | 86368 | tgtaacattatgcaacctggaagcc | D21207 |
| 1161 | gaagtccacacctgacaatgctgtgc | AA124192 | 43765 | ccaggtctcaacacaagagaagaac | U52842 | 86369 | atttatgcaacctggaagccttaaga | D84655 |
| 1162 | acctgactgtgtcgaagctg | AA124192 | 43766 | aaagttgcaacttcagtctcccat | U52842 | 86370 | gagcaactcttactgttaacaat | D84655 |
| 1163 | tggaaacgcacaaaacccagaagag | W44037 | 43767 | cctccattcactctacagacagag | L36829 | 86371 | cctacagtccccgtatctcaaa | D84655 |
| 1164 | cacaaaaaccaagaagactacgcaggg | W44037 | 43768 | tttctgacataaactcatgactaat | L36829 | 86372 | tgtccccgtatctcaaacgtca | D84655 |
| 1165 | gggccagtgccacacatctggagga | W44037 | 43769 | acataaactcatgactaatctttgt | L36829 | 86373 | ctgtatcttcaaaacgtcaactttt | D84655 |
| 1166 | gccagtgccacacatctggaggat | W44037 | 43770 | taaaactcatgactaatcttttgtca | L36829 | 86374 | tctgttcaggtaccccttccac | D84655 |
| 1167 | ccagtgccacacatctggaggatga | W44037 | 43771 | actcatgactaatctttgtcaatc | L36829 | 86375 | tgtcaggtaccctcactgtgct | D84655 |
| 1168 | cagtgccacacatctggaggatga | W44037 | 43772 | gactaatctttgtcaatcatgaac | L36829 | 86376 | cctccatgtcctccatggggctat | D84655 |
| 1169 | gtgccacacatctggaggatgaga | W44037 | 43773 | taatcttttgtcaatcgaactttt | L36829 | 86377 | ccagactagcgtcgtgcagtcaa | D84655 |
| 1170 | ccacacatctggagatgaggaagg | W44037 | 43774 | gtcccagccattttgtatatgttg | L36829 | 86378 | catgaaaatcaccactgccgattat | D84655 |
| 1171 | cacacatctggaggatggccaaa | W44037 | 43775 | atatctatacatcacaaagttata | L36829 | 86379 | aatcaccactgccgtcgtgtgcc | D84655 |
| 1172 | aagtgtcaggcactgatggccaaa | W44037 | 43776 | tttacgtctgggggcagtttctgt | L36829 | 86380 | actagtgccgtgaagtctctacc | D84655 |
| 1173 | gtgtcaggcactgatgcccaaagg | W44037 | 43777 | ttcatttaagtctttgcaatggat | L36829 | 86381 | tgaagtctaccgcttgacatg | D84655 |
| 1174 | tgtcctcctagacagcagcgcgtc | W44037 | 43778 | tcactccatagacacagcagccgctc | L36829 | 86382 | ctctcccgtttgactatggtgc | D84655 |
| 1175 | aagagtacgcaggcaggcccagctg | W44037 | 43779 | ccctacacagagcgggtccccagg | L36829 | 86383 | cagccacgaagtactgatgtcgggg | D84655 |
| 1176 | caggcactgatgccaaatgggata | W44037 | 43780 | gtcgcccacagcagccattgtac | L36829 | 86384 | gcgtcatgactgctgtcaaaaa | D84655 |
| 1177 | ttctggcggtcaagcaggattccat | W44037 | 43781 | aggcagcccatgtacacttcagcg | X96793 | 86385 | tgagtgctcggtcaccaccacctgg | X98014 |
| 1178 | cgtcaagtcaggatccattctgta | W44037 | 43782 | cagccattgtacacttcacgtga | X96793 | 86386 | tcacacaactggctgagctcacaag | X98014 |
| 1179 | tggtcaggtcatctctatga | W44037 | 43783 | ggacttgaccgatacaagtctgag | X96793 | 86387 | gcatatccaagtgctgagggtcaggagct | X98014 |
| 1180 | cagtgcatcttaaagatga | W44037 | 43784 | atacaagtgggtggtgtctc | X96793 | 86388 | cccaagatgcagggtgggaggagagc | X98014 |
| 1181 | caggcccccaagactgctgagggcat | W44037 | 43785 | aggctgcatagcagccaactaaggt | X96793 | 86389 | tgagagcatgccccattaaacgc | X98014 |
| 1182 | agtccaatctggaaacatgcaaa | M77167 | 43786 | tgtcttcgtgtacagctcagggaa | X96793 | 86390 | ctcttgacacacagcaacagcctggttg | X98014 |
| 1183 | aggcccaagactgctgagggcatt | M77167 | 43787 | cagagggccctggctctccagggaac | X96793 | 86391 | ccatctcagaaatctcacgactcagag | X98014 |
| 1184 | gccaagactgctgaagggcattgct | M77167 | 43788 | ccctgctctccagggaactggga | X96793 | 86392 | agaatctacgactcagagaccac | X98014 |
| 1185 | ctgctgagggcattgtgagtggct | M77167 | 43789 | gcagtagcccaggaactttgaccga | X96793 | 86393 | tgagtgctcgtcaccaccactgg | X98014 |
| 1186 | ttctggcgttcaagcaggattccat | M77167 | 43790 | gccggtggactgaccgataacaag | X96793 | 86394 | tcacacaactggctgagctcacaaa | X98014 |
| 1187 | cgtcaagtcaggatccattcgta | M77167 | 43791 | ggacttgaccgatacaagtctgag | X96793 | 86395 | gcatatcccaagtgctgagcctcaggagt | X98014 |
| 1188 | tggtcatcttaaagagatga | M77167 | 43792 | atacaagtgggtggtgttctc | X96793 | 86396 | cccaaagtccaggagtcgagagc | X98014 |
| 1189 | cagtgcatcttaaagatgcaaa | M77167 | 43793 | tgtcttcgtgtacagctcaggaa | X96793 | 86397 | tgagagcatgcccctaaaaacgc | X98014 |
| 1190 | taaatgacatttcagactttgag | M77167 | 43794 | ccgactccgaggcccctgctgcc | X96793 | 86398 | ctcttgacacacagcctggttg | X98014 |
| 1191 | acatttcagactttgagatgaa | M77167 | 43795 | ttgcagcccacgcggttgtctgcc | X96793 | 86399 | gacaacagcctggttcagccgcattta | X98014 |
| 1192 | acttgtatcatttcacctcg | M77167 | 43796 | ceggactaactgcccaagccagattc | X96793 | 86400 | gcctcagttcagcctgcattta | X98014 |
| 1193 | tatctatttcacctgatctca | M77167 | 43797 | taactgccaacagccagattcctga | X96793 | 86401 | gggagatctcacctcctcgcatg | X98014 |
| 1194 | ttaaatcacaatttgtcatagt | M77167 | 43798 | ccaagccagattcctgaataaag | X96793 | 86402 | tcgttgcacacaggcacgacctcaat | X98014 |
| 1195 | ttgatcaaaggcacaaaacatga | M77167 | 43799 | ctctccaggaactggaaagagaga | X96793 | 86403 | accaggtccatgggtgtctga | X98014 |
| 1196 | agcaggatcaatctgtaaaataac | M77167 | 43800 | ggctagaccctgatcctaatccca | X96793 | 86404 | ttccttgacctgccatattggctg | X98014 |
| 1197 | attccattcgtaaatacctgtaat | M77167 | 43801 | gacccgtctactgtatcctggaa | X96793 | 86405 | gacctttgccattatggctgtca | X98014 |
| 1198 | tgtagtctgctcatccatca | M77167 | 43802 | gtctactgtatcctggaatggac | X96793 | 86406 | agcaatatgggctgtcactcct | X98014 |
| 1199 | ctgtctgatctccactacattat | M77167 | 43803 | atctggctctgagaatgcagcagga | X96793 | 86407 | aaactcagccatgaagaccaccacta | X98014 |

| SEQ ID NO | sequence | DBAxnID | SEQ ID NO | sequence | DBAxnID | SEQ ID NO | sequence | DBAxnID |
|---|---|---|---|---|---|---|---|---|
| 1200 | tgcatccatactacattatgctat | M77167 | 43804 | tttatgttcaccctttgcaaagt | X96793 | 86408 | tctctaatctactcctccaacaat | AA106532 |
| 1201 | catactacattatgctatggtctc | M77167 | 43805 | tctctgaacaacagcagatgcc | X96793 | 86409 | taatctctactcctccaacaatgaag | AA106532 |
| 1202 | acattatgctatggtctcagtgtc | M77167 | 43806 | cgtcgctgaccatcgcgatggtt | AA023081 | 86410 | tgaactgcctatcggaacatagcat | AA106532 |
| 1203 | ttgctatggtctcagtgtcatctct | M77167 | 43807 | cccggctgccagcaggttcatctg | AA023081 | 86411 | aactgcctatcggaacatagcatga | AA106532 |
| 1204 | ttgctgtctatggtttagcctgta | M16449 | 43808 | cagtgcctgtacaacaaagcctg | AA023081 | 86412 | gcctatcggaacatagcatgaccat | AA106532 |
| 1205 | gctgctatggtttagcctgtaggt | M16449 | 43809 | gccagttacaacaaagcctggaagc | AA023081 | 86413 | atagcatgaccatagcgcgaggacg | AA106532 |
| 1206 | gcgttttcgacttggaagaacat | M16449 | 43810 | gttacaacaaagcctggaagctaga | AA023081 | 86414 | agcatgaccatagcgcgaggacgcg | AA106532 |
| 1207 | ttttctgacttggaagaacattct | M16449 | 43811 | tacaacaaagcctggaagctagacg | AA023081 | 86415 | catcgaccgaaagcctcttagaat | AA106532 |
| 1208 | acatctctgtagttctaagtgt | M16449 | 43812 | caacaaagcctggaagctagacgttagacg | AA023081 | 86416 | acagtacacgcgcctcaggaaca | AA106532 |
| 1209 | tacagagccgaactgcctcgtggt | M16449 | 43813 | gaagctagacgccgcacctatgcaaa | AA023081 | 86417 | agtacacgcgcctcaggaaacagg | AA106532 |
| 1210 | actgcctcggtcctgggcttca | M16449 | 43814 | ctagacgcgcacctatgcaaacaca | AA023081 | 86418 | aggcgccacttaacaacaacgtgacga | AA106532 |
| 1211 | gcctctgtcctgggctttcagg | M16449 | 43815 | agacgcgcacctatgcaaacacaca | AA023081 | 86419 | tgtaatagactacatcacagcctt | AA106532 |
| 1212 | tcgtggtcccggtgcttcagggag | M16449 | 43816 | acgcgcacctatgcaaacacacagg | AA023081 | 86420 | atctctactctccaacaatgaaggc | AA106532 |
| 1213 | cagcgttctgcctgagagcat | M16449 | 43817 | gcgcacctatgcaaacacacacggg | AA023081 | 86421 | ctactctccaacaatgaaggcgcag | AA106532 |
| 1214 | ccagttcgcctgagagcattg | M16449 | 43818 | cggtcgccagcaggttcatctgt | AA023081 | 86422 | actctccaacaatgaaggcgcagag | AA106532 |
| 1215 | gttctgcctgagagcattgcaa | M16449 | 43819 | gctgccccagcaggttcatctgctcc | AA023081 | 86423 | gagaccaaatgcgcaactactacga | AA106532 |
| 1216 | atggtttgactgtaggtcatgct | M16449 | 43820 | cccagcaggttcatctgctcc | AA023081 | 86424 | gaccaaatgcgcaactactacgaga | AA106532 |
| 1217 | ttgcaagaagctggcctgaattc | M16449 | 43821 | cagcaggttcatcgtctcctttccc | AA023081 | 86425 | aaatgcgcaactactacgacggt | AA106532 |
| 1218 | ttagcctagtcatgctgctagc | M16449 | 43822 | aggttcatctgtctctttccgact | AA023081 | 86426 | atgcgcaactactacgacggtga | AA106532 |
| 1219 | tagctagtgtcaggggcaatgag | M16449 | 43823 | ctttcccgactgcagcgccagttac | AA023081 | 86427 | gcaactactacgagacgggaactg | AA106532 |
| 1220 | ctatgcactagtatccagactttt | M16449 | 43824 | cccgactgcagcgccagttacaaca | AA023081 | 86428 | cctgcgagttcagctgtctac | AA106532 |
| 1221 | tgcactagtattccagactttta | M16449 | 43825 | tgcagcgccagttacaacaaagcct | AA023081 | 86429 | cagctgctcatcgaatgcatgggg | AA106532 |
| 1222 | ttttgagttcagctgaatgtcat | M16449 | 43826 | ttcatagcagcagttaagtgacgga | X70296 | 86430 | aaagcctgctgccactttacaagga | AA106532 |
| 1223 | gttcagctgaattgcatcccgttt | M16449 | 43827 | tggalgcctgggatgctgctgtgaa | X70296 | 86431 | tcttttgactgctttgaatgt | X80502 |
| 1224 | cagcctgaattgcatcccgttggg | M13990 | 43828 | gctgctgcaagttcatcttgttca | X70296 | 86432 | gcactgctttgaatgcttccact | X80502 |
| 1225 | aattgcagaaacactctgaaagac | M13990 | 43829 | tgtcaagttcagcatcttgttcattc | X70296 | 86433 | attgaagccgtgtgaattagactg | X80502 |
| 1226 | attctgcagaaacactctgaaagacc | M13990 | 43830 | caagttcagcatcttgttcattc | X70296 | 86434 | ataataaaccgactccccatgtgaat | X80502 |
| 1227 | ctgaaagaccaccatcaggttag | M13990 | 43831 | gttcagcatcttgttcattccg | X70296 | 86435 | aaccgactccccatgtgaatggggaa | X80502 |
| 1228 | tgaaagaccaccatcaggtttagc | M13990 | 43832 | atcctgtgtatatgtgcattcta | X70296 | 86436 | cctctcacttgtatatgtcctca | X80502 |
| 1229 | gaaagaccaccatcaggttttagca | M13990 | 43833 | ctagcaaaagccgtagcctcttcgt | X70296 | 86437 | gatataagtcctcaaccaggagagc | X80502 |
| 1230 | aagaccaccatcaggttttagcaag | M13990 | 43834 | gcaaaagccgtagcctcttcgtgtg | X70296 | 86438 | gtcctcaaccaggagagctctgc | X80502 |
| 1231 | agaccaccatcaggttagcaagc | M13990 | 43835 | aaagccgtagcctcttcgtgtgtg | X70296 | 86439 | cttagccaagggatcagaatctt | X80502 |
| 1232 | gaccaccatcaggttttagcaagct | M13990 | 43836 | gtagcctctcgtgtgtttctg | X70296 | 86440 | actcgtcacactgctaaggaac | X80502 |
| 1233 | acccaccatcaggtttagcaagcta | M13990 | 43837 | tatactgatgtgtcactaaaata | X70296 | 86441 | tggcctaagaactccaaatggaaa | X80502 |
| 1234 | cccaccatcaggttttagcaagctag | M13990 | 43838 | atgagcaggccggttcacgatgtc | X70296 | 86442 | aatagtctccagaacgaacaacccata | X80502 |
| 1235 | tttgcagaaacactctgaaagactg | M13990 | 43839 | ccggttcacgatgtctagaagatt | X70296 | 86443 | atccagaacgaaccatagacaat | X80502 |
| 1236 | gaaaacactctgaaagaccaccatc | M13990 | 43840 | gttcacgatgtctagaagatttct | X70296 | 86444 | aagaaccatagacaacatcggaa | X80502 |
| 1237 | aacactctgaaagaccaccacate | M13990 | 43841 | ttcttaactactgatcagttatc | X70296 | 86445 | accataacaactggcaaagcct | X80502 |
| 1238 | acactctgaaagaccaccatcagg | M13990 | 43842 | ctactgatcatatctaggttaac | AA020620 | 86446 | agacaatctggcaaaagcctgtctgc | X80502 |
| 1239 | cactctgaaagaccaccatcaggt | AA016708 | 43843 | tctcgagtattgctgtcgtcaag | AA020620 | 86447 | tctggccaagctgtctgccactta | X80502 |
| 1240 | actctgaaagaccaccatcaggtt | AA016708 | 43844 | gtatttgctgctgtcagtcagc | AA020620 | 86448 | cctcctgtcttcacgaactagt | X80502 |
| 1241 | ctctgaaagaccaccatcaggttt | AA016708 | 43845 | ttgtgctgctcaagttcagcatc | AA020620 | 86449 | ttctcagtcttcacgaactcagtca | X80502 |
| 1242 | tctgaaagaccaccatcaggttta | AA016708 | 43846 | tgatcaaggccatctcatctccaa | AA020620 | 86450 | aggccctgcagagaccacactctgcatga | X83562 |
| 1243 | gtgttcgatccagccgagcagtaca | AA016708 | 43847 | tcaaggccatctcatctccatcaacaa | AA020620 | 86451 | tcagaggacacactctgccatgaa | X83562 |
| 1244 | ttcgatccagccgagcgagcagaca | AA016708 | 43848 | aacgcaacaaatcatcaacatcaggga | AA020620 | 86452 | gcacttaccatactgccttgat | X83562 |
| 1245 | accacgagagcagagacaacctga | AA016708 | 43849 | cgcaacgcaaatcatcacagggagaa | AA020620 | 86453 | ctttgatataagctccttgtgcact | X83562 |
| 1246 | gacagagacaactgactcgcggtt | AA016708 | 43850 | aacagcaaatcatcagggagactttt | AA020620 | 86454 | ctccttgtcacttgctctgctct | X83562 |
| 1247 | ctgactcgcagttttcgactag | AA016708 | 43851 | atttggttctaagccgcatgagaa | AA020620 | 86455 | tgtatcatctgatccatcacag | X83562 |
| 1248 | actgcagtttcagatctaggt | AA016708 | 43852 | tggtgctcaagcgcgatgatgagaactg | AA020620 | 86456 | gtatcatcacagcattaggcgttgg | X83562 |
| 1249 | aaatgcttaacgaccttcagacag | AA016708 | 43853 | gaggcttgaacaacagctcattta | AA020620 | 86457 | atcaagcattaggcgttggtggcata | X83562 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 1250 | aacgacctcagagagcaagaactcc | AA016708 | 43854 | gctctgacaacagctcatttacag | AA020620 | 86458 | gcattaggcgtggtcatagacac | X83562 |
| 1251 | gcagaagaacctcgctcaaaatc | AA016708 | 43855 | acaagctcatttacagacattagc | AA020620 | 86459 | gtgcatagcaacaacagttgctca | X83562 |
| 1252 | gaagaactccgctcaaaattcacag | AA016708 | 43856 | agctcatttacagacattagcaaac | AA020620 | 86460 | gctcttcacgaactcagctaagatc | X83562 |
| 1253 | ctcctgctcaaaattcacgaggtgt | AA016708 | 43857 | tcatttcagacattatgcaacact | AA020620 | 86461 | ctcagctaagatctcctgaccaca | X83562 |
| 1254 | ctcctgctcaaaattcacgaggt | AA016708 | 43858 | tcctcatcttcaacaaccacggaa | AA020620 | 86462 | atcagtccccttcatagctgcact | X83562 |
| 1255 | gatccagcgcagtcagtacaagtgg | AA016708 | 43859 | tcttcaacaaccacggaagccgcg | AA020620 | 86463 | catagcctgcactggccaatccaga | X83562 |
| 1256 | gtgtcgaactcaagcaccaagatg | AA016708 | 43860 | ggctccaagttctaccagccta | AA020620 | 86464 | ctgcactggccaatccaagaagt | X83562 |
| 1257 | ggagttgccctcatcttcaatcacg | AA016708 | 43861 | tctccaagttctaccagccctag | AA020620 | 86465 | tgtgccttgccttgcagttcgca | X83562 |
| 1258 | gtgccctcatcttcaatcacgaga | AA016708 | 43862 | ccaagtctaccagcctatagta | AA020620 | 86466 | cttgcagtttgccttgcagttcgca | X83562 |
| 1259 | gccctcatcttcaatcacgagaggt | AA016708 | 43863 | agtctaccagcctatagtgaaga | AA020620 | 86467 | gttcgcatcttcggatcattcttg | X83562 |
| 1260 | atctcaatcacgagaggtcttt | AA016708 | 43864 | accagcctatagtgaagacacga | AA020620 | 86468 | tccggatccatggactatatctgcaga | AA116773 |
| 1261 | ttcaatcagagagggtctttttggc | AA016708 | 43865 | aagacacgcaacagcaaatcatcag | AA020620 | 86469 | ccatggactatctgcagagtttcc | AA116773 |
| 1262 | cggggaccaaagcagcagaagagacaca | AA016708 | 43866 | tatactaccacaaaccacgtacaca | AA020620 | 86470 | tgccctgcaaggaggaggagacatag | AA116773 |
| 1263 | ggcaccaaagcagcagaagacaacc | AA016708 | 43867 | gtacaacactagttcaaatgctctc | L41495 | 86471 | cccctgcaaggaggaggagacatag | AA116773 |
| 1264 | ctgtcgcctagcaccatggaagc | AA068780 | 43868 | ttacccaagtgctctattccgggt | L41495 | 86472 | aagccacctggcctatcggccatgt | AA116773 |
| 1265 | ttgtcgcctagcaccatggaagcc | AA068780 | 43869 | aagtgctctattccggtgagaaga | L41495 | 86473 | gcccatcggcctatcggcatgttc | AA116773 |
| 1266 | tagcaccatggaagccacgcaa | AA068780 | 43870 | tcttatccggtgagaagaccta | L41495 | 86474 | ccatcggcctatcggcatgttc | AA116773 |
| 1267 | agcaccatggaagccacgcaagcaag | AA068780 | 43871 | gagaagaacctcactccatgatt | L41495 | 86475 | atctggctatcggcatgtctctg | AA116773 |
| 1268 | gaaccatggaagccacgcaagcaagt | AA068780 | 43872 | aacctcactccatgattggggaag | L41495 | 86476 | catgttctcggatatgtggacaat | AA116773 |
| 1269 | caagctgccacactggtatgttg | AA068780 | 43873 | actccatgattggggaaggaatgg | L41495 | 86477 | tgtctctggatatgtggacaatcc | AA116773 |
| 1270 | gccaactcggtatgttggagatc | AA068780 | 43874 | gcgatcaccgacaccacagagac | L41495 | 86478 | atgtggacaatccaagaagacacaa | AA116773 |
| 1271 | ccaactcggtatgttggagatcc | AA068780 | 43875 | accggacaccacagagactaggat | L41495 | 86479 | atattcgaggagactttggcttat | AA116773 |
| 1272 | caactcggtatgttggagatcca | AA068780 | 43876 | ctcctgagccagaattgtccagtgg | L41495 | 86480 | atggactactcgagagtctccag | AA116773 |
| 1273 | actcggtatgttggagatccaa | AA068780 | 43877 | agccagaattgccagtggttgaaa | L41495 | 86481 | ttatctgcagagtttccaggacaat | AA116773 |
| 1274 | tgtgcggtagcaccatggaagcca | AA068780 | 43878 | ttcaaatgctccattgggtagaga | L41495 | 86482 | atctcagagtttccaggacaatga | AA116773 |
| 1275 | gtcggcctagcaccatggaagccac | AA068780 | 43879 | tgtctcacttgggcaaggggtct | L41495 | 86483 | tcaaaccaggctaccctgggacagc | AA116773 |
| 1276 | tcgccttagcaccatggaagccacc | AA068780 | 43880 | tccggatctcatctgtgctg | L41495 | 86484 | ctgggaacagcccttgctcactatg | AA116773 |
| 1277 | gccttagcaccatggaagccacca | AA068780 | 43881 | catctgtgctgcctgctgcctt | L41495 | 86485 | acagccttgctcactatgtac | AA116773 |
| 1278 | gccttagcaccatggaagccaccaa | AA068780 | 43882 | gttgctgccgcctgccttagccc | L41495 | 86486 | agccttgctcactatgtacag | AA116773 |
| 1279 | ccttagcaccatggaagccaccaag | AA068780 | 43883 | gctgcctgccttagcccagactg | L41495 | 86487 | tttgctcactatgatacaggtca | AA116773 |
| 1280 | cttagcaccatggaagccaccaagc | AA068780 | 43884 | ctgccttagccagactggtgatt | L41495 | 86488 | gcgctgccgaattctcacctgca | AA116773 |
| 1281 | ttagcaccatggaagccaccaagca | AA068780 | 43885 | ctacgttaccaagtgctctatt | L41495 | 86489 | ccgaattctcacctgcaagatat | X99946 |
| 1282 | tatacgcctggggtaatgagaggtg | X03919 | 43886 | aagacctactttcaccagctactg | AA020650 | 86490 | aacgttgccctcagctaccatg | X99946 |
| 1283 | acgtcctggggtaatgagaggtggct | X03919 | 43887 | acctactctaccagctgtgatg | AA020650 | 86491 | accattggccctcatgataaatg | X99946 |
| 1284 | tcctacacggcctatacttagt | X03919 | 43888 | gtcctctactactcagccaccaaga | AA020650 | 86492 | gtgccctcatgcataaatgaagtcc | X99946 |
| 1285 | tacacggcctatactttagtatg | X03919 | 43889 | ctctactactcagccaccaagaacg | AA020650 | 86493 | atctctacacactaagccgaaaaca | X99946 |
| 1286 | acggcctatactttagtatagacg | X03919 | 43890 | tactactcagccaccaagaacgga | AA020650 | 86494 | cttaatttgagccctggctgtttga | X99946 |
| 1287 | atactttagtatagcctgtatacat | X03919 | 43891 | tactagccaccaagaacggca | AA020650 | 86495 | ttgagctggctgtttgaaaattg | X99946 |
| 1288 | tatttgtcatgttttgtgcataga | X03919 | 43892 | gccaccaagaacggcatcctgtacc | AA020650 | 86496 | tcaccgcaaaacaatctaagtcat | X99946 |
| 1289 | atatttagtctgcacctagagca | X03919 | 43893 | accaagaacggcatcctgtaccgag | AA020650 | 86497 | aatctaaagtcatctcacaggccaac | X99946 |
| 1290 | aggtctgcacctagagca ttga | X03919 | 43894 | aaggcatcctgtaccgagttggtg | AA020650 | 86498 | tgtttgtgccaacttccaa | X99946 |
| 1291 | gctgcacctagagcactttgaaat | X03919 | 43895 | atcctgtaccgagttgtagtgtg | AA020650 | 86499 | ttgctgccaactccaataaat | X99946 |
| 1292 | agcactttgaaatacctccattga | X03919 | 43896 | ctgtaccgagttgtgatggtg | AA020650 | 86500 | ttcttcacctgcaagatatcttca | X99946 |
| 1293 | actttgaaatacctccatgttgag | X03919 | 43897 | taccgagttgtgatggtgtacc | AA020650 | 86501 | ccaaacttccaataaatttcgttg | X99946 |
| 1294 | ggctctgcggccgattagactg | X03919 | 43898 | tatgatcaagaatacgcgagatttcg | AA020650 | 86502 | acctgcaagatatttccggagga | X99946 |
| 1295 | tcttgcggccgattagactagaa | X03919 | 43899 | caagattcgcagattgcagttccc | AA020650 | 86503 | acagatcgcagtacgatgatga | X99946 |
| 1296 | tcacacctagaagtactgtaagaatac | X03919 | 43900 | aagttcaaatctcgtgtgagctgt | AA020650 | 86504 | tcagaatcgcatgatggagcac | X99946 |
| 1297 | agaatacctcaatgtttgaggggga | X03919 | 43901 | aaatttctgtgtgaggctgccgc | AA020650 | 86505 | aggacactgccaagctgatgtac | X99946 |
| 1298 | atacctcaatgtttgaggggcatgt | X03919 | 43902 | ttcgtgggagctgtgccgctctgg | AA020650 | 86506 | ctgccaagctggatgtactgaaga | X99946 |
| 1299 | tcgttagctactactaattcct | X03919 | 43903 | gccctgtctgctggatgaggcaaa | AA020650 | 86507 | atcagaaccacaagctgaccaaga | X99946 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 1300 | tactctactaattctacacggcct | X03919 | 43904 | cccaggtcctggagcagtcgagg | AA020650 | 86508 | tgaaccaactgattaagcaggcag | X99946 |
| 1301 | tctactaattctacacggcctgta | X03919 | 43905 | agggtctggagcagtcgaggacc | AA020650 | 86509 | tcctgtccagcaattgtcgagct | U76832 |
| 1302 | tgtgagaactgggccgatccatg | W44201 | 43906 | atgaccacctgggtcagtcgaagc | U33535 | 86510 | aattgtcgagtcatcaacaagtg | U76832 |
| 1303 | aactgcgccggatccatgtaactg | W44201 | 43907 | ccgcagtcacggactggatcatt | U33535 | 86511 | agaacatccgagctcggccgacta | U76832 |
| 1304 | tgcaggcagctccatcgctcagct | W44201 | 43908 | aactaacacaggaatgtgtgttcag | U33535 | 86512 | tcctgagctcggccgactacggga | U76832 |
| 1305 | agctcaccaaagcagtagccgc | W44201 | 43909 | cttccaacctctataaacatgtgga | U33535 | 86513 | agacagtcaagatagcctagagaa | U76832 |
| 1306 | ccaaagcagtagccgcaccactgct | W44201 | 43910 | aacatgtggacaccggaaggagata | U33535 | 86514 | aagtcatgatgccatctgtctc | U76832 |
| 1307 | cactgctcactcgcatagcatgg | W44201 | 43911 | ctagacagtggacctgacaaagt | U33535 | 86515 | tgattgccatctggtctctgtcac | U76832 |
| 1308 | tgctcactctcgcatagcatggct | W44201 | 43912 | cagtggacctgacaaagtgacaag | U33535 | 86516 | gtgtctgctcactgtctccatct | U76832 |
| 1309 | tcactctcgcatagcatggctgtg | W44201 | 43913 | atatttcaagccaagctgacaaag | U33535 | 86517 | ctgttctcatcttggctgtcatcat | U76832 |
| 1310 | tggatactttccaaattgtcat | W44201 | 43914 | gacagtgtcttcactgagcccta | U33535 | 86518 | tcatcttgctgtcatcattggcat | U76832 |
| 1311 | atactttctccaaattgtcatcta | W44201 | 43915 | gtcttcactgagcccttaaaacat | U33535 | 86519 | tggctgtcatcattggcatcatccat | U76832 |
| 1312 | ctttctccaaattgtcatctacct | W44201 | 43916 | taaccactataaatgtttcatgc | U33535 | 86520 | tcatcattggcatcaccataaacgt | U76832 |
| 1313 | tcttccaaattgtcatctacctgg | W44201 | 43917 | ccactataaatgtttcatgcggtg | U33535 | 86521 | tcgagtcatcaacaagtgcaactc | U76832 |
| 1314 | tggcgccgatccatgtaactgttc | W44201 | 43918 | tagagatcttcccaacgtactat | U33535 | 86522 | tggcatcaccaaccgttggataa | U76832 |
| 1315 | tccaaattgtcatctacctggtga | W44201 | 43919 | ggaaagaccacagccgcgttcggcat | U33535 | 86523 | tcatcaacaagtgcaactcaactg ca | U76832 |
| 1316 | cgccggatccatgtaactgttccag | W44201 | 43920 | acagcctcggcatctcggaatt | U33535 | 86524 | caatgcgcgaatacggaagaga | U76832 |
| 1317 | atccatgtaactgttccagcagag | W44201 | 43921 | gcctggtcagcaattcgcgggtgga | U33535 | 86525 | tcctgaaggacacgcaggtgactcg | U76832 |
| 1318 | catgtaactgttccagcagaggctg | W44201 | 43922 | ttcggtgtggacagtggactcta | U33535 | 86526 | tctctgcgcgcacagtagatcca | U76832 |
| 1319 | gttccagagggtgggccaaga | W44201 | 43923 | acagtggactctactcggcatgaa | U33535 | 86527 | gcagtatccgagagctccatgatgat | U76832 |
| 1320 | ccccagagggctgagtgcctg | W44201 | 43924 | gactctactccggcatgaacgagaa | U33535 | 86528 | tccgagtccatgagatcttac | U76832 |
| 1321 | acgacggactctgagtggcctgtgc | W44201 | 43925 | tctacctccggcatgaacgagaaggg | U33535 | 86529 | tgatcaaccgcatcgaagaaagaacat | U76832 |
| 1322 | acgaactcgagtggcctgcatc | W44201 | 43926 | ctcctgggagcttattggagcgg | U53584 | 86530 | tttgtaccccagatgctgcaag | U31966 |
| 1323 | aacgcaatgctgagggttaaagg | W44201 | 43927 | gttcctaaactctaaggcttcagtg | U53584 | 86531 | agatgctgcaagagtggctctcct | U31966 |
| 1324 | atgctaggctgttaaaggggttaag | M12289 | 43928 | ctgctgtatgtggatgcagtg | U53584 | 86532 | ggtgcagtcgtccagaatctt | U31966 |
| 1325 | ccaaatcgcgcagtaaacaca | M12289 | 43929 | tgctgatgcagtgcctagaagggg | U53584 | 86533 | cctgtccagaatcctgccaggaaa | U31966 |
| 1326 | gagtaacacatcgcagagaag | M12289 | 43930 | tttgacaacctgttcaaggtgat | U53584 | 86534 | gtccagaatccttgccaggaaactc | U31966 |
| 1327 | gtaacacatcgcagagaggaag | M12289 | 43931 | ccaactcctggaacagtgtgctt | U53584 | 86535 | cagaatcctgccaggaaactcaat | U31966 |
| 1328 | acacatcgcagaggaggaagct | M12289 | 43932 | tcctgaacagtgtgctttccgt | U53584 | 86536 | aatcctgccagaaactcaatgcag | U31966 |
| 1329 | acatctgcagaggaggaaggct | M12289 | 43933 | tctgctgccaggtgtgacttaga | U53584 | 86537 | cctgccaggaaactcaatgacag | U31966 |
| 1330 | gctgccaagggggctgaaggaagca | M12289 | 43934 | acttagaactccgtcctgagtagat | U53584 | 86538 | ggccctttgcctcagatgcagag | U31966 |
| 1331 | ggtcgtctgggggtcactgcctc | M12289 | 43935 | ccggagcatcacagctacaagg | U53584 | 86539 | cctttgcctcagatgcagaggg | U31966 |
| 1332 | tcgctgctgggtcactgcctc | M12289 | 43936 | cagtacgacggcctgaaggcacag | U53584 | 86540 | tttgcctccagatgcagaggggcct | U31966 |
| 1333 | tcactgcctctcgtgttactt | M12289 | 43937 | cagacggctgggggctgggacacgtccgta | U53584 | 86541 | agactgctgaaggccaaggaaagc | U31966 |
| 1334 | ttttctctactgctgactaataa | M12289 | 43938 | cagccattttctgtagcaggacct | U53584 | 86542 | caaggagctgctcctctaataaaa | U31966 |
| 1335 | agaatgctccggtcgcaggacct | M12289 | 43939 | tcctctaacggaaggcacaattca | U53584 | 86543 | tctaataaaaccccaaggcagagtg | U31966 |
| 1336 | aatgtgctccggtcgcaggacctgg | M12289 | 43940 | caattcagtcgttcagaaccagga | U53584 | 86544 | gaatgtccagcatggaggtctc | U31966 |
| 1337 | gaggaacaatcagccaaccctgg | M12289 | 43941 | ttcagaacaaccagaccaacctag | U53584 | 86545 | tgtgccagcatgtggagtcagg | U31966 |
| 1338 | gaggttcaccacaaatcagccag | M12289 | 43942 | acaccaacatcagtcgcaggctgt | U53584 | 86546 | gtccagcatggtgagtcagggcc | U31966 |
| 1339 | ggttcaccacaaatcagccgcagg | M12289 | 43943 | acatcagtcaggctgtgtgacaag | U53584 | 86547 | aaactcaggctggagtcgcagag | U31966 |
| 1340 | ttcaccacaaatcagccagagta | M12289 | 43944 | gatccaagctagccattctccttc | U53584 | 86548 | tgaagagggaccacacagaggagtg | U31966 |
| 1341 | cacaccaaaatcagccgcagtaa | M12289 | 43945 | acattaactcaggcattctttctc | U53584 | 86549 | cgagcacacagaggaggagtg | U31966 |
| 1342 | caccaaaatcagccagagtaaca | M12289 | 43946 | ctgctgttctctgtctgt | U53584 | 86550 | tccattgagatgccagctggcct | AA107731 |
| 1343 | agatgccaaggcatacgtgagc | W44217 | 43947 | cctcagccgccacagttaatgcgac | L01991 | 86551 | atgccagctgctcgatcagcct | AA107731 |
| 1344 | attggccaaggcatacgtgagtt | W44217 | 43948 | tcagccgccacagttaatgcgaccac | L01991 | 86552 | atttccaaagtcgacgggtcct | AA107731 |
| 1345 | tctgacatccctagtcaata | W44217 | 43949 | tgttgctccatcaaagaagaccta | L01991 | 86553 | tccaagtcgcgggtcctat | AA107731 |
| 1346 | tgacatccctagtcagtcaatag | W44217 | 43950 | aggtcaaggccaccacagatggagg | L01991 | 86554 | tccttatccgaacgagagtga | AA107731 |
| 1347 | atccctagtcagtcaatagga | W44217 | 43951 | atgccaccagtgagcagtcag | L01991 | 86555 | tccccgaacgagagtgacctct | AA107731 |
| 1348 | atccctagtcagtcaataggaact | W44217 | 43952 | gatccacgcagccatttctaacatca | L01991 | 86556 | accttcaagcattggggctgagt | AA107731 |
| 1349 | tatgctgtgaactttctttagcagg | W44217 | 43953 | tttctaacatccccctttgtcagg | L01991 | 86557 | ttctaagcattgggcgtgagtcaa | AA107731 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 1350 | cttgtgaacttctcttagcaggcag | W44217 | 43954 | acccttgtcaggttatatgtcgt | L01991 | 86558 | taagcattcgggctgagttcaagaa | AA107731 |
| 1351 | aactctttagcaggcgagtgaactc | W44217 | 43955 | tcctactgttctttattgtaaatgc | L01991 | 86559 | agctcctccatctcttcttcagga | AA107731 |
| 1352 | cttcttagcaggcgaggagaatct | W44217 | 43956 | ttattgtaaatgcttgtgggtgata | L01991 | 86560 | tctattctcttcaggatgtagt | AA107731 |
| 1353 | tcttagcaggcgaggagaactga | W44217 | 43957 | atgcttgtgtagaaggctttt | L01991 | 86561 | attctctctcaggatgtacg | AA107731 |
| 1354 | tcctgcgtgcatagtgcatatgcc | W44217 | 43958 | ctcccagtcagccaccaggaaatgt | L01991 | 86562 | ctctgatcacgcctagctcatgtt | AA107731 |
| 1355 | tgccaaggccatactgactgagcttgc | W44217 | 43959 | ccagtcagccaccaggaaatgtgt | L01991 | 86563 | tgatcagcctagctccatgttgag | AA107731 |
| 1356 | atacgtgagcttgcacagagct | W44217 | 43960 | atgctacagcactaaagtgctact | L01991 | 86564 | gaaacacgcgctgactgtgctaa | AA107731 |
| 1357 | tgagcttgcacgcagcctgacca | W44217 | 43961 | atgtcacgtgtgaacacaataa | L01991 | 86565 | acacagcgctgactgttgctaacca | AA107731 |
| 1358 | agctgcacacgagcctgacatc | W44217 | 43962 | aaactcagtcgactgtgtcgcc | L01991 | 86566 | tgtactttgctaacaactccacca | AA107731 |
| 1359 | cacacgagcctgacatccctagt | W44217 | 43963 | ctcagctgaactgttgctgcctat | L01991 | 86567 | aaactgagcctaatttccaagtgct | AA107731 |
| 1360 | cacgagcctgacatccctagtca | W44217 | 43964 | cagctgaactgttgctgcctatcaa | L01991 | 86568 | ctgagctaatttccaagtgctgac | AA107731 |
| 1361 | cgagcctgacatccctagtcaag | W44217 | 43965 | aactgttgctgcctatcaaagaaga | L01991 | 86569 | ctaattccaagtgtcgacgcgggt | AA107731 |
| 1362 | agcctctgacatccctagtcaagtc | W44217 | 43966 | tcccggctccaaagtgagagtc | U53591 | 86570 | catcccagatcagccattacttt | AA107731 |
| 1363 | atgcaccttgtttgccaagaagc | M91602 | 43967 | cctggctccaaagtgagagctcaa | U53591 | 86571 | cagatcagccattacttgctac | U36788 |
| 1364 | ccttgttcccaagaagcgaatag | M91602 | 43968 | tcctattgccacctgccgtgctaa | U53591 | 86572 | atgaatgccttttgaccgccatga | U36788 |
| 1365 | gaccagatgtttgcagccttccc | M91602 | 43969 | aatcttttccgtataaggtat | U53591 | 86573 | ttgaccggcagactggatcatcaa | U36788 |
| 1366 | cctgcaattccgcaattctgatt | M91602 | 43970 | ttccttcagttcatagggttatagtg | U53591 | 86574 | actgaatcaataacgttgtgggcac | U36788 |
| 1367 | gacgttaccgcaatctgattata | M91602 | 43971 | ggtagtaatctctcatttccag | U53591 | 86575 | tcatcaatctgtggcacagagt | U36788 |
| 1368 | ttggtccacatcattacccacgag | M91602 | 43972 | tagtaatctctcatttatccagca | U53591 | 86576 | accagttcactatctgatgtgcg | U36788 |
| 1369 | gtcacatcattacccagagaag | M91602 | 43973 | atctctctattatccagcactca | U53591 | 86577 | tcactatctggatgtgctcgc | U36788 |
| 1370 | aaggactgaggcctgaaccacagcc | M91602 | 43974 | ctctccatattatcccagcactcaa | U53591 | 86578 | tcctggatgtgcgctgcctga | U36788 |
| 1371 | gccctgaaccacacgcctcagtgc | M91602 | 43975 | ctctattatccccagcactcaaaaa | U53591 | 86579 | atcatttctcgcatatgggacag | U36788 |
| 1372 | ctgaaccacagcctcagttgacca | M91602 | 43976 | gtccagactggctcggaatatgag | U53591 | 86580 | tctctgcagtaggacagaatgaa | U36788 |
| 1373 | tctcatccaggctgtgcgcaaa | M91602 | 43977 | atatgcagcagacaacatgatatact | U53591 | 86581 | ctttggtggggctggactgcgtaact | U36788 |
| 1374 | ccatccaggctgtgcgcaaataa | M91602 | 43978 | atgcagcaagcttgcattgtacag | U53591 | 86582 | ttactttgctacctcaagagaga | U36788 |
| 1375 | atcccaaggcattcaagctgttg | M91602 | 43979 | ttcaagcttgatgttacagtacag | U53591 | 86583 | tgctacctcaagaaggagggctcatc | U36788 |
| 1376 | ctcaaagcattcaaggtgttgatc | M91602 | 43980 | tgttaatgttgcccaccttggg | U53591 | 86584 | caattccaagagctgactctgagaa | U36788 |
| 1377 | aaggctgactatgtcgggggatgc | M91602 | 43981 | tgtgtgccaccttggaagaag | U53591 | 86585 | gggaaggccttcatcttcatgagtg | U36788 |
| 1378 | gcfgactatgtcgggggatgctga | M91602 | 43982 | aatgccaatcctaagccctattgc | U53591 | 86586 | ccctcatgctcatgagtgcctg | U36788 |
| 1379 | gagatgtgaccacaagcagagaa | M91602 | 43983 | tgccaattcctaagcctcattgca | U53591 | 86587 | atgctcatgagtgcctggcc | U36788 |
| 1380 | ctgaccacaagcagagaggtct | M91602 | 43984 | taagtccatcgcaccctgcgcgtg | U53591 | 86588 | atgaggtcctgtggccatcgt | U36788 |
| 1381 | accacaagcagagaggttctccca | M91602 | 43985 | agtccatgccacctgcgccgtgct | U53591 | 86589 | atccaccagagcaagaatcgttc | U36788 |
| 1382 | atcgaccgagatgtcgagccttc | M91602 | 43986 | acagacgccaatcatacgactacagtt | AA020692 | 86590 | cgagagccaacatcgactgcggtgaa | U77083 |
| 1383 | ccccatttcgatgatgtcgatat | M91602 | 43987 | gcaccacacgactacgcttcatctg | AA020692 | 86591 | ccaacatgactgggtgaaggagaa | U77083 |
| 1384 | ctatttcgatgatgtcgatat | M63903 | 43988 | atcgagtcgagccaccaaacaagaa | AA020692 | 86592 | caggagctcagacaccagcatccta | U77083 |
| 1385 | tttccatctcgttgcggcatt | M63903 | 43989 | gtcgagccaacaacagcaacaatt | AA020692 | 86593 | caccagcatcctactctcaaggatg | U77083 |
| 1386 | tcctactctgttgccggcatgct | M63903 | 43990 | ccaaccaacaagaacaattcatcaa | AA020692 | 86594 | tccagctcggagccagcctagct | U77083 |
| 1387 | gttgccgcatttgtgatttctag | M63903 | 43991 | acaatttcatcaaatcagactcttt | AA020692 | 86595 | agccagctccttcctaactgtcag | U77083 |
| 1388 | tatactttgtagtctcagtcgggt | M63903 | 43992 | tcatcaaatactcagactcttcaaat | AA020692 | 86596 | cctagctcctaactgtcaggctgac | U77083 |
| 1389 | actttgtagtctcagtcggttga | M63903 | 43993 | atatcagacttcttcaaatcagaat | AA020692 | 86597 | tcctaactgctaggctgacggacac | U77083 |
| 1390 | tagtctcagtcggtgattcat | M63903 | 43994 | ttcaaatcagaatcttccaacactt | AA020692 | 86598 | ctcagggaagccccagctctgaagct | U77083 |
| 1391 | gtgttgattccatcatggaaata | M63903 | 43995 | tcctccaacatttcggacgggct | AA020692 | 86599 | agagctcccgaatgcttactat | U77083 |
| 1392 | tatgttgtacatactgccaagaat | M63903 | 43996 | aacaatttctgaggggttcatag | AA020692 | 86600 | tccctgaatgctttactatccctg | U77083 |
| 1393 | catactgccaagaatgtcctgca | M63903 | 43997 | ttctggacgggcttcatagtagacc | AA020692 | 86601 | attccagaaccaaagaaatcaacaagg | U77083 |
| 1394 | acgtcccaagaatgtcctgcaagt | M63903 | 43998 | tacgtcacgtcctttgcaagt | AA020692 | 86602 | tattcaaggttcacagaacag | U77083 |
| 1395 | aatagagccaactatttgtatgta | M63903 | 43999 | tgcaatgctgaattcagagtcta | AA020692 | 86603 | gcagttagttcctgttcgagaac | U77083 |
| 1396 | tgcttctttccctctggaa | M63903 | 44000 | acagttcatctgggttttgcccac | AA020692 | 86604 | agtcctggttcctgagaaccactg | U77083 |
| 1397 | cctcctgtcctggaactgtcgcca | M63903 | 44001 | tcatctgggttatgccaacggatg | AA020692 | 86605 | tgagaaccactgtcccagtatgac | U77083 |
| 1398 | gaactgtcgcaccgtgatcca | M63903 | 44002 | atgcaacggatggttcctgccat | AA020692 | 86606 | ccactgtcccagtatgaccctct | U77083 |
| 1399 | gtcgcaccgtgatccagtcctg | M63903 | 44003 | ggttcctgcagtgaagaactct | AA020692 | 86607 | gtatgaccacccttactactctcagc | U77083 |

| SEQ ID NO | sequence | DBAxnID | SEQ ID NO | sequence | DBAxnID | SEQ ID NO | sequence | DBAxnID |
|---|---|---|---|---|---|---|---|---|
| 1400 | gtgtgatccgtctcctgctctggct | M63903 | 44004 | ttgaagaactcttaaccagttgct | AA020692 | 86608 | ttactatctcagcagcctgctgcagg | U77083 |
| 1401 | cagatccagtgaagggttctgt | M63903 | 44005 | aactcttaaccagttgctgaatct | AA020692 | 86609 | tctcagcagcctgcagggtctct | U77083 |
| 1402 | aagggtttctgtcttgatgcttca | M63903 | 44006 | ttaaccagttgctgaatcttgaa | AA020692 | 86610 | ttttctctcatccaatcctgaaag | AA107785 |
| 1403 | aactcagatggcgtctaagatcat | W44163 | 44007 | aacacactgcgaactctgaggtttg | U41636 | 86611 | tctcatccaatcctgaaagcat | AA107785 |
| 1404 | ggcgctcaagatcatccgcgggtg | W44163 | 44008 | acacactgcgaactctgaggttg | U41636 | 86612 | ttagtgctcgagctagatccgccag | AA107785 |
| 1405 | aggacatcctcaacaatctgaatga | W44163 | 44009 | atgtagttcaccctgtagagata | U41636 | 86613 | tttcccggcatccaaaatcatggc | AA107785 |
| 1406 | catcctcaacaatctgaatgatgcc | W44163 | 44010 | tgtagttcaccctgtagagatagt | U41636 | 86614 | cggaccatccaaaatcatggctcctag | AA107785 |
| 1407 | tcctcaacatctgaatgatgccat | W44163 | 44011 | gtagttcaccctgtagagatagatg | U41636 | 86615 | catccaaaatcatggctctagtt | AA107785 |
| 1408 | atgatcagctgctagctgctgtag | W44163 | 44012 | atagatgtcttatctagtgt | U41636 | 86616 | ccaaaatcatggctctagtttcag | AA107785 |
| 1409 | gagtcagctgctagctgctgtagag | W44163 | 44013 | agatgtcttattctagtgtgtga | U41636 | 86617 | aaatcatggctctagtttcagaag | AA107785 |
| 1410 | gtcagctgctagagctgctgtagagct | W44163 | 44014 | gatgctcatttagtgtgtgat | U41636 | 86618 | tcatggctcctagttcagagatc | AA107785 |
| 1411 | ctagctgctgtagagctgctgacc | W44163 | 44015 | tgctctatcttagtgtgtgatca | U41636 | 86619 | tggctcctagttcagagatctgc | AA107785 |
| 1412 | agctgctgtagagctgctgaccgt | W44163 | 44016 | gctcttatcttagtgtgtgatcaa | U41636 | 86620 | agtgatgagcgctgcctggccctg | AA107785 |
| 1413 | tgtagagctgctgacgtggggaac | W44163 | 44017 | tctattctttagtgtgtgatcaaca | U41636 | 86621 | tgcctggccctggttcctgagtt | AA107785 |
| 1414 | taagalcatccgcggggtcgacga | W44163 | 44018 | gtgatcaacagtcttcggtcaaat | AA020700 | 86622 | tcatctccaatcctgaaagcatg | AA107785 |
| 1415 | aagatcatccgcggggtcgacgag | W44163 | 44019 | cactgaactcttgaggtttggagt | AA020700 | 86623 | tctccaatcctgaaagcatgtgcc | AA107785 |
| 1416 | atcatccgcggggtcgacgagagc | W44163 | 44020 | ggagtttcgctcaggcaaacaagt | AA020700 | 86624 | ccaatcctgaaagcatgtgccctg | AA107785 |
| 1417 | agctgcgtcggacgagctg | W44163 | 44021 | gagtttcgctcaggcaaacaagtt | AA020700 | 86625 | atcctgaaagcatgtgccctgagtt | AA107785 |
| 1418 | agctgcgagctaggccgagaatcca | W44163 | 44022 | gtttcgctcaggcaaacaagtgc | AA020700 | 86626 | ctgaaagcatgtgccctgagggc | AA107785 |
| 1419 | gagaatccactaatgtcaggacat | W44163 | 44023 | ttcgctcaggcaaacaagttgctt | AA020700 | 86627 | aaagcatgtgccctgaggggcata | AA107785 |
| 1420 | gaatccactaatgtcaggaccatcc | W44163 | 44024 | tcgctcaggcaaacaagttgctt | AA020700 | 86628 | tgtgccccgaggggcataaaccg | AA107785 |
| 1421 | atcactaatgtcaggaccatcc | W44163 | 44025 | tctaacctaccagaaatgtg | AA020700 | 86629 | tggttatgtctgagctagatcggc | AA107785 |
| 1422 | gtgcaggacatcctcaacaactgc | W44163 | 44026 | aaatgtagttcaccctgtagaga | AA020700 | 86630 | gtcactgtggctggttcctagttg | U30838 |
| 1423 | ttaaatgtacatctccaactgtc | W44163 | 44027 | atctgcctgcctgcacggactatg | AA020700 | 86631 | tggttatcagtgctgcgtgggcg | U30838 |
| 1424 | tttttcatgcgtcacacgaag | M84918 | 44028 | tgcctgcctgcacggactatgt | AA020700 | 86632 | ctaatgctcacgtatgtcagtta | U30838 |
| 1425 | agctgatcctgagtgcggcagggc | M84918 | 44029 | ttccggaccattccaggaggaagag | AA020700 | 86633 | atggctcacgtatgtcagttacag | U30838 |
| 1426 | tgatcctgagtgcggcaggc-gctct | M84918 | 44030 | gaagtcatcatccgtgaacaacaaag | AA020700 | 86634 | acagattgccagctcagggtctaat | U30838 |
| 1427 | ttcctttcctcatagcagggtg | M84918 | 44031 | gtcatcatccgtgaacaacaaagt | AA020700 | 86635 | gattgccagctcagggtctaatctt | U30838 |
| 1428 | ttgttgtcacttctcgagcct | M84918 | 44032 | atcatcctgaacaacaaagagtgtg | AA020700 | 86636 | tgccagctcagggtctaatcttct | U30838 |
| 1429 | acagttgcggaaggccactcaggc | M84918 | 44033 | atcctgaacaacaaagagtgtgaca | AA020700 | 86637 | gtctaatcttctggtctaatactt | U30838 |
| 1430 | ggaaggccactcaggtcaggtgta | M84918 | 44034 | tgtgacaattctaccacaacttcaca | AA020700 | 86638 | caaatcctgtgtcctagcataa | U30838 |
| 1431 | ttatctccaggcatgctgtagt | M84918 | 44035 | gacacattctaccacaacttccaca | AA020700 | 86639 | cctgtgtccctagcataatccag | U30838 |
| 1432 | tctcccaggcatgctgtgtgtgca | M84918 | 44036 | gaggacaccaccagggagaagtct | AA020700 | 86640 | cctagcataatccacgaggtcttg | U30838 |
| 1433 | cccaggcatgctgtagtgcaaca | M84918 | 44037 | gacaccaccagggagaagttctgct | AA020700 | 86641 | atccacgaggtcttgagattacaa | U30838 |
| 1434 | atttcctcaagctggcgagtcaggtg | M84918 | 44038 | ttctgctatagagtcaactcgtaact | AA020700 | 86642 | ttatcagtgctgccgtgctgggcc | U30838 |
| 1435 | tttcatgcggctcacagcgaaggcc | M84918 | 44039 | tgaaggaccattccgcgtcactg | AA020700 | 86643 | gttaaatgctaccaccatgat | U30838 |
| 1436 | gctcacggaaggccactgcact | M84918 | 44040 | aaggaccatccccgtcgactgta | AA020700 | 86644 | aaatgctaccaccatgatgaa | U30838 |
| 1437 | cacaggaaggccactgcactcg | M84918 | 44041 | catccccgtcgactgctgtg | AA020700 | 86645 | tgtgctaccaccatgtgaaaa | U30838 |
| 1438 | gaaggccactgcactctgcgca | M84918 | 44042 | ggacttccaaggctgacgaccgcat | AA020700 | 86646 | ttatgaaaacgtgccatgtgtgc | U30838 |
| 1439 | acctcactggccagctgatcct | M84918 | 44043 | atgtgcctcagttcggaccattc | AA020700 | 86647 | tattcaccatcattgaataactt | U30838 |
| 1440 | tcactgggcagctgatcctga | M84918 | 44044 | tggctcagtcggaccaattcag | AA020700 | 86648 | gtaacccaaacatgacaaattat | U30838 |
| 1441 | ctggccagctgatcctgagtg | M84918 | 44045 | cctcagtccggaccattcaggaga | AA020700 | 86649 | accccaacatgacaaatatgat | U30838 |
| 1442 | cagagctgatccgtgagtcgcagg | M84918 | 44046 | cagttccggaccattccaagaagg | AA020700 | 86650 | cccaagccacagcagtgtacaaggt | U30838 |
| 1443 | gtttgcaacagcgacaattga | D14552 | 44047 | gctaacccagtcctgccaacagga | D63644 | 86651 | tctcgagttcgccgtcgttgg | M33934 |
| 1444 | aattgacatccaaacaaaggaat | D14552 | 44048 | cccagtctgccaacagggactcag | D63644 | 86652 | gagttccggagcagtgcaggacaa | M33934 |
| 1445 | tctgcaggttaccatggccgc | D14552 | 44049 | gaggacttgcgacctgcat | D63644 | 86653 | tcgttcctacctgattgctggcat | M33934 |
| 1446 | gggacgttaccatggccgctgatgt | D14552 | 44050 | ggcatgctccccatttctgagt | D63644 | 86654 | tgattgctggcatccagcatttcctg | M33934 |
| 1447 | ctgatgctcctaaagcatccagcg | D14552 | 44051 | ccatttctgagttctagtcaggcaa | D63644 | 86655 | ctggcatccagcattcctgcaaga | M33934 |
| 1448 | aagccatccagtgcgataatgcccca | D14552 | 44052 | ggcttactgcccagcgctatta | D63644 | 86656 | tccagcattcgtcagacattgg | M33934 |
| 1449 | tgaccagcagggtgaaactctcgga | D14552 | 44053 | tactgccagacgtcattatcagc | D63644 | 86657 | attccgtcagacgtcattgccaa | M33934 |

| SEQ ID NO | sequence | DBAxnID | SEQ ID NO | sequence | DBAxnID | SEQ ID NO | sequence | DBAxnID |
|---|---|---|---|---|---|---|---|---|
| 1450 | tcatcagcaggctgaggatgacaa | D14552 | 44054 | ccagaagcctattatcatgccataga | D63644 | 86658 | agagttaaccaagctcaggcat | M33934 |
| 1451 | atgacaacggtaccagcagagacat | D14552 | 44055 | gctattatcatgccatagatgccca | D63644 | 86659 | taaccaagtcagccatgacgta | M33934 |
| 1452 | tctttgggtcaccctcaggacata | D14552 | 44056 | tggacatgcatcacctggctcaa | D63644 | 86660 | acagcctccattgtacgagaacg | M33934 |
| 1453 | accgcctatagatcgagtccatcgc | D14552 | 44057 | tggcactccatggctctaaccaca | D63644 | 86661 | aacagatccagtatatgccttgaat | M33934 |
| 1454 | ttagatctgagtccatcgcctccat | D14552 | 44058 | taaatccattgaataatcatt | D63644 | 86662 | gctttggtccgtcgtatgctga | M33934 |
| 1455 | acatcccaacacaaaggaatgaatcc | D14552 | 44059 | aacaggactccaggtttgctgaga | D63644 | 86663 | gtgttcgttattgctgatgagg | M33934 |
| 1456 | ttctgtcttcgggtgtgacaatc | D14552 | 44060 | tcccaggtcagccagcagcatcacg | D63644 | 86664 | atattgccaaagcttggctcttgg | M33934 |
| 1457 | tagatcatatcacagagagagagaac | D14552 | 44061 | tcgcaacagccgcctggccagactg | D63644 | 86665 | ctcttggggcttccacgtcatgat | M33934 |
| 1458 | aggagacctgcaggccaagaagaacaa | D14552 | 44062 | cagcagcctggccagacgaagtt | D63644 | 86666 | gggcttccacagtcatgatgggctc | M33934 |
| 1459 | ccctgcaggccaagaacaagggcgt | D14552 | 44063 | ttccaggacatgctaccatgccgg | D63644 | 86667 | tggacaaacatctcagcagccagaa | M33934 |
| 1460 | aggaacagctgccgagtcgtgta | D14552 | 44064 | gacatgctaccccatgccgggcgacc | D63644 | 86668 | aacatcagcagcagcagaaccgata | M33934 |
| 1461 | gccatatttaatgctcgcggggacgt | D14552 | 44065 | ccgagcaggggactggcaactata | D63644 | 86669 | gccagaaccgatactacagtgaagc | M33934 |
| 1462 | ttatgtctgcgggagacgttaccat | D14552 | 44066 | actggcaactataacatcgaggact | D63644 | 86670 | ctgacgttgcagccctgctcgatg | U30840 |
| 1463 | gaacaagccaatgctcatctcacca | M74753 | 44067 | atgggaacatcgctccatacacct | D63644 | 86671 | tgtcagccctgctcgatgccagaa | U30840 |
| 1464 | caagccaatgctcatctcaccaagt | M74753 | 44068 | gctccatacaccttcaggtggtag | D63644 | 86672 | agcccctgtagatgccaggctac | U30840 |
| 1465 | agccgatgtgtgggtccatgaaaacg | M74753 | 44069 | gatgtcaccaaaatgctgtgttag | D63644 | 86673 | atctgatccagtcccagatgaaa | U30840 |
| 1466 | tgagcaagaccctcctggtcaggc | M74753 | 44070 | gaagccaagctctagcacactatata | D63644 | 86674 | atccagtcccagatgaaagttgga | U30840 |
| 1467 | agacctcctggtcagggcagagaga | M74753 | 44071 | tggatccgagtcgtaccaagctt | D63644 | 86675 | attgtgactccgacctgcgaacc | U30840 |
| 1468 | cctcctgtcagggcagaagatat | M74753 | 44072 | cgagtctggtaccaagcttgatgca | D63644 | 86676 | acttcccgcatcgaaccctgtg | U30840 |
| 1469 | ttcgtggctctgacaattctactt | M74753 | 44073 | cggtaccaagcttgatgcatagctt | D63644 | 86677 | ccgcatcgaaccctggtgtcaga | U30840 |
| 1470 | gctcgtgcaattctactaattc | M74753 | 44074 | ttcatagtgtcacctaaaatagct | D63644 | 86678 | gtccagatcctatctggaaac | U30840 |
| 1471 | ccagtatcactttccacatgcaa | M74753 | 44075 | ataggtggtaatcatcaggtcata | D63644 | 86679 | atccatctgtcgaagcatgtac | U30840 |
| 1472 | cgtatcactttccacacatgcaataa | M74753 | 44076 | attgttatccgctccacatccaca | D63644 | 86680 | ccacctggtgaaaggagatgttt | U30840 |
| 1473 | ttcactttccacacatgcaataaagt | M74753 | 44077 | tcacaattccacacaacatagagc | D63644 | 86681 | ttagactgatcctcacacctgtc | U30840 |
| 1474 | aatgctcactccaagttgcct | M74753 | 44078 | aagcctcagctaatgaatgagagc | D63644 | 86682 | gccctgctgatgccaagaacgttca | U30840 |
| 1475 | aatgctcatctcaccaagttcagga | M74753 | 44079 | tacacctgcaggtgtagcatg | D63644 | 86683 | ggtggccacagttggccctggccagga | U30840 |
| 1476 | gctcatctcaccaagttcaggaaag | M74753 | 44080 | tggaccaaacagccagagctacct | D63644 | 86684 | cacagttggccctggccagactgaat | U30840 |
| 1477 | cctctgcacgttctcaggacactg | M74753 | 44081 | caaacgccagactaccttatccc | D63644 | 86685 | tgccaggtacctcagaatt | U30840 |
| 1478 | aagcccagcatgctgagctagaagag | M74753 | 44082 | tccctgcacgttactgcggggactg | D63644 | 86686 | atagctacctcagaatttagcta | U30840 |
| 1479 | atcgcaagaatcgcaagctcaataaac | M74753 | 44083 | gacatgtacctgggggactggtcagt | D63644 | 86687 | ttagactccaggtacagcagaaccc | U30840 |
| 1480 | gcaaagaccccgtgactcacctca | M74753 | 44084 | tcccctcttcagatcaaattat | D63644 | 86688 | ccattcagagggtacagcagaaacc | U30840 |
| 1481 | acctcacctctagcccggatggtg | M74753 | 44085 | tctctcagatcaaattcattcaagg | D63644 | 86689 | gaacaggaaaccccattccagaa | U30840 |
| 1482 | acctcagccgaatgctggttggtccatg | AA166601 | 44086 | ttaaaagatgtcaccacaaatgctg | D44443 | 86690 | gaattatgaaccaccaacaaccagge | AA107752 |
| 1483 | attaaacagagcgcatcatcgctg | AA166601 | 44087 | agaattccattacgacataatctg | D44443 | 86691 | ttatgaaccaacaaccagccat | AA107752 |
| 1484 | ttaaacagagcgcatcatcgctgag | AA166601 | 44088 | ccatacgacataatctcatgaa | D44443 | 86692 | aatcctgggcctgtggaaactac | AA107752 |
| 1485 | attcatactgacagttcagttagt | AA166601 | 44089 | ataacaactgatcaggatagtagta | D44443 | 86693 | atcctgggctgctgaaactcact | AA107752 |
| 1486 | tcatcactgacagttcagttgtc | AA166601 | 44090 | acactgacgatgatgatgtagtgatag | D44443 | 86694 | tgctgaaactcactgaagattg | AA107752 |
| 1487 | atcactgacagttcagttagtt | AA166601 | 44091 | gtagtgatagcccaccagtagccttaa | D44443 | 86695 | gaaactcactgaagattcgaactt | AA107752 |
| 1488 | atatgaccaacagatagaagattct | AA166601 | 44092 | atagcccaccagcagtagccttaacaa | D44443 | 86696 | gatcgaacttttctagtggccgcg | AA107752 |
| 1489 | atgaccaacagatagaagattccta | AA166601 | 44093 | gcctttaacacagctctcagacca | D44443 | 86697 | tcgaactttcttagtggccgagcga | AA107752 |
| 1490 | attcctacagagagcaagctcggtt | AA166601 | 44094 | acacagtctctcagacagatttt | D44443 | 86698 | gaactttctgagactgctgatatt | AA107752 |
| 1491 | tagattgcaacagtcatgctgga | AA166601 | 44095 | acagtctctcagacagagttttgc | D44443 | 86699 | ctgagcgattgacactgctgatatt | AA107752 |
| 1492 | gattgccaacagtcatgctggga | AA166601 | 44096 | acgtctctcagacagagtttggc | D44443 | 86700 | gcgattgacactgctgatattaca | AA107752 |
| 1493 | ttgccaacagtcatgctggaagatc | AA166601 | 44097 | gtctctcagacagagtttggcatc | D44443 | 86701 | caagccccattcaggtgattattctg | AA107752 |
| 1494 | tgccaacagttgcatgctggagatct | AA166601 | 44098 | tctcagacagagtttgcatcgt | D44443 | 86702 | tatgaaccaacaaccaggccatt | AA107752 |
| 1495 | acagagttgcatcgctggaagtaca | AA166601 | 44099 | tacgacataatcgtcattgaacaa | D44443 | 86703 | atgaaccaacaaccaggccatg | AA107752 |
| 1496 | gccaacagttgcatgctggagatcct | AA166601 | 44100 | tgcatagttatccagctttggtacc | D44443 | 86704 | tgaaccaacaaccaggccatga | AA107752 |
| 1497 | agagcgcatcatcgctgtgtacaag | AA166601 | 44101 | ttaaagtgcctcgatcaaggatacag | D44443 | 86705 | cacaacaaccaggccattgaaaat | AA107752 |
| 1498 | agcgcatcatcgctgtgtacaagt | AA166601 | 44102 | aagtgcctcgatcaaggatgaccc | D44443 | 86706 | ccaacaaccaggccattgaaatg | AA107752 |
| 1499 | cgcatcatcgctgtagtacaagctag | AA166601 | 44103 | gggcaatagacaccaatccgaagga | D44443 | 86707 | agttgagcaggaatcctggggctgct | AA107752 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 1500 | gtacaagctagtagtcctggtgt | AA166601 | 44104 | caatagacccaatccgaaggaaga | AA020683 | 86708 | gaagcgaatccggggcgctgaa | AA107752 |
| 1501 | acaagctagtagtcctggtggtiga | AA166601 | 44105 | acaccaatccgaaggaagaatgcgct | AA020683 | 86709 | aagcgaatccggggcgctgtgaaa | AA107752 |
| 1502 | aagctagtagtcctggtgtgata | AA166601 | 44106 | atgcgctgctactgccaaagaa | AA020683 | 86710 | aacttcaatgcaggaggccacaag | U30839 |
| 1503 | gaattcatcactgacagttcagtta | AA166601 | 44107 | cgctgcgtgctactgccaaagaa | AA020683 | 86711 | tagagatcactgtccctgcgaaat | U30839 |
| 1504 | aatggtactctcaagtcatcacaa | W46084 | 44108 | atacaatgattttcacgtgttgt | AA020683 | 86712 | tgtcctcagccaacaacgtagtgtc | U30839 |
| 1505 | actctcaagtcatcacaaagtccga | W46084 | 44109 | tggtaatctcctctagtttgct | D78644 | 86713 | tcagcaacaacgtagtgtcatgtta | U30839 |
| 1506 | ttctttgacgctgagatcaagaagc | W46084 | 44110 | tagacatttctattgcttctaaata | D78644 | 86714 | cccgtcgtacaccgtgcctgca | U30839 |
| 1507 | gaactgctactccccatattagt | W46084 | 44111 | tcttcctatgctacagtta | D78644 | 86715 | tcctgcatgtccagtccactttc | U30839 |
| 1508 | ctgctactccccatattagtgtc | W46084 | 44112 | ttccctatgctacagttaatc | D78644 | 86716 | atgtccagtccagtccactttccatgg | U30839 |
| 1509 | ctactcccccatattagtgtctca | W46084 | 44113 | gttaatctattgccatcctga | D78644 | 86717 | cagtccactttccatggcctttg | U30839 |
| 1510 | ctcccatattagtgtcaggctgc | W46084 | 44114 | aatcttattgccatcctgaacca | D78644 | 86718 | tgtgccacattcagttgatatcagct | U30839 |
| 1511 | cccatatttagtgtcaggctgc | W46084 | 44115 | cttattgccatcctgaaccaca | D78644 | 86719 | gttatatcagctctgctactgaa | U30839 |
| 1512 | catatttagtgtcaggctgcgt | W46084 | 44116 | attgccatcctgaaccacaaatg | D78644 | 86720 | tcagtctgcctagtgaaggct | U30839 |
| 1513 | atttagtgtcaggctgcgtttaga | W46084 | 44117 | tgccatcctgaaccacaaatgtgt | D78644 | 86721 | tctgtctagtgagctgtttgtt | U30839 |
| 1514 | taggtctcaggctgcgttagaga | W46084 | 44118 | catccctgaacacaaatgtgtatt | D78644 | 86722 | atcactgcctgaaatgaagag | U30839 |
| 1515 | tgtctcaggctgcgttagagaaaga | W46084 | 44119 | ccctgaaccacaaatgtgtatttag | D78644 | 86723 | cttcccacacgtgaagtctagagatt | U30839 |
| 1516 | ctcaagtcatcacaaagtccgagta | W46084 | 44120 | tatatctcctaggtttgctga | D78644 | 86724 | tacagatcatccaatggagatgct | U30839 |
| 1517 | aagtcatcacaaagtccgagtatga | W46084 | 44121 | caltcttttctaaagaccgctgct | D78644 | 86725 | aattgtcatgtttgccacattc | U30839 |
| 1518 | tcacaaagtccgagtatgatgaat | W46084 | 44122 | tcttttctaaagaccgctgtctgc | D78644 | 86726 | catgttttgccacattcagtga | U30839 |
| 1519 | ctgcgtcgtactcactgggagt | W46084 | 44123 | ttttctaaagaccgctgtctgtcgtg | D78644 | 86727 | tgtgccacattcagttgatgtctg | U30839 |
| 1520 | cgtactctcatcgtgggagtccatta | W46084 | 44124 | aagaccgctgcttgctataagctac | D78644 | 86728 | acatttcagttgatgtctgcagagt | U30839 |
| 1521 | tccattaaaggactctttgacgctg | W46084 | 44125 | acgcgtctcttgctatagctactaa | D78644 | 86729 | taaatatgtcctcagcaacaacgt | U30839 |
| 1522 | attaaggactctttgacgctgaga | W46084 | 44126 | ctataagctctaacgcggcattgg | D78644 | 86730 | gtagctttccaaccagcctgagg | U30839 |
| 1523 | aaggactctttgacgctgagatca | W46084 | 44127 | gttaacaacctgtgggcctgtga | D78644 | 86731 | ttctcaaccagcctgagggntct | U30839 |
| 1524 | cctaagtccacatctgctcaggc | W46084 | 44128 | acgaattccaggtgcctgagcag | AA020714 | 86732 | atccagttgccgaaggaaccgagc | U52461 |
| 1525 | ttcgtcctggcgaattcctg | L00923 | 44129 | gaattccaggtgcctgagcagt | AA020714 | 86733 | gaccagcagccgtggaagctgccca | U52461 |
| 1526 | gaccctgatgtgcaacagtgtatcc | L00923 | 44130 | agatccaagatcggcagcgtgta | AA020714 | 86734 | atgttctactcttcctcagcagct | U52461 |
| 1527 | gcacagtgatcacaccccaggtcat | L00923 | 44131 | atcaccccagaagatcggcagtcag | AA020714 | 86735 | tactcttcctcagctagcag | U52461 |
| 1528 | ttagctttgaaactgcatgaaag | L00923 | 44132 | caccccagaagatcgggcgtgcacg | AA020714 | 86736 | gttctcccaaggacagacataagccacg | U52461 |
| 1529 | agccgttcagactgggagatctctct | L00923 | 44133 | agatcgcgtgcacgttccagca | AA020714 | 86737 | gacataagcacgctctcgagct | U52461 |
| 1530 | cgttcagactgggagatctctct | L00923 | 44134 | gcgtcacgcgttcagcagcgtct | AA020714 | 86738 | tggctccaccaactgcagaagcaga | U52461 |
| 1531 | tggcagatctcttgatgtgca | L00923 | 44135 | acgcgtccagcagcgtctggct | AA020714 | 86739 | caccaactgcagaagcagatgacg | U52461 |
| 1532 | cagatcttcttgatgtgcaata | L00923 | 44136 | tcgttcagcagcgtctggctgtgt | AA020714 | 86740 | catttcatatggcgtgaaggctg | U52461 |
| 1533 | atcttcttgatgtgcaataaaa | L00923 | 44137 | aaatgcgacgaacctgaacatcc | AA020714 | 86741 | gcaacactgccaattaaagttcag | U52461 |
| 1534 | acatccaagatcgttcagaagtt | L00923 | 44138 | atgcgacgaacctgaacatctg | AA020714 | 86742 | aaccagcgagggagtctccatca | U52461 |
| 1535 | tgttctctattggaggataaatgt | L00923 | 44139 | caggtgccgagcagctccagt | AA020714 | 86743 | gagtctccatcaacgtcattgctg | U52461 |
| 1536 | cattaaacatacatcattatgttca | L00923 | 44140 | gcggaacctgaactgaacaactggt | AA020714 | 86744 | cccaaatcaaatagcccatcataa | U52461 |
| 1537 | ttaaacatacatcattatgttca | L00923 | 44141 | acgcatttcataactgacct | AA020714 | 86745 | tcaaataagccatcataagcctga | U52461 |
| 1538 | aacatacacatttatggttcagat | W46087 | 44142 | cgcggtcagctccatgcggtca | AA020714 | 86746 | aagccatataagcctgacatttct | U52461 |
| 1539 | tattgttcagatcgtttcacct | W46087 | 44143 | tgagcagtccatgtggtgtcaga | AA020714 | 86747 | agcctgacattctctgatgcc | U52461 |
| 1540 | gtcactgaacagggctgtagaatg | L00923 | 44144 | agcagtccatgtggtgtcaga | AA020714 | 86748 | acatttctcggatgccaccatt | U52461 |
| 1541 | aatgtttctccgttcccagagaa | L00923 | 44145 | catgtcggttcagatgaagagc | AA020714 | 86749 | gatgccaccattgtacactgcca | U52461 |
| 1542 | gcttgttccgttccagaagca | L00923 | 44146 | agggccagattccaccccgaagatcgg | AA020714 | 86750 | tgtcctacatcttctacaacggga | AA107742 |
| 1543 | agatggacctgatgtgcacagt | L00923 | 44147 | gcgcagatcacccagaagatcgcg | AA020714 | 86751 | gtcctacatcttttacaactggccaag | AA107742 |
| 1544 | ctgtagactctcagtccagcca | W46087 | 44148 | caggatcacccagaagatcggcgg | AA020714 | 86752 | aacgcagtcgaacactcggccaac | AA107742 |
| 1545 | actgcttccgtttccagaagacat | W46087 | 44149 | acgcattttccataactgacct | U58471 | 86753 | acgcagtggaacactggccaac | AA107742 |
| 1546 | cctacagctactctcttgcctc | W46087 | 44150 | cgcggtgttccagctcccgagc | U58471 | 86754 | caggtggaacactggccaacgtg | AA107742 |
| 1547 | tacagctactctctttgcctccaa | W46087 | 44151 | ctccctctccgtggagagcatct | U58471 | 86755 | aggcgaacactcggccaacgtag | AA107742 |
| 1548 | agctactcttttgcctccagaa | W46087 | 44152 | caagactcctccacattccaa | U58471 | 86756 | gtgcgaacactggccaacgtgaga | AA107742 |
| 1549 | ttcctttgcctccagaagtca | W46087 | 44153 | acctccaacgccagagagttgg | U58471 | 86757 | gcgaacactggccaacgtgagag | AA107742 |

TABLE 1-continued

| SEQ ID NO | sequence | DBAxnID | SEQ ID NO | sequence | DBAxnID |
|---|---|---|---|---|---|
| 1550 | tctttgcctccaagaaagtccagtc | W46087 | 44154 | cctccaacaggccagagagttggt | U58471 | 86758 | cgaacactcggccaacgtgagaagt | AA107742 |
| 1551 | ttgcctccaagaaagtccagtcga | W46087 | 44155 | tccaacaggccagagagttggtaa | U58471 | 86759 | gaacactcggccaacgtgagaagtc | AA107742 |
| 1552 | aagtccagtcggatggccagatgt | W46087 | 44156 | ccaacaggccagagagttggtaag | U58471 | 86760 | cactcggccaacgtgagaagtccac | AA107742 |
| 1553 | ctcatgaagctgcagcatgcatcac | W46087 | 44157 | ggtgctgactctcgggatagtgct | U58471 | 86761 | actcggccaacgtgagaagtccaca | AA107742 |
| 1554 | cagccctccgggctgagccatggaagc | W46087 | 44158 | gtgctgagtctcgggatagtgtctc | U58471 | 86762 | catctcttacaacgggaagacccag | AA107742 |
| 1555 | ccctccgggctgagccatggaagctct | W46087 | 44159 | caaacaacagacacagagcttcca | U58471 | 86763 | ggagtcatgtctcacgaatcgg | AA107742 |
| 1556 | gtccttcagcagccaagacatgaa | W46087 | 44160 | agttgtatctcttcctccgaag | U58471 | 86764 | gagcatgtctcaggaatcggt | AA107742 |
| 1557 | ctttcagccagacagtgaagta | W46087 | 44161 | agctctccagagccgggcgtgtct | U58471 | 86765 | tgcctgctcgagaacgcagtgcg | AA107742 |
| 1558 | ttagaaccgagccatctctgtaa | W46087 | 44162 | gagagccaagccaattgtaactag | U58471 | 86766 | ccctgctcgagaacgcagtgcgaa | AA107742 |
| 1559 | gaaccgagccatctctgctaaagg | W46087 | 44163 | gctctccagacgcggcgtgtctctt | U58471 | 86767 | ctgtctcgagaacgcagtgcgaaca | AA107742 |
| 1560 | gagccatctctgctaaaggcatgac | W46087 | 44164 | tctccagagcgggcgtgctcctac | U58471 | 86768 | tgtctcgagaacgcagtgcgaacac | AA107742 |
| 1561 | ccatctctgctaaaggcatgacctt | W46087 | 44165 | ctccagagcggcgtgctcttctacc | U58471 | 86769 | tctcgagaacgcagtgcgaacactc | AA107742 |
| 1562 | gcatgacctagtgaccccctaca | W46087 | 44166 | cagagcggcgtgctcttaccgt | U58471 | 86770 | agccggaacacggtgagatgtacga | AA107388 |
| 1563 | tgaccccctacgactcttcctt | W46087 | 44167 | gcttgcctcgggactcgcctct | U58471 | 86771 | acaatatctgaacagcctctca | AA107388 |
| 1564 | tgatatcaccacatgtgacatgc | W46087 | 44168 | ttgcctctgggactgcctctct | U58471 | 86772 | gcaaggtcacctcctggaaggcctcc | AA107388 |
| 1565 | atatcaccacatgttggacatgca | W46087 | 44169 | tgcctctgggactgcgcttctctc | U58471 | 86773 | ccaagaggctggtgtccaaggatga | AA107388 |
| 1566 | gagcactcctactggacatgcaa | W46087 | 44170 | aaatcagctccatacaacgctccg | U58471 | 86774 | actttgtgagtgttggttgtctgc | AA107388 |
| 1567 | gcactctactggagatccaatcga | W46087 | 44171 | ctgcgacagtccgtcactagga | AA021664 | 86775 | tgttggtgtcctgctgtcatggga | AA107388 |
| 1568 | actcctactggagatccaatcgaa | W46087 | 44172 | tccaagatcaacgcgagcaagaatc | AA021664 | 86776 | ttggttgtcctgctgtcatgggacc | AA107388 |
| 1569 | tcctactggagatccaatcgagatg | W46087 | 44173 | ccaagatcaacgcgagcaagaatca | AA021664 | 86777 | ttgtcctgctgtcatgggaccttgg | AA107388 |
| 1570 | ctactgggagatccaatcgagatgag | W46087 | 44174 | acagagtactgtctcgattggg | AA021664 | 86778 | cctgctcatggggactcttgggaa | AA107388 |
| 1571 | cgaacaagaaccagaccaaaagtt | W46087 | 44175 | cagagtactgtctcgattggga | AA021664 | 86779 | tgctgtcatggggacctttgggaaga | AA107388 |
| 1572 | caaagatacagcagccctaagata | W46087 | 44176 | gagtactgtctcgatttgggag | AA021664 | 86780 | ctgtcatggggacctttgggaagaag | AA107388 |
| 1573 | tatcagccctaagatacagagaa | W46087 | 44177 | tgtctcgatttgggaagttgaga | AA021664 | 86781 | ttgactttggaccttgtatgagt | AA107388 |
| 1574 | tcagcagccctaagatacagagaat | W46087 | 44178 | ttaaacaagatccagtcactgagg | AA021664 | 86782 | tattctgaacaagcctcccagttg | AA107388 |
| 1575 | agcagccctaagatacagagaagtt | W46087 | 44179 | acagatccagtcactggagatcaa | AA021664 | 86783 | gacttttgacctgtgattgagttc | AA107388 |
| 1576 | atcaccacacagttgacatgcaaga | W46087 | 44180 | cagatccagtcactggagatccaag | AA021664 | 86784 | ttctgaacaagcctctccagttgaa | AA107388 |
| 1577 | caccacatgttggacatgcaagaca | W46087 | 44181 | gatccagtcactggagatccaagag | AA021664 | 86785 | ctgaacaagcctctccagttgaaac | AA107388 |
| 1578 | agcacatgcaatcagtcatccaa | W46087 | 44182 | ccgacagtccgtcactgtgggaa | AA021664 | 86786 | gaacaagcctccagttgaaacca | AA107388 |
| 1579 | acagatccaatcaagtcatcaaag | W46087 | 44183 | atccagtcactggagatccaagaggg | AA021664 | 86787 | gcctcccagttgaaaccaatatt | AA107388 |
| 1580 | agactccaatcaagtcatcaaaacg | W46087 | 44184 | gacagctccgtcactatggaagata | AA021664 | 86788 | atattacaaactcgggcaaggcacct | AA107388 |
| 1581 | actcaatcaagtcatcaaaagcg'tg | W46087 | 44185 | acagctccgtcactatggaggat | AA021664 | 86789 | tacaaactcgggcaaggcacctcctg | AA107388 |
| 1582 | aagatagaagcactcctactggagat | W46087 | 44186 | agctccgtcactatgaggatga | AA021664 | 86790 | aactcgggcaaggcacctcctggaag | AA107388 |
| 1583 | gatagaagcactcctactggagatcc | W46087 | 44187 | gctccgtcactatgaggatgaa | AA021664 | 86791 | gtaccaggcattctgacaggatgc | AA107388 |
| 1584 | agatgtacctcagaaaccagaggt | W46087 | 44188 | aatttcagagggatccaagatcaa | AA021664 | 86792 | accaggcattctgacaggatgcag | AA107807 |
| 1585 | tgaaagcacaactcagtgactgac | W46087 | 44189 | ggatccaagatcaacgcgagcaaga | AA021664 | 86793 | ggcttaatgtccaactttcagcag | AA107807 |
| 1586 | tgagtatctatcctacgctcctga | W46093 | 44190 | gatccaagatcaacgcgagcaagaa | AA021664 | 86794 | aatcaggggcctgcattgtccaacc | AA107807 |
| 1587 | gtatctatcctacgctcctgaga | W46093 | 44191 | ctacgacctcctgggctccactat | S70056 | 86795 | ctgcattgccaacgaaatgcttc | AA107807 |
| 1588 | ccttacgctcctgagatcctctac | W46093 | 44192 | agctccgtgctactcttaggga | S70056 | 86796 | attgtccaacgaaatgcttcctga | AA107807 |
| 1589 | tacgctcctgagatcctctacgat | W46093 | 44193 | agaatactgcatgccgtcaccagc | S70056 | 86797 | tgccaacgaaatgcttcctgaag | AA107807 |
| 1590 | gctctcgagatttcctccacgatcag | W46093 | 44194 | gcctatctgggctgggtctc | S70056 | 86798 | tccaacgaaatgcttcctgaagga | AA107807 |
| 1591 | gagatcctcctacgatcagaagtat | W46093 | 44195 | tcctgctgtggcttccatgtatg | S70056 | 86799 | atgcttccgaaggacctaacaat | AA107807 |
| 1592 | attcctctacgatcagaagtactgac | W46093 | 44196 | ggtcacccatcaaatgcttcatggt | S70056 | 86800 | gcttcctgaaggacctaacaagtgc | AA107807 |
| 1593 | ctcctacgatcagaagtactccatgtg | W46093 | 44197 | ccatcaaatgcttcatggtccactac | S70056 | 86801 | aaggacctaacaagtgccagaaat | AA107807 |
| 1594 | gtcactgccttctgttttgggtg | W46093 | 44198 | aatgcttcatggtcactatgtttg | S70056 | 86802 | ggacctaacaagtgccagaagttg | AA107807 |
| 1595 | gcctctgttttggagttgccagt | W46093 | 44199 | tgttaagacctgctgcttggttt | S70056 | 86803 | ccagccatctgacaggatgcagaa | AA107807 |
| 1596 | cacaacttcagtgactgacttacta | W46093 | 44200 | gaccctgctgctttgtcatag | S70056 | 86804 | gcatttctgacaggatgcagaggag | AA107807 |
| 1597 | ttcagtgactgacttactaaactac | W46093 | 44201 | ttcatagtatctttaacctgagtaa | S70056 | 86805 | aggagatcacagcctagccacctagc | AA107807 |
| 1598 | tgacttactaaactacttttctg | W46093 | 44202 | gtatcttaacctgagtaaatctg | S70056 | 86806 | gagatcacagcctagccactgcac | AA107807 |
| 1599 | tgacttactaaactacttttctggct | W46093 | 44203 | gcctgctacttcttaggagtcacc | S70056 | 86807 | gatcacagcctagccactagcacga | AA107807 |

| SEQ ID NO | sequence | DBAxnID | SEQ ID NO | sequence | DBAxnID | SEQ ID NO | sequence | DBAxnID |
|---|---|---|---|---|---|---|---|---|
| 1600 | ctttctggctccagaggtcttact | W46093 | 44204 | cctcagccatggctgtcttgggcc | S70056 | 86808 | tcacagctagactcagcaagatg | AA107807 |
| 1601 | ggctccagaggttcttactgggag | W46093 | 44205 | ccatgctgtcttggccctgaaga | S70056 | 86809 | gtgggtccaatctgggcttaatgtc | AA107807 |
| 1602 | gaaccaatactactgtgaagctgt | W46093 | 44206 | actaatgtcatctcagtctgtaagc | S70056 | 86810 | gtccaatctgggcttaatgtccaac | AA107807 |
| 1603 | gcaaatcacgcagagagcctgagtat | W46093 | 44207 | tcagtctgtaagccctgtaagtc | S70056 | 86811 | tggagctactgcctgccccagga | |
| 1604 | ttcccaaagttggaagccaagtcat | M33212 | 44208 | cctctgaaagcttcggcaaaatg | S70056 | 86812 | tggcacccaagaaggccaagaag | |
| 1605 | aattgttccggatgactgaccagg | M33212 | 44209 | ctccagtcagcttcctaacattt | S70056 | 86813 | atcttcggacacttgcagccat | |
| 1606 | atctctggcagtggaagactctc | M33212 | 44210 | gtcagcttcctaacattttgaga | S70056 | 86814 | ccatggccgtcaatgtgaagaa | |
| 1607 | ctgtctcattctgtaatagtaa | M33212 | 44211 | aagcccacatttgaggtggctcat | AA021692 | 86815 | tgggccgtcaatgtgaagaatga | |
| 1608 | gtctcattctgtaatagtaata | M33212 | 44212 | aagcccacatttgaggtggctcatc | AA021692 | 86816 | atgaggaactgacgctatgatgaa | |
| 1609 | tgagaacttcctactgtgttga | M33212 | 44213 | gcaagacatacattccactaggt | AA021692 | 86817 | aactgacgctatgatgaaggaagc | |
| 1610 | cttccctactgtgtttgataaatg | M33212 | 44214 | caagacatacattccactaggtc | AA021692 | 86818 | aagcagtgggccatcaacttcac | |
| 1611 | ttccctactgtgtttgataaatg | M33212 | 44215 | agacatacatttccactatgtgcg | AA021692 | 86819 | ccagtggccatcaacttcactgt | |
| 1612 | tcccctactgtgtttgataaaatgt | M33212 | 44216 | catacatttccactatgtcggtt | AA021692 | 86820 | ggcccatcaactcactgtcttcct | |
| 1613 | tccctactgtgtttgataaaatgtg | M33212 | 44217 | acatttccactatggtcggttcag | AA021692 | 86821 | ccatcaactcactgtcttcctgac | |
| 1614 | algcctgttagttcaaggatgg | M33212 | 44218 | cattccactatggctcggttcagg | AA021692 | 86822 | tcaacttcactgtcttcctgaccat | |
| 1615 | tgcctgttagttcaaggatga | M33212 | 44219 | ttccactatggctcggtttcaggaat | AA021692 | 86823 | aagggagctcaacgtctctccat | |
| 1616 | atgtttccggatgactgaccagga | M33212 | 44220 | aaaatctgacgtcaatgcaattatcc | AA021692 | 86824 | ggagtcaacgtctctccatgtt | |
| 1617 | gttccggatgactgaccaggaggc | M33212 | 44221 | atctgacgtcaatgcaattatccat | AA021692 | 86825 | ccaagtctctccatgtttgacca | |
| 1618 | ttccggatgactgaccaggaggcta | M33212 | 44222 | cgtcaatgcaattatccattattta | AA021692 | 86826 | acgtcttccatgtttgaccagac | |
| 1619 | tccggatgactgaccaggaggctat | M33212 | 44223 | gcccacattgaggtcatctcta | AA021692 | 86827 | tctctccatgtttgaccagactca | |
| 1620 | atgactgaccaggaggctattcaag | M33212 | 44224 | attgaggtggctcatctagaacctg | AA021692 | 86828 | tgtttgaccagactcagatccagga | |
| 1621 | aggctattcaagatctctggcagtg | M33212 | 44225 | ggtggctcatctagacctgccaaga | AA021692 | 86829 | ttgaccagactcagatccaggagtt | |
| 1622 | gctattcaagatctctgcagtga | M33212 | 44226 | gtgctcatctagacctgccaaga | AA021692 | 86830 | aggatctgggacacttcgagc | |
| 1623 | atccagatctctcgcagtgga | M33212 | 44227 | gctcatctagacctgccaagaatgt | AA021692 | 86831 | tggagctactgcctgccccaga | |
| 1624 | actactaatgtctctcctgtgg | L30104 | 44228 | tcatctagacctgccagaatgtat | AA021692 | 86832 | gggagctactgcctgccccagga | |
| 1625 | gacgatgacttctcttcagtgaca | L30104 | 44229 | catctagacctggcaagaatgtata | AA021692 | 86833 | ggcacccaagaaggccaagaaag | |
| 1626 | cccatcgcaacgcagtggccacg | L30104 | 44230 | tctagacctggcaagaatgatata | AA021692 | 86834 | gcacccaagaaggccaagagaaagg | |
| 1627 | ttgcaacgcgtggccacggagagt | L30104 | 44231 | taatactttcaaagttctcacaag | Z37164 | 86835 | taagacatggcacccaagaaggcca | |
| 1628 | acacacaaagatgcattaaaca | L30104 | 44232 | caaagttctcacaaggatgaagctgt | Z37164 | 86836 | aagacatggcacccaaggaaggccaa | |
| 1629 | gatccaaagtggctgcctggaga | L30104 | 44233 | tgaagtccctgctgtaagagatag | Z37164 | 86837 | agacatggcacccaagaaggccaag | |
| 1630 | aatctgatccaattccaaggttg | L30104 | 44234 | ggctattaaacttggccactaatgct | Z37164 | 86838 | gacatggcacccaagaaggccaaga | |
| 1631 | aaggttgcactcactactcaaga | L30104 | 44235 | tattaaacttggccactatgtgca | Z37164 | 86839 | acatggcacccaagaaggccaagag | |
| 1632 | cagtactcaagaaccatctctact | L30104 | 44236 | cactaatgctcagtcactactaga | Z37164 | 86840 | catggcacccaagaaggccaagaga | |
| 1633 | ttcaagaaccatctactgtctcca | L30104 | 44237 | taatgctgcagtcactactaaga | Z37164 | 86841 | atggcacccaagaaggccaagaga | |
| 1634 | aaccatctctactgtctccactaaa | L30104 | 44238 | tgcagtcactgtactaagagttggat | Z37164 | 86842 | tggcacccaagaaggccaagaagg | |
| 1635 | ccaagaccaagaatcgcaataaaca | L30104 | 44239 | agtcactgtactaagagttgatcag | Z37164 | 86843 | tggagctactgccttgccccagga | |
| 1636 | gactttctcagcgacaagacca | L30104 | 44240 | catcatggcaaaaccagctgggagg | Z37164 | 86844 | gggagctactgccttgccccagga | |
| 1637 | ctctcagcgacaagaccaagatg | L30104 | 44241 | tgtactctgcgggtgtacaataa | Z37164 | 86845 | ggcacccaagaaggccaagaagaag | |
| 1638 | actaccagttcaggctgctgtatg | L30104 | 44242 | actctgctgggtgtacaataaaatg | Z37164 | 86846 | gcacccaagaaggccaagaaggccaag | |
| 1639 | tcattccaggcctgcgacggttc | L30104 | 44243 | agttctcacagagggatacagtctt | Z37164 | 86847 | taagacatggcacccaagaaggccaa | |
| 1640 | ggctttccggatgcagttgacca | L30104 | 44244 | ggataaggctgttgacctgccggagt | Z37164 | 86848 | aagacatggcacccaagaaggccaa | |
| 1641 | ccggatgcagttgaccagcggcg | L30104 | 44245 | taaacaaatcacatatggagctg | Z37164 | 86849 | agacatggcacccaagaaggccaag | |
| 1642 | ttcttggctcacgaacaacctcc | L30104 | 44246 | aatcacatcatatggagacgtgt | Z37164 | 86850 | gacatggcacccaagaaggccaaga | |
| 1643 | tttgatccatcgcacgagtgg | L30104 | 44247 | agagacgtgtcctgggctgaacag | Z37164 | 86851 | catggcacccaagaaggccaagag | |
| 1644 | gagcagcagttgcactttgacag | M30514 | 44248 | gttgaagcgattccacgggcactg | Z37164 | 86852 | acatggcacccaagaaggccaagag | |
| 1645 | tgagcgagtctgttcaccaagccat | M30514 | 44249 | agcgattccacgcactgccagaa | Z37164 | 86853 | atggcacccaagaaggccaagaga | |
| 1646 | tcctccctgggccttggggaggtcgct | M30514 | 44250 | ttctggtgaaggccaatgaagtt | Z37164 | 86854 | tggcacccaagaaggccaagaagg | |
| 1647 | gctgagtgtcttctgtgggaatta | M30514 | 44251 | aagtcctggcaittgatctgaccgt | X84311 | 86855 | tggatttcagaacatcagttgcaa | |
| 1648 | aggcttccctgggaagatagagga | M30514 | 44252 | tggcattttgatctgaccgttcaac | X84311 | 86856 | cccaatctggcacctgattcac | AA107868 |
| 1649 | caccactgacttgacagtctga | M30514 | 44253 | cagaaacacttctgcattacgg | X84311 | 86857 | ctgattcacgcattgggtatgct | AA107868 |

TABLE 1-continued

| SEQ ID NO | DBAxnID | sequence | SEQ ID NO | DBAxnID | sequence | SEQ ID NO | DBAxnID | sequence |
|---|---|---|---|---|---|---|---|---|
| 1650 | M30514 | tgacttgagcagtctgataggc | 44254 | X84311 | atgagattgcctgcctgagtga | 86858 | AA107868 | tggattcacgcattgggtatggtc |
| 1651 | M30514 | cacttgaagcctcaagagctctgc | 44255 | X84311 | ctgccgaatgagctgcataaagc | 86859 | AA107868 | ggattcacgcattgggtatggctcc |
| 1652 | M30514 | ctaagagctctgcctttcctgatgt | 44256 | X84311 | acaaggcttgaagtaccctgcacgt | 86860 | AA107868 | gattcacgcattgggtatggctcct |
| 1653 | M30514 | gctcgtgcctttcctgatgcattga | 44257 | X84311 | tcatgagccgcctgagttcttcc | 86861 | AA107868 | ctcctacatagtctcggaagaactt |
| 1654 | M30514 | tttcctcgccatttgtaagatt | 44258 | X84311 | agccgcctgagttcttccctgca | 86862 | AA107868 | tcctacatagtctcggaagaactg |
| 1655 | M30514 | ctatatttctaactatgtatgta | 44259 | X84311 | ttggccacacagcaggcttgctct | 86863 | AA107868 | cgttcacatagtctcggaagaaggctatagctc |
| 1656 | M30514 | gagtcgtcttcctagccatgctctc | 44260 | X84311 | gcaggctgtctgaggttctgag | 86864 | AA107868 | cgttcacagagggcgtataggtcc |
| 1657 | M30514 | tcatctgtggcactgctggcatct | 44261 | X84311 | ggccaactaaggcagttgtacata | 86865 | AA107868 | gttcacagagggcgtataggtccc |
| 1658 | M30514 | ctgcdggcatctcctcatggccca | 44262 | X84311 | gtacataacaccttcacatgagaa | 86866 | AA107868 | ggcgctataaggtccccttgggtct |
| 1659 | M30514 | gcatctctcatggccactacaa | 44263 | X84311 | tcctccttcagtacctaaggcgtca | 86867 | AA107868 | atctggggcacactggattcacgca |
| 1660 | M30514 | tcctcatggccctactacaaccaagt | 44264 | X84311 | tgagcctctggaagtgaccgtt | 86868 | AA107868 | gggcacactggattcacgcattggg |
| 1661 | M30514 | tgcctgacctgccgtccccgaga | 44265 | X84311 | ttcctggaacgtgaccgttctgaa | 86869 | AA107868 | gggcacactggattcacgcattgggt |
| 1662 | M30514 | acctgccttgccagactgggtgaccga | 44266 | X84311 | aagctgaccgtctgaagtatct | 86870 | AA107868 | gcacactgcgattcacgcattgggta |
| 1663 | M30514 | cttgccagactgaggccaccaa | 44267 | X84311 | tgctgcagcagcttactgctggc | 86871 | AA107868 | cacactggattcacgcattgggtat |
| 1664 | AA168633 | atcacagccaaggtgcagtacatca | 44268 | X84311 | cttactgcctgcaaatatatgt | 86872 | AA107871 | acactggattcacgcattggtatg |
| 1665 | AA168633 | attcattactgccaggaaagtgtg | 44269 | X84311 | gacactctggccagaaaacacttgc | 86873 | AA107871 | cactggattcacgcattggtatgg |
| 1666 | AA168633 | caccaagtgctcgtcgtgtaccac | 44270 | X84311 | tctgaccgaaaacattgctgcatt | 86874 | AA107871 | actggattcacgcattggtatggc |
| 1667 | AA168633 | caattggctctgctcgtgtaccacgag | 44271 | X84311 | acgacagctgaccatcgtagtctc | 86875 | AA107871 | cagccagcaggtctggagcatat |
| 1668 | AA168633 | tggctctgtgtaccacgaggtc | 44272 | X84311 | cgcagctgaccatcgtagtctcgg | 86876 | AA107871 | cccagcaggtctggagcatagta |
| 1669 | AA168633 | tgtcgtaccacgaggtcatcaac | 44273 | X84311 | tacaccagtgatgatcaaggaatgc | 86877 | AA107871 | aacacaatgtgcgctggaaatga |
| 1670 | AA168633 | ccgtgtaccagaggtcatcaacgcc | 44274 | X84311 | tcaagaatgtgctggagagatgc | 86878 | AA107871 | acaatgtgcctggaaattgaatc |
| 1671 | AA168633 | gtaccacgaggtcatcaacgccatg | 44275 | X84311 | ggagatcatcgcaagcaagagtacat | 86879 | AA107871 | atgtgcctggaaatgaatctgc |
| 1672 | AA168633 | cgaggtcatcaagccatgcagtgc | 44276 | X84311 | agatcatcgcaagcaagagatcca | 86880 | AA107871 | ttctcaggggaaccatgggatcca |
| 1673 | AA168633 | ggtcatcaaagccatgcagtgcagg | 44277 | X84311 | atcattcgcaagcaagagtacatgc | 86881 | AA107871 | ctcagggaaccatggggatccatgc |
| 1674 | AA168633 | catcaacgccatgcagtcgcaggtgt | 44278 | X84311 | tacatcaagacagaccatgccatgcc | 86882 | AA107871 | aggaaccatggagaatccatgccgga |
| 1675 | AA168633 | cgccatcagtgccaggtgcagtgtg | 44279 | X84311 | acgagcatggcctacacatgtagat | 86883 | AA107871 | gaaccatggagaatccatgccgggag |
| 1676 | AA168633 | aagtgccagcaaaagctgtgatact | 44280 | X84311 | ggcctacatcgtagatgctttaac | 86884 | AA107871 | ccatggagaatcatggcgagacgat |
| 1677 | AA168633 | tgtgccaggcaaaagctgtgactccca | 44281 | X84311 | cctacatctagatgctttaaccg | 86885 | AA107871 | atgggatccatgcgggagacgat |
| 1678 | AA168633 | aaagctgtgatactccattgacatcg | 44282 | X84311 | gatgctttaacgctagtatagacgct | 86886 | AA107871 | ggatccatgcggagacgatcaaaa |
| 1679 | AA168633 | gctgtgtatactcattgacatcgag | 44283 | X84311 | agctgaccatcgctggagat | 86887 | AA107871 | acagggcctggacattacgcattgtagac |
| 1680 | AA168633 | gtgtactccattgacatcgagatg | 44284 | X84311 | gtatagacgctacgtaggtggtga | 86888 | AA107871 | agtctggagcatatgagacatt |
| 1681 | AA168633 | gcctgcactgcaccaatggctct | 44285 | X84311 | gacatcgtagtctcggagatgcta | 86889 | AA107871 | atatgtagacatttccgaacacaa |
| 1682 | AA168633 | ctgcactgcaccaatggctctgtc | 44286 | X84311 | ccatcgtagtctcggagatctata | 86890 | AA107871 | tgtagacatttccgaacacaatg |
| 1683 | AA168633 | gcactgcaccaatggctctgtgg | 44287 | X84311 | atcgtagtctcggagatgctataga | 86891 | AA107871 | agacattcccgaacacaatgtgcg |
| 1684 | D76440 | aggtcaccagggcactgatcatcca | 44288 | AA022321 | cgtagtctcggagagatctatagatg | 86892 | AA107871 | catttcccgaacacaatgtgccgct |
| 1685 | D76440 | alagtttcgaccatactaggct | 44289 | AA022321 | ccgttcccgaagttgaatcagtt | 86893 | AA107871 | tcccgaacacaatgtgccgctgga |
| 1686 | D76440 | gcaacagaccgcagacaagagaaa | 44290 | AA022321 | gaatcaggtgccggaggtacaca | 86894 | AA107871 | ccgaacacaatgtgcctggaaat |
| 1687 | D76440 | aggcctttcctatagcttcac | 44291 | AA022321 | atcaggtggccgaggtaccaca | 86895 | AA107871 | cggcactgaccaatactaggcc |
| 1688 | D76440 | ttctcatatgacttcaactgcac | 44292 | AA022321 | ctggttgcactgctgtctgagcctg | 86896 | AA107871 | ctgtaccaatacataggccaggag |
| 1689 | D76440 | atatgactttcaactgcacaggaag | 44293 | AA022321 | ggtctgagctctgtgaatgaagtaa | 86897 | AA107871 | ccaaacctgccagttgaagcctctg |
| 1690 | D76440 | cttcaactgcacaggaagcatcca | 44294 | AA022321 | tagcatataggcacctttggaa | 86898 | Z26580 | tccaagccaagttggaccctgtgta |
| 1691 | D76440 | tgaactgactgctcagttgtagg | 44295 | AA022321 | cttaagcacatagtctaaccgc | 86899 | Z26580 | ccagtggaccctgtatggagg |
| 1692 | D76440 | ggactgttcagttgtaggtccactta | 44296 | AA022321 | agagtcctaacgctcccatcccag | 86900 | Z26580 | ggaccctgtatggaggatgaagc |
| 1693 | D76440 | ttctcagtgtaggcactagcaccc | 44297 | AA022321 | tcctccagtcaaggagagctcccaag | 86901 | Z26580 | cactgtagcaccatgcctggtac |
| 1694 | D76440 | gcaactgcaccttttacaaaacat | 44298 | AA022321 | aagtaagtagctcctgcagctctg | 86902 | Z26580 | catttcctgtccaatgtag |
| 1695 | D76440 | agccacccttacaaaacatgtatgc | 44299 | AA022321 | gtagctcctgcagctctgaaaatt | 86903 | Z26580 | ctgccctggggagaaagtgctgtc |
| 1696 | D76440 | tctgaccatactagggctgtgtaa | 44300 | AA022321 | atglaggccagatgctcaattc | 86904 | Z26580 | agtgctgtgactgcccagagttag |
| 1697 | D76440 | ccatactagggctgtgtaagggtg | 44301 | AA022321 | atgctcaattcttgctaccaggac | 86905 | Z26580 | gctgtgcactgcccagagttaggag |
| 1698 | D76440 | tagagtatcccacagtgcacactgtga | 44302 | AA022321 | ttgcaccaggacgccccatgaaa | 86906 | Z26580 | gctgtgcccagagttaggagacg |
| 1699 | D76440 | atcccaaatccacagtgcagtattt | 44303 | AA022321 | gtttgccattttctctgaacag | 86907 | Z26580 | caatactgcacataggccggatgggatg |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 1700 | ttttccatacagtgctttgtacct | D76440 | 44304 | atataacagtcactgtatcccatc | Z26580 | 86908 | gtcattgagatctcatagaagact | X97650 |
| 1701 | atacagtgctttgtacctgtaat | D76440 | 44305 | cagctcactgtatcccatctgtcct | Z26580 | 86909 | ctcatagaagactcatctgctggt | X97650 |
| 1702 | tctgtctcttttgtatgggactgat | D76440 | 44306 | tcccatctgtcctgagtgggtcac | Z26580 | 86910 | cttcatgccaggaaggtctcttc | X97650 |
| 1703 | ttaacagcaacgcagatacgagcaa | D76440 | 44307 | ctctgaaagtgccccattttatag | Z26580 | 86911 | gaaggtcttccaggaaacatatg | X97650 |
| 1704 | gatggtcctacgacattctgactga | D76440 | 44308 | ctctggctccaaataatcattttct | Z26580 | 86912 | ctctttccaggaaacatgtggaga | X97650 |
| 1705 | ggtcctctacgacattctgacatc | W45807 | 44309 | ctccaaataatcattttcttctt | Z26580 | 86913 | aagatctgatgtcatccaccagc | X97650 |
| 1706 | caagttcagcctctagcagatac | W45807 | 44310 | ttcactactctgatagcactatagg | Z26580 | 86914 | tgggatccaaacctgccatggaa | AA107887 |
| 1707 | caatgacattcattcttggctgccc | W45807 | 44311 | atctgatgacactatagggggacct | Z26580 | 86915 | ctggcgactaggcctctgtggcaga | AA107887 |
| 1708 | cattttcattctggctgccctctgag | W45807 | 44312 | cgcatcagtagccgacgccgaagag | Z26580 | 86916 | tggcgactaggcctctgtggcagag | AA107887 |
| 1709 | ttcattctggctgccctctgagaac | W45807 | 44313 | atcagtagccgacgccgaagagac | X17500 | 86917 | aagccaaagagctccaacaagcacg | AA107887 |
| 1710 | ctggctccctgagaactacacag | W45807 | 44314 | gctgctcatctgcagcaggcggtg | X17500 | 86918 | gccaaagagctccaacaagcacga | AA107887 |
| 1711 | gccctctgagaactacacgagaat | W45807 | 44315 | cctgcagcaggcggtgcaggtcatc | X17500 | 86919 | ccaaagagctccaacaagcacgaa | AA107887 |
| 1712 | tgatttctatgacatgtcgaaca | W45807 | 44316 | gcaggtcatccggcctggcgagcag | X17500 | 86920 | caaagagctccaacaagcacgaagg | AA107887 |
| 1713 | ttctatgacatgtcgagccgtcagt | W45807 | 44317 | cgggcacctgtgagccgtcacagtt | X17500 | 86921 | aagagctccaacaagcacgaagga | AA107887 |
| 1714 | ctatgacatcgtcgaacatgtcgga | W45807 | 44318 | gcacctgtgagccgtcacagttct | X17500 | 86922 | aagagctccaacaagcacgaaggga | AA107887 |
| 1715 | catgtcgaacatcgtcggaagagag | W45807 | 44319 | gtgagccgtcacagttctcttgtt | X17500 | 86923 | agagctccaacaagcacgaaggaa | AA107887 |
| 1716 | ccgcctttctggatgtggaggaag | W45807 | 44320 | ggaccatcgtccaaccatatctgc | X17500 | 86924 | gagctccaacaagcacgaaggaaa | AA107887 |
| 1717 | ccttttctggaggatgagcgc | W45807 | 44321 | gtcatcagagcggttcgtgatgag | X17500 | 86925 | agctccaacaagcacgaaggaaaa | AA107887 |
| 1718 | cctgaagcagttcctcgtcggaac | W45807 | 44322 | tgagcaggtcctcatcgaagcatg | X17500 | 86926 | gcgactaggcctctgtggcagaga | AA107887 |
| 1719 | gaagcagttcctcgtcggacatc | W45807 | 44323 | tctccatcgaagcatgacagagag | X17500 | 86927 | cgactaggcctctgtggcagagaa | AA107887 |
| 1720 | gtccctctgagaatcatcgacca | W45807 | 44324 | ggaactgaaggtcccaccacgcgc | X17500 | 86928 | gactaggcctctgtggcagagaatc | AA107887 |
| 1721 | ggacatcaaccagagtgtcaagtt | W45807 | 44325 | caagccgaccacgcagtacagatgag | X17500 | 86929 | agttcaagccaaagagtccaacaa | AA107887 |
| 1722 | catcaaccagagtgtcaagtttcag | W45807 | 44326 | cattaacagaggcttccgggagctg | X17500 | 86930 | gttcaagccaaagagctccaacaag | AA107887 |
| 1723 | tgtcaagtttcagcctctagcag | W45807 | 44327 | catgtccgtgcacctcaagtcg | X17500 | 86931 | ttcaagccaaagagctccaacaagc | AA107887 |
| 1724 | cactgcctctgacatacgagct | X74671 | 44328 | ccagctcgacctcaagtcggataag | X17500 | 86932 | tcaagccaaagagctccaacaagca | AA107887 |
| 1725 | ctcctgacataccgagctgcat | X74671 | 44329 | gcacctcaagtcggataaggcggca | X17500 | 86933 | caagccaaagagctccaacaagcac | AA107887 |
| 1726 | agaagagcaaagcaactcgagaggca | X74671 | 44330 | gcgcagaccaagctgctcatctg | X17500 | 86934 | aaggaatgcctgctctatcattt | AA107893 |
| 1727 | cggcctggacgtcctacacagtga | X74671 | 44331 | gaccaagctgctcatctgcagcag | X17500 | 86935 | aggaatgcctgctctatcatttt | AA107893 |
| 1728 | agagctcagagaggggcgggcccag | X74671 | 44332 | cctgttcggtccaatctatctag | X17500 | 86936 | ggtatcctcagcactgaccaagac | AA107893 |
| 1729 | atacccatttaaaagtactactctga | X74671 | 44333 | cggtccaatcctatcatgcaagat | U62523 | 86937 | gtatcctcagcactgaccaagaac | AA107893 |
| 1730 | agctcactctgcagagcgccaagtc | X74671 | 44334 | gggtatctgcagtccaagcccac | U62523 | 86938 | tatcctcagcactgaccaagaccg | AA107893 |
| 1731 | ctcgagagccagtcccagtcccgagt | X74671 | 44335 | tctcggccagtccaagcaagtc | U62523 | 86939 | cctcagcactgaccaagaccgcg | AA107893 |
| 1732 | ctgcagacatcgtcgtctgacca | X74671 | 44336 | aagccacgtccaggaaaactgcgt | U62523 | 86940 | cctcagcactgaccaagaccgcga | AA107893 |
| 1733 | acatctgctctcgtcgaccaacca | X74671 | 44337 | tgtttccacaggacactttgctgc | U62523 | 86941 | tcagcactgaccaagaccgcgaga | AA107893 |
| 1734 | ctctgagttgaggtcgccgtgcca | X74671 | 44338 | acactttgctgcaatctcagacct | U62523 | 86942 | agcaactgaccaagaccgcgagaga | AA107893 |
| 1735 | agttttccacaagttgtctaggt | X74671 | 44339 | tccatcagctccaaagtaaaaccga | U62523 | 86943 | cacttgaccaagaccgcgagagaga | AA107893 |
| 1736 | acatacggagctgacattatgc | X74671 | 44340 | aaccgaaaagctaaactgcatgg | U62523 | 86944 | acttgaccaagaccgcgagagaga | AA107893 |
| 1737 | cgagcttgacatttgcaggt | X74671 | 44341 | gaattgacagtctcgcctgtc | U62523 | 86945 | ctgaccaagaccgcgagagagact | AA107893 |
| 1738 | ttatgctgacagctgcattcga | X74671 | 44342 | tattgacagtcctcgcctgtc | U62523 | 86946 | ggtatacctaacctgctgttag | AA107893 |
| 1739 | ctgacagttgcattgcatctgcat | X74671 | 44343 | tctgcccctgtcctgtgaaaat | U62523 | 86947 | gtatacctaacctgctgtttatg | AA107893 |
| 1740 | gcttgcattttgacttcaagaagaa | X74671 | 44344 | gagaccaaatgctcactatgtaggg | U62523 | 86948 | tatacctaacctgcgttattatgg | AA107893 |
| 1741 | cattgctcaaggatacggacat | X74671 | 44345 | agggcactaatacaccccatggct | U62523 | 86949 | acctgcgttattgggtatccta | AA107893 |
| 1742 | tgaaggagctttccatgagatgaa | X74671 | 44346 | acacacagtcgttccacagga | U62523 | 86950 | ttatgggtatcctcagcactgacc | AA107893 |
| 1743 | gacttttcatggagatagagaaaga | X74671 | 44347 | tgtttccacaggacactttgctgc | U62523 | 86951 | tatgggtatcctcagcactgacca | AA107893 |
| 1744 | ctgtcaacatagacatagacaca | W45834 | 44348 | acactttgctgcaatctgcagagact | U62523 | 86952 | atgggtatcctcagcactgaccaa | AA107893 |
| 1745 | tgctcacacatagcacagcagga | W45834 | 44349 | tttagctgagtgtgttgagggctc | U62523 | 86953 | gggtatcctcagcactgaccaaga | AA107893 |
| 1746 | ttttcatctgagagtcgcaggag | W45834 | 44350 | ctgagtcacagcccagggacttg | U62523 | 86954 | cacatgctcaggaccatagatgaa | AA107893 |
| 1747 | gatgctaccgagcgaaatctgctc | W45834 | 44351 | aatttcactgatagatggcccag | U62523 | 86955 | ctcaggaccatagatgaactatta | AA107893 |
| 1748 | ttgcttccgtcacacagttatagtt | W45834 | 44352 | cctcacgaacacactgagcctctt | X85169 | 86956 | agagcctgccaaggctgccctggac | U26459 |
| 1749 | tcaactaccaaattcgaactggc | W45834 | 44353 | gaaccacctgagcctctgggta | X85169 | 86957 | ggctgcctgccctggacctgg | U26459 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 1750 | actaccaaattcagaacttggccag | W45834 | 44354 | tccctcctgactgccagtggaagt | X85169 | 86958 | ccccttatcaaacctgatgctgtt | U26459 |
| 1751 | ttcagaacttggccaggaagatcaa | W45834 | 44355 | atcagtggacccttagtcaagtcca | X85169 | 86959 | acacgaattgctcaatgcatgagtc | U26459 |
| 1752 | agatcaatcagtccatcgtctggat | W45834 | 44356 | tctatagagggccctgccactgc | X85169 | 86960 | attgctcaagcatgagtcgcaac | U26459 |
| 1753 | atcagtccatcgtcggattggag | W45834 | 44357 | ccgtccagcgcctgcgtctggag | X85169 | 86961 | atgagtgcaaccttcaacagga | U26459 |
| 1754 | agtccatcgtctggattggaggcat | W45834 | 44358 | gcataaatgtctcgccacgtga | X85169 | 86962 | ctgcaaccttcaacagggagccctc | U26459 |
| 1755 | ccatcgtctggattggaggcatct | W45834 | 44359 | atgtctctgccacgctgactgtc | X85169 | 86963 | aagtctaatatgtcggtgctgt | U26459 |
| 1756 | tcaacatagcacagaccaggatcc | W45834 | 44360 | ctgccacgtcgactgcagaatt | X85169 | 86964 | aaatagtcggtgctgttttaat | U26459 |
| 1757 | atagcacagaccaggatcccaactg | W45834 | 44361 | actgtccaagattgtgtgagaggca | X85169 | 86965 | ggtcaaggccgttctacgcta | U26459 |
| 1758 | gcacagaccaggatcccaactggg | W45834 | 44362 | agaggcagtcagccagggtgtcttc | X85169 | 86966 | caaggatgacctctgctttgaat | U26459 |
| 1759 | cagaccaggatcccaactgggaggc | W45834 | 44363 | ttcctctgctacttttgagatgag | X85169 | 86967 | gtcaaggccctgttctatcgtat | U26459 |
| 1760 | agacatgaaacagccctgatcctg | W45834 | 44364 | ggataccacagcacagcctagcttt | X85169 | 86968 | tgacctctgctgtgaatgagatc | U26459 |
| 1761 | catgaaacagccctgatcctgtcc | W45834 | 44365 | ccagcagccgtagcttttttcagt | X85169 | 86969 | tgagatctcagcacttcctgcctg | U26459 |
| 1762 | gaaacagccctgatcctgtcctt | W45834 | 44366 | ctccctcgggagttggggatcag | X85169 | 86970 | cactctgcctgatggaggagag | U26459 |
| 1763 | ttctgtttcatctggagagtctg | W45834 | 44367 | gggccactgtagcctcaggaacct | X85169 | 86971 | caagcccagatagctccggatc | U26459 |
| 1764 | aactcagtacgtcctggaagag | M35131 | 44368 | actgtagccctcaggaactgccaag | X92664 | 86972 | aggtccggatcctccgtccacag | U26459 |
| 1765 | atgatagtctctgtagccgaagt | M35131 | 44369 | aatgtctccagttattacgcag | X92664 | 86973 | gtccagcttttagaccaaaaatag | U26459 |
| 1766 | tcttgttttccaaagagtgtcag | M35131 | 44370 | gtccagttattacgcagtggcag | X92664 | 86974 | tctccaggcctctgcaagagct | U26459 |
| 1767 | tgcccactacacgtcctggaagag | M35131 | 44371 | ttattacacaggggctccctc | X92664 | 86975 | atgctgtaccttaagcttgtca | U26459 |
| 1768 | tggccactgaaccacgccagggtgt | M35131 | 44372 | gtcaactatacttggtccaacagtt | X92664 | 86976 | aggccagtctcgggcactgatgaa | U26459 |
| 1769 | cacgccaggtgtactctccactga | M35131 | 44373 | tatactgtccaccagttcgta | X92664 | 86977 | ctatcttattatagctcgatgt | U26459 |
| 1770 | aggggtactctccactgaagtcca | M35131 | 44374 | agtcactgcctgatatctgtaaa | X92664 | 86978 | gcctatgtaccaccagtagaataa | U26459 |
| 1771 | tactctccactgaagtccactttca | M35131 | 44375 | ctggagtcgtcttgtactattca | X92664 | 86979 | tatgtaccaccagtagaataagg | U26459 |
| 1772 | ccactgaagtccactttcaattgct | M35131 | 44376 | ctcatttgttcccttgtacagat | X92664 | 86980 | ttatctgtactctactcactccaa | U57343 |
| 1773 | aagtccactttcaattgttccag | M35131 | 44377 | tgttcccttgtacagattgcaac | X92664 | 86981 | gtactatctctactcaaatactgt | U57343 |
| 1774 | acttccagttccatgcaatag | M35131 | 44378 | ttgcaaccgcggatcctgggtc | X92664 | 86982 | tatctactcaaatactgtgactc | U57343 |
| 1775 | aattgttccagtcaataaaaccaa | M35131 | 44379 | catagccactcagatatttgaccaac | X92664 | 86983 | cttactcaaatactgttgactcgt | U57343 |
| 1776 | gcttctgttagccgaacgtgatga | M35131 | 44380 | aacataattcacatcattgtatgc | X92664 | 86984 | actcaaatactgttgactcgtaca | U57343 |
| 1777 | atgtgaacgtacgctaacacac | M35131 | 44381 | attcacacatttgtatgcagtgtg | X92664 | 86985 | atactgttgactcgtacattaaag | U57343 |
| 1778 | gcattatttctgatgtccaact | M35131 | 44382 | ttcccactgctgcgatcttat | X92664 | 86986 | ctgttgactcgtacattcaattat | U57343 |
| 1779 | atttcctgtatgcccaactgacaga | M35131 | 44383 | ctgtcgcggatcttataagctt | X92664 | 86987 | ccagctcctgggcactgatgaagt | U57343 |
| 1780 | tgtatgtccaactgacagatgaacg | M35131 | 44384 | tggtccacccaggttctgtatatgaa | X92664 | 86988 | ctcatalatgatgtctccggaattc | U57343 |
| 1781 | tccaactgacagatgaccgcaataa | W45896 | 44385 | agccttacaaatacggacttcctgt | X92664 | 86989 | atgtaactagcatctgtagct | U57343 |
| 1782 | gtgtaacctattcctgaatgcctt | W45896 | 44386 | ggatatcacattttctcagattat | X92664 | 86990 | cttagcagcatgctagcttttcat | U57343 |
| 1783 | tctgaatgcctttgttctcccaa | W45896 | 44387 | cacattttctcagattatcattt | X92664 | 86991 | agcatctgagttttcattgtgg | U57343 |
| 1784 | cagaagcgatgatgacctctgacaag | W45896 | 44388 | ttcttcagattatccattaagcca | X92664 | 86992 | gtgttatatccagctggagatca | U57343 |
| 1785 | agacgatgatgacctctgacagaga | W45896 | 44389 | agattatccattaagccaccaaag | X92664 | 86993 | tgagagatcaccttcaaaaggcca | U57343 |
| 1786 | gatcaacgactatcgcgttagtc | W45896 | 44390 | ttttccgtccagaatctcactgc | X92664 | 86994 | ttcaaaaggccagcctactctatt | U57343 |
| 1787 | atcaacgactatcgcgttagtcg | W45896 | 44391 | aatctatctgcaacatcacactg | X92664 | 86995 | cccagcctactctattatagctgca | U57343 |
| 1788 | gactatcgcgtattagtcgagtcgc | W45896 | 44392 | caacatcaacagtcaggagtcatc | AA021860 | 86996 | tatgcaaagagccactcttgtgtt | AA107984 |
| 1789 | ctatcgcgtattagtcgagtcgcag | W45896 | 44393 | gtcttcacagccaacgtgcagat | AA021860 | 86997 | cgcaaagcgcactcttgttatg | AA107984 |
| 1790 | cgtattagcgcgtcgagtcgcagtgaa | W45896 | 44394 | gcttcacagccaacgtgcagatta | AA021860 | 86998 | aacgtctctagctaaagcagcac | AA107984 |
| 1791 | gtattagcgcagtccgagtttgggt | W45896 | 44395 | acgagacttcccagccatccgtaa | AA021860 | 86999 | aaagatagactactgcctggaacga | AA107984 |
| 1792 | attagtgcgagtgcagtcgagtttcc | W45896 | 44396 | ccgagacttccgacatccgtacaac | AA021860 | 87000 | gcatgactactgcctggaacgacca | AA107984 |
| 1793 | ttagtcgagtcgcagttgcgtcca | W45896 | 44397 | agacttccagcagtccgtacaacac | AA021860 | 87001 | atgaactccgtagatactaca | AA107984 |
| 1794 | agtcgagtcgcagttgcggtccatc | W45896 | 44398 | gacttccagcagccgtcacacacg | AA021860 | 87002 | atgactacgtagatacacagta | AA107984 |
| 1795 | cgagtcgcagttgcggtccatcgc | W45896 | 44399 | cttccagcactccgtacacacgct | AA021860 | 87003 | acatcagtatcgtgtatgata | AA107984 |
| 1796 | acgatcgattgcctctgacaagag | W45896 | 44400 | tttccagatccgtacaacacgctg | AA021860 | 87004 | tacagatcgtgtatgtataaca | AA107984 |
| 1797 | cgatcgattgacctctgacaagagt | W45896 | 44401 | tccagatccgtacaacacgctgaa | AA021860 | 87005 | tgtgataacacctatgtatgatcat | AA107984 |
| 1798 | agtcgatgacctctgacaagagttg | W45896 | 44402 | ccgagatccgtacaacacgctgaag | AA021860 | 87006 | gataacacctatgtatgatcatga | AA107984 |
| 1799 | gatgatgacctctgacaagagttgcag | W45896 | 44403 | agcatccgtacaacacgctgaagta | AA021860 | 87007 | aacacctatgtatgatcatgtactt | AA107984 |

| SEQ ID NO | sequence | DBAxnID | SEQ ID NO | sequence | DBAxnID | SEQ ID NO | sequence | DBAxnID |
|---|---|---|---|---|---|---|---|---|
| 1800 | ttgcagctgatcaacgactactcgg | W45896 | 44404 | gcatccgtacaacagctgaagtac | AA021860 | 87008 | gagccactctgtgttatgccaggc | AA107984 |
| 1801 | cagctgatcaacgactatcgcgtat | W45896 | 44405 | cttcaacgccaacggtgcagattac | AA021860 | 87009 | acggtccagacgccgctggcaatgct | AA107984 |
| 1802 | gctgatcaacgactatcgcgtatta | W45896 | 44406 | cacagccaacggtgcagattacagg | AA021860 | 87010 | gctccagacgcctggcaatgctgat | AA107984 |
| 1803 | ctgatcaacgactatcgcgtattag | W45896 | 44407 | aacacagagctgaacagccgctcaa | AA021860 | 87011 | ccagacgccgcaatgctgatcgatac | AA107984 |
| 1804 | actcggtcatccgtgttgaatga | M61909 | 44408 | cacagagctgaacagccgctgcaag | AA021860 | 87012 | gccatccaatgctgatcacgcgaatga | AA107984 |
| 1805 | ttgatagctcctgctcggtaggga | M61909 | 44409 | ggaagccatgtcgttctggaacga | AA021860 | 87013 | tcacgaatgaacgctcctatgcta | AA107984 |
| 1806 | agcacatgggggccgctcttcgt | M61909 | 44410 | gaagccatgtcgttctggaacgag | AA021860 | 87014 | cgaatgaacgctctatgctaaag | AA107984 |
| 1807 | ctgcagctctccatgctgagctgt | M61909 | 44411 | agccatgtcgttctggaacgagtc | AA021860 | 87015 | atgaacgtctctatgctaaagcat | AA107984 |
| 1808 | gctcccatgctgagctgtggccaa | M61909 | 44412 | gaacgagacttccagcatccgtac | AA021860 | 87016 | gggttcgcaaacattgcgtgaagt | AA107984 |
| 1809 | ttgctgccgcctccagaatcagg | M61909 | 44413 | agcccttgctgttccactgccgcg | AA021860 | 87017 | ttcgccaaacattgcgtgaagtgca | W14830 |
| 1810 | ttagtcgagacatcccgctccc | M61909 | 44414 | tgtccactgccgcagattccgcg | AA021860 | 87018 | aagctgcggcagcgttcaacg | W14830 |
| 1811 | tttccaaggcctaatagcagggca | M61909 | 44415 | ctgcatccaccgagggtctgctt | AA021860 | 87019 | cagcgttccaccgctgtgaaggacc | W14830 |
| 1812 | ctagaatgctcagccacaagacag cc | M61909 | 44416 | gcatctccaccgaggtctgcttat | AA021860 | 87020 | ttcaccgctgtgaggaccagtatt | W14830 |
| 1813 | tggactctgctcttctagctcg | M61909 | 44417 | gtcgtctttgggtgcgatgaatg | AA021860 | 87021 | gaccagtattacgctgtggatgct | W14830 |
| 1814 | cttgctcttctagctctgaactaa | M61909 | 44418 | ctttggtgcgatgaatgtgcact | AA021860 | 87022 | cagtattacgctgtggattgctaca | W14830 |
| 1815 | cttctagctctgaactaatataaatg | M61909 | 44419 | gaatgtgcactgcgaccaacgtgg | AA021860 | 87023 | aaaggctccagtgtgggtggcctatg | W14830 |
| 1816 | gagatcctccatctccagctt | M61909 | 44420 | atgtgcactggcaccaacgtgac | AA021860 | 87024 | agtgtggcctatgaaggacaat | W14830 |
| 1817 | gagccatgcctaggccatatagcc | M61909 | 44421 | gtgcactccggcaccaacgtggaccc | AA021860 | 87025 | ggacaatccggcacgactactgat | W14830 |
| 1818 | tgcctaggccatatagccttacta | M61909 | 44422 | ctgccgactgccggcgatgcttt | AA021860 | 87026 | tcctggcacgactactgcttccact | W14830 |
| 1819 | tatagccttactacaagtgtctc | M61909 | 44423 | ccggatgccgggcgatgcttgcca | AA021860 | 87027 | cacgactacttgcttcactgcaaaa | W14830 |
| 1820 | tacaacttgatccaagcagtgctc | M61909 | 44424 | cgatgcttgccacggcagcacct | AA021860 | 87028 | tgcaacaaggccatcacatctggag | W14830 |
| 1821 | ttgatccaagcagtgctcccaaga | M61909 | 44425 | tcccactgccgggacagctcggct | AA021860 | 87029 | tactgcttccactgcaaaaatgct | W14830 |
| 1822 | caaagcagtgctcccaagacagct | M61909 | 44426 | ccactgccgggcagagctcggctgg | AA021860 | 87030 | ggaatcacttaccaggatcagccct | W14830 |
| 1823 | agcagctccacgtgtgctgccgg | M61909 | 44427 | ctgcacgcaccagatgcatc | AA021860 | 87031 | atcacttaccaggatcagcccggc | W14830 |
| 1824 | aaagccatatttgtaggccgtgcac | M61909 | 44428 | ctacgcaccagatgcatctcac | AA021860 | 87032 | taccagatgcagtttccatgccg | W14830 |
| 1825 | aagccatatttgtaggccgtgcaca | W45901 | 44429 | acgcaccagagtcgcatctccacg | AA021860 | 87033 | gatccgcctgcagtccgagtgct | W14830 |
| 1826 | tgagcgctcaagcaggagaggatt | W45901 | 44430 | ccaccagagtctgcatctcaccgag | AA021860 | 87034 | tgtgttacctgctctaagaagctgg | W14830 |
| 1827 | agcagctcaaggcaggagaggattag | W45901 | 44431 | gagtctgcatctcaccgagggtgt | AA021860 | 87035 | acctgctctaagaagctggctgggc | W14830 |
| 1828 | tgaatctctcaattaagaactgga | W45901 | 44432 | gctcgcatctcaccgagggtgtcc | AA021860 | 87036 | tctaagaagctggctgggcagcgtt | W14830 |
| 1829 | gaatctctcattaagaactggat | W45901 | 44433 | gtcttacatgattgtctgcaca | AA021860 | 87037 | cgactacactcaatgtaggcctica | W14830 |
| 1830 | aatctctacattaagaactggatg | W45901 | 44434 | cttacatgattgtctgcacaga | X92665 | 87038 | ctacactcaaatgtaggccttcagg | AA107961 |
| 1831 | atctctacattaagaactggatga | W45901 | 44435 | gtccattgatcagcttaaattgt | X92665 | 87039 | tggaaccaccaggagactgctgtgg | AA107961 |
| 1832 | tctctacattaagaactgggatgac | W45901 | 44436 | tttgttacctgtatatgtaaaatg | X92665 | 87040 | gcattgtagttccagaagtcggag | AA107961 |
| 1833 | gagagttttccccttggatcaat | W45901 | 44437 | aatggacacctggctacaagaccacc | X92665 | 87041 | tgttagttccagaggtcggagtggg | AA107961 |
| 1834 | agccatatttgtaggccgtgcacag | W45901 | 44438 | ggacacctggctacaagaccaccatg | X92665 | 87042 | ttccagaggtcggagcggacgaaa | AA107961 |
| 1835 | ccatatttgtaggccgtgcacaga | W45901 | 44439 | cacctggctacaagaccaccatgg | X92665 | 87043 | gttcagccaggcaggaggaagag | AA107961 |
| 1836 | atatttgtaggccgtgcacagaa | W45901 | 44440 | gctacaagaccacgatagttaatg | X92665 | 87044 | cagtccaggcaggaggaaagaact | AA107961 |
| 1837 | tatttgtaggccgtgcacagaaaa | W45901 | 44441 | acaagaccaccatgtagttaatgat | X92665 | 87045 | aacagactcgagtcgcctgt | AA107961 |
| 1838 | atttgtaggccgtgcacagaaaaa | W45901 | 44442 | taccttaagctgtaactgtaatg | X92665 | 87046 | agactctgcagtcgcctatagt | AA107961 |
| 1839 | agtttgcagctcaagcaggaggag | W45901 | 44443 | gttagacttctacgtctgcattt | X92665 | 87047 | tcagtctgcctgtagttggaaag | AA107961 |
| 1840 | gttcagctcaagcaggaggaggat | W45901 | 44444 | tagactttacgtctgcatttgtg | X92665 | 87048 | agtcgcctgtagttggaaagcaa | AA107961 |
| 1841 | ttgagcagctcaagcaggaggat | W45901 | 44445 | tgattgtgtcacagaagagagc | X92665 | 87049 | cactcaatgaggcctcaggtga | AA107961 |
| 1842 | ctagtgctgctagagcgtggttc | X55315 | 44446 | agactttcactgctgcatttgcc | X92665 | 87050 | aagggcaaacctctctgcagttggt | AA107961 |
| 1843 | tagagcgtggttcccatgtgaatgg | X55315 | 44447 | tttgttctcaacgaagagagctgc | X92665 | 87051 | gcaaacctctctgcagttgctcta | AA107961 |
| 1844 | tgctctccatggcagctgattct | X55315 | 44448 | atatattcagtcttactcccag | X92665 | 87052 | aacctctgcagttggctacca | AA107961 |
| 1845 | tgattcctggtgcagttccact | X55315 | 44449 | ttattcagtcttactcccagatt | X92665 | 87053 | tcctgcagttggctaccacgtgc | AA107961 |
| 1846 | ttctctgaggcctgcagcaaggt | X55315 | 44450 | ttcagttactctccaggatttg | X92665 | 87054 | agttgctcaccacgctgcgcgga | AA107961 |
| 1847 | gtaggcctgcagcaaggttgctc | X55315 | 44451 | atctgctacagtagacaaatcgt | X92665 | 87055 | ctgcgtgaccaccaccaggacgat | AA107961 |
| 1848 | ctgcagcaaggtttgctcactga | X55315 | 44452 | actgtgttccattgatcagcttaa | X92665 | 80756 | ccgtggaccaccaccaggaccgatcg | AA107961 |
| 1849 | tttgtcactgcatcagctgtag | X55315 | 44453 | tgtgtccattgatcagcttaaatt | X92665 | 87057 | agaagatgccaccaagccgcatact | AA107997 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 1850 | cactgcatcagtgctgtaggacca | X55315 | 44454 | catcccgagctctgtgtcatagcc | AA030190 | 87058 | agatgccaccaagcgcatactaag | AA107997 |
| 1851 | aactcagctgcgaaggatcctgc | X55315 | 44455 | cccggagctctgtcatagccagc | AA030190 | 87059 | agaaccaggcttggtgctgacactg | AA107997 |
| 1852 | ggaacaagcactaccactgagcca | X55315 | 44456 | cgactagccctgccagcagccac | AA030190 | 87060 | ggtgccctctgcaggatgtgg | AA107997 |
| 1853 | taccactgagccacacatacata | X55315 | 44457 | ccttgcagcagccacactagaggc | AA030190 | 87061 | cctctgcaggatgtgtgcaggct | AA107997 |
| 1854 | gtggttccagtggatgagat | X55315 | 44458 | tggcagccacatgccagcaga | AA030190 | 87062 | tctgcaggatgtgcaggctgag | AA107997 |
| 1855 | gcatgacttaggctgaagaaacc | X55315 | 44459 | cagagccacatgccagggccagagc | AA030190 | 87063 | gatgcatacgtgtgctgagcca | AA107997 |
| 1856 | acattgacacctcgcgctgcact | X55315 | 44460 | tcagccagcacctggtcatgaag | AA030190 | 87064 | tgcaactgtgtctgagccaaag | AA107997 |
| 1857 | cttatatgctgaagaagcactgt | X55315 | 44461 | gccagcacctgtgtcatgaagcag | AA030190 | 87065 | atactgtgtgctgagccaagtgg | AA107997 |
| 1858 | ttgagctagctgctggctgcagg | X55315 | 44462 | agcacctgtgtcatgaagcagca | AA030190 | 87066 | gtggccagtctactccttggctg | AA107997 |
| 1859 | gatgtcttcatccctgcctgggt | X55315 | 44463 | gcagcaattctcttcagcccgctt | AA030190 | 87067 | gccaggtctactccttggctgcaa | AA107997 |
| 1860 | tgctgaccgaggtgaatgctctt | X55315 | 44464 | gcaattcttcagccgctggc | AA030190 | 87068 | aggtctactccttggctgcaatga | AA107997 |
| 1861 | ggtgaatgctctccatgcagct | X55315 | 44465 | gagtgatctctgccttcagcagcc | AA030190 | 87069 | tgccaccaaggcatactcaagaga | AA107997 |
| 1862 | caltgaagtgctcatcttgatgag | W45951 | 44466 | ctgtgtcatagccagcttggaatga | AA030190 | 87070 | cacccaagcgatactaagaagg | AA107997 |
| 1863 | tgaagtgctcatcttgatgaggt | W45951 | 44467 | catctgactcagccaggtccaaagg | AA030190 | 87071 | agtctcacacaggtcccacaacaca | AA107997 |
| 1864 | ggtctccttaaagaatcctgtcgg | W45951 | 44468 | tgtcatagccagcttggagtagcaa | AA030190 | 87072 | acacaggtcccacacacagaaccaa | AA107997 |
| 1865 | ctccttaaagaatcctgtcggata | W45951 | 44469 | catagccagcttggagtagcaacct | AA030190 | 87073 | caggtcccaacacagaaccaggc | AA107997 |
| 1866 | cttaaagaatcctgtcggatatt | W45951 | 44470 | ggagtagcaacctaccacatgtga | AA030190 | 87074 | cccaacacagaaccaggcttggtg | AA107997 |
| 1867 | gaatcctgtcgggatatttgaac | W45951 | 44471 | gcaacctcatcacctgcatgtagcc | AA030190 | 87075 | caacagaaccaggcttggtcgctg | AA107997 |
| 1868 | tcctgtcgcgatatttgaacagc | W45951 | 44472 | acctcatcacctgcatgtagccctt | AA030190 | 87076 | cagaaccaggcttggtcgctgaca | AA107997 |
| 1869 | gaacagcaacacagatgtcgctccc | W45951 | 44473 | tcatcacctgcatgtagccctggc | AA030190 | 87077 | taaatgccgtgctctccaggcaca | AA107997 |
| 1870 | tccctcctgcgaagagttcata | W45951 | 44474 | cctcgtagccctttgccagcage | AA030190 | 87078 | gtgctccaggccgcacacaggtattt | AA107997 |
| 1871 | cttcctgcgaagagttcataacgg | W45951 | 44475 | tctgaacttcctgatgctgcactg | AA030190 | 87079 | acagtggctattccttcaagcacat | AA107997 |
| 1872 | agagtcatacggatccggcctaat | W45951 | 44476 | actttccgatgctgcactggtacac | AA030190 | 87080 | atttcctcacgcacatgttcctta | AA107999 |
| 1873 | gttcatacggatccggcctaatgg | W45951 | 44477 | aggccaagctggactagagacccctg | AA030190 | 87081 | tcacgcacatgttcctactg | AA107999 |
| 1874 | catgctctctgccggtctccata | W45951 | 44478 | tttatgccactgaagtaatttga | AA030190 | 87082 | tcacgcacatgttcctactg | AA107999 |
| 1875 | gctctctgccggtctccacatga | W45951 | 44479 | aattgccctttgtctcactaa | AA030190 | 87083 | acattgttcctactgctaagaagcaa | AA107999 |
| 1876 | cttctgccaccatgcacatgatgag | W45951 | 44480 | agcccttgctcactaaaacag | AA030190 | 87084 | taacgaaccatctaaaagagatcat | AA107999 |
| 1877 | ctcgggccaccatgacacagatgaggtg | W45951 | 44481 | ttgtgctcactaaaacaaggatcac | AA030190 | 87085 | aagagatcatatcctacaggcgagt | AA107999 |
| 1878 | gaaagatctggctctgctccctta | W45951 | 44482 | ggatcacatttaactgtggcaaac | AA030190 | 87086 | agatcatatctacagccagctga | AA107999 |
| 1879 | agatctggcttcgtccctgcaga | W45951 | 44483 | gttgccccatgcgggacacatgaacatt | AA030190 | 87087 | tatcctacaagcagctgcattgat | AA107999 |
| 1880 | tctggcttcgtccctaaagaat | W45951 | 44484 | cccatgcgggacacagacaggaacatt | AA030190 | 87088 | acaggcagctgcatgtgatgatga | AA107999 |
| 1881 | ttcggcttcctaaagaatcctgg | W45951 | 44485 | gaacatttggattccaaggaggga | AA030190 | 87089 | tcaggcacacaggtatccgaga | AA107999 |
| 1882 | tcctctgcaggatgatggttaagc | W45951 | 44486 | tttgattccaaggagcaaagag | AA030190 | 87090 | ataacctctgagctgtgctgcat | AA107999 |
| 1883 | atggttaagccatgcctgccagagca | W45951 | 44487 | tgatgccgcactgtacacacaaacc | AA030190 | 87091 | cttctgagctgtgctgcatcatgt | AA107999 |
| 1884 | agctctgtactgtaagctgctggtga | M86829 | 44488 | tgcactgtacacacaacaaagag | AA030190 | 87092 | ctgagctgtgctgcatcattgtcga | AA107999 |
| 1885 | tccctagctcaggctgcagtct | M86829 | 44489 | tgactagctcttactggcacac | AA030190 | 87093 | agctgtgtctgcatcattgtcgacag | AA107999 |
| 1886 | gctcaggctcgtcagttctgagttt | M86829 | 44490 | gagctcttactggcacacaaag | AA030190 | 87094 | gctcattgtcgacatggcta | AA107999 |
| 1887 | gctcgtcagttctagttacctga | M86829 | 44491 | ttactgcacacagaagtcctag | AA030190 | 87095 | gcatcattgtcgacgtggctatc | AA107999 |
| 1888 | cagtctgagttcttacctctt | M86829 | 44492 | ggcaacctactataagccagcact | AA030190 | 87096 | tcattgtgacagtggctattcctt | AA107999 |
| 1889 | ttctgagttcttacctgagtcttta | M86829 | 44493 | tacctataagcccagcacttggag | AA030190 | 87097 | ggacgagacctgcttcacctgcag | AA107999 |
| 1890 | catctccaagggttatcaagat | M86829 | 44494 | acagtcatctgaactatacaggga | AA030190 | 87098 | ggaccgttcacctgccagccgc | AA107999 |
| 1891 | agatactcagagaactgcgaaatg | M86829 | 44495 | aacgctggtcaggaggacggagactgt | AA021852 | 87099 | tgtgtcccagccactgcaagaacag | AA107999 |
| 1892 | tgtatgcttgcattgtatatggaa | M86829 | 44496 | tcaggagtcctctctgctaactc | AA021852 | 87100 | cacagcctgcaagaagcagtatct | AA107999 |
| 1893 | agaactgtgcatcaagtatgtat | M86829 | 44497 | gcttagcgtccttggtcgaaagcaaa | AA021852 | 87101 | gctatctggcaacgcttcacagca | AA107999 |
| 1894 | gttaagccaltgtcctgagacaaaa | M86829 | 44498 | tagctcctggtcctgagacaaagat | AA021852 | 87102 | tgagttccalactgccgaccgc | U77040 |
| 1895 | ccatgctcctggagacaaagtaact | M86829 | 44499 | cgtctcctggaagacaaagatcta | AA021852 | 87103 | tccatactgcctgacctgcttcgt | U77040 |
| 1896 | tcttaagggctgctgtcgagtctc | M86829 | 44500 | tgcaatgtagcctgtctgttacca | AA021852 | 87104 | tcattgtgacagtggctattc | U77040 |
| 1897 | ctgagtcctcactcaagtggctgg | M86829 | 44501 | gtagctggtctgtgttaccaggggga | AA021852 | 87105 | tttcgggaagccacgaccactgcttaac | U77040 |
| 1898 | cctcactcaagtggctgggatgct | M86829 | 44502 | gtggtcttgttaccagggcagca | AA021852 | 87106 | ccaacgactgttttaactgtaag | U77040 |
| 1899 | tcaaggctgaggctctgtccta | M86829 | 44503 | ggtctgttaccaggggcagcacag | AA021852 | 87107 | cttcctgcagagagatgactc | U77040 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 1900 | tgtccagctctgctactgtaagcta | M86829 | 44504 | cttgttacagggggcagcacaggca | AA021852 | 87108 | tattgaagggcacagaagccac | U77040 |
| 1901 | cctagctctgtactgaagctatgt | M86829 | 44505 | ggcctgtcctgcaggatgagatgg | AA021852 | 87109 | cttcacgctcagcgctgccagcag | U77040 |
| 1902 | tgaccttgctgtcctctgccctg | M77677 | 44506 | cttgtcctgcaggatgagatgcca | AA021852 | 87110 | aggcggcacagaagccacagcgcgt | U77040 |
| 1903 | ttgctgctctgccctgagtca | M77677 | 44507 | ggaagtcctctcctgtcaactcga | AA021852 | 87111 | caagaticcattcatacctaaggagaat | U77040 |
| 1904 | aactgagctctgggcacgtgatgcc | M77677 | 44508 | agtcctctctgctaactcgtcgca | AA021852 | 87112 | tcagaatcgtgctgcctgctat | U77040 |
| 1905 | tgatgcctaccaggccatgatgt | M77677 | 44509 | ccttctctgctaactcgcagcagca | AA021852 | 87113 | cttctcgtgcctgctctatgagaag | U77040 |
| 1906 | atgatgtaccagacagacccctgagcc | M77677 | 44510 | gagccacccaagtcgccatggtgc | AA021852 | 87114 | gtgcaaaagctatcaccacagga | U77040 |
| 1907 | gctagctctcagtcctcattactg | M77677 | 44511 | ccatggctcagccgcattagcgtc | AA021852 | 87115 | tatcaccacaggagggttacttac | U77040 |
| 1908 | cttctcagctcattactggagag | M77677 | 44512 | ctgccagccgcttagcgtccgtgc | AA021852 | 87116 | tacttacggagcagccctggac | U77040 |
| 1909 | agctccattactggcagaagggccc | M77677 | 44513 | ccagccgcttagcgtccgtggcga | AA021852 | 87117 | gcagcctggccaccaaggaatgctt | U77040 |
| 1910 | atactggctgagaggggccttctt | M77677 | 44514 | gccgttagcgtccgtggctggaaagc | AA021852 | 87118 | tgtacatccagcaggtgacaacatc | U77040 |
| 1911 | tgccgctctttttgctcagtttgc | M77677 | 44515 | ctgcaaccacagtatacactcat | AA021852 | 87119 | aggtgacaacatcatctgtgcagc | U74815 |
| 1912 | ccttttgctcagttgttctcaca | M77677 | 44516 | ccatgtataacctcatcctagag | AA021852 | 87120 | agatctggtgttctgatgtgcc | U74815 |
| 1913 | cttcagttcttcttccatgatt | M77677 | 44517 | tgctcatagcagagagagccatct | AA021852 | 87121 | tggcattgtgactcttcagctaa | U74815 |
| 1914 | gtctctgccctgaggtcactgcag | M77677 | 44518 | tgatcttcatctctggaggactc | AA021852 | 87122 | catctgactcttcagctaagccaac | U74815 |
| 1915 | gacagcctcggaagactcatattgggaa | M77677 | 44519 | tctctcattctgtgagggactcata | AA021852 | 87123 | actcttctcaagctccaacacacta | U74815 |
| 1916 | ctactaggcaaccacaactgaggaa | M77677 | 44520 | tcaatcctggagagactcatta | AA021852 | 87124 | gggttgctccacacagaatcctc | U74815 |
| 1917 | ggaccacaactgaggaatagaat | M77677 | 44521 | aggactcatactctaggtgatcgca | AA021852 | 87125 | acacgaatcctccaatagaatccca | U74815 |
| 1918 | aatttgctccaaatgacaccagaa | M77677 | 44522 | actctagtgattgcaatggcgcat | AA021852 | 87126 | cctgtctcctgatctcagcctccag | U74815 |
| 1919 | ctctccaaatgacaccaagaagccag | M77677 | 44523 | attgcaatgggcatgaagatgct | AA021852 | 87127 | ttcctgattcagctccagcaactg | U74815 |
| 1920 | ggttaaatagcaccacatatcct | M77677 | 44524 | tgaagatgctccatctgcagctg | AA021852 | 87128 | gcaactgccagcctgacctaca | U74815 |
| 1921 | aatagcaccacatatctggtaa | M77677 | 44525 | ggctgtgcatcaacaccgatgct | AA021852 | 87129 | ttgataccaagtcacccactgagt | U74815 |
| 1922 | aggccaacagttctgtatatgggg | M77677 | 44526 | gcatccaaccacgatgctggagga | AA021852 | 87130 | caacatactgggcagctatgac | U74815 |
| 1923 | tccatgttccgtggcatgaccca | M77677 | 44527 | tgtatacactcatccctagatgg | AA021852 | 87131 | tgacctggatctttccaccagca | U74815 |
| 1924 | tgccagctgactttccaggtca | M77677 | 44528 | atacaactcatcctctagaatgttc | AA021852 | 87132 | ttccacaaccatacaaagtgctg | U74815 |
| 1925 | ttccaggtcaagctcatccggtctgt | M77677 | 44529 | tcatccctagagtgggtccatt | AA021852 | 87133 | caagccatacaaagtgctgaggcac | U74815 |
| 1926 | ctgtatagtcctactcagctcca | M77677 | 44530 | tcccgcctcaatctaagaaccatg | AA021852 | 87134 | agtgctgaggccaccaagaagaagcc | AA107137 |
| 1927 | ctatcagtctcagaggccaggtca | M77678 | 44531 | cctcaatctaagaaccatcataaa | AA021852 | 87135 | agcaaccaccggcgtccgcagttcgg | AA107137 |
| 1928 | agtcctcagaggccaggtcaagtgc | M77678 | 44532 | taaacatagcgtgtcagaagct | AA021852 | 87136 | ctgcacctggagactctgaggctcc | AA107137 |
| 1929 | tgtcagctgacttccaggtca | M77678 | 44533 | tgaatccggtctcatagcacgaga | AA021852 | 87137 | tatcgtgccatggcatggtgac | AA107137 |
| 1930 | ttccaggtcaaagatgaatctga | M77678 | 44534 | atccggtctcatagcacgagagaga | AA021852 | 87138 | cctgctcgaaccatgctggtg | AA107137 |
| 1931 | aatctgaaatgtcccattggctagt | M77678 | 44535 | aaagctctgtggactcttgaggct | AA021852 | 87139 | tcgggcaaccacggcgtccgcagttcgg | AA107137 |
| 1932 | tcccccaacaaggggtatgggat | M77678 | 44536 | agctctgctggactctgaggctcc | AA021852 | 87140 | agcaaccaccggcgtccgcagttcgg | AA107137 |
| 1933 | tgactttccgggtgtactgtcctg | M77678 | 44537 | aaccaccattcgtatcagtttcta | AA021852 | 87141 | ctgcacctggagtactacgctttaca | AA107137 |
| 1934 | ttgcatcagaggagtctgacctgttc | M77678 | 44538 | ccacattcgtatcagtttaat | AA021852 | 87142 | gcacctggatgcctttacagagag | AA107137 |
| 1935 | tttcctgggcatgaaccatactgg | M77678 | 44539 | accattcgtatcagttctctccaacat | AA021852 | 87143 | ctggagtaccgctttacagagag | AA107137 |
| 1936 | alactgggctgctctggcttgag | M77678 | 44540 | aagtagtgcatactctccaaccat | AA021852 | 87144 | agtaccgctttacagagctcag | AA107137 |
| 1937 | ggctgctctggcttgagctctac | M77678 | 44541 | gtagtgcatactctccaaccatgga | AA021852 | 87145 | taccgctttacagctcagca | AA107137 |
| 1938 | ctctgggctgagctctacaacatac | M77678 | 44542 | agtgcatactctccaaccatagga | AA021852 | 87146 | ccgcttttacaagctcagcacg | AA107137 |
| 1939 | gtttaccagcctcatatctccagt | M77678 | 44543 | catactctccaaccataggaagct | AA021852 | 87147 | gctttacagctcagcagcagcag | AA107137 |
| 1940 | tcatatctccagtctctgcatgcc | M77678 | 44544 | tactctccaaccataggaagcgt | AA021852 | 87148 | ttacaagctcagcagcacgacgag | AA107137 |
| 1941 | ctccagtctctgcatgccctgggaa | M77678 | 44545 | tactctccaaccataggaagcgat | AA021852 | 87149 | gcagtcagcacgagagggggtc | AA107137 |
| 1942 | aaactgccagcagggcatccag | M77678 | 44546 | cttctccaaccataggaagcatg | AA021852 | 87150 | gaccagtccaggggtcctgatggtg | AA107137 |
| 1943 | agtccaggctgccgaaaagagccc | M77678 | 44547 | tctccaaccataggaagcgatgttg | AA021852 | 87151 | agtgcctaggaaagaatctgta | AA107137 |
| 1944 | aagtgaccacctcattctggggg | L09104 | 44548 | acctgccgagtgctgccaggaa | AA021852 | 87152 | gtacgtgctatcaagctggagcc | AA107137 |
| 1945 | tggactacaaggctgttgggagag | L09104 | 44549 | cgagtgctgccccgaagtctgtcc | AA021852 | 87153 | acgtgctatcaagctgggccat | AA107137 |
| 1946 | gactacaaggctgtgggagaagct | L09104 | 44550 | ctgccaggaagtctgtccgtccg | AA021852 | 87154 | ggctatcaagctggagccatcaag | AA107137 |
| 1947 | ctacaaggctgttgggagaagctgg | L09104 | 44551 | ctgatcttgctcaactgtggagc | AA021852 | 87155 | ctatcaagctgagccacccaagtc | AA107137 |
| 1948 | cctccctgttgaagctgatgaagg | L09104 | 44552 | tcttgctaaacttgggagcttt | AA021852 | 87156 | ggcccacagtcgaactggagac | AA107137 |
| 1949 | ttgacgggtcatgttgttcgact | L09104 | 44553 | ttttttaaccaagcacagagta | AA021852 | 87157 | acagctgcacctggattaccgctt | AA107137 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 1950 | gacgtgtcagtgttctgacctgt | L09104 | 44554 | ggaaaaccaccattctgatcagtt | AA021858 | 87158 | agtatgtcataccaatgctcttgta | U04269 |
| 1951 | tcatgtttgtgacctgtatttca | L09104 | 44555 | acctagaacgcatcctgcacagcgt | Z48670 | 87159 | caatgccttgtcacctgtgtg | U04269 |
| 1952 | atgtgttctgacctgtatttcaca | L09104 | 44556 | aacgcatcctgcacgcgtgcacct | Z48670 | 87160 | ggttgtgcactgatctcagaagga | U04269 |
| 1953 | cacccagctagaataaagacacct | L09104 | 44557 | atctattaacaattcgatgcgaagg | Z48670 | 87161 | tgcactgatctcagaagaatgctta | U04269 |
| 1954 | tgggacatcaacagctgaccagt | L09104 | 44558 | acactgctatccgtttaacgttgag | Z48670 | 87162 | ttgtaatttctcttcctcatagga | U04269 |
| 1955 | ggacatcaacagtcgaccagtgg | L09104 | 44559 | cgcagtctgctggaattccaaaat | Z48670 | 87163 | tttctatagaatccagttcattc | U04269 |
| 1956 | acatcaacaagcttcgaccagtgggg | L09104 | 44560 | agagactcaaacgaactatgcaaaat | Z48670 | 87164 | atccagttcatttctatgtacctat | U04269 |
| 1957 | ggcagctctgtgacctccatg | L09104 | 44561 | tccaaactccagaaagacatccta | Z48670 | 87165 | ttcatttctatgtacctatgctgag | U04269 |
| 1958 | ctagaataaactccagccgccct | L09104 | 44562 | catcctaatttactgacatgtt | Z48670 | 87166 | tacctatgctgagaatcctgcgccaat | U04269 |
| 1959 | agttggcctggactacaaggctgtt | L09104 | 44563 | tctgtgacatgttttcagttacctc | Z48670 | 87167 | taagagccaatacttccttagaatg | U04269 |
| 1960 | ttgggcctggactacaaggctgttgg | L09104 | 44564 | catgtttcagttacctctaggtg | Z48670 | 87168 | gccaatacttcctagatgatgcaa | U04269 |
| 1961 | cctagatacaaggctgtggggaga | L09104 | 44565 | tacctctaggtgaagcctccagga | Z48670 | 87169 | acttctagatgatgcaataaaata | U04269 |
| 1962 | aagccttgtcatcgaagggaacca | AA050852 | 44566 | gaagcctcaggagactctctcttac | Z48670 | 87170 | tagtaaacaatcgatcctgatccaa | U04269 |
| 1963 | cctgtcatcgaagggaccatgg | AA050852 | 44567 | acaggtgcacctctaccacacagt | Z48670 | 87171 | gatcctgatccaagtttctcatttt | U04269 |
| 1964 | gaggacttctcaaggagcactaca | AA050852 | 44568 | tctaccacatagtcaaagagaagg | Z48670 | 87172 | tcctatctcaggttggctgctatga | U04269 |
| 1965 | gacttctcaaggagcactacactg | AA050852 | 44569 | tttacataaacgaagtatgcatt | Z48670 | 87173 | ctcaggttggctgctatgagaccaaa | U04269 |
| 1966 | aaggagcactacactgacctgaagg | AA050852 | 44570 | tgagcatcgacgttgaaggaaagat | Z48670 | 87174 | acttacactgccttggcctcttct | U04269 |
| 1967 | gagcactacactgacctgaaggacc | AA050852 | 44571 | tctccataaacacacaggcctctct | Z48670 | 87175 | ctctctctctgtgaggtatata | U04269 |
| 1968 | cactacactgacctgaaggacgcc | AA050852 | 44572 | taacacacaggcctctctgtggaa | Z48670 | 87176 | accagcatacagtgtgcactg | U04269 |
| 1969 | tttactggcctgggaataatacgc | AA050852 | 44573 | acaggcctctctgtggaaatacca | Z48670 | 87177 | attacaggtgtgcactgatctca | U04269 |
| 1970 | gtgaaatacatgcactccagaacag | AA050852 | 44574 | aataccacatcatcattacaatt | Z48670 | 87178 | cctactccatgacaacatactg | U04269 |
| 1971 | tacatgcactcagaccagtggttg | AA050852 | 44575 | tcctcttggggcaagctgactc | Z48670 | 87179 | ttatctgtatcacatcgtttc | U04269 |
| 1972 | cactcagaccagcagtggtctaagg | AA050852 | 44576 | ccaagctgactccacgtccatcga | D29678 | 87180 | atgatgccatggcgactggagaagac | U29055 |
| 1973 | tcaggaccaggttgctatgtct | AA050852 | 44577 | aatggcctgccatgaccaagctgcc | D29678 | 87181 | ccattccaaccttgaatcgttacag | U29055 |
| 1974 | tcggaccatggccacactggagcgca | AA050852 | 44578 | tgcaacaaggctgcagactaaggcc | D29678 | 87182 | caacctgaatcgttacgacgtatag | U29055 |
| 1975 | atggccaacagtgcgcgcaacttca | AA050852 | 44579 | caatgtaccccagtacaacatcct | D29678 | 87183 | gcgatagaatcctatccaactactaac | U29055 |
| 1976 | gccaacagtgcgcgcaccttcatg | AA050852 | 44580 | catcctggctgaacgtgcgccaa | D29678 | 87184 | gcatatcctatccaactactaac | U29055 |
| 1977 | aacagtgcgcgcaccttcatgcca | AA050852 | 44581 | gggacctgaacctattgaaggtaa | D29678 | 87185 | ttccttcacttattgctgaaccaa | U29055 |
| 1978 | cgccttgtgtcaggttctgc | AA050852 | 44582 | tgttgcagaacctattgaaggtaa | D29678 | 87186 | tcactattgctgaaccaagagcgac | U29055 |
| 1979 | aagtttctgcaggcttcagaggaa | AA050852 | 44583 | agtgtaaacctgtcgcagcgatctc | D29678 | 87187 | attgcgaaccaagagcacaattcc | U29055 |
| 1980 | caggcttcagaggacctctcaagg | AA050852 | 44584 | acccctgcagcgcatctcagagagc | D29678 | 87188 | gaaccaagagcacaatcccattaa | U29055 |
| 1981 | gcttcagaggacctctcaaggagc | AA050852 | 44585 | tgcagcgcatctcagagaggagc | D29678 | 87189 | aaattgtgcatttctgggccatt | U29055 |
| 1982 | caaacagttcgaggattccaag | W46016 | 44586 | catagcgctctgaacccagtggc | D29678 | 87190 | tcacatctgttcctcctccaagag | U29055 |
| 1983 | gttcctgaggattccaaggaaacag | W46016 | 44587 | tgtactccagctccatcgacatgtg | D29678 | 87191 | ctgttccttctccaagagtggccg | U29055 |
| 1984 | cttgtgcacaaggactttagccggt | W46016 | 44588 | ccacagtcgcatcgacatgtggctcagc | D29678 | 87192 | tcctctggtatgatgactcaa | U29055 |
| 1985 | tgtgcacaaggactttagccgctgc | W46016 | 44589 | ggtcacgccgtgcatcttgcaga | D29678 | 87193 | cactcaaagtgacagagcaggtgt | U29055 |
| 1986 | gcacaaggactttagccgctgcaactgcctg | W46016 | 44590 | ccggcccatcttgccgcagagctgc | D29678 | 87194 | tcttagcggacacgacaaccgagt | U29055 |
| 1987 | cttagccgctcgaactgctgatc | W46016 | 44591 | gcatcttgcagagctgctaatgc | D29678 | 87195 | ctggacacgacaaccgagtcagctg | U29055 |
| 1988 | agccgctcgcaactgctgatcagt | W46016 | 44592 | tctccctggccaatgatgtggata | D29678 | 87196 | acgaacaaccgagtcgctgcttggg | U29055 |
| 1989 | tcgcaactgctgatcagtgccag | W46016 | 44593 | tggatgaccagtcgaaganggattctt | D29678 | 87197 | tggaacagggtcctggacagctt | U29055 |
| 1990 | caacgcctgatcagtgccagagg | W46016 | 44594 | tgctagcaaccgacgatgaggaaca | D29678 | 87198 | ctaacaggtggcctggactacatcaa | U29055 |
| 1991 | ctgccagtgccagagggccag | W46016 | 44595 | ttagccgcaacgcttgtagtgt | D29678 | 87199 | tggaatacacaaagtcacctggaa | D50095 |
| 1992 | cgcactgggcctgagccaaggatgta | W46016 | 44596 | cagcaacgcttgtagtgtcactct | D29678 | 87200 | tggtcattgcctctcgcaacagctg | D50095 |
| 1993 | tgagtactccactccgccaggcc | W46016 | 44597 | agagaattcgcagcgccctagcctgga | D38379 | 87201 | ttgccttcgcaacgctgcag | D50095 |
| 1994 | cctagcaccaaaacagaaggtggcc | W46016 | 44598 | gccatgggcagggagtcaggacaacg | D38379 | 87202 | tctgcaacactcgtcgcagcgaacc | D50095 |
| 1995 | cagcaccaaaacagaaggtggcctg | W46016 | 44599 | tagatgacgactctgccgctggc | D38379 | 87203 | gcgaacctgcacatgtcaccat | D50095 |
| 1996 | catgggacaccgtccaacaaccgc | W46016 | 44600 | tctgccctggccctgacctgttt | D38379 | 87204 | ctgtgcacagtcacattggct | D50095 |
| 1997 | gagcaactgtccaacaaccgttg | W46016 | 44601 | cctgacctgctttccaacactgttt | D38379 | 87205 | acatgttcaccatttgctgggcta | D50095 |
| 1998 | gacctgtccaacaaccgcttgtg | W46016 | 44602 | tgcactccactctgtcactgcaga | D38379 | 87206 | tggctacaactccactccacgctgaa | D50095 |
| 1999 | gtccaacaaccgcttgtgcacaag | W46016 | 44603 | cactctccacctgttgtcacatgt | D38379 | 87207 | tcatctaccccgctgcaacgagaa | D50095 |

| SEQ ID NO | sequence | DBAxnID | SEQ ID NO | sequence | DBAxnID | SEQ ID NO | sequence | DBAxnID |
|---|---|---|---|---|---|---|---|---|
| 2000 | caacaacgctttgtcacaaggac | W46016 | 44604 | ccacctgtattctgcagtccag | D38379 | 87208 | atgtccaaggatgtcacatgtgg | D50095 |
| 2001 | caaccgctttgtcacaaggacta | W46016 | 44605 | tctccagcctgtgctatagtgcc | D38379 | 87209 | gggtcgtagaccctgagcctag | D50095 |
| 2002 | ctgtgccaccaagaactgtcagc | M63445 | 44606 | ttgctataglgccactgaatgc | D38379 | 87210 | acatcaaagtcaactgaagaggct | D50095 |
| 2003 | tcgtgccaccaagaactgtcagca | M63445 | 44607 | cgcttgtgctcactcgggca | D38379 | 87211 | aagtcacctgaagaggctcgctc | D50095 |
| 2004 | gttggctttcctgtaagctatccag | M63445 | 44608 | agtgcccacctgaatgtcaataaag | D38379 | 87212 | tccgtcacattccagacagtatgt | D50095 |
| 2005 | ttggctttcctgtaagctatccag | M63445 | 44609 | tcactctgggcctagtgtgcgct | D38379 | 87213 | cacattccagacagtatgtccgg | D50095 |
| 2006 | ttccgtaagctatccaggagtt | M63445 | 44610 | attaatgctctaaacatgcaata | D38379 | 87214 | ccagacagtatgtcggttgca | D50095 |
| 2007 | ttccgtaagctatccaggagctg | M63445 | 44611 | cagctattattcagggcctacctg | D38379 | 87215 | ggattcctatttcatcttctcat | D50095 |
| 2008 | cctgtaagctatccaggagcttggg | M63445 | 44612 | ggaaacctgactttatcacagag | D38379 | 87216 | ccatattcatctctctcatggtcat | D50095 |
| 2009 | ctgtaagctatccaggagctggt | M63445 | 44613 | cctgacttattcacagaaggcgc | D38379 | 87217 | tcttcatgtcatctgcctctgcaa | D50095 |
| 2010 | gtaagctatccaggagcttggtta | M63445 | 44614 | cagcatctcggacttgctctgt | D38379 | 87218 | tcggaagtccagtccaataggttt | D50095 |
| 2011 | agctatccaggagctggttaata | M63445 | 44615 | ctctgagacttgtctgtagaaag | D38379 | 87219 | ctgctgaccaagtcagcagagtgca | D50263 |
| 2012 | gctatccaggagcttgggtaatat | M63445 | 44616 | atggttcgtcgcctgcagtcg | AA022006 | 87220 | gacctcagctttctctagctccata | D50263 |
| 2013 | taaatatagcatcgtcggggt | M63445 | 44617 | cgtcgtcctcgcagtcgtctct | AA022006 | 87221 | agtttctctagctccctagtctag | D50263 |
| 2014 | gtgccaccaaagaactgtcagagc | M63445 | 44618 | tgtgccagccaggacgaaactgg | AA022006 | 87222 | tcccagtcgcactttaacctaggg | D50263 |
| 2015 | tgccaccaaagaactgtcagcagct | M63445 | 44619 | gaaccagagttcactgaaaccg | AA022006 | 87223 | cagctgcacttaacctaggggag | D50263 |
| 2016 | ccaccaaagaactgtcagcagctgc | M63445 | 44620 | gaaacggaatgcctcctcctgggg | AA022006 | 87224 | cctctgtccctgatatgctgtac | D50263 |
| 2017 | caaagaactgtcagcagctgcctgc | M63445 | 44621 | gaatgcctcctgccggtgaaagg | AA022006 | 87225 | ctgtccctgatatgctggtaccat | D50263 |
| 2018 | agaactgtcagcagctgcctgcacg | M63445 | 44622 | tgccttcctgccggtgaaagcgaat | AA022006 | 87226 | atgctggtaccatgtgttgtgtcca | D50263 |
| 2019 | tgtcagcagctgcctgcacgtctt | M63445 | 44623 | agcgaattcctagacaacctggaaca | AA022006 | 87227 | ttgtttgtccagggatgccagc | D50263 |
| 2020 | gtcagcagctgcctgcacgtcttc | M63445 | 44624 | gaattcctagacaacctggaacaa | AA022006 | 87228 | tttgtcaggggatgccagctca | D50263 |
| 2021 | cagcagctgcctgcacgtcttcac | M63445 | 44625 | agagaacacgctcaccagcaca | AA022006 | 87229 | taactagtccatctcccctggaac | D50263 |
| 2022 | tctcggaaaccgtagccctgcagg | W55117 | 44626 | cactgccaccagccacaaatactgcg | AA022006 | 87230 | ctgactcaagtgcagagtgcactg | D50263 |
| 2023 | tcggaaaccgtagccctgcagca | W55117 | 44627 | tgcaccccgccacaaatactgcgacc | AA022006 | 87231 | ctccctggaatcttagctctct | D50263 |
| 2024 | tagcctgcagcctgtgaccaa | W55117 | 44628 | ctgcctgcagtgcctctggg | AA022006 | 87232 | tctggaaccttaggaaagtagctg | D50263 |
| 2025 | agccctgcagcatgctgtgaccaac | W55117 | 44629 | cctctcagtcgcgctctggggct | AA022006 | 87233 | gtagctgcagccagcctgctgct | D50263 |
| 2026 | gccctgcagcatgctgaccaact | W55117 | 44630 | ctgcagtcgcgtcctcggggctgct | AA022006 | 87234 | gccggtctctgaaagaggtgatg | D50263 |
| 2027 | ccctgcagcatgctgaccaactg | W55117 | 44631 | ttgcaccgcgtccatccagaac | AA022006 | 87235 | gatggtccatctccatccaccctgga | D50263 |
| 2028 | cctgcagcatgctgaccaactga | W55117 | 44632 | cccactgcagtcagagaaaaacagt | AA022006 | 87236 | tctccaccgggaccataggtgg | D50263 |
| 2029 | ttgcagcatgctgaccaactgact | W55117 | 44633 | tacctaaaaacagtcagtgcgtt | AA022006 | 87237 | actgacctcagttctctagctcc | D50263 |
| 2030 | tgcagcatgctgaccaactgactg | W55117 | 44634 | aacagtcagtgctgttcttgtgcc | AA022006 | 87238 | attaccaaggacatgttgaagaag | D50263 |
| 2031 | ggtctcggggctgaccaaccacagaa | W55117 | 44635 | tctttgtgccaggacagaaac | AA022006 | 87239 | gccctgcgagcttgggctgatgatg | D50263 |
| 2032 | tctctgggagcagaaccacacagaagc | W55117 | 44636 | gcctacactcgtccatccagcag | AA022006 | 87240 | ttaccgtttgtacacagagagcct | D26089 |
| 2033 | ctctgggagcagaaccacacagaagca | W55117 | 44637 | atcccgtccattcaagcaacgagc | AA022006 | 87241 | acacagagagctaagcccagttt | D26089 |
| 2034 | cggaaaccggtagccctgcagcat | W55117 | 44638 | ctaactgaggaggagctgaatct | AA022006 | 87242 | ctgtgcctttgtgtgttgcaatgc | D26089 |
| 2035 | gaaaccggtagccctgcagcatgg | W55117 | 44639 | gaaatctctgtgagatagagaga | AA022006 | 87243 | gtaccatgtcatgctgtgatgtagagg | D26089 |
| 2036 | aaaccggtagccctgcagcatggc | W55117 | 44640 | atctctgtgagatagagaaacg | AA022006 | 87244 | gctagtccttactgtgrgggacat | D26089 |
| 2037 | aaccggtagccctgcagcatggct | W55117 | 44641 | tcctctgacagaatgatgcgctg | AA022006 | 87245 | tataactgcagccgtacatcttt | D26089 |
| 2038 | accggtagccctgcagcatggctg | W55117 | 44642 | tgacagaactgatgcgctggaatta | AA022006 | 87246 | tggcagccgtacatccttttactg | D26089 |
| 2039 | ccggtagccctgcagcatggctga | W55117 | 44643 | atgcatgcctaaagcctaacctcac | AA022006 | 87247 | ccgtacactcttttactgtgatatga | D26089 |
| 2040 | cggtagccctgcagcatggctgac | W55117 | 44644 | catgctcaaaagcctaacctcaaac | AA022006 | 87248 | atcctttactgtgatatgatgggct | D26089 |
| 2041 | ggtagccctgcagcatggctgacca | W55117 | 44645 | taactgcctcaaacttaaatagtat | AA022006 | 87249 | tccataactatttagaacaaag | D26089 |
| 2042 | cttgccctgcctgcagtttc | M36660 | 44646 | atctatccaatttccccatgtaaat | X01023 | 87250 | gatttctaacacgtgactgggaaga | D26089 |
| 2043 | tttcgccttgttccacaaggatag | M36660 | 44647 | tatccaatttccccatgtaaatag | X01023 | 87251 | gctgcatggccctgcagtgcactac | D26089 |
| 2044 | gctattagttaccctctctgtgttt | M36660 | 44648 | gacgagacaagctcacctctgaaa | X01023 | 87252 | tggcatggcagtccactgaggtcactcac | D26089 |
| 2045 | ttgctcaaacaatggctgagggact | M36660 | 44649 | cacaagctcacctctgaaggact | X01023 | 87253 | tagagtcactcactgttattgc | D26089 |
| 2046 | ctcaaacaatggctgagggactaac | M36660 | 44650 | ctcacctgaaaggactaattga | X01023 | 87254 | aggcagtatccactaactataaacct | D26089 |
| 2047 | cagtgactgcacagccgtgcgggat | M36660 | 44651 | caaaactgcgaacagttcgaaact | X01023 | 87255 | actataaaacctcttcatctg | D26089 |
| 2048 | tgcactgcacaggccggggatgc | M36660 | 44652 | aaacttcgaacagttctgaacctg | X01023 | 87256 | taaacctcgttcctcgaatgt | D26089 |
| 2049 | ctgacacaagccgggggatgtgctct | M36660 | 44653 | cagctcgaaacttctggtgcataaa | X01023 | 87257 | tgcctcttaccgtgttgtacacaga | D26089 |

TABLE 1-continued

| SEQ ID NO | DBAxnID | sequence | SEQ ID NO | DBAxnID | sequence | SEQ ID NO | DBAxnID |
|---|---|---|---|---|---|---|---|
| 2050 | M36660 | acaagcctcggggattgctctcca | 44654 | X01023 | gcataaactgacctaactgaagag | 87258 | U27457 |
| 2051 | M36660 | agcctcggggattgctctccagct | 44655 | X01023 | actgacctaactgaggaggagctg | 87259 | U27457 |
| 2052 | M36660 | tctccgcctcattctgctatctt | 44656 | J00612 | tgttccggcaacggagatgaaca | 87260 | U27457 |
| 2053 | M36660 | cgcctcatctgctattcttct | 44657 | J00612 | agtacgtcatggtgcacttccgctg | 87261 | U27457 |
| 2054 | M36660 | tgcctcatgcgtttttgatagtt | 44658 | J00612 | acaagcgttacggtggcttcatgac | 87262 | U27457 |
| 2055 | M36660 | cctcatgcgttttgatagtctg | 44659 | J00612 | gtggttcatgacctccgagaagag | 87263 | U27457 |
| 2056 | M36660 | agtctgccacggcgtggacngca | 44660 | J00612 | tcatgacctcgaagagccagac | 87264 | U27457 |
| 2057 | M36660 | tctgccacgcggtggacagcaaa | 44661 | J00612 | agaagagccaagcgccccctggtac | 87265 | U27457 |
| 2058 | M36660 | ttcttcgggctagctggctaaat | 44662 | J00612 | cgccctggtgacgctctcaagaa | 87266 | U27457 |
| 2059 | M36660 | cgggctagcctggctaaatgcatc | 44663 | J00612 | cgctcttcaagaacgccatcatcaa | 87267 | U27457 |
| 2060 | M36660 | gctagcctggctaaatgcatccaa | 44664 | J00612 | tcaagaacgccatcatcaagaacgc | 87268 | U27457 |
| 2061 | M36660 | ccactgtgctaatgtacctct | 44665 | J00612 | acgcatcatcaagaacgcgcacaa | 87269 | U27457 |
| 2062 | M29211 | atgcggaccacacagactagtgag | 44666 | J00612 | tcatcaagaacgcgcacaagaagg | 87270 | U27457 |
| 2063 | M29211 | ttgagtcaactcaaggatgattga | 44667 | J00612 | agaacgcgcacaagaaggcccagtg | 87271 | AA108106 |
| 2064 | M29211 | tcctaatgcatttgtctctcggacc | 44668 | J00612 | tcatgggtcacttcgctgggaaccg | 87272 | AA108106 |
| 2065 | M29211 | gacctgcatttcttaatgcatagt | 44669 | J00612 | gcccaggaacgacagcagtgctgg | 87273 | AA108106 |
| 2066 | M29211 | cctgcatttcttaatcgattagtcca | 44670 | J00612 | gcagtcagggaacgctcagcgag | 87274 | AA108106 |
| 2067 | M29211 | ttcttaatgcattagtccaattgt | 44671 | J00612 | cagagccgcagtccacgcgagggcaa | 87275 | AA108106 |
| 2068 | M29211 | ctcaacaatatcaccagctgaagcc | 44672 | J00612 | cgagtccacgcgagggcaagcgtc | 87276 | AA108106 |
| 2069 | M29211 | aaatatcaccagctgaagcctataga | 44673 | J00612 | agggcaagcggtctactactccatgga | 87277 | AA108106 |
| 2070 | M29211 | atcaccagctgaagcctatagagta | 44674 | J00612 | agcgctcctactccatgagcactt | 87278 | AA108106 |
| 2071 | M29211 | tcaccagctgaagcctatagactac | 44675 | J00612 | cctactccatggagcactccgctg | 87279 | AA108106 |
| 2072 | M29211 | caccagctgaagcctatagactacg | 44676 | J00612 | ttttcattatatctcgaatgagttcca | 87280 | AA108106 |
| 2073 | M29211 | accagctgaagcctatagagctacga | 44677 | J00612 | ttattgctacactgcgatcagcagc | 87281 | AA108106 |
| 2074 | M29211 | ctacatatagggaccccctcaatgt | 44678 | J00612 | tgaccctcatgtgaatttcgaa | 87282 | AA108106 |
| 2075 | M29211 | ccattataggagcccctcaattgact | 44679 | J00612 | gtgaattctgtcaacctcaggaatg | 87283 | AA108106 |
| 2076 | M29211 | ttatggacccctcatgtactcct | 44680 | J00612 | tctgtcaacctcaggaatgttaacg | 87284 | AA108106 |
| 2077 | M29211 | tgggaccccctcatgtactccat | 44681 | J00612 | gtttgctctttggaatatagctgt | 87285 | AA108106 |
| 2078 | M29211 | gaccccctcattgtactcctaat | 44682 | J00612 | tgtacattgcacgtaggttttga | 87286 | AA108106 |
| 2079 | M29211 | cccccattgtactcctaatgtatt | 44683 | J00612 | gtttaggctggccttaaactcacag | 87287 | AA108106 |
| 2080 | M29211 | tcattgtactcctaatgtattgt | 44684 | J00612 | cttaaactcacagtctctgcctc | 87288 | AA108106 |
| 2081 | M29211 | tcattgtactccaatgatttgct | 44685 | J00612 | gtctctgctcagcctcgagt | 87289 | AA108106 |
| 2082 | W46716 | gaaagttggcctgtgtgtgtctga | 44686 | M60285 | tgcttgatttacggatgtgggccag | 87290 | AA108106 |
| 2083 | W46716 | aagttggcctgtgtgtgtgctgagt | 44687 | M60285 | gattacgtgatttggggccagaaatac | 87291 | AA108106 |
| 2084 | W46716 | aagggatatcctccacctgctcaa | 44688 | M60285 | ctacactggatcagcagcctgcaa | 87292 | AA108106 |
| 2085 | W46716 | ggggatatcctccacctgctcaaca | 44689 | M60285 | aatactgggccatttcattagagga | 87293 | AA108106 |
| 2086 | W46716 | ggatatcctccacctgctcaacagc | 44690 | M60285 | gctagctacaggtcagttgaagg | 87294 | AA108106 |
| 2087 | W46716 | atcctccacttgctcaacagcacaa | 44691 | M60285 | ggaagacctcaagctctgcaaagg | 87295 | AA108106 |
| 2088 | W46716 | tcacctgctcaacagcacaacaca | 44692 | M60285 | agaggttagcctttgtgctgacta | 87296 | AA108106 |
| 2089 | W46716 | accctgctcaacagcacaacaagg | 44693 | M60285 | ttgttgctactaggtcttcgtg | 87297 | AA108106 |
| 2090 | W46716 | ctgctcaacagcacaacaaggcca | 44694 | M60285 | tgtactaggctctctgctcatgtc | 87298 | AA108110 |
| 2091 | W46716 | tgctcaacagcacaacaaggccag | 44695 | M60285 | cctgctgctcggagagtttct | 87299 | AA108110 |
| 2092 | W46716 | ctcaacagcacaacaaggccaagg | 44696 | D64160 | cttgataccgaattgcagcagagaa | 87300 | AA108110 |
| 2093 | W46716 | caacagcacaacaaggccaaggcac | 44697 | D64160 | tatcaccccagcttactcacaactcc | 87301 | AA108110 |
| 2094 | W46716 | agtggccccatggtgatgaggact | 44698 | D64160 | acctccaagaaacgcaagtgtc | 87302 | AA108110 |
| 2095 | W46716 | agctggctcttctatgacta | 44699 | D64160 | acagcaaggtccttgctgctgag | 87303 | AA108110 |
| 2096 | W46716 | ctgtctggctctcatagactc | 44700 | D64160 | agtgctctttgtactgctgccttat | 87304 | AA108110 |
| 2097 | W46716 | ggtcttggctctcatagacact | 44701 | D64160 | cttgctactgagcctatctccct | 87305 | AA108110 |
| 2098 | W46716 | tcttggctctcatagactatcaa | 44702 | D64160 | tcctctaatacattcttaataaga | 87306 | AA108110 |
| 2099 | W46716 | ttgctctctatagactatcagaga | 44703 | D64160 | ggcaagtccccacagttcaagcttcaa | 87307 | AA108110 |

| SEQ ID NO | sequence | DBAxnID | SEQ ID NO | sequence | DBAxnID | SEQ ID NO | sequence | DBAxnID |
|---|---|---|---|---|---|---|---|---|
| 2100 | agaagagccctcgtgaggtcaccat | W46716 | 44704 | tcccacgtaagcttccaataaag | D64160 | 87308 | gccaacttccacatgcagtgctcaa | AA108110 |
| 2101 | aagagccctcgtgaggtcaccaga | W46716 | 44705 | gactgtcatggccagttatccacta | D64160 | 87309 | ttccacatgcagtgctcaagcgtta | AA108110 |
| 2102 | cagatgctgtcctggagccggcata | L03814 | 44706 | cagttatcacatcgttgtagcaat | D64160 | 87310 | cacatgcagtgctcaagcgttacgt | AA108110 |
| 2103 | ctagagtcagttcctccgatgagga | L03814 | 44707 | tcacacgtttagcaatgtatga | D64160 | 87311 | atgcagtgctcaagcgttacgttcag | AA108110 |
| 2104 | cctgccaggagatcctccgcctt | L03814 | 44708 | tcccagccactcactcttaagaaa | D64160 | 87312 | tgtccaagcgttacgttcagatgtcag | AA108110 |
| 2105 | gattctccgccttatgtcgggagac | L03814 | 44709 | tatctctgtcggactcatctcata | D64160 | 87313 | tcaagcgttacgttcagagatgattt | AA108110 |
| 2106 | ggagatctagacatcgctgcacat | L03814 | 44710 | attatttgcatttgcatttgcaatg | D64160 | 87314 | tggttctcgatagcgtcggacatgtag | AA108110 |
| 2107 | ctagcatctgcacatcctg | L03814 | 44711 | tgcatttgcatttgcaatgtgaaga | D64160 | 87315 | tcgatagccggacatgtaggatcgt | AA108110 |
| 2108 | tctgctgcacattctctgctggt | L03814 | 44712 | tattatacccaaggagggccgag | D64160 | 87316 | aattcagcgaacaatgtggaactg | AA108110 |
| 2109 | tgccacattctctgctgctgatgaac | L03814 | 44713 | catcggatcctggagaactggagtt | D64160 | 87317 | agttatcatggccacaaaccgaata | U39302 |
| 2110 | gctctgtatgaacctccaaactgga | L03814 | 44714 | actgaatccaggacctctccaagaa | D64160 | 87318 | gatggcctgcgggaaggcagaaag | U39302 |
| 2111 | ccctcaaactgagactccaagtcca | L03814 | 44715 | tccaggacctccaagaacagcaa | D64160 | 87319 | ctatctctagtggccacagtgtc | U39302 |
| 2112 | aggaacctagagccaggacatgga | L03814 | 44716 | cctcgaacaggcatcggtgcctag | D64160 | 87320 | ccattccagtcattttgccag | U39302 |
| 2113 | cctagagccaggacatgggatagaga | L03814 | 44717 | aacagcatcggtgccgtaggaagtg | D64160 | 87321 | tccagttcattttgccagtagaaa | U39302 |
| 2114 | tcagcttcctccgatgaggaaatg | L03814 | 44718 | ttcatcaggatgccaagtgcttg | D64160 | 87322 | agccgtatcgtgagggacaactgtg | U39302 |
| 2115 | gtgcgcaaccactgtttgaccatt | L03814 | 44719 | gtgcttgcttttacatcggctgcttt | D64160 | 87323 | cactgcctccatatgtgttggt | U39302 |
| 2116 | ctgtttgaccattcacctgtcag | L03814 | 44720 | catccgctgcttggaacaatcagg | D64160 | 87324 | gcctccatatgtgttggtcattgt | U39302 |
| 2117 | gaccattccacgctgcagcaccag | L03814 | 44721 | attggccagtatctttccagtaaca | D64160 | 87325 | atatgttggtcattgtgccgtg | U39302 |
| 2118 | ttgccgctgccagtgactcctag | L03814 | 44722 | cagtatctttccagtaacacagggatc | D64160 | 87326 | tgttggtcattgccgtgctctc | U39302 |
| 2119 | cagtgactcctaggcccacatgcct | L03814 | 44723 | ctttccagtaacagggatcataaag | D64160 | 87327 | tgccgtgctctctactccccat | U39302 |
| 2120 | cacagccccacagtggacgatgtca | L03814 | 44724 | aagatgccacactctccgctatc | D64160 | 87328 | catggccacaaaccgaatagaaact | U39302 |
| 2121 | ctgtgttccacatggaaaagagca | L03814 | 44725 | gccacacttctcgtatcgggtc | D64160 | 87329 | tttggatccagcacttatcaggca | U39302 |
| 2122 | cacacaacatatggccaagtg | W46723 | 44726 | cttctccgtatcgggtcctccag | D64160 | 87330 | caggccaggccatttgacagaaag | AA108121 |
| 2123 | caaacaatatggggccaaggtgct | W46723 | 44727 | gcgtatctggtcctccagacaca | D64160 | 87331 | gcgtatcttcagatcacacag | AA108121 |
| 2124 | cgtactacatgacagttggtgcaa | W46723 | 44728 | tttctcagatcatcaatcctgcca | D64160 | 87332 | cttccagatcaccacgaggatg | AA108121 |
| 2125 | ttttcagccatcattcaggaccg | W46723 | 44729 | agatccatcaatcctgccattgtct | D64160 | 87333 | caccagcaggatgacaactggtgat | U39302 |
| 2126 | gacccccatcattcaggaaccggcaag | W46723 | 44730 | atcaatcctgccattgtctgccgt | D64160 | 87334 | tgacctctgcgggcgacatcaag | U39302 |
| 2127 | accccatcattcaggaaccggcaag | W46723 | 44731 | atgtctgccgtatgaagcaggga | D64160 | 87335 | tggctgagccctgctgtgggaacgc | U39302 |
| 2128 | ccccatcattcaggaaccggcaagcg | W46723 | 44732 | agcattgccaatcatgactgttca | D64160 | 87336 | gatgccaatcaggcctctatggcaa | U39302 |
| 2129 | ccatcattcaggaaccggcaagcgg | W46723 | 44733 | agcaacttgactggcacgaaggt | D64160 | 87337 | atggcaactaggccttctatggcaa | AA108121 |
| 2130 | atcattcaggaaccggcaagcgcgct | W46723 | 44734 | tcagatgtcccacaagtgatgcag | D64160 | 87338 | caagccaactaggaactccggacaagca | AA108121 |
| 2131 | tcattcaggaaccggcaaggcgcta | W46723 | 44735 | catagtcttccttcatcagcgatg | D64160 | 87339 | agcctaggaactccggacaagca | AA108121 |
| 2132 | attcaggaccgggcaaggcgcagtctagc | W46723 | 44736 | cctggccactgctgcacgagtcatc | AA021926 | 87340 | gcctaggaactccggacaagcaga | AA108121 |
| 2133 | ttcaggaccggcaaggcgtagca | W46723 | 44737 | ctggcacctgctgcacgagtcatcg | AA021926 | 87341 | gcctaggaactccggacaagcagaa | AA108121 |
| 2134 | caaccatatgggccaaggtctgac | W46723 | 44738 | gagtcatcttggtgatgccacact | AA021926 | 87342 | ctaggaactccggacaagcagaaag | AA108121 |
| 2135 | aggaccggcaaggcggctagcaagc | W46723 | 44739 | agtcacttggtgatgccacactg | AA021926 | 87343 | taggaactccggacaagcagaaagg | AA108121 |
| 2136 | aggcctgaccccgagctgtacgcg | W46723 | 44740 | tggatgcgcacactgccgaagtcaa | AA021926 | 87344 | gaagcgagtcctgtgtctggtgttg | AA108121 |
| 2137 | ggtgtcgaccccgagctgtacgcg | W46723 | 44741 | ggagcgcacactgccgaagtcaac | AA021926 | 87345 | tggcaactaggcctctatggcaaa | AA108121 |
| 2138 | cgtcgaaggtgacgccgaagcgg | W46723 | 44742 | gatgccgcacactgccgaagtcaact | AA021926 | 87346 | ggcaactaggcctctatggcaaaaa | AA108121 |
| 2139 | ctgcgtagacaatgcgggcccacc | W46723 | 44743 | atgccgcacactgccgaagtcaactg | AA021926 | 87347 | caactaggcctctatggcaaaaat | AA108121 |
| 2140 | caccgtacatcatgacatggg | W46723 | 44744 | tggccacactgccgaagtcaactgc | AA021926 | 87348 | caactaggcctctatggcaaaaaat | AA108121 |
| 2141 | cccgtacatcatgacaagtgggtg | W46723 | 44745 | gcgcacactgccgaagtcaactgcc | AA021926 | 87349 | agatcaagcctaggaactccggaca | AA108121 |
| 2142 | ccgtacatcatgacaagtgggtgc | W46723 | 44746 | cgcacactgccgaagtcaactgcct | AA021926 | 87350 | gatcaagcctaggaactccggacaa | AA108121 |
| 2143 | ttgacagttgtccaggccca | M58691 | 44747 | gcacactgccgaagtcaactgcctc | AA021926 | 87351 | atcaagcctaggaactccggacaag | AA108121 |
| 2144 | cttccaggcccaagtctctgttg | M58691 | 44748 | tggatcctgcacgtcaactgcctc | AA021926 | 87352 | tcaagcctaggaactccggacaagc | AA108121 |
| 2145 | tctcctgaatctaagtgctgtga | M58691 | 44749 | ggccctctgcacgagtcatcgtt | AA021926 | 87353 | gaatccagaacaatcagggaacgt | AA108121 |
| 2146 | agccggtccaataactatccta | M58691 | 44750 | gcacctgctgagagtcatcgtt | AA021926 | 87354 | agaggccatcagggaacgtgcaggg | AA108121 |
| 2147 | ttttactagacctgaagtcagtg | M58691 | 44751 | cactgcctgcagagtcatcgtttg | AA021926 | 87355 | cacatgccctagtgaaccccacatgt | U70068 |
| 2148 | tagacctgaagtcagtgctcggt | M58691 | 44752 | acctccaagccagtcacttgg | AA021926 | 87356 | cacatgcagcctgcctcttctt | U70068 |
| 2149 | ctgaagtcagtgctcggtgtcga | M58691 | 44753 | cacctccaagccagtcacttggtg | AA021926 | 87357 | ctgcctctctgctggtcaaag | U70068 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 2150 | tggtcgaagctctcctgagaatcc | M58691 | 44754 | acctccaagccgagtcacttgtgg | AA021926 | 87358 | gtgctcgaccaatgctcgactcca | U70068 |
| 2151 | ctgagaatccgtgctcaaattc | M58691 | 44755 | cctccaagccgagtcacttggtga | AA021926 | 87359 | gaccaatgctcgactccagcctct | U70068 |
| 2152 | gtgctcaaattccctcctaaagca | M58691 | 44756 | caggaggacccaacagttgagcgg | X85993 | 87360 | agcctttcacgccacattgaagt | U70068 |
| 2153 | aatatattgctaccgtacaagtcta | M58691 | 44757 | acccagaagtgctgagctgagccgca | X85993 | 87361 | tttcacgccacattgaagttaggg | U70068 |
| 2154 | atatgctaccgtacaagtctatt | M58691 | 44758 | cttagtgttcctcgaaagtcat | X85993 | 87362 | gcatcaccgatcttccaggattg | U70068 |
| 2155 | gcttattatggtacccaggctggc | M58691 | 44759 | gttccctgaaagttcatatggt | X85993 | 87363 | tgggcaacacgcctcacagaaatca | U70068 |
| 2156 | tattatggtacccaggctggctt | M58691 | 44760 | tatggttcctcttttgcctgaga | X85993 | 87364 | ccaagctccacagaaatcaagataa | U70068 |
| 2157 | accccaggctggtttgaactcaat | M58691 | 44761 | tggttccttcttttgcctgagaata | X85993 | 87365 | cggccacactaaatgcaggctgta | U70068 |
| 2158 | tgaactcaataataatcctgcttag | M58691 | 44762 | aatgtcattgccatcgaaagaga | X85993 | 87366 | agcccaggggagtcaggccaggt | U70068 |
| 2159 | caatataatcctgccttagcctt | M58691 | 44763 | tgcatcagcaaagccattttattga | X85993 | 87367 | tagagctgactccttcattctcta | U70068 |
| 2160 | tataatcctgccttagcctttcca | M58691 | 44764 | atcagcaaagccattttattgaagc | X85993 | 87368 | ctgactcctccatcctcagtgatg | U70068 |
| 2161 | tccaagttctggggttacaggtatg | M58691 | 44765 | ttggctaccagcactcgtgttgta | X85993 | 87369 | cctlcatlctcagtgatgtttgac | U70068 |
| 2162 | caactcggtctctggaacttaa | M58691 | 44766 | accagcactcgtgttgtatgtact | X85993 | 87370 | gtttgacaacaacagatagtagcg | U70068 |
| 2163 | tcttatatgggtcctaagagga | M58691 | 44767 | agcactcgtgttgtatgtactgga | X85993 | 87371 | ccaaaggatatccaagcaaggat | U70068 |
| 2164 | ggcatccagcaagcaaagaggcaac | L13732 | 44768 | catttcatggcattatgtggatgt | X85993 | 87372 | tgtccactgtcaccctagcccagg | AA108088 |
| 2165 | tccagttccagaacaacctcaaaaca | L13732 | 44769 | ttcaggcattatgtggatgtttac | X85993 | 87373 | actcagtggggcgtctccacaa | AA108088 |
| 2166 | cagaacaacctcaaacagaactgcca | L13732 | 44770 | actttccagcagggcttttcctagt | X85993 | 87374 | cgctctccaaaggcctctggt | AA108088 |
| 2167 | aacacctcaaacagaactgccacaa | L13732 | 44771 | ggcttctlcagtataccaacgctt | X85993 | 87375 | attcctgagaccggcactccaaaat | AA108088 |
| 2168 | tcaaacagaactgccacaactccat | L13732 | 44772 | tataccaacgctgacagatcac | X85993 | 87376 | gagaacgcactccaaaatgccc | AA108088 |
| 2169 | aacagaactgccacaactccattgt | L13732 | 44773 | gatgttcacgtccgctgacttagtg | X85993 | 87377 | tccctcaaacatcagaagagctgg | AA108088 |
| 2170 | agaactgccacaactccattgtctc | L13732 | 44774 | gtccgctgacttagtgttccctg | X85993 | 87378 | aagttgcaagctgaggcagcaga | AA108088 |
| 2171 | acaactccattgtctcactccagt | L13732 | 44775 | cgctgacttagtgttccctgaaa | X85993 | 87379 | tcttgcaagctgaggcagcagatag | AA108088 |
| 2172 | actccattgtctcactccagctgt | L13732 | 44776 | tccaggagacaaccaactcctag | D63679 | 87380 | gggaagcagctcctcaacttagttgg | AA108088 |
| 2173 | ttgtcactccagctcgtcgaaga | L13732 | 44777 | agtttcgcaaccagcatgtacct | D63679 | 87381 | aagcgctcctcaacttagttggtca | AA108088 |
| 2174 | cactccagctcgtcggaagaatgaag | L13732 | 44778 | cttgacatccccaagaagagttac | D63679 | 87382 | ctcaactctgggtcattgtgtcag | AA108088 |
| 2175 | agacacagcagcaatlggaggtc | L13732 | 44779 | ctactgatatactctagtttgtta | D63679 | 87383 | ttagtggtcattgtcatgtgatg | AA108088 |
| 2176 | cttacctcggaatatgacacat | L13732 | 44780 | atatactctagtttgttagactgt | D63679 | 87384 | attggtcatgttgatgctggagaaa | AA108088 |
| 2177 | atgaaccattctlatccaccacac | L13732 | 44781 | tttgttagactgtccaagaagaatg | D63679 | 87385 | tcctcaaaggcctctggtggtgat | AA108088 |
| 2178 | ccattctlatccaccacaactaga | L13732 | 44782 | agtgtgttgtctgcatgctgtc | D63679 | 87386 | caaaggcctctggtgatgatgtg | AA108088 |
| 2179 | ttctlatccaccacaactaagagac | L13732 | 44783 | gttgtctgcatgctgctgtc | D63679 | 87387 | agggcctctggtgatgatggagc | AA108088 |
| 2180 | tcaactgaaggtgactccagttccc | L13732 | 44784 | tagacaaattcacacaattgcatgg | D63679 | 87388 | gctctctggatgatgagcgta | AA108088 |
| 2181 | ggtgactccagttccccagaacaccct | L13732 | 44785 | caacattgcatggctctcctttcaa | D63679 | 87389 | gagcgtactctcctaacatcctg | AA108088 |
| 2182 | gactccagttccagaacacctcca | L13732 | 44786 | tgcatggctctclttcaaaaagtg | D63679 | 87390 | cgtacttcctaacatcctgaga | AA108088 |
| 2183 | ctaaaatcacacactggtgtccta | L13732 | 44787 | ttcagactaagtgtagaagaacagta | D63679 | 87391 | cctaacatcctgagaccggcactc | AA108088 |
| 2184 | aatltcacactgaglggtcctaaagt | W47695 | 44788 | tgtacctgttaccaagacaacagta | D63679 | 87392 | aacattcctgagaccggcactccaa | AA108088 |
| 2185 | ccagttcaaagtcctcgatgtaga | W47695 | 44789 | tgttaccaagacaacagtacgtcat | D63679 | 87393 | aatgtctccatcaggccttcactat | AA108088 |
| 2186 | agtctcaaagtcctcgatgtagatg | W47695 | 44790 | aacagtacgtactgacaatagcca | D63679 | 87394 | gtctccatcaggccttcactatct | AA108088 |
| 2187 | tctcaaagtcctcgatgtagatgt | W47695 | 44791 | ttttaatcctlgacagtttgcat | D63679 | 87395 | ttatgacgaggctgaccggttcag | AA108088 |
| 2188 | aaagtctccgatgtagatgtagtg | W47695 | 44792 | aaccttgacagtttgcatgtgatg | U01840 | 87396 | ttgcagtttcccgccagatgtc | AA108088 |
| 2189 | agtctccgatgtagatgtagttgtt | W47695 | 44793 | tgtatgctatcactcattggctac | U01840 | 87397 | tcccgcatgctgtggccaactt | AA108088 |
| 2190 | gggcctgagtggcctcaaaagtg | W47695 | 44794 | gctatcactcattggctactlgaca | U01840 | 87398 | cgccatgtctgtgggcaacttaga | AA108088 |
| 2191 | ctgcactcaaagtcgaagtaaaaatc | W47695 | 44795 | actcactgaagtctactlgacataggca | U01840 | 87399 | atctggtctgtcatcacacacg | AA108088 |
| 2192 | atctccaaagtcaagaactaacag | W47695 | 44796 | ggacctcattcacagaagttacag | U01840 | 87400 | tgtgctacgtcatcacacacgcga | AA108088 |
| 2193 | aaatgtactttccagatgagaat | W47695 | 44797 | gttacagcacgatgtcaacgccgg | U01840 | 87401 | tcatcacacacggcgaggaagaga | AA108088 |
| 2194 | atgtactttccagatgagaatt | W47695 | 44798 | acgatctggcccggtgagtca | U01840 | 87402 | tgtgtctctcatacctggagtca | X65979 |
| 2195 | ttcacactggtcctaagtta | W47695 | 44799 | agatactlgcaggtggtcaggcag | U01840 | 87403 | atacctggagtcagccaagatggggg | X65979 |
| 2196 | attgaattlcctgagggtgagat | W47695 | 44800 | tttgcaggtggtcaggtcagtcagg | U01840 | 87404 | cagtttgcaactcctaagttaa | X65979 |
| 2197 | ttgaatattccgagggagatg | W47695 | 44801 | gggcctgcagcgaactgacattag | U01840 | 87405 | atcaggccttcactlgcactgtcg | X65979 |
| 2198 | gaatatttccgagggagagatgt | W47695 | 44802 | acacgcttccagagacacacttag | U01840 | 87406 | gggcacttgctcactgggtcg | X65979 |
| 2199 | atlcctgagggtlgagatltgatacca | W47695 | 44803 | ttcagagacacactatggagagcc | U01840 | 87407 | cctltgctcactgggtccataaa | X65979 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 2200 | gattgataccagtctcaagctcct | W47695 | 44804 | aggaagacactcccgatgagctat | U01840 | 87408 | tcaagggacggaccagagagac | X65979 |
| 2201 | ttgatacagtctcaaagctcctga | W47695 | 44805 | acactccgatgagctattttcgt | U01840 | 87409 | ctatactgcagccttcaaagtgtt | X65979 |
| 2202 | taccagtctcaaagtcctgatgta | W47695 | 44806 | gagctattttcgtcacttcttctc | U01840 | 87410 | tactgcacgccttcaaagtgttga | X65979 |
| 2203 | tctccgtttgatatctgttgca | W47695 | 44807 | taactcacacggctaaagaagcaat | U01840 | 87411 | tgcacgccttcaaagtgttgacac | X65979 |
| 2204 | ctgtttgcaagtctcatgaagatg | W47695 | 44808 | ccgccggctcacatcgatgagatc | U01840 | 87412 | agttatgcacggaggctgaccggtt | X65979 |
| 2205 | gatccaggcctcatacagtgcttt | W47695 | 44809 | ccttaaccactgctgggtgcagcc | U01840 | 87413 | ttcagtgcacggggaatttgaccca | AA108166 |
| 2206 | ccagcctccatacacgtgcttcac | W47695 | 44810 | ccacgtgctcctcctggagccatc | U01840 | 87414 | caaagtctcatggtatcgctggctc | AA108166 |
| 2207 | gcgcctcatacagtgcttcaccg | W47695 | 44811 | acgcaggtcgtcctcgagccatc | U01840 | 87415 | tatcgctgctcaaccaatgtgact | AA108166 |
| 2208 | catacagtgcttcaccgagccac | W47695 | 44812 | tctgtcctcgagccatcaacag | U01840 | 87416 | atcgctggctcaaccaatgtgactg | AA108166 |
| 2209 | ctgggtctctgccataatctc | W47695 | 44813 | ctcatggatcctgaacctgtgct | U01840 | 87417 | tggctcaaccaatgtgactgggat | AA108166 |
| 2210 | ccttctgccataatctcctctaa | W47695 | 44814 | tgaacctggtctgataagaagtct | U01840 | 87418 | ggctcaaccaatgtgactgggata | AA108166 |
| 2211 | tctgccataatctcctctaagat | W47695 | 44815 | tgccacaagtggagcctaaggaa | U01840 | 87419 | gctcaaccaatgtgactggggataa | AA108166 |
| 2212 | gccctaaatctcctctaagatctg | W47695 | 44816 | ttataaacctgcacgaaccactg | U01840 | 87420 | ctcaaccaatgtgactggggataat | AA108166 |
| 2213 | aattctctctaagatctggcgctg | W47695 | 44817 | actctgccagaacacctgtttc | AA022083 | 87421 | tcaaccaatgtgactgggggataatg | AA108166 |
| 2214 | ctaagatctggcgctgttgaagaa | W47725 | 44818 | agcctcgagctgttgcagcagtc | AA022083 | 87422 | caaccaatgtgactggggataaagt | AA108166 |
| 2215 | agagcactgctcatggagactctt | W47725 | 44819 | gttgcacagtcttcagaagcct | AA022083 | 87423 | aactggacatattccaaatgacct | AA108166 |
| 2216 | gcactgctcatggagactcttgag | W47725 | 44820 | cgagctctgcaaacctgaccgca | AA022083 | 87424 | cctggacatattccaaatgaccctg | AA108166 |
| 2217 | ctgtctatggagactcttgaggcg | W47725 | 44821 | agctctgcaaacctgaccgcagt | AA022083 | 87425 | aaagctctatggtatcgctggctca | AA108166 |
| 2218 | ggtgtaactgctctccatactt | W47725 | 44822 | cttctgcaaacctgaccgagtcg | AA022083 | 87426 | aagctctatggtatcgctggctcaa | AA108166 |
| 2219 | cttcctcatatctgaagaaagcaga | W47725 | 44823 | tctgcaaacctgaccgcagtcgg | AA022083 | 87427 | agctctatggtatcgctggctcaac | AA108166 |
| 2220 | aagcagatgccagatccagcgcctc | W47725 | 44824 | tgggctcaccgctgctaaggag | AA022083 | 87428 | tatggtatcgctggctcaaccatg | AA108166 |
| 2221 | cagagctcagatccagcgcctcata | W47725 | 44825 | ggcagctcaccgctgctaaggaga | AA022083 | 87429 | atggtatcgctggctcaaccaatgt | AA108166 |
| 2222 | actgcagatccagcgcctctacag | W47725 | 44826 | cagctcaccgctgctaaggagagt | AA022083 | 87430 | tggtatcgctggctcaaccaatgtg | AA108166 |
| 2223 | ccccatctcaagtccgcctcgagg | W47725 | 44827 | gctcaccgctgtaaggaggagtct | AA022083 | 87431 | ggtatcgctggctcaaccaatgtga | AA108166 |
| 2224 | catcccacaagttaactgaa | W47725 | 44828 | tctgcagaacactgttttc | AA022083 | 87432 | gtatcgctggctcaaccaatgtgac | AA108166 |
| 2225 | ggagccatcgatgcacactgct | W47725 | 44829 | gaaacctgtgttctctgtttca | AA022083 | 87433 | gtccctcagctggcctcggagct | AA108166 |
| 2226 | agccatctgatgccacaactgctac | W47725 | 44830 | gaccacaatgtgaccggagcccc | AA022083 | 87434 | tcctcatgctggcctcggagcctt | AA060105 |
| 2227 | gatgccacaactgctacccttgcc | W47725 | 44831 | ccacaatgttgtgaccggagcccg | AA022083 | 87435 | catgctggcctcggagcctgcc | AA060105 |
| 2228 | taccctgctagctctctgagcg | W47725 | 44832 | tgtgtgaccggagccctgaagctg | AA022083 | 87436 | catggctcggagaacactcaagaa | AA060105 |
| 2229 | cagctgcatcaagctcctgctg | W47725 | 44833 | ttggaccggagcctgagcgtt | AA022083 | 87437 | tctaaggctcatcctgagagaact | AA060105 |
| 2230 | cacgcatcaagtcctgctgctg | W47728 | 44834 | gaccggagccctgagctgtgcag | AA022083 | 87438 | ctaaggctcatcctgagagaactg | AA060105 |
| 2231 | cagatcaagctcctgctgctggg | W47728 | 44835 | ggagccctgagctgtcgcagc | AA022083 | 87439 | taaggctcatcctgagagaactgc | AA060105 |
| 2232 | gatcaagctccctgctgctggcc | W47728 | 44836 | cagggcctctgagccctgagatc | AA022083 | 87440 | aggtccatcctgagagaactggcta | AA060105 |
| 2233 | ccttgctgacactgactgctggt | W47728 | 44837 | gtgattcatccccagtggccagcat | U25652 | 87441 | ggtccatcctgagagaactggctac | AA060105 |
| 2234 | ctcagcagcctaactctgtggtgg | W47728 | 44838 | ggatctctgtgggatccaaacattt | U25652 | 87442 | catgctggcatcggagcctgcc | AA060105 |
| 2235 | tcctcacaagcttttaactgaagtc | W47728 | 44839 | gatccaacattccgttcgtatt | U25652 | 87443 | catggcatggagaacactcaagaag | AA060105 |
| 2236 | ctccaagcttttaactgaagctcag | W47728 | 44840 | ttctaaagcacaaaacacttccat | U25652 | 87444 | tggccatggagaacactcaagaaga | AA060105 |
| 2237 | agctttaactgaagctcagatcg | W47728 | 44841 | agcacaaaacacttccataattag | U25652 | 87445 | ggccatggagaacactcaagaagaa | AA060105 |
| 2238 | aactgaagctcagatcggccaagat | W47728 | 44842 | ctcctgtattctgaattgccaaa | U25652 | 87446 | gccatcggagaacactcaagaagaag | AA060105 |
| 2239 | ctcagactggccaagatggagcca | W47728 | 44843 | tggattgccaaacaccaccattga | U25652 | 87447 | catcggagaacactcaagaagaaga | AA060105 |
| 2240 | cagactggccaagatggagccatc | W47728 | 44844 | ccataactctacaactctg | U25652 | 87448 | ctttcaaggctccatcctgagagaac | AA060105 |
| 2241 | aagatggagccatctgatgccaca | W47728 | 44845 | attatttctgcatccatctact | U25652 | 87449 | aatcagagaacttgcaccggggcg | AA060105 |
| 2242 | ttgagccatctgatgccccattcct | W47728 | 44846 | tctgcaatccatctacacatatata | U25652 | 87450 | ctgagcaatcctgcgcagagatctgc | U77630 |
| 2243 | gggcacttctgagcccccattcct | M21532 | 44847 | atccatctacatataatagcaaac | U25652 | 87451 | gcataagcctcattactactgaact | U77630 |
| 2244 | ttctgagccccattccctgcgg | M21532 | 44848 | catccagttgcagcatccgta | U25652 | 87452 | taagcctactactgaactct | U77630 |
| 2245 | caggccagaacccagaaagcaggg | M21532 | 44849 | agtgtcgcatcctgacaatgg | U25652 | 87453 | gcctcattactactgaacttcca | U77630 |
| 2246 | atatgtcggtcaacaccagggcg | M21532 | 44850 | ccagatcccgtacaatgggcaagg | U25652 | 87454 | tccaaacctagcggaacctgca | U77630 |
| 2247 | taacagttaatccctgcctgctt | M21532 | 44851 | tcccgtacaatgggcaaggctacc | U25652 | 87455 | tgcaaagcttgtgtcagccaaag | U77630 |
| 2248 | cagttaattccctgccgctcca | M21532 | 44852 | gctatccaggtagtgtctgctcatc | U25652 | 87456 | aatgttgtgtcagccaaggta | U77630 |
| 2249 | ctatccgccccaaggatggaatgca | M21532 | 44853 | tgttgccatcataaggagactcca | U25652 | 87457 | tgcagccaaggtaactatagta | U77630 |

| SEQ ID NO | sequence | DBAxnID | SEQ ID NO | sequence | DBAxnID | SEQ ID NO | sequence | DBAxnID |
|---|---|---|---|---|---|---|---|---|
| 2250 | aggatctgctgaactcagttcg | M21532 | 44854 | tgccatcataaggactccagttcc | U25652 | 87458 | aatgtctcagcaaggtgtaaggttg | U77630 |
| 2251 | atcctgctgcactcagttccgag | M21532 | 44855 | agataggatctgtgcgatccaa | U25652 | 87459 | gcgcctgattatcgcctgggatga | U77630 |
| 2252 | cccagacacaagctcctgagagtt | M21532 | 44856 | ctgttctgtttgaatcctatgt | AA022093 | 87460 | cctgattatcgcctgggatgaaga | U77630 |
| 2253 | agaacaagctcctgagagttcta | M21532 | 44857 | ctctgttttgaatccctatggaa | AA022093 | 87461 | tgcagagatccgcctggctgcccct | U77630 |
| 2254 | gagagttctagccatcctgggcctc | M21532 | 44858 | tgatgtggtccatcgcgggaggt | AA022093 | 87462 | aaaccaataaacgtctccaatgctg | U77630 |
| 2255 | tgagcccattcctgcaggttc | M21532 | 44859 | tgagttgtccatcgcgggaggaactaac | AA022093 | 87463 | gatctgcctggctgccctaggga | U77630 |
| 2256 | tggcaggttcaccgaccaggaagg | M21532 | 44860 | tacctgcacagtgacctgcatc | AA022093 | 87464 | cagaggaaccaagaccaagccagg | U77630 |
| 2257 | aggaaggcttcttcaacctgctgac | M21532 | 44861 | cttgcacagtgacctgcatcc | AA022093 | 87465 | ccaagaccaagccaggctcatgcca | U77630 |
| 2258 | aaggctctcaacctgctgaccca | M21532 | 44862 | gcacagtgacctgcatccctt | AA022093 | 87466 | catgccagaaccgagacttacagg | U77630 |
| 2259 | cccacgtgcaggcggatcggatgga | M21532 | 44863 | ctgcatcctcttagaagaagccac | AA022093 | 87467 | gccttgccgctcataaactggttt | U77630 |
| 2260 | agcgcgtgttcctgcaggctgg | M21532 | 44864 | tagaagaagccacactcctcgaatt | AA022093 | 87468 | gctcataaactggtttccacgggg | U77630 |
| 2261 | cctgcaggctgggcaggccagaa | M21532 | 44865 | ctgcctccaaggttcctcaagtca | AA022093 | 87469 | gttctcacgggcataagcctcat | U77630 |
| 2262 | ggccaggccagaaccccagaaagcca | M21532 | 44866 | tcctcaagagttcctaagtcaagg | AA022093 | 87470 | ctgctcacacaactggtgaccatggac | U07808 |
| 2263 | gtttgtcacatgataccaagatgt | X13664 | 44867 | tcaagagcttccacttcaaggcca | AA022093 | 87471 | acacacctgaccatggaccctggg | U07808 |
| 2264 | aagatgtaactcagctcagtaattc | X13664 | 44868 | atccctatgtgaagcgttccattaa | AA022093 | 87472 | ctgtccccagctgccaagtgt | U07808 |
| 2265 | gattacaggccaattccaccacaca | X13664 | 44869 | gcttcctaagtcaaggccaagtatt | AA022093 | 87473 | tccccccagctgtcccaagtgcc | U07808 |
| 2266 | gactgagctcgtcctaatgagttt | X13664 | 44870 | gcctaaatgacatcaccaaaaga | AA022093 | 87474 | ctgtgccaagtgccgccggtgcc | U07808 |
| 2267 | catcacctgaaactaatcagaaag | X13664 | 44871 | ctaccaacctgatcaattgctgc | AA022093 | 87475 | tgccaagtgtgcccggggctgcatc | U07808 |
| 2268 | gctaacactgggctcattcacatgg | X13664 | 44872 | acctgatcaattgctgctgaaaa | AA022093 | 87476 | caagtgcagtcgtcgtccccgaaac | U07808 |
| 2269 | ctcattcacatgggtttgcattcc | X13664 | 44873 | tcaatttgcttgctgaaaatgtcg | AA022093 | 87477 | tccctgaaaccaccctatggccagcg | U07808 |
| 2270 | gcattctaggcaaactaaactgct | X13664 | 44874 | gattaagcaataaccaaggagtcgt | AA022093 | 87478 | ctgaaaccaccctatggccagcggga | U07808 |
| 2271 | tgcctttacaacaaggctcagtca | X13664 | 44875 | gcaatacccaaggagtcgttctgc | AA022093 | 87479 | cccacctatggcagcgggagagatc | U07808 |
| 2272 | caaggctcagtcatcttcctgaagc | X13664 | 44876 | cctttctaccagtgagtgtcca | AA022093 | 87480 | aagtgactacacagtacctgagtca | U07808 |
| 2273 | ctgctgagaccagcacttggtctg | X13664 | 44877 | gatctgggccaatgtcatcttgtta | AA022093 | 87481 | cacaglacctgagtcaaggagtta | U07808 |
| 2274 | agaccagcacttggtctgttttgt | X13664 | 44878 | caatgtcatcttgttatacagaagc | AA022093 | 87482 | gaccaggaccctgggggaatgcacg | U07808 |
| 2275 | aatggccattttctctgatctt | X13664 | 44879 | gggcaatcttctcctgacgaatc | AA022093 | 87483 | cacgtatgtcgtggggatccgc | U07808 |
| 2276 | ctctctgatctgtaataccttaaa | X13664 | 44880 | tctttctcctgacgaatcaatctg | AA022095 | 87484 | aggagatctgcatcgcggagataat | U07808 |
| 2277 | ataacaggatctgtcgtgtagtcc | X13664 | 44881 | ttctcctgacgaatcaatctggcc | AA022095 | 87485 | gatctgcatcgcgggagataattgc | U07808 |
| 2278 | ggatcttgctgtagtcctagctg | X13664 | 44882 | aatcaatctggccacagaaatcata | AA022095 | 87486 | ttgcaaatgcacaacctgcagcgt | U07808 |
| 2279 | ctagctggcctcaaaatcacaattac | X13664 | 44883 | cataaatccacatatgctgtacaa | AA022095 | 87487 | atgcaacctgcagctgtaaaacc | U07808 |
| 2280 | ggcctcaaactcacaatactctcc | X13664 | 44884 | atatgctgtacaagcctcttattag | AA022095 | 87488 | cacaacctgcagctgtaaaacctgt | U07808 |
| 2281 | aaactcacaatactctctcctgatc | X13664 | 44885 | tgctgtacaagcctcttatagatt | AA022095 | 87489 | aaccttgcagctgtaaaaaacctgct | U07808 |
| 2282 | ctctcctgatcaatcccaagt | X13664 | 44886 | tgtacaagcctcttatagattcca | AA022095 | 87490 | agccttgctgggggctagtactact | U07808 |
| 2283 | tgtatgtcagcctgctccggaagtg | X13664 | 44887 | ctctttatagattccagtgcattca | AA022095 | 87491 | cttgctgggggctagtactactata | U39473 |
| 2284 | tttctcatcgctgacgttggcac | W47743 | 44888 | ttatagatccagtgcattcatag | AA022095 | 87492 | cggatctttccattgctagagcaaa | U39473 |
| 2285 | tgaaccgctgcagcagcggaagtg | W47743 | 44889 | tggatcatttcgatcttcaggtta | AA022095 | 87493 | agactgaagcttgctccagagttat | U39473 |
| 2286 | gaaccgctgcagcagcggaagtg | W47743 | 44890 | atcatttcgatcttcaggttagcc | AA022095 | 87494 | atcaaggctgagctgctgtacaaga | U39473 |
| 2287 | aaccgcgtgcaggcagcggaagttggtcat | W47743 | 44891 | tcgatcttcaggttagccgtagca | AA022095 | 87495 | ttactaaaccagttgcagtactgt | U39473 |
| 2288 | acgcgcggcagcggaagttggtcatc | W47743 | 44892 | ttcaggttagccgtagcattggca | AA022095 | 87496 | ctaaaccagttgcagtactgtgagg | U39473 |
| 2289 | ccgcggcggcagcggaagttggtcatcc | W47743 | 44893 | tttagccgtagcattggcaatttct | AA022095 | 87497 | cagttgcagtactgtgagaggccag | U39473 |
| 2290 | cgccggcagcggaagttggcac | W47743 | 44894 | ttattcattccaaagcaagctgg | AA022095 | 87498 | ggcatcccacgtggtggccatcatttg | U39473 |
| 2291 | ttctcatcgtgacggtggcact | W47743 | 44895 | cattccaaagcaagctggtttca | AA022095 | 87499 | ccactggccatcattggtgtgag | U39473 |
| 2292 | ctcatcggtgacggtggcactgc | W47743 | 44896 | ctgttttcatcgatgggcaatctt | AA022095 | 87500 | gtggccatcattggtgagcaggaac | U39473 |
| 2293 | tcatcgtgacggtggcactgct | W47743 | 44897 | gatgcccgttaagaaaaatgcagc | U34920 | 87501 | gccatcattggtgagcaggaactca | U39473 |
| 2294 | catcggtgacggtggcactgcta | W47743 | 44898 | atgcagctggccctgcctcccagag | U34920 | 87502 | ctagactatactgggtcatct | U39473 |
| 2295 | agctggtgacggaacgaagtgaa | W47743 | 44899 | cggctggcctgcagctccgta | U34920 | 87503 | ccatctgcaactggaacaactat | U39473 |
| 2296 | aagtgaaccgctgcagcgaagttg | W47743 | 44900 | ctggcctgatgtttcgtatct | U34920 | 87504 | gactactatactgggtcatctatg | U39473 |
| 2297 | agtgaaccgcctggcagcgaagttgg | W47743 | 44901 | ccttgatgcttgcgatcttatcg | U34920 | 87505 | tatactgggtcatctatgaggcag | U39473 |
| 2298 | gtgaaccgcctggcagcgaagttggt | W47743 | 44902 | tgatgcttgcgatcttatcgtag | U34920 | 87506 | gtgctgcagatgccaaccaagtg | U39473 |
| 2299 | gccgatgctccgcagcgcgagaagct | W47719 | 44903 | tgcttcgtactctatctgtagaga | U34920 | 87507 | ctgctcagatgcaaccaagctg | U39473 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 2300 | ccgatgtcgacagcgagaagctc | W47719 | 44904 | cttgtctatacaaacacgcctg | U34920 | 87508 | atgccaaccagctggggaagagc | U39473 |
| 2301 | aagtgcagggctcctcgctggaa | W47719 | 44905 | cttgccttctagactcagcttaa | U34920 | 87509 | tacgaggcctggttggcatgttg | U39473 |
| 2302 | tggtcttgcctcaaatccacggga | W47719 | 44906 | gccttctagagctcagcttttaa | U34920 | 87510 | ggcatgtttgacccaagggcgca | U39473 |
| 2303 | gtcttgcctcaaatccacggaga | W47719 | 44907 | ttctagactcagcttttaaccagg | U34920 | 87511 | gtatacagcagttgctgagaaac | U27455 |
| 2304 | tttgcctcaaatccacgggagatt | W47719 | 44908 | tagactcagcttttaaccaggga | U34920 | 87512 | tcatcatcatgccaatgaagactc | U27455 |
| 2305 | ttgcctcaaatccacgggagattt | W47719 | 44909 | tctccagagcaccaccatctaagg | U34920 | 87513 | tgtcagctcataccaaagaaat | U27455 |
| 2306 | caaatccacgggagattttctgag | W47719 | 44910 | tccagagcaccaccatctaaggca | U34920 | 87514 | cagtcataccaagaaatactga | U27455 |
| 2307 | ctctcaagatctgtgggtgacactcc | W47719 | 44911 | cagtttaacccctgtgagctcagt | U34920 | 87515 | acggctggtgcctactgacag | U27455 |
| 2308 | ggtgacactccatggccagtactat | W47719 | 44912 | attgcactagatcatgtcttgacag | U34920 | 87516 | tggtgcctactgacaggccct | U27455 |
| 2309 | gtgacactccatggccagtactatg | W47719 | 44913 | ctagacatgtcttgacaggtcctg | U34920 | 87517 | cagaagactgagcctttcgtgct | U27455 |
| 2310 | acactccatggccagtactatgacc | W47719 | 44914 | catgtctgacaggtcctgagatc | U34920 | 87518 | gataattctcccaggacagtgt | U27455 |
| 2311 | atgtccgaacagcgagaagctcaac | W47719 | 44915 | gtctttgacaggtctgagattccc | U34920 | 87519 | tggcctttcgagccaattccagga | U27455 |
| 2312 | gctccgacagcgagaagctcaacct | W47719 | 44916 | cctgagattcctcggctgtgcct | U34920 | 87520 | aaccacactcagtgaccacttcat | U27455 |
| 2313 | acagccgagaagctcaacctggattc | W47719 | 44917 | atcattggccctgggtgatggctc | U34920 | 87521 | gtgaccacttcatgtgaagactt | U27455 |
| 2314 | cgagaagctcaactggattccatc | W47719 | 44918 | cattgggccctgggtgatggctctg | AA022099 | 87522 | agacattgtgaagctactgaaggt | AA022099 |
| 2315 | gctaacctggattccatcatcggg | W47719 | 44919 | gccgttgccatgttgacggtgagag | AA022099 | 87523 | tggtgcctttgatgctctacatgcc | AA022099 |
| 2316 | tcaacctggattccatcatcggga | W47719 | 44920 | gccatgttgacggtgagagctcaca | AA022099 | 87524 | ctttgatgctctacatgccggcca | AA022099 |
| 2317 | cctgattccatcatcggggcctg | W47719 | 44921 | ccggttcatcattggcttcagcgca | AA022099 | 87525 | tgctcacatgccggccaaatgg | AA022099 |
| 2318 | tgcaagtcagggtctccggctgg | W47719 | 44922 | gcttcagcgcaccatgccatcgt | AA022099 | 87526 | ttcctcacccgatcattgagtc | AA022099 |
| 2319 | tgctactttgctcgttctctgtc | M96823 | 44923 | accagtccatcgttgctgcagt | AA022099 | 87527 | ctacccgatcattgagtccagagc | AA022099 |
| 2320 | cttgctctctctgttcctcagat | M96823 | 44924 | ccagtccatcgttgctcagtta | AA022099 | 87528 | ttgagtccagagcgatttgcct | AA022099 |
| 2321 | ctgcctctgtggagcaatgatct | M96823 | 44925 | atgtccatcgtgtcgtcagtag | AA022099 | 87529 | ccagatttgcctgctgcagctccaa | AA022099 |
| 2322 | atgatctcaattcctttggtggct | M96823 | 44926 | atcgttgctcagttatggggctta | AA022099 | 87530 | ttgcctgcagctcagctcataccaa | AA022099 |
| 2323 | cccagatatgctcacacccctagct | M96823 | 44927 | cgttgctgcagttatggggctatt | AA022099 | 87531 | gctcttgcacattctcggcat | AA022099 |
| 2324 | tatgctcacacccctagctgaggtc | M96823 | 44928 | ttgctgcagttatggggcttaatgc | AA022099 | 87532 | cttgcacattctcggcatct | AA022099 |
| 2325 | ccaacctgctctgggtcctgtaaa | M96823 | 44929 | gggccctggtgatggctctgctcc | AA022099 | 87533 | ttactactactagctgggtgttc | AA022099 |
| 2326 | ctgctcaggctctgaaaatggt | M96823 | 44930 | tgatggctgctctcacattgcc | AA022099 | 87534 | gatgtctcagtcatatcgcgatatcg | AA107289 |
| 2327 | aactccccggctcaggccacact | M96823 | 44931 | tctgctctcacatgccagtat | AA022099 | 87535 | gtctcagtcatatcggatatcggaa | AA107289 |
| 2328 | gctcctctgtgccccagttcca | M96823 | 44932 | ctgctccacatgccagttaca | AA022099 | 87536 | gatatcgcattgtacgccgcagc | AA107289 |
| 2329 | tccaaatatagccggcacaaataa | M96823 | 44933 | tcattcgtgactacagtacctggt | AA022099 | 87537 | attggtacgcgcagcagtgtctc | AA107289 |
| 2330 | tatagccggcacaaataacatta | M96823 | 44934 | tcgtgtgactacagtacctggtaaa | AA022099 | 87538 | ggtacgcgcagcagtgtctcata | AA107289 |
| 2331 | tcgtcctgttccaggctcagct | M96823 | 44935 | gacagtagcctgcacttaacttt | AA022099 | 87539 | ccgcagtcagttgtcctatagtcgtc | AA107289 |
| 2332 | tcagcctctgctgttctcaccta | M96823 | 44936 | taaatgtggccgttgccatgttgaac | AA022099 | 87540 | cagtgttcatatgtcgtctgtat | AA107289 |
| 2333 | cttcctactctagtctcactgaat | M96823 | 44937 | agagtcaaccaggcaacaccgtagg | U43836 | 87541 | tgttctcatatgtcgctctgtatct | AA107289 |
| 2334 | aggtgcactggatcacaggacctg | M96823 | 44938 | gtgacaagctgcttttccagactcca | U43836 | 87542 | catagtcgtctgtgatatcggcccg | AA107289 |
| 2335 | actggatcacaggacctggttag | M96823 | 44939 | atctccagagctgccatctaacaa | U43836 | 87543 | aagagctgatctccatgtgccat | AA107289 |
| 2336 | tcacaggacctggttagtgtctc | M96823 | 44940 | cagagtgccatctaacaattgtca | U43836 | 87544 | tgatcccacatgccattagtac | AA107289 |
| 2337 | gaccttggcttagtgtctcgactc | W47721 | 44941 | tgccactaacaattgtcaaggaac | U43836 | 87545 | tcacatgccattagtactacct | AA107289 |
| 2338 | gtgctctgactcgcctctgtgg | W47721 | 44942 | aaggaacctcatgtccacctcagg | U43836 | 87546 | ttagtacgtacccatgcagtcat | AA107289 |
| 2339 | gtcttggttcagcattgctggag | W47721 | 44943 | cctcacgtccaccgtcaggggccag | U43836 | 87547 | gtaagtaccccatgcagtcatcga | AA107289 |
| 2340 | tctgggttcagcactggaagt | W47721 | 44944 | gtctcacctcaggggccaggtact | U43836 | 87548 | cgtacctccatgcagtcatgatta | AA107289 |
| 2341 | acatctcgggatataacagcatcta | W47721 | 44945 | cctcaggggccaggtactctctcta | U43836 | 87549 | attaagcacgtagccagtgtcag | AA107289 |
| 2342 | cattctcggggataaacgcatcat | W47721 | 44946 | tctctcaacttaaccacctgtcaa | U43836 | 87550 | gagtactcatgtactagctggat | AA107289 |
| 2343 | taacgcatctagtaaccagcaaata | W47721 | 44947 | ccaccctgctcaagtgagcatctc | U43836 | 87551 | ggaacttcacacgtgagaccagac | AA107289 |
| 2344 | aggtgcacacaacaaggacggcaaa | W47721 | 44948 | acactcaactgtgataaagagat | U43836 | 87552 | ctcagctgagaccagacaactag | AA107289 |
| 2345 | gtgcacacaacaaggacggcaaact | W47721 | 44949 | agctgcttccagactcaccggcc | U43836 | 87553 | atctccggtggaggcgtgactc | U64199 |
| 2346 | tgcacacaacaaggacggcaaact | W47721 | 44950 | tttcagactccacgggccggttg | U43836 | 87554 | gagcggctgacctcatgttaac | U64199 |
| 2347 | gcacacaacaaggacggcaaactc | W47721 | 44951 | gcttttaggccctgcttcacagg | U43836 | 87555 | ctgactctagatccctcagagcat | U64199 |
| 2348 | cacaagacaaggacggcaaacttca | W47721 | 44952 | atggccctgcttcaaggagaaga | U43836 | 87556 | ggtatgactccctcatgagtaatg | U64199 |
| 2349 | cagcacaacaaggacggcaacttcagat | W47721 | 44953 | ctgctccaggggaggaagatggag | U43836 | 87557 | gactccctaaggtcaagtaatgaggtt | U64199 |

| SEQ ID NO | sequence | DBAxnID | SEQ ID NO | sequence | DBAxnID | SEQ ID NO | sequence | DBAxnID |
|---|---|---|---|---|---|---|---|---|
| 2350 | acggcaaacttcagattggagacaa | W47721 | 44954 | gcacaggcgaacctcctcagtcgg | U43836 | 87558 | gtacctcatttatctgcccagttc | U64199 |
| 2351 | tggttcagcattgctggaggtgtgt | W47721 | 44955 | tagagagctctcgccatctttta | U43836 | 87559 | catttatctgcccagttctcactc | U64199 |
| 2352 | gttcagcattgctggaggtgttgga | W47721 | 44956 | tcgccatctttatctccagagct | U43836 | 87560 | gaagacaagccagctgtcgtcggat | U64199 |
| 2353 | ttcagcattgctggaggtgtgaa | W47721 | 44957 | tgcctcctggattcctggatccag | U47281 | 87561 | tagcttccaataggtacttaagtc | U64199 |
| 2354 | tcagcattgctggaggtgttggaaa | W47721 | 44958 | cctggattcctggatccaggtcag | U47281 | 87562 | atacacaactggtatcatatag | U64199 |
| 2355 | cagcattgctgaggtgttggaaac | W47721 | 44959 | ctgcctgctgaattgaaaacagca | U47281 | 87563 | agcagagaccctgactcaaaactgg | U64199 |
| 2356 | agcattgctgaggtgttggaaacc | W47721 | 44960 | ccaagaagcctggtcttctgaccaa | U47281 | 87564 | aaaggacccaagatagatcatgctc | U64199 |
| 2357 | gcattgctgaggtgttggaaacca | W47721 | 44961 | agcctgcttcttgaccaaccgtct | U47281 | 87565 | ttgacagtcaccccagtgaactacc | U64199 |
| 2358 | cacatccttgggataacagacatct | W47721 | 44962 | gctctctgaccaaccgtctctgcta | U47281 | 87566 | ccagtgaactaccttcctagccatg | U64199 |
| 2359 | tttattacaatcatctcctcaatag | W47721 | 44963 | acgtctgtctatcatagggaacca | U47281 | 87567 | ccctccaacatagaagatctgtcac | U64199 |
| 2360 | ttattacaatcatctcctcaatagc | AA071834 | 44964 | tctgtctatcatagggaccatctggc | U47281 | 87568 | gaagatctgccacaactgagatctg | U64199 |
| 2361 | acactcagtgcgccactgactaatc | AA071834 | 44965 | atcatagggaccatctggctgagcc | U47281 | 87569 | gaggctgaccccactgatcttttg | U64199 |
| 2362 | cactcagtgcggcactgactaatca | AA071834 | 44966 | ctgagccacagcccacaaagatgc | U47281 | 87570 | actgatcttttgactgagacac | U64199 |
| 2363 | actcagtgcggcactgactaatcaa | AA071834 | 44967 | cgggacctgcagatgcacttaata | U47281 | 87571 | attttgcatcaagtctcctcgcc | U64199 |
| 2364 | ctcagtgcggcactgactaatcaaa | AA071834 | 44968 | ctcgagtgcactaataagglatc | U47281 | 87572 | tccactggtgagaaccctgcagg | U78085 |
| 2365 | tcagtgcggcactgactaatcaaac | AA071834 | 44969 | ccaggacgcttctggaaggagtc | U47281 | 87573 | gagaaccctgcaggtcctggtga | U78085 |
| 2366 | agtgcggcactgactaatcaaact | AA071834 | 44970 | cacagacctggcctgactggcc | U47281 | 87574 | ctcattaatgtgccaaggcctcc | U78085 |
| 2367 | cagcaaccgactacactcagtgcgg | AA071834 | 44971 | gctggccaacttcttgcttttgtc | U47281 | 87575 | aatgtcgccaagggctcctccaatt | U78085 |
| 2368 | agcaaccgactacactcagtgcggc | AA071834 | 44972 | caactcttgcttttgtcaacag | U47281 | 87576 | agggctctccaattcctatgcca | U78085 |
| 2369 | gcaaccgactacactcagtgcggca | AA071834 | 44973 | cttttgtctcaacgctgctg | U47281 | 87577 | ggctcctccaattcctatgccatca | U78085 |
| 2370 | caaccgactacactcagtgcgggca | AA071834 | 44974 | tttgtcaacgctgctgaaccca | U47281 | 87578 | aatcctatgccatcaagaagaaag | U78085 |
| 2371 | aaccgactacactcagtgcggcact | AA071834 | 44975 | ctgctgaaccactgattatgtc | U47281 | 87579 | tcctatgccatcaagaagaaagatg | U78085 |
| 2372 | actacactcagtgcggcactgacta | AA071834 | 44976 | actgattatgttctgcaggccgg | U47281 | 87580 | aagtcaaccgtgatttcccagct | U78085 |
| 2373 | ctacactcaglgcggcactgactac | AA071834 | 44977 | ctgagcagttcacaaagggtgca | U47281 | 87581 | tctaaccgtcgattttcccagctgct | U78085 |
| 2374 | tacactcagtgcggcactgactaat | AA071834 | 44978 | agcttcacaaagggtggaaggat | U47281 | 87582 | aaccgtcgatttccagctgcgc | U78085 |
| 2375 | ctcacctatggagacaagatctt | AA071834 | 44979 | tgtctctcttatcccagagt | U47281 | 87583 | ccagctgctgctccctaaataactg | U78085 |
| 2376 | agatcttatggacacataccctgt | X16995 | 44980 | ctgtgtcctcactgcgaatgcgac | D45858 | 87584 | aacctctgcaggtctgcgtgaatg | U78085 |
| 2377 | cattttaacacataccactctgt | X16995 | 44981 | cctcactgtgaatgtgacagacca | D45858 | 87585 | gtgaatcaggccatgctggctgct | U78085 |
| 2378 | ttttttaacacataccactctgta | X16995 | 44982 | tgtcgcagaccaaatcctgatgtc | D45858 | 87586 | caggccatgctggctgcacagg | U78085 |
| 2379 | cacatacactctgtgtaaataag | X16995 | 44983 | cagacaatcctgatgctccctga | D45858 | 87587 | atctggctgtggcacagggggctc | U78085 |
| 2380 | atacactcctggtgtaaataagctg | X16995 | 44984 | aatcctgatgctccctgaacagac | D45858 | 87588 | gctcgtgaggctgcttccggaaca | U78085 |
| 2381 | gcggagctccaactgagatctctt | X16995 | 44985 | tgatgccctgaacagacaccccc | D45858 | 87589 | gcttccggaacatcaagaaca | U78085 |
| 2382 | tccgctcctctcactgtcatcta | X16995 | 44986 | gccgctcaacctcaccagaaata | D45858 | 87590 | atcaagaacatcgccgagtgcctg | U78085 |
| 2383 | gtacataactgtcactcaagaaggt | X16995 | 44987 | gctatcatccaagaaataaacaca | D45858 | 87591 | aagatcatttccagatggacaaac | AA139606 |
| 2384 | cataactgtcactcaagaaggtgat | X16995 | 44988 | atcaccagaaataaaacactctgt | D45858 | 87592 | aagatacaaccagatgacaacac | AA139606 |
| 2385 | aactgtcactcaagaaggttgatga | X16995 | 44989 | ttggaccaggcacctcaggaaccca | D45858 | 87593 | tccaggatgacaacaccttcct | AA139606 |
| 2386 | tgtattctcggattaataagg | X16995 | 44990 | tcctgccgactgtgaactcatct | D45858 | 87594 | attgatcctcagtgccggaagg | AA139606 |
| 2387 | cttctgcaccatgccttagg | X16995 | 44991 | tgtgaactcatctcctgagccat | D45858 | 87595 | ttccagtccggaaggtggcttta | AA139606 |
| 2388 | ctgtcaccaccatgcctttag | X16995 | 44992 | ctcatctctcgaagccataatgtc | D45858 | 87596 | aaggtggcttaccatccgcaatg | AA139606 |
| 2389 | cagcctggttttgagctaagactga | X16995 | 44993 | tcctgaagccataatgtccgagcg | D45858 | 87597 | gtggctttaccatcgcaatgtct | AA139606 |
| 2390 | agactgacgtaacctccactccag | X16995 | 44994 | aagccataatgtgcactgtgtaga | AA021930 | 87598 | cttacatctgaatgtctccatca | AA139606 |
| 2391 | ctcctccgaagatgataaga | X16995 | 44995 | tccgagccatctgcatcgaggagtt | AA021930 | 87599 | accatcgcaatgctccatcacct | AA139606 |
| 2392 | tattgtctatcctccagctcag | X16995 | 44996 | ggccccgctcctgtttcagggttgg | AA021930 | 87600 | atctcaagtctccatcacctgt | AA139606 |
| 2393 | agctcagtcctggcctctgtgt | X16995 | 44997 | aactgccccaaagcaatgaagaggc | AA021930 | 87601 | gtctccatcacctgtcaaaaga | AA139606 |
| 2394 | tcgatcctggcctctcgtgttttt | X16995 | 44998 | aggctgtagtgactgtgtgaaga | AA021930 | 87602 | agatgccccaactgcaggaaaatg | AA139606 |
| 2395 | agcagtcactcaacctggccaatca | M34381 | 44999 | tccgagccatcctcactcggggag | AA021930 | 87603 | atggccccaactgcaggaaatggaa | AA139606 |
| 2396 | ctcacactgccaatcagttgggct | M34381 | 45000 | gcagccaactgaggatcacaatg | AA021930 | 87604 | tccatggactcctcgctagtgg | AA139606 |
| 2397 | cactgctggctctccatgcat | M34381 | 45001 | gatatcaatgctgcagctgacca | AA021930 | 87605 | catgaactcctctgctagtgggct | AA139606 |
| 2398 | ggcctctggctccatgccattcaaactga | M34381 | 45002 | aggctgcctgctctctagtgact | AA021930 | 87606 | ttgtgctgctctcataacca | AA139606 |
| 2399 | ctctccagtctctaagactccatagagga | M34381 | 45003 | ctgcctctcttagtgacttgc | AA021930 | 87607 | tgtgctctcctcataaccaagacta | AA139606 |

TABLE 1-continued

| SEQ ID NO | DBAxnID | sequence | SEQ ID NO | DBAxnID | sequence | SEQ ID NO | DBAxnID |
|---|---|---|---|---|---|---|---|
| 2400 | M34381 | tcccatgcattcaaactgaggcacc | 45004 | M34381 | ttctagttgacttgcacctgtctt | 87608 | AA139606 |
| 2401 | M34381 | gcattcaaactgaggcaccagccct | 45005 | M34381 | tagttgacttgcacctgtctcag | 87609 | AA139606 |
| 2402 | M34381 | tcctggggalgctgrggccaagg | 45006 | M34381 | actttgcaccigtcttcaggctgcc | 87610 | AA139606 |
| 2403 | M34381 | tcaggagcctggcctgtcgtcact | 45007 | M34381 | cacctgtctcaggctgccaggga | 87611 | AA139606 |
| 2404 | M34381 | gcctgtccctgtcgtcactcatcat | 45008 | M34381 | agaagccagcaggcaccacttct | 87612 | AA107510 |
| 2405 | M34381 | cctgtcgtcactcatcatttgt | 45009 | M34381 | ttcccagatccgtcttccattg | 87613 | AA107510 |
| 2406 | M34381 | tgtcactcatcatttgtcttaaa | 45010 | M34381 | cccagatcctgtcttccattgagc | 87614 | AA107510 |
| 2407 | M34381 | acatcagcttgggctgggctagca | 45011 | M34381 | ctgtctccagttgagctgccaac | 87615 | AA107510 |
| 2408 | M34381 | ccaatcagttgggctagagaagga | 45012 | M34381 | tcttccattgagctgctccaacat | 87616 | AA107510 |
| 2409 | M34381 | atcagttgggctagagaagagtt | 45013 | M34381 | tccattgagctgctccaacactctc | 87617 | AA107510 |
| 2410 | M34381 | ttgagatccacgaagaagagta | 45014 | M34381 | ctacgaagatcaaccggacgcgtt | 87618 | AA107510 |
| 2411 | M34381 | attccaaccgagaagaagatagaggc | 45015 | M34381 | atcaaccggagcgttccagccat | 87619 | AA107510 |
| 2412 | M34381 | tggcaccccaggcctatggaagccc | 45016 | M34381 | gcttccggccatcctgcatcgg | 87620 | AA107510 |
| 2413 | M34381 | acttactagtccctttcctag | 45017 | M34381 | tgtatctataggtctttttgatggg | 87621 | AA107510 |
| 2414 | M34381 | cgtcactgctcggggctcccatg | 45018 | M34381 | atctataggtcttttgaggctg | 87622 | AA107510 |
| 2415 | M34381 | tattcacttttcagacatgataca | 45019 | J03733 | aacacattatgtgttgggaagagg | 87623 | AA107510 |
| 2416 | M34381 | tcagctgtgaagcagtcgttgtag | 45020 | J03733 | cacacattatgtgttgggaagagga | 87624 | AA107510 |
| 2417 | M34381 | cacttctaggagacatctgaag | 45021 | J03733 | acacttatgtgttggggaaggaat | 87625 | AA107510 |
| 2418 | M34381 | tctgaagtcctgcctgcagaaacc | 45022 | J03733 | agttatttacatagtcctgaagag | 87626 | AA107510 |
| 2419 | M34381 | gtcctgcctgcagaaacctgact | 45023 | J03733 | gttattttacatagtcctgaagagc | 87627 | AA107510 |
| 2420 | M34381 | gcctcagaaacctgactgttccc | 45024 | J03733 | ttatttacaatgtctgaagagt | 87628 | AA107510 |
| 2421 | M34381 | tgttcctcaacctgtgactccat | 45025 | J03733 | attttacatagtcctgaagagctaa | 87629 | AA107510 |
| 2422 | M34381 | ctcaacctgtgactccaattgcatc | 45026 | J03733 | ttttacatagtcctgaagagctaaa | 87630 | AA107510 |
| 2423 | M34381 | ttgcacacactagtaacagttg | 45027 | J03733 | tacatagtcctgaagagctaaagac | 87631 | AA107510 |
| 2424 | M34381 | atcatacaactggtcaactt | 45028 | J03733 | acatagtcctgaagagctaaagaca | 87632 | AA107510 |
| 2425 | M34381 | caaacacggcagtcaactcctgta | 45029 | J03733 | tctataggtcttttgatgggctga | 87633 | AA107510 |
| 2426 | M34381 | cggcagtcaactcctgtaataat | 45030 | J03733 | tcttttgatgggctgaacatagaa | 87634 | AA107515 |
| 2427 | M34381 | ttaggttgcccatggaaaat | 45031 | J03733 | atagaagcaaacacacattatgtgtt | 87635 | AA107515 |
| 2428 | M34381 | ccaacatcgcacagtctgctgtgt | 45032 | J03733 | tagaagcaaacacacacttatgttg | 87636 | AA107515 |
| 2429 | M34381 | cagtctgtgtgtgcaggaagaacc | 45033 | J03733 | gaagcaaacacacattatgtgttgga | 87637 | AA107515 |
| 2430 | M34381 | agaaccacggcctggatctga | 45034 | J03733 | aagcaaacacacattatgtgtgggaa | 87638 | AA107515 |
| 2431 | M34381 | cagcatcagtctgctagccatcc | 45035 | J03733 | agcaaacacacttatgtgtggggaa | 87639 | AA107515 |
| 2432 | M34381 | tttgttgcccagagtctgtgtga | 45036 | J03733 | caaacacacttatgtgtgggaaga | 87640 | AA107515 |
| 2433 | M34381 | gtcaactgcctaggaccggttggc | 45037 | J03733 | attatgacatacaaactgactg | 87641 | AA107515 |
| 2434 | M34381 | catggccactccagagagaccat | 45038 | J03733 | atgacatacaaaactgactgctcc | 87642 | AA107515 |
| 2435 | M34381 | ccagtgagctccgattctgcta | 45039 | J03733 | actgtcctagcattgaacattgc | 87643 | AA107515 |
| 2436 | M63850 | tggattctgtgtgaccagcacactc | 45040 | M63850 | cttgctcctagcattgaacattgc | 87644 | AA107515 |
| 2437 | M63850 | tgacctctgctcctatgccctct | 45041 | M63850 | ttgctcctagcattgaacattgta | 87645 | AA107515 |
| 2438 | M63850 | ttctatgcctctatcctcatag | 45042 | M63850 | tgtcctagcattgaacattgctaa | 87646 | AA107515 |
| 2439 | M63850 | tatcctatcatagataacattccc | 45043 | M63850 | gctcctagcattgaacattgctaaa | 87647 | AA107515 |
| 2440 | M63850 | atcatagtaaatcttccagagcc | 45044 | M63850 | ctcctagcattgaacattgctctag | 87648 | AA107515 |
| 2441 | M63850 | ctcactcattccaactattcctg | 45045 | M63850 | tcctagcattgaacattgctaaaaa | 87649 | AA107515 |
| 2442 | M63850 | tcattccactattcctgaaata | 45046 | M63850 | tgacatacaaaactgactgctcct | 87650 | AA107515 |
| 2443 | M63850 | ttctgaaaatatccccgagaga | 45047 | M63850 | acatacaaaactgactgctcctag | 87651 | AA107515 |
| 2444 | M63850 | aatgaaattccagcctgactttct | 45048 | M63850 | catacaaaaactgactgctcctagc | 87652 | AA107515 |
| 2445 | M63850 | gccttgatttctcctgtgacctg | 45049 | M63850 | atacaaaactgactgctctaaaa | 87653 | AA107515 |
| 2446 | M63850 | acttttctgtgcacctgatggga | 45050 | M63850 | tacactacaaaactgactgctctaga | 87654 | AA107515 |
| 2447 | M63850 | caccatcctgaatgccagttgcat | 45051 | M63850 | aaactgactgctcctagcatgaa | 87655 | U41568 |
| 2448 | M63850 | aatgcaagtcccagggggaaag | 45052 | M63850 | actgactgtctcctagcatgaac | 87656 | U41568 |
| 2449 | M63850 | tatctggaccagtcctcattc | 45053 | M63850 | actgactgtctcctagcatgaaca | 87657 | U41568 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 2450 | gaccagttccttcatttcaggtgg | M63850 | 45054 | ttcacgagcagttgtcacttacga | X83930 | 87658 | gtaaaatccctcgtctccatactg | U41568 |
| 2451 | ttccttcatttcaggtgggactct | M63850 | 45055 | acaccacagtcatgatgtcagt | X83930 | 87659 | atccctgtccatactggcttct | U41568 |
| 2452 | ggacttctgatccaggaagacaaa | M63850 | 45056 | tgagcaccaattcctccgactctga | X83930 | 87660 | ctgtccatacggcttcttgtgaa | U41568 |
| 2453 | agctcctcagtgcagctgtgtataa | M63850 | 45057 | cctcgactcgacatcgattatga | X83930 | 87661 | gcaaacaaatcactattctgtata | U41568 |
| 2454 | gctcctcgactctggcctctatg | M63850 | 45058 | attatgactcctcaacgactggg | X83930 | 87662 | aaatcactatttcgtatatctcta | U41568 |
| 2455 | agtcaggcaacagttcctcctgccg | M29395 | 45059 | acggctcagatcccaccaggagaact | X83930 | 87663 | ctattctgtatatctcaagagtg | U41568 |
| 2456 | cttgcgcctctgatccaagaag | M29395 | 45060 | cagatcccaaggaggaactcatcat | X83930 | 87664 | ttactgagcacatccgatgatgca | U41568 |
| 2457 | tgcctccactagtgatcgaccg | M29395 | 45061 | aggaactcatcatcctaggggttctgg | X83930 | 87665 | agcaacatccggatgatgcagaagaga | U41568 |
| 2458 | tgtgatctgaccgctcttaacca | M29395 | 45062 | ccaacctcattgcaacctgatcag | X83930 | 87666 | agtaccagatcagatccgctgaact | U41568 |
| 2459 | ctgaccgctcttaacacatagacc | M29395 | 45063 | caacctgatcagaacaccggacact | X83930 | 87667 | agatcagatccgtgaactgaacag | U41568 |
| 2460 | gctcttttaacacatagacctagcc | M29395 | 45064 | ccctgatttccaaggagtgacacca | X83930 | 87668 | gatccgtgaactgaacagtgccct | U41568 |
| 2461 | taacacatagacctagccgtgtcc | M29395 | 45065 | tttccaaggagtgacccagactct | X83930 | 87669 | ctgaactgaacagtgcccttttcct | U41568 |
| 2462 | cttagccgtgtcatgcaagtgga | M29395 | 45066 | tgtcagtgcttaatctgtcgcgga | X83930 | 87670 | gtgcccttttcctgctgagattcat | U41568 |
| 2463 | accagttgccccctgggtccgcatg | M29395 | 45067 | attctgtcgcggtggctcccactaa | X83930 | 87671 | tcgtcactgaactctttttcaggcc | U41568 |
| 2464 | tgtggtccgcatgcttactgagcaa | M29395 | 45068 | agatggccaccatgcatgacgtgaa | X83930 | 87672 | tttgaactgaggcccctggcggtg | U41741 |
| 2465 | ccgcatgcttactgagcaaagacc | M29395 | 45069 | ccacatgatcgacgtgaagaaaga | X83930 | 87673 | gccctggcgttgccagtcgtcagt | U41741 |
| 2466 | cctccacatcactgtacct | M29395 | 45070 | cacagacaactgcacatctcag | X83930 | 87674 | tacctggctgctgggaagcaggc | U41741 |
| 2467 | cccactgtcattgtgtgttctaa | M29395 | 45071 | tgcacatctacggctacgagggcgc | X83930 | 87675 | ctgagtactctggggagcaggctta | U41741 |
| 2468 | acatcatcagtgtgtacttaagtt | M29395 | 45072 | tctacggctacgagggcgcgagtc | X83930 | 87676 | agtactctggggagcaggcttactc | U41741 |
| 2469 | ttgctaataactggggggtcatag | M29395 | 45073 | gttccctgagccaccaatttcctccga | X83930 | 87677 | gctagctgcgtatcccagagagt | U41741 |
| 2470 | aaagcaactgtctctcttatgtagg | M29395 | 45074 | ctgggcatgctcagctggacataca | X83930 | 87678 | agctggctcatccaggagtaga | U41741 |
| 2471 | acgttcctctatgtaggatcagc | M29395 | 45075 | tgggactgtcagctggacatacag | X83930 | 87679 | tggctgtatcccagagtagaagg | U41741 |
| 2472 | catctgtaactccaattccaggga | M29395 | 45076 | gctgactccctacattatgcagc | X83930 | 87680 | gaggccctacagaaggctcggag | U41741 |
| 2473 | taactccaattccaggatccagt | M29395 | 45077 | ctgtactccctacattatgcagct | X83930 | 87681 | gccctacagaaggctcgagcca | U41741 |
| 2474 | agacagtctttgccagtcagatccagt | M29395 | 45078 | tgtactccctacattatgcagct | X83930 | 87682 | cctacagaaggctctggagccagg | U41741 |
| 2475 | tctttgccagtcgtaagaggaaaa | M29395 | 45079 | gtactccattacattatgcagctc | X83930 | 87683 | ggctctggagccaggagaactgta | U41741 |
| 2476 | gcaacaacagcagtaccatatc | M29395 | 45080 | tactccattacattatgcagcttcg | X83930 | 87684 | ccttgcacactgctctgctgctct | U41741 |
| 2477 | gcagtaccatatcgcacagcaacag | M16362 | 45081 | tccattacattatgcagctcgaaa | AA022148 | 87685 | tgcatgctgtcctctgctggaa | U41741 |
| 2478 | tcaacaacagctctaataccag | M16362 | 45082 | ccctacattatgcagctctaatacaca | AA022148 | 87686 | atgtcgtctccttgcgaaacac | U41741 |
| 2479 | acagctctaataccagcacag | M16362 | 45083 | ccttacattatgcagctcgaaaaa | AA022148 | 87687 | ttcctgtcggaacactgaccacac | U41741 |
| 2480 | caccaacatattggacgctactga | M16362 | 45084 | ttacattatgcagctcgaaaaca | AA022148 | 87688 | gtcgcggcctagtactccactg | U41741 |
| 2481 | catattggacgctactgagtcact | M16362 | 45085 | gatcctgagctgctggaagc | AA022148 | 87689 | ggctcctcctttcctggagcagaa | U41741 |
| 2482 | tggaGctactgagtcacttggagg | M16362 | 45086 | gggcatgctcagctggacatacaga | AA022148 | 87690 | tctccttctcggagcagaagtt | U41741 |
| 2483 | ctactgagtcacttggaggaactgc | M16362 | 45087 | ggcatgctcagctggacatatacaga | AA022148 | 87691 | tccttctctggagcagaagttaag | U41741 |
| 2484 | cttgtacactgagtgggccagcc | M16362 | 45088 | catgctcagctggacatacagaaat | AA022148 | 87692 | tggtcctactaggcagtccagttt | U41741 |
| 2485 | cccagcttcttgcttaatccccagt | M16362 | 45089 | atgctcagctggacatacagaaatt | AA022148 | 87693 | gagtccagttctgctgtcat | U41741 |
| 2486 | cctttcctaggcgagctcagtgact | M16362 | 45090 | aaatggctgtactccctacattat | AA022148 | 87694 | tttccttactgtcactccagatta | U41741 |
| 2487 | tcctaggcgagctcggacagatggtt | M16362 | 45091 | aatggctgtactccctacattatgca | AA022148 | 87695 | acagataaccctgaaggccgatgc | U73029 |
| 2488 | ccatatccgaagcaaccagcagag | M16362 | 45092 | tggctgtactccctacattatgca | AA022148 | 87696 | aaacctgaaggcagatgctgaatc | U73029 |
| 2489 | gatgctacggcaaacagcagcaaca | M16362 | 45093 | ggctgtactccctacattatgcag | AA022148 | 87697 | tcctccacagttctcagttgat | U73029 |
| 2490 | cagcaggcagagaggcagcagtcct | M16362 | 45094 | tctgaagtccatatgtcagatat | AA022148 | 87698 | ccacagttcagtttgtagttcat | U73029 |
| 2491 | gagcagcaaacgccccagcttg | M16362 | 45095 | agattatcacgtaacactgcatga | AA022148 | 87699 | ttccagttgtatgtcatgtagca | U73029 |
| 2492 | gcaacagcccgcagtttcgttgtccg | M16362 | 45096 | tcaaaagctgttttgccaacctgc | AA022148 | 87700 | ttgctccactatgtctgctg | U73029 |
| 2493 | gcccgcagcttggcgccaactt | M16362 | 45097 | gctgtttgccaactgccgcaggcac | AA022148 | 87701 | tatgttctgctgactgccaa | U73029 |
| 2494 | ggtcggcaacttcacacaacagtc | M16362 | 45098 | tttgccaacctgcaggcacggtccg | AA022148 | 87702 | ctgttgacctgcactgccaacttga | U73029 |
| 2495 | gccaactctcaacaacagctctaat | M16362 | 45099 | aacctgcaggcacggtcagggaat | AA022149 | 87703 | gactgactgccaactggaaagtca | U73029 |
| 2496 | tgaatatctcgatgctgagcagctgtg | M16362 | 45100 | cgaataggatgcgttgggaagtt | AA022149 | 87704 | cttgcatcttttcggaatgctggg | U73029 |
| 2497 | atatctcgatgctgagcagctgggcag | W47892 | 45101 | tctgtcattgcaatatcactagcag | AA022149 | 87705 | tatgttcttaactactcatgagaactg | U73029 |
| 2498 | gatttctctcactaaagggcagagga | W47892 | 45102 | attgacttgactactgccagctgtttat | AA022149 | 87706 | gaggacactacagcagcagatctt | U73029 |
| 2499 | agccaaattcttctgctttctag | W47892 | 45103 | atatcactagcagcttataagcca | AA022149 | 87707 | acactactgcagatctccttctg | U73029 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 2500 | ccaaattattctgtcttctagtat | W47892 | 45104 | gctttataagccactaggctgtct | AA022149 | 87708 | ggatctctctgtcatattcagta | U73029 |
| 2501 | tttccagaatactacagctctctg | W47892 | 45105 | taagccactagcgtgttccgcag | AA022149 | 87709 | tctcttgcatatcagtaagcttt | U73029 |
| 2502 | tccagaatacagctctttgcat | W47892 | 45106 | tcacgtaacaactgcatgataagtg | AA022149 | 87710 | gtagataccaagtcccagggctc | U73029 |
| 2503 | cagaatacagctctgcatgac | W47892 | 45107 | tccttatagcttcttcactcgcg | AA022149 | 87711 | ctaagttcccaatgctcccattca | U73029 |
| 2504 | actacagctcttgcatgacaacctg | W47892 | 45108 | tagctttcactcagcgtatcca | AA022149 | 87712 | cagctgtcttctccgcctcatt | U73029 |
| 2505 | acagctcctgcatgacaacctgaag | W47892 | 45109 | tcttcactcagcgtatccagtctg | AA022149 | 87713 | tgaatctctgaccgttcagaaga | AA107591 |
| 2506 | gctctgtcatgacaacctgaagtct | W47892 | 45110 | ctcagcgtatccagtctgcaattg | AA022149 | 87714 | gaatcctgacctgttcagaaggaa | AA107591 |
| 2507 | cttgcatgacaacctgaagtctctc | W47892 | 45111 | gtatccagtctgcaattgcatcat | AA022149 | 87715 | tgcctaagggcaactaagggatct | AA107591 |
| 2508 | agcagctgggcagtatgcggaacag | W47892 | 45112 | agtctgcaattgcatcatcaaaag | AA022149 | 87716 | ggcacctaagggatctgtgcatta | AA107591 |
| 2509 | gcatgacaacctgaagtctctcctg | W47892 | 45113 | gcatcatcaaaagctgctttgcca | AA022149 | 87717 | atcttgcatatctttaacgagt | AA107591 |
| 2510 | ttgsggacaggaccatccaggaggc | W47892 | 45114 | cgtgtcgcccagaatgtgactc | AA022149 | 87718 | tgtgcatatatcttaacgagttta | AA107591 |
| 2511 | cggcaggaccaccagaggctga | W47892 | 45115 | caattacctgccagctgatccgc | AA022149 | 87719 | cgagtttagccacactctaaag | AA107591 |
| 2512 | acaggaccaccaggaggctgacca | W47892 | 45116 | aaggtcatctgctcaggggcaag | AA022149 | 87720 | gagtttagccacactctaaagg | AA107591 |
| 2513 | ccatccaggaggctgaccaagatgg | W47892 | 45117 | atctgctgcagggcaagtggat | AA022149 | 87721 | tttagccacactctaaagggtg | AA107591 |
| 2514 | gtgccatatttacagaattcgt | W47892 | 45118 | atccggatcctggtagatgatggatgg | AA022149 | 87722 | tctgcccgtgtgaagtccccttc | AA107591 |
| 2515 | gcatccgatttcttcactaagggc | W47892 | 45119 | atccggtagatgatggccctct | AA022149 | 87723 | agactcgttcaaacaccagtga | AA107591 |
| 2516 | tccgatttcactaaggcgaa | W47892 | 45120 | ttcgctccgcctctagtaatctaa | AA022149 | 87724 | gactcgttcaaacacctagtgat | AA107591 |
| 2517 | atgcatcatctaccggaccctat | W47892 | 45121 | caggcctctagtaatctaagggtca | AA022149 | 87725 | atctctgacctgttcagaagaag | AA107591 |
| 2518 | tgcatcatctaccggaccctatc | W47863 | 45122 | gcaagcccgaacatctatgcagcat | L39373 | 87726 | actcgttcaaacacctcagtgatt | AA107591 |
| 2519 | cgagagtcgctcatcggcgtaaat | W47863 | 45123 | ccggacatctatgcagcattgt | L39373 | 87727 | aaatctaccggagaatgcctgc | AA107591 |
| 2520 | acgagtcgctcatcggcgtaaatgc | W47863 | 45124 | atctatcagcattgtgtcccag | L39373 | 87728 | atctacctggagaatgcctgct | AA107591 |
| 2521 | cgagtcgctcgcgtaaatgct | W47863 | 45125 | gcagcatttgtgtcccagagtgc | L39373 | 87729 | tctacctggagaatgcctgccta | AA107591 |
| 2522 | gagtcgctcatcggcgtaaatgtca | W47863 | 45126 | tgcggacccgagtgaacacatgtat | L39373 | 87730 | ctacctggagaagccttgcctaa | AA107591 |
| 2523 | gtcgctcatcggcgtaaatgctacc | W47863 | 45127 | cagcatttgtccaggagtgcc | L39373 | 87731 | gaggaatgcctgccaaggggaac | AA107591 |
| 2524 | cgctcatcggcgtaaatgctacc | W47863 | 45128 | tgaacacatgatgctctaaatac | L39373 | 87732 | gaatgcctgccaagggcaccta | AA107591 |
| 2525 | ctcatcggcgtaaatgctaccggcg | W47863 | 45129 | catgtactctaaatacctgctc | L39373 | 87733 | atgcctgcctaagggcaacctaag | AA107591 |
| 2526 | gtaaatgctaccggcgaaggtgtcg | W47863 | 45130 | ctatgaccagttccgctactgctg | L39373 | 87734 | gcttaccccacaagtgtgtcgaag | AA107591 |
| 2527 | taaatgctaccggcgaaggtgtcg | W47863 | 45131 | ccagttccgctactgctggaaaat | L39373 | 87735 | ctaaagctgctgacgaggtccg | AA107591 |
| 2528 | atgctaccggcgaagggtcggacg | W47863 | 45132 | tccctaccgggagcccaagacact | L39373 | 87736 | tctacctctacgatgagcagcc | AA107591 |
| 2529 | acgagtcgctcatcggcgtaaatgc | W47863 | 45133 | gcgccagaaccaaggctcagatgga | L39373 | 87737 | gtcagccatagcctgtcctggg | AA107591 |
| 2530 | atcatctaccggaccctcatcacg | W47863 | 45134 | gaaccaggctcagatgaaggtca | L39373 | 87738 | ctgttcctgggtagcctgcatc | AA107591 |
| 2531 | atctaccggaccctcatcacgat | W47863 | 45135 | taattggctgcaaggagagatca | L39373 | 87739 | gtagcctgcatcgacagctgtat | AA107591 |
| 2532 | acccgggaccctcatcacgcgatga | W47869 | 45136 | atggagaaccttgcatgtatcgatcg | L36244 | 87740 | ctgcatcgacagtgtatcccc | AA107591 |
| 2533 | ccgggccatcgacgagtcgctcat | W47869 | 45137 | tgatgaacctacctatcaaagaga | L36244 | 87741 | ctgggtctactgcagcatctga | AA107591 |
| 2534 | cgggggccatcgacgagtcgctcatc | W47869 | 45138 | actactcagaagactctaggcttcc | L36244 | 87742 | tctactgcagcatctctgagcact | AA107591 |
| 2535 | ccatcgacgagtcgctcatcggcgt | W47869 | 45139 | acgacattcaggacattcaaagtt | L36244 | 87743 | gcagcatctcgagcaacctgaacag | AA107591 |
| 2536 | atcgacgagtcgctcatcggcgtaa | W47869 | 45140 | cattgcaccccctgtcatggtcgaa | L36244 | 87744 | ttgaactcgtgtcgtcgcagt | AA107591 |
| 2537 | atgagagtcgctcatgtgatgaat | W47869 | 45141 | atccctcagcctatggggcaaaag | L36244 | 87745 | tgctggcgagtcagtaagttggac | AA107591 |
| 2538 | agcccgactgttcgatgaact | W47869 | 45142 | gatcagcgatgcatgaacaagt | L36244 | 87746 | tgagctgcgagggctcagtaggaa | AA107591 |
| 2539 | gcccgactgttcgatgaactc | W47869 | 45143 | ccctctcctgttgctgataga | L36244 | 87747 | gtaaagcctgtggctcacacagtggg | AA107591 |
| 2540 | gtcataggctcttctcatgatccc | W47869 | 45144 | aggccatctcgaccggaatgatct | L36244 | 87748 | tcacaacgtcgtggaacctcctgat | D50060 |
| 2541 | cataggctctctcatgatgcccgtc | W47869 | 45145 | tgatctgactaatctcagtaaca | L36244 | 87749 | agctggaacctcctgcatcaccaa | D50060 |
| 2542 | ataggctctcctcatgatgcccgtc | W47869 | 45146 | tgactaatctcaggtaacatgaagt | L36244 | 87750 | cgtgcagaatgcgatgagacctt | D50060 |
| 2543 | gtcgttagcccgcactgttgtcg | W47869 | 45147 | acagctccccttgatgggccag | L36244 | 87751 | ccgatgagacctctgcgagatgt | D50060 |
| 2544 | tcgttagcccgcactgttgtcga | W47869 | 45148 | ggaacactctaggctcatgccttgc | L36244 | 87752 | tgaagtcaatcggctcgagaagcg | D50060 |
| 2545 | agcccgcactgttgcgatgaact | W47869 | 45149 | gagtgaactctcgtttgctgcac | L36244 | 87753 | tcttcatccagttgctgccgcac | D50060 |
| 2546 | gcccgcactgttgctgatgaactc | W47869 | 45150 | actcctgtttgctgccaccatga | L36244 | 87754 | aatcagtagccctgagcattaac | D50060 |
| 2547 | ccgcactgttgctgatgaactcc | W47869 | 45151 | tgtttgctgccaccatgaatttg | L36244 | 87755 | tagccctgagccattaacagcagt | U68058 |
| 2548 | cgcactgttgctgatgaactcca | W47869 | 45152 | aattttgccactctcgggctgag | L36244 | 87756 | gctcctctaaatcaaaccatttg | U68058 |
| 2549 | tgaatcagccgcctgctgtctact | W47869 | 45153 | gccactctgggtgagtcactc | L36244 | 87757 | tcctctaaatcaaaccattgtg | U68058 |

| SEQ ID NO | sequence | DBAxnID | SEQ ID NO | sequence | DBAxnID | SEQ ID NO | sequence | DBAxnID |
|---|---|---|---|---|---|---|---|---|
| 2550 | cgcctlgcggtctcactggtgatca | W47869 | | cttcgttccggtactgtgatgta | L36244 | 87758 | catgatgtgcaccagggtgttatt | U68058 |
| 2551 | gcctlgcggtctcactggtgatcat | W47869 | 45154 | tctaactcagatgactgctcccga | X80937 | 87759 | gcatgtgcaccagggtgttatttaa | U68058 |
| 2552 | tggacagctcataggtcttctcatg | W47869 | 45155 | gactgctcccgatctgggaggt | X80937 | 87760 | tttaagctcattgcacattcaagttg | U68058 |
| 2553 | ggacagctcataggtcttctcatga | W47869 | 45156 | ttgtgactgtgccattattga | X80937 | 87761 | ctaggctcattggcctagacattat | U68058 |
| 2554 | gacagctcataggtcttctcatgt | W47869 | 45157 | atgtacaaagcctgtcgcatcc | X80937 | 87762 | ggctcattggcctagacattatgat | U68058 |
| 2555 | cagctcataggtcttctcatgatgc | W47869 | 45158 | ctlgctgactccgtccggtgtaca | X80937 | 87763 | tcattgctagacattatgatttg | U68058 |
| 2556 | agctcataggtcttctcatgatgcc | W47869 | 45159 | gcatccgtccggtgtacaacatcc | X80937 | 87764 | tttaagctccatcaagatgctaa | U68058 |
| 2557 | cctgtagtcccaagggtcacctg | W47869 | 45160 | atatttgctggcaatatgaagaat | X80937 | 87765 | gctccatcaagatgctcaataaag | U68058 |
| 2558 | gccaggtcccaagggtcacctgg | W47869 | 45161 | tttcattacaaatgtctgatgtg | X80937 | 87766 | ccctgggccataaacagcagtgt | U68058 |
| 2559 | tcccagactacacaggccacggct | M55171 | 45162 | tacaaatgtctgatgtgtgttaac | X80937 | 87767 | cattaacgcagtgtctcttctggca | U68058 |
| 2560 | acaggccacggctctgagcgaaag | M55171 | 45163 | tgtctgatgttggttaactaatt | X80937 | 87768 | taacagcagtgtctcttctggcaagt | U68058 |
| 2561 | gtgagagaccttagctgggtggag | M55171 | 45164 | ctaattttgccaggaccatattg | X80937 | 87769 | tattccacgagcattagagatgaact | U68058 |
| 2562 | ttaccctgaagaacattgagggt | M55171 | 45165 | ttgccaggaccatattgatcaag | X80937 | 87770 | taactagacatcgtgttatctct | U68058 |
| 2563 | tgaccccagatatataggggaataa | M55171 | 45166 | taggcagcagatctcactgctcaag | X80937 | 87771 | tgtatctctatagctctgctt | U68058 |
| 2564 | aaacaagtcaaacactactgata | M55171 | 45167 | gccagatctcactgtcaagtgagtg | X80937 | 87772 | ctctatagctctgcttcctctaaa | U68058 |
| 2565 | agtcaaacatctgataatcata | M55171 | 45168 | tctcactgtcaagtgagtggcccca | X80937 | 87773 | agctcgttccttctaaatcaaac | U68058 |
| 2566 | tttgcattctaatgaatggatcg | M55171 | 45169 | gtccctgtggctctgaagacaaat | X80937 | 87774 | cagtgccaggctgggcagtgcctc | U75839 |
| 2567 | ggatctgctgcttttcacaagga | M55171 | 45170 | tcccacactcaaagtgagcgacaa | X80937 | 87775 | ggagctgcttccagacagtgggcga | U75839 |
| 2568 | gcttgcttttcacaaggaataa | M55171 | 45171 | aagtgagcgacaaaccgcaggag | X80937 | 87776 | ccagccatgggtcaagaggtgtg | U75839 |
| 2569 | ctccaagcaagcctttgtggaa | M55171 | 45172 | tgttgcctctgccattgcactgt | X80937 | 87777 | tgttcctacatgttaaggagctg | U75839 |
| 2570 | atgatctgtgactgcaggtcgaa | M55171 | 45173 | gcactgttgctcctggccatt | X80937 | 87778 | ttcactgaaaacgcfggactgcac | U75839 |
| 2571 | gcaagcagcctttgtggaacataca | M55171 | 45174 | tattacccagaaagtgggagct | X80937 | 87779 | cgtggactgcacatctccaacagc | U75839 |
| 2572 | ctcagccaatcacagtcagacagg | M55171 | 45175 | ttaccccagaaagtgggggctgg | X80937 | 87780 | ctctgaccagtacaaggctactc | U75839 |
| 2573 | ctcagccaatcacagtcagacagg | M55171 | 45176 | atagagccaaaacgcggatcagctgg | X80937 | 87781 | ccaaggcctacctccaggactggtg | U75839 |
| 2574 | ggctgtcacccaataagagacac | M55171 | 45177 | agagccaaaacgcggatcagctgg | X80937 | 87782 | catgagctccaggctaggccagcaat | U75839 |
| 2575 | ctgggcccagaagaaacacagt | M55171 | 45178 | agccaaaacgcggatcagctggaa | X80937 | 87783 | cttccagccacgaaatactcga | U75839 |
| 2576 | acacagtgccagtccaggtaagt | M55171 | 45179 | aagtgttgcagagcccagcctga | X80937 | 87784 | actcagtcgtaccaataaagcagt | U75839 |
| 2577 | tgcagtcccaggtaagccctag | M55171 | 45180 | ttgcagaggccagcctgatcat | AA022172 | 87785 | cgtgtacccaataaagcagttatgc | U75839 |
| 2578 | agatttcccatgcgcagtctgtgc | AA125097 | 45181 | agaggcccagcctgatcata | AA022172 | 87786 | cctcagcccctgcctggccagtactg | U75839 |
| 2579 | gatttcccatgcgcagtctgtgc | AA125097 | 45183 | agaggcccagcctgatcattataga | AA022172 | 87787 | gccctgcggctagtctgatgcc | U75839 |
| 2580 | gcagtctgtgcttaccaaataat | AA125097 | 45184 | aggcccagcctgatcattataga | AA022172 | 87788 | agatctgatgccttcatggaagga | U75839 |
| 2581 | cagtctgtgcttaccaaataata | AA125097 | 45185 | ccaagaacagcagctggctt | AA022172 | 87789 | gatgccttcatggaaggaagtga | U75839 |
| 2582 | taatataacacattcctcagtcgt | AA125097 | 45186 | ccaagaacagcagctggctt | AA022172 | 87790 | tctgtggtcatgggggaaatg | U75839 |
| 2583 | atataacacattcctcagtcgtla | AA125097 | 45187 | ggatgatacagcaggacaggaa | AA022172 | 87791 | gtcatgcatgggggaaatgtggccc | U75839 |
| 2584 | tataacacattcctcagtcgttat | AA125097 | 45188 | atgacaccagacaggagacagg | AA022172 | 87792 | gtggccccaggaaccagccatggggtc | U75839 |
| 2585 | ataacacattcctcagtcgttata | AA125097 | 45189 | gacaccagacaggacaggagcaagc | AA022172 | 87793 | ccagaccagccatggcaagagg | U75839 |
| 2586 | acacattcctcagtcgttataaag | AA125097 | 45190 | caggaagcaaagccccctattgata | AA022172 | 87794 | aaatgtttcatgaaggtcaagc | AA107615 |
| 2587 | cacattcctcagtcgttataaagt | AA125097 | 45191 | ggaagcaaagccccctattgataga | AA022172 | 87795 | tgtttccagaaggtcaagccaaaa | AA107615 |
| 2588 | acctlgccatagtaacctccactg | AA125097 | 45192 | aagcaaagccccctattgatagagc | AA022172 | 87796 | cacattggcttacaaactggcaaa | AA107615 |
| 2589 | ttgccatagtaacctccactgcct | AA125097 | 45193 | ccaagcccccatagtagagca | AA022172 | 87797 | tttatgcttagaaggtctgtg | AA107615 |
| 2590 | atttccccatgcagtctgtgct | AA125097 | 45194 | attgatagccggatcag | AA022172 | 87798 | ttatgcttagaaggtctgtgct | AA107615 |
| 2591 | ttcccatgcgcagtctgttta | AA125097 | 45195 | actcctgctcctgttagcttta | AA022172 | 87799 | tgccttagaaggttctgtgctata | AA107615 |
| 2592 | ttcccatgcgcagtctgtttac | AA125097 | 45196 | gcacccagacgagctgataattc | U49739 | 87800 | aatccgctggctaaggagacaattcc | AA107615 |
| 2593 | tcccatgcgcagtctgtttacc | AA125097 | 45197 | gcttcacacaaatctaggaaatt | U49739 | 87801 | atccgctggctaaggagacaattccg | AA107615 |
| 2594 | ccatgcgcagtctgtttaccaa | AA125097 | 45198 | ttcaacaaatctatggaaattgat | U49739 | 87802 | ctcgtgccaccattggcttacaaa | AA107615 |
| 2595 | catgcgcagtctgtttaccaaa | AA125097 | 45199 | tgatttcctactaataattgaa | U49739 | 87803 | tctgaccacattggcttacaaact | AA107615 |
| 2596 | atgcagtctgttttaccaaaat | AA125097 | 45200 | gaggctgtcttactgcttagctta | U49739 | 87804 | tctgaccacattggcttacaacta | AA107615 |
| 2597 | cgcagtctgttgcttaccaaatag | AA125097 | 45201 | gctgcttactgcttagactacc | U49739 | 87805 | ctgaccacattggcttacaaactag | AA107615 |
| 2598 | aggcgctactcaggaaaagctga | W47969 | 45202 | ctgttagacttacccctctggt | U49739 | 87806 | tgaccacattggcttacaaactagg | AA107615 |
| 2599 | aagctcgtactctgctatccgtcc | W47969 | 45203 | cttaccctgttggctgcttgcatt | U49739 | 87807 | gaccacattggcttacaaactaggc | AA107615 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 2600 | taacctcaggactgctgctagcct | W47969 | 45204 | accctgcgttggtcctgctgattgat | U49739 | 87808 | accacaatggcttacaaactaggca | AA107615 |
| 2601 | caggacatgctgctagccttcttgg | W47969 | 45205 | ctcgtggtccgtgattgatggc | U49739 | 87809 | ccacatggcttacaactaggcaa | AA107615 |
| 2602 | atgctgctagccttctgggactat | W47969 | 45206 | tggtcctgattgatggcagaggt | U49739 | 87810 | tcttcggcccgtcaatcatgaaga | U10440 |
| 2603 | ctagcctctggagctatttgccac | W47969 | 45207 | cccagacagagctgataatttctg | U49739 | 87811 | actctggaagcactgccgggatat | U10440 |
| 2604 | gcctctggagactattggcacgac | W47969 | 45208 | ctgataattctgtctgccacactg | U49739 | 87812 | aggaaaactctgaggaccgggattt | U10440 |
| 2605 | ggactatttggcacgactgcagaaa | W47969 | 45209 | cttgctctgcacactgaccaccta | U49739 | 87813 | actctgaggaccggcattgtgga | U10440 |
| 2606 | ctattggcacgactgcagaaagt | W47969 | 45210 | cacactgaccacctattgctgagt | U49739 | 87814 | accaaatgcctgactcgtcagacaa | U10440 |
| 2607 | ttggcacgactgcagaaatgttgc | W47969 | 45211 | atgtccagcgtccgtgattaacgag | U49739 | 87815 | actcgtgacaacatcaggctgggtt | U10440 |
| 2608 | cagtcaaaatcgtactacagaactg | W47969 | 45212 | ctgatttttggctgtttcacac | U49739 | 87816 | ggaaggacctgctgcagaagatc | U10440 |
| 2609 | aaatcgtactacagaactgatcatc | W47969 | 45213 | tattttggctgtttcacacaaa | U49739 | 87817 | acgctggcactgtggagcagagcgc | U10440 |
| 2610 | ctgtatccgtccgcccagaattag | W47969 | 45214 | ctgttccacaaaatctaggaa | U49739 | 87818 | tggacgagcgccaagaagccgg | U10440 |
| 2611 | ctatccgtccgtccagaattgtat | W47969 | 45215 | atgtccagccatgccatgaagaac | U49739 | 87819 | gccttgcccagacgtaaactagc | U10440 |
| 2612 | catgcctcagaaggactgatccacaga | W47969 | 45216 | catgcctgaagaacctgatccacaga | U49739 | 87820 | agatacactgcttatgaagca | U10440 |
| 2613 | agttcactcttgaggaacagga | W47969 | 45217 | tgtgtcaccaatgctgtgaccttc | U49739 | 87821 | atcacgcttatgaagcaagaag | U10440 |
| 2614 | atgacgaaatttctcctgtatgagag | W47969 | 45218 | taccaatgctgtgacctctcagtctt | U49739 | 87822 | agaagaactgccggatatggaaga | U10440 |
| 2615 | acgaatttctcctgtatgagagaac | W47969 | 45219 | tgctgacctcagtcttaatccc | U49739 | 87823 | aagcgagtcagccaagtgaatttt | U10440 |
| 2616 | gagcatttccaataacctcaggaca | W47969 | 45220 | gttgactccatccatctcaag | U49739 | 87824 | tcgacttcagaatcataagcccct | U10440 |
| 2617 | caataacctcaggacatgctgctag | W47969 | 45221 | tctcatcctcatctcaagggctcc | U49739 | 87825 | agccctgcgaggcaggatacgaatg | U10440 |
| 2618 | tgacctcatgaatcctcgcctctg | M84005 | 45222 | cctcatcttcaagggtctgagcc | U49739 | 87826 | gcagctgccgagttctactacag | U10440 |
| 2619 | gtggcttaggcaactcgtgattca | M84005 | 45223 | gggctcctgagcctttaacatgc | U49739 | 87827 | ccccaagagcgcctgcaaggtgct | U10440 |
| 2620 | ttgctcaggcaggtgatgaagatccg | M84005 | 45224 | ggctacactttcagtcaggat | U49739 | 87828 | agagcgctgcaagtgcggcgca | U10440 |
| 2621 | tagtgttcctctatggctctcgc | M84005 | 45225 | actttcatggctcaggattcatct | U49739 | 87829 | tgccttaattggtctcaggcaa | U10440 |
| 2622 | ttcctctatggctctcgatcta | M84005 | 45226 | catggctcaggattcatctgaaggg | X91824 | 87830 | cagctactcagttcttcttcagtcc | X91824 |
| 2623 | gctctcgatctaggtgtatctgct | M84005 | 45227 | tgaagacctgatcaccagatgctga | X91824 | 87831 | tgatgcctttcgtcttctcaaccgca | X91824 |
| 2624 | atgggtatctctccagctaagag | M84005 | 45228 | caccagatcgaggcgctgtcta | X91824 | 87832 | tatatctggacccatgaagcttcatc | X91824 |
| 2625 | atctgctcccagctaagagcagtaa | M84005 | 45229 | atgctgaggctgtctatctgcttga | X91824 | 87833 | atgaagctcatccgcctttaggag | X91824 |
| 2626 | tctactctggtcacaccatggt | M84005 | 45230 | aggctgaggctgtctatcctgcttatga | X91824 | 87834 | gttatacgctagctcgagggcaa | X91824 |
| 2627 | tccagataagcgtcatccgtgtcc | M84005 | 45231 | ctgctatccgtctcaaggtgaatcc | X91824 | 87835 | cagctgtagctcgaggcaacagaga | X91824 |
| 2628 | tcacaccaggtgaatccgtccat | M84005 | 45232 | atccgcttaagtccatggtt | X91824 | 87836 | acagactacaacattgctgcaca | X91824 |
| 2629 | cgctcactatactctaagaacaa | M84005 | 45233 | ctatgagtccatgcctggct | X91824 | 87837 | actacaacattgctgcacagagcc | X91824 |
| 2630 | taggcaactccgtgattcagtcaac | M84005 | 45234 | agtccatgcctgtgctaccaat | X91824 | 87838 | acattcgtcacaagcgcagagag | X91824 |
| 2631 | ctccagctccattgtcggaca | M84005 | 45235 | acctccgagccatgcgctcacaa | X91824 | 87839 | cagacccaatatcctggccagagac | X91824 |
| 2632 | taccgccatgattaaattggcctg | M84005 | 45236 | tgagccatgctcacaagtcaag | X91825 | 87840 | ccaatacttctggcacggaaggag | X91825 |
| 2633 | acacaagtccaatgaggcggtgct | W48442 | 45237 | tccaatactagcccaacagaagaca | X91825 | 87841 | tccttgccaggatctggaaggatg | X91825 |
| 2634 | ctgtggccaagaaggtcatcct | W48442 | 45238 | gatgctgagcctcaattgcattct | X91825 | 87842 | gtctaaccgccaattgtcagtct | X91825 |
| 2635 | tccagataagcgtcatccgtctc | W48442 | 45239 | gctgagcctcaattgtcatccgtt | X91825 | 87843 | ccgccaattgtcagtctcatgt | X91825 |
| 2636 | taaggtcatcctcggtctcttactg | W48442 | 45240 | cctcaattgcattcgttggggaata | X91825 | 87844 | aatttgcagtcattcgttgccaat | X91825 |
| 2637 | tcatcctggtctcttactgcttcat | W48442 | 45241 | atactatgcccctaatatcacagtcc | X91825 | 87845 | gtctcagtggcacggtcatggtgca | X91825 |
| 2638 | gcctattgtctcaactactggcgag | W48442 | 45242 | ctatgcctcaaatacacagtcccac | X91825 | 87846 | atgactgagggcttttccgctctg | X91825 |
| 2639 | tttgctccaactactggcaggcac | W48442 | 45243 | ccctaaatacacagtccccactc | X91825 | 87847 | gctcttgtgcaggtctgcactga | X91825 |
| 2640 | gtcctgacagctcctagctcacact | W48442 | 45244 | aatatcacagtcccactctcatt | X91825 | 87848 | tcactgacacagtgaaatttgt | X91825 |
| 2641 | gagccaggttcatcctgtcgtcc | W48442 | 45245 | ttaatcctataattgtgggtcct | X91825 | 87849 | ccaaccagctgtataactgtga | X91825 |
| 2642 | agccaggttcattgcttgttgcta | W48442 | 45246 | atccattaatgttgtgggtctcggg | X91825 | 87850 | cctgctcgattactccttactacaga | AA107705 |
| 2643 | gccccaggtcattgctcgttgcgac | W48442 | 45247 | atggtctcaagtcaagaacacacc | X91825 | 87851 | tgattacttcctacaggaacatgg | AA107705 |
| 2644 | ccccaggtcattgcttgttctacg | W48442 | 45248 | tgttgggctctggtctagaattc | X91825 | 87852 | gctcttgtcaggtctgctacctatt | AA107705 |
| 2645 | caggtcattcgttgctgctacgtg | W48442 | 45249 | ctctacaagtcaagaacccctgtgac | X91825 | 87853 | tcaaggacaggcaacaggaaacat | AA107705 |
| 2646 | aggttcattcgttggctacgtgg | W48442 | 45250 | acagtcaagacaccctgtgacac | X91825 | 87854 | ggaacatccttggacgcagaagg | AA107705 |
| 2647 | tgcgctatgacacgcgatgtgggagaa | W48442 | 45251 | gacaccctgacaccaaggttcct | X91825 | 87855 | tcctctgacgcagaaggtcacat | AA107705 |
| 2648 | ctgctatgacacgcagatggtgggagat | W48442 | 45252 | acctggtgacaccaaggttcctgag | X91825 | 87856 | cagaaggtcacatcatccaacatcga | AA107705 |
| 2649 | gaacctcaaagtcaggaatcaggaac | W48442 | 45253 | ctcaactgtcactcaatactagcc | X91825 | 87857 | gtcatccaacatccaactggttgg | AA107705 |

TABLE 1-continued

| SEQ ID NO | DBAxnID | sequence | SEQ ID NO | DBAxnID | sequence | SEQ ID NO | DBAxnID | sequence |
|---|---|---|---|---|---|---|---|---|
| 2650 | W48442 | gctccaactactggcaggcaccatg | 45254 | W48442 | aactgtcactccaatactagcccaa | 87858 | X91825 | tcatccacatcgactttggcttcat | AA107705 |
| 2651 | W48442 | actactggcaggcaacatggtcctg | 45255 | W48442 | tgtcactccaatactagcccaacag | 87859 | X91825 | acatcgactttggcttcatccttc | AA107705 |
| 2652 | W48442 | ctactgcaggcaccatggtcctga | 45256 | W48442 | ggaagccaacttcactgtatcctca | 87860 | AA022139 | gaaacctgggcttgagacatcagc | AA107705 |
| 2653 | W48442 | accatgtcctgaccagactagct | 45257 | W48442 | agccaacttcactgtatcctcaatg | 87861 | AA022139 | tcgagacatcagcgttaagctgac | AA107705 |
| 2654 | W48442 | ccatggtcctgaccagactagtc | 45258 | W48442 | tccctcaggtgtccctcatcattaa | 87862 | AA022139 | actcctcaaggaacatgcagtta | AA107705 |
| 2655 | W48442 | catggtcctgaccagactagtca | 45259 | W48442 | ctcaggtgtccctcatcattaacta | 87863 | AA022139 | agcgttaagctgaccacagaagtt | AA107705 |
| 2656 | W48442 | atggtcctgaccagactagctcac | 45260 | W48442 | aggtgtccctcatcattaactatga | 87864 | AA022139 | gcagttataccactgcaggcatcct | AA107705 |
| 2657 | W48442 | ggtcctgaccagactagctcacac | 45261 | W48442 | tgtccctcatcattaactatgatct | 87865 | AA022139 | ataccactgcaggcatcctcagtgc | AA107705 |
| 2658 | W48442 | acagctctgtcactaccaagctta | 45262 | W48442 | ccctcatcattaactatgatctcc | 87866 | AA022139 | catcctcagtgccagccaatt | AA107705 |
| 2659 | X73359 | gctcctgtcactaccaagttacac | 45263 | W48442 | tcattaactatgatctcccaataa | 87867 | AA022139 | tcagtgccagcgcaatttgtgca | AA107705 |
| 2660 | X73359 | ttcctgcagtattctatgcta | 45264 | X73359 | ttaatatgatctcccaataaacag | 87868 | AA022139 | cccagccaatttgtcaaagctg | AA107705 |
| 2661 | X73359 | atagctatcatctcagaaggaaaa | 45265 | X73359 | atgatctcctaataacagagaatt | 87869 | AA022139 | tgtgcaaagctgtgctgctactg | AA107705 |
| 2662 | X73359 | gctatcatctcagaaggaaagaaa | 45266 | X73359 | alctcctaataacagagaatigta | 87870 | AA022139 | aaagtgtgctgctactgcttggt | AA107705 |
| 2663 | X73359 | aggaagcccagagggtgtctgtcat | 45267 | X73359 | tgtacatacacagaagattgggagac | 87871 | AA022139 | gtctcctctgagctgctcttc | AA107705 |
| 2664 | X73359 | aagcccagagggtgtctgtcatagg | 45268 | X73359 | caactttcactgtatcctcaatgcat | 87872 | AA022139 | ttcctcgagctgcctctacgtgg | AA108524 |
| 2665 | X73359 | cttgttgtcgcctggtctcgt | 45269 | X73359 | cttcactgtatcctcaatgcatgaa | 87873 | AA022139 | ctgtaaatgctctccaacaatgc | AA108524 |
| 2666 | X73359 | tgttggtcgcctggtctctgtca | 45270 | X73359 | cactgtatcctcaatgcatggaga | 87874 | AA022139 | atgctccacaacaatgcaacagc | AA108524 |
| 2667 | X73359 | tcgcctggtctctgtccagaggc | 45271 | X73359 | tgtatcctcaatgcatggagacatg | 87875 | AA022143 | ctctccacaacaatgcaacagccgg | AA108524 |
| 2668 | X73359 | cctggtctctgtccagaggtcaaa | 45272 | X73359 | gggccgccagagtgcttatttctac | 87876 | AA022143 | caccatgagccgccagatgacaac | AA108524 |
| 2669 | X73359 | tggtctctgtccagaggtcaaggc | 45273 | X73359 | cgcagagtgcttattctcaga | 87877 | AA022143 | acaatgcaacagcgcggccagccgt | AA108524 |
| 2670 | X73359 | gtctgctgtgcacctgggccta | 45274 | X73359 | ttctcagagtgcttactcaggg | 87878 | AA022143 | atgcaacagccagcgcggact | AA108524 |
| 2671 | X73359 | ttcaactttccctggccacagc | 45275 | X73359 | ctacagatgtctgggcaggggggt | 87879 | AA022143 | ggagctctgaccatgcagctg | AA108524 |
| 2672 | X73359 | atttcctggccacagcccaccaat | 45276 | X73359 | ttcaggccgttcctacatgtatat | 87880 | AA022143 | ccgatgagccgccagtgacaac | AA108524 |
| 2673 | X73359 | agccaccaatctggcccgaaagt | 45277 | X73359 | aggcgtcctacatgtatatgcgt | 87881 | AA022143 | cctgctctccatggttctct | AA108524 |
| 2674 | X73359 | tctcgccagaagtacacacgc | 45278 | X73359 | tgatcgtgaacatgctggcc | 87882 | AA022143 | tctctcatggttctctgttacc | AA108524 |
| 2675 | X73359 | tgcactgcaacctgctagtcccag | 45279 | X73359 | tctgtggcacactgctggcctg | 87883 | AA022143 | cttcagctgccttctacggtggctg | AA108524 |
| 2676 | X73359 | aagcattgctctggacctgtgcagtg | 45280 | X73359 | catctggctgctggtgtg | 87884 | AA022143 | cgagctgcctttctacgctggctgccc | AA108524 |
| 2677 | X73359 | tcttctgtgccagattctag | 45281 | X73359 | gctggcctgtctgtgtgcgagcc | 87885 | AA022143 | ttctacgctgccaagctcgg | AA108524 |
| 2678 | M17030 | ggtcattagttccagaggeggtac | 45282 | M17030 | gcgagcatcctcatctgctgcta | 87886 | AA022143 | ggggcgccaatccatcagatac | AA108524 |
| 2679 | M17030 | cattagtgtccagaggcaggag | 45283 | M17030 | agccatcctcagtctgctact | 87887 | AA022143 | tcctcatgagattacctgtaga | AA108524 |
| 2680 | M17030 | atccctagtgcatgtatgattatg | 45284 | M17030 | gtctctgctactcttttcgtcca | 87888 | AA022143 | tccatgagattacccctgtagaaat | AA108524 |
| 2681 | M17030 | gtaatlgtttgctcatttagaaat | 45285 | M17030 | cagatacctttacaLcaagttagat | 87889 | AA022143 | atgagattacccctagaaatcg | AA108524 |
| 2682 | M17030 | acactctctcatttacaacctct | 45286 | M17030 | atacctttacatcaagttagatag | 87890 | AA022143 | tggctgcaatactcctcacaacaa | AA108524 |
| 2683 | M17030 | ctctctcaatttacaacctgtga | 45287 | M17030 | ccttacatcaagttagatgggga | 87891 | AA022143 | gcttataaacttagcctcagggc | AA120244 |
| 2684 | M17030 | atttacaacctgtgaatgacattg | 45288 | M17030 | ggtccatgtatatcggtgaaatt | 87892 | AA022143 | tataaacttagcctcagggctca | AA120244 |
| 2685 | M17030 | tacaacctgtgaatgacatttggt | 45289 | M17030 | cggtgaaatlgtccaacgctctc | 87893 | AA022143 | catcagctcctgctttgtatactg | AA120244 |
| 2686 | M17030 | aacctgtgaatgacatttgggtac | 45290 | M17030 | tccaacgctcagggggagcactt | 87894 | AA022143 | cagctcctgctttgtatactgag | AA120244 |
| 2687 | M17030 | tatcatacaacttgttcctccactaa | 45291 | M17030 | aaccgctcagggggagcactt | 87895 | AA022143 | agagactgcggaactgaggagcc | AA120244 |
| 2688 | M17030 | aacattaacacttgttcttacaatg | 45292 | M17030 | tggcacttttcatcagctggccatc | 87896 | AA022143 | caaagcgccgaactcagcaactaatgaa | AA120244 |
| 2689 | M17030 | attaaacactlgttcttacaatgct | 45293 | M17030 | cactttcatcagctggccatgc | 87897 | AA022143 | gaactgcggccactcagcaactgcct | AA120244 |
| 2690 | M17030 | gggaatcatggtgtcatggtatc | 45294 | M17030 | tcatcaggtccatcgcaagggc | 87898 | AA022143 | actggcccactcagcaaacgcctcat | AA120244 |
| 2691 | M17030 | tcatgtatccctgtcgacagacta | 45295 | M17030 | atccatccatcgcaagggg | 87899 | AA022143 | ggccactcagcaacgcctcattg | AA120244 |
| 2692 | M17030 | tggtatccctgtcgacagacta | 45296 | M17030 | aittatctggccaattatgatctg | 87900 | AA022143 | tcagaacgctcattgtcaag | AA120244 |
| 2693 | M17030 | tgctgacagactacttcaacctgcct | 45297 | M17030 | gaagatccttgactgagactagta | 87901 | AA022193 | gcaactgcctcattgtcaaggac | AA120244 |
| 2694 | M17030 | tgacagactacttcaactcctgtctcca | 45298 | M17030 | ccctcttgactcgagaccggaaatgct | 87902 | AA022193 | aaacttgctcaaggagagtg | AA120244 |
| 2695 | M17030 | tgctcagaagccaaagtttgatg | 45299 | M17030 | ctcctcagagaccggaaatgctat | 87903 | AA022193 | aaacttgctccaggtccagat | AA120244 |
| 2696 | M17030 | ccctcgtcttttagcaataagaata | 45300 | M17030 | ccttcagaacggccggaaatgctatgg | 87904 | AA022193 | tcatttgtcaaggagctgggctct | AA120244 |
| 2697 | M17030 | gtaaacacatccctagtcatggt | 45301 | M17030 | gagcagtccctgagcagtgccagca | 87905 | AA022193 | cagctcagggctccagatcgtta | AA120244 |
| 2698 | W47953 | gtcctttagtctcttttggacactt | 45302 | W47953 | agtccctgagcagtgccagcacaga | 87906 | AA022193 | ctcaggggctccagatcgttagt | AA120244 |
| 2699 | W47953 | gtcctcttgacacttccaaatat | 45303 | W47953 | tcctgagcagtgccagcacagatt | 87907 | AA022193 | cagggctccagatcggttagctgca | AA120244 |

TABLE 1-continued

| SEQ ID NO | DBAxnID | sequence | SEQ ID NO | DBAxnID | sequence | SEQ ID NO | DBAxnID |
|---|---|---|---|---|---|---|---|
| 2700 | W47953 | ttcagaagcttgccaacaactccta | 45304 | AA022193 | tgagcagtgccagcacagatttgg | 87908 | AA120244 |
| 2701 | W47953 | agaagctgccaacaactcctatgc | 45305 | AA022193 | agcagtgccagcacagatttgggg | 87909 | AA120244 |
| 2702 | W47953 | agcttgccaacaactcctatgcatg | 45306 | AA022193 | cagtgccagcacagatttgggggt | 87910 | AA120244 |
| 2703 | W47953 | ttgccaacaactcctatgcatgcaa | 45307 | AA022193 | gtgccagcacagatttgggggtt | 87911 | AA120244 |
| 2704 | W47953 | ccaacaactcctatgcatgcaaaca | 45308 | AA022193 | ccettgactgagactagtaggag | 87912 | AA120244 |
| 2705 | W47953 | acaactcctatgcatgcaaacacc | 45309 | AA022193 | gccagcacagatttggggttca | 87913 | D83146 |
| 2706 | W47953 | catgcaaacacctgaagtcaatc | 45310 | AA022193 | acaacctgctcgggcgactgga | 87914 | D83146 |
| 2707 | W47953 | gcaaacacccgaagtcaatccta | 45311 | AA022193 | aacctctgctcgggcgactgagg | 87915 | D83146 |
| 2708 | W47953 | ctgagtcaatcctattgaaaat | 45312 | AA022193 | gctgcaagggcgtatgggggtct | 87916 | D83146 |
| 2709 | W47953 | ttcaatcctatttgaaaatctcca | 45313 | AA022193 | tgcacaagggcgtatgggggtctgt | 87917 | D83146 |
| 2710 | W47953 | tctttgaacacttccaatatcgg | 45314 | AA022193 | tatggggctctgtctgatgacaa | 87918 | D83146 |
| 2711 | W47953 | caagtccctccaacaatccaacct | 45315 | AA022193 | gtagccaagcaactgggcgttga | 87919 | D83146 |
| 2712 | W47953 | gacacttccaaatatcgggcgat | 45316 | AA022193 | gcaactggcgttggaagtccct | 87920 | D83146 |
| 2713 | W47953 | cgatgacgtgcaaaaccgaggctgc | 45317 | AA022193 | atgacagactctgaagtgctga | 87921 | D83146 |
| 2714 | W47953 | tgacgtgcaaaaccgaggctgctcg | 45318 | U49861 | catgtgtccaattgccactata | 87922 | D83146 |
| 2715 | W47953 | tggatagccaatccatcgttcat | 45319 | U49861 | tctctggccactgagccaaagctt | 87923 | D83146 |
| 2716 | W47953 | tagcaatcctcatcgtttcatgaa | 45320 | U49861 | gcactgatgccaaagcttataact | 87924 | D83146 |
| 2717 | W47953 | caatcctcatcgtttcatgaaaca | 45321 | AA022193 | tgccatglaggcccgtgtcactc | 87925 | D83146 |
| 2718 | W47953 | ttattcagaagctgccaacaactc | 45322 | U49861 | gtaggccctgtcactctgtcct | 87926 | D83146 |
| 2719 | W47953 | tatgcatctgcagtcagcgaggt | 45323 | U49861 | gtcactctgtcctccgggtcacag | 87927 | D83146 |
| 2720 | W47953 | cgaggtcactgcaatctataaat | 45324 | U49861 | ctgcctcctgggtcacagtgct | 87928 | D83146 |
| 2721 | W48544 | gcaaatatcatcagcgacatcgacaa | 45325 | U49861 | tcctggtccacagtgctcttcactg | 87929 | D83146 |
| 2722 | W48544 | aatatcatcagcgacatcgacaatt | 45326 | U49861 | ttcactgtctttgtttcgatagc | 87930 | D83146 |
| 2723 | W48544 | atatcatcagcgacatcgacaattg | 45327 | U49861 | gtcttttgttttcgatagcattga | 87931 | D83146 |
| 2724 | W48544 | tatcatcagcgacatcgacaattg | 45328 | U49861 | gcttcatctcatgtctgccct | 87932 | AA108230 |
| 2725 | W48544 | tcatcagcgacatcgacaatttgca | 45329 | U49861 | tccaatttgccactatagaccca | 87933 | AA108230 |
| 2726 | W48544 | catcagcgacatcgacaatttgcag | 45330 | U49861 | tttgccactatagaccaatgta | 87934 | AA108230 |
| 2727 | W48544 | atcagcgacatcgacaattgcagc | 45331 | U49861 | acttatagaccaatgtatatgc | 87935 | AA108230 |
| 2728 | W48544 | taggcaccccggacgcagtgcgcta | 45332 | U49861 | ataatgtgaacatggttgtgca | 87936 | AA108230 |
| 2729 | W48544 | caccccgggacgcagtgcgctactgg | 45333 | U49861 | tgttctgcttgtaggaaccatagaa | 87937 | AA108230 |
| 2730 | W48544 | accgggacgcagtgcgctactggt | 45334 | U49861 | tttccatgcaacatagaatcttca | 87938 | AA108230 |
| 2731 | W48544 | agggtcatcgcaatctataaaatgt | 45335 | U49861 | atctcatctactccctactact | 87939 | AA108230 |
| 2732 | W48544 | agggtcatcgcaatctataaaagt | 45336 | U49861 | ctaccatctgaaatagattgcaat | 87940 | AA108230 |
| 2733 | M88355 | gtcatcgcaatctaggggtgtgg | 45337 | AA022196 | gaggaatctatccatatgaggcaa | 87941 | AA108230 |
| 2734 | M88355 | tcatctgcaatctataaaatggt | 45338 | AA022196 | gaatctatccatatgaggcaacag | 87942 | AA108230 |
| 2735 | M88355 | tccagcaatatcatcagcgacatc | 45339 | AA022196 | ggctttgtggacatcctaagcagg | 87943 | AA108230 |
| 2736 | M88355 | cccagcaatatcatcagcgacatcg | 45340 | AA022196 | tttgtggacatcctaagcaggaa | 87944 | AA108230 |
| 2737 | M88355 | cagcaatatcatcagcgacatcgac | 45341 | AA022196 | gacatcctaagcaggaagaggaga | 87945 | AA108230 |
| 2738 | M88355 | agcaatatcatcagcgacatcgaca | 45342 | AA022196 | aaggcagttgcaactgtgggggcca | 87946 | AA108230 |
| 2739 | M88355 | ccatactcacggcgatcctcagac | 45343 | AA022196 | attctgtgtctattgatgcaggtc | 87947 | AA108230 |
| 2740 | M88355 | tcaactacggcgatcctcgactga | 45344 | AA022196 | ggtcagtgtcctcctgtctata | 87948 | AA108230 |
| 2741 | M88355 | gctgtcgactgggatatgcgca | 45345 | AA022196 | catgagtcctttgctatataag | 87949 | AA108230 |
| 2742 | M88355 | gtgctgaccctggatatgcgcaagt | 45346 | AA022196 | tccctgtcctataaagaaggcattt | 87950 | AA108230 |
| 2743 | M88355 | gacctggatatgcgcaagtgctct | 45347 | AA022196 | tattttgagcagactgagcagtg | 87951 | AA108230 |
| 2744 | M88355 | gccaacgcatctgctcagcgcccgg | 45348 | AA022196 | tttgagccagactgagcagtgaag | 87952 | AA108234 |
| 2745 | M88355 | acagccatctgctcagcgcccggatg | 45349 | AA022196 | tcctatccatagaggcaacagaag | 87953 | AA108234 |
| 2746 | M88355 | ggcatctgctcagcgcccggatggt | 45350 | AA022196 | tgtaagtacaatcccaagtatcctg | 87954 | AA108234 |
| 2747 | M88355 | atctgctcagccccggatggctgcc | 45351 | AA022196 | aagtacaatcccaagtatcctgttg | 87955 | AA108234 |
| 2748 | M88355 | tcggaccccgagctcgccttctgg | 45352 | AA022196 | tacaatcccaagtatcttgttgcta | 87956 | AA108234 |
| 2749 | M88355 | tgagcccactctctgggaatacctt | 45353 | AA022196 | cccaagtatcttgtcaatgaca | 87957 | AA108234 |

TABLE 1-continued

| SEQ ID NO | DBAxnID | sequence | SEQ ID NO | DBAxnID | sequence | SEQ ID NO | DBAxnID | sequence |
|---|---|---|---|---|---|---|---|---|
| 2750 | M88355 | cgttcccatggccactgcagaa | 45354 | AA022196 | tatctcgttgctaatgacaccggct | 87958 | AA108234 | taacaggctaggcagctcaatcg |
| 2751 | M88355 | cctacagcggatctcagactgagca | 45355 | AA022196 | gttgctaatgacaccggcttgtgg | 87959 | AA108234 | gctaggcagctcaatcgcttaa |
| 2752 | M88355 | acagccggatctcagactgagca | 45356 | AA022196 | aatgacaccggctttgggacatcc | 87960 | AA108234 | gcagctcaatcgtttaacaacaa |
| 2753 | M88355 | gatctcagactgagcaacatcgcca | 45357 | U17698 | atttacattgactcagtgaaaggaa | 87961 | AA108234 | tcaatcgctttaacaacactgtta |
| 2754 | M88355 | ctcagactgagcaacatcgccatgg | 45358 | U17698 | tacattgactcagtgaaaggaaaat | 87962 | AA108234 | atggcatcatcctgggactlatta |
| 2755 | M88355 | agactgagcaacatcgccatggcct | 45359 | U17698 | agaccatgttcctaccaaatcaat | 87963 | AA108234 | tcatcctgggactlattaacagcgg |
| 2756 | M88355 | ctgcttggcttactggctcgact | 45360 | U17698 | ccatgttcctaccaaatcaatgat | 87964 | AA108234 | tggctggccctgatggtatcat |
| 2757 | M88355 | ggcttactggctgacctcggcct | 45361 | U17698 | ttgttcctaccaaatcaatgattcc | 87965 | AA108234 | gtatcatctactatccaagcctga |
| 2758 | M88355 | agggctgtcgtgacctggatatgc | 45362 | U17698 | ttcctaccaaatcaatgattccata | 87966 | AA108234 | tctactatctcaagcctgactgtc |
| 2759 | W48010 | atcggccaccgatgggctgcacact | 45363 | U17698 | ctaccaaatcaatgattccatattt | 87967 | AA108234 | agcctgacttggtcaaagctagggtc |
| 2760 | W48010 | tcggccaccgatgggctgcacactg | 45364 | U17698 | actatgtccatlagcacccagatagc | 87968 | AA108234 | caaagctagggtctcctcaggtatg |
| 2761 | W48010 | gatgatcgaccgcaacctcgggag | 45365 | U17698 | atgtcatlagcacccagatagcttt | 87969 | AA108234 | tagggtctccagagctgcccctg |
| 2762 | W48010 | atgatcgaccgcaacctcggggagg | 45366 | U17698 | atlatgcattlccttttgaagcaa | 87970 | AA108234 | atgcttggaccagatttcttc |
| 2763 | W48010 | aaattatccacgagctggctactc | 45367 | U17698 | atgcattlccttttgaagcaaaatgt | 87971 | Y09585 | ggaccagatttctcttcttagg |
| 2764 | W48010 | aattatccacgagctggctactca | 45368 | U17698 | gcatttcctttltgaagcaaaatgt | 87972 | Y09585 | accagcacagcacacatcgattag |
| 2765 | W48010 | attatccacgagctggctactcag | 45369 | U17698 | acttgatgcaacacgcacttg | 87973 | Y09585 | acacacagcatgaggacaga |
| 2766 | W48010 | ttatccacgagctggctactcaga | 45370 | U17698 | atgcaacacgcacttgtgtc | 87974 | Y09585 | ccatctgccagatctgccctg |
| 2767 | W48010 | tatccacgagctggctactcagga | 45371 | U17698 | caacacatgcactttgtgtctcc | 87975 | Y09585 | gttcaaccaaccattaatggatc |
| 2768 | W48010 | acgaggctgactcaggagagaaga | 45372 | U17698 | cactttgtgtcctgattcaa | 87976 | Y09585 | gtcggtlcaactcaccagcaactlc |
| 2769 | W48010 | aggctggctactcaggagaagaagtg | 45373 | U17698 | acttcttgtatataagactgtac | 87977 | Y09585 | tcacagcaacttcctcttgggtc |
| 2770 | W48010 | cggccaccgatgggctgcacactga | 45374 | U17698 | tataagactgtactgctlaggatat | 87978 | Y09585 | caactlcttggttggctgctca |
| 2771 | W48010 | ggccaccgatgggctgcacactgag | 45375 | U17698 | aagactgtactgctlaggatattaa | 87979 | Y09585 | ctcctttggctgtcagccagt |
| 2772 | W48010 | gccaccgatgggctgcacactgagc | 45376 | U17698 | gttctatgtagggttgcaga | 87980 | Y09585 | tgglgctcagccagtgatact |
| 2773 | W48010 | caccgatgggctgcacactgagcgc | 45377 | U17698 | cctgtctatcaccaaccctgg | 87981 | Y09585 | gactcgtltctctgctggcta |
| 2774 | W48010 | accgatgggctgcacactgagcgct | 45378 | U17698 | tgctatccaaacctggacagtc | 87982 | Y09585 | ggactgttttccttctggct |
| 2775 | W48010 | ccgatgggctgcacactgagcgctg | 45379 | U17698 | gatcctgccatgttgaccgactg | 87983 | Y09585 | tctctccaaggcttccaagca |
| 2776 | W48010 | aggatgatcgaccgcaacctccggg | 45380 | U17698 | gccactgttgaccgactgcaaat | 87984 | Y09585 | cacatcgatgaggacgagaccaa |
| 2777 | W48010 | ggatgatcgaccgcaacctccggga | 45381 | U17698 | agcactagctgacgagtatgaaggcc | 87985 | Y09585 | caaggttccaagagagagggcaa |
| 2778 | M62860 | cctgctctcttgttgctg | 45382 | U17698 | agtttgcaatggtgtccagcacc | 87986 | Y09585 | agaccaaggccaagactttatg |
| 2779 | M62860 | ctctctctttggtgctctcca | 45383 | U17698 | ctgcgtatctataagccgtgtt | 87987 | Y09585 | ctttatgtcatcatgggctgtt |
| 2780 | M62860 | ggtctcagatgacatctctttacc | 45384 | U17698 | tatcctataagcgtlcatgc | 87988 | Y09585 | tcatgggctgctctgttctgtg |
| 2781 | M62860 | ctcagatgacatctctttacctgg | 45385 | U17698 | actcaccccatgcatacggactcctg | 87989 | Y09585 | ttgtggaccctttcatagactacac |
| 2782 | M62860 | tgacatcttlacctggccgctac | 45386 | U17698 | ccactgcatacggactctgcctata | 87990 | Y09585 | ggactgcttlccttctgctlggcta |
| 2783 | M62860 | calctcatlctttacctggctaccag | 45387 | U17698 | catacggactctgcctatagcaatt | 87991 | Y09585 | ttctcatgcctltgaataagtc |
| 2784 | M62860 | ctctttacctggctactcagcct | 45388 | U17698 | gactctgcctatagcaattggtat | 87992 | Y09585 | ctttcagacggcctltctcatcat |
| 2785 | M62860 | ccgagatgccatttcgatlttccac | 45389 | U17698 | aactgctlggatcaacaccccat | 87993 | X91043 | aatgaatgcatccaggctctgaaa |
| 2786 | M62860 | catttcgatltlccactagccaag | 45390 | U17698 | ctlgatcaacagccccattccatg | 87994 | X91043 | agcatccatggtatccagaglct |
| 2787 | M62860 | ttcgatltlccactagccaagga | 45391 | U17698 | agctgagtlccctaagctgcaagtt | 87995 | X91043 | ctttaactctgggggatttagcg |
| 2788 | M62860 | gatttlccactatgccaagggacaa | 45392 | U17698 | tggtttcatlgactlcgtatgact | 87996 | X91043 | taactctcggggagattagctgaaa |
| 2789 | M62860 | clatgccaagggacaaccttacatc | 45393 | U17698 | catlgactlcgtatgactlctgta | 87997 | X91043 | ttccttcctgtatgtgactgtag |
| 2790 | M62860 | tlcttggctgtctcagcctg | 45394 | U17698 | ggaattttlcgatttcagaagag | 87998 | X91043 | atgtlcactgtaggggtcttagaa |
| 2791 | M62860 | ggtgtctctcagcctggccatt | 45395 | U17698 | atttcacgaagatgctgccatt | 87999 | X91043 | tgcactgtagggcttagaaatgg |
| 2792 | M62860 | gtctcagcctggccatgtggtt | 45396 | U17698 | cgaaggatcctgccatgttgac | 88000 | X91043 | tgaagactgcctctggagccagg |
| 2793 | M62860 | tccagcctggccatlggttac | 45397 | U17698 | tagcagaagcaccatggtatctga | 88001 | X91043 | agcctcaaggctcaggcttca |
| 2794 | M62860 | agcctggccattgtggttacacg | 45398 | U17698 | cagaagcaccatggtatctgagag | 88002 | X91043 | ggcttcatcctcgcaccaacaaat |
| 2795 | M62860 | aatctatlggtgcgtgggctcccag | 45399 | U17698 | tlctgattgctacgcaagattt | 88003 | X91043 | gccagctaaaacactctgtgacact |
| 2796 | M62860 | ctgctccttgtcccagtgaatgg | 45400 | U17698 | tgctatlgcccaagattgcttlc | 88004 | X91043 | gtaaacactctgtgacactgaagaa |
| 2797 | M62860 | ctccttcgtcctgaatgggggc | 45401 | U17698 | ctatlgcccaagattgcttlat | 88005 | X91043 | atccatlggttatcacgagctcct |
| 2798 | W48055 | tcagctccaatgaatltggctct | 45402 | U17698 | ttgcccaagatltgcttlctatga | 88006 | X91043 | ggttatcacgagtctcctgcc |
| 2799 | W48055 | gctccaatgaatltggctctta | 45403 | U17698 | atlttgtctltctatgcacgtaltgta | 88007 | X91043 | tcagctccggtacttcaaaccctg |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 2800 | ctcatcattatatcgtcctactg | W48055 | 45404 | tgctttctatgcacgtattgtcaa | D14636 | 88008 | tcaaacctgaccactactgctgcg | X91043 |
| 2801 | atcattatatcgtcctactactgcta | W48055 | 45405 | aattgtgcttgtgccacaggtcat | D14636 | 88009 | cactctgctgccgagaaaactcc | X91043 |
| 2802 | atatgtcctacactgtctaatctgg | W48055 | 45406 | gcttgtgccacaggtcatgatcgt | D14636 | 88010 | ccctgccatgcgacatgttgcag | X91043 |
| 2803 | tacactgctaatctgctgatcgcc | W48055 | 45407 | ttgtgccacaggtcatgatccgtga | D14636 | 88011 | gccatgcacatgttgcaggcgatc | X91043 |
| 2804 | actgctaatctggctgcatgccta | W48055 | 45408 | tgccacaggtcatgatcgtggaa | D14636 | 88012 | catcgacatgttgcagggcatcatg | X91043 |
| 2805 | gctgcatgcctactgtcgagagga | W48055 | 45409 | aagcaaccatggtatctgagagagc | D14636 | 88013 | gactctacgcaggagaaccctg | X91043 |
| 2806 | tgcctacgtgggaggatggtct | W48055 | 45410 | gatccccaagcttagaattgtt | D14636 | 88014 | ccatctgtcattttaaacagtc | X99572 |
| 2807 | tccccatagaaagtgcagaagacc | W48055 | 45411 | tgtggagacttcttcgtctgt | D14636 | 88015 | tgattcccagtactctgacaaatg | X99572 |
| 2808 | agtgcagaagaactgcgccaagacgac | W48055 | 45412 | tgtcgttactcatgttatcaa | D14636 | 88016 | tagctcagatgtcttttgccatc | X99572 |
| 2809 | gcagaagaactgcgccaagacgacaga | W48055 | 45413 | tttactctagtttcaaataatg | D14636 | 88017 | cagatgtctttgcgccatcagcact | X99572 |
| 2810 | tcaccagatcctgtcaggtcgcga | W48055 | 45414 | tatatcagccaaaaccataactac | D14636 | 88018 | ggccatcagcacctgcaagaaggag | X99572 |
| 2811 | cccagatcctgtcaggtcggattg | W48055 | 45415 | gtctactgttctaggtttctgtgg | D14636 | 88019 | gaggagccctgtgtttgatgaata | X99572 |
| 2812 | agatcctgcaggtcggattgttg | W48055 | 45416 | ttttctgattgatattgcccaaga | D14636 | 88020 | tagtaggtgccactcgattgtttc | X99572 |
| 2813 | tcctgtcaggtcggattgttggag | W48055 | 45417 | cctgcgtccgtgggtcccatatct | D14636 | 88021 | ctcgattgttcctgcggctggcaa | X99572 |
| 2814 | tggtctcacactcatcattat | W48055 | 45418 | ggtccatatctggtcccaacgaa | D14636 | 88022 | aatgtcatgagttattgtctct | X99572 |
| 2815 | ttcttcacactcatcattatgt | W48055 | 45419 | atgtcacttacgtttgggcattgt | D14636 | 88023 | agcactgatcaattcccatccact | X99572 |
| 2816 | ttcacactcatcattatcgtcct | W48055 | 45420 | cttacgtttgggcattgtgagctg | D14636 | 88024 | ctgaagcactgccgtcatgtttata | X99572 |
| 2817 | acactcatcattatcgtcctaca | W48055 | 45421 | gaaggtctcttgtctcccaacaca | D14636 | 88025 | ctgtcattttaaacagtcactgt | X99572 |
| 2818 | aaagtccaatcattgtacgtgtg | L14751 | 45422 | ctctgtttctcaacacacatgctg | U47810 | 88026 | cactgcttttgtcaagttcgtcaac | X99572 |
| 2819 | atcattgtacgtgtgagttgggaa | L14751 | 45423 | ttttctcaacacaatgtcgaagcta | U47810 | 88027 | tttgtcaagttcgtcactgttgc | X99572 |
| 2820 | agagccaggctaccgcgattagga | L14751 | 45424 | gtatagttagttcctccagagctg | U47810 | 88028 | aagttgctgccactgttgcccacta | X99572 |
| 2821 | caggctaccgcgattaggagtagaa | L14751 | 45425 | ttagttctccagagctgccaaga | U47810 | 88029 | ttgattgacctagtgtcatggtaa | X99572 |
| 2822 | cccctgtttccatcgtgatgta | L14751 | 45426 | aagcaactccactggctagtccta | U47810 | 88030 | atggtaaagccacatttccatcatgcaa | X99572 |
| 2823 | ttcccatgggtaggatggact | L14751 | 45427 | tttttagaatctgccatataacta | U47810 | 88031 | aagccacattccatgcaatgggg | X99572 |
| 2824 | ccctcaggagagacaacctct | L14751 | 45428 | aatctgccatataactaccaataa | U47810 | 88032 | cattccatgcaatgcggctaggt | X99572 |
| 2825 | caagagacaaactctgagagctaa | L14751 | 45429 | catactgttccaaacgaatgacag | U47810 | 88033 | gcaatgctgcagctggctaggactaa | X99572 |
| 2826 | gagacaaaactctgagagctaatgt | L14751 | 45430 | accaaaaagtctactcactcaggtg | U47810 | 88034 | atgtctgcagctggctaggactct | AA108443 |
| 2827 | gagctaatgtcaggtccctggagac | L14751 | 45431 | taggcaactgtctcagtttacc | U47810 | 88035 | tcaatagcctggactctcgggagac | AA108443 |
| 2828 | ctgctggcacaggtggggaaccat | L14751 | 45432 | actgctctcagttttaccagagtcg | U47810 | 88036 | gagaccaagactccaatgctacca | AA108443 |
| 2829 | tctcttatctccaagcatgaga | L14751 | 45433 | ctcagtttaccagatcgctacta | U47810 | 88037 | agaccaagactccaatgctaccat | AA108443 |
| 2830 | ccgactcctatgcgagacagtgcca | L14751 | 45434 | tttaccagatcgctactatgaaga | U47810 | 88038 | accaagactccaatgctaccatgt | AA108443 |
| 2831 | atgagaacagccggtccattccgca | L14751 | 45435 | aggataccaaccaaatgtcactacgt | U47810 | 88039 | agacttccaatgctaccatgtctg | AA108443 |
| 2832 | cagacagtccgcatcctgccaagg | L14751 | 45436 | aggataccaaccaaatgtcactacgt | U47810 | 88040 | agactccaatgctaccatgtctgt | AA108443 |
| 2833 | acagtccgccatcctgccaagtc | L14751 | 45437 | ccaagcaactgctgagtgctgcacca | U47810 | 88041 | cttccaatgctaccatgtctgata | AA108443 |
| 2834 | gccatcctgccaagtaccctaggc | L14751 | 45438 | ggcactgctgagtgctgcaccaaag | U47810 | 88042 | accatgtctaccatgtctggttgaa | AA108443 |
| 2835 | gtaccctaggctgaccctcagcctcc | L14751 | 45439 | gaatattccactaattacggacaag | U47810 | 88043 | catgtctgatacttgttggttaat | AA108443 |
| 2836 | ctgagatctcagcctcccagatccaa | L14751 | 45440 | tattccactaattacggacaagctc | U47810 | 88044 | gtaatgctgagtcgcgatgcacatcg | AA108443 |
| 2837 | ttgagtctcccagatccaaggggga | L14751 | 45441 | tccactaattacggacaagctctc | U47810 | 88045 | actctgagaactgcagacctcaata | AA108443 |
| 2838 | atgaccctcaaggatgccatactat | W48926 | 45442 | actaattacggacaagctctcgt | AA022241 | 88046 | tgagaactgcagacctcaatagccg | AA108443 |
| 2839 | acctcaaggatgccatactatctg | W48926 | 45443 | caagcctcctgtcacttttagtca | AA022241 | 88047 | gaaactgcagacctcaatagccgaa | AA108443 |
| 2840 | agaaggatgccatactatctgtgc | W48926 | 45444 | gctcctctgctcactttttagt | AA022241 | 88048 | actgcagacctcaatagccggact | AA108443 |
| 2841 | acagatccagagggctgtgcat | W48926 | 45445 | ccctcgctcatttagtcagttaca | AA022241 | 88049 | actgcagacctcaatagccggactc | AA108443 |
| 2842 | gacatccgagggctgcatgcatgg | W48926 | 45446 | ctgtcactttagtcagttacacca | AA022241 | 88050 | ctgcagacctcaatagccggactcc | AA108443 |
| 2843 | cagagggctgtcatgaggtcatg | W48926 | 45447 | ttagtcagttacacaagagttatc | AA022241 | 88051 | gcagacctcaatagccggactcctg | AA108443 |
| 2844 | agaggctgtcatgaggtcatgg | W48926 | 45448 | gtcagttacacaagagtattctt | AA022241 | 88052 | gacctcaatagccggactccggg | AA108443 |
| 2845 | ggcttgctcatgaggtcatggagc | W48926 | 45449 | tgctgccaaagagggggctggaac | AA022241 | 88053 | aagagctgttgccacgcaccgga | AA108443 |
| 2846 | ttgctgcatgagtcatgagcagc | W48926 | 45450 | tgcaccaaagagggggctggaacgaa | AA022241 | 88054 | cgtttgccacgcaccggcagga | Y09632 |
| 2847 | aattgccaggcacgtgagttccca | W48926 | 45451 | gaaagctgcatgcgtgctctga | AA022241 | 88055 | agccctgccaaaagcgctggga | Y09632 |
| 2848 | attgcccagcacgtgagttccca | W48926 | 45452 | agctcgcatgcgtctctgaaac | AA022241 | 88056 | acctacctgccaaagctcaacgac | Y09632 |
| 2849 | tgccaggcacgtgagttccagc | W48926 | 45453 | ctctgcatgctgctctgaaacacc | AA022241 | 88057 | ctgcaaagtctcaacgacgacagc | Y09632 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 2850 | aggatgccatactatctgtcttt | W48926 | 45454 | atggctgctgaaccaccagccac | AA022241 | 88058 | aagtcaacagacagcagccctat | Y09632 |
| 2851 | ggatgccatactatctggtcttt | W48926 | 45455 | ctgaaacaccagccacaggaatcc | AA022241 | 88059 | aacagacagcagccctatgcgcgg | Y09632 |
| 2852 | tggccatactatctggtcttgtg | W48926 | 45456 | atctgagggttcaggaaagatc | AA022241 | 88060 | ccttatgcgcggattctgctca | Y09632 |
| 2853 | gccatactatctggtcttttgtgt | W48926 | 45457 | gccatgctgcagggcatgacatctg | AA022241 | 88061 | atggtttgccctgaggttgtca | Y09632 |
| 2854 | ccatactatctggtcttttgttg | W48926 | 45458 | tctggcatgaactacctcagtaatc | AA022241 | 88062 | ttggccagctgttagctgataagt | Y09632 |
| 2855 | atactatctggtcttttgttggc | W48926 | 45459 | atcacaattagtccacgggaact | AA022241 | 88063 | ttaagcttcagcatacaccagaac | Y09632 |
| 2856 | ctggtcttttgttggctgctgct | W48926 | 45460 | tggctgccgaaacatctcggtga | AA022241 | 88064 | atacaccgaactgtattcagaat | Y09632 |
| 2857 | gtcttttgttggctgctgctga | W48926 | 45461 | gctgccagaaacatctcggtaat | AA022241 | 88065 | ccacgcaaccgggcagggaaacct | Y09632 |
| 2858 | atgctactccaaagacagagcagt | W48926 | 45462 | ctgccagaaacatctcggtgaatc | AA022241 | 88066 | tcgtcaagcattaaccaactgtgat | Y09632 |
| 2859 | cctccaaagacagagcagtacgtgg | W47946 | 45463 | gccagaaacatctcggtgaatcaa | AA022241 | 88067 | cttaatcaagcagaaccagaccctg | Y09632 |
| 2860 | catatcattgactgatacctgtaat | W47946 | 45464 | ccagaaacatctcggtgaatcaaa | AA022241 | 88068 | gaccctggctgagctgcagaataac | Y09632 |
| 2861 | atcattgactgatacctgttgtgtt | W47946 | 45465 | aacatctcggtgaatcaaaacctg | AA022241 | 88069 | cattgctgcagtatcacacactgtg | Y09632 |
| 2862 | taatatgcaacggcacagctagttt | W47946 | 45466 | acatcttcggtgaatcaaaaactgt | AA022241 | 88070 | gtatcacactgctaaagctccaa | Y09632 |
| 2863 | tatgcaacggcacagctagtttttc | W47946 | 45467 | gacagccctgaagccattgccatg | AA022242 | 88071 | gctaaagctcaaggccaagcctct | Y09632 |
| 2864 | gcaacggcacagctagtttttctga | W47946 | 45468 | agccctgaagccatgccattgccatgg | AA022242 | 88072 | tccaaggcaaggctctgccaaa | Y09632 |
| 2865 | cagctagtttttctgatctggataa | W47946 | 45469 | ctgcatgaactacctcagtaatca | AA022242 | 88073 | gctccatttcaacgctcggagca | Y09632 |
| 2866 | ctagtttttctgatctggataaag | W47946 | 45470 | ggcatgaactacctcagtaatca | AA022242 | 88074 | atttcaacaagctcggagcatga | D86603 |
| 2867 | agtcaacatctgaactatatttca | W47946 | 45471 | gcatgaactacctcagtaatcacaa | AA022242 | 88075 | ggaggcctgctgtcatcctcagtatt | D86603 |
| 2868 | agaataaatcaacagacaactct | W47946 | 45472 | atgaactacctcagtaatcacaat | AA022242 | 88076 | tatcctcagtattgactaggagtt | D86603 |
| 2869 | aatctcaacagacaactctattctg | W47946 | 45473 | tgaactacctcagtaatcacaatta | AA022242 | 88077 | aagtgtatcatcgttccgtttctc | D86603 |
| 2870 | cttcacaaggcgaggtgggtagatg | W47946 | 45474 | aactacctcagtaatcacaatatg | AA022242 | 88078 | atcatgtccctgttctcagttct | D86603 |
| 2871 | aacagacaactctattctgattata | W47946 | 45475 | tacctcagtaatcacaattatgtcc | AA022242 | 88079 | cagttcgttccctcttttagtcc | D86603 |
| 2872 | gatgctcatggtccattggacgctat | W47946 | 45476 | acctcagtaatcacaattatgtcca | AA022242 | 88080 | tgccccgagagctgcacactgcac | D86603 |
| 2873 | gtcattggtcattggacggcgctagat | W47946 | 45477 | ctttccattcgccttttgtcatg | AA022242 | 88081 | ctgcacactgcacaaggctgtcgat | D86603 |
| 2874 | atggtcattggacggctatgatggt | W47946 | 45478 | ttccattcgccttttgtcatttg | AA022242 | 88082 | actgcacaaggctgtcgatcatctc | D86603 |
| 2875 | tttgatgcatgcacacatatgg | W47946 | 45479 | tgtctcccaaactctcgtttcaga | AA022242 | 88083 | tgtcgatcatcatttgcaggtcg | D86603 |
| 2876 | gatgcatgcacacatatcattgact | W47946 | 45480 | gtctcccaaactctcgtttcagag | AA022242 | 88084 | cagctcattgaatccagtgaagaa | D86603 |
| 2877 | gcatgccacatatcattgactga | W47946 | 45481 | tctcccaaactctcgtttcagagat | AA022242 | 88085 | caagctggagctcatcgcacgcagt | D86603 |
| 2878 | cacatatcattgactgatcctgt | W47946 | 45482 | tcccaaactctcgtttcagagatg | AA022242 | 88086 | aagagcccttcctactgcggagcagt | D86603 |
| 2879 | actagccacatctggacacacacg | W47946 | 45483 | caaactctcgtttcagagatgtga | AA022242 | 88087 | ttgaactctaatgcctgcacctc | D86603 |
| 2880 | cacggtcaccatggtcagcgctgat | W74814 | 45484 | aactcctgttttcagagatgtgaac | AA022242 | 88088 | gcactcagtcctccaaagtccag | D86603 |
| 2881 | gggctcttcatccaccaacaggtg | W74814 | 45485 | ttcctgttcagagatgtgaacct | AA022242 | 88089 | ctcaaagtccagtcatggctgtg | D86603 |
| 2882 | tcttcatccaccaacaggtcgcgctg | W74814 | 45486 | gatgtgaacctttatcccccaaag | AA022242 | 88090 | agtccagtcatggctgttgacctg | D86603 |
| 2883 | tcatccaccaacaggtgcgtgtg | W74814 | 45487 | tgtgaacctttatccccaaagt | AA022242 | 88091 | gcatgtggttgacctgaggctg | D86603 |
| 2884 | tccaacaggtgcgctgttggcc | W74814 | 45488 | atcagagaacccaactcctccatg | AA022242 | 88092 | ccacgtggcctgctgagctgaggc | D86603 |
| 2885 | acagggcgctgttggccacacagc | W74814 | 45489 | catcggcctttgtcatagggaca | AA022242 | 88093 | aatctcaaactcacctaccctgctgc | AA108506 |
| 2886 | caagggaacacactcagtgcagtg | W74814 | 45490 | atcggcctttgtcatagggacag | AA022247 | 88094 | ttccaaactcacctactctgcag | AA108506 |
| 2887 | cggaacacatcgaatgctggg | W74814 | 45491 | tcggcctttgtcatagggacaga | AA022247 | 88095 | gacagaagaccctaggtggtac | AA108506 |
| 2888 | aacacatcgagtgcagctggag | W74814 | 45492 | cctttgtcatagggacagaatct | AA022247 | 88096 | cagaagaccctattggtgtacag | AA108506 |
| 2889 | catgcagtgcagtgcagggaccag | W74814 | 45493 | cccaaactctgcctagaaggacat | AA022247 | 88097 | caagaaccccttaggtggtacagt | AA108506 |
| 2890 | ggccatagtgtacgcactgctgct | W74814 | 45494 | ccaaactccgcctagaaggacatg | AA022247 | 88098 | agaagaaccagcgagactccctca | AA108506 |
| 2891 | cagctgatgtcagcagactcag | W74814 | 45495 | aggacatgcccatgtctcccaa | AA022247 | 88099 | accagcgagactgtactccctca | AA108506 |
| 2892 | cgtacgactgtctgcatgcacgaa | W74814 | 45496 | acatgaccccatgtctcccaaact | AA022247 | 88100 | cagcgagactctgtactccctcaga | AA108506 |
| 2893 | tcagccgcacactctctccc | L75822 | 45497 | atctggaacgtcactgctgccaagg | L75822 | 88101 | gcgagactctgtactccctcagatt | AA108506 |
| 2894 | cgtcaacaatcattacctgggc | L75822 | 45498 | gtgtcttgctgtgaggtcatcg | L75822 | 88102 | gagactctgtactccctcagattt | AA108506 |
| 2895 | aatcattacctcggggcctggtg | L75822 | 45499 | ccatgcctctgagtaggtcatcg | L75822 | 88103 | gactctgtactccctcagattgct | AA108506 |
| 2896 | cattaccttcggcctgctggact | L75822 | 45500 | gcctctgagctaaggtgtctcag | L75822 | 88104 | gtactcccctcagattgtgagg | AA108506 |
| 2897 | tacctctgggcctggtgtgactgag | L75822 | 45501 | gtagctaaggtgctctcagacagcc | L75822 | 88105 | acctactgctcgcaggactcactca | AA108506 |
| 2898 | tgggccttgctgactgtgggactca | L75822 | 45502 | cttcagacgccgacagctataac | L75822 | 88106 | ctccctcagatttgctgagggtc | AA108506 |
| 2899 | tgaggactccaaggctggtggtcttt | L75822 | 45503 | gacacgccgacagctataaccgct | L75822 | 88107 | ctacctctgcgaagactcactcagt | AA108506 |

| SEQ ID NO | sequence | DBAxnID | SEQ ID NO | sequence | DBAxnID | SEQ ID NO | sequence | DBAxnID |
|---|---|---|---|---|---|---|---|---|
| 2900 | atgaatactggccccaggggctg | X56824 | 45504 | tctgcctgacacacttcttaac | L75822 | 88108 | acctgctgcaggactcactcagtgg | AA108506 |
| 2901 | gtgaactgtccaatgtggcctc | X56824 | 45505 | ccactaacacttattacagccagc | L75822 | 88109 | gctgcaggactcactcagtggtgac | AA108506 |
| 2902 | gtctgagccagtgccatggttg | X56824 | 45506 | acactttatcagcagctggttt | L75822 | 88110 | caggactcactcagtggtgacagca | AA108506 |
| 2903 | gtaagccatcatgttgactgaccac | X56824 | 45507 | tattacagccagctggtttacaca | L75822 | 88111 | ggactcactcagtgtgacagcaag | AA108506 |
| 2904 | atccatgttgactgaccacgactgc | X56824 | 45508 | gataacacttacaagactatctacaa | L75822 | 88112 | tcactcagtggtgacagcaagccc | AA108506 |
| 2905 | tgaccacgactgtgtccccagtg | X56824 | 45509 | ttgagctgtgaggtcatcggaatcc | L75822 | 88113 | gtgacagcaagaccctatggtgt | AA108506 |
| 2906 | cccagtgccatggccactttgatat | X56824 | 45510 | cctgtccatcggaacaaggtaa | L75822 | 88114 | gactcggtcgcgttcaaggcacccttcg | AA108508 |
| 2907 | gccatggccacttgatatccgttt | X56824 | 45511 | gatcactctggagttcagcggacag | L75822 | 88115 | tgcgttcaaggacctttcgcgaggat | AA108508 |
| 2908 | ttgatccgttccagacattct | X56824 | 45512 | cggacgaactgtgctggtgacc | L75822 | 88116 | tcagaggctgttgactcggtggtg | AA108508 |
| 2909 | tttcccagttctaccagagtaatg | X56824 | 45513 | ttgcctgtgaccgggaaaatctgg | L75822 | 88117 | gaaagctgtaactgctgcaggctt | AA108508 |
| 2910 | cagttctaactctgtgtgaata | X56824 | 45514 | gagtgccacgcatccaaactcccaag | L75822 | 88118 | aagctgtaactgctgcaggcttc | AA108508 |
| 2911 | tggtctcaactctgctgaaatc | X56824 | 45515 | tccaactcccaagggcagccttccg | L75822 | 88119 | aagctgaactgcagctgcaggcttcc | AA108508 |
| 2912 | ggcctctctctgtaagggagaat | X56824 | 45516 | cagttataacctcgaatccatgca | L75822 | 88120 | tgtaactgcgccaggcttccagct | AA108508 |
| 2913 | gagaatctgcctgctctctc | X56824 | 45517 | tacaaatctgcataagtacataa | L75822 | 88121 | gtaactgcctgcaggcttccagctg | AA108508 |
| 2914 | ctgcctggctctcttcctggc | X56824 | 45518 | catatacctttcagaatacaaatg | L75822 | 88122 | taactgctgcaggcttccagctga | AA108508 |
| 2915 | tggctctctctctggggcctaa | X56824 | 45519 | tcaagcaaatcttccacagtgttc | L75822 | 88123 | aactgctgcaggcttccagctgac | AA108508 |
| 2916 | cacatcagcagctggctgaactt | X56824 | 45520 | agcaaatcttccacagttgtcaag | L75822 | 88124 | ggtacctcttattcagaagatccg | AA108508 |
| 2917 | ttgaaacagcagcccaaatcctg | X56824 | 45521 | aaatcttccacagttgttcaagaat | L75822 | 88125 | gtacctccttattcagaagatccgg | AA108508 |
| 2918 | aatctgcagcagagcccaaaact | X56824 | 45522 | gaatcttcaaaggcacacctcggt | L75822 | 88126 | gcgttcaaggacctttcgcggaggatc | AA108508 |
| 2919 | gcagcagagcccaaaactggcctg | X56824 | 45523 | tctctaaaggcacacctcgtctt | L75822 | 88127 | ttcaaggacctcgcggaatcttc | AA108508 |
| 2920 | aaatgttcatcaagaacctggac | X56824 | 45524 | ttagcttccagtccaaaaccattca | L75822 | 88128 | gacctcgcggagatctccagaag | AA108508 |
| 2921 | tgtcttcatcaagaacctggaca | W48104 | 45525 | tccagtccaaaccattcagccgtg | AA022064 | 88129 | cttcgcgaggatcttcagaactgat | AA108508 |
| 2922 | tttctcgcctttgaaacatctg | W48104 | 45526 | aaaccattcagccgtgcaaatgcag | AA022064 | 88130 | ctgataacttcgttttggtcagag | AA108508 |
| 2923 | ctctgcctttgaaacatctgtcc | W48104 | 45527 | ccattcagccgtgcaaaatgcagctg | AA022064 | 88131 | tgataacttcgtttttggtcagat | AA108508 |
| 2924 | tggaaacatctgtcctgtaagtg | W48104 | 45528 | agccgtgcaaatgcagctgaaacca | AA022064 | 88132 | ttcgtttttggttcagtaggctg | AA108508 |
| 2925 | caatctgcctgtaagtggctgt | W48104 | 45529 | atacctttcactcgttacaatga | AA022064 | 88133 | ttcagcttttgactcgggt | AA108508 |
| 2926 | ctgtcctgcaaggtggctctgat | W48104 | 45530 | aatacaaatgccaattgaacatga | AA022064 | 88134 | ggactccgtcgcgatgaagtaccct | AA108509 |
| 2927 | gtcctgtaaggtggctgtgatgag | W48104 | 45531 | aatgttgttcactctgaatctg | AA022064 | 88135 | tccgtcgcgatgaagtaccctcct | AA108509 |
| 2928 | cggctcaaggcctatgctttgt | W48104 | 45532 | gctttgttcactctgaatctg | AA022064 | 88136 | agatgccgaacacactggttgtac | AA108509 |
| 2929 | ctcgaaggctatgctttgtcac | W48104 | 45533 | gtcactctgaatctgatgttgca | AA022064 | 88137 | gtcggacacactggttgatgcctac | AA108509 |
| 2930 | ctatgcttttgtcacttcgagacc | W48104 | 45534 | cactctgaatctgatgatgtgca | AA022064 | 88138 | cggacacactggttgatgcctacaa | AA108509 |
| 2931 | atgtttgtcacttcgagaaac | W48104 | 45535 | ggaaacattcaagcaaatcttcca | AA022064 | 88139 | cacacactggtgatgctactaaatgca | AA108509 |
| 2932 | cttcatcaagaacctggacaaatcc | W48104 | 45536 | cattcaagcaaatcttccacagttg | AA022064 | 88140 | ggttgatgcctacaatgcagccct | AA108509 |
| 2933 | tgcttgttcactcgagaccca | W48104 | 45537 | tatacctactctcgttacaatggct | AA022064 | 88141 | ttgatgcctacaatgcagcctcta | AA108509 |
| 2934 | caagaacctgacaaatccatagaac | W48104 | 45538 | tacttccgttacaatggtcactaa | AA022064 | 88142 | tgcctacaatgcagcctctcagtcc | AA108509 |
| 2935 | gaaacctggacaaatccatagacaac | W48104 | 45539 | ccaggacagctgctgtcttgtccc | AA022064 | 88143 | caatgccctcagtccagtcagctt | AA108509 |
| 2936 | caaatctagacaacaggcactg | W48104 | 45540 | tgcctgtagccaacttcctccagt | AA022064 | 88144 | atgcagcctcagtccagtccagtgg | AA108509 |
| 2937 | agacaacaggcactgtatgacact | W48104 | 45541 | gtagccaacttcctccagttatggc | AA022064 | 88145 | agccacagtggttgaaacacga | AA108509 |
| 2938 | gtatgacacttctctgcttgga | W48104 | 45542 | cccactctggatatctgaccttg | AA022064 | 88146 | cgtctgatgagtaccctcctat | AA108509 |
| 2939 | tgacacttctctgcttgggaaac | W48104 | 45543 | tctgtatctgacctgaccca | AA022064 | 88147 | tgcgatgagtacctccttatcagc | AA108509 |
| 2940 | cacttctgccttgaaacatc | W48104 | 45544 | tatctgacctgacctcagctt | AA022064 | 88148 | cgatagctacccctcttatcagcaa | AA108509 |
| 2941 | gacatcaccgctcctgtttg | W48104 | 45545 | acctcgactcagctttagagga | AA022064 | 88149 | agtactcacacagaatcatgaacac | AA108509 |
| 2942 | cagcaccacatggggcatcagagac | X14045 | 45546 | gactcagccttagaggacatggc | U37091 | 88150 | tagcttcccaagatgtcggacac | AA108509 |
| 2943 | gctgacaatggcctcacagaaatca | X14045 | 45547 | atgaggaactggctgtgtggcgcac | U37091 | 88151 | ttccaagatgtcggacacactg | AA108509 |
| 2944 | gaaatcaagactctgcctttc | X14045 | 45548 | tgtgcacacttaccgcctt | U37091 | 88152 | ctccaagatcggacacactggt | AA108509 |
| 2945 | gtcctttcctgaaagccatgc | X14045 | 45549 | cgttacaatggcctcactcagtgat | U37091 | 88153 | caagatctggacacactggttgat | AA108509 |
| 2946 | ttcctgaaaagccatgccaaccag | X14045 | 45550 | aatggctcactcagtgatccaaaat | U37091 | 88154 | cagaagctcactgacaataatgtca | AA108509 |
| 2947 | cgaaaaggccatgccaaccagaccatg | X14045 | 45551 | accacaacccaactgatgatgactg | U37091 | 88155 | ctcactgacaataatgtcagcttc | AA108509 |
| 2948 | gccatgccaaccagaccatgcaggc | X14045 | 45552 | tctctctgcttgacctgacca | U37091 | 88156 | ggtgcccgaaaagcgcattcaca | D86604 |
| 2949 | caaccagaccatggcaggcaacaca | X14045 | 45553 | gtgacgtcatctgactgtaca | U37091 | 88157 | accccgaccatgaaataagtacctggaca | D86604 |

| SEQ ID NO | DBAxnID | SEQ ID NO | sequence | DBAxnID | SEQ ID NO | sequence | DBAxnID |
|---|---|---|---|---|---|---|---|
| 2950 | X14045 | 45554 | cccatcaagatccacaaaaccagt | U37091 | 88158 | ttctggtactcggtctagcaaacat | D86604 |
| 2951 | X14045 | 45555 | gaattctcaaaaatctgtactatg | U37091 | 88159 | aatagcctgctgatatgagagtat | D86604 |
| 2952 | X14045 | 45556 | ctgcagccgctggaaaacgccag | U37091 | 88160 | cttttcaaacacttcatatgtctga | D86604 |
| 2953 | X14045 | 45557 | tcccagtactagacggctgtgtca | U44795 | 88161 | cagattgccatcagaggctggagt | D86604 |
| 2954 | X14045 | 45558 | agaacatggactccaagctccagg | U44795 | 88162 | ttcatgcctttggcaaaaagtcta | D86604 |
| 2955 | X14045 | 45559 | ccgtagctgcctcctgtctgcatg | U44795 | 88163 | taagtatccaagtactgaggtag | D86604 |
| 2956 | X14045 | 45560 | gctgcctcctgtccatgcattcc | U44795 | 88164 | ttccaacttgaggagccgaagatc | D86604 |
| 2957 | X14045 | 45561 | tcctgctgcatgcattcgatgtctc | U44795 | 88165 | gaagatcagccctgctgctgaccttta | D86604 |
| 2958 | X14045 | 45562 | gcattccgtgcagtactacacag | U44795 | 88166 | aatgtcagtcttccggagccacc | D86604 |
| 2959 | X14045 | 45563 | ggtctgcagtactaccagtaggta | U44795 | 88167 | agcctgctgcacctagaagaa | D86604 |
| 2960 | X14045 | 45564 | cagtactacacagtaggtatgacaca | U44795 | 88168 | tgagacaactgtcacctggctcccc | D86604 |
| 2961 | X14045 | 45565 | atgcacactggcacgtaggacagt | U44795 | 88169 | ccattctcaaaadcgcagtctct | D86604 |
| 2962 | W89599 | 45566 | atgagcacgtaggacacgtgaatg | U44795 | 88170 | ttcaaactgccagttctctagcgtc | D86604 |
| 2963 | W89599 | 45567 | caicattggcactgtgctcactg | U44795 | 88171 | tagcgtcaccacagcattgggtctc | D86604 |
| 2964 | W89599 | 45568 | cctgtgagcaccctgctctggttc | U44795 | 88172 | caccacagcattgggtttctctcc | D86604 |
| 2965 | W89599 | 45569 | cgactccacactgctagtcctg | U44795 | 88173 | ggggttcttctccacagcatacagc | D86604 |
| 2966 | W89599 | 45570 | ctgtagctcctggatagcccaac | U44795 | 88174 | ctgtttgcctgcccgaaaagcaga | D86604 |
| 2967 | W89599 | 45571 | ggaagctacggcctgtgaagctgt | U44795 | 88175 | cttcaaattgccagaaatatgg | D86604 |
| 2968 | W89599 | 45572 | tacggcctgtgaagtgttctaggg | U44795 | 88176 | aaattgccagaaatatgggaggagc | D88792 |
| 2969 | W89599 | 45573 | tctatggactttctgctattctg | U44795 | 88177 | gaaacagccgcacttggcactggg | D88792 |
| 2970 | W89599 | 45574 | gactttcctgctatatctgtaag | U44795 | 88178 | gccagcactggcactggggcacac | D88792 |
| 2971 | W89599 | 45575 | cctgctatttctgtaaggggaaga | U44795 | 88179 | cactgggcatcacgcagctgccgt | D88792 |
| 2972 | W89599 | 45576 | gagactccacaagaaactcaagagg | AA022254 | 88180 | actcacagcgctcaagcacacg | D88792 |
| 2973 | W89599 | 45577 | tcaggtccgtcggctggggtgac | AA022254 | 88181 | gcacacgaattcactcactgatcctg | D88792 |
| 2974 | W89599 | 45578 | tggcacagatcttggaagatc | AA022254 | 88182 | gaattcactacatcgattctggaacct | D88792 |
| 2975 | W89599 | 45579 | attttgaaggatgaccgggcctg | AA022254 | 88183 | actatctgattctggaacttcagg | D88792 |
| 2976 | U04055 | 45580 | cgggcctgctctcccatgacattt | AA022254 | 88184 | gatctggaacctttcagaggtctccc | D88792 |
| 2977 | U04055 | 45581 | cctcaagcaccaacacattctgg | AA022254 | 88185 | ggaacctttcagaggtctccctag | D88792 |
| 2978 | U04055 | 45582 | caagcaccaacacattttcggtga | AA022254 | 88186 | ttcagaggtctccctataggtagtc | D88792 |
| 2979 | U04055 | 45583 | acacattttggtgataccagg | AA022254 | 88187 | gtcggagtctacaaatctgactga | D88792 |
| 2980 | U04055 | 45584 | tattttactgcatatcaccagtctg | AA022254 | 88188 | ccctgtcatgctcagttaatggtg | D88792 |
| 2981 | U04055 | 45585 | tttactgcatatcaccagtctgaa | AA022254 | 88189 | ttcatgctcagttaatggtgtgaacc | D88792 |
| 2982 | U04055 | 45586 | actgcatatcaccagtctgaaag | AA022254 | 88190 | gtgaacccagtaagcacagacagaga | D88792 |
| 2983 | U04055 | 45587 | gcatatcaccagtctggaaaaggat | AA022254 | 88191 | acagagaatccattaccaaactg | D88792 |
| 2984 | U04055 | 45588 | tatcaccagtctggaaaaggatcag | AA022254 | 88192 | cattaccaaactgcagatggcgttt | D88792 |
| 2985 | U04055 | 45589 | cgacagatctggaagatcatc | AA022254 | 88193 | caaactgcagatggcgtttatgcgg | D88792 |
| 2986 | U04055 | 45590 | gagatctggaagatcatcccaaca | AA022254 | 88194 | gctcactactgtgaaacgccagca | D88792 |
| 2987 | U04055 | 45591 | catccgcaagaaatacagcaaata | AA022254 | 88195 | acactctacctgctgtaaatgata | D88792 |
| 2988 | U04055 | 45592 | ccgaagaaatacagccaaaatca | AA022254 | 88196 | aatgataccatcaactcctga | D88792 |
| 2989 | U04055 | 45593 | caagaataccagccaaaatcattt | AA022254 | 88197 | cttcagactaatcacagcagcg | L29006 |
| 2990 | U04055 | 45594 | gaaataccagccaaaatcattttg | AA022254 | 88198 | tcacagccgtctgtcctca | L29006 |
| 2991 | U04055 | 45595 | ataccagccaaaatcattttgaggtg | AA022254 | 88199 | gtctgctccatcacagaaccca | L29006 |
| 2992 | U04055 | 45596 | ccagccaaaatcattttgaggatg | U50595 | 88200 | tccttcatcagaaccccagtctt | L29006 |
| 2993 | U04055 | 45597 | tgcagaaatctgctgctgaagaa | U50595 | 88201 | ctcatctcctttgatctggatga | L29006 |
| 2994 | U04055 | 45598 | gctgcagtcctgttccagtctt | U50595 | 88202 | ttcctttgatctggatgaaaacga | L29006 |
| 2995 | U04055 | 45599 | tctgagccatgccatgccgg | U50595 | 88203 | agtccacgtcacagggcgttgag | L29006 |
| 2996 | U04055 | 45600 | gccatgcatgcagggccgaagcct | U50595 | 88204 | gtctcacagggcgttgagccagt | L29006 |
| 2997 | U04055 | 45601 | gaagcctgatacaacagagatgac | U50595 | 88205 | gctgagccagttgaaggatttta | L29006 |
| 2998 | U04055 | 45602 | acagagatctgctgtaagcat | U50595 | 88206 | ccctactccattagtgactat | L29006 |
| 2999 | U04055 | 45603 | acaggacatcatctgcaaagcat | U50595 | 88207 | ataccatccatcctgcaaagtct | L29006 |

TABLE 1-continued

| SEQ ID NO | DBAxnID | sequence | SEQ ID NO | DBAxnID | sequence | SEQ ID NO | DBAxnID |
|---|---|---|---|---|---|---|---|
| 3000 | U04055 | ctctattcaggtcatacacaccac | 45604 | U50595 | tcctgaaagatccaactgataa | 88208 | L29006 |
| 3001 | W48026 | tgcatccgaggaaccacaacc | 45605 | U50595 | ctgataaccccgggcacacagcaa | 88209 | L29006 |
| 3002 | W48026 | tcccactttggggtcaccatgcct | 45606 | U50595 | gggcacacgcaacctcacatcct | 88210 | L29006 |
| 3003 | W48026 | actgacttcagtgctgggcagagc | 45607 | U50595 | acagcaacctactactccacgg | 88211 | L29006 |
| 3004 | W48026 | gacttcagtgctgggcagcggcct | 45608 | U50595 | acatcctcacgggtcaccagagcag | 88212 | L29006 |
| 3005 | W48026 | cggccctggagctggtctcactt | 45609 | U50595 | atgtctgcctggaagctggcct | 88213 | L29006 |
| 3006 | W48026 | ccctcggagctggtctcactttgg | 45610 | U50595 | cacgggtcaccagagcagctactga | 88214 | L29006 |
| 3007 | W48026 | ctggtcttcacttggccctctg | 45611 | U50595 | ctggcctgactcagacatcctcat | 88215 | D88793 |
| 3008 | W48026 | gcccctctttggggtcctcactgtca | 45612 | U50595 | ggatcccagttcgcacagcaggt | 88216 | D88793 |
| 3009 | W48026 | cctctttggggtcctcactgtca | 45613 | U50595 | caggttctgcacagcaggtgatcca | 88217 | D88793 |
| 3010 | W48026 | gtcactccgggtctgctcaacatca | 45614 | U50595 | tcctggtcagtttgaacgtgt | 88218 | D88793 |
| 3011 | W48026 | tcgctcaacatcagccagctgatca | 45615 | U50595 | tcaggtttgaacgctgtggtgagaat | 88219 | D88793 |
| 3012 | W48026 | aacatcagccaccgatacacaccat | 45616 | U50595 | cctttgacttcactatgagactgt | 88220 | D88793 |
| 3013 | W48026 | cactttgggtcaccatgcctgtc | 45617 | U50595 | ctatttgagactgtggtgtctgca | 88221 | D88793 |
| 3014 | W48026 | gtcaccatgcctgctcgggtgctat | 45618 | U50595 | ttttaccactgcagtaccagtagcc | 88222 | D88793 |
| 3015 | W48026 | accatggctgtcgggtctatgt | 45619 | U50595 | ttaccactgcagtaccagtagccag | 88223 | D88793 |
| 3016 | W48026 | attgcctgcggtctatagtgtc | 45620 | U50595 | gcatccagacgagaaaggcgtgt | 88224 | D88793 |
| 3017 | W48026 | tagtgtcacccctagttcaacaagt | 45621 | U50595 | gcctgcagtcccagcgcagactttt | 88225 | D88793 |
| 3018 | W48026 | tgtcacccctagttcaacaaagtagc | 45622 | AA022273 | ctgcagtccccagcgcagactttct | 88226 | D88793 |
| 3019 | W48026 | cacccctagttcaacaagtagcag | 45623 | AA022273 | agtccccagcgcagactttcttc | 88227 | D88793 |
| 3020 | W48026 | gatactgacttactgctggagagc | 45624 | AA022273 | gctcccagcgagactttccttca | 88228 | D88793 |
| 3021 | M23998 | gcccagcaactctgagtctatggt | 45625 | AA022273 | ctcccagcgcagacttttcttcttcag | 88229 | D88793 |
| 3022 | M23998 | ccagcaactctgagtctatggtat | 45626 | AA022273 | agcgcagacttctcttcagccct | 88230 | D88793 |
| 3023 | M23998 | acactaatctcagacagctctgta | 45627 | AA022273 | cgcagacttttcttcagccccgt | 88231 | D88793 |
| 3024 | M23998 | actactctgagactgacgtctgta | 45628 | AA022273 | gcagactttctcttcagccccgtt | 88232 | D88793 |
| 3025 | M23998 | ctaattccagacagtctctgtaggg | 45629 | AA022273 | cagacttttctttcagcccgttc | 88233 | D88793 |
| 3026 | M23998 | aattccagacagtctctgtagggca | 45630 | AA022273 | taccactgcagtaccagtagccagt | 88234 | D88793 |
| 3027 | M23998 | atticcagacagtctctgtagggca | 45631 | AA022273 | accactgcagtaccagtagccagta | 88235 | D88793 |
| 3028 | M23998 | tccagacagctctgtaggcagtt | 45632 | AA022273 | ccactgcagtaccagtagccagtag | 88236 | D38218 |
| 3029 | M23998 | ccagacagctctgtaggcagtt | 45633 | AA022273 | actgcagtaccagtagccagtagcc | 88237 | D38218 |
| 3030 | M23998 | tagggcagtttcctgccatgtataa | 45634 | AA022273 | ctgcagtaccagtagccagtagccc | 88238 | D38218 |
| 3031 | M23998 | agggcagttcctgccatgtataat | 45635 | AA022273 | tgcagtaccagtagccagtagccca | 88239 | D38218 |
| 3032 | M23998 | ggcagtttcctgccatgtataatata | 45636 | AA022273 | gcagtaccagtagccagtagcccag | 88240 | D38218 |
| 3033 | M23998 | cagcaactcgagctctatgtatt | 45637 | AA022273 | agtaccagtagccagtagcccaggg | 88241 | D38218 |
| 3034 | M23998 | gcaactctgagtctatggtatatcct | 45638 | AA022273 | gaactaagttctgctctgtgagaaaa | 88242 | D38218 |
| 3035 | M23998 | caactctgagtctatggtatctctct | 45639 | U52945 | gaagttactcattccacagcccccac | 88243 | D38218 |
| 3036 | M23998 | ccagctctgctgtggtgtacgagac | 45640 | U52945 | gacctactgcacatgtctgtcag | 88244 | D38218 |
| 3037 | M23998 | agctctgctgtggtgtacgagaca | 45641 | U52945 | catgtctgcagtgtggagaccag | 88245 | D38218 |
| 3038 | M23998 | gctctgtgctgtggtgtacgagacca | 45642 | U52945 | gtgctgtcagctggagaccgactc | 88246 | D38218 |
| 3039 | M23998 | aggacctaatctcagacatgctct | 45643 | U52945 | ggagacctcgtagaccctaaagcat | 88247 | D38218 |
| 3040 | M23998 | gacactaatctcagacatgctctgt | 45644 | U52945 | gacccgactcccgtaaagcattct | 88248 | D38218 |
| 3041 | W48179 | acgagcaaggctcgcgctcaagccgc | 45645 | U52945 | catcagtgaacccaacaataagtta | 88249 | D38218 |
| 3042 | W48179 | gagcaaggctcgcgctcaagccgcg | 45646 | U52945 | cagtagaaccacacaataagttatg | 88250 | D38218 |
| 3043 | W48179 | gtccgcatccagaggaacaaggccg | 45647 | U52945 | ttattaatgcacttctaccctg | 88251 | D38218 |
| 3044 | W48179 | ccgcatccagaggaacaaggccgcg | 45648 | U52945 | atgcactttctacccctgtaageg | 88252 | D38218 |
| 3045 | W48179 | gcttcgcgagagaggaagcagca | 45649 | U52945 | ttctctaccctgtaaggctgtg | 88253 | D38218 |
| 3046 | W48179 | cttcgcgagagctgaagcagcag | 45650 | U52945 | acagccccacctgtataaacagattc | 88254 | D38218 |
| 3047 | W48179 | ggaagccgtactcgtcaagctaat | 45651 | U52945 | gcccactgtataaacagattctaa | 88255 | U63337 |
| 3048 | W48179 | gaagcgtactcgtcaagctaatg | 45652 | U52945 | atcctaaatctgtatgcagggaaa | 88256 | U63337 |
| 3049 | W48179 | aagccgtactcgtcaagctaatgg | 45653 | U52945 | attgaagacactatctttacctg | 88257 | U63337 |

| SEQ ID NO | sequence | DBAxnID | SEQ ID NO | sequence | DBAxnID | SEQ ID NO | sequence | DBAxnID |
|---|---|---|---|---|---|---|---|---|
| 3050 | agccgtacttcgtcaagctaatgg | W48179 | 45654 | gtcatagacctgatgatgttcctga | U52945 | 88258 | caccaatgagccaggttcctagcct | U63337 |
| 3051 | gccgtacttcgtcaagctaatgga | W48179 | 45655 | cagttccagctaaggcgcactaatgc | U52945 | 88259 | ttcctttgaagctcagttcttga | U63337 |
| 3052 | ccgtacttcgtcaagctaatggga | W48179 | 45656 | ggcctagtgacctctactgacatg | U52945 | 88260 | ttggaagtcagttctgagtgtc | U63337 |
| 3053 | tcagccgcagcagtctgcatccgt | W48179 | 45657 | cttagtgacctctactgacatgc | U52945 | 88261 | ttcttgagttcagagaggcctcat | U63337 |
| 3054 | cgtacttcgtcaagctaatggat | W48179 | 45658 | cctgcatactagacctcctcttta | U52945 | 88262 | ttgccgtcctccctgagacagg | U63337 |
| 3055 | gagcagctcgtcgtcgcatccagaga | W48179 | 45659 | agtagctctagctcctaaacatcc | L37297 | 88263 | tcctcctgagacgcagtcagatgcag | U63337 |
| 3056 | agcagctcgtcgtcgcatccagagga | W48179 | 45660 | tcataatcttcaaacacattggta | L37297 | 88264 | agcaggatgcggccaggagacat | U63337 |
| 3057 | cagctcgtcgtcgcatccagaggaa | W48179 | 45661 | tcttccaaccacattggtattact | L37297 | 88265 | tgccatgcacttggattttgt | U63337 |
| 3058 | agctcgtccgatccagaggaacaa | W48179 | 45662 | aaccacattggtattacctgcgtg | L37297 | 88266 | ctgtcccagtgtcgttaatat | U63337 |
| 3059 | ctcgtccgcatccagaggaacaagg | W48179 | 45663 | aggacgaaccctgtagacctcctgc | L37297 | 88267 | ctgttcatcggttcacagggcaa | U63337 |
| 3060 | tcgtccgcatccagaggaacaagc | W48179 | 45664 | gaaccttagtgactctgctctctg | L37297 | 88268 | atcaggttcacagggcaaggagaa | U63337 |
| 3061 | cgtccgcatccagaggaacaagcc | W48179 | 45665 | ctctctgcctagtcaatgcgaacacc | L37297 | 88269 | gcaatcttactgtttctggtctg | U63337 |
| 3062 | cattgactccagcattggagagtt | W48179 | 45666 | gcctagtcactgtgaccaccaaatgc | L37297 | 88270 | tactgttttctggtgctgactgct | U63337 |
| 3063 | gatcatcaattctgggcactcgat | M64863 | 45667 | tcactgtgaccaccaaatgccccttt | L37297 | 88271 | tttctcggtcgtgactgctacaccc | U63337 |
| 3064 | ggcctgtcgtcgcagaggtttgac | M64863 | 45668 | caaatgcccccttacctaccagat | L37297 | 88272 | tacaccaggaacttgccctcacta | U63337 |
| 3065 | caaacagctgcccgtctctgtgggt | M64863 | 45669 | tcacctgtgaggcctatagagag | L37297 | 88273 | caggactgccctcactaagcaaa | U63337 |
| 3066 | tctgatcgaccctttcaaagtgaaa | M64863 | 45670 | tctagtccaaaacatccatacct | L37297 | 88274 | tttgccctcactaagcaaatgacc | U63337 |
| 3067 | aatcacagtcgcgaacaatgggaag | M64863 | 45671 | cattgctcctctgctgggcct | L37297 | 88275 | ggctccattggacatcccagtaccc | U60328 |
| 3068 | tagcaactcagaggccgaatctaacg | M64863 | 45672 | tcctgcttaccctctatctgaaac | L37297 | 88276 | attggacatcccagtaccgatcca | U60328 |
| 3069 | gccgaatctaacgctccgatccat | M64863 | 45673 | ctgaaacctaatgattcttccag | L37297 | 88277 | gatacctcgatagaggatgggaat | U60328 |
| 3070 | tctaacgtccggatccatgcctg | M64863 | 45674 | ttgattcttcaagccaagttcaa | L37297 | 88278 | taatttggcgtctgtccaggaa | U60328 |
| 3071 | ccaatcttagagtgcctccaacaa | M64863 | 45675 | agagccaaagtcctgcccacatcag | L37297 | 88279 | tggcgtcgtccaggaaaagttg | U60328 |
| 3072 | ttagagtgcctccaacaatcctcc | M64863 | 45676 | ctgccacactagttcactactcataat | L37297 | 88280 | gctgatgaaccaacttcaccaccaag | U60328 |
| 3073 | tctactgtcagcaatgaagggtga | M64863 | 45677 | acatcagttcactcattaatttcaa | L37297 | 88281 | aggttccacacgacgatctcaccag | U60328 |
| 3074 | caatctgcgggcagtcatcacagat | M64863 | 45678 | acttcaacacagtgaacaacattga | L37297 | 88282 | ccacacgagatctcaagatactc | U60328 |
| 3075 | ggaccagcagatcggttatgcct | M64863 | 45679 | tcaacacactgaacaacattgatgt | L37297 | 88283 | caaagcagcaagcagccccacgtg | U60328 |
| 3076 | tatgccgagcgttctagatcca | M64863 | 45680 | gaattcatgaacattggagttcag | L37297 | 88284 | gtaccaggagatccgtctgatggtc | U60328 |
| 3077 | tgagcgttctagatccaacagga | M64863 | 45681 | aagagactggctgctactcaaagtt | L37297 | 88285 | aaatgcttatgctgtgttatgac | U60328 |
| 3078 | aacaggaagccatctcattacaccc | M64863 | 45682 | agactggctgctactcaaagttgtg | L37297 | 88286 | gcaaggctaaaacctgagatcaag | U60328 |
| 3079 | ctcggagctgtcccgatcgtgtc | M64863 | 45683 | ctggctgctactcaaagtgtgggag | L37297 | 88287 | cctaaacctgagatcaaggatgtc | U60328 |
| 3080 | agctcggagctgcccgatcgtgtga | M64863 | 45684 | gatttagccatggtgtaggtgaaaa | L37297 | 88288 | gcaactcaatccaatctgcact | U60328 |
| 3081 | ggagctcttatctcatcggcctg | M64863 | 45685 | ttagcaacagttcgacagtaga | L37297 | 88289 | gcaactccatcggtcactacctg | U60328 |
| 3082 | ttttcagggccaacatggcaagaag | M48222 | 45686 | gagactcccagtttcgtggaatgt | L37297 | 88290 | ggtcactacctggttgcagctacag | U60328 |
| 3083 | ttcagggccaccatggcaagaagta | W48222 | 45687 | actccatgtgtgaagttat | L37297 | 88291 | gttcagctacagataccggatagggat | U60328 |
| 3084 | agaagtccgatctttctggtcggag | W48222 | 45688 | tttgtcatgccatgtacaacact | L37297 | 88292 | gctctggggcagcagatgatgaag | U60328 |
| 3085 | tctttctggtcggaggaagaaatct | W48222 | 45689 | gtcatactagttcatacaacactatt | L37297 | 88293 | gcagctatgaaggccgttagggcca | U60328 |
| 3086 | gaaatctctagttcggtctcggtc | W48222 | 45690 | acacactgaacaacatgcatggat | L37297 | 88294 | gcgctaggcccattggctgctgaac | U60328 |
| 3087 | aatcctagttcggtctcggtctcca | W48222 | 45691 | gacaagacccatcctgtctgtcagc | L37297 | 88295 | aagcttgctctgctgctgttg | U60328 |
| 3088 | tctagttcggtctcggtctcca | W48222 | 45692 | accatctgtcctgtcttccct | L37297 | 88296 | ctggcctgctcgtttgttaagc | U60328 |
| 3089 | tagttggtctcggtctccacgag | W48222 | 45693 | catctgctcctgtcttccctag | M72394 | 88297 | atggattaccggcctggtgcatg | U60329 |
| 3090 | tggttcctccacgagaggaag | W48222 | 45694 | aaccccagttgtaattctgtgctg | M72394 | 88298 | tacgggcctgggcatagcgag | U60329 |
| 3091 | ttcggtccacgaggaagcctg | W48222 | 45695 | ctgtgaatttcgtgtgtaggatga | M72394 | 88299 | gcctgggcagcgagatgagag | U60329 |
| 3092 | cggtctccacgagagaagcctgaa | W48222 | 45696 | aatttctgcctgggatcaagc | M72394 | 88300 | gcagctatgggggcgttagggcca | U60329 |
| 3093 | gaatggcagctccagttccaaca | W48222 | 45697 | atgatcaagccattgaattccatg | M72394 | 88301 | gcgggctaggcagggtgctgaac | U60329 |
| 3094 | caggcatggtccaagaagtagt | W48222 | 45698 | gttcactctgatcaataagtgcca | AA023187 | 88302 | ctgaggcctctactgctgcgtt | U60329 |
| 3095 | gccacatggccaagaagtagtggat | W48222 | 45699 | ataagtccaaagtcccaaggatct | AA023187 | 88303 | gcttctatgctgagcttatcata | U60329 |
| 3096 | gataggctcgggtgtcctgtgcc | W48222 | 45700 | atttcacagacgtcaatggatcat | AA023187 | 88304 | gagcttttcatatcatcagcagca | U60329 |
| 3097 | gtcctggtcgccgtaatgcgaga | W48222 | 45701 | atgggatcattatcccacacagt | AA023187 | 88305 | tatcatatcagcagcaactaga | U60329 |
| 3098 | tccctggtccgtcctaatgcgaga | W48222 | 45702 | ggatcattatcccacagcagtcg | AA023187 | 88306 | atcatcagcagcaactagaagaaa | U60329 |
| 3099 | tgcctggtccgcctaatgcgaagtccg | W48222 | 45703 | ccacagcagtcggctctatctc | AA023187 | 88307 | gtcgactccaaagaagaagtgca | U60329 |

TABLE 1-continued

| SEQ ID NO | DBAxnID | sequence | SEQ ID NO | DBAxnID | sequence | SEQ ID NO | DBAxnID | sequence |
|---|---|---|---|---|---|---|---|---|
| 3100 | W48222 | gtgccgctaatgcgagaagtcgat | 45704 | W48222 | cagtcggtgtctattctcttaggt | 88308 | AA023187 | gtaatcacatgatccagcacctga | U60329 |
| 3101 | W48222 | cgagaagtccgatcttctgctgcg | 45705 | W48222 | tcggtgctctatctctaggtgag | 88309 | AA023187 | atccagcaactgatcccaagattg | U60329 |
| 3102 | W48073 | atgcctgtatacactgctgacgt | 45706 | W48073 | ttccatatagccctgctgaggga | 88310 | AA023187 | atcccaagattgaggatggaaatg | U60329 |
| 3103 | W48073 | cgcctgatacacgctgacgtcg | 45707 | W48073 | catatatagccctgctgaggaaga | 88311 | AA023187 | gcttccgacaacaatccaagt | U60329 |
| 3104 | W48073 | tgaccgtcgcactgcagtccgtcg | 45708 | W48073 | aagtgtccggtgtagcgtacgt | 88312 | AA023187 | cagacaaccattccaagtactyct | U60329 |
| 3105 | W48073 | accgtcgcactgcagtccggctact | 45709 | W48073 | atatctgcttaatggattgagtg | 88313 | AA023187 | tactttccagaacgaggggatgctg | U60329 |
| 3106 | W48073 | cctgtcgcactgcagtccggctacg | 45710 | W48073 | gccaaagtcccaaggatctccaat | 88314 | AA023187 | gacaccatgtaatggattaccggg | U60329 |
| 3107 | W48073 | gtcgcactgcagtccggctactgc | 45711 | W48073 | gcaactccactggcatttgcc | 88315 | AA023187 | tgtaccggttgacctgcaacgactg | AA108790 |
| 3108 | W48073 | tcgcactgcagtccggctactgct | 45712 | W48073 | aaagtcccaaggatcttcacatgga | 88316 | AA023187 | accggttgacctgcaacgactgcg | AA108790 |
| 3109 | W48073 | aaggcggaacttccaaggcatctctc | 45713 | W48073 | gtccaaggatcttcacatgacca | 88317 | AA023187 | acgacagctgcccacagagcgcat | AA108790 |
| 3110 | W48073 | tccaaggcatctccggagcgaag | 45714 | W48073 | atcttcacatggaccacgctccac | 88318 | AA023187 | acagctgcccacagagcgcatcct | AA108790 |
| 3111 | W48073 | tctccggagcgaagctatgctgacg | 45715 | W48073 | ttcacatgaccacgctccacggg | 88319 | AA023187 | ggcccacagagcatccttcalgt | AA108790 |
| 3112 | W48073 | cgaagtcatgctgactcatctgtg | 45716 | W48073 | accttgagcctatttcacagacgt | 88320 | AA023187 | ccacagaggcatcctcatgtcc | AA108790 |
| 3113 | W48073 | agctatgctgacgtcatctgtgca | 45717 | W48073 | tttgagcctatttcacagagcnaa | 88321 | AA023187 | tgtccagacgactgtcagcagtc | AA108790 |
| 3114 | W48073 | gcctgtatacactgctgaccgtgc | 45718 | W48073 | gagcctatttcacagacgtcaatgg | 88322 | AA023187 | ccacagacgactgtcagcagcgtc | AA108790 |
| 3115 | W48073 | gctatgctgacgtcatctgtgcca | 45719 | W48073 | ccgtcctgcaaacttgcttgc | 88323 | AA023187 | cagagacgctcagcagtcgtccca | AA108790 |
| 3116 | W48073 | tgtatacactgctgcgtgcaca | 45720 | W48073 | tcctctgcaaactgtcgttgcaca | 88324 | AA023187 | acgactgcagcagtgtcccagca | AA108790 |
| 3117 | W48073 | tatacactgctgaccgtcgcactgc | 45721 | W48073 | gcatgtccactaggtacgtgagcac | 88325 | AA023187 | ttacctgcaacaccaattcccacaa | AA108790 |
| 3118 | W48073 | atacactgctgaccgtcgcactga | 45722 | W48073 | tgtccactaggtacgtgagcaccgt | 88326 | AA023187 | ggaactgtcctcgcgcatcacga | AA108790 |
| 3119 | W48073 | acactgctgaccgtcgcactgagt | 45723 | W48073 | aggccacacagcacggaccagatgc | 88327 | AA023187 | tgacctgcaacgactgccgaactat | AA108790 |
| 3120 | W48073 | ctgctgaccgtcgcactgacgtccg | 45724 | W48073 | ccacacagcacggaccagatgccta | 88328 | AA023187 | cctgcaacgactgccgaactatgac | AA108790 |
| 3121 | W48073 | tgctgaccgtcgcactgacgtccgg | 45725 | W48073 | gaccagatgctatccaggtgtgcg | 88329 | AA023187 | cgcaatgcacagcacttatcga | AA108790 |
| 3122 | W48073 | ctgaccgtcgcactgacgtccgt | 45726 | W48073 | cagtcactcatgccgaagtacaa | 88330 | AA023187 | aatgcacagcacttatcgacca | AA108790 |
| 3123 | W48073 | ttaaaggatgccatgctacagg | 45727 | X01237 | ctcactcatgccgaagtactga | 88331 | AA023187 | ccatccacaggtcacgacagctg | AA108790 |
| 3124 | X01237 | gatgccatgctacagaggtctg | 45728 | X01237 | actctcatgccgaagtacatgga | 88332 | AA023187 | tccacacaggtcacgacagctgcc | AA108790 |
| 3125 | X01237 | ctggcccagtgaaattctatccage | 45729 | X01237 | catggcccgaagtacatgagccgt | 88333 | AA023187 | aggtgcacagacagtggccacaga | AA108790 |
| 3126 | X01237 | aatttcatccagccagttgttgac | 45730 | X01237 | tacatgagccctgaaacctgtgg | 88334 | AA023187 | tgcacgacagctgccacagagcg | AA108790 |
| 3127 | X01237 | gttggacctggcacctacaactgaa | 45731 | X01237 | cggtcctccacacagaacgccagga | 88335 | AA023187 | gccttcaaggctcatcgtgctca | AA108790 |
| 3128 | X01237 | cctgcaccaatgaaatctca | 45732 | X01237 | tccaacagaaagccaggcatgattagg | 88336 | AA023187 | gccttcaaggctcatcgtgctcag | AA108814 |
| 3129 | X01237 | cactcacaaatgaaatctcacctac | 45733 | X01237 | atgtaggccaccgcacgcgtgta | 88337 | AA023187 | agcaaccgcacgttggagttctccg | AA108814 |
| 3130 | X01237 | tctatcttggccctcatagggtcc | 45734 | X01237 | gcaccgctgtaacagccggacag | 88338 | AA023187 | gcaaccgcacgttggagttctccga | AA108814 |
| 3131 | X01237 | cctcatagggtccatatctccagg | 45735 | X01237 | ctgtaacagccgcgaccaggaaat | 88339 | AA023187 | ttggagtccgaaatttgctgt | AA108814 |
| 3132 | X01237 | cttcctccattcgcaagcctg | 45736 | X01237 | agctgaagcgccatgctccactag | 88340 | AA023187 | gagttcgcgaaatttgctggg | AA108814 |
| 3133 | X01237 | ttccattcgcaagcctgctgca | 45737 | X01237 | tgaagcgccatgtccactaggta | 88341 | AA023187 | tctccgaaatttgctgtggggaaaa | AA108814 |
| 3134 | X01237 | tccagctacctgaagacaagaagg | 45738 | X01237 | agcgccgcatgtccactaggtacgt | 88342 | X85802 | gttccagcatttgaaggtttatgg | AA108814 |
| 3135 | X01237 | tacgctacctgaagacaagaaggccagt | 45739 | X01237 | gggcttcagccacattcaaaataag | 88343 | X85802 | aagtacgccaaaggcgaagctaaca | AA108814 |
| 3136 | X01237 | tccttgctgtattgactcagg | 45741 | X01237 | tctttgacactttaaagagtctg | 88344 | X85802 | aagtacgccaaaggcgaagctacagt | AA108814 |
| 3137 | X01237 | ctgtctattgactccagggctgaga | 45742 | X01237 | tcatgctcggtcaccaagctgcc | 88345 | X85802 | gtacgccaaaggcgaagctacagt | AA108814 |
| 3138 | X01237 | tatgactctcaggggctgagacacaat | 45743 | X01237 | tctggtcaccaagctgcccagaa | 88346 | X85802 | tacgccaaaggcgaagctacaggtg | AA108814 |
| 3139 | X01237 | ttttactctgtagctaggggtcg | 45744 | X01237 | ctcagaacccattgctctctcct | 88347 | X85802 | ctcaaggtcatcgctgctcagta | AA108814 |
| 3140 | X01237 | tctctagtagtgctggtcccgaa | 45745 | X01237 | ttgaccccagatgtccagatgtt | 88348 | X85802 | aaggctcatcgctgctcagtacagc | AA108814 |
| 3141 | X01237 | tctctgctggcccagcgaattcta | 45746 | X01237 | ccagatgcccagatgttgccagtg | 88349 | X85802 | cgctcagtacagcggggcatca | AA108814 |
| 3142 | W48081 | cataatttccgaaatccccagtgtgc | 45747 | W48081 | tgtccctgtcttcgtctgtc | 88350 | X85802 | ctcagtacagcgggggcatcaggtcc | AA108814 |
| 3143 | W48081 | aatttccgaaatccccagtgtgc | 45748 | W48081 | cttccctcctatggagtgatag | 88351 | X85802 | tcagtacagcgggggcatcaggtccg | AA108814 |
| 3144 | W48081 | ttcttcgccccgaccccatag | 45749 | W48081 | ttctttcactgtttatctacaga | 88352 | X85802 | ttgggcaaagcaacccgcacgtgga | AA108814 |
| 3145 | W48081 | tttctgccccgaccccatatctga | 45750 | W48081 | gattcaacactgcactaagggggaa | 88353 | X85802 | gggcaaagcaacccgcacgtggagt | AA108814 |
| 3146 | W48081 | ccctgacctgccatagtcactctga | 45751 | W48081 | tcaaactgcactaagggggaaatg | 88354 | X85802 | caaagcaacccgcacgttggagtct | AA108814 |
| 3147 | W48081 | tgacctgccatagtcactctgatac | 45752 | W48081 | atctgactcgttgctcaatgaggtttattc | 88355 | X85802 | accaaagccagatgcagactgagtg | AA108814 |
| 3148 | W48081 | cctgcatagtcactctgatacct | 45753 | W48081 | ctcgttgctcaatgaggtttattg | 88356 | X85802 | gatggtcccacttcaagaagcgca | U60330 |
| 3149 | W48081 | gccatagtcactctgatacctgag | | | cactcctgccagcagtagacacagggac | 88357 | X85802 | gaggatctgccgcactgtcacag | U60330 |

TABLE 1-continued

| SEQ ID NO | DBAxnID | sequence | SEQ ID NO | DBAxnID | sequence | DBAxnID |
|---|---|---|---|---|---|---|
| 3150 | W48081 | atagtcactctgatacctgagcc | 45754 | X85802 | cagtacaggcacagccaagccac | 88358 | U60330 | gactatgccgcactgcacgaga |
| 3151 | W48081 | gtcactctgatacctgagcccaa | 45755 | X85802 | aagccaccataggccagccggagt | 88359 | U60330 | tatcgccgcactgcacgagatig |
| 3152 | W48081 | actctgatacctgagcccaagtc | 45756 | X85802 | ccataggccagcctgagtctttt | 88360 | U60330 | gaatacatcagcctccggtcatca |
| 3153 | W48081 | ctccgcgtctctggcttccacaca | 45757 | X85802 | gccagcctgagtctttcatgct | 88361 | U60330 | agcctccgctcatcatccagagc |
| 3154 | W48081 | ctgcgtcttggcttccacacce | 45758 | X85802 | tcttttcatgctgagtccacccaa | 88362 | U60330 | aatcagtatgtcactctccatgaca |
| 3155 | W48081 | ttccgaatccagtgctgctgtgat | 45759 | L43567 | tatgcaaatcctcgaatctacatg | 88363 | U60330 | tatgtcactctccatgacatgatcc |
| 3156 | W48081 | cgaaatccagtgctgctgtgatccc | 45760 | L43567 | gcaaatcctcgaatctacatggta | 88364 | U60330 | actctccatgacatgtcctgaaaa |
| 3157 | W48081 | aatccagtgctgctgtgatccctt | 45761 | L43567 | cacaggacctcaccatggatggag | 88365 | U60330 | aagatcaaacgcccccggagcagca |
| 3158 | W48081 | tgcctgaacgcgggaacatctcatt | 45762 | L43567 | aggacctcaccatgggatggagctg | 88366 | U60330 | acacgtactggggccaggccagg |
| 3159 | W48081 | ggaacatccatctcctggagcct | 45763 | L43567 | acctcaccatgggatggagctgtat | 88367 | U60330 | ggtccacttacaagaagcgcaggt |
| 3160 | W48081 | acatctccatctcctggagcctct | 45764 | L43567 | tccaacgcaggagtcaggacctga | 88368 | U60330 | gtgttttgatgccaatggagttga |
| 3161 | W48081 | tctcatcctcggagcctcttct | 45765 | L43567 | gatacaaattctactagtctgtat | 88369 | U60330 | tttgtgatgccaatggagttga |
| 3162 | W48081 | cattctcctgagcctcttctgc | 45766 | L43567 | cggtctatactgtgcaagatcggcta | 88370 | U60330 | gtaaaaccgagattcggctgctgta |
| 3163 | W48081 | ccaacaagcaactcaagctacggg | 45767 | L43567 | tctatactgtgcaagatcggccta | 88371 | U60330 | gagattcggctgctgatcgagaaat |
| 3164 | W48081 | agcaactcaagctacgggggcctat | 45768 | L43567 | attactgtgcaagatcggcctacta | 88372 | U60330 | ctgttgattccagaatagaagatg |
| 3165 | W48081 | cagtcagctgacactcaggatacg | 45769 | L43567 | gtgcaagatcggcctactactgatta | 88373 | U60330 | gatactttcgaccagatttcta |
| 3166 | W48081 | tcagctgacactcaggatacggcc | 45770 | L43567 | caagatcggcctactactgattacga | 88374 | U60330 | atagctaaaataccccatggggagg |
| 3167 | W48081 | gctgacactcaggatacggccaga | 45771 | L43567 | aatcctcgaatctacatacagtaaat | 88375 | U65313 | acctccacgaggtgggcatgacacag |
| 3168 | W48081 | tcaggatacggccagagcagtag | 45772 | L43567 | tgagatcacagttctcttctacagt | 88376 | U65313 | aggtacgcttcaaggagacagcgtcg |
| 3169 | W48081 | gggatacggccagagcagcctagggt | 45773 | L43567 | gatcacagttctctacagttact | 88377 | U65313 | gacacagcctttttgatcattctt |
| 3170 | W48081 | tacggccagagcagctatggttctt | 45774 | L43567 | agttcctccacagttactgagcac | 88378 | U65313 | acagcctttgatcattcttga |
| 3171 | W48081 | agctatggttctttatgacagca | 45775 | L43567 | tctctcacagttactgagcacaca | 88379 | U65313 | ttgatcatttcttgatgtgaaaag |
| 3172 | W48081 | tatggttctttatggacagacc | 45776 | L43567 | ctctacagttactgagcacacagga | 88380 | U65313 | atcatttcttgatgtgaaaagcat |
| 3173 | W48081 | tctttatggacagaccaaaaact | 45777 | L43567 | agttactgagcacaaggacctcac | 88381 | U65313 | gcatcttgttatcagttaaatt |
| 3174 | W48081 | tcttatgacagaccaaaactact | 45778 | L43567 | tgagcacacagagaccctccaccac | 88382 | U65313 | cattattccccaattcacaacag |
| 3175 | W48081 | gggctactccacagagagcagtcag | 45779 | L43567 | ctcacgcatgtcatattagtcc | 88383 | U65313 | ttcccaatttcacaacaggattca |
| 3176 | W48081 | ctccaacagagcagtcagcctgcctat | 45780 | AA023244 | cacgcatgtagtccattagtctt | 88384 | U65313 | aattcacacaggatltcatattgtaa |
| 3177 | W48081 | ccaacagagagcagtcagcctatggc | 45781 | AA023244 | gctttcactcgaggcagtccagag | 88385 | U65313 | ttcaacacaggattcatatgttaa |
| 3178 | W48081 | acagagagcagtcagccctatggcccaac | 45782 | AA023244 | ttcactcgaggcagtccagagac | 88386 | U65313 | tatctaaactgtctacaacaaaat |
| 3179 | W48081 | gagcagtcagccctatggccaacag | 45783 | AA023244 | tcactcggaggcagtccagagaca | 88387 | U65313 | gcttcacaggagacagcgtcgttgaag |
| 3180 | W48081 | cagtcagccctatggccacagagtt | 45784 | AA023244 | gcagtcagagacaaccactctgtt | 88388 | U65313 | caggagagcgcgtgaagtcccac |
| 3181 | W48081 | tcagccctatggccaacagagtaca | 45785 | AA023244 | tccagagacaaccactctgtctcg | 88389 | U65313 | gaagtccactgtggccagtttg |
| 3182 | W48081 | ggccagtcagtgacactccagagat | 45786 | AA023244 | cagagacaaccactctgtctcgga | 88390 | U65313 | ttggcagtttggcagtgtgaccta |
| 3183 | W48081 | gccatctgctgagcaatgatgt | 45787 | AA023244 | gagacaaccactctgtctcgaccgc | 88391 | U65313 | gtggtacctaactactgtgtttgc |
| 3184 | W48081 | gccagacttaagtctcttctcac | 45788 | AA023244 | accactctgtctcgaccgccctgg | 88392 | U65313 | cctaactcatcgtgtttgcatttctt |
| 3185 | W48081 | atgatcgtttcctgagggaca | 45789 | AA023244 | ctgtctcgaccgccgaactgc | 88393 | U65313 | tcatcgtttgcatlcttgttaag |
| 3186 | W48081 | tggcagtctttttcatgtagt | 45790 | AA023244 | tgtagtccatttagtctgcagttt | 88394 | U65313 | tgtgacacgcctttttgatcatt |
| 3187 | W48081 | ttagtctggcggaggcagctgctgtgat | 45791 | AA023244 | tagtccattagtcctgcagtt | 88395 | AA108891 | cacaacttagccaacggagaagca |
| 3188 | W48081 | agccatgtcgacctgctgcct | 45792 | AA023244 | tagtccatttagtcctgcagttt | 88396 | AA108891 | caacttagccaacgagaagcage |
| 3189 | W48081 | gtctgacctgctgtggccatagggcc | 45793 | AA023244 | gtccatttagtctgcagttca | 88397 | AA108891 | atttgcttcctgtctaatcctgc |
| 3190 | W48081 | ggtgcctagggcctagtggccct | 45794 | AA023244 | ccaatttagtctgcagttcact | 88398 | AA108891 | ttgctcctgtctaatcctgcta |
| 3191 | W48081 | ctgctagcctggagcgctgag | 45795 | AA023244 | ttagtctgcagttcactggga | 88399 | AA108891 | ttcctgtctaatcctgtcaatgag |
| 3192 | W48081 | agccctgtgaggctgaggtcga | 45796 | AA023244 | tcctgcagtttcactggaggca | 88400 | AA108891 | cctgtctaatctgtcaatgagaa |
| 3193 | W48081 | actggaggccttctaactgtcat | 45797 | AA023244 | ctgcagttttcactcgggaggcgt | 88401 | AA108891 | gctaatctgtcaatgagaaca |
| 3194 | W48081 | ctaactgtcatattcaaatagcgac | 45798 | AA023244 | cagtttttcactcggggaggcgtccag | 88402 | AA108891 | gtctaatctgtcaatgagaaca |
| 3195 | W48081 | tctctcctcccacgtgcagtga | 45799 | AA023244 | ctattgtcacataaggttaccaag | 88403 | AA108891 | tcgtcaatgagaacacccgaaggc |
| 3196 | W48081 | attaatgccaacgtctaactg | 45800 | D21850 | tcacataaacgttaccatggaaact | 88404 | AA108891 | gtcaatgagaacaccccgaaggccataga |
| 3197 | W48081 | gatcacacttaagtatgacacgga | 45801 | D21850 | ctggtgccaaagaccaatcatcaga | 88405 | AA108891 | atgagaacaccctgaaggcataga |
| 3198 | W48081 | tgaacatttctaactcaggaccgaga | 45802 | D21850 | ctgcaaagaccaatcagattcagt | 88406 | AA108891 | acacctgaaggcataggaaggcat |
| 3199 | W48081 | aatcaaaattcgctcgcagactt | 45803 | D21850 | aagaccaatcagattcagtaatgc | 88407 | AA108891 | acttagccaacgagaagcagcac |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 3200 | aattctgtctcggcagactccctt | L22144 | 45804 | aatcctgggtcattgctcggctat | D21850 | 88408 | tttagccaacggagaggcagcacca | AA108891 |
| 3201 | gctccgcagactctcccttcagga | L22144 | 45805 | ggtcattgctcggctatcttcat | D21850 | 88409 | caaatgatgccggctgatcacaa | AA108891 |
| 3202 | cagacttctccttcaggatgatcg | L22144 | 45806 | tttgctcggctatcttcatgaacc | D21850 | 88410 | atgacaggaggtgccagcctgcc | AA108891 |
| 3203 | tatgcccaattcctcaattgttaat | U09928 | 45807 | gaaacgtgctgcactgagaatcct | D21850 | 88411 | ctgccctaggactgacagtgctt | AA108891 |
| 3204 | cattcctcaattgttaattgctcc | U09928 | 45808 | tgccaccagcctgagagtcctgtg | D21850 | 88412 | tgaggcacttcattgcttcctg | AA108891 |
| 3205 | caaagccaactgcgatgaggaaggac | U09928 | 45809 | cagcctgagagtcctgtcagaga | D21850 | 88413 | aggacacttcattgcttcctgtc | AA108891 |
| 3206 | gaaggactcggctttggcataaa | U09928 | 45810 | ctgattctgactcacactacc | D21850 | 88414 | tcattgcttcctgtctaatctcg | AA108891 |
| 3207 | aggtctgcagacagcagcagagac | U09928 | 45811 | ccactcaagatcaacttcagacgt | D21850 | 88415 | ccctatactggggagacacagatg | AA108891 |
| 3208 | agctgggctaccgagagactgcc | U09928 | 45812 | caagatccactctcagaagtcaacc | D21850 | 88416 | cctactccatggccagacagtcaa | U65593 |
| 3209 | gctacctgagagactgtcccagaaa | U09928 | 45813 | caaccgcactctgctgcaaagag | D21850 | 88417 | tggatctctcccaactgctcgcca | U65593 |
| 3210 | ccaacaacctcctatgcatataa | U09928 | 45814 | atccaacactcactgaatgcaaaag | D21850 | 88418 | caactgctgccagctaggctgcac | U65593 |
| 3211 | accttcctatgcatatagatgtc | U09928 | 45815 | gatctacactgcccgctgtgac | D21850 | 88419 | gctgcaccgtggccaactagtgct | U65593 |
| 3212 | agatgtctcagtgtcttatcatta | U09928 | 45816 | ccccgtctgtgacgtccttagg | D21850 | 88420 | ccgtgggccaactagctataggcctg | U65593 |
| 3213 | gtctttatcattaaacaccaagcag | U09928 | 45817 | ctgtgacagctccttagggaaag | D21850 | 88421 | gccaactagtatagcctgggtgct | U65593 |
| 3214 | atcattaaacaccaagcaggactgc | U09928 | 45818 | ggatcactgtgtgccaaagacca | D21850 | 88422 | tgtccagtcgagacagctgatgaa | U65593 |
| 3215 | ttgctgggcctggcctggctagct | U09928 | 45819 | aggtgtccactcgacatccagctg | D21850 | 88423 | aacatctgggctccctacaggtgct | U65593 |
| 3216 | tcattaaacaccaagcaggactgct | U09928 | 45820 | gtgtccactctcgacatcagctgct | D21850 | 88424 | tgggctccctcatcagggtcgtgcaa | U65593 |
| 3217 | tgggctggctagccaggccaaatgt | U09928 | 45821 | gaaactgtacagcagaagtcaggc | D21850 | 88425 | tgagtcagctgacgcgcaaacgtgt | U65593 |
| 3218 | taaatgttgttctcgtgccca | U09928 | 45822 | actggtaccagcagaagtcaggcac | D21850 | 88426 | atgcgctctgggaacaaatcgca | U65593 |
| 3219 | cttgtttctgtctgtgcccaaaga | U09928 | 45823 | gattatgacacatccaaactggct | D21850 | 88427 | ccatggccagaacagtcaatctgat | U65593 |
| 3220 | tctccgtctgcccaagaaaaggca | U09928 | 45824 | tttatgacacatccaaactggctc | D21850 | 88428 | gaacaaatcgcattccaagagtag | U65593 |
| 3221 | aaaggcaggctccgtgtgggaagt | U09928 | 45825 | ttatgacacatccaaactggctc | D21850 | 88429 | agtcaatctgatcctctcgtgtg | U65593 |
| 3222 | aggctccgtgtggaagtcacaga | U09928 | 45826 | atgacacatccaaactggctctgg | D21850 | 88430 | ctgtgcgagcaaggagagaacca | AA108925 |
| 3223 | agccccaagccaactggcgatgag | U09928 | 45827 | cttattactgccagtgggagcag | D21850 | 88431 | ctgagctaccacaaaatggcgt | AA108925 |
| 3224 | cgcgtgcacatgggactagag | U09928 | 45828 | ttattactgccagtgcaagtgcag | L43568 | 88432 | gcgagcctcattactgcaagtalga | AA108925 |
| 3225 | tctgcactgggactagaggctttct | U09928 | 45829 | actgccagcagtggaggcagtaacc | L43568 | 88433 | gagtccgatacttcgcaaagccac | AA108925 |
| 3226 | accagacacatcacactggatt | U50413 | 45830 | ctgcacagcagtgagccagtaaccca | L43568 | 88434 | aagccactgtcaagggctaccagtg | AA108925 |
| 3227 | acacaactcacactggattattcc | U50413 | 45831 | agaaggtcaccatgacctgcagtgc | L43568 | 88435 | cactaggcagaggtgggtggatct | AA108925 |
| 3228 | catcacactggattattcctt | U50413 | 45832 | gaaggtcaccatgacctgcagtgc | L43568 | 88436 | taaactataatcaaccaattaatgct | AA108925 |
| 3229 | tatcagagacgccgcgtcgctcacg | U50413 | 45833 | aggccaccatgacctgcagtgcag | L43568 | 88437 | aactataatcaaccaattaatgct | AA108925 |
| 3230 | ggtcgtcacgcaggcagcacttg | U50413 | 45834 | gtgccagctcaagtgaagttacatg | L43568 | 88438 | ttcaacacacaaaaggacgaccat | AA108925 |
| 3231 | tctgctcacgcaggcacacttgaga | U50413 | 45835 | tgccagctcaagtgtaagttacatg | L43568 | 88439 | ttacacttattacccactatccat | AA108925 |
| 3232 | acatgatgcagctgctgtcggagga | U50413 | 45836 | acatgatgccagctacccagaagtc | L43568 | 88440 | tacacttattaccccactatccta | AA108925 |
| 3233 | gagtcgtcacagggactgagag | U50413 | 45837 | catgaactggtaccagcagaagtca | L43568 | 88441 | cactttattaccccactatccataat | AA108925 |
| 3234 | taaactatcaagtcagcaaccaac | U50413 | 45838 | tgaactggtaccagcagaagtcagg | L43568 | 88442 | ttattacccactattccataatcct | AA108925 |
| 3235 | tatcaagtcagcaaccaaccaaccaa | U50413 | 45839 | gtgatgtccaggttacttgtgta | AA041645 | 88443 | attaccactatccattatccataatcctag | AA108925 |
| 3236 | acagcgtccactggactgtggatg | U50413 | 45840 | acgcgtccacatagatcttgtac | AA041645 | 88444 | ttaccactatccattatcctag | AA108925 |
| 3237 | aaaatgcaaaaatctcctctgcag | U50413 | 45841 | aacaggattctcatgtagaggcagg | AA041645 | 88445 | taccctatccatatcctaggt | AA108925 |
| 3238 | ctctccgtgcaggaacaaaggaggcc | U50413 | 45842 | ctccgacgtggtcatataagg | AA041645 | 88446 | cttataatcaaccaattaatgctat | AA108925 |
| 3239 | caaaggccttaaccatggtgct | U50413 | 45843 | cgcacgtggtcgtcaatatagaga | AA041645 | 88447 | ttataatcaaccaattaatgctat | AA108925 |
| 3240 | agaggccttaaccatggtgt | U50413 | 45844 | tcaatataggaacccccaggggt | AA041645 | 88448 | tataatcaaccaattaatgctattc | AA108925 |
| 3241 | gaaggcttaccacgtcacgttggg | U50413 | 45845 | ataaggaaccccccagggctgca | AA041645 | 88449 | ataatcaaccaattaatgctattca | AA108925 |
| 3242 | tggtcagcctgtgtagccctggggt | U50413 | 45846 | cccaggagcaactgagcccccaataa | AA041645 | 88450 | taatcaaccaattaatgctattcca | AA108925 |
| 3243 | tggtgaaccagcagacatcacactg | U50413 | 45847 | aggagcacctgagccccataagca | AA041645 | 88451 | aatcaaccaattaatgctattcaac | AA108925 |
| 3244 | tcgagcctgcactggactcactt | M33960 | 45848 | tgagcccaataagcagcaagtaca | AA041645 | 88452 | atcaaccaattaatgctattcaaca | AA108925 |
| 3245 | gagtcgcactggactcacttcaa | M33960 | 45849 | gcccaataagcagcaagtacaca | AA041645 | 88453 | tcaaccaattaatgctatcaacac | AA108925 |
| 3246 | ctagaggccactctgcatcgtta | M33960 | 45850 | aagtacacatcgtctggctcc | AA041645 | 88454 | tacctagaacagaaccagttcagag | AA108925 |
| 3247 | cactctgcatcgtatgtgtgt | M33960 | 45851 | gcatcacatagctcgtggctacga | AA041645 | 88455 | ctgcttccaagtgttagagaatagc | U68535 |
| 3248 | tctgcatcgtatgtctccacgg | M33960 | 45852 | atcatgtggcgtgtcggttac | AA041645 | 88456 | acctccataattctagatgatatga | U68535 |
| 3249 | gcatcgtatgtctccacgagaa | M33960 | 45853 | tccacatagatctgtacagaaag | AA041645 | 88457 | accccagctcagacaaatgtgtt | U68535 |

TABLE 1-continued

| SEQ ID NO | DBAxnID | sequence | SEQ ID NO | DBAxnID | sequence | SEQ ID NO | DBAxnID |
|---|---|---|---|---|---|---|---|
| 3250 | M33960 | cttttcattatgcactgcagcca | 45854 | AA041645 | agaataaatccacaggctggtccaa | 88458 | U68535 |
| 3251 | M33960 | atgcactgcagccacacaccgtg | 45855 | AA041645 | aatccacaggcgtggtccaaatacca | 88459 | U68535 |
| 3252 | M33960 | cactggcagccacacaccgtgtac | 45856 | AA041645 | caggctggtccaaatacccaacacg | 88460 | U68535 |
| 3253 | M33960 | gccacacaccgtaccatagggc | 45857 | AA041645 | gctggtccaaatacccaacactgaa | 88461 | U68535 |
| 3254 | M33960 | tagggccccaaatgtggggtcacat | 45858 | AA041645 | aataccaacatgtgaacaggattc | 88462 | U68535 |
| 3255 | M33960 | tgtggggtcacalgctctgaattt | 45859 | AA041645 | accaacatgtgaacagattccta | 88463 | U68535 |
| 3256 | M33960 | cactgcactcactcaatgtgtgc | 45860 | AA041645 | catactgaacctacactggggcaaa | 88464 | U68535 |
| 3257 | M33960 | tgactcactcaatgtcatttcc | 45861 | AA041645 | ttgattccgccaacggatcaatat | 88465 | U68535 |
| 3258 | M33960 | actcaatgtcatttccggctgc | 45862 | AA041645 | gtcacctaatggacgagggctctt | 88466 | U68535 |
| 3259 | M33960 | tcaatgtcatttccggctgcgt | 45863 | AA041645 | ctacacagagggtcctccgcatca | 88467 | U68535 |
| 3260 | M33960 | cggctgcgtattggagcagtgaac | 45864 | AA041645 | cagaggtcctccgcattcagaacat | 88468 | U68535 |
| 3261 | M33960 | gacagcagctctcgglcaaccacct | 45865 | AA041645 | tcctccgcattcagaacatctact | 88469 | U68535 |
| 3262 | M33960 | agcagctcctggtcaaccacctig | 45866 | AA041645 | gcatcagaacatctatccgagtaa | 88470 | U68535 |
| 3263 | M33960 | tggtcaaccacttagtagataat | 45867 | AA041645 | agccatcaggtgacaacgglatat | 88471 | U68535 |
| 3264 | W48325 | gatgttcacgacggaatggcata | 45868 | L48514 | tcgtaggcaacttataccagaaagc | 88472 | L48514 |
| 3265 | W48325 | tgtgggtcacgacggaatggcatatc | 45869 | L48514 | gcactttataccagaaagccttgta | 88473 | L48514 |
| 3266 | W48325 | accagacagatggcgtcagctgalg | 45870 | L48514 | tataccagaaagccttgtactgga | 88474 | L48514 |
| 3267 | W48325 | ccagacagatgcgctcagctgatga | 45871 | L48514 | cctigacgtgaactcaaatgt | 88475 | L48514 |
| 3268 | W48325 | agacagatgcgctcagctgatgaag | 45872 | L48514 | tcaatattcacctgataaaaagta | 88476 | L48514 |
| 3269 | W48325 | cagatgcgctcagctgatgaaggac | 45873 | L48514 | atgctcagttgctgacatactggc | 88477 | L48514 |
| 3270 | W48325 | agatgcgctcagctgatgaaggaca | 45874 | L48514 | acgtigctgacatactggcccatga | 88478 | L48514 |
| 3271 | W48325 | acggtcttctaaccgtatcaact | 45875 | L48514 | tactggcccatgaaatcatgttt | 88479 | L48514 |
| 3272 | W48325 | cggtcttctaaccgtatcaactg | 45876 | L48514 | aggttctgcagttgggcacgctggt | 88480 | L48514 |
| 3273 | W48325 | gtcttctataccgtatcaactga | 45877 | L48514 | attatctattgatcctccggg | 88481 | L48514 |
| 3274 | W48325 | tcttctataccgtatcaactgca | 45878 | L48514 | ctattgatcctctctccggacat | 88482 | L48514 |
| 3275 | W48325 | tctataccgtatcaactgcaagtt | 45879 | L48514 | tcggctgtcacctaatggcagag | 88483 | L48514 |
| 3276 | W48325 | gaatggcatatcacaccagacgat | 45880 | L48514 | tccactgctcactggcggcgagaa | 88484 | AA023285 |
| 3277 | W48325 | ctataccgtatcaactgcaagtt | 45881 | L48514 | ctgcagctcattcctcaaccgtt | 88485 | AA023285 |
| 3278 | W48325 | atggcatatcacaccagacagat | 45882 | L48514 | gatcctttcattcatcgatac | 88486 | AA023285 |
| 3279 | W48325 | tggcatatcacaccagacagatgc | 45883 | L48514 | ctctttcatttcatcgatcatacga | 88487 | AA023285 |
| 3280 | W48325 | gcatatcacaccagacagatgcg | 45884 | L48514 | tttcattcatctgcatcgacacag | 88488 | AA023285 |
| 3281 | W48325 | catatcacaccagacagatgcgctc | 45885 | L48514 | cattcatctgcatcgacacagag | 88489 | AA023285 |
| 3282 | W48325 | tatcacaccagacagatgcgctcag | 45886 | L48514 | atcgcatacccagacagaaggcgct | 88490 | AA023285 |
| 3283 | W48325 | atcacaccagacagatgcgctcagc | 45887 | L48514 | tgcatacgacagaaggcgctccca | 88491 | AA023285 |
| 3284 | W48325 | acaccagacagatgcgctcagctga | 45888 | L48514 | ccgacgaaggcgctccaaactig | 88492 | AA023285 |
| 3285 | W48325 | caactccttgatgtctgcccta | 45889 | L48514 | gaaggcgctccaaactigcccag | 88493 | AA023285 |
| 3286 | M69222 | agtgactaggtcggctgttcta | 45890 | L48514 | tccaaactigccccaggcctgaag | 88494 | AA023285 |
| 3287 | M69222 | agagccatcacatggctcgggtg | 45891 | L48514 | ccaggcctigaaggcacggtagg | 88495 | AA023285 |
| 3288 | M69222 | atcagcatggltcggggttggg | 45892 | L48514 | agctagctgcttcactcgtaaagc | 88496 | AA023285 |
| 3289 | M69222 | gaaggtctcttgaggctaggcaa | 45893 | L48514 | cttgaaggcacgglgatgcattg | 88497 | AA023285 |
| 3290 | M69222 | ttctctggaagcgcaagaggtgc | 45894 | L48514 | ctgttcactcgtaaagctattacc | 88498 | AA023285 |
| 3291 | M69222 | ttcaagtlaaggcgcactgtgtg | 45895 | L48514 | cttcactcgtaaagcttaatccc | 88499 | AA023285 |
| 3292 | M69222 | gctcgacttcacctgttaaacatgg | 45896 | L48514 | tctgtaaagcttatcctctgcgc | 88500 | AA023285 |
| 3293 | M69222 | cttcactcgttaaacatggctgcct | 45897 | L48514 | gtaaagcttatccctctgcgtcc | 88501 | AA023285 |
| 3294 | M69222 | ctgttaacatggcctttgaat | 45898 | L48514 | aagcttatccctctgcgtcctgg | 88502 | AA023285 |
| 3295 | M69222 | aacatggctgcttgaataaagga | 45899 | L48514 | tcgctcctggatctcttcattca | 88503 | AA023285 |
| 3296 | M69222 | aaagtctgaaactgcgctcagctggt | 45900 | L48514 | ctcctggatcttcattcatct | 88504 | AA023285 |
| 3297 | M69222 | atgtcaacccaaagaaagaacggaca | 45901 | L76193 | gtcaagttgtggcccaaggattca | 88505 | J03877 |
| 3298 | M69222 | actaglagcttatctcicagcag | 45902 | L76193 | gatccagtctgccaaggaatca | 88506 | J03877 |
| 3299 | M69222 | aggtatctatctcagcagatgc | 45903 | L76193 | gatatttgcaggcgcaccta | 88507 | J03877 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 3300 | cagccagatatgcccaactctt | M69222 | 45904 | atctataatcctgagggcctccag | L76193 | 88508 | tgccaagctactactgaaagtc | J03877 |
| 3301 | gatatgcccaacactcctaatgta | M69222 | 45905 | tgtcagataagccaggtgagca | L76193 | 88509 | aaagctactactgaagtcacag | J03877 |
| 3302 | actcctaatgtacctccagagcca | M69222 | 45906 | acactgtatgcgaacaacggctctg | L76193 | 88510 | cctacctactgaaagtcacagt | J03877 |
| 3303 | taatgtacctccagagccacagca | M69222 | 45907 | tatgcgaacaacggctctgcttc | L76193 | 88511 | tacctactgaaagtcacagatca | J03877 |
| 3304 | acctccagagccatcagcatggttt | M69222 | 45908 | agcacgtgctctgtatcata | L76193 | 88512 | cctactgaaagtcacagatcatg | J03877 |
| 3305 | ccgtatccacttaactgagtgagc | AA162205 | 45909 | actatattccaaagctctgtact | L76193 | 88513 | tggtgttctccaggaaccgtatca | U73378 |
| 3306 | tatccacttaactgagtgagcaaa | AA162205 | 45910 | aaagctgtactgtgacctctaga | L76193 | 88514 | cacagcaaacaattaattctcata | U73378 |
| 3307 | ggatgatctagctctgccaaggctc | AA162205 | 45911 | ctgtactgtgacctctagatcttc | L76193 | 88515 | catttctgtgtgtgaaggatat | U73378 |
| 3308 | tgatctagctctgccaaggctctgc | AA162205 | 45912 | tgtgacctctagatcttctaaaac | L76193 | 88516 | tatgaccccatgtcccagacacatt | U73378 |
| 3309 | tctagctctgccaaggctctgcaga | AA162205 | 45913 | agtctgccaacggaatcacagtct | L76193 | 88517 | cccatgtcccagacacattacatc | U73378 |
| 3310 | agctctgccaaggctctgcagagac | AA162205 | 45914 | gccaaaggaatcacagtcactag | L76193 | 88518 | tcccagacacattacatcataact | U73378 |
| 3311 | tctgccaaggctctgcagagaccca | AA162205 | 45915 | ggaatcacagtctcactagacaga | L76193 | 88519 | caaaggtctctcctgactagca | U73378 |
| 3312 | ccctgtccccaatctgctggccatt | AA162205 | 45916 | aagttgtctatgtagctgatgtaa | L76193 | 88520 | tctcctcctgacctagcatcaaa | U73378 |
| 3313 | tgttgcccaactactcacttgc | AA162205 | 45917 | gatttaacctcagtgaaggtcaltc | L76193 | 88521 | tctgacctagctacacagaaaag | U73378 |
| 3314 | tgcccaatctggccattcacctg | AA162205 | 45918 | gtcattcagctggggacccttagtgg | L76193 | 88522 | aatcttacatgactgtcaagccat | U73378 |
| 3315 | ggccattcacctgcctgaaccaatc | AA162205 | 45919 | gataacctgaccgtgctccagcca | L76193 | 88523 | tacatgactgtcaagccatcttt | U73378 |
| 3316 | ctaacacacgcttcgccagagc | AA162205 | 45920 | gttgctccagccacggagatatt | L76193 | 88524 | gactatctgaacatgtgaaaaatt | U73378 |
| 3317 | tctgtgggtccaaccactcattgc | AA162205 | 45921 | ctggatacaacattcactgactccta | L76193 | 88525 | tgttcagacacagctgaattcccc | U73378 |
| 3318 | tgggtccaaccactcattgctgt | AA162205 | 45922 | acacattcactgactctacagaa | Z22111 | 88526 | tatgacatttcacacacataagt | U73378 |
| 3319 | gtccaaccactcattgctgtaca | AA162205 | 45923 | gtactagctacaacaagttcaa | Z22111 | 88527 | ctgttgaactcatctaattcaat | U73378 |
| 3320 | caaccactcattgctgtacagcc | AA162205 | 45924 | actagctacaacagaagttcaaggc | Z22111 | 88528 | taactcatcaattcaattactg | U73378 |
| 3321 | ccacttcattgctgtacagcctta | AA162205 | 45925 | tagctacaacagaagttcaaggc | Z22111 | 88529 | tttcaatttactgttaccagcagag | U73378 |
| 3322 | ctcattgctgtacagcctact | AA162205 | 45926 | gtagacaaatctccagcacgct | Z22111 | 88530 | gttaccagcagctgcgtgtgtt | U73378 |
| 3323 | ttgctgtacagccttactggc | AA162205 | 45927 | aaatctccagcacagcctacatgc | Z22111 | 88531 | agcagagtcgctgttgttgtct | U73378 |
| 3324 | aattttgtagtgcagagggatgat | AA162205 | 45928 | atctctacacagccactgacatgc | Z22111 | 88532 | gttgttgttctccattcacatga | U73378 |
| 3325 | aaagtggctcgcagaacgtcctgaa | AA162205 | 45929 | ctctcagacacagccacatgcagct | Z22111 | 88533 | tccattcacatgaaattctattaa | U73378 |
| 3326 | agactgtccgaactcatctctcaa | M55561 | 45930 | ctgcgtctactactgtgcagaga | Z22111 | 88534 | gcgtgagccatcccactcctgc | D31943 |
| 3327 | acaagccactacggcttctcttctgt | M55561 | 45931 | tctactactgtgcagagagatta | Z22111 | 88535 | gtagctcgaatgctcctgggccat | D31943 |
| 3328 | ggcctcatcatcacgcctcaagggt | M55561 | 45932 | tactactgcaagagagattact | Z22111 | 88536 | caccaggcttcatagagctgcgtt | D31943 |
| 3329 | atccatcacgatgcgggcggctcc | M55561 | 45933 | actgactctacaacatgaactgggta | Z22111 | 88537 | gatgctatccaaggcgcagatgttag | D31943 |
| 3330 | catcgatgcgggctcgctggagttc | M55561 | 45934 | tgcatcctccaaacatggggtgaag | Z22111 | 88538 | gcttatccaagggcccagaatgtag | D31943 |
| 3331 | cctcttcttgccaatactaatg | M55561 | 45935 | agagctgagggattgaagcgtgt | Z22111 | 88539 | caagggccgagatgtagtctcct | D31943 |
| 3332 | cttaatgtgcctcttccctcagc | M55561 | 45936 | agctgagtggtgaggacgtgta | Z22111 | 88540 | gtagctctgtgtccgttcctg | D31943 |
| 3333 | tgaaggcgcagttctgaagccccg | M55561 | 45937 | tgttaatcctacgcaatggtagtt | Z22111 | 88541 | gctccttgtccgtctcctg | D31943 |
| 3334 | ctgctgccaacaactagccgagag | M55561 | 45938 | ttaatcctagcaatggtggtgctag | Z22111 | 88542 | ttgtctcgtttcctgccctaggaag | D31943 |
| 3335 | ceaacacaatagccgaagacatcc | M55561 | 45939 | aatcctagcaatggtggtactagct | Z22111 | 88543 | cctgctaggaagttgctgccgact | D31943 |
| 3336 | cgtgaccccgcactagggccacaata | M55561 | 45940 | tgggtagcttacaaacagaagtc | Z22111 | 88544 | taggaagttgctgcacgtgagaga | D31943 |
| 3337 | tcctgaactcatcctcaagctgc | M55561 | 45941 | ctaccatatatcatgactgggta | X54352 | 88545 | tacatacaccatacaagacttta | D31943 |
| 3338 | ctctcaaagctgtcctccagagccag | M55561 | 45942 | atatatctacatgacttgaggacagag | X54352 | 88546 | tgaaatgtcctgggccatccacct | D31943 |
| 3339 | aagctgtctccagagccaggaagat | M55561 | 45943 | tgctgacccaggagactaccaccgc | X54352 | 88547 | gtcctgggccatccacctgcgtat | D31943 |
| 3340 | gatgaagagtttctctctcctc | M55561 | 45944 | caccaggctaccacccgtgactg | X54352 | 88548 | tccccaagctttggagtgtgccac | D31943 |
| 3341 | cactcatcatctctggttgtgatt | M55561 | 45945 | gagctaaccacgcagcactttg | X54352 | 88549 | tctcccagcctcttttggaggt | D31943 |
| 3342 | catttctctggtttctgattcgata | M55561 | 45946 | tgtctatgccagccaactgatgaa | X54352 | 88550 | ctcctcacaggcgcagcaaccatggct | D31943 |
| 3343 | aggatccttgggacactactacg | M55561 | 45947 | tggcagccaactgcatgaaaccaag | X54352 | 88551 | acaggccgcaccatgcttcatag | D31943 |
| 3344 | cttgggacactactacgccgt | M55561 | 45948 | catcaagcagtgcacaatcatat | X54352 | 88552 | cagcaccatggcttcatatagctgg | D31943 |
| 3345 | ggaagatacccctccctgggcc | M55561 | 45949 | actgacataccgcagcatcgtaa | X54352 | 88553 | atgcaccagaagaacattaaaag | AA108874 |
| 3346 | gaagtatgcctcacctttggggct | M28666 | 45950 | tacacattgacttcattgatct | X54352 | 88554 | tgcgtcaccagaagaacattaaaga | AA108874 |
| 3347 | ggctcatctcttttagagaaagtc | M28666 | 45951 | tgaatttatcttctgaggtgaata | X54352 | 88555 | agccatctcgacgatgagcgtgagt | AA108874 |
| 3348 | ctcatctcttttagagaaaggccat | M28666 | 45952 | aatgattcactaatctgccttg | X54352 | 88556 | ccatctcgacgatgagcgtgagtac | AA108874 |
| 3349 | gaaagtctcatgccaatcttgaatg | M28666 | 45953 | agcctaattagccgctgggcctg | X54352 | 88557 | | AA108874 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 3350 | agtccatgccaatcttgaatgtaa | M28666 | 45954 | tcactaatcgtcctaattggtgcc | X54352 | 88558 | catctcgacgatgagcgtgagtacc | AA108874 |
| 3351 | gtccatgccaatcttgaatgtaac | M28666 | 45955 | aattagccgctgcctgccagag | X54352 | 88559 | tctcgacgatgagcgtgagtaccgc | AA108874 |
| 3352 | ccatgccaatcttgaatgtaacca | M28666 | 45956 | gcctctgccagagtacaggaaatca | X54352 | 88560 | taccgcttcacattccgaaggcag | AA108874 |
| 3353 | catgccaatcttgaatgtaaccaa | M28666 | 45957 | aggcaccagctccgcaggcgaa | X54352 | 88561 | ccgcttcacattccgaaggcagcagac | AA108874 |
| 3354 | tggttctctgatagagttggggaa | M28666 | 45958 | ttagtcttgccaccagcatgcctg | X54352 | 88562 | cttcacattccgaaggcagacgat | AA108874 |
| 3355 | gttcttctgatagagttggggaaga | M28666 | 45959 | tttgccaccagcatgccgaccaca | X54352 | 88563 | ttcacattccgaaggcagcagacgatg | AA108874 |
| 3356 | ttctctgatagagttgggggaagt | M28666 | 45960 | accagcatgcctgaccacagtatc | X54352 | 88564 | cacattccgaaggcagcagacgatgtc | AA108874 |
| 3357 | gatatgcctgaccacagtgagctcca | M28666 | 45961 | gagcattgcctgaccacaggagctac | X54352 | 88565 | acattccgaaggcagcagacgatgct | AA108874 |
| 3358 | tatgcctcacctgggggcctccata | M28666 | 45962 | ttgtcttcagccaggatgtccc | X54352 | 88566 | ageacttaaatggcatcctgataaa | AA108874 |
| 3359 | atgcctcacctgggggcctccatat | M28666 | 45963 | atgccctccagccttgacatgg | X54352 | 88567 | gcatcctgataaaaatccagaaaat | AA108874 |
| 3360 | tcacctgggcctccatatctgcc | M28666 | 45964 | tccagttacaagcgaaggcacact | X54352 | 88568 | attcaaagaagtcgccgaggcatat | AA108874 |
| 3361 | cctggggcctccatatctgccttt | M28666 | 45965 | tccccaaaggcaccagtgctcagg | AA023402 | 88569 | ttagacggcaggtgcaaggtcaagccatc | AA108874 |
| 3362 | ctccatatctgccttcctcagta | M28666 | 45966 | aaggcaccgatgcctagagtcttga | AA023402 | 88570 | aggtgcaagccatctgacgatgag | AA108874 |
| 3363 | tccatatctgccttcctcagtag | M28666 | 45967 | attttcacaaacatggactgtcca | AA023402 | 88571 | ggtgcaagccatctgacgatgagc | AA108874 |
| 3364 | catatctgccttcctcagtagtt | M28666 | 45968 | tgtctcatctgccctctcagcc | AA023402 | 88572 | tgcaagccatctgacgatgagcgt | AA108874 |
| 3365 | ggtcaggccctgaacactgaccag | M28666 | 45969 | atctggccttcagccgttgt | AA023402 | 88573 | aagccatctcgacgatgagcgtgag | AA108874 |
| 3366 | ggcctgaacactgaccagagtcc | M28666 | 45970 | ttcagccgttagttagactcct | AA023402 | 88574 | ggccatctcgaaggttcctgt | AA108874 |
| 3367 | gaagccaaactgcacagataaagg | W83658 | 45971 | tagttagactcctctgtagagga | AA023402 | 88575 | tcgcaaagggcgccttcccagagg | X84325 |
| 3368 | gccaacatgcacagataaaggtgt | W83658 | 45972 | tagagatcttccatctgctct | AA023402 | 88576 | tgcacctccaaatctggaacagc | X84325 |
| 3369 | gctgcactgatgcctactgtg | W83658 | 45973 | tgctggcctcacagagccagtt | AA023402 | 88577 | tagacctcgtaaggacaaggtgct | X84325 |
| 3370 | gctgactgatgcctactgtgagg | W83658 | 45974 | gcctgacatggccacttgattcc | AA023402 | 88578 | tgaccaccaggggccacgatat | X84325 |
| 3371 | ttgatgcctactgtgaggcactg | W83658 | 45975 | cagagcccagtcttggcattcct | AA023402 | 88579 | cctaccacaggggccaagatatggc | X84325 |
| 3372 | gcctactgtgaggcacatgccacag | W83658 | 45976 | gccaactgattccggttcaggacat | AA023402 | 88580 | gttcagctcggctccatgacaacgt | X84325 |
| 3373 | gcactgtgaggcacatgccacag | W83658 | 45977 | tgattccgttcaggacatcctct | AA023402 | 88581 | cagctcggctccatgacaacggga | X84325 |
| 3374 | gccaagaagacccctcgagaccc | W83658 | 45978 | aggacatcctcctcgagagtct | AA023402 | 88582 | aagcagtcttccagaagacaaaccga | X84325 |
| 3375 | gttctctgcgccatccttaagc | W83658 | 45979 | tcctcttcctgagagtctcatgg | AA023402 | 88583 | cagtcttcaggagcagcagaagt | X84325 |
| 3376 | cttctgccatccttaagtctct | W83658 | 45980 | ttcctgagtcttcatggcgtaca | AA023402 | 88584 | tggctctcagcagtcgcagacataa | X84325 |
| 3377 | cttgaacactgaccagagtctcga | W83658 | 45981 | agagtcttcatgggtacagagcgt | AA023402 | 88585 | tcagcagtcgcagacataacttttg | X84325 |
| 3378 | gaaactgaccagagtctctgaaga | W83658 | 45982 | tgagtgccagttacaacgcgagge | AA023402 | 88586 | gggccttcccagagagctacagtcc | X84325 |
| 3379 | atggccagcaacaccaccgccagca | W83658 | 45983 | agaattgcgttagcctgcataaa | AA023402 | 88587 | agagctacagtcccacagtgttga | X84325 |
| 3380 | gccagcaacaacaccgccagcatag | W83658 | 45984 | attgtcgttagcctgcataaactc | AA023402 | 88588 | gctacagtcccacagtgttgagcg | X84325 |
| 3381 | aacacgccagcatagcacaagcca | W83658 | 45985 | cgatctcagcctgtgggtcccgac | Z30174 | 88589 | gtcccacagtgttgagcgctaaa | X84325 |
| 3382 | gccagcatagcacaagccagcaagcca | W83658 | 45986 | gatagactggcttgtacttgtagt | Z30174 | 88590 | agccgtataatgccactctcgcagat | X84325 |
| 3383 | gcacaagccaggaagtctggtagaac | W83658 | 45987 | ccacaggtagcacagtaaagagt | Z30174 | 88591 | atgccactctgcagatgaaggtaa | X84325 |
| 3384 | atggaagccaactgcgacagataa | W83658 | 45988 | cgtgttccactgcgacattgtga | Z30174 | 88592 | ccactctgcagatgaaggtaaacc | X84325 |
| 3385 | cgcctcatggatctctggtagtt | W83658 | 45989 | gtcttccactgcgacattgtgat | Z30174 | 88593 | ctgttgcacctccaaatctgcgacac | X84325 |
| 3386 | cctcatggatctctggtagttgg | W48382 | 45990 | gtgatattccactctaactaacgc | Z30174 | 88594 | cagaggccactgggcgtgttgctg | U51037 |
| 3387 | ttggccattaatcatccaatgca | W48382 | 45991 | tcaaagcaaacctctaaatcaa | Z30174 | 88595 | cctgccagtcgagtgagagaaccatgtg | U51037 |
| 3388 | gtgaccattaatcatccaatgcatc | W48382 | 45992 | caccaaaccctctaaatcaatgagaac | Z30174 | 88596 | gagcctcagtcgtgactgatttcaaa | U51037 |
| 3389 | gaccattaatcatccaatgcatcag | W48382 | 45993 | aaacctctaaatcaatgagacaac | Z30174 | 88597 | tcctgtgtattcgtttaagagagc | U51037 |
| 3390 | ccattaatcatccaatgcatcagg | W48382 | 45994 | acctctaaatcaatgagacaacc | Z30174 | 88598 | gagccatcagttagctatcagaatc | U51037 |
| 3391 | attaatcatccaatgcatcaggctg | W48382 | 45995 | gttagcctcgataaactcctgcag | Z30174 | 88599 | ccatcagttagctatcagaattcag | U51037 |
| 3392 | taatcatccaatgcatcaggctga | W48382 | 45996 | aatcaatgagacaaccaccaacatt | Z30174 | 88600 | attttgacttagctgtactgt | U51037 |
| 3393 | atcatccaatgcatcaggctgtaat | W48382 | 45997 | cctgcataaactccgagtgactg | Z30174 | 88601 | tttgacttagctgtactgtgtgat | U51037 |
| 3394 | catccaatgcatcaggctgtaatgt | W48382 | 45998 | taaacctccgatgactgaaagtg | Z30174 | 88602 | ggacttagctgtactgtgatatt | U51037 |
| 3395 | tccaatgcatcaggctgtaatgtct | W48382 | 45999 | actctcccgatgactgaaaggtt | Z30174 | 88603 | ttttaggccaacatgacaggttg | U51037 |
| 3396 | caatgcatcaggctgtaatgtctg | W48382 | 46000 | ggtacacagttcttagtgttca | Z30174 | 88604 | gaggatctactgctgtacactaat | U51037 |
| 3397 | tcatgatctcctgtagttgcg | W48382 | 46001 | tgtttcatcagaatcacgcagagtc | Z30174 | 88605 | gatctactgctgtacactaataa | U51037 |
| 3398 | catgatctcctgtagttgcataaagttcag | W48382 | 46002 | atcagaatcacgcagagtcatatgg | Z30174 | 88606 | gccatcatggaacaaccatgtgaaa | U51037 |
| 3399 | agtcatccgggacatcaagttcagcc | W48382 | 46003 | atcacgcagagtcatatgaattaa | Z30174 | 88607 | agtcatggaacaaccatgtgaaaat | U51037 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 3400 | ggaacatcaagttcagcctaggggt | W48382 | 46004 | actctataaagacettgtgtgagc | AA064208 | 88608 | tcctgatttccagctcagctggagcca | U51037 |
| 3401 | tgcagatatacatcacgacgtgaggag | W48382 | 46005 | ctataaagacettgtgtgagccaa | AA064208 | 88609 | tttccagctcatggagccagcgtt | U51037 |
| 3402 | cagatatacatcacgacgtgaggag | W48382 | 46006 | tggtattctgcagcatttctggct | AA064208 | 88610 | ccagctcatgggagccagcgttgaa | U51037 |
| 3403 | gatatacatcacgacgtgaggagat | W48382 | 46007 | ttctgcagcatttctgctgatgtc | AA064208 | 88611 | tcttgctgttgttagctgaatg | U51037 |
| 3404 | tacatcacgacgtgaggagatcagt | W48382 | 46008 | tgcagcatttctggctgatgtccgg | AA064208 | 88612 | ctctgtccaagccagaagagttgat | U51037 |
| 3405 | tgtacgcatggaagcgggagtctt | J02700 | 46009 | agcatttctgctgatgtccggcc | AA064208 | 88613 | tgattcttgcacatgaattgtcaca | U51037 |
| 3406 | gagtcttcactggggcgaggttgc | J02700 | 46010 | gcccaaaggatggctgtaatggt | AA064208 | 88614 | ctttggagcgcttctctgctcatg | D87990 |
| 3407 | cctggctggttgtgacgactca | J02700 | 46011 | taatttaacttctgtatcattgaa | AA064208 | 88615 | gctcaatctgcaccctgatgga | D87990 |
| 3408 | cgactcagcacatcgcagagtgtt | J02700 | 46012 | tttaacttctgtatcattgaact | AA064208 | 88616 | catcatctataacatcctgctctt | D87990 |
| 3409 | agcacatctgcagagtgtcctgtc | J02700 | 46013 | tatatttaggacctatccagcagta | AA064208 | 88617 | ctataacatcctgctcttggcctg | D87990 |
| 3410 | tcctgccgtgccatgcagactc | J02700 | 46014 | gactatccacgcagtaaaatgaaa | AA064208 | 88618 | gaccagtgcctgggtcagagctt | D87990 |
| 3411 | cctgccgtgccatgcagactc | J02700 | 46015 | ctatccacgcagtaaaaatgaaaat | AA064208 | 88619 | tgcctgcagagtttatctc | D87990 |
| 3412 | ccatgcagactctgctaagaat | J02700 | 46016 | agaccttgtgtgagccaagtgatc | AA064208 | 88620 | gagtttatcttcatgacagtcgtg | D87990 |
| 3413 | agactctgctaagaattagatg | J02700 | 46017 | cctgtgtgagccaagtgatcagt | AA064208 | 88621 | catgacagtcgtgtacttccggtcc | D87990 |
| 3414 | gagtaaagacactccacctcacacc | J02700 | 46018 | ccaagtgcagtgtgaggaatc | AA064208 | 88622 | gaagttcacctcaccatcttgctct | D87990 |
| 3415 | ttcacctcacactcgaagtcgt | J02700 | 46019 | attcgggcaatgttaaagtg | AA064208 | 88623 | cctggtcctgtctgatgccaag | D87990 |
| 3416 | tcacacctgaagttctttaaagg | J02700 | 46020 | tagttctcatccagtcacaaacag | AA064208 | 88624 | tatttatcgaacagggcatcttg | D87990 |
| 3417 | ctgacctgcacagagcctggggtca | J02700 | 46021 | ttctacatccagtcacagcaggat | AA064208 | 88625 | ctcgaacagttgcatcttgggaaaa | D87990 |
| 3418 | gtggaactcatcagcgctcagt | J02700 | 46022 | tacatccagtcacacaggatgt | AA064208 | 88626 | gtcctgacccttgatgaactgaca | D87990 |
| 3419 | actgggcctctactccacagaacc | J02700 | 46023 | cagtcaacagaggatgtgttat | AA064208 | 88627 | aacctgatggatgactgacagggtt | D87990 |
| 3420 | gtttcgaacctgcagttgaaa | J02700 | 46024 | gtccttgcctatatagaacagaaa | AA064208 | 88628 | actgcaacggttccagggaaccat | D87990 |
| 3421 | acacattgccatcttcagccaag | J02700 | 46025 | cttgccctatgaacagaaacag | AA064208 | 88629 | ttaccaacagttccaaccacatg | D87990 |
| 3422 | ttgcccatctcagccagaagact | J02700 | 46026 | cttgcaacactttccacagtgaaaat | X83202 | 88630 | aacaggtccacacacatgatgttg | D87990 |
| 3423 | cagtcctcacactttgcattgt | J02700 | 46027 | acacttttgcaacagagaaagtaatt | X83202 | 88631 | ttggtccagttctgtgggct | D87990 |
| 3424 | gatgtccctgccggttgtgtgac | J02700 | 46028 | tgtcacaaaccactttgggctgca | X83202 | 88632 | tggatcctttctgtgggagctc | D87990 |
| 3425 | tttgtaacgctacatgcacggct | W48402 | 46029 | aaaccacttttgggctgcagttgtg | X83202 | 88633 | cccgaccatcatatacatcacctg | D87990 |
| 3426 | gtaacgctacatgcacgctctgtc | W48402 | 46030 | cttgggcctcagttggaactg | X83202 | 88634 | aacataatctcgacgcctctac | U36575 |
| 3427 | gctactgcgtttggcagatcgc | W48402 | 46031 | tgggctgcagttgtgaacttgatt | X83202 | 88635 | cgacgcttctactctgaccgtt | U36575 |
| 3428 | gctactgcgtttgcccagatcgc | W48402 | 46032 | gttgtatcgcagtgctgaactgac | X83202 | 88636 | ctgaccaaagctcattccaactc | U36575 |
| 3429 | ttcgctttgcagatctgtactca | W48402 | 46033 | tcggcttttaccctcaccactgaa | X83202 | 88637 | aaagcctcatcccaactcaccagg | U36575 |
| 3430 | ttggcagatcgctactcattctg | W48402 | 46034 | ttacctcacactgaatgaaacaatg | X83202 | 88638 | tcattccaactccaccaccaggatcg | U36575 |
| 3431 | gcagatctgctactcattctgga | W48402 | 46035 | cctcacactgaatgaaacaatgata | X83202 | 88639 | caccaggatgctgaactggagagc | U36575 |
| 3432 | gatctgctactcattctggacct | W48402 | 46036 | gcctcatacttcagtaagcctacc | X83202 | 88640 | tgcgctgcagagaactggtgagaa | U36575 |
| 3433 | ctactcattctgggacctccctgg | W48402 | 46037 | taccacaaagtatctttccagag | X83202 | 88641 | atagccacagactggttcattt | U36575 |
| 3434 | ctcattctgggacctccctgggag | W48402 | 46038 | ccacaaagtatctttccagagata | X83202 | 88642 | tctcttccaaaggcaaacagcctt | U36575 |
| 3435 | gagcctttgccagttgtctgaag | W48402 | 46039 | aagtatctttccagagataccaaa | X83202 | 88643 | tccaaagccaaacagcctttgccctg | U36575 |
| 3436 | gagcctgtttgccagtgtctgaag | W48402 | 46040 | tatctttccagagatacacaaatt | X83202 | 88644 | tgcccaactctcagccttagtt | U36575 |
| 3437 | gccagttgtctgaagcagtacaga | W48402 | 46041 | cttccagagatacaacaaatttg | X83202 | 88645 | tatctaccagatcagtatgttatt | U36575 |
| 3438 | acagtacatgcagtggtgtcgaa | W48402 | 46042 | gggtacacccttcatcatgagaaaattc | X83202 | 88646 | ctgaaacagctgcatgcgcacagt | U36575 |
| 3439 | tgcacggtgtcgaaggtcctcc | W48402 | 46043 | gaaattctgcaacactgcacagt | X83202 | 88647 | gccgcacagtgcacagtgcacgc | U36575 |
| 3440 | gagcctggcctgcaaggttcctac | W48402 | 46044 | tagtctcacttgctctctcagctga | X83202 | 88648 | gcatggcaacagcaagcaggtcacg | U36575 |
| 3441 | cctgcaaggttcctactccatcc | W48402 | 46045 | cttcactgcttcctcagctgacct | AA023390 | 88649 | ctgctgccgcaaacagcatctta | U36575 |
| 3442 | gcaaggttcctactccatatggctg | W48402 | 46046 | tctcatcctacagagatggagtgc | AA023390 | 88650 | ccgccaaacagatctctgcgtt | U36575 |
| 3443 | aggttcctactccatatggctact | W48402 | 46047 | atctctcacagagagatggggagctcatttt | AA023390 | 88651 | cactctagccgttgtcatggtgac | U36575 |
| 3444 | catatggctgacttcgttggcag | W48402 | 46048 | atctacacagagtggagtcattt | AA023390 | 88652 | agaaaagcaactgcctgctgacca | U36575 |
| 3445 | agctggcctgagagctcatctgt | W48402 | 46049 | tcctacacagagtggagtcattc | AA023390 | 88653 | tgcctgctgaccaagcctcattt | U36575 |
| 3446 | gactggcgctactgctgttaac | W61537 | 46050 | ggagtcatttccttattgatggggt | AA023390 | 88654 | tcacatcaggtatacgctgatcact | U36575 |
| 3447 | aagttgagctgcctggcctccgg | W61537 | 46051 | gagtcatttccttattgatggggtg | AA023390 | 88655 | catcagctataccgatcactagg | AA109180 |
| 3448 | tccagtccagtcctggcctgtata | W61537 | 46052 | agtcatttccttattgatgggggtg | AA023390 | 88656 | tgcgctctgacttctctgatata | AA109180 |
| 3449 | cggcccgtgactgactgactgtataga | W61537 | 46053 | tcattccttattgatgggggtgcaa | AA023390 | 88657 | gctctgacttctctgatatatgg | AA109180 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 3450 | gccgctgactgactgagtatagaca | W61537 | 46054 | catttccttattgatggggtgcaaa | AA023390 | 88658 | acttcctgtatatggagatgt | AA109180 |
| 3451 | agaatcgcgactgaccgccagc | W61537 | 46055 | ttccttattgatgggggtgcaaatg | AA023390 | 88659 | gagatgtcatccaatatcaatat | AA109180 |
| 3452 | gcgactgaccgccagcctgtc | W61537 | 46056 | ttcacttgcttccagctgacccg | AA023390 | 88660 | tcatctccaatatcaatatctgcag | AA109180 |
| 3453 | actgtaccgccagtcctgttcagtg | W61537 | 46057 | ttctcagctgaccctgtgtctcca | AA023390 | 88661 | ccaatatcaatatctgcagagcct | AA109180 |
| 3454 | tgtaccgccagtcctgttcagtgt | W61537 | 46058 | ttcaaagtccagtctcccagtccgt | AA023390 | 88662 | tcaaatatctgcagagcctggagga | AA109180 |
| 3455 | taccgccagtcctgttcagtcga | W61537 | 46059 | agtccgtcggctgtgtatagaagag | AA023390 | 88663 | atatctgcagagccctggaggaaca | AA109180 |
| 3456 | ccgcagtcctgttcagtcgatg | W61537 | 46060 | gtccgtctggctgtgataagaagt | AA023390 | 88664 | tctgcagcccggaggaacacag | AA109180 |
| 3457 | ctgactactgtcgttgtaacca | W61537 | 46061 | tccgtctggctgtgatagaagagtg | AA023390 | 88665 | gagccctggaggaacacaggttaag | AA109180 |
| 3458 | gagctactgtctgttgtaaccaga | W61537 | 46062 | aagagtgacctctcctctcacc | AA023390 | 88666 | cagagctataccgatcactaggaga | AA109180 |
| 3459 | gctactgtctgttgtaaccagacc | W61537 | 46063 | ctctcatcctacgcaggagtgagt | AA023390 | 88667 | tataccgatcactaggagactgtcct | AA109180 |
| 3460 | tgtgtctaaccagacccaaagtg | W61537 | 46064 | gtcgcgagattcatcaccctggaa | AA023390 | 88668 | acgtcctccgtgacgtcgatgccaa | AA109180 |
| 3461 | ctgttctaaccagacccaagtgag | W61537 | 46065 | cgcgagattcatcacctcggaact | AA023390 | 88669 | tccggacgtgatgccaagccct | AA109180 |
| 3462 | gttgctaaccagacccaagtgagct | W61537 | 46066 | ttattcaagcatcgacgataagc | AA023390 | 88670 | atgccaaggcctggtcgcctga | AA109180 |
| 3463 | ctaaccagaccaaagtgagctgc | W61537 | 46067 | attcaagcatctgcagataagctg | AA023390 | 88671 | ccaaggcctggtcgcctgactt | AA109180 |
| 3464 | caaggtgagctgcctgtggctcc | W61537 | 46068 | aagcatctgcagataagctgcagg | AA023390 | 88672 | aggcctggtgcgtctgactttct | AA109180 |
| 3465 | ccaaagctgactgctgctggccag | AA020101 | 46069 | gcatctgcagataagctgcaggcc | AA023390 | 88673 | tggtgcgtctgacttctcttgat | AA109180 |
| 3466 | gctctgccagctgagtgccggaa | AA020101 | 46070 | atctgcagataagctgcaggccac | AA023390 | 88674 | caagccatgactacgactgggaacc | AA109196 |
| 3467 | accagttccagaatgtgattcgga | AA020101 | 46071 | acgataagctgcaggccacggcggg | AA023390 | 88675 | gccatgactacgactgggaacccg | AA109196 |
| 3468 | gttccgaatgtgattcgatgaa | AA020101 | 46072 | taagctgcaggccacggcggccaa | AA023390 | 88676 | ggtcaatcaaacgtgcctacctc | AA109196 |
| 3469 | tgcacctcgccgttattggcagc | AA020101 | 46073 | agctgcaggccacggcgggccaag | AA023390 | 88677 | gctaccttcccgacttgaatctg | AA109196 |
| 3470 | ccctcgccgttattggcagcaacac | AA020101 | 46074 | gccaatgatagcactcgtgttgg | AA023390 | 88678 | cttccgaactggaatctggtagca | AA109196 |
| 3471 | agaatcaggcgcactgcgactttgt | AA020101 | 46075 | caatgatagcactcgtgttggcg | AA023390 | 88679 | ccgacttgaatctggtagcaaca | AA109196 |
| 3472 | gaatcagggcgcactgcgactttgg | AA020101 | 46076 | cgagattcatcaccctcggaacta | AA023390 | 88680 | tctggtagcaacaatcccgtccgtg | AA109196 |
| 3473 | cgacttgtgaagctccgcaacatg | AA020101 | 46077 | agatcatcaccctcggaacttatt | AA023390 | 88681 | ggagttgcaacaatcccgtccgtgaag | AA109196 |
| 3474 | actttgtgaagctccgcaacatgt | AA020101 | 46078 | tcatcaccccggaacttattcaag | AA023390 | 88682 | gaagtgaccgtggcctgaaatatt | AA109196 |
| 3475 | ctttgtgaagctccgcaacactgtc | AA020101 | 46079 | atcaccctcggaacttattcaagca | AA023390 | 88683 | tatttaatgcagcgatggatagc | AA109196 |
| 3476 | ttgtgaagctccgcaacatgctcat | AA020101 | 46080 | caccctcggaacttattcaagcatc | AA023390 | 88684 | ttaatgcagcagatggattagcct | AA109196 |
| 3477 | tgggcccatggtgagatccggaagt | AA020101 | 46081 | cctcggaacttattcaagcatctg | AA023390 | 88685 | tactacactgtcgtcacagggt | AA109196 |
| 3478 | tgtgaagctccgcaacatgctcatg | AA020101 | 46082 | gaacttattcaagcatctgcacgat | AA023390 | 88686 | ataggcctcagtgttgtatactaca | AA109196 |
| 3479 | tgcccatggaatccggaagctgaa | AA020101 | 46083 | acttattcaagcatctgcacgataa | AA023390 | 88687 | gttgtatactacactgtcgtgtcac | AA109196 |
| 3480 | tgggatccacgtgtaccagttcca | AA020101 | 46084 | taccatgagcatctacacagaaag | AA023390 | 88688 | gtatactacactgtcgtgtcacagg | AA109196 |
| 3481 | ggatccacgtgtaccagtttccaga | AA020101 | 46085 | acgtcagcagcatggaggcacggt | X95685 | 88689 | tactacactgtcgtcacagggt | AA109196 |
| 3482 | tccacgtaccagtttccagaatg | AA020101 | 46086 | caatcatcagacagagagctgacaa | X95685 | 88690 | gtgctgcacagggctctcaattcg | AA109196 |
| 3483 | acgtgtaccagtttcagaatgtga | AA020101 | 46087 | caggtcacagacagacattgggataa | X95685 | 88691 | ctgtcacagggctctcaattcggtg | AA109196 |
| 3484 | cggttaccagttccagaatgtgat | AA020101 | 46088 | actatgccaggactacgtccatac | X95685 | 88692 | cagggtccaattcgattgccaatca | AA109196 |
| 3485 | gtaccagtttccagaatgtgattc | AA020101 | 46089 | gccaggactacgtccatacacagaa | X95685 | 88693 | tctcaattcggtgcaatcaaagttg | AA109196 |
| 3486 | ggcctggccattgctgttgaaggc | AA003323 | 46090 | cacagaagtcatcatcccgactt | X95685 | 88694 | ctgcatgagaccctggatcatctca | U66865 |
| 3487 | ctggccattgctgttgaaggccca | AA003323 | 46091 | ctgtgcttcggggatcatccagcatgc | X95685 | 88695 | gagaccctggatcatctcatcaag | U66865 |
| 3488 | gtagttcaggagccaggtgactag | AA003323 | 46092 | ttcgggatccagatcatgcggccc | X95685 | 88696 | ctggttccggctgcacagccgca | U66865 |
| 3489 | gtcttcaggcaggttcaacagagc | AA003323 | 46093 | acatccaggcagtcgccattc | X95685 | 88697 | gtcacgccgcagcaaggagagct | U66865 |
| 3490 | cacatactgatagcccttgtgg | AA003323 | 46094 | agcagtcatttgcaaggaaccc | X95685 | 88698 | gagagctgcaggccacctcaaggt | U66865 |
| 3491 | atacctgatagccccttctgttgc | AA003323 | 46095 | cttaccctgggtcgtttagcagc | X95685 | 88699 | tgcaggccacctcaaggtcagcaa | U66865 |
| 3492 | cctgatagccccctgctgtgggcctg | AA003323 | 46096 | gcacggttccacttcaaatgacact | X95685 | 88700 | gccacctcaaggtcagcaaacagaa | U66865 |
| 3493 | gtggttcccgtcgtggacgccg | AA003323 | 46097 | ttccacttcaaatgacatcagctta | X95685 | 88701 | tgtcaggcccttctacctgctct | U66865 |
| 3494 | gccccttactgctgctcagtctta | AA003323 | 46098 | cagcttagtcagcccacaaaggcagc | X95685 | 88702 | gccctgttgctctgactcact | U66865 |
| 3495 | ttactttctcagctgagctc | AA003323 | 46099 | atgcaggccacaaaggcagcctaac | X95685 | 88703 | taacccgatctctggactgctgga | U66865 |
| 3496 | ctgttctagtcttcagagatgcagg | AA003323 | 46100 | ccacaaaggcagctctaaccatgtt | X95685 | 88704 | cgatccggactgctggaacagc | U66865 |
| 3497 | tttctagtcttcagagatcagggtt | AA003323 | 46101 | aggcagctctaaccatgtttccaac | X95685 | 88705 | gactgcagcgacgatgagccac | U66865 |
| 3498 | gaaggcccccagcaaggctgcgatct | AA003323 | 46102 | ccatgtttccacaatcatcagaca | X95685 | 88706 | ctcatctatttaggcccccaga | U66865 |
| 3499 | ggcccccagcaaggctgagatcttt | AA003323 | 46103 | tctcaacaatcatcagacagaggagct | X95685 | 88707 | cctatttaggcccccagacacacta | U66865 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 3500 | gctgagatctttcgaggaccgaa | AA003323 | 46104 | ccggccattcaacttctccggag | AA023491 | 88708 | ttaggcccagcacactccagagaca | U66865 |
| 3501 | gatggctccgtgtgtggccctag | AA003323 | 46105 | ggatccatccgcatctagagac | AA023491 | 88709 | agccctcagagatatcatcgtgtta | U66865 |
| 3502 | ggtctccgtgtgtgtggcctactag | AA003323 | 46106 | caatgggacctacaagcctgtgtga | AA023491 | 88710 | ctgacagtctataacctgaaccgca | U66865 |
| 3503 | tcctgtgtggcctacgtagttc | AA003323 | 46107 | tggaacctacacagctgtgatgg | AA023491 | 88711 | gtctataacctgaaccgcaccactc | U66865 |
| 3504 | gtggctacgtagtcaggaggccag | AA003323 | 46108 | ccagcctcgaagatatcccaga | AA023491 | 88712 | accactccggagtgaggatcgttc | U66865 |
| 3505 | tacgtagttcagaggccaggtgact | M95564 | 46109 | tctgaagcatatcccagatttcta | AA023491 | 88713 | cacaacacaaaaagttcctagagg | U66865 |
| 3506 | cacactccgttaacaacaga | M95564 | 46110 | gcatatcccagattctcacaaca | AA023491 | 88714 | tttctgcgtgctctccaagtct | L35236 |
| 3507 | ctgtttaacaacagcatgcttgt | M95564 | 46111 | tatccccagatctcacaacactg | AA023491 | 88715 | cgtgctctccaagatctgtatca | L35236 |
| 3508 | atgtctgagatatacactgaagct | M95564 | 46112 | cccagatctcacaacactggaa | AA023491 | 88716 | ctgtaactgccctcaaatgccatg | L35236 |
| 3509 | tctgagatatacactgaagctgaa | M95564 | 46113 | atctcacaacactggaaatcaa | AA023491 | 88717 | ctgcccttcaaatgcctgaggagg | L35236 |
| 3510 | tgagataccacctgaagctgaatc | M95564 | 46114 | ctctcgttctacctgcaggctgc | AA023491 | 88718 | agatccgcatgtcttgtatcaa | L35236 |
| 3511 | accaactgaagctgaattccactc | M95564 | 46115 | ctgttctacctgcaggctgttt | AA023491 | 88719 | tatttcaaacagcactagaggatgct | L35236 |
| 3512 | tgaagctgaatccaccttcatagta | M95564 | 46116 | tccatccgcatctagagacact | AA023491 | 88720 | acttagagatgctcctgtcagtgtc | L35236 |
| 3513 | ctctcctaccgtgtattactgc | M95564 | 46117 | ctaccgtcaggctgcttttagca | AA023491 | 88721 | agatgctcctgtcagtgtcctccag | L35236 |
| 3514 | ctgttacctgtatactacatgat | M95564 | 46118 | tgtgatagttgcccccaggaccaac | AA023491 | 88722 | ggctccaccaagacacacaccgggg | L35236 |
| 3515 | gttacctgtatactacatgat | M95564 | 46119 | gcccaggaccaacggtccaaccat | AA023491 | 88723 | catggccatttcatgatcatt | L35236 |
| 3516 | aggcttactttgttcttagaagat | M95564 | 46120 | tctcaacaatgttcagcgctggatc | AA023491 | 88724 | ccattcatgatcattatcctg | L35236 |
| 3517 | cttacttgttctttagagatagc | M95564 | 46121 | ctggatcccctgagaacaggactgc | AA023491 | 88725 | atctattactctgacataatccat | L35236 |
| 3518 | ttcctcatgagtcatgtgacagt | M95564 | 46122 | gaacaggactgttggtgtctcct | AA023491 | 88726 | aagttctgtatccaagctgagctga | L35236 |
| 3519 | atgttttgttctcatgagtcatg | M95564 | 46123 | ggtgtctccttttagctacaat | AA023491 | 88727 | aacttctagttgcgctgcttggt | L35236 |
| 3520 | ctttgttctcatgagtcatgtga | M95564 | 46124 | gtctccctttttagctacaatg | AA023491 | 88728 | tttcctccagcagtgcttactaca | L35236 |
| 3521 | ttcctcatgagtcatgtgacagt | M95564 | 46125 | aggctccttgtcactccaagtcag | AA023491 | 88729 | tccagagtgcttactacacaagac | L35236 |
| 3522 | aattatgacgccagttggaggagga | M95564 | 46126 | ctgttcactccaagtcaggagagg | AA023491 | 88730 | agtgcttactacacaagacacaaatca | L35236 |
| 3523 | tatggacgcagttggaggtatta | M95564 | 46127 | cattcaaatcagtccttcggggac | AA023491 | 88731 | ttaagtggctgcgaaccagcaccagaacc | L35236 |
| 3524 | tccagcagttgcgaggaaaacc | M95564 | 46128 | tcaaatcagtccttcggggacgt | AA023491 | 88732 | ggctacgcgaaccagcaacctgtaac | L35236 |
| 3525 | tcatatggccagctgctaaaga | M95564 | 46129 | cagtcttctggggacagttactg | AA023491 | 88733 | agcaacctgaactgccctcaaat | L35236 |
| 3526 | ctacatctcaaaactctagtgtc | D26352 | 46130 | cagtttactgctttggctggaaat | AA023506 | 88734 | tgggctcgaagctgctgagtctcg | AA124831 |
| 3527 | ataactcatgccaagccaactgttt | D26352 | 46131 | tttactgctttggcgtggaaatga | AA023506 | 88735 | cgaagctgcttgagtctgacttg | AA124831 |
| 3528 | aaccaactattgactccagctggc | D26352 | 46132 | actgtctttggctggaaatgaagcc | AA023506 | 88736 | tcctaatgcttgccctcatgcctggg | AA124831 |
| 3529 | actattgactccagctggttggta | D26352 | 46133 | tgaagctgcaggatcgcgggccccac | AA023506 | 88737 | tgcttgcctcatgcctggacaaac | AA124831 |
| 3530 | ccagatgacataactatgtctga | D26352 | 46134 | agttgcacgcagcgtcctcggctc | AA023506 | 88738 | cccagtggttgccatccagcatat | AA124831 |
| 3531 | taactatgtctgatctatgcctat | D26352 | 46135 | tcggctcacgttcctggcccctg | AA023506 | 88739 | ggtggttgccatccagcatatcaa | AA124831 |
| 3532 | tgtctgatctatgcctatattcc | D26352 | 46136 | ggctctggggccatctgaggaagca | AA023506 | 88740 | gttgccatccagcatatcaataa | AA124831 |
| 3533 | atctctatgcctatatttccaagaag | D26352 | 46137 | gctaggccggtcgcagttccccagg | AA023506 | 88741 | ataatgccaacctccaatgtaatgt | AA124831 |
| 3534 | tgccctatttccaagaagtctact | D26352 | 46138 | ccggctgcagttccccagggctact | AA023506 | 88742 | ccaacctccaatgtaatgttaat | AA124831 |
| 3535 | gtctactgccagagatgtgaccat | D26352 | 46139 | gctgcagttccaggctactgt | AA023506 | 88743 | acctccaatgtaatgttgaaatgca | AA124831 |
| 3536 | gtcatattctgtgtcctcga | D26352 | 46140 | tcccaggctactgttccaaggcgg | AA023506 | 88744 | gcttaaatatttcttcatacaag | AA124831 |
| 3537 | gtgtgtctgattaaactcaatg | D26352 | 46141 | caggctactgttccaaggggga | AA023506 | 88745 | ttcttcataaagtttgctaatgc | AA124831 |
| 3538 | accatagactgctcacccaagcac | D26352 | 46142 | ggggccagaccattcaaatcagt | AA023506 | 88746 | agctgttgagtctgactttgct | AA124831 |
| 3539 | aaagcaacctctgctgttctatc | D26352 | 46143 | agaccattcaaatcagtcctttcct | AA023506 | 88747 | agtctcgacttgtctcctgcgct | AA124831 |
| 3540 | cctggctgctctatctggcg | D26352 | 46144 | accattcaaatcagtcctttcggg | AA023506 | 88748 | gacttgtctcctgctgtctagg | AA124831 |
| 3541 | atggtcgcctctgaagcaccaa | D26352 | 46145 | aaattctgactgatccagtttga | AA023506 | 88749 | gtctcctgctaggactgt | AA124831 |
| 3542 | tctgcctgaagcaccaaatatca | D26352 | 46146 | tggactgatcagtttgaacctca | AA023506 | 88750 | tcctgctgctaggactgtcct | AA124831 |
| 3543 | gcaccaaatcaacagttaatat | D26352 | 46147 | aactcctgtccttttgtcttcag | AA023506 | 88751 | tgctgctgctaggactgtctcctaat | AA124831 |
| 3544 | tattctgaaagatctcctagaga | D26352 | 46148 | acactttacctgctcctctcctg | AA023506 | 88752 | taggactgcctaatgctgcctc | AA124831 |
| 3545 | actccctagagattagtgtactg | D26352 | 46149 | gcccaggtagccctgtgataatcc | AA023506 | 88753 | gactgctcaatgcctaatgtgcctcag | AA124831 |
| 3546 | gcttctaggtgtcatggaatggga | D26352 | 46150 | gtagcctgtgataatcccaagctt | AA023506 | 88754 | ctgcctatgctggagaaatgtcgt | AA124831 |
| 3547 | atattgctatttcaactataagc | X16133 | 46151 | ctgtatataaacccaagcttagggcg | AA023506 | 88755 | gtgccagtgtataccaggcctca | AA124831 |
| 3548 | aatgaaccgtctcaggataaagat | X16133 | 46152 | gtccttatatatcatccgcttaag | X66196 | 88756 | ttgaagcagatcctccttttaacct | Y07836 |
| 3549 | tgaatcctgttacccttcccat | X16133 | 46153 | aatatcattctcctgtcttaagctcct | X66196 | 88757 | ggaatctgctgcgcttttcct | Y07836 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 3550 | tcctcattaactgtaaggaatat | X16133 | 46154 | atcctcgttaagctcctttgggat | X66196 | 88758 | cacgaaggttcctgatgcagag | Y07836 |
| 3551 | aatgtgttacctatctgttgtc | X16133 | 46155 | gcttaagctccttttgggatgctgg | X66196 | 88759 | ttcctgagtcgagagatcagcc | Y07836 |
| 3552 | tatcttgtgttctggaaaatgcct | X16133 | 46156 | gctccttttgggattgctgtaagac | X66196 | 88760 | ccctgcagaccccacagagaagattc | Y07836 |
| 3553 | gaacaattctacctccaagtgt | X16133 | 46157 | tgatccagtttgaacctcaaaagt | X66196 | 88761 | tgcagaaccccagagaagattcaga | Y07836 |
| 3554 | caatcttcatcctaagtgttca | X16133 | 46158 | agcattgcagcatcagcctgtgca | X66196 | 88762 | ttcctctgcacaaggagacacg | Y07836 |
| 3555 | tcttctacctaagtgttcagga | X16133 | 46159 | gcaagcatcagcctgcagcaca | X66196 | 88763 | gatagcctgacatcagatgacagac | Y07836 |
| 3556 | ttcaggaaccaactcgcattggaa | X16133 | 46160 | ctgtgcacgcacacccgagtctgg | X66196 | 88764 | gactgatgcacatctcgggcgtt | Y07836 |
| 3557 | aggaaccaactcgcattgtgaatt | X16133 | 46161 | cctgccaactgaaggtccttagcag | X66196 | 88765 | agcacatctgggcgttccctac | Y07836 |
| 3558 | tctatttcaactatagccttgta | X16133 | 46162 | aggtccttagcaggacacaactct | X66196 | 88766 | ttataccaggcctcaacaactcag | Y07836 |
| 3559 | attttcaactataagcctttgacag | X16133 | 46163 | ttagcaggacacaactctgcttcc | X66196 | 88767 | tccagcttcatgaaccagacaaga | Y07836 |
| 3560 | tcaactataagcctttgacaggat | X16133 | 46164 | ggacacaactctgcttccttttgt | X66196 | 88768 | agctcatgaaccagacacaagatac | Y07836 |
| 3561 | cttttgacacaggattcctgctgacga | X16133 | 46165 | gccaataacactgaccgagcgctgtt | X66196 | 88769 | atgaaccagacaagatccgactc | Y07836 |
| 3562 | acaggattctcactgacgaaaaca | X16133 | 46166 | caataactgaccgagcgctgtc | X66196 | 88770 | cctttgcacatctgccctgact | Y07836 |
| 3563 | ttctcactgagcaaaaccaagaaca | X16133 | 46167 | tacgtgttcacgatgccgaagcga | X66196 | 88771 | gactcttggcgctgtccaggctt | Y07836 |
| 3564 | ctgagcaaaaccaagaccaaaacaga | X16133 | 46168 | acgtgttcacgatgccgaagcgac | X66196 | 88772 | tgcttgtccaggttgaagcaga | Y07836 |
| 3565 | gaatgtgacgtctgtctcccca | X16133 | 46169 | tgttcacgatgccgaagcgaccga | X66196 | 88773 | ttgctcaggcttgaagcagatcc | Y07836 |
| 3566 | gggccaccacatatgactcgcttca | X16133 | 46170 | gttcacgatgccgaagcgaccgac | X66196 | 88774 | cgcaagtcgaacgaggagcttctacg | AA109508 |
| 3567 | caccacatatgactcgcttcagac | W48463 | 46171 | ttcacgatgccgaagcgaccgacg | X66196 | 88775 | cctctacgcctgaaggtgctgca | AA109508 |
| 3568 | tagattctaacagtcgaactcga | W48463 | 46172 | cacgatgccgaagcgaccgacgag | X66196 | 88776 | agaacgcaagtgctgttgaagaac | AA109508 |
| 3569 | gctcgaacttgtcatcagaattatga | W48463 | 46173 | acgatgccgaagcgaccgacgagg | X66196 | 88777 | tggcctgcggtaatctttccagaa | AA109508 |
| 3570 | gtcctgcttaaacgactgctga | W48463 | 46174 | cgatgccgaagcgaccgacgagga | X66196 | 88778 | tgcggtaatcctttccagaaccgaa | AA109508 |
| 3571 | ctgcttaaacgactgctgaaat | W48463 | 46175 | gatgccgaagcgaccgacgaggag | X66196 | 88779 | tcctttccagaaccgagaaactct | AA109508 |
| 3572 | gctttaaacgactgctgaaatga | W48463 | 46176 | atgccgaagcgaccgacgaggagc | X66196 | 88780 | tccagaaccagagaaactctaatt | AA109508 |
| 3573 | ttaaacgactggctgaaatgtagg | W48463 | 46177 | gccgaagcgaccgacgaggagcc | X66196 | 88781 | aaactctaatttgtgcttgactatg | AA109508 |
| 3574 | tgtactcatagctggatcctaat | W48463 | 46178 | gccgatctcaagcttcatcgggt | X66196 | 88782 | acctctaatttgtgcttgactatg | AA109508 |
| 3575 | actcatagctggatcctaattg | W48463 | 46179 | catctcgatcaagcttcatcgggtcg | AA023458 | 88783 | taatttgtgcttgactatgtcacg | AA109508 |
| 3576 | catagctggatcctaatttgaa | W48463 | 46180 | tctctgatcaagcttcatcgggtcg | AA023458 | 88784 | atttgtgcttgactatgtcacgg | AA109508 |
| 3577 | agctggatcctaatttggaaagt | W48463 | 46181 | atcaagcttatcgggtgccccgat | AA023458 | 88785 | ggagctcttccatcacgg | AA109508 |
| 3578 | cagttcctaagctggccagactag | W48463 | 46182 | caccatatgactgcctcagactta | AA023458 | 88786 | aagagcgaccacatcatgccaga | AA109508 |
| 3579 | ttcctaagctggccagactattg | W48463 | 46183 | caaagttatcgggtgccccgatag | AA023458 | 88787 | gctctcttcatccatcacgggaa | AA109508 |
| 3580 | cagttactctcagcattttgaagg | W48463 | 46184 | gatacgtgtcacgatgccccgaagc | AA023458 | 88788 | gagcaggaccacatcatgcgcagaac | AA109508 |
| 3581 | tagcgaatctctcagtcttttaga | W48463 | 46185 | ctgagaagccaaggcccaggagactcaa | AA023458 | 88789 | aggaccacacatcatggcagaacg | AA109508 |
| 3582 | ctgaatctctcagttcttagatc | W48463 | 46186 | cagagcccaaggcccgaggactcaactc | AA023458 | 88790 | aggaccacatcatggcagaagccaa | AA109508 |
| 3583 | aatctctcagttctttagatcaa | W48463 | 46187 | tacgttgtggcctggccagcaatg | AA023458 | 88791 | gaccacatcatggcagaacgcaacgtg | AA109508 |
| 3584 | ctctcagttcttagatctcaacag | W48463 | 46188 | ggcctgcagcaatgcgggtccaga | AA023458 | 88792 | ccacatcatggcagaagccaaacgtg | AA109508 |
| 3585 | ctttagatttcaacagctcgaactc | W48463 | 46189 | tttacatagctagccactcatcag | W13166 | 88793 | tccctaagaacgcaagcgcgtgaa | AA109508 |
| 3586 | cagttcctaagctggccagactag | W48463 | 46190 | atgtacagctaactgcagactac | W13166 | 88794 | gcagaaggcaagttgcgctgttgaaga | AA109508 |
| 3587 | ttcctaagctggccagactattg | W48463 | 46191 | tacagcaccatcatagagctacaag | W13166 | 88795 | cctttccaattgtgcacctct | AA109508 |
| 3588 | caggactcttgcactgacat | W48464 | 46192 | agcaccatcatatgagctacaagaga | W13166 | 88796 | aatccatcacaccttctggagag | D10215 |
| 3589 | tctgctcactgacatctgctgc | W48464 | 46193 | accatctagagctacaagaacag | W13166 | 88797 | tcactatacgaattctactaagg | D10215 |
| 3590 | gctcactggacatcgcctggc | W48464 | 46194 | aatagctacaaagtcaccctcatcc | W13166 | 88798 | attcctaaaatctgctactc | D10215 |
| 3591 | acatcgctggcacagctggagga | W48464 | 46195 | agctacaaagtcaactgccatcctctga | W13166 | 88799 | tactattaacattcctaagatgct | D10215 |
| 3592 | tctgcctgcacagctggaggagt | W48464 | 46196 | caggaccagggctgtgctactgga | W13166 | 88800 | taacattcctaagatgttcctga | D10215 |
| 3593 | aggagctggcaccctaatgtgtt | W48464 | 46197 | agcaagccaggactcaactcaga | W13166 | 88801 | tcctaagatgcttgaaaagc | D10215 |
| 3594 | agctgcaccctaatgtgttcca | W48464 | 46198 | agccaggcgtcgctactggat | W13166 | 88802 | gtgtgttccaactttggactgtgga | D10215 |
| 3595 | ccccttagtgttccagactgc | W48464 | 46199 | caggccaggcctcaactcaagaact | W13166 | 88803 | tccaactttgactggtggccgta | D10215 |
| 3596 | ttaatgttccagacagtgcacg | W48464 | 46200 | caggactcaactcaagaacttgatcc | W13166 | 88804 | tctttcagtactactctcgagata | D10215 |
| 3597 | atgttccagacagtgcacagaat | W48464 | 46201 | gactcaactcagaactgatccctg | W13166 | 88805 | cagtactactctcgagataagaacc | D10215 |
| 3598 | ctaagctggccacagtatggtgtgga | W48464 | 46202 | ctgcagcagacttccgagcgaat | W13166 | 88806 | atctctgcaagacattaagttt | D10215 |
| 3599 | ccagactatggtgtcctccag | W48464 | 46203 | cagcagacttccgagcgatcagt | W13166 | 88807 | tcagcacctcgtgtgaggaaatcct | D10215 |

| SEQ ID NO | sequence | DBAxnID | SEQ ID NO | sequence | DBAxnID | SEQ ID NO | sequence | DBAxnID |
|---|---|---|---|---|---|---|---|---|
| 3600 | gctgctccctcattgacttcctga | W48464 | 46204 | ccagacttccggagcgatcagttcc | W13166 | 88808 | agtacatccaatatcaacaggtcac | D10215 |
| 3601 | attgactccgagagtggtcagaa | W48464 | 46205 | gacttccggagcgatcagttccggg | W13166 | 88809 | tccaatatcaacaggtcaccatcc | D10215 |
| 3602 | cagcagagcaatgccgtacagcct | W48464 | 46206 | tagcggcttggtagtcaggcaaa | AA023595 | 88810 | ttcatcccagatacctgagcta | D10215 |
| 3603 | cacgctccaaaggcaagtgtcctga | W48464 | 46207 | cagtggatccccacaaggcgccaga | AA023595 | 88811 | tacctgcagctactggtacccag | D10215 |
| 3604 | ccaaaggcagtgtcctgagcgccac | W48464 | 46208 | ggtgcacctccaggcctgcttcgtc | AA023595 | 88812 | tgagctactggtacccagtaagga | D10215 |
| 3605 | agtgctcgagccacccattgtgg | W48464 | 46209 | cgtcctgcgtcatggttgaactg | AA023595 | 88813 | cctccaaatgctcactacgag | D10215 |
| 3606 | cactcgccaggaagagagcgtga | M91380 | 46210 | tcctgcgtcatggttgaactggt | AA023595 | 88814 | caaatgctcactacagattcta | D10215 |
| 3607 | cagctcttaggatggtacacat | M91380 | 46211 | cctgctgcatggttgaactgt | AA023595 | 88815 | gacagccaacatctgataacaagc | X97986 |
| 3608 | ctggtcatctgaacaagacaatt | M91380 | 46212 | tcatggttgaactggtgggcatgt | AA023595 | 88816 | tacaagcatgtcgtggactct | X97986 |
| 3609 | aatttgtctgcctagtgtctgtg | M91380 | 46213 | ttgaactggttgggcatgtgcgtca | AA023595 | 88817 | ttacacagactgcaaactttcact | X97986 |
| 3610 | ttgctcgcctagtgtctgtgcc | M91380 | 46214 | aactgtggttggcatgtgcgtcaggt | AA023595 | 88818 | cacagactggcaaactttcactcaa | X97986 |
| 3611 | cgctcatgcagtccagatttcatcc | M91380 | 46215 | atgtgcgcaggttgtagccgatgc | AA023595 | 88819 | gcaaacttcactcaacctcggctt | X97986 |
| 3612 | ggagagtcaagacagcaatgccat | M91380 | 46216 | tgtggtgcaggttgtagccgatgc | AA023595 | 88820 | tcaacctcggcttgggtgaagaatcc | X97986 |
| 3613 | gagctcaagacagcaatgccatcat | M91380 | 46217 | gtgcgtcaggttgtagccgatgcct | AA023595 | 88821 | acctggcttggtgaagaatccatt | X97986 |
| 3614 | ctcacgacagcaatgccatcatca | M91380 | 46218 | gtggatctccacaagcgccagaat | AA023595 | 88822 | gtgaagactaacgttcgcccatataa | X97986 |
| 3615 | acagcaatgccatcatcaaaagttt | M91380 | 46219 | tggatctccacagagcgccagaat | AA023595 | 88823 | actacgttcgcccatataactatga | X97986 |
| 3616 | gcaatgccatcatcaaaagttttgc | M91380 | 46220 | tccacaagcgccagaattggtgca | AA023595 | 88824 | ttcgccatataactatgaaggcaa | X97986 |
| 3617 | atgccatcatcaaaagttttgc | M91380 | 46221 | ccacaagcggccagaattggtgcac | AA023595 | 88825 | aaggctccatggctgatctgtggg | X97986 |
| 3618 | tgatctggagatcagagggtgcc | M91380 | 46222 | acaagcggccagaattggtgcacct | AA023595 | 88826 | ctgtgggctgcgatgatcggca | X97986 |
| 3619 | cccacacatgatgataaaaactt | M91380 | 46223 | agaattgtgcacctccaggcctgc | AA023595 | 88827 | tgtggggactctggtgtcaagga | X97986 |
| 3620 | ttgaaagtcaatccttctttgaga | M91380 | 46224 | aattgttgcacctccaggcctgct | AA023595 | 88828 | gactctgggtcaaggaatcaa | X97986 |
| 3621 | gtcaatccttttctttgacactcc | M91380 | 46225 | attggtgcacctccaggcctgttc | AA023595 | 88829 | aatcaaacacagcaaagtttgag | X97986 |
| 3622 | gagacactcgaataaactatggag | M91380 | 46226 | tctgctctagccttaaccacacca | AA023595 | 88830 | aaggccacactggagtccaacaag | X97986 |
| 3623 | ggagatttctgcatagaaagtg | M91380 | 46227 | tttaaccacaccacctggaggaa | U02554 | 88831 | gcctggccgatatgcttacacagac | X97986 |
| 3624 | gatttctgcatagaaagttgg | M91380 | 46228 | cctatcaatcatgccctcttcact | U02554 | 88832 | tggccgatatgcttacacagactgg | X97986 |
| 3625 | ttttctggtcatcgaaccag | M91380 | 46229 | tgccctcttcactactgccaggcct | U02554 | 88833 | ccgatatgcttacacagactggcaa | X97986 |
| 3626 | cagaccctgcgcagcaggcatacctgc | M91380 | 46230 | tgtcgaatgcctcatcttagcct | U02554 | 88834 | tgcttacacagactgcaaacttc | X97986 |
| 3627 | tacctgcccaggtgtctatgca | M27347 | 46231 | gaatgcctcatcttagcctggaa | U02554 | 88835 | gttgcctatgggatgacgaatatcg | AA109527 |
| 3628 | attgcctccaagtggagcttccg | M27347 | 46232 | ctcatcttagccttgaactcaa | U02554 | 88836 | ttcgccttgatgacgaataatcg | AA109527 |
| 3629 | tccaactggaggactccggagtcc | M27347 | 46233 | actggaactgactggaaccag | U02554 | 88837 | tcgaacaacgggtctccgcatgg | AA109527 |
| 3630 | caagatggcttagcttgcaatg | M27347 | 46234 | aaactgcactgggaaccaggagtat | U02554 | 88838 | gaacaacgggctcccggcatgtggc | AA109527 |
| 3631 | ggtctcttagcttgcaatgaactg | M27347 | 46235 | gtgctgctaagctgcatgcatag | U02554 | 88839 | acaacgggctcccggcatgtggcaa | AA109527 |
| 3632 | tatgtcgacgagcctgggctccat | M27347 | 46236 | ttctcagaactgcataaaactgttg | U02554 | 88840 | ctcccgcatgtgcaagccgggc | AA109527 |
| 3633 | cctggagctccatcccctaatactg | M27347 | 46237 | ctgtcccataaagtgtacacacac | U02554 | 88841 | gctttcggggcagaacgaatggct | AA109527 |
| 3634 | gctccatcccctaatactgcaacag | M27347 | 46238 | cacaccaactgctgtaacaggct | U02554 | 88842 | ctttcggggcagacagcctggggctg | AA109527 |
| 3635 | tccctaatactgcaacagcaggt | M27347 | 46239 | tagcaagcaatgcccacactgcag | U02554 | 88843 | ggaaggactctctagtgggtgaca | AA109527 |
| 3636 | atactgcaacagcaggaggaaatg | M27347 | 46240 | agcagtgccaccacagcaggggctt | U02554 | 88844 | ggaaggactctcatgtggggtgca | AA109527 |
| 3637 | gcaactgactactgaatcagata | M27347 | 46241 | tgctgagataagcctgggaacc | U02554 | 88845 | gaaggactcctatggggtgcaa | AA109527 |
| 3638 | gtgtctatagcatctgtcctccagt | M27347 | 46242 | gagataagcctgggaacctgccca | U02554 | 88846 | aaggacttcctatgtggtgacaag | AA109527 |
| 3639 | tccagetctcttactgggggctcct | M27347 | 46243 | agccctggaacctgccotcaact | U02554 | 88847 | atgacgaatatcggcctgcgctgg | AA109527 |
| 3640 | tcctcttactgggggctccttga | M27347 | 46244 | caccacctcttggtcaaccggtc | U02554 | 88848 | tgacgaatatcggcctgcgctgg | AA109527 |
| 3641 | tactgggggctcctcttgaagaata | M27347 | 46245 | gtcaacacctgtctgttttatg | U02554 | 88849 | acgaatatcggcctgcgcgtggtc | AA109527 |
| 3642 | cagtagctcgacgagtgaccactttg | M27347 | 46246 | ctgctgctcgggaggcttcattt | U02554 | 88850 | cgaatatcggcctgcgcgtggggtg | AA109527 |
| 3643 | gctgcgacgagtgaccagcttg | M27347 | 46247 | gagcttcatttcctctcgatct | X53802 | 88851 | gaatatcggcctgcgctgggtgcgt | AA109527 |
| 3644 | accgtctccaacagactctcgtt | M27347 | 46248 | ttcaacggctggactactagga | X53802 | 88852 | atatcggcctgcgctgggtgcgtcgt | AA109527 |
| 3645 | tctgcttcacattcctgatgaata | M27347 | 46249 | gaactgttgccgttcctccaaga | X53802 | 88853 | cgctcgaacaacgtctccggcatg | AA109527 |
| 3646 | agaaatagcaaagtcgcggcagagat | W54905 | 46250 | ctgttgctgttttctccaagac | X53802 | 88854 | gtcgaacaacgggctcccggcatgt | AA109527 |
| 3647 | tgctgcaggaactgcgagagaacac | W54905 | 46251 | gtttcctcaagagctctggaagagg | X53802 | 88855 | cttccacgetggacatccgcttag | AA109527 |
| 3648 | acggtgcaagtgccgacgagttccgca | W54905 | 46252 | tctccaagagtctggaagaggccg | X53802 | 88856 | acagctgggacatccgcttagcga | AA109531 |
| 3649 | atgcctccaagtgccgagcatgt | W54905 | 46253 | gccgtcactgcacactactgtat | X53802 | 88857 | ttctagaggtacccattcagggctg | AA109531 |

| SEQ ID NO | sequence | DBAxnID | SEQ ID NO | sequence | DBAxnID | SEQ ID NO | sequence | DBAxnID |
|---|---|---|---|---|---|---|---|---|
| 3650 | ccaagttgccgagcatgtcttccg | W54905 | 46254 | tgcacactactgtatgaacccteac | X53802 | 88858 | ctagagagtaccattcaggctgtc | AA109531 |
| 3651 | tgccgagcatgtcttccgcacttt | W54905 | 46255 | acactactgtgaacccteactgc | X53802 | 88859 | agaggtaccattcaggctgtcat | AA109531 |
| 3652 | ageatgtcttccgcacttitgacac | W54905 | 46256 | ctactgtatgaaccctcactgccca | X53802 | 88860 | aggtaccattcaggctgtcatca | AA109531 |
| 3653 | tcttccgcacttigaccaacacag | W54905 | 46257 | accctgcgaccaagtgcagtaac | X53802 | 88861 | accatcagggctgtcatcaggca | AA109531 |
| 3654 | gcacttigaccaacacagegacgg | W54905 | 46258 | tcatttcettcgatcctcaggac | X53802 | 88862 | ccattcagggctgtcatcaggatc | AA109531 |
| 3655 | ccaacagcgacggcaacactgcactt | W54905 | 46259 | tcctcttcgatctcaggacttcagg | X53802 | 88863 | ggctgtcatcaggcatcccgaggct | AA109531 |
| 3656 | gcgacggcaacactgcacttccggga | W54905 | 46260 | tcgatctcaggacttcaggcgaaaa | X53802 | 88864 | cgtcatcaggcatcccgaggctct | AA109531 |
| 3657 | tcgacttcgggagttcatcatcgc | W54905 | 46261 | atctcaggacttcaggcgaaaagcg | X53802 | 88865 | gtcatcaggcatcccgaggctctaa | AA109531 |
| 3658 | agaacacgagttctctgagctgca | W54905 | 46262 | ccacgtcctcatggtactgctgg | X53802 | 88866 | catcaggcatcccgaggctctaagg | AA109531 |
| 3659 | ccgagttctctgagctgagctacta | W54905 | 46263 | gccattgctgatttcaactggactg | X53802 | 88867 | ctgggacattgcttagcagatcca | AA109531 |
| 3660 | agctgggctacgagttgtgtacaa | W54905 | 46264 | tctgatttcaactggactggagcta | X53802 | 88868 | caggcatccggagtctctaaggta | AA109531 |
| 3661 | tcctgaaggactgcccgactggcat | W54905 | 46265 | gatttcaactggactggagctacta | X53802 | 88869 | gggacattgcttagcagatccagg | AA109531 |
| 3662 | aggactgcccgactggcatcctcaa | W54905 | 46266 | tcctccgccgacgagtaggccgc | X53802 | 88870 | catcgttagcagatccaggaggct | AA109531 |
| 3663 | gcccgactggcatcctcaagtgga | W54905 | 46267 | gactaacctaacatggccgcacaga | AA023589 | 88871 | ttcgcttagcagatccaggaggctt | AA109531 |
| 3664 | ctggcatcctcaacgtggatgagtt | W54905 | 46268 | aagtcctatcgaagctggccctga | AA023589 | 88872 | cgcttagcagatccaggaggctlcaa | AA109531 |
| 3665 | tcctcaacgtggatgagttcaagaa | W54905 | 46269 | tcctaacgaagctggcctgaagt | AA023589 | 88873 | cttagcagatccaggaggcttcaag | AA109531 |
| 3666 | gaaacgtgtcagcacagaatcat | W54905 | 46270 | tatcggaagctggcctcaagtac | AA023589 | 88874 | agatccaggaggcttcaaggagaa | AA109531 |
| 3667 | aaccgttccagcacagaatcatcc | W48477 | 46271 | aagctggcctgaagtatcacccig | AA023589 | 88875 | atccaggaggcttcaaggagcaacg | AA109531 |
| 3668 | atcctgacctgcctgacctgtcct | W48477 | 46272 | ctggcctgaagtatcacccigaca | AA023589 | 88876 | gtactgacgactgcagctatggc | AA109531 |
| 3669 | cctgtgacctggtctctctagtg | W48477 | 46273 | ctgaagtatcacccigacaagaacc | AA023589 | 88877 | ctgacgactgcagctatggctag | AA109531 |
| 3670 | tgctgacctggtctctctagta | W48477 | 46274 | aagtacccigacaagaaccctg | AA023589 | 88878 | cacgttctctgcgagtcegtca | AA109531 |
| 3671 | tggctctctagtgaccggtgg | W48477 | 46275 | tatcaccctgacaagaaccctgata | AA023589 | 88879 | gttcttgtcgagtcgtcaatt | AA109531 |
| 3672 | ttcaacctgcgaagcacaagttig | W48477 | 46276 | cctgacaagaaccctgataaccccag | AA023589 | 88880 | cttgcggagtcctgtcaattcca | AA109531 |
| 3673 | caacctgcgaagcacaagttigca | W48477 | 46277 | gacaagaaccctgataaccccagag | AA023589 | 88881 | agtcctgcaattccagcctgact | AA109531 |
| 3674 | gaagctctgtgcctgatgaacag | W48477 | 46278 | taacctaacatggccgccagtgagc | AA023589 | 88882 | cctctgataccagcggtgtaac | AA109531 |
| 3675 | aagtcttgcctgatgagcagaa | W48477 | 46279 | cctaacatggccgaccagagcagc | AA023589 | 88883 | ctgggataccatgcggtgtaacctgt | AA109531 |
| 3676 | gtcttgtccctgatgagcagaag | W48477 | 46280 | aacatggccgaccagagcagcgct | AA023589 | 88884 | ggatacatgcggtgtaacctgt | AA109531 |
| 3677 | ttgtcccctgatgagcagaagg | W48477 | 46281 | ctctcactcegggagaatcattat | AA023589 | 88885 | catggtgaacctgtagaaatgct | AA109531 |
| 3678 | ccgtgtccagcagaatcatcctt | W48477 | 46282 | gaatcattaccatgtcttggac | AA023589 | 88886 | gtgtaaccctgtagaaatgctg | AA109531 |
| 3679 | gtgtccagcacagaatcatccttg | W48477 | 46283 | taccatgtcttgactggacaaga | AA023589 | 88887 | tagaaatgctcgatcagcgctact | AA109531 |
| 3680 | ccagcacagaatcatccttggaaaa | W48477 | 46284 | gacaagaatgcaacctcagatgaca | AA023589 | 88888 | acagcactgcagctagcgctagttc | AA109531 |
| 3681 | cagcacagaatcatccttggaaaagg | W48477 | 46285 | aatgcaacctcagatgcattaaaa | AA023589 | 88889 | gaaatgctcgatcagcggctactac | AA109531 |
| 3682 | cacagaatcatcctggaaaaggag | W48477 | 46286 | catccaaatatgctgctcaggtg | X87671 | 88890 | ctgcagctagcgctagttcaccgtg | AA109531 |
| 3683 | cagaatcatcctggaaaaggagag | W48477 | 46287 | ctcaaatagcctgctcatcaggtg | X87671 | 88891 | cagctatgctagttcaccggta | AA109531 |
| 3684 | gacccaactgtggagattgatg | W48477 | 46288 | tcctcccagatgccctgtccag | X87671 | 88892 | gttcaccgtgacgcgggtcatgg | AA109531 |
| 3685 | ttcaatctgacctgcctactg | W48477 | 46289 | tccagatgcccttgtccaggc | X87671 | 88893 | cacgtgtaccgcggtcatggatc | AA109531 |
| 3686 | actaggaagcctcatccgaccaat | W48477 | 46290 | ggcccctgccagccttggcc | X87671 | 88894 | gglacgcggttcatggatcggatc | AA109531 |
| 3687 | tcatccgaccaatgtgtaaacgc | W48477 | 46291 | tttcctctccactigagctg | X87671 | 88895 | acgcggttcatggatcacg | AA109531 |
| 3688 | caccccagccgagtgcagccagta | W48477 | 46292 | tcctcttccactigagctgggt | X87671 | 88896 | cgggatcacgttctgctcgagtc | AA109531 |
| 3689 | catttaaggccagtccagttgact | L01695 | 46293 | tccggcaggttcaaggagagctac | X87671 | 88897 | tcaaggttgctcaccagggaagaga | AA109531 |
| 3690 | ctctctctttgtaaatacatgcatt | L01695 | 46294 | acagactigcegttccagaagaa | X87671 | 88898 | ttgtcaccaggagaaagcg | AA109531 |
| 3691 | ctctctctttgtaagtccatcc | L01695 | 46295 | gactigcegttccagaagact | X87671 | 88899 | ctgtttacagttctgaggtatac | X99104 |
| 3692 | tctgtgaagtccatccatgtc | L01695 | 46296 | ttgcctgttccagagagacttt | X87671 | 88900 | ttggggtctgtggactaggaatag | X99104 |
| 3693 | gaagtccatcccatggtcattaga | L01695 | 46297 | tctigccaatgtattitttgtaagc | X87671 | 88901 | tcctatttccagtcgactatctg | X99104 |
| 3694 | catccatggtcatttgaccgcc | L01695 | 46298 | gcctgcccagtggaccaggagta | X87671 | 88902 | ttctccagtcgacatatcgacact | X99104 |
| 3695 | cattagctgccatcctgaaccgc | L01695 | 46299 | tgctcaggggaccaggagact | X87671 | 88903 | agtgcactactgaccactcctca | X99104 |
| 3696 | acctgccactctgaaccgcatgta | L01695 | 46300 | cgccagggctcatttcagaga | X87671 | 88904 | agacaaccccagcgaccacctgca | X99104 |
| 3697 | aggcccctgctatgccagagatca | L01695 | 46301 | cctcattcagacgagtaagca | X87671 | 88905 | cacactttcggtccctgaccta | X99104 |
| 3698 | tctctgtaacgtctgaggctte | L01695 | 46302 | agaaggagcaggcctcctacctg | X87671 | 88906 | ctctccaggtattlgcatggacca | X99104 |
| 3699 | taaacgtctgaggtctccttctag | L01695 | 46303 | gtaagcaggccccctccctacctggag | X87671 | 88907 | gcatlgattcttggactigaggaac | X99104 |

TABLE 1-continued

| SEQ ID NO | sequence | DBAxnID | SEQ ID NO | sequence | DBAxnID |
|---|---|---|---|---|---|
| 3700 | ctctgaggtcttcctcaggatgta | L01695 | 46304 | tcctacctggcaggtcctcattgtc | X87671 | 88908 | ctcttaactgaattgctgttcagt | X99104 |
| 3701 | ggtcttcctcagatgatatcttat | L01695 | 46305 | gcaggtcctcattgtccttcct | X87671 | 88909 | atattgagtctccagttactg | X99104 |
| 3702 | agcagctagcccagtacaagcagg | L01695 | 46306 | agtatgactcatccagagacagaag | AA023559 | 88910 | tagtctccagttactgctaaca | X99104 |
| 3703 | gtattaccagttaatgtgacacag | L01695 | 46307 | atgactcatccagagacagaagat | AA023559 | 88911 | cctcagttactgctaacatctcca | X99104 |
| 3704 | agcaactiggcaccagagcgag | L01695 | 46308 | aactgatgcctgatgtcggctac | AA023559 | 88912 | ttacttgtcaacatctcattcct | X99104 |
| 3705 | ttgagcaccccagagcgagtgcagc | L01695 | 46309 | actgcatgcctgatgtcggctatcg | AA023559 | 88913 | gctaacatccattcctaggta | X99104 |
| 3706 | gaaggctcagtactacctgccgat | W48490 | 46310 | atgcctgatgtcggctatcgagcta | AA023559 | 88914 | atcctcattccttaggatagatggg | X99104 |
| 3707 | tcagtactacctgccgatggccagc | W48490 | 46311 | cctgatgtcggctatcgagcctaccg | AA023559 | 88915 | gtctctcctggctgttacagtgt | X99104 |
| 3708 | gcgtcaggcctgactgattggc | W48490 | 46312 | ctgatgtcggctatcgagctaccgg | AA023559 | 88916 | cctggcgttcagtgtctgtg | X99104 |
| 3709 | gtcaggcctgactgattggcgag | W48490 | 46313 | atgtcggctatcgagctaccggca | AA023559 | 88917 | tatcagtgtcgtttgctgcaga | AA110543 |
| 3710 | gcctgacttgattggcgaggagagt | W48490 | 46314 | gtcggctatcgagctaccggccaac | AA023559 | 88918 | agtgtgtctttgctgcagagataa | AA110543 |
| 3711 | tatcatgagggtgtggtcgct | W48490 | 46315 | tcggctatcgagctaccggcaacc | AA023559 | 88919 | tggaacatcacttataagagaggag | AA110543 |
| 3712 | ccatgagggtgtggtcgct | W48490 | 46316 | ggctatcgagctaccgccaacg | AA023559 | 88920 | aggagaatcctatctcaagatagg | AA110543 |
| 3713 | tgagggtgcgtttgtgctaccag | W48490 | 46317 | gctatcgagctaccggccaaccgg | AA023559 | 88921 | gagaatcctctcaagatagataagg | AA110543 |
| 3714 | ggtgtctatcacagaagtcagac | W48490 | 46318 | ttagataatgcactgccagatgag | AA023559 | 88922 | atccttcatcaagatagatgaag | AA110543 |
| 3715 | gtcgctatccagaagtcagacatg | W48490 | 46319 | agataatgcactggcagatgagct | AA023559 | 88923 | tgccctgggttctgtgccattaac | AA110543 |
| 3716 | cgctatccagaagtcagacatggat | W48490 | 46320 | gataaatgcactggcagatgagt | AA023559 | 88924 | ccctggggtctgtgcagtaacga | AA110543 |
| 3717 | tatccagaagtcagacatggatta | W48490 | 46321 | taatgcactgcagatgagagctgg | AA023559 | 88925 | ggtgttcgtgccattaagatagt | AA110543 |
| 3718 | gtactactgccccgatggcagacc | W48490 | 46322 | aatgcactgcgatgagagctgg | AA023559 | 88926 | tgttctgtgccattaacgatagtga | AA110543 |
| 3719 | ctactgccgatggcagcaccatt | W48490 | 46323 | tgcactgccagatagagctgggg | AA023559 | 88927 | ttctgccattaacgatagtgaa | AA110543 |
| 3720 | tggcagcaccattgcagtggccct | W48490 | 46324 | actgcgcagatgagcttggggaga | AA023559 | 88928 | ggctaacctatgacacactgaac | AA110543 |
| 3721 | caccattgcagttgcccttccag | W48490 | 46325 | tgaactgcatgcctgatgtcggcta | AA023559 | 88929 | tgtgctttgtctgcagagtaaaa | AA110543 |
| 3722 | tgagattggccctccagttccgg | W48490 | 46326 | aacatgaccggcgcagctagccc | AA023669 | 88930 | ctatacctatgacacatctgactg | AA110543 |
| 3723 | ggccccctgagctctgtcaggtccgg | W48490 | 46327 | accatgaccggcgcgacgtagcct | AA023669 | 88931 | tgtgtttgtcagatgaaaaac | AA110543 |
| 3724 | tgagctgtgctcaggctgtcaggct | W48490 | 46328 | gtagccctcgagctgtcagcct | AA023669 | 88932 | gaaagctgaacctcatcgtgac | AA110543 |
| 3725 | gctgcgttcaggctgactgatt | W48490 | 46329 | agccctctcactgctgggagaccgg | AA023669 | 88933 | aagctgaaccctcatcgtgact | AA110543 |
| 3726 | cattccgcagttgcagaaccagg | W48490 | 46330 | gccttctcactgtggagaccga | AA023669 | 88934 | aacctcatcgtgacgtgtccggg | AA110543 |
| 3727 | ttgcaagaccagggaccgcgttattac | M29464 | 46331 | ttctcactgctgggagaccgatctg | AA023669 | 88935 | cctcatcgtgacgtgccgggaa | AA110543 |
| 3728 | ttgcaaggtggccaaagtgagtat | M29464 | 46332 | tctccactgctgggagaccgatctgg | AA023669 | 88936 | atgcattgaacactcatttaataga | AA110543 |
| 3729 | acaccctggggtgtcatgtcgcgacc | M29464 | 46333 | tcactgctgggagaccgatctggaa | AA023669 | 88937 | attggacatcacttaataggaga | AA110543 |
| 3730 | tgcatgtgcgacctccaactgaac | M29464 | 46334 | actgctgggagaccgatctgggaac | AA023669 | 88938 | tgtaggccctcaagaatgacgtcc | AA110543 |
| 3731 | tgacatcctgaacatactgatgt | M29464 | 46335 | tgctgggagaccgatctgggaacca | AA023669 | 88939 | ccagtatcatccactccactcgcag | Y07941 |
| 3732 | tcctgaactcatacttagtggct | M29464 | 46336 | aagggtagtaccctagggctgcacga | AA023669 | 88940 | atttgcctcagttccatatctaa | Y07941 |
| 3733 | tggttgctcaatgcaatgtgctg | M29464 | 46337 | acgagcctcagtcggcgtcatg | AA023669 | 88941 | ctcctagttccatatctaaaacag | Y07941 |
| 3734 | ttcattgccaatgtgcgtgccgt | M29464 | 46338 | catgaccgtgcgcagctagccctt | AA023669 | 88942 | tttggactgtcgcagcgtcggga | Y07941 |
| 3735 | gccaatgtgcgtgccgttttgttc | M29464 | 46339 | gtgccgcagctagccttccactg | AA023669 | 88943 | ctgcgcagctgcagggaccctcc | Y07941 |
| 3736 | cagtgtcgtgctttcagtgtgaca | M29464 | 46340 | tgccgcagctagcccttctcactg | AA023669 | 88944 | actgcctgtccactgtgatga | Y07941 |
| 3737 | ctccttgtcacagaagtgcagaaac | M29464 | 46341 | cgcagctagcccttctcactgc | AA023669 | 88945 | cttgctcatcgtgatgagaacct | Y07941 |
| 3738 | cattagagatacctgagcaggccag | M29464 | 46342 | gcagctagcccttctcactgctg | AA023669 | 88946 | ttgtgctgaacggccccagttcct | Y07941 |
| 3739 | cgagatacctgagcaggttgac | M29464 | 46343 | cagcgtagccttctcactgctgg | AA023669 | 88947 | gaaacgggccagttcctcttgtatg | Y07941 |
| 3740 | atggccaactccgatctggccc | M29464 | 46344 | ggcgtacgccttctcactgcgggag | AA023669 | 88948 | gatacaacatgtatttgcttgtca | Y07941 |
| 3741 | caacttcgatctgcccccatgt | M29464 | 46345 | cgtagccctcctcactgctgggaga | AA023669 | 88949 | ccatgtattgcttgtcaaaatat | Y07941 |
| 3742 | gggctgactgctgcgtgtaacaac | M29464 | 46346 | ttgcatgggtgatcgcgccgcca | AA023669 | 88950 | taggttcaccattgctttgggat | Y07941 |
| 3743 | ctgtgtaaccacagcgtgaact | M29464 | 46347 | taatccgaccttcatatcggaact | AA023665 | 88951 | aggcttaagatacccagaggtcag | Y07941 |
| 3744 | cagagggtcacggccagccttca | M29464 | 46348 | tgtattacggcagcaggttcctca | AA023665 | 88952 | taagatccagaggtcaggctcaa | Y07941 |
| 3745 | cgtcaagtcgcagcgcttccaggc | M29464 | 46349 | tattagccgagcaggttcctcaggc | AA023665 | 88953 | ggaactcctcatgatcccaagct | Y07941 |
| 3746 | cctcacactggtataatgtcttcctg | J05185 | 46350 | ccgagcaggttcctcaggtcactc | AA023665 | 88954 | atgatctcaagctggccatggcc | Y07941 |
| 3747 | accaattcgcatcatcgtgagg | J05185 | 46351 | aggttcctcaggtcactcgaact | AA023665 | 88955 | tgtgcctcattccaggaaaaat | Y07941 |
| 3748 | ggatcatgcatcctgtcaagggg | J05185 | 46352 | ctcaggtccaggtcactactgat | AA023665 | 88956 | cttggacttctgtatccgacactt | Y07941 |
| 3749 | tcaagctgaggtactgtcaaggccg | J05185 | 46353 | aggctcactcatcggaactactgatctt | AA023665 | 88957 | gtatccagactatatctcattggtt | Y07941 |

| SEQ ID NO | sequence | DBAxnID | SEQ ID NO | sequence | DBAxnID | SEQ ID NO | sequence | DBAxnID |
|---|---|---|---|---|---|---|---|---|
| 3750 | caggactaccgaccagccggctatg | J05185 | 46354 | cggaactactgatcttggacattgg | AA023665 | 88958 | actlgactgaagcctgtcgctcta | Y09419 |
| 3751 | taccgacagccggctaggccaca | J05185 | 46355 | aactactgatcttggacattggctt | AA023665 | 88959 | tgactgaagccgtcgctctatga | Y09419 |
| 3752 | ctgtggctgcgattccttccag | J05185 | 46356 | tactgatcttggacattggcttgc | AA023665 | 88960 | ccatagccgtatagccatcaaat | Y09419 |
| 3753 | gatctcttccagcatgcctgtggc | J05185 | 46357 | tcttggacattggcttgctgtgt | AA023665 | 88961 | tatgccgtatagccatcaaatgt | Y09419 |
| 3754 | tttccagcatgcctggcctgtgt | J05185 | 46358 | ggacttcatatgcgaactgcaggt | AA023665 | 88962 | tatgccatcaaatgtcaggcaac | Y09419 |
| 3755 | aatgaaatgcccattctcaggcat | J05185 | 46359 | tatcggaactgcaggtacgcgcgga | AA023665 | 88963 | gtcaggcaactgctcatgaattcct | Y09419 |
| 3756 | atgccattctcaggcattctac | J05185 | 46360 | tgcaggtacgcgggatgcgccagt | AA023665 | 88964 | caactgctcatgaattccttcagt | Y09419 |
| 3757 | attcttcaggcattctaccataat | J05185 | 46361 | aggtacgcgggatgtgccgcagt | AA023665 | 88965 | ctgctcatgaattcctttcagtgt | Y09419 |
| 3758 | ttcatctgaaggcattcatcttt | J05185 | 46362 | tacgcgggatgatgccgcagtcg | AA023665 | 88966 | caattagacagcccagcaaagactg | Y09419 |
| 3759 | atgctcatgccagctactgtt | J05185 | 46363 | cagccagacatctgctgagtgtct | AA023665 | 88967 | gacagcccagcaaagactgcagaat | Y09419 |
| 3760 | actgttcaccatggcagaacctcc | J05185 | 46364 | gtcaaagagccgcgtctggt | AA023665 | 88968 | gcagaatgcactgaccctagaat | Y09419 |
| 3761 | ttcaacatggcagaacctccgagt | J05185 | 46365 | taagagcagcccgcgttctggtt | AA023665 | 88969 | tcaagaccttaattggacatg | Y09419 |
| 3762 | tctgcctggtaggaagttggc | J05185 | 46366 | ttgaccgcaagacattgctgaact | AA023665 | 88970 | ctgaagcctgtcgctagaaga | Y09419 |
| 3763 | ctctgggtctgtggcactctccac | J05185 | 46367 | cattgctgaactgccacatcgg | AA023665 | 88971 | aacagctgggggctgtatgtcc | Y09419 |
| 3764 | tctccacctgtcctagtgtgcca | J05185 | 46368 | ccgatgacatgccgtatagagagtt | AA023665 | 88972 | gggctgtatgtctgtggaatt | Y09419 |
| 3765 | catttaacctggggatctatgcatc | J05185 | 46369 | gtggttctgccttcacaaatgca | AA023665 | 88973 | attgtcctgggaattcctcaaaga | Y09419 |
| 3766 | aggcgttgccagttccaacgccag | AA071689 | 46370 | aatgtcatgtctcactagaaga | AA023665 | 88974 | tctgtgccctcatacttggaatt | Y09419 |
| 3767 | gcggttgcccagttccaacgccagt | AA071689 | 46371 | atgtctacttcatagaagaaccaaa | AA023665 | 88975 | gtgtgtcgggcaacttcctgac | Y09419 |
| 3768 | ttcgtcaccttccctgactgt | AA071689 | 46372 | tgtgttgctagtgtactctg | AA023665 | 88976 | tcctgacctccatatgccgtatag | Y09419 |
| 3769 | tcacctttccctgacttgctctcat | AA071689 | 46373 | tcggtactgactatctgtaaata | AA023665 | 88977 | cctcatatgccgtatatgccatca | Y09419 |
| 3770 | tccctgacttcctctcatcttga | AA071689 | 46374 | ctttcgccactgacgacaaagcca | AA023665 | 88978 | actccgattccattcatggcctt | Y09419 |
| 3771 | cctgactgcttcattcatcttttgagt | AA071689 | 46375 | gcactgacgacaaagccagtgtag | AA023665 | 88979 | ttcccgatccatttcattggcctct | Y09419 |
| 3772 | catcttgagtttatcttggaggc | AA071689 | 46376 | acagacaaagccagtgtaggttgt | AA023665 | 88980 | ttatccgatgatgatttaggact | AA110549 |
| 3773 | tttgagttatcttggaggcctgg | AA071689 | 46377 | tagcttcagttatgcacagtgta | AA023665 | 88981 | atgaactcacagcaggcggaaaca | AA110549 |
| 3774 | agttatcttggaggcctgctgtg | AA071689 | 46378 | ctgaatccgcacattcggaccaa | AA023665 | 88982 | agaactcacagcaggcggaaaca | AA110549 |
| 3775 | tttatcttggaggcctgctgtga | AA071689 | 46379 | tcggcacattcggaccaatatatt | AA023665 | 88983 | acttcacagcaggcggaaacaaa | AA110549 |
| 3776 | tctgtgtctgcttcctgccaca | AA071689 | 46380 | tccatcaagtcccctgacaaaaca | AA023665 | 88984 | agaattcactgtagcacaggcatc | AA110549 |
| 3777 | tgtgtctgcttctgccaccactc | AA071689 | 46381 | aagtcccctgacaaaacgaggggcag | AA023665 | 88985 | aatccatgctagacacaggcatctc | AA110549 |
| 3778 | gtgtccagtccaagccagctcg | AA071689 | 46382 | ttttctagaaactcatgcttgac | AA023665 | 88986 | ttcactgacacaggcatctcag | AA110549 |
| 3779 | cccggcgagcagttcgggtggcag | AA071689 | 46383 | tagaaacttcatgcttgacacacc | AA023665 | 88987 | ctgtagacacaggcatctcagtgta | AA110549 |
| 3780 | gggcagcagttcgggttggcagcagcacc | AA071689 | 46384 | caccagtattaaccattcccgatga | AA023665 | 88988 | gtagacacaggcatctcagtgtaaa | AA110549 |
| 3781 | cagcagttcgggttggcagcacct | AA071689 | 46385 | tattaaccattcccgatgacatgcg | AA023665 | 88989 | agacacaggcatctcagtgtaatt | AA110549 |
| 3782 | tgcccagttcgctcccgtcttgt | AA071689 | 46386 | atgcagccctagatcgtcttggcc | AA023665 | 88990 | ccggattccactcatggccttctta | AA110549 |
| 3783 | cccagttcgctcccgtcttcgtca | AA071689 | 46387 | atctgtcttggcagcccaccgaa | AA023665 | 88991 | ggattccattcatggccttcttaac | AA110549 |
| 3784 | cagtggcttctcccgtcttcgtcacc | AA071689 | 46388 | tggtcatgcagccccagccatctgg | AA023665 | 88992 | attccattcatggccttcttaactt | AA110549 |
| 3785 | gtggcttctccgtcttcgtcacct | AA071689 | 46389 | aggcctgccaaggtcattgtgcagt | AA023665 | 88993 | tccatcatggccttcttaacttag | AA110549 |
| 3786 | ataccgctaggcaagaaatacaa | AA071689 | 46390 | tgcctgccatctctgggcaagat | AA023665 | 88994 | cattcatggccttcttaactagtc | AA110549 |
| 3787 | acctgtcatcgcaagattggatgc | AA071689 | 46391 | ccatctctggggcaagattaaagg | AA023665 | 88995 | ttcatggccttcttaacttagtcct | AA110549 |
| 3788 | aacatgccacaagaggagcaggagc | J05186 | 46392 | aagactctgtctcggtatga | AA023665 | 88996 | catggccttcttaacttagtcctg | AA110549 |
| 3789 | aggcaccagcactagtggacagca | J05186 | 46393 | tgtgctcagggttatgatatcaa | AA023665 | 88997 | tcttaactagtccttgaacaactg | AA110549 |
| 3790 | gacaggcattgccaccaaggcacgtg | J05186 | 46394 | atatcaacagccaaggtagagaagtc | X76652 | 88998 | ggcagatccagacctcgtcccaca | AA109774 |
| 3791 | caccaagcaagtggccaaggtga | J05186 | 46395 | aagtgaactcccaagaaatacacat | X76652 | 88999 | cagcagaccgacctcgtcacaaa | AA109774 |
| 3792 | tttgttaatgccacctaggtct | J05186 | 46396 | actcccaaggaaatacacatgctcc | X76652 | 89000 | gctctcggaatatcccagcatcat | AA109774 |
| 3793 | taatgccacctatgcgtgaatac | J05186 | 46397 | aggaaataacacatgcttccaattaa | X76652 | 89001 | tcgaatatcccagcatcatcctt | AA109774 |
| 3794 | cacctatgcgtgaatactgaata | J05186 | 46398 | ctttgcaccagcaacatgtataaa | X76652 | 89002 | cccagcatctctgagcttatgcc | AA109774 |
| 3795 | actattactcagtatctctcag | J05186 | 46399 | aggctcctccagagacattgtataa | X76652 | 89003 | gcatcatcctcctgagcttatgcc | AA109774 |
| 3796 | tactcagtatctctcagacaat | J05186 | 46400 | cagcagacatccagggtcaccaccat | X76652 | 89004 | atcatcctcctgagcttatgccac | AA109774 |
| 3797 | agtatctctcagacaaataagttt | J05186 | 46401 | acatccaggtcaccactatcgga | X76652 | 89005 | tccttcctgagcttatgccacgaag | AA109774 |
| 3798 | tggatctactgccaagacatcac | J05186 | 46402 | aggtcaccactactggagaaact | X76652 | 89006 | cttcctgagcttatgccagaagct | AA109774 |
| 3799 | ctactgccaacgcatcaccaacga | J05186 | 46403 | agtgttcgaacgtcaacgagctga | X76652 | 89007 | tccgagcttatgccacgaagctga | AA109774 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 3800 | ccaacgatcaccaacgaccaata | J05186 | 46404 | gccacgcagcagcaacgcaacggcac | X76652 | 89008 | gcttatgccagaagctgagatcaa | AA109774 |
| 3801 | acatcaccacgaccaatataagt | J05186 | 46405 | acagcaacggcactgagatggtcag | X76652 | 89009 | ttatgccacgaagctgagatcaatg | AA109774 |
| 3802 | gttccctaccactcattgtctc | J05186 | 46406 | aattcaccaagaagttgcacatgtc | AA023740 | 89010 | agacctcgtccacaaactcaactc | AA109774 |
| 3803 | ctaccatctattttgctcccagtg | J05186 | 46407 | tcaccaagaagttgcacatgtccca | AA023740 | 89011 | tttaaacagcagtgcctttgatatc | AA109774 |
| 3804 | tctattttgctcccagtggggacaa | J05186 | 46408 | agatgttgccaaaatccttgactac | AA023740 | 89012 | taaacagcaggcgcttgatatcgt | AA109774 |
| 3805 | tagatgaacatgccacaagaggag | J05186 | 46409 | tgttgccaaaatccttgactacaag | AA023740 | 89013 | ccacgctcgatgagacctggcaaa | AA109774 |
| 3806 | aggcgtcctcactgcggaagcaag | W48504 | 46410 | tgccaaaatccttgactacaagtgt | AA023740 | 89014 | accgtcgatgagacctggcaaagt | AA109774 |
| 3807 | ggcgtcctcactgcggaagcaaga | W48504 | 46411 | gtgtgtctcagatctaaggctgcc | AA023740 | 89015 | ctcgatgagacctgcaaagtactg | AA109774 |
| 3808 | gaagcaacggcctggtgaagaaggag | W48504 | 46412 | cagatctaaggctgccgggatccca | AA023740 | 89016 | atgaccgtctcggaatatccaga | AA109774 |
| 3809 | agcaacggcctggtgaagaaggag | W48504 | 46413 | atctaaggctgccgggatcccagca | AA023740 | 89017 | gaccgctcgcgaatatccagca | AA109774 |
| 3810 | gaggagttccacagacctgaagcc | W48504 | 46414 | taaggctgcgggatcccagaga | AA023740 | 89018 | tccaggcctcaaggaagctagagc | AA109774 |
| 3811 | ggagttccacagacctgaagccaa | W48504 | 46415 | tgccaggacccagcacagttgcag | AA023740 | 89019 | ctagagctgcagcagtcaacca | AA109799 |
| 3812 | gagttccacagacctgaagccaga | W48504 | 46416 | cgggatcccagcacagcacatggga | AA023740 | 89020 | ctcatttcattggtgctcttct | AA109799 |
| 3813 | gttcccacagacctgaagccagagg | W48504 | 46417 | agcagcacatggagccctagaagattg | AA023740 | 89021 | gtcattgtggtcctcttcctgt | AA109799 |
| 3814 | ttcccacagacctgaagccagagga | W48504 | 46418 | gcctcgaacatagggtgtgag | AA023740 | 89022 | gtgggtcctcttcctcctgtcctgtgga | AA109799 |
| 3815 | cccagacctgaagccaggaaggag | W48504 | 46419 | tggcccccgaacgcattagtgcctc | AA023740 | 89023 | ctcttcttcctgtcctgatgcca | AA109799 |
| 3816 | ccacagacctgaagccagccaaag | W48504 | 46420 | aacgcattagtgcctcaaggtgcag | AA023740 | 89024 | ttcctggcatgccccatcttca | AA109799 |
| 3817 | gagttccacagacctgaagccaga | W48504 | 46421 | gcattagtgcctcaggaaatctccg | AA023740 | 89025 | atgccaatctcagtgccaatgcct | AA109799 |
| 3818 | gttcccacagaccctgaagccagagg | W48504 | 46422 | ttagtgcctcaggaaatctccgctt | AA023740 | 89026 | agtgccaatgcctgcgggcatatg | AA109799 |
| 3819 | cagactgaagccagaggaagttggc | W48504 | 46423 | cctcaggaaatctccgcttaagttg | AA023740 | 89027 | aatgcctggcatatgacacgg | AA109799 |
| 3820 | ctctcacgtcggaagcagaaccaag | W48504 | 46424 | caggaaatctccgcttaagttgcag | AA023740 | 89028 | gcatatgacacggttctgccgaga | AA109799 |
| 3821 | gaacattgcagcagcaccggctg | W48504 | 46425 | tccgcttaagttgcaggcgaatgaa | AA023740 | 89029 | gtttctgccagaaacactctcag | AA109799 |
| 3822 | aacattgcagcagcaccggcctgg | W48504 | 46426 | gctcgcagtcgttcaggccgcgtg | AA023740 | 89030 | ctgcacagtctcaaccagcagcag | AA109799 |
| 3823 | cattgcagcagcaccggcctggtg | W48504 | 46427 | acgtgcagtccggtcacatcagcct | AA023740 | 89031 | tcaaccagcagcaggggtgcagaa | AA109799 |
| 3824 | attgcagcagcaccggcctggtga | W48504 | 46428 | gccgcgtgcctgcttacgttaagtac | AA023740 | 89032 | atccaagcatcagagcagtgt | AA109799 |
| 3825 | tgcagcagcaccggccctggtgaag | W48504 | 46429 | cgttaagtactcgcttcggagcat | AA023740 | 89033 | agtggtcgtcgcaacctgatcg | AA109799 |
| 3826 | agcagcaccggcctggtgaagaag | W48504 | 46430 | taagtactcgcttcgggagcatcaa | AA023740 | 89034 | tctgcgtccaacctgatcgccaga | AA109799 |
| 3827 | gtctgcaccattgggatgctgctat | M97900 | 46431 | gtactcgcttcgggagcatcaacac | AA023740 | 89035 | gtgatccgcatgccattgcattg | AA109799 |
| 3828 | gtctgcaccattgggatgctgctat | M97900 | 46432 | ctcgcttcggagcatcaacacg | AA023740 | 89036 | gtgaacctgtcgtccaagaagtcg | AA109799 |
| 3829 | acatggcaaccaatcttgtcagg | M97900 | 46433 | cgctcggagcatcaacacgtgaag | AA023740 | 89037 | cgcatgcatgtcattgcatggtgtcc | AA109799 |
| 3830 | caaccaatcttgtcaggtggatg | M97900 | 46434 | ttcggagcatcaacacgtgaagacc | AA023740 | 89038 | cctgacctttgcagtcgtgtgc | AA109799 |
| 3831 | atcttgttcaggtggatggatggga | M97900 | 46435 | atcaacacgtgaagaccaaggaa | AA023740 | 89039 | cttatgagaccactalgggcata | AA109799 |
| 3832 | aaactacatctccctgtgaca | M97900 | 46436 | atcaacacgtgaagaccaaggaaggaa | AA023740 | 89040 | ctacaggcttcagaagctgaggcct | U46463 |
| 3833 | calcttccctgtagacacaaaagt | M97900 | 46437 | tcaacacgtgaagaccaaggaagg | AA023740 | 89041 | actacaactcatggcgcctgg | U46463 |
| 3834 | aaatggtgcaatccaccaaacag | M97900 | 46438 | tgacctggtcatcagcctga | AA023740 | 89042 | actctcatggtcctgtgacatgg | U46463 |
| 3835 | ttttctcaatgtaatcaccctact | M97900 | 46439 | accctgtcacatcagccttgaggc | AA023740 | 89043 | atggtgcctgacatgagagtc | U46463 |
| 3836 | caatgtaatcacctacatgtggaa | M97900 | 46440 | ctgtcacatcagccttgaggcgt | AA023740 | 89044 | catgcttactgagtctctgct | U46463 |
| 3837 | aatcaccctacatgtggaaatagca | M97900 | 46441 | tcggaatccgacatagagcgtgat | AA023740 | 89045 | tacttaggatcttcgtctgtgta | U46463 |
| 3838 | atgtcttttttgggaagagacaga | M97900 | 46442 | gagatccgacatacgagctgattgc | AA023740 | 89046 | ggatcttgtctgtcgtaggaccgg | U46463 |
| 3839 | gtgtatctcctgattgctcacatt | M97900 | 46443 | atccgacatacgagctgattgctcg | AA023740 | 89047 | ataatactcacagcagctcacagt | U46463 |
| 3840 | tctcctgattgctcacattgtggtg | M97900 | 46444 | catacgagctgattgctcgcgcgtg | AA023740 | 89048 | ctcagctccagtcacatgtgtagt | U46463 |
| 3841 | gaattaacagccagccagccatcat | M97900 | 46445 | agctgatctgctgcgcgtctg | AA023740 | 89049 | gcagctcacatggtagtggtttc | U46463 |
| 3842 | acagccagccatcattgcagaccag | M97900 | 46446 | gacctgaagccctcaaacatgacagt | AA023740 | 89050 | gggcatatcttctagctgcatatt | U46463 |
| 3843 | agccagccatcattgcagaccaag | M97900 | 46447 | cctgaagctcaacatgacagtgga | U25708 | 89051 | atcttcctagctgcatatccalga | U46463 |
| 3844 | cagatcagccatcagcatcagtgg | M97900 | 46448 | cagtccctttggcctgatcct | U25708 | 89052 | aacactgcacctttgccatgtc | U46463 |
| 3845 | atgcatccacatgatatacatgc | M97900 | 46449 | tccccttggcctgatcctcct | U25708 | 89053 | tccaaacgcaaccaatcgctaatg | U46463 |
| 3846 | tgtatacatggcaaccaatcttg | M97900 | 46450 | ccctttggcctgatcctcctat | U25708 | 89054 | agcaaccaatgctaatgcacacc | U46463 |
| 3847 | ctcagttcatcaacttccatcta | M97900 | 46451 | ccttttgcctgatcctcctag | U25708 | 89055 | gctaatgcacaccacacgcctig | U46463 |
| 3848 | cagttcatcaacttccatctg | W48519 | 46452 | ttgtggcctgatcctcctatgcag | U25708 | 89056 | cctgatgcctgatgcctgaagcaaaaaa | U46463 |
| 3849 | tgaatgcatcaaccaatatggca | W48519 | 46453 | gtgggccatcaaccatgcagaa | U25708 | 89057 | caagtctacagggtccagaagagctg | U46463 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 3850 | aatgacatcaaccaatatggcaga | W48519 | 46454 | cctgatccttcctatgcagaacta | U25708 | 89058 | ataagcaacaaggcttcaggagaga | AA117787 |
| 3851 | atgacatcaaccaatatggcagag | W48519 | 46455 | tgatccttcctatgcagaacctacc | U25708 | 89059 | agcaacaaggcttcaggagagatca | AA117787 |
| 3852 | gacatcaaccaatatggcagaggc | W48519 | 46456 | attacatagaattcttatactggg | U25708 | 89060 | agcataatgaactcctggttaattg | AA117787 |
| 3853 | atcaaaccaatatggcagaggccgt | W48519 | 46457 | acaatacgaattctatatcgggtgt | U25708 | 89061 | gttatgtcctctctctatctggaa | AA117787 |
| 3854 | tcaaaccaatatggcagaggccgc | W48519 | 46458 | ctgtaagcctcacatgacagtgaa | U25708 | 89062 | attgtcctcttctatctggaatgg | AA117787 |
| 3855 | aaccaatatggcagaggccgtccaa | W48519 | 46459 | taagcctcaacatgacagtgaagg | U25708 | 89063 | gtcctctcttatctggaatggtag | AA117787 |
| 3856 | atatggcagaggccgtccaaagaag | W48519 | 46460 | ctcaacatgacagtgaaggccgaga | U25708 | 89064 | ctcttctatctgaatgtagcta | AA117787 |
| 3857 | tatggcagaggccgtccaaagaagt | W48519 | 46461 | tagggcctcaacctcctgctgg | U25708 | 89065 | atgttacgcacgctacataagata | AA117787 |
| 3858 | cagaggccgtccaaagaagaagag | W48519 | 46462 | cctcccgaagctgaaaactgag | U25708 | 89066 | ttacgcacgtacataaagatatg | AA117787 |
| 3859 | ttcatcaacttcccatctgtgt | W48519 | 46463 | tgagcctgaatccttatgagggct | U25708 | 89067 | aaccagatgagacttcacgaagatg | AA117787 |
| 3860 | tcatcaacttcccatctatgtg | W48519 | 46464 | tgttacagttcccctttggccctg | U25708 | 89068 | gacctcacggaagatgccaggaag | AA117787 |
| 3861 | tcaacttcccatctatgtggagag | W48519 | 46465 | tacagtcccctttgggcctgatc | U25708 | 89069 | tctacgaagatgccaggaagaat | AA117787 |
| 3862 | aacttccccatctatgtgtggagta | W48519 | 46466 | cgttagtccatctcctatccaaaa | U25708 | 89070 | tattctatagttttgaggaagaga | AA117787 |
| 3863 | acttcccatctatgtgtggagtag | W48519 | 46467 | agtccatctcctatgccaaaatcaa | AA023764 | 89071 | atcagatgggcgctcaggtggact | AA117787 |
| 3864 | tttcccatctatgtggagtagca | W48519 | 46468 | actgtgggcgctcagtggatgtca | AA023764 | 89072 | agatggggcgctcaggtggactata | AA117787 |
| 3865 | ttcccatctatgtggagtagcaa | W48519 | 46469 | ggcttgtcagtggagtcagagtc | AA023764 | 89073 | ctgagtctatgcctcacaccata | AA117787 |
| 3866 | cccatctatgtggagtagcaaga | W48519 | 46470 | ctgctcagtggagtcagagttcat | AA023764 | 89074 | gagtctatgcctcacaccatatc | AA117787 |
| 3867 | gtgctccgtcctacatgggtgatgg | W48519 | 46471 | agagaagacactacacatagaatta | AA023764 | 89075 | tctatgcctcacaccatatcagt | AA117787 |
| 3868 | ctgtcctagggtgatgggaacaa | W48519 | 46472 | agaagacactacacatagaattatg | AA023764 | 89076 | cacaccatattcagtggtttagca | AA117787 |
| 3869 | tggatgcgtgtcagatgtgtca | M32484 | 46473 | aagactactacacatagaattatggg | AA023764 | 89077 | accatatcagtggtttagcataa | AA117787 |
| 3870 | gggcaaccagtccctgaacatt | M32484 | 46474 | cctactacaagaatatgggagt | AA023764 | 89078 | tcatgaatcgttcagtggtgtat | AA117787 |
| 3871 | gaacattgagtgtcctgctgtcg | M32484 | 46475 | tggcagttgccagcagtgtgaaag | AA023764 | 89079 | tgaatctgttcagtggtttatgac | AA117787 |
| 3872 | tcgagttgtcctgctgtcgctggagt | M32484 | 46476 | cagttgccagcagcgtgaaaagcaca | AA023764 | 89080 | acgcagtccagctatcaagaattatg | AA162233 |
| 3873 | gcccttttgtccaccgagatttg | M32484 | 46477 | tatctcaacctcgtaaatgtat | AA023764 | 89081 | tttgcctgtcgaagtactgatttc | AA162233 |
| 3874 | ttgcgaccgagatttgattga | M32484 | 46478 | tccatctctatgccaaaatcaagt | AA023764 | 89082 | gcctgtcgaagtactgatttcaca | AA162233 |
| 3875 | atcacatatgccggctatgacagcc | M32484 | 46479 | catcctatgccaaaatcaagtcgtg | AA023764 | 89083 | tactgatttcacaagcaggactat | AA162233 |
| 3876 | tatgcggctatgacagcctact | M32484 | 46480 | tctcctatgccaaaatcaagtcgtg | AA023764 | 89084 | tgatttcacaagcaggactatat | AA162233 |
| 3877 | ggctatgacagccctactcttcaa | M32484 | 46481 | atgccaaaatcaagtcagctgggaaat | AA023764 | 89085 | agataacaggggtccagttgcat | AA162233 |
| 3878 | ccttacttttcagaatcagcaat | M32484 | 46482 | gggaaatccatcatgactgctggg | AA023764 | 89086 | gttgcatccctactgctgcttgat | AA162233 |
| 3879 | atgaccagttgctgaggcactga | M32484 | 46483 | tccatcatgactgtgggctgtcca | AA023764 | 89087 | gcatccctactgctgtgatcaag | AA162233 |
| 3880 | cagtttgcgaggcactgagagccca | M32484 | 46484 | tcatggactgtggggctgtcagtgg | AA023764 | 89088 | tcccctactgctgtgatcacaag | AA162233 |
| 3881 | ggtcgcccagactgactgagagga | M32484 | 46485 | atggactgtggggtcgtcagtgat | AA023764 | 89089 | tactgtgtttgatcacaagcctgaa | AA162233 |
| 3882 | cccagcatcgactgagaaagaactgga | M32484 | 46486 | agatttctaccacatctactgg | AA023764 | 89090 | ttatgcaacttcattaactaccgg | AA162233 |
| 3883 | agtccattttgcagggcactaattc | M32484 | 46487 | cttacaccatctactgacctgtgg | X94908 | 89091 | tcacaagctgaatggtggtcttat | AA162233 |
| 3884 | ttttgcaggcactaattccttga | M32484 | 46488 | cacagtttacacagtctgctgag | X94908 | 89092 | cattaactaccggtccctgatgtct | AA162233 |
| 3885 | agccgcactaatttcttgatgtccc | M32484 | 46489 | agagccacacacacagttggctc | X94908 | 89093 | taactaccggtccctgatgtctgca | AA162233 |
| 3886 | atgtcccaaggggatcttgatag | W48530 | 46490 | aaatcaagctgctgatagcatcct | X94908 | 89094 | ctaccggtccctgatgtctgcgac | AA162233 |
| 3887 | acactgctgaacctgcaacaactg | W48530 | 46491 | ctgtagatcgtgaacgaagcac | X94908 | 89095 | gtccctgatgtctgcagacaatgta | AA162233 |
| 3888 | tctgaacctgcaacaacattgcaa | W48530 | 46492 | gcatcctagaaacgcaagaggatctc | X94908 | 89096 | cctgatgtctgcagacaatgtacgc | AA162233 |
| 3889 | gatctgtcatcgaccagctcata | W48530 | 46493 | gcatcatttcggggctttatcat | X94908 | 89097 | agacaatgtacgccagcagtactca | AA162233 |
| 3890 | gtattgaatgcctcggctcagcgc | W48530 | 46494 | gggctttatcatctgctggttgtc | X94908 | 89098 | caatgtacgccagcagtatcaaga | AA162233 |
| 3891 | tagcatgctgtggttaagggaa | W48530 | 46495 | tctgcaggagctctttggaccca | X94908 | 89099 | tgtcttcgcatcaagcacaga | AA162233 |
| 3892 | tggacatgctcaacctacgtctc | W48530 | 46496 | actctcattaacccgtcatcta | X94908 | 89100 | cttctcagatcaagcacaaagattg | AA109831 |
| 3893 | gacatgctcaacctactgtcttcct | W48530 | 46497 | tcatcacactgtgttcaacgaaga | X94908 | 89101 | tactcttcagagaccttacgtcgg | AA109831 |
| 3894 | tgctcaacctacgtctctcccag | W48530 | 46498 | ccaatactactgtgtgcggccctt | X94908 | 89102 | ttctcagagaccttaagtcggggcg | AA109831 |
| 3895 | tccaggctgcgcaggaggactct | W48530 | 46499 | cctgtgcctctatatccatc | X94908 | 89103 | tctcagagacctttacgtcgggcga | AA109831 |
| 3896 | gcaggactcctgacatccttatac | W48530 | 46500 | tctatatccatccatctgctcat | X94908 | 89104 | cctgatcagtctaccagaggggt | AA109831 |
| 3897 | aggactcctgacatcctttataccg | W48530 | 46501 | tcccatccatctgctcattatcct | X94908 | 89105 | atcagctctaccagagggcgtgtcc | AA109831 |
| 3898 | tgaactgcaacatgtacgg | W48530 | 46502 | tgctcattatccgtatggcgcat | X94908 | 89106 | cagcctgaccatgagggcgtgccat | AA109831 |
| 3899 | tgaactgcaacatgtcaaca | W48530 | 46503 | tgtatggccgcatatacgggccgc | X94908 | 89107 | agctctaccacatgaggcggtgccata | AA109831 |

TABLE 1-continued

| SEQ ID NO | DBAxnID | sequence | SEQ ID NO | DBAxnID | sequence | SEQ ID NO | DBAxnID | sequence |
|---|---|---|---|---|---|---|---|---|
| 3900 | W48530 | cctgacatccttatacc ggctcag | 46504 | X94908 | ggaag gcttcaccacggcacagct | 89108 | AA109831 | taggacgacactgctgatgaagaggt |
| 3901 | W48530 | aactg caacaacattgtcaacatg | 46505 | X94908 | gcttcacacaggcacagcttatcac | 89109 | AA109831 | ggacgacactgctgatgaagaggct |
| 3902 | W48530 | cctg caacaacattgtcaacatgac | 46506 | AA023769 | ctgattacccgcgaaatatcctga | 89110 | AA109831 | agacacagctgatgaagcagc gattctg |
| 3903 | W48530 | caacaacatgtcaacatgactga | 46507 | AA023769 | gattacccg caaatatcctgacg | 89111 | AA109831 | ttctccagcatcaagcaccagattga |
| 3904 | W48530 | acaacatgtcaacatgactgaat | 46508 | AA023769 | agtaccagttccagcaaccagccag | 89112 | AA109831 | tcagcatcaagcacacaggattgagat |
| 3905 | W48530 | aacattgtcaacatgactgaatc | 46509 | AA023769 | agttccagcaccagccagtcagga | 89113 | AA109831 | agcatcaagcacacaggattgagattg |
| 3906 | W48530 | cattgcaacatgactgaatcaag | 46510 | AA023769 | ccagcaccagccagtcaggaggag | 89114 | AA109831 | gcatcaagcacacaggattgagattga |
| 3907 | W48530 | gcgatctgctcatcgaccagctca | 46511 | AA023769 | ccagcaccagccagtcaggaggatg | 89115 | AA109831 | agattggctccttctgtatgata |
| 3908 | W48876 | gtctcgaggacacgacgggatccgcag | 46512 | AA023769 | agctccctgcggctgtgttgaac | 89116 | AA109831 | attgagtccttctgtatgataat |
| 3909 | W48876 | tcgaggacacgacgggatccgcag | 46513 | AA023769 | ctccctgcggctgtgttgaaca | 89117 | AA109831 | gagtccttctgtatgataatact |
| 3910 | W48876 | agagcttccacggctaagccatt | 46514 | AA023769 | tgtttgaacacttgtcatgatgca | 89118 | AA109831 | agtccttctgtatgataatactt |
| 3911 | W48876 | cacggctaagccattgcctct | 46515 | AA023769 | tttgaacacttg ccatgatgcagc | 89119 | U57324 | atctgcaggaggccaggcgaggtcc |
| 3912 | W48876 | caggctaagccattgcctctccat | 46516 | AA023769 | tgaacacttgcatgatgcagcgg | 89120 | U57324 | agtttacactctagccatatat |
| 3913 | W48876 | cggctaagccattgcctctccatt | 46517 | AA023769 | aacacttgccatgatgcagcggga | 89121 | U57324 | aaggctcttcaggg atgaggctcg |
| 3914 | W48876 | taagccattgcctctccatttggt | 46518 | AA023769 | tctgacggttgatggcatccgg | 89122 | U57324 | tccacgtctgtaagtctccaggat |
| 3915 | W48876 | agccattgcctctccatttggtgc | 46519 | AA023769 | cttcgagtgcatccggacaactg | 89123 | U57324 | tctgtaagctccaggagatcag |
| 3916 | W48876 | attgcctctccatttggtgccgct | 46520 | AA023769 | tcgatgcatccggacaacgtga | 89124 | U57324 | cccgttgcagtcatgaatgtccc |
| 3917 | W48876 | tgcctctccatttcggtcgcgttc | 46521 | AA023769 | gatgcatccggacaacgtggatg | 89125 | U57324 | catgaatgtcccagtgctgtgtt |
| 3918 | W48876 | cctctccatttcggtcgcgttct | 46522 | AA023769 | gcatccggacaacgtggatgcagc | 89126 | U57324 | ttagaagccaagtcctgtctcttctattt |
| 3919 | W48876 | tccatttcggtcgcgttctttat | 46523 | AA023769 | ccggaacaacgtgatgcagccctg | 89127 | U57324 | gccaagtctgtccttatt ctgcag |
| 3920 | W48876 | cgacggatccgcagccattaggga | 46524 | AA023769 | caagc gatgcagcctgccctc | 89128 | U57324 | tcctgttctatttcgcagtgact |
| 3921 | W48876 | gggatccgcagccattagggaatgg | 46525 | AA023769 | gccattagtacagtggccgggagc | 89129 | U57324 | tcttattcttcgagtgactgctggg |
| 3922 | W48876 | gatccgcagccattagggaatgct | 46526 | AA023769 | ccaaagtcataccattggccgtag | 89130 | U57324 | ttctg cagttgactgctgggaagttgg |
| 3923 | W48876 | ggtaaccttaag cagcattg cctt | 46527 | AA023769 | gtcatacattggagcgggaacgtt | 89131 | U57324 | tgtcgtgttactctgatgagga |
| 3924 | W48876 | taaccttaag cagcattg cctcc | 46528 | AA023769 | gttccagctgtgctctgtgtgca | 89132 | U57324 | accaataaacag atgctccgctgg |
| 3925 | W48876 | ctttaagcagcattgcctccagt | 46529 | AA023769 | tctcctatccctatccatcaga | 89133 | U57324 | ccctggctaccgctctgtca |
| 3926 | W48876 | cttcagctgcttagttttcaca | 46530 | X69867 | ctatccttatccatcagagagt | 89134 | U57324 | acctgctg tcaccagactgcagc |
| 3927 | W48876 | gcttgtttagttttcacaagaaga | 46531 | X69867 | ctatccatcagagagtgttccctt | 89135 | U57324 | ctgt caccagactgcagctgcct |
| 3928 | W48876 | gcttgcgcttcaaaatgccggat | 46532 | X69867 | ttcttagcctctataccaaccca | 89136 | U57324 | accagactgcagctg ccgctcga |
| 3929 | W48902 | aaggacgacaagccatccgagctc | 46533 | X69867 | accccacagagacaatgattctcag | 89137 | U57324 | cttggatgctcagcaagcaaggc |
| 3930 | W48902 | atgacatcagcaactttgcaatt | 46534 | X69867 | ttctcagcttgaagcgggccctcac | 89138 | U57324 | tgctcagcaagcaaggtctcttca |
| 3931 | W48902 | aaattaatgagctcactg gatcaa | 46535 | X69867 | gcctcacctgaagcttgataaaac | 89139 | U57324 | gcaagcaaggtctctcaggg atg |
| 3932 | W48902 | attaatgagctcactgtgatcaag | 46536 | X69867 | cgtgttccagcaggtgtcttcaag | 89140 | M32502 | tctagggctgctaatgctggctg |
| 3933 | W48902 | atgagctcactgtgatcaaagagt | 46537 | X69867 | tgglggcttgtttgatggag acat | 89141 | M32502 | tcagccactttcctgttgtgca |
| 3934 | W48902 | gagctcactgtgatcaaagagtcg | 46538 | X69867 | ttggcaaacacaccatgccttcta | 89142 | M32502 | ctggataagctgtgtgtgagacact |
| 3935 | W48902 | atcaaagtcgacactgggctgg | 46539 | X69867 | ccttctacagaaggacg tgacagac | 89143 | M32502 | agacactgagcagaacggatacaa |
| 3936 | W48902 | caaagagtcgacactgggctggcc | 46540 | X69867 | attggctccattctgcactagcc | 89144 | M32502 | attacagctcttcatatctatg |
| 3937 | W48902 | ctccagccctcggattggctgc | 46541 | X69867 | ctccattctgcactagcagcagaaa | 89145 | M32502 | tacaagtctcttcatatctatg |
| 3938 | W48902 | ccagccctcggatttgctgcgcag | 46542 | X69867 | tctgcactggcagcagaaacctgcc | 89146 | M32502 | gtcatgttccggggctgtattcaag |
| 3939 | W48902 | agccctcggatttgctgcgcagac | 46543 | X69867 | cattgttagacctcacatg gaca | 89147 | M32502 | cattgtaattatctc gccatagtc |
| 3940 | W48902 | ggagacaagccatccgagctctg | 46544 | X69867 | ttagactcacatgtgacaagttg | 89148 | M32502 | tatcctgccatatgcaggtaatag |
| 3941 | W48902 | cccctggattggctgcgagacaa | 46545 | X69867 | ttagtactgtcctcctcaggag | 89149 | M32502 | cctaccatagtcaggtaatagcat |
| 3942 | W48902 | acgacaagccatccgagctctgga | 46546 | X69867 | caacatcccagatgtgttcacgg | 89150 | M32502 | tccctaccaacctgctatcccaaa |
| 3943 | W48902 | catccgagctctgg atgaagggat | 46547 | X69867 | caaaggcagccctcatggtggca | 89151 | M32502 | ccaacctctgtatccaaagttg |
| 3944 | W48902 | tccg agtcctggataagaacttatg | 46548 | Z18278 | ttcaacaggactacacagtcgtt | 89152 | M32502 | gccactcttccctgttgcagt |
| 3945 | W48902 | gatatcgcttgcaaacttatg | 46549 | Z18278 | aggagctacacagtgcttcaagg | 89153 | M32502 | ctgttgcagtgcttgcagtgccaagc |
| 3946 | W48902 | acttatgccagatcaagcaggt | 46550 | Z18278 | agtgctttcaaggtcttctcca | 89154 | M32502 | tttgcagttggcttgccaagcagg |
| 3947 | W48902 | agtacttattgcagatcaagcaac | 46551 | Z18278 | ttcaaggtcttctccaagcaac | 89155 | M32502 | cctgctgccactcttccaccatg |
| 3948 | W48902 | cttattcgaggacatgcaggt | 46552 | Z18278 | ttcttcaagcaacaatgagagacca | 89156 | M32502 | catgtgaccaatgagcactgctta |
| 3949 | W48905 | cagtgcgaccatggcctcg | 46553 | Z18278 | gagtgcttcccatagctgta | 89157 | M32502 | tgtgacatgagcactgctctagg |

| SEQ ID NO | sequence | DBAxnID | SEQ ID NO | sequence | DBAxnID | SEQ ID NO | sequence | DBAxnID |
|---|---|---|---|---|---|---|---|---|
| 3950 | tgaaaacttctgcgatcaacag | W48905 | 46554 | gcttgtagctcagtgggtatatg | Z18278 | 89158 | gaccatgagcactgctctaggaca | M32502 |
| 3951 | gtcatcgcacagtctcagtcggca | W48905 | 46555 | gtccatgaaccttgcaggctgcc | Z18278 | 89159 | tctccttccgaagttgaaatcaa | M32502 |
| 3952 | catcgcacagtctcagctgtgga | W48905 | 46556 | tgaaccttgcaggctgccagctg | Z18278 | 89160 | tactctaccaagctcttcagtgt | AA109782 |
| 3953 | gcaagacggccacctcagtatttc | W48905 | 46557 | tttgcaggctgccagctgtcttg | Z18278 | 89161 | cctcaccatagctctttcagtgtaa | AA109782 |
| 3954 | aagaggccacctcagtatttcag | W48905 | 46558 | gtgttgtgctctgtcggttccctt | Z18278 | 89162 | ggaccactctgtctccttcatg | AA109782 |
| 3955 | gacggccacctcagtatttcagtc | W48905 | 46559 | tgctggttccctttcttcgtcacag | Z18278 | 89163 | cactctggtctccttcatgaagaa | AA109782 |
| 3956 | cggccacctcagtatttcagtcct | W48905 | 46560 | ttccttctgtcacagagctca | Z18278 | 89164 | gaatttcaggcgattggaagaatca | AA109782 |
| 3957 | cacctcagtatttcagtccttcag | W48905 | 46561 | ttcttctgcacagagctcatcagtc | Z18278 | 89165 | agaatcagttcactgtagcccagta | AA109782 |
| 3958 | cctttcagtatatttcagtccttcagt | W48905 | 46562 | ttcctgggttgtatttctaatt | Z18278 | 89166 | aatcagttcactgtagcccagtag | AA109782 |
| 3959 | ttcagtatttcagtccttcagtgt | W48905 | 46563 | tctaattcctttcttcaacccactca | Z18278 | 89167 | tcagttcactgtagccagtatgag | AA109782 |
| 3960 | cagtatttcagtccttcagtgtctg | W48905 | 46564 | atctacacagcatcaacaggagct | Z18278 | 89168 | agttcactgtagcccagtatgagaa | AA109782 |
| 3961 | accttctgcgatcaacagcgtgct | W48905 | 46565 | acagcattcaacagagactacggca | Z18278 | 89169 | ttcactgcccagtatgagaaatt | AA109782 |
| 3962 | tacccaggagcagaccaacaggatgg | W48905 | 46566 | aatttgatgtggggcacgtgccaa | Z18278 | 89170 | cactgtagcccagtatgagaaatt | AA109782 |
| 3963 | ctctcggatcaacagcgtgctat | W48905 | 46567 | ttttgatgtggggcacgtgccaata | Z18278 | 89171 | ctgtagcccagtatgagaatttga | AA109782 |
| 3964 | tctcggatcaacagcgtgctatca | W48905 | 46568 | tgtgactttgggcattgtagatccat | Z18278 | 89172 | ctaccatagctctttcagtgtaatg | AA109782 |
| 3965 | tgcgatcaacagcgtgctatcaag | W48905 | 56569 | caccacgctgtgacattaaagggtc | Z18278 | 89173 | gatcaacactgaagtttagatcag | AA109782 |
| 3966 | atccaacagcgtgctatcaagcaga | W48905 | 46570 | gtcatatacacagtttgaacacac | Z18278 | 89174 | accatagctctttcagtgtaatgaa | AA109782 |
| 3967 | ccaacagcgtgctatcaagcagata | W48905 | 46571 | catatacagcacagtttgaacacac | Z18278 | 89175 | tagctctttcagtgtaatgaaggag | AA109782 |
| 3968 | aacagcgtgctatcaagcagataat | W48905 | 46572 | tttgaacacactatcgtttgctgc | Z18278 | 89176 | gtgcaaattacactactatgatgaa | AA109782 |
| 3969 | atgtcatcgcacagtctcagtctgg | W48905 | 46573 | tgaacactatactgttgctgctcca | Z18278 | 89177 | gcaaattacactactatgtctcct | AA109782 |
| 3970 | taccacaggcagcaaccaacaggatggg | W48905 | 46574 | aacacactaactgttgctgtctcac | Z18278 | 89178 | agagatgaccactctgtgtcctct | AA109782 |
| 3971 | acaccaggagcatggcagggaagatc | U35312 | 46575 | ctatactgttcgtccaactgtaa | Z18278 | 89179 | agatgaccactctgtgtcctctt | AA109782 |
| 3972 | tatgagacactgtgtatgtgcgactgg | U35312 | 46576 | atacgttcgctccaactgtaaag | AA023796 | 89180 | atggaccactctgtgtcctctca | AA109782 |
| 3973 | acactgctgtatgtgcgactgg | U35312 | 46577 | tgttgctccaactgtaaagaagt | AA023796 | 89181 | ttcaaggctagcctgagctactta | AA109782 |
| 3974 | ccatgattgtgcgcagactctct | U35312 | 46578 | gtacccttgctccgaagtag | AA023796 | 89182 | cttctcccagaagagcagagagcc | U18119 |
| 3975 | tttgtccagagacttctcaggg | U35312 | 46579 | cctttcctctgccgaagtagcgtc | AA023796 | 89183 | agtcatctaccagctcaggctgggag | U18119 |
| 3976 | tcaggagagccaggccatggattgag | U35312 | 46580 | ttgcctctgccgaagtaggctga | AA023796 | 89184 | catctaccagctcaggctgggaag | U18119 |
| 3977 | agccaggccatggatgatgaagaaga | U35312 | 46581 | tgccgaagtaggctggatcgtt | AA023796 | 89185 | caggagcctcgcgagaatctcct | U18119 |
| 3978 | aaactgccctctaatacaggcactc | U35312 | 46582 | agtaggccgatcgtgggagaaat | AA023796 | 89186 | tcgcctgaatctctcattgcaac | U18119 |
| 3979 | cctctaatacagccactcaatgga | U35312 | 46583 | taggcgatcgctggagagaagtaa | AA023796 | 89187 | tcattgcaccaggtcgacctctc | U18119 |
| 3980 | atacaggcacctcaatggattataa | U35312 | 46584 | ggcgatcgctgggagagaagataat | AA023796 | 89188 | gggtgcaacagtgccaacaagagatg | U18119 |
| 3981 | ggacaatctgttcttcactcgtt | U35312 | 46585 | tctgtgactggcattgtagat | AA023796 | 89189 | gtgcaacagtgccaacaagatgtca | U18119 |
| 3982 | tcttcaacaggttctactcagttcc | U35312 | 46586 | gggagtcaatccctatctacaagg | X15830 | 89190 | caccagtcaacaaagattactactg | U18119 |
| 3983 | atacgatgtctgcagtcagataccacac | U35312 | 46587 | tcaatcctatctacaaggaaagag | X15830 | 89191 | tgccacaaagatcatcactggttaag | U18119 |
| 3984 | acaccactacacagatcgcatgcg | U35312 | 46588 | taccaatgctgtgctttctgctac | X15830 | 89192 | tagaagcctttggtctgtaagact | U18119 |
| 3985 | caaggcatcaacaagacaaccgcatct | U35312 | 46589 | ctgtgcttctgctacattagaata | X15830 | 89193 | gcccagaaagtagcagagagcccca | U18119 |
| 3986 | gctcaacaagaaccgcatctggaga | U35312 | 46590 | tgctttcgtacattgaataaaa | X15830 | 89194 | gcagccccagagccgatccagccta | AA109597 |
| 3987 | catcaacaagaaccgcatctggaga | W48921 | 46591 | atacatggttctctgcagttt | X15830 | 89195 | gagagcccaggatccagccatacc | AA109597 |
| 3988 | ccgctctcgcgcagtatgagga | W48921 | 46592 | ctcagattctcagttttgggt | X15830 | 89196 | cctgtcacctctatcctgtcagg | AA109597 |
| 3989 | ctctcagcagtatgagacactgt | W48921 | 46593 | ttgggttatgctgtttgggccaagt | X15830 | 89197 | tgtacccctatccgtcaggatg | AA109597 |
| 3990 | taagctgccgtactctggtattgtta | W48921 | 46594 | tatgcgttggccaagtctcgtaa | X15830 | 89198 | tgtctgactggggaaccaagtcaa | AA109597 |
| 3991 | gccgtactcctggtatttgagata | W48921 | 46595 | ggtgacacatctactctgcgtt | X15830 | 89199 | gaaccaagtcatctaccccaggtcag | AA109597 |
| 3992 | aaatctgattggctgaagctgga | W48921 | 46596 | gacacatctcactctgctctt | X15830 | 89200 | ccaagtcatctaccccaggtcaggt | AA109597 |
| 3993 | aatctgattggctgaagctgaa | W48921 | 46597 | acatctcactcgtcgtttcttaat | X15830 | 89201 | tagattccatcaatactattaccca | AA109597 |
| 3994 | atctgattggctgaagctgaagg | W48921 | 46598 | gtatgtagaaaacccatccaatgctt | X15830 | 89202 | attccatcaatactattaccatg | AA109597 |
| 3995 | tctgattggctgaaagctgaagg | W48921 | 46599 | aaccacatccaatgcttatgtcag | X15830 | 89203 | ttagtatccaatcatatgctaat | AA109597 |
| 3996 | ctgattggctgaaagctgaaggt | W48921 | 46600 | ccatccaatgcttatgtcatgct | X15830 | 89204 | gtatcaaactcataatgctaattca | AA109597 |
| 3997 | tgattggctgaaagctgaaaggtg | W48921 | 46601 | gtcatagagcccgtgagttgacacag | X15830 | 89205 | tcaaactcataatgctaattcacac | AA109597 |
| 3998 | attggctgaaagctgaaggtgt | W48921 | 46602 | catagagcccgtgagttgacacatg | X15830 | 89206 | aactcataatgctaattcacacagc | AA109597 |
| 3999 | ttggcctgaaagctgaaggtgtgc | W48921 | 46603 | aagcagtctctgccctccataccc | X15830 | 89207 | tcataatgctaattcacacagatc | AA109597 |

| SEQ ID NO | sequence | DBAxnID | SEQ ID NO | sequence | DBAxnID | SEQ ID NO | sequence | DBAxnID |
|---|---|---|---|---|---|---|---|---|
| 4000 | gtactcggtattgttagagatacag | W48921 | 46604 | tccttgctccatccaatgcctgt | X15830 | 89208 | taatgctaattcacacgcatcagg | AA109597 |
| 4001 | tcacaggtcaccagattcgccaaa | W48921 | 46605 | ttgcctccataccaatgcctgtgct | X15830 | 89209 | tgctaattcacacagcatcaggacg | AA109597 |
| 4002 | cacaggtcaccagattcgccaaa | W48921 | 46606 | ctgttccgtatacaatggatagaa | X67348 | 89210 | taattcacacagcatcaggacgaac | AA109597 |
| 4003 | acaggtcaccagattcgccaaaat | W48921 | 46607 | cactaccacctgagggtcacagt | X67348 | 89211 | ttcacacagcatcaggacgaacatg | AA109597 |
| 4004 | cctaaatctgattggcctgaaagc | W48921 | 46608 | taattcagtagacacgggcagttaa | X67348 | 89212 | acacagcatcaggacgaacatgaac | AA109597 |
| 4005 | cttaaatctgattggcctgaaagct | W48921 | 46609 | ctctaccaggagccctcctctcaat | X67348 | 89213 | tccatcaatactataccatcgctc | AA109597 |
| 4006 | ttaaatctgattggcctgaaagctg | W48921 | 46610 | caggaggcctctcaatgttact | X67348 | 89214 | aatactataccatcgctcaatag | AA109597 |
| 4007 | taaatctgattggcctgaaagctgg | W48921 | 46611 | gaggcctctcaatgttacctac | X67348 | 89215 | aatactataccatcgctcaatacg | AA109597 |
| 4008 | gctcagtaccacctggtgcctcac | W48921 | 46612 | caatgttactcaccctaaaggctg | X67348 | 89216 | ataccatcgctcaatacgcctaat | AA109597 |
| 4009 | cagttaccacctggtgcctcactgt | M77174 | 46613 | tgttactcaccctaaaggctgaca | X67348 | 89217 | cccatcgctcaatacgcctaatcaa | AA109597 |
| 4010 | agagtccccatgtcctggcagtgt | M77174 | 46614 | cagtaattcgtctcaaacatagt | X67348 | 89218 | atcgctcaatacgcctaatcaacaa | AA109597 |
| 4011 | gctcgccctcagagctgcaaggga | M77174 | 46615 | ttctgctctaaacatagtgggtaag | X67348 | 89219 | acaatcgtctcgagaacttaccaata | AA109597 |
| 4012 | agaccaactcttcccagaatcgct | M77174 | 46616 | taagctacagcaaatcgtacagt | X67348 | 89220 | gtctcgagacttaccaaatactgact | AA109597 |
| 4013 | ccaactcttcccagaatcgctaga | M77174 | 46617 | aatcgttacatgtatctattaag | X67348 | 89221 | tgactlacttagaggcctccaccaaa | AA109641 |
| 4014 | cagtcgagacctcagtcttggaagg | M77174 | 46618 | cacactgcagggtcacagtgtcact | X67348 | 89222 | cttacttagaggcctcaccaaactg | AA109641 |
| 4015 | ccatcgggagcctgaggacctgac | M77174 | 46619 | ctcctcagccagaaagcaaggactg | X67348 | 89223 | tagcccatcctggtcccaggaag | AA109641 |
| 4016 | ggttaagcaggccgacgtggtggctc | M77174 | 46620 | aaactgcttagactccgacactgt | X67348 | 89224 | tagtgtcccaggaagaaggatgga | AA109641 |
| 4017 | cagactgtgggtctgggtcctaga | M77174 | 46621 | ctggctagactctgcacagctata | X67348 | 89225 | aggagtcctgtcatgcgtagc | AA109641 |
| 4018 | actgtggtcctgggtcagaagg | M77174 | 46622 | tagaactcctgacagttataaccaca | X67348 | 89226 | tcctgctcatgtcgtagcaatag | AA109641 |
| 4019 | gaaccccctggcgtctttcctgat | M77174 | 46623 | cctgacagtctataaccacagaacag | X67348 | 89227 | gtgaccgacaagttctggacagt | AA109641 |
| 4020 | ccacctggtcctcactgtcaaact | M77174 | 46624 | gactctactaattcagtagacacg | X67348 | 89228 | accgacaagttctggacagttcgat | AA109641 |
| 4021 | ggccatggtgagccactgttctgg | M77174 | 46625 | tctacctaattcagtagacacgggc | X67348 | 89229 | agacaagttctcggacagttgctca | AA109641 |
| 4022 | catggtgagccactgttctggggag | M77174 | 46626 | cggaccagaattgctgtggtctca | AA023087 | 89230 | caagttctcgacagttgctcacac | AA109641 |
| 4023 | tgagccactgttctggggagcagag | M77174 | 46627 | agaattgctgtgttcagtagcc | AA023087 | 89231 | gttctggacagttgtcacactac | AA109641 |
| 4024 | gccacctgttctggggagcagagga | M77174 | 46628 | agagcagctgcttcagtagacg | AA023087 | 89232 | ctcggacagttgctcactactg | AA109641 |
| 4025 | acccacctagccagaggttccatgt | M77174 | 46629 | gacgcagctgcttcagatgaacga | AA023087 | 89233 | acttagagggcctcaccaaaaactcgt | AA109641 |
| 4026 | ctagccagaggttccatgtcctgg | M77174 | 46630 | acgcagctgcttcagatgaacgag | AA023087 | 89234 | aggcctcaccaaactgcgtctcaat | AA109641 |
| 4027 | ggccagaggttccatgtccttggag | M77174 | 46631 | cgcagctgcttcagatgaacgagc | AA023087 | 89235 | cctcaccaaactgcgtctcaatgtc | AA109641 |
| 4028 | gtcctggtcaatgatctatatacat | M34141 | 46632 | agctgcttcagatgaacgacgag | AA023087 | 89236 | caccaaactgcgtctcaatgtcgat | AA109641 |
| 4029 | aactcccaactgaatgtctagaa | M34141 | 46633 | gctgcttcagatgaacgacgaac | AA023087 | 89237 | caaactgcgtctcaatgtcgatgag | AA109641 |
| 4030 | ttggagccacactagatctctcaa | M34141 | 46634 | gaattgctcgggtctcagtagcct | AA023087 | 89238 | gcgtcaatgtcgatgaggcatt | AA109641 |
| 4031 | ggagccacactagactcttccaa | M34141 | 46635 | aattggtcgggtctcagtagcctc | AA023087 | 89239 | atttgatcagctggtcgcgcgtc | AA109641 |
| 4032 | acactagactcttccaaagatgt | M34141 | 46636 | attggtcgggtctcagtagcctcc | AA023087 | 89240 | ataagaactctctagcccatct | AA109641 |
| 4033 | atggactcatctatgatctggttg | M34141 | 46637 | ttggtcgggtctcagtagcctccg | AA023087 | 89241 | tccagggcaactttcagatct | AA109641 |
| 4034 | gactcatctatgatctggttggaa | M34141 | 46638 | cgtgaagacgcagctgctttcagat | AA023087 | 89242 | tcaagacaactccattgtctggg | U69599 |
| 4035 | tcatctatgatctggttggaaacc | M34141 | 46639 | gaagacgcagctgctttcagatga | AA023087 | 89243 | gcatctgcattgctgctggct | U69599 |
| 4036 | atccagatcttttgctggcagt | M34141 | 46640 | gaagacgcagctgcttcagatgaa | AA023087 | 89244 | tgcattgctctggcctgacgg | U69599 |
| 4037 | cagatcttgctgtggcagctgt | M34141 | 46641 | aagacgcagctgcttcagatgaac | AA023087 | 89245 | gcttcacctgttcctcaaataca | U69599 |
| 4038 | tgtgggcagctgttctcatgaagct | M34141 | 46642 | cagtagcggggcgggcctggtctccc | AA023087 | 89246 | aatccaaagcgagtgaagtactg | U69599 |
| 4039 | ggcagctgtttcatgaagctaat | M34141 | 46643 | tgactgagggcggcctggtccgta | AA023107 | 89247 | atctaaagaaccaagaccaattcat | U69599 |
| 4040 | ttcccaactgaagtcatagaa | M34141 | 46644 | gtcaggtgaagcaactcttcgaaa | AA023107 | 89248 | cagaccaattcatctagaggtctt | U69599 |
| 4041 | aattggtcatttcgtctcagt | M34141 | 46645 | agcaactctcgaaagtgaatgaga | AA023107 | 89249 | cagcaatccaattagaggtctt | U69599 |
| 4042 | ttcctgttcagtgaatgaccacag | M34141 | 46646 | aactcttcgaaagtgaaatgagca | AA023107 | 89250 | aattcatcttagaggtctggacaa | AA109641 |
| 4043 | aaccagtgtccagcaagaattgctg | M34141 | 46647 | ctaccgatgtacctggaagcagg | AA023107 | 89251 | tgtcaattatttcttccagaaaa | U69599 |
| 4044 | ccagtgtccagcaagaatgcctg | M34141 | 46648 | ccgagtacctggaagcagggagc | AA023107 | 89252 | ttatttcttccagaaaaggagcg | U69599 |
| 4045 | agcaagaattgctgcccaaact | M34141 | 46649 | gagccatgactttcactacattat | AA023107 | 89253 | gcaactccattgctgggcaact | U69599 |
| 4046 | tgcctgcccaaactactgctacg | M34141 | 46650 | ccatgactttcactacattatga | AA023107 | 89254 | ccattgctgggcaatctgaagcc | U69599 |
| 4047 | tacgtctacgccaaaggtcaaggca | M34141 | 46651 | tgactttcactacattattgaca | AA023107 | 89255 | aaatccgaccacatggcctctgag | U69599 |
| 4048 | tggtctgcagcaacttccagatag | W48951 | 46652 | ctttttcactacattatgcacgg | AA023107 | 89256 | ccgcaggctgcagcaagtcatcct | U69599 |
| 4049 | tggctgcagcaacttccagatagc | W48951 | 46653 | ttcactacattatgcacgggggt | AA023107 | 89257 | ggctgcagcaagtcatcctgattcc | U69599 |

| SEQ ID NO | sequence | DBAxnID | SEQ ID NO | sequence | DBAxnID | SEQ ID NO | sequence | DBAxnID |
|---|---|---|---|---|---|---|---|---|
| 4050 | tgtgtaccggtatgccaaggcaag | W48951 | 46654 | cctggtctccgtagccaggagat | AA023107 | 89258 | agcaagtcatccgattccgttggg | U69599 |
| 4051 | gtgtaccggtatgccaacggcaagt | W48951 | 46655 | ctccgtagccaggaagatggtgct | AA023107 | 89259 | tcatcctgattccgttgggcatct | U69599 |
| 4052 | taccggtatgccaacggcaagtt | W48951 | 46656 | agatggtgctgacgatgatcgc | AA023107 | 89260 | cgttgggcatctccgattgctgct | U69599 |
| 4053 | taccggatgccaacggcaagttg | W48951 | 46657 | tgacgatgatcgccgtgacgatcggga | AA023107 | 89261 | cccagtctgtgagatgcgagaaat | U76716 |
| 4054 | cggtatgccaacggcaagttgtat | W48951 | 46658 | cctcgtcaggaggacgagcagc | AA023107 | 89262 | gtactgalgctactcagcagcga | U76716 |
| 4055 | ggtatgccaacggcaagttgtat | W48951 | 46659 | gccggaacttcaacagtatcagag | AA023107 | 89263 | ccaagccggcgactggatgacta | U76716 |
| 4056 | tatgccaacggcaagttgtatcc | W48951 | 46660 | gggaccttcaacgtatcagagtca | AA023107 | 89264 | aagccccggcactggatgactactc | U76716 |
| 4057 | tatgccaacggcaagttgtatcc | W48951 | 46661 | ttcaacagtatcagagctaa | AA023107 | 89265 | tggatgactactcagagccggt | U76716 |
| 4058 | atgccaacggcaagttgtatccc | W48951 | 46662 | atctgalccgtcgtgtcaccg | AA023107 | 89266 | gcacctctgagcgctctctgggccg | U76716 |
| 4059 | ggctgcagccaacttccagatagcg | W48951 | 46663 | gctgtgtccacggtggagtccaaa | U08110 | 89267 | ccctcgggcgatacactgatgtgga | U76716 |
| 4060 | ctgcagccaacttccagatagcgg | W48951 | 46664 | gctgaaccacatgttgggcctact | U08110 | 89268 | tgggccgatacactgatgtggacac | U76716 |
| 4061 | tgcagccaacttccagatagccga | W48951 | 46665 | accacagttgggcctactctga | U08110 | 89269 | gcatgcaccccaatcggtgacct | U76716 |
| 4062 | gcagccaactccagatagcggag | W48951 | 46666 | acatgttgggcctactctgaggg | U08110 | 89270 | cgggtgacctgccctccaagatcg | U76716 |
| 4063 | gcagccaactccagatagcggagt | W48951 | 46667 | tgttgggcctactctgagggttt | U08110 | 89271 | ggagcaacagacaacagacagta | U76716 |
| 4064 | cagccaactccagatagccgggagtg | W48951 | 46668 | ctgtgactcccgaatgggctgctt | U08110 | 89272 | gctactcagacagcgaacactacct | U76716 |
| 4065 | agccaactccagatagccgagtgg | W48951 | 46669 | cttcccgaatgggctgctggccac | U08110 | 89273 | ggagcacagcaacagacagtag | U76716 |
| 4066 | ttgtaccggaagttccaacggcaa | W48951 | 46670 | ctgcctgccggagctcactctga | U08110 | 89274 | gaaatgacctcagtaccatctga | U76716 |
| 4067 | gcttcaggcctgctagctcggt | W48951 | 46671 | ctgtgcccggagcttcaaaataa | U08110 | 89275 | atgacctcagtaccatctctgatac | U76716 |
| 4068 | aggcctgctagctcctggtcactgg | X74937 | 46672 | gcttcaaaataaacgtcatctgtg | U08110 | 89276 | acctcagtaccatctctgataccag | U76716 |
| 4069 | agalgggccacgtgctctgtcatt | X74937 | 46673 | caaataaacgtcatctgtgtagttg | U08110 | 89277 | tgaagcctcagcctgctctgrgga | U76716 |
| 4070 | tgggccacgtgatctgtcattca | X74937 | 46674 | accctgcctaaccatgtgact | U08110 | 89278 | agggctcagcctctgtgctgggacc | U76716 |
| 4071 | acagtgatcgtcattctaaatagg | X74937 | 46675 | tctgccttaaccatgtgactgga | U08110 | 89279 | cctctgtcgcggacccaaagcccg | U76716 |
| 4072 | agccttgtctccttatgtagac | X74937 | 46676 | cttaacatgtgactgaggagca | U08110 | 89280 | tgctgtgcagaccccaaagccccgact | U76716 |
| 4073 | cctctatgtagactactgcttctca | X74937 | 46677 | aacagtgactgaggagcagcagc | U08110 | 89281 | gccctgcacagagagggagatgc | U76716 |
| 4074 | tgtagactactgcttctcaagacat | X74937 | 46678 | ggcagtccccgcagctgaacca | U08110 | 89282 | tgcatttcgtgatacgttgccca | U12283 |
| 4075 | ctatgtctgttgtcagaaagtc | X74937 | 46679 | aggccctcaatgcctgaaccacat | U08110 | 89283 | tcacttatagtgggctcatcaggag | U12283 |
| 4076 | acatcccatcctgacatggtgaaa | X74937 | 46680 | cctaatgctgaaccacatgttggg | U08110 | 89284 | ttatagtggctcatcaggagc | U12283 |
| 4077 | gaaatccaggtctcgggtctgatt | X74937 | 46681 | aatgctgaaccacatgtggggct | U08110 | 89285 | tgcctcctggtctctagaggtatt | U12283 |
| 4078 | atccaggtctgtattaat | X74937 | 46682 | ttctttgacaggttcatcgctgga | X65582 | 89286 | tcctcctggtctctagaggtatt | U12283 |
| 4079 | ccctgctagtctggtcactggggg | X74937 | 46683 | ttcatccgtgatcttgtagcacc | X65582 | 89287 | cttggctctagaggtatlgagaga | U12283 |
| 4080 | tgctagtctggtcactgggacaa | X74937 | 46684 | atctacctataccttgccctcaag | X65582 | 89288 | ctggtctctagaggtatlgagaca | U12283 |
| 4081 | tggcactggggacaagggaaata | X74937 | 46685 | cccagtcttcccactgctgtt | X65582 | 89289 | ctggaccttgcaggaggccat | U12283 |
| 4082 | accaactttcaggcctcaagggagc | X74937 | 46686 | catccactgcccttctgaaagct | X65582 | 89290 | tattaacgcaataaactggccag | U12283 |
| 4083 | cttcaggcctcaggccagagctc | X74937 | 46687 | cctcttgaaagtctgtctggcct | X65582 | 89291 | actgcaataaactggccaatgtggc | U12283 |
| 4084 | tctcacctgtctgtgtccaata | X74937 | 46688 | gaaagctgtctgctggctgcacca | X65582 | 89292 | tgcaataaactggccagtgtgccc | U12283 |
| 4085 | cacctgtctgtccctaaatagat | X74937 | 46689 | tgtctgtgcctgcaaccagtccctg | X65582 | 89293 | caataaactggccagtgtggcccg | U12283 |
| 4086 | tctgttccctaaatagatgggcca | X74937 | 46690 | ctgtatctctatccaggggatc | X65582 | 89294 | catttctgatacgttgcccact | U12283 |
| 4087 | ttccatcatlcgcatggccatlt | M83344 | 46691 | ttcctatccatccaggggacct | X65582 | 89295 | tctgttgatacgttgcccactacc | U12283 |
| 4088 | ccatlcatlcgcatggccatligg | M83344 | 46692 | atctcaggagatcagagaccgtagagc | X65582 | 89296 | tgttatacgttgccactacc | U12283 |
| 4089 | aacctlgttacctcactcaggatga | M83344 | 46693 | tgagaccgccatatcatgcccaa | X65582 | 89297 | ctcctccagtcgaaaacgatgccca | U12283 |
| 4090 | ctgttacctcactcaggatgatac | M83344 | 46694 | atcgtlaccgccatgctcggc | X65582 | 89298 | caccgccatcacttatagtgggc | U12283 |
| 4091 | gttacctcactcaggatgatact | M83344 | 46695 | ctccacccatcgggtctaata | X65582 | 89299 | agccatcacttatagtgggctcat | U12283 |
| 4092 | atgatactctcaagttctalccaaa | M83344 | 46696 | cccatcgtgtgctaataggacc | X65582 | 89300 | cccatcacttatagtgggctcatca | U12283 |
| 4093 | atactctcaagttctatccaaata | M83344 | 46697 | gctaataggacctgcctagccgccgt | X65582 | 89301 | catcacttatagtgggctcatcagg | U12283 |
| 4094 | ctctcaagttctatccaaattaatg | M83344 | 46698 | tcaaggagatcagacctgcgccgt | X65582 | 89302 | acttgcggagctcagaccagctgct | U79163 |
| 4095 | tcaagttctatccaaattaatg | M83344 | 46699 | tgcagctagaccagctagtacac | X65582 | 89303 | tctccggcttggcccaaggcaa | U79163 |
| 4096 | agttctatccaaattaatgatgct | M83344 | 46700 | gccctccccaaatcaggacaga | X65582 | 89304 | tttggccacgctacgtgaaggtggg | U79163 |
| 4097 | gtctatccaaattaatgatgcct | M83344 | 46701 | ctcccaaaatcaggacagaaggact | X65582 | 89305 | gcagctgcttcagcaagcgctcctg | U79163 |
| 4098 | ttctatccaaattaatgatgctc | M83344 | 46702 | gacttacctactlcgctctct | Z22923 | 89306 | gcttcagcaagcgtcctctc | U79163 |
| 4099 | tlcattcgcatggccattggccat | M83344 | 46703 | gcatgcgccgatgccgtgggggctt | Z22923 | 89307 | gcttcagcaagcgtcctgcttgt | U79163 |

TABLE 1-continued

| SEQ ID NO | sequence | DBAxnID | SEQ ID NO | sequence | DBAxnID |
|---|---|---|---|---|---|
| 4100 | cagttccattcctccatcgcttt | M83344 | 46704 | tttctcaggatctctggaaaccca | Z22923 | 89308 | gcaagcgtcctgctctgtgccga | U79163 |
| 4101 | ttcccttctacagatgatcaagc | M83344 | 46705 | aagatccaggggttctgaagacaag | Z22923 | 89309 | agccatccaagtctgtgcacctcac | U79163 |
| 4102 | cccttctcacagatgattcaagcat | M83344 | 46706 | aggccaacagagccaagtattggag | Z22923 | 89310 | catccaagtctgtgcacctcaagt | U79163 |
| 4103 | tatataccatgcagccattttgga | M83344 | 46707 | ggtagcttcctcctggagtacca | Z22923 | 89311 | ggattcctccatccagtaccccatcat | U79163 |
| 4104 | ataccatgcatgccattttgaaac | M83344 | 46708 | ttacccctatttattctcctggact | Z22923 | 89312 | acccatcatttcgagtgaaggc | U79163 |
| 4105 | tgcatgccattttggaacctggtta | M83344 | 46709 | ccctatctattctctggacttat | Z22923 | 89313 | tcatttcgagtgtaagtgtcctg | U79163 |
| 4106 | tggaacctggtacctcactccagga | M83344 | 46710 | atacctggagtggcagttcttagg | Z22923 | 89314 | gcttggccaaggcaagaaacagcg | U79163 |
| 4107 | tgtgagctacctgatggccatggag | W48962 | 46711 | tcttagccacgcctgctattgcct | Z22923 | 89315 | aacagcgcgtgagcaagaagctgag | U79163 |
| 4108 | gtgggctacctgatggccatggaga | W48962 | 46712 | taggccagccctgctattgcctgc | Z22923 | 89316 | agatggctgtgggcacagacctt | U79163 |
| 4109 | cagatccgcagcgtcatgcagaag | W48962 | 46713 | cagtattaaacatccatcttcct | Z22923 | 89317 | agacctctgccggtgctgtacgc | U79163 |
| 4110 | agcatccgcagcgtcatgcagaagt | W48962 | 46714 | ctcacagagcctgggtccatcaagg | Z22923 | 89318 | cggtcgtagcgggtggaatgacct | U79163 |
| 4111 | catccgcagcgtcatgcagaagtat | W48962 | 46715 | gggtccatcaagggggccatgagcaa | Z22923 | 89319 | tgcgtacgcgtggaatgacctagg | U79163 |
| 4112 | atccgcagcgtcatgcagaagtatc | W48962 | 46716 | gggccatgacaacaccaggacaca | Z22923 | 89320 | taggcagccgtttgccacgcta | U79163 |
| 4113 | ccgcagggtcatgcagaagtatcta | W48962 | 46717 | tgtctagggtcacttctgggtggac | Z22923 | 89321 | gccgctttggccacgctagcgtaa | U79163 |
| 4114 | cgcagcgtcatgcagaagtatctag | W48962 | 46718 | tcactttgggtgacatgtactcc | Z22923 | 89322 | acagtctgccatcacgactctgtc | AA109760 |
| 4115 | aagatctctcagagagttaggat | W48962 | 46719 | ggacatgtactccagaccagagg | Z22923 | 89323 | catcacgactctgctcggcagatc | AA109760 |
| 4116 | gatcttctcacagaagttaggatac | W48962 | 46720 | catgtactccagaccaggaggta | Z22923 | 89324 | catgactgcatatgcacagactg | AA109760 |
| 4117 | atctcttcacagaagttaggataga | W48962 | 46721 | gtactccagaccagaggaggctagat | Z22923 | 89325 | atatggcacagactcgatggataag | AA109760 |
| 4118 | ctctcacagaagttaggataccgtg | W48962 | 46722 | accaatggttcctcagctgtagt | Z22923 | 89326 | tggacagactcgatggataaggc | AA109760 |
| 4119 | gagctacctgatggccatggagaag | W48962 | 46723 | agctagtgctctgccctgggca | Z22923 | 89327 | cacagactctgctcgagacgat | AA109760 |
| 4120 | agctacctgatggccatggagaaga | W48962 | 46724 | aactagtcgacactggaatcatgg | Z22923 | 89328 | agtcaacacagtaagaagacact | AA109760 |
| 4121 | ctacctgatggccatggagaagagc | W48962 | 46725 | ctagtcgacacctggaatcatgggc | Z22923 | 89329 | gtaagacactggacagctgacaac | AA109760 |
| 4122 | gcgcgcccagcaagaagatcctgc | W48962 | 46726 | agtcgacacctgaatcatgggctg | Z22923 | 89330 | tcgagcagctgacaccgctctgtcag | AA109760 |
| 4123 | caagagatcctgctgccagagccc | W48962 | 46727 | tcgacacctggaatcatgggctga | Z22923 | 89331 | gctcgtgacacctctgcaggtc | AA109760 |
| 4124 | gaaagatcctgctgccagagcccagc | W48962 | 46728 | gacacctggaatcatgggctgaac | Z22923 | 89332 | cgctcaggtcgctcgggaactcg | AA109760 |
| 4125 | agagccagatccgcagcgtcatgc | W48962 | 46729 | cacctggaatcatgggctgaccgc | Z22923 | 89333 | ggactcgtcggtgacactgctcca | AA109760 |
| 4126 | gccagatccgcagcgtcatgcag | W48962 | 46730 | tggaatcatgggctgcaccgcagcg | Z22923 | 89334 | cacgactctgctgcgacgatcgca | AA109760 |
| 4127 | tgagtccctcacctgctctctcagt | W48962 | 46731 | gaatcatgggctgcaccgcagcg | Z22923 | 89335 | tgacactctccaggaagctgctga | AA109760 |
| 4128 | ctcagctgacactggaattctac | M83348 | 46732 | ggctgcaccgcagcgaggatgaaaa | Z22923 | 89336 | gacgatcgcactgctggccacatc | AA109760 |
| 4129 | tacagccacattggagtcatgtc | M83348 | 46733 | ctgaccgcagcgaggatgaaaac | Z22923 | 89337 | gctggccaccatcgcagcccaggca | AA109760 |
| 4130 | tcatgtctgaatgctggatatt | M83348 | 46734 | ctgtagtgcctdgccctggggcag | Z22923 | 89338 | catctgagccaggcaggaggctccg | AA109760 |
| 4131 | atgagaccaggacctaaaatgagac | M83348 | 46735 | tgcaccgcagtgaggatgaaaaca | Z22923 | 89339 | gtgtcactcggtactccgag | AA109760 |
| 4132 | atgagactctgtctccaaaggaaaa | M83348 | 46736 | actgccgcccagccagttgcga | Z22923 | 89340 | gctgttcactcgtactccgaagc | AA109760 |
| 4133 | ctctgtctccaaaggaaacagaca | M83348 | 46737 | gcaagtcgcacaactagtcgcaaac | Z22923 | 89341 | tcggtactgccagatgcatgactga | AA109760 |
| 4134 | atatatagccagtcatgcagaatacca | M83348 | 46738 | aagtgcgcacaactagtcgcacact | Z22923 | 89342 | gtactgcagagcatgactgcatat | AA109760 |
| 4135 | tacatggccaatccatttgagagc | M83348 | 46739 | gtgccacaacaactagtcgacacctgg | Z22923 | 89343 | actgaattcacctaacgcaagatg | AA109760 |
| 4136 | gagccccaaacttgagtctgctg | M83348 | 46740 | gccacaactagctgggcgctgaa | Z22923 | 89344 | gtcttaaagccaggtcacttgctgg | AA109760 |
| 4137 | tttgagtcgtcgttaaatgttgc | M83348 | 46741 | gcacaactagtcgacacctggaat | Z22923 | 89345 | agcattcagtgattcctgcctgtc | U79776 |
| 4138 | atgttgcaggtgtttgaatagaaata | M83348 | 46742 | acaactagtgcgaccctggaatcat | Z22923 | 89346 | ttcctgcctgtctcaagagagtag | U79776 |
| 4139 | agcgaccagtgaattccatccgt | M83348 | 46743 | agcacatcgaaccacaaaacaggt | AA023145 | 89347 | tattagcatcattcaact | U79776 |
| 4140 | gaaataatgtctctgtccatatcc | M83348 | 46744 | ggtgacactcgtgaaccatcggcaatg | X75926 | 89348 | acatttattcaacttctgctt | U79776 |
| 4141 | tggaatctcatccgttggatctc | M83348 | 46745 | catgcccgtcattggctggcata | X75926 | 89349 | atcaactttgcactttgtgata | U79776 |
| 4142 | aatctcatccgttggatcttcaat | M83348 | 46746 | cctgtcatgtcttgccatagcatct | X75926 | 89350 | tttgtggcactttgtgatacaaatg | U79776 |
| 4143 | gtgacactccttcatcctataaa | M83348 | 46747 | atggcttgccatagcattcgta | X75926 | 89351 | ttgggtgctctactatgccat | U79776 |
| 4144 | tgtcagttaccactccaggtacagc | M83348 | 46748 | ctcctaagcagcaaagattgacagc | X75926 | 89352 | ctactaagcttcatatttctgaca | U79776 |
| 4145 | ttaccactccagtgaccgccaccatt | M83348 | 46749 | tagcaagccaaactgggctgccaccatt | X75926 | 89353 | tgccatatttctgacacttaag | U79776 |
| 4146 | ctcaggtacagccaccattgtgagt | M83348 | 46750 | ggctcaaagcgctcagttcaggt | X75926 | 89354 | tatttctgacacttaagaaagaa | U79776 |
| 4147 | aggtacagccaccattgtgagtcat | M83348 | 46751 | gtgcatttacacggcaggtctgg | X75926 | 89355 | aagccaggtcaactgctgctgctggaa | U79776 |
| 4148 | ttcggatccattgtaacactcct | AA110197 | 46752 | tttggctgactgtctcctaacaca | X75926 | 89356 | attcattttgatgcaccagttgcaaa | U79776 |
| 4149 | atgctaacatctaccatgcctgaaga | AA110197 | 46753 | gtcctcaacaagatgggtacac | X75926 | 89357 | accaagctgcaagagtccgtccc | U79776 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 4150 | ttaacagatcacaaagtgtcagc | AA110197 | 46754 | ggtacactacacctgagatcctc | X75926 | 89358 | ttgccaagatgtcctgtccctactg | U79776 |
| 4151 | tcacaaagtgtcagccatcatcaa | AA110197 | 46755 | gtactagtgccaagttgctcagaa | X75926 | 89359 | aagtcctgtccctactgatgtgt | U79776 |
| 4152 | caaacgtgtcagccatcatcaagcc | AA110197 | 46756 | agtgccaagttgctcagaaagtctg | X75926 | 89360 | ttcttatagctgctacatgtttg | U79776 |
| 4153 | gtctgcagctgtctgaagtgaa | AA110197 | 46757 | ccgcctacgttgctcagatctat | X75926 | 89361 | gttctttcattgcactgagcattc | U79776 |
| 4154 | tgtcagctcgtctgaaggaggt | AA110197 | 46758 | tactgtcggttgacatcattaaata | X75926 | 89362 | ttcattgcactgagcattcagtgat | U79776 |
| 4155 | aggtgcagccgctgctgacctgcc | AA110197 | 46759 | tctctcttgatgagctgctgtgt | X75926 | 89363 | cctaggaaggctgcacctgacctg | U03421 |
| 4156 | tgcagccgctgctgacctgccag | AA110197 | 46760 | gagctgctgtgtggctgctcgta | X75926 | 89364 | gaacctgaccttgactgggccgtg | U03421 |
| 4157 | tgccagcaacctgaagcaatcgt | AA110197 | 46761 | ctgtgtggctgctgttgacaaat | X75926 | 89365 | gtgcatcgagaacctgaagagcag | U03421 |
| 4158 | ccagcaacctgaagcaatcgtat | AA110197 | 46762 | tgtgcatcctctaaccaggtact | X75926 | 89366 | caictgagaccctgaagaggacgt | U03421 |
| 4159 | gcaaacctgaagcaatcgtgctaga | AA110197 | 46763 | ctgatgagccagaggacctgacac | X75926 | 89367 | agaccctgaagagcaggaactgag | U03421 |
| 4160 | ctaacactacctgatgaagaagg | AA110197 | 46764 | atgaagcctcatcagctcgagga | X75926 | 89368 | tgagatcctgggtctgggggtcct | U03421 |
| 4161 | gggcaagaaagacctgactactgg | AA110197 | 46765 | caagagccacatcagggatgcagt | X75926 | 89369 | gggtctgggtctcatgagaaatct | U03421 |
| 4162 | accagaaagacccctgactactggga | AA110197 | 46766 | tagtcacactgccaggccctggga | X75926 | 89370 | tatgaaatcgttcacagtgctctc | U03421 |
| 4163 | aagaccctgactctggtgactcct | AA110197 | 46767 | cgaattgtgccaaggctggcctgg | X75926 | 89371 | gaaatcgttcacagtgtctctctc | U03421 |
| 4164 | gtgacctctgagacgttagtaga | AA110197 | 46768 | atgtggccaaaggctggcctggcc | X75926 | 89372 | atctgttcacagtgtctcctcact | U03421 |
| 4165 | ggtctctataggcccgccaaaga | AA110197 | 46769 | acctcccaggtgacatgggctgc | X75926 | 89373 | tgttcacgtgttcctccacttcc | U03421 |
| 4166 | ctctcatcaggcccgccaaagatt | AA110197 | 46770 | tgacatggctgccccaagtatct | X75926 | 89374 | cagtgtctcctcactcctacatt | U03421 |
| 4167 | caggccccagccaaagatttctcatca | AA110197 | 46771 | caagatcctgtgactctctcgc | X75926 | 89375 | gactcgactgtgactcgggactgaa | U03421 |
| 4168 | gtgaaagccactctagggggtgca | M15668 | 46772 | gtatccctgactctttctgcagc | X75926 | 89376 | tcgactgtgaactggggactgaaac | U03421 |
| 4169 | gccacttctaggggttgcatcacta | M15668 | 46773 | tgtgactttctctgcagcgccgc | X75926 | 89377 | gactgaaaccaccacatcgatacgc | U03421 |
| 4170 | accaatgtcattgtagaggcgtc | M15668 | 46774 | gactctctgcaggcgcggccaag | X75926 | 89378 | acaccagcagacagtctttccag | U03421 |
| 4171 | atattcgctctagaaggaagtga | M15668 | 46775 | tcatcagcttgaggaaagagcgggc | X75926 | 89379 | cccagtagacgtctttccagtag | U03421 |
| 4172 | aaaggctgagctctctctgacgt | M15668 | 46776 | tgcagccgccgccaagtcaccagg | X75926 | 89380 | agtagacagtctttccagtagacc | U03421 |
| 4173 | ctctctgacgtatgtacctctg | M15668 | 46777 | tccgcttcggggaagaggggccca | X75926 | 89381 | tagacagtcttccagtaggactgg | U03421 |
| 4174 | tatgagcctgactaggcttctgtc | M15668 | 46778 | ctctcaacactgatacgcctgctg | X75926 | 89382 | tgggcatctgagaacccgaagag | U03421 |
| 4175 | gcctcgttagctttcgtcactcac | M15668 | 46779 | acactgatacgtctgctgaccatc | X75926 | 89383 | tgactattcctgggggattgatta | U03421 |
| 4176 | cactcacttggtgcatcagcatg | M15668 | 46780 | atacgctctgaccatcaagagc | X75926 | 89384 | attacgccagttgacattggta | U03421 |
| 4177 | ttgactgcattgcaatctgatga | M15668 | 46781 | cgctcctgaccatcaagagccac | X75926 | 89385 | cccatcataaatgggccgggtat | U03421 |
| 4178 | ctgatgaaattccccagctgaagtc | M15668 | 46782 | tctgctgaccatcaaagagccacatc | X75926 | 89386 | gcagcatccatagctgctgcga | U03421 |
| 4179 | aaaattccccagctgaagtctgaaga | M15668 | 46783 | catcaagagccacatcaaggatgca | X75926 | 89387 | gcatcctaagctgtctgcgatga | U78103 |
| 4180 | tgctcctaagctaacctgctgtttt | M15668 | 46784 | catcagcagcctgaaccgaacacac | AA023919 | 89388 | tcatagctgctgcgatgatgccag | U78103 |
| 4181 | taagctaacctgctgtttctccacat | M15668 | 46785 | tccagcctgaaccgaacacacct | AA023919 | 89389 | cgtctgcgatgatgccagcattg | U78103 |
| 4182 | tgtgccacagacttaacagtgcaa | M15668 | 46786 | aaggccctacctggaaccggaatgca | AA023919 | 89390 | gcgatgatgccagcattggggatg | U78103 |
| 4183 | aggccaagcatctcagctgtctta | M15668 | 46787 | ccgtggaccagatgcaggtgtca | AA023919 | 89391 | aattagctgtgtctgtaaaatag | U78103 |
| 4184 | agcatctcagctgctctactgcat | M15668 | 46788 | gtggacccagatgcaggtgtcaga | AA023919 | 89392 | atgtatcttgctagtaagggcacat | U78103 |
| 4185 | tcagctcgctactgcatcgatcat | M15668 | 46789 | accaaggcaggtgtcagaggcc | AA023919 | 89393 | ttttcagtcattggatcagtggc | U78103 |
| 4186 | cgtcttactgcatcagatgctgtt | M15668 | 46790 | tcagaggccgaggcagcgatgtgccac | AA023919 | 89394 | gtactgtctctgctcggacttta | U78103 |
| 4187 | gctggttctcagatccatttaa | M15668 | 46791 | gcagcaggccaacgatgtgccga | AA023919 | 89395 | acagccagtgacattggtacat | U78103 |
| 4188 | cagacccctgagactgcacttga | W48999 | 46792 | agcagggccaacgatgtgccgacc | AA023919 | 89396 | agatgctcattggcaatcaggt | U78103 |
| 4189 | ccatggaacagtcctgacaaggc | W48999 | 46793 | caggattacactctctacctggagct | AA023919 | 89397 | aagatcctcataaagccaaatgcaac | U78103 |
| 4190 | agtacacatccaactaacatgacaac | W48999 | 46794 | ggattacactctcctactctgggagct | AA023919 | 89398 | atcctaagccaacactgcacaac | U78103 |
| 4191 | caactatgacaacatgacaaggccat | W48999 | 46795 | tactatctctacctggagctgaga | AA023919 | 89399 | aagccaaatgcacaacactgaccca | U78103 |
| 4192 | ctatgacaaagtgcccaggcaatctc | W48999 | 46796 | tggaaccgaacacctgtatgt | AA023919 | 89400 | ccaaatgcaacaactgaccatca | U78103 |
| 4193 | caagctcccaggcaatcatgcc | W48999 | 46797 | cacgtatgtgtgggaccggtg | AA023919 | 89401 | caacactgacccatcataaatgtgg | U78103 |
| 4194 | cccagggcaatcatgccagctg | W48999 | 46798 | acgggtcctaacaaccatgtgca | AA023919 | 89402 | cactgacccatcataaatgtggc | U78103 |
| 4195 | caatcatgctcagccggctggcc | W48999 | 46799 | gtgcctacaaccccatgtgcacta | AA023919 | 89403 | acctttgctgagtcgctaga | U78103 |
| 4196 | tctcatgctcagccggctgcctg | W48999 | 46800 | gcctacaaccccatgtgcgacctag | AA023919 | 89404 | ttttgtctgagtcgctagaggc | U78103 |
| 4197 | cctgcgttcctcagaggccagagtgctc | W48999 | 46801 | acacaccccatgtgcacctatgaa | AA023919 | 89405 | agctggcttcaaccagcctgagg | AA109998 |
| 4198 | agaccgagtgctctgcgatgccag | W48999 | 46802 | acaccccatgcacctatgtgaacc | AA023919 | 89406 | ggcttcaaccagccctgaggtgacg | AA109998 |
| 4199 | cctgcgatgcagaagagacgggcacg | W48999 | 46803 | ccccatgcgcacctatggaacgt | AA023919 | 89407 | aaccagcctgatggtgacggcagag | AA109998 |

| SEQ ID NO | sequence | DBAxnID | SEQ ID NO | sequence | DBAxnID | SEQ ID NO | sequence | DBAxnID |
|---|---|---|---|---|---|---|---|---|
| 4200 | tggacatgtccctgacaaggcaga | W48999 | 46804 | gagatcgtcagtcggtcctctggag | AA023922 | 89408 | cagctcgaggtggacggcagagtc | AA109998 |
| 4201 | acatgtccctgacaaggcagaggc | W48999 | 46805 | tcgtcagtcggtcctctggagacag | AA023922 | 89409 | aagtcggctactctgctttgga | AA109998 |
| 4202 | aggcagccctggtggccaaggaact | W48999 | 46806 | acatgtcgtctgcgagtagtag | AA023922 | 89410 | tctgggtacttctgctttggaaag | AA109998 |
| 4203 | cagccctggtggccaaggaactgcg | W48999 | 46807 | attgtcgtctgcgagtagtagcc | AA023922 | 89411 | gggctactctgctttggaaagctg | AA109998 |
| 4204 | ccaaggaactgcggtccgctgctaga | W48999 | 46808 | tgtcgtctgcgagtagtagcat | AA023922 | 89412 | ctactctgctttggaaagctgct | AA109998 |
| 4205 | aactgcggaccgctgctgaagaggc | W48999 | 46809 | tcgtctgcgagtagtagccatca | AA023922 | 89413 | cttctgctttgaaagctgcgcgg | AA109998 |
| 4206 | ctgaccctccaaagtcacaca | W48999 | 46810 | gtagtagccatcaagtcagattg | AA023922 | 89414 | aaagctgcgggaacacgagggg | AA109998 |
| 4207 | taaagtcacactaccaactatgac | W48999 | 46811 | tagccatcaagtcagattgtgga | AA023922 | 89415 | gagtcgctgaggccaccagtc | AA109998 |
| 4208 | actgctttccaagtctcgaatat | W49003 | 46812 | gccatcaagtcagattgtggaga | AA023922 | 89416 | gctgcggggaacactgaggggtc | AA109998 |
| 4209 | tttccaagtctctgaatatcttgg | W49003 | 46813 | catcaagtcagattgtggagag | AA023922 | 89417 | aggccaccagttcctcacagtcag | AA109998 |
| 4210 | ctgtcctccagtcgaaccagctat | W49003 | 46814 | tggctccgatcgagagcgactct | AA023922 | 89418 | cagttctccacgctcagcagagc | AA109998 |
| 4211 | tccagtcgaaccagctatccctg | W49003 | 46815 | gcgacttctacaagatgatgtagtg | AA023922 | 89419 | gttcctccagctcagcagctgg | AA109998 |
| 4212 | tgaaccagctatccctggagtct | W49003 | 46816 | cagtacgcgttgcgacatttgtg | AA023922 | 89420 | cacagtcagaggtgcaagaaa | AA109998 |
| 4213 | acccagctatcccctggagtcttgg | W49003 | 46817 | gctaccgcggttgcgacatttgcgtc | AA023922 | 89421 | gaaagtcagtcaacactgaggaacc | AA109998 |
| 4214 | cagtatcccctggagtcttggtgg | W49003 | 46818 | taccgcgttgcgacatttgcgtctg | AA023922 | 89422 | agtcagtcaacactgaggaaccaca | AA109998 |
| 4215 | ttggtggccctaccccattggcat | W49003 | 46819 | ccgcgttgcgacatttgctgctgt | AA023922 | 89423 | gagacgcggtcgtcctgaagaggct | AA109998 |
| 4216 | ggaacatcgcaaccaactagctgac | W49003 | 46820 | gcgttgcgacatttgctctgct | AA023922 | 89424 | tacacacaggtcacttctgcc | AA109998 |
| 4217 | acaagctgacctctcaactcctt | W49003 | 46821 | gttcgacatgtcgtctgctgagg | AA023922 | 89425 | accacaggtcacttcttcgcctga | AA109998 |
| 4218 | ttgggatcatcacatgctctcgg | W49003 | 46822 | tgcgacatgtcgtctgctgaggta | AA023922 | 89426 | acgtgactgggcttcagatggag | AA109998 |
| 4219 | ggatcatccacatgctgttcgggt | W49003 | 46823 | cgacatttgcgtctgctgagggt | AA023922 | 89427 | gtgactgggcttcagatgaggcg | AA109998 |
| 4220 | ccaagtctgaatatcttggtc | W49003 | 46824 | catgatatctttgaccttctcat | AA023922 | 89428 | actgggctccagatgagccgccc | AA109998 |
| 4221 | gggtcgcctgagcctttccacca | W49003 | 46825 | atgtatctttgaccttctcagtg | | 89429 | cccacaggcactgagtacgagactc | AA109998 |
| 4222 | atatcttggctcatcatgagcgt | W49003 | 46826 | ttgaaactctcgtttggatgtag | | 89430 | gagtacgagacctctcactgctaagt | AA109998 |
| 4223 | tcttttggtcatcatggagcgtacg | W49003 | 46827 | tgatatctttgacctctcagta | | 89431 | gagactctcacgtctaagtttcact | AA109998 |
| 4224 | tacggcaagttcaccatagagaa | W49003 | 46828 | gatatctttgacctctcagat | | 89432 | actctcactgctaagtttcactcg | AA109998 |
| 4225 | caagttcaccatagagaactggaa | W49003 | 46829 | atatctttgacctctcagatg | | 89433 | gctaagttcacttcgtggactg | AA109998 |
| 4226 | tgttcaccatagagaactgacggaa | W49003 | 46830 | tatctttgacctctcagtgatga | | 89434 | aagttcacttcgtggactggctg | AA109998 |
| 4227 | tcaccatagagaactgacggagga | W49003 | 46831 | acctctcagtgatgagctggact | | 89435 | tttcacttcacttcgtggactggct | AA109998 |
| 4228 | cgctcctggaagttctgctctcca | W49003 | 46832 | cctctcagtgatgagctggactg | | 89436 | ggtgcacttctgccctgatcaact | AA109998 |
| 4229 | gaaccaagtctcatgatgaagt | W49003 | 46833 | ctctcagtgatgagctggactga | | 89437 | tcgggactggctctcagagc | AA109998 |
| 4230 | cctccaatgcgtgtcaccatat | M17299 | 46834 | gactgaaactctcgttgatg | | 89438 | actctcgccgatcaactcccagg | AA109998 |
| 4231 | ccgtatgctgcgtgtcgtcatca | M17299 | 46835 | ctttattaccactactgatgtct | | 89439 | atccagtccctgaagcaggcgcc | AA109998 |
| 4232 | gccatcaatatcacattcagcaagt | M17299 | 46836 | tattaccactacttgatgcctcat | AA166524 | 89440 | gtacagagctcccgatccccatgcca | AA109999 |
| 4233 | aatatcacattcagcaagtctat | M17299 | 46837 | gctaccctcgagtagctgctggg | AA166524 | 89441 | accatccacctgaccttgcagatcgcg | AA109999 |
| 4234 | acattcagcaagtctaattctgtc | M17299 | 46838 | accctctcgagtagctggggtcc | AA166524 | 89442 | gccgcgtcgacctggtgaatgaga | AA109999 |
| 4235 | catcacattgttagtctctcaa | M17299 | 46839 | ctctcgagtagctgcggtcctga | AA166524 | 89443 | cagcctgaccctggtgaatgagacg | AA109999 |
| 4236 | tcttcaagatctcatcaggatttc | M17299 | 46840 | ctgagtagctgctggtgctga | AA166524 | 89444 | aatgagacgtgactgggtccag | AA109999 |
| 4237 | agatctcatcaggatttcccacgt | M17299 | 46841 | acagctgcacactgtctcaaaagt | AA166524 | 89445 | gtacacacttagttacttcattg | AA109999 |
| 4238 | catcaggatttcccacgtcctc | M17299 | 46842 | gctgcacacgtgcttcaaaaggtacg | AA166524 | 89446 | gttacttcattgctccgttggt | AA109999 |
| 4239 | aggaaacattccatgctcaactatt | M17299 | 46843 | gacactgctttcaaaagggtaccggaa | AA166524 | 89447 | ttgaacacgtatttcccagtcca | AA109999 |
| 4240 | cattctgtcaactattaaagaa | M17299 | 46844 | aactgaggagctgcagtgctgcagt | AA166524 | 89448 | atgcagttcttctttggcctt | AA109999 |
| 4241 | ctactgtcgccaaatgggggac | M17299 | 46845 | agctatgcagttcgagttgggatt | AA166524 | 89449 | tcttggccttttcctgctcagca | AA109999 |
| 4242 | tagaggcctcagcaacatgtaatt | M17299 | 46846 | tatgcagttcgagttggggattatc | AA166524 | 89450 | gtgccttcctgctcgttcagca | AA109999 |
| 4243 | aatgtactgctctcgttttcctgc | M17299 | 46847 | atgctccactcgatgtggactga | AA166524 | 89451 | tcagcattccagcctgtggcagt | AA109999 |
| 4244 | cttctccgttcctgcacag | M17299 | 46848 | ctgaccgcgggcagaaaaggaatac | AA166524 | 89452 | attctcagctcgtcagtaaagag | AA109999 |
| 4245 | cgcacagcagaaccaactcac | M17299 | 46849 | caccgtcggaaaacgggatcattg | AA166524 | 89453 | ctctccagtcgtgttcctggat | AA109999 |
| 4246 | ctatatctcaacattgttaacctc | M17299 | 46850 | caggtctccagctcgagggtcgg | AA166524 | 89454 | ttacactgttagacactatttta | AA109999 |
| 4247 | tgaatcaagacgcctatgctgctg | M17299 | 46851 | gacggcaggcgctgttggagacta | U79523 | 89455 | tgttagaacactattttcagaact | U79523 |
| 4248 | aagccgactatgtcgtgtg | M17299 | 46852 | aggcgtgtttgtggagctcacctcc | U79523 | 89456 | acactattttcagaatctgaatgt | U79523 |
| 4249 | gaccgctgctgtaccagtagctact | W49039 | 46853 | ctgctttgtggaagctcagcactct | U79523 | 89457 | tcatttggccgttggcgtttggt | U79523 |

| SEQ ID NO | sequence | DBAxnID | SEQ ID NO | sequence | DBAxnID | SEQ ID NO | sequence | DBAxnID |
|---|---|---|---|---|---|---|---|---|
| 4250 | cctgctgtaccagtagctactcag | W49039 | 46854 | tgtgggagctaccctctgagtagt | AA166524 | 89458 | ctaccagttcactccagtgccatg | U79523 |
| 4251 | ttttctgacacaagaacttgtaagc | W49039 | 46855 | aactacaccacgagagaggatct | X56518 | 89459 | gttcactccagtgccatgtcttta | U79523 |
| 4252 | cagcggtacctagtagctgataaac | W49039 | 46856 | tacacaaggaggaggaggatcttg | X56518 | 89460 | tccaggccattgtctttatatgaa | U79523 |
| 4253 | ggatctatactctgctacactgtgaa | W49039 | 46857 | aatcgcttctcccaaattgctca | X56518 | 89461 | ctcttccagttagcgtcaaagcc | U79523 |
| 4254 | tctatactctgtacactggaaag | W49039 | 46858 | ttttctcccaaattgtcaggcca | X56518 | 89462 | agcgctcaaagccctaatggaagtt | U79523 |
| 4255 | atactctgctacactggaaatgaag | W49039 | 46859 | cccaaattgtcagcgccacgata | X56518 | 89463 | aatagcctattctgcttgaaca | U79523 |
| 4256 | ctctgctacactggaaatgaagggg | W49039 | 46860 | ttgctcagccgaccgatactctgg | X56518 | 89464 | cctattctgcttgaacacacgtat | U79523 |
| 4257 | gacatgtctggttttgtaataata | W49039 | 46861 | ctcagcgccacgatactctgacg | X56518 | 89465 | cctttgacatcgcatgccatggatc | AA110022 |
| 4258 | atgctggtgtctggagcatcgat | W49039 | 46862 | acgatactctggacgagggcagcg | X56518 | 89466 | ctttgacatcgatgccatcggatc | AA110022 |
| 4259 | gtgctgctggagcatcgatacgagg | W49039 | 46863 | gcccgagccctagctgtatataca | X56518 | 89467 | atgccatcgatgcgcttaagctcac | AA110022 |
| 4260 | tctgctggagcatcgatacgagggga | W49039 | 46864 | gccctagctagtatatacactatt | X56518 | 89468 | tgccatcgatcgttaacgtcact | AA110022 |
| 4261 | gctgtaccagtagctactcagttc | W49039 | 46865 | catcttctgcatgtctgggctaag | X56518 | 89469 | ccatcgatcgcttaacgtcacgc | AA110022 |
| 4262 | gtaccagtagctactcagttcatt | W49039 | 46866 | cttctgcatgtctgggctaagctc | X56518 | 89470 | catcgatcgcttaacgtcactgct | AA110022 |
| 4263 | cccagtagctactcagttcattact | W49039 | 46867 | tactgaccaatttgcccgcacag | X56518 | 89471 | atcggatcgttaacgtcactgctg | AA110022 |
| 4264 | agtagctactcagttcattacttcc | W49039 | 46868 | tggaccaatttgcccgcacaggg | X56518 | 89472 | tcggatcgttaacgtcactgctgc | AA110022 |
| 4265 | tactcagttcattacttccaacaga | W49039 | 46869 | cccaatgacccctcgagactccaaat | X56518 | 89473 | ggatcgcttaacgtcactgctgccg | AA110022 |
| 4266 | tcagttcattacttccaacagaag | W49039 | 46870 | cctcgagactccaaatctccaaga | X56518 | 89474 | atcgcttaacgtcactgctgccgac | AA110022 |
| 4267 | gttcattacttccaacagaaggttg | W49039 | 46871 | cgagactccaaatctccacagtgc | X56518 | 89475 | gtataagatcaccattgccaacgac | AA110022 |
| 4268 | tacttccaacagaaggttgaaccat | W49039 | 46872 | tccaaatctccacagtggccacgt | X56518 | 89476 | tataagatcaccattgccaacgaca | AA110022 |
| 4269 | gagctataagcctctggctctct | W49039 | 46873 | acctgcgcttctgaatcgctttc | X56518 | 89477 | tttgacatcgatcgcatcggatcgc | AA110022 |
| 4270 | taagcctctggcttctctactgtg | W49039 | 46874 | tggaatcgctttctcccaaatgc | X56518 | 89478 | ttgacatcgatcgcatcggatcgc | AA110022 |
| 4271 | gggcatcagaaaccctgaaactgggg | W49039 | 46875 | ttttctgctggccatacccgtcctg | X56518 | 89479 | gacatcgatgccatcgatgcatcgctta | AA110022 |
| 4272 | tagatagctgagcccacctgtggg | J03293 | 46876 | ctgctggccatacccgtcctgtgt | AA028322 | 89480 | acatcgatcccatcgatgcgcttaa | AA110022 |
| 4273 | agcaagaacaggcgtcataactgt | J03293 | 46877 | cataaagtcttccatctgctcctcg | AA028322 | 89481 | catcgatgccatcgatgcttaac | AA110022 |
| 4274 | aacagcgctataactgctagct | J03293 | 46878 | aaagtcttccatctgctcttcgaag | AA028322 | 89482 | atcgatcgcccgatcgctaacg | AA110022 |
| 4275 | cgctcataactgtctagctaget | J03293 | 46879 | gtcttccatctgctcttcgaagca | AA028322 | 89483 | cgatgccatcggatcgcttaacgtc | AA110022 |
| 4276 | taactgtctagctaagttatgat | J03293 | 46880 | catctgctcttgaagccatcacag | AA028322 | 89484 | gatgccatcggatcgctaacgtca | AA110022 |
| 4277 | ttcaaggtcattgtggctacacaa | J03293 | 46881 | ctgtcttgaagccatcacgggt | AA028322 | 89485 | tgacctgactgacctgatgatga | AA110022 |
| 4278 | gtcattgtggctacacaaggagct | J03293 | 46882 | ctcttcaagccatcacgggctcc | AA028322 | 89486 | aaatcatcagctgccccactgag | AA110022 |
| 4279 | attgtggctacacaaggagctga | J03293 | 46883 | acgggtctctgcgcctcctag | AA028322 | 89487 | acatgaccggcaaatgcaagtcctag | AA110022 |
| 4280 | gtgctcctgatatacatagaatt | J03293 | 46884 | gtggccagtactctgacatcgggc | AA028322 | 89488 | ccggcaaatgcaagtcctgatgac | AA110022 |
| 4281 | ttctggctctctactgtgcactt | J03293 | 46885 | gtggtgctcatatctggcctcg | AA028322 | 89489 | gcaaatgcaagtcctggatgactcc | AA110022 |
| 4282 | tactgtgcaccttgttgatgtcta | J03293 | 46886 | gtgctcattatctggcctctcg | AA028322 | 89490 | aatgcaagtcctgatgactccatg | AA109910 |
| 4283 | gcaccttgttgatgtctatagtt | J03293 | 46887 | aacaggactctgatctggctccga | AA028322 | 89491 | agtcctgatgactccatgtccgga | AA109910 |
| 4284 | tttagctgcatgcattttatgtaac | J03293 | 46888 | aggactctgatctggctccgaact | AA028322 | 89492 | cctggatgactccatgtccggagag | AA109910 |
| 4285 | atgtaaccacatgcatgcagtacc | J03293 | 46889 | actcgatcgtgctccgaactac | AA028322 | 89493 | ggatgactccatgtccggagagaag | AA109910 |
| 4286 | taaccacatgcagtacactgt | J03293 | 46890 | ctgatcgtgctccgaactac | AA028322 | 89494 | gtatgtaacttctccagaggca | AA109910 |
| 4287 | cccacatgcatgcagtacctgga | J03293 | 46891 | atctgcgtcgaactatcccaca | AA028322 | 89495 | tgtactaactctccagaggcaagt | AA109910 |
| 4288 | tgcatgcagtaccgtagagtcac | J03293 | 46892 | tggctccgaactatcccaacaag | AA028322 | 89496 | ttctccagaggcaagttcaaggtt | AA109910 |
| 4289 | ctcgaggccaggtccgcagagat | J03293 | 46893 | ccgaactatcccaacaagagcata | AA028322 | 89497 | tggctcccacctgaggataacaga | AA109910 |
| 4290 | ccaggtctccgcagagatcctagctg | W48975 | 46894 | tatcccaacaagagcataaagtct | AA028322 | 89498 | ctgccccacctgaggataacagatgt | AA109910 |
| 4291 | gctgaactgtggcagctcctcg | W48975 | 46895 | ccaagtccccagaaatgtccctgct | AA028322 | 89499 | cagatgtcactccggactgctagg | AA109910 |
| 4292 | tgaactgctggcgatggtctcgat | W48975 | 46896 | agtcccagaaatgtccctgctgag | W75353 | 89500 | agtcacttccgactgctaggggg | AA109910 |
| 4293 | aactgctgcgatggtctcgatgc | W48975 | 46897 | tgtcttggtcagctttgtagcac | W75353 | 89501 | atggcatgtataccaccttagttga | AA109910 |
| 4294 | ctgttggcgatggtcgatgcc | W48975 | 46898 | tcagctttgtcatgcatgctac | W75353 | 89502 | tgtataccacttaggtgacatgac | AA109910 |
| 4295 | cgttggcgatggtcgatgccc | W48975 | 46899 | tagcatccagtctacagaaagct | W75353 | 89503 | ataccacttaggtgacatgaccagg | AA109910 |
| 4296 | cggccccgtgccactgcaatgtagc | W48975 | 46900 | catccatgtctacagaaagctgt | W75353 | 89504 | ccactagttgacatgaccggcaa | AA109910 |
| 4297 | gcccgtgccactgcaatgtagcag | W48975 | 46901 | ccatgtctacagaaagcctgagccc | W75353 | 89505 | tcagagtctcacaaactgtcccct | AA109910 |
| 4298 | cgtgccactgcaatgtagcagct | W48975 | 46902 | agagcagcgcctgagcctggtaag | W75353 | 89506 | gagcctccacaatctgcctctagg | AA109912 |
| 4299 | tgcactgcaatgtagcagctgc | W48975 | 46903 | tggagccactggtgaccagaaccag | W75353 | 89507 | ggaccactggcccctcaagagtgacta | AA109912 |

TABLE 1-continued

| SEQ ID NO | sequence | DBAxnID | SEQ ID NO | sequence | DBAxnID |
|---|---|---|---|---|---|
| 4300 | actgcaatgtagcagctctgcgagc | W48975 | 46904 | agcccactgtgaccagaaccaggga | W75353 | 89508 | cactggcctcaagagtgactacat | AA109912 |
| 4301 | gctccagagatctagctgagt | W48975 | 46905 | tgcacagaaccaggacagatggca | W75353 | 89509 | ccctcaagagtgactacattagtct | AA109912 |
| 4302 | tgcaattgtagcagctctgcgagcc | W48975 | 46906 | acagatggcagttctggggcc | W75353 | 89510 | actacattagtctgctgcctcaag | AA109912 |
| 4303 | tcgcagagatcctagctgaggtgg | W48975 | 46907 | ccccagaaatgtccctgctaggtg | W75353 | 89511 | acattagtctgctgcctcaagcac | AA109912 |
| 4304 | ggtcgccgatgtcacggttccta | W48975 | 46908 | cagaaatgtccctgctgaggtgg | W75353 | 89512 | ttagtctgctgcctcaagcacta | AA109912 |
| 4305 | tcgccggatgcacggttctctaa | W48975 | 46909 | tgtccctgctgaggtgcaggccag | W75353 | 89513 | tggcctcaagcacttactagccac | AA109912 |
| 4306 | ttacggggtgcagctgctgctgaac | W48975 | 46910 | tgtgaggtgcaggccacgggacct | W75353 | 89514 | gcacttactagccacggcctacat | AA109912 |
| 4307 | tgcagcggcgcgaactcgtggc | W48975 | 46911 | catcagtctccctttcgtcgtgt | W75353 | 89515 | cttacctagccacggcctcatctt | AA109912 |
| 4308 | gggtcgctgaactcgtggcgatg | W48975 | 46912 | cagctccctttctgtcgtgctt | W75353 | 89516 | acctagccacggcctcacatctagt | AA109912 |
| 4309 | tcgctgaactcgtggcgatggtct | W48975 | 46913 | ctgtcgctgtctggtcagttgt | W75353 | 89517 | tcctcaaactgtccctaggggtg | AA109912 |
| 4310 | gctatctgcctgcctgatctgga | W48975 | 46914 | tgctgtctctgttcagcttgtagc | W75353 | 89518 | actgtccctaggggtgcctgagt | AA109912 |
| 4311 | tgcctgcctgatctggaatcctc | J02980 | 46915 | cgcagccaggtcaaggtgagagc | AA023975 | 89519 | ggcctagctctgtccatatctgg | AA109912 |
| 4312 | tatattccagaccctgcaactc | J02980 | 46916 | gagatgtccaagagctgatgcagc | AA023975 | 89520 | agctctgccatatctgggaacgg | AA109912 |
| 4313 | caacctccatggacaattccagatc | J02980 | 46917 | catcacatgatgcagcgctgga | AA023975 | 89521 | tctctgcatatctgggaaccggta | AA109912 |
| 4314 | aacattccagatctgacctctc | J02980 | 46918 | cacatgattgcagcgctgggacatg | AA023975 | 89522 | ctgcatatctggaacgggaatga | AA109912 |
| 4315 | gaaacactgcgcccatagtcacggc | J02980 | 46919 | gcttctgccacagatgttgttg | AA023975 | 89523 | tatctggaaggtgagtgagtggcc | AA109912 |
| 4316 | ccatagtcacgccagtctccaagc | J02980 | 46920 | gcgcacacgcgatgttgtcactca | AA023975 | 89524 | tctggaacctggcctcaagtgta | AA109912 |
| 4317 | cagglctgctcaggatgagactccc | J02980 | 46921 | gatgttgttgcactcaggcgcagc | AA023975 | 89525 | agaagtcagaagccatgtgtca | AA109912 |
| 4318 | ggaagaactcagccgagcagga | J02980 | 46922 | gcactcaggcgcatgccggtactac | AA023975 | 89526 | aagtcagaagccatgttgtcaga | AA109912 |
| 4319 | attgcagagactgccaaccttta | J02980 | 46923 | ctcaggcgcatgccggtactacagg | AA023975 | 89527 | atggcaaggtcgtctgccagcggc | AA109912 |
| 4320 | cgccaaccttctgccaagtggctc | J02980 | 46924 | aggccatgccgactacagctg | AA023975 | 89528 | gtcagccagccgcggtgaact | AA109912 |
| 4321 | ccctcactgaagtgctctctgt | J02980 | 46925 | atgccggtactacaggctgcgcgg | AA023975 | 89529 | cgctcggcagccgcgttgaactg | AA109912 |
| 4322 | gcctgtatctgaatcctcaatggg | J02980 | 46926 | gtactacaggctgcgcgctgcgga | AA023975 | 89530 | ctctggcagccgcgttgaactgag | AA109912 |
| 4323 | aatcctcatgggccagattcctgg | J02980 | 46927 | atgctcaagagctgatgcagctta | AA023975 | 89531 | ctggaccgcagcaagcaagggaaa | AA109912 |
| 4324 | ccatggccagattcctgctgc | J02980 | 46928 | ctgatcagcttatcgttcctgcc | AA023975 | 89532 | gggcacggcccctcaagtga | AA109912 |
| 4325 | ttccctgctcgcctttattccta | J02980 | 46929 | atgcagttatcgttctaggcgcgac | AA023975 | 89533 | gcatgttcagcgactgagggacacgg | AA109912 |
| 4326 | agttatgctgccctttgccagcagt | J02980 | 46930 | atcgttctaggccgacaactccaca | AA023975 | 89534 | atgcttcagcgactgcacgaget | AA109912 |
| 4327 | agcaggttctctctggggcaggga | J02980 | 46931 | gtctaggccgacaactccacagc | AA023975 | 89535 | gcttcagcgactgcacacgagcttt | AA109912 |
| 4328 | tttctctctgggcgcaggaca | J02980 | 46932 | ggccgacaactccacaagctgtgc | AA023975 | 89536 | ttcagcgactgacacgagcttc | AA109912 |
| 4329 | gcacagattcccaaagcacctatt | J02980 | 46933 | caactccacaagcttctgctgatc | AA023975 | 89537 | gtccgaagccatgtgtcagag | AA109912 |
| 4330 | ccgagcctgcgtctactgatgc | J02980 | 46934 | aagcttctgctgcatcacatgatg | AA023975 | 89538 | ctcagaagccatgttgtcagaagct | AA109912 |
| 4331 | ctcgtgctctactgatggccagctg | W49034 | 46935 | gctgaactcatcctgcttggaaag | AA108035 | 89539 | ggaagtgcatcctccatggagaaca | AA109721 |
| 4332 | caacttcatcaaggtgttaggcaaa | W49034 | 46936 | acctatctgcttggaaagtcctgg | AA108035 | 89540 | aagtgcatcctccatggagaacacg | AA109721 |
| 4333 | cttcatcaaggtgttaggcaagtta | W49034 | 46937 | ccctgctgtggttcaaacttg | AA108035 | 89541 | ggtcatcctcatggagaacacgt | AA109721 |
| 4334 | catgggctgcaggctcaaggttaag | W49034 | 46938 | gaaagtgcatcaattctgaaatgt | AA108035 | 89542 | tcatcctcatggagaaacgctg | AA109721 |
| 4335 | gctggctgcaggctcaaggtaaggat | W49034 | 46939 | tgcatcaattctgaatgtcaaaca | AA108035 | 89543 | atctccatggagaaacgctgtgg | AA109721 |
| 4336 | tgaagtctatgctgaaggtctta | W49034 | 46940 | ctgtcagatcctgtgatcacaca | AA108035 | 89544 | cctccatggagaaacgctgtggtc | AA109721 |
| 4337 | agtctatgctgtgaaggtcctaaag | W49034 | 46941 | agatccctgtgatcatcataa | AA108035 | 89545 | agttactcctttaaagtatgatg | AA109721 |
| 4338 | catcctgcaggagtacgactggac | W49034 | 46942 | atttaagaatgcctccagegagct | AA108035 | 89546 | ttacttccttaaaagtatgatgcct | U79550 |
| 4339 | cctgacgagctgaagtcatcaat | W49034 | 46943 | ccttcaggagctgaagtcatcaat | AA108035 | 89547 | acattccctggtgtgtcccatgtc | U79550 |
| 4340 | tgacgagctgactgaagtcgacgaga | W49034 | 46944 | catcaatattctgcttgataaatg | AA108035 | 89548 | ccctcaagtcgccttcaatgact | U79550 |
| 4341 | cagacgactgaactgacgagag | W49034 | 46945 | caaccatctcgaggtcactacatt | AA108035 | 89549 | tgtcttaatgactgtgtagttgaa | U79550 |
| 4342 | gtcgtctacgtcgagccagctggca | W49034 | 46946 | attccagctgagactggaaca | AA108035 | 89550 | cggttaataagccacgcctatatca | U79550 |
| 4343 | gtcatctctgccagctggcaagc | W49034 | 46947 | tgtgaaagtctgggccaataatgtg | AA108035 | 89551 | ttaatagccacgcctatattcaacc | U79550 |
| 4344 | tactgaggccagctggcaagcct | W49034 | 46948 | ccttgccaataaagtcgcattg | AA108035 | 89552 | gcaagcctatattcaaccagaata | U79550 |
| 4345 | tgatgccagctggcaaggcctgc | W49034 | 46949 | gccaataatgctgccattgagtcaa | AA108035 | 89553 | acgcctatattcaaccagaatactt | U79550 |
| 4346 | ccagctggcaaggccctgcgagaac | W49034 | 46950 | aatgctccattgagtcaactcaa | AA108035 | 89554 | cctatattcaaccagaatacttgtg | U79550 |
| 4347 | gcgctgggcctggatgagtttcaac | W49034 | 46951 | gccattgagtcaacctcactctg | AA108035 | 89555 | atatttcaaccagaatacttgtgaaa | U79550 |
| 4348 | tgagttcaactcatcaaggttta | W49034 | 46952 | gagtcaacctcactctgggcactc | AA108035 | 89556 | ttcaaccagaaatacttgtgaaatca | U79550 |
| 4349 | gtcaacttcatcaaggtgttaggc | W49034 | 46953 | acctcactctgggcactcctgctg | AA108035 | 89557 | atgtatgatgcctggtgtcatcag | U79550 |

| SEQ ID NO | sequence | DBAxnID | SEQ ID NO | sequence | DBAxnID | SEQ ID NO | sequence | DBAxnID |
|---|---|---|---|---|---|---|---|---|
| 4350 | tgtctggtggtacctggctgcagaa | W49037 | 46954 | cttctgggcactcctgctgctggtg | AA108035 | 89558 | gatgcctggtgtcatcagtgaatg | U79550 |
| 4351 | ctggtggtacctggctgcagaaggt | W49037 | 46955 | gccacagtcatcattagaagaagcag | AA039136 | 89559 | gtgaatgacagcctttctggatta | U79550 |
| 4352 | ctaccatggcttccaggcctga | W49037 | 46956 | attgtgattgacacctcaggtgggac | AA039136 | 89560 | gacagcctttctggattacctaca | U79550 |
| 4353 | ccctcatgctggacagtggtgcatct | W49037 | 46957 | gcagtgctcatagtcaggccctac | AA039136 | 89561 | agcctttctggattacctacaatg | U79550 |
| 4354 | tcatgctggcagtggtgcatctga | W49037 | 46958 | atagctcaggcctacacaactatta | AA039136 | 89562 | gacaaacttcaaacattcctggtgc | U79550 |
| 4355 | tgcatctgaagagtccctccacct | W49037 | 46959 | gctcaggcctacacaaactattaact | AA039136 | 89563 | cttcaacattcctggtgcgtgtcc | U79550 |
| 4356 | tgaagagtccctccacctttgcag | W49037 | 46960 | actattaactacgcgagacgatg | AA039136 | 89564 | caaacattcctggtgcgtgtgcccat | U79550 |
| 4357 | tccacctttgcagcaacccgcgaag | W49037 | 46961 | tgagccacacagctcgaaggta | AA039136 | 89565 | ttctctgcggaatcacacatggcggc | AA110046 |
| 4358 | ttgggctagtiggctgctgactgat | W49037 | 46962 | gccacacagtcgaaggctaaaa | AA039136 | 89566 | gcggaatcacacatggcggctgggac | AA110046 |
| 4359 | ggctagttggctgctgactgatcct | W49037 | 46963 | aacgcagcagcaacctgggaaagg | AA039136 | 89567 | ctcaatcggctgctcagtaaagcgg | AA110046 |
| 4360 | ttggctgctgactgatcctcatccc | W49037 | 46964 | gcagcagcaacctgggaaagagctg | AA039136 | 89568 | tcaatcggctgctcagtaaagcggg | AA110046 |
| 4361 | tcatcctgcatggcgcgctgttac | W49037 | 46965 | ccagagcagtctaccatgtctctcc | AA039136 | 89569 | caatcggctgctcagtaaagcgggg | AA110046 |
| 4362 | gtgggtactggctgcagaaggttat | W49037 | 46966 | ggacagtctaccatgtctctccctg | AA039136 | 89570 | aatcggctgctcagtaaagcggggg | AA110046 |
| 4363 | ctgcatggccgctgtacctatcc | W49037 | 46967 | attgacacctcaggtggaccctg | AA039136 | 89571 | tagagcaatgcaatgccatttt | AA110046 |
| 4364 | aggttatccagctcggcgctgactgaa | W49037 | 46968 | gacctcatgtcgcagactgtag | AA039136 | 89572 | aggaaatactccaaggcagctcac | AA110046 |
| 4365 | aagggaattctgccctgtcgaga | W49037 | 46969 | atgtgtgccagatgtagctgctg | AA039136 | 89573 | ggaaatactccaaggcagctcaca | AA110046 |
| 4366 | attcttgccctgtcgagaatcttg | W49037 | 46970 | tcgtgcagagtcgtagctgctgca | AA039136 | 89574 | gaaatactccaaggcagctcacag | AA110046 |
| 4367 | gccctgtcgagaatcttgaacct | W49037 | 46971 | tgcagagtcgtagctgctggcacca | AA039136 | 89575 | cggaatccaccatgcgggctgggacc | AA110046 |
| 4368 | cttgaacctccatgcagcagaatgg | W49037 | 46972 | gtagctgtggccaccagagatgg | AA039136 | 89576 | gaatcaccatgcggctgggaacct | AA110046 |
| 4369 | tgcaagctacccatggccttccagg | W49037 | 46973 | gctgctggcaccagagagatggcag | AA039136 | 89577 | aatcaccatgggggctgggaccctg | AA110046 |
| 4370 | aagctaccccatggcctccaggcct | W49037 | 46974 | atggcagtcatagtcagtcagcc | AA039136 | 89578 | caaggctcaatcgctgctcagtaa | AA110046 |
| 4371 | ttatttgttgccttcctgtccaag | W49037 | 46975 | ccccgtcgtcagaggtgctgcagaga | AA024005 | 89579 | aaggctcaatcggctgctcagtaaa | AA110046 |
| 4372 | attuggtgcctccctgtccaagct | M13945 | 46976 | ccccggtcagagtgctgcagaga | AA024005 | 89580 | aggctcaatcgctgctcagtaaag | AA110046 |
| 4373 | tgttgcccccgtttatttgtcatg | M13945 | 46977 | gttgcagtcagaggagccggaagaa | AA024005 | 89581 | gctcaatcggctgctcagtaaagc | AA110046 |
| 4374 | tgcccccggttatttgtcatgt | M13945 | 46978 | tgcagtcagaggagccggaagaag | AA024005 | 89582 | gtcaatcggctgctcagtaaagcg | AA110046 |
| 4375 | agtgggtcctaggggtctgctgactgt | M13945 | 46979 | gaaggaggacccagagctgacaag | AA024005 | 89583 | tgcatagcaagctgctgtgatcca | AA110046 |
| 4376 | gtctagggtctgctgactgactata | M13945 | 46980 | aagcagaccaggaaggtgacaagc | AA024005 | 89584 | atgtgaagccatccaatgcctcat | D87115 |
| 4377 | ctagggtctgctgactgactataa | M13945 | 46981 | cagaccagaaggtgtcaagctcc | AA024005 | 89585 | cagcggaccagtctccccgagt | D87115 |
| 4378 | ggtctgctgactgtactataagacag | M13945 | 46982 | aagcgctgacaagctccacagagc | AA024005 | 89586 | tgtgacttcactagccagtgcct | D87115 |
| 4379 | gctgctgactgactgtactaagacagt | M13945 | 46983 | ggctgacaagctccacgagagcac | AA024005 | 89587 | acttcactacaagcctaaggaa | D87115 |
| 4380 | ggatcctctcggggctgtgtttg | M13945 | 46984 | tgacaagctccagggagcacgag | AA024005 | 89588 | taaggaagaaccccgcagagagcgat | D87115 |
| 4381 | ctctgggctgtgtgttgagcagg | M13945 | 46985 | dacaagctccagggagcagcacgaga | AA024005 | 89589 | agaacccgagagcgatgagcta | D87115 |
| 4382 | tttgagcaggtgctgccccgctggt | M13945 | 46986 | gctccagaggctgcagagcctg | AA024005 | 89590 | tgagctcgagctgatgagaaca | D87115 |
| 4383 | tttggtgcctcctgtccaagt | M13945 | 46987 | ccgggtcagtgctgcagaagcc | AA024005 | 89591 | tggaaccaccatcctcacctgca | D87115 |
| 4384 | tggttgcctcctgtccaagttcc | M13945 | 46988 | ctccacgggagcacgagagcctg | AA024005 | 89592 | tcttcacttgcacaaaactaagaa | D87115 |
| 4385 | tgcctcctgtccaagttcactg | M13945 | 46989 | aaccaggcgcagccccaaggac | AA024005 | 89593 | agacagaccattgcccttgtgaa | D87115 |
| 4386 | cttcctgtccaagttcactgact | M13945 | 46990 | aacaggcgcagccccaaggacag | AA024005 | 89594 | gggtaccttttagagcacaatgga | D87115 |
| 4387 | tgtccaagttcactgactgtact | M13945 | 46991 | cagcgcccaaggacgatgacagga | AA024005 | 89595 | tcctcatcaacaaggaagggcatgt | D87115 |
| 4388 | gtccaagttcactgactgtactgc | M13945 | 46992 | gagcccccaaggacgacgacaggaaa | AA024005 | 89596 | caatgatgctggctgcaagccta | D87115 |
| 4389 | agcttcacctgactgttgccccgg | M13945 | 46993 | agccccaaggacgatgacagaaag | AA024005 | 89597 | actgcccaagcttacagcccctga | D87115 |
| 4390 | gcttcacctgactgttgccccggt | M13945 | 46994 | aaacggttgcagtcagaggagc | AA024005 | 89598 | acatgccccgagagatcaaccc | D87115 |
| 4391 | ccacaatcaaccatactttctac | W49072 | 46995 | aacgagttgcagtcagaggagcc | AA024005 | 89599 | agatggccattcgcgatctccctta | D87115 |
| 4392 | caatacaacccatatttctcaccaa | W49072 | 46996 | gcatccacgaaacccacctataacag | AA024005 | 89600 | tcccttatgctgtctgggggcacacc | D87115 |
| 4393 | tacaaatctccacacaactaatca | W49072 | 46997 | atccacgaaaccaccataacgca | X13297 | 89601 | atgagtcttgggggcaccgttcca | D87115 |
| 4394 | aaatctcacacaactaaatcaaca | W49072 | 46998 | tggatcaggcgcctccagtccttc | X13297 | 89602 | gcacaccgttccagccagctgaagca | D87115 |
| 4395 | caatcaacaactaaaatccaatc | W49072 | 46999 | gatcaggcctccagttcctcca | X13297 | 89603 | gagcggccaccatccaccaaggg | D87115 |
| 4396 | ctaatcaacaaatcccaatcct | W49072 | 47000 | tcagggcctccagttctttccaaa | X13297 | 89604 | catccatccaaggtgaacaaa | AA154742 |
| 4397 | aattccaatcctctgtataact | W49072 | 47001 | cgcctcagttccttccaaatcat | X13297 | 89605 | gaaatcggccaagtccaagacata | AA154742 |
| 4398 | ctcttgctataacttctacacaat | W49072 | 47002 | tccagttcctttccaaatcattcct | X13297 | 89606 | atcggccaagtcccaagacatactt | AA154742 |
| 4399 | ttgctataaccttctacacaattac | W49072 | 47003 | tccttccaaatcattcctgcccaa | X13297 | 89607 | caaagacatattctgtgaagaa | AA154742 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 4400 | taaccttctacacaattacacacatta | W49072 | 47004 | ctttccaaatcattcctgcccaaag | X13297 | 89608 | agacatactttctgctgaagaagta | AA154742 |
| 4401 | cctctacacaattacacattactc | W49072 | 47005 | tgcccaaagcttgatttgttactc | X13297 | 89609 | gtggtctcagtctctgaaaaactc | AA154742 |
| 4402 | cacacaacaattcaaaaccttca | W49072 | 47006 | tcagacatgtctaccttaactg | X13297 | 89610 | gtctcagtctctgaaaaactcctt | AA154742 |
| 4403 | catacttctccaccaaacacattat | W49072 | 47007 | agacatgtctaccttaactgta | X13297 | 89611 | tctgaaaactcctgccaaccag | AA154742 |
| 4404 | actttctcaccaaacacattalcct | W49072 | 47008 | gtccaccgtaaatgtlctaagtcc | X13297 | 89612 | cctgccaaccagacagtcaaaat | AA154742 |
| 4405 | ttctcaccaaacacattatcctaca | W49072 | 47009 | ctgctcgcctctagcacacaactg | X13297 | 89613 | tgccaaccagacagtcaaaatgc | AA154742 |
| 4406 | ceaaacattalcctatcatcacaa | W49072 | 47010 | gctctgcctctagcacacaactgtg | X13297 | 89614 | caaccagacagtcaaaatgtctt | AA154742 |
| 4407 | aacacattatcctacatcacaaact | W49072 | 47011 | tctagcacaacadtgtgaacgttt | X13297 | 89615 | gttcttttctgctagccaaaggat | AA154742 |
| 4408 | acattatcctacatcacaaatct | W49072 | 47012 | gcacacaacadtgtgaacgttttgtg | X13297 | 89616 | tctgtctagccaaaggattcgaaa | AA154742 |
| 4409 | tacatcacaaactttctaccalca | W49072 | 47013 | aactgtgaacgttttgtggatcagc | X13297 | 89617 | cagccattcctctagacgacaaa | AA154742 |
| 4410 | atcacaaaactttctaccatacaat | W49072 | 47014 | ttttggatcagcgcctccagttcc | X13297 | 89618 | ttctctagacgacaaaaagcag | AA154742 |
| 4411 | agatcttgaatctcagggtcgaact | W49072 | 47015 | tgtggatcagcgcctccagttcct | X13297 | 89619 | aacatactgagatcgatgatccca | AA154742 |
| 4412 | tctgaatctcagggtcgaactctc | W49072 | 47016 | taccatccactgatcacacaga | X13297 | 89620 | gagatcgatgatcccacactcggaa | AA154742 |
| 4413 | tcaaatctgcgcagagtgaagtgg | M59821 | 47017 | acctcaacctagaccacactgcaatg | AA024009 | 89621 | acatctgaatctgggatgaaatcg | D30785 |
| 4414 | cccggacttgtcaaactagatgat | M59821 | 47018 | ccgagctgctcacaggtcgcagca | AA024009 | 89622 | tacaacaacagcaaccagaagatc | D30785 |
| 4415 | caacctagatgatcgcctgctggcgtgg | M59821 | 47019 | cagagctcacagtgcgcagcatc | AA024009 | 89623 | aaccaagaatcacagtccagata | D30785 |
| 4416 | cctagatgatcgcctgctggacc | M59821 | 47020 | ccgagccatacgaacacctgtgg | AA024009 | 89624 | aacaccctcaactgtcggaagtga | D30785 |
| 4417 | ccgctggtcgtagttgctgcgtag | M59821 | 47021 | cagcccatagagaatctgtgcagt | AA024009 | 89625 | tatccagaacaagtgtagagag | D30785 |
| 4418 | gttgctcgtagacacagctctct | M59821 | 47022 | tagaagctgatccactagatgg | AA024009 | 89626 | ggcatggtctgtcggcagcagca | D30785 |
| 4419 | ggtgcgtagacacagctctctcgg | M59821 | 47023 | agctcgatccactagatggcgac | AA024009 | 89627 | gctgcagtgccaggtgctgactcag | D30785 |
| 4420 | gcgtagacacagctctctcgggca | M59821 | 47024 | ctctgatccactagatgggact | AA024009 | 89628 | caggatcacctcatgggctcag | D30785 |
| 4421 | actaccggagtttacaatgtcag | M59821 | 47025 | ctgatccactagatgggactgt | AA024009 | 89629 | atcacctcagggctcagaccct | D30785 |
| 4422 | tttacaatgtcagctaggaaaataa | M59821 | 47026 | gatccactagatgggactgtct | AA024009 | 89630 | tcatgggctcagaccctgcggaa | D30785 |
| 4423 | tcgaactctctaggggccaggctgc | M59821 | 47027 | atgccgacagcagctcgtgac | AA024009 | 89631 | cctggctacaccaaaatctgcc | D30785 |
| 4424 | tcgccctcacagtccgcagctt | M59821 | 47028 | ctcaactagccaccctgccatgtg | AA024009 | 89632 | accaaatctgccgtactacacct | D30785 |
| 4425 | gccccctacagtgggcacctgtg | M59821 | 47029 | acctagaccacctgccaatgtggga | AA024009 | 89633 | accatgacaacagggactgatct | D30785 |
| 4426 | agtgggcacgctgtcaagcggtc | M59821 | 47030 | ctagaccacctgccaatgtgggatg | AA024009 | 89634 | gaagtcacagtcacgatalaatgc | D30785 |
| 4427 | ggtgtggcaagcggtcagagtgcg | M59821 | 47031 | agaccacctgccaatgtggaatgaa | AA024009 | 89635 | tcaataaacaccaattgttggcc | D30785 |
| 4428 | ggtcagagttgctcatggagacaga | M59821 | 47032 | accacctgccaatgtgggatgaact | AA024009 | 89636 | cgactgcagaactcagcaaacctg | D30785 |
| 4429 | gtcatgagagacgcggggtgtlc | M59821 | 47033 | ctacgtgcagagctcgcgagcgtgct | AA024009 | 89637 | cagaactcagcaaacctggggaca | D30785 |
| 4430 | cctgactgaaccaatcaaatctgc | M59821 | 47034 | acgtgcagagctcgcgagcgtctca | AA024009 | 89638 | tcagcaaacctcggggacaaggtga | D30785 |
| 4431 | acctcccaaaatcaatgtgtgac | AA067362 | 47035 | agctctggggtttggtctgctgcc | AA024009 | 89639 | aagcggtccaacgccaatctga | D30785 |
| 4432 | tgtggtgacgtgaactgggaaaag | AA067362 | 47036 | agctctcggggtttggtctgctgct | AA024009 | 89640 | gtccaggtccaatctgtgccca | D30785 |
| 4433 | gttcctgactgcattgctgccct | AA067362 | 47037 | ggtttggtctgctctctggacaa | X14971 | 89641 | tgtcccaaagttggccagaagtgca | D30785 |
| 4434 | gtactgcattgctgccctctgtc | AA067362 | 47038 | tgcccagcagttctgagccctgga | X14971 | 89642 | actgcaccagcctcaagagaact | D30785 |
| 4435 | cattgctgccctcttgctctatgt | AA067362 | 47039 | agcagttctgagccctggacttgcc | X14971 | 89643 | caggccaactgccacgccgcggag | AA154337 |
| 4436 | tgccctctgctcatgttggttac | AA067362 | 47040 | tctgagccctggacttgcccgtgta | X14971 | 89644 | gccgttcctggactgtacgaaaacag | AA154337 |
| 4437 | ccttctgctctatgttggttacacg | AA067362 | 47041 | gagcctggacttgcctggtlat | X14971 | 89645 | altcatttgacagtccattgagt | AA154337 |
| 4438 | cctctaccggatagtgcaaactg | AA067362 | 47042 | ccctgactgcctgccctgtatggc | X14971 | 89646 | ttcatttgacagtccattgagtt | AA154337 |
| 4439 | tagtatgcaaactgcccatgatc | AA067362 | 47043 | ccagttgccagcgagccgggaga | X14971 | 89647 | tcatttgacagtccattgagttg | AA154337 |
| 4440 | caaactgcccatgatcgcgaact | AA067362 | 47044 | cctcagtgcggcagccaaaagagc | X14971 | 89648 | catttgacagtccattgagttgc | AA154337 |
| 4441 | gcccatgcccatgactttat | AA067362 | 47045 | gtcactcgtcgtgttacattcc | X14971 | 89649 | atttgacagtccattgagttg | AA154337 |
| 4442 | gccatgatgacttatttgtact | AA067362 | 47046 | ctgctgctgtttacattcaatttaagggg | X14971 | 89650 | atttgacagtccattgagttgg | AA154337 |
| 4443 | gcatgtccatagttgattactcc | AA067362 | 47047 | tccaggggccgtgtatattgtgag | X14971 | 89651 | tttgacagtccattgagttgc | AA154337 |
| 4444 | tgtcctataggtgttactccct | AA067362 | 47048 | actttggggtctggaatcatcca | X14971 | 89652 | ttgacagtccattgagtttggt | AA154337 |
| 4445 | tgattactcctcttctgccacagtc | AA067362 | 47049 | gaatcatcgacgaaggccctgca | X14971 | 89653 | ttgacagtccattgagttggct | AA154337 |
| 4446 | ctctctcgcagtctacgttc | AA067362 | 47050 | ccaatgccaccagcccaaatgtaccg | X14971 | 89654 | tgacagtccattgagttggctc | AA154337 |
| 4447 | ctacgttacgttcagtcttgtg | AA067362 | 47051 | cctcgcaccacaagaagagccgt | X14971 | 89655 | gacagtccattgagttggctica | AA154337 |
| 4448 | tacgttgcagtcttgtccg | AA067362 | 47052 | tgcgcaccagagactgctgcct | X14971 | 89656 | gtgtccggtatcgaaaacaggga | AA154337 |
| 4449 | gttgcagtctttgtccgtac | AA067362 | 47053 | aagagcctgtcccgtcactgtg | X14971 | 89657 | tgtccggtatcgaaacaggac | AA154337 |

| SEQ ID NO | sequence | DBAxnID | SEQ ID NO | sequence | DBAxnID | SEQ ID NO | sequence | DBAxnID |
|---|---|---|---|---|---|---|---|---|
| 4450 | tgtgttcctgtactgcattgctgcc | AA067362 | 47054 | gtcactgtgtgagctgctggccca | X14971 | 89658 | gtcctcggtatcgcgaaaacaggcact | AA154337 |
| 4451 | gtcgagattgccattgccataagg | J02935 | 47055 | agctgctggccagccagttctgagc | X14971 | 89659 | tcctcggtatcgaaaacaggcactt | AA154337 |
| 4452 | attgcccattgccataagggcagt | J02935 | 47056 | aaagcaaagcatccgatggaacacag | X14971 | 89660 | ggacatctacgacaaatatggcaaa | AA154337 |
| 4453 | atctgagccttcctcagtgtata | J02935 | 47057 | gaagttgaccccgaatcctgcaaatt | X14971 | 89661 | gaccctctagcacaaatatggcaaag | AA154337 |
| 4454 | accttccagtcagcccacagaaccac | J02935 | 47058 | acgcgtctccaaggactatgtgaat | X14971 | 89662 | acatctacgacaaatatgccaaga | AA154337 |
| 4455 | gacagaaccgctctgctgctgtct | J02935 | 47059 | cagttctagtccgcagaccagaaga | X14971 | 89663 | aattcatttgacgtccattgag | AA154337 |
| 4456 | ttgcttcgaacgccgtcattagac | J02935 | 47060 | tagtccgagaccagagatcagc | X14971 | 89664 | acactgccaattcatcatggggc | AA110098 |
| 4457 | ctgaacgccgtcattagaccactta | J02935 | 47061 | atcaggctcttgttgtcgcgctc | X14971 | 89665 | gccaattcatcatgggagcactgat | AA110098 |
| 4458 | attagaccaactatgtcatgagtac | J02935 | 47062 | tcgttgctttgtaccacactga | X14971 | 89666 | agtgaatgtcccgcaagtgtcctc | AA110098 |
| 4459 | atgtcatgagtactccaacccaggt | J02935 | 47063 | gtctttgtaccacactgcagataaa | X14971 | 89667 | gaatgtcccgcaagtgtcctccatg | AA110098 |
| 4460 | tgagtactccaaccaggttcaca | J02935 | 47064 | ataccacctgcagataaaacaccccc | X14971 | 89668 | tgcccgcaagtgtcctccatgcag | AA110098 |
| 4461 | ttcagaatgtctccagcaatta | J02935 | 47065 | acacccttgctgaaaactgccat | X14971 | 89669 | gcaagtgtcctcatgcagatggga | AA110098 |
| 4462 | atgtctccagcaatttaagtgcc | J02935 | 47066 | tgaaaactgccattcacggcgacctc | X14971 | 89670 | agtgtcctccatgcagatgggagcg | AA110098 |
| 4463 | tactctcggagaactgccctgctca | J02935 | 47067 | aaatcagggcagtcctgtggttcaa | X14971 | 89671 | aggactgatagcctgctggcagt | AA110098 |
| 4464 | aaaccccaggctgcttccgcttacg | J02935 | 47068 | gaccgaatctgcaaatttcgtgg | X14971 | 89672 | actgatagcctgctgtggcagtgac | AA110098 |
| 4465 | aggctctcggcccctgcaggaca | J02935 | 47069 | ttcgtggtcgtcggcataaatacaca | X14971 | 89673 | ggatagcctgctgcagtgacctt | AA110098 |
| 4466 | aagaggaactcacattacgaag | J02935 | 47070 | ggctcgtgttgcctggaacca | X14971 | 89674 | tagcctgcttggcagtgacctgc | AA110098 |
| 4467 | ttttggctcaactggatctgatgg | J02935 | 47071 | cgcctggagccaaacctgcaagctc | X14971 | 89675 | cttcatcccgtcatcagtgcctcg | AA110098 |
| 4468 | tccaacttgatctgatggaccccg | J02935 | 47072 | gagccaaacctgcaagctcagatgt | X14971 | 89676 | aattcatcatgggagcactgatgca | AA110098 |
| 4469 | ttggatctgatgaccccggccaagt | J02935 | 47073 | aacctgccaagctcagatgtatagac | X14971 | 89677 | tcgagggatagcccccggttggcacc | AA110098 |
| 4470 | ctgatgaccccggccagtagatgt | J02935 | 47074 | ctcacctgccagcaaagaca | X14971 | 89678 | tgatagcccgttggccaccacact | AA110098 |
| 4471 | ggccatgccaaatgcagccatgaag | J02935 | 47075 | tgcgtaccagcaaagacaccgtct | X14971 | 89679 | cactacaaccaacctggagcagcct | AA110098 |
| 4472 | caatgccaaatgcagccatgaagaa | W49091 | 47076 | gatctctcgatcaagctctcgagag | AA024092 | 89680 | tacaaccaacctggagcagcctcag | AA110098 |
| 4473 | atactagacgtatacatagtcttc | W49091 | 47077 | tccttgatcaagctctcgagagt | AA024092 | 89681 | caacctggagcagcctcaggtcatt | AA110098 |
| 4474 | gcagttgagcacctactctctcgt | W49091 | 47078 | ctcgagctcgaggtgcgcagtgctc | AA024092 | 89682 | tgaccttcggggatcttttgaat | AA110098 |
| 4475 | agtttgagcacctactctctcgtag | W49091 | 47079 | cgatcgagtcgcgcagtgcttcag | AA024092 | 89683 | cccaggtgaatgtcccgcaagtgtcc | AA110098 |
| 4476 | tgagcacctactctctcgtagactc | W49091 | 47080 | atcgagtcgtcgcagtgcttcagcg | AA024092 | 89684 | tccttcaaggtacgagccagtccaa | AA110098 |
| 4477 | ctctgtagactctgttggaaatac | W49091 | 47081 | ccagtcgtcgcagtgcttcagcgt | AA024092 | 89685 | caacagtccaaaatgtacagaca | AA110098 |
| 4478 | ctcgtagactctgttggaaatacaa | W49091 | 47082 | cggatactccgctcgctgcccc | AA024092 | 89686 | gcttagtgcaagccctgttgccccc | AA110098 |
| 4479 | gtagaacattctcatgtcgattc | W49091 | 47083 | cgctgctcagccgcgcgatcgtagagg | AA024092 | 89687 | tagtgcaagccctggttgcccaga | AA110098 |
| 4480 | agaacattctcatgtcgattctg | W49091 | 47084 | gctcagccgcgatcgtagagggcta | AA024092 | 89688 | tggttgcccagaaccaagtgat | U69488 |
| 4481 | aacattctcatgttcgatttctggg | W49091 | 47085 | tcagccgcgatcgtagagggctacg | AA024092 | 89689 | cccagaaccaagtatgttatg | U69488 |
| 4482 | catttctcatgttcgattctgggaa | W49091 | 47086 | agcccgatcgtagagggctacgcg | AA024092 | 89690 | tgttatgtaccctgacctaagtt | U69488 |
| 4483 | attatattgccagatacacactcg | W49091 | 47087 | agatgacgttggccaccagctt | AA024092 | 89691 | tactttcggttggataaagatg | U69488 |
| 4484 | tatattgccagatacacactgtc | W49091 | 47088 | cttcgatcaagctctcgagaggta | AA024092 | 89692 | agtcgatagctgggcaggagagaacc | U69488 |
| 4485 | tattgccagatacacactgtctt | W49091 | 47089 | cttgccacacgtctcgagctgat | AA024092 | 89693 | ttaagagcagcccagatggaaacat | U69488 |
| 4486 | gccaggaacacgtcgtctggtg | W49091 | 47090 | tcaagctcgagaggtgatccgtg | AA024092 | 89694 | atctgcccagctcttgctgatta | U69488 |
| 4487 | cagagaacacgtcgtctggtgca | W49091 | 47091 | gctccgagaggtgatcctgcgagt | AA024092 | 89695 | gctcttgctgattaaggctgtt | U69488 |
| 4488 | gacacacgtcgtctggtgcaacaa | W49091 | 47092 | ggtgatccgtgttgctcgatcgagt | AA024092 | 89696 | cctcactatgaacaacaacatcct | U69488 |
| 4489 | cacgtcgtctggtgcaacaatact | W49091 | 47093 | atccgtgttgctcgatcgagtcgtc | AA024092 | 89697 | cactatgaaccacaacaatccggt | U69488 |
| 4490 | cgtcgtctggtgcaacaatact | W49091 | 47094 | ccgtgtttgctcgatcgagtcgtgc | AA024092 | 89698 | gaaccaaacctcggttcggtaaat | U69488 |
| 4491 | atcatctaggggcttgctcaaaca | M25811 | 47095 | gtgtttgctcgatcgagtcgtgcag | AA024092 | 89699 | aagagagccgcgtcttgttgtg | U69488 |
| 4492 | ctttgctaaacagcatatgaaatc | M25811 | 47096 | gttgctcgatcgagtcgcgcagtg | AA024092 | 89700 | tatattgagcttggtcgttatgc | U69488 |
| 4493 | cccacatccactagagatgaaaaa | M25811 | 47097 | gatgagtcatcccattatggtcgca | U08215 | 89701 | cttggtctgtatgcttggaatg | U69488 |
| 4494 | ccattctcagttctcattgaacgc | M25811 | 47098 | gaggtcatcccattatggtcgcca | U08215 | 89702 | tggtcgttgtatgcttggaatgtt | U69488 |
| 4495 | tcagttctattgaacggcacatgt | M25811 | 47099 | ggatcttacaggtgacgtgcacag | U08215 | 89703 | aatgcttaggcaagcccgttggtgc | U69488 |
| 4496 | cctattgaacggacatgtggaact | M25811 | 47100 | gtgacgtgacagaccaagaaccg | U08215 | 89704 | gtgaaggtctgtcaggctctgatta | AA110113 |
| 4497 | atacttatgtcgacatcaactct | M25811 | 47101 | tgcacagacaagacacgccaagt | U08215 | 89705 | gtccaggcctctcagatccactcg | AA110113 |
| 4498 | tatgctgacatcaactctttgatgt | M25811 | 47102 | tgcacattactgtgagtgcat | U08215 | 89706 | actcaggctctgatctcggaccgctc | AA110113 |
| 4499 | gacatcaactctttgatgtctt | M25811 | 47103 | gaggtcatcctcgactcctcagat | U08215 | 89707 | gcgacatatctcgacggccttgca | AA110113 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 4500 | aacttctttgtagttgtctgctaga | M25811 | 47104 | tcctgactcttcagataaaccaaga | U08215 | 89708 | acatatctcgacggctcagcaaca | AA110113 |
| 4501 | atgtgtcttgctcagaaggatttta | M25811 | 47105 | tgactcttcagataaaccaagatgg | U08215 | 89709 | tctcggacggctcagcaacaactga | AA110113 |
| 4502 | ttttgcgagtgcatcatgctgaatgga | M25811 | 47106 | ataatatcaacataaatttgtttg | U08215 | 89710 | ctcggaggctcagcaacaactga | AA110113 |
| 4503 | gtcattctaatctctggagatga | M25811 | 47107 | taataaactgcttttcaatgaagg | U08215 | 89711 | ctacgcattattcagcttattcaa | AA110113 |
| 4504 | tctaatctctgggatgatgactctc | M25811 | 47108 | taaactgcttttcaatgaaggtat | U08215 | 89712 | atttcagcttattcagtcatcgt | AA110113 |
| 4505 | gagatgactctcaatccagggtgc | M25811 | 47109 | gtcatcctattgggtcagccatag | U08215 | 89713 | cagcttattcaagtcatcgctggcc | AA110113 |
| 4506 | actcttcaatccaggggccatcag | M25811 | 47110 | ttcacagtacgttcctcctcggga | U08215 | 89714 | aacagacattttccagctgttctgc | AA110113 |
| 4507 | ccatcagtaatcatgccactgtca | M25811 | 47111 | cgaagacgcacacactgcaggccc | U08215 | 89715 | acagacattttccagctgttctga | AA110113 |
| 4508 | gtaalcatgccactgttcacgagtg | M25811 | 47112 | ctgaactctatgagtctgagggga | U08215 | 89716 | ctcaggctgtcagatcactgcg | AA110113 |
| 4509 | atgcactgttcacgagtgtgtta | M25811 | 47113 | gaacttcatatggtctgaggggaaga | U08215 | 89717 | tcaggctctgtcagatcactgcga | AA110113 |
| 4510 | atgactagcctcagtccctctaga | M25811 | 47114 | caggttgtactcaggacttagata | U08215 | 89718 | tctgtcagatcactcggcacatat | AA110113 |
| 4511 | tggcctctgcattggctccataat | W49135 | 47115 | atattagcgttcttactatgaaaa | U08215 | 89719 | tctgtcagatcactcggcacatat | AA110113 |
| 4512 | cctcttgcattggctccataatgat | W49135 | 47116 | ttagctgttctacttatgaaaagg | U08215 | 89720 | gtcatcactcggacatatctcg | AA110113 |
| 4513 | gagtacacgcattcaacacatgac | W49135 | 47117 | cttttccacgcctctctcaatg | U08215 | 89721 | cagatcactcggacatatctcgga | AA110113 |
| 4514 | ttcaacacatgacgatgagatta | W49135 | 47118 | ttcaatgacatcgtccaggccatcc | X54424 | 89722 | agatcactcggcgacatatctcggac | AA110113 |
| 4515 | taatgtgaatccaagccacaaagg | W49135 | 47119 | acagggccatcacacaagtcatta | X54424 | 89723 | tcactcgcgacatatctcggacgc | AA110113 |
| 4516 | gaatcacagccacaaaaggacgaat | W49135 | 47120 | accatcaacaacatcattaaagtc | X54424 | 89724 | gcatccggccccacacagctgg | AA110113 |
| 4517 | gacgaatctgagcctaatgatgt | W49135 | 47121 | aaagttctgaatccacagaagcaac | X54424 | 89725 | ggccacacagcgggtcattccca | AA110117 |
| 4518 | gaatctgagcctaatgatttgtgat | W49135 | 47122 | ctgaatccacagaagcaacagctgc | X54424 | 89726 | ttgatcaagtcaccatactactcta | AA110117 |
| 4519 | tctgagcctaatgatgtgatcct | W49135 | 47123 | cggatcaagctcacatataatcaca | X54424 | 89727 | atcactccatactcatatctcataa | AA110117 |
| 4520 | taatgatgttcgttggctcaagaa | W49135 | 47124 | aagctcacatataatcacaaggct | X54424 | 89728 | tcaccatactatctcataagtcag | AA110117 |
| 4521 | tgttcgttggctcaagaagctct | W49135 | 47125 | aatcacaaaggctcggcaatgcaag | X54424 | 89729 | ccatactatctcataatgtcagtga | AA110117 |
| 4522 | agaagctctcaggcatcttaggag | W49135 | 47126 | tgcagcaccatctcattcttacc | X54424 | 89730 | tactatctcataatgtcagtgagctcac | AA110117 |
| 4523 | gcatttggctccataatgatagtgct | W49135 | 47127 | ctatcccactcaatcaaaggaatt | X54424 | 89731 | tatctcataatgtcagtgagctcac | AA110117 |
| 4524 | ttggctccataatgatagtgctgca | W49135 | 47128 | taccagtccgcagaagagctgagag | X54424 | 89732 | agctcactgcagaaatgcacagat | AA110117 |
| 4525 | catcaatctgttccatagatctaa | W49135 | 47129 | ccctcatcacagcacagagctaaga | X54424 | 89733 | tcactgcagaaatgcacaggatat | AA110117 |
| 4526 | ttcgttccatgatctcaaccgcgt | W49135 | 47130 | gcctcaacagcacagagctagaca | X54424 | 89734 | gatataaacagcaggtggttctc | AA110117 |
| 4527 | tgttccatgatctcaaacgcgtagt | W49135 | 47131 | gcagtaccaaagacattccagctgc | X54424 | 89735 | aaccaggcaggggttcttcgacag | AA110117 |
| 4528 | tcccatgatctaaacgctagtcag | W49135 | 47132 | ccaaagacattccagctgcagttc | X54424 | 89736 | ctttcaaccctgcttccagg | AA110117 |
| 4529 | ctaaacgctagtcagcaacggagt | W49135 | 47133 | acatccagctgcagttctgctc | X54424 | 89737 | ggttctcgacagatacctactgc | AA110117 |
| 4530 | aacgcgtagtcagcaacggagtaca | W49135 | 47134 | cctagcagcagcgtgtcccagcct | X54424 | 89738 | tgagtcaacctgcttctcagggac | AA110117 |
| 4531 | tagtcaacttctcagtggtgt | L11332 | 47135 | agcagcgtgcccagcctttaata | X54424 | 89739 | tcctctgtgggaagaagtggcccc | AA110117 |
| 4532 | aactttctcagtggtgctctgta | L11332 | 47136 | ccagcttaatacaggagcatca | X54424 | 89740 | tgatgctgtggcatcaaact | AA110117 |
| 4533 | aatggccatcaaactcccattagaag | L11332 | 47137 | gagcagcgtacaagccctcagg | X54424 | 89741 | agatgtcatatagactgcttgatca | AA110117 |
| 4534 | caatcaaactcccattagacaaag | L11332 | 47138 | gcgctaacagccctcaggcagtt | X14206 | 89742 | tgtccatatagactgcttgatca | AA110117 |
| 4535 | ttcattctccacagatattcaca | L11332 | 47139 | ctactgccacactcaggggagac | X14206 | 89743 | ccatatagactgcttgatcacgt | AA110117 |
| 4536 | cttcccacagatattcacatggtaa | L11332 | 47140 | atctcaggagaccgattgctta | X14206 | 89744 | tgcttgatcacgtcaccatactac | AA110117 |
| 4537 | atcacatgtaaacctcacatggtcat | L11332 | 47141 | atctgctgcaacgacacatgccctg | X14206 | 89745 | cttgatcacgtcaccatactactac | AA110117 |
| 4538 | cccacgtgccctgcctttaatctt | L11332 | 47142 | tgtcaacgacactgccctgctgat | X14206 | 89746 | cttctgcagcttttggaaacaggt | AA110117 |
| 4539 | tgccctgctttaatcttaactc | L11332 | 47143 | cgacactgccctgctgtataatgag | X14206 | 89747 | aacaggtgtccgtcgctgctgagg | AA110117 |
| 4540 | ttaactcaacagctccgtgataact | L11332 | 47144 | gtacactgtcgcacatttgcag | X14206 | 89748 | atgttgaacggttgtaccagtgcc | AA110117 |
| 4541 | caacagtccgtgataacttgagc | L11332 | 47145 | tgtcatgacatttgcagttgat | X14206 | 89749 | gtggttctatttatgtgacctg | U79738 |
| 4542 | gtccctgataactttgagcattctt | L11332 | 47146 | tctcaaaatcctgcgaaactcaag | X14206 | 89750 | ttatgtgaccgttctctcctggac | U79738 |
| 4543 | ctctcctcaatgagctgagaatc | L11332 | 47147 | ataacctgctgaaactcaagtcaat | X14206 | 89751 | tgtgaccctgttcctctgaccaa | U79738 |
| 4544 | gagaatcccacctgagaactttcat | L11332 | 47148 | ttttaagacatcctcggtaatg | X14206 | 89752 | gttcctcctgaccaatctccctgt | U79738 |
| 4545 | ccaactcgagaacttcatacatgg | L11332 | 47149 | caagcctcaggcagcttcacac | X14206 | 89753 | ccaatcctcggtgtgcaagcga | U79738 |
| 4546 | ctttcatcaatgtgtgataagccta | L11332 | 47150 | caccgtgcgtgtgtatgaattc | X14206 | 89754 | atctcccgtgttgcaagtcgaaag | U79738 |
| 4547 | aagcctataccactgcagctaaat | L11332 | 47151 | ctcaggcagcttcacaaccgagg | X14206 | 89755 | ccagcctcatttctgttcct | U79738 |
| 4548 | atatacactgcagctaaatcctag | L11332 | 47152 | tgtctttctttactgaccagtc | X14206 | 89756 | tcaaccactgcagcgctgtgggac | U79738 |
| 4549 | gctaaatcctgccacagctgataa | L11332 | 47153 | caggacaccaacttgctgataa | X14206 | 89757 | agttgtccgtctgtcgcagatt | U79738 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 4550 | tcctcagcacagctgataacatcat | L11332 | 47154 | caccaacttgctgcatcctgtcg | X14206 | 89758 | ttgtccgtctgctgcaggattcaa | U79738 |
| 4551 | acctcaagctctggggtatcgaccg | M20473 | 47155 | gacaggctacatgttggaaaggg | X14206 | 89759 | gttctgtgcaggattcaagtgagg | U79738 |
| 4552 | tcgaccgtgacagttactacaggcgcat | M20473 | 47156 | gatctacttgcgacatggtgtcc | X14206 | 89760 | aggcctagaactcagtgcttaggg | U79738 |
| 4553 | atgacttctacatcatccacagagg | M20473 | 47157 | tgcaaactgccaacacatccag | Z33637 | 89761 | cagtgcctaggggtaaggcgtca | U79738 |
| 4554 | tctacatcatcacagaggcactgc | M20473 | 47158 | cctcactctggttctgctccaag | Z33637 | 89762 | aaggctgcagttggaccggcggt | U79738 |
| 4555 | gcactgcttcagtcctccagcgag | M20473 | 47159 | ctctgggttctgctccaggaactct | Z33637 | 89763 | gctgtcagcttgacggctggtacc | U79738 |
| 4556 | cctcgactacttgggagggatgc | M20473 | 47160 | tcctggcattgttttgatccatcc | Z33637 | 89764 | gtcagctggacggctggataccagt | U79738 |
| 4557 | agattgcctgctgaatcggcc | M20473 | 47161 | ttttgatccatcccttgtccat | Z33637 | 89765 | caagactgctgactattgttgac | U79738 |
| 4558 | atcggccccgtgcagccactgtggt | M20473 | 47162 | tgtgtgaccagccaatgccctgtc | Z33637 | 89766 | tgacttagtcccagcgaaggctat | U79738 |
| 4559 | tagaccggcctgttttgagcgtgt | M20473 | 47163 | tagacagggcccaaagtgtgccctt | Z33637 | 89767 | tgtcccttatgaatcagatacaag | Z11997 |
| 4560 | gctctggatcctgaagaggaacat | M20473 | 47164 | agagtcctccgagccatgaagag | Z33637 | 89768 | ttagtaccaattgtccaatacatt | Z11997 |
| 4561 | tccaagctacaacagcttcatctc | M20473 | 47165 | cctcctgccaagaagaaatata | Z33637 | 89769 | ccattgtccaatacattgcttttt | Z11997 |
| 4562 | tcatctcctaactgtctgagcctg | M20473 | 47166 | tggactccagtttatagttgct | Z33637 | 89770 | ttttataagacccaaactcatcat | Z11997 |
| 4563 | gctacaggccatccatccatggaaag | M20473 | 47167 | atgagtaccctgccagcacagagg | Z33637 | 89771 | ataagacccaaactcatcattcattaat | Z11997 |
| 4564 | agttcctcagcaaagtctccatcct | M20473 | 47168 | tcccttcaatctaccacagctctgg | Z33637 | 89772 | tccatlcaattaatcaggtttaatct | Z11997 |
| 4565 | tcgcaaagttctcatcctagaatc | M20473 | 47169 | caatctaccccagtcctggtgccaa | Z33637 | 89773 | gattatcgttcttaaagtgccag | Z11997 |
| 4566 | aagtctccatcctagaatccctga | M20473 | 47170 | gttctgtccaagaatctgcctg | Z33637 | 89774 | taattttcacgcgttttgtgatgga | Z11997 |
| 4567 | tagaatccctggagaagtgggaacg | M20473 | 47171 | gttcaggcacgtgtctttactt | Z33637 | 89775 | tttcacgcgttttgtgatggagtg | Z11997 |
| 4568 | ctgtagctgatgccctggagcctgt | M20473 | 47172 | ttggaagtcccagctctgactcta | Z33637 | 89776 | tgaacatgagtctgatgatacta | Z11997 |
| 4569 | ctgatgcctgagcctgtgcagtt | M20473 | 47173 | gtcccagtcctgactctataccag | Z33637 | 89777 | ccttagtccagggaaggctatcac | Z11997 |
| 4570 | ccctgagccctgcagttgaaga | M20473 | 47174 | agtcctgactctataccagtattgc | Z33637 | 89778 | tcccagccgaggctatcacaagaac | Z11997 |
| 4571 | cggttttgcacattgggctttat | M20473 | 47175 | gactctataccagtatgctgagc | Z33637 | 89779 | tcacaagacgctgcgtaaagct | Z11997 |
| 4572 | ttttgcacattgggctttatatg | W49158 | 47176 | tcccttactgccagcagccagaatg | Z33637 | 89780 | caagaacgctggcgtaaagcttg | Z11997 |
| 4573 | ctttgcacgaggaaatttcaat | W49158 | 47177 | cccaaatcttcattgttttgat | Z33637 | 89781 | ctgtaaagcttgcccttctatcta | Z11997 |
| 4574 | gaaatttcaatggtcccctgcgg | W49158 | 47178 | tgccacttgcaccagaagaatt | Z33637 | 89782 | agcttgcccttctatctagatatg | Z11997 |
| 4575 | atttcaatgtgccctgtgggtc | W49158 | 47179 | ttgcaccccagaaaatttccaatgag | Z33637 | 89783 | tttgcccttctactctagatatgat | Z11997 |
| 4576 | tcaatgtgccctgtgggatcaag | W49158 | 47180 | ctactaaccagagctgaactaaggc | Z33637 | 89784 | tataactgtgtttgtccccttatga | Z11997 |
| 4577 | caatgtgccctgtgggatcaagc | W49158 | 47181 | ctaaccagagctgaactaaggctgc | Y00516 | 89785 | gagtcctgacactcattagcactg | Y00516 |
| 4578 | tgtgccctgtgggatcaagcc | W49158 | 47182 | gaactaaggctgctccatcaacact | Y00516 | 89786 | catgctccaacagacagaagatt | D49730 |
| 4579 | tgtcccctggggatcaagccgagag | W49158 | 47183 | ctgccacccactgtcatgtgaaga | Y00516 | 89787 | tcctagataactccagacataagat | D49730 |
| 4580 | gtccctggggatcaagccgagagt | W49158 | 47184 | cctaccccacttgctatgaagaggg | Y00516 | 89788 | ataactccagacataagatactcaa | D49730 |
| 4581 | ccctggggatcaagccgagagtct | W49158 | 47185 | ggtcttcaggctctttccccalcact | Y00516 | 89789 | ttctlcacatttccatccacacag | D49730 |
| 4582 | agaggtctaaatttctgagggaaga | W49158 | 47186 | cttcaggtcttttccccalcactctt | Y00516 | 89790 | cacacagcagggccagaacacagag | D49730 |
| 4583 | ttgacattgtgggctttatatgaa | W49158 | 47187 | atgtaaaatgccatccctttccag | Y00516 | 89791 | tctgagcctgtgtcgtccttca | D49730 |
| 4584 | cacattgtgggctttatatgaaaaa | W49158 | 47188 | cgggactgccaataaacaactattt | Y00516 | 89792 | gtctgttccttcatgaatgtatgat | D49730 |
| 4585 | aagccattggaaagccgagagat | W49158 | 47189 | cactgccaataaacaactattaag | Y00516 | 89793 | cctttgttctggctgtacaatg | D49730 |
| 4586 | agatctatgccaaagccgaagaga | M19960 | 47190 | caccccagaaatttccaatggag | Y00516 | 89794 | gttcttggctgtacaatgggctg | D49730 |
| 4587 | atctatgccaaagcgaagaagaag | M19960 | 47191 | agccctgcaggccctgctctaaact | Y00516 | 89795 | ggtaacactccacacagggttgt | D49730 |
| 4588 | tatgccaaagcgaaagaagaagtt | M19960 | 47192 | cctgcaggcctctgctctaaggcc | Y00516 | 89796 | actcacctcagagtgttgtgaa | D49730 |
| 4589 | gaagccgatcttgcagcacggaga | M19960 | 47193 | agccagtgaatctctctcatct | Y00516 | 89797 | atttcagacatttctggata | D49730 |
| 4590 | tctttgcacgcaggaaatttcaa | M19960 | 47194 | atctctcatctctaaccagcc | Y00516 | 89798 | attttaaacatccatggaccagac | D49730 |
| 4591 | gactgtacagaggcctgctgcca | M19960 | 47195 | tctctlcatctaaccatgcctac | Y00516 | 89799 | catggaccagccacataagtagtc | D49730 |
| 4592 | tccctaaatcaattctgatgacc | M19960 | 47196 | cttcatctaaccatgcctactaa | Y00516 | 89800 | ggtagtctgtcaccagatgtt | D49730 |
| 4593 | cagctgccatccacctctgccgtg | M19960 | 47197 | ccatgccaaccagagctgaac | Y00516 | 89801 | ctgtgctaccacagtgttaacact | D49730 |
| 4594 | actgcaacccaagtcgatgtggc | M19960 | 47198 | tcatatgggcacagctgtgctc | Y00516 | 89802 | ttagtaccctgcggtgaatccaga | D49730 |
| 4595 | gcaaccaagtctgatgtgttt | M19960 | 47199 | ggtacaccgctgatgctgactg | AA024180 | 89803 | agatctaagctcctagataactc | D49730 |
| 4596 | agtctgaattgtctttctctcaa | M19960 | 47200 | tagacattcttttccaagaagtc | AA024180 | 89804 | taagtcctagataactccagaca | D49730 |
| 4597 | gtgctttttcctccaatagaaagt | M19960 | 47201 | tattctttccaagaagtctgagtc | AA024180 | 89805 | ggaccaccccaatctcgaggctgagg | L47335 |
| 4598 | tgcgtcaacctgtgtgtctcaaagg | M19960 | 47202 | ctgagtcctgcatatagctcatc | AA024180 | 89806 | cccaatctcgaggctgggcagtac | L47335 |
| 4599 | gatgagactctcctgcaacgtgt | M19960 | 47203 | agtcctcgcatatagctcatctcc | AA024180 | 89807 | gtggcattccaggggtgactttgct | L47335 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 4600 | acttcctcttgaacagtgtgctgtt | M19960 | 47204 | ccttcgcatatagctcatctcctg | AA024180 | 89808 | gcattccaggttgacttttgctcct | L47335 |
| 4601 | tcctcttgaacagtgtgctgtgta | M19960 | 47205 | atagctcatctcctggagaagatg | AA024180 | 89809 | ggtgactttgtccgttccgct | L47335 |
| 4602 | tcttgaacagtgtgctgtaaac | M19960 | 47206 | gctcatctccttggagaagtgat | AA024180 | 89810 | gactttgttcctgttcctgtccc | L47335 |
| 4603 | caattcgatgagaccgtggtgaac | M19960 | 47207 | ttattgtcagccatgtctcagtac | AA024180 | 89811 | aagcctactcactgggcaccatgt | L47335 |
| 4604 | agccaaactgaccgtcaaggacgcc | M19960 | 47208 | tcagccatgtctcagtacttctga | AA024180 | 89812 | cttcactgggcaccatgttcag | L47335 |
| 4605 | agccaaactgaccgtcaaggaaagg | M19960 | 47209 | atgctcagttacttctgatgagtc | AA024180 | 89813 | accagttttgcagccattgctgcgg | L47335 |
| 4606 | ctgaccgtcaaggaaggaactgg | M19960 | 47210 | cgtgctgatgctgacgaataagt | AA024180 | 89814 | atgtttgcagccattgctgcggta | L47335 |
| 4607 | cagtggtccatgccaattgctcct | M19960 | 47211 | cagtgacttcgatgagtcgatccg | AA024180 | 89815 | tttgcagccattgctgggctactt | L47335 |
| 4608 | tggtcatgccaattgctctgtg | M19960 | 47212 | atatttgtacacataggactgtg | AA024180 | 89816 | gccattgctgggctacttcactcc | L47335 |
| 4609 | catgccaattgtctctgtcatcag | M19960 | 47213 | tttctgtacacataggggactggat | AA024180 | 89817 | aatctggggctgaggcagtacctg | L47335 |
| 4610 | ttctagcttagctgtcagctgtcca | M19960 | 47214 | cgtacacataggggactgtggatcac | AA024180 | 89818 | taagtaaaccacaggtcgccttg | L47335 |
| 4611 | cctagctgcagctgtccatcact | M19960 | 47215 | taaggacttttgcctgcctccacgat | AA024180 | 89819 | gcagtacctgctgaaccaggggtg | L47335 |
| 4612 | ccttgctgggtgactgcgggcaccgg | W49163 | 47216 | ctgcctcacgattgcttcagtctg | AA024180 | 89820 | agccttgagcaggcgaggagagtg | L47335 |
| 4613 | ttgactggcgggcaccggtacacaa | W49163 | 47217 | cctttcacgattgctttcagtctgtt | AA024180 | 89821 | gctccgcaggcaggcagagagtcgtg | L47335 |
| 4614 | cacagttcattatccgtcatgtat | W49163 | 47218 | cgattgcttcagtcgttgtcagt | AA024180 | 89822 | tagtcagctgtggaacatgctgag | L47335 |
| 4615 | agttcattatccgtcatgtatgc | W49163 | 47219 | ctcagagccaccatcacgccaggt | AA024180 | 89823 | tcagctggcgaacatgctgagcag | L47335 |
| 4616 | ttattccgtcatgtatgccatccg | W49163 | 47220 | agcagcaccatcacgccaggtga | AA024180 | 89824 | acatgctggcgaggtgcaggggcat | L47335 |
| 4617 | ttccgtcatgtatgccatccgagtc | W49163 | 47221 | ttcaaaagctgtacacagcgagat | AA024180 | 89825 | tgagcagccaggtggcattccagg | L47335 |
| 4618 | cgtcatgtatgccatccgagagtc | W49163 | 47222 | tcgtacacagcgagatcaagtcctg | AA024180 | 89826 | tagccacaggtgacagtcaggaca | L47335 |
| 4619 | catgtattgccatccgagtcgcc | W49163 | 47223 | gcgaatcaagtcctgctgaaggaa | AA024180 | 89827 | gaccaaggatcaatggggatgaac | L47335 |
| 4620 | ttgatgaccttgactttcatagg | W49163 | 47224 | agatcaagtcctgctgaaggaatga | AA024180 | 89828 | gggcttcaggaacttcacctccaaag | L47335 |
| 4621 | atgaccttgacttcatatggga | W49163 | 47225 | tcaatgcctgctaaggaatgatgc | AA024180 | 89829 | accaagccacttgagggtctct | U57344 |
| 4622 | acttgacttcttcataggggatga | W49163 | 47226 | atcttctggcacaaccgtataatc | AA024180 | 89830 | aagagccacttgagggtctctcaa | U57344 |
| 4623 | ttgacttcttcataggggatgaagc | W49163 | 47227 | ttctttggcacaaccgtataatccg | AA024180 | 89831 | ccacttgagggtctctcaaggcaa | U57344 |
| 4624 | acaacaagctcggactcacgcaggcaa | W49163 | 47228 | gccacaacgtatatccggaagtatt | AA024180 | 89832 | aagacaaagcctccagttcctgcac | U57344 |
| 4625 | agctcggactcacgcaggccactga | W49163 | 47229 | ccgtatatccggaagtattgtccag | AA024180 | 89833 | tgccccaggaaccttaagcagaaaactg | U57344 |
| 4626 | gctacgcaggccaaccagtgagccaca | W49163 | 47230 | tgtccagtttttggctacagctagcc | AA024180 | 89834 | actggccaaggctgaagaagatg | U57344 |
| 4627 | acgcaggccaaccagtgagccacagtt | W49163 | 47231 | accatcacgccaggttgaccgagt | AA024180 | 89835 | gggtccaccggatccaatgttggaa | U57344 |
| 4628 | caggccaaccagtgagccacagttcat | W49163 | 47232 | atcacgccaggtttgaccgagtctt | AA024180 | 89836 | tcacctgatccaatgtttgaaga | U57344 |
| 4629 | gcaacactgagccacagttcattat | W49163 | 47233 | ttgaccgagtctttggcaaagtat | AA024180 | 89837 | tggaagaatcccatctccctgg | U57344 |
| 4630 | ctggccacagttcattaccgtc | W49163 | 47234 | gcaagttatcagccaataagact | AA024180 | 89838 | ttacctatagaggctggggtlcaaag | U57344 |
| 4631 | agccacagttcattattccgtcatg | W49163 | 47235 | ttatccgccaataagacttcaaaa | AA024180 | 89839 | ctgactgtgaccaccccaggcctgcac | U57344 |
| 4632 | ctaaggctcgaactctccaaggtgg | W48965 | 47236 | tccagccaataagacttcaaaagct | AA024180 | 89840 | actgtaccaccgcctgcaccta | U57344 |
| 4633 | ggtgatcctacgtggaaagacta | W48965 | 47237 | taagacttcaaaagctctacacg | AA024180 | 89841 | cttgacctaattggtccctgcctg | U57344 |
| 4634 | gaaatgagcggttgagatcgtag | W48965 | 47238 | gactttcaaaagctctacacagcga | AA024180 | 89842 | cctaattggtccctgctggtcttg | U57344 |
| 4635 | gagatgcaggattcctacagccc | W48965 | 47239 | cacatccgcacagactgttttgagt | L48015 | 89843 | ctgcttccttggggttcaggact | U57344 |
| 4636 | atcgcaggattccctactagcctcc | W48965 | 47240 | cgcacagactgttttgagtcgtaca | L48015 | 89844 | ctggctctttgggttcaggatcca | U57344 |
| 4637 | gggattcctactagcctccagatcl | W48965 | 47241 | cggtgctcgagatccgggtct | L48015 | 89845 | gtccttgggtcaggactltcact | U57344 |
| 4638 | ccctacagcctccagatctgggaca | W48965 | 47242 | gctgcagatccgtcctccgggc | L48015 | 89846 | tgcagcaacaggggccactgcgca | U57344 |
| 4639 | gacacacgcggacacgggaaaagttca | W48965 | 47243 | tccgggctgccccagatgatgagag | L48015 | 89847 | aacaggggccactgcgcaagctgc | U57344 |
| 4640 | gctactaccgcgggtgccccagggtg | W48965 | 47244 | ctcactccatccagagaagcca | L48015 | 89848 | ttccactccacgagctctgcagct | U57344 |
| 4641 | taccgggtgccccagggtgagcagg | W48965 | 47245 | aagccaagtgaatttcactaccca | L48015 | 89849 | ttcacctccacgagctctttgga | U57344 |
| 4642 | gaggcagcgaatgagcggaactc | W48965 | 47246 | attcactcagtccccagggccaccagc | L48015 | 89850 | atgaagtcctgcaccatgccat | U57344 |
| 4643 | aatggagcggaactctcaaccat | W48965 | 47247 | accagggtcctgcctaaagtgt | L48015 | 89851 | cgcccaaccgttttgactcagatcl | U57344 |
| 4644 | gatcctacgggagaactagcc | W48965 | 47248 | ctgctaaagttgtgtggggcag | L48015 | 89852 | cgcccaaccatttcaggatggtg | U57344 |
| 4645 | ccaccgggtlgaatactact | W48965 | 47249 | aaagttgctggggtcaggaagaca | L48015 | 89853 | tctttctcaaaggggttgagagatg | U79748 |
| 4645 | ggaaagctagccatccatccaggt | W48965 | 47250 | atccagccaaaatacagctgtgct | L48015 | 89854 | gtgtttgctcgtcttagcag | U79748 |
| 4646 | actagcctcattcacagttatgca | W48965 | 47251 | acagacatcgggccttggcctag | L48015 | 89855 | gctgccttgctctcttagcagagagaa | U79748 |
| 4647 | agcctcattcacagttatgcaaga | W48965 | 47252 | atccaggcctttggcctagtctat | L48015 | 89856 | ttgctggcgagctcttgga | U79748 |
| 4648 | ctcattcacagttatgcaagaatg | W48965 | 47253 | atccgccgggaccatcaatg | L48015 | 89857 | cagtttgctgctgagtctccctgct | U79748 |
| 4649 | gattacaaggccacgattgcgtag | | | | | | | |

TABLE 1-continued

| SEQ ID NO | DBAxnID | sequence | SEQ ID NO | DBAxnID | sequence | SEQ ID NO | DBAxnID |
|---|---|---|---|---|---|---|---|
| 4650 | W48965 | aaggccacgattgcgtagacttig | 47254 | L48015 | atcaatggcattgtggaggattaca | 89858 | U79748 |
| 4651 | W48965 | gccacgattgcgtagacttgaaa | 47255 | L48015 | aggccaccttctatgacatggtac | 89859 | U79748 |
| 4652 | L28035 | gccaccctttgatggggaagatgag | 47256 | L48015 | cctttctatgacatgtgaccaatg | 89860 | U79748 |
| 4653 | L28035 | tcaagccatcatggaacaacgtgtc | 47257 | L48015 | tatgacatgtgaccaatgaccca | 89861 | U79748 |
| 4654 | L28035 | gccagaccgttggttctagccagc | 47258 | L48015 | cctaaccggctggctgcagatccgg | 89862 | U79748 |
| 4655 | L28035 | ccgcttgtctctagccagcatcgac | 47259 | AA024231 | actgggctactcgctgacagtgacg | 89863 | U79748 |
| 4656 | L28035 | agccagcatcgaccaagctgattc | 47260 | AA024231 | tgggctacctgctgacagtgacgg | 89864 | U79748 |
| 4657 | L28035 | catccaccaagctgattcaggge | 47261 | AA024231 | tgaatgcagcacctctagacttta | 89865 | U79748 |
| 4658 | L28035 | ccaagctgattccaggccttacc | 47262 | AA024231 | aatgtcagcacctctagacttaca | 89866 | U79748 |
| 4659 | L28035 | gaaccggactgctgtgcaccagat | 47263 | AA024231 | tcagcacctctagacttacaggt | 89867 | U80036 |
| 4660 | L28035 | gccgtgcctgtcatgtaatcctat | 47264 | AA024231 | cgactggcccagcgtcatgctcctg | 89868 | U80036 |
| 4661 | L28035 | gcctgtcatgtaatctcatctgtg | 47265 | AA024231 | actgggcccagcgtcatgctctgag | 89869 | U80036 |
| 4662 | L28035 | catgtaatctcatctgccgcgcta | 47266 | AA024231 | tggcccagcgtcatgctctgcagtg | 89870 | U80036 |
| 4663 | L28035 | gctgtaaccaccatcactacccctag | 47267 | AA024231 | gcccagcgtcatgctgtgagagtt | 89871 | U80036 |
| 4664 | L28035 | ggaacaaactgtcacctatcccaag | 47268 | AA024231 | caggtcatgctgagagttggag | 89872 | U80036 |
| 4665 | L28035 | aactgtcacctatcccaagtcactt | 47269 | AA024231 | catgctcgagagttgagggcaag | 89873 | U80036 |
| 4666 | L28035 | ttcccggaagctgtggccatctgc | 47270 | AA024231 | aaggcagacgcgccagatactaccat | 89874 | U80036 |
| 4667 | L28035 | tgtgggccatcgcaaaggttcctg | 47271 | AA024231 | ggctacctgctgacagtgacggtct | 89875 | U80036 |
| 4668 | L28035 | catgcaaaggttctgaccaag | 47272 | AA024231 | ctacctgctgacagtgacggtctct | 89876 | U80036 |
| 4669 | L28035 | gcaccaggaaaagcctgggtca | 47273 | AA024231 | gctgacagtgacggtctctgcagat | 89877 | U80036 |
| 4670 | L28035 | tcatgctttccgttcgatcgat | 47274 | AA024231 | tgacagtgacggtctctgcagatgg | 89878 | U80036 |
| 4671 | L28035 | actggaaatgtcacctccttcaga | 47275 | AA024231 | cttctggagccacgatgcccggac | 89879 | U80036 |
| 4672 | W48968 | ccaagccagacacgcgaacaggagac | 47276 | AA024231 | gatgcccgggactatgctgatggat | 89880 | U80036 |
| 4673 | W48968 | aagccagacacgcgaacaggagacta | 47277 | AA024231 | tgcccggactatgctgatgggatca | 89881 | U80036 |
| 4674 | W48968 | gctagttcagcggaacaggagccg | 47278 | AA024231 | aatgaatgtcagcacctctagatc | 89882 | U80036 |
| 4675 | W48968 | ctgagttctgtcatggaagccgt | 47279 | AA024231 | agctccctatcacgacctgtgcc | 89883 | U80036 |
| 4676 | W48968 | tgagttctgtctcatggaagccgtg | 47280 | AA024231 | accettctatgaggactagagaga | 89884 | U80036 |
| 4677 | W48968 | agttcgtctcatggaagccgtgg | 47281 | Z23143 | tctgacagtgatactgtgggacag | 89885 | U80036 |
| 4678 | W48968 | gttctgtctcatggaagccgtgagt | 47282 | Z23143 | gaattcacagaagcatcgttagcc | 89886 | U80036 |
| 4679 | W48968 | ttctgtctcatggaagccgtgagta | 47283 | Z23143 | agcatcgttagccccaagcctgaac | 89887 | AA110061 |
| 4680 | W48968 | tcgtctcatggaagccgtgagtacc | 47284 | Z23143 | ccaagccttgaacgttagcctactg | 89888 | AA110061 |
| 4681 | W48968 | cgtctcatggaagccgtgagtacca | 47285 | Z23143 | cttgaacgttagcctactgcccagt | 89889 | AA110061 |
| 4682 | W48968 | agccgtgagtaccatgccgagacta | 47286 | Z23143 | tgagttcagactttctgcgaagaga | 89890 | AA110061 |
| 4683 | W48968 | gccgtgagtaccatgccgagactat | 47287 | Z23143 | cagacttctggaagagacgcagg | 89891 | AA110061 |
| 4684 | W48968 | agccagacgcgaacagagactgc | 47288 | Z23143 | accagaaacacgattcatcatgg | 89892 | AA110061 |
| 4685 | W48968 | aacaggagacgcctcattcagac | 47289 | Z23143 | ggattcatcaaggtctctgaggag | 89893 | AA110061 |
| 4686 | W48968 | acaggagacgcctcattcagacc | 47290 | Z23143 | tgctttctaagaaagccctgatt | 89894 | AA110061 |
| 4687 | W48968 | aatggcgtcggtctgagttgtcct | 47291 | Z23143 | cattccccaatcgatggacagttga | 89895 | AA110061 |
| 4688 | W48968 | tggctgctgagttcgtctcatg | 47292 | Z23143 | atgagtgtctcaggcagatggggaa | 89896 | AA110061 |
| 4689 | W48968 | ggctggctgagttcgtctctcatgg | 47293 | Z23143 | gtctcaggcagatgggaagttat | 89897 | AA110061 |
| 4690 | W48968 | ctcggcagttgtctcatggaa | 47294 | Z23143 | tgacagagtgctggggcgcagaatcc | 89898 | AA110061 |
| 4691 | W48968 | cggctgagttgtctcatggaagc | 47295 | Z23143 | ccettgccaaaatgtcggaagttcca | 89899 | AA110061 |
| 4692 | W48968 | cgagcagttggttctcatggaagc | 47296 | Z23143 | ccaaaatgtcagatgtcccaggacat | 89900 | AA110061 |
| 4693 | W49178 | agtaccaagatgctatgccggacga | 47297 | Z23143 | tgtcagagtcccaggacaattaaact | 89901 | AA110061 |
| 4694 | W49178 | ctcagttctccatcgcccgtg | 47298 | Z23143 | ttaaactctgacgtcgatactgt | 89902 | AA110061 |
| 4695 | W49178 | cagttctcatcgcccgtgta | 47299 | AA024290 | ggctccaggctccaaacagccatg | 89903 | AA110061 |
| 4696 | W49178 | tccatctgcccgtgactccagtg | 47300 | AA024290 | tgccaggtccaaacagccatgtt | 89904 | AA110061 |
| 4697 | W49178 | ccatctgcccgtgactccagtgt | 47301 | AA024290 | tcaagctctcaagaaccaagttcac | 89905 | AA110061 |
| 4698 | W49178 | catctgcccgtgactccagtgc | 47302 | AA024290 | tctctaagaccaagttcacagttcc | 89906 | AA110061 |
| 4699 | W49178 | gtgtactccagtgtctttctgctgg | 47303 | AA024290 | ctaagaaccaagttcacagttccctg | 89907 | AA110277 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 4700 | gtgtgtctgtttgcaatggga | W49178 | 47304 | agaccaagtlcacagttccctggct | AA024290 | 89908 | cgaactgtggcagtcatgcgcgat | AA110277 |
| 4701 | tgtgtctgtttgccaatggag | W49178 | 47305 | agttcacagttccctgctgccaga | AA024290 | 89909 | gatcataatccctgtcgtcttgag | AA110277 |
| 4702 | gtgtctgtttgccaatggagt | W49178 | 47306 | tcacagttccctggctgccagaaga | AA024290 | 89910 | ataatccctgtcgtctgagact | AA110277 |
| 4703 | tgttctgtttgcaatgggag | W49178 | 47307 | ttcaccacgtttaatgcagataac | AA024290 | 89911 | aatccctgtcggttctgagcactic | AA110277 |
| 4704 | taccaagtcgtatcgcaatgg | W49178 | 47308 | aagccgtcattcctgatgactatt | AA024290 | 89912 | tccctgtcggttctgagcacttcg | AA110277 |
| 4705 | ccaagatgctatcgcggacgaggg | W49178 | 47309 | ccgctcattcctgatgactattgtg | AA024290 | 89913 | tcggttcgagcacttctgcagagt | AA110277 |
| 4706 | aagatgctatcgcggacgaggaaga | W49178 | 47310 | ctcattcctgatgactatgtgtca | AA024290 | 89914 | ggtctgagcactctgcagagtca | AA110277 |
| 4707 | agatgctatcgcggacgaggaagag | W49178 | 47311 | caggctccaaacagccatgcttaga | AA024290 | 89915 | tcttgagcacttctgcagagtcatg | AA110277 |
| 4708 | gattagatccctcagcttcctcat | W49178 | 47312 | ccaaacagccatgcttagcgcat | AA024290 | 89916 | ttgagcacttctgcagagtcatgaa | AA110277 |
| 4709 | attagatccctcagcttcccatc | W49178 | 47313 | agccatgctgagccattgggaat | AA024290 | 89917 | gcacttctgcagagtcatgaatcctc | AA110277 |
| 4710 | ttagatccctcagcttccatct | W49178 | 47314 | agccattgggaatcccacggcaca | AA024290 | 89918 | actctgcagagtcatgaatctcaa | AA110277 |
| 4711 | agatccctcagcttctccatctgc | W49178 | 47315 | tgggaatcccacggcacaggtgcc | AA024290 | 89919 | acgtcagacagcatttgggatat | AA110277 |
| 4712 | taggaactcgacctgagtctgagt | W49178 | 47316 | gaatccccacggcacagtggcagg | AA024290 | 89920 | gtactggactcagggcaccgatca | AA110277 |
| 4713 | ctcgacctgagtctgtagttacaga | M63554 | 47317 | tcccacggcacagtggccaggttt | AA024290 | 89921 | tggactcagggcaccgatcataaat | AA110277 |
| 4714 | ttgaaacaaatctacctatgtaga | M63554 | 47318 | gatcaagctctcaagaccaagtt | AA024290 | 89922 | gactcagggcaccgatcataatcct | AA110277 |
| 4715 | tgaactatggcctattgagacaa | M63554 | 47319 | tggccacagtcctcattcacgg | AA024290 | 89923 | ctcagggcacgatcataatcctgcgt | AA110277 |
| 4716 | atctcgataatcctattacaacat | M63554 | 47320 | ccagctcctattcacagtgagc | AA024290 | 89924 | ggcaccgcataatccctgtcggt | AA110277 |
| 4717 | ctattacaacatccaacagttca | M63554 | 47321 | tgtlatcacagatgctcagtggacc | X61172 | 89925 | caccgatcataatccctgtcggtct | AA110277 |
| 4718 | acaacatccaacagttcaagtcc | M63554 | 47322 | cacagatgctcagtggaccaagact | X61172 | 89926 | ccgatcataatccctgtcggttctg | AA110277 |
| 4719 | aatctcctgttaactatgctgat | M63554 | 47323 | tgctcagtggaccaagacgtctcg | X61172 | 89927 | aagtcctggagactggtcgagact | AA110277 |
| 4720 | cactgtlcacatgcattttgtaa | M63554 | 47324 | cattgaattatcatcccgtgtctt | X61172 | 89928 | gcaacgttgctgatgcctcca | AA110277 |
| 4721 | tgaaccagtgctaagactgtgtga | M63554 | 47325 | aattatcatcccgttcgtgtgt | X61172 | 89929 | ggagcatcacactgactgcagtac | AA110277 |
| 4722 | atacccagagacatatactatattac | M63554 | 47326 | gtgtcttgctgtactcgtgctgaa | X61172 | 89930 | cttatgaggtcactcactcaccaacc | D85845 |
| 4723 | ctattactaatgcatgcgggccat | M63554 | 47327 | ttgctgctgtgtcgaagtgtt | X61172 | 89931 | cctacaatttcatgccacattatac | D85845 |
| 4724 | aggaagctgctcatatctccat | M63554 | 47328 | tactcgtgctgtcgaagttt | X61172 | 89932 | tgccacaattatacctgcaagtct | D85845 |
| 4725 | tatatctccataagagtgctttca | M63554 | 47329 | agtgttcacagtcctttgtctag | X61172 | 89933 | atgtgcattcaactccctttcagc | D85845 |
| 4726 | atgaatctcatttagcccccactg | M63554 | 47330 | ttcacagtccttgctcagaagaa | X61172 | 89934 | atgttcctgtagacctgagctatga | D85845 |
| 4727 | dcattagcccccaactgatgtt | M63554 | 47331 | ccttattccacaggtgaagcaagaac | X61172 | 89935 | ctgtagacctgtgatcactcccta | D85845 |
| 4728 | tgttaagtacgttcttctggatata | M63554 | 47332 | cagaaactctatgtaaccagcaagc | X61172 | 89936 | acctgactgattcctactccca | D85845 |
| 4729 | gtatgccttctggatataagaacag | M63554 | 47333 | ctctatgtaaccagcaagcttcgc | X61172 | 89937 | gcattggaactcagtcaatacgat | D85845 |
| 4730 | agaggcctgtcttgatctaagtca | M63554 | 47334 | gtaaccagcaagctctgcttttta | X61172 | 89938 | gaactcagctcaatagatctctc | D85845 |
| 4731 | ttgatctaagctcattgagggctagc | M63554 | 47335 | acattacaacactgggaaatgaag | X61172 | 89939 | tggttcgtggatgcctccaactggg | D85845 |
| 4732 | tgtatcagttgaactactltaagtag | M63554 | 47336 | ctgggttcttctggcacaggggca | X61172 | 89940 | gctcaatagatctctctgattag | D85845 |
| 4733 | atatttcatttcatgatgaatctcc | X61434 | 47337 | tcctctggcacacagtgggcagtcagc | X61172 | 89941 | aatcttcaattgtgactctactact | D85845 |
| 4734 | gcaatggccaatgtcccacagtaacaa | X61434 | 47338 | agtcagccacactcagaccgaca | AA024320 | 89942 | caatttgtgactctactatctgt | D85845 |
| 4735 | caatgtccccacagtaacaaataaatg | X61434 | 47339 | ataagtatgcctgggccgaaagat | AA024320 | 89943 | tctctgtccacagcttcaactatca | D85845 |
| 4736 | gatttcagttgtccacctgtattt | X61434 | 47340 | tccgcagttgcctggcgccgaaagat | AA024320 | 89944 | gctcaactacgtgtccagggct | D85845 |
| 4737 | ctgaatactctgtgctagcaagtt | X61434 | 47341 | ceatcagtcctctgtgaggaagt | AA024320 | 89945 | gccctcttatggccatatggaaac | D85845 |
| 4738 | tactctgtgctagcaagttctggt | X61434 | 47342 | aagtagccatcaagctcgaatgt | AA024320 | 89946 | tgaaacattctctccatccaa | D85845 |
| 4739 | ttaaatccaagaacatgctaatact | X61434 | 47343 | tgaagacgaaacatcccagtcca | AA024320 | 89947 | ctttggagccatccactcgactg | D85845 |
| 4740 | ccaagaacatgctaatcatgtgttc | X61434 | 47344 | agaagaaacatcccagcccacat | AA024320 | 89948 | gcaagacgcaatcaaaccactgg | U65418 |
| 4741 | taatcatgttctagtatgctca | X61434 | 47345 | cccagctccacagagcaagtt | AA024320 | 89949 | cctgaatcaacactgccaatg | U65418 |
| 4742 | tgctacaaattctctggtagttg | X61434 | 47346 | tcatgagctgctgtggcccaacct | AA024320 | 89950 | aggactatcgtccagatccacat | U65418 |
| 4743 | aaattctgtgtggtgtat | X61434 | 47347 | tgtggccaacctggatgaccttt | AA024320 | 89951 | atgctgcagatccacatccactgt | U65418 |
| 4744 | ttaagtccagaaccctgtata | X61434 | 47348 | ggccaaccttggatgcactictcaa | AA024320 | 89952 | tccatccgaaggccgaacaaagc | U65418 |
| 4745 | tactgccctcctacgtgcaagt | X61434 | 47349 | atgacctctcaactctgttccg | AA024320 | 89953 | tcaccgtgaacactcatctccgtg | U65418 |
| 4746 | attgacagcagtcctagtcatage | X61434 | 47350 | tcttcaacttcgttccgacagt | AA024320 | 89954 | tgtggatccgctcacgagacatgc | U65418 |
| 4747 | agcagtcctagtcatatgcacacac | X61434 | 47351 | gtgctcctttgagacatctacct | AA024320 | 89955 | acacgaacatgccctgcaagtgtcc | U65418 |
| 4748 | attgaaatctatctgagaccttc | X61434 | 47352 | tcaactcctgtcccggacagttag | AA024320 | 89956 | acatcgctcaagtgtcccaaaat | U65418 |
| 4749 | aatcctatcgaagaccttctctcca | X61434 | 47353 | gctccttgagacatctaccggg | AA024320 | 89957 | tcaagccccctcaagaagtactgct | U65418 |

TABLE 1-continued

| SEQ ID NO | DBAxnID | sequence | SEQ ID NO | DBAxnID | sequence | SEQ ID NO | DBAxnID |
|---|---|---|---|---|---|---|---|
| 4750 | X61434 | atctgagacctctctccactatc | 47354 | AA024320 | cctttggagacatctacctgggtgc | 89958 | U65418 |
| 4751 | X61434 | ctctccactatctgcatgtgttt | 47355 | AA024320 | gagacatctacctgggtgccatcat | 89959 | U65418 |
| 4752 | J04847 | atttccaatgtgaaacagtcatca | 47356 | AA024320 | acactacctgggtgccatcatgc | 89960 | U65418 |
| 4753 | J04847 | aacaatgtcatcaattcgactgcc | 47357 | AA024320 | tctacctgggtgccatcatgcctc | 89961 | U65418 |
| 4754 | J04847 | tcattctcaacgagaggaacataa | 47358 | AA024320 | tggggtgccatcatgcctctgtga | 89962 | U65418 |
| 4755 | J04847 | cattctcaacgagaggaacataa | 47359 | AA024320 | gtgccatcatgcctctgtgagga | 89963 | U65418 |
| 4756 | J04847 | gtgccatcttggctagaaacatgg | 47360 | X63240 | cggcagcccagagctgcgggacct | 89964 | U65418 |
| 4757 | J04847 | agtggtgacggtccaagagcagat | 47361 | X63240 | cctcagcgctggggaccccgg | 89965 | U65418 |
| 4758 | J04847 | ttcagcagtggccgtgctagcaac | 47362 | X63240 | tgctcatccggagacctaccaag | 89966 | U65418 |
| 4759 | J04847 | tcagcagtggccgtgctagcaacag | 47363 | X63240 | agacctaccaagccaacactgcca | 89967 | U65418 |
| 4760 | J04847 | agtggccgtgctagcaacagtcgca | 47364 | X63240 | gctacgggaaccacgtgggtcgt | 89968 | U65418 |
| 4761 | J04847 | ggccgtgctagcaacagtcgcagcg | 47365 | X63240 | accagtggtgctgctgctaaaaat | 89969 | U73915 |
| 4762 | J04847 | gagccatggcagcagcagagaggggtt | 47366 | X63240 | tggtgctgctaaaaatgcaggc | 89970 | U73915 |
| 4763 | J04847 | agcaggtggcagcagcagagaggggttg | 47367 | X63240 | cctacgcgggcaagctgctcatcag | 89971 | U73915 |
| 4764 | J04847 | catgtcatcaatttcgactggcta | 47368 | X63240 | agtcgctcatcagcctgtccgagga | 89972 | U73915 |
| 4765 | J04847 | atgtcatcaatttcgactggcta | 47369 | X63240 | tgctcatcagcctgtccgagagc | 89973 | U73915 |
| 4766 | J04847 | gtcatcaatttcgactggcctagtg | 47370 | X63240 | tgtccgaggaggcatcagccgcga | 89974 | U73915 |
| 4767 | J04847 | tcatcaattcgactgcctagtga | 47371 | X63240 | acatggtagccaccgagtgcggctg | 89975 | U73915 |
| 4768 | J04847 | atcaattcgactgcctagtgaca | 47372 | X63240 | cggcctctagcgctgctccaa | 89976 | U73915 |
| 4769 | J04847 | tcaattcgactgcctagtgacat | 47373 | X63240 | tgcatgcctgtgtcccaacgactc | 89977 | U73915 |
| 4770 | J04847 | accctcattcaacgagaggacta | 47374 | X63240 | tagcgctgtgtcccaacgactccg | 89978 | U73915 |
| 4771 | J04847 | cctcattctcaacgagaggaacat | 47375 | X63240 | tgctgtctaaaggcgctgcaggg | 89979 | U73915 |
| 4772 | M57958 | ttaacgaaacaatcagtccgtcctg | 47376 | X63240 | tgctaaaggcgctgcagggcttacg | 89980 | U73915 |
| 4773 | M57958 | tcagtcgctccttttcgagtact | 47377 | X63240 | taaaggcgctgcagggcttacgggc | 89981 | U73915 |
| 4774 | M57958 | atctcgtccgaaatcgaagaaaca | 47378 | X63240 | agcgtcagtgctcatccgcagca | 89982 | U73915 |
| 4775 | M57958 | ttttcatacagggcatagtctcg | 47379 | X63240 | gtcagtgctcatcccgagaccta | 89983 | U73915 |
| 4776 | M57958 | ggcatagtctcgctcggatttcactc | 47380 | AA027404 | gccatcatgacgaagacgagacgagaag | 89984 | U73915 |
| 4777 | M57958 | atagtctcggtcgatttcactcact | 47381 | AA027404 | ccatcatgacgaagacgagaga | 89985 | U73915 |
| 4778 | M57958 | gtctcggtcgattcactcact | 47382 | AA027404 | agcgtcatcacaaccgagcag | 89986 | U73915 |
| 4779 | M57958 | gtcgattcactcactacgacatc | 47383 | AA027404 | ctgtcatctacaaccgagcagc | 89987 | U73915 |
| 4780 | M57958 | gatttcactcactacgacatctga | 47384 | AA027404 | gtcatctacaaccgagcagcgga | 89988 | X14805 |
| 4781 | M57958 | ttcactcactacgacatctgaaca | 47385 | AA027404 | tcatctacaaccgagcagcgggaga | 89989 | X14805 |
| 4782 | M57958 | cacttacgatcatctgaacagaatgt | 47386 | AA027404 | atctacaaccgagcagcgggagagt | 89990 | X14805 |
| 4783 | M57958 | ttacgacatctgaacagaatgtaaa | 47387 | AA027404 | ctacaaccgagcagcgggagagtt | 89991 | X14805 |
| 4784 | M57958 | gagtactacagggtcctcctcagtga | 47388 | AA027404 | acaaccgagcagcgggagagttctt | 89992 | X14805 |
| 4785 | M57958 | aggggtcctcagtcactactcagtgt | 47389 | AA027404 | aacccgagccagcgggagagttctgg | 89993 | X14805 |
| 4786 | M57958 | ttaggccctcattatctgtaagt | 47390 | AA027404 | agtttctgggggcacctccaagag | 89994 | X14805 |
| 4787 | M57958 | cctcattatctgtaagtataacg | 47391 | AA027404 | tttctgggggcacctccaagag | 89995 | X14805 |
| 4788 | M57958 | accttcaacacgtctggatcctcg | 47392 | AA027404 | agaagaaalcttccaccagagcct | 89996 | X14805 |
| 4789 | M57958 | ttcaacacgtctggatcctggtg | 47393 | AA027404 | tccttccaccagactgcggcgagt | 89997 | X14805 |
| 4790 | M57958 | aacacgtctgatctggggcaa | 47394 | AA027404 | cttccaccagacctgccggcgagtgg | 89998 | X14805 |
| 4791 | M57958 | tggatctggggcaaatctgagga | 47395 | AA027404 | caccagacctgccgagtggaagc | 89999 | X14805 |
| 4792 | W49194 | agcagtcgcctgaactggtgtgg | 47396 | AA027404 | ccagagcctgccgagtggaagctg | 90000 | X14805 |
| 4793 | W49194 | gccttgaactggtgttctgatgt | 47397 | AA027404 | agagcctgccgagtggaagctgtt | 90001 | X14805 |
| 4794 | W49194 | ctctgccccagtatagaccccaa | 47398 | AA027404 | agcctgccgagtggaagctgttca | 90002 | X14805 |
| 4795 | W49194 | ctgttgctccaatttgaccac | 47399 | AA027404 | cctggccagtggaagctgttcat | 90003 | X14805 |
| 4796 | W49194 | ttgtgctcaatttgaccactg | 47400 | AA027420 | ggtcctggacgaagccacagcccga | 90004 | X14805 |
| 4797 | W49194 | tctcaattgaccactctctt | 47401 | AA027420 | cacagccgagtggattgatagacg | 90005 | X14805 |
| 4798 | W49194 | ttcccatcacgccttgagggaaa | 47402 | AA027420 | cgcacaggccgtgcaccatcatg | 90006 | X14805 |
| 4799 | W49194 | cccatcacagccttgggaaatca | 47403 | AA027420 | gctgcaccatcatggacgagtgac | 90007 | X14805 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 4800 | atcacgcctlgagggaaatcaaga | W49194 | 47404 | gcaccaccatggacagtgacaag | AA027420 | 90008 | ctgttccaagctcagcactgccat | Z47352 |
| 4801 | atcaagatlctacagctcctaaaac | W49194 | 47405 | caccatcatggacagtgacaagata | AA027420 | 90009 | caagctcagcactgccatgaaccag | Z47352 |
| 4802 | aagatlctacagtctcctaaacatg | W49194 | 47406 | cctagacacggcaagatlgttgaa | AA027420 | 90010 | aatcccggtgaagggcaagctgctg | Z47352 |
| 4803 | cagtcctaaaacatgcagaatgtgg | W49194 | 47407 | cagtcctgaagaactgctgccaat | AA027420 | 90011 | gcagacaactcctgagccacaagg | Z47352 |
| 4804 | gttctgatgtctctgctcctgata | W49194 | 47408 | caatatggglccctlctacttgatg | AA027420 | 90012 | cacaaggcgcctgccatgggg | Z47352 |
| 4805 | ctgatgtctctgctcctgatacga | W49194 | 47409 | tatgglgtccctlctacttgalggcc | AA027420 | 90013 | gctgcctgcaatggglgccatt | Z47352 |
| 4806 | ctgtcctgatacagagaattggat | W49194 | 47410 | tccctlctacttgatggccaaggaa | AA027420 | 90014 | tctccatggaactctctgtctcc | Z47352 |
| 4807 | tctcctgatacgagaattggatlcc | W49194 | 47411 | gaaccacacaggagctctagacagt | AA027420 | 90015 | tggaactctctgtctccctcttt | Z47352 |
| 4808 | ggaaccatcacacaggaacgatlct | W49194 | 47412 | agcgccagtggatctagacagaga | AA027420 | 90016 | cctcttlccctlatgtcaacgtg | Z47352 |
| 4809 | accatcacacacaggaacgatlctctc | W49194 | 47413 | gacggatgcctcatlcagacgcacc | AA027420 | 90017 | gctgtccaaggctgtgatatgttttg | Z47352 |
| 4810 | caggaacgatlctctgcctgct | W49194 | 47414 | ggatagccatlcagacgaccatc | AA027420 | 90018 | tgtttgattcaggctctatgtagc | Z47352 |
| 4811 | ttccaacctgtccctcagtataga | W49194 | 47415 | catccggaacagttctcccagtgc | AA027420 | 90019 | gatlcagctctatgtagcatcctc | Z47352 |
| 4812 | cactgtggtlgcgcgtggccctlg | W49194 | 47416 | gaacgagtlcccagtlccacgcacggtc | AA027420 | 90020 | cagcaggccatgaacagccagcc | Z47352 |
| 4813 | tgaacgcgcctggccatgctca | W49194 | 47417 | ccagtgcacggtcatcactactcga | AA027420 | 90021 | altcaggctctatgtagcatcctct | Z47352 |
| 4814 | cagtctatgtcttcactcacgcagac | W49194 | 47418 | cacggtcatcactalcgcacacagg | X56007 | 90022 | ccagaacactgtcacaacgtggcc | Z47352 |
| 4815 | tctatgtcttcactcacgcagactgc | W49194 | 47419 | catcactatcgcacacagggtcgcac | X56007 | 90023 | cactggtcacaacgtggccacgag | Z47352 |
| 4816 | tctcctcagcgccaagtggccactg | W49194 | 47420 | cactlgttgcacagagaagatgaa | X56007 | 90024 | ccacgagctccatgaagaagctc | Z47352 |
| 4817 | ctgagccgccaagtggccactggt | W49194 | 47421 | tgagaacctggccacttlgtcatg | X56007 | 90025 | gtccctcatgaagaagctgtggcc | Z47352 |
| 4818 | cgccaagtlgggcactggcttcacag | W49194 | 47422 | cgctgccaatatlgccacagacgat | X56007 | 90026 | agacaacttlcctgtcatcagag | Z47352 |
| 4819 | actggctcacagcttlctgtctct | W49194 | 47423 | ggacaagttgctgccgtggccgcc | X56007 | 90027 | ctttlcctgtcatcagagggcgag | Z47352 |
| 4820 | ggcttcacagcttlctgtctgta | W49194 | 47424 | ccacactcctgtggatgctctg | X56007 | 90028 | ggagcaaatcccgtgaaggggcaag | Z47352 |
| 4821 | gcttctcttctgtatactaaagg | W49194 | 47425 | tctctgtgalgcttctcggaatgt | X56007 | 90029 | cagacctgctcagagaggacaaag | Z47352 |
| 4822 | tctlgtctgtatactaaaggttg | W49194 | 47426 | caacttctcacctagcctgatgcc | X56007 | 90030 | aagctgatccacgaagglgtgcc | Z47352 |
| 4823 | tgtctgtatactaaaggttgctt | W49194 | 47427 | ctagcctgatgccacacaatttcc | X56007 | 90031 | cagagctcggtccatlgtaccagc | Z47352 |
| 4824 | acgcgctctggccatgctcagat | W49194 | 47428 | tgatgccacacaatltccaacatc | X56007 | 90032 | ctggccatlgtaccaggccagcta | Z47352 |
| 4825 | gttgcttlattgtcaccatltcaat | W49194 | 47429 | caacatcttccaacttagcttage | X56007 | 90033 | catlgtaccaggcagcctagccag | Z47352 |
| 4826 | gctccttlggccatgctcagatatc | W49194 | 47430 | ctccaacttagcttagccagaga | X56007 | 90034 | tgcctlaggccccagccagctgac | Z47352 |
| 4827 | tggccatgctcagatatcctcaag | W49194 | 47431 | acctlagtlagccagacagagaga | X56007 | 90035 | aggtccccagccagctgacacagaagg | Z47352 |
| 4828 | cccatgctcagatatcctcagcga | W49194 | 47432 | ccttggccactlgtcatgtcct | X56007 | 90036 | cagcagctgacagaagggggctct | Z47352 |
| 4829 | atgctcagatatcctcaagcgaaac | W49194 | 47433 | ccactgctlcatgtcatgttcgct | X56007 | 90037 | ttctccacagagctgggglgcag | Z47352 |
| 4830 | tatcctcaagcgaaacatccagcag | W49194 | 47434 | tgtcatgttlccctgctaatlggcagc | X56007 | 90038 | ccacagagctggggtgcagccccaa | Z47352 |
| 4831 | cctcaagcgaaacatccagcagtac | W49194 | 47435 | tcctactatggcaaaagtlccat | X56007 | 90039 | ggtcagcccaacatgtgatllg | Z47352 |
| 4832 | gtacaacagcttlgtgcatgctgcc | W49194 | 47436 | ctatactcagcctltggcggctgta | X56007 | 90040 | gcccaacatgtgatlltgaatgag | Z47352 |
| 4833 | aagatggatgccacacgccaatgatg | M73329 | 47437 | tgttgaatgccgatcaagcggtgta | X56007 | 90041 | atccacgaaggtggtgccacactct | Z47352 |
| 4834 | gatgccacacgccaatgatgtgctt | M73329 | 47438 | atgccgtcatcaagcgtgccaatat | X56007 | 90042 | cacatctgtcgcgggatgatgtc | Z47352 |
| 4835 | tttatlagtctactcaacgaagaag | M73329 | 47439 | catcaacgctgccaatatlgccaca | X56007 | 90043 | tatgtcgggatgctcgaaata | Z47352 |
| 4836 | gaggacctctaaagcaacgcccaaa | M73329 | 47440 | gaatltcaacgcacaacatlccg | X56007 | 90044 | aacacattctatgacatlgggccg | D17571 |
| 4837 | gacctctaaagcaacagcccaatgc | M73329 | 47441 | cgcaacatcgatcccatgagc | X74216 | 90045 | gacatcggccgagtlgggccca | D17571 |
| 4838 | ctctaaagcaacagcccaatgcacc | M73329 | 47442 | cagagtlcgttlgacccactlcaacc | X74216 | 90046 | gggccctgccgagtttlgggccgtg | D17571 |
| 4839 | aacagcccaaatgcacccactlatata | M73329 | 47443 | tgcttlgacccacttlcaacctact | X74216 | 90047 | tggccctlaggccgagccgctgtcc | D17571 |
| 4840 | ggactctlaccagaagagcaa | M73329 | 47444 | gccctlcaaggctgtgtgacaaagt | X74216 | 90048 | ctlaggcagccgctlccatlgta | D17571 |
| 4841 | ggataaactgttlctlagctgtaaat | M73329 | 47445 | aacagcacagcacacagcagtgaca | X74216 | 90049 | gtggaaacctgtccatlgagc | D17571 |
| 4842 | tctctaaacttgttctltagctgcac | M73329 | 47446 | gacaacagcgccaaaagcagtgaca | X74216 | 90050 | cctgtccatlgaggccagatgacaa | D17571 |
| 4843 | tgttlctlagctgcactgttgaaa | M73329 | 47447 | gggaacagccacctcactgctgct | X74216 | 90051 | ctggcatccatlgctcaggatcacc | D17571 |
| 4844 | ttagctgcactgttlgaaaataaacaa | M73329 | 47448 | agccactcctactgctgctact | X74216 | 90052 | ggatcaccatlgaggtcc | D17571 |
| 4845 | gccatgccaatgatgtgcttctc | M73329 | 47449 | tctactgctgctactcgcgt | X74216 | 90053 | atcaccatcattcgaggtcccca | D17571 |
| 4846 | acagccaatgatgtgcttctccat | M73329 | 47450 | tgctgctactcgctgtlgcgc | X74216 | 90054 | aaccaaggtlcacatatagtctg | D17571 |
| 4847 | gtgccttctccatgaagtcaagg | M73329 | 47451 | tcccgagtlcctccgatlgctctc | X74216 | 90055 | agtgctgctllcactgctgcac | D17571 |
| 4848 | tcccatatgaagtcaagggttttc | M73329 | 47452 | cattcagtlgaccctlcaatggagacaagtg | X74216 | 90056 | gctgctlgttlcactgctgcaccaa | Y07711 |
| 4849 | tttccaaccagccaacagaagctaa | M73329 | 47453 | gatccaatgagcaagtlgggcaagaa | X74216 | 90057 | ttcactgctgccaccatlgcccttg | Y07711 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 4850 | tcaccagccaacaagaagctaactc | M73329 | 47454 | atgtcctggccacaaaacagatct | X74216 | 90058 | gtgcttgctgaggtagaagccta | Y07711 |
| 4851 | ccagccaacaagaagctaactccaa | M73329 | 47455 | ctggccacaaaacagatcgcaaag | X74216 | 90059 | cctgctctgctgctaggttgtg | Y07711 |
| 4852 | aagctaacctccagaatgtatgaa | M73329 | 47456 | actgacctgctgctccaggacgat | X74216 | 90060 | cgtctaggttggccacagctaag | Y07711 |
| 4853 | gcaatccttactccagaaaacagcg | M14647 | 47457 | aactcgcgccaatctactctgg | X74216 | 90061 | ctctcgatggccacgtccttgcg | Y07711 |
| 4854 | ctaactccagaaaacaggcggcaag | M14647 | 47458 | aatcctatccggacctggcatcc | X74216 | 90062 | atggccacgtccttgtcggaagg | Y07711 |
| 4855 | ttctggtcgtcatggtcagattgc | M14647 | 47459 | gagcctggcatccagagttgcttga | X74216 | 90063 | cactgaggccagtccttgcctcac | Y07711 |
| 4856 | aacaggtgtctctagaaccttatgc | M14647 | 47460 | gaaggcaccagctgaaggaacatcc | X74216 | 90064 | tgaggccagtcctgcctcacct | Y07711 |
| 4857 | agaacctgtagaacgcgtgcgca | M14647 | 47461 | tgaaggaacatccactttaagag | AA027445 | 90065 | tgccctgaccaggcctcagcatg | Y07711 |
| 4858 | tacctcaggtcctgaagttgtctg | M14647 | 47462 | cgaaccaatgagctgttcatgacg | AA027445 | 90066 | cctcagcatggcctacaagtattga | Y07711 |
| 4859 | gatgttcataacaactgctgaa | M14647 | 47463 | aaccaatgagctgttcatgacgtt | AA027445 | 90067 | catggcctacaagtattgaggctcc | Y07711 |
| 4860 | tgctgaacatctatccctctct | M14647 | 47464 | gttcatgacgttatactgagtc | AA027445 | 90068 | tgggctcaaccctgcctctg | Y07711 |
| 4861 | atccctctctgtctcttagaag | M14647 | 47465 | ttcttgaaaagctccacactcgg | AA027445 | 90069 | tgggccagtatcgtgctgtctcca | Y07711 |
| 4862 | tgtctctagaaggtccctggtgat | M14647 | 47466 | ttgaaaagctccacactcggtgag | AA027445 | 90070 | cccagatcgcgctgctgctccagg | Y07711 |
| 4863 | tcgtgatctagacctttcaaagcacc | M14647 | 47467 | aaagtccacactcggtgagtcat | AA027445 | 90071 | gcatctacgaccggggcctcgcg | U78109 |
| 4864 | ttggtgcctttctagatgagttgt | M14647 | 47468 | agctccacactcggtgagtcatga | AA027445 | 90072 | tctacgacctgggcctcggcgcct | U78109 |
| 4865 | aacgcggagcaagtccaccagaca | M14647 | 47469 | ccacactctggtgagtcatgaggtt | AA027445 | 90073 | gccgaccggcctatgaggagacgaggt | U78109 |
| 4866 | actgatctttgcaaatgctaaatt | M14647 | 47470 | acactctggtgagtcatgaggtgt | AA027445 | 90074 | cgacggcctatgaggacgaggtgtc | U78109 |
| 4867 | gtccaccagacacatcggaagacc | M14647 | 47471 | actctgggtgagtcatgaggttgtc | AA027445 | 90075 | cctctcggagtgcacgccgcta | U78109 |
| 4868 | tccatcactatttcaagcctggg | M14647 | 47472 | ggaacatccactttaagagctgt | AA027445 | 90076 | gccgctaccacgcgcaagagct | U78109 |
| 4869 | gctcttccacatgtacctgatatc | M14647 | 47473 | catcactttaagagctgtatat | AA027445 | 90077 | gacccgtcgagaactgactcac | U78109 |
| 4870 | ccacagtacctgatactctgtgt | M14647 | 47474 | tccacttttaagacgctgtatatac | AA027445 | 90078 | cctcgctagaactgactcacata | U78109 |
| 4871 | gtacctgatactctgtgtcaagaa | M14647 | 47475 | gctgtatatacatccatccacctt | AA027445 | 90079 | gaactgacttcacataaagtgtggg | U78109 |
| 4872 | taccagagctgttgcaagtgact | M14647 | 47476 | catccaactgcatcacaaataag | AA027445 | 90080 | ctgactcacataaagtgtggaac | U78109 |
| 4873 | tatactttcgtcgtcatgtcag | M14647 | 47477 | tctccactgcatcacaaataagtt | AA027445 | 90081 | agtatcgctctgctccagggcc | U78109 |
| 4874 | agctacggcattcgtacagact | W49285 | 47478 | tccactgcatcacaaataagtag | AA027445 | 90082 | ttcgaaacttctccggctgc | U78109 |
| 4875 | cctacagaaatccggcattcgtaca | W49285 | 47479 | cactgcatcacaaataagttagac | AA027445 | 90083 | gagagacttttctccctgggtccg | U78109 |
| 4876 | taagacaatggctgcttagccaag | W49285 | 47480 | tgcctctgcagcctacactggcat | AA027445 | 90084 | tgggctacacgtcggatgagaccgt | U78109 |
| 4877 | acaatggctgcttagccaaggcca | W49285 | 47481 | tagataaccataccctcttct | AA027445 | 90085 | tctaacagtcggatgagaccgtgt | U78109 |
| 4878 | gctgcttagccaaggccatcgaaa | W49285 | 47482 | tattttctaacgcdggactgagc | D16141 | 90086 | acacgtcggagaacggtcgtgtt | U78109 |
| 4879 | tgcttagccaaggccatcgaaaag | W49285 | 47483 | tctaacgctgaactgagcdggcca | D16141 | 90087 | cggcatcacgaccdggccttcg | U78109 |
| 4880 | ttagccaaggccatcgaaaagacg | W49285 | 47484 | gcctgactgacgctggccagtcatt | D16141 | 90088 | tccgatcacgacctgggccttcg | U78109 |
| 4881 | gtgtattttcacacctgatgaca | W49285 | 47485 | actgagctgccagtcatttctaaag | D16141 | 90089 | cgtcgcgtcatggtggagcatcatc | U78109 |
| 4882 | gttattttcacacctgaccttgat | W49285 | 47486 | ctggccagtcatttctaaagcagttt | D16141 | 90090 | cgtctgcatgttcctttccttcact | U78109 |
| 4883 | tttttcacacctgatgacaat | W49285 | 47487 | tggtacttgctccggccgttgg | D16141 | 90091 | caactctcacaaactctccctgagg | D50096 |
| 4884 | cacacctgatgacaatgagaaga | W49285 | 47488 | gtatgtggtcctgactagag | D16141 | 90092 | caactctgctgtccaggagccaa | D50096 |
| 4885 | atgcaatgttccagtctcttat | W49285 | 47489 | tgtggctcctgactagagactgt | D16141 | 90093 | tctgtccaggagccaaagccga | D50096 |
| 4886 | caagaaatccggcattcgtacagact | W49285 | 47490 | atgggcttccctgagatgccacct | D16141 | 90094 | tgatgctgagaccggttgtggagca | D50096 |
| 4887 | gaaatccggcattcgtacagactg | W49285 | 47491 | gtagagtccacctcggcttctcg | D16141 | 90095 | atttacagaaatcatctccatcc | D50096 |
| 4888 | aatccggcattcgtacagactgaa | W49285 | 47492 | gcaggcatgacctcggttgctccc | D16141 | 90096 | cagaaatcatctcatctccctag | D50096 |
| 4889 | gggtctatcgcgctgaggtta | W49285 | 47493 | tcgtccacctcggtcttgcct | D16141 | 90097 | atcatcctttaggtagaccatta | D50096 |
| 4890 | ggtgtatcgcgctgaggttaca | W49285 | 47494 | cttaacgaccgaaccdgtgactagt | D16141 | 90098 | agatctaccaagatccacgagct | D50096 |
| 4891 | ctatcagcgctgaggttacactga | W49285 | 47495 | acgagcccgctgactgatgctgggc | D16141 | 90099 | taccaagatccacggaggaagctggacag | D50096 |
| 4892 | atcagcgctgaggttacactgagg | W49285 | 47496 | cactccataccgtactctccttttc | D16141 | 90100 | gatccacgagagcttgacagaatgt | D50096 |
| 4893 | atgctgctccaggtgagaagt | W49285 | 47497 | atacctacttcctctccttccag | D16141 | 90101 | tgcctcgtttaccgcggactgaga | D50096 |
| 4894 | actcagttatcactgtcagttcg | W49285 | 47498 | tacttcctttcctccaagcagagt | D16141 | 90102 | cgtctaggttggggtttatgccaat | D50096 |
| 4895 | tcagttatcactgtcagttctgca | W49290 | 47499 | cttctcctcaagcagagtatttt | D16141 | 90103 | cagaagcttccatgcgtaccaa | D50096 |
| 4896 | tgcagtttcccaaagtgcctggaa | W49290 | 47500 | cacgccatgggcctctgagagat | D16141 | 90104 | cttccgatggcgtaccaacagctc | D50096 |
| 4897 | tcccaaagtgcctgaagaacgcgag | W49290 | 47501 | atgggcctctgagagatcccttaga |  | 90105 | acagtcttcactgcaagctgca | D50096 |
| 4898 | gaaacatggcgcgttgatgctcaa | W49290 | 47502 | agatcctagaatcccagtgggtccc |  | 90106 | cttccgcaagttgcaagccac | D50096 |
| 4899 | acatggcgcgttgatgctcaacac | W49290 | 47503 | gatcctagatcgaggcgggtccct |  | 90107 | ctgcaagctgcaagcgcaacactct | D50096 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 4900 | tggatgtcaacaccgtgttcaagga | W49290 | 47504 | atcctagatccagcggtgccctc | | 90108 | gcttgcaagccacaacctccacaa | D50096 |
| 4901 | ggatgtcaacaccgtgttcaaggag | W49290 | 47505 | tgggcctccgagagatccttagat | | 90109 | gctaggtatcgcagcaggaaccg | AA119868 |
| 4902 | gatgtcaacaccgtgttcaaggagt | W49290 | 47506 | gggcctccgagagatccttagatc | | 90110 | ctctaggtatcgcagcaggaaccga | AA119868 |
| 4903 | tgtcaacaccgtgttcaaggagtta | W49290 | 47507 | ggcctccgagagatccttggaga | | 90111 | gggcctggcttccgatcttggaga | AA119868 |
| 4904 | gtcaacaccgtgttcaaggagttag | W49290 | 47508 | gcctccgagagatccttagatcc | | 90112 | ggcctggcttccgatcttggaagaa | AA119868 |
| 4905 | tcaacaccgtgttcaaggagttagt | W49290 | 47509 | cctcctgagagatccttagatccag | | 90113 | gctggcttccgatcttggagaat | AA119868 |
| 4906 | agtttataccttcgagttcgcagt | W49290 | 47510 | ctccgagagatccttagatccagc | | 90114 | cctggcttccgatcttggagaatg | AA119868 |
| 4907 | tactctgagttcgcagttttcc | W49290 | 47511 | agagatccttagatccagcggtgcc | | 90115 | ctggcttccgatcttggagaatgt | AA119868 |
| 4908 | actctgagttcgcagttttccca | W49290 | 47512 | gagatccttagatccagcggtgcc | | 90116 | tggcttccgatcttggagaatgtg | AA119868 |
| 4909 | ctctgagttcgcagttttcccaa | W49290 | 47513 | tgggcctccgagagatccttagat | | 90117 | ggcttccgatcttggagaatgtga | AA119868 |
| 4910 | tctgagttctgcagttttcccaaag | W49290 | 47514 | gggcctccgagagatccttagatc | | 90118 | gcttccgatcttggagaatgtgaa | AA119868 |
| 4911 | ctgagttctgcagttttcccaaagt | W49290 | 47515 | atcctagatccagcggtgccctc | | 90119 | ttccgatcttggagaatgtgaagg | AA119868 |
| 4912 | tgagttctgcagttttcccaaagtg | W49290 | 47516 | tcctagatccagcggtgccctcc | | 90120 | taagtctgaattgatgtggcctcgg | AA119868 |
| 4913 | ctgcagttttcccaaagtgctgga | W49290 | 47517 | ccttagatccagcggtgccctcca | | 90121 | aggtatcgcagcaggaaccgaagta | AA119868 |
| 4914 | tgtagagcagatccttggtatg | M98502 | 47518 | cttagatccagcggtgccctccaa | | 90122 | ggatcgcagcaggaaccgaagtac | AA119868 |
| 4915 | gcagattccttgcgtattggtcaac | M98502 | 47519 | ttagatccagcggtgccctccaac | | 90123 | gtatcgcagcaggaaccgaagtacg | AA119868 |
| 4916 | tcttttacattatgctgtgcaggt | M98502 | 47520 | tagatccagcggtgccctccaacc | | 90124 | tatcgcagcaggaaccgaagtacgc | AA119868 |
| 4917 | tgctgtgcaggtgtacagttagt | M98502 | 47521 | agatccagcggtgccctccaacca | | 90125 | atcgcagcaggaaccgaagtacgcc | AA119868 |
| 4918 | tgaggcacactgtctgaactctg | M98502 | 47522 | gatccagcggtgccctccaaccag | | 90126 | accattgggctgcttccgatctt | AA119868 |
| 4919 | gaatatgctacatctgtccggtca | M98502 | 47523 | atccagcggtgccctccaaccagg | | 90127 | cattgggctgcttccgatcttg | AA119868 |
| 4920 | gctacactggtccgtcagtgtga | M98502 | 47524 | tccagcggtgccctccaaccagga | | 90128 | tgggcctggcttccgatcttggag | AA119868 |
| 4921 | gtcatgccgttgcaaagcaacat | M98502 | 47525 | ggcctccgagagatccttagatc | | 90129 | tcccgtctgcaaccagcaggcagg | AA119868 |
| 4922 | ttattagcttgcagaagaagaga | M98502 | 47526 | gcctccgagagatccttagatcc | | 90130 | tctgcaaccagccaggcaacta | AA110440 |
| 4923 | aaacagcaggaaccagtgctaggc | M98502 | 47527 | cctccgagagatccttagatcca | | 90131 | tgaacaaacttgtgtcaagcaggg | AA110440 |
| 4924 | ggtatacacatatatccgactct | M98502 | 47528 | ctccgagagatccttagatccag | | 90132 | gtccgagacactctggtctcc | AA110440 |
| 4925 | agcagcctagtctacgtgtaggaa | M98502 | 47529 | agagatccttagatccagcggtgc | | 90133 | aggcacttcggtcttccgtgatg | AA110440 |
| 4926 | tccctgtattggtcaaccatcct | M98502 | 47530 | gagatccttagatccagcggtgcc | | 90134 | ttctggttccgtgatggtctg | AA110440 |
| 4927 | ccatcctagttcgtctatagct | M98502 | 47531 | agatccttagatccagcggtgccc | | 90135 | tgggtcccgtgatggggtcgtca | AA110440 |
| 4928 | tagtctgtctatagctctatta | M98502 | 47532 | gatcctggttcgactttgctg | | 90136 | gggtctcaggcatccagcagga | AA110440 |
| 4929 | taaactcaaaaccactgagtact | M98502 | 47533 | cctgaagctgacttggtgtt | | 90137 | agggcatccagcaggaaccgggcaa | AA110440 |
| 4930 | ttggtaatctcaaactcatgatag | M98502 | 47534 | tgaagctgacttggtgtcac | | 90138 | aagaaccggggcaatggctgcatgc | AA110440 |
| 4931 | atctcaaactcattgatagtagagc | M98502 | 47535 | ttcagcgtgttctacctgatgct | | 90139 | accgggcaatggctgcatgtcaca | AA110440 |
| 4932 | cctctcgattttcatgaagattcat | M98502 | 47536 | agcgcgttctacctgatgatctgga | | 90140 | atggctgcatgtcacagaagataag | AA110440 |
| 4933 | cggtcatgatcatcttacattat | M98502 | 47537 | gcgttctacctgatgatctgagc | | 90141 | gcaaccaggcaggcaactacttctt | AA110440 |
| 4934 | tatagaaaacaccctgggtgaagg | M98502 | 47538 | ttctacctgatgatctggagcgtt | | 90142 | aggcaggcaactacctctggctg | AA110440 |
| 4935 | gccaggcagtcatcaggagagacc | L29503 | 47539 | ctgatgatctggagcgttgcacag | | 90143 | caggcaactacctctggtctgtca | AA110440 |
| 4936 | tattctccaagaccacagcctg | L29503 | 47540 | atctggagcgttgcacagttgac | | 90144 | gcaactacctctggtctgcagg | AA110440 |
| 4937 | ttccaagcaacagcctaagttgg | L29503 | 47541 | acagattgactaatcctaatcgac | | 90145 | ttctggctggggagtacagt | AA110440 |
| 4938 | gaccacagccttgactgggaagaat | L29503 | 47542 | gattgactaatcctatacagag | | 90146 | atgttgccaataatcgcgctgcca | AA110440 |
| 4939 | gaagagccccaaatacggggaaag | L29503 | 47543 | ctaatcctatacagcaggattgtc | | 90147 | ttgccaatcgctcgctgcatct | AA110440 |
| 4940 | tgagcacctgaaccaaaacctggag | L29503 | 47544 | atacagcaggatgttgttgcgggcg | | 90148 | aaggctcctggaacaatgggcatga | AA110440 |
| 4941 | atctcgtttggccgctggggga | L29503 | 47545 | ctggtctggctgcaggaagaac | | 90149 | tctgagcctcgacagacccttca | AA110440 |
| 4942 | tatgttccacacctcgtgccctc | L29503 | 47546 | gtcctggtctgcagaaggaacaag | | 90150 | ctgcagtcctgacgacccttcat | AA110440 |
| 4943 | tatttctcgagaaccaatgtgtt | L29503 | 47547 | gatgctcctgaagactgtcgg | | 90151 | ctgttttcactccaagtagctga | AA110440 |
| 4944 | tactactggtgctgtaccgacac | L29503 | 47548 | gcttcctgaagactgttcggt | | 90152 | ctgttcactccaagtagttgaa | AA110440 |
| 4945 | cagacacaaacagcctaggtgctaa | L29503 | 47549 | tgcaagcttgtttgccgttcaga | | 90153 | tgtttcaccccaagtagctgaaa | AA110440 |
| 4946 | cagtcatcgaccaaccactgca | L29503 | 47550 | cctgtttggcgctcagagaataat | | 90154 | ttcactccaagtagctgaaaaag | AA110440 |
| 4947 | ctatgcaccagagtaataccagagt | L29503 | 47551 | gctcaatgattcagcgccgttctacc | | 90155 | tcactcccaagtagctgacaccttcat | AA110440 |
| 4948 | tgccaccaggatacgcgcacttc | L29503 | 47552 | caattgattcaggccgttcactga | | 90156 | tgcagtcgagacccttcatc | AA110440 |
| 4949 | ccaggatacgcaacttccatcatt | L29503 | 47553 | gcctgcaagccctcgcgatct | AA027491 | 90157 | cctgacgacccttcatccagggt | AA110440 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 4950 | gcacttcatcatgtgaactataga | L29503 | 47554 | ttgaagaagccttgcgatatcct | AA027491 | 90158 | tgacagacccttcatcccaggttt | |
| 4951 | ctatagaacatcaactctgcaaatg | L29503 | 47555 | gtcaccatgccgttgactgaatg | AA027491 | 90159 | cttcatcccaggglttcagtcctg | |
| 4952 | aacatcaaactctgcaaatgtggat | L29503 | 47556 | gatgatcatgcctctcagctccgg | AA027491 | 90160 | ttcatcccagggttctagtcctgt | |
| 4953 | aactctgcaaatgtggatatttct | L29503 | 47557 | gatcatgcctctctagctccgta | AA027491 | 90161 | tcatcccaggglttcagtcctgt | |
| 4954 | gatttgctgtcattcccaaagt | M37335 | 47558 | gcctctagctccggctacgcggag | AA027491 | 90162 | gtcccgttcactcccaagtagctt | |
| 4955 | ttgctgtcattcccaaagtgct | M37335 | 47559 | gtttgagcagcccaagatccggcga | AA027491 | 90163 | tcctgttcactcccaagtagctg | |
| 4956 | cattccttaaaatctcacatgca | M37335 | 47560 | tgagcccaagatccggcgaacgc | AA027491 | 90164 | tagtcagggactcctcccctctgca | |
| 4957 | tccctaaaatctcacatgcacac | M37335 | 47561 | gcagcccaagatccggcgaacagc | AA027491 | 90165 | agtcaggactcctcccctctgca | |
| 4958 | cttaaaatctcacatgcacaca | M37335 | 47562 | caagatccggcgaacgacgagagc | AA027491 | 90166 | gtccctgacagaccctcatcccag | |
| 4959 | agttaatcaactgcaagtgttcct | M37335 | 47563 | tcagctgagcgtcagcagtgttt | AA027491 | 90167 | cctgacagaccctcatcccaggt | |
| 4960 | taatcaactgcaagtgttccttca | M37335 | 47564 | gctgagtcgcagcagtgttcct | AA027491 | 90168 | cctatcccaggglttcagtcctg | |
| 4961 | tcaactgcaagtgttccttcattt | M37335 | 47565 | acgaagcttcgagatactcctgct | AA027491 | 90169 | ttcatcccaggglttcagtcctgt | |
| 4962 | actgcaagtgttccttcattctg | M37335 | 47566 | aagccttcgatactcctgtctc | AA027491 | 90170 | tcatcccaggglttcagtcctgt | |
| 4963 | gcaagtgttccttcattctgata | M37335 | 47567 | tccgatactcctgctctcctgtat | AA027491 | 90171 | tcctgttcactcccaagtagctg | |
| 4964 | tccttcattctgataagaagaattt | M37335 | 47568 | tgcctatctgccacttcgggtaga | AA027491 | 90172 | cctgttcactcccaagtagcttga | |
| 4965 | tttagaaactctcattactacaaatg | M37335 | 47569 | ctatctgccacttcggttagagaa | AA027491 | 90173 | ctgtttcactcccaagtagcttga | |
| 4966 | tgctgtcatcccaaagtgcttc | M37335 | 47570 | tctgccacttcggtagaggatct | AA027491 | 90174 | ttcactcccaagtagctgaaaag | |
| 4967 | cattccccaaagtgcttctgctg | M37335 | 47571 | gtagtgtcaccatgcccgttgaac | AA027491 | 90175 | tcactcccaagtagctgaaaaggt | |
| 4968 | ccaaagtcttctgctgttgaa | M37335 | 47572 | gttgtcaccatgcccgttgactgg | AA027491 | 90176 | ccctctgcagtcccctgcacgaccc | |
| 4969 | aagtgcttctgtcgttgaaga | M37335 | 47573 | aagctcgggccatgagcacttac | AA027491 | 90177 | ccctctgcagtcctgcacgaccct | |
| 4970 | tgcttctgcgttgaaagagat | M37335 | 47574 | ggcctagcacttaccaggcatt | AA027491 | 90178 | cctctgcagtcctgcacgaccct | |
| 4971 | acttgagacttgtctgggcaat | M37335 | 47575 | caccagacaggatgctctacaac | AA027491 | 90179 | tctgcagtccctgacagacctca | |
| 4972 | tgagacttgtggccaatata | M37335 | 47576 | tcctgctccaactagagccagag | AA027491 | 90180 | ctgcagtccctgacagacccttat | |
| 4973 | gaaaccatcaagatcaaggaaggt | M37335 | 47577 | caactagagccagagtctcaga | Z22216 | 90181 | tgcagtccctgacagacccttcatcc | |
| 4974 | caagaagaacctctagcacagatct | W49298 | 47578 | ctagagcccagagtcttcagaa | Z22216 | 90182 | cagtccctgacagaccctcatccc | |
| 4975 | agaagaacctctagcacagatctag | W49298 | 47579 | gagcccagagtcttcagaagaaga | Z22216 | 90183 | agtccctgacagacccttcatcca | |
| 4976 | gctgactgcgaggttgcagattgg | W49298 | 47580 | tggcgctgctggctctttttcaga | Z22216 | 90184 | cacatcaacatcttcctaatcgcaa | |
| 4977 | ctgactgcgaggttgcagatttgt | W49298 | 47581 | cgcgctgtgggtcttttcagaggt | Z22216 | 90185 | catcaacatcttcctaatcgcaac | |
| 4978 | actgtctcctcaactggatgct | W49298 | 47582 | gctctttcagaggttccagcca | Z22216 | 90186 | cgcaaccggtcaactgatgtagag | |
| 4979 | taacctgatgctgtgtctgtgct | W49298 | 47583 | tcttttcagaggttccaggcaagg | Z22216 | 90187 | aaccggtcaactgatgatgagatgt | |
| 4980 | aacctgatgctgctgttgtgctg | W49298 | 47584 | aggttccagccaagggcatgacaag | Z22216 | 90188 | gctgcttcgattgcctgtgctt | |
| 4981 | ctggatgctgtctgttgtctgtat | W49298 | 47585 | catgagcactaccaggcattt | Z22216 | 90189 | cttcgatttgcctgtgctttagag | |
| 4982 | ttgctgtctgtatccggaaag | W49298 | 47586 | ttcccaggccaagggcatgcaagctt | Z22216 | 90190 | tcgaatgtgcctgctcttaagaa | |
| 4983 | tgtctgtctgtatccggaaag | W49298 | 47587 | cacttaggccaggcattttacagac | Z22216 | 90191 | gtgcctgctgttagagaagctggaa | |
| 4984 | agtctatcaacagttggagattt | W49298 | 47588 | ttacgcaggcattttacagaccac | Z22216 | 90192 | agactatgctgacgatcagtgagtg | |
| 4985 | gtctatcaacagttgggagattt | W49298 | 47589 | gtagctgcgcaagccccaagtta | Z22216 | 90193 | tatgctgacgatcagtgagtggc | |
| 4986 | gaagaacctctagcacagatcagc | W49298 | 47590 | gctgcaggccccaagccccaagttagg | Z22216 | 90194 | tatgctgacgatcagtgagtggccc | |
| 4987 | gaacctctagcacagatctgaa | W49298 | 47591 | aacctcagcacagacacccgctc | Z22216 | 90195 | tgctgacgatcagtgagtggccca | |
| 4988 | acctctagcacagatctgact | W49298 | 47592 | tgctgcatcaccagacaggatgg | Z22216 | 90196 | catcttccaatcgcaaacgtagat | |
| 4989 | tctagcacagatctagctgactcg | W49298 | 47593 | cataaccaggaccagggatgctccac | Z22216 | 90197 | tcctaaatcgcaaacgtagattg | |
| 4990 | ctagcacagatctagctgactgcg | W49298 | 47594 | ataacctgaagtgctgacatcac | X15267 | 90198 | ttcctaaatcgcaaacgtagattg | |
| 4991 | gatctagctgaggttgcag | W49298 | 47595 | aaacctgaagtgctgacatcacag | X15267 | 90199 | atcgaaactagatgtgcaagt | |
| 4992 | ctagctgactgcgaggttgcagatt | W49298 | 47596 | ctgacatcacagagcaggccctgc | X15267 | 90200 | ggcaagtgcagcaaccggtcaac | |
| 4993 | tagctgactgcgaggttgcagatt | W49298 | 47597 | tcgaatcacagagcaggccctgca | X15267 | 90201 | caagtgcacagcaaccggtcaactg | |
| 4994 | caaggcgggctcgccaatacttg | L28835 | 47598 | cgaatcacagagcaggccctgcac | X15267 | 90202 | agtgcaagacaaccggtcaactgat | |
| 4995 | agccgctcgccaatacttctc | L28835 | 47599 | catccagagcagcaggccctgcactct | X15267 | 90203 | tgcacgaccaaccggtcaactgatgt | |
| 4996 | tctgctgcttcttctgcatg | L28835 | 47600 | cagagcaggccctgcactctcgtt | X15267 | 90204 | agattccatgctcaaacactgaa | |
| 4997 | cagtgctttgtgtccagatgagg | L28835 | 47601 | agcaggccctgcactctgctttct | X15267 | 90205 | attctccatgctcaaacactgaaaa | |
| 4998 | gggcctctgcaatgaactgacgggg | L28835 | 47602 | gcccctgcactctcgtttctggag | X15267 | 90206 | taacaaccttcatgcacttaggct | |
| 4999 | gatgtgacccttcagtcatc | L28835 | 47603 | gactgagtacaccttcccactact | X15267 | 90207 | cttatgctgtggttctggcttac | |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 5000 | gacaccttgcagttcatcaacatc | L28835 | 47604 | actgagtacaccttccacttactg | X15267 | 90208 | tatggctggttctggcttaacag | AA110466 |
| 5001 | ttgcagttcatcaacatcaactat | L28835 | 47605 | ctgagtacaccttccacttactga | X15267 | 90209 | gtttcggcttacagagtgcgccga | AA110466 |
| 5002 | caacatcaactatgtgccccgcag | L28835 | 47606 | acccgaagtgctgacatcacaga | X15267 | 90210 | ggcttacagagtgcgccgatttca | AA110466 |
| 5003 | ggtgctctttgccaacatggcagt | L28835 | 47607 | ccctgaagtgctgacatcacacag | X15267 | 90211 | cttacagagtgcgccgatttcaga | AA110466 |
| 5004 | ctttgcaacatggcagtctgtc | L28835 | 47608 | ctgaagtgtcgacatcacagaca | X15267 | 90212 | tacagagtgcgccgatttcaggtt | AA110466 |
| 5005 | caacatggcagctctgttctgtat | L28835 | 47609 | tgaagtgctgacatcacagagcag | X15267 | 90213 | cagagtgcgccgatttcaggttga | AA110466 |
| 5006 | atactgtctgctctaaagctctac | L28835 | 47610 | gaagtgctgacatcacagagcagg | X15267 | 90214 | gtgcgccgatttcaggttgactaa | AA110466 |
| 5007 | gctcaccccggtgctcaccaagca | L28835 | 47611 | agtgctgacatcacagagcaggcc | X15267 | 90215 | cgattttcaggttgactaagacgtg | AA110466 |
| 5008 | gctcaccaaagcagtcagcagggc | L28835 | 47612 | gtgctgacatcacagagcaggccc | X15267 | 90216 | tccatgctcaaacactgaaaataag | AA110466 |
| 5009 | caaagcagtcagcagggcatttg | L28835 | 47613 | tgctcgacatcacagagcaggccct | X15267 | 90217 | catgctcaaacactgaaaataagag | AA110466 |
| 5010 | agtcagcagggcatttgtcagc | L28835 | 47614 | gatcagccgatgcaaattgtgagc | X15267 | 90218 | tgctcaaacactgaaaataagagca | AA110466 |
| 5011 | tctggccaacgcgattgagaagaag | L28835 | 47615 | agagaagccgatgcaaattgtgag | X15267 | 90219 | gttttggccactatattaagactg | AA110466 |
| 5012 | tgtcaaggtccactggtcactac | L28835 | 47616 | gtgttgactgctgcaacgatgaaa | X15267 | 90220 | ttgagccactatattaagactgt | AA110466 |
| 5013 | tgccccaactttctgctgctgtc | L28835 | 47617 | tgttgactgctgcaacgatgaaag | X15267 | 90221 | tatatgaacttaacaaccttcacgc | AA110466 |
| 5014 | tgcctctgcctgaaagacactcagg | W49108 | 47618 | gttgactgctgcaacgatgaaagc | AA027544 | 90222 | gaacttaacaaccttcacgcact | AA110466 |
| 5015 | ctctgcctgaaagacactcaggaca | W49108 | 47619 | ttgactgctgcaacgatgaaagcg | AA027544 | 90223 | cttaacaaccttcagcacttatgg | AA110466 |
| 5016 | agccttacgctcaacatgaacggggg | W49108 | 47620 | tgactgctgcaacgatgaaagcgc | AA027544 | 90224 | atctgcctcaggcagcctagccgtt | AA110471 |
| 5017 | gggccaacgagagggcctgccttct | W49108 | 47621 | actgtctgcaacgatgaaagcggc | AA027544 | 90225 | tctgcctcaggcagcctagccgttg | AA110471 |
| 5018 | ccaacgagagggcctgcctgctgcc | W49108 | 47622 | aaagctgccgccatgtgccgcactg | AA027544 | 90226 | tggtgatccaaggcagctcaagcatg | AA110471 |
| 5019 | agtcctcgaacctgtgatcctcga | W49108 | 47623 | tggccgccatgtcgcgcactgtgt | AA027544 | 90227 | gtgagatccacaggcagtcaagcag | AA110471 |
| 5020 | gctgatccggacactggagctagca | W49108 | 47624 | ggccccatcgcgcactgtggt | AA027544 | 90228 | tgagatccacaggcagtgcatgagg | AA110471 |
| 5021 | gatctcggaacaccgtagcacgc | W49108 | 47625 | cgccatgtcgcactgtgtgact | AA027544 | 90229 | gagatccacaggcagtgcatgaggt | AA110471 |
| 5022 | acacacgtagcacgcgccaacagt | W49108 | 47626 | gccatgtcgcactgtgttgactg | AA027544 | 90230 | atacggggttctcgcaggagcag | AA110471 |
| 5023 | cacacgtagcacgcgccaacagtaac | W49108 | 47627 | catgtcgcactgtgttgactgc | AA027544 | 90231 | ataggttctcgcaggagcagtatg | AA110471 |
| 5024 | agcacgccaacagtaacgtgtgt | W49108 | 47628 | atgtgcgcactgtgttgactgtct | AA027544 | 90232 | gggttcgccaacagtaatg | AA110471 |
| 5025 | acgcccacagtaacgtgtgtgcg | W49108 | 47629 | tgtgcgcactgtgttgactgtctg | AA027544 | 90233 | ggtttcctgcaggagcagtattgt | AA110471 |
| 5026 | tgcctgaaagacactcaggacacaa | W49108 | 47630 | tcatagcagatcgctctcgtacaa | AA027544 | 90234 | ttcctgcaggagcagtattgtggc | AA110471 |
| 5027 | cgccacagtaagtggtgcgcc | W49108 | 47631 | tagcagatctgctctcgtacaa | AA027544 | 90235 | ttcctgcaggagcagtattgtggct | AA110471 |
| 5028 | gacaactgagacaagcctgagaa | W49108 | 47632 | ttagttaatttccatgctctcag | X66091 | 90236 | tgcctcagccagctagccgttgg | AA110471 |
| 5029 | actcaggacacaagcctgagaatgg | W49108 | 47633 | aatttccatgctcttcagactggaa | X66091 | 90237 | gcctcaggccagcctagccgtttgga | AA110471 |
| 5030 | tcgtctccgccagtttgatga | W49108 | 47634 | ttccatgctctcagactgtgatat | X66091 | 90238 | cctcaggccagcctagccgtttggag | AA110471 |
| 5031 | ttctccgccagtttgatgagag | W49108 | 47635 | ctatcttccagactgtgatatgt | X66091 | 90239 | tcaggccagcctagccgtttggagct | AA110471 |
| 5032 | tccgcccagtttgatgagagaca | W49108 | 47636 | ctatctgctctgttttgtgtgaaa | X66091 | 90240 | caggccagcctagccgttggagctt | AA110471 |
| 5033 | agagacagcctacgctcacatgaa | W49108 | 47637 | acatttcaatcattttaggattgtc | X66091 | 90241 | ggcagcctagccgtttggagctg | AA110471 |
| 5034 | gacagcctacgctcacatgaacgg | W49330 | 47638 | tatgactccaagtctattgtcaca | X66091 | 90242 | agttggggcagcgctgagatatg | AA110471 |
| 5035 | acgaagtcgcgtgactgttagga | W49330 | 47639 | tccaagtctattgtcacagatgaa | X66091 | 90243 | gcagcctcgagatatgtgtggaga | AA110471 |
| 5036 | agtcgcgtgactcttagcaaata | W49330 | 47640 | cagtatgacctatactagaaggc | X66091 | 90244 | tcctgacacgtcatcaagtacct | AA110471 |
| 5037 | cgatcatcacacattctggtgta | W49330 | 47641 | tattgacctatactagaagatgagg | X66091 | 90245 | tggaactgtcatcaagtaccgcc | AA110471 |
| 5038 | atcatcacacattctagtgcgtaat | W49330 | 47642 | tcgctctcgtacataagagtatgg | X66091 | 90246 | ggctacagtcagggcctaaactca | AA110471 |
| 5039 | catcacacattctagtggctaatg | W49330 | 47643 | tgtatacgttccttattcacttag | X66091 | 90247 | tcaggcctaaactcaggagcacag | D38614 |
| 5040 | tcacacattctagtgcgtaatgg | W49330 | 47644 | ctttaactcagtacaatctttcatt | X66091 | 90248 | cctaaactcaggagcacagccatag | D38614 |
| 5041 | atgtcgctcgtttgtcagacga | W49330 | 47645 | tttaattcaagctgtttgttcaga | X66091 | 90249 | ctcaaggacagccataagtgggg | D38614 |
| 5042 | ttgttgcagacgcatgactacata | W49330 | 47646 | tgtaatatcctttctcctaacatc | X66091 | 90250 | agtcattgcccagtttctggact | D38614 |
| 5043 | gcagagcgactgactacatagacga | W49330 | 47647 | atccctttctcctaacactactact | X66091 | 90251 | ccattgcccagtttctggactgt | D38614 |
| 5044 | gacgcatgactacatagacatgatga | W49330 | 47648 | tcctaacatctacattccctcag | X66091 | 90252 | gactgtggacctgctgaccatt | D38614 |
| 5045 | gactacatagcacgaaggtgcta | W49330 | 47649 | tcccctcatgtcttgtaacttta | X66091 | 90253 | ttgttgacctgctggaccaattgcc | D38614 |
| 5046 | ctacatagcacatgacaaggtgctaag | W49330 | 47650 | ggtctaccgcatgaggatgatgag | X66091 | 90254 | ctgctcgaccattcgtctgcttc | D38614 |
| 5047 | ctgcgtgacttcttaggagaaata | W49330 | 47651 | tgatgagcaactccagaccttc | X66091 | 90255 | tgtctctgctctgtgagctaccac | D38614 |
| 5048 | ggtcagtgctatacctctag | W49330 | 47652 | tatcacctgaggcaaagttcttgg | Z14252 | 90256 | acactgtcaagtacctgcctgg | D38614 |
| 5049 | aagtcgtatctcgctgagacatgg | W49330 | 47653 | ctctcagagctgtttgtacact | Z14252 | 90257 | tcatcaagtacctggcctgggccact | D38614 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 5050 | gtcgctacccttgtagacatggcg | W49330 | 47654 | gtcctactattgcccaggatctga | Z14252 | 90258 | agtacctgcctggccactgcagga | D38614 |
| 5051 | catggcggcacagatgctgcacag | W49330 | 47655 | atctggattacccctggcgggctgatg | Z14252 | 90259 | gatatgggtcagcaccaggagccc | D38614 |
| 5052 | cacaggtcgctgcacgaaatggctt | W49330 | 47656 | attacccgggctgcgatgctgac | Z14252 | 90260 | aagccatagtcctagatctatccg | D38614 |
| 5053 | ggtcgctgcacagatggcttagat | W49330 | 47657 | gtctgacgcgggcttgtcgaggc | Z14252 | 90261 | ccatagtctagatcatccgccc | D38614 |
| 5054 | tcgctgcacgaaatggcttagatcg | W49330 | 47658 | ggagctattgcccagcctgggta | Z14252 | 90262 | gtgtgacccctcaggccctgtctg | D38614 |
| 5055 | gatctggaaccacgtctgattg | L28836 | 47659 | aatggacctcgaacctgactgt | Z14252 | 90263 | cccacagagcctgccaaggtcagg | D38614 |
| 5056 | tgattgtggtccaaacgctgtgg | L28836 | 47660 | gtactgtacctgatcctgcaagc | Z14252 | 90264 | cttctgaagtccttggccatgtat | X92352 |
| 5057 | agtttgccattttgatgaatgcac | L28836 | 47661 | ttacctgatcctgcaaggcgttaa | Z14252 | 90265 | ctgaagtcctgtgccatgtatcta | X92352 |
| 5058 | aatgcacaagtcggtcagtgtgga | L28836 | 47662 | ggccactctgtgccagcctctca | Z14252 | 90266 | cctgtcatttgcagtaaatatg | X92352 |
| 5059 | aggactacattacagccactgctg | L28836 | 47663 | tctgtgtgccagctctcagccga | Z14252 | 90267 | atgcctaagaggcctgcatatgatt | X92352 |
| 5060 | acagccactgctggaaggttggcat | L28836 | 47664 | cagcctgcttgtgcgccactg | Z14252 | 90268 | cctaagaggcctgcatatgattgag | X92352 |
| 5061 | tctttaccgttctcacagaaatg | L28836 | 47665 | tgctttggcgccacttgatgccc | Z14252 | 90269 | aggcttcgattgtatgtgactgtg | X92352 |
| 5062 | ccgtttctcacagaaatgccttg | L28836 | 47666 | gatgccaatagggaggcctccagat | Z14252 | 90270 | cttcgatttgatgtgactgtgata | X92352 |
| 5063 | ctcacagaaatgccttggaagca | L28836 | 47667 | gtatccatgttccagactgggaa | Z14252 | 90271 | tttatcattgacatgtgagttacag | X92352 |
| 5064 | gccttttgaagcaccacagctacta | L28836 | 47668 | catgttccagactggggaaagttca | Z14252 | 90272 | aatatgtcctgtgaattgtaa | X92352 |
| 5065 | ggaagcaccagagtcgagagacta | L28836 | 47669 | acatlccgatgcgctgctattac | Z14252 | 90273 | tggaacttactaagagtgctttg | X92352 |
| 5066 | accacagagtactacctgcatatgga | L28836 | 47670 | agaatcttaagcgcgtggccaagga | Z14252 | 90274 | atttcatatctgtcattcactga | X92352 |
| 5067 | agttatggcctctttttggaggcag | L28836 | 47671 | aatcttaagcgcgtggccaaggagc | AA153569 | 90275 | tcatatctgtcattcactgaaaa | X92352 |
| 5068 | tttatgtctccgaccctatat | L28836 | 47672 | tttttctactgcaagcacatgtgac | AA153569 | 90276 | attaatctggcgtgaatatat | X92352 |
| 5069 | ttcctcgcgaccctatatgaccct | L28836 | 47673 | tttctactgcaagcacatgtgacta | AA153569 | 90277 | tggaaacttactaagagtgctttg | X92352 |
| 5070 | tgacccctggaacactgagagacca | L28836 | 47674 | tactgcaagcacatgtgactagat | AA153569 | 90278 | cctcctaagaagtgctttgctattt | X92352 |
| 5071 | ggatctgaccagtgtcgtgaagga | L28836 | 47675 | ctgcaacgacatgtgactagatta | AA153569 | 90279 | cttatcctctagtgctttggccaa | X92352 |
| 5072 | ctgaccagtgctgaagagtactt | L28836 | 47676 | atttagtgccgcatttgtgaaa | AA153569 | 90280 | atcctctagtgctttggccaattg | X92352 |
| 5073 | atgacagttgggccaatcctga | L28836 | 47677 | ttagtgccgcattttgtgaaata | AA153569 | 90281 | ctctaggcttggccaatgact | X92352 |
| 5074 | agttggccactttgaatccgaga | L28836 | 47678 | agtgcctgcattttgaaatatg | AA153569 | 90282 | gtgcttgcaatgactgacttattg | X92352 |
| 5075 | tcgggccactgctgagcgcagaga | L28836 | 47679 | gtaactttagccatgacctgaatc | AA153569 | 90283 | ctttggccaatgacttattgtgc | X92352 |
| 5076 | cgggccactgctgagcgcagcacaca | W57339 | 47680 | aacttagccatgacctgaatctat | AA153569 | 90284 | agctgtaccaggcgtctctgt | AA110453 |
| 5077 | cagacaccatgctgagcgcccgcgaaag | W57339 | 47681 | ctttagccatgacctgaatctatt | AA153569 | 90285 | ctgtaccaggcgtctctgtctgga | AA110453 |
| 5078 | cagacaccatgctgagcgcccgcgaaaca | W57339 | 47682 | caagagttccgcatcatgaaaa | AA153569 | 90286 | tcctgatcaactccaggaagag | AA110453 |
| 5079 | caccatgctgagcgcccggaaagcca | W57339 | 47683 | ttagccatgacctgaatctattt | AA153569 | 90287 | tcctgatcaactccaggaagaga | AA110453 |
| 5080 | catggccgcggaaaagccaaggag | W57339 | 47684 | agagttccgcgcatcatgaaaaag | AA153569 | 90288 | ctgatcaacttcaggaagagaag | AA110453 |
| 5081 | caaatcatctggaactcggaaag | W57339 | 47685 | agtccgcgccatcatgaaaaagac | AA153569 | 90289 | aaggtcttgacgatggtgatga | AA110453 |
| 5082 | aaatlcatctggaactcggaaga | W57339 | 47686 | ttcctgcgcatcatgaaaagacca | AA153569 | 90290 | tcttlgacgatggtgaagtgaacag | AA110453 |
| 5083 | aaatlcatctggaactcggaagaa | W57339 | 47687 | aagaccagcctcattaagatcagt | AA153569 | 90291 | aacagatttgccagggatgccca | AA110453 |
| 5084 | tcatctggaactcggaagaagga | W57339 | 47688 | gaccagcctcattaagatcagtgt | AA153569 | 90292 | acagatttgccagggatgccat | AA110453 |
| 5085 | catctggaactcggaagaagaagag | W57339 | 47689 | acggtctattaagatcagtgttct | AA153569 | 90293 | agatttgccagggagatgccattg | AA110453 |
| 5086 | gtttaagtcctctgttcactgtg | W57339 | 47690 | tctttttcactgcaagcacagtg | AA153569 | 90294 | tttttgccagggagatgccattgt | AA110453 |
| 5087 | gggccactgcctgagcagcaccat | W57339 | 47691 | taagctattgccgcaacatact | AA153569 | 90295 | aggaggcccatccactcatgcctgg | AA110453 |
| 5088 | cactgctgagcgcagcacccc | W57339 | 47692 | cagcaagcgtggcctgagagatcaga | X56007 | 90296 | tgtactaccaggctgtgctctgat | AA110453 |
| 5089 | actgctgagcgcagcaccatgccg | W57339 | 47693 | gagtacgtatcaccgtgctcttcag | X56007 | 90297 | tactaccaggctgtctctgatca | AA110453 |
| 5090 | ctgctgagcgcagcaccatgccccgc | W57339 | 47694 | gtatcagtcagctgcgctctc | X56007 | 90298 | actaccaggctgtctctgatcaa | AA110453 |
| 5091 | ctgctgagcgcagcaccatgcccgcga | W57339 | 47695 | gctcgttcagtttgagcctctc | X56007 | 90299 | taccaggctctctctgatcaact | AA110453 |
| 5092 | tgagcgcagcaccatgccccgcgga | W57339 | 47696 | ctttcagttgagcctctcaggagg | X56007 | 90300 | caggctgtctctgtcgatcaactca | AA110453 |
| 5093 | agagcaccatggccccgcggaaaa | W57339 | 47697 | gttgagcctcagagggttcct | X56007 | 90301 | aggctgtctctgatcaacttcag | AA110453 |
| 5094 | caccaccatggcccgcggaaag | W57339 | 47698 | tcttcttaggtctaccgagactct | X56007 | 90302 | ctgtctctgatcaacttcagga | AA110453 |
| 5095 | ctaccaccttcaagccagtccaccg | W49346 | 47699 | ttaggtctaccagaccctcaccct | X56007 | 90303 | gtctctgatcaactccaggaaga | AA110453 |
| 5096 | cctcaaggccgtcagatgactggg | W49346 | 47700 | tcaccctctgtcttttccaat | X56007 | 90304 | ccgagggccaccatggttacaca | AA110506 |
| 5097 | cactcagtcagatgactgggc | W49346 | 47701 | ttccaatctgttcagtcagtac | X56007 | 90305 | agccgcccatggttacacagag | AA110506 |
| 5098 | tcgtcagtgactgggcagac | W49346 | 47702 | tctgtttcagtactgacctgggg | X56007 | 90306 | ggaagcctgccatctcaatact | AA110506 |
| 5099 | gtcagatgactctggggacgcgc | W49346 | 47703 | gacccatgcagacctggctgtagat | X56007 | 90307 | cttcattcattcatttcaatactgggc | AA110506 |

| SEQ ID NO | sequence | DBAxnID | SEQ ID NO | sequence | DBAxnID | SEQ ID NO | sequence | DBAxnID |
|---|---|---|---|---|---|---|---|---|
| 5100 | agatgactcgggacgacgacgaa | W49346 | 47704 | tgcagacctgctgtagatccagga | X56007 | 90308 | gtcatcttcaatactctgggccat | AA110506 |
| 5101 | tgactcgggacgacgacgaagagct | W49346 | 47705 | gcgctctgctgggcttctatccc | X56007 | 90309 | atcttcaatactctgggccatggt | AA110506 |
| 5102 | ctctggggacgacgaagagagcct | W49346 | 47706 | ctatccctctatgtctagttc | X56007 | 90310 | tttcaatactctgggccatgtggg | AA110506 |
| 5103 | cgagagcctgctgccctgctgac | W49346 | 47707 | ctaggctcttctgtgtctgag | X56007 | 90311 | ctccactttcatctgcttcgtt | AA110506 |
| 5104 | agagcctgctgccctgctgacaac | W49346 | 47708 | ttatcctcacattcagccctct | X56007 | 90312 | cacctttcatctgcttcgttggt | AA110506 |
| 5105 | tgctgccctgctgacaacagtgat | W49346 | 47709 | cattcagccctgtccgagget | X56007 | 90313 | cttttcatctgcttcgttggtgc | AA110506 |
| 5106 | gctgccctgctgacaacagtatc | W49346 | 47710 | tttcgaagtaacctatctagtct | X56007 | 90314 | tggctctggcagtcaggtcaag | AA110506 |
| 5107 | caaggctgcagatgggaccgt | W49346 | 47711 | ttttctcgtgacccaatggcctga | X56007 | 90315 | taaagtgactcaaagcgaatcatt | AA110506 |
| 5108 | ctgccctgctgacaacagtgatct | W49346 | 47712 | tctcgtgacccaatggcctgagcc | X56007 | 90316 | ttacacagactccctcgggca | AA110506 |
| 5109 | ccgtcagcaatgatcaccgttctg | W49346 | 47713 | caggccctccagaaacagttgtag | AA049662 | 90317 | cacagagtcctcctcgggcattt | AA110506 |
| 5110 | gcaatgatcaccgttctgagttg | W49346 | 47714 | gccctccagaaacagttgtagcca | AA049662 | 90318 | tggtgagttccagctcatgga | AA110506 |
| 5111 | atgagcctgctgagttgcc | W49346 | 47715 | gtagcaagctgtagatgatgaagtt | AA049662 | 90319 | gttccagctcatgagaagcctg | AA110506 |
| 5112 | gatcaccgttctgagttggccaa | W49346 | 47716 | attcgattagcttcatccggtc | AA049662 | 90320 | cccagcctcatggaagcctgca | AA110506 |
| 5113 | caaggctacgtgatgaacaact | W49346 | 47717 | gattagcttcatccggtcttcatc | AA049662 | 90321 | agcctctcatggaagcctgtcatct | AA110506 |
| 5114 | gatgaacactcagtcagatgactct | W49346 | 47718 | tagcttcatccggtcttcatctct | AA049662 | 90322 | cttcatggaagcctgtcatcttc | AA110506 |
| 5115 | gaacactcagtcagatgactctgg | W49346 | 47719 | cttcatccggtcttcatctcaat | AA049662 | 90323 | catggaagcctgtcatcttcaat | AA110506 |
| 5116 | gagccagtccaccagcatt | W49346 | 47720 | cttcatcttattctactagaagt | AA049662 | 90324 | ctgctgctgcaactagtaagacct | AA110506 |
| 5117 | cactggcagtcccaccagcagc | M88299 | 47721 | ctctctaggtggacattaaaccat | AA049662 | 90325 | gctgctcgcaactagtaagacctgg | AA110514 |
| 5118 | ggacgatgctactgcaggtggt | M88299 | 47722 | attaaacatcgtccaaagtacatg | AA049662 | 90326 | atgtctaccgagctacgcgccgct | AA110514 |
| 5119 | cgatgtctactgcaggtgggtacc | M88299 | 47723 | gacccaaatggctgctgagcccagaga | AA049662 | 90327 | cgcctgctgctgctaggatactaga | AA110514 |
| 5120 | ctactgccaggtgggtaccagcagc | M88299 | 47724 | aaaccatcgtccaaagtacatga | AA049662 | 90328 | cctgctgctaggatactagaa | AA110514 |
| 5121 | ctgcaggttgggtaccgtgagcgt | M88299 | 47725 | cccaaatgggctgagcccagaacac | AA049662 | 90329 | tgctgctgctaggatactagagt | AA110514 |
| 5122 | taccgttgagcgctgacacacgca | M88299 | 47726 | aatgggctgagcccagagacacga | AA049662 | 90330 | cgaatagaactcgcagctggcaagg | AA110514 |
| 5123 | caaggttcagacagcgtcagtga | M88299 | 47727 | ctgagcccagagacacgaggggtg | AA049662 | 90331 | tagactgcagctgcaaggaacg | AA110514 |
| 5124 | gcttcagacagcgtgcagtga | M88299 | 47728 | gagctgcgtagaagggcagctg | AA049662 | 90332 | ggaactgcagctgcaaggaacgac | AA110514 |
| 5125 | tcagaccacgcgtgcagtgatgcg | M88299 | 47729 | ttactgtcaaagcagccctccaga | AA049662 | 90333 | actcagctgctgcaaggaacgacat | AA110514 |
| 5126 | gagaaccaccgctgctgctgcc | M88299 | 47730 | ctgcaaagcagccctccagaaac | AA049662 | 90334 | gccactgcagtgcaggtgcgtcgta | AA110514 |
| 5127 | gacctggccaggtgccgagccattcag | M88299 | 47731 | aagcagcccctccagaaacagttg | AA049662 | 90335 | tgctcgcaactagtaagacctgtaag | AA110514 |
| 5128 | tagctgcaaaggcgccgaggccattag | M88299 | 47732 | cttcaatcctctatctactgcgg | X15643 | 90336 | tcctgcaactagtaagacctgtaag | AA110514 |
| 5129 | cgccaaagacaggcggccacgtc | M88299 | 47733 | tatctactgcgggatccagattc | X15643 | 90337 | tagtaagaccgagacagcggcaac | AA110514 |
| 5130 | gcaggaaatcaccaactggccgac | M88299 | 47734 | ctgtcaaggtactgtccagttt | X15643 | 90338 | atcgtgaatcagctcgagaaggagc | AA110514 |
| 5131 | aatcaccaactggccgacagc | M88299 | 47735 | aggtactgtgcctagctagcgt | X15643 | 90339 | cgtgaatcagctcgagaaggagcagca | AA110514 |
| 5132 | caactggccgacagctacagcgccta | M88299 | 47736 | tgtgcctagcctttagcgttgactcc | X15643 | 90340 | tgaatcagctcgagaaggagcagca | AA110514 |
| 5133 | ctgccgacagctacagctgaa | M88299 | 47737 | tagcttaggtttgactccaagga | X15643 | 90341 | gggcagcatgtctaccgagctacg | AA110514 |
| 5134 | catccagacagcgacgccgacgat | M88299 | 47738 | tacaaatgactgcactgtaatac | X15643 | 90342 | agcagcatgtctaccgagctacgcg | AA110514 |
| 5135 | ccagcagcagacgccgacgtc | M88299 | 47739 | tagctgccactgtaatacaggctt | X15643 | 90343 | cagcatgtctaccgagctacgcgc | AA110514 |
| 5136 | atcatgaagactccaatcgga | W49353 | 47740 | gtaatacaggctttctactctta | X15643 | 90344 | aggaaccaagtatccgccatag | AA110514 |
| 5137 | catgaagactctcaaatgtgaaga | W49353 | 47741 | ctcctgacagacactaaccagta | X15643 | 90345 | ctgaaccgagtctgatgcacatt | U73460 |
| 5138 | catgaagactctcaaatgtggaag | W49353 | 47742 | attttttagctgcaacaagaagag | X15643 | 90346 | agtgtcggaagaccctggagtct | U73460 |
| 5139 | atatgattgagcccattgtgagta | W49353 | 47743 | tatagttcagttctctgtaga | X15643 | 90347 | agaactcaccatttctttgccagc | U73460 |
| 5140 | tatgattgagcccattgtgagtat | W49353 | 47744 | tgcttttcaagagtctctgcct | X15643 | 90348 | caccatgtcttgccagccctgaa | U73460 |
| 5141 | tgattgagcccattgtgagtatg | W49353 | 47745 | ttaagagtctctgcctgccagg | X15643 | 90349 | aagatagacagccccagtacctc | U73460 |
| 5142 | gattgagcccattgtgagtagt | W49353 | 47746 | tcgcaggtctcctttgaaactat | X15643 | 90350 | tgcccagacctcctgtctccgt | U73460 |
| 5143 | attgagcccattgtgagtagtg | W49353 | 47747 | ctctagcaatagcaacgcgaagag | X15643 | 90351 | cctgtctccgtgtatactagcta | U73460 |
| 5144 | ttgagcccattgtgagtagtgt | W49353 | 47748 | caatagcaacggcagaaccgagactac | X15643 | 90352 | tctccgtgatactagctatccta | U73460 |
| 5145 | gagcccattgtgagtatgttc | W49353 | 47749 | cagaacggactacacaagggagagctac | X15643 | 90353 | tgtatactagctatcctactacc | U73460 |
| 5146 | agcccattgtgagtatgtttcca | W49353 | 47750 | gggagcaaaacctgtcagtgggg | X15643 | 90354 | cctactgctgtcggcagctg | U73460 |
| 5147 | gccccattgagtatgtcttaa | W49353 | 47751 | acaggaactgctgtgagatccc | X15643 | 90355 | tgtactgctgggcagctgcatcc | U73460 |
| 5148 | agtattgtgtccacgctgaaga | W49353 | 47752 | acgatgactagaccagggggtta | X72862 | 90356 | aacataatccaggaggacttagcaag | U73460 |
| 5149 | tgaagactccaaatcgaagaag | W49353 | 47753 | ctctcttccgagagaagtgtcta | X72862 | 90357 | cagctgcatccatgcttctggtag | U73460 |

| SEQ ID NO | sequence | DBAxnID | SEQ ID NO | sequence | DBAxnID | SEQ ID NO | DBAxnID |
|---|---|---|---|---|---|---|---|
| 5150 | gtatgtcgttccacagctgaagaa | W49353 | 47754 | catgttcctccacaaatcactctgt | X72862 | 90358 | U73460 |
| 5151 | aagactctcaaaatcggaagaagtt | W49353 | 47755 | actctgtctccaggctcgtgtctc | X72862 | 90359 | U73460 |
| 5152 | agactctcaaaatcggaagaagtt | W49353 | 47756 | ggctcgtgtctcggttagtttga | X72862 | 90360 | U73460 |
| 5153 | agaagttcagagctgtgagaga | W49353 | 47757 | gtgtctcgattagttgagagcag | X72862 | 90361 | U73460 |
| 5154 | aagttcagagctgtgagatact | W49353 | 47758 | tgaggttcatccctggctcctcac | X72862 | 90362 | U73460 |
| 5155 | agcttcagagctgtgagatacta | W49353 | 47759 | ctatggctctcaagcaccatcttg | X72862 | 90363 | U73460 |
| 5156 | tatatgattgagcccatgtgagt | W49353 | 47760 | ctctcaagcaccatctggaccat | X72862 | 90364 | U73460 |
| 5157 | tgtgcaagctgaagccttgttgaa | W49353 | 47761 | aagcaccacatctggaccatctcta | X72862 | 90365 | AA111635 |
| 5158 | gcaagctgaagccttgttgaacaa | W49353 | 47762 | calcttgaccatctcacaatag | X72862 | 90366 | AA111635 |
| 5159 | ctctgcgggtgccgaggatgtgta | W49353 | 47763 | tctacctcacagttagacttcaag | X72862 | 90367 | AA111635 |
| 5160 | agtagggacaacggcaccacacacg | X66602 | 47764 | gaacttactcactactactccta | X72862 | 90368 | AA111635 |
| 5161 | gtgcagcgccgtccagtgaactc | X66602 | 47765 | cactactactccagcagttcagcagt | X72862 | 90369 | AA111635 |
| 5162 | tgcagacgcccgtccagtgaacta | X66602 | 47766 | ccaactgctgacgccctggga | X72862 | 90370 | AA111635 |
| 5163 | agagcccgtccagtgaactcaagc | X66602 | 47767 | cctatggcctggaggccgccagt | X72862 | 90371 | AA111635 |
| 5164 | gcccgtccagtgaactcaagcggg | X66602 | 47768 | tgccagtccctgcctatgttgtgc | X72862 | 90372 | AA111635 |
| 5165 | tggtccacagtcttcctggagact | X66602 | 47769 | tccctgcctatgttgtctgtag | X72862 | 90373 | AA111635 |
| 5166 | gtccacagtcttcctggaccct | X66602 | 47770 | tgctttctaacctgatgatgac | X72862 | 90374 | AA111635 |
| 5167 | ccacagttcctggaccctgt | X66602 | 47771 | ccgtagctgcctcacacgaatgga | AA027667 | 90375 | AA111635 |
| 5168 | ctgttccctccactctgattg | X66602 | 47772 | ctgcctcaacagaatgagataagtt | AA027667 | 90376 | AA111635 |
| 5169 | caagctgaagccttgttgaacag | X66602 | 47773 | tgattgtccaaccgcgaacaattgcc | AA027667 | 90377 | AA111635 |
| 5170 | aagagcagactcatctcgggccag | X66602 | 47774 | tgtccaccgcgaacaattgccatg | AA027667 | 90378 | AA111635 |
| 5171 | cgtcaaggggctcgagagccat | X66602 | 47775 | acggcaacaatgccatgccacgt | AA027667 | 90379 | AA111635 |
| 5172 | gtcaaggggctcgagagccatt | X66602 | 47776 | gcggacaattgccatgcacgtgac | AA027667 | 90380 | AA111635 |
| 5173 | ctaagccctcggccaggagatcac | X66602 | 47777 | caccactcctaagctgcg | AA027667 | 90381 | AA111635 |
| 5174 | tccctggacagctacagctgg | X66602 | 47778 | ctcctagattacgctgtctc | AA027667 | 90382 | AA111635 |
| 5175 | tcgcggacagttacagctggagaa | X66602 | 47779 | ctctagattacgctgtctctga | AA027667 | 90383 | AA111635 |
| 5176 | cgggacagttacagctgagaa | X66602 | 47780 | acgtcttctctgacttaaagac | AA027667 | 90384 | AA111635 |
| 5177 | ccacaggccgccgttagtcgg | X66602 | 47781 | ctgctctcgacttaagagcgt | AA027667 | 90385 | U75680 |
| 5178 | ggcgccagttagtcgggtgaca | X66602 | 47783 | ttctctgacttaaagacggtt | AA027667 | 90386 | U75680 |
| 5179 | gtaggcalcttcagctgtgtcgga | X66602 | 47784 | agttctaggggctgaacgaccacgt | AA027667 | 90387 | U75680 |
| 5180 | agctcctctgtgagagacaataaaaa | X66603 | 47785 | tctaggcctgaacgaccacgtgat | AA027667 | 90388 | U75680 |
| 5181 | ctccctctgtacataccaaggtct | X66603 | 47786 | cgctgaacgaccacgtgatcaacgt | AA027667 | 90389 | U75680 |
| 5182 | ctgtacatacaaggtctgagtaa | X66603 | 47787 | acgaccacgtgatcaacgtcaacgt | AA027667 | 90390 | U75680 |
| 5183 | agctcttagggagccctcttcagtg | X66603 | 47788 | tgatcaacgtacctgggcgaaaatgc | AA027667 | 90391 | U75680 |
| 5184 | gtcttgacaagcacagctgtgga | X66603 | 47789 | gcgaaaaatgctaccctccatgacgac | AA027667 | 90392 | U75680 |
| 5185 | gacaagcagctggtgagaagcggg | X66603 | 47790 | tttccagcatcatgatgtccacg | AA027667 | 90393 | U75680 |
| 5186 | aagccaagcgcgatcgaggcgag | X66603 | 47791 | tcatgattgccacgcggacaat | AA027667 | 90394 | U75680 |
| 5187 | agalagctgtgtgtacgtattact | X66603 | 47792 | agtctccttgctgataactgcaga | AA027667 | 90395 | U75680 |
| 5188 | ctgtgtgtacgtattactgtatac | X66603 | 47793 | atatcaatggcttactatggacat | AA027667 | 90396 | U75680 |
| 5189 | gttgacaacctgctgctaccctatgt | X66603 | 47794 | tgctgcacgacggagcgatacacac | AA027667 | 90397 | U75680 |
| 5190 | aactgctaccctactagtacatc | X66603 | 47795 | tacacacaactcggaagaccaaactt | AA027678 | 90398 | U75680 |
| 5191 | tacactctctagatgaagactg | X66603 | 47796 | gaagaccaaaatctcggctatcatga | AA027678 | 90399 | U75680 |
| 5192 | agactgctcaacaatggtgc | X66603 | 47797 | caaactcgctatcatgagatct | AA027678 | 90400 | U75680 |
| 5193 | accaaagactctggcctatg | X66603 | 47798 | tcggctactgagactcattcaa | AA027678 | 90401 | U75680 |
| 5194 | agactgctcctatggccag | X66603 | 47799 | agactattcaactcatccatcat | AA027678 | 90402 | U75680 |
| 5195 | cccagttcagtcacctcagtcg | X66603 | 47800 | tattcaactcatcatggagct | AA027678 | 90403 | U75680 |
| 5196 | gcgctgctcaggagtgagaaac | X66603 | 47801 | actcatccatcatggagctcattc | AA027678 | 90404 | U75680 |
| 5197 | tctacctctcaatgtgttaacca | W49367 | 47802 | ccatcaggagctccattcagctg | AA027678 | 90405 | U77356 |
| 5198 | tacctctctcaatgttaaccaat | W49367 | 47803 | tccattcagctgcatccacaagc | AA027678 | 90406 | U77356 |
| 5199 |  |  |  |  |  | 90407 | U77356 |

TABLE 1-continued

| SEQ ID NO | DBAxnID | sequence | SEQ ID NO | DBAxnID | sequence | SEQ ID NO | DBAxnID | sequence |
|---|---|---|---|---|---|---|---|---|
| 5200 | W49367 | tgacttccttgccagtgtcacaag | 47804 | AA027678 | tactatgtgcatcacactgact | 90408 | U77356 | gtcactgctctgttcctgaaa |
| 5201 | W49367 | gacttccttgccagtgccagtcacaagc | 47805 | AA027678 | ttcagcgtgcatcccacaagccacc | 90409 | U77356 | gtgtcctgtttcctgaaatatgaa |
| 5202 | W49367 | ctccttgccagtgtcacaagcca | 47806 | AA027678 | gtgacatcacactggactaagaaag | 90410 | U77356 | attgtagcgacccagactgtagag |
| 5203 | W49367 | ttccttgccagtgtcacaagccag | 47807 | AA027678 | tgacacggcacctccacatcac | 90411 | U77356 | gcgacccagactgtagagatttt |
| 5204 | W49367 | ccttgccagtgtcacaagcagca | 47808 | AA027678 | cttccacatcatcccagaagactat | 90412 | U77356 | tttgggtacalctgctgtgtggaaa |
| 5205 | W49367 | cttgccagtgtcacaagccagca | 47809 | AA027678 | catcatcccagagactatccactt | 90413 | U77356 | gaactgtacttagtggctgtcat |
| 5206 | W49367 | ttgccagtgtcacaagccagcaa | 47810 | AA027678 | cccagaagactatccactgctgca | 90414 | U77356 | tacttagtggctgtcatgctctg |
| 5207 | W49367 | cagtgccaagccagccagcaaga | 47811 | AA027678 | agactaccactgctgcacgagg | 90415 | U77356 | tgtlcatgctctgagttaggtatt |
| 5208 | W49367 | gtgtcacaagccagccaagcaagat | 47812 | AA027678 | tccactgctgcacgacggggagat | 90416 | U77356 | atgaatactatccatgtaataagca |
| 5209 | W49367 | tgtcacaagccagccaagcaagattc | 47813 | AA027678 | caattagccactgcgcttatcgaga | 90417 | U77356 | acatacacacacctacctctcatg |
| 5210 | W49367 | ctctcaatggttaaccaatagt | 47814 | X78684 | gccactgccgttatcgagaagagtc | 90418 | U77356 | cttacctcatgcgtgttacct |
| 5211 | W49367 | ttcttcaatggttaaccatagic | 47815 | X78684 | ttgcaaactgtcataccatgaac | 90419 | U77356 | tctcatgcggttttacctgtcgtg |
| 5212 | W49367 | gttaaccaatagtcaggcctcagca | 47816 | X78684 | aactgtcataccactgaactgagt | 90420 | U77356 | agtggctcactgcctgggatcta |
| 5213 | W49367 | ttaaccaatagtcaggcctcagcag | 47817 | X78684 | ttatgttgactgtggattttccca | 90421 | U77356 | tcactgcctgggatctttacctgg |
| 5214 | W49367 | caatagtcaggcctcagagaaac | 47818 | X78684 | gtggatttccactgaccaaagctt | 90422 | U79525 | gggtcaccacagttctcctagga |
| 5215 | W49367 | gcctcagcagaaaacttcctttc | 47819 | X78684 | actggtattacctcagttattcatgc | 90423 | U79525 | ccaccgctctctagagaacagct |
| 5216 | W49367 | gcagaaaacttcctttcgcacta | 47820 | X78684 | attacctcagtttattcatgcctgt | 90424 | U79525 | tctctctttaggaaacagtcgttct |
| 5217 | W49367 | tttgacttccttgccagtgtcaca | 47821 | X78684 | tcagttattcatgcactgctatcata | 90425 | U79525 | aggagcttcaccaagatgctcgtctt |
| 5218 | W49367 | cttctccaagtgtccccaagccgtct | 47822 | X78684 | ttcatgcactgttatcatcatacaagatc | 90426 | U79525 | tcaccaagatgctcgttctgaaatg |
| 5219 | W49367 | gcccaagccgtcgtgccagagat | 47823 | X78684 | tatcatacgatctctctactatgt | 90427 | U79525 | ccgagcttctacaacagcgaggcagg |
| 5220 | W49367 | cgccaaggacgtttagccgcc | 47824 | X78684 | acagatctctctatagtgttctat | 90428 | U79525 | ctgtgaccaacatacaggccacat |
| 5221 | W49367 | gccatgacgacgttatgcgct | 47825 | X78684 | ttagggctctccaagcctcatgatt | 90429 | U79525 | tacacgatgccgtgcatgccct |
| 5222 | W49367 | acgagttttatgccctgggagact | 47826 | X78684 | ctcttcaagcctcatgattgtacaa | 90430 | U79525 | atgccctgaacatgctgcgcagttt |
| 5223 | W49367 | gacgtttatgccctgggggagctg | 47827 | X78684 | tgtacaacctactgaaatatgacca | 90431 | U79525 | tgaacatgcgccagtttgtggg |
| 5224 | W49367 | cacactgccccgtctctgccagtga | 47828 | X78684 | acctactgaaatatgaccactgct | 90432 | U79525 | gaagttaccgcaaccattgcaga |
| 5225 | W49367 | cactgccccgtctgtgatgtacc | 47829 | X78684 | tatgacacgactgttatgttgttgtgt | 90433 | U79525 | accgcaaaaccattgcagaccctg |
| 5226 | W49367 | actgccccgtctgtgcagtgacc | 47830 | X78684 | tgttgtactgctctgttctcca | 90434 | U79525 | aaccattgcagaccctgttatgca |
| 5227 | W49367 | tgtgcagtgaccctgcagtgggtt | 47831 | X78684 | tactgctgtctgtgcctatatagac | 90435 | U79525 | caacacctccaagaaccttgactt |
| 5228 | W49367 | tgcagtgaccctgcagtgggtte | 47832 | X78684 | cagtagctgctttcaagtcat | 90436 | U79525 | agacctttgaatttcagaag |
| 5229 | W49367 | gcagtgaccctgcgagtgggttc | 47833 | X78684 | tggttaccatttcggcgtctga | 90437 | AA027694 | gagaccagtacccctgaacctcac |
| 5230 | W49367 | tcccaggcctctgcgacgagatc | 47834 | AA027694 | ttacaacttttcgggcgtctgctaaa | 90438 | AA027694 | ctctgaaccctcacctgggaatgtcc |
| 5231 | W49367 | ccaggccgtctgcgcacgagatcac | 47835 | AA027694 | aactatggtctcacaattcatgaag | 90439 | AA027694 | ttgctccgggaagtggagacatgc |
| 5232 | W49367 | caagccgctgcgacgagatcacc | 47836 | AA027694 | ctatggctcacaattcatgaagaa | 90440 | AA027694 | gggaatgcttccacaagccccctgaat |
| 5233 | W49367 | agccgctgcgacgagatcaccggc | 47837 | AA027694 | atggcttcacaatttcatgaagaatt | 90441 | AA027694 | acgcccactgaatttgcacaagc |
| 5234 | W49367 | gtctgcgcacgagatcaccggcctg | 47838 | AA027694 | aggtgacctgccctgctgtcgtgaa | 90442 | AA027694 | acaaggcggctcagtttcaagttg |
| 5235 | W49367 | ctgcgcacgagatcaccggcctgc | 47839 | AA027694 | gacctgccctgctgtcgtgaacct | 90443 | AA027694 | actctctcagtaaaatgcaggcaa |
| 5236 | W49367 | gcgacgagatcaccggcctggac | 47840 | AA027694 | cgtgcctgcctgctgtcgaacctg | 90444 | AA027694 | caggcaagcaaccccagctgcttcaca |
| 5237 | W49367 | acgagatcaccggcctggccgacg | 47841 | AA027694 | cctgctcgtgtcgaacctgt | 90445 | AA027694 | agtacgacttttgttggccaccag |
| 5238 | W49376 | ataaggcctcaatacgagaagcagg | 47842 | AA027694 | tcctgcgtcctgtcgaacctgatggtg | 90446 | AA142505 | acagactttcgtgtgggcaccagtga |
| 5239 | W49376 | gtacaagagccgcattacacgatgt | 47843 | AA027694 | gtctgcgtgaacctgatgtgaaac | 90447 | AA142505 | gccactggataaaccagtcacagaa |
| 5240 | W49376 | gcacaagaccgcgcacaagcgcg | 47844 | AA027694 | acaacttttgcgctgatagaagg | 90448 | AA142505 | actgataaaccagtcacagaagtc |
| 5241 | W49376 | acaagagaccgcacaagccgcgt | 47845 | AA027694 | ctttctgcgctgtgataaagggtc | 90449 | AA142505 | ggataaaccagtcacagaagtctc |
| 5242 | W49376 | gacaccgagccaagccgctgcac | 47846 | AA027694 | ttgttgggcacctgacagaagttg | 90450 | AA142505 | acccagtcacagaagtctctgca |
| 5243 | W49376 | caccgagccaaagccgctgcacag | 47847 | AA027694 | tgtttgggcaccctgacgaagttg | 90451 | AA142505 | agtcacagaagtctctgcaggc |
| 5244 | W49376 | ccgagccaaagccgctgcacagga | 47848 | AA027694 | gtttgggcaccgcagaagtgcag | 90452 | AA142505 | aagtctctcgaggcattaggta |
| 5245 | W49376 | gacgcaaagccgctgccagaacg | 47849 | AA027694 | tggggcacctgacgaaagtgcagaag | 90453 | AA142505 | tctctcgaggcattaggtactg |
| 5246 | W49376 | cgcaaagccgctgcacaggacgag | 47850 | AA027694 | atcacgcaactaggcttcacaat | 90454 | AA142505 | ctctggcgtttggagcagggat |
| 5247 | W49376 | caaagcgccgctgcacaggagaga | 47851 | AA027694 | cacagcaactatggcttcacaatc | 90455 | AA142505 | caacttatccataatgatcgaca |
| 5248 | W49376 | acggcgctgcacggacgagggga | 47852 | AA027694 | gcaactatggcttcacaattcatga | 90456 | AA142505 | ctttaatccaattagatcgacactg |
| 5249 | W49376 | tgcacggacgaggacgagaaagc | 47853 | AA035870 | aggcccaggccgaccagatagcgc | 90457 | AA142505 | ctgtggccaccagtgaagataca |

| SEQ ID NO | sequence | DBAxnID | SEQ ID NO | sequence | DBAxnID | SEQ ID NO | sequence | DBAxnID |
|---|---|---|---|---|---|---|---|---|
| 5250 | aagagccgcatacacgatgctaacc | W49376 | 47854 | gcccaggctcgaccagatagccg | AA035870 | 90458 | tcatcgccgttttcaagtcaccag | AA142505 |
| 5251 | gagccgcatacacgatgctaaccga | W49376 | 47855 | tgccccgaagtggcaggacagtg | AA035870 | 90459 | ctttcaagtcaccagagacctgat | AA142505 |
| 5252 | gccgcatacacgatgctaaccgag | W49376 | 47856 | gactgtgcggactccgagcctg | AA035870 | 90460 | ttcaagtcaccagagacctgatagt | AA142505 |
| 5253 | cgcatacacgatgctaaccgagag | W49376 | 47857 | ggtcttcattcattcacccttcatct | AA035870 | 90461 | aagtcaccagagacctgatagtgc | AA142505 |
| 5254 | cgatgctaaccgagagcgccgaga | W49376 | 47858 | tttcattcattcacccttcatctgcta | AA035870 | 90462 | tagttgcagaggctcagaagctg | AA142505 |
| 5255 | atgctaaccgagagcgccgcacag | W49376 | 47859 | tcattcattcacccttcatctgctacg | AA035870 | 90463 | agaagctcgaggcctggcccctgg | AA142505 |
| 5256 | cgccgcacaagaccgacgcaaag | W49376 | 47860 | attcatcaccttcatctgctacgtg | AA035870 | 90464 | aacagagacatgcgccctgggca | AA142505 |
| 5257 | ccgcacaagaccgacgcaagcg | W49376 | 47861 | tcatcaccttcatctgctacgtgt | AA035870 | 90465 | aacagagcatccttttcacttcga | AA142505 |
| 5258 | tttctagtccagctgctgcagaaact | W49376 | 47862 | atcacccttcatctgctacgtggt | AA035870 | 90466 | agagcatcctttcacttcactga | AA142505 |
| 5259 | cccattctcattaagttttgcat | M26391 | 47863 | cacccttcatctgctacgtggtgtcc | AA035870 | 90467 | agtcctgtcatatcataatgactaag | L32372 |
| 5260 | agagatcctgctcgagattctta | M26391 | 47864 | ttcatcgctacgtggtgtccccg | AA035870 | 90468 | cataagactaagcacactgacat | L32372 |
| 5261 | gatcctgctcgagatttcttaaag | M26391 | 47865 | tcgacagatagggccgctatgtgg | AA035870 | 90469 | aatgactaagcacactaactgcatcaa | L32372 |
| 5262 | cctgctcgagattcttaaagctg | M26391 | 47866 | gaccagatagccgctatgtggcc | AA035870 | 90470 | gcacacttgacatcaactgcatcaa | L32372 |
| 5263 | agattctcttaaagctgcagacactg | M26391 | 47867 | ccagatagccgctatgtggccc | AA035870 | 90471 | ttgaactcaactgcatcaagatgtg | L32372 |
| 5264 | tttcttaaagctgcagacactgcac | M26391 | 47868 | agatagccgctatgtggcccccg | AA035870 | 90472 | tcaactgcacaagatgtggacctgt | L32372 |
| 5265 | cttaaagctgcagacactgcactat | M26391 | 47869 | acgagccagaccgcgatccaga | AA035870 | 90473 | gtatttcacagacaaactggcttt | L32372 |
| 5266 | gctgcagacactgcactattggttt | M26391 | 47870 | agagccagaccgatcccagagtcc | AA035870 | 90474 | ttttcaaagccaaatatgtaaatg | L32372 |
| 5267 | gcagacactgcactattggtttgt | M26391 | 47871 | agcccgatccagagtccgcgcatgg | AA035870 | 90475 | aatgatccgtcttaacattg | L32372 |
| 5268 | tgaaactataacatttcaaatgtcat | M26391 | 47872 | catggcccccgaagtgcaagacag | AA035870 | 90476 | gtatcctgtttttaacatttgtg | L32372 |
| 5269 | tatacattcaaatgtctatgtct | M26391 | 47873 | attgattaccccagcgaagactggtc | X78682 | 90477 | tctacttcgatgtcagagggaagcgt | L32372 |
| 5270 | tcttcattaagttttgcatgatcat | M26391 | 47874 | taccccagcgagagctaactgcatcaa | X78682 | 90478 | acatgcacgtaacactgaagtac | L32372 |
| 5271 | agtttgcatgatcatcacacagat | M26391 | 47875 | ctctgcgaggggtgactccaaggc | X78682 | 90479 | gaagtactcatcaactgaagtc | L32372 |
| 5272 | gcatgatcatcacacagattagtta | M26391 | 47876 | tgactccaaggccgctgagctgatc | X78682 | 90480 | ctatccattaactgaagtcttgta | L32372 |
| 5273 | tcatcacacagattagtttt | M26391 | 47877 | caaggccgctgagctgatcgccaac | X78682 | 90481 | gttccgcagccactattagtc | L32372 |
| 5274 | ccatatctcaggtctttttgctagt | M26391 | 47878 | cgctgcgatcgcaactgctg | X78682 | 90482 | tccgcagccactattgtgctct | L32372 |
| 5275 | tactctagtctttgctagtgagtc | M26391 | 47879 | gctgatcgcaactgctgctggccacg | X78682 | 90483 | actatttgtcctgattcata | L32372 |
| 5276 | ttctagtctttgctagtgagtc | M26391 | 47880 | tcggaacatcactactcgccagcg | X78682 | 90484 | attgtagtctcttgattcataatg | L32372 |
| 5277 | ttcaagatcctgctcgagattc | M26391 | 47881 | ctaactgcgggggccagtcgtg | X78682 | 90485 | tccctcatccttttgactagaccac | W41817 |
| 5278 | gaggctccaagatcatccaccat | M26391 | 47882 | cggcctccatcagtcgaatgacgc | X78682 | 90486 | tccctcatccttttgactagacacgt | W41817 |
| 5279 | ccaagatcatccaccatcaagag | M90316 | 47883 | ccatcatgtgaatgacgccttcct | X78682 | 90487 | tagaaccactttgccagcccactt | W41817 |
| 5280 | ccaacaccaagtcgccgatagcct | M90316 | 47884 | tgctgaatgacgccttcctctgcc | X78682 | 90488 | agaccacttttgccagcccacctg | W41817 |
| 5281 | accaagtcgccgatagcctctcctt | M90316 | 47885 | tgacctcacagagccgaggcaaca | X78682 | 90489 | gaccactttgccagccccacttga | W41817 |
| 5282 | aactctgctccaccatcagctaa | M90316 | 47886 | attggggcttaccctggaatgacgtg | X78682 | 90490 | accacttttgccagcccacttgat | W41817 |
| 5283 | gctctccaccatcagctaaagggac | M90316 | 47887 | cctggatcgacgtgcccgacacat | X78682 | 90491 | cactttgccagcccaccttgatca | W41817 |
| 5284 | ccagtcccatcaggtggagccaagagt | M90316 | 47888 | tgacgtgtcctgacacatctgacc | X78682 | 90492 | cttttgccagcccacctgatcatg | W41817 |
| 5285 | gagccaagagtcccaagggaagga | M90316 | 47889 | gtccctgaccacatctgaacttcggg | X78682 | 90493 | ttgccagcccaccttgatcatgt | W41817 |
| 5286 | aggcaagatcccaaccgatccaa | M90316 | 47890 | tctgacctcggaaggagttcaca | X78682 | 90494 | tgccagcccaccttgactcatgttgc | W41817 |
| 5287 | cactgccccatgctgaatgctcag | M90316 | 47891 | gggcagccatatctctgaggct | X78682 | 90495 | cacttgatcatgttgcctgcatc | W41817 |
| 5288 | tgctcagatctcgcgggtcctgccc | M90316 | 47892 | catcatctctgtgaggggtactcc | X78682 | 90496 | accttgatcatgtcgctgcatc | W41817 |
| 5289 | ctgttacgggatccctcatttgtg | M90316 | 47893 | tatctatactgtcagtcgaagtca | U03457 | 90497 | cctcatccttgactagaccactt | W41817 |
| 5290 | gcaccccatctggaagtggggtacaa | M90316 | 47894 | atacgtcagtgcaagtcaagaccaa | U03457 | 90498 | cctcatccttgactagaccactttt | W41817 |
| 5291 | tgccactggacatgggaagtacga | M90316 | 47895 | taccaagtgggaaccatttcattc | U03457 | 90499 | tcatccttgactagaccactttg | W41817 |
| 5292 | agggctcagcaccatagaccatgtt | M90316 | 47896 | ttcattccaactcaggcattgaaa | U03457 | 90500 | tcctttgactagaccactttgcca | W41817 |
| 5293 | cagcaccatagaccatgttcgtac | M90316 | 47897 | cccaacctaggcattgaaaatctgt | U03457 | 90501 | ctttgactagaccacttttgccagc | W41817 |
| 5294 | ccatgttcgatcggatagactc | M90316 | 47898 | ttagattgagctttctgcagggg | U03457 | 90502 | ttgactagaccacttgccagc | W41817 |
| 5295 | ttgcatcggatagactccggcg | M90316 | 47899 | tgagctttctcggagcatgat | U03457 | 90503 | tgactagaccacttttgccagccc | W41817 |
| 5296 | cctggatagactccggccgatgcc | M90316 | 47900 | tttctctgagggggcatgatccatg | U03457 | 90504 | tgactagaccactttgccagcca | W41817 |
| 5297 | cagccctgaccaagaaattgcttcc | M90316 | 47901 | cgtttcaagtcgtgtctccata | U03457 | 90505 | tcacggctgtctgaagaatgaaaa | W41817 |
| 5298 | tgtcagaactgcgctgcgcaagg | AA041982 | 47902 | ataatatgctgaactgtatttat | U03457 | 90506 | agatacgtccacttagaattcaaatt | D88315 |
| 5299 | tcagaactgcgctgcgcaaggag | AA041982 | 47903 | tattttatcataactgctgttaga | U03457 | 90507 | atatatagccgttccaggactgt | D88315 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 5300 | atggctttgtgcacatagaggacaa | AA041982 | 47904 | tcataactgctgcttatgagccgga | U03457 | 90508 | agtggctttcaggactgtcacagt | D88315 |
| 5301 | aggacaagacgcgctgaggatgca | AA041982 | 47905 | aagaccatagagcaccttacaggag | U03457 | 90509 | ggccttcagctgactgtcacagtaac | D88315 |
| 5302 | caagacggccgctgaggatgccata | AA041982 | 47906 | atagagcaccttacaggagtagag | U03457 | 90510 | ctttcaggactgtcacagtaacact | D88315 |
| 5303 | agacgccgctgaggatgccatacg | AA041982 | 47907 | cacctacaggagctagagatggct | U03457 | 90511 | ggactgtcacgtaacacttatt | D88315 |
| 5304 | aggatgcatacgtaacctgcacca | AA041982 | 47908 | tggagcagtctcaaatcaaatata | U03457 | 90512 | ctgtcacagtaacacttattacca | D88315 |
| 5305 | cctgcaccactacaagctgcacgga | AA041982 | 47909 | atactggccctgctgaatttcca | U03457 | 90513 | tcacagtaacacttattacagag | D88315 |
| 5306 | tgcaccactacaagctgcacggagt | AA041982 | 47910 | gccgtctgaatttccagtctcct | U03457 | 90514 | cactttattacagagctaatgtt | D88315 |
| 5307 | ccactacaagctgcacggagtgaac | AA041982 | 47911 | tctgaattttccagtcctcatgg | U03457 | 90515 | atcttgtgtgttactgcctaat | D88315 |
| 5308 | actacaagctgcacggagtgaacat | AA041982 | 47912 | agctcctcattggattttaccaga | U03457 | 90516 | tgtgtgttactgcctaatgcttt | D88315 |
| 5309 | tacaagctgcacggagtgaacatca | AA041982 | 47913 | gaacatctcaaacatgatgccaca | U03457 | 90517 | agcctagccatctggctcaatctgt | D88315 |
| 5310 | gacctgcaggtatccatgcggctgt | AA041982 | 47914 | aacgatgccacatcaacagaaccga | X78683 | 90518 | ctagccatctggctcaatctgttta | D88315 |
| 5311 | ggtatccatgcggctgtggagat | AA041982 | 47915 | ggcacactgtccagcttggagag | X78683 | 90519 | atctggctcaatctgtttaaactg | D88315 |
| 5312 | tcattgaaatcgcccgggatgccgc | AA041982 | 47916 | gcccaggcatcatgtggactgat | X78683 | 90520 | gttctgctcattataccactattct | D88315 |
| 5313 | ggagatcgctcactctgagcag | AA041982 | 47917 | tatctgcccctgtcgattaaggaag | X78683 | 90521 | cataatcataaggaccctccaacatt | D88315 |
| 5314 | agatccgctcactctgagcagta | AA041982 | 47918 | gactgagaccagtccccttcagagtc | X78683 | 90522 | cataaggaccctccaacactgaatac | D88315 |
| 5315 | actcttgagcagtacggaaggtg | AA041982 | 47919 | cagagggttccttccctcctgtt | X78683 | 90523 | gacctcaacactgaatacataatc | D88315 |
| 5316 | tcttcgagcagtacggagaggtgct | AA041982 | 47920 | ctttccctccctgtgttggctg | X78683 | 90524 | ctcaacactgaatacataatcta | D88315 |
| 5317 | ttatggctttgtgcacatagaggac | AA041982 | 47921 | gtgatttctccgtgatttctcacag | X78683 | 90525 | tatcatactgataaacttagtact | AA116372 |
| 5318 | gcccagatccccagaatgtaaaccag | W51344 | 47922 | tctccgtgatttctacagcctga | X78683 | 90526 | ttttgtctgtgctactagtagtcc | AA116372 |
| 5319 | aatgtaaaccaggccaaaatggctg | W51344 | 47923 | tgatttctacagcctgagcctct | X78683 | 90527 | tctccttacttataggcagtgtga | AA116372 |
| 5320 | ggtcagagcccccagaccacagcg | W51344 | 47924 | gggagataaccaccatgccaggaatt | X78683 | 90528 | cctttacttaggcagtgtgacaga | AA116372 |
| 5321 | gcagagccccagaccttcagcag | W51344 | 47925 | cgcacatcacagaaccgatctat | X78683 | 90529 | gaaagtcaagcttccaaaagaaga | AA116372 |
| 5322 | gcagcccagaccttcagcagaggct | W51344 | 47926 | gagataaccaccacgccaggaattc | X78683 | 90530 | gtcaagcttccaaaagaagaagca | AA116372 |
| 5323 | cagacctcagagatggctcccagg | W51344 | 47927 | atccatcacagcgatatctcaca | X78683 | 90531 | aagcaacttgtccatgtggggttg | AA116372 |
| 5324 | acctcagcagatggctcccagtc | W51344 | 47928 | gaaccgaatctatctcacagctgac | X78683 | 90532 | gcaacttgccatgtggggttgta | AA116372 |
| 5325 | gatggctccaggtcagaatgtgg | W51344 | 47929 | aatctatctcacagctgacaacct | X78683 | 90533 | cttgtccatgtggggttgtaccca | AA116372 |
| 5326 | ggctccaggtccaggatgtggagt | W51344 | 47930 | tctcacagctgacaacctgtctg | X78683 | 90534 | attatgctacttccatattgca | AA116372 |
| 5327 | tccgttccgggaactgaggagt | W51344 | 47931 | agctgacaacctgtctgaatcta | X78683 | 90535 | ttatagctaccatattgcact | AA116372 |
| 5328 | tctgctccggtccagtaactact | W51344 | 47932 | caacctgtctgaatctacaagat | X78683 | 90536 | atagctccatattgcactag | AA116372 |
| 5329 | gctccggtccagtaaccactctga | W51344 | 47933 | aagtgacagcctccatttaaggataag | X78683 | 90537 | tgtctgctactagtagtccag | AA116372 |
| 5330 | gtaaacaggccaaaatggctgacg | W51344 | 47934 | tggcgttggcgtcatgtgtcgtga | AA028273 | 90538 | tgtgctactagtgtccagcagtat | AA116372 |
| 5331 | aaccaggccaaaatggctgacgtag | W51344 | 47935 | catgtgtctgtgacggagacgccgg | AA028273 | 90539 | tgctactagtgtccagcagtatc | AA116372 |
| 5332 | atggctgacgtagggaccacgtcag | W51344 | 47936 | ttggctgcttagcctgcctgggc | AA028273 | 90540 | ctactagtgtccagcagtattcca | AA116372 |
| 5333 | accagttgcaggtactctgaactg | W51344 | 47937 | ggctgcttagcctgcctgggctc | AA028273 | 90541 | actagtagtccagcagtattcca | AA116372 |
| 5334 | ggtatcctcagaaactgacggtgcag | W51344 | 47938 | gctgcttagcctgcctgggctcc | AA028273 | 90542 | cagcagtattccatgtcccatctc | AA116372 |
| 5335 | atctctgaaactgacggtgcagcag | W51344 | 47939 | gcttagcctgcctgggctccaa | AA028273 | 90543 | gtcatctccttacttataggga | AA116372 |
| 5336 | tctgaaactgacggtgcagcagccc | W51344 | 47940 | gctccacggctgcctgagggtctc | AA028273 | 90544 | cccatctccttacttatagggag | AA116372 |
| 5337 | gaaactgacggtgcagcagcccaga | W51344 | 47941 | ctccacggctgcctgagggtct | AA028273 | 90545 | taatactcaggatgcgacgaatac | AA110627 |
| 5338 | gatgcagttcgtcagaagagag | W46015 | 47942 | cacggctgcctgagggtctctgca | AA028273 | 90546 | atactcaggatgcgacgaatacaa | AA110627 |
| 5339 | gaagtcagttagcagcagggcag | W46015 | 47943 | cggctgcctgagggtctctgcagc | AA028273 | 90547 | agcccgctgcggcagagcagtgcaa | AA110627 |
| 5340 | tactcattacggtgcaattgctc | W46015 | 47944 | ctgcctgagggtctctgcagcc | AA028273 | 90548 | ccctgcgagagcagtgcaacaa | AA110627 |
| 5341 | tccattacggtgcaattgctctgt | W46015 | 47945 | acgccagcgacctgagtcggc | AA028273 | 90549 | cctgcggcagagcagtgcaacaa | AA110627 |
| 5342 | gtgcaattgctctgtttgctaalg | W46015 | 47946 | attgtgtcgacggagagccggt | AA028273 | 90550 | cctgcggcagagcagtgcaacaaa | AA110627 |
| 5343 | caattgctctgtttgctaatgctg | W46015 | 47947 | tcgtggttccgcgtgcagctgttg | AA028273 | 90551 | agcagtgcaacaaactcacagtgga | AA110627 |
| 5344 | cttctgtttgctaatgctgttgc | W46015 | 47948 | tggttccgcgcagctggctg | AA028273 | 90552 | gcagtgcaacaaactcacagtgaca | AA110627 |
| 5345 | ctgttgctaatgctgttgcaa | W46015 | 47949 | gttccgcgcagctggctggt | AA028273 | 90553 | gtgcaacaaactcacagtggacaca | AA110627 |
| 5346 | tttgctaatgctgttgcaaatta | W46015 | 47950 | tttccgcggcagctgttggctgctt | AA028273 | 90554 | gcaacaaactcacagtggacacaga | AA110627 |
| 5347 | gctaatgctgttgcaaattaaac | W46015 | 47951 | tccgcggcagctgttgctgctgttta | AA028273 | 90555 | caatcacagtggacacagatatc | AA110627 |
| 5348 | aatgctgttgcaaattaaactg | W46015 | 47952 | ctgtggctgtttagcctgctgcg | AA028273 | 90556 | actactggacacagatatccgc | AA110627 |
| 5349 | cacccacagggtaagaacaagagc | W46015 | 47953 | gttggctggcttagcctgcctggg | AA028273 | 90557 | ggaaacctccatacctgagtacct | AA110627 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 5350 | gtcagcttagcgagcagggcaggt | W46015 | 47954 | tcgatctcatgtcaccaccagaa | X17501 | 90558 | gaaactctgcatacgagtacctg | AA110627 |
| 5351 | caagagacatctcagcattgcttaga | W46015 | 47955 | tcacaccacagaacaagtctacatt | X17501 | 90559 | aactctgcatacgagtacctgaa | AA110627 |
| 5352 | agcttaggcgagcaggcaggttcct | W46015 | 47956 | ttcacaggatcctgttaacctgaca | X17501 | 90560 | tcctgcatacgagtacctgaagc | AA110627 |
| 5353 | ttagcgagcaggcagcagttcctac | W46015 | 47957 | tgttaacctgacaagaactctctc | X17501 | 90561 | cctgcatacgagtacctgaagcc | AA110627 |
| 5354 | tcctagcgatgtcactgaaggc | W46015 | 47958 | tctctcaccaagaaggcaactg | X17501 | 90562 | gcatacgagtacctgaagccctg | AA110627 |
| 5355 | ttacgatgtgtcactgaaggcaac | W46015 | 47959 | acagagtcttgccttcatccctagc | X17501 | 90563 | ataccgagtacctgaagccctgct | AA110627 |
| 5356 | tataattacccgataattagagatt | W46015 | 47960 | cttcatccctagcagtgtcctagc | X17501 | 90564 | tacgagtacctgaagccctgct | AA110627 |
| 5357 | agagattactcatttacggtgcaat | W46015 | 47961 | ccagcgaacaactctggctctattt | X17501 | 90565 | tcctcatcgggttgctgatattac | AA110735 |
| 5358 | gattactcatttacggtgcaattgc | W46015 | 47962 | gagttgcatgcatgtcctatgaaa | X17501 | 90566 | tcatcggtgttgctgatatacata | AA110735 |
| 5359 | tgatctgcgcgcacaaagacagag | X12789 | 47963 | acaagcacagaacctgtacagtgc | X17501 | 90567 | ttctacttagtgtggctgaaatgtt | AA110735 |
| 5360 | gcgccacaaagacagagatctcc | X12789 | 47964 | acaggacctgtacagtgctccacc | X17501 | 90568 | tgtgctgatgcacagacctctagg | AA110735 |
| 5361 | aggactgagttcatcctagggga | X12789 | 47965 | cctgtacagtgctccaccactgac | X17501 | 90569 | tgctgatgcacagacctctagggag | AA110735 |
| 5362 | gagttcatcctatgggactact | X12789 | 47966 | ctacatttacacctgccaagtcag | X17501 | 90570 | tgatgcacagacctctagggagaag | AA110735 |
| 5363 | atcctatgggactactagccct | X12789 | 47967 | gcaatcctgtaagcagcaagaacga | X17501 | 90571 | acagacctctagggagaagatgagg | AA110735 |
| 5364 | actcactagccctgcttcagctac | X12789 | 47968 | acacagtgactcactcactcg | X17501 | 90572 | tcttagcagtcagtcacgcttacg | AA110735 |
| 5365 | tagccctggcttcagctaggaatg | X12789 | 47969 | tagccagatctctggagtagtg | X17501 | 90573 | tagcagtctagtctacgcttacggat | AA110735 |
| 5366 | tggcctttcaggtactgaatgagctcc | X12789 | 47970 | gatcttctgagtatgttggactgc | X17501 | 90574 | ctagctcacgttaccgatgggaag | AA110735 |
| 5367 | gtccagctctctgatgtctgtgcc | X12789 | 47971 | caacttgctagtggtcacaacact | X17501 | 90575 | gtctaagcttacgatgggaagcag | AA110735 |
| 5368 | tgatgctgtgtccaagtgaatggcc | X12789 | 47972 | tggtcacaacactcatcattcacag | X17501 | 90576 | tacgttacgatgggaagcaggtc | AA110735 |
| 5369 | aatgccactgaagtcctgccaagc | X12789 | 47973 | tcatcattcacaggatcctgttaac | X17501 | 90577 | catatccatcactgataatccatc | AA110735 |
| 5370 | cactgaagtcctgccaagctagctc | X12789 | 47974 | agaccaagaatgccgccatcgtagt | AA028220 | 90578 | atccatccactgataatcccatcc | AA110735 |
| 5371 | gaaccgcaaactcaaccgcctgcag | X12789 | 47975 | accaagaatgccgccatcgtagtgg | AA028220 | 90579 | gtaattcagcgcgttacagtcttt | AA110735 |
| 5372 | actgaagtcctgccaactagtcc | X12789 | 47976 | gattagctccagaacagcgccccag | AA028220 | 90580 | attcagcgcgttacagtcttcag | AA110735 |
| 5373 | caacatcaaccgcctgcaggagatt | X12789 | 47977 | attagctccagaacagcgccccagc | AA028220 | 90581 | tacagctttcagalacgtcctgt | AA110735 |
| 5374 | caacgcctgcaggagattgaagcc | X12789 | 47978 | tagctccagaacagcgccccagcag | AA028220 | 90582 | tcagatacctcctgtctactag | AA110735 |
| 5375 | tgaagccctcaaaggccagagggca | X12789 | 47979 | agctccagaacagcgccccagcaga | AA028220 | 90583 | gatacgtcctgttctactagt | AA110735 |
| 5376 | cctcaaaggccagagggcatcgttg | X12789 | 47980 | tccagaacagcgcccagcagaact | AA028220 | 90584 | ctgttctacttagtgtgctgaaat | AA110735 |
| 5377 | tcatacgaagaccaccagcgggtac | X12789 | 47981 | acgccccagcagaactgaagt | AA028220 | 90585 | ttcggatccatgcgggctctacgacc | AA110735 |
| 5378 | gaagaccaccagcgggtactactagga | X12789 | 47982 | acgccccagcagaactgaagttgg | AA028220 | 90586 | atgcggctctacgacctgtgacg | AA110774 |
| 5379 | caccagcgggtactactgaggactg | X12789 | 47983 | gcgccccagcagaactgaagttgaa | AA028220 | 90587 | gtgcctggaacctatgtgatgc | AA110774 |
| 5380 | ccaacacagccatggggaagatcac | W78478 | 47984 | gcccagcagaactgaagttggaat | AA028220 | 90588 | aaccttatgtgatgcctggacgac | AA110774 |
| 5381 | aacacagccatggggaagatccga | W78478 | 47985 | cccagcagaactgaagttggaatt | AA028220 | 90589 | gtgcggaacgacctggggttcaaga | AA110774 |
| 5382 | gctctatgcagccaacttcgaggt | W78478 | 47986 | ccaagaagccatcgtagtggga | AA028220 | 90590 | cggaacgactctgggcttcaagaaga | AA110774 |
| 5383 | tctatgagcagccaacttcgaggt | W78478 | 47987 | agaatgccgccatcgtagtggag | AA028220 | 90591 | acgactctggggcttcaagaagaag | AA110774 |
| 5384 | tatgagcagccaactttcgaggt | W78478 | 47988 | aatgccgccatcgtagtggaagtg | AA028220 | 90592 | ggctatgacaagccaactgtggccg | AA110774 |
| 5385 | tgagcagccaacttcgaggtc | W78478 | 47989 | atgccgccatcgtagtggaagttgg | AA028220 | 90593 | aagccacctgtgccgcgtgacgctta | AA110774 |
| 5386 | gccccaacttcgaggtcagtgc | W78478 | 47990 | gccgccatcgtagtggaagttgga | AA028220 | 90594 | ccaacttgggccgtgacgcttagc | AA110774 |
| 5387 | ccaacttcgaggtcagtgcagtact | W78478 | 47991 | cgccatcgtagtggaagttggaca | AA028220 | 90595 | cctgggccgtgacgcttatgcaac | AA110774 |
| 5388 | aacttcgaggtcagtgcagtactt | W78478 | 47992 | aagacggagtgacagtgctaga | AA028220 | 90596 | aagcttatgcaacagctcaaggcca | AA110774 |
| 5389 | ctcgaggtcagtagctcctg | W78478 | 47993 | aagattagctccagaacagcgccc | AA028220 | 90597 | atctaagaccttgatcgacctac | AA110774 |
| 5390 | tcgaggtcgcagtactctcgg | W78478 | 47994 | gtacacttcccgggtgatgctcagc | X55573 | 90598 | atgcaacagctcaaggcccatgcctg | AA110774 |
| 5391 | gcaggtgccagtactccgtc | W78478 | 47995 | cacttccgggtgatgctcaacag | X55573 | 90599 | gaccttgatcgacctacgaccc | AA110774 |
| 5392 | caccagcatggggaagatcacctt | W78478 | 47996 | ggacatgtcgggggacgtcacaca | X55573 | 90600 | accttcacctgaacgtgacagcaga | AA110774 |
| 5393 | ggcttccaagggcccactatgagtg | W78478 | 47997 | gtctgcgggacggcacagtccta | X55573 | 90601 | acctgaacgtgacagcagaggcctt | AA110774 |
| 5394 | cttccaagggcccactatgagtca | W78478 | 47998 | gacgtcacagtctagagaaagtc | X55573 | 90602 | caagagccttagccgggagttgct | AA110774 |
| 5395 | tccagggcccactatgagtcagc | W78478 | 47999 | ggtatccaaagccaactgaagcag | X55573 | 90603 | ttagccggagttgctcggtgctt | AA110774 |
| 5396 | cagggcccactatgagttcagcagc | W78478 | 48000 | gtatttctacgagacaagtgtaat | X55573 | 90604 | tgctcggtcctggaacttatgt | AA110774 |
| 5397 | gggcccactatgagtgcagcaacg | W78478 | 48001 | gcaatcgaactaaccaatcgtat | X55573 | 90605 | tcgggtgcctggaacttatgtgta | AA110774 |
| 5398 | gccccactatgagtgcagcaccgc | W78478 | 48002 | atgcgaactaccccatctatgtt | X55573 | 90606 | acatttgtccacctgctggtg | AA110812 |
| 5399 | atgctctatgagcagccaacttcg | W78478 | 48003 | aattgctggccattcattaaggata | X55573 | 90607 | acagatgtctccattgcagaccggc | AA110812 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 5400 | gtatccacttggtgctgctgc | M18208 | 48004 | ttcctgtatgtacactgaccatt | X55573 | 90608 | gctgacacttgcggtacaactgtc | AA110812 |
| 5401 | ctgctgcagccctgcaggga | M18208 | 48005 | tgtatgtacactgaccattaaaag | X55573 | 90609 | gacacttggtacaatcgtcacg | AA110812 |
| 5402 | cagttggcttgattcctgctg | M18208 | 48006 | ttcccgggtgatgctcagcagtcaa | X55573 | 90610 | acttggtacaatctgtcacgcg | AA110812 |
| 5403 | tgctctgcgccctggagctgaagc | M18208 | 48007 | gatgctcagcagtcaagtgccttg | X55573 | 90611 | acaatctgcgccgtgacaaac | AA110812 |
| 5404 | gctctgcccaatgacttgcagctct | M18208 | 48008 | gctcagcagtcaagtgccttggag | X55573 | 90612 | atctgtcacgccgtgacaaactic | AA110812 |
| 5405 | cccaatgacttgcagcctctg | M18208 | 48009 | tctactcttctgctggaggaatac | X55573 | 90613 | gctgacaaactictctcagctgcg | AA110812 |
| 5406 | agactigcagcctctctgttca | M18208 | 48010 | actcttctgctggaggaataca | X55573 | 90614 | aaacttctcagctgcgctacca | AA110812 |
| 5407 | agcccgtggctgtaggagagtacag | M18208 | 48011 | ttacctgagtgccaaacatgtct | X55573 | 90615 | cttctcagctggcgctaccagag | AA110812 |
| 5408 | agtacaggtccagtcttcctctg | M18208 | 48012 | ggatgccgcaaacatgtctagagg | X55573 | 90616 | ctctcagctgcgctaccagagtt | AA110812 |
| 5409 | ggtccagtcttctctcgcagtct | M18208 | 48013 | cgcaaacatgtctatgagggttcgg | X55573 | 90617 | tcagctgcgctaccagagtttatg | AA110812 |
| 5410 | ttgcaacaacctgtccctgcaaa | M18208 | 48014 | cctcagtcgcaggtctaggcagtcc | X69619 | 90618 | gtgacctccattgagaccggctga | AA110812 |
| 5411 | gctccctgcaaactaaataaagca | M18208 | 48015 | acagttcttgcagttcaaggac | X69619 | 90619 | acctccattgagaccggctgaatg | AA110812 |
| 5412 | atgtaccaggcgactatcgtgacac | M18208 | 48016 | cattaaccactacgcatgagggt | X69619 | 90620 | attgagacgcggtgaatgtggatt | AA110812 |
| 5413 | gactatgcgacactgagcgagatgg | M18208 | 48017 | ccactaccgcatgaggggtcacagc | X69619 | 90621 | tttgcttgattcacaaggaacgga | AA110812 |
| 5414 | tatgaaactcagctccgcagataca | M18208 | 48018 | ctaccgcatgaggggtcacagcccc | X69619 | 90622 | cgcatggtacttgtgggatgtga | AA110812 |
| 5415 | ctctccagatatcatcaacacactga | M18208 | 48019 | cttigccaaccttaagtcatgctgt | X69619 | 90623 | gatgacatggctgacacttgcggta | AA110812 |
| 5416 | agatacatcaacacactgaccaggc | M18208 | 48020 | tgccaacttaagtcatgctgtgtg | X69619 | 90624 | gacatggctgacacttgcggtacaa | AA110812 |
| 5417 | acacactgaccaggcctaggtatggga | M18208 | 48021 | gctgagaccatgtcatgctgtat | X69619 | 90625 | atggtgacacttgcggtacaactc | AA110812 |
| 5418 | aacacaggtgacttcctggagtgc | M18208 | 48022 | catgtcatgctgtattacgatgat | X69619 | 90626 | actccagctaccaacagatgcctg | M64404 |
| 5419 | ggtggactcctggagttgcagctct | M18208 | 48023 | tggctcctagagtcgccaagtc | X69619 | 90627 | agcctaccaacagatgcctgaagaag | M64404 |
| 5420 | atatcatgatgcaggaggatg | M18208 | 48024 | ctgctcctagagtcgccaagtccca | X69619 | 90628 | tgtcctgactgttcctgccag | M64404 |
| 5421 | tatcatcatgcaggaggatgc | M81475 | 48025 | tgctccaggtcccagagaaaatggat | X69619 | 90629 | ctgcagacaatgaactctggagat | M64404 |
| 5422 | cctgtgcacagcaggggtcccaa | M81475 | 48026 | gatcatgctccctgctatacg | X69619 | 90630 | acacgcacgtgcagcacatgctat | M64404 |
| 5423 | ccaacctagagcaaatcacattt | M81475 | 48027 | tgctccctgctatcacgccaat | X69619 | 90631 | acgtgcacgtgcagcacatgctat | M64404 |
| 5424 | caacctagagcaaatcacatta | M81475 | 48028 | ctctgactcagcgccaattagt | X69619 | 90632 | atgcaactgcatgtatiggtcc | M64404 |
| 5425 | accctagagcaaatcacatttat | M81475 | 48029 | ggagtgccaagccacatagcagg | X69619 | 90633 | tgtattgggctccccaaggatgaa | M64404 |
| 5426 | attgtaatttcagtcgcattattc | M81475 | 48030 | aagccacatagcggcacctctgg | X69619 | 90634 | ggatgaaccctcttggcttagaa | M64404 |
| 5427 | ttgtaattcagtcgcattattctg | M81475 | 48031 | cttcactcaaacagtcattaaccac | X69619 | 90635 | ggttattcgtgtcacgaaagtt | M64404 |
| 5428 | taatttcagtcgcattattctgtaa | M81475 | 48032 | ccactcaacagtcattaacacac | X69619 | 90636 | gaaagtttctacctcatccctgaa | M64404 |
| 5429 | aaatcagtcgcattattctgaag | M81475 | 48033 | aaacagtcattaaccactacgcatg | X69619 | 90637 | ctcatccctgacttggctitat | M64404 |
| 5430 | tcagtcgcattattctgiaagaa | M81475 | 48034 | cctgcttcacagatattattccag | AA163866 | 90638 | gaagaagttcctcactactctgcaaa | M64404 |
| 5431 | tcagtcgcatttattctgiaagaaa | M81475 | 48035 | cctgttcacagatattattccag | AA163866 | 90639 | cactactgcaaaatgtggctctcag | M64404 |
| 5432 | caccccaggggcgtcaggaaggaaccg | M81475 | 48036 | ttaacgccacagatggcactggt | AA163866 | 90640 | atgtggctccaggcccttccgat | M64404 |
| 5433 | gaaagcccgtaatgactcaggagcc | M81475 | 48037 | taacgccacagatggcactggtg | AA163866 | 90641 | cttcagccctctgatgtrgatg | M64404 |
| 5434 | agcccgtaatgactcaggggcctg | M81475 | 48038 | aacgccacagatggcactggtgg | AA163866 | 90642 | ggccctctgatgatgaatgaa | M64404 |
| 5435 | cccgtaatgactcagggccctgt | M81475 | 48039 | acacgccacagatggcactggtggc | AA163866 | 90643 | atctaatcatticttgaccatt | M64404 |
| 5436 | gtaatgactcaggggccctgcagc | M81475 | 48040 | cagccacagatgggactggtggca | AA163866 | 90644 | tcatttatcattcttaacctgaa | M64404 |
| 5437 | taatgactcaggggccctgcagca | M81475 | 48041 | ccacagatggcactgggtggccaggtc | AA163866 | 90645 | ttctaacctgaaacatggaaagt | M64404 |
| 5438 | actcaggggccctgcagcagat | M81475 | 48042 | ccacagatggcactggtggcaggtc | AA163866 | 90646 | gaggacagctgctgtagtgtata | AA110992 |
| 5439 | aggccctggcagcacagatgggt | M81475 | 48043 | acagatggcactggtggcaggtcca | AA163866 | 90647 | gatagctgcgctgtagtgtataagg | AA110992 |
| 5440 | cgtacaagcagtcgcacagcagat | M81475 | 48044 | cagatggcactgggtgcaggtccat | AA163866 | 90648 | gatggctagcggttagtagccaag | AA110992 |
| 5441 | tgctatatttgcactgatctaat | M68915 | 48045 | tggcaggtccattctacgagatgga | AA163866 | 90649 | cttagtagccaagttgccagatct | AA110992 |
| 5442 | gcttctaccaactcacacattcct | M68915 | 48046 | tgctttcacagatattatccagga | AA163866 | 90650 | agccaagttgccagatctcactg | AA110992 |
| 5443 | tcacaaactcctgacagcttgca | M68915 | 48047 | cttcacagatattattccagatt | AA163866 | 90651 | caagttgccagatctcactgc | AA110992 |
| 5444 | aactctctgacgtgtcatgatct | M68915 | 48048 | ttcacagatattatttccaggttca | AA163866 | 90652 | gttgccagatctcactgcact | AA110992 |
| 5445 | ttgtgaaactgtcacctgtactg | M68915 | 48049 | tggtgacttaacgccacagatgg | AA163866 | 90653 | cagatctcactgcgactgggtct | AA110992 |
| 5446 | tccacctgactgctgaatacg | M68915 | 48050 | gggacttaacgccacagatggcat | AA163866 | 90654 | atcttcactgtgcactgggtct | AA110992 |
| 5447 | aatccgacactgcctgtgaatt | M68915 | 48051 | gtgacttaacacgccacagatggcat | AA163866 | 90655 | tgactgtcactgggtctggaaga | AA110992 |
| 5448 | ttgctccagttgcccaagaatcct | M68915 | 48052 | acttaacacgccacagatggcact | AA163866 | 90656 | atggtaagtgctctggccaggcctt | AA110992 |
| 5449 | tgcccaagatctgggccgcatggt | M68915 | 48053 | acttaacacgccacagatggcactg | AA163866 | 90657 | agtgctgcatggccaggccttggccgag | AA110992 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 5450 | tgaagccgctcctcttcacaaaa | M68915 | 48054 | aatttgcgcagggatccaagatg | AA028462 | 90658 | catcatggaagcaccacttgacatg | AA110992 |
| 5451 | cgctcctcttcacaaaagtgatg | M68915 | 48055 | attgccagcgggatccaagatgg | AA028462 | 90659 | ccacttgacatgctacactgttc | AA110992 |
| 5452 | atttgcactgatctaatcctaaa | M68915 | 48056 | gctccggcgaccatgcagagcctt | AA028462 | 90660 | ctttgcactgtacactgtcgg | AA110992 |
| 5453 | tcaaactccagtgaccatgagga | M68915 | 48057 | ctcggccgaccatgcagagcctt | AA028462 | 90661 | catgctaccactgtcggctacaac | AA110992 |
| 5454 | atgaggaattcctgtatgaaagt | M68915 | 48058 | tcggccgaccatgcagagcctttc | AA028462 | 90662 | gctacactgtcggctacaactat | AA110992 |
| 5455 | aattcctctgtatgaagtctact | M68915 | 48059 | cggccgaccattgcagagcctttc | AA028462 | 90663 | acactgttcggctacaactatggc | AA110992 |
| 5456 | caattcctctggaaggactgaggg | M68915 | 48060 | ccgaccattgcagagcctttccaa | AA028462 | 90664 | gttcggctacaactatggcaaatac | AA110992 |
| 5457 | gatcaagctatatccggaattgat | M68915 | 48061 | cgaccattgcagagcctttcccaa | AA028462 | 90665 | caaatacatggcacactgctgatg | AA110992 |
| 5458 | gctatatccggaattgatcaaggc | M68915 | 48062 | gaccattgcagagcctttcccaaa | AA028462 | 90666 | gaggcctcaggagaagctgaagctgaacta | AA110992 |
| 5459 | cacagcgctactccaactccacaaa | M68915 | 48063 | accattgcagagcctttcccaaacg | AA028462 | 90667 | actgatggctcacacagtacggaa | AA110992 |
| 5460 | gagcacagaagcagcaccagagctc | M68915 | 48064 | ccattgcagagcctttcccaaacgg | AA028462 | 90668 | attttgcactgcactattgaacatgacc | AA111021 |
| 5461 | agcacagaagcagcaccagagctcc | W51418 | 48065 | cattgcagagcctttcccaaacgga | AA028462 | 90669 | tgcactgcactattgaacatgacct | AA111021 |
| 5462 | cccacagaaaaaccagctgaaggtg | W51418 | 48066 | ttgtggcagcgggatccaagatgc | AA028462 | 90670 | cactgcactattgaacatgaccct | AA111021 |
| 5463 | cccacagaaaaaccagctgaaggtga | W51418 | 48067 | tggcagcgggatccaagatggca | AA028462 | 90671 | cactattgaacatgacccctgccaga | AA111021 |
| 5464 | ccacagaaaaaccagctgaaggtgat | W51418 | 48068 | tggcaagctcggcgaccattgca | AA028462 | 90672 | aacatgacctgccagaaatgcaaa | AA111021 |
| 5465 | cacagaaaaccagctgaaggtgatc | W51418 | 48069 | gcaaagctcggccgaccattgcaga | AA028462 | 90673 | catgacctgccagaaatgcaaagg | AA111021 |
| 5466 | acagaaaaccagctgaaggtgatca | W51418 | 48070 | caaagctcggccgaccattgcagag | AA028462 | 90674 | tgacctgccagaaatgcaaaagga | AA111021 |
| 5467 | cagaaaaccagctgaaggtgatcaa | W51418 | 48071 | aaagtctcggccgaccattgcagagc | AA028462 | 90675 | accctgccagaaatgcaaagggaat | AA111021 |
| 5468 | gaaaccagctgaaggtgatcaact | W51418 | 48072 | aagctcggcgaccattgcagagcc | AA028462 | 90676 | gtcctgaagctcagatgaagttca | AA111021 |
| 5469 | aaccagctgaaggtgatcaactg | W51418 | 48073 | agctcggccgaccattgcagagcct | AA028462 | 90677 | gtcaaaccaggcgtccggcagag | AA111021 |
| 5470 | aaaccagctgaaggtgatcaactgg | W51418 | 48074 | gttgaccaccaggcgaaactgta | AA028462 | 90678 | gatggctcacacagtacggaaagac | AA111021 |
| 5471 | gcacagaagcagcaccagagctcct | W51418 | 48075 | gaccacacaggcgaaactgtactc | AA028462 | 90679 | gctcacacagtacggaaagactaca | AA111021 |
| 5472 | accagagctcctgccacatctctg | W51418 | 48076 | atctctatgaggtagatgttctaa | X69620 | 90680 | ctgcgcactgcgtgtcgttcct | AA111021 |
| 5473 | ccagagctcctgccacattctcgg | W51418 | 48077 | gatgttctaaacaatcctcgagtg | X69620 | 90681 | gccactgcgtgtcgttcctt | AA111021 |
| 5474 | cagagctcctgccacttctcgtg | W51418 | 48078 | aatcctctgcagttcccactctct | X69620 | 90682 | ttccttccatttgcactgcacta | AA111021 |
| 5475 | ctcctgccacattctcggttggga | W51418 | 48079 | ggcctgcagttgtcagggtataag | X69620 | 90683 | tcctttccattttgcactgcacta | AA111021 |
| 5476 | tcctgccacattctcggttggga | W51418 | 48080 | ctgcagttgtccgtacacccagaagg | X69620 | 90684 | ctttccatttgcactgcactatt | AA111021 |
| 5477 | tgggcagccacttctctggggc | W51418 | 48081 | ttctgtccgtacacccagaagg | X69620 | 90685 | ttccatttgcactgcactatga | AA111021 |
| 5478 | tgggcagccacttctctggccgc | W51418 | 48082 | gtcgtaagtccccaccttagtt | X69620 | 90686 | gcaattagcggtgcagcttacct | AA051500 |
| 5479 | tgaagttaattcctctggccgtcc | W51418 | 48083 | cccacagactgcgtgctaagta | X69620 | 90687 | attagcggtcagttacctttac | AA051500 |
| 5480 | aatgtaattcctctgcctgcctgcctt | M55617 | 48084 | atttttacgtcatgtacagtataag | X69620 | 90688 | ccatgttgcacagcctgccagcag | AA051500 |
| 5481 | ccaggtctgcgtgggcagtccaga | M55617 | 48085 | ttacgtcatgctacagtataagaca | X69620 | 90689 | tgtggtcacagcctgccagcagcaa | AA051500 |
| 5482 | caggtctgcgtgggcagtcccagaa | M55617 | 48086 | ttttgctctttctcaagcaagtga | X69620 | 90690 | agcctgccagcaagaagaccacctgg | AA051500 |
| 5483 | gtctgcgtgggcagtcccagaaga | M55617 | 48087 | tccttttctaagagaatgaatgtt | X69620 | 90691 | ctgcagcagaagagaacactgggtc | AA051500 |
| 5484 | tctgcgtgggcagtcccagaaagaa | M55617 | 48088 | atgattgcttcaatgttgcactg | X69620 | 90692 | cacctcagttggaagtagcagaatgc | AA051500 |
| 5485 | aaagctgacctgcgtgcaatacaga | M55617 | 48089 | ttcaatgttgcactgatctagtg | X69620 | 90693 | gctcttaggagactctgctagctt | AA051500 |
| 5486 | aagctgacctgcgtgcaatacaga | M55617 | 48090 | gttgcactgatctagtgcatggt | X69620 | 90694 | cttaggagactctgctatgctt | AA051500 |
| 5487 | cctgacctggtgcaatcagagt | M55617 | 48091 | actgactagttgcatggttagtca | X69620 | 90695 | aggagactctgctgctatgctgcc | AA051500 |
| 5488 | ctgacctgcgtgcaatcagagtct | M55617 | 48092 | agaaggccagcgggatcagattaat | X69620 | 90696 | gactctgctgctatgctgccag | AA051500 |
| 5489 | acctgcgtgcaatcagagtcttca | M55617 | 48093 | gaggccatctctatgagtagatg | AA028484 | 90697 | tgctgctatgctgccacaaatg | AA051500 |
| 5490 | acctggtcaatcagagtcttcaa | M55617 | 48094 | tgcatttgcttgcagatcaatt | AA028484 | 90698 | agggctgcagttcagcctttacaac | AA051500 |
| 5491 | cctcgcgtccttctgacttat | M55617 | 48095 | ccttttgcttgcagatcaattc | AA028484 | 90699 | gcttgcagttctactaacaca | AA051500 |
| 5492 | ctgcctgcgtcctctgactttca | M55617 | 48096 | tcttttcataaacatttcaagaat | AA028484 | 90700 | tgtcagttaccttaccaacacaga | AA051500 |
| 5493 | ctgcctcttgactttatcaagcc | M55617 | 48097 | ttttcataaacattctaagaatcct | AA028484 | 90701 | cagcttacttacaacacagagggt | AA051500 |
| 5494 | tttatcaagccgggaagatgtgcc | M55617 | 48098 | aacattctaagaatcctgatgagaa | AA028484 | 90702 | acttaacacagagggctccagct | AA051500 |
| 5495 | agggacagaacctacctcagataca | M55617 | 48099 | acatttctaagaatcctgatgagaaa | AA028484 | 90703 | ttacaacacagagggctccagctgtt | AA051500 |
| 5496 | gtgacagaacctacctcagatacac | M55617 | 48100 | atttctaagaatcctgatgagaaaac | AA028484 | 90704 | caacacagaggggtccagctgttcac | AA051500 |
| 5497 | tgcagaacctacctcagatacact | M55617 | 48101 | ttctaagaatcctgatgagaaaact | AA028484 | 90705 | cagccatgttgcacagcctgccag | AA051500 |
| 5498 | acctccaggctgcgtgggcagtcc | M55617 | 48102 | ggaaatgaaacaccaccattaaagc | AA028484 | 90706 | aagatgctccctgctgctcga | AA049017 |
| 5499 | atcagaaggaccatgctggttac | W51428 | 48103 | gaaatgaaacaccaccattaaagcc | AA028484 | 90707 | ccctgtgctgctgaagaagaggc | AA049017 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 5500 | aggaccatgctgtgttacaaggcg | W51428 | 48104 | atgaaacaccaccattataagcccct | AA028484 | 90708 | atgcctgagtgctacatccgtgcca | AA049017 |
| 5501 | ctatcttgacaaccgaaccatgag | W51428 | 48105 | tgaaacacaccattataagccctg | AA028484 | 90709 | gagtgctacatccggcagcacca | AA049017 |
| 5502 | ctcttgacaaccgaaccatgagtca | W51428 | 48106 | ctttttgcttgcagatcaattca | AA028484 | 90710 | tgctacatccggcaccaccatca | AA049017 |
| 5503 | ttgacaaccgaaccatgtcatca | W51428 | 48107 | aacaccaccattataagccctggca | AA028484 | 90711 | tacatccgtggcagcaccatcaagt | AA049017 |
| 5504 | acaacgaaccatgagtcatcaccc | W51428 | 48108 | cagatcaatttcatcttttcataa | AA028484 | 90712 | cgtggcagcaccatcaagtaccgc | AA049017 |
| 5505 | acgaaccatgagtcatcaccctca | W51428 | 48109 | agatcaatttcatcttttcataa | AA028484 | 90713 | ggcagcaccatcaagtaccgcgca | AA049017 |
| 5506 | gaaccatgagtcatcaccctcatcc | W51428 | 48110 | atcaatttcatcttttcataaa | AA028484 | 90714 | agcaccatcaagtaccgcgcatcc | AA049017 |
| 5507 | ccatgagtcatcaccctcatcagg | W51428 | 48111 | tcaatttcatcttttcataacat | AA028484 | 90715 | atcaagtaccgcgcatccctgatg | AA049017 |
| 5508 | acccctcatccaggtcagattgtcga | W51428 | 48112 | caatttcatcttttcataaacat | AA028484 | 90716 | aagtaccgcgcatccctgatgagaca | AA049017 |
| 5509 | ctcatccaggtcagattgtcgagca | W51428 | 48113 | ttcatcttttcataaacattcta | AA028484 | 90717 | tacctgcgcatccctgatgagatca | AA049017 |
| 5510 | atccaggtcagattgtcgagcatg | W51428 | 48114 | catcttttcataaacattctaaga | AA028484 | 90718 | aagacagcgcagaatcacccatgc | AA049017 |
| 5511 | accatgctgtgttacaaggcgagg | W51428 | 48115 | tatttccacatggaatagacttta | AA119194 | 90719 | cgcatccgatgagatcattgaca | AA049017 |
| 5512 | aagcctttcatgtgtataggcata | W51428 | 48116 | cacagcaggcaggagcgatttcac | AA119194 | 90720 | gcgagaatcaccccatgctggtga | AA049017 |
| 5513 | atggctccaaagccaatatctac | W51428 | 48117 | ctactacagaggaggcaatggccatc | AA119194 | 90721 | gagactacaagggcatctggtgagt | AA049017 |
| 5514 | gcttccaaaagccaatatctactct | W51428 | 48118 | aatggcatcatgctagtgtatgac | AA119194 | 90722 | acctacaagggcatctggtgagct | AA049017 |
| 5515 | tccaaaagccaatatctactctga | W51428 | 48119 | agtgtatgacatccacaaggtaaa | AA119194 | 90723 | aacgggcatctgggagctgtgaca | AA049017 |
| 5516 | agccaatatctactctgacaacg | W51428 | 48120 | gtgtatgacatccacaaggtaaaa | AA119194 | 90724 | calctggagctgtgacaactga | AA049017 |
| 5517 | caatatctactctgacaaccgaac | W51428 | 48121 | gtatgacatcacccaacggtaaaagc | AA119194 | 90725 | tggatgaacatcaacctccgggag | AA049017 |
| 5518 | tatctactctgacaaccgaaccat | W51428 | 48122 | tatgacatcacccaacggtaaaagt | AA119194 | 90726 | atctgcacgtccgggatggtgaca | AA049017 |
| 5519 | cagctggtctttctggactcct | W51428 | 48123 | tgacatcaccacaacggtaaaagctt | AA119194 | 90727 | gaatggctgccttacaatgacagaga | AA049017 |
| 5520 | gcttgtcttttctggactccgg | W51428 | 48124 | gacatcaccaacggtaaaagtg | AA119194 | 90728 | atggcctccattacaatgacagaa | AA049017 |
| 5521 | gctttgccaagtgcgcggcccttt | W51430 | 48125 | catccaacggtaaaagcttggag | AA119194 | 90729 | atattccgaagtctaaltccgt | AA111135 |
| 5522 | agcggcccttgcctgctgcctgcgattggc | W51430 | 48126 | aacatcagcaagtggcttagaaaca | AA119194 | 90730 | agatagccagtccttcaagtgta | AA111135 |
| 5523 | cggcccttgcctgctgattggct | W51430 | 48127 | acagccaggccaggagcgatttcaca | AA119194 | 90731 | agccagtccttcaagtgtatctg | AA111135 |
| 5524 | gccccttgcctgctgaattggcct | W51430 | 48128 | ggagcgatttcacccatcacaacac | AA119194 | 90732 | agccagtccttcaagtgtatctg | AA111135 |
| 5525 | tttgccctgattgcctggcctgt | W51430 | 48129 | gagcgatttcacacccatcacaacct | AA119194 | 90733 | ccagtcctccaagtgtatctgacc | AA111135 |
| 5526 | ctgattggctgctgctgtgacaagaa | W51430 | 48130 | acaacctcctactacagaggagcaa | AA119194 | 90734 | agtcctcaagtgtatctgaccat | AA111135 |
| 5527 | gattggctgctgctgtgacaagagt | W51430 | 48131 | acctcctactacagaggagcaatg | AA119194 | 90735 | gtgtatctgaccatctctggc | AA111135 |
| 5528 | ttggctgctgctgacaaagaagtc | W51430 | 48132 | acctcctactacagaggagcaatgg | AA119194 | 90736 | gtaccatctctggcgaagcgaa | AA111135 |
| 5529 | tgacaagaagctgcccgtccgat | W51430 | 48133 | ctcctactacagaggagcaatggac | AA119194 | 90737 | accatctctgggccaagctgaagg | AA111135 |
| 5530 | acgcacagaggagagaagcgctcc | W51430 | 48134 | tcctactacagaggagcaatgggca | AA119194 | 90738 | tctctgggccaagctgaaggagag | AA111135 |
| 5531 | taccccctgggagtagactgatac | W51430 | 48135 | ccaactgcctgggaagcaagat | X71788 | 90739 | ggcctgcttacaatgacagaatg | AA111135 |
| 5532 | cccctctggagactgtgatactg | W51430 | 48136 | gggacacctgggctaagagaagacg | X71788 | 90740 | cctgcttacaatgacagaatggca | AA111135 |
| 5533 | gatactggagcacatcataggccagg | W51430 | 48137 | gctccatgcatacatagggaagt | X71788 | 90741 | atgggcaacctccacatcctg | AA111135 |
| 5534 | ctggagcacatcataggccaggcttt | W51430 | 48138 | ctagtacactcaagccaaccatgt | X71788 | 90742 | cctccacatcctgtacaagaa | AA111135 |
| 5535 | cacatctaggccaggcttttggcaa | W51430 | 48139 | ggatcccacctgggaaacccaatgt | X71788 | 90743 | catcctgtacatcagaatggta | AA111135 |
| 5536 | cattctaggccaggctttggcaagt | W51430 | 48140 | tccccacctgggaaaccaatgctata | X71788 | 90744 | tctcctgtacatcagaatggtgata | AA111135 |
| 5537 | tctaggccaggctttggccaagtga | W51430 | 48141 | aaccaatgctatagctttcagagact | X71788 | 90745 | tcctgtacatcagaatggtgatatt | AA111135 |
| 5538 | aggcttttggcaagtgagcgcct | W51430 | 48142 | caatgtatgacgtcttcagagatgta | X71788 | 90746 | tgtatttccggaagtgctaatttct | AA111135 |
| 5539 | cagaaatcctgatgacattacgaat | W51430 | 48143 | ttcagagactgtatccatttgcag | X71788 | 90747 | tacattcccagtgaatcctgggcta | AA118687 |
| 5540 | aaatcctgatgacgcttttgaa | W51430 | 48144 | gactgtatccatttgcagaaccgt | X71788 | 90748 | acatttcccagtgaatcctggcta | AA118687 |
| 5541 | gtcccagacgccgctcctttgatc | W51433 | 48145 | tgatcctcattgcagaaccgtgaa | X71788 | 90749 | gaacagtccttcagtgactgaatca | AA118687 |
| 5542 | tccaagacgcgctcctttgatgct | W51433 | 48146 | cccagcatccaacaaccagctggga | X71788 | 90750 | tccttcagtgactgaatcatgcat | AA118687 |
| 5543 | cccagagacgcgctcctttgatctca | W51433 | 48147 | tctgtcttcattggcagaggcaa | X71788 | 90751 | atgtcatccagaagacagtctcctt | AA118687 |
| 5544 | ccagagacgcgctccttttgatcat | W51433 | 48148 | tgtctttcattaggcagaggcaat | X71788 | 90752 | tccaagacgtcctcctgcataa | AA118687 |
| 5545 | caagacgcgcctcctttgatctat | W51433 | 48149 | taagaagccaactgggcaggcaagcc | X71788 | 90753 | agacagtcctcgcataaagctct | AA118687 |
| 5546 | aagacgcgctcctttgatctattg | W51433 | 48150 | gaagccaactggcgcaggcaagtcc | X71788 | 90754 | tcctttgcataaagctcgaaggtt | AA118687 |
| 5547 | agacgcgctcctttgatctattg | W51433 | 48151 | caagtccaaacccggaagcag | X71788 | 90755 | tgcataaagctcaaggtgtgca | AA118687 |
| 5548 | gacgcgctcctttgatctattga | W51433 | 48152 | gaggttaccacctcacatagaaccag | X71788 | 90756 | aagctcaaggtcgtgcatgact | AA118687 |
| 5549 | gcgcgctcctttgatctattgaaaa | W51433 | 48153 | ggtaccactcacatggaaccaagag | X71788 | 90757 | ttgttatctgatctgacc | AA118687 |

TABLE 1-continued

| SEQ ID NO | DBAxnID | sequence | SEQ ID NO | DBAxnID | sequence | SEQ ID NO | DBAxnID |
|---|---|---|---|---|---|---|---|
| 5550 | W51433 | ttgtatgtcgcagagtttatca | 48154 | X71788 | actcacatggaaccagaggaagctg | 90758 | AA118687 |
| 5551 | W51433 | aatcctgatgacattacgaatgaag | 48155 | X70472 | tgctcaaccaggttcctacaagc | 90759 | AA118687 |
| 5552 | W51433 | ctgcccctatgaccatgcctggaa | 48156 | X70472 | ctgcccctatgaccatgcctggaa | 90760 | AA118687 |
| 5553 | W51433 | agcattttctgttgaaggacaatt | 48157 | X70472 | tgagtctagctttgggaagttcctg | 90761 | AA118687 |
| 5554 | W51433 | catttttctgttgaaggacaattag | 48158 | X70472 | acaaggtccactcctgggcctgct | 90762 | AA118687 |
| 5555 | W51433 | tcttttgtcccaagacgcgctcct | 48159 | X70472 | tgtcctccaccaatgctagaaga | 90763 | AA118687 |
| 5556 | W51433 | tttgcccaagacgcgctcctttg | 48160 | X70472 | caggctctcatccagtcggcctca | 90764 | AA118687 |
| 5557 | W51433 | ttgtcccaagacgcgctcctttga | 48161 | X70472 | ctcatccagtcagactcctcag | 90765 | AA118687 |
| 5558 | W51433 | tgtcccaagacgcgctcctttgat | 48162 | X70472 | ggcctcatccagactcctgttag | 90766 | AA118687 |
| 5559 | W51433 | gtatccaagaagccccgaatacat | 48163 | X70472 | atctcagatcctgcttaggatggg | 90767 | AA118687 |
| 5560 | X04418 | ccccgaatacatcctatcaagagc | 48164 | X70472 | cctcgtccgttgtacactgc | 90768 | U03645 |
| 5561 | X04418 | aaatctgtcttgccgcaacacat | 48165 | X70472 | ctcctgttggtacactgcccaca | 90769 | U03645 |
| 5562 | X04418 | acaccattctgcctgcggcaggca | 48166 | X70472 | cactgccccacaataaaatgccat | 90770 | U03645 |
| 5563 | X04418 | gcctgcgcaggcattccacaagt | 48167 | X70472 | cccatgtccctggaagacgggcctg | 90771 | U03645 |
| 5564 | X04418 | ggtgccaaatgccccatcaaacaa | 48168 | X70472 | aagaccagtctctcatgcaggagaa | 90772 | U03645 |
| 5565 | X04418 | actgctaaaccaccaticagtccat | 48169 | X70472 | agctctctcaggagaaagccg | 90773 | U03645 |
| 5566 | X04418 | aaaccacattcagtcatctt | 48170 | X70472 | ggcagctcctggccgcctgaagtc | 90774 | U03645 |
| 5567 | X04418 | acattcagtccatctcttctgaga | 48171 | X70472 | tcctgagccgcctgaagtccagcca | 90775 | U03645 |
| 5568 | X04418 | agtccatctcttctgagatgaca | 48172 | X70472 | caagagccgggctcatgtttacag | 90776 | U03645 |
| 5569 | X04418 | ttgcttatagttttcagtcagtc | 48173 | X70472 | gtgaccagttcaggatgtcttcg | 90777 | U03645 |
| 5570 | X04418 | tgcatgctggtgcaattgctc | 48174 | X70472 | aactacttaggtggcagaagtcacg | 90778 | U03645 |
| 5571 | X04418 | aatacatcctatcaagagccaaga | 48175 | AA028396 | ccacatcccgactgaactgga | 90779 | U03645 |
| 5572 | X04418 | agcagctctgtagaggagttgagaa | 48176 | AA028396 | ctcccagactggaactggagttgtc | 90780 | U03645 |
| 5573 | X04418 | agataattagccaggctactccga | 48177 | AA028396 | tgaagccaactgcagctccctt | 90781 | U03645 |
| 5574 | X04418 | ttagccaggctatcctgagccaa | 48178 | AA028396 | tcccacagtcattatgtactccc | 90782 | U03645 |
| 5575 | X04418 | atgggatctacttgtttggtcaca | 48179 | AA028396 | agtcattattgtacttctcctgat | 90783 | U03645 |
| 5576 | X04418 | ttgttggtcacacttccatccct | 48180 | AA028396 | cattatgtactttcctgatg | 90784 | AA028396 |
| 5577 | X04418 | ggtcacacttccatccacaagg | 48181 | AA028396 | tgtactctcctgatgtggtaggaa | 90785 | AA028396 |
| 5578 | X04418 | aatccaaaacttgtcttggccaa | 48182 | AA028396 | tctcctgatgtgtaggaagtcctt | 90786 | AA028396 |
| 5579 | X04418 | agctagacgccccgactgtccagtg | 48183 | AA028396 | ggaagtcctgggctcaaaggtgat | 90787 | AA111168 |
| 5580 | W51466 | cgcagcgagccgcagccggcagaaacc | 48184 | AA028396 | agtcctgggctcaaaggtgatggc | 90788 | AA111168 |
| 5581 | W51466 | atcaggctcgtccagccggaa | 48185 | AA028396 | cctcatcccctggagaccggattgta | 90789 | AA111168 |
| 5582 | W51466 | catagaaaactgcccctttcacag | 48186 | AA028396 | catccccgaaacggttgtagcc | 90790 | AA111168 |
| 5583 | W51466 | taggaaactgcccctttcacagag | 48187 | AA028396 | tggagttgtacctgactactgga | 90791 | AA111168 |
| 5584 | W51466 | ccttttcacagaggctcttcatgac | 48188 | AA028396 | tgtagccaacattgtcgaacagc | 90792 | AA111168 |
| 5585 | W51466 | ttcacagaggctctcatgactct | 48189 | AA028396 | agttgtcacctgacttactggagt | 90793 | AA111168 |
| 5586 | W51466 | cagaggctctcatgactcttgg | 48190 | AA028396 | tgtcacctgacttactgagctgag | 90794 | AA111168 |
| 5587 | W51466 | gaggctctcatgactctttggct | 48191 | AA028396 | acttactggactgagggtctg | 90795 | AA111168 |
| 5588 | W51466 | ctcttcatgactctttggctcaa | 48192 | AA028396 | gggtcgttcctgcagacgaagg | 90796 | AA111168 |
| 5589 | W51466 | cttcatgactctttggctcaagga | 48193 | AA028396 | tctgttcctgcagcagacgaaggt | 90797 | AA111168 |
| 5590 | W51466 | tcatgactctttggctcaaggga | 48194 | AA028396 | gttcctgcagcagacgaaggtgtc | 90798 | AA111168 |
| 5591 | W51466 | cagcagcagccgaggccatggaaccgc | 48195 | AA028396 | cctgcagcagacgaaggctgccag | 90799 | AA111168 |
| 5592 | W51466 | cgggccagccaactggtccatgc | 48196 | AA028396 | tagcagacgtccagccggaatacta | 90800 | AA111168 |
| 5593 | W51466 | ccaactggtccatggcctgcatg | 48197 | AA028396 | agcagacgtccagcggatactaa | 90801 | AA111168 |
| 5594 | W51466 | tcatgactctttggctcaaggga | 48198 | AA028479 | atgtcaagtagtcttcagagtca | 90802 | AA111168 |
| 5595 | W51466 | ctgtcgatgccctgaacggact | 48199 | AA028479 | tcttcaagtagtcttcaagaac | 90803 | AA111168 |
| 5596 | W51466 | cgatgccccctgaacggactgaagga | 48200 | AA028479 | tagttcatcaagaacaaactatg | 90804 | AA111168 |
| 5597 | W51466 | atgcccctgaacggactgaaggagg | 48201 | AA028479 | gatgtcatgacgcattgtggcga | 90805 | AA111168 |
| 5598 | W51466 | tcaggctcttgtcaaggccgg | 48202 | AA028479 | tcaagaacagttcgttcatggc | 90806 | AA111168 |
| 5599 | K03237 | cgttcgaacagttgagagtc | 48203 | AA028479 | agaacagttgtcttcatggctga | 90807 | AA111209 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 5600 | gctccatatgctgctagcctggaaa | K03237 | 48204 | acaagcttcgttcatgctgtgataa | AA028479 | 90808 | cgctgtcgttcgagctactcccag | AA111209 |
| 5601 | caattcctaaaatctgctcttctt | K03237 | 48205 | aagcttcgttcatgctgctgataaac | AA028479 | 90809 | aagttacttccaaagtgctgtggag | AA111209 |
| 5602 | cctaaaatctgctcttttatgat | K03237 | 48206 | cttcgttcatggctgataaactgt | AA028479 | 90810 | tacttccaaagtgctgtgggaggac | AA111209 |
| 5603 | atctctgctcttctatgatgatgtc | K03237 | 48207 | ttcgttcatgctgataaactgta | AA028479 | 90811 | cttccaaagtgctgtgaggcacaa | AA111209 |
| 5604 | tgatgtctgctactctgaatttga | K03237 | 48208 | cagacacgtccagtggatactaaac | AA028479 | 90812 | tggaggcacaatcaccggtcggac | AA111209 |
| 5605 | ctgctactctgaatttgagatatt | K03237 | 48209 | gacacgtccagtccggatactaaactt | AA028479 | 90813 | ggcacaatcaccggtcggacacag | AA111209 |
| 5606 | agatattacatgatccatcttttgg | K03237 | 48210 | gtagctatcacatgctcagagt | AA028479 | 90814 | cacaatcaccggtcggacacacag | AA111209 |
| 5607 | tacatgatccatcttttggaatct | K03237 | 48211 | tatcatcaacatgctcagagtctca | AA028479 | 90815 | caatcaccggtcggacacagagct | AA111209 |
| 5608 | atccatcttttggaatctcttctta | K03237 | 48212 | atcatcaacatgctcagagtctcaa | AA028479 | 90816 | atcaccggtcggacacagagtct | AA111209 |
| 5609 | tctctagtcttgcacttgaata | K03237 | 48213 | atcacatgctcagagtcttcagta | AA028479 | 90817 | gccgttcaggcgcaacagagtcgg | AA111209 |
| 5610 | agtcttgcacttgaatatatgat | K03237 | 48214 | cacatgctcagagtcttcaagtagt | AA028479 | 90818 | ttccagggcaacagagtcgggac | AA111209 |
| 5611 | agaatgccctataaggatcctatca | K03237 | 48215 | acatgctcagagtcttcaagtagtt | AA028479 | 90819 | ctgttgcttgagctactcccaggc | AA111209 |
| 5612 | taggatcctatcaaaggcgaagcc | K03237 | 48216 | agaggagtccatccctacttccac | AA028479 | 90820 | tgcttgagctactcccaggcttct | AA111209 |
| 5613 | agacctctagagtacatcataaga | K03237 | 48217 | cttccagagatctacagtgaccgg | AA028479 | 90821 | cttcgagctactcccaggcttctga | AA111209 |
| 5614 | tgaagcatccgacctgcgtcatgat | K03237 | 48218 | tctcctgaaacatctggaagttacc | AA028479 | 90822 | tcgagctactcccaggcttctgaag | AA111209 |
| 5615 | ctccctgaagtcgctgatataagaa | K03237 | 48219 | tattatcaacatcactctgcccact | AA028479 | 90823 | gagctactcccaggcttctgaagtt | AA111209 |
| 5616 | cctgctatgacctagaacaagtt | K03237 | 48220 | cactctgcccactggagttccgatt | AA028479 | 90824 | tactccccaggcttcgaagttactt | AA111209 |
| 5617 | tattgacctagaaacagttgattt | K03237 | 48221 | gccactggagttcgcatcgcttgctg | AA028479 | 90825 | cttcgaagttacttccaaagtgct | AA111209 |
| 5618 | tctagtcaattcctaaaatctcg | K03237 | 48222 | tggagttcgatctgctggagttg | AA028479 | 90826 | tgaagttacttccaaagtgctgtgg | AA111209 |
| 5619 | tgtagacaagtcgcgcaagagttc | W51476 | 48223 | tccgattctgctggagttgatgaa | AA028479 | 90827 | tgccaatgatgcctctgcccgggct | AA111212 |
| 5620 | aggagcttccattcaggagcaacactg | W51476 | 48224 | tggagctccaccagttcctggcgcaac | AA028479 | 90828 | caatgatgcctctgcccgggctgta | AA111212 |
| 5621 | acaagcctccaacatctataagtg | W51476 | 48225 | gcctccaccagttcctggggcaaccag | AA028479 | 90829 | atgctgatgtaccaaccaccaaaggg | AA111212 |
| 5622 | cgcctccaacatctataagttgaa | W51476 | 48226 | gttcctgggcaaccagcaggaggccatc | AA028479 | 90830 | atgatgtaccaaccaccaaaagccac | AA111212 |
| 5623 | ctgatcactaagctggagtcctcc | W51476 | 48227 | catccaggcagccattaagaaagtg | AA028479 | 90831 | atgtaccaaccaaaaggcacctg | AA111212 |
| 5624 | catccatcaagctgggctccttcat | W51476 | 48228 | ctacaggaccgagggtactaagatg | AA028479 | 90832 | taccaaccaaaggccacctgagc | AA111212 |
| 5625 | cactaagctggagtccttcattcag | W51476 | 48229 | tgtgccctggatcaactccacgt | AA028479 | 90833 | caaacaccaaaaggcacctgcgcgat | AA111212 |
| 5626 | gctggagtccttcattcaggaggcac | W51476 | 48230 | ctggatcaactgccacgttcagaa | AA028479 | 90834 | caaacaaaaggcacctgagcgattg | AA111212 |
| 5627 | ggagcttcattcaggaggcaactg | W51476 | 48231 | tcaactgccacgttcagaaagctg | AA028479 | 90835 | aaggcaccgagcgattgatgatca | AA111212 |
| 5628 | cttcattcaggaggcaactgcccgggtc | W51476 | 48232 | cattcgatatcgtcacgggaat | AA028479 | 90836 | gcacctgagcgattgatgtcatg | AA111212 |
| 5629 | cattcaggaggcaactgccgggtcatc | W51476 | 48233 | gatatctctcacggaatagcagt | AA028479 | 90837 | ttcctgatgcagcaggctgagcaggctg | AA111212 |
| 5630 | tcaggagcaactgccgggtcatcggg | W51476 | 48234 | tagcagtagagctcctgaaacat | AA028479 | 90838 | tgcagcagcaggctgagtgat | AA111212 |
| 5631 | gttccactgctgtggcagcaacaac | W51476 | 48235 | tagagctcctgaaacatctggaa | AA028479 | 90839 | tgcccggctgtagagctatgcac | AA111212 |
| 5632 | ccactgctgtggcagcaacaactct | W51476 | 48236 | cagctctcacggatgggaggcctga | AA028593 | 90840 | tgttggcacatctgttcagcccaac | AA111212 |
| 5633 | tggcagcaacactctcagactgctg | W51476 | 48237 | agctctcacggatggggaggcctgag | AA028593 | 90841 | ggcacatctgttcagcccaaccag | AA111212 |
| 5634 | agcagccgctgtggtccctgacag | W51476 | 48238 | cacagtctttgtgatgaatctagt | AA028593 | 90842 | acatctgttcagcccaaccaggca | AA111212 |
| 5635 | tggcctgacagctgctgtaagac | W51476 | 48239 | ctagttccagagccaggagcacg | AA028593 | 90843 | tctgttcagcccaaccaggcagat | AA111212 |
| 5636 | tcctgacgctgtaagactg | W51476 | 48240 | tagttccagagccaggagcga | AA028593 | 90844 | tgttcagcccaaccaggcagatgc | AA111212 |
| 5637 | ctgacagctgtaagactgtggt | W51476 | 48241 | agttccagaggcaggagcacgat | AA028593 | 90845 | gcccaaccaggcagatgcggatgc | AA111212 |
| 5638 | taactggctgtgggtaagcgggacac | W51476 | 48242 | gttccagagccaggagcacgatg | AA028593 | 90846 | agatgccggatcgatgataccaac | AA111212 |
| 5639 | actctggaatcctgccatccgc | AA107455 | 48243 | tttccagagccaggaggcacgatgt | AA028593 | 90847 | ggacatgccgttcacttcgcgaaga | AA111212 |
| 5640 | ccaactggaacttcacagtaga | AA107455 | 48244 | ttccagagccaggagcacgatgtt | AA028593 | 90848 | catgccgttcacttcgcgaaggataa | AA120716 |
| 5641 | agtccactggaactctccccgt | AA107455 | 48245 | tccagagccaggagcacgatgttt | AA028593 | 90849 | attggtgcgctactccattaatg | AA120716 |
| 5642 | ccctgtgtcaaggctggcatcat | AA107455 | 48246 | cagagccaggaggcacgatgttt | AA028593 | 90850 | ggtgacgtactccattaatgatgctg | AA120716 |
| 5643 | tttgtgccaaggctggcatcattgc | AA107455 | 48247 | gagccctgcgtgctagagattacg | AA028593 | 90851 | gctactccattaatgatgctgtca | AA120716 |
| 5644 | aggctggcatcattgcctctgccg | AA107455 | 48248 | ctctcaggtggaggcctgagtt | AA028593 | 90852 | gctactccattaatgatgctgtca | AA120716 |
| 5645 | ctggcatcattgcctctgccgc | AA107455 | 48249 | tctccaggatggaggcctgagttg | AA028593 | 90853 | actccattaatgatgctgtcaatg | AA120716 |
| 5646 | gcatcattgcctctgccgagtg | AA107455 | 48250 | aggcccacagtctttgtgatga | AA028593 | 90854 | aatcttttgtctgactatggctacc | AA120716 |
| 5647 | ctgcccgagctgggagacgcgctt | AA107455 | 48251 | gagccctgcgtcgtgtagagattacg | AA028593 | 90855 | cttttgtgactatggctaccatc | AA120716 |
| 5648 | tccacacctgcaaggatgagca | AA107455 | 48252 | gccccacagtcttttgtgatgaat | AA028593 | 90856 | gactaggctaccatctcagagggga | AA120716 |
| 5649 | acactcgcaagatgagaagagg | AA107455 | 48253 | gccccacagtcttttgtgatgaact | AA028593 | 90857 | taccatctcagaggaacgaggtgc | AA120716 |

| SEQ ID NO | sequence | DBAxnID | SEQ ID NO | sequence | DBAxnID | SEQ ID NO | sequence | DBAxnID |
|---|---|---|---|---|---|---|---|---|
| 5650 | gctgcatcacaatcaaatccaccgc | AA107455 | 48254 | cccacagctctttgtgatgaactca | AA028593 | 90858 | ctctacaattggattcactgaacgaa | AA120716 |
| 5651 | tagatcagatccgtgccatcatgga | AA107455 | 48255 | ccacagctctttgtgatgaactcag | AA028593 | 90859 | gccgttcacttgcgaaggataactc | AA120716 |
| 5652 | atcagatccgtgccatcatggaacaa | AA107455 | 48256 | gctagcatatccttccacttccag | X53532 | 90860 | aggataactcctgacatcatcataa | AA120716 |
| 5653 | agatccgtgccatcatggaacaaga | AA107455 | 48257 | atatcctccacttccagctgggg | X53532 | 90861 | ataactcctgacatcatcataaacc | AA120716 |
| 5654 | acaagaaagccaacatccggaacat | AA107455 | 48258 | ccccaaactactgaagaatgacat | X53532 | 90862 | attggtcacttgatcgaatgtctcc | AA120716 |
| 5655 | aagccaacatccggaacatgtcgcagt | AA107455 | 48259 | atgacatttggcactgtctcctgaa | X53532 | 90863 | cacttgatcgaatgtctccaagga | AA120716 |
| 5656 | acatccggaacatgtcagtcatcgc | AA107455 | 48260 | tttggcactgtctggaaccacat | X53532 | 90864 | atcgaatgtctccaaggaaggtct | AA120716 |
| 5657 | tcatcgccatggaccacggccgcaa | AA107455 | 48261 | accaagtcactcactagccaggtc | X53532 | 90865 | gaatgtctccaaggaaggtctctg | AA120716 |
| 5658 | tggaaccaagccaagtcacgcgtgc | AA107455 | 48262 | ggaccctgattctacattcactttc | X53532 | 90866 | gtcctgccaacaaggggfgaaattg | AA120716 |
| 5659 | aagccaagcaacatggccagataccg | AA062269 | 48263 | tgattctacattacattcaaatgt | X53532 | 90867 | gtgtaaggcacctaagccagatgca | AA120716 |
| 5660 | ccagccaacatggccagataccatg | AA062269 | 48264 | tacattacattcaaatgttactg | X53532 | 90868 | tgtaaggcacctaagccagatgcac | AA120716 |
| 5661 | gccgcgtcatcacaccataaggtg | AA062269 | 48265 | tatttctgtcatcatgggaaatgca | X53532 | 90869 | tgatcgactgcgaaggaggggatat | W07963 |
| 5662 | gccgtcatcacaccataaggtgtaa | AA062269 | 48266 | gggtcttgagacctggctagagt | X53532 | 90870 | agagagcgtttgcctgccaagaa | W07963 |
| 5663 | gctcatacaccataaggtgtaaaa | AA062269 | 48267 | acctggctagagtgaccatgtggt | X53532 | 90871 | agcgggtttggccctggccaagatgga | W07963 |
| 5664 | tagcaagtccatcaaactctgcgg | AA062269 | 48268 | tccacttccaggctggagctg | X53532 | 90872 | cggtttggccctggccaagatggact | W07963 |
| 5665 | caagtccatcaaaatcctgcgtga | AA062269 | 48269 | tagacagttccatctaaaagcac | X53532 | 90873 | ggtttggccctggccaagatggactc | W07963 |
| 5666 | gtccatcaaaatcctgcgtgagaa | AA062269 | 48270 | agttcatctaaaagcacttcagg | X53532 | 90874 | tggcctggccaagatgggactccagg | W07963 |
| 5667 | catcaaaatcctgcgtgagaattt | AA062269 | 48271 | catctaaaagcacttcaggtcaaa | X53532 | 90875 | agcacagacaggatcgcagggaact | W07963 |
| 5668 | aactcctgcgtgagaatttaccag | AA062269 | 48272 | aaggcaaccagcttgggfgctgtca | X53532 | 90876 | ggcacagacaggatcgcagggaactg | W07963 |
| 5669 | atttaccagactctcaagagcatct | AA062269 | 48273 | accagctgggtgtcaccttgc | X53532 | 90877 | ggaactgcattagcctggctgc | W07963 |
| 5670 | ttaccagactctcaagagcatctgc | AA062269 | 48274 | accttgccaagtttctaatactgt | X53532 | 90878 | gtaaggcacctaagccacagcaac | W07963 |
| 5671 | gcaccatggccagataccgatgctg | AA062269 | 48275 | ttctaatactgtatgtctgatagc | X53532 | 90879 | taaggcacctaagccagatgcacca | W07963 |
| 5672 | ccatgccagataccgatgctgcgt | AA062269 | 48276 | atatttgtgccctgcctgcgct | X87096 | 90880 | aaggcacctaagccagatgccaccag | AA111149 |
| 5673 | tggccagataccgatgctgccgag | AA062269 | 48277 | ctgcctacgcgggtggalactgtgc | X87096 | 90881 | aggcacctaagccagatgcaccagg | AA111149 |
| 5674 | ccagataccgatgctgccgcagaa | AA062269 | 48278 | ccctcagtctaggagagccgtga | X87096 | 90882 | ggcacctaagccagatgcaccagga | AA111149 |
| 5675 | gataccgatgctgccgcagcaaaag | AA062269 | 48279 | ctctcaactacaactgccagtgctct | X87096 | 90883 | gcacctaagccagatgcaccaggag | AA111149 |
| 5676 | acgatgctgccgcagcaaaagcag | AA062269 | 48280 | caactgccagtgtctccccatga | X87096 | 90884 | ccacctaagccagatgcaccaggagg | AA111149 |
| 5677 | gatgctgccgcagcaaaagcaggag | AA062269 | 48281 | ctgcagtgtctctcccatgag | X87096 | 90885 | atgalcgaggfggcagggaggta | AA111149 |
| 5678 | gcgctgccgcagcaaaagcaggag | AA062269 | 48282 | taagtcctagggcctcaactgcc | X87096 | 90886 | aatgtgaggtcaaccacagcagt | AA111149 |
| 5679 | accccagattctgagctgcagc | W51489 | 48283 | atgcagcgccctgctgatcttgat | X87096 | 90887 | attgtaggftcaaccacagcagg | AA111149 |
| 5680 | gatctgagctgcagccctggctc | W51489 | 48284 | ggacactgctgctattgatcttgat | X87096 | 90888 | accgctattagccagatgtgtc | AA111149 |
| 5681 | cagtagccagcagccctggctcga | W51489 | 48285 | tgtgctattcgatctgattgtcga | X87096 | 90889 | cgcctttattagccagattgtgtc | AA111149 |
| 5682 | gtcgtgaccgcagattgtgatgt | W51489 | 48286 | gctatttgcagccagattgtcttc | X87096 | 90890 | gcctattagccagattgtgtctc | AA111149 |
| 5683 | gctgaccgcagattgtgatgtcgt | W51489 | 48287 | atcgatcttgattgtcgaagagt | X87096 | 90891 | ccttattagccagattgtgtctcca | AA111149 |
| 5684 | ttgattcgtcttgcgaacagaaag | W51489 | 48288 | gtgcttcgatatcgatgccgaacg | X87096 | 90892 | ctattagccagattgtgtcttccat | AA111149 |
| 5685 | tcgtctgcaacagaaagcacgaa | W51489 | 48289 | cttcgatatcgatgccgaacggge | X87096 | 90893 | ttattagcagattggccctgaatgtgatctt | AA111149 |
| 5686 | ttctcaacagaaagcacgaatga | W51489 | 48290 | ctgatcgatgccgaacggccgttga | X87096 | 90894 | tgatttggccctgaaatggtgatctt | AA111149 |
| 5687 | actccgagcacgtccgtgcgtgtc | W51489 | 48291 | cagccgaactgcgttgatccgtct | X87096 | 90895 | gatttggccctgaatggtgatctta | AA111149 |
| 5688 | tgcgagacgctcccgtcgtcatc | W51489 | 48292 | ccgttgatccgctccaggagaaatg | X87096 | 90896 | atttggccctgaatggtgatctta | AA111149 |
| 5689 | caccttcatccgcagccacgagga | W51489 | 48293 | tgatccgctccaggagaatgggc | X87096 | 90897 | ttggccctgaatggtgatcttacag | AA111149 |
| 5690 | cttcatccgcagccagcaggacga | W51489 | 48294 | tccatgaccgcccaaggaaccac | X87096 | 90898 | ttgatggctcaaccacagcagtgg | AA111149 |
| 5691 | tctgagctcagcctggctcta | W51489 | 48295 | ggaccgctcgaggcaggaagaag | AA028701 | 90899 | gtaggtcaaccacagcagtggaa | AA111149 |
| 5692 | ctgcagcctggcttctccgtca | W51489 | 48296 | tttgaaatgtcaccacgctgtga | AA028701 | 90900 | tcaaccacagcagtggaaactggg | AA111149 |
| 5693 | tctcttcctcacagcagcacgcagt | W51489 | 48297 | ttgaatggtcaccagctgctggc | AA028701 | 90901 | aaccacagcagtggaaactggga | AA111149 |
| 5694 | acgtcaccacagcagtgaagt | W51489 | 48298 | accagctgcagctgccgcagttc | AA028701 | 90902 | atggagaactccaattccatccgca | AA111149 |
| 5695 | accgcaccacagtgaagtccgggg | W51489 | 48299 | ctgctgcagccgcagttcataatgg | AA028701 | 90903 | gagaactccaattccaatccgcacca | AA111149 |
| 5696 | cttgcgttccagccaacagc | W51489 | 48300 | tgctgcggccagtctaatgga | AA028701 | 90904 | ctaaccgcttattagccagatg | AA111149 |
| 5697 | gttccagtagcaacagctcgcc | W51489 | 48301 | gctgcagccgcagttcataatgac | AA028701 | 90905 | taaccgcttattagccagatgtg | AA111149 |
| 5698 | ccagtagcaacagtctgcgccagc | W51489 | 48302 | ctggcagccgcagttctaatggaca | AA028701 | 90906 | tgcfgccaccggagcgagaggga | AA111356 |
| 5699 | gcaccgaatcactgcgcttcgagtgccagg | AA073984 | 48303 | tggcagccgcagttcttatgggacat | AA028701 | 90907 | agctgcgaccagcatttgtcgcfgaag | AA111356 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 5700 | cactgagtcgcccaggtgtcggga | AA073984 | 48304 | ggcagccgcagtctaatggcatc | AA073984 | 90908 | tgattgcatcaatgactgtgggcaa | AA111356 |
| 5701 | ttgaaaatgtcccacctgtcattc | AA073984 | 48305 | gcagccgcagttctaatggacatct | AA073984 | 90909 | attgcatcaatgactgtgggcaaag | AA111356 |
| 5702 | atgtcccacctgtcattccaacacc | AA073984 | 48306 | cagccgcagttctaatggacatct | AA073984 | 90910 | gatgtcagtgctcttcccgatg | AA111356 |
| 5703 | ctcaccactacctcattagtatcta | AA073984 | 48307 | cgtttgacgacgaatacctgaagtg | AA073984 | 90911 | tgtcagtgctcttcccgatgg | AA111356 |
| 5704 | accactacctcattagtatctaccg | AA073984 | 48308 | tgaaatggtcaccacgtctggca | AA073984 | 90912 | tcagtgctcttcccgatgtg | AA111356 |
| 5705 | tcattagtatctaccgggataagct | AA073984 | 48309 | gaaatgtcaccacgctgctggcag | AA073984 | 90913 | agtgctctctcctgatgtgtga | AA111356 |
| 5706 | ttagtatctaccgggataagctctt | AA073984 | 48310 | aaatgtcaccacgctgctggcagc | AA073984 | 90914 | ctctctcctgatgtgtgaactg | AA111356 |
| 5707 | gtatctaccgggataagctctctt | AA073984 | 48311 | aatggtcaccacgctgctggcagc | AA073984 | 90915 | ctcttcctgatgtgtgaactgca | AA111356 |
| 5708 | gggataagctctctttgtgtctgt | AA073984 | 48312 | atggtcaccacgctgctggcagccg | AA073984 | 90916 | cttcctgatgtgggtgaactgcatg | AA111356 |
| 5709 | ataagctctctttgtgtctgtgat | AA073984 | 48313 | tggtcaccacgctgctgcagccgc | AA073984 | 90917 | tccctgatgtggtgaactgcatgca | AA111356 |
| 5710 | tctcttttgtgtctgtgatacagac | AA073984 | 48314 | gtcaccacgctgctgcagccgcag | AA073984 | 90918 | ctgcggacatttgctgctgaagca | AA111356 |
| 5711 | tgagtcgccaggtgtcgggaaaat | AA073984 | 48315 | tcaccacgctgctggcagccgcagt | AA073984 | 90919 | ggacatttgctgctgaagcagagagc | AA111356 |
| 5712 | tgatccacagtctattctcataaa | AA073984 | 48316 | aaagttctctgccagagacact | AA073984 | 90920 | acatttgctgctgaagcagagagc | AA111356 |
| 5713 | tccacagtctattctcataaactg | AA073984 | 48317 | tctctcctgagagacactgaagta | AA073984 | 90921 | atttgctgctgaagcagagccgag | AA111356 |
| 5714 | gtctatttctataaactgctctgg | AA073984 | 48318 | tgaactcttattgattgctcaaacgt | AA073984 | 90922 | tttgttgagctcggccacagataaa | AA111356 |
| 5715 | ttctcataaactgctctggggacat | AA073984 | 48319 | ggaactctcattcttattcagctag | AA073984 | 90923 | tggagtcgccacagataaaggaa | AA111356 |
| 5716 | taaactgctctggggacattttct | AA073984 | 48320 | caatctcttattcagctagaatc | AA073984 | 90924 | tcaaaatcttaccacaccaagaa | AA111356 |
| 5717 | actgctctggggacattttctaga | AA073984 | 48321 | ccacagattcgcctgtctttct | AA073984 | 90925 | gatctttgagctgaaggcagagtt | AA111356 |
| 5718 | gcgttgtaagccagtcagtgtgtga | AA073984 | 48322 | agaaccgtctaccagtgacctctg | AA073984 | 90926 | atctctgagtgtgaagccagcctgt | AA111366 |
| 5719 | cggacacagtgccccaaggacaag | J05261 | 48323 | gtctaccagtgacctctgattatg | J05261 | 90927 | agcctgctaagaggggatgtccat | AA111366 |
| 5720 | catgtcccccaggacaagcctga | J05261 | 48324 | cagtgacctctgattatgatttga | J05261 | 90928 | tttgttttgagccagtgagtcccag | AA111366 |
| 5721 | gcaaccatggaaatctcagtactga | J05261 | 48325 | ctgcaaaactctctctcctcctag | J05261 | 90929 | tttgtagcagtgagccagaacaagg | AA111366 |
| 5722 | catggaaatctcagtactgatcca | J05261 | 48326 | atcgtctgctcgagctgaatfg | J05261 | 90930 | ctctgctgccctgccaggctagg | AA111366 |
| 5723 | tcctgactaaaactgccagact | J05261 | 48327 | gtttttgccatgtcaaaagccat | J05261 | 90931 | ctcaggctaggtgccaggggct | AA111366 |
| 5724 | actaaaactgctggggacaitctcaca | J05261 | 48328 | ccgatgacctctctccagta | J05261 | 90932 | tgccaggctggtcctccagata | AA111366 |
| 5725 | cagactctcacagctggtgatc | J05261 | 48329 | tctccactagaacactggatctt | J05261 | 90933 | tggctcctaggcaggggtagt | AA111366 |
| 5726 | agcctgtgcatcccagccttgggc | J05261 | 48330 | cactgaacctggatctcaacac | J05261 | 90934 | ctctaggatcaggggtagttcag | AA111366 |
| 5727 | ggtcacagacagtcctaggaacaag | J05261 | 48331 | ggatctccaacacggaggctcatcc | J05261 | 90935 | tgctggttgggccagcagt | AA111366 |
| 5728 | catgctccccaggacaagcctga | J05261 | 48332 | ccgaggtctcatccttccctatact | J05261 | 90936 | gtgtttgggccgaccagtcagtct | AA111366 |
| 5729 | cagacagtcctaggaacaagtgagca | J05261 | 48333 | ctatactccgtgacagaagaagga | J05261 | 90937 | tttgggccgagccagtcagtctctg | AA111366 |
| 5730 | gtgggcacttgtccggccatcgt | J05261 | 48334 | tctgctcgctccccactgcatac | J05261 | 90938 | ggagtcccataccagtcctcactt | AA111366 |
| 5731 | ccaggaaccccacaagagctagagaga | J05261 | 48335 | taatcttttcgtgtaatcagaca | J05261 | 90939 | ccgagctgcagctgctgcgagtgt | AA111366 |
| 5732 | ggcacaagctgagctgctttacc | J05261 | 48336 | tgctaccaagggcaacaaggtgggt | J05261 | 90940 | cagctccagctgcctgctgggtgt | AA111322 |
| 5733 | gcctcgagctgctttaccatgtc | J05261 | 48337 | agggcaactgtcagccgaaggaat | J05261 | 90941 | tcctcacttgacctgctgggct | AA111322 |
| 5734 | agctgctttaccatgtcctcgag | J05261 | 48338 | aatgcaaattctcagactctaacct | J05261 | 90942 | tcacttgacctgctgggcctct | AA111322 |
| 5735 | ctcgagttctgaacaagagcct | J05261 | 48339 | ccaaagaacaccacttggatcagt | J05261 | 90943 | cctgacctgctgggcctccttga | AA111322 |
| 5736 | gttctgaacaagagcctactga | J05261 | 48340 | gaccacttgagatcaagtaggacca | J05261 | 90944 | tgagactgcctgttgttgttg | AA111322 |
| 5737 | agagcctactgatagttccgctg | J05261 | 48341 | aatatctttcaggatggagggacca | J05261 | 90945 | agctacctgttgttgttgttg | AA111322 |
| 5738 | atagctctccggaccttgaaaatccc | J05261 | 48342 | atactaattatacccctgcaaagc | J05261 | 90946 | taccatgtttgtgttttggcag | AA111322 |
| 5739 | ttctgctcgcaaccatggaaatcctc | J05261 | 48343 | attatacccctgcaaagcccaac | J05261 | 90947 | tggatagctttcttgctgcagaga | AA111322 |
| 5740 | gttagagccctgctgggtgatcgtt | W49913 | 48344 | ccttgcaaagcccacttgaact | W49913 | 90948 | gctttgctgcgcagggaccct | AA111322 |
| 5741 | tagagccctgctgggtgatcgtttct | W49913 | 48345 | ccctgcaaagcccaacttgaatc | W49913 | 90949 | atgctcccggctgattgaagagtc | AA111322 |
| 5742 | gaagacatctctgaggttggg | W49913 | 48346 | gcaaaagcccaacttgaatctctt | W49913 | 90950 | tggtcaactaacagatccccacaga | AA111322 |
| 5743 | gacatctctgaggttgggcctg | W49913 | 48347 | ttgaaatctcttaggactatcgtc | W49913 | 90951 | cacagatcccacacagatccagga | AA111322 |
| 5744 | tctctctgaggttgggcctgtgt | W49913 | 48348 | tatccacgctccatagggtagacta | W49913 | 90952 | cacagatccacacagaagctgcagtg | AA111322 |
| 5745 | ttctctgaggttgggcctgtgta | W49913 | 48349 | ccaacgccatcaaggatggcctggc | W49913 | 90953 | gcccaagatcaagactgtggacat | AA111322 |
| 5746 | cgaataccaaggagaccaatgagacg | W49913 | 48350 | ccatcaaggatgccctggctaget | W49913 | 90954 | gcatgatcctcagaacactgtggacat | AA111322 |
| 5747 | actttatgtcgccatgcgggaacttg | W49913 | 48351 | cactctctggccaggagtttaatct | W49913 | 90955 | tgatcctccagaagccatccgccg | AA111322 |
| 5748 | tttatgtcgccatgcgggaacttg | W49913 | 48352 | ttaatctcttgcaatgttaagtcc | W49913 | 90956 | gccgaattcacaaggggagcatg | AA111322 |
| 5749 | tgccatgcgggaacttgaattgg | W49913 | 48353 | aggggccacagcagctcagctatg | W49913 | 90957 | gcggagtccatgccactttcag | AA111322 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 5750 | acttgagtggacaatgctgccagt | W49913 | 48354 | agcagatacaacctgttaagga | X93035 | 90958 | ccatgcctacctttcagaaacat | AA111322 |
| 5751 | gagacctgcgggtggatcgttcct | W49913 | 48355 | tacacaacctgtaaggaatgcaa | X93035 | 90959 | ttctgtcgcagcagagaccctgaa | AA111322 |
| 5752 | gatcgtctccggttcgtatcg | W49913 | 48356 | ttatgtgaccatgtggtgttaaat | X95591 | 90960 | ttgctgcagcagagaccctgaagga | AA111322 |
| 5753 | tcgttctccggttcgtattcgtg | W49913 | 48357 | gattcctttgaattcatgtataa | X95591 | 90961 | tctttgatgccactcacggcttgt | AA111322 |
| 5754 | gttctcgttctgtattcgtggg | W49913 | 48358 | tatctgtagcctgcgaggtgaagg | X95591 | 90962 | ttgtgatggccactcacggcttgtt | AA111322 |
| 5755 | aacattcctatgaagctactgaag | W49913 | 48359 | tgtgacctgcgaggtgtaaggacat | X95591 | 90963 | ccactcacggcttgttacctcga | AA111322 |
| 5756 | cattcctatgaagctactcgttctg | W49913 | 48360 | gacttaaataccactcgttctg | X95591 | 90964 | ctcacggcttgttatcctgatgc | AA111322 |
| 5757 | ttccttalgaagctactgaagaaca | W49913 | 48361 | aataccactcgttctgttcgt | X95591 | 90965 | acggcttgttatcctgatgctcc | AA111322 |
| 5758 | ctgaaggacatctctcgaggttg | W49913 | 48362 | taccccactcgttcgttcagtta | X95591 | 90966 | ccctgatgctcccggctgattga | AA111322 |
| 5759 | tgttgtgatgctctgtcctaaact | L02241 | 48363 | cactctgtttctgtcagttagttc | X95591 | 90967 | atgccacatccaaggagatcgcaga | AA111422 |
| 5760 | tggatgcctgctccttaaactgca | L02241 | 48364 | ctgttctgtcagttagttcaaca | X95591 | 90968 | tgccacatccaaggagatcgcagac | AA111422 |
| 5761 | gccccacacaaatccactgctctac | L02241 | 48365 | gttctgtcagttagttcaacatg | X95591 | 90969 | ccattcgaggtgtgcagagtgcc | AA111422 |
| 5762 | tatatgctaattcgtctagtga | L02241 | 48366 | ttcgtctgtatattcaaagtcaaa | X95591 | 90970 | catcgaggtgtcggagatgcg | AA111422 |
| 5763 | atgcttaattcgtctagtgagtt | L02241 | 48367 | ctgtacttaattctcatgttcca | X95591 | 90971 | atcgaggtgtgcgtggatgcgt | AA111422 |
| 5764 | aattctgtcttagtgagttggaaca | L02241 | 48368 | taaatttacacattacattctgtgat | X95591 | 90972 | tcgaggtgtcggagatgccgtc | AA111422 |
| 5765 | tttcaccatatttccgtaaaatat | L02241 | 48369 | aatttacacattacattgtgatac | X95591 | 90973 | gtccctgcgatgcagccagagactc | AA111422 |
| 5766 | tgtaacactaaacatctctagga | L02241 | 48370 | tttacacattacattgtgatacg | X95591 | 90974 | tccctgcgatgcagccagagactcc | AA111422 |
| 5767 | aaagtattctccactcgactcgaat | L02241 | 48371 | tttcatatataagcatcatgatgtg | X95591 | 90975 | ccctgcgatgcagccagagactcg | AA111422 |
| 5768 | gtattttccatctagcctgaatga | L02241 | 48372 | tatctataagcagttgtgaaatcc | X95591 | 90976 | cctgcgatgcagccagagactcgt | AA111422 |
| 5769 | atctagcctgaatgtactgtaaatt | L02241 | 48373 | gaaatccaaaatgttctctgtaaca | X95591 | 90977 | ctgcgatgcagccagagactccgtc | AA111422 |
| 5770 | cattatgaccccatacataacataaaat | L02241 | 48374 | aatccaaaatgttctgtaaacatt | X95591 | 90978 | gccacatccaaggagatcgcagaca | AA111422 |
| 5771 | gctctgtcctaaacgtcagcatga | L02241 | 48375 | tgttctgtaaacattgtagtgt | X95591 | 90979 | ccacatccaaggagatcgcagacact | AA111422 |
| 5772 | ctgtcctaaactgcagcatcagcatgac | L02241 | 48376 | ccaacctctaccatgagagatcgcc | AA028748 | 90980 | ccacatccaaggagatcgcagacact | AA111422 |
| 5773 | tgttactttcaaattgcaccaagg | L02241 | 48377 | caacctctaccatgagagatcgcca | AA028748 | 90981 | acatccaaggagatcgcagacactt | AA111422 |
| 5774 | tactttcaaattgcaccaaggaag | L02241 | 48378 | ggatgctcccagagagaccacgga | AA028748 | 90982 | cagcagagtccattcgaggttgc | AA111422 |
| 5775 | attgcaccaaggaaggacacactg | L02241 | 48379 | gatgctcccagagagaccacgat | AA028748 | 90983 | agcagagtccattcgaggttgct | AA111422 |
| 5776 | ggaacactgtttatgccccaacaa | L02241 | 48380 | tgcctcccagagagaccacacgtg | AA028748 | 90984 | gtccattcgaggtgtcgagatg | AA111422 |
| 5777 | cacactgtttatgccccaacaaat | L02241 | 48381 | gcctcccagagagaccacgatga | AA028748 | 90985 | tccattcgaggtgtcggagatgc | AA111422 |
| 5778 | gtttatgccccaacaaatccactg | L02241 | 48382 | ctccccagagagaccacgatcgatga | AA028748 | 90986 | tgaaggctcgtaactaccggc | AA111422 |
| 5779 | actccctattattgccctctgct | L02241 | 48383 | aggagaccacgtcatcatgatga | AA028748 | 90987 | aggctcgtaactaccggcatg | AA111422 |
| 5780 | tttctggtagttctgacatgatg | Z14986 | 48384 | ccagatgcacatgaagtcac | AA028748 | 90988 | catggagctcagttcgacaccaca | AA111262 |
| 5781 | tatctgtctgatctgtaatgagca | Z14986 | 48385 | ccgatcgacatcgaagtcacactg | AA028748 | 90989 | gaggctcagttcgacaacgac | AA111262 |
| 5782 | gtaattgacacgcacacttattga | Z14986 | 48386 | acatcatgaagtcacggaggacat | AA028748 | 90990 | tcgaagtccgaactgccagaacgat | AA111262 |
| 5783 | agcacacacctatttgaattgct | Z14986 | 48387 | aagtcacggaagcatcctgcaag | AA028748 | 90991 | gagatcgaacgccaggacgatcca | AA111262 |
| 5784 | acagcacctatttgaatttgctatt | Z14986 | 48388 | accctaccatgagagatcgccatc | AA028748 | 90992 | atccgaacgccaggacgatccaggg | AA111262 |
| 5785 | tatttgagggcagttgcttatta | Z14986 | 48389 | cctccacatgagatcgccatca | AA028748 | 90993 | cacgcgtgccactgtgagagaagt | AA111262 |
| 5786 | ggtgccataatttctctgttgt | Z14986 | 48390 | tctaccatgagatcgccatcaca | AA028755 | 90994 | ggtgccactgtgagagaagttga | AA111262 |
| 5787 | aaaagtattctgtaccacatgta | Z14986 | 48391 | ctaccatgagatcgccatcaca | AA028755 | 90995 | agtgcaatatcacaagttggatc | AA111262 |
| 5788 | tgtatttctgtaccaacatgaagc | Z14986 | 48392 | atgagagatcgccatccaatact | AA028755 | 90996 | gcaatatcacaagttgatcgta | AA111262 |
| 5789 | atttcgtaccacaatgtaagcttc | Z14986 | 48393 | tgagatcgccatccaacaatcactg | AA028755 | 90997 | atatcacacaaagttgatcgtaagg | AA111262 |
| 5790 | tctgtaacacacaatgtaagcttcaat | Z14986 | 48394 | ctggagctttcaacccgggtcag | AA028755 | 90998 | ctctcgtaactgaccggcatgct | AA111262 |
| 5791 | ttctaaacagagtcgttagttg | Z14986 | 48395 | gacgctttcaaccctggtcacga | AA028755 | 90999 | tcgtaactgaccgcatgctaag | AA111262 |
| 5792 | ttggaacactgctcgactctttct | Z14986 | 48396 | cactgctcatttgcagcgctgag | AA028755 | 91000 | gcctgaacagctgcggaactcgttc | AA111262 |
| 5793 | gaacactgctctgactctctacaa | Z14986 | 48397 | ctgctcatttgcgcgcgtcagtc | AA028755 | 91001 | acagtcgcgaactcgttcatcggg | AA111262 |
| 5794 | ttctacacgtgtlgattgaaggct | Z14986 | 48398 | ggatcagtagctcgatttgcacag | AA028755 | 91002 | acggaactcgttcatcgggaggtc | AA111262 |
| 5795 | gcttctgcagttgatctcgtg | Z14986 | 48399 | atcagtccgcatttgcacagtc | AA028755 | 91003 | gaactcgttcatcggagctcagc | AA111262 |
| 5796 | ttcggtcagcttatclcgtcgatt | Z14986 | 48400 | cagtagctccgatttgcacagt | AA028755 | 91004 | ctcgttcatcgggagtcagctc | AA111262 |
| 5797 | ggtcagcttatcgtctgatctcg | Z14986 | 48401 | gtagctccgattgccacagttg | AA028755 | 91005 | gtccatcggaggctcagttcgac | AA111262 |
| 5798 | cttatctctgcgattcgtaatga | Z14986 | 48402 | agctccgattgccacagtttgat | AA028755 | 91006 | atgcaaactgcaaagcaaggccgct | AA111262 |
| 5799 | acgcagttcaccgcagcgagcctgtgc | M94632 | 48403 | ctgcattttgcacagtcttgtat | U08373 | 91007 | caaaactgcaaagcaaggccgctctg | U08373 |

TABLE 1-continued

| SEQ ID NO | DBAxnID | sequence | SEQ ID NO | DBAxnID | sequence | SEQ ID NO | sequence | DBAxnID |
|---|---|---|---|---|---|---|---|---|
| 5800 | M94632 | aacccactctgctgtctgctgagg | 48404 | AA028755 | cgcattgcacagtctgctgatatct | 91008 | gtgtccaggacagtgactgcgcatc | U08373 |
| 5801 | M94632 | ccaacaggcactctagacagagca | 48405 | AA028755 | cattgcacagtctttgatatctg | 91009 | acagtgactgcgcatctgcacaaac | U08373 |
| 5802 | M94632 | ggcactctagacagagcaatctct | 48406 | AA028755 | tttgcacagtctttgatatcttgat | 91010 | gtgactgcgcatctgcacaaactct | U08373 |
| 5803 | M94632 | ttgtgccagcccacaggctggc | 48407 | AA028755 | tatcttgattattgctatgccacg | 91011 | gcgcatctgcacaaactctttctaa | U08373 |
| 5804 | M94632 | cccagaggctgcttgtctggag | 48408 | AA028755 | gctcatttgtgcagcgtgatgccac | 91012 | catctgcacaaactctttctaagta | U08373 |
| 5805 | M94632 | ggaaccgcttcctgtgcacagggc | 48409 | AA028755 | tctgtattgctatgccacaga | 91013 | ctgcacaaactctttctaagtatct | U08373 |
| 5806 | M94632 | gtgagacagccagccacgccgtttg | 48410 | AA028755 | ctgtccgccacactggatgctgc | 91014 | aaactctttctaagtatctagcaat | U08373 |
| 5807 | M94632 | gtgcacatctccacagaaacagaa | 48411 | AA028755 | gtgccgcccacacttggatatgctg | 91015 | ctctttctaagtatctagccaatgtt | U08373 |
| 5808 | M94632 | aacagaactcatgcactgaccgc | 48412 | AA028755 | gtccgccacacttggatgctgga | 91016 | atctagcaatgttactcttcagac | U08373 |
| 5809 | M94632 | ttagcgtgtaatgcctgaggaata | 48413 | AA028755 | cacactggatctgcggatcagta | 91017 | tagcaatgttactcttcagacact | U08373 |
| 5810 | M94632 | tgtaatgcctgaggaataaagtgt | 48414 | AA028755 | cactggatctgcggatcagtagc | 91018 | gcaaagcaaggcgctctggaacaa | U08373 |
| 5811 | M94632 | ggccatgcagcatctgtgtggac | 48415 | AA028755 | tggtatcgtggatcagtagctgc | 91019 | caaggcgctctggaacaagatgca | U08373 |
| 5812 | M94632 | gagcatctcgtttgaacacgcct | 48416 | AA028755 | atcggctggatcagtagctgcatt | 91020 | gaaggcccagagaagccagaagat | U08373 |
| 5813 | M94632 | tgtggacacgcctgtgaatgaccct | 48417 | AA028755 | ggtcgctcatctgcagtgcccg | 91021 | tgatgagagcccaggatctggagac | U08373 |
| 5814 | M94632 | caogcctgtgaatgacccgtcact | 48418 | AA028755 | ttcatctgcagtgccggctlct | 91022 | tgagagcccaggatctggagacgcc | U08373 |
| 5815 | M94632 | tgtgaatgacccgtcacttacce | 48419 | AA028755 | aagggctctccagggttgacag | 91023 | gagcccaggatctggagacgccca | U08373 |
| 5816 | M94632 | tttaccctaactacagatatgca | 48420 | AA028755 | aagggctgcatttaccaggggactg | 91024 | cccactgaagtcattgcggaagagg | U08373 |
| 5817 | M94632 | tacagcatatgcatgccaggccggg | 48421 | AA028755 | cgcatttaccaggggcactgaagccg | 91025 | tctagagtcaggtgtccaggacag | U08373 |
| 5818 | M94632 | tgctggccaccaagaccggaagagg | 48422 | AA028755 | ggcactgaagccgacagcatctca | 91026 | atctactactcagaaagttactg | AA111263 |
| 5819 | W49956 | tggttgatctggctctgagaat | 48423 | AA028755 | gacagcatctcagcggattcctca | 91027 | ttaccagagaactctcctaagcaa | AA111263 |
| 5820 | W49956 | tgatcggtggctctgagaatcatt | 48424 | AA028755 | atctcagcggatctccatttcc | 91028 | tgtcaacagagtctaggaatggt | AA111263 |
| 5821 | W49956 | gcttcagacaccataggagtggcaa | 48425 | AA028755 | ttcctcatttccctccgctgag | 91029 | caatgattcatgagccagaaccog | AA111263 |
| 5822 | W49956 | ttcagacaccataggagtggcaaga | 48426 | AA028755 | ccctggccgagctgggggatctgc | 91030 | atgatcatgagccagaaccogga | AA111263 |
| 5823 | W49956 | gggccaagatccaccctgccaggtg | 48427 | AA028755 | ccgaactctgcaaagtgaaggggt | 91031 | gatcatgagccagaaccogcata | AA111263 |
| 5824 | W49956 | atcccaactgccaggccaagtggcg | 48428 | AA028755 | ttctgcacacgccagtggttct | 91032 | catgagccaacccgcatattc | AA111263 |
| 5825 | W49956 | tcagtgacttgacctgtacctgct | 48429 | AA028755 | tgtgcagtccggctctattact | 91033 | tgagccagaaccogcatattctt | AA111263 |
| 5826 | W49956 | agtgacttgacctgtacctgctgg | 48430 | AA028755 | gtgcccgcctctcaactccaagtgct | 91034 | agcccagaaccogcatattctct | AA111263 |
| 5827 | W49956 | tgacttgacctgtacctgctgtc | 48431 | AA028755 | tattacttccacttccaagtgatct | 91035 | cccagaaccogcatattctct | AA111263 |
| 5828 | W49956 | acttgacctgtacctgctgtcct | 48432 | AA028755 | ttccaagtgatctccaagtggacc | 91036 | ccgcatattcttctttaagacg | AA111263 |
| 5829 | W49956 | tggccctgactcaggcccaggg | 48433 | AA028755 | gtgatctccaagtgggaccttgtc | 91037 | gcatattcttcttcttaagagc | AA111263 |
| 5830 | W49956 | gcctgactcaggcccagaggccaggat | 48434 | AA028755 | tgggaccttgtcgtttatcaagt | 91038 | accagaaactctccttaagcaagt | AA111263 |
| 5831 | W49956 | actggtggctctgagaatcatct | 48435 | AA028755 | gattcctgagtttctctaacaca | 91039 | ctcctcaagcaagtaccaagactca | AA111263 |
| 5832 | W49956 | agaatcattctgattactgcttcag | 48436 | AA028755 | gactggttccaggatgtatgaccgta | 91040 | ctctcaagcaagtaccaagactca | AA111263 |
| 5833 | W49956 | tcattctgattactgcttcagacac | 48437 | AA028755 | acgcttccagatgtatgaccgtac | 91041 | tacccaagactcatctgatgttccg | AA111263 |
| 5834 | W49956 | attctgattactgcttcagacaca | 48438 | AA028755 | gaaggccttcctgtatgaccggg | 91042 | agactcatctgatgttccgaagaga | AA111263 |
| 5835 | W49956 | tctgattactgcttcagacaccata | 48439 | AA028755 | aaggccttcctgtatgaccgggc | 91043 | actcatctgatgttccgaagagaat | AA111263 |
| 5836 | W49956 | tgattactgcttcagacaccataggg | 48440 | AA028755 | ggcctcctgtatgaccgggctg | 91044 | tcatctgatgttccgaagaattg | AA111263 |
| 5837 | W49956 | tactgcttcagacaccataggagtg | 48441 | AA028755 | gcctcctgtatgaccgggcctga | 91045 | tgtgcacacagagttactaggaagg | AA111263 |
| 5838 | W49956 | ctgcttcagacaccataggagtggc | 48442 | AA028755 | ctcctgtatgaccggcgctggc | 91046 | cctccactgactgcaggaactacaa | AA111263 |
| 5839 | W49956 | ggggtctttcctgcagagaaatt | 48443 | AA028755 | ttccagtggcgggctgggaa | 91047 | tccactgactgcaggaactacaaga | AA111263 |
| 5840 | W49959 | agcagtgcaacatcgttcagaga | 48444 | AA028730 | ccgtgatgacgcgggctggaaaa | 91048 | catactgctggaaatggagctg | AA111386 |
| 5841 | W49959 | aatactgtgccagaaatctagaa | 48445 | AA028730 | ctgtgatagacgggcggctggaaatg | 91049 | atcatgtctggaaatgggaactgg | AA111386 |
| 5842 | W49959 | gaaatggccaccagcatttgcaaac | 48446 | AA028730 | ctgtgtatagacgggcggctggta | 91050 | gtctctggaaatggagctgtgacc | AA111386 |
| 5843 | W49959 | atgggaccacgcattgcaaacatg | 48447 | AA028730 | aatgggctgcatggctgctggta | 91051 | tgtgacttccaccatggggagtgg | AA111386 |
| 5844 | W49959 | ggaccacgcattgcaaacatgcc | 48448 | AA028730 | atggcgtcatggctgctgtat | 91052 | tgggctctggctgatctatcccaaa | AA111386 |
| 5845 | W49959 | cgcattgcaaacatgaccttcaa | 48449 | AA028730 | ctgggcagcagtctactaaccgcg | 91053 | ggctctgctctgatctatcccaaag | AA111386 |
| 5846 | W49959 | tgcaaacatgaccttcaaagcacag | 48450 | AA028730 | tcgtcatgctgctggtatcgtca | 91054 | gctctctgctgatctatcccaaagg | AA111386 |
| 5847 | W49959 | catgaccttcaaagcacagtggatc | 48451 | AA028730 | atgctgcagaccgtgggcacagaca | 91055 | tcgtcagactctgatctatcccaaaggag | AA111386 |
| 5848 | W49959 | gaccttcaaagcacagtggatccct | 48452 | AA028730 | ctgcagaccgtgggcacagaacgg | 91056 | ctgcttggtctatcccaaaaggagc | AA111386 |
| 5849 | W49959 | agcacaggagaccctgctcatca | 48453 | AA028730 | tgcagaccgtgggcacagaacgga | 91057 | aatgttccatggagacataa | AA111386 |

| SEQ ID NO | sequence | DBAxnID | SEQ ID NO | sequence | DBAxnID | SEQ ID NO | sequence | DBAxnID |
|---|---|---|---|---|---|---|---|---|
| 5850 | gtggatccgtctattcaaaagt | W49959 | 48454 | tgggcacgacaacggaccagagaac | AA028730 | 91058 | ccactgactgcaggaactacaagag | AA111386 |
| 5851 | agtgcacacatgcttcagagacac | W49959 | 48455 | ggcacgacaacggaccagagaact | AA028730 | 91059 | actgactgcaggaactacaaggaga | AA111386 |
| 5852 | cacatcgttcagagacacagcaac | W49959 | 48456 | agaacctagtattagtagaag | AA028730 | 91060 | ctgactgcaggaactacaagaggac | AA111386 |
| 5853 | atgcttcagagacacagcaactat | W49959 | 48457 | tagaaggcctcgtgtatgacgc | AA028730 | 91061 | cactagacacatgtctctgaaa | AA111386 |
| 5854 | gagacacagcaactatagcacagcgg | W49959 | 48458 | atttcaccagaactccgctcat | AA028730 | 91062 | ctaggacatcatgtctctggaatg | AA111386 |
| 5855 | acacagcaactatagcacagcgcgg | W49959 | 48459 | agaactccgagctcattgaacatct | AA028730 | 91063 | taggacatcatgtctctggaaatgg | AA111386 |
| 5856 | cagcaactatagcacagcgcggt | W49959 | 48460 | acaacttcattagcacacatgaaagt | AA028730 | 91064 | ggaacatcatgtctctggaaatggag | AA111386 |
| 5857 | ctatagcacgcgcggtgtataaac | W49959 | 48461 | caaagcagtatgcggtcatgcaggggatg | AA028730 | 91065 | gacatcatgtctctggaaatggagc | AA111386 |
| 5858 | tagcacagcgcggtgtataaacacc | W49959 | 48462 | tgtactgcagtagctccgtga | AA028730 | 91066 | tctactacaattcagccactgggaa | AA111386 |
| 5859 | tatcacaaaggtcatcacaggtg | L00654 | 48463 | actgcagtagctctagcctgtacaa | AA028784 | 91067 | ctactacaattcagccactgggaaa | AA111494 |
| 5860 | aaaggtctcatcacaggtgacaatg | L00654 | 48464 | gcagtagctctagcctgtacaaaca | AA028784 | 91068 | atgcacccgattaactacactgga | AA111494 |
| 5861 | gttcctccagcagtcgtcctg | L00654 | 48465 | aacacgcgaagattcacgctcgata | AA028784 | 91069 | gccaccgatttaactacactgatg | AA111494 |
| 5862 | atgctgcttcctgccgggtggcat | L00654 | 48466 | agattcacgctcgataaacccatag | AA028784 | 91070 | ccacgatttaactacactggatt | AA111494 |
| 5863 | catctgagtccaattctctgcc | L00654 | 48467 | acgctcgataaaccatcaggagagc | AA028784 | 91071 | accgatttaactacactcgatgtgg | AA111494 |
| 5864 | caattctgcctccactcaagt | L00654 | 48468 | aaaccatagagagcccatagaggggg | AA028784 | 91072 | ccgatttaactacactggatgtggg | AA111494 |
| 5865 | ttctgcctccactcaagtagctac | L00654 | 48469 | gaggtccctattcatctccatgaa | AA028784 | 91073 | taatttactaccgaagggagtac | AA111494 |
| 5866 | cttccactcaagtagctacactgag | L00654 | 48470 | actcacagctcattgaacactctaac | AA028784 | 91074 | atttttactaccagagagagatgct | AA111494 |
| 5867 | tagtacactgagccaggccgcgctc | L00654 | 48471 | cctatctactcctagaacacctg | AA028784 | 91075 | ttttactacccagaaggagtctctg | AA111494 |
| 5868 | gcgctctcgtatgctcctcaatat | L00654 | 48472 | agctcattgaacatctaacagtcca | AA028784 | 91076 | ggccgcctcgtgaaagttgtatat | AA111494 |
| 5869 | ctctgctatgcctcaatttaaaatgcg | L00654 | 48473 | atctaacagttcaccgcaagcctt | AA028784 | 91077 | cgcccctcgtgaagttgtatatga | AA111494 |
| 5870 | tatgcctcaatataaatgcgttaaag | L00654 | 48474 | taacagttcaccgccaagccttcaa | AA028784 | 91078 | actacaatcgccactgggaatg | AA111494 |
| 5871 | gacaatgttccacatgccgagatg | L00654 | 48475 | acggcaagctttcaaagtcaacag | AA028784 | 91079 | ctacaatgttcagccactggggaatgc | AA111494 |
| 5872 | atgcctcaatataataagcgttaaagc | L00654 | 48476 | tcaagtcaacaggtgtggacgagt | AA028784 | 91080 | ccaaatcagccactggggaaatgccca | AA111494 |
| 5873 | gtccaatgtcgcgagatgcatgc | L00654 | 48477 | attccagctacaacttcattagaca | AA028784 | 91081 | caattcagccactgggaaatgccac | AA111494 |
| 5874 | gacatgcgtgtgtgtggggaatgaag | L00654 | 48478 | gctacaacttcattagacacatgaa | AA028784 | 91082 | attcagccactggggaaatgccaccg | AA111494 |
| 5875 | gtcacctattactggaactgatcc | L00654 | 48479 | ctgtggtcaccaacctccagggca | AA028784 | 91083 | ttcagccactgggaaatgccaccga | AA111494 |
| 5876 | caccactgtgccccaaaggactctct | L00654 | 48480 | actacacatcgcatacggcaacct | AA028784 | 91084 | gaaatgccaccgatttaactacact | AA111494 |
| 5877 | tatgtcccccaaaggactctcgtca | L00654 | 48481 | tagagggtcccacagcgtctctc | AA028784 | 91085 | atgccaccgatttaacctccagatg | AA111494 |
| 5878 | gactctgagtcactcaagatga | L00654 | 48482 | acagcgtctctcggttcctact | AA028784 | 91086 | atgtgcacatggtgacctccagatg | AA111494 |
| 5879 | acactccaggatgacctcgttcctc | L00654 | 48483 | tgttcccgactagaacggcaggt | AA028784 | 91087 | gtgacctccagattgtggagctga | AA111494 |
| 5880 | tacaggcccaagccgtgccaactc | M90388 | 48484 | ccgactgaacggcaaggcgctc | AA028784 | 91088 | ctgtgcccagctgacaggagctg | AA111592 |
| 5881 | ccgtgcaaactctctactagcta | M90388 | 48485 | aagctcacctcgtgttcctgatccat | AA028784 | 91089 | cccagctgacaggagctgaaaatg | AA111592 |
| 5882 | gcaagcctacagaacgtgtcagcc | M90388 | 48486 | tgggccctgtctctcagatt | AA028784 | 91090 | aaacgaatgcatcatcatgggggtga | AA111592 |
| 5883 | ttcagccaaaaatccagctcct | M90388 | 48487 | ctccctagggttctgggaacca | AA028784 | 91091 | accatcatgggtgatctcagtt | AA111592 |
| 5884 | attccagtctcttctgaatttgg | M90388 | 48488 | tctctgggaaccacctaatggtatt | AA028784 | 91092 | atctcagttttagggccatggcga | AA111592 |
| 5885 | ggaacccgccatcagtcgtggaatat | M90388 | 48489 | tggtattatccgtgggcattat | AA028784 | 91093 | actgcctttctcatgggccccat | AA111592 |
| 5886 | tgtaacgcacctgatttataag | M90388 | 48490 | catttatcaatacttagagacta | AA028784 | 91094 | ctttctcatgggcccccattgagtg | AA111592 |
| 5887 | gcacctgatttataagaatatt | M90388 | 48491 | catcgatatcgggccaacctgtgcgt | X66295 | 91095 | tcatgggcccccatgatgtgcctgaa | AA111592 |
| 5888 | aaattgtaccgtcagataaagctac | M90388 | 48492 | atacggccaacctgtgcgtgcacct | X66295 | 91096 | tggggccccatgatgtgcctgaagga | AA111592 |
| 5889 | ttccagcaaactgtatttcatat | M90388 | 48493 | ccaacctgcgtgcactgaacct | X66295 | 91097 | aggagttgtcaccctgacacaga | AA111592 |
| 5890 | ttcctatatttcactgggaactgc | M90388 | 48494 | tgaaacctcaaactgccaggggc | X66295 | 91098 | acctcagattggaagctgaaga | AA111592 |
| 5891 | atatttcactgggaactgccaataa | M90388 | 48495 | tcaacctccaggtggccagctt | X66295 | 91099 | ccctgacacagacattaaggtcac | AA111592 |
| 5892 | ctagctatctgaaccacacagagaa | M90388 | 48496 | ccagctctgcgaccacatggtcaa | X66295 | 91100 | gatattcgtcagatcagaatcca | AA111592 |
| 5893 | atcctgaaaccacagaactacac | M90388 | 48497 | tctgtgaccacatgttcaacacgaa | X66295 | 91101 | attcgtccagatcagatcccaact | AA111592 |
| 5894 | aaaccagagaactccactccc | M90388 | 48498 | tgttcaacagcaagcaggtcagtc | X66295 | 91102 | cagatcaaacttcagccaagctag | AA111592 |
| 5895 | cagagaacctcacatctctaaaca | M90388 | 48499 | tacgtaattcctacagacgaactt | X66295 | 91103 | atcagatcccaacttcagcaagcccag | AA111592 |
| 5896 | catcttctaacacaatttgaggac | M90388 | 48500 | atgatcagtcacagcaagttaa | X66295 | 91104 | agatccaacttcagcaagccgaat | AA111592 |
| 5897 | gtaattctcaccaagccaagcc | M90388 | 48501 | ctataatttctgatgggcgtg | X05475 | 91105 | aacttcagccaaagccagaaattaatgg | AA111592 |
| 5898 | ctcccaccaagcaagctacaga | M90388 | 48502 | ttctctgatgggcagtgcctgg | X05475 | 91106 | ttaatgcatctcgtcgcccagc | AA111592 |
| 5899 | caccaagcaagctacagaagtgt | M90388 | 48503 | gcctgatcagtccgcccaatgtgt | X05475 | 91107 | cccatgcactgcagtcagtcacacagga | AA114552 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 5900 | ctgtacttcattgaactggataa | M13685 | 48504 | gaatggcctgcgaaatccatcaaac | X05475 | 91108 | ctgcagtcgcacgcatgactgtt | AA114552 |
| 5901 | agacaatctaaacattctaggc | M13685 | 48505 | cctcgaaatccatcaacaatata | X05475 | 91109 | ggcattcaggagcacaagaacctg | AA114552 |
| 5902 | gttccatccagtactaaatgcttac | M13685 | 48506 | atcaaacaatatagccttcaggaaa | X05475 | 91110 | cattcacgaggcacaagaacctga | AA114552 |
| 5903 | tgcttaccgtgaccctggctt | M13685 | 48507 | caatatagccttcaggaaacaaagc | X05475 | 91111 | aaactgtctcaagctctacgattc | AA114552 |
| 5904 | ttcagcgtgcactcagttccgtagg | M13685 | 48508 | tatagccttcaggaaacaaagcaaa | X05475 | 91112 | actgtctcaagctctacgattcag | AA114552 |
| 5905 | gtgcactcagttccgtaggattcca | M13685 | 48509 | aagcaaacctggttcacagaagcaag | X05475 | 91113 | tgtctcaagctctacgattcagag | AA114552 |
| 5906 | tcagttccgtaggattccaaagcag | M13685 | 48510 | cccaggacttccaacttagtcatct | X05475 | 91114 | gtctcaagctctacgattcagaga | AA114552 |
| 5907 | aagcagaccgtagctgtctgcttg | M13685 | 48511 | ctgtaaacatcaacccgtatacat | X05475 | 91115 | ctcaagctctacgattcagagaagc | AA114552 |
| 5908 | gaccccctagctgtctttgaatctg | M13685 | 48512 | ctttccaacttagcatcttacctg | X05475 | 91116 | caagctctacgattcagagaagca | AA114552 |
| 5909 | tagctgtctttgaatctgcatgta | M13685 | 48513 | acatcaccccgataacatcataga | X05475 | 91117 | agctctacgattcagagaagccatt | AA114552 |
| 5910 | gcatgtacttcacgttttctatat | M13685 | 48514 | cccgtgataacatcatagatgatgt | X05475 | 91118 | ccaattagcctgtaaacgcaatgt | AA114552 |
| 5911 | gttgctatcagacgtgacattaaat | M13685 | 48515 | tggcaaacctccagtctctcatcag | X05475 | 91119 | gcagtcagccacggcatgactgttaa | AA114552 |
| 5912 | tctaaacattcttaggctgcaga | M13685 | 48516 | cagctccatcagtcaaagaatgtc | X05475 | 91120 | agtcagcacggcatgactgttaact | AA114552 |
| 5913 | gaagtaggccattccaaagtggg | M13685 | 48517 | tatataatctcattccttgaaaat | X05475 | 91121 | taagcaagttctgtcaaggcccat | AA114552 |
| 5914 | aatctgctacatgattgttaaatca | M13685 | 48518 | aaagtgctaccacatgctcaaatgg | X05475 | 91122 | tcaaggccatttcgaagttggcca | AA114552 |
| 5915 | acccccagcagacataaactgcgata | M13685 | 48519 | gctaccacgtctaaatggagtac | X05475 | 91123 | ggccatttcgaagttgccaatg | AA114552 |
| 5916 | tgcgataccctcagttgcactgt | M13685 | 48520 | caggggtcatcgctcagtgcaggt | X05475 | 91124 | gggcgcagcattcacgaggcaca | AA114552 |
| 5917 | agctgcactgtggattctgtat | M13685 | 48521 | tgcatcgtctgcagagttgacag | X05475 | 91125 | cgacggcattcacgaggcacaagaa | AA114552 |
| 5918 | atataaacataactcaagcttat | M13685 | 48522 | aaatccttaccgtgataagaacag | X05475 | 91126 | acggcattcacgaggcacaagaacc | AA114552 |
| 5919 | ctggccgttccatccagtactaaat | M13685 | 48523 | gctgtatcgttcactcagggacc | X05475 | 91127 | caaagctacaccttcttcttggact | AA114552 |
| 5920 | ggtccgttccagctgtcttgctg | M13685 | 48524 | atactggggacctggctgtacata | X05475 | 91128 | tacaccttcttggactgactta | AA114552 |
| 5921 | gttcagccggtctgtctgaccctg | M13685 | 48525 | tagctacactgttggatacaacct | X05475 | 91129 | tctggtacagttgtaatgatagg | AA114576 |
| 5922 | tcccccaattcgcagcacccaggga | M13685 | 48526 | tgtgataccaacctggggttgctga | X05475 | 91130 | tgcagacttccagttcttctcg | AA114576 |
| 5923 | atccgcagaccaagggatctttc | M11900 | 48527 | ttttgctcaaactatctcatct | X05475 | 91131 | agactttccagttcttctcg | AA114576 |
| 5924 | cagacacagggatcttccagagt | M11900 | 48528 | tctcaaactatctcatct | X05475 | 91132 | ctttcctctgttcttctg | AA114576 |
| 5925 | atctttccagagtttgggcctctg | M11900 | 48529 | actactacatgttcttctca | X05475 | 91133 | gatgctcaaatctcttctcgc | AA114576 |
| 5926 | tcctcagttaaccagaagcctcga | M11900 | 48530 | atgtctttcttagatgctcaag | X05475 | 91134 | atctcttctctcgagctctgtt | AA114576 |
| 5927 | tcagtaaaccagaagcctctgaaag | M11900 | 48531 | ttttctagatgctctaagctata | X05475 | 91135 | cctctctcgagtctgttctaat | AA114576 |
| 5928 | aaccagaagcctctgaagacacaggga | M11900 | 48532 | gacatattcagacgtatgacacgg | U49112 | 91136 | tctctcagcgattcttaatcaa | AA114576 |
| 5929 | tccctcctgtttctcaactgcacg | M11900 | 48533 | ttcagacgtatgacacgggatcagg | U49112 | 91137 | ctgcagtcgcagttcttaatcaagca | AA114576 |
| 5930 | ttcaactgtcacgcaggggtcagaa | M11900 | 48534 | cgctatgacacggatcaggatggct | U49112 | 91138 | cagctggtctctaatcaagcagct | AA114576 |
| 5931 | aactgtcacgcaggggtcagaactg | M11900 | 48535 | gagcaatatctccatggtctca | U49112 | 91139 | tctctctgactgactaatccac | AA114576 |
| 5932 | gagctacgccaggggtcagagtgt | M11900 | 48536 | tatctccatggtctcagcattg | U49112 | 91140 | tctggtctatacaagcagctgat | AA114576 |
| 5933 | ctatgctcaagaggcaggtgatgaa | M11900 | 48537 | tccatggtcttcagcattgtataac | U49112 | 91141 | gactgattaatccactccttcaat | AA114576 |
| 5934 | tgataaactttcagagcctagaccag | M11900 | 48538 | aacagacaagcacgcatgcaaaaga | U49112 | 91142 | tgactaattcaacctctccaatggt | AA114576 |
| 5935 | tgaactttcagagcctctagaccaga | M11900 | 48539 | gatgccaaatcctacctgaggtgata | U49112 | 91143 | cttaatcaacctcttcaatggtggg | AA114576 |
| 5936 | tcagagcctagaccagacaccaaat | M11900 | 48540 | aggctgcagctcattgaaggtgca | U49112 | 91144 | caggagtcgcacctgcactctggta | AA114576 |
| 5937 | gagcctagaccagacaccaaatcag | M11900 | 48541 | tgaaggtcagctccagccccagtca | AA028875 | 91145 | gcatgccacctgacttcgtactaag | AA114576 |
| 5938 | cctagaccagacaccaaatcagaaa | M11900 | 48542 | tggtcagccctgtaggaagaggtt | AA028875 | 91146 | tgccactgcactctggtacagtt | AA114576 |
| 5939 | aggtcccaattcgagatccaggaccacag | M11900 | 48543 | gacctggaaacaccctgtgatg | AA028875 | 91147 | ctgactctgtacagttggtaat | AA114576 |
| 5940 | gcagttaccaagagccctggca | AA117812 | 48544 | tgtggaaacaccctgtgatggcct | AA028875 | 91148 | gaccttccggttcctggtcatgctg | AA114576 |
| 5941 | agcttaccaagagcctcgcaca | AA117812 | 48545 | ggaaacaccctgtgatgcctgg | AA028875 | 91149 | cctggtcatgctgagatgaccct | V01527 |
| 5942 | gccctctgcacagatggaagaaga | AA117812 | 48546 | accctgtgatggcctggacag | AA028875 | 91150 | cactccgactcagtctagcatgg | V01527 |
| 5943 | ccctctgcacagatggaagaagaa | AA117812 | 48547 | gactggcctggggacaggccctgc | AA028875 | 91151 | gactcagatgctagcatgtactat | V01527 |
| 5944 | tcagagctccagatggaagaaga | AA117812 | 48548 | tgatggctcagcccgaggcagcagc | AA028875 | 91152 | cctcactctgtgatctgagtcc | V01527 |
| 5945 | gagccctagactgacagaccacaccagca | AA117812 | 48549 | acacagcccctgcgaaggcagccagca | AA028875 | 91153 | ctctgtgatctgagtccccagt | V01527 |
| 5946 | agagctccatgagccgcatgageagcaa | AA117812 | 48550 | cgaaggcagccagcactgaggagcag | AA028875 | 91154 | gagctcccagatctcgtctag | V01527 |
| 5947 | agctcagcggccatgagccatt | AA117812 | 48551 | aaggcagccagcactgaggagcagge | AA028875 | 91155 | tctgtctagctctgctctg | V01527 |
| 5948 | cagtgcagccatgagcaaatgaaa | AA117812 | 48552 | aaggtgtcagcccccatagatgat | AA028875 | 91156 | tctagctcgtctctggatt | V01527 |
| 5949 | caggggcgccatgagcaaatgaaaa | AA117812 | 48553 | aggtgtcagcccatagatgatc | AA028875 | 91157 | gggattccagagactccatctg | V01527 |

TABLE 1-continued

| SEQ ID NO | DBAxnID | sequence | SEQ ID NO | DBAxnID | sequence | SEQ ID NO | DBAxnID | sequence |
|---|---|---|---|---|---|---|---|---|
| 5950 | AA117812 | agcgcggccatgagcaaatgaaaaa | 48554 | AA028875 | gtgtcagcccccatagatatgatcgg | 91158 | V01527 | tccagagactccatctgtgtacagc |
| 5951 | AA117812 | tttagagcacgcacaaagaatta | 48555 | AA028875 | tgtcagcccccatagatatgatcggt | 91159 | V01527 | gactccatctgtgtacagccgcacc |
| 5952 | AA117812 | gcttaccaagagccctctggcacag | 48556 | AA028875 | gtcagcccccatagatatgatcggtg | 91160 | V01527 | cctgaaggcccccatcactgtggag |
| 5953 | AA117812 | cttaccagagccctctggcacaga | 48557 | AA028875 | tcagcccccatagatatgatcggtgc | 91161 | V01527 | ggcacagtctgatctgccctggagc |
| 5954 | AA117812 | taccaagagccctctggcacagatg | 48558 | AA028875 | agcccccatagatatgatcggtgcca | 91162 | V01527 | gtctgcctggagcaagatgtgtggc |
| 5955 | AA117812 | accaagagccctctggcacagatgg | 48559 | AA028875 | atatgatcggtgccaaacgccgtgg | 91163 | V01527 | ggtgatctcctcgggcttggcctt |
| 5956 | AA117812 | ccaagagccctctggcacagatga | 48560 | X06340 | ctgcgtgggcacgtgcatctggacc | 91164 | V01527 | agggctcctgcagtgactcagagtg |
| 5957 | AA117812 | aagagccctctggcacagatggaag | 48561 | X06340 | acgtgcatctggaccacagaaggctg | 91165 | V01527 | gtttgactcagttgactgctcag |
| 5958 | AA117812 | agagccctctggcacagatggaaga | 48562 | X06340 | ttggaatggctccctccttagaa | 91166 | V01527 | aagaccttgaatgtctgctccgaa |
| 5959 | AA117812 | gagccctctggcacagatggaagaa | 48563 | X06340 | gaatggctccctcctttagaaga | 91167 | V01527 | ctccgaatctctgactgccagtcca |
| 5960 | AA117812 | gaggccacagcagaggaccccctca | 48564 | X06340 | tggctccctccttagaaagagc | 91168 | AA114591 | gaaaccacactatgatcatctgggc |
| 5961 |  | cacagcagagaccccctcaaggccc | 48565 | X06340 | gagaagctacaggcactggccct | 91169 | AA114591 | ctatgatctcacagcaatacggtc |
| 5962 |  | gccacagcagaccccactcaagg | 48566 | X06340 | aagcctacagggcactgcctggt | 91170 | AA114591 | catcctcgagatgcggtcacata |
| 5963 |  | cccacagaggccacagccgcgcg | 48567 | X06340 | cctacagggcactgcctggtaca | 91171 | AA114591 | agagtaccggttccgctttggagg |
| 5964 |  | gccacagccgagccccctcaagg | 48568 | X06340 | cactgcctggtacatttctga | 91172 | AA114591 | ccgcttgtgaggcgaggtccatc |
| 5965 |  | caacaggcccacagccgagaccccac | 48569 | X06340 | tggtacatttctgacatttcg | 91173 | AA114591 | ctttggtgggaggtctccattt |
| 5966 |  | gccacagccgagccactcaagg | 48570 | X06340 | ctgacatttcttgaggcctccacat | 91174 | AA114591 | cttccccaatggctcctgttaca |
| 5967 |  | agccgcagccactcaaggcccaca | 48571 | X06340 | acatttctgaggcctcacatggg | 91175 | AA114591 | caatggctctcgttcactgccc |
| 5968 |  | gccacaccccaacggaggccccaca | 48572 | X06340 | catctgaccagaaggctggactgt | 91176 | AA114591 | ggtggacaaacccgagccgacctct |
| 5969 |  | caggaggccacacaacactctc | 48573 | X06340 | ggactgtgagccttttccgatgaag | 91177 | AA114591 | ctgagcgacctctggctccacagtg |
| 5970 |  | gccacagcaaacacctctctctggc | 48574 | X06340 | ctgtgagcctttcgatgaaggat | 91178 | AA114591 | ctctggctccacagtgccacata |
| 5971 |  | cacctcctctggctgaaaccccca | 48575 | X06340 | gactctgacgacaacatgatcccca | 91179 | AA114591 | ctggctccacagtggtccacatagg |
| 5972 |  | gaggccacagccgagcccgagacccctca | 48576 | X06340 | ctctcagccgggaaatgtcaaagg | 91180 | AA114591 | ggaatccaacagagagtcatgggcaac |
| 5973 |  | cacccaaggtccacgccgagacc | 48577 | X06340 | ctctgccctctcagggcttgaactt | 91181 | AA114591 | tggctccacagtggctccacatagga |
| 5974 |  | caccccccaacagcccgagaccccgagca | 48578 | X06340 | agggcttgaactgtctccgatgcc | 91182 | AA114591 | atcccacagtcatggccaacatc |
| 5975 |  | caacaggagcccacagccagcgata | 48579 | X06340 | gatgccctggggtgactttcccact | 91183 | AA114591 | agtcatgggccaacatccaggtggta |
| 5976 |  | gaggccacagcagccgatacccta | 48580 | X06340 | ttaccactgtccagggatcgccga | 91184 | AA114591 | catgggcaacatccagttgtgtagaa |
| 5977 |  | cacagcaggagataccctcaaggcc | 48581 | X06340 | accactgtccaaggatcgccgatg | 91185 | AA114591 | caacatccagtggtgaagagacg |
| 5978 |  | gaggcccaagccgagccccctca | 48582 | X06340 | cagttcctgatacagattccgcag | 91186 | AA114591 | gacgcaggcatcctcgagagtac |
| 5979 |  | caacaggcccacagccgagaccccac | 48583 | X06340 | gttcctgatacagattcggcatggc | 91187 | AA114591 | gcaggtccatcctcgagagtacggc |
| 5980 |  | cacagcaaacacctctctggctgg | 48584 | X06340 | tcctgatacagattcggcatggcta | 91188 | AA114591 | ggtcatcctcgagagtacggctc |
| 5981 |  | acagcaaacacctctctggctga | 48585 | AA030066 | gatacagattcggcatggctaagga | 91189 | AA114540 | acgcaaaatcggttacagcacatga |
| 5982 |  | cctctctggctgaaaccccacaag | 48586 | AA030066 | tacagattcggcatggctaaggacg | 91190 | AA114540 | ccaaaatcgttacagccacatgacag |
| 5983 |  | ctcctctggctggaaaccccacaa | 48587 | AA030066 | cagattcggcatggctaaggacgat | 91191 | AA114540 | cggttattcccaatgtcagttcag |
| 5984 |  | tcctctggctgaaaccccacaaggc | 48588 | AA030066 | gttttaactgctgtggctctgga | 91192 | AA114540 | ttattccaatgtgtcagttcagatc |
| 5985 |  | cacaaggcagagaccccaggacctca | 48589 | AA030066 | ttaagtgagcactcctgcaacgag | 91193 | AA114540 | ttcccaatttgtcagttcagatccaa |
| 5986 |  | acaaggcagagccccaggacctca | 48590 | AA030066 | aagtgagcactcctgcaacgagta | 91194 | AA114540 | attgtcagttcagatccaaaaacagc |
| 5987 |  | ggccccacagcccgagccccctctgg | 48591 | AA030066 | gcactcctgcaacgagtagaactc | 91195 | AA114540 | tcagatccaaaaacgacgtcttaa |
| 5988 |  | gccccaagcaaacacctctctgg | 48592 | AA030066 | cactgtccaagggatccgcatgat | 91196 | AA114540 | cagcacgcttaaacatttactgc |
| 5989 |  | acaaggcagaaccccaggacctcag | 48593 | AA030066 | ctgtccaagggatccgcatgatta | 91197 | AA114540 | cattttactgctaaccagattgatga |
| 5990 |  | cacgcaaaacacctctctggctgg | 48594 | AA030066 | acgtactcagagacatagtaggctg | 91198 | AA114540 | ttactgctaaccagattgatgaaat |
| 5991 |  | acacgcaaacacctctctggctga | 48595 | AA030066 | tactcagactagtgaaggcgtt | 91199 | AA114540 | atgtcgacaagttgggatta |
| 5992 |  | cacctctctggctgaaaccccaca | 48596 | AA030066 | agtaattcagctacagggtgaccag | 91200 | AA114540 | tccagcgacaagtttgggattatct |
| 5993 |  | cctctctggctgaaaccccacaag | 48597 | AA030066 | taattcagctacagggtgaccagcg | 91201 | AA114540 | aaatcggttacgccatgacagtgt |
| 5994 |  | ctcctctggctgaaaccccacaag | 48598 | AA030066 | attcagctacagggtgaccagcga | 91202 | AA114540 | tcggttacagccatgacagtctc |
| 5995 |  | tcctctggctgaaaccccacaaggc | 48599 | AA030066 | gccagttcctgatacagattcggaa | 91203 | AA114540 | gttacgccatgacagtgctcggt |
| 5996 |  | aggcccaccacgcccgagcccgagaccccag | 48600 | AA030066 | cagcctggatctggaaaagagag | 91204 | AA114540 | acagccatgacagtgtctcggtat |
| 5997 |  | cgaaagcagaccccgagccgagactca | 48601 | X73985 | agggtcctggcctgatagacag | 91205 | AA114540 | atgacagtgtctcggttattcc |
| 5998 | W50027 | ggaaccatgacgcccgagggaagg | 48602 | X73985 | atgagttccctgctgtatgatta | 91206 | AA114540 | atgacagtgtctcggttatccca |
| 5999 | W50027 | gtgcaacgggcactggttgttg | 48603 | X73985 | agtccttcctgctgtatgatttggc | 91207 | AA114540 | acagtgtctcggttattccaattg |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 6000 | cagcttccagcttgttggaaga | W50027 | 48604 | aggcttcgagtccacagagtgga | X73985 | 91208 | tctcggtattccaattgtcagtt | AA114540 |
| 6001 | aagacctattatcagatcaaccac | W50027 | 48605 | ctctggagtcccacagagtggactc | X73985 | 91209 | tcttgaactctgagacaaccctt | AA114638 |
| 6002 | acctattatcagatcaaccaccaa | W50027 | 48606 | tggactcctcctctgctgcgca | X73985 | 91210 | ggactctgcagacaacccttgacg | AA114638 |
| 6003 | caagatctcatggttggcgatga | W50027 | 48607 | cggactccagttctgccaccag | X73985 | 91211 | agatggctccgaatggcttaca | AA114638 |
| 6004 | ggatccatggttggcgatgaggga | W50027 | 48608 | acttccagttctgccaccagctt | X73985 | 91212 | gatggctccgaatggcttacagc | AA114638 |
| 6005 | tctcatggttggcgatgaggcaagt | W50027 | 48609 | tctctgccaccagctgcttaatga | X73985 | 91213 | tggctcctgcaatggcttacagcat | AA114638 |
| 6006 | aagtgagctgcgctccatgtggag | W50027 | 48610 | tgccccaccagctgcttaatgatct | X73985 | 91214 | tcctgcaatggcttacagcatta | AA114638 |
| 6007 | tgagctggctccatgtggaggtg | W50027 | 48611 | ccaccagctgcttaatgatctagc | X73985 | 91215 | tcctgcaatggcttacagcattag | AA114638 |
| 6008 | gggctccatgtggaggaactac | W50027 | 48612 | gtccttaggcctgatagacagttg | X73985 | 91216 | tggctacagcattacgccgacta | AA114638 |
| 6009 | gaactacccgatgagaacggcatc | W50027 | 48613 | acagtgtgcctgcgtggtcacg | X73985 | 91217 | gcttacagcattacgccgcactagg | AA114638 |
| 6010 | caaggcactggtttgtgaagtgt | W50027 | 48614 | gtgtgcctgggtcacggt | X73985 | 91218 | ttacagcattacgccgcactaggc | AA114638 |
| 6011 | atatgcaggctcaacttccagaa | W50027 | 48615 | aagcttctgctctcgcgcgat | X73985 | 91219 | gccgcagcctgcgagacagtgtgg | AA114638 |
| 6012 | tgcaggctctaacttccagaacac | W50027 | 48616 | ctgtcgtctccgcgatgcatga | X73985 | 91220 | tgctgcctagtcaacctaacgcg | AA114638 |
| 6013 | ctctaacttccagaacagcttc | W50027 | 48617 | tctccgctgcgatgcatgagttcct | X73985 | 91221 | acctcgagacaaccctgacgag | AA114638 |
| 6014 | taacttccagaacacagcttcca | W50027 | 48618 | ccgctgcgatgcatgagttcctcg | X73985 | 91222 | tctgcagacaaccctgacgggc | AA114638 |
| 6015 | cttccagaacacagcttccagct | W50027 | 48619 | tgcatgagttcctgcctgtatgat | X73985 | 91223 | tgcagacaaccctgacgggccgg | AA114638 |
| 6016 | agaacacagcttccagcttggtt | W50027 | 48620 | cagacactcagtgatacccttgtt | X73985 | 91224 | aagctgcagacagcctgcagactt | AA114638 |
| 6017 | acacagcttccacgcttggtga | W50027 | 48621 | ctcagttgataccaccccttcatcca | X63615 | 91225 | atgagcctggcagaccctggcctg | AA114638 |
| 6018 | tacaggcctctcaattgaggga | W50027 | 48622 | aaagctcgctgtggataattg | X63615 | 91226 | tgccagttcaccaggatggctcctg | AA114638 |
| 6019 | aataglaccaggcctagagtgt | W78418 | 48623 | gacaattctttgcatgaccctca | X63615 | 91227 | ccagttcaccaggagtgctcctga | AA114638 |
| 6020 | agagcacacactgttcagcttgt | W78418 | 48624 | aattctttgcatgaccctctaa | X63615 | 91228 | agttcaccaggatggctcctgcaat | AA114638 |
| 6021 | gagcacacactgttcagctgtatg | W78418 | 48625 | tttgcatgaccctaaagacgag | X63615 | 91229 | actggttcatgcactgtcatgt | AA114648 |
| 6022 | gcacacactgttcagctgtatggct | W78418 | 48626 | tgacctctaaagagcaggacactc | X63615 | 91230 | ggttccatgcactgcatggttgc | AA114648 |
| 6023 | cacacactgttcagctgtatggct | W78418 | 48627 | gacactcctgctctaacgctagg | X63615 | 91231 | tgggcacaccctgtacctgctgcg | AA114648 |
| 6024 | cacactgttcagctgtatggcttg | W78418 | 48628 | ctaactgctaggtgttgcagttg | X63615 | 91232 | tgctgccacaccgccacagaaggaa | AA114648 |
| 6025 | acactgtcagctgtatggcttg | W78418 | 48629 | actgctgcagtactggtgccctc | X63615 | 91233 | gcaacccgccacagaagaacactc | AA114648 |
| 6026 | actgttcagctgtatggctgcc | W78418 | 48630 | ttctgagcctgaggtgtacaa | X63615 | 91234 | aaccactcagagaaggcagcagga | AA114648 |
| 6027 | ctgtcagctgtatggctgcc | W78418 | 48631 | ttttgttgctgcgggaactgca | X63615 | 91235 | agaaggccagcaggcagcaggga | AA114648 |
| 6028 | agctgtatggctttgccccgggtg | W78418 | 48632 | ggatacaccctttcatccaacgt | X63615 | 91236 | aggacaggacaagcttctgcctc | AA114648 |
| 6029 | ctgacccgccatgttggttgat | W78418 | 48633 | ctttcatccacactgtcccaggac | X63615 | 91237 | aggacaaggaacaagcttctggcctc | AA114648 |
| 6030 | tagtaccaggcctatgagtggt | W78418 | 48634 | gtaaacactgccaggctccactg | X63615 | 91238 | cccctgatcatccacctggagaa | AA114648 |
| 6031 | agtaccaggcctatgagtgtggc | W78418 | 48635 | caggctccactgagtgcccaagg | X63615 | 91239 | catccacctggagaacagctggag | AA114648 |
| 6032 | taccaggcctagagtgtggcct | W78418 | 48636 | cccaaggccatgaaacagtggcag | X63615 | 91240 | ccacctggagaacagctggagccc | AA114648 |
| 6033 | accaggcctagagtgtggtggcctg | W78418 | 48637 | ccttgtatctccacaagctgcct | X63615 | 91241 | atgcactgcatggtgcctgt | AA114648 |
| 6034 | ctatgagtgtggcctgaggcaa | W78418 | 48638 | tgttatctccacaagctgccgtc | X63615 | 91242 | cactgcatggtgcctgttc | AA114648 |
| 6035 | tatgagtgtggcctgaggcag | W78418 | 48639 | ctccacaaagtgcctgtcggat | AA030144 | 91243 | ttctgccacaggaagtggtaca | AA114648 |
| 6036 | gcaaggcacacactgttcagctgt | W78418 | 48640 | cataacaacagttatcttccacca | AA030144 | 91244 | cttgccacaggaagtgtacagta | AA114648 |
| 6037 | caagacacactgttcagctgta | W78418 | 48641 | ttctccaccaagacaaagacaag | AA030144 | 91245 | tcctggcttggctacgttcctat | AA114615 |
| 6038 | ctttccactgagccacaccta | L27439 | 48642 | tggactccagtgccacactcca | AA030144 | 91246 | tggctaccgttcctatccgtgct | AA114615 |
| 6039 | actgagccacaccctcactgaaa | L27439 | 48643 | tgccacactccacacttaaggcct | AA030144 | 91247 | ccgttcctatcctgtcgtggcac | AA114615 |
| 6040 | agttcatgtgttctcatggg | L27439 | 48644 | cacacttcaacctgaatggcctct | AA030144 | 91248 | tgttgccagcaccctgtacct | AA114615 |
| 6041 | aagttacatgtctatcttgtaat | L27439 | 48645 | aacctgaatggctcttacctgaggg | AA030144 | 91249 | gcttacctgctccgaagctacg | AA114615 |
| 6042 | ttacatgtctatcttgtaatgaa | L27439 | 48646 | ctgaatggctctctacctgaggggtc | AA030144 | 91250 | tactctgctccgaagctacgga | AA114615 |
| 6043 | cargtctatcttgtaatgaaga | L27439 | 48647 | aggggtcccatataggctatggcga | AA030144 | 91251 | gatcctctgatcgaaaatgct | AA114615 |
| 6044 | ttgatcgtttcagggtgcatcgc | L27439 | 48648 | ggtcccataaagtagctagcgaatg | AA030144 | 91252 | ctccctgattcgaaaatatgctgt | AA114615 |
| 6045 | atcgtttcagggtgcatcagccgc | L27439 | 48649 | gggtacaactacgtcgcaaggtt | AA030144 | 91253 | cattacaataaggtctccagacaat | AA114615 |
| 6046 | gtgatcagccgctctgctgccatt | L27439 | 48650 | tacaactacgctgcaaggttctg | AA030144 | 91254 | aaggtctccagacaatgcagacaca | AA114615 |
| 6047 | catcagccgcttcgtcattga | L27439 | 48651 | tacagctgcaaggtttctgagatga | AA030144 | 91255 | gtctcagacaatgcagacacattc | AA114615 |
| 6048 | agatatgtcatcacatgaaacat | L27439 | 48652 | accaagccaagaccaatgacagga | AA030144 | 91256 | cacactgcactgattgccgca | AA114615 |
| 6049 | tgtcatcacatgaaacataaa | L27439 | 48653 | aatgcagtactccagctgtg | AA030144 | 91257 | cgcactgtattcgcgcaacaatc | AA114615 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 6050 | tgagccaacacttcactgaaatat | L27439 | 48654 | gacggcagtacttccagctgtgcca | AA030144 | 91258 | agtattcgccgcacaaatccagaga | AA114615 |
| 6051 | gccaacacttcactgaaatatga | L27439 | 48655 | agtacttccagctgtgccatgggtt | AA030144 | 91259 | attcgccgcacaaatccagagaaag | AA114615 |
| 6052 | agattttccaaggagcagcacatg | L27439 | 48656 | acttccagctgtgccatgggttacc | AA030144 | 91260 | gtggcctacttggaatccatatca | AA114615 |
| 6053 | tgttgtctcaatcagttctatca | L27439 | 48657 | tccagctgccatggttaccatg | AA030144 | 91261 | tctgctctcgaagctacgcgcactt | AA114615 |
| 6054 | agatcactcaacctaagctgctgag | L27439 | 48658 | tgtgccatggttaccatggagcct | AA030144 | 91262 | cgaagtacggcacttaccgctgcg | AA114615 |
| 6055 | aacctaagctgctgagcacaaa | L27439 | 48659 | atgggttaccatggagcctgtgt | AA030144 | 91263 | agctacggcacttaccgctgcgacc | AA114615 |
| 6056 | agctgctgagcacacaaggtcag | L27439 | 48660 | tttctgaagctcggggcgcatcac | AA030144 | 91264 | gaccgtgaactagccatggctgtgc | AA114615 |
| 6057 | tgggcgccatccttaatggtcgga | L27439 | 48661 | catccacaggcctgcagaagctg | AA030144 | 91265 | ctagccatggctgtgcaacctcacc | AA114615 |
| 6058 | catactgagatggtccttgagatga | L27439 | 48662 | gtcaacctgattgtcagaagacgc | X51971 | 91266 | gccatggctgtgcaacctcaccagg | AA114615 |
| 6059 | agcatcgagcaccgaacaactcaga | L27439 | 48663 | cagaagacgcctatccacgttcgga | X51971 | 91267 | atggctgtgcaacctcaccaggatc | AA114615 |
| 6060 | gcttcgctagaaactccagaact | M38314 | 48664 | ccggccagtatccacgttccggaca | X51971 | 91268 | caacctcaccaggatcctccctgatt | AA114615 |
| 6061 | gctagaaaactccagaactccagg | M38314 | 48665 | agccagtccacgttccggacac | X51971 | 91269 | ttgctctgataattaccctcta | AA114666 |
| 6062 | cagaaattcaggccaagccctcca | M38314 | 48666 | cagtatccacgttccggacactct | X51971 | 91270 | tgtctgtcgataattaccctcta | AA114666 |
| 6063 | accttaagctgggccaggaggaag | M38314 | 48667 | ctatccacgttccggacactctgt | X51971 | 91271 | attaccctctatagctgatgtcaac | AA114666 |
| 6064 | gatactgttccgagctcgattctt | M38314 | 48668 | tccaagttccgacactcttgtct | X51971 | 91272 | taccctctatagctgatgtcaacta | AA114666 |
| 6065 | ctggctttccaggcctctgtga | M38314 | 48669 | aggtcttaatctcaggatgaagtct | X51971 | 91273 | accctctatagctgatgtcaactaa | AA114666 |
| 6066 | ggagagctaccactctactatatct | M38314 | 48670 | tcttaatctcaggatgaagtcgta | X51971 | 91274 | ccctctatagctgatgtcaactaaa | AA114666 |
| 6067 | ctaccactctactatatctagcatc | M38314 | 48671 | tttccagttgccagggccaccgac | X51971 | 91275 | ctctatagctgatgtcaactaaag | AA114666 |
| 6068 | tagcatccacaggtcgtctagaaac | M38314 | 48672 | acacaacaggtgccatgggaccct | X51971 | 91276 | actaaaagtatcgtcgagcatg | AA114666 |
| 6069 | tgcccagaaaccgtgggaagtcgt | M38314 | 48673 | acacaggtgccatgggaccccttg | X51971 | 91277 | aaagtatcgtctgagcatgccac | AA114666 |
| 6070 | accatgctaccctttccatccggat | M38314 | 48674 | ctgcctgccggattactgaa | X51971 | 91278 | tcgacatgccacgggcaactca | AA114666 |
| 6071 | gctaccttttcatcgctccactg | M38314 | 48675 | ccgccactctgagtcagtcaccgta | X51971 | 91279 | ttcaccaaaataactagcaccatg | AA114666 |
| 6072 | tttccatcgctccactggccacg | M38314 | 48676 | ccacttctgagtcagtcaccgta | X51971 | 91280 | tcaccaaaataactagcaccatga | AA114666 |
| 6073 | atggctccactgcatcgtgtgt | M38314 | 48677 | cttgctgagtcagtcaccctgattg | X51971 | 91281 | gtctcgataattaccctctata | AA114666 |
| 6074 | tatgactaccagggctcctgacgg | M38314 | 48678 | gagtcagtcaccgatggtcagaa | X51971 | 91282 | ctcgcgataattaccctctatagc | AA114666 |
| 6075 | cggctccgacggcctataagccag | M38314 | 48679 | tcagtcacctgattgtcagaaga | X51971 | 91283 | tcgtcgataattaccctctatagt | AA114666 |
| 6076 | agcatcccgtagtctgaggcttcg | M38314 | 48680 | gctgcagcctaatggtgagagagatg | D10576 | 91284 | tcgataattaccctctatagctgat | AA114666 |
| 6077 | cctagtctgaggcttctgctaga | M38314 | 48681 | gggagatgacccctcaagcagttcctt | D10576 | 91285 | cgataattaccctctatagctgatg | AA114666 |
| 6078 | catggtgcccacattggcttccaag | W50004 | 48682 | ttttctcatgccagctgctaagctc | D10576 | 91286 | gataattaccctctatagctgatgt | AA114666 |
| 6079 | tggtgcccacattggcttcaaggg | W50004 | 48683 | cttcatgccagctgctaagctcaag | D10576 | 91287 | taattaccctctatagctgatgca | AA114666 |
| 6080 | acctgggccaaggtcagaagagc | W50004 | 48684 | catgccagctgctaagctcaaggaa | D10576 | 91288 | aattaccctctatagctgatgtcaa | AA114666 |
| 6081 | ctgggccaaggtctcagaagagctg | W50004 | 48685 | ccagctgctaagctcaaggaagaga | D10576 | 91289 | ggctacacacacctttctgcaggag | AA114781 |
| 6082 | gtatgctggccaacacaaggccagcca | W50004 | 48686 | ccgcatgcggggcactggtgctt | D10576 | 91290 | ctacacacacttttctgcaggagag | AA114781 |
| 6083 | atgctggccaacacaaggagcagccatt | W50004 | 48687 | ccatgtcgggcactggctggctgag | D10576 | 91291 | agaatccagactcaacagtatggtga | AA114781 |
| 6084 | tgagcaacaccagagcactgctg | W50004 | 48688 | ggtgctgagctgtgctcaacgat | D10576 | 91292 | aatccagactcaacagtatggtgaac | AA114781 |
| 6085 | agcaacaccagagccattgctgta | W50004 | 48689 | gcttgagctgctgcaacgatgaa | D10576 | 91293 | cagactcaacagtatggtgaacttat | AA114781 |
| 6086 | caaacacagagccatgctagg | W50004 | 48690 | tgagctgtgctgcaacgatgaaagc | D10576 | 91294 | ggaccaaacaatggctgccaatgct | AA114781 |
| 6087 | acaacacgagccatgctaggct | W50004 | 48691 | tctcaccgtcgttgtacctgtt | D10576 | 91295 | accaaacaatggctgccaatgctca | AA114781 |
| 6088 | agccattgctgtaggctgggctc | W50004 | 48692 | gatgaccccaagcagttccttgat | D10576 | 91296 | caaacaatggctgccaatgctcaga | AA114781 |
| 6089 | acatggcctagaaggatatg | W50004 | 48693 | gaccctcaagcagttccttgatacc | D10576 | 91297 | atggctgccaatgctcagaagaata | AA114781 |
| 6090 | gtgccccacattggctcagggtt | W50004 | 48694 | cctcaagcagttccttgattactt | D10576 | 91298 | atggctgccaatgctcagaagaatataa | AA114781 |
| 6091 | ggccattaaccaccagatcccacc | W50004 | 48695 | caagcagttccttgattacttag | D10576 | 91299 | ctgcaagctcagaagaataaatt | AA114781 |
| 6092 | catttaattaccagatcccacctg | W50004 | 48696 | attggagatcaccatgtcgcccaag | D10576 | 91300 | caagaaatcaagaaccttttcaag | AA114781 |
| 6093 | ttaattaccagatcccacctgt | W50004 | 48697 | gggatcaccatgtcgtcccagggc | D10576 | 91301 | acacaccttctgcaggagagct | AA114781 |
| 6094 | atgcccactggtaccactgg | W50004 | 48698 | gatcaccatgtcgtcccagggtg | D10576 | 91302 | acaccttctgcaggagagagctc | AA114781 |
| 6095 | catccacctggtaccactggtg | W50004 | 48699 | ttcttttctcatgccagctgctaag | D10576 | 91303 | acactttctgcaggagagctctt | AA114781 |
| 6096 | cacctggtgggaacctggccaagg | W50004 | 48700 | gcacaccacagttctggaattc | D10576 | 91304 | acctttctgcaggagagctcttg | AA114781 |
| 6097 | cgacctgggccaaggtctcagagaa | W50004 | 48701 | tctcaccgtcgttgtacctgt | D10576 | 91305 | ctttctgcaggagagagctctgtg | AA114781 |
| 6098 | ctgtttcgaatgtcaggcagg | L34611 | 48702 | aagcacattcccagccagtcat | X61397 | 91306 | gagagttctcgtgatgaaaggaa | AA114781 |
| 6099 | gtctggagccgctgacactgga | L34611 | 48703 | attccagagcccaagtcatttattt | X61397 | 91307 | gagcttctcgtgatgaaaggaaga | AA114781 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 6100 | cgctccagccaattgagaacgaaacc | L34611 | 48704 | cccagagccaagtcattattcct | X61397 | 91308 | gaagaatccagactcacgtatggt | AA114781 |
| 6101 | gaacgaaaccataccagttactgg | L34611 | 48705 | atatgctcactagtgtatttctga | X61397 | 91309 | tggagccatcagagatccacaaagt | AA114788 |
| 6102 | aaccataccagttactatgacagtt | L34611 | 48706 | gttgatctaacaacagcttagaaca | X61397 | 91310 | catcagagatcacaaagtgtgaga | AA114788 |
| 6103 | cataccagttactatgacagttccc | L34611 | 48707 | tgaactacaacgcttagaacatca | X61397 | 91311 | ccgtcagacgcaaactcatatagat | AA114788 |
| 6104 | aacagtcatgtgactgggcatcaag | L34611 | 48708 | tctacaacagcttagaacatcaaaa | X61397 | 91312 | gtcagacgcaaactcatatagattg | AA114788 |
| 6105 | gccagagttggctggctgctcatt | L34611 | 48709 | atatacttatgcatatcgaatgt | X61397 | 91313 | cagagcgcaaactcatatagattgta | AA114788 |
| 6106 | agagttggctggctgctcattcag | L34611 | 48710 | agcatacaagtaatagcttgttc | X61397 | 91314 | gacgcaaactcatatagatgtaac | AA114788 |
| 6107 | ctggctgtcattcaggactggacc | L34611 | 48711 | atagcttgtttccatatagaaata | X61397 | 91315 | cagcctccggctgggttaaacag | AA114788 |
| 6108 | gctgctattcaggactggaccaag | L34611 | 48712 | accacagtctcggaattcatacct | X61397 | 91316 | tcactctgcagatccgcctggggt | AA114788 |
| 6109 | gtctattcaggactggaccaggttg | L34611 | 48713 | atccactagtatactatgttaattt | X61397 | 91317 | tgtcgcagatccgcgctttggggtttga | AA114788 |
| 6110 | ccgctggacactggcattggactca | L34611 | 48714 | ggaatttcatacatcgcacatacg | X61397 | 91318 | tcgagatccgcctggggttgaca | AA114788 |
| 6111 | ctggacactggcattggacttccag | L34611 | 48715 | catacttttgcacatactgctgtt | X61397 | 91319 | gcagatccgcctggggttgacatt | AA114788 |
| 6112 | tagcagctacagtactatgcccaatg | L34611 | 48716 | actttgcacatactgctgtttgct | X61397 | 91320 | ccgcctggggttgacattactcat | AA114788 |
| 6113 | cagctacacagtctatggcccaatggt | L34611 | 48717 | tttgcacatactgctgttgctcat | X61397 | 91321 | tgggaacatctccggaccgtcagac | AA114788 |
| 6114 | tggcccaatggtcacacacagt | L34611 | 48718 | catactgctgtgttcttatgttgag | X61397 | 91322 | ggaacatctccggaccgtcagacgc | AA114788 |
| 6115 | cccaatggtcacacacgagtgtg | L34611 | 48719 | actgctgtgttcttatgttgtgtagaaa | X61397 | 91323 | aacatctccggaccgtcagagcgca | AA114788 |
| 6116 | gtcacacagtgtgaccaatgtg | L34611 | 48720 | taagaaaagcacatcccagagcca | X61397 | 91324 | catccggaccgtcagacgcaaac | AA114788 |
| 6117 | gaccaatgggcccccgcagga | L34611 | 48721 | caccaggacatcgaaagcggaact | X61397 | 91325 | tctccggaccgtcagacgcaaactc | AA114788 |
| 6118 | aagatccgatttgggctgtag | W50088 | 48722 | gttttcatccgccctcgtcgaac | X92346 | 91326 | tccggaccgtcagacgcaaactcat | AA114788 |
| 6119 | attttgggctgtagaagagacgg | W50088 | 48723 | gacatgcctgatgccagcacatt | X92346 | 91327 | ccggaccgtcagacgcaaactcata | AA114788 |
| 6120 | tggttctgccttcctacagtc | W50088 | 48724 | cctgatgccagccacattcatcact | X92346 | 91328 | gaccgtcagacgcaaactcatatag | AA114788 |
| 6121 | gccttcttcctacagtctcctcact | W50088 | 48725 | tgccagccacattctacctggactg | X92346 | 91329 | gtgccccggcccagcattcagg | AA114788 |
| 6122 | tttccttacagtctcctcatcta | W50088 | 48726 | ccacatctacctggacgaggtgc | X92346 | 91330 | cccaaacctgaggccaaagctgtg | L34570 |
| 6123 | tacagtctcctcatcctactcca | W50088 | 48727 | cctgctcaggtgctatgtcccaaga | X92346 | 91331 | tgcagtggggaaccctttccaag | L34570 |
| 6124 | agctcctccatctcatctatgatg | W50088 | 48728 | caggtctatgtcccaagagccata | X92346 | 91332 | ttccaagccgcgttccaagtc | L34570 |
| 6125 | ctcctcatctcatctatgatgaag | W50088 | 48729 | gaaactgcctgagattaacttctc | X92346 | 91333 | caagagcccgcttccatatgctgc | L34570 |
| 6126 | atctcatctatgatgaagtccgaa | W50088 | 48730 | ctttccattcaaccccagtggtgcct | X92346 | 91334 | gctttccatagctgctgatgtgaa | L34570 |
| 6127 | gaagtccgaaagtcatcctccgggc | W50088 | 48731 | tattttctagtctaggtggggac | X92346 | 91335 | ttcatatgctcgtctagtgaaccac | L34570 |
| 6128 | gtccgaaagtcatccgccgggt | W50088 | 48732 | tctagtgctagtgggcacagcagg | X92346 | 91336 | acatgttacaactgctatgaat | L34570 |
| 6129 | aagctcatcctcgcgggggaccctg | W50088 | 48733 | gtcgaactgcccccggaagatccctca | X92346 | 91337 | tgttaacactgctctatgaatcaa | L34570 |
| 6130 | acgcgtggctgccttcctgctctt | W50088 | 48734 | cggaagatctccagctgagtagagc | X92346 | 91338 | ttacacactgcttaagaatcaaata | L34570 |
| 6131 | ctggcctccttcctgcttcactgcc | W50088 | 48735 | gtaggcctctgggtccaagtggg | X92346 | 91339 | aatagatctcaagcctttaatagat | L34570 |
| 6132 | gttggcctccgaatgtaccactctca | W50088 | 48736 | ggccgagcctttccacagctctg | X92346 | 91340 | agatctcaagccttaatagatcta | L34570 |
| 6133 | ctccgaatgtaccactcaaggtca | W50088 | 48737 | ttacagctcttgggcctaggatgt | X92346 | 91341 | tgaggccaaagctgtgctgaaggag | L34570 |
| 6134 | cgaattgtaccactcaaggtcacgt | W50088 | 48738 | gtgcctccaattggtgctcagccc | X92346 | 91342 | gctgctgcctggataaggaaatt | L34570 |
| 6135 | atgtaccactcaaggtcacgtggt | W50088 | 48739 | ccaattggtcttcagccctggccc | X92346 | 91343 | ttggacatacctttatgagtaccg | L34570 |
| 6136 | ccactcaaggtcacgtggtttct | W50088 | 48740 | gaaacatgcatccaggggcctgtctc | X92346 | 91344 | accttatagctacctgcggccgcagc | L34570 |
| 6137 | aaggtcacgtggtttctgtgcct | W50088 | 48741 | agaattcctacgtttatgtggcat | X92346 | 91345 | tttatacaagaccaactcaagtgcat | L34570 |
| 6138 | agacccctttaagcatgtgtgtg | X69019 | 48742 | tctctagtttatgcgaatcaatta | AA030251 | 91346 | caagacaactcaagtgcatccgt | L34570 |
| 6139 | gacccctttaagcatgtgtgttg | X69019 | 48743 | tactctgagtctgcagattcatct | AA030251 | 91347 | gaccactcaagtgcatccctgcct | L34570 |
| 6140 | tttgcttgctttaaggccattggg | X69019 | 48744 | actctgagtctgcagaatcatga | AA030251 | 91348 | agtgcatccgtgctggagcccg | AA114623 |
| 6141 | atatttgcaagggtgatgtctggt | X69019 | 48745 | cttctgagtctgcagaattcatga | AA030251 | 91349 | gatgcaatgcaactccctgcctt | AA114623 |
| 6142 | tgatggtctggttgggtgaattc | X69019 | 48746 | ttctgagtctgcagaatcatcgac | AA030251 | 91350 | gcacctccgtgcctcctcaagag | AA114623 |
| 6143 | catcctttcctaggcctttgca | X69019 | 48747 | agatcatcgactctgcaatggtg | AA030251 | 91351 | aacaaggccactacaaattcgtg | AA114623 |
| 6144 | atcctcttcctaggcctttgcat | X69019 | 48748 | gattcatcgactctgcaatggtg | AA030251 | 91352 | aaggccactacaaattcgtggct | AA114623 |
| 6145 | tcttttcctaggcctttgcattga | X69019 | 48749 | attcatcgactctgcaatggtggc | AA030251 | 91353 | ggaaatacaccactttggctgcat | AA114623 |
| 6146 | cctaggcctttgcattgaaatg | X69019 | 48750 | ttcatcgactctgcaatggtggct | AA030251 | 91354 | acaccacttggctggcatccaatg | AA114623 |
| 6147 | cctaggcctttgcattgaaaatg | X69019 | 48751 | tctctgactctgcaatggtggcta | AA030251 | 91355 | ctttggccgatccaatggtgtc | AA114623 |
| 6148 | ctaggcctttgcattgaaatgc | X69019 | 48752 | catctgactctgcaatggtggtac | AA030251 | 91356 | tggctggcaatcaatggtgtcatt | AA114623 |
| 6149 | taggcctttgcattgaaatgcac | X69019 | 48753 | ctctcactgttatgcgaatcaattac | AA030251 | 91357 | ctggcatccaatggtgtcatttg | AA114623 |

| SEQ ID NO | sequence | DBAxnID | SEQ ID NO | sequence | DBAxnID | SEQ ID NO | sequence | DBAxnID |
|---|---|---|---|---|---|---|---|---|
| 6150 | cccctttaagcatgtgtgtgtct | X69019 | 48754 | atctgactctgcaatgtggctacc | AA030251 | 91358 | caattgctagtgcaagcaggctg | AA114623 |
| 6151 | ttgtcttagcatgtacctgctggg | X69019 | 48755 | aatcaattacttctgagtctgcaga | AA030251 | 91359 | ttgctagtgcaagcaggtgctgatg | AA114623 |
| 6152 | tcttagcatggtacctgctgggttt | X69019 | 48756 | atcaattacttctgagtctgcagat | AA030251 | 91360 | caagcaggtgctgatgtggaatgcag | AA114623 |
| 6153 | ttagcatggtacctgctgggtttgt | X69019 | 48757 | tcaattacttctgagtctgcagatt | AA030251 | 91361 | cctcctgcctcctccaagagaca | AA114623 |
| 6154 | tagcatggtacctgctgggtttgtt | X69019 | 48758 | caattacttctgagtctgcagattc | AA030251 | 91362 | cgaaaaatcacacctcttatgtcag | AA114623 |
| 6155 | catggtacctgctgggtttgttgt | X69019 | 48759 | aattacttctgagtctgcagattca | AA030251 | 91363 | cctgtgcctcctccaagagacactg | AA114623 |
| 6156 | tggtacctgctgggtttgttgtg | X69019 | 48760 | attacttctgagtctgcagattcat | AA030251 | 91364 | cctccaagagaacactgctttaa | AA114623 |
| 6157 | tgcctgcttgctttaaggccat | X69019 | 48761 | ttacttctgagtctgcagattcatc | AA030251 | 91365 | tcctcaagagacactgctttaaccca | AA114623 |
| 6158 | tgtttccatgcatgaaagacgctg | X69019 | 48762 | aacatataccttaataaggcagtgca | AA030251 | 91366 | gacactgcttaaccatagcagcag | AA114623 |
| 6159 | cagcaagccaaacatgtgtgggaagcc | L10106 | 48763 | atatacctaataaggcagtgcatat | AA030068 | 91367 | actgcttaaccatagcagcagcagaca | AA114623 |
| 6160 | gagccagtcagtgtaacctgta | L10106 | 48764 | algattttgccactgtacaagttga | AA030068 | 91368 | actgcttaaccatagcagcagcagaca | AA114623 |
| 6161 | cctgtactgcacgcagagatttta | L10106 | 48765 | attttgccactgtacaagttgacca | AA030068 | 91369 | accatagcagcagcagcagaagccact | AA114623 |
| 6162 | actgatcagtttctgtgactgtat | L10106 | 48766 | tgccactgtacaagttgaccatt | AA030068 | 91370 | gacaaatttgaccttgacttcaagc | AA114623 |
| 6163 | tcagttctgtgactgtatgagagc | L10106 | 48767 | tacaagttgaccattctgggctc | AA030068 | 91371 | caaatttgaccttgacttcaagcgc | AA114811 |
| 6164 | tgagagcatccacatttcatgccac | L10106 | 48768 | aagttgaccattctgggctcgat | AA030068 | 91372 | gattgaaatcatctctgggcgtgct | AA114811 |
| 6165 | catccacatttcatgccacctaatt | L10106 | 48769 | ttctaatctcatcttactgcat | AA030068 | 91373 | ttgaaatcatctctgggcgtgctgc | AA114811 |
| 6166 | ctccgcttttcgtagagcagtac | L10106 | 48770 | ttaatctcatcttactgcatcaa | AA030068 | 91374 | tgaaatcatctctgggcgtgctgct | AA114811 |
| 6167 | gtagagcagtcgacacacattgcat | L10106 | 48771 | atctcatcttctactgcattgactc | AA030068 | 91375 | gaaatcatctctgggcgtgctgctc | AA114811 |
| 6168 | cagtaccacacatttcatgcactt | L10106 | 48772 | tctctactgcattgactcctcgg | AA030068 | 91376 | aaatcatctctgggcgtgctgctct | AA114811 |
| 6169 | ccacacattgcactgcacttgtaag | L10106 | 48773 | actgcattgactcctcgcgctgtg | AA030068 | 91377 | atcatctctgggcgtgctgctgg | AA114811 |
| 6170 | tcgttttgcatgatgtgggctta | L10106 | 48774 | gttgaagctccgtcacaatcgcca | AA030068 | 91378 | tcatctctgggcgtgctgctgga | AA114811 |
| 6171 | ttgctatgatggcgttagagtac | L10106 | 48775 | tgactccctcggcctgtggattct | AA030068 | 91379 | catctctgggcgtgctgctctgat | AA114811 |
| 6172 | aagagtacctggagtctcatagtc | L10106 | 48776 | aagctccgtcacaaatcgccact | AA030068 | 91380 | atctctgggcgtgctgctctcgatt | AA114811 |
| 6173 | cctggggtccatagtcctgag | L10106 | 48777 | aattataccaacaacagctagag | AA030068 | 91381 | tctctgggcgtgctgctctcgatta | AA114811 |
| 6174 | gtcctatagtcgctgagactatt | L10106 | 48778 | ttataccaacaacagctagagcc | AA030068 | 91382 | tgacctgactcaagcgccaccg | AA114811 |
| 6175 | atagttcgtgagactattgcaga | L10106 | 48779 | tacaacaaacagcctagagcccaaa | AA030068 | 91383 | accgcccaggcgtcatcacaaga | AA114811 |
| 6176 | ttgcagagcatccaagccagaaatcc | L10106 | 48780 | cagcctagagcccaaatatctgcct | AA030068 | 91384 | ccgcaggcgtcatcacaagaga | AA114811 |
| 6177 | cattgctcgtcgagccagcgctg | L10106 | 48781 | gcccaaatatctgccttgtaagtga | AA030068 | 91385 | cgcaggcgtcatcacaagagagt | AA114811 |
| 6178 | caatgtcacctacaaccactcgg | L10106 | 48782 | atatctgccttcgtaggtgatgatt | AA030068 | 91386 | gcaggcgtcatcacaagagaggt | AA114811 |
| 6179 | tgtcacctacaaccactcttggc | W50102 | 48783 | tgccctccgcatgtacaacctcgt | AA030068 | 91387 | ccaggcgtcatcacaagagagagt | AA114811 |
| 6180 | cctcttctttgataattacgagcac | W50102 | 48784 | acctcgtgtgtgcgcgcagagaata | AA030256 | 91388 | ggctgtcatcacaaagagagtgat | AA114811 |
| 6181 | ttagcagcacaaacaacagcgtcgt | W50102 | 48785 | accgaggttcaacctgatgctggg | AA030256 | 91389 | tgatgaaatcatctctggggcgtc | AA114811 |
| 6182 | cagcacaaacaacagcgtcgtcaag | W50102 | 48786 | cgcactgcccttcggagaactagcgt | AA030256 | 91390 | atttactatggctgtctctgcgc | AA114811 |
| 6183 | gcacaaacaacagcgtcgtcaagaag | W50102 | 48787 | ctgccctcggagactagcgtgg | AA030256 | 91391 | tctcccagggaatgctcgtcgt | AA116282 |
| 6184 | caacaaacaacagcgtcgtcaagaagac | W50102 | 48788 | ctgccctcggagactagcgtgg | AA030256 | 91392 | gtttggctcttttccagataacact | AA116282 |
| 6185 | caacagcgtcgtcaagaagatcccac | W50102 | 48789 | ctgccctcggagactagcgtgcg | AA030256 | 91393 | ttcttttccagataacactgcactt | AA116282 |
| 6186 | cgtcaagaagatcaccctggaggtg | W50102 | 48790 | agactaggggggactcatggcg | AA030256 | 91394 | tgcactgcgtctctgccctgcat | AA116282 |
| 6187 | agatatggcatccatcgtcagag | W50102 | 48791 | gactaggtgggggactccatgagt | AA030256 | 91395 | tgcgtctctgcctgcatacatcg | AA116282 |
| 6188 | cgtgctcattggtgttaacatat | W50102 | 48792 | ctaggtgggggactccatggagtg | AA030256 | 91396 | gtctctgcctgcatacatcgtct | AA116282 |
| 6189 | gttaacatatggctgctgggagaa | W50102 | 48793 | cgactccatgagtggttggaa | AA030256 | 91397 | tctctgcctgcatacatcgtcttg | AA116282 |
| 6190 | ctacaactctcggtgactacgaa | W50102 | 48794 | tccatgagtggttgggaagact | AA030256 | 91398 | cctgatacacatcgtcttgttgtt | AA116282 |
| 6191 | caaccactcggtgactacgaatgt | W50102 | 48795 | tcgtgtgcgcaccgagaatagcag | AA030256 | 91399 | gtctttgttcttctagcaaga | AA116282 |
| 6192 | ccactctggagactacgaatgtcac | W50102 | 48796 | ctgtcgccaccgggctactggaaga | AA030256 | 91400 | tttgttgttcttctagcaagatgc | AA116282 |
| 6193 | ctctggagactacgaatgtcacgtc | W50102 | 48797 | tgctggcccaccgggctactgaagag | AA030256 | 91401 | tcttctagcaagatgcagtcgtaggg | AA116282 |
| 6194 | cgactaagtgcacgtcacctgcgt | W50102 | 48798 | ctggccaccgggctactggaagagc | AA030256 | 91402 | gaatgctggtctgtctttgcctct | AA116282 |
| 6195 | ctacgaatgcacgtcaccgtcc | W50102 | 48799 | tggccaccggctactggaagaggt | AA030256 | 91403 | tgctggtctgtctttgcctccca | AA116282 |
| 6196 | atgtcaacgtctacgctctcctc | W50102 | 48800 | gccaccggctactggaagagctac | AA030256 | 91404 | gtctgtttttgcctccaggcaat | AA116282 |
| 6197 | tctcctctttgataattacgag | W50102 | 48801 | gagacaaccgagggtcaacctgat | AA030256 | 91405 | cttgcctctccaggcaatcctagc | AA116282 |
| 6198 | tgaggctttactgtcacccteatc | L09562 | 48802 | gtcagattgtgccctgccctgc | AA030256 | 91406 | ctccaggcaatcctagcctgat | AA116282 |
| 6199 | ctttactgtcaccctcatcagcaaa | L09562 | 48803 | gtcagattgtgccctgccctgc | X52886 | 91407 | tccaggcaatcctagcctgaattt | AA116282 |

| SEQ ID NO | sequence | DBAxnID | SEQ ID NO | sequence | DBAxnID | SEQ ID NO | DBAxnID |
|---|---|---|---|---|---|---|---|
| 6200 | agcagtttcgcaggaatgttgtgt | L09562 | 48804 | cagattgctgccctcgcctgctg | X52886 | 91408 | tcctagcctgaatttcaagcccct | AA116282 |
| 6201 | taccacctgtccagcagctagag | L09562 | 48805 | cctccaactctggcctgcaaaggc | X52886 | 91409 | ttcctgttggcttctttccagat | AA116282 |
| 6202 | tgtgttccaggtgcaaaaatgatc | L09562 | 48806 | ccaactctggcctgcaaaggcctg | X52886 | 91410 | tgggaactgaccgacatctggaaga | AA116344 |
| 6203 | acaataccagttgtctaccaaagca | L09562 | 48807 | actctggcctgcaaaggcctgaag | X52886 | 91411 | gaactgaccgacatctggagactc | AA116344 |
| 6204 | tgtctacaaagcaagctcagttg | L09562 | 48808 | ctggcctgcaaaggcctgaaggtg | X52886 | 91412 | agttcacagtcgcggagccagccaag | AA116344 |
| 6205 | caaagcaatgctcagcttgatcagt | L09562 | 48809 | cctcctgggaaggcatgcctcagcc | X52886 | 91413 | tcacagtgccgagcagccaaggat | AA116344 |
| 6206 | agaggaatcagacccgcagagagc | L09562 | 48810 | aaggcatgcctcagccgctgggtaga | X52886 | 91414 | cagtgccgagcagccaaggatgtg | AA116344 |
| 6207 | atcagaccctgcagagagcatggag | L09562 | 48811 | gccatgcctcagcctggtagaagt | X52886 | 91415 | tgccgagcagccaaggatgtaatg | AA116344 |
| 6208 | catggatgtctgggtgactagtc | L09562 | 48812 | tcctgggctaggcagctgggagca | X52886 | 91416 | cgcagagaagccatcgctgcggcagt | AA116344 |
| 6209 | actcattgtaaactctgagact | L09562 | 48813 | cctgggctaggcagctgggagcaa | X52886 | 91417 | agagaagccatcgctgcagcgcatcg | AA116344 |
| 6210 | cctcatcagcaaagacaggctagc | L09562 | 48814 | ctaggcagctgggagccaagtga | X52886 | 91418 | gccatcgctggcagtcgcatgcta | AA116344 |
| 6211 | agacaggctatgcctctgcaatgaa | L09562 | 48815 | cccagtaccgaggctgccttcaaa | X52886 | 91419 | atccgttggccagtccgatgctatg | AA116344 |
| 6212 | gctatgcctctctgaatgaagaaccta | L09562 | 48816 | agtacacgaggctgcctcaaaggc | X52886 | 91420 | gcttggccagtccgatgctatgtaac | AA116344 |
| 6213 | agaacaaattatcatccatgactc | L09562 | 48817 | ggctgcctcaaaggccctactgg | X52886 | 91421 | tggcagtccgatgctattgaacatg | AA116344 |
| 6214 | aattatcatccatgactcatcct | L09562 | 48818 | ccctactgtttaatagctgtga | X52886 | 91422 | ctgaccgacatctggagactccat | AA116344 |
| 6215 | atggcctaacccagcagtccccata | L09562 | 48819 | tgccgcccttgctgtgtgggcagt | X52886 | 91423 | cagtccgatgctattgaacatgaga | AA116344 |
| 6216 | taaccagatgcccctataagtagt | L09562 | 48820 | cctttgctgtgtgggcagtactg | X52886 | 91424 | cgacatctggagactccatactga | AA116344 |
| 6217 | taccttgaactgatcaatgtcatc | L09562 | 48821 | cagtactctgaagcaggcaaatggg | X52886 | 91425 | catctggagactccatactgagaga | AA116344 |
| 6218 | cgcacgctgggagcatccagaaggg | X17463 | 48822 | tactctgaagcaggcaaatgggtct | X52886 | 91426 | ctggagactccatactgagaaaag | AA116344 |
| 6219 | accagaagatgcgcgcgcgctcgcg | X17463 | 48823 | ggtgatgcccacaatcagcgtcatg | X52886 | 91427 | taaatgtcaggagtgtggaaggc | AA116344 |
| 6220 | ctcaaccgagggtcagcctggctta | X17463 | 48824 | gatgcccacaatcagcgtcatgaga | X52886 | 91428 | atgtcaggagtgtggaaggcctt | AA116344 |
| 6221 | gggtcagcctggctagttggccacg | X17463 | 48825 | atcacgaaaagctgttcatagaag | X52886 | 91429 | ctggaaggcctttgctctcgtcgta | AA116344 |
| 6222 | tcagcctggctagttggccacgtg | X17463 | 48826 | gaggacaactatagtctccgatgcgc | X52886 | 91430 | ctttattcaacagtcacaacctcatt | AA116344 |
| 6223 | gctggcttagtggccacgtgtctt | X17463 | 48827 | actatagtctccgatgcgcacc | X52886 | 91431 | aaggcttagcctctaggggtcaca | AA145535 |
| 6224 | tgcttagtggccacgtgtcttcct | X17463 | 48828 | atatgtctcgatgcgcaccatgagc | X52886 | 91432 | ttagctccctaggggtcagcactgga | AA145535 |
| 6225 | cttagtggccacgtgtctctctg | X17463 | 48829 | gtccgatgcgcaccatgcagttc | X52886 | 91433 | agctccacaggaaccggatccattc | AA145535 |
| 6226 | gtctgcgctggcaccttgtatt | X17463 | 48830 | gtccgatgcgcaccatgactctc | X52886 | 91434 | tccacaggaaccggatccatcactaccac | AA145535 |
| 6227 | tgggctgcgcaccttgtatattgaa | X17463 | 48831 | tccgatgcgcaccagcttc | X52886 | 91435 | ggatccatcacctacgattaccac | AA145535 |
| 6228 | cgctggccactttgtatattgaa | X17463 | 48832 | caccatgagctctcagctctgc | X52886 | 91436 | tatcgctggactcctttcatctgt | AA145535 |
| 6229 | tgggaccttttgtatattgaatgc | X17463 | 48833 | catgagctctcagctctgctgtc | X52886 | 91437 | cctctctatcctggacatcttatc | AA145535 |
| 6230 | tgggcaactacggcaagacaggcga | X17463 | 48834 | gagctctccagctctcgctgctg | X52886 | 91438 | ctttcatctggggcatcctatctc | AA145535 |
| 6231 | gaactacggcaagacaggcgagt | X17463 | 48835 | gccacaatcagtcgtcatgagatac | AA030294 | 91439 | ctggccatccttatcctcttagcaag | AA145535 |
| 6232 | agagaagctcacctcacagttcag | X17463 | 48836 | ctcctgtcgttggtgccgtcagc | AA030294 | 91440 | catcctcatcctagcaagaa | AA145535 |
| 6233 | agctcacctaccagttcagcgggga | X17463 | 48837 | cacaatcagtcgtcatgagatactg | AA030294 | 91441 | tatcatcctagcagagatgtcga | AA145535 |
| 6234 | tcacctaccagttcagcgggcgaagt | X17463 | 48838 | tgtaaagtctgggctcatgttcggg | AA030294 | 91442 | gtccctagggtgcacagtcggacat | AA145535 |
| 6235 | actgatccgccgcagaagcgcgccag | X17463 | 48839 | ggcataacttctgcagctctgggcc | AA030294 | 91443 | gtgccgagcagccggacattggggtc | AA145535 |
| 6236 | gcctcaaccaggcgctgggccacc | X17463 | 48840 | ataacttctgcagctctgggccacc | AA030294 | 91444 | cacgctggacactgggggtctc | AA145535 |
| 6237 | gacctcaaccaggcgacctggctgc | X17463 | 48841 | actcttgcagtctgggccacc | AA030294 | 91445 | acatttgggggtctcgtcaacg | AA145535 |
| 6238 | agagtgaagccacctggatcaacg | X17463 | 48842 | ctccactgatcacgaaaggcctgt | AA030294 | 91446 | ctttctgtcaacaggggacagcgtga | AA145535 |
| 6239 | tgaaggccacctggatcaacgttga | W50000 | 48843 | ccactgatcacgaaaggcctgttca | AA030303 | 91447 | ctgtcaacaggggacagcgtgaatg | AA145535 |
| 6240 | gcctgggctgcggaggtgacacat | W50000 | 48844 | ggctccatggtgactagagtta | AA030303 | 91448 | cctcccagcagtcgcagaagct | AA145535 |
| 6241 | ttgagttctgtgctaccaatgggg | W50000 | 48845 | ttcaaaatgtccggctccgcagca | AA030303 | 91449 | cctcccagcagtcagaagct | AA145535 |
| 6242 | gagttctgtaccaatgggaa | W50000 | 48846 | ctgcacacggtagttcaacacg | AA030303 | 91450 | tgcagaagtccacaggaaccggat | AA145535 |
| 6243 | tctgtaccaatgggaacag | W50000 | 48847 | gtgttctaacagcaaggcgcaccacc | AA030303 | 91451 | agctcgccattcctccaccatg | AA145535 |
| 6244 | acagcaagctgcctgaagtcat | W50000 | 48848 | ttctaacagcaaggcgccaccttg | AA030303 | 91452 | tcctcaccatgtgttttcacatg | U04334 |
| 6245 | caagctgcgcctgaagtcagcag | W50000 | 48849 | taacagcaaggcgcaccacctgag | AA030303 | 91453 | gtcgccagccagacatggtacc | U04334 |
| 6246 | agctgcgcctgaagtcatgcagga | W50000 | 48850 | caccacctggctgcccattgcg | AA030303 | 91454 | tgcagacatgtacctctagg | U04334 |
| 6247 | gcgcctgaagttcatgcagactta | W50000 | 48851 | actgacatagcccagcaggtagcgg | AA030303 | 91455 | tggtacctctaggacaccacacaga | U04334 |
| 6248 | acagacacttgtcaactgaacga | W50000 | 48852 | gaccatacgcaggctagcggata | AA030303 | 91456 | ccaaagctgtgctcagcccaattca | U04334 |
| 6249 | ggacacttgtcaactgaactgagt | W50000 | 48853 | atagccaggtagcgggatacg | AA030303 | 91457 | ctgtctgctcagcattcaagcaga | U04334 |

TABLE 1-continued

| SEQ ID NO | DBAxnID | sequence | SEQ ID NO | DBAxnID | sequence | SEQ ID NO | DBAxnID | sequence |
|---|---|---|---|---|---|---|---|---|
| 6250 | W50000 | gccacctgtgatcaacgttgagccg | 48854 | AA030303 | gatatcgtctctgaccggttaagg | 91458 | U04334 | tcagccaatttcaagcagcagatttga |
| 6251 | W50000 | cacttgatcaacgttgagccgcca | 48855 | AA030303 | gctctcgaccggttaaggagcaag | 91459 | U04334 | ttacagcccggaatgagcaactga |
| 6252 | W50000 | ttggatcaacgttgagccgagcc | 48856 | AA030303 | cgcagcaccaaagagcagtggca | 91460 | U04334 | atgagcaactgacctgccttatga |
| 6253 | W50000 | atcaacgttgagccgagcccactg | 48857 | AA030303 | agcaacaccaaagagcagtggcaccg | 91461 | U04334 | cttatgaataccttcaagccgaccg |
| 6254 | W50000 | caacgttgagccgagccactgt | 48858 | AA030303 | aagcagtggaccgtcaatgaca | 91462 | U04334 | tcaagccagccgcatagagaacag |
| 6255 | W50000 | gcagccactgctcgagccgaggacctg | 48859 | AA030303 | agcagtggaccgtcaatgacatac | 91463 | U04334 | cccagcatgctgccatcaaccagg |
| 6256 | W50000 | agcccactgctcgagccgaggacctgcc | 48860 | AA030303 | agtggcaccgtcaatgactaccg | 91464 | U04334 | atgctgccatcaaccagggccagct |
| 6257 | W50000 | cactgctcgaggaggacctgccggg | 48861 | AA030303 | accgtcaatgactatacccgtcaag | 91465 | U04334 | ccatcaaccagggccagctggactg |
| 6258 | W50000 | tcacatgacggcgctgtgcacaagc | 48862 | AA030303 | ctgtgggtctgcacacggtagt | 91466 | U04334 | tacctaatgctccatgcacaatgag |
| 6259 | W50000 | gctgtgcacaagccctacaactgct | 48863 | AA030303 | ctgggtgcacacggtagtgtct | 91467 | U04334 | tggggtgctacctgatgcagaa |
| 6260 | W50000 | atgctgagctcggttatattccg | 48864 | AA030303 | gcttatgattccaagcagatgaac | 91468 | U04334 | cgctacctgatgtcgaagaaggcctg |
| 6261 | L04649 | attttcgaccacatgaaggtgcaca | 48865 | AA030303 | gatgaacctgtacaccctcccaaattc | 91469 | U04334 | tgcagaaggcctgtcttcagatgac |
| 6262 | L04649 | tgtccaatgggcagcttgagcgagcag | 48866 | AA030303 | caaggccatgctgcaactgactgatgaa | 91470 | U04334 | ctatcacatgcgacctgggcgct |
| 6263 | L04649 | cctggtgagctccaagttgatggg | 48867 | X70533 | tgtgctgcctgctcgccaccaatggc | 91471 | AA116479 | ttatctgccctaagtctctgttat |
| 6264 | L04649 | ggaaagtctcttggtacagtctc | 48868 | X70533 | ctccgaatcatccacctccagtac | 91472 | AA116479 | tctgcctaagtctctgttatgtt |
| 6265 | L04649 | tcacgactctcatcaaccaaggag | 48869 | X70533 | caagtacaacagccgcttcatctc | 91473 | AA116479 | tctcttcatagagctctatatc |
| 6266 | L04649 | ctctcatcaaccaaggaggcctcca | 48870 | X70533 | gccctcatctctggccttgac | 91474 | AA116479 | cttcatcatagagctctatatctg |
| 6267 | L04649 | atcaaccaaggagcctccagacaga | 48871 | X70533 | catcttcctggcctttgacagtac | 91475 | AA116479 | catcatagagctctatatctggtt |
| 6268 | L04649 | caaggagcctccagacagagaggag | 48872 | X70533 | cctggccttgacaagtacacatgg | 91476 | AA116479 | agagctctatatctggttaatgaa |
| 6269 | L04649 | gcctccagacagagaggaggagaa | 48873 | X70533 | aaaccatgtgccatctgacttga | 91477 | AA116479 | gctctatctggttaatgaagta |
| 6270 | L04649 | aactgctcccactgtggccaagagct | 48874 | X70533 | tgggccatcgacttgagcaacgtc | 91478 | AA116479 | cttggcaacttaacaatttcaat |
| 6271 | L04649 | tgtgggcaagagctctccgccgg | 48875 | X70533 | catctgacttgagcaacatgagaagt | 91479 | AA116479 | tcaaaacctgcagaactattatcat |
| 6272 | L04649 | gatcacctcaacagtcacgtcagac | 48876 | X70533 | catcccaaattccatgtctgact | 91480 | AA116479 | agctgccatcagacgactcggaacatc |
| 6273 | L04649 | caagtgcactcaacagcagcggcct | 48877 | X70533 | ctccatgtcgatacctatgacctt | 91481 | AA116479 | tgccatcagacgtcgggaacatcaaa |
| 6274 | L04649 | cactcaacagcagcgggcctcaaat | 48878 | X70533 | gtctcgataccctagaactt | 91482 | AA116479 | catcagacgtcgggaacatcaaatag |
| 6275 | L04649 | acagagcggcctcaaatgtgaga | 48879 | X70533 | tgacctttcaagatgtgctggcagat | 91483 | AA116479 | ctaagtcttcgttatgttcagagc |
| 6276 | L04649 | gctacgaaggatgcctccgagcgc | 48880 | X70533 | tcaagatgctggcagatgtgggc | 91484 | AA116479 | tttcctgatgcgccgaaccca |
| 6277 | L04649 | gctccatgtcatgtctgggcaaga | 48881 | X70533 | tgtgctgcagatgtgggccatagg | 91485 | AA116479 | agtctcgttatgtcagagctcga |
| 6278 | W50127 | agatgcaagagctgcccaagaga | 48882 | X70533 | gttcaacaacaatctgatttcgca | 91486 | AA116479 | cttctgttatgttcagagctcggca |
| 6279 | W50127 | gatgacaagagctcgcccaagaaga | 48883 | X70533 | aacgtactccacaaggccatgctg | 91487 | AA116479 | ttatgttcagagtcggcactgcag |
| 6280 | W50127 | atacaatacgacgtgctgcagggt | 48884 | AA030276 | aacttcccagccacaaggccatgg | 91488 | AA116479 | ggcactgcagctgtgaatctgtct |
| 6281 | W50127 | tacaatacgacgtgctgcagggtc | 48885 | AA030276 | cttcccagccaggaatccattgggt | 91489 | AA116479 | gctgaatctgtctctcatcata |
| 6282 | W50127 | aatacgacgtgcgtgcagggtctga | 48886 | AA030276 | ttgcctactccgaagtctgacat | 91490 | AA116479 | gtgaatctgctctcatcatagag |
| 6283 | W50127 | taccgactgcgtgcagggtctgtca | 48887 | AA030276 | ggattttgccataatcgagcct | 91491 | AA116479 | aatctgtctctcatcatagagtc |
| 6284 | W50127 | acgacgtgcgtgcagggtctgacac | 48888 | AA030276 | atttgccaataatcgagcctgt | 91492 | AA116335 | taacttcctagctgctaaggagaaa |
| 6285 | W50127 | cgactgcgtgcagggtctgacacac | 48889 | AA030276 | tgccaataatcgagcctgtaga | 91493 | AA116335 | cttcctagctgctaaggagaaatcc |
| 6286 | W50127 | gactgcgtgcagggtctgacacaca | 48890 | AA030276 | tgccataatcgagcctgtagat | 91494 | AA116335 | ttacctgaagccacctattctgac |
| 6287 | W50127 | tctgacacacacagtaaagccccagag | 48891 | AA030276 | ccaataatcgagcctgtagattg | 91495 | AA116335 | cctcagaagccacctattctgactcc |
| 6288 | W50127 | ctgacacacagtaaagcccagaga | 48892 | AA030276 | caataatcgagcctgtagattgc | 91496 | AA116335 | cagaagcacctattctgactccacc |
| 6289 | W50127 | gacacacacagtaaagcccaggagatc | 48893 | AA030276 | taatcgagcctgtagattgccca | 91497 | AA116335 | cacctattctgactccacctcgaga |
| 6290 | W50127 | gacacagtaaagcccaggagagca | 48894 | AA030276 | gcttgtagattgcccagtgtaaa | 91498 | AA116335 | ttctgactccacctcggaaccaag |
| 6291 | W50127 | acacacagtaaagcccaggagatcc | 48895 | AA030276 | tgtagattgcccagtgtaaaagg | 91499 | AA116335 | ctccacctcggaaccaaggataact |
| 6292 | W50127 | caagagtcgcccaagaagaagcaag | 48896 | AA030276 | ttccagccaggaatccattgggtt | 91500 | AA116335 | cacctcgaaccaaggatactctt |
| 6293 | W50127 | aagagtctgcccaagaagaagcaagg | 48897 | AA030276 | ccgaccaggaatccattgggttggc | 91501 | AA116335 | agatgttcacgatttgactacgt |
| 6294 | W50127 | caagaggtcgggaactgactgac | 48898 | AA030276 | agccaggaatccattgggttggcg | 91502 | AA116335 | tccaagatttgactacgttcgta |
| 6295 | W50127 | gacctgatgaccctcaagaaggag | 48899 | AA030276 | gaatccattgggttggcgactg | 91503 | AA116335 | attttgactacgttgcattggtg |
| 6296 | W50127 | cctggatgacctcaagaaggaagtg | 48900 | AA030276 | aatccattgggttggcgcactgc | 91504 | AA116335 | gaaatcctgagcggccgcctggggc |
| 6297 | W50127 | cggaaataccaatacgacgtcgctgc | 48901 | AA030276 | ccatgggttggccgactgtctcac | 91505 | AA116335 | actacgttgctgattggttaagt |
| 6298 | W50167 | gaaatacaatacgactgcgtgca | 48902 | AA030276 | taaaagttgctactccgaagtct | 91506 | AA116335 | tccggttaaccgactgaggtgct |
| 6299 | W50167 | cagttcacccagctgactctg | 48903 | AA030276 | agagttgctactccgaagtctag | 91507 | AA116335 | taaccgactgaggtgctcaatgga |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 6300 | gttcaccaaggctgtactcttgga | W50167 | 48904 | catgtgactgtgaccagcagatcga | X57111 | 91508 | cgactggagtgctctaatggacaa | AA116335 |
| 6301 | cagtggacaccctcactcagtactcg | W50167 | 48905 | accagcagatcgacagctgtaccta | X57111 | 91509 | agccaccatttgtacctaccattag | AA116335 |
| 6302 | tctacagtactgccctggctcag | W50167 | 48906 | caccgcagtctcaagtgagattga | X57111 | 91510 | caccattgtacctaccattagaagg | AA116335 |
| 6303 | tacagctactgccctggctcagtg | W50167 | 48907 | agattgaaccgcctcatgatgagg | X57111 | 91511 | cattgtacctaccattagaagacg | AA116335 |
| 6304 | cagctactgccctggctcagtgc | W50167 | 48908 | aacgcctcatgatcagggctattc | X57111 | 91512 | atgaatttacctcagaagcacctat | AA116335 |
| 6305 | gctactgccctggctcagtgcaa | W50167 | 48909 | gtcaggctcatcctaccagagacat | X57111 | 91513 | ggcttggtgctcagagagagacaagt | AA033499 |
| 6306 | tactgccctggctcagtgtcaaca | W50167 | 48910 | gctattcctacaggacattcagaa | X57111 | 91514 | tctcagctaggaagacacggcgctg | AA033499 |
| 6307 | gccctggctcagtgtcaacagtaa | W50167 | 48911 | cctaccaggacattcagaaagcttt | X57111 | 91515 | tgtctcacgagatgtacctgaat | AA033499 |
| 6308 | cctggctcagtgtcaacagtaagg | W50167 | 48912 | aagcttgtcattgcccacaacaa | X57111 | 91516 | cacgatgacctgaatctgtctgc | AA033499 |
| 6309 | ttggctcagtgtcaacagtaagggc | W50167 | 48913 | tggtcattgcccacaacaacatttga | X57111 | 91517 | gatgacctgaatctgtctgctgcctt | AA033499 |
| 6310 | ctcagtgtcaacagtaagggccact | W50167 | 48914 | ttgcccacaacaacattgagatggc | X57111 | 91518 | gaatctgtgcctgattcctg | AA033499 |
| 6311 | tcaccaaggctgtacctcttggaga | W50167 | 48915 | tttcttctcctgctcactgagccac | X57111 | 91519 | tctgtgccttgatcctggccg | AA033499 |
| 6312 | tggttctctttcgttctaatac | W50167 | 48916 | agatcagacagctgtacctacgaagc | X57111 | 91520 | ctgccttggatctctggcgctggtc | AA033499 |
| 6313 | gcttcctctttcgttctaatacg | W50167 | 48917 | cccaagcacgtcgtgtacagaaaa | X57111 | 91521 | cctggatctcggcgctgctcac | AA033499 |
| 6314 | tcttttcgttctaatacgtaatc | W50167 | 48918 | ggaatctggccacagctcacacgag | X57111 | 91522 | tggatcctggcgtgctgtcactct | AA033499 |
| 6315 | tttcgttctaatacgtaatcag | W50167 | 48919 | tggccacgctcacacagtactgg | X57111 | 91523 | ccactctgcaaggccgagaccag | AA033499 |
| 6316 | tttctaatacggtaatacagccag | W50167 | 48920 | ccctgtcatctccaatgccag | X57111 | 91524 | tgtcaaggccgaccaagaagtg | AA033499 |
| 6317 | taatacgtgatactacacctctacagt | W50167 | 48921 | tgtctttgatgtgacctacaa | X57111 | 91525 | agacacggcgtggaaccatggac | AA033499 |
| 6318 | atcagtgaaccctctacagtac | W50167 | 48922 | cattcctcggaatcaactcga | X57111 | 91526 | gctgaaccatggacacctcatat | AA033499 |
| 6319 | acagttcaaactgtctttgatcgg | W50167 | 48923 | aagccagtactatcaacaaggctcg | X57111 | 91527 | tccaatcccgcaaggctgatgt | AA033499 |
| 6320 | aactgctctgatcgggaacagcag | W50167 | 48924 | gtgcagtccaccaaggcttgtg | X57111 | 91528 | atccgcaaggctgatgctgcagcc | AA033499 |
| 6321 | acaatgccaggtaatcctgtggg | M89777 | 48925 | ttccaccaaggctctcggtgacctg | W43968 | 91529 | ctcatgggaacacctggcctcaca | AA033499 |
| 6322 | taatcctgtggggaacaagtgtga | M89777 | 48926 | acgcagacgggtatccagcgtgaa | W43968 | 91530 | tcacagctctgctcagc | AA033499 |
| 6323 | tctgaccctgtgggaatgatggccgag | M89777 | 48927 | cagacgggtatccagcgtggaacta | W43968 | 91531 | ctggtctgctcacgatgtac | AA033499 |
| 6324 | tacgctgagatggggccgaggct | M89777 | 48928 | gctatccagcgtggaactaagaaca | W43968 | 91532 | gtcgtctcagcagatgtacctg | AA033499 |
| 6325 | agttctggaggcctggccaagga | M89777 | 48929 | actaagaacaattaccgatgagag | W43968 | 91533 | ctcttacatcctactacactaca | AA116410 |
| 6326 | aggttctggagcgcctggtggacat | M89777 | 48930 | aattaccgatgagctgccctg | W43968 | 91534 | tctcttcatctcctactacactacaa | AA116410 |
| 6327 | tcgaggccgtggtggacatctg | M89777 | 48931 | cccccaggatgccatcaaaacggag | W43968 | 91535 | cactacacattatcatcactccaaa | AA116410 |
| 6328 | tggaacatctgtgacacagatgaa | M89777 | 48932 | ccaggatgccatcaaaacggagtca | W43968 | 91536 | actacacattatcatcactcacta | AA116410 |
| 6329 | acaatgccaggtaatcctggtccag | M89777 | 48933 | catgccttggaaccagaaggtcca | W43968 | 91537 | tacaacattatcatcactcaaaaca | AA116410 |
| 6330 | gctcagccccaggcagccaatggaaa | M89777 | 48934 | tccaatcagaaaagcctgtacacct | W43968 | 91538 | acaacattatcatcactcaaaacat | AA116410 |
| 6331 | ctgccttcgcgagcacagtgggat | M89777 | 48935 | cagaaaagcctgtacacctctatgg | W43968 | 91539 | acattatcatcactcaaaaacatcc | AA116410 |
| 6332 | acagccggagccagcgcagctgttag | M89777 | 48936 | caccaaggcttcggtgacctggcta | W43968 | 91540 | acattatcactcaaaacatccc | AA116410 |
| 6333 | ccttctggagcacagtggcatcga | M89777 | 48937 | ttccggacctggctatccctcaagcca | W43968 | 91541 | ttatcactcactcaaaacatcccta | AA116410 |
| 6334 | gcatcgactcaaggtcaagacgt | M89777 | 48938 | ggtgacctgctatctccaagccca | W43968 | 91542 | atcatcactcaaaactccccttaaa | AA116410 |
| 6335 | tcaagcgactacgacacgacaa | M89777 | 48939 | gctatcctcaagccaggcaacaag | W43968 | 91543 | tctcatcactcaaaactccccttaaaa | AA116410 |
| 6336 | cagaggccgagagggctcaccggac | M89777 | 48940 | aaagtgctcaggtcagcatcggac | W43968 | 91544 | tttcacaaactactactcccatc | AA116410 |
| 6337 | cctactacggagactatgggtt | M89777 | 48941 | caggtcagcatcggaccggcatgc | W43968 | 91545 | tcttacatctactactacaaca | AA116410 |
| 6338 | accaggagtcttcacgcgtgca | M89777 | 48942 | agagaaaccgtcaccgcagca | W43968 | 91546 | cttacactctactactacactacaat | AA116410 |
| 6339 | cgcagtcaaaaactattcctggga | M89777 | 48943 | accacgcagaggtatcagcgtg | W43968 | 91547 | atctctactacactacaacattat | AA116410 |
| 6340 | tatactctgaggaattactttggtg | M29475 | 48944 | cgacaacttatctttggtcagagt | AA030364 | 91548 | atcctactacactacaacattatca | AA116410 |
| 6341 | gctaaggtctactatttcacagg | M29475 | 48945 | gacaacttatctttggtcagagt | AA030364 | 91549 | tcctactacactacaacattatcat | AA116410 |
| 6342 | gagactctccaatgccagcttg | M29475 | 48946 | gtggactccagccttgtcgtgc | AA030364 | 91550 | ctactactacaacattatcatca | AA116410 |
| 6343 | ctccatgccagccttggttaaact | M29475 | 48947 | tggactcagtcctagatgtcgtggcg | AA030364 | 91551 | ctactactacacaacattatcatcatctc | AA116410 |
| 6344 | tgatacatttgttcaatggcttcc | M29475 | 48948 | actcactagtatgctgcatcggac | AA030364 | 91552 | tacactacaacattatcatcactca | AA116410 |
| 6345 | atttgttcatagtcatcagt | M29475 | 48949 | actcactagtatgctgtcagtcta | AA030364 | 91553 | aaaccctgcaacagtagccattggtg | AA116677 |
| 6346 | tgttcaatggtcacgagtca | M29475 | 48950 | agaatttgactgctgcagggtt | AA030364 | 91554 | aaatggccaccatgcaattgacacaagg | AA116677 |
| 6347 | cacgagtcttactcttcctctgag | M29475 | 48951 | ttccagttgacactcactgggt | AA030364 | 91555 | aaatgccattccaattgacacaagg | AA116677 |
| 6348 | gagctactttcctctcgaggg | M29475 | 48952 | tccagtgacactccactggtg | AA030364 | 91556 | atgcattccaattgacacaaggt | AA116677 |
| 6349 | gtttagacaccaggatgcatgtac | M29475 | 48953 | gggcacagtcaggcatggggacac | AA030364 | 91557 | gccattccattccaattgacacaaggtgt | AA116677 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 6350 | tagacaccaggatgcaatgtactat | M29475 | 48954 | ggcacagctcaggcatgggcacact | AA030364 | 91558 | cattccaattgacacaaggctgtct | AA116677 |
| 6351 | aggactatattccatgtcaaatg | M29475 | 48955 | cacagctcaggcatgggcacactgc | AA030364 | 91559 | aattgacacaaggctgtctgaacct | AA116677 |
| 6352 | aaggtctcactatttcacaggctg | M29475 | 48956 | acaacttatcttggtcagagtgg | AA030364 | 91560 | ttgacacaaggctgtctgaacctg | AA116677 |
| 6353 | gtctcactatttcacaggctgacc | M29475 | 48957 | caacttatcttggtcagagtgt | AA030364 | 91561 | caaggctgtctgaacctgtgaatg | AA116677 |
| 6354 | tcactatttcacaggctgacctg | M29475 | 48958 | ttatcttggtcagagtggtgctgg | AA030364 | 91562 | aggctgtctgaacctgtgaatgt | AA116677 |
| 6355 | tttcacaggctgacctgaattg | M29475 | 48959 | atctttggtcagagtgtgctgca | AA030364 | 91563 | tgtctgaacctgtgaatggtacct | AA116677 |
| 6356 | tcacaggctgacctgaattgaga | M29475 | 48960 | ctttggtcagagtgtggctggcaac | AA030364 | 91564 | tcaaattgaaaggccccctgagattg | AA116677 |
| 6357 | caggctgacctgaattgagactc | M29475 | 48961 | tgctggcaacaactgggccaaagg | AA030364 | 91565 | tggttgccacatgctgaacccaatt | AA116677 |
| 6358 | gaattgagactccaatgccagc | M29475 | 48962 | caaatggggcaaaggcaactatacg | AA030364 | 91566 | gtgccacacatgctgaaccccaattgc | AA116677 |
| 6359 | tttgagactctccaatgccagcctt | M29475 | 48963 | ggttggactcagtcctagatgctgtg | AA030364 | 91567 | ccatgctgaaccccaattgctaaaat | AA116677 |
| 6360 | gagctactgcggagttcggctcacc | W50181 | 48964 | gccacggccgcatcgggtaagcaccg | X05021 | 91568 | atgctgaaccccaattgctaaaatgc | AA116701 |
| 6361 | agatctcaggagcatgttgtcagaa | W50181 | 48965 | gcacgtaagcaccggcaagcaccacc | X05021 | 91569 | gctgaacccaattgctaaaatgcct | AA116701 |
| 6362 | taagcaggtctgggatgggccaca | W50181 | 48966 | aaactggagttgtccccatcatga | X05021 | 91570 | ctaaaatgctgggtccaaggaatg | AA116701 |
| 6363 | atgtggccacactcagctgctgaa | W50181 | 48967 | tgctcccatcatgattgattgtcg | X05021 | 91571 | tgcctgggtccaaggaatgaaatt | AA116701 |
| 6364 | ccacacttcagctgtgtgacacagg | W50181 | 48968 | ctccalcatgatgttgttgtcgatc | X05021 | 91572 | tcaccgaaaaaatgccatccaat | AA116701 |
| 6365 | acttcagctgctgacacaggcttt | W50181 | 48969 | atgttgtcgatcaggctactacaa | X05021 | 91573 | caaatcagtgctggcacgctccgt | AA116701 |
| 6366 | ttcagctgctgacacaggcttct | W50181 | 48970 | caggctactacaaagtctgggccaa | X05021 | 91574 | acacagaccacatatgttaagtt | AA116701 |
| 6367 | cagctgctgacacaggcttctg | W50181 | 48971 | gctactacaaagtctgcggcaaggg | X05021 | 91575 | tgtccccaaatcttcaagtctggga | AA116701 |
| 6368 | tgctgacacaggcttctgagca | W50181 | 48972 | ctaagcaacctgtcatcgtgaaggc | X05021 | 91576 | ccccaaatcttcaagtctgggatgc | AA116701 |
| 6369 | ctgacacaggcttctgagcaag | W50181 | 48973 | ctgcatcgtgaaggccaaattctt | X05021 | 91577 | caaatctcaagtctggatgctgc | AA116701 |
| 6370 | acacaggcttctgagcaaggcga | W50181 | 48974 | cccaattctcagaagagctgaa | X05021 | 91578 | atctcaagtcgggatgctgccac | AA116701 |
| 6371 | acaggcttctgagcaaggcgat | W50181 | 48975 | aattcttcagcagaagctgagga | X05021 | 91579 | aagtcgggatgctgccacagtgga | AA116701 |
| 6372 | atctcagagacatgtgcagaagt | W50181 | 48976 | tcggtaagcaccgcaagcaccaagcag | X05021 | 91580 | atatgatcctcgtaagaaccatgtt | AA116701 |
| 6373 | aggcttctgagcaaggcgatgc | W50181 | 48977 | gtaagcaccgcaagcaccaagcagga | X05021 | 91581 | tgatctcgtaagaaccatgtt | AA116701 |
| 6374 | cagaagcctgcgttctgcgag | W50181 | 48978 | tgcggcattaccacttgaagaggaa | X05021 | 91582 | tctccgtaaaccccatgtgtgag | AA116701 |
| 6375 | ctgctggtctgccgggaaagtc | W50181 | 48979 | ggcattaccacttgaagaggaacca | X05021 | 91583 | ccgtaagaaccatgtgtgagaga | AA116701 |
| 6376 | tggtctgccgggaaagtcatct | W50181 | 48980 | accagctgtcgcccaacagtcaa | X05021 | 91584 | taagaaccatgttgagagatgc | AA116701 |
| 6377 | tgtctgccgggaaagtcatctt | W50181 | 48981 | agagttctgccaacagtcaactt | X05021 | 91585 | cgagacatatcgtaagttgc | AA116701 |
| 6378 | aagtcatctcatggagaacatgctg | W50181 | 48982 | tctgccaacagtcaacttgataa | X05021 | 91586 | accacatatgtgaagttgctca | AA116701 |
| 6379 | gtcatctcatggagaacatgctgg | W50181 | 48983 | aaccgtggacatggtcagggaga | X05021 | 91587 | ttgctcagtttaagagaagatcta | AA116701 |
| 6380 | tccatggcaaggtagctcagggtg | W50181 | 48984 | ggtaacaaccgagccaagatgtgc | X05021 | 91588 | agaagtatcaccgctgtataagctg | AA116701 |
| 6381 | cccccaaaacagaactcaggagcag | W50181 | 48985 | tgtgaatctgctggccctcgtc | X05021 | 91589 | tctatcaccgctgtataagctg | AA116701 |
| 6382 | caggtttaccacgcctgtgccatgc | W50181 | 48987 | gttcatctgaaagcgggggcatctg | X05021 | 91590 | atcaccgctgtataagctgtag | AA116701 |
| 6383 | aagtcgacgaccctcagctcatgg | W50181 | 48988 | catctgaaagcgggggcatctgat | X05021 | 91591 | accgtcgtgtataagctgtataag | AA116701 |
| 6384 | cacgaccctcagctcatgggccatca | W50186 | 48989 | tctgatgcctcctacagagcgac | X05021 | 91592 | gtaggagtgcccaaatcttcaagt | AA116710 |
| 6385 | atgggcatcatcccccgatcgcc | W50186 | 48990 | gcctcctctacagagccacaatggc | X05021 | 91593 | attccggatccatgatccagacagca | AA116710 |
| 6386 | atccccggatcgcccgagacatct | W50186 | 48991 | tctacagagccacaatggctctgac | X05021 | 91594 | catcaccaactacctgggccagtg | AA116710 |
| 6387 | cggatcgcccgagacatctcacc | W50186 | 48992 | acagagccacaatggctctgacg | X05021 | 91595 | tgtccaaggagctgtctcaagagtg | AA116710 |
| 6388 | ttcaaccacactctcatggat | W50186 | 48993 | caatggctgacgctggtgcac | X05021 | 91596 | tgccaaggagctgtctcaagagtaca | AA116710 |
| 6389 | aaccacatctactccatggatgaga | W50186 | 48994 | tgctgacgctggtgcacagc | X05021 | 91597 | caacggagctgctcaagagtaca | AA116710 |
| 6390 | aacctgagttccacattagaggtg | W50186 | 48995 | cgctggtgcacagctgccatc | X05021 | 91598 | ctctcggggcctattgcagtg | AA116710 |
| 6391 | ttactgataagatccgtgacctt | W50186 | 48996 | gtggcacagctgccctctgtcaga | X05021 | 91599 | cagctgcctgccaggccatcatg | AA116710 |
| 6392 | taagatccgtgaccttttgaatgg | W50186 | 48997 | aatctgctgggccctctgcagattg | X05021 | 91600 | gtccctgcaggccattcatgc | AA116710 |
| 6393 | gttaccacgcctgcccatgcga | W50186 | 48998 | gccctgcagattgccagagga | X05021 | 91601 | gtcctgcaggccattcatgtc | AA116710 |
| 6394 | tacaaggctgccatgcagatcg | W50186 | 48999 | ctcgcagattgccaaagacg | X05021 | 91602 | cggcaggccattcatgtcaac | AA116710 |
| 6395 | tgtgccatgcagatcgccaagaacg | W50186 | 49000 | cagattgcccagagaccacagagcc | X05021 | 91603 | caggccattcatgtcaccaggccc | AA116710 |
| 6396 | gtcaaagagcgcctttgctgctgctaca | W50186 | 49001 | cagattgcccagagaccacagagccc | X05021 | 91604 | atcatgtgcaccaggcccacacc | AA116710 |
| 6397 | ggctcaaacgcacaattttgctt | W50186 | 49002 | ggccagagaccatcagcaccactt | X05021 | 91605 | caccaactacctggcaccagtgt | AA116710 |
| 6398 | attttgcttatgacagacatct | W50186 | 49003 | aggaccatcagcaccttcagaa | X05021 | 91606 | ctacctgcaccagtgtctgat | AA116710 |
| 6399 | cagacatcctcaggggaaaacgcaca | W50186 |  |  |  | 91607 | cctgcaccagtgtctgagtgtc | AA116710 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 6400 | ggaaagctgcacgaccctcagctca | W50186 | 49004 | cggcacaggttccggctggtggct | | 91608 | ggcacaagtctgtctagtgcagc | AA116710 |
| 6401 | ttgagaaagcccaggactttagctga | X15788 | 49005 | ggcacaggttccggctggtggctt | | 91609 | gtctgctagtgtcagcccagcgct | AA116710 |
| 6402 | aagcccaggactttaggctgaagaggt | X15788 | 49006 | gcacaggttccggctgtggtggctt | | 91610 | tgctagtgtcagcccagcgctgtc | AA116710 |
| 6403 | atctcagatgcctgcaaacaatgg | X15788 | 49007 | tctcggtggcttcgatttttggcgt | | 91611 | tgtcagcccagcgctgcagcagt | AA116710 |
| 6404 | gatgcctgcaaacaatggcactag | X15788 | 49008 | tggcttcgatttttggcgtcagt | | 91612 | cgctgcagagtgcaacggcaagacc | AA116710 |
| 6405 | acaatggcactagagagctgcccaa | X15788 | 49009 | ttcgatttttggcgtcagtagtcg | | 91613 | tctcaacggttaccatgcaagacc | D00208 |
| 6406 | ttgtggactcagcgccatctg | X15788 | 49010 | gatttttggcgtcagtagtcgcgg | | 91614 | ttaccatggcaagaccctggagga | D00208 |
| 6407 | gacttcagccgccatctgggtttc | X15788 | 49011 | tgggtaacaaccgagccaagatgtt | | 91615 | tctttgagggctgcccagataagga | D00208 |
| 6408 | agcggccatctgggtttccacaca | X15788 | 49012 | cggcacaggttccggctggtggct | | 91616 | agtgaagactcctgcatgaagtgt | D00208 |
| 6409 | ggtcctcatagccaactcagcgca | X15788 | 49013 | ggcacaggttccggctggtggctt | | 91617 | gatctccgttggctgtgagata | D00208 |
| 6410 | ccatagccaactcagcgcagaggc | X15788 | 49014 | gcacaggttccggctggtgggctt | | 91618 | ccctggcgtggagatagtgcct | D00208 |
| 6411 | ccaactcagccgcagggcctgcttg | X15788 | 49015 | tctggctttcgatttttggcgt | | 91619 | tgagatagtgccttactctggcttc | D00208 |
| 6412 | ggcctgcttgctcctctgggcc | X15788 | 49016 | tggcttcgatttttggcgt | | 91620 | gatagtgccttactctggcttctc | D00208 |
| 6413 | agctcaagctgcattgcctgagtga | X15788 | 49017 | ttcgatttttggcgtcagtgcg | | 91621 | ttactctggcttctcgcacatgt | D00208 |
| 6414 | agctgcattgcctgagtgagaacat | X15788 | 49018 | gatttttggcgtcagtagtcgcgg | | 91622 | tggcttcttcgcacatgtcacagt | D00208 |
| 6415 | aagcatcaccgccgccagcaagggt | X15788 | 49019 | tgggtaacaaccgagccaagatgt | | 91623 | cgcacatgtcacagtgcacggctgagcaa | D00208 |
| 6416 | tgcagcgtgcagaggcctgctgt | X15788 | 49020 | ttcatccagaatgcaatgatcacg | | 91624 | acatgtcacagtgcagcaaatt | D00208 |
| 6417 | tgcgcacgcagtaggtaggtcca | W50073 | 49021 | tcattccagaatgcaatgatcacgg | | 91625 | taattgtccacctccacaaata | D00208 |
| 6418 | ctgagcttactgcggcctcgtgg | W50073 | 49022 | cagtgtcacagttacacacaggatact | | 91626 | ttgtgtccaactccacaaataca | D00208 |
| 6419 | cccacactctttcatcctagatgct | W50073 | 49023 | agtgtcacagttacacacaggatact | | 91627 | aagctgcattccagaaaggtgatgag | D00208 |
| 6420 | tctttcatccagatgcctgcaaaa | W50073 | 49024 | tgtcacagctacacacaggatactgt | | 91628 | aagttgactccaggagtactgt | D00208 |
| 6421 | cctgatcagctgtggtcactga | W50073 | 49025 | gtcacagctacacacaggatactgtg | | 91629 | gtgtctctgctcctgccatgccat | D00208 |
| 6422 | tgtatcagctgtggtcacctgcac | W50073 | 49026 | cacagctacacacaggatactgtggt | | 91630 | tctcctgccctgcattgccatgat | D00208 |
| 6423 | gtacccgcactgagagaaaatgcagg | W50073 | 49027 | agctacacacaggatactgtggtg | | 91631 | gcattgcatgtgcaatgaatt | D00208 |
| 6424 | ttggactccaggcgcacacatca | W50073 | 49028 | gctacacaggatactgtggtgt | | 91632 | aatctttgagggctgcccagatga | D00208 |
| 6425 | atcctggccaaccatcatcaaagc | W50073 | 49029 | acacaggatactgtggtgtac | | 91633 | ctaacatcccggctttgtagg | D00208 |
| 6426 | cctggccaaccatcatcaaagctg | W50073 | 49030 | tgtgttaccacaaatgaagaaccca | | 91634 | aagtgccactgcgtcgcccttgt | D00208 |
| 6427 | ggccaaccatcatcaaagctaggt | W50073 | 49031 | acacaaaatggaagaaccctacagtg | | 91635 | cttagcagcttcgattccaagt | D00208 |
| 6428 | ccaaccatcatcaaagctaggtaa | W50073 | 49032 | aatgatgaggcacctcacagcctag | | 91636 | tttgtatgccaggccagcctctag | D00208 |
| 6429 | aaccatcaaagctaggtaag | W50073 | 49033 | aaatggaagaaccatcagtgcact | | 91637 | tcagctcactcagaggatcctg | D00208 |
| 6430 | ccatcatcaaagctaggtaagt | W50073 | 49034 | gatgacggcacctcacacaggggcc | | 91638 | caggagattcctgacctctgggat | D00208 |
| 6431 | tgaacctgctaacaattccaactg | W50073 | 49035 | tacagtcaggtcagtgtcacagt | | 91639 | aggattcctgacctctgggatat | D00208 |
| 6432 | tgctacaatttccaactgccaaaa | W50073 | 49036 | acagtcaggtcagtgtcacagcta | | 91640 | cctgaccctgggattatgtctcc | D00208 |
| 6433 | ctgggtcactgcaacctttgt | W50073 | 49037 | agtcaggtcagtgtcacagtaca | | 91641 | gaccctgggatatgtcctcga | D00208 |
| 6434 | gtgggtcactgcaacctctttgttg | W50073 | 49038 | caggtcagtgtcacagtacacag | | 91642 | ggattatgtcctcgacattgggaa | D00208 |
| 6435 | tcacctgtcaacctcttgtgtacc | W50073 | 49039 | aggtcagtgtcacagtacacacag | | 91643 | ttatgtctccgacattgggaaacac | D00208 |
| 6436 | ctgaacctttgttgtacccgca | W50073 | 49040 | tccagtcacagtacacacaggata | | 91644 | tgctcctgacactcaccgaggg | D00208 |
| 6437 | gcaacctcttgttgtacccgcat | W50073 | 49041 | ttttcaaggaagcgacaggttct | | 91645 | cctttgagacactcaccgagg | D00208 |
| 6438 | cctttgttgtacccgcactgaga | W50073 | 49042 | ggtcttctcgagtgcgggcgaagca | | 91646 | gttttcagttttgctctcgtggag | U12570 |
| 6439 | tctttgttgtacccgcactgagaa | W50073 | 49043 | actctggccagttcatagccaaagt | | 91647 | ttgcttccttgtgaggctgaagt | U12570 |
| 6440 | tgtttgtacccgcactgagaaaatg | W50073 | 49044 | gaattgacctgtccatgaatgcctt | | 91648 | ctttcatttgaagccgaggctctg | U12570 |
| 6441 | aagctgcctgcctggatatccgca | W50073 | 49045 | acctgtccgtcctggatattg | | 91649 | ccgctcctaaagctggagtcttc | U12570 |
| 6442 | gctgcctgcctggatatcctgatt | X57528 | 49046 | tgtccatgatagccttaagtttgaa | | 91650 | cctggctcttgtctggaggaagcc | U12570 |
| 6443 | acgggtacacgcctgagcaagaca | X57528 | 49047 | ccatagccttaagttgaacat | | 91651 | ggctcttttgtgaggaggagctta | U12570 |
| 6444 | cggtacacgcctgagcaagaacaa | X57528 | 49048 | tgaacattagctgacctctgtt | | 91652 | tctttgctggaggagggctaagt | U12570 |
| 6445 | gacacaatgaccttctcagatggac | X57528 | 49049 | ttagctgacctctgtaaacat | | 91653 | taatgaccaagtaacttttgatga | U12570 |
| 6446 | acaatgaccttctcagatggactga | X57528 | 49050 | ttcaattccatacaattcagtgt | Z31553 | 91654 | atgttgctgggtgaggaccacaaagg | AA116752 |
| 6447 | atgaccttctcagatgatgaccc | X57528 | 49051 | atttcatacaatcagttgatt | Z31553 | 91655 | cagatacatagcatccacgtgtgc | AA116752 |
| 6448 | actgctaggttcagttgcatctgcc | X57528 | 49052 | attcaagttctttcatacatg | Z31553 | 91656 | cagatcacatagcatccacgtgtgc | AA116752 |
| 6449 | ggactcgtcagttgccatctgccta | X57528 | 49053 | tctcggggggggcgaagcagca | Z31553 | 91657 | atcacatagcatccacgtgctga | AA116752 |

| SEQ ID NO | sequence | DBAxnID | SEQ ID NO | sequence | DBAxnID | SEQ ID NO | sequence | DBAxnID |
|---|---|---|---|---|---|---|---|---|
| 6450 | gaccgacaggaccggagcagccag | X57528 | 49054 | tctgatgcggctgaagcagcagag | Z31553 | 91658 | gcatccacgtgctgagcttatag | AA116752 |
| 6451 | atgaagatcacagaccttcggagca | X57528 | 49055 | cattatcaaagcagcaccaaggaaa | Z31553 | 91659 | catccacgtgctgagcttataga | AA116752 |
| 6452 | aagatcacagaccttcggagcatca | X57528 | 49056 | ctgttaagcattccccattgctgat | Z31553 | 91660 | tccacgtgctgagcttatagaaa | AA116752 |
| 6453 | gcctgccggatatcctgatcctgc | X57528 | 49057 | agccatcccattgctgatgaactc | Z31553 | 91661 | ccacgtgctgagcttatagaaaa | AA116752 |
| 6454 | ctggatatcctgatcctggaatct | X57528 | 49058 | cccattgctgatgaactcggggcc | Z31553 | 91662 | aagaggatcgtgtctcgtggga | AA116752 |
| 6455 | gatatcctgatcctggaatctgca | X57528 | 49059 | atttgctgatgaactcggggccagt | Z31553 | 91663 | agatggatcgtgtctcgtgggaa | AA116752 |
| 6456 | atcctgatctcgaatctgcacgc | X57528 | 49060 | tgaactcggccagttcatagcaa | Z31553 | 91664 | atggatcgtgtctcgtgggaag | AA116752 |
| 6457 | ctggaatctgcacgcggtacca | X57528 | 49061 | cctcgaagccggatctctcctgt | Z31553 | 91665 | gaccacaaaaggagcaccaatggaa | AA116752 |
| 6458 | ctggaatctgcacgcggtacagc | X57528 | 49062 | cgaagcctcggatctctccggtcaa | Z31553 | 91666 | tggatcgtgtctcgtgggaagct | AA116752 |
| 6459 | cgaatctgcacgcggtacagcctg | X57528 | 49063 | tctcctggtcaactgaatgtcttg | Z31553 | 91667 | ggaagcagctggcttcactgtgtac | AA116752 |
| 6460 | tgcacgcggtacacgcctgagcaag | X57528 | 49064 | tctcctggtcaactgaatgtcttgg | AA030267 | 91668 | tggcttcactgtgtacgtgagtatc | AA116752 |
| 6461 | ccgtgctacctgctgaagtac | X57528 | 49065 | tcctggtcaactgaatgtcttggg | AA030267 | 91669 | tgagtactccagacatcatctaggggg | AA116752 |
| 6462 | tgtacctgctgaagtacagact | X57528 | 49066 | tcaactgaatgtcttgggaaaag | AA030267 | 91670 | ttctcggttcggggtcatacagac | AA116752 |
| 6463 | gcttagctgctgatccacttgaccca | M34476 | 49067 | aaaggtttgaccgaccagcatgtac | AA030267 | 91671 | ctcggtcttggggtcatacagatc | AA116752 |
| 6464 | tagtgatccacttgaccctgaccagg | M34476 | 49068 | aaggttgaccgaccagcatgtaag | AA030267 | 91672 | gtcatacagatcacatagcatccac | AA116752 |
| 6465 | ccaacttgaccgaggaagcctct | M34476 | 49069 | agcgttgaccgaccagcatgtaagg | AA030267 | 91673 | catacgatccacatcatctacccagt | AA116752 |
| 6466 | ccttgaccagaggaagcctctatt | M34476 | 49070 | gccgttgaccgaccagcatgtaagga | AA030267 | 91674 | tactgagccaccaaaactgagcgg | AA116778 |
| 6467 | tgaccccagaggaagcctctattat | M34476 | 49071 | aagcctcgatctcctggtccaact | AA030267 | 91675 | tggagccaccaaaactgagcgggat | AA116778 |
| 6468 | atattagctgccaaataagatcc | M34476 | 49072 | ctcgatctcctggtcaactgaat | AA030267 | 91676 | catgccaacagttgcattccattccac | AA116778 |
| 6469 | ctaaccgcgtgtcgcatatgctg | M34476 | 49073 | tcggatctcctggtcaactgaatg | AA030267 | 91677 | gtccaacagttgcattccattcaag | AA116778 |
| 6470 | cccccgtcgttgcatatgctgagt | M34476 | 49074 | cggatctcctggtcaactgaatgt | AA030267 | 91678 | cagttgcattccatcaagtctg | AA116778 |
| 6471 | gcgtgttcgcatatgctgagttt | M34476 | 49075 | ggatctcctggtcaactgaatgtc | AA030267 | 91679 | tttgcattccatcaagtctgagg | AA116778 |
| 6472 | tgttcgcatatgctgagtttcta | M34476 | 49076 | gatctcctggtcaactgaatgtct | AA030267 | 91680 | catcaagtctgaggtccagcacc | AA116778 |
| 6473 | acctcgtgaagtacagcactcat | M34476 | 49077 | atctcctggtcaactgaatgtctt | AA030267 | 91681 | gaaggcatcatctacagactct | AA116778 |
| 6474 | gaagtacagcactcatctcgaagct | M34476 | 49078 | ttctcctggtcaactgaatgtcttt | AA030267 | 91682 | aggcacatcatctacagactctgt | AA116778 |
| 6475 | tccattactctgtctgtgcctg | M34476 | 49079 | ctccagttctcagccaccggtagtg | AA030267 | 91683 | cacatcatctacagactctggaga | AA116778 |
| 6476 | ccctcatctcagccatcaggccagg | M34476 | 49080 | ccagttctcagccaccggtagtgtg | AA030267 | 91684 | atctacagactctggagagacagcac | AA116778 |
| 6477 | tcatctcagccatcagccaggggcc | M34476 | 49081 | aattatgtaacctgcagggtgtgcttt | AA154451 | 91685 | tacagactctggagagacagcactg | AA116778 |
| 6478 | gccctctcacacagagaggggcca | M34476 | 49082 | ttatgtaaccctgcagtgtgcttttc | AA154451 | 91686 | agccaccagactgagagggtggc | AA116778 |
| 6479 | tcctagcctctaccctgat | M34476 | 49083 | atgaaccctggagtgtgctttttca | AA154451 | 91687 | tggcatccaccagactgagagggatg | AA116778 |
| 6480 | gctgctagctgatccccacctgac | M34476 | 49084 | gtaacctggagtgtggcactttttgcagt | AA154451 | 91688 | catcaccagactgaggagtgagatg | AA116778 |
| 6481 | gctgaccatccagtcatccagtcc | W41501 | 49085 | ccaggtggcacctttgcttctg | AA154451 | 91689 | gtcttcctttgggccgaccag | AA116778 |
| 6482 | catccagttcatccagtcctactttt | W41501 | 49086 | tggtgcacctttttgtctgagtt | AA154451 | 91690 | tcctttgggccgaccagtccaac | AA116778 |
| 6483 | cacaaagatcctgactggacggc | W41501 | 49087 | agaaccccaggtgtcagaggggtgcg | AA154451 | 91691 | ttgggccgaccagtccaacagt | AA116778 |
| 6484 | cactgtgaccggcatcctggacggg | W41501 | 49088 | gtgcgtcctgcctgaatcaaagggt | AA154451 | 91692 | gggccagaccatgccaacagttg | AA116778 |
| 6485 | tgcaccgtgacatcctggacact | W41501 | 49089 | gcgtctgcctggaatcaaagggtct | AA154451 | 91693 | gaccatgccaacagttgcattcc | AA116778 |
| 6486 | tggccatgcgggacgaggtacatg | W41501 | 49090 | ttttgcagttactgcatgtgt | AA154451 | 91694 | tgtcatccagcattgcacagcac | AA116778 |
| 6487 | cggatacatgcgtggcgacaggtac | W41501 | 49091 | agttctcagccacgcgtagtgtgcg | AA154451 | 91695 | gtcatccagcattgcacagcaca | AA116756 |
| 6488 | gtacatgcgtggcgacaggctc | W41501 | 49092 | ttctcagccaccggtagtgtgcag | AA154451 | 91696 | cagcaacgtgaggcatgagaagc | AA116756 |
| 6489 | tgcgtgcaacggctctcgtcggtg | W41501 | 49093 | ctcagccaccggtagtgtgcgagca | AA154451 | 91697 | aagcagcagatgcggaagtaccgtg | AA116756 |
| 6490 | cggctcctgtcggttttgccatt | W41501 | 49094 | cagccaccggtagtgtgcgagcagt | AA154451 | 91698 | cagcagatgcggaagtaccgtgacaag | AA116756 |
| 6491 | cctgctctgttttgccattacaac | W41501 | 49095 | gcctccggttgctgattttcat | AA154451 | 91699 | gatgcgaagcgtaccgtgacaag | AA116756 |
| 6492 | gtttgcattaacgacagcagagt | W41501 | 49096 | ccggcttgtcgatttcatgaagtt | AA154451 | 91700 | atgcggaagctaccgtgacaaga | AA116756 |
| 6493 | ccagtcatccagtccactttgtg | W41501 | 49097 | tttgttctttcaaacgaaatgt | AA154451 | 91701 | acgtaccgtgacaagattgaggt | AA116756 |
| 6494 | ccagtcatccagttctgcgactat | W41501 | 49098 | tgtcttcaaacgaaatttgtcg | AA154451 | 91702 | gattgaggctgactgccaagaac | AA116756 |
| 6495 | gtcctactttgctcgtgactatgat | W41501 | 49099 | gagatctccttttgcactacaaag | Z31555 | 91703 | attgaggctgactgccaggcactct | AA116756 |
| 6496 | ctactttgtctgtgactatgatccc | W41501 | 49100 | tctcccatgtccctgtgtca | Z31555 | 91704 | ctgccaggacatcttgaacgatgt | AA116756 |
| 6497 | tcccaccatgaagattcctacaca | W41501 | 49101 | ggcatgaatccattcagaccatga | Z31555 | 91705 | tgccaggacatcttgaacgatgttc | AA116756 |
| 6498 | accatgaagattcctacacaca | W41501 | 49102 | aatcccatcagaccatgactgaag | Z31555 | 91706 | catccagcattcgacagcaccac | AA116756 |
| 6499 | tgaagattcctacacaagatctgc | W41501 | 49103 | attcagaccatgactgaagtcga | Z31555 | 91707 | atctccagcattcgacagcacaacg | AA116756 |

| SEQ ID NO | sequence | DBAxnID | SEQ ID NO | sequence | DBAxnID | SEQ ID NO | sequence | DBAxnID |
|---|---|---|---|---|---|---|---|---|
| 6500 | ttcctacaaagatctgcactgtg | W41501 | 49104 | gttcgagccagacaggtgaaggagt | Z31555 | 91708 | ctccagcattgcacagcacaacgtg | AA116756 |
| 6501 | ccggctcggctgcaaccatgatca | W51262 | 49105 | attgactgttgcaaggcagta | Z31555 | 91709 | tccagcattgcacagcacaagtga | AA116756 |
| 6502 | cggctcggctgcaaccatgatcaa | W51262 | 49106 | tgtttgcacaaggcagtaacgta | Z31555 | 91710 | cagcattgcacagcacaagtgagg | AA116756 |
| 6503 | aaccatgcaaccacttcctggag | W51262 | 49107 | cagcagatctctcttgccacccaga | Z31555 | 91711 | agcattgcacagcacaacgtgagc | AA116756 |
| 6504 | accatgatcaagcacttcctggag | W51262 | 49108 | cttgccaccagatggttaggatga | Z31555 | 91712 | cattcgacagcacaacgtgaggcat | AA116756 |
| 6505 | tggagttcagagccacgttggtc | W51262 | 49109 | gatgacatccgtaagcctggagaat | Z31555 | 91713 | acagcacaacgtgaggcatgagaag | AA116756 |
| 6506 | agttcagagccacgtgtggtccc | W51262 | 49110 | actgtaccattaccactgtgacta | Z31555 | 91714 | tttggatccatgcctgaagaagat | AA116793 |
| 6507 | agttcagagccacgtgtggtccca | W51262 | 49111 | catgatgcctgtgtcatccgga | Z31555 | 91715 | ggatccatgcctgaagaagatagg | AA116793 |
| 6508 | gttcagagccacgtgtggtcccag | W51262 | 49112 | gccctgtgtcatccggaacctca | Z31555 | 91716 | tattaatgctgattcttccatagaa | AA116793 |
| 6509 | ttcagagccacgtgtggtcccagc | W51262 | 49113 | tgtgtcatccgaacctcatcctg | Z31555 | 91717 | tgctgattcttccatagaaggaaat | AA116793 |
| 6510 | cagtcagcagtactctgtaccag | W51262 | 49114 | aacctcatccgtgacaacgtgtg | Z31555 | 91718 | tgattcttcatagaaggaaattac | AA116793 |
| 6511 | agtcagcagtactctgtaccagc | W51262 | 49115 | gccgaaatatcctggcgccctggcag | Z31555 | 91719 | ttacactctaagagttgattgcaca | AA116793 |
| 6512 | gtcagcagtactctgtaccagcc | W51262 | 49116 | atatctgccctggcgcagtcagc | Z31555 | 91720 | agttgattgcaccactgatgtac | AA116793 |
| 6513 | cggctcggctgcaaccatgatcaag | W51262 | 49117 | gcagacaagtgccaacttggaac | Z31555 | 91721 | tgattgcacaccactgatgtacagc | AA116793 |
| 6514 | gctcggctgcaaccatgatcaagca | W51262 | 49118 | tttgaatgcctgaaggtcatcc | Z31555 | 91722 | ttgcacaccactgatgtacagctta | AA116793 |
| 6515 | tcggctgcaaccatgatcaagcat | W51262 | 49119 | agagagtcccctacatgatgccatc | Z31555 | 91723 | agtgtacaacctaacacaaagagctg | AA116793 |
| 6516 | cggctgcaaccatgatcaagcactt | W51262 | 49120 | gtcctacatgatccatcatgat | Z31555 | 91724 | caacctaacaaagagctgcaaagc | AA116793 |
| 6517 | gctgcaaccatgatcaagcacttc | W51262 | 49121 | catcgccgcacaacttccaggcatt | Z31555 | 91725 | gctgcaaagcccagatgaaggttt | AA116793 |
| 6518 | ctgcaaccatgatcaagcactcc | W51262 | 49122 | cgcaaacttcaggccattgtgtgg | Z31555 | 91726 | ttgttttcaagctgggatgcagaa | AA116793 |
| 6519 | tgcaaccatgatcaagcactctg | W51262 | 49123 | agccatggctgcatcaacgctctg | Z31555 | 91727 | gtttgcaagctgggatgcagaagaa | AA116793 |
| 6520 | gcaaccatgatcaagcactcctg | W51262 | 49124 | ggtgcatcaacgctctgacacga | Z31555 | 91728 | cctcttgttcctactgaagtggca | AA116793 |
| 6521 | ggcatcactctatgggcaaagtgtt | M33581 | 49125 | agctctcgaggctgcatgcctttatt | Z31555 | 91729 | tggttctactgagtcgcagggaa | AA116793 |
| 6522 | aagtttactcagacatgggccacct | M33581 | 49126 | tgaggctgcatgccttattgtcc | Z31555 | 91730 | ggaacattcaagactcctaccaagag | AA116793 |
| 6523 | catageggttccaggttcagtag | M33581 | 49127 | cctattgtccgtggatgagact | Z31555 | 91731 | acattcaagactcctaccaagagga | AA116793 |
| 6524 | tcagccatgtgacctgccatcaaag | M33581 | 49128 | cactgagatcctcctaccatca | Z31555 | 91732 | actcctacaagagcgagtgtggct | AA116793 |
| 6525 | atgtgcactcatgcaaatgccatac | M33581 | 49129 | tccatcagctggccgtggcagagc | Z31555 | 91733 | cctacaagagcgaggtggcttat | AA116793 |
| 6526 | actcatgcaaatgccatacatgcag | M33581 | 49130 | ggtctgctggttcactgaggtt | Z31399 | 91734 | aacatctgcaaggtagtggcagtcc | AA116633 |
| 6527 | gcaaatgccatacatgcagaagtat | M33581 | 49131 | atalgccaaggcctggagatatt | Z31399 | 91735 | atctgcaaggtagtggcagtccgg | AA116633 |
| 6528 | tgtgcacacacgcacacattaac | M33581 | 49132 | acagctatgtgacaacgctggcttt | Z31399 | 91736 | tcatctactgcaggtgaattgaga | AA116633 |
| 6529 | cacacacgcacacattaaccaacga | M33581 | 49133 | caagctgcttgatgcccaaacaac | Z31399 | 91737 | catcctactgccaggtgaattgaa | AA116633 |
| 6530 | cgcaacattaaccaacgactagca | M33581 | 49134 | tgatgccacaaacatcctcaacaagc | Z31399 | 91738 | atctcactgccaggtgaattgagaa | AA116633 |
| 6531 | tcgtactgaaactcactacaatga | M33581 | 49135 | cacaacatgcgggtcgacaagcgcgg | Z31399 | 91739 | tccactgcaggtgaattgagaaaa | AA116633 |
| 6532 | tgaaactcactacaatgtatactta | M33581 | 49136 | caacaagcatgcgaaggagtatggtgat | Z31399 | 91740 | ctcactgcaggtgaattgagaaaag | AA116633 |
| 6533 | tactgacaatggcacctgagttc | M33581 | 49137 | acacgcacagggaggtatgtggtat | Z31399 | 91741 | tcctgtccgaagtggaacaatag | AA116633 |
| 6534 | gacatgggccacctgagttcagatcc | M33581 | 49138 | tgagaacatgccgacaacttccag | Z31399 | 91742 | tcctggtgccgaagtggacaatag | AA116633 |
| 6535 | cctatacactaaggtctctgcct | M33581 | 49139 | cgatgtcctgtcgcaggtcgtatgg | AA030557 | 91743 | gacaatatggctccattggcagca | AA116633 |
| 6536 | ttgtaatgccacactacgacaag | M33581 | 49140 | gtcgccgttatgggtcctgctc | AA030557 | 91744 | acaatatggctccatggcagcaa | AA116633 |
| 6537 | cagatcctgcaggtcagaggcaga | M33581 | 49141 | tatagttcattgtaccgctacacta | AA030557 | 91745 | caatatggctccattggcagcag | AA116633 |
| 6538 | ctgaggtccagtcgctggcaaac | M33581 | 49142 | atagttcattgtaccgctacacta | AA030557 | 91746 | catctgcaaggtagtccagttcagc | AA116633 |
| 6539 | tggcctgcaaacagctagcaac | M33581 | 49143 | agttcattgtaccgctacactaatg | AA030557 | 91747 | atctgcaaggtagtggcagttcgca | AA116633 |
| 6540 | gccaaacagctgcaactagcccg | M33581 | 49144 | tcattgtaccgctacactaatgatt | AA030557 | 91748 | tagtgccgctagatctacta | AA116633 |
| 6541 | ctatagtagatgccaaccatcct | L46815 | 49145 | cattgtaccgctacactaatgattc | AA030557 | 91749 | cagtccgcgctagatctaaattga | AA116633 |
| 6542 | catcctactgaaagagcacagct | L46815 | 49146 | tgtaccgctacactaatgattccg | AA030557 | 91750 | agtccgcagtagatctaaattgac | AA116633 |
| 6543 | tcctatacactataggtctctgct | L46815 | 49147 | taccgctacactaatgattccgtg | AA030557 | 91751 | gtccgcagtagatctaaattgacg | AA116633 |
| 6544 | acctatagctgtcctctgccagg | L46815 | 49148 | accgctacactaatgattccgtgt | AA030557 | 91752 | tccgcagtagatctaaattgacga | AA116633 |
| 6545 | caaagctggctctctatgattag | L46815 | 49149 | cgctacactaatgattccgtgtct | AA030557 | 91753 | gctcatccgcaggtgaattga | AA116633 |
| 6546 | gtggctcctctatgattagaaatac | L46815 | 49150 | tacactaatgattccgtgtctg | AA030557 | 91754 | gaacttaatccaatatatgaaag | AA116633 |
| 6547 | gaaatacctgcaggatgaaggaccc | L46815 | 49151 | gtcgtatgctctcgtccgttc | AA030557 | 91755 | ttaatccaatatatgaaagccct | AA116789 |
| 6548 | aggatggcccctagtcgggctgtt | L46815 | 49152 | acactaatgattccgtgtctcgc | AA030557 | 91756 | gagcacagctgtgtgtatattg | AA116789 |
| 6549 | ctgccctgaggaacaacgtcac | L46815 | 49153 | tcgtatgctctcgtctccgttcg | AA030557 | 91757 | atacaagaacctgaacctcgatg | AA116789 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 6550 | acgtcacattccttcatggtgga | L46815 | 49154 | tgcacctgccggatacctgatgc | AA030557 | 91758 | acaagaacctgaacctctgatgcc | AA116789 |
| 6551 | cattctcatgctggattaacg | L46815 | 49155 | ggataccctgatgccgtcctctag | AA030557 | 91759 | gaacctgaacctctgatgccatct | AA116789 |
| 6552 | cttcatggctggatttaagtatgtg | L46815 | 49156 | gacggtctcgtagtcgagtgtatag | AA030557 | 91760 | cgtgaacctctgatgccatccac | AA116789 |
| 6553 | ttctctgccatcagaggacacaaa | L46815 | 49157 | cggtctcgtagtcgagtgtatagt | AA030557 | 91761 | tgaacctctgatgccatcccacag | AA116789 |
| 6554 | tactttctagcatccagccgcaca | L46815 | 49158 | ggtctcgtagtcgagtgtatagtc | AA030557 | 91762 | aacctctgatgccatccacagt | AA116789 |
| 6555 | ctagcatctcagcagcacagactag | L46815 | 49159 | tctcgtagtcgagtgtatagtcat | AA030557 | 91763 | cctctgatgccatccacagtta | AA116789 |
| 6556 | tctcagcagcacagactagcagcag | L46815 | 49160 | atgccagcagttgcctggaagcc | AA108956 | 91764 | tgatgccatccacagtttattaa | AA116789 |
| 6557 | cagcagcacagactagcaggaaga | L46815 | 49161 | ccagcagttgtgcctgaagccta | AA108956 | 91765 | tcttactcagttctttcaccgatg | AA116789 |
| 6558 | ggttgccatcctttctccta | L46815 | 49162 | aacctcatcaagttcaggaaggaag | AA108956 | 91766 | atatatgaaagccctcttagactg | AA116789 |
| 6559 | ccatctcctttcctctatacactat | L46815 | 49163 | ctagaggcacacggcactgggtcc | AA108956 | 91767 | ttacttcagttctttcaccgatgat | AA116789 |
| 6560 | ccttttcctataccatataggct | L46815 | 49164 | cacggcgactggtccgagtgttg | AA108956 | 91768 | atgaaagccctcttagacgtgcaa | AA116789 |
| 6561 | gccgctgacgacggaacgaaatg | AA060409 | 49165 | attggctgccaccaccgccaccattg | AA108956 | 91769 | tagaagtgcaaaagccatggaagag | AA116789 |
| 6562 | ccgctgacgacggaacgaaaatgg | AA060409 | 49166 | agcaccattgccacgctgctccag | AA108956 | 91770 | gacgtgcaaaagccatggagaagct | AA116789 |
| 6563 | tgtctctcagatgaactaaagac | AA060409 | 49167 | attgccagctgctctcaggatggtc | AA108956 | 91771 | tgcaaaagccatgagagaagctagac | AA116789 |
| 6564 | gtctctcagatgaactaaagacg | AA060409 | 49168 | tctcaggatgctgagtgttatt | AA108956 | 91772 | ttagaagacgtcacagctgtgtgta | AA116789 |
| 6565 | ctctccagatgaactaaagacgaa | AA060409 | 49169 | tttattttgaccctgacgatgcct | AA108956 | 91773 | agaagacgtcacagctgtgtata | AA116789 |
| 6566 | agacgaactaccgagcggcacgt | AA060409 | 49170 | tggaactggagatgcctcagca | AA108956 | 91774 | aagcagctcacagctgttgtatatt | AA116789 |
| 6567 | taaatacaacatgatgatggcaga | AA060409 | 49171 | tgtgacgatgctcaggcaatatgt | AA108956 | 91775 | aaagttgcagctgctccctgcaca | AA116789 |
| 6568 | aataccaacatgtagatggcagagt | AA060409 | 49172 | gcagttgctggaagccttatag | AA108956 | 91776 | cttccctgcacaaacgagacagaca | W08028 |
| 6569 | atgccagagtctgtaccgcctctg | AA060409 | 49173 | gatgcctcaggccaatatgtgtcac | AA108956 | 91777 | ctctccattccggaaacgtgcatttta | W08028 |
| 6570 | atggcagagtctgtaccgcctctg | AA060409 | 49174 | gtgcctgaagccttatagaccaac | AA108956 | 91778 | ttcattccgacgtgcatttacca | W08028 |
| 6571 | ggcagagtctgtaccgcctctgt | AA060409 | 49175 | atgaccaacatcaggcagaaaac | AA108956 | 91779 | gacgtgcatttaccacaacctgcagc | W08028 |
| 6572 | gcagagtctgtaccgcgcctctgtt | AA060409 | 49176 | gaccaacatcaggcagaaaccaacca | AA108956 | 91780 | gtgcatttaccaacctgcacgcggg | W08028 |
| 6573 | gagtctttgtgggttgatgtg | AA060409 | 49177 | ccatgggcagaaaccaattaca | AA108956 | 91781 | catttaccaacctgcacgcggggca | W08028 |
| 6574 | gaaaccacaatgctgctattataa | AA060409 | 49178 | cccaattacactcaagaagtttgcat | AA108956 | 91782 | tttaccaacctgcagggggcgca | W08028 |
| 6575 | caaggataaagcctgtgtgtctg | AA060409 | 49179 | aagtttgtcatcaggtggctgtgaca | AA108956 | 91783 | accaacctgcagcggggcagtcatg | W08028 |
| 6576 | atgaacgcctgggtctgctggatga | AA060409 | 49180 | gacaactccatcaagctatggagg | AA108956 | 91784 | aacctgcagcggggcagtcatgtc | W08028 |
| 6577 | agctcgggggtctctccagatga | AA060409 | 49181 | atctccagccgctcggggagaagga | AA108956 | 91785 | ctgcaggcggggcagtcagtcttt | W08028 |
| 6578 | gggtgtctccagatgaactaaa | AA060409 | 49182 | ccgagcccagcaccctacctgaa | AA030569 | 91786 | ccattcgaacgaagatgacttg | W08028 |
| 6579 | gggtgtctccagatgaactaaag | AA060409 | 49183 | gaacctggagccagcagccactgaa | AA030569 | 91787 | ccctgcacaaacgagcagacatca | W08028 |
| 6580 | ggtctctccagatgaactaaaga | AA060409 | 49184 | gcacatccagccgcctgcgggaa | AA030569 | 91788 | cctgtaagctgagctcggacagag | W08028 |
| 6581 | cctcaggtccactgcagataaagatg | AA060409 | 49185 | atctccagccgcctcaagctatgggagg | AA030569 | 91789 | aaacggacagcatcacagtgtca | W08028 |
| 6582 | ggcacctatgctcgtgtggccaccc | L33412 | 49186 | atctccagccgcctcggagaagga | AA030569 | 91790 | acagacacatggtcaaggcct | W08028 |
| 6583 | taaggcacccagatgcgctccactg | L33412 | 49187 | ccgagccccagcagccactgaa | AA030569 | 91791 | ttcctgacctgacactcagcctg | W08028 |
| 6584 | caccgatgccagctgtgtgatgg | L33412 | 49188 | gaacctggagccagcagccactgaaga | AA030569 | 91792 | gacactcagcctctctcttcatcc | W08028 |
| 6585 | gatccggctgtgctgtggccctag | L33412 | 49189 | ctgcagccagccagccactgaagacacg | AA030569 | 91793 | actcagcctgtctctcttcattccgg | W08028 |
| 6586 | gcctgtgatggccatggccctag | L33412 | 49190 | ggcagccagccactgaagaacg | AA030569 | 91794 | cagcctgtctctcttcattccgaag | W08028 |
| 6587 | caattcctctgaggcactcct | L33412 | 49191 | cagccagccactgaagacgca | AA030569 | 91795 | cctgtctctcttcattcggagtgc | W08028 |
| 6588 | ctccttgaggcactccttccaa | L33412 | 49192 | gccagccactgaagacacgcacatt | AA030569 | 91796 | attggcgcttgtgtacatggagt | W08028 |
| 6589 | gaggcactccttccaaccccagag | L33412 | 49193 | agtccaacaagaacatattactgga | AA030569 | 91797 | tgttcgaaagaaccaagatggag | W08028 |
| 6590 | acgaggcccacatcagatccatgctg | L33412 | 49194 | ccagcaagaacatatacctgaacgt | AA030569 | 91798 | ctctgcaagctgaagctgggaagaa | W08033 |
| 6591 | gcccacatgatccatgctgagtaaa | L33412 | 49195 | agaacataatccgaacgtggccgt | AA030569 | 91799 | aagtcggtggcctcatctgtgaa | W08033 |
| 6592 | atgatccatgctgagtaaacatttg | L33412 | 49196 | aacatatacctgaacgtggccgtga | AA030569 | 91800 | gtctgggtgccatctctgtgaagc | W08033 |
| 6593 | ggacctcaggaagccctcctgtca | L33412 | 49197 | catatacctgaacgtggccgtgaac | AA030569 | 91801 | ctggtgccctcatctctgaagcct | W08033 |
| 6594 | caggaagccctccgtcagcatca | L33412 | 49198 | tataccctgaacgtggccgtgaacac | AA030569 | 91802 | cagcctgtctcttcattccgaag | W08033 |
| 6595 | agccctctgcagcatgcagagtca | L33412 | 49199 | tacctgaacgtggccgtgaacacgca | AA030569 | 91803 | gtgcctcatctgtgaagcctttg | W08033 |
| 6596 | cctgtcagcatgggtcacagaaa | L33412 | 49200 | caaaccgtgccaacacagagaggt | AA030569 | 91804 | gcctcatctgtgaagcctttgtgaa | W08033 |
| 6597 | acagaaaccgcgatgagggccag | L33412 | 49201 | ttgaaccttgcctgcatgcataac | D12644 | 91805 | catatctgtgaagcctttgtgaacg | W08033 |
| 6598 | ctgagcccgctggggatctcg | L33412 | 49202 | ttgcgtgcattcatacctcatgagt | D12644 | 91806 | catctgtgaagccttgtggaacga | W08033 |
| 6599 | gccctgctcgtggggatccctct | L33412 | 49203 | ctaaggctattgaccctagatttct | D12644 | 91807 | tactggccttttcatttatctataa | W08033 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 6600 | ggaccgtaagagcgcaccgatcgag | L33412 | 49204 | gattaattacattcctgttttgtga | D12644 | 91808 | ttttgagatggccacgagagctgc | W08033 |
| 6601 | agaggaacctgaatccatcttcaatga | W50092 | 49205 | taattacattcctgttgtgactg | D12644 | 91809 | taattacctaagattacaaatcag | W08033 |
| 6602 | ggaacctgaatccatctcaatga | W50092 | 49206 | cattcctgttgtgactgtaaatt | D12644 | 91810 | tgagatggccacgagagctgctctg | W08033 |
| 6603 | tcatcatcactgtcatggacaaga | W50092 | 49207 | tacattttacgtattgagacat | D12644 | 91811 | agatggccacgagagctgctctgca | W08033 |
| 6604 | aagacaagctcatgtcaatgacgt | W50092 | 49208 | taattttcaggatgtgcatatca | D12644 | 91812 | atggccacgagagctgctctgcaag | W08033 |
| 6605 | acaagctcatgtgcaatgacgtcat | W50092 | 49209 | gacatagctgctgaccattccatc | D12644 | 91813 | ccacgagagctgctctgcaagctag | W08033 |
| 6606 | gcaatgacgtcatgtcaagatcta | W50092 | 49210 | ggaccatccatcttatgttaaag | D12644 | 91814 | gagagctgctctgcaagctagacgt | W08033 |
| 6607 | tcattgcaagatctacctgtcctg | W50092 | 49211 | ttccatctatgtttaagaaatct | D12644 | 91815 | gagctgctctgcaagctagacgtgg | W08033 |
| 6608 | ttggcaagatctacctgtcctggaa | W50092 | 49212 | tatacatgcagtgtgtgccag | D12644 | 91816 | tgctgcaagctagacgtgggaag | W08033 |
| 6609 | gcaagatctacctgtcctggaagat | W50092 | 49213 | cgtgcatgcataccatcatgagtgat | D12644 | 91817 | gaatgccagcttccggatgttg | W08033 |
| 6610 | agatcggacaggtgaggtgaagca | W50092 | 49214 | catgcataccatcatgagtgatgt | D12644 | 91818 | tgccagcttccggatgttg | AA116951 |
| 6611 | aagacatgatcgctgtcccggca | W50092 | 49215 | atacctcatgagtgattgtacatac | D12644 | 91819 | tcctgagcagtgtgcagcagaac | AA116951 |
| 6612 | ctcgtcccgcatgcgtgttgctca | W50092 | 49216 | tgtacatacttgcctactcctag | D12644 | 91820 | tgaagcagtgtgcagcagaactct | AA116951 |
| 6613 | acctgaatccatctcaatgagtc | W50092 | 49217 | ctactcctagagacactcgtgctta | D12644 | 91821 | gcagcagaactctctcatcaactct | AA116951 |
| 6614 | tgaatccatctcaatgagtctt | W50092 | 49218 | ctagagacactcgtgctactcatc | D12644 | 91822 | gcagaactctctctcatcaactctggt | AA116951 |
| 6615 | tttacatacccactgatttctgag | W50092 | 49219 | cttactcatcctctgtgcctggc | D12644 | 91823 | gaactctctctcaactctggtagg | AA116951 |
| 6616 | taccactgatttctgaggaggtc | W50092 | 49220 | actccatcctctgtgcctggtaa | D12644 | 91824 | ctctctatcaactctggtaggccg | AA116951 |
| 6617 | attttctgaggaggtccatcat | W50092 | 49221 | cagccaggctggagaggctgccaag | D12644 | 91825 | tctatcaacttctggtaggccgctg | AA116951 |
| 6618 | ggggtccatcatcatcatcactgt | M83380 | 49222 | tttgcgggcttccaagtggtgccg | D16464 | 91826 | atcaacttctggtaggccgtgagt | AA116951 |
| 6619 | agtccatcatcatcatcactgtcat | W50092 | 49223 | cactctgggacttccatgtggagacg | D16464 | 91827 | aacttctggtaggccgctgagtgct | AA116951 |
| 6620 | ccatcatcatcatcatcactgtcat | W50092 | 49224 | ttccgacctcatgtggagccgtgg | D16464 | 91828 | ttctggtaggccgctgagtgctgca | AA116951 |
| 6621 | ctctcatcatgttgacctgctgc | W50092 | 49225 | gagaccgtgggaactgaggaggct | D16464 | 91829 | ccagcttccggagatgttgaga | AA116951 |
| 6622 | gcaccactctgccatgctgtgg | M83380 | 49226 | gaactgagaccgtcaggccactgct | D16464 | 91830 | gcagacccgcagtcttgccaagt | AA116951 |
| 6623 | ccattccgaagccaacctga | M83380 | 49227 | tcagccatgctacccgtaaagtc | D16464 | 91831 | gacccgcagtcttgccaagtatg | AA116951 |
| 6624 | attccgaagccaacctgatcagc | M83380 | 49228 | agtgactgaacactgcactgcattg | D16464 | 91832 | cccgcagtctgccaagtatgcag | AA116951 |
| 6625 | atcagtcttccagtcctctcat | M83380 | 49229 | gactcatgcactgcattgtat | D16464 | 91833 | gcagctctggccaagtatggaag | AA116951 |
| 6626 | cttccagttcctctcatctgaatcg | M83380 | 49230 | tgaccatgcactgcattgtata | D16464 | 91834 | gtaaaggcctctcgaagcagctgtg | AA116951 |
| 6627 | tcatccgaatctggacatctgcagc | M83380 | 49231 | catattgattgcgctttgtatta | D16464 | 91835 | aaggcctctgaagcagctgtgcag | AA116951 |
| 6628 | tgagccatttacagaaatgctgag | M83380 | 49232 | attgattgcgcctttgtattataa | D16464 | 91836 | gcctctgaagcagctgtgcagctgcag | AA116951 |
| 6629 | gctcctgcagtgagccccttctca | M83380 | 49233 | cgggttccaagtggtgccgggctcct | D16464 | 91837 | agatcttgggccggatgcccat | AA116951 |
| 6630 | gcagatggaccccttcagatctcagggacag | M83380 | 49234 | tgacggccaaattgcctttcatc | D16464 | 91838 | tgccatttgtgtgctcgaagctt | U12785 |
| 6631 | ggaccccttcagagcagatctc | M83380 | 49235 | ggtcaccccggtcacaccacagcaac | D16464 | 91839 | acatcactgcgccacttgccctt | U12785 |
| 6632 | cttctcaggacagatctctcagagat | M83380 | 49236 | cccggtctacacacacccagcaacgggg | D16464 | 91840 | tgagtctctgcggaatgaagaagc | U12785 |
| 6633 | ctgaactctttgcagtcgggtga | M83380 | 49237 | ggtcatacacccagcaacagtggaa | D16464 | 91841 | gccaagcaagatgcccccgatg | U12785 |
| 6634 | ggtactgctagcctgttgggcagca | M83380 | 49238 | tcctaaggcagtgtcaacctccagt | D16464 | 91842 | gacacttgtttgtctggtgtctg | U12785 |
| 6635 | ggcagcaacatgttctccaaccagt | M83380 | 49239 | taacgcagtgtcaacctccagtgcc | D16464 | 91843 | tgttttgcggctgctgtcctg | U12785 |
| 6636 | ggcctctcaacttccagggcctgag | M83380 | 49240 | cgcagtgctgtcaaccctccagtggctcc | D16464 | 91844 | tgtctcaaggcctcatcctggct | U12785 |
| 6637 | ccaggggccctagacacgtagcctc | M83380 | 49241 | atgcctctcgaaggtgaccgc | D16464 | 91845 | ttgctcaggagcctcatcctggct | U12785 |
| 6638 | cctgagccagtagcctctgagtg | M83380 | 49242 | tatttttgccaagttcaagtgat | Z31557 | 91846 | acggagcctcatctaccgaaggtctc | Z31557 |
| 6639 | tagcctctgaggttacagaggagc | M83380 | 49243 | atggtttctctaaataaggcatg | Z31557 | 91847 | catgctcaactaccccggaaggctctc | Z31557 |
| 6640 | gtatagcactccattccgaagccca | M83380 | 49244 | ttctccaataaggcatgtgaca | Z31557 | 91848 | ctgctgtttcgaagcgatgaga | Z31557 |
| 6641 | gaagcactgactgaaccattgtc | W50213 | 49245 | acatgactgtaagcctagcccttg | Z31557 | 91849 | tgtgtgttcgaagcttgaatga | Z31557 |
| 6642 | actgactgaaccattgtcctgtc | W50213 | 49246 | gaattttcatgccaactcaggctac | Z31557 | 91850 | gtgttgaagcttggatggaggccat | Z31557 |
| 6643 | atgcaagtatctcactccttgtca | W50213 | 49247 | ctatgccaactcaaggtccaggaga | Z31557 | 91851 | ttatcaaccacgcgcaagaaggccct | Z31557 |
| 6644 | aacttaccgttctgtatgccag | W50213 | 49248 | caactcaggctacaaggagaccccag | Z31557 | 91852 | tggacttcatgtttccaacaa | Z31557 |
| 6645 | ccgttctgtatgccaagtaccca | W50213 | 49249 | ttgaaattatccacactagcctg | Z31557 | 91853 | tctatgtctcccaacaatgacaa | Z31557 |
| 6646 | ctgtatgccagtaccacagcgcag | W50213 | 49250 | ctccgttaacatgtaagatcct | Z31557 | 91854 | tgtctccacaatgacaagtgat | Z31557 |
| 6647 | tgtccagtaccacagcagaggcc | W50213 | 49251 | catgtaagatcctgccagtgtaaa | Z31557 | 91855 | acgtcattgttcatcactgtgcc | U12785 |
| 6648 | gaccccagagctccagcagaggctg | W50213 | 49252 | agacctgccagtgtaaaacacat | Z31557 | 91856 | ttgttcactcactgccccatt | U12785 |
| 6649 | acagcagagctccagcgtctctc | W50213 | 49253 | tgtcaagcttcaagtgattggaa | Z31557 | 91857 | caacatcccaacagcagaaccg | AA117004 |

TABLE 1-continued

| SEQ ID NO | DBAxnID | sequence | SEQ ID NO | sequence | DBAxnID | SEQ ID NO | sequence | DBAxnID |
|---|---|---|---|---|---|---|---|---|
| 6650 | W50213 | gaggtccagctgtctccaagtac | 49254 | ggacatttgacacctattcaaatta | Z31557 | 91858 | aacattcccaacaagcagacaccga | AA117004 |
| 6651 | W50213 | ccagctgctcctcaagtactatca | 49255 | ttgacacctattcaaattatacgt | Z31557 | 91859 | ccgacttcaacaactaatcctgaac | AA117004 |
| 6652 | W50213 | ctattcaggagaccagtgttcaa | 49256 | gacacctcaaagcagctcttttcaa | Z31557 | 91860 | gactttcaacaactaatcctgcaac | AA117004 |
| 6653 | W50213 | ccgttctctgctgcagctgaat | 49257 | caaagcagctcttttcaaccact | Z31557 | 91861 | ctttcaacaactaatcctgcaacca | AA117004 |
| 6654 | W50213 | ctctgctgcagctgaattgagtt | 49258 | ttttcaaccactgaacaagatgt | Z31557 | 91862 | tttcaacaactaatcctgcaaccaa | AA117004 |
| 6655 | W50213 | ttgagttgccaagctcagtcagtg | 49259 | accactgaacagatgttagct | Z31557 | 91863 | tcaacaactaatcctgcaaccaacc | AA117004 |
| 6656 | W50213 | tgccaagctcagtcagtgactcaa | 49260 | agatgtttagctacaccgatacaa | Z31557 | 91864 | caacaactaatcctgcaaccaacct | AA117004 |
| 6657 | W50213 | gtcagtgactcaacctgatgctcat | 49261 | gggatgtcgccacagtccaggcaa | AA030482 | 91865 | acaactaatcctgcaaccaacctg | AA117004 |
| 6658 | W50213 | gactcaacctgatgctcatgtcact | 49262 | gccacagtccaggcaaccacaagg | AA030482 | 91866 | aactaatcctgcaaccaacctgt | AA117004 |
| 6659 | W50213 | acctgatgctcatgtcactgtct | 49263 | ctcagcctttgcaggaggattta | AA030482 | 91867 | ctaatcctgcaaccaacctgtgta | AA117004 |
| 6660 | W50213 | tgctcatgtcactgtctgaagaa | 49264 | ttactagggcgcatcaggggctct | AA030482 | 91868 | taatcctgcaaccaacctgtgtaa | AA117004 |
| 6661 | W50213 | ggaacactggttcatccttttctg | 49265 | actaggggcatcatgggctgtgg | AA030482 | 91869 | acattcccaacaagcagacaccgac | AA117004 |
| 6662 | W50213 | atccttatctcggcctctacgtg | 49266 | ggccatcatgggctctgtgaattcc | AA030482 | 91870 | aatcctgcaaccaacctgtgtaat | AA117004 |
| 6663 | J00621 | ggctctccatgccagtgacatccca | 49267 | calcatgggctctgtgaattccaga | AA030482 | 91871 | altcccaacaagcagacaccgactt | AA117013 |
| 6664 | J00621 | tgcaccttcatccgcaagttctat | 49268 | gaattccagaaggtcacaagcagag | AA030482 | 91872 | ttcccaacaagcagacaccgacttt | AA117013 |
| 6665 | J00621 | cttcatccgcaagttctatacagag | 49269 | tcaacaaggcagaggcccaggggta | AA030482 | 91873 | tcccaacaagcagacaccgactttc | AA117013 |
| 6666 | J00621 | tcggcataacactcgtctggattc | 49270 | aatggaggcctcgactcgctggc | AA030482 | 91874 | caacaagcagacaccgactttcaac | AA117013 |
| 6667 | J00621 | taacaatcggttggattcgcctg | 49271 | cctcgactcgctgcgcaagaccaca | AA030482 | 91875 | acaagcagacaccgactttcaacaa | AA117013 |
| 6668 | J00621 | cagtaacctaggccaagccaagt | 49272 | cgactctggccaagaccaagt | AA030482 | 91876 | caagcagacaccgactttcaacaac | AA117013 |
| 6669 | J00621 | ccctaggccaagccaagctggact | 49273 | acagtccaggcaaccacgagaggta | AA030482 | 91877 | caccgactttcaactaactcctg | AA117013 |
| 6670 | J00621 | gccaagccaagctggcactcttgg | 49274 | cacaattcgtacaaactgaaagga | AA030482 | 91878 | tcaacatcggcatcgagggctcga | AA117013 |
| 6671 | J00621 | tggcactcttgggggccatttgtct | 49275 | gtccaggcaaccacgagagggtagga | AA030482 | 91879 | caacatcggcatcggggggctcgac | AA117013 |
| 6672 | J00621 | ttttgtcgcttgtcccaacatg | 49276 | gccaaccacagaggggtaggagctcag | AA030482 | 91880 | atggtgactgacactccaagccct | AA117013 |
| 6673 | J00621 | tacgagctcccgaagttgatcatg | 49277 | aggagctcagttcatgcatgcatg | AA030482 | 91881 | tggtgactgacactccaagccta | AA117013 |
| 6674 | J00621 | ctccctgaagttgatcatcgaagcc | 49278 | agctcagtcatgcatgcatgg | AA030482 | 91882 | ggtgactgcactccaagccctga | AA117013 |
| 6675 | J00621 | cagggctacacactcagctggatcc | 49279 | gattgcatttctcagaaaagtgc | AA030482 | 91883 | gtgactgcactccaagccctact | AA117013 |
| 6676 | J00621 | ctacacactcagctggactgactac | 49280 | ttgcatttctcagaaaagntgac | AA030482 | 91884 | gagccctccaattccagacaccga | AA117013 |
| 6677 | J00621 | actcagctgactgactacgtgcta | 49281 | ctgatgtgctctcagctcttctg | AA030482 | 91885 | gccctccaattccagacaccgaag | AA117013 |
| 6678 | J00621 | cagtacgactgtgctcagtat | 49282 | tcggcacgatggtgactggatatg | AA030590 | 91386 | cttccaattccagacacgaaggag | AA117013 |
| 6679 | J00621 | cggtcacagatcccaacaagagaga | 49283 | gaattcctaattaaccaaacgac | AA030590 | 91887 | ttccaattccagacaccgaaggagg | AA117013 |
| 6680 | J00621 | acagtaatcccaacaagagaggacaag | 49284 | attgattgctgtttccaaccacta | AA030590 | 91888 | tccaattccagacaccgaaggaggg | AA117013 |
| 6681 | AA071777 | cttaggacacactggctgtgctccct | 49285 | tgattgctgtgttccaacactag | AA030590 | 91889 | aacatcggcatggggggctgacc | AA117013 |
| 6682 | AA071777 | tgtgctgctctgctcatggacaag | 49286 | aggacattatactgctttgcaaag | AA030590 | 91890 | ctgactggaccctcatgctgac | AA117013 |
| 6683 | AA071777 | agtcagtatgtcatcctgaacgcg | 49287 | gacattatactgctttgcaaaaa | AA030590 | 91891 | tgactggaccctcatggtgact | AA117013 |
| 6684 | AA071777 | cagtatgtcatcctgaaagcgctg | 49288 | ttctaccagagacaggacactttca | AA030590 | 91892 | acctggaccctcatggtgactga | AA117013 |
| 6685 | AA071777 | tattgcatcctgaacgcgctggac | 49289 | ctaccagagacaggacacttcagt | AA030590 | 91893 | cctggaccctcatggtgactgac | AA117013 |
| 6686 | AA071777 | atcctgaacgcgctggacgtcgtg | 49290 | gacccagagacaggacactttcagtgggactgg | AA030590 | 91894 | tggaccctcatggtgactgac | AA117013 |
| 6687 | AA071777 | ctggaacgcgctggacgtcgtgact | 49291 | caggacacttcagtgggactgtg | AA030590 | 91895 | ggaccctcatggtgactgacact | AA117013 |
| 6688 | AA071777 | gaacgcgctggacgtcgtgactgtt | 49292 | ggacactttcagtgggactggctc | AA030590 | 91896 | catggtgactgacactccaagcc | AA117013 |
| 6689 | AA071777 | gctggacgtcgtgactgttgaactc | 49293 | acacttcagtgggactggcttt | AA030590 | 91897 | gtcctgtgactgtgtgcatac | AA117013 |
| 6690 | AA071777 | tgttgaactctaccctcgacacaag | 49294 | ttaacccaaatgcaggtcctgccg | AA030590 | 91898 | ccgtcgaggactggtgcataag | AA117013 |
| 6691 | AA071777 | ggcctcggttcctcgacacgcctg | 49295 | cccaaatgcaggtcctgccgtat | AA030590 | 91899 | agtgtctccttaatagaattag | AA116993 |
| 6692 | AA071777 | cggttcctcgaatgcctgtgtaag | 49296 | caaatgcaggtcctgccgctataa | AA030590 | 91900 | atgaaggtcatctacgagagact | AA116993 |
| 6693 | AA071777 | tctgctcatggacaagatggccagg | 49297 | aatgcaggtcctgccgctataat | AA030590 | 91901 | tagaatctgtctatggcgtattct | AA116993 |
| 6694 | AA071777 | cctgaatggcctgttgaagctggca | 49298 | tgcaggtcctgccgctataattg | AA030590 | 91902 | atcttgtctagggtattctgaag | AA116993 |
| 6695 | AA071777 | gtcctgttcctgctctccctg | 49299 | caggtcctgccgctataattgat | AA030590 | 91903 | cttgtctatgggtattctgaagca | AA116993 |
| 6696 | AA071777 | cttcctgtttttggaacagtgag | 49300 | ggtcctgccgctataatttgatg | AA030590 | 91904 | gtatctgaagcattcactaaaggt | AA116993 |
| 6697 | AA071777 | cctgttttggaacagtagtca | 49301 | tcctgccgctataatttgattgct | AA030590 | 91905 | tctgaagcattcactaaaggttcac | AA116993 |
| 6698 | AA071777 | gtcaggatcctgctctgc | 49302 | ggcgttccggttgtcaacgtga | X65453 | 91906 | ggttcacagtgtttcagctgactg | AA116993 |
| 6699 | AA071777 | agccatgatcgctctgcctt | 49303 | gcaagccaagtgatccacagagtg | X65453 | 91907 | ttcacagtgttcagctgactgcc | AA116993 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 6700 | catgatcgctctgctctgcctttt | AA071777 | 49304 | tgctgcagtctcctactacaca | X65453 | 91908 | cacagtgttcagctgctgctgccaa | AA116993 |
| 6701 | cgctctgctgcctttgggga | AA071777 | 49305 | tccctacagacaagtcagtagga | X65453 | 91909 | cagtactcatacaacttcgatct | AA116993 |
| 6702 | tctcccacattaaaatgaaaactgc | M80360 | 49306 | tttataacctaggatcctcctcat | X65453 | 91910 | cagttgttcagctgtactgccaaga | AA116993 |
| 6703 | gattcaaactgtacaaacaactct | M80360 | 49307 | gtaccccaaggcacatagactgg | X65453 | 91911 | gtacatcataacttcgatctct | AA116993 |
| 6704 | aggttctggtgcctacattacag | M80360 | 49308 | tgctcctaagaacttacaactga | X65453 | 91912 | atcatacaacttcgatctctgatg | AA116993 |
| 6705 | ttgtgcctacattatcagggggc | M80360 | 49309 | ctaagaacttacaactgaaacagc | X65453 | 91913 | catacaacttcgatctctgatgac | AA116993 |
| 6706 | cagtgcctattaggttcagacaat | M80360 | 49310 | cactgattcagacaaccagaaaaga | X65453 | 91914 | caacttcgatctctgatgactgga | AA116993 |
| 6707 | ttgacaacaggctaatctgacagga | M80360 | 49311 | ccataatacacagatgacagagctc | X65453 | 91915 | tcgatctcgatgactgagagata | AA116993 |
| 6708 | taatctgacaggaacctactttgt | M80360 | 49312 | cagctcacaatctgtatggttgac | X65453 | 91916 | gatctctgatgactgagaggaggg | AA116993 |
| 6709 | ataatgccaagggttgctcaccaaa | M80360 | 49313 | tgttatggttgacctgggctcctg | X65453 | 91917 | tgagtgtctccttttaatagaatt | AA116993 |
| 6710 | tttgctcaccaaacacataaacgt | M80360 | 49314 | atcccacagagttgcttctcatct | X65453 | 91918 | gctaaatatccaatcaagcagtctc | AA116993 |
| 6711 | agaggcagagcacagaaggaaag | M80360 | 49315 | agagttggcttctcalctttggct | X65453 | 91919 | aatatcaatcaagcagtctctgaa | AA117064 |
| 6712 | aatgctgtcatcttttaacagct | M80360 | 49316 | ggctctcatctttggcttactca | X65453 | 91920 | gaacgctggagaaatcgtgaagaa | AA117064 |
| 6713 | gtcatcttttaacagctgaaggt | M80360 | 49317 | tcatctttggcttactcaaactct | X65453 | 91921 | tgacttgtctgatctcggagtat | AA117064 |
| 6714 | aactgtacaaaacaactctgtggca | M80360 | 49318 | ttactcaaactcgaacagtgcgct | X65453 | 91922 | agttgttctgatctcggagtatct | AA117064 |
| 6715 | caactctgtggcacaagccgtctct | M80360 | 49319 | aaactgaacagtgcgtgtccta | X65453 | 91923 | agtactctgtcacattgctgggtggt | AA117064 |
| 6716 | tgtgggtctccttttgagatgct | M80360 | 49320 | tgaacagtgcgtgctctaggctgc | X65453 | 91924 | tcttgtcacattgctgtggtagtt | AA117064 |
| 6717 | cttccttctgagatggctctgctc | M80360 | 49321 | gtgcgtcctaggctgccagcagg | X65453 | 91925 | ttgtcacatttgctggtgtagttcc | AA117064 |
| 6718 | atggctctgctctgtgaagggagc | M80360 | 49322 | ccaactatcctgatacaacagtg | X65453 | 91926 | tcccaagctgaaccacaatgactgg | AA117064 |
| 6719 | cttttcaggctctgtcctcctgct | M80360 | 49323 | caactatcctgatacaacagctga | X65453 | 91927 | ccaagctgaaccacaatgactgat | AA117064 |
| 6720 | gtctccattttctaggcagtacat | M80360 | 49324 | acagtcgacctcattccgatacc | X65453 | 91928 | gctgaaccacaaatgactgattaag | AA117064 |
| 6721 | atttctctaggcagtacattcata | M80360 | 49325 | agctgacctcattccgatactt | X65453 | 91929 | tgaaccacaatgactgattaagca | AA117064 |
| 6722 | gcttgctccaccaagaaggcttga | AA071856 | 49326 | gctgacctcattccgatacctt | X65453 | 91930 | tatccaatcaagcagtctcgaaaa | AA117064 |
| 6723 | ttttgctcaccaagaaggctttgag | AA071856 | 49327 | gcctaagatacctcaaagaagcag | X65453 | 91931 | caatcaagcagtctctgaaaaatat | AA117064 |
| 6724 | agcccagaggccagtcccccagaag | AA071856 | 49328 | ataccctaaagataccaagaagagag | X65453 | 91932 | aatgactcaaagtctcggcgtctg | AA117064 |
| 6725 | gaacgccaatccagggatcaagtgt | AA071856 | 49329 | cgtcgcacatctggcctctcgact | X65453 | 91933 | acctaaagtctcgggctcgtgcata | AA117064 |
| 6726 | acgccaatccagggatcaagtgtt | AA071856 | 49330 | gtcgcacatctggcctctcgacta | X65453 | 91934 | ctaaagtctcggggctctgcataca | AA117064 |
| 6727 | atcaagtgttcctctgtgcgtccc | AA071856 | 49331 | cgcacattcggcctctcgactc | X65453 | 91935 | agtctcggggctctgcatacaata | AA117064 |
| 6728 | tgtgccttcccagtctgggtagag | AA071856 | 49332 | cacattcgccctctgcgactcgg | X65453 | 91936 | tctcgggcgtctgcatacaataaccc | AA117064 |
| 6729 | tgcctcctaggctgggtagagat | AA071856 | 49333 | attcggcctctgcgactcgggc | X65453 | 91937 | gcgctcgatacaataaacctgaaag | AA117064 |
| 6730 | cgtcctaggctgggtagagatga | AA071856 | 49334 | aactatcctgatacaacagctgac | X65453 | 91938 | cgcaaccaactgaaacgcccgatg | AA117064 |
| 6731 | ccctaggctgggtagagatgactga | AA071856 | 49335 | ctatcctgatacaacagctgacct | X65453 | 91939 | caaccaactggcctaggcgccaga | AA117074 |
| 6732 | cccttaggctgggtagagatgactga | AA071856 | 49336 | atcctgatacaacagctgacctca | X65453 | 91940 | tagcaacctggcctaggcgctagga | AA117074 |
| 6733 | ggcccagaggccgcagtgtggca | AA071856 | 49337 | cctlgatacaacagctgacctcatt | X65453 | 91941 | cttagaggagctggggccacaagtacct | AA117074 |
| 6734 | tgctcaccaagaaggctttggaaga | AA071856 | 49338 | ctlgatacaacagctgacctcattt | X65453 | 91942 | agagctggggccacaaagtacct | AA117074 |
| 6735 | agaggcccaatggaagtltgggactg | AA071856 | 49339 | tgtatacaacagctgacctcattc | X65453 | 91943 | acgctggggccacaaagtacctga | AA117074 |
| 6736 | cattgccttcagctcagagcct | AA071856 | 49340 | caacagctgacctcattccgata | X65453 | 91944 | ctgggggccacaaagtacctgatgt | AA117074 |
| 6737 | ttgccttcagctcagagccta | AA071856 | 49341 | aacagctgacctcattccgatac | X65453 | 91945 | tgggccacaaagtacctgatggt | AA117074 |
| 6738 | ttctcagctcagagcctcagccag | AA071856 | 49342 | aaggccaagcgccgccaaccagaga | X65453 | 91946 | cggccacaaagtacctgatggtgga | AA117074 |
| 6739 | ctcagctcagagcctcagcccagag | AA071856 | 49343 | tgtcggccgagaacgaagaagtgc | X61800 | 91947 | tgccacaaagtacctgatggtgag | AA117074 |
| 6740 | tcagagccctttggaccggaagcagtg | AA071856 | 49344 | gtcggccgagaacgaagaagtgcga | X61800 | 91948 | tgcctagccgccaaggctgacg | AA117074 |
| 6741 | agagcctcagagccaggccagtgc | AA071856 | 49345 | tgggcactgactgcgagaagct | X61800 | 91949 | agagctgccgaaggctgacggccag | AA117074 |
| 6742 | tgtcctagagacacaccgggg | AA071856 | 49346 | gcactgactgcgagaagctata | X61800 | 91950 | aacccaactgaaacgcccgatgcag | AA117074 |
| 6743 | agaggacacccgggccacagt | W50324 | 49347 | agcatttctacgtctattaccat | X61800 | 91951 | tgcattgctacctagcacctggc | AA117074 |
| 6744 | cgagaaccattaactcactgctacc | W50324 | 49348 | ttctacgtctattaccatgcagc | X61800 | 91952 | cattgctacctagcacctggt | AA117074 |
| 6745 | gctcaccagcttaccattaccag | W50324 | 49349 | tacgtctattaccattgcagctaa | X61800 | 91953 | attgctacctagcacctggcta | AA117074 |
| 6746 | cagccagcctttggaccgagagtca | W50324 | 49350 | gtctattaccattgcagctaaggt | X61800 | 91954 | ttgctgtacctagacctggctag | AA117074 |
| 6747 | gcctttgaccgagagtcacatccc | W50324 | 49351 | ttattaccattgcagctaaggtaca | X61800 | 91955 | gctgtacctagacctggcctagcc | AA117074 |
| 6748 | gaccgagagtcacatccattacca | W50324 | 49352 | ttaccattgcagctaagglacatt | X61800 | 91956 | tgtaccttagacctggccctaggg | AA117074 |
| 6749 | agagtcacatccattaccatcg | W50324 | 49353 | gacattccgacagacttttgtaga | X61800 | 91957 | taccttagacctggccctaggggct | AA117074 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 6750 | cattacaccatgacctgctggca | W50324 | 49354 | gagcagctcaccggacctggctg | X61800 | 91958 | cgccacagtgtcgtgttgctgtc | AA117128 |
| 6751 | gactctgcggccagtgatgctggat | W50324 | 49355 | actctgacgacctataccteagac | X61800 | 91959 | cacagtgtcgtgttgctgtcgtc | AA117128 |
| 6752 | calctcaccatcaggctgaacatt | W50324 | 49356 | gccgcccgaatcgctagttlcttg | X61800 | 91960 | gctcttctacacgctgaatattcc | AA117128 |
| 6753 | accatcacgtgaacatttcagatg | W50324 | 49357 | gctagtttcttggacctgccgc | X61800 | 91961 | ctacacgtcgaatattccataatc | AA117128 |
| 6754 | taatgtgtcggggacctgagactcagt | W50324 | 49358 | ttccttggacctgcggacgac | X61800 | 91962 | gtcgaatattccataatcctccag | AA117128 |
| 6755 | cctggagacaactgccaaactgcca | W50324 | 49359 | tttgggacctgcgagcgacagaag | X61800 | 91963 | cataatcctccagtctgccctagtt | AA117128 |
| 6756 | gacaacctgccaaactgccatttcag | W50324 | 49360 | acctggcgagccgacgaagctgcag | X61800 | 91964 | aatcctccagtctgccctagttca | AA117128 |
| 6757 | tccaaactgccatttcagatcaag | W50324 | 49361 | gaagcgcagctggggactggact | X61800 | 91965 | aaactgtacgtcatttcccagatg | AA117128 |
| 6758 | cctgccatttcagatcaagcctcc | W50324 | 49362 | gatatgatgcgggccgtgcgtagaa | X61800 | 91966 | cttgtacgtcatttcccagatgtc | AA117128 |
| 6759 | atttcagatcaagcctccgagaac | W50324 | 49363 | atatgatgcgggccgtgcgtagaa | AA030635 | 91967 | ttcccagatgctgtctgcgattt | AA117128 |
| 6760 | gatcaagcctccgagaaccattac | W50324 | 49364 | tgatcacggtcgtatggaagccca | AA030635 | 91968 | gatgctgtctgcgatttagtgcc | AA117128 |
| 6761 | gccttccgagaaccattactcactg | W50324 | 49365 | tgatcacggtctgtatgaagcgcaac | AA030635 | 91969 | gctgctgtctgcgatttagtggccaac | AA117128 |
| 6762 | tcttttctgacttaaactgagt | W50324 | 49366 | tcgtagaagcccaacgatgatg | AA030635 | 91970 | tgctgctgtcatctatttcagggg | AA117128 |
| 6763 | ctcctgacttaaactgagttcctga | W76814 | 49367 | gtatgaagcccaacgagtgatgaa | AA030635 | 91971 | tgttgactgtgccattaagtcggca | AA117128 |
| 6764 | gcatctgtagtgacgattggagagg | W76814 | 49368 | tggaagcccaacgagtgatggagat | AA030635 | 91972 | cttgccattaagtcggcacggtat | AA117128 |
| 6765 | cccggtctcaggcgagctagccgcca | W76814 | 49369 | ggaagcccaacgagtgatggagatg | AA030635 | 91973 | cattaagtcggcacggtatcgtgga | AA117128 |
| 6766 | gagtccaggcagctagcgagtcagc | W76814 | 49370 | aagcccaacgagtgatggagatgaa | AA030635 | 91974 | taagtcggcacggtatcgtgacag | AA117128 |
| 6767 | agcagtccagcacgcgccacaag | W76814 | 49371 | agcccaacgagtgatggagatgaat | AA030635 | 91975 | gtacagagtatctatcaagctc | AA117128 |
| 6768 | agccacgcgccacaaaggaggcgcc | W76814 | 49372 | acacgttatagggctgagtacg | AA030635 | 91976 | cagtagtatctatcaagtctc | AA117128 |
| 6769 | cccaaatgtcctggccatgaaagg | W76814 | 49373 | gtcacactggcgataagatgacag | AA030635 | 91977 | tatcaagctcttctacagctgaat | AA117128 |
| 6770 | caatgctcctggccatcgaaaggaa | W76814 | 49374 | atgatgggcgcgtgctagaagc | AA030635 | 91978 | aatcctagaatcagagtcgagtctc | AA162093 |
| 6771 | atgtcctcctggccatcgaaaggaa | W76814 | 49375 | tgatgcgggccgtgcgctagaagc | AA030635 | 91979 | gagtctctcgtgactgccatta | AA162093 |
| 6772 | gtcctcgccatcgaaaggaagagc | W76814 | 49376 | gtgcgctagaagcctacacgcgcg | AA030635 | 91980 | caggacaacacctatccgagatcc | AA162093 |
| 6773 | cctcggccatcgaaaggaagaagct | W76814 | 49377 | tgcgctagaagcctacacgcgcga | AA030635 | 91981 | gacaacacctatccgagatcgc | AA162093 |
| 6774 | tgactaaactgagttcctgacat | W76814 | 49378 | cgctagaagcctacacgcgcga | AA030635 | 91982 | acctatccgagatcgcgctcta | AA162093 |
| 6775 | actgagttcctgacatttcggaa | W76814 | 49379 | tagaagcctaccagccgaggtga | AA030635 | 91983 | tatcctgagatcctgcgtctaacc | AA162093 |
| 6776 | tgagttcctgacatttctggaaag | W76814 | 49380 | agcctaccagccgcgaggtgatcac | AA030635 | 91984 | cctgagatcctgcgtctaacctag | AA162093 |
| 6777 | aggcatttctacctgcatctgact | W76814 | 49381 | aggtatcacggtgtatggaagcc | AA030635 | 91985 | gagatcctgcgtctaacctaggat | AA162093 |
| 6778 | gcatttctacctgcatctgtga | W76814 | 49382 | agaggactctactcagacagtgat | AA030635 | 91986 | ctgcgtctaacctaggtgtgt | AA162093 |
| 6779 | atttctacctgcatctgtagtgacg | W76814 | 49383 | catggttacttgccatggccaag | AA030635 | 91987 | cgctctaacctaggatcggtgtgt | AA162093 |
| 6780 | ttctacctgcatctgtagtgacgat | W76814 | 49384 | ctgctggagatgctgagaagccc | X55038 | 91988 | tctaacctaggatcggttgttgc | AA162093 |
| 6781 | acctgcatctgtagtgacgattgga | W76814 | 49385 | gaagcccaggcttcacaacgct | X55038 | 91989 | aacctaggatcggttgtgtgcagc | AA162093 |
| 6782 | gagatgatctcctatgagggaat | W76814 | 49386 | caggcttcagcaacgcttcgcca | X55038 | 91990 | tctcttcgtgactgccattagta | AA162093 |
| 6783 | gatcctatgagggaattgactt | W50329 | 49387 | ggcttcagcaacgcttcgcaggt | X55038 | 91991 | cttcgtgactgccattagtaaag | AA162093 |
| 6784 | cctgagatgcaactagacaagt | W50329 | 49388 | tttcagcaacgcttcgccaggtcc | X55038 | 91992 | aaagttcagctcagcaaaggggcgg | AA162093 |
| 6785 | tgccaactagacaagtcaacagatca | W50329 | 49389 | cgcttcagcaacgcttcgccaggtccag | X55038 | 91993 | ggaccgaaccagacctggaaaatgct | AA162093 |
| 6786 | caactagacaagtcacagatcatga | W50329 | 49390 | ttcgccaggtccaggctccaggt | X55038 | 91994 | ccgaaccagacctggaaatgctca | AA162093 |
| 6787 | tggtctacagatcccagatcaga | W50329 | 49391 | aggttccaggctccaggctgaa | X55038 | 91995 | aaatgcttaggcttatacagaga | AA162093 |
| 6788 | tctacagaatccaagatcgaaac | W50329 | 49392 | caggtccaggctctgagacaggcc | X55038 | 91996 | tgcttcaggctttatacagagaag | AA162093 |
| 6789 | acagaatccaagatcgaaactct | W50329 | 49393 | atttagccctggcccaggcactg | X55038 | 91997 | atgcaggaacaacctatccgaga | AA162093 |
| 6790 | gaatccaagatcagaaactctgaa | W50329 | 49394 | ggcttacttgccatggctcaagg | X55038 | 91998 | tgctgcatcgcagaaggagaact | AA117151 |
| 6791 | tccaagatcagaaactctgaagat | W50329 | 49395 | cccatgatgaccgagttgcaagt | X55038 | 91999 | gcttgcagcagaaggagaactt | AA117151 |
| 6792 | aaactcgaagattctcatggaaa | W50329 | 49396 | gaagaaccatgcaggcaggcggca | X55038 | 92000 | gcacgccgcgttgttcacaagt | AA117151 |
| 6793 | actcgaagattctcatggaaga | W50329 | 49397 | acatcaaagctgagctgctggacat | X55038 | 92001 | cacgcccgcttggtcttacaagtt | AA117151 |
| 6794 | gaattgactctcaactccatacc | W50329 | 49398 | tcaaagctgagctgctggacatag | X55038 | 92002 | gtcctctgacaacgcaattca | AA117151 |
| 6795 | ttgactctcaactccatacccgt | W50329 | 49399 | ctgagctgctgaacagctgacc | X55038 | 92003 | cttctgacaactgaattcaaac | AA117151 |
| 6796 | actctacactcccataccgtgct | W50329 | 49400 | ctccgcccaaggcagctgctgagaag | X55038 | 92004 | ttcctgacaacactgaatcaaaca | AA117151 |
| 6797 | tgtgactgtccgtggcacatgggac | W50329 | 49401 | aactctgggcagctgctgagaatgg | X55038 | 92005 | cctgacaacactgaattcaaacaa | AA117151 |
| 6798 | gactgtccgtggcacatggaccct | W50329 | 49402 | gccggagaccctttcagagctctt | AA031244 | 92006 | aagtgtcctatgtgagagctata | AA117151 |
| 6799 | tgtccgtggcacatgaccctga | W50329 | 49403 | ggaggaccctttcagagctctt | AA031244 | 92007 | gtgtgacctctatgtgagagctaag | AA117151 |

| SEQ ID NO | sequence | DBAxnID | SEQ ID NO | sequence | DBAxnID | SEQ ID NO | sequence | DBAxnID |
|---|---|---|---|---|---|---|---|---|
| 6800 | gtggcacatggaccctgtagagaag | W50329 | 49404 | ctctctcttcgtcctttcctgctaa | AA031244 | 92008 | tgacctctatgtgagagctaagtag | AA117151 |
| 6801 | ggccctgagagctgccaactagaca | W50329 | 49405 | tcgtccttcctgctaactccgctt | AA031244 | 92009 | gacctctatgtgagagctaagtagt | AA117151 |
| 6802 | acctgaaacacatcaccaagtgaa | W50138 | 49406 | tcctcatctttcgttcagcccgg | AA031244 | 92010 | ttaaacctttgaagacattgactga | AA117151 |
| 6803 | aacacatcaccaagtgaagcctg | W50138 | 49407 | ctcatctttcgttcagccgagg | AA031244 | 92011 | tgttttctggttcaagcgatgaa | AA117151 |
| 6804 | tgcccatgttggagtcatgcctga | W50138 | 49408 | tcggtccttcgtcctcgtttctac | AA031244 | 92012 | tgttttctggttcaagcgatggaac | AA117151 |
| 6805 | tgagctcatgctgagaagagagc | W50138 | 49409 | ggccgcgcatcactacacgcagaa | AA031244 | 92013 | ttttcttgttcaagcgatggaactt | AA117151 |
| 6806 | agctcatgctgagaagagagccac | W50138 | 49410 | cgcatcactacacgcagaatcatgg | AA031244 | 92014 | ttctgttcaagcgatggaactta | AA117151 |
| 6807 | ccactgccgaggtgtctccggca | W50138 | 49411 | catcactacacgcagaatcatgga | AA031244 | 92015 | gtctcaagaagcactaggcacagcc | AA117151 |
| 6808 | ccgctgagtgctccggcatcctg | W50138 | 49412 | tcactacacgcagaatcatggaga | AA031244 | 92016 | agaagactaggcacagcccgctg | AA117151 |
| 6809 | agtgctccggcatcctggctgaa | W50138 | 49413 | actacacgcagaatcatggagaacg | AA031244 | 92017 | taggcacagcccgctggtcttaca | AA117151 |
| 6810 | gtcccgcatcctggctgaatcc | W50138 | 49414 | agacctttcagagctcttgat | AA031244 | 92018 | caaatgatgcgggctcggcagtat | AA116977 |
| 6811 | tccggcatcctggctgaatcctaa | W50138 | 49415 | cctttcagctcttgact | AA031244 | 92019 | aaatgatgcgggctcggcagatc | AA116977 |
| 6812 | atcctggctgaatcctaagccagc | W50138 | 49416 | ttttcagagctcttgtagactg | AA031244 | 92020 | atgctgattcgggtcaacatggagg | AA116977 |
| 6813 | ggctgaatcctaagccagccctgc | W50138 | 49417 | ttttcagagctcttgtagactggg | AA031244 | 92021 | tgctgatcgggtcaacatggaagga | AA116977 |
| 6814 | acatccaccaagttgaagcctggg | W50138 | 49418 | ctttgatgactttggggtgtcttctcg | AA031244 | 92022 | gctgatcgggtcaacatggaggat | AA116977 |
| 6815 | tcaccaagttgaagcctgggtct | W50138 | 49419 | tgactttgggtgtcttctccggcagct | AA031244 | 92023 | ctgatcgggtcaacatgagagatc | AA116977 |
| 6816 | tgaagcctggggtctctccgaagt | W50138 | 49420 | acttgggtcttctccggcagttc | AA031244 | 92024 | gatcgggtcaacatggaggattc | AA116977 |
| 6817 | gtctctgaggtctcgtgggaga | W50138 | 49421 | ttcagacaccagggtcccgactca | AA031244 | 92025 | tcaacatggaggatcgcgggacag | AA116977 |
| 6818 | ttctgaggttctggtgagaagta | W50138 | 49422 | acgccacgctccgtgagagtacc | AA031244 | 92026 | aacatggaggatcgcgggacaga | AA116977 |
| 6819 | tcacagattcctgctgccatgtt | W50138 | 49423 | gctccgtgagagtaccaccgagttc | AA031244 | 92027 | aacatggaggatcgcgggacagac | AA116977 |
| 6820 | cagatttcctgccgccatgtgaa | W50138 | 49424 | ctatgccagagatataggggaccag | AA031244 | 92028 | aattgagcgggctcggcagtatcc | AA116977 |
| 6821 | tgtgccatgttgagctcatgcc | W50138 | 49425 | ggcacacgcagatgaccacacagcgca | AA031244 | 92029 | attgatgcgggctcggcagtatcct | AA116977 |
| 6822 | catcctcagatactcatatgcaag | W50138 | 49426 | gccagatgacacacgcgcaagaga | AA031244 | 92030 | ttgatgcgggctcggcagtatcctt | AA116977 |
| 6823 | aagatgtggattcatacggtgtga | M31314 | 49427 | gatgcaccacgcagcaagagaacac | AA031244 | 92031 | tgatgcgggctcggcagtatccctg | AA116977 |
| 6824 | tgaacacgttctctatgtgaaat | M31314 | 49428 | agaacacacatttcctactc | AA031244 | 92032 | ggctcggcagtatcttggggagact | AA116977 |
| 6825 | tgaaatacacaggctgcagagaa | M31314 | 49429 | atggctgtgtcactatgacgaca | AA031244 | 92033 | tgaaacgaggctcactgcgactttg | AA116977 |
| 6826 | aagcaaatccttcagcaagttag | M31314 | 49430 | catgtatcctataccgtgtcgta | AA031244 | 92034 | aaacgaggctcactgcgactttgtg | AA116977 |
| 6827 | atticcttcagcaagttagaaggcga | M31314 | 49431 | gtatcctctataccgtgtctgtcg | AA031244 | 92035 | tgaagctcgggagatgcgattcg | AA116977 |
| 6828 | taacgccactgcgagccagaccac | M31314 | 49432 | tctcctatacgtgtctgtaatgct | AA031244 | 92036 | cactcagccaggccgaccaggccga | AA116977 |
| 6829 | cgcccgatgactcggaagctcagt | M31314 | 49433 | tacggtgtctaatgctgtgtc | AA031244 | 92037 | agacagccgagctgctctagagaca | W08049 |
| 6830 | atggacctgaagctcagtgggtga | M31314 | 49434 | tgagagtaccaccgagttctcctg | AA031244 | 92038 | cagagaccctaatctggtgaacga | W08049 |
| 6831 | ccctcccagtgacagtacgg | M31314 | 49435 | cctgagtactcatctatgctatc | AA031244 | 92039 | atccctacagcatacagctct | W08049 |
| 6832 | gttgaccctgaaactgtgggaccat | M31314 | 49436 | gtgagtactcatcatctatcatg | AA031244 | 92040 | cctcacagacgatacagctctggc | W08049 |
| 6833 | ggaaccatggcgaactctaaat | M31314 | 49437 | agtactcatctatgctatcatgt | AA031244 | 92041 | ctacagacgatacagctctggctga | W08049 |
| 6834 | ctgattctactggtgtgaggtagc | M31314 | 49438 | tgctatcatgtgatctactagccaga | AA031244 | 92042 | atacagctctggctgatatcacacc | W08049 |
| 6835 | aggtagccactgaggagacagcagtgt | M31314 | 49439 | tatcatgatctactatgccagacag | AA031244 | 92043 | cagctctgcgtatatcacacctc | W08049 |
| 6836 | caacgactccagtgtcgctcctg | M31314 | 49440 | aagtcaaagcctcaggcggccgaa | AA031244 | 92044 | ctgatatcaccaccttccacagatga | W08049 |
| 6837 | agtgagctcaagtgcagcctgtcc | M31314 | 49441 | tcccatcctgatgatgatgcagtc | AA031244 | 92045 | cacttcaccacttcacagatagctgg | W08049 |
| 6838 | agctccaagctgctggtggctccagtc | M31314 | 49442 | ggtgagtactcacatctatgctatc | AA031244 | 92046 | ccacagatccaagctgtgacaa | W08049 |
| 6839 | ttcacatcctgtttatctgcagt | M31314 | 49443 | gtgactgagtcactcatgtact | AA031244 | 92047 | ctactgagatgccgggatgagaa | W08049 |
| 6840 | tttatctgtcagtgggaatatgtt | M31314 | 49444 | ccctcgagggtcttgaggatcag | AA031244 | 92048 | cagatgcagctgtagacaaat | W08049 |
| 6841 | ttcgttgaacaggtctctagt | M31314 | 49445 | ttcctgaggtcttgaggatcagg | AA031244 | 92049 | acaatatgctgttctgggcagaa | W08049 |
| 6842 | gcgcgggcaacgactccaggttgc | AA120695 | 49446 | aagtcaaagccttcaggcggccaga | AA031244 | 92050 | tgcgttctctggggcagaaggcctt | W08049 |
| 6843 | caagactccagtgtcgtcctcg | AA120695 | 49447 | tcccatcctgatagatgcagtc | AA031244 | 92051 | tctggggcagaaggcctgctgct | W08049 |
| 6844 | tttaactactggaggactttg | AA120695 | 49448 | cccatcctgatatagctcagctc | AA031244 | 92052 | ttgcttgcaatcagcatccctc | W08049 |
| 6845 | aactactggagacttttgcaa | AA120695 | 49449 | ccatccctgatatgatcagctcc | AA031244 | 92053 | tcttgcaatcagcatccctga | W08049 |
| 6846 | tactctgagacctttctgcaacag | AA120695 | 49450 | gatagatgcagctccataacccc | AA031244 | 92054 | ctgactggctaccccctaggggtgca | W08049 |
| 6847 | gagagcttctgcaacaggagagaa | AA120695 | 49451 | atagatgcagctcccataaccccct | AA031244 | 92055 | atgtgcctgagacatttcacacaga | W08049 |
| 6848 | ctcttgcaacaggagacaaaggtg | AA117183 | 49452 | tagatgcagctcccataacccctg | AA031244 | 92056 | aatcacgagactctcagaaatccg | AA117183 |
| 6849 | ctcttgcaacaggacacaaaggtg | AA117183 | 49453 | gcccttgaacagggccataatgaa | X51983 | 92057 | atacagagaactctcagaatctga | AA117183 |

| SEQ ID NO | sequence | DBAxnID | SEQ ID NO | sequence | DBAxnID | SEQ ID NO | sequence | DBAxnID |
|---|---|---|---|---|---|---|---|---|
| 6850 | aaaggccgctcactcaggggag | AA120695 | 49454 | tgactgacctccgcatgatcgggc | X51983 | 92058 | tcagagctcttcgcgataatacac | AA117183 |
| 6851 | gttacgtaccttcagagtcatg | AA120695 | 49455 | actgacctcgcatgatcgggcct | X51983 | 92059 | agagctattcgcgataatacacat | AA117183 |
| 6852 | agtaccttcagagtcatgagccag | AA120695 | 49456 | tgacctccgcatgatcgggcctgc | X51983 | 92060 | gagctcttcgcgataatacacatg | AA117183 |
| 6853 | accttcagagtcatgagccagagt | AA120695 | 49457 | cccgctcctccgaggtcttgag | X51983 | 92061 | agctcttcgcgataatacacatgt | AA117183 |
| 6854 | cttccagtgggtcttctgccaggtc | AA120695 | 49458 | ccgctcctccgaggtcttgagg | X51983 | 92062 | ctcttccgcgataatacacatgtgt | AA117183 |
| 6855 | tttcagagtcatgagccagagttg | AA120695 | 49459 | cgctcttcctgaggtcttgagga | X51983 | 92063 | tcttccgcgataatacacatgtgtc | AA117183 |
| 6856 | gtgctctcgcaggtcaaggcgct | AA120695 | 49460 | gctcttccgagggtcttgaggat | X51983 | 92064 | cttccgcgggtcttgaggat | AA117183 |
| 6857 | cttctcgcaggtcaaggcgcgtc | AA120695 | 49461 | tcttctcgaggtcttgaggatca | X51983 | 92065 | tgtcgttccaagagcactctac | AA117183 |
| 6858 | ctcgcaggtcaaggcgcgtcgac | AA120695 | 49462 | tacatcacatgtttcactgct | X51983 | 92066 | gtgttccaagagcacttctaca | AA117183 |
| 6859 | acgcattcatatctatcgttgagt | AA120695 | 49463 | gcagcagctgcagccactgcaggtt | AA168900 | 92067 | tgttccaagagcacttctaccc | AA117183 |
| 6860 | acatcatatctatcgttgagtta | AA120695 | 49464 | atagctatggcagctcaaatggcag | AA168900 | 92068 | cacgagaacctcagaatctcgaaa | AA117183 |
| 6861 | ttcatatcatcgttgagtttaact | AA120695 | 49465 | gcagctcaaatggcagccctgcaag | AA168900 | 92069 | gttctcaagagcactctacacca | AA117183 |
| 6862 | atatctatcgttgagtttaactact | AA120695 | 49466 | gctcaaatggcagccctgcaagcta | AA168900 | 92070 | acgagactctcagaatctcgaaaa | AA117183 |
| 6863 | tgaaatctcctgctaacagactca | X01450 | 49467 | caaatggcagccctgcaagctaaag | AA168900 | 92071 | cgagaactctcagaatctcgaaaaa | AA117183 |
| 6864 | gtaacagacctcaagaaggagacag | X01450 | 49468 | caagctaaaggcctggccagagactg | AA168900 | 92072 | agaactctcagaatctcgaaaaact | AA117183 |
| 6865 | tgtactggagccctcatcatg | X01450 | 49469 | aaagcctgccagagactggcatag | AA168900 | 92073 | gaactctcagaatctcgaaaaactt | AA117183 |
| 6866 | tgggagccctttcatcatgatctta | X01450 | 49470 | actggcatagcagtgccagctact | AA168900 | 92074 | ctctcagaatctcgaaaaacttca | AA117183 |
| 6867 | catcatgatcttaatctgactgtt | X01450 | 49471 | ggcatagcagtgcccagctactaca | AA168900 | 92075 | ctcagaatctcgaaaactttcaga | AA117183 |
| 6868 | aaagcgtctcgggtatctctcactc | X01450 | 49472 | atagcagtgcccagctactacaacc | AA168900 | 92076 | atctcgaaaaacttcagagctctt | AA117183 |
| 6869 | ttacatcattcagtctcacctgtaa | X01450 | 49473 | gcagtgcccagctactactacaaccag | AA168900 | 92077 | ttggcttccagtcaggttaatcttt | AA117183 |
| 6870 | cattcagtctcacctgtaactaaca | X01450 | 49474 | gttcttaatgttgctcacctgtaa | AA168900 | 92078 | gcttccagtcaggttaatcttgca | AA117183 |
| 6871 | gcttaactgtgacaaccacatcact | X01450 | 49475 | gtgccagtactacaaccagcagag | AA168900 | 92079 | cgcagaaacaagatcattgcattgca | AA117183 |
| 6872 | ctgtacaaccacatcactgttacc | X01450 | 49476 | cttaatgttgctgcactgttgcat | AA168900 | 92080 | aaccaagatcattgcagctct | AA117183 |
| 6873 | aaccacatcactgttacctgaagt | X01450 | 49477 | aatgttgctcactgttgcacag | AA168900 | 92081 | caagatccatttgcagtcttca | AA117183 |
| 6874 | accacgtatcatgtaactacaac | X01450 | 49478 | gctgcactgttgcatcagcaacgc | AA168900 | 92082 | ttctccacctgttcctgcgaccaca | W08050 |
| 6875 | taaatctctgagctgacaggcat | X01450 | 49479 | ggaaccagggttactctcagatatg | AA168900 | 92083 | ttcacctgttcctgcgaccacgc | W08050 |
| 6876 | gcttgacaggcatcctccacacagg | X01450 | 49480 | acgcagttactctcagatgctca | AA168900 | 92084 | tggttctcgaccacagcctctcag | W08050 |
| 6877 | caggatcctccacacagcaggattttc | X01450 | 49481 | caggttacctccagatagctagg | AA168900 | 92085 | ttccgaccacagccttccagat | W08050 |
| 6878 | atagttttcctcgaagccaccatgct | X01450 | 49482 | actcctcagaagctatgcagctgt | AA168900 | 92086 | tcggaccacagcctccagaatctg | W08050 |
| 6879 | tcctctagaacaccagctacagac | X01450 | 49483 | gcctggatccagaagggaggcccac | AA168900 | 92087 | gaccacagccttccagaatctgacac | W08050 |
| 6880 | tccacgccacgaagctctctgtac | X01450 | 49484 | aaccacagtaccagcctggagagaca | AA168900 | 92088 | gaatctgacagaatctgctgagatta | W08050 |
| 6881 | gccgaagctctgtgtacatttcc | X01450 | 49485 | cgacgctgaagcattttataga | AA168900 | 92089 | ccctactcagaaacaagctgatg | W08050 |
| 6882 | tcgtacatctgtactggagagc | X01450 | 49486 | tcctcgtgacccaaggttcattt | X16440 | 92090 | agatacactgtgagtgtgctgctc | W08050 |
| 6883 | aggccgagctgaggacatctgcag | X01450 | 49487 | tctagggcatccactcattcaca | X16440 | 92091 | tccactccaatcattgtggggag | W08050 |
| 6884 | acatcgcagtgagtgactgtgaact | W50367 | 49488 | gcatccactcatttcacagagtaa | X16440 | 92092 | gggcagagccccagtcgcctcattc | W08050 |
| 6885 | cttctgaagttgcactgctctcctga | W50367 | 49489 | tgatgctcagctcctcctgaa | X16440 | 92093 | catgagccccagtcgcttcattcgca | W08050 |
| 6886 | tgtcaaatccccagcagtcgtacca | W50367 | 49490 | ttcctgccaattaggctccgaca | X16440 | 92094 | gagcccagtccttcattcgcagaa | W08050 |
| 6887 | caaactccagcagtcgtaccaaga | W50367 | 49491 | tcccatggccgacatacccagat | X16440 | 92095 | cagtcttcattcgcagaaccaag | W08050 |
| 6888 | actcccagcagtcgtaccaagagc | W50367 | 49492 | taggctccgatacccagtagtctc | X16440 | 92096 | ttcattcgcagaaaccaagatctca | W08050 |
| 6889 | gcctgctgaatttctcagtct | W50367 | 49493 | ccatctccaaaatactcatctt | X16440 | 92097 | tgttaaccattcgaataatcaga | W08050 |
| 6890 | tggctctgaatttctcagtcttta | W50367 | 49494 | aatactcatctttgtctagttatt | X16440 | 92098 | accattcgaatatacagatctggc | L19932 |
| 6891 | ctctgaattctcagtcttttacta | W50367 | 49495 | agtaacgctgaggacgcagacata | X16440 | 92099 | attctgaaagccttgccatggttc | L19932 |
| 6892 | tgaatttctcagtcttttactag | W50367 | 49496 | gagaccagacatagcctgactgggc | X16440 | 92100 | gaaagcctggcatgttctgtaaa | L19932 |
| 6893 | attctcagtctttactagagat | W50367 | 49497 | agacatagcctgactgggcatcact | X16440 | 92101 | ctgtaaagctctgtaccgctggag | L19932 |
| 6894 | tctcagtctttactatagatct | W50367 | 49498 | agtagtactgtctctgccaatcc | X16440 | 92102 | tgtaccgctggagaaacggatcac | L19932 |
| 6895 | tctgcagtgacgttctgaactgtt | W50367 | 49499 | tactgtctgccaatcccgaagtt | X16440 | 92103 | gcatcactaaagctatgaggtgaa | L19932 |
| 6896 | tactcattccaatgctaaccatgc | W50367 | 49500 | cactctgcccagtgcccaagatgt | X16440 | 92104 | actgttctcagtaatgtcttgt | L19932 |
| 6897 | tcattctcaatgctaaccatgcaga | W50367 | 49501 | ccctgggaatctagcacacaggat | X16440 | 92105 | tctgtcaagtatgtctgtgtccac | L19932 |
| 6898 | tcaatgctaaccatgcagaaagcaa | W50367 | 49502 | tggaatcctagcacaggatcagaga | X16440 | 92106 | aagtatgtctgtgtccacacatg | L19932 |
| 6899 | atgctaaccatgcagaaagcaaagt | W50367 | 49503 | cgactgacactcagaactag | X06368 | 92107 | gtcttgtccacacatggttga | L19932 |

TABLE 1-continued

| SEQ ID NO | DBAxnID | sequence | SEQ ID NO | DBAxnID | sequence | SEQ ID NO | DBAxnID | sequence |
|---|---|---|---|---|---|---|---|---|
| 6900 | W50367 | ctaaccatgcagaaagcaaagtt | 49504 | X06368 | tgaacttcagaacatgagggtct | 92108 | L19932 | tagaatccgaattccgagtgtga |
| 6901 | W50367 | ggtacctctgaagttgcatctgg | 49505 | X06368 | tcctgacagatgcttagactacag | 92109 | L19932 | atctggcagtcatagcttggcacca |
| 6902 | W50367 | atccttctgaagttgcatctggga | 49506 | X06368 | gtactgagcgggcagctaaaaagtg | 92110 | L19932 | gggccatggtgcattgtaataa |
| 6903 | W50374 | cattccatcgttgcgtgtgaac | 49507 | X06368 | gccctgcacttcagactggaagt | 92111 | L19932 | cagtcatagcttgccaccaaattc |
| 6904 | W50374 | ttccatcagcttgcgtggaactt | 49508 | X06368 | tcacttagacgtgaagtatgggg | 92112 | L19932 | tagcttggcaccaaattccgaaag |
| 6905 | W50374 | ccagcaatcccgagctggg | 49509 | X06368 | tgcaaggctgaccacacacaaaa | 92113 | L19932 | ccgaaagacctctgaaagcatgaa |
| 6906 | W50374 | caatcccgagctgcagctgggcag | 49510 | X06368 | aaccgtgtctcctccaagtctg | 92114 | L19932 | gcatgaattcctgactgctgccaag |
| 6907 | W50374 | atcccgagcagctgggcaggat | 49511 | X06368 | gtgctcctccaagtcgactgt | 92115 | L19932 | tgactgtgccaaggcctgataagg |
| 6908 | W50374 | atcccgagcagctgggcaggtct | 49512 | X06368 | gactgctccaattaatcgtcaa | 92116 | L19932 | tgccaaggctgataaagggaacta |
| 6909 | W50374 | gccaggatcctactgctcacga | 49513 | X06368 | tcctcaattaactgtcaacattaa | 92117 | L19932 | tcttggagctcacaaatgtgaatca |
| 6910 | W50374 | aggatctctactgctcacgata | 49514 | X06368 | ctgcaacattaaactaacagtcat | 92118 | W83337 | tggcatccgcgatgattggcgct |
| 6911 | W50374 | gatctctactgctcacgataag | 49515 | X06368 | ttccagagcctggccatcactgc | 92119 | W83337 | ctgcatccatgcacgaattctc |
| 6912 | W50374 | tcctactgctcacagataagacag | 49516 | X06368 | cattaaactaacagtcattaacatc | 92120 | W83337 | catcgtcaccaacgtggcctgcaa |
| 6913 | W50374 | ctactgctcacagataagacagg | 49517 | X06368 | gggccatcacgccagtggggtct | 92121 | W83337 | tcgtcaccaacgtggcctgcaatg |
| 6914 | W50374 | actgctcacagataagacaggac | 49518 | X06368 | ggttctcacagtgctagcctctat | 92122 | W83337 | cgtcaccaacgtggcctgcaatga |
| 6915 | W50374 | cccatcagattcgcgtgaactgg | 49519 | X06368 | tgctgcctataattactacgc | 92123 | W83337 | tcaccaacgtggcctgcaatgag |
| 6916 | W50374 | ctgctcacagataagacaggacc | 49520 | X06368 | cctctatatttactatgccaactgg | 92124 | W83337 | tggcctgcaatgagcaaaactgg |
| 6917 | W50374 | caagatcgtgcacgctgggtgatt | 49521 | X06368 | caactggtgcaccctagttctctt | 92125 | W83337 | aactgacgtaaactacactcagcta |
| 6918 | W50374 | agatcgtgcacgctgggtgattcg | 49522 | X06368 | gtgcaccctagttctcttctcca | 92126 | W83337 | ctgacgtaaactacactcagctagt |
| 6919 | W50374 | tgtacagctgggtgattcgcaggga | 49523 | X06368 | cgtcccaaactctggttccaatg | 92127 | W83337 | tgacgtaaactacactcagatagtc |
| 6920 | W50374 | tacagctgggtgattcgcaggga | 49524 | X06368 | cctgcatgcgacggtgaacttgt | 92128 | W83337 | acgtaaactacactcagctagtcga |
| 6921 | W50374 | cagctgggtgattcgcaggattcc | 49525 | X06368 | gcatgcgacggtgaacttgtggcg | 92129 | W83337 | cgtaaactacactcagctagtcgat |
| 6922 | W50374 | tgattcgcaggattccaaaatccc | 49526 | X06368 | tgctcacacccgcaagttgagtc | 92130 | W83337 | tgtccgctccatgcacgaattctca |
| 6923 | W50374 | gtggctccgttccgacacaatccccg | 49527 | X06368 | tttacttcctcaggaggagagagaa | 92131 | W83337 | tccgctccatgcacgaattctcagc |
| 6924 | W50374 | atgagcccttggcagatgtccagge | 49528 | X06368 | actttcctcagggatgagaagacag | 92132 | W83337 | gttcgtctgcatcgtcaccaacgt |
| 6925 | W50374 | cagatgccagcgctgctccca | 49529 | X06368 | acatgtttctgcgtgtgcggctgga | 92133 | W83337 | ttcgtgtgcatcgtcaccaacgtg |
| 6926 | X60103 | ctcaataccgaagcacatcattgt | 49530 | X06368 | tgttctgcgtgtgcgggcgact | 92134 | W83337 | tcgtgtgcatcgtcaccaaacgtggc |
| 6927 | X60103 | accagaagcacactcattggccctg | 49531 | X06368 | agtttaccagtgcacacaaggcctat | 92135 | W83337 | gtggtcatcgtcaccaaacgtggcc |
| 6928 | X60103 | agcacatcattggcctgaagg | 49532 | X06368 | ttaccagtgcacaaagcctatat | 92136 | W83337 | gtgcatcgtcaccaaacgtggcctg |
| 6929 | X60103 | tccacttgatgctactgtaggg | 49533 | X06368 | ccagtgacacaaagcctattatcaa | 92137 | W83337 | gcatcgtcaccaaagtggcctgca |
| 6930 | X60103 | ttgatgctactgtaggctcac | 49534 | X06368 | acacaaagcctattatcaacaaagt | 92138 | AA117227 | gacgagggcagcgagccaaggctg |
| 6931 | X60103 | cataggccaaacagtgagatgct | 49535 | X06368 | caaagcctattatcaacaaagttgc | 92139 | AA117227 | aaggctgccacgcgtgaccctgaag |
| 6932 | X60103 | gttcctgccatgtcccagtccca | 49536 | X06368 | tgcgacggctgaacttggcgtct | 92140 | AA117227 | ctgctgccaacgcgtgacgt |
| 6933 | X60103 | gtcctgtcatgctccagatccc | 49537 | X06368 | aaagcctattatcaacaaagttgct | 92141 | AA117227 | tgtccaacgcgatgacgtaccc |
| 6934 | X60103 | tgtcatgctccagatccctctt | 49538 | X06368 | tgaacttgtgcgtctcatgct | 92142 | AA117227 | tccaacgcattgacgtgaccccgc |
| 6935 | X60103 | ctcccagatcctctctgtgtgta | 49539 | X06368 | acttttgcgtctgcatgtctcta | 92143 | AA117227 | aggcattgacgtgaccgcagaa |
| 6936 | X60103 | atgtcacctgcaagaacaggagaag | 49540 | X06368 | ttgtggctcgtctcatgtctcac | 92144 | AA117227 | ttgacgtaccgcagaagaggtt |
| 6937 | X60103 | gtcaacagcaagatctgcctgca | 49541 | X06368 | tcggctctgcatctcatcaccg | 92145 | AA117227 | tgaccgcagaagagtttgatga |
| 6938 | X60103 | aggccagctgccctgcacatcac | 49542 | X06368 | gctctgtctcatctacaccccgaa | 92146 | AA117227 | gagatgatccattgctgctggtgg |
| 6939 | X60103 | acatcactgactgccactgaaggg | 49543 | X06368 | tgctcatgctcaccgcaagtt | 92147 | AA117227 | gttgagaataccactcactgtaat |
| 6940 | X60103 | ctgactgccactgaagggcaactc | 49544 | X06368 | tcatgctcacaccgcaagttga | 92148 | AA117227 | ccactcactgaatttgctactt |
| 6941 | X60103 | gcaactcaagtatccaactgtga | 49545 | X06368 | ccctcagctcagtgaaacgcaa | 92149 | AA117227 | actcactgaatttgcttacgc |
| 6942 | X60103 | actgtgactacagaagaccactcaata | 49546 | X06368 | gttggacagctgcttcactacag | 92150 | X53028 | ctgacacgtgacccctgcggagagag |
| 6943 | X60103 | agaccactcaataacgaagacat | 49547 | X06368 | acgagcctttcactgaaggaccaca | 92151 | X53028 | gggtcacttcaaacagcggatcac |
| 6944 | X60103 | taaacgttcgtccaatgggtgtg | 49548 | X06368 | gacaccattgattccaccaaggga | 92152 | X53028 | acttcaaacaggatcactgccaga |
| 6945 | W50375 | tggcttcaatggtgtgtgatcca | 49549 | X06368 | attgattccaccacaggcaaagc | 92153 | X53028 | ttcaaacaggatcactgcgacca |
| 6946 | W50375 | gcctgatgccagttccagttcgcgccgaa | 49550 | X06368 | tcacccacaggcagaagcagaatt | 92154 | X53028 | aacaggatcactgcagacctgct |
| 6947 | W50375 | ctgatgccagttgccgagcgcgcga | 49551 | X06368 | atcttgcagaatgctaatgccat | 92155 | X53028 | atcactgcagacctgtccaaacg |
| 6948 | W50375 | tgcccgttgccgagcgaaaagtc | 49552 | X53028 | atgcaatggatgctcagcgtgactgt | 92156 | AA117227 | ctgacgcctgctgccaacggcat |
| 6949 | W50375 | gccagtgccgagcgaaaagtcat | 49553 | X53028 | tgtgactagcgtgactgtagcgta | 92157 | AA117227 | gcagacctgctccacgcggcattg |

TABLE 1-continued

| SEQ ID NO | sequence | DBAxnID | SEQ ID NO | sequence | DBAxnID |
|---|---|---|---|---|---|
| 6950 | agtagagatcgcaccactatttat | W50375 | 49554 | atctctcctgcaaaatagatgtttc | X53028 | 92158 | tgcacgacacagtcatctccaagtg | AA117284 |
| 6951 | tagagatcgcaccactatttatg | W50375 | 49555 | atgtttcagtgtctgtgacaatga | X53028 | 92159 | gcacgacacagtcatctccaagtgc | AA117284 |
| 6952 | gagatcgcaccactatttattgat | W50375 | 49556 | acaatgaccgttactgtgttga | X53028 | 92160 | aagccttgcatatcatagtacact | AA117284 |
| 6953 | tgcaccactatttatgaag | W50375 | 49557 | ccagctgcttcactacagaagaag | X53028 | 92161 | gccttgcatatcatagtacactcc | AA117284 |
| 6954 | gcaccactatttatgatgaagt | W50375 | 49558 | gcttcactacaggaaggaggcagac | X53028 | 92162 | tgcatatcatagtacactccaagta | AA117284 |
| 6955 | accactatttatgatgaagttg | W50375 | 49559 | tttctacgactcggagggacagatg | X53028 | 92163 | gcatatcatagtacactccaagtac | AA117284 |
| 6956 | gtgattccatatccagtcgccagg | W50375 | 49560 | gggcctccacaggaggcaaacgat | X53028 | 92164 | atatcatagtacactccaagtacat | AA117284 |
| 6957 | gattccatatccagtcgccaggt | W50375 | 49561 | tcaccaggaggcaaacgatgaaag | X53028 | 92165 | tatcatagtacactccaagtacatc | AA117284 |
| 6958 | ttccatatccagtcgccagggtg | W50375 | 49562 | ccagagagttcgacggcggaagag | X53028 | 92166 | atcatagtacactccaagtacatca | AA117284 |
| 6959 | ccatatccagtcgccagggtggt | W50375 | 49563 | cttggctgcgatgatctggaactc | X53028 | 92167 | catagtacactccaagtacatcaaa | AA117284 |
| 6960 | atccagtcgccagggttggtgtca | W50375 | 49564 | gttcagccagcggggcgacagttg | X53028 | 92168 | atagtacactccaagtacatcaaag | AA117284 |
| 6961 | ccagttcgccagggttggtcaat | W50375 | 49565 | ggagccaagttcagccagtggtcg | AA030895 | 92169 | ggcaaagccttgcaaatcaaagtt | AA117284 |
| 6962 | agttcgccagggttgtgtcaatat | W50375 | 49566 | agccaagttcagccatgcatggcgat | AA030895 | 92170 | acgacacagtcatctccaagtgcat | AA117284 |
| 6963 | ttcgccagggttgtgtcaatatgg | W50375 | 49567 | ctctctctatcctggcactgacgg | AA030895 | 92171 | cgacacagtcatctccaagtgcata | AA117284 |
| 6964 | ctgagtctgcagtcctgcgaggagat | W50375 | 49568 | tctctctatcctggcactgacggt | AA030895 | 92172 | gacacagtcatctccaagtgcataa | AA117284 |
| 6965 | agtctgcagtcctgaggagatccc | W50375 | 49569 | tctcctatcctggcactgacggtga | AA030895 | 92173 | cacagtcatctccaagtgcataaaa | AA117284 |
| 6966 | tacagaagatctggcccagagat | W50375 | 49570 | ccatatcctggcactgacggtgatct | AA030895 | 92174 | acagtcatctccaagtgcataaaat | AA117284 |
| 6967 | agatctgggcccagagatctgga | W50375 | 49571 | ctatcctggcactgacggtgatctc | AA030895 | 92175 | cagtcatctccaagtgcataaaata | AA117284 |
| 6968 | tctgggcccgagatcttggact | W50375 | 49572 | tcctggcactgacggtgatctcag | AA030895 | 92176 | taaagccctgcatatcatagtaca | AA117284 |
| 6969 | aggtggatctccatactgccaagg | W50375 | 49573 | ctgcactgacggtgatctcatgtg | AA030895 | 92177 | aaagccctgcatatcatagtacac | AA117284 |
| 6970 | tggatctccatactgccaaggct | W50375 | 49574 | tggcactgacggtgatctcatgtgg | AA030895 | 92178 | tacaattacaactccaactctttag | AA117284 |
| 6971 | atcctcactcgccaaaggtctttt | W50375 | 49575 | gcactgacggtgatctcatgtggtt | AA030895 | 92179 | tattacaatcaactcttaagggact | AA117284 |
| 6972 | tccatctgccaaaggtctttccg | W50375 | 49576 | cactgacggtgatctcatgtggttc | AA030895 | 92180 | gcttgcagacttggagtcgagcaggt | AA117286 |
| 6973 | gtcttttccggtcagtcccag | W50385 | 49577 | gccaagttcagccatgtcgcagtc | AA030895 | 92181 | agactttggagtcgcagtcaactt | AA117286 |
| 6974 | tcccagtgggccgtccaagtccag | W50385 | 49578 | tgacggtcatctcggtctcc | AA030895 | 92182 | ctttggagtcgcaggtcaacttaca | AA117286 |
| 6975 | ggccgtccactgcgatctatgagc | W50385 | 49579 | caagttcagccatggtgcgatccg | AA030895 | 92183 | aaggtcaacttacagatacccatggca | AA117286 |
| 6976 | ctgagtccactggcgagatcccagc | W50385 | 49580 | gttcagccatggtgcgatccgaaa | AA030895 | 92184 | tcaacttacagataccatgccaaag | AA117286 |
| 6977 | gtctgaggggcctgccgtaag | W50385 | 49581 | tttcagccatggtgcgatccgaaac | AA030895 | 92185 | aacttacagatatcatcggcaaagg | AA117286 |
| 6978 | cagtctgcgaaggggcctgcgccat | W50385 | 49582 | cagccatgtgcgatccgaaagag | AA030895 | 92186 | cagataccatggcaaagaggaatac | AA117286 |
| 6979 | tcctgaggagatccagccatcat | W50385 | 49583 | gccatgtgcgatccgaaagaagct | AA030895 | 92187 | ggctccgaagttattcaggaaatt | AA117286 |
| 6980 | agggagatccagccatcatgctcat | W50385 | 49584 | tgctgccgggctctccctatcctg | AA030895 | 92188 | acatctggtctcgggaataactgc | AA117286 |
| 6981 | agatccccagccatcagctatcacaa | W50385 | 49585 | ggctctccctatcctggcactgac | AA030895 | 92189 | aactgccatagaaatggctgaagga | AA117286 |
| 6982 | tcccagccatcagtctatacagaa | W50385 | 49586 | ctgcctcatgagaccacagccc | AA030895 | 92190 | tacaatccaacttaaggagctaga | AA117286 |
| 6983 | cagccatcagtctatacagaat | W50385 | 49587 | tcatgagacaccagccctg | AA030895 | 92191 | actagaatacctcatttatgaga | AA117286 |
| 6984 | ccatcagtctatacagaagatcgt | W50385 | 49588 | gccctgaagggcctcaatcact | Y00746 | 92192 | tagaatacctcattttatgaaaa | AA117286 |
| 6985 | cctgcactcgtgcccaaaatcatg | U00677 | 49589 | gggaggccttcaatcacctagagct | Y00746 | 92193 | tacacgagatatcaaggcgggaaa | AA117286 |
| 6986 | tccaaaacgatgtcttttatcatc | U00677 | 49590 | atccactagagctgcgaagtccga | Y00746 | 92194 | acacgagatatcaaggcgggaaat | AA117286 |
| 6987 | acctggcgacgagtcggggtgt | U00677 | 49591 | tagagctgcagtcgagtctggc | Y00746 | 92195 | atatttgctaaacacgaagggcca | AA117286 |
| 6988 | gagtctcgctgtgtggcagct | U00677 | 49592 | tgacagagctggccagtatggcat | Y00746 | 92196 | tatttgctaaacacgaagggccat | AA117286 |
| 6989 | ggcttgttgggcagccttcctac | U00677 | 49593 | agctgccagtatggcatcattta | Y00746 | 92197 | gctaaaacagaaggccatgccaaag | AA117286 |
| 6990 | accagtgcctttctaagagatat | U00677 | 49594 | tcatttagtcagatccctgctgt | Y00746 | 92198 | aaagctccaagatgggtgaaagt | AA117313 |
| 6991 | gtacacagaagccattccgagccctg | U00677 | 49595 | agtcagaccctgctatgctgaggcc | Y00746 | 92199 | agctccaagatgggtgaaagtc | AA117313 |
| 6992 | agaagccattccgagccctgaacct | U00677 | 49596 | atccctgctatgtgagcctgggaa | Y00746 | 92200 | atttcaggaaggctctcgttta | AA117313 |
| 6993 | ggcctcaagcaccctgagatctc | U00677 | 49597 | tgccaacctgagaattgtaatag | Y00746 | 92201 | ttcaggaagctccgttagtg | AA117313 |
| 6994 | taagcacctgagatctgcagc | U00677 | 49598 | ccagccaagtttcgacagtccaga | Y00746 | 92202 | caggaagctccgtgtgagtag | AA117313 |
| 6995 | agatctgcagcgagctctg | U00677 | 49599 | agggtcactgcagtgtctgccag | Y00746 | 92203 | gggaagctccgttagtgagcc | AA117313 |
| 6996 | ctgagtctcgcagtcagttgcgca | U00677 | 49600 | ccatgaacctgggcagcacccaagg | Y00746 | 92204 | gaagctccgttagtggccta | AA117313 |
| 6997 | gctcttgcctagaactgaagcct | U00677 | 49601 | gaccacactaagttaagcacgcgga | Y00746 | 92205 | agctccgtgttagtgagcctaa | AA117313 |
| 6998 | tgcaccagtccttctaagaggatcagat | U00677 | 49602 | tcattagtcagacctgtgcatgt | Y00746 | 92206 | ctccgttagtgagcctaaagc | AA117313 |
| 6999 | tgtcctctgcgactgcctgctg | U00677 | 49603 | aaaccaggcagttcaaggcaagcc | Y00746 | 92207 | ctccgttagtgagcctaaagcac | AA117313 |

| SEQ ID NO | sequence | DBAxnID | SEQ ID NO | sequence | DBAxnID | SEQ ID NO | sequence | DBAxnID |
|---|---|---|---|---|---|---|---|---|
| 7000 | tctgctgactgcctgcctgctgtctggg | U00677 | 49604 | tcacgtcatctgcctgcctgggagc | Y00746 | 92208 | tagtgagctaaagcaccaaggca | AA117313 |
| 7001 | gggcctcagaaccagcctgaagaa | U00677 | 49605 | tcatctgccctggaggccttcaa | Y00746 | 92209 | gtgagcctaaagcaccaaggcaac | AA117313 |
| 7002 | cagagaccagcgtgaggaagcagaa | U00677 | 49606 | tagcttggctgacaggagagccagg | X67083 | 92210 | ctctccaagatgggtgaaagttcac | AA117313 |
| 7003 | agcagaactcagaccgggaacaggg | U00677 | 49607 | cagagtcaacgcacatcccaaag | X67083 | 92211 | tggaacagagtccagtgtttataa | AA117313 |
| 7004 | actcagaccgggacagcgagtctg | U00677 | 49608 | gcctgcaccaagcatgaacagtggg | X67083 | 92212 | gacacagagtccagtgttataatc | AA117313 |
| 7005 | tccaatcagttcactctgaacaag | K02927 | 49609 | ggaagtgtaccccagcaccatcgcgc | X67083 | 92213 | aagattgcattcacagagtggatg | AA117313 |
| 7006 | gaaacacagcagccatggtgtgctct | K02927 | 49610 | atcgcgcaagtggccagccatggac | X67083 | 92214 | gatgtcattcacagaggtggattgaa | AA117313 |
| 7007 | aaagccagtttgatattaggaaatc | K02927 | 49611 | ccaagcatggacccctgccactgcac | X67083 | 92215 | ttgcattcacagaggttgattgaacc | AA117313 |
| 7008 | aatactaaagagccttcctgcaaat | K02927 | 49612 | atgtgacccctgcactgcactgcaca | X67083 | 92216 | gccaactatgctgtgatgcatatt | AA117313 |
| 7009 | ccttcctgcaaatagtgaggagact | K02927 | 49613 | ccctgcactgcactgcacatgacggtaca | X67083 | 92217 | caactatgctgtgatgcatattc | AA117313 |
| 7010 | agtctcgtctccagcttcctccg | K02927 | 49614 | ctctgcacatagagctacatagacggtaca | X67083 | 92218 | agtcctttatcaagctgcacctg | AA117363 |
| 7011 | ttccctgcctggccattctcagttt | K02927 | 49615 | cttgcacatagacgttacatcagtgtttt | X67083 | 92219 | gtcacctgaacgtagaatccaggt | AA117363 |
| 7012 | gcctggccattctcagtttggccaa | K02927 | 49616 | atgttattactgtccatgtccag | X67083 | 92220 | acagtcctctcacagacagactcc | AA117363 |
| 7013 | ccattcagtttgggcaaagagat | K02927 | 49617 | tattactgtccagtcagtaaagt | X67083 | 92221 | agtcctctcacagacagactcctc | AA117363 |
| 7014 | caagcaattactcatcagctaaaga | K02927 | 49618 | gctctccagattccagtcagagttc | X67083 | 92222 | cttcacagacagactcctcagag | AA117363 |
| 7015 | attactcatcagctaaagactctttg | K02927 | 49619 | cagattccagtcagagttctatggc | X67083 | 92223 | cttcacagacagactcctcagaggc | AA117363 |
| 7016 | gtctagacaaactctatagctcat | K02927 | 49620 | agagttatatggcccaggagagga | X67083 | 92224 | tcacagacagactcctcagaggcg | AA117363 |
| 7017 | agcagccatggtgtgctcttggag | K02927 | 49621 | tggcacagctagctgaagagaacga | X67083 | 92225 | ttttagcaggcaaatgtatatgtc | AA117363 |
| 7018 | catgggtgtgctcttggagaacaga | K02927 | 49622 | agaacgacgcggctcaagcaggaagaat | X67083 | 92226 | atgtatatgtccacatatctcgga | AA117363 |
| 7019 | ttatcagcagcctgctggacgtg | K02927 | 49623 | agaccaacggcgggctctgatcga | X67083 | 92227 | gtatatgtccacatatctcggatgt | AA117363 |
| 7020 | gcagctctgttgacgtgcctgcc | K02927 | 49624 | tgatcagccatggtcagcctgca | X67083 | 92228 | atatgtccacatatctcggatgct | AA117363 |
| 7021 | agggagccacgactactacgtactgt | K02927 | 49625 | tggtcagcctgcaccaagcatgaac | X67083 | 92229 | atgtccacatatctcggatgctgc | AA117363 |
| 7022 | cttacagtactgtttctcacacagtg | K02927 | 49626 | tgctttcacagtcagttaaacc | X67083 | 92230 | cacctgaacgtagaatccaggtat | AA117363 |
| 7023 | gtactgtttctcacacagtaaata | K02927 | 49627 | ttcacagtcagttaaacctcacagtct | X67083 | 92231 | gtccacatatctcggatgctgeat | AA117363 |
| 7024 | tttctcacagtaaatatcattt | K02927 | 49628 | cagagtttcactcacattcctct | X67083 | 92232 | agaatccagtatgcacatgcctat | AA117363 |
| 7025 | gtgaccgtcagcctgctttcg | K02927 | 49629 | ccctttacaagaatgtcaagtg | X67083 | 92233 | tccaggtatgcacatgcctacat | AA117363 |
| 7026 | gcaccgatccagctgcttttcgcc | X15666 | 49630 | aggatcactgttccattcagaagaa | D17384 | 92234 | ttatacagagcgagcctccttca | AA117363 |
| 7027 | accggtcctggccagcaaagctg | X15666 | 49631 | actgttccattcagaagaatgggac | D17384 | 92235 | atacagagcgacagtcctcttcaca | AA117363 |
| 7028 | ccgggtcctggccagcaaagctgcg | X15666 | 49632 | atgggaacagctgaccaggatccag | D17384 | 92236 | acaggcgacagtcctcttcacaga | AA117363 |
| 7029 | tggccagcaaagctgcgaggagaat | X15666 | 49633 | cacagtcgacaggatccagtgctg | D17384 | 92237 | aggagacagtcctcttcacagacaga | AA117363 |
| 7030 | gccagcaaagctgcgaggagaatct | X15666 | 49634 | gatccagtcgctgagtctggatttcatc | D17384 | 92238 | cgacagtcctcttcacagacagact | AA117363 |
| 7031 | aatctccaagactccgccgagctg | X15666 | 49635 | atggcagcctttaaatactatctat | D17384 | 92239 | ataccaattcagcaccttaattgt | AA117363 |
| 7032 | gggcctactaaccccagctgagg | X15666 | 49636 | gcctaaatacttattctattgct | D17384 | 92240 | ctagcacctaattgtaccctgct | AA120054 |
| 7033 | gggcctactaaccccagcgttgagg | X15666 | 49637 | tattgtgatctgtacctaagaataa | D17384 | 92241 | cgtctgtatgtgccgccacacac | AA120054 |
| 7034 | ctactaaccccagcgttgaggtga | X15666 | 49638 | taaataccttgcagctactgctgcta | D17384 | 92242 | aacacacagcactgacaaattcatt | AA120054 |
| 7035 | actaaccccagcgttgaggtgagagc | X15666 | 49639 | ctgttcagctactgctacaaagca | D17384 | 92243 | cactctttccgatccttgtctaa | AA120054 |
| 7036 | accccagcgttgaggatgagccgtt | X15666 | 49640 | ctgctacacagcatggctgatttca | D17384 | 92244 | tgctaatacactctttaacgtatac | AA120054 |
| 7037 | ttccagctgttgcctgtctc | X15666 | 49641 | atggctgattcagtgctgctttc | D17384 | 92245 | tctcacttccacagctatataatc | AA120054 |
| 7038 | catctgctgaccagcagcagctgcag | X15666 | 49642 | gatttcagtgctgctttcatataa | D17384 | 92246 | cacttccacaagctatataatcctcc | AA120054 |
| 7039 | gctgaccagcagctgcagtgt | X15666 | 49643 | agtgctgctttcatataatgggtg | D17384 | 92247 | ttccacacgctatatataatcctcatt | AA120054 |
| 7040 | tgacctaaccagcgttgcagttcg | X15666 | 49644 | ttcaacattccacagtttcact | D17384 | 92248 | agctatataatctccattggaagc | AA120054 |
| 7041 | gaaagactcacccggctgacaag | X15666 | 49645 | attcaccacagtttcactcacat | D17384 | 92249 | ctatataatccattggaagcaag | AA120054 |
| 7042 | agcgactcaccagcgtgacaagga | X15666 | 49646 | atgtactgcactactagacaca | D17384 | 92250 | tataatctccattggaagcaaggcc | AA120054 |
| 7043 | tacccggctgacaaggagaaacac | X15666 | 49647 | actgactgcactactagacacaggt | Z50013 | 92251 | ttgtacctcggcttgtcagcaat | AA120054 |
| 7044 | accaccggtgacaaggagaacacgc | X15666 | 49648 | tgacctggtccgtgctgagttgag | Z50013 | 92252 | tacctcggctgtcagcaatcag | AA120054 |
| 7045 | gctgctcacctatcgatgatagcc | W50285 | 49649 | ggctgctgcactgtgagtctcgg | Z50013 | 92253 | tgtttagcaatcagcacatttga | AA120054 |
| 7046 | gcctctcactttatcgatgatagcc | W50285 | 49650 | tcgcactgtgagtctgcgcaggggc | Z50013 | 92254 | tagcaatcagcacattggactc | AA120054 |
| 7047 | tttagcgctcagctgctctct | W50285 | 49651 | tgtgactcgcaggcccaggac | Z50013 | 92255 | cagcaatcagcacattggactccc | AA120054 |
| 7048 | gccctcggccattagccgc | W50285 | 49652 | tcaggaacctgctcgcagctaggc | Z50013 | 92256 | tcgacattgactcccgtcga | AA120054 |
| 7049 | gccctctgccattgccattaggggt | W50285 | 49653 | tcgcagtgccatccacacatt | Z50013 | 92257 | gcacatttgactccccgtctgatag | AA120054 |

TABLE 1-continued

| SEQ ID NO | DBAxnID | sequence | SEQ ID NO | DBAxnID | sequence | SEQ ID NO | DBAxnID |
|---|---|---|---|---|---|---|---|
| 7050 | W50285 | ctctcgccattgctaggggtcta | 49654 | Z50013 | ctatgcatccctactattgaaaca | 92258 | AA120054 |
| 7051 | W50285 | tgcgccattgcttaggggtctagccg | 49655 | Z50013 | catccctacattgaaacatcagcc | 92259 | AA117444 |
| 7052 | W50285 | gcattgctttaggggtctagccgat | 49656 | Z50013 | ctatacactagtccgtgattcgg | 92260 | AA117444 |
| 7053 | W50285 | ttgcttaggggtctagcgagtcgg | 49657 | Z50013 | actagtccgtgagattcgcagcat | 92261 | AA117444 |
| 7054 | W50285 | ggaacaggatctcatcgacgtccgc | 49658 | Z50013 | ctacttagacacagcaggtcaagaa | 92262 | AA117444 |
| 7055 | W50285 | ggatccatcgacgtccgctcac | 49659 | Z50013 | agagtatagtgccatgcgggaaccag | 92263 | AA117444 |
| 7056 | W50285 | catccatcgacgtccgctcacgaatgg | 49660 | Z50013 | tgtattgccatcaacaacaccaag | 92264 | AA117444 |
| 7057 | W50285 | tcacctatcgatgtagcccgcgaa | 49661 | Z50013 | tgccatcaacaacaccaagtcctc | 92265 | AA117444 |
| 7058 | W50285 | cgtccgctcacgaatggaagtcg | 49662 | Z50013 | caccaagtcctcgaggacatccat | 92266 | AA117444 |
| 7059 | W50285 | tatcgatgtagcccgcgaacgtcgt | 49663 | Z50013 | cgaggacatccatcagtacgagggag | 92267 | AA117444 |
| 7060 | W50285 | cgatgtagcccgcgaacgtcgttga | 49664 | Z50013 | catccatcacagtacaggagcagatc | 92268 | AA117444 |
| 7061 | W50285 | tgtagcccgcgaacgtcgttgagcg | 49665 | Z50013 | caagtgacctgcgctcgcact | 92269 | AA117444 |
| 7062 | W50285 | agcccgcgaacgtcgttgagcgcct | 49666 | Z50013 | tgagatgttcagttcctgctcatt | 92270 | AA117444 |
| 7063 | W50285 | ccgggaacgtcgttgaggcctgca | 49667 | Z50013 | gatgctcagttcctgctcattag | 92271 | AA117444 |
| 7064 | W50285 | cgaacgtcgttgaggcctgcagt | 49668 | Z50013 | cattggactctcatgtgcgagaccca | 92272 | AA117444 |
| 7065 | W50285 | acgtcgttgaggcctgcagctgct | 49669 | Z50013 | cttcatgtcgagaccccatgccag | 92273 | AA117444 |
| 7066 | W50285 | cggagcgtatccgcttccatccg | 49670 | Z50013 | gtgcagagaccacgccaggatggt | 92274 | AA117444 |
| 7067 | W50285 | ggagagctatccgctccatccga | 49671 | Z50013 | tgtctggcttcctagccattgcact | 92275 | AA117444 |
| 7068 | W50285 | aaacctgccggagcccgatgaagct | 49672 | Z50013 | ctggattccctagcccattgcactgca | 92276 | AA117444 |
| 7069 | W50288 | accctgccggagccgatgaagcta | 49673 | Z50013 | gctctagccattgcactgcaggt | 92277 | AA117444 |
| 7070 | W50288 | accctgccggagccgatgaagctat | 49674 | Z50013 | tcctagccattgcactgcaggtgg | 92278 | AA117444 |
| 7071 | W50288 | ccctgccggagccgatgaagctat | 49675 | Z50013 | tagccattgcactgcaggtgggaac | 92279 | AA117444 |
| 7072 | W50288 | ctgccggagccgatgaagctatagga | 49676 | Z50013 | ccattgcactgcaggtgggaacatg | 92280 | AA117446 |
| 7073 | W50288 | tgccggagccgatgaagctatggat | 49677 | Z50013 | ttgcactgcaggtgggaacatgcg | 92281 | AA117446 |
| 7074 | W50288 | tgtaccagaagaactagaaaagca | 49678 | Z50013 | gcttcagttcctgctcattagga | 92282 | AA117446 |
| 7075 | W50288 | agagcgaaaccttagtctgatgca | 49679 | Z50013 | tgtaggctccgtcgtcgatttgtt | 92283 | AA117446 |
| 7076 | W50288 | agagcgaaaccttagtctgatgcata | 49680 | Z50013 | aggccgccgtcgatttgttgcc | 92284 | AA117446 |
| 7077 | W50288 | ggaaaccttagtctgatgatcat | 49681 | Z50013 | ctccgtcgcgtcgatttgttgccggt | 92285 | AA117446 |
| 7078 | W50288 | gagcagctatccgcttccatccgac | 49682 | Z50013 | cgtcgtcgatttgttgccggt | 92286 | AA117446 |
| 7079 | W50288 | agcagctatccgcttccatccgacg | 49683 | Z50013 | attgttgccggcccatagac | 92287 | AA117446 |
| 7080 | W50288 | gcagctatccgcttccatccgacgt | 49684 | Z50013 | cgggcccatggactcatgtgc | 92288 | AA117446 |
| 7081 | W50288 | tatccgcttccatccgacgtgcaaa | 49685 | AA031030 | tgccctcatggactcatgtcgcag | 92289 | AA117446 |
| 7082 | W50288 | atccgcttccatccgacgtgcaaa | 49686 | AA031030 | tcctacaagattcaggtaggttgc | 92290 | AA117446 |
| 7083 | W50288 | gcttccatccgacgtgcaaacc | 49687 | AA031030 | ttaggcggttgccatgaacctg | 92291 | AA117446 |
| 7084 | W50288 | tgcaaacctgccggagccgatgaa | 49688 | Y00864 | gttaccgcgtctgttgaaacatg | 92292 | AA117446 |
| 7085 | W50288 | caaacctgccggagccgatgaagc | 49689 | Y00864 | acccggtcgtttgaaacatgt | 92293 | AA117446 |
| 7086 | M96760 | gaaacctgcagggttatcaggca | 49690 | Y00864 | tactaagggccaccaccatgaga | 92294 | AA117446 |
| 7087 | M96760 | cctcccaaggaagttctagcgagg | 49691 | Y00864 | agggggccaaccatgagaattttg | 92295 | AA117446 |
| 7088 | M96760 | acaatcgttactcagactcagga | 49692 | Y00864 | ctttcagttgctgattgaat | 92296 | AA117446 |
| 7089 | M96760 | tatcttttcctggggctgaaag | 49693 | Y00864 | tcagttgctgattgaattt | 92297 | AA117446 |
| 7090 | M96760 | tttcctggggctgaaagatacatac | 49694 | Y00864 | tttgaatattccgagcccatgagt | 92298 | AA117446 |
| 7091 | M96760 | gcccacacgactcggctgaggagg | 49695 | Y00864 | gaatattccgagcccatgaatcc | 92299 | AA117446 |
| 7092 | M96760 | aagccagcacctggctgaggccccac | 49696 | Y00864 | tgagcccatgagtcctgaaaatat | 92200 | AA117446 |
| 7093 | M96760 | cctcccaaggaagttctagctgagg | 49697 | Y00864 | gtgtccaagtgttgacagttctga | 92301 | AA117453 |
| 7094 | M96760 | atccaggtcgtccggaacccagt | 49698 | Y00864 | atcgttccgactgagtcgtcact | 92302 | AA117453 |
| 7095 | M96760 | aaccaccaggttgaagaacagatga | 49699 | Y00864 | aactgttcagtctgaagaattc | 92303 | AA117453 |
| 7096 | M96760 | atgtttcagcatccagatttctaca | 49700 | Y00864 | tcgacttagtgctacactcttgca | 92304 | AA117453 |
| 7097 | M96760 | ctagcatccagattctacaataaag | 49701 | Y00864 | tgagtgctacacctctgcactttc | 92305 | AA117453 |
| 7098 | M96760 | tcaaggcacacgagaagtattctgg | 49702 | Y00864 | gtgctacacctctgcacctttcaa | 92306 | AA117453 |
| 7099 | M96760 | gctgcacctattgctgcagattc | 49703 | Y00864 | tcttgcacctttccaaagtaagctg | 92307 | AA117453 |

| SEQ ID NO | DBAxnID | SEQ ID NO | sequence | DBAxnID | SEQ ID NO | sequence | DBAxnID |
|---|---|---|---|---|---|---|---|
| 7100 | M96760 | 49704 | tgcacttccaaagtaagctgtt | Y00864 | 92308 | tctcagcgtcctgcctgctgga | AA117453 |
| 7101 | M96760 | 49705 | ttggagtcctggtcatgtacga | Y00864 | 92309 | cgtccgctcctgctgctggacagaaa | AA117453 |
| 7102 | M96760 | 49706 | acgagactgtcaccagttaccgc | Y00864 | 92310 | cctgctccgtcctggacacagaagaa | AA117453 |
| 7103 | M96760 | 49707 | cagtcggggactgcatgcaggtacct | AA031112 | 92311 | gctcctgctggacagaagaagga | AA117453 |
| 7104 | M96760 | 49708 | atgcggggacctgtccagaggcc | AA031112 | 92312 | aacatgtcaaactctggagattgt | AA117453 |
| 7105 | M29015 | 49709 | taccctgcacctgctgcacatct | AA031112 | 92313 | gattgtcatgagcgtgcagtcac | AA117453 |
| 7106 | M29015 | 49710 | accgtgcacctggtcgcacatcg | AA031112 | 92314 | tgttcatgcgctgcagtcactca | AA117453 |
| 7107 | M29015 | 49711 | cgtgcacctggctgcaatctggcc | AA031112 | 92315 | ttcatgagcgtgcagtcactcaag | AA117453 |
| 7108 | M29015 | 49712 | gtgcacctggtgcacatctggcc | AA031112 | 92316 | agcgtgcagtcactcaatggggatt | AA117453 |
| 7109 | M29015 | 49713 | tgcacctggctgcacatctggccag | AA031112 | 92317 | cagtcactcaatgggattcttacc | AA117453 |
| 7110 | M29015 | 49714 | gcacctggctgcacatctggccgg | AA031112 | 92318 | gtagggaccccagccaatagccaatc | AA117453 |
| 7111 | M29015 | 49715 | tgcgagtaccgtccagaggcct | AA031112 | 92319 | acccaggccaatatgccaaccagg | AA117453 |
| 7112 | M29015 | 49716 | ctgtccagaggcctttataccgtg | AA031112 | 92320 | tgcagtcggcgcctcatcagaacaa | AA117418 |
| 7113 | M29015 | 49717 | tgttccagaggccttataccgtgc | AA031112 | 92321 | agtcggccgtcatcagaacaatga | AA117418 |
| 7114 | M29015 | 49718 | caggagcttataccgtgcacctg | AA031112 | 92322 | ttcctccagttcaaggtacagga | AA117418 |
| 7115 | M29015 | 49719 | ctttataccgtgcacctggtcgac | AA031112 | 92323 | taaagatgccctgctgtgatg | AA117418 |
| 7116 | M29015 | 49720 | ttataccgtgcacctggtgcaca | AA031112 | 92324 | agagtgccctgctgtgtgata | AA117418 |
| 7117 | M29015 | 49721 | tgtcaccccatgtgattttgtaaatc | AA031112 | 92325 | gagtgccctgctgtgtgtgtataac | AA117418 |
| 7118 | M29015 | 49722 | agaactatttctgcaatcgcaaa | AA031112 | 92326 | gtccctgctgttggtgatacaa | AA117418 |
| 7119 | M29015 | 49723 | atctatttctggcaatcgcaaact | AA031112 | 92327 | ccctgctgttgggtgatacaacga | AA117418 |
| 7121 | M29015 | 49724 | tattttctggcaatcgcaaactg | AA031112 | 92328 | ccctgctgttggtgataaacgag | AA117418 |
| 7122 | M29015 | 49725 | ttctggcaatcgcaaaactgtgt | AA031112 | 92329 | gatacacgagggcgctaagttc | AA117418 |
| 7123 | M29015 | 49726 | gtgagactcacctagtttgaatt | AA031112 | 92330 | ataacacgagggcagcctaagttg | AA117418 |
| 7124 | M29015 | 49727 | tcctctggtatattgcctatg | AA031112 | 92331 | gctgcctcatcagaacaatgac | AA117418 |
| 7125 | M29015 | 49729 | cctcctgtatattgcctatg | AA031112 | 92332 | gctgcctcatcagaacaatgac | AA117418 |
| 7126 | AA033424 | 49730 | tgtgattgctcaatcccagttgtg | AA031112 | 92333 | tggcctcatcagaacaatgacac | AA117418 |
| 7127 | AA033424 | 49731 | gtgattgctcaatcccagttgg | AA031112 | 92334 | cactcaggctgctgttcctgggtc | AA117418 |
| 7128 | AA033424 | 49732 | tgattgctcaatcccagttgga | AA031112 | 92335 | ctcaggctgctgtccggtctc | AA117418 |
| 7129 | AA033424 | 49733 | gattgtcaatcccagttgtgac | AA031112 | 92336 | agcctgctgttcctgggtctcaac | AA117418 |
| 7130 | AA033424 | 49734 | attgctcaatcccagttgtgact | AA031112 | 92337 | ggctgctgttcctgggtctcaact | AA117418 |
| 7131 | AA033424 | 49735 | agaatggcccctgacggtatggagc | AA031112 | 92338 | ctgctgttccctgggctctcaactc | AA117418 |
| 7132 | AA033424 | 49736 | ttgctcaatcccagtgttgac | AA031112 | 92339 | ctgttcctggctctcaactctc | AA117418 |
| 7133 | AA033424 | 49737 | gcgcactggtcgtcagttgactg | AA031112 | 92340 | aagccaatcccagttggacgtga | AA117418 |
| 7134 | AA033424 | 49738 | gaatggccctgacggtatggagc | AA031112 | 92341 | tcaaggtgtctcctccagttcagg | AA117418 |
| 7135 | AA033424 | 49739 | gtatggacccggacgtctatctgag | AA031115 | 92342 | tccaacaattctgtctcgtattt | AA117418 |
| 7136 | AA033424 | 49740 | tggagccggagcgtctactgagagt | AA031115 | 92343 | aattctgtctggtattcattga | AA117418 |
| 7137 | AA033424 | 49741 | gagccggagcgtctactgagagtaa | AA031115 | 92344 | aagacatcttgcacatgaccat | U10871 |
| 7138 | AA033424 | 49742 | agccggagcgtctactgagagtaac | AA031115 | 92345 | tcttgcacatgaccatgctgtg | U10871 |
| 7139 | AA033424 | 49743 | gccgacgtctactgagagtaacg | AA031115 | 92346 | cacatgaccatgctgtgttaggg | U10871 |
| 7140 | AA033424 | 49744 | ccggagctgtctactgagagtaacgt | AA031115 | 92347 | ggctgttccagggactggactcg | U10871 |
| 7141 | AA033424 | 49745 | cgctcctggaagtccaatcattgg | AA031115 | 92348 | gttcaggactgaactgaactgctca | U10871 |
| 7142 | AA033424 | 49746 | gctccctggggttctggccaatga | AA031115 | 92349 | ggactgaactagaacggccagaa | U10871 |
| 7143 | M23453 | 49747 | tgtcctggggttctggccaatgag | W13236 | 92350 | tcttcatcagaagacaaggggaacga | U10871 |
| 7144 | M23453 | 49748 | tccctggggttctggccaatgaga | W13236 | 92351 | tcagtaataccacctcagttaaaata | U10871 |
| 7145 | M23453 | 49749 | cctctggggttctggccaatgaaac | W13236 | 92352 | gcaggaacccgaatcattggagc | U10871 |
| 7146 | M23453 | 49750 | ctctggggtctggccaatgaaact | W13236 | 92353 | aatcattggagcccagaaggaggc | U10871 |
| 7147 | M23453 | 49751 | ctgggttctggccaatgaaactgg | W13236 | 92354 | ggccaggttcacctcagttggtc | U10871 |
| 7148 | M23453 | 49752 | ttcggccaatgagaaactgctct | W13236 | 92355 | gtctcacccacctcagtgtcagttc | U10871 |
| 7149 | M23453 | 49753 | caatagaactgctccccgagcc | W13236 | 92356 | cacctcagtgcagtcaactcc | U10871 |
|  |  |  |  |  | 92357 | catgccatccatcagagtgggtta | U10871 |

TABLE 1-continued

| SEQ ID NO | sequence | DBAxnID | SEQ ID NO | sequence | DBAxnID |
|---|---|---|---|---|---|
| 7150 | gagccatttcttcagccaaacatcc | M23453 | 49754 | aatgagaacctgcctctcggagcc | W13236 | 92358 | atcccatcaagatgggttagtagca | U10871 |
| 7151 | ccatttctcagccaaacatcccat | M23453 | 49755 | atgagaacctgcctctcggagcc | W13236 | 92359 | gtgatttccaacaattcgctctgg | U10871 |
| 7152 | catttctcagccaaacatcccata | M23453 | 49756 | ctcctggaagtccaatcattgggt | W13236 | 92360 | catcacggaggcaccaccgacagc | W08014 |
| 7153 | attctcagccaaacatcccatat | M23453 | 49757 | tcctggaagtccaatcattgggct | W13236 | 92361 | aggaggcaccaccgacagctgccca | W08014 |
| 7154 | ttctcagccaaacatcccatatt | M23453 | 49758 | cctggaagtccaatcattgggctc | W13236 | 92362 | cattacagttctttgaggatgtt | W08014 |
| 7155 | ttctcagccaaacatcccatattt | M23453 | 49759 | gaagtccaatcattgggctctgtcc | W13236 | 92363 | tatcagttcttgaggatgtttgac | W08014 |
| 7156 | tcttcagccaaacatcccatattt | M23453 | 49760 | agtccaatcattgggctctgtcc | W13236 | 92364 | gctccaactgggcctcgtcgtgt | W08014 |
| 7157 | cttcagccaaacatcccatattta | M23453 | 49761 | gtccaatcattgggctctgtcct | W13236 | 92365 | gtgaaatatccaacaacgaggcca | W08014 |
| 7158 | gggtcaaatgccctggaactggaa | M23453 | 49762 | caatcattgggctctgtcctctg | W13236 | 92366 | tataccaacaacggccaattgaa | W08014 |
| 7159 | tgtcaaatgccctggaactggagt | M23453 | 49763 | aatcattgggctctgtcctctggt | W13236 | 92367 | aacgaggccaattgatggtggtgaa | W08014 |
| 7160 | gtcaaatgccctggaactggagtt | M23453 | 49764 | tgatctgccacaggaccacagtgcca | W13236 | 92368 | agatatacgatcattgacaagtca | W08014 |
| 7161 | tcaaatgccctggaactggagtta | M23453 | 49765 | atctgccacaggaccagtcgaag | W13236 | 92369 | tatacgcatcatgacaagtcaggt | W08014 |
| 7162 | aattatggagcattgctctcagcca | M23453 | 49766 | cttcacgcgagccacttagctt | W13236 | 92370 | acgatcattgacaagtcaggttcc | W08014 |
| 7163 | attatggagccattcttcagccaa | M23453 | 49767 | ttcacgcgagccacttagcttgt | W13236 | 92371 | tgacaagtcaggttccacagtcacc | W08014 |
| 7164 | ttatggagccattcttcagccaaa | M23453 | 49768 | gacgagccacttagcttgtccac | W13236 | 92372 | aggcaccacccgacagtgcccagt | W08014 |
| 7165 | atggagccattcttcagccaaaca | M23453 | 49769 | cggagcccacttagctgtccacat | W13236 | 92373 | gtcaggttccacagtcaccgctgct | W08014 |
| 7166 | gaccaagtcgtctagaagttgct | M23453 | 49770 | gagcccacttagctgtccacagt | W13236 | 92374 | caccacgaagtcgcccagtgaa | W08014 |
| 7167 | caagtcgtctagaagttgctgac | M23453 | 49771 | gccacactagcttgtccacatgat | W13236 | 92375 | caccgacagtcgcccagtggaagc | W08014 |
| 7168 | agctcgcaaacatctgatctgctt | W50468 | 49772 | actagcttgtccacatgtactca | AA031158 | 92376 | cagctccagttggaagctggtcc | W08014 |
| 7169 | gctcgcaaacaatcgatctgctt | W50468 | 49773 | ttagctgtccacatgtatctcaat | AA031158 | 92377 | ccccacatgggtctccgtgatg | W08014 |
| 7170 | gctcgcaaacaatcgatctgttc | W50468 | 49774 | agctgtccacatgtatctcaatg | AA031158 | 92378 | gggtctccgtgatgttgacc | W08014 |
| 7171 | tccgcaaacaatcgatctgcttc | W50468 | 49775 | ctgtccacatgtatctcaatgca | AA031158 | 92379 | gctcctgtatggttgacact | W08014 |
| 7172 | cgcaaacaatcgatctgcttccct | W50468 | 49776 | tctgccacagtgaccagtccaagc | AA031158 | 92380 | gaccactgtccgagaatagtggga | W08014 |
| 7173 | gcaaacaatgctcgatctgctccct | W50468 | 49777 | tgtccaccagttatctcaatgcaac | AA031158 | 92381 | taatctcacgctgtgccagact | AA117492 |
| 7174 | acaatgcgatcgcttcccttgc | W50468 | 49778 | aggaccagtccaaggccaatcagat | AA031158 | 92382 | tccccatcagacgcggaatga | AA117492 |
| 7175 | tctgccaccggacacatgccgt | W50468 | 49779 | gaccagtccaaggccaatcagatct | AA031158 | 92383 | ggcctcaaagctcatccattctt | AA117492 |
| 7176 | ctgccaccgggacacatgccgtc | W50468 | 49780 | ccagtccaaggcaatcagatcttt | AA031158 | 92384 | ctctcaaagctcatccattctga | AA117492 |
| 7177 | acgtgtcctagaagttgctgacc | W50468 | 49781 | taaagttcgtggatggaatgccaac | AA031158 | 92385 | tcaaagctcatccattctttgagc | AA117492 |
| 7178 | aagtcgtctagaagttgctgacc | W50468 | 49782 | gatgaatgccaacttttcagcgag | AA031158 | 92386 | aagctcatccattctttgagacct | AA117492 |
| 7179 | ccgtgggcatcatgccgccaacag | W50468 | 49783 | tgaatgccaacttttcagacggagc | AA031158 | 92387 | ctcatccattctttgagaccatcac | AA117492 |
| 7180 | gtcgtctagaagttgctgaccct | W50468 | 49784 | aatgccaacttttcagacggagccca | AA031158 | 92388 | atcatttctttgagaccatcactg | AA117492 |
| 7181 | agttgctgacctaaatgctctgt | W50468 | 49785 | cgtggagactcctcatcaaggagacaa | Z49916 | 92389 | tcttttgagaccatcactgggga | AA117492 |
| 7182 | gttgctgacctaaatgctctgtt | W50468 | 49786 | agactacaacggctttcctgctc | Z49916 | 92390 | tctttggaccatcacttggggagaa | AA117492 |
| 7183 | ttgctgacctaaatgctctgttgta | W50468 | 49787 | gagggcatttcaacctgagcct | Z49916 | 92391 | ttgagaccacactggggagat | AA117492 |
| 7184 | ctgacctaaatgctctgttagtc | W50468 | 49788 | cattcaacctgagcccttcag | Z49916 | 92392 | ccatcactttggggaagaattgcacca | AA117492 |
| 7185 | cctaaatgctctgttagtccaag | W50468 | 49789 | caacctgagcccttcacggtcaca | Z49916 | 92393 | caccattgagcgggaatgaata | AA117492 |
| 7186 | cgagctcgcaaacaatgatctgc | W50468 | 49790 | gagcccttcaggttcacagatcac | Z49916 | 92394 | agaattgcaccgacagaacaactcc | AA117492 |
| 7187 | ttgtataacaccctccatgcttca | W54878 | 49791 | gctccgacaatgcctgtgaccag | Z49916 | 92395 | cattcagccggaatgaatatct | AA117492 |
| 7188 | tataacaccctccatgcttcagca | W54878 | 49792 | tgttctgagacacatgcccagag | Z49916 | 92396 | tggaatatcatttccagaaaatt | AA117492 |
| 7189 | gagaagtcagtcgtccgtcaaatcc | W54878 | 49793 | gagacacagcccagatggcaaac | Z49916 | 92397 | aattcttcctaaggctagaagact | AA117492 |
| 7190 | agtcagtcgtccgtcaaatccccaa | W54878 | 49794 | ggcaaacccagacccgtcaatccat | Z49916 | 92398 | tttttgatgccaacaaagcgtttagg | AA117492 |
| 7191 | ctcagtcgtcaatccaaatga | W54878 | 49795 | ccagacccgaatccatcgtt | Z49916 | 92399 | tagatgccaaagcgtttaggctg | AA117492 |
| 7192 | agctccgtcaatccaatgatt | W54878 | 49796 | cctgaatccatcgtttaattag | Z49916 | 92400 | atgccaaaagcgtttaggctgta | AA117492 |
| 7193 | tccgtcaatccaaatgatttag | W54878 | 49797 | caacggcttcctgctgctgcc | Z49916 | 92401 | acgggcctctcaagctcatccatt | AA117492 |
| 7194 | gtcaaatcccaaatgatttatgaga | W54878 | 49798 | tgtgctgtccagagaactggag | Z49916 | 92402 | cgccgggaactcagagtccactga | W29527 |
| 7195 | aaatcccaaatgatttatgagatta | W54878 | 49799 | ctcgagcgtctcaccggttgcc | Z49916 | 92403 | gccccgaactcagagtccactgac | W29527 |
| 7196 | atgaacattcgttcgcattggta | W54878 | 49800 | gcgtctcaccgggtttgcccaagg | Z49916 | 92404 | tcagagtccactgactttccgca | W29527 |
| 7197 | atccgtttcgcattggtaacagca | W54878 | 49801 | aaatgccaggacggaggcaagaggge | Z49916 | 92405 | ttttgacagtgccaactgcaagcaag | W29527 |
| 7198 | cgtttgcattggttaacagcaaag | W54878 | 49802 | gagcaattccatcatgtaacttcaca | Z49916 | 92406 | ttgacagtgccaacgtcaagcaagt | W29527 |
| 7199 | acaccctccatgcttcagcatcacg | W54878 | 49803 | tgagctgctgccaacagccccat | Z49916 | 92407 | tgacagtgccaacgtcaagcaagtg | W29527 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 7200 | cctccatgcttcagcatatacgtca | W54878 | 49804 | tccactgaagctgaggcgcattttc | Z49916 | 92408 | gacagtgccaagtcaagcaagtgg | W29527 |
| 7201 | tgcttcagcatctacgtcatgggca | W54878 | 49805 | tggcttcctgtataatgtcaaaa | X78874 | 92409 | acagtgccaacgtcaagcaagtgga | W29527 |
| 7202 | ttcagcatctacgtcatgggcattg | W54878 | 49806 | agacctgactattgcaatagaaagt | X78874 | 92410 | cagtgccaagtcaagcaagtggac | W29527 |
| 7203 | agcactacgtcatgggcatgtcc | W54878 | 49807 | tggctgccagtgcctgtaact | X78874 | 92411 | agtgccaagtcaagcaagtggacg | W29527 |
| 7204 | tacgtcatgggcatggcctggaat | W54878 | 49808 | gtgccttaactcacaacgacgc | X78874 | 92412 | gtgccaacgtcaagcaagtggacgt | W29527 |
| 7205 | gtcatgggcatggtcctggaatgga | W54878 | 49809 | tcaacacgagcgcctccttggcatt | X78874 | 92413 | tgccaacgtcaagcaagtggacgtg | W29527 |
| 7206 | atgggcatggcctggaatggatca | W54878 | 49810 | agatatcctccgtcataggcccag | X78874 | 92414 | ccggaactcagagtccactgact | W29527 |
| 7207 | cagaggtaccaatcattccagt | W54878 | 49811 | cctccgtcatatggcccagacggca | X78874 | 92415 | ccggaactcagagtccactgactt | W29527 |
| 7208 | taccaattcattccagttgctc | W54878 | 49812 | tcatatgcccagacggcaaaccaa | X78874 | 92416 | gcgaactcagagtccactgactttt | W29527 |
| 7209 | tgctcggtagctgggtgattggaaga | K02060 | 49813 | gtcaactgagtcctgtagatgagg | X78874 | 92417 | cgaactcagagtccactgactttc | W29527 |
| 7210 | agacactgcaacattactcactg | K02060 | 49814 | aatagacaatcttaatctgcgg | X78874 | 92418 | gaactcagagtccactgactttcc | W29527 |
| 7211 | acactgcaacattactcactgaa | K02060 | 49815 | acaatcttaatctgcgggaactg | X78874 | 92419 | aactcagagtccactgactttccg | W29527 |
| 7212 | actcgcaacattactcactgaagg | K02060 | 49816 | ctttaactcggggactgctccat | X78874 | 92420 | actcagagtccactgactttccgc | W29527 |
| 7213 | tctgcaacattactcactgaaggcc | K02060 | 49817 | cagttcggtggtgtttgcacag | X78874 | 92421 | ctcagagtccactgactttccgcc | W29527 |
| 7214 | tgcaacattactcactgaaggctg | K02060 | 49818 | gtgttttgcacagcatatctcatct | X78874 | 92422 | caattcggttcgaggcgtcacagt | W08057 |
| 7215 | caacattactcactgaaggcctgag | K02060 | 49819 | gcatactccatctctccagcagaa | X78874 | 92423 | attcggttcgaggcgtcacagtga | W08057 |
| 7216 | attactcactgaaggccgtgagacgc | K02060 | 49820 | tccatctctccagcagaaagtcca | X78874 | 92424 | tccctggcacactccgtga | W08057 |
| 7217 | ctcactgaaggcctgagacgcagcc | K02060 | 49821 | tctctccagcagaaagtccacggcca | X78874 | 92425 | cgtttgcaaagcagtcacgcactg | W08057 |
| 7218 | cactgaaggcctgagacgcagcccc | K02060 | 49822 | aagcatcctgacatagagccctttt | X78874 | 92426 | tttccgcaaagcagtcacgcactga | W08057 |
| 7219 | cccatttcattccagttgctcgg | K02060 | 49823 | catgagcccttttacgttgacagac | X78874 | 92427 | tttccaaagcagtccactgag | W08057 |
| 7220 | ccatttcattccagttgctcgta | K02060 | 49824 | agacatcttcgaaagctggtcg | X78874 | 92428 | gcaaagcagtcacgcactgagccg | W08057 |
| 7221 | tttcattccagttgctcggtagc | K02060 | 49825 | aattatggaaccagtggggctg | X78874 | 92429 | aaagcagtcacgcactgagcgcga | W08057 |
| 7222 | tcatttccagttgctcggtagctg | K02060 | 49826 | gagaccagtggggctgtctgtgtca | X78874 | 92430 | aagcagtcacgcactgagcgcgat | W08057 |
| 7223 | atttccagttgctcggtagctgct | K02060 | 49827 | ggataaaacagaacccatagagc | X78874 | 92431 | agcagtcacgcactgagcgcggat | W08057 |
| 7224 | ccagttgctcggtagctgctggt | K02060 | 49828 | taacagaacccatagagcagttgtg | X78874 | 92432 | cagtcacgcactgagcgcggatctc | W08057 |
| 7225 | agttgctcggtagctgctggtgatt | K02060 | 49829 | aaccccatagagcagtgtgaacaat | X78874 | 92433 | agtcacgcactgagcgcggatctca | W08057 |
| 7226 | tttgctcggtagctgctggtgattgaa | K02060 | 49830 | tagatcccacagtgtttctgtgga | X78874 | 92434 | ttcggttcgcggcgtcacagtgaa | W08057 |
| 7227 | gttgctaccactactatgacgat | W50352 | 49831 | acatgtttcgtcctggataggg | X78874 | 92435 | gtcacgcactgcgcgggatctcaa | W08057 |
| 7228 | tgctaccactactatgacgatgc | W50352 | 49832 | gttcttgctccggatagtgagtt | Z22649 | 92436 | tcggttcgaggcgtcacagtgaag | W08057 |
| 7229 | cgatgtaccaaggttcgacgtttg | W50352 | 49833 | tgctccggatagtgagttgaaagg | Z22649 | 92437 | tgttggatacctgcaagcacga | W08057 |
| 7230 | tgttccgacgtgggcttagcactc | W50352 | 49834 | cccagcatctcaatactatttca | Z22649 | 92438 | tttcctatcctgagggcacactt | W08057 |
| 7231 | ttccgacgtgggcttagcatctcag | W50352 | 49835 | catcttcaatactatcacgatg | Z22649 | 92439 | tccctatcctgagggcacactttc | W08057 |
| 7232 | ggcttagcatctcaggaaggccaag | W50352 | 49836 | tattttcacgtatgacaggtgcagg | Z22649 | 92440 | cctatcctgagggcacacttccg | W08057 |
| 7233 | atctcaggaatggacctgtctg | W50352 | 49837 | gtgccacagtatcacctcctcct | Z22649 | 92441 | tatcctgagggcacacttccgtg | W08057 |
| 7234 | gaatggaccctgtctggcttccgt | W50352 | 49838 | cagtatcacctccctcctcgttct | Z22649 | 92442 | atcctgagggcacacttccgtgg | W08057 |
| 7235 | atggaccctgtctggcttccgtat | W50352 | 49839 | gccaatctggagctagaacccagt | Z22649 | 92443 | tgatgttcctggatagatgccctt | AA117646 |
| 7236 | ggaccctgtctggcttccgtatag | W50352 | 49840 | caactgctagtcgtggcaaaactagg | Z22649 | 92444 | ttcctggatagatgccctgcct | AA117646 |
| 7237 | tctggcttcctgtatagcagatgaa | W50352 | 49841 | agccttagcagttccctcctat | Z22649 | 92445 | atctggacactagggtatacttc | AA117646 |
| 7238 | ttggcttcctgtatagcagatgaat | W50352 | 49842 | tgagccttcccctccatcacga | Z22649 | 92446 | cctgttcgttctaagtttcacat | AA117646 |
| 7239 | ctaccactactatgacgatgccc | W50352 | 49843 | ttttccctcatctacgaagtg | Z22649 | 92447 | agatgccctctgcctcagttcatt | AA117646 |
| 7240 | taccactactatgacgatgccgg | W50352 | 49844 | cctcatctacgaagtggatatat | Z22649 | 92448 | taagttttcacattctaat | AA117646 |
| 7241 | cactatgacgatgccgcgacgatg | W50352 | 49845 | tcagtcccacaaacaagctacta | AA032836 | 92449 | gttttcacattctaatttgccatct | AA117646 |
| 7242 | actatgacgatgccgcgacgatga | W50352 | 49846 | atgcccacaaacaagtctatt | AA032836 | 92450 | ttcacattctaattgccatctgac | AA117646 |
| 7243 | tatgacgatgccgcgacgatgtacc | W50352 | 49847 | atatgcccgaggacatagccaaag | AA032836 | 92451 | atcgaccagagttcaggccattag | AA117646 |
| 7244 | acgaggtcgggacgatgtaccaggt | W50352 | 49848 | tgccgaggacatagccaagctgg | AA032836 | 92452 | tgaccagagttcaggccattaggg | AA117646 |
| 7245 | gatgccggacgatgtaccaggtgt | W50352 | 49849 | gacatagccaagctggtgcagtt | AA032836 | 92453 | ttcaccattagggaaaggccag | AA117646 |
| 7246 | tgccggacgatgtaccaggtgtc | W50352 | 49850 | gaacctggccgttcactgagtcag | AA032836 | 92454 | aaggccagttgtgtaggaggattat | AA117646 |
| 7247 | gccaactccatcagccagatgacag | M12130 | 49851 | ggtccacgatatgatccatgaagca | AA032836 | 92455 | agatgccctctgcctcagttcatt | AA117646 |
| 7248 | tcccccagatgacagcgatgagga | M12130 | 49852 | tgaagcagagaccttcacgcttact | AA032836 | 92456 | tgcctctgcctcagttcatttgt | AA117646 |
| 7249 | ggactcactcagccactgcaggt | M12130 | 49853 | actgttccgatggccactcccaag | AA032836 | 92457 | tctgcctcacttgcttcatga | AA117646 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 7250 | actgaccagctgcaggtttgtt | M12130 | 49854 | tgttccgatgccactgcccaagaa | AA032836 | 92458 | tcagttcattgcttcatgattctgc | AA117646 |
| 7251 | ccagctgcaggtttgtacctg | M12130 | 49855 | gccactgcccaagaagccatagaaa | AA032836 | 92459 | cattgcttcatgattctgtttga | AA117646 |
| 7252 | tccaacatgaaggtctctgcttcc | M12130 | 49856 | cactgcccaagaagccatagaaatg | AA032836 | 92460 | tgcttcatgattctgctgttgaagg | AA117646 |
| 7253 | accatgaaggtctctgcttcctgt | M12130 | 49857 | cacaaacaagtctactaattcggaca | AA032836 | 92461 | attctgctgaaggtttgctgga | AA117646 |
| 7254 | atgaaggtctctgcttcctgtgac | M12130 | 49858 | caagtctactattcggacaaatacg | AA032836 | 92462 | tagacaatctggcaactaggtgt | AA117646 |
| 7255 | gcttctgtgacttgattgggata | M12130 | 49859 | tctactattcggacaaatacgacga | AA032836 | 92463 | tttctaccagagagactgaaaat | AA117646 |
| 7256 | gtgcctgctctgggtcatacacctg | M12130 | 49860 | tactattcggacaaatacgacga | AA032836 | 92464 | agaacagaccagctgacacaaaac | U03723 |
| 7257 | cctgctgcagtcatacacctgatc | M12130 | 49861 | agttcgaataccggcagtcatatt | AA032836 | 92465 | ataccaccttctaattgctcaag | U03723 |
| 7258 | catacacctgatctggaagtaacaa | M12130 | 49862 | ttcgaataccggcagtcatattgc | AA032836 | 92466 | gaaatttcgagctcactctct | U03723 |
| 7259 | cagacaacctcggtgcctgtgtgt | M12130 | 49863 | aataccggcatgtcatattgcccga | AA032836 | 92467 | tcggagctcactctctcttccctg | U03723 |
| 7260 | acaacctcggtggcctgtgtgtcac | M12130 | 49864 | taccggcatgtcatattgcccgagg | AA032836 | 92468 | ttctcccggggacaagtcagag | U03723 |
| 7261 | tcggtggccgtgtgcactccct | M12130 | 49865 | ttcactacacagttctagaggatg | AA032836 | 92469 | ttccctggacaagtcagagtat | U03723 |
| 7262 | tcccttgtacataactcctgtgac | M12130 | 49866 | ggctgtactaaacacactggaaat | X52046 | 92470 | caactgttctaatgcaaaggctgtg | U03723 |
| 7263 | tgacaaaacctctggaagttctgg | M12130 | 49867 | gccaaactctgaaacccagcaa | X52046 | 92471 | ctgttctaatgcaaaggtggag | U03723 |
| 7264 | ctgtcctcactcatgctgtctg | M12130 | 49868 | aaaccacactcatgttcatctg | X52046 | 92472 | ttctaatgcaaaggctggagact | U03723 |
| 7265 | ctctactgctgtctggactca | M12130 | 49869 | catcatgttcatctgttttaa | X52046 | 92473 | caaaagatgcactgcatacagtaa | U03723 |
| 7266 | tactcatgctgtctggactcactg | M12130 | 49870 | gtttaatcttatcaaccagtgaa | X52046 | 92474 | acgatgcactgcatacagtaatat | U03723 |
| 7267 | cttacttcacaatatgctacgaa | M12130 | 49871 | atctatcaaccagtgcaagtgaac | X52046 | 92475 | acagaccccagctgacacaaaagca | U03723 |
| 7268 | atatgctacagaacatctaggctga | J03776 | 49872 | tcaaccagtgcaagtgaccaactaa | X52046 | 92476 | ccagctgacacaaaacagcagtcagt | U03723 |
| 7269 | ctgcgccaagactattctaatgtg | J03776 | 49873 | tttgcgttcaaccaccaataca | X52046 | 92477 | gctgacaaaacgcagtcagttgt | U03723 |
| 7270 | ctatttctaatggtgtgatatat | J03776 | 49874 | accaccaataccaggtcaaatgctt | X52046 | 92478 | gacacaaaacgcagtcagttgtcca | U03723 |
| 7271 | ctatgattttctcattcacaataat | J03776 | 49875 | caattccaacttcaaaatgtctcaa | X52046 | 92479 | aaacgacagtcagttgtccatactta | U03723 |
| 7272 | caatgataccatatcaactgaaccttc | J03776 | 49876 | caacttcaaaatgtctcaatgctgc | X52046 | 92480 | agtcagttgtccatactaccttct | U03723 |
| 7273 | tacccataaactgaacctctgttat | J03776 | 49877 | actaaacacactggggaatgtggca | X52046 | 92481 | ttgtccatactactctcaattg | U03723 |
| 7274 | taactgaacctctgttatgttgtg | J03776 | 49878 | gaatatcaaacacgcaaggcaatga | X52046 | 92482 | tccatactacctctaattgctc | U03723 |
| 7275 | aacttctgttatgttgtgaaatgt | J03776 | 49879 | caaacacgcaaggcaatgagactac | X52046 | 92483 | tcttaaagattctcggcaggtgc | AA117715 |
| 7276 | ctctatttgcttctagcagatagaa | J03776 | 49880 | gcaatgagactaccatcatagata | AA032912 | 92484 | cttaaagattctgcagctggcagtggca | AA117715 |
| 7277 | ttgcttctagcagatagaaggatc | J03776 | 49881 | agactaccacatagatatctgcac | AA032912 | 92485 | cagagtattccctttcaggag | AA117715 |
| 7278 | ttctaccctttgttgaccacacat | J03766 | 49882 | cccatatgcagcagtccacccatg | AA032912 | 92486 | cagagctattccctttcaggag | AA117715 |
| 7279 | aacatcaggctgaaactcatacaa | J03766 | 49883 | atagatatctgcacctatgcacattg | AA032912 | 92487 | ttactgaccacgtgatctgggaat | AA117715 |
| 7280 | atgtgcaggcacactctgtaag | J03766 | 49884 | ccctatgacatttgggggtccgatc | AA032912 | 92488 | tacttgaccacgtgatcgggaatt | AA117715 |
| 7281 | ccagtgcaactctgtaagttgggga | J03766 | 49885 | cgcacctactatagatatctggga | AA032912 | 92489 | tgaccacgtgatctgggaattaca | AA117715 |
| 7282 | cacactctgtaagttgggatggtgc | J03766 | 49886 | cacctcactatagatatctgggaa | AA032912 | 92490 | tgaccacgtgatcgggaattacac | AA117715 |
| 7283 | tgctgctgattgctatgtggca | J03766 | 49887 | taggagccatagcagcacatctat | AA032912 | 92491 | gccttaaagaccaggtccaggggat | AA117715 |
| 7284 | gttctatggcactgaggaaacta | J03766 | 49888 | ggagccccatagcagcagcatctatag | AA032912 | 92492 | gaccaggtccaggcgatttctag | AA117715 |
| 7285 | tagatcttcatgctggatatta | J03766 | 49889 | cccatagcagcagcatctatagaaga | AA032912 | 92493 | ttaaaagattcctggcaggtggcat | AA117715 |
| 7286 | ttctcagtctggatatagatccc | J03766 | 49890 | catagcagcacatctatagaaagaca | AA032912 | 92494 | aagattctgcaggtgggcatcgcg | AA117715 |
| 7287 | acacactggaatgcactgctgcagaa | W50513 | 49891 | tagcagcacatctatagaagacacc | AA032912 | 92495 | agtgaaatccccaaggcaggcagagct | AA117715 |
| 7288 | tgaatgcactgctgcagaagttac | W50513 | 49892 | catctataaagacacctagcggaa | AA032912 | 92496 | gtgaaaatccccaaggcagagagcta | AA117715 |
| 7289 | cgaactatctataccgaagatcga | W50513 | 49893 | tctatagaagacacctagcggaagc | AA032912 | 92497 | gaaaatcccaaggcagaggtctat | AA117715 |
| 7290 | actatctataccgaagatcgaga | W50513 | 49894 | tatagaagacacctagcggaagtt | AA032912 | 92498 | tcccaaggcagagctatttccct | AA117715 |
| 7291 | atctataccgaagatcgagaagac | W50513 | 49895 | agacacctagcggaagcttagagt | AA032912 | 92499 | gggcagcagtattccccttcagga | AA117715 |
| 7292 | tataccgaagatcgagaagacgtt | W50513 | 49896 | acaacctagcggaagcttagagtga | AA032912 | 92500 | ggcagagctattccccttcagaa | AA117715 |
| 7293 | agaagacgtttcccagctgtatgc | W50513 | 49897 | tgggaaactcacattccagagat | AA032912 | 92501 | aatgctccgcttaaggtacggcagtg | AA117721 |
| 7294 | agagtttcccagctgtatgcct | W50513 | 49898 | ggaaaactcacatttcagagatgt | AA032912 | 92502 | gctccgcttaaggtacggcagtgg | AA117721 |
| 7295 | cgttcccagctgtatgccttac | W50513 | 49899 | ctcacattccagagatgctcg | AA032912 | 92503 | gcatgtaatcaccgttttgcaca | AA117721 |
| 7296 | ttcccagctgtatgccttcaccat | W50513 | 49900 | cacatttccagagatgctctggcgg | AA032912 | 92504 | atagtaatcacctgtttgcacatg | AA117721 |
| 7297 | cccagctgtatgccttcaccatctg | W50513 | 49901 | actgaagctaactgtgtggaggt | AA032912 | 92505 | tagtaatcacctgtttgcacatgg | AA117721 |
| 7298 | agctgatgccttcacactctgcct | W50513 | 49902 | agtcctaggagccccatagcagc | AA032912 | 92506 | gtaatcacctgtttgcacatgtt | AA117721 |
| 7299 | atgcactgcgagaagttactga | W50513 | 49903 | ctactagagcccatagcagcacat | AA032912 | 92507 | atcacctgtttgcacatgttctg | AA117721 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 7300 | tgccttcaccatctgcctggctg | W50513 | 49904 | actaggagcccatagcagcacatct | AA032912 | 92508 | tcacctgttttgcacatggttctga | AA117721 |
| 7301 | agtttactgagctcgagaggcaaa | W50513 | 49905 | gcagccatgcgacactacatcgt | AA032956 | 92509 | cctgtttgcacatggtctgaacca | AA117721 |
| 7302 | ttactgagctcgagaggcaacaa | W50513 | 49906 | cgacactacatcggttcatcgata | AA032956 | 92510 | tgttttgcacatggtctgaacaca | AA117721 |
| 7303 | acaatgcattcaagtcaccagatgc | W50513 | 49907 | caatcgctataaggttccacctg | AA032956 | 92511 | gttttgcacatggttctgaacacag | AA117721 |
| 7304 | atgcattcaagtcaccagatgatt | W50513 | 49908 | gttcacctgtcacagaatcactgc | AA032956 | 92512 | ttgcacatggttctgaacacagtc | AA117721 |
| 7305 | tcaagtcaccagatgcattcgaagt | W50513 | 49909 | gtcacagaatcactgcgaagtcat | AA032956 | 92513 | ccgcttaaggtacggcagtggagag | AA117721 |
| 7306 | tcctacgaactatctataccgcaa | W50513 | 49910 | gaatcactgcgaagtcatgtgcaa | AA032956 | 92514 | cacatggttcgaacacagtcactt | AA117721 |
| 7307 | ctacgaactatctataccgccaagat | W50513 | 49911 | ttacacgccataacggtactgaagg | AA032956 | 92515 | tggagagttcgcctgcatagtaat | AA117721 |
| 7308 | cctgcattttgtcagcacggccac | W50513 | 49912 | ataacggtactgaaggcaggactat | AA032956 | 92516 | gagagttcgcctgcatagtaatca | AA117721 |
| 7309 | cggccacagttgtcatgactcagg | U00678 | 49913 | gcaggatctatcagccatagacatc | AA032956 | 92517 | agagttcgcctgcatagtaatcac | AA117721 |
| 7310 | gatatggcttcaaatgggtaga | U00678 | 49914 | tctagccatagacatctgataata | AA032956 | 92518 | agttccgctgcatagtaatcacct | AA117721 |
| 7311 | gctcttcaaatgggtagagggtga | U00678 | 49915 | ataataacttatcctagagcataca | AA032956 | 92519 | tccgcctgcatagtaatcacctgtt | AA117721 |
| 7312 | gtgcagagcctgagctccttgatt | U00678 | 49916 | acttatcctagagcataacatgtcct | AA032956 | 92520 | ccgcctgcatagtaatcacctgtt | AA117721 |
| 7313 | agcgcctgattgcagcaggggtagcc | U00678 | 49917 | tacatcggtcatcgatatcacgg | AA032956 | 92521 | cctgcatagtaatcacctgttttgc | AA117721 |
| 7314 | ctgtgtccctcgctgtcagttgagt | U00678 | 49918 | gtgtcatcgatatcacggaagatg | AA032956 | 92522 | aggggttccggactgtagaccag | AA117730 |
| 7315 | tcaggcctctcgctgtcagttcaga | U00678 | 49919 | gaagatccgatgacgcatctcct | AA032956 | 92523 | tgtccggactgtagaccagtctt | AA117730 |
| 7316 | ctcctgctctgtcagactaaca | U00678 | 49920 | cgcatgacgcgatcctcctgaa | AA032956 | 92524 | aatgctctactttgtcggaatgt | AA117730 |
| 7317 | agtcagactaacagtaccagaggc | U00678 | 49921 | cgcatctcctcgatgctgtgac | AA032956 | 92525 | tgtcgtcactttgtcggaatgtgg | AA117730 |
| 7318 | tcttaacctgagataggttccatc | U00678 | 49922 | aatgaaactacagcaatctgagcac | AA032956 | 92526 | tcgtcactttgtcggaatgtggga | AA117730 |
| 7319 | gataggttcatcctgatacatct | U00678 | 49923 | actacagcaatctgagcactgaga | AA032956 | 92527 | aggaattcatggcagtggggcacta | AA117730 |
| 7320 | catgtgtcagactcaggtaagt | U00678 | 49924 | gagataaatcactgcctataaggg | AA032956 | 92528 | cgaattcatggcagtggggcactacg | AA117730 |
| 7321 | tccatcctgatacatcttcaactc | U00678 | 49925 | gcatggagccctgagcgtggcactg | AA032956 | 92529 | aattcatgcagtggggcactacggg | AA117730 |
| 7322 | ctgaagacatcctgttgttttct | U00678 | 49926 | tggagccctgagcgtggcactgagc | AA139256 | 92530 | tcatgcagtggggcactacgggtg | AA117730 |
| 7323 | tctgaaacactcactataaaaacct | U00678 | 49927 | ccctactctgctgagttaggcctg | AA139256 | 92531 | tggcagtgggcactaccgggtgtcc | AA117730 |
| 7324 | aacacttcactaataaacctcaagat | U00678 | 49928 | tactgcctgagttaggcctgtcca | AA139256 | 92532 | ggcactacggtgctccattccgac | AA117730 |
| 7325 | ttaatatctgatatctcagagt | U00678 | 49929 | tgagttaggcctgccagacagccct | AA139256 | 92533 | cactacgggtgctccattccgactg | AA117730 |
| 7326 | tctgatatctctgagagttcta | U00678 | 49930 | aggcctgccagacagccctgcaat | AA139256 | 92534 | ttccgactgtatgaccagtctgt | AA117730 |
| 7327 | aacagctctcagttctagttctc | U00678 | 49931 | agacagccctgcaatcgtgcgc | AA139256 | 92535 | tacgggtccatccgactgagt | AA117730 |
| 7328 | gtctctagatttctcggagtgtac | U00678 | 49932 | caatctgcgcttcatccaccagga | AA139256 | 92536 | actgtatgaccagtctgtctgt | AA117730 |
| 7329 | cactggcattgtctgctccctgg | U00678 | 49933 | gcatgcacatattgcaccaggca | AA139256 | 92537 | tgtatgaccagtctgtctgcggtga | AA117730 |
| 7330 | catgtctgctcctgctgcccaag | M20632 | 49934 | acatattgcaccagcgacccctgc | AA139256 | 92538 | tatgaccagtctgtctgtgtgaat | AA117730 |
| 7331 | ctttgctaaggcaccttgatgcc | M20632 | 49935 | ttattgcaccagcgacccctgcac | AA139256 | 92539 | tgaccagtctgtgctggtgaatgt | AA117730 |
| 7332 | taaggccacttgatgccatcctcc | M20632 | 49936 | acccctgcacacacctgcgta | AA139256 | 92540 | accagtctgtgctggtgaatgtcg | AA117730 |
| 7333 | tgagccatcttcaagacttacagc | M20632 | 49937 | cagtatttctactatgagaccat | AA139256 | 92541 | cagtctgtgctggtgaatgtctg | AA117730 |
| 7334 | catctcaagactttcagcttacatg | M20632 | 49938 | gcacacactatttgtgaccatg | AA139256 | 92542 | tgaatgtctactttgtcggaat | AA117730 |
| 7335 | caccaagtctcccttatcaggaattc | M20632 | 49939 | tatctactacgagaccatgtg | AA139256 | 92543 | attgttaacgcatctagttaagt | AA117730 |
| 7336 | gtctcctttacaggaatctcggat | M20632 | 49940 | tactgagccagtgagtcgagtg | AA139256 | 92544 | ttgttaacgcatctagttaagtg | AA117663 |
| 7337 | ggaattctcggatcatctgtgaaa | M20632 | 49941 | ccagtgagcgagtgcagttg | AA139256 | 92545 | gttcccaagctgatgtgaatagga | AA117663 |
| 7338 | caccagatctctgtcagaggacc | M20632 | 49942 | gtccggatcagagcctccaagcgc | AA139256 | 92546 | aatgctttcgtcatttgatcatga | AA117663 |
| 7339 | agtctgctcaggaccaggcct | M20632 | 49943 | tccagactcaagcgtcctctgttg | AA139256 | 92547 | tgatcttttgtcatgattaggctca | AA117663 |
| 7340 | tccaggtggctaccacaataagg | M20632 | 49944 | gagcctcaagcgtctcttgtcac | AA139256 | 92548 | gatctttgtcatgattaggctcat | AA117663 |
| 7341 | ctctgctgtgcccaagaagtc | M20632 | 49945 | tcttgcacctccatttcctact | AA139256 | 92549 | tcttttgcatgattagctctat | AA117663 |
| 7342 | tcctgtgcccaagaagtctcgat | M20632 | 49946 | ggactgatccagccatctcgtctt | X66405 | 92550 | tcatgattagcctcatctccctaac | AA117663 |
| 7343 | gaagctcctgatgatggccgtata | M20632 | 49947 | ccgtgggtcttcacaccatcactg | X66405 | 92551 | taggtcatctcctaactgtgt | AA117663 |
| 7344 | cctgatgatggcggtatagatgac | M20632 | 49948 | agggtgctcagtgacctacaatgc | X66405 | 92552 | aggctcatctcctaactgttgtat | AA117663 |
| 7345 | ctgtacactttcagcagaggctgc | M20632 | 49949 | ttccatctgaaagcaaagtgcta | X66405 | 92553 | ggctcatctcctaactgttgtata | AA117663 |
| 7346 | cacttcagccagagctgtgcactgc | M20632 | 49950 | cacaccagaggcttagcttggaca | X66405 | 92554 | ctcatcccctaactgtgtatat | AA117663 |
| 7347 | agccagaggctgcactgccaccctg | M20632 | 49951 | ttggacagttccactcaagtgtcc | X66405 | 92555 | tgtttaacgcatctcagttaagtga | AA117663 |
| 7348 | aggctgcactgcacctgggac | M20632 | 49952 | ccaagttgctcgtcgaatcaa | X66405 | 92556 | tttaacgcatctcagttaagtgaac | AA117663 |
| 7349 | gcctggctcttcatcgtgggca | W50536 | 49953 | agtgtcctgcagaatcaatccaga | X66405 | 92557 | ttaacgcatctcagttaagtgaact | AA117663 |

TABLE 1-continued

| SEQ ID NO | sequence | DBAxnID | SEQ ID NO | sequence | DBAxnID |
|---|---|---|---|---|---|
| 7350 | cctggtgcttcatcgttgggcac | W50536 | 49954 | ctgtcagaatcaatccagagcttc | X66405 | 92558 | atatctgattgttcgttcctccaag | AA117663 |
| 7351 | cttcatcgttgggcactagccgtgc | W50536 | 49955 | gaatcaatccagagcttctccctc | X66405 | 92559 | tgttcgttctccaagctgatgtga | AA117663 |
| 7352 | ttcatcgttgggcactagccgtgcc | W50536 | 49956 | gtaatctgatccaagccagctatct | X66405 | 92560 | tgtcgttccaagctgatgtgaa | AA117663 |
| 7353 | tcatcgttgggcactagccgtgcg | W50536 | 49957 | tgatccaagccagctatctgcta | X66405 | 92561 | tccgttctccaagctgatgtgaata | AA117663 |
| 7354 | catcgttgggcactagccgtgccg | W50536 | 49958 | tgtcttcaccatcactgcagtt | X66405 | 92562 | tcgttctccaagctgatgtgaatag | AA117663 |
| 7355 | tcgttgggcactagccgtgccgcct | W50536 | 49959 | cacaccatcactgcagttccgtct | X66405 | 92563 | ctaactccgctgcagcattgtcat | AA124193 |
| 7356 | cggtgacgtctctggtcggcacaact | W50536 | 49960 | atcactgcagttccgtctgtgtc | X66405 | 92564 | ccgctgcagttgtcatctggga | AA124193 |
| 7357 | ggtgacgtctctggtcggcacaactg | W50536 | 49961 | tgtgttcttccatgctcaaca | X66405 | 92565 | tatatggatttgccaactgcctgg | AA124193 |
| 7358 | gtgacgtctctggtcggcacaactgc | W50536 | 49962 | tccatgctcaacatgaagcagacct | X66405 | 92566 | tgcctggacacctcacctcacagag | AA124193 |
| 7359 | tgacgtctctggtcggcacaactgg | W50536 | 49963 | cagacttctcatgagttcagcttg | X66405 | 92567 | gttctcacatcctctggatgcc | AA124193 |
| 7360 | gacgtctctggtcggcacaactgcgg | W50536 | 49964 | tgagttcagcttgctgattaggc | X66405 | 92568 | cacatcctctggatgcccagagg | AA124193 |
| 7361 | ctgtgctctcatcgttgggact | W50536 | 49965 | ttcacaggtgcttgtcagtgact | X66405 | 92569 | gatgcccagaggccagagttct | AA124193 |
| 7362 | tggtgctctcatcgttgggacta | W50536 | 49966 | caagagaccaggctagaaggagcagc | AA032900 | 92570 | ccagaggccagtctttagttggcgca | AA124193 |
| 7363 | ggtgctctcatcgttgggcactag | W50536 | 49967 | cagctgtaccagcaggcactgaggc | AA032900 | 92571 | gccagagttctaagttggccggacctg | AA124193 |
| 7364 | gtgctctcatcgttgggcactage | W50536 | 49968 | atccgacaatcaggcgcctgctcac | AA032900 | 92572 | tcctcgttaaccactggagactg | AA124193 |
| 7365 | tgctctcatcgttgggcactagcc | W50536 | 49969 | caatcagccggtctcaggtgct | AA032900 | 92573 | tgtgctaaccactggagactggag | AA124193 |
| 7366 | gctctcatcgttgggcactagccg | W50536 | 49970 | tcacgtctggccaccggtcctat | AA032900 | 92574 | tgctaaccactggagactggagttg | AA124193 |
| 7367 | ctctcatcgttgggcactagccgt | W50536 | 49971 | gtctggccaccgctctattacctg | AA032900 | 92575 | ctgcagcattgtcatctgggagtc | AA124193 |
| 7368 | tctctcatcgttgggcactagccgtg | W50536 | 49972 | tggccaccggtcctattacctgct | AA032900 | 92576 | caactggacctggagttgctgacc | AA124193 |
| 7369 | atccttaatattccagatgaaaagg | W50536 | 49973 | agccgtcttacgcaccggcctggtc | AA032900 | 92577 | cagcattgtcatctgggagtcac | AA124193 |
| 7370 | agtaacacattgagccactgatta | W50536 | 49974 | cgctctacaacggccggtcaac | AA032900 | 92578 | ttgtcatctggagtccaacagta | AA124193 |
| 7371 | ctataccaaggacaggggtagtga | W50536 | 49975 | cttacagacgcgctcggtcaactc | AA032900 | 92579 | agtcacacagtagaggggccgtc | AA124193 |
| 7372 | tctgctccaagtccccaggtgcat | W50536 | 49976 | cctggtcaactcacctcagcagag | AA032900 | 92580 | ccacactagaggggccgtcctt | AA124193 |
| 7373 | gctcctaagtcccccaggtgcatcca | W50536 | 49977 | cttcacctcagcagtctgcagc | AA032900 | 92581 | cctcccgctctttagtctatgg | AA124193 |
| 7374 | tcccccaggtgcatccaattttcaa | W50536 | 49978 | ctgtacagcagcagtgtcagc | AA032900 | 92582 | tccctgctctttagtctatgg | AA124193 |
| 7375 | ccaggtgcatccaattttcaactt | W50536 | 49979 | cacccccgcaagttgcagcagag | AA032900 | 92583 | ctgtcttagtctatatgggat | AA124193 |
| 7276 | tcaacttaccaaagatctctccct | W50538 | 49980 | taccagcagggcactgaggcgcca | AA032900 | 92584 | cggaatactgggcctccatctcgg | AA124193 |
| 7377 | ttaccaaagatctctcctcatct | W50538 | 49981 | caggaccactgaggctgccccaaccaga | AA032900 | 92585 | gaatactggcctccatcttcgga | AA120173 |
| 7378 | ccaaagatctctccttcatctat | W50538 | 49982 | cgaggccactggaaatggcgaga | AA032900 | 92586 | tgcacaataaccaaccttagcca | AA120173 |
| 7379 | aagatctctcctcatctat | W50538 | 49983 | aaacctgacatcccgacaatcag | AA032900 | 92587 | accttagccagaccaccttgccctct | AA120173 |
| 7380 | atctcctcatctatcaata | W50538 | 49984 | ctggacatccgacaatcagcgc | AA032900 | 92588 | cttagccagaccaatttgcctcttg | AA120173 |
| 7381 | aaacacattgagccactgattaagc | W50538 | 49985 | gacatcatccgacaatcagcgccg | AA032900 | 92589 | ttagccagaccaatttgccctctgaa | AA120173 |
| 7382 | tctcctcattcctatcaaataat | W50538 | 49986 | atcatccgacaatcagcgctgct | AA032900 | 92590 | agccagaccatttgccctctgaacta | AA120173 |
| 7383 | ccagtcagcacccatccaggatgccg | W50538 | 49987 | tgccccgatttggactcactgac | AA032900 | 92591 | agaccatttgccctctgaacatta | AA120173 |
| 7384 | gacagcagcaccatccaggatgccggc | W50538 | 49988 | gtactcactgaacagagcattct | U00674 | 92592 | cattgcccttctgaacattttacgt | AA120173 |
| 7385 | ageaccatccaggatgccggcctat | W50538 | 49989 | attcataccttctgtccaattaca | U00674 | 92593 | cctcaaaacttccagttctgctg | AA120173 |
| 7286 | atccaggatgccggctatataccaag | W50538 | 49990 | aattacactgtaattcaccagtt | U00674 | 92594 | tcaaaacttcccagttctgctgac | AA120173 |
| 7387 | caggatgccggctataccaaggaac | W50538 | 49991 | agctgtaattaccatgttaaaag | U00674 | 92595 | gttcgctgctgtgtggtgacgt | AA120173 |
| 7388 | gatgccggctataccaaggacagg | W50538 | 49992 | atgggccctccaaagctgcaacat | U00674 | 92596 | actggcctccatcttcggcaccga | AA120173 |
| 7389 | gccggctataccaaggacacagg | W50538 | 49993 | aaagtgcacaaatgccctcaatta | U00674 | 92597 | ttggcctccatcttcggcacgaaa | AA120173 |
| 7390 | gccggctataccaaggacacagagt | W50538 | 49994 | tgcccttcaaattacggaggctgga | U00674 | 92598 | tatttcaaaatggagcatgctgtc | AA120173 |
| 7391 | ctctctacacttgcagaattgatt | M12600 | 49995 | ataccttcaactgtgaaacatg | U00674 | 92599 | tcggaatgtcatggaggacag | AA120173 |
| 7392 | tctctacacttgcaggatgat | M12600 | 49996 | taacttgttgaatctatgccagg | U00674 | 92600 | catgtcatggagacgatgttc | AA120173 |
| 7393 | caggtccttgtttcctcatcga | M12600 | 49997 | gcttggaatctatgccaggagaaaaa | U00674 | 92601 | ccgatgttctgggttgcacataaa | AA120173 |
| 7394 | ggtccttgtttcctcatcgagga | M12600 | 49998 | tttgtcactgctgtaaagcaactatt | U00674 | 92602 | gatgttctgggttgcacaataaa | AA120173 |
| 7395 | ttgtttcctcatcgaggagagcg | M12600 | 49999 | agatccagctgttttccagcataaa | U00674 | 92603 | tgtctcggttgcacaataaccaa | AA120173 |
| 7396 | ttcctcatcgaggagagcgagc | M12600 | 50000 | ttggctactccgttgagccacctt | U00674 | 92604 | gatattccaaatgtcctccagtc | AA120173 |
| 7397 | ctccatcgaggatgcgagcgaga | M12600 | 50001 | tactcgttgagcaccttccctga | U00674 | 92605 | atttccaaatgctccagtctgg | U10355 |
| 7398 | gagcagacttgcctcagtttctg | M12600 | 50002 | gcaccttccctggtctgtcacga | U00674 | 92606 | tgaattattcactgcctgcagaag | U10355 |
| 7399 | tcgggctttgatcacagtaagg | M12600 | 50003 | tcccgagcttgtcagaaatcat | U00674 | 92607 | attcactgcctgcagaagccctcag | U10355 |

TABLE 1-continued

| SEQ ID NO | DBAxnID | sequence | SEQ ID NO | DBAxnID | sequence | SEQ ID NO | DBAxnID | sequence |
|---|---|---|---|---|---|---|---|---|
| 7400 | M12600 | ggatgtcatgtcgtcgctagaat | 50004 | M12600 | agctgtcacagaacacatttaaac | 92608 | U10355 | cactgctgtcagaagctccagtgt |
| 7401 | M12600 | catggtcgtcgcctagaatcaactt | 50005 | M12600 | aacactgaaacagtgctgtctg | 92609 | U10355 | ctgtcagaagctcagtgtggccta |
| 7402 | M12600 | tacacttctgcaggaattgatccg | 50006 | M12600 | gccttaattcatacctttctgcca | 92610 | U10355 | gcctcagtgtggcctaagatactcc |
| 7403 | M12600 | ttaaaaccaaatgacattcattttg | 50007 | M12600 | cacctactctgtcctgcatggc | 92611 | U10355 | cctcagatactcctatttaccattg |
| 7404 | M12600 | gattccgagatacctagtagtttg | 50008 | M12600 | acctactctgtcctagtcgatggt | 92612 | U10355 | aagatacctctatttaccattgtga |
| 7405 | M12600 | tgtgagagagactcccactgctccctg | 50009 | M12600 | gtcctagtcgatggctgctccaaaa | 92613 | U10355 | atactcctatttaccattgtgaagt |
| 7406 | M12600 | gagagatgcccactgctgtcctg | 50010 | M12600 | tcctagtcgatggctgctccaaaa | 92614 | U10355 | ctcctatttaccattgtgaagtgt |
| 7407 | M12600 | tccctggttagtcactttgcagttgca | 50011 | M12600 | cctagtcgatggctgctccaaaaag | 92615 | U10355 | aacctagctagcaattcagttagg |
| 7408 | M12600 | gtttggttagccattggcaggtgt | 50012 | M12600 | ctagtcgatggctgctccaaaaga | 92616 | U10355 | tcccaaatgcctccagtcgttt |
| 7409 | M12600 | ttaactctgtgccagcagggtcctt | 50013 | M12600 | tagtcagatggctgctccaaaagac | 92617 | U10355 | atttgtatacagtctcatcataagaa |
| 7410 | M12600 | acctctgccagcagggtccttgt | 50014 | M12600 | agtcagatggctgctccaaaagaca | 92618 | U10355 | tgatacagtctcatcataagaaggg |
| 7411 | L07296 | ghagctgtctgtacacagtgactaa | 50015 | L07296 | gtcagatggctgctccaaaaagacaa | 92619 | U10355 | ttcataaatacagcaaacaagttga |
| 7412 | L07296 | atcacaatgaggcaacgcctcgcc | 50016 | L07296 | tcagatggctgctccaaaaagacaaa | 92620 | U10355 | gttccatcacatgtgagtcatgtaa |
| 7413 | L07296 | acatacacaacacgtgccagtcacca | 50017 | L07296 | cctactctgtcctagtcgatggctg | 92621 | AA117906 | ccatcacatgtgagtcatgtaaaat |
| 7414 | L07296 | ctagaaccacacgctgctgttcga | 50018 | L07296 | ctactctgtcctagtcgatggctgc | 92622 | AA117906 | tcacctgaaccatggtctgtgaa |
| 7415 | L07296 | cctaagacacgctgctgttctga | 50019 | L07296 | tactctgtcctagtcgatggctgct | 92623 | AA117906 | tcttgaattattcactgcctgcag |
| 7416 | L07296 | cctcactgggtcttcctccctga | 50020 | L07296 | actctgtcctagtcgatggctgctc | 92624 | AA117906 | aaatctgcggcaatcatgaaacttac |
| 7417 | L07296 | tcttctctagaggcctggatctga | 50021 | L07296 | ctctgtcctagtcgatggctgctcc | 92625 | AA117906 | atctgcggcaatcatgaacttacta |
| 7418 | L07296 | ctctagagcctgatctgatctgat | 50022 | L07296 | tctgtcctagtcgatggctgctcca | 92626 | AA117906 | cagcaccttgagtgtgaaatggta |
| 7419 | L07296 | agcctgatctgatctgtggat | 50023 | L07296 | ctgtcctagtcgatggctgctccaa | 92627 | AA117906 | aagactgtatgccaccaatggtca |
| 7420 | L07296 | gatcgatctgtcgggatctgtc | 50024 | L07296 | tgtcctagtcgatggctgctccaaag | 92628 | AA117906 | gactgtatgccaccaatggtcaat |
| 7421 | L07296 | attgtctgagattcgtcaaggaa | 50025 | L07296 | agctgatctgttccactctgtga | 92629 | AA117906 | ctggatgtcaccaatggtcaatct |
| 7422 | L07296 | tcaaactctgtcctgaacgatccc | 50026 | L07296 | ttcgtttccattctgagtgtca | 92630 | AA117906 | tatgccacaatgcaatctgag |
| 7423 | L07296 | ctcgccctgagtgttgagaagaa | 50027 | L07296 | gtaaacactctacctctgcaatt | 92631 | AA117906 | tgcaccaatggcaatctgagc |
| 7424 | L07296 | cagaagatcgggcgctgttgtaaag | 50028 | L07296 | aacacttcactctgcagattcc | 92632 | AA117906 | caccaatggcaatctggagccca |
| 7425 | L07296 | gaattactcatcaaagatcatct | 50029 | L07296 | actcttcctctgcagattcctcc | 92633 | AA117906 | atggtcaatctggagcccaaccag |
| 7426 | L07296 | actcatcaaagatcatctgaaaa | 50030 | L07296 | ctcccagtagcaagtaagtagctg | 92634 | AA117906 | ggtcaatctggagcccaaccaggta |
| 7427 | L07296 | agaagcccaatcaataactgttcta | 50031 | L07296 | tcatgtatttcattttgttaagag | 92635 | AA117906 | tcaatctggagcccaaccaggtacc |
| 7428 | L07296 | ccaatcaataactgttctagatcct | 50032 | L07296 | tcgtattcattttgctaagagat | 92636 | AA117906 | caatcagaactaactaccacacga |
| 7429 | L07296 | tgttctagatcctgtcccaataa | 50033 | L07296 | gatctgaattctctttcctggaat | 92637 | AA117906 | atcatgaactactaccacagcacc |
| 7430 | L07296 | agatcctagtccccaataactgaag | 50034 | L07296 | tctagttctgtcaacaaatgcct | 92638 | AA117906 | catgaactactaccacagcacctt |
| 7431 | L07297 | ggtcacagctggcaggagacgatgaat | 50035 | L07297 | tcctccatggctgccattgatcc | 92639 | AA117906 | tgaacttactaccacacgacctga |
| 7432 | L07297 | tagctgcttgggaggcagagagcat | 50036 | L07297 | tcctcatggcctgcattgatcacc | 92640 | AA117906 | cttactaccacaggcacctttgagttg |
| 7433 | L07297 | agacatcttgccattcgcaaag | 50037 | L07297 | tgttccactctggagtgctagga | 92641 | AA117906 | tactaccacagcaccttgagttg |
| 7434 | L07297 | cttgtccattgccaaagctcttg | 50038 | L07297 | tcatgcctgcattgatccaccctgt | 92642 | AA117906 | ctaccacagcaccttgagttgtgaa |
| 7435 | L07297 | ccattgtcaaaagctctgtgcggct | 50039 | L07297 | ttccacttcgtagtgctaggacta | 92643 | AA117906 | accacagcaccttgagttgtgaaat |
| 7436 | L07297 | gcaaaagctgtctgggctgcagtg | 50040 | L07297 | cactgtggagtgctaggacatag | 92644 | AA117906 | gaggacctccagctcagcttcag |
| 7437 | L07297 | tgagaagctgggcagctgaggttct | 50041 | L07297 | acggttctgcactgcccctg | 92645 | AA117906 | cctattccagtctcaggaagcg |
| 7438 | L07297 | cagcagcctgagttttctcatccag | 50042 | L07297 | tctgctcactgctccctgtaaaca | 92646 | AA117906 | ccttttggctgccaacaagctga |
| 7439 | L07297 | cctgagttcttctcatccagatatcc | 50043 | L07297 | gtccactgccctgtaaacactctta | 92647 | AA117906 | ttttggctgccaacaagctgatt |
| 7440 | L07297 | cggattctctggttcgttaaag | 50044 | L07297 | cactgcctgccctgctaaacacactctta | 92648 | AA117953 | ttttggctgccaacaagctcgatta |
| 7441 | L07297 | tctctggttctgtaaagacttag | 50045 | L07297 | tctgtaaacactctttactctgcag | 92649 | AA117953 | ttggtgccaacaagctcgattaa |
| 7442 | L07297 | gactagtttggagctcatgcatgaaag | 50046 | L07297 | tttcagtgtattcccactctgtaag | 92650 | AA117953 | tggctgccaacaagctcgattaagg |
| 7443 | L07297 | agagcatgctagccacttaattc | 50047 | L07297 | cagcgtattcccactgctctaagga | 92651 | AA117953 | ggctgccaacaagctcgattaagga |
| 7444 | L07297 | ctgacgccagcagcatcatcatgggtac | 50048 | L07297 | tgaatcgatacaccctgccttcatg | 92652 | AA117953 | gctgccaacaagctcgattaaggaa |
| 7445 | L07297 | ttaagtttctgcttgatgaact | 50049 | L07297 | atcgatacacctgtccctctcatgaat | 92653 | AA117953 | tgccaacaagctcgattaaggaaagc |
| 7446 | L07297 | cccagtgccaatccccactgagacgag | 50050 | L07297 | gatacacctgctccttcatgaatggt | 92654 | AA117953 | aagctcaaggagccactctgagtctg |
| 7447 | L07297 | gaatccccactgagacgcctgca | 50051 | L07297 | cctgtcttcatgaatggttcgaga | 92655 | AA117953 | agctcaaggaggagcacctgagtctg |
| 7448 | L07297 | ctgtgctctggctgcactccaccag | 50052 | L07297 | ctgtggctctgtgctgagagtg | 92656 | AA117953 | tatcccagtcttcaggaagcgct |
| 7449 | L07297 | ctctggtgcactccaccagccagga | 50053 | L07297 | tcagaaccaggacacgcttgataag | 92657 | AA117953 | atttcccagctcttcaggagcgccta |

TABLE 1-continued

| SEQ ID NO | DBAxnID | sequence | SEQ ID NO | DBAxnID | sequence | SEQ ID NO | DBAxnID |
|---|---|---|---|---|---|---|---|
| 7450 | L07297 | gtgactcaccaggcaggactagac | 50054 | X66223 | gaaccaggacacgcttgataaggt | 92658 | AA117953 |
| 7451 | X66223 | aggcaccacatccaaggccactaggc | 50055 | X66223 | taaggttcctgaaggtgtggact | 92659 | AA117953 |
| 7452 | X66223 | tgccttctgatgccgcggtgga | 50056 | X66223 | ggttcctgaagcgtgtggactgt | 92660 | AA117953 |
| 7453 | X66223 | acactggcacctcgtttggaatgcc | 50057 | X66223 | tccgtaagcgtgtggactgtgata | 92661 | AA117953 |
| 7454 | X66223 | cacctcgtttggagtgccccatct | 50058 | X66223 | cgtattccacttgctcaagagactc | 92662 | AA117953 |
| 7455 | X66223 | tgtttgagtgccccatctggcct | 50059 | X66223 | cccactgctaagagactccgaat | 92663 | AA117953 |
| 7456 | X66223 | ggagtgcccatctggcctgtcag | 50060 | X66223 | agatgctagtcctgttcagaact | 92664 | AA117980 |
| 7457 | X66223 | cccatctggcctgtcagagtcct | 50061 | X66223 | tgtctagtcctgttcagaactgc | 92665 | AA117980 |
| 7458 | X66223 | tgttcagagtcctggtaccagtta | 50062 | X66223 | ctagtcctgttcagaactggctga | 92666 | AA117980 |
| 7459 | X66223 | ggaatccaccggatcaagaagga | 50063 | X66223 | gtcgggttcagaactggctgaagc | 92667 | AA117980 |
| 7460 | X66223 | aggccgtatcctcctgggtcatagc | 50064 | X66223 | ctcctcaatggcatgaatcgata | 92668 | AA117980 |
| 7461 | X66223 | tatcctctgggtcatgatacct | 50065 | X66223 | ctcctaatggcatgaatcctgagga | 92669 | AA117980 |
| 7462 | X66223 | tcatagtccatataaggcgccg | 50066 | X66223 | gatcactcatgtcatcctgtggct | 92670 | AA117980 |
| 7463 | X66223 | cctatgggcccaaagatgcatca | 50067 | X66223 | cactcagtcatcctgtggctgaa | 92671 | AA117980 |
| 7464 | X66223 | ctgccatcttactcatgtgcc | 50068 | X66223 | gcaactgcgagaccgagaagta | 92672 | AA117980 |
| 7465 | X66223 | atcttactcatgcttgccttgc | 50069 | X66223 | actgctcgagaccgagaagtagga | 92673 | AA117980 |
| 7466 | X66223 | gctcaaggctagcgtgctgtacc | 50070 | X66223 | agaagtaggaatccctcagaggag | 92674 | AA117980 |
| 7467 | X66223 | aggctatgctgctgcatcccggag | 50071 | X66223 | aggaatccctctgagcagtcctg | 92675 | AA117980 |
| 7468 | X66223 | ttcagcaactggagtgcaagagt | 50072 | X66223 | aatccctctgagcagtcctggaa | 92676 | AA117980 |
| 7469 | X66223 | gctgggttctgacatcccacatgg | 50073 | X66223 | ccctcgagcagtcctggaaact | 92677 | AA117980 |
| 7470 | X66223 | catcccacatggccacctctgttgg | 50074 | X66223 | gcagtcctggaaactgcgaaacag | 92678 | AA117980 |
| 7471 | X66223 | ggttcgtccgaatgcatcctg | 50075 | X66223 | ctacagttatgtcgcccagatta | 92679 | AA117980 |
| 7472 | X66223 | ttccgtccaggatgccatcgctg | 50076 | X66223 | cagttatgtcgcccagattagta | 92680 | AA117980 |
| 7473 | X66223 | cccctcgagggagactcttcga | 50077 | X66223 | caagtagcaacgatgggtcaaag | 92681 | AA117980 |
| 7474 | X66223 | tgcaccctcgagccctataccaag | 50078 | X66223 | tcatgtcatttcctggctgaagga | 92682 | AA117980 |
| 7475 | X66223 | caccctcgagccctataccaagcag | 50079 | X66223 | tgacaccgatgggtcaaagtggatc | 92683 | AA117980 |
| 7476 | X66223 | ggcctataccaagcagaagtatccg | 50080 | X66223 | catccgtggctgaaggatagt | 92684 | W29730 |
| 7477 | X66223 | gaagtatccaggaacactgcaggcag | 50081 | X66223 | atatgttatcggcagctgattaaa | 92685 | W29730 |
| 7478 | X66223 | tccgaacagcctacctgaagttgcc | 50082 | X66223 | tattaacacattccaatccagga | 92686 | W29730 |
| 7479 | X66223 | caagctctgcgctcctcgct | 50083 | X66223 | taaacacattccaatccagagaga | 92687 | W29730 |
| 7480 | X66223 | cattggagacactcccatcgacacg | 50084 | X66223 | acacattccaatccaggaagagat | 92688 | W29730 |
| 7481 | X66223 | tggagacactcccatcgacagctc | 50085 | X66223 | ttttattcagcaactgctgcgagac | 92689 | W29730 |
| 7482 | X66223 | cctgccccaaagtgatgctgt | 50086 | X66223 | tattcagcaactgctgcgagac | 92690 | W29730 |
| 7483 | X66223 | ccagtgcacagagcagcgctcac | 50087 | X66223 | agtgtgccactacgcccagagaat | 92691 | W29730 |
| 7484 | X66225 | agtcggtccatcttgacagagtc | 50088 | X66225 | ccatacgcccagagaaatgacagg | 92692 | W29730 |
| 7485 | X66225 | cggtccatcttgacagagtcctt | 50089 | X66225 | gtgtccacgaacaggaggagtctc | 92693 | W29730 |
| 7486 | X66225 | cttcgacagagtcctttacagttg | 50090 | X66225 | tgggtactcattctgatgcacact | 92694 | W29730 |
| 7487 | X66225 | cgacagagtcctttacagagttggg | 50091 | X66225 | ctcattctgatgcacactggagct | 92695 | W29730 |
| 7488 | X66225 | agtcctttacagagttggtgccaag | 50092 | X66225 | tctgatgcacactggagctcgggac | 92696 | W29730 |
| 7489 | X66225 | catcgtgtgtttaaccagatgcc | 50093 | X66225 | gcaggcactgatgtcaactgcgagc | 92697 | W29730 |
| 7490 | X66225 | cggtcgtttaaccagttggccaag | 50094 | X66225 | tggcaggcctagaggactcaga | 92698 | W29730 |
| 7491 | X66225 | gggcattccagaagattaccaag | 50095 | X66225 | tcactttttgcaacgagtcagc | 92699 | W29730 |
| 7492 | X66225 | agtggtttcctatcgggttctg | 50096 | X66225 | gctgaccaccgtgaaccagacctg | 92700 | W29730 |
| 7493 | L06463 | taccaggatcatacaaagtacaac | 50097 | Z35167 | aatcaggcaggtgccaggttgcatg | 92701 | W29730 |
| 7494 | L06463 | gatcataccaaagtacaaaggccaag | 50098 | Z35167 | caggtgccaggttgcagttcgaagac | 92702 | W29730 |
| 7495 | L06463 | accaagtacacatgagctctgtg | 50099 | Z35167 | tgacaggtcctactgcgtcagt | 92703 | W29730 |
| 7496 | L06463 | gtacaccatgagctcgtgccatc | 50100 | Z35167 | gtcctactgcgtcagtgcggt | 92704 | AA117973 |
| 7497 | L06463 | catgagctcgtgccatcgattc | 50101 | Z35167 | ctggctcgcagtgcgcgctccct | 92705 | AA117973 |
| 7498 | L06463 | ctcgtgccatctgatctctgggt | 50102 | Z35167 | tcctatgatgccactctcagggaa | 92706 | AA117973 |
| 7499 | L06463 | ctgattccttgagccaagatgg | 50103 | Z35167 | gatgccactctcagaggaagagatc | 92707 | AA117973 |

| SEQ ID NO | sequence | DBAxnID | SEQ ID NO | sequence | DBAxnID | SEQ ID NO | sequence | DBAxnID |
|---|---|---|---|---|---|---|---|---|
| 7500 | aagggaccacgtgcatgaagaat | L06463 | 50104 | agagatcgctcttacatcagccgc | Z35167 | 92708 | agaatcatatcgcaaacgcctgca | AA117973 |
| 7501 | tagaaacactactcacctgataa | L06463 | 50105 | ccgttcatcacgccgctgtgcg | Z35167 | 92709 | atcatatctcgcaaacggctgcaagg | AA117973 |
| 7502 | acactactcacctgataaaatgt | L06463 | 50106 | ggtccacgttcaggaccaatccatc | Z35167 | 92710 | atatctgcaaacggctgcaaggtgg | AA117973 |
| 7503 | tcctatacgggtctcgatgaca | L06463 | 50107 | gctgccttcgcgttcagttaccat | Z35167 | 92711 | tctgcaaacggtgcaaggtgata | AA117973 |
| 7504 | actggttctctgatgacagaccca | L06463 | 50108 | tgccttcatgttcgcaacattaa | Z35167 | 92712 | gcaaacggcgtcaaggtggataact | AA117973 |
| 7505 | ttctgatgacagaccaaagtc | L06463 | 50109 | gccagactattcagattccacactg | Z35168 | 92713 | aactccttcactcactgctgaatcag | AA117973 |
| 7506 | gatgacagaccaaagtctctct | L06463 | 50110 | agattccacactgtcctcaggggtg | Z35168 | 92714 | tcctactcactggtgaatcagaac | AA117973 |
| 7507 | ctccgtcaccacatctcgcag | L06463 | 50111 | ccttcatgatgcatacaagtgcagg | Z35168 | 92715 | tcactcactggtgaatcagaacccc | AA117973 |
| 7508 | gttcaccaacatcttcagaactc | L06463 | 50112 | aaggtctggccaagccctaacctc | Z35168 | 92716 | atggaatcctcaagaacactggtcc | AA117973 |
| 7509 | caccatcttcagaacttcgtttc | L06463 | 50113 | gcaattactacgctttggctgcg | Z35168 | 92717 | ttcaagaacatgtcccttcagcaag | AA117973 |
| 7510 | tatcaatgagtccctaccaccagg | L06463 | 50114 | caattcgtacagctttggctggc | Z35168 | 92718 | gtccctcagccaagccctgtgattc | AA117973 |
| 7511 | tggagctgcctgacaaatactgagcg | | 50115 | gctttggctggccactgtgatat | Z35168 | 92719 | cctcagcaagccctttgatttcgaa | AA117973 |
| 7512 | ggactgctgacaaatactgagcgt | | 50116 | ggctggccactgttgatagtcaga | Z35168 | 92720 | cagcaagccctttgatttcgaaatg | AA117973 |
| 7513 | ctattagtcagtaggttgtgctgg | | 50117 | acatgtttcacaaacctcagtcaga | Z35168 | 92721 | caagccctgtgattcgaaatggag | AA117973 |
| 7514 | tattagtcagtaggtttgctgg | | 50118 | gtatagccgatgtcaagttagcat | Z35168 | 92722 | gccctttgattcgaaatggagaga | AA117973 |
| 7515 | ggcttctctactaggaaacactg | | 50119 | tcatgtctcaacattaacaacgt | Z35168 | 92723 | gaccggatctctgctgatcttagaa | AA117973 |
| 7516 | gcttctctactaggaaacactg | | 50120 | cagagcccatgcctggcaatgatga | Z35168 | 92724 | atgctggccagtctaatgaatttttg | AA117973 |
| 7517 | gacgtcctgacaaatactgagcgtc | | 50121 | ccatgccaatgaacatgaaccct | Z35168 | 92725 | tgctggccagtctaatgaatttggc | AA117973 |
| 7518 | actgcctgacaaatactgagcgtcc | | 50122 | caatgaacatgaaccccctgaaggg | Z35168 | 92726 | aggccttccagattggcccagacc | AA118029 |
| 7519 | gcgtctcctattagtcagtaggt | | 50123 | acatggaaccccctgaaggagacagag | Z35168 | 92727 | gccttccagattgcgggccagaccg | AA118029 |
| 7520 | cgtcctccattagtcagtaggtt | | 50124 | gacagaatccagccattcattgg | Z35168 | 92728 | ccttccagattgcggccagaccgg | AA118029 |
| 7521 | gtcctcctattagtcagtaggt | | 50125 | agccattcattagtcgatgtcagt | Z35168 | 92729 | cttccagattcgggccagaccggt | AA118029 |
| 7522 | ctcctattagtcagtaggttgtgc | | 50126 | tcgcttcagccagactatica | Z35168 | 92730 | ttccagattgcggccagaccggtg | AA118029 |
| 7523 | tcctattagtcagtaggttgct | | 50127 | ggtgctcaacctgctgggagctggtt | Z35168 | 92731 | tcctttggcgggacgcgaataatg | AA118029 |
| 7524 | ccttattagtcagtaggttgtgctg | | 50128 | caaccgctggagcgtcacctg | Z35168 | 92732 | tgaccccattgctaattcccccaat | AA118029 |
| 7525 | ctcacccagccaggatgaagcta | | 50129 | tgtacctggcctccgtctctggccg | Z35168 | 92733 | ggtaaccaaggccttccagattgcg | AA118029 |
| 7526 | tctcaccccagccaggatgaagctac | | 50130 | ctggcgtccactcctcaaaggcac | X57971 | 92734 | gtaaccaaggccttccagatgcgg | AA118029 |
| 7527 | ctattagtcagtaggttgct | | 50131 | tccttcaaaggcacctcagagacaac | X57971 | 92735 | taaccaaggccttccagattgcggc | AA118029 |
| 7528 | cctattagtcagtaggttgtctg | | 50132 | cattcgtcggcagggaacctggtc | X57971 | 92736 | accaaggccttccagattgcggcca | AA118029 |
| 7529 | ctattagtcagtaggttgtctgg | | 50133 | cctggtcacagatgttctggaata | X57971 | 92737 | ccaaggccttccagattgtgggccag | AA118029 |
| 7530 | tattagtcagtaggttgtgctggg | | 50134 | tggaatacctggagccttgtgatg | X57971 | 92738 | caaggccttccagattgcgggccaga | AA118029 |
| 7531 | gcttctctactaggaaacactg | | 50135 | aggacaccggtgcttaccagaaatg | X57971 | 92739 | aaggccttccagattgcgggccagac | AA118029 |
| 7532 | gcttctctactaggaaacactga | | 50136 | ctggcgcttaccagaatgtgacaac | X57971 | 92740 | ttctgacgcaggtgcatgagtta | AA123463 |
| 7533 | tggactgcctgacaaatactgagcg | | 50137 | cagaatggacataccagactg | X57971 | 92741 | tcatcaaaggatacatcggccaaa | AA123463 |
| 7534 | ggactgcctgacaaatactgagcgt | | 50138 | gtgacactaccagactgggtcaca | X57971 | 92742 | caaatccttgcagtactaccggt | AA123463 |
| 7535 | gactgcctgacaaatactgagcgt | | 50139 | cagtgcctcagactcctacccctga | X57971 | 92743 | tgcagtactaccggttcccgacat | AA123463 |
| 7536 | actgcctgacaaatactgagcgtcc | | 50140 | caacggctctcatccaccctgagcag | X57971 | 92744 | gcagtactaccggttcccgacatg | AA123463 |
| 7537 | gcgtcctcctattagtcagtaggt | | 50141 | atccagagcagaactgggccaac | X57971 | 92745 | actacctgttcccgacatggga | AA123463 |
| 7538 | cgtcctcctattagtcagtaggt | | 50142 | ggccaacttgaccacagagagaga | X57971 | 92746 | ctacctggtccgacatggatgat | AA123463 |
| 7539 | gtcctcctattagtcagtaggttg | | 50143 | caacagctcgatccaagaagcag | X57971 | 92747 | actggttcccgacatggatgatgaa | AA123463 |
| 7540 | ctcctattagtcagtaggttgc | | 50144 | ctctgcatccaagaagaagcatatgtg | X57971 | 92748 | cctgtccgacatgatgatgaa | AA123463 |
| 7541 | tctccaaggctgctcccacga | W50665 | 50145 | ggctaatgtcactcaacagctgc | X57971 | 92749 | tggttcccgacatgatgatgaaga | AA123463 |
| 7542 | ctggctcccgatcagactctatgctcag | W50665 | 50146 | tcaacagagctgcccgagggcac | X57971 | 92750 | ggttcccgacatgatgatgaagaa | AA123463 |
| 7543 | tgcacgctgcgattcagcggaaag | W50665 | 50147 | tggctggctgactgtctgtt | X61675 | 92751 | ttcccgacatgatgatgaagaagg | AA123463 |
| 7544 | tgttacacatcaccacgcctgcg | W50665 | 50148 | tggctggactgtctgtttccag | X61675 | 92752 | agatgacatccgccaatccttg | AA123463 |
| 7545 | caccagctgcgaattcagcgagg | W50665 | 50149 | acatggctccggaagaatccaga | X61675 | 92753 | tgacatcggccaatcccttgcag | AA123463 |
| 7546 | atgaggaccgctgtctaaaactaggt | W50665 | 50150 | atccagacgctcggccactggga | X61675 | 92754 | actacctgttcccgacatggata | AA123463 |
| 7547 | gaccagctgtctaaactgaact | W50665 | 50151 | aagttccaaacggcagattcc | X61675 | 92755 | catcggccgacatgatgat | AA123463 |
| 7548 | agccgctctctaaacttgaccttca | W50665 | 50152 | aaggttcatccacagcactatg | X61675 | 92756 | tctggccaaatccctgcagtacta | AA123463 |
| 7549 | ccgtcctaaactgaacttccaatg | W50665 | 50153 | tcatccacatgcactacccagaa | X61675 | 92757 | ctggccaaatccctgcagtactac | AA123463 |

| SEQ ID NO | DBAxnID | sequence | SEQ ID NO | DBAxnID | sequence | DBAxnID |
|---|---|---|---|---|---|---|
| 7550 | W50665 | gtcctaaacttgaccttcaatgact | 50154 | W50665 | acatgactatagccagaagccaga | 92758 | ggccaaatccctgcagtactacct | AA123463 |
| 7551 | W50665 | ctaaacttgaccttcaatgactgca | 50155 | W50665 | actatagccagaagccagaatgcc | 92759 | gccaaatccctgcagtactaccg | AA123463 |
| 7552 | W50665 | aacttgaccttcaatgactgcaagg | 50156 | W50665 | agccagagtacgccagtggagcctc | 92760 | agcctttcacatggtagttacta | AA118053 |
| 7553 | W50665 | cccagactactgctcagtgcagc | 50157 | W50665 | ttagtaaggccagcagcaagcaag | 92761 | gcctttcacatgtagttactaa | AA118053 |
| 7554 | W50665 | ttgacctcaatgactgcaagggca | 50158 | W50665 | tgtcagtgtgatcctccagcag | 92762 | agataagaaccctgcaaacatagtc | AA118053 |
| 7555 | W50665 | actctatgctcagtgcagccgctg | 50159 | W50665 | gactgtctgttctcagccggc | 92763 | ataagaaccctgcaaacatagtcag | AA118053 |
| 7556 | W50665 | tgtcagtgcagccgcgtgtgaa | 50160 | W50665 | gatccctcctttagggaggccag | 92764 | tagaaacctgcaaacatagtcgt | AA118053 |
| 7557 | W50665 | gtgcagccgcgtgtgaatgcaaa | 50161 | W50665 | gcctcagtgaactctaccacctggg | 92765 | aaacccctgcaaacatgtcagtgtg | AA118053 |
| 7558 | W50665 | ccagtctcttgctcgggcaaga | 50162 | W50665 | ctgaactctaccacctggcctggaa | 92766 | accctgcaaacatagtcagtgtggg | AA118053 |
| 7559 | W50665 | ctctcggtcacgtctgcagatgatc | 50163 | W50665 | agagatccgacgcgctttgccaa | 92767 | ggaagcctttcacaatagtagcct | AA118053 |
| 7560 | W50665 | gtcacgtctgcagatgatctggagt | 50164 | W50665 | cccctgacttcaatcagtgcctaaa | 92768 | agcctttcacaatagtagcctcta | AA118053 |
| 7561 | W50665 | ctggagtgcagccctggaactccagc | 50165 | W50665 | acttcaatcagtgcctaaagaacag | 92769 | gcctttcacaaatagtagcctctaa | AA118053 |
| 7562 | W50665 | gaaataccgcgcgtcgtcagtgt | 50166 | W50665 | gcctaaagaacagtccggagagga | 92770 | ctttcacaatagtagcctctaaat | AA118053 |
| 7563 | W50665 | atacgggccgtcagtgtacga | 50167 | W50665 | agaacagtccggagagaattctt | 92771 | tttcacaatagtagcctctaaatt | AA118053 |
| 7564 | W50670 | ttcgtccggttcacgcaactcga | 50168 | AA033161 | tgcctgctggttgccaattccag | 92772 | tttcacatgtagttatctataac | AA118053 |
| 7565 | W50670 | gttgcacgacaactgaccgaaga | 50169 | AA033161 | cctgctgttgccaattccaggag | 92773 | ataccttaaaaggacactcaccagat | AA118053 |
| 7566 | W50670 | ttgcacgacaactgaccgaagag | 50170 | AA033161 | ttcagcctgcctcagtcattccg | 92774 | cctaaaaggacactcaccagataga | AA118053 |
| 7567 | W50670 | tgcacgacaactgaccgaagagg | 50171 | AA033161 | agcctgagctccagtcattccggag | 92775 | aggacactcaccagatagaaacct | AA118053 |
| 7568 | W50670 | gcacgacaactgaccgaagaggc | 50172 | AA033161 | ctgagctcagtcattccggagacc | 92776 | acactcaccagatagaaaacctgc | AA118053 |
| 7569 | W50670 | cacgacaactgaccgaagaggca | 50173 | AA033161 | agcctcagtcattccggagacctg | 92777 | acactcaccagatagaaacctga | AA118053 |
| 7570 | W50670 | acgacaactgaccgaagaggcat | 50174 | AA033161 | ctcagtcattccggagaccctga | 92778 | ctcaccagatagaaacctgcaaac | AA118053 |
| 7571 | W50670 | cgcgtcacgtacattccgt | 50175 | AA033161 | agtcattccggagaccctgcctga | 92779 | caccagatagaaacctgcaaacat | AA118053 |
| 7572 | W50670 | gcgtcgtcacgtacattccgtg | 50176 | AA033161 | cattccggagacctgcctctgatgg | 92780 | attcatgacagattccactaaccga | AA118062 |
| 7573 | W50670 | cgtcacgtacattccgctgg | 50177 | AA033161 | ttgtgctttatcgtaaggcaca | 92781 | ttcatgacagattccactaaccgac | AA118062 |
| 7574 | W50670 | gcgtcacgtacattccgtga | 50178 | AA033161 | aaggcaaacatttgccaggagtc | 92782 | gccaacgtcgcttgtgagcgat | AA118062 |
| 7575 | W50670 | tcgtcacgtacattccggac | 50179 | AA033161 | acatttgctgagcgctagtgac | 92783 | ccaagctgctttgggagcgatt | AA118062 |
| 7576 | W50670 | gtcacgtacattccgctggaccg | 50180 | AA033161 | gctggttgccaattccaggagcta | 92784 | caacgtcgctttgtggagcgatg | AA118062 |
| 7577 | W50670 | tcacgtacattccggctggaccgc | 50181 | AA033161 | ttgccaattccaggagctaacctca | 92785 | agtctgctttgggagcgatgct | AA118062 |
| 7578 | W50670 | cacgtacattccggctggaccgct | 50182 | AA033161 | ccaattccaggagctaacctcaagg | 92786 | cgtctgcttttgggagcgatgctg | AA118062 |
| 7579 | W50670 | ctttccaaggagctgagaacatgt | 50183 | AA033161 | attccaggagctaacctcaaggaga | 92787 | gtctgctttgggagcgattgctga | AA118062 |
| 7580 | | ggcgagcctacactgacatgaagga | 50184 | AA033161 | ggagctaacctaaggagagaggctt | 92788 | ctgctttgggagcgattgcgaac | AA118062 |
| 7581 | | ccaattactacagacctctggact | 50185 | AA033161 | gcagcagtccaccctcagggaaca | 92789 | tatcacttagcctatgacgaatatt | AA118062 |
| 7582 | | actacagacctctggactgcctgc | 50186 | AA033161 | acttcaggaacacctgaccatgg | 92790 | atcacttagcctatgacgaatatt | AA118062 |
| 7583 | | actgagtgctctctattagttcag | 50187 | AA033161 | tcaggaacacctgaccatggccatg | 92791 | cacttagcctatgacgaatatt | AA118062 |
| 7584 | | tctggggtctctctattaggaacact | 50188 | AA033161 | gatgtcatgccattgggaggcag | 92792 | catgacagattccactaaccgagc | AA118062 |
| 7585 | | ctcctataggaacactgaacact | 50189 | AA033161 | tatgccatctgggagcagccacca | 92793 | atgacagattccactaaccgacgcc | AA118062 |
| 7586 | | tgaaatgctctggggcacaata | 50190 | AA033161 | agaatgaccacgctctctgcatta | 92794 | tgacagattccactaaccgacgccg | AA118062 |
| 7587 | | tgctctggggcacaagtatac | 50191 | AA033161 | accacgctctctgcattaatgac | 92795 | agcaagccaacgtctgcttgt | AA118062 |
| 7588 | | atgtgatccccaagggttca | 50192 | AA033161 | acgctctctgcattaatgacgt | 92796 | gcaagtggccaacgtcgctttgtg | AA118062 |
| 7589 | | gtatcccacaaggtttcgaatgg | 50193 | AA033161 | ctctctgcattaatgcactgctg | 92797 | caagtggccaagtgctgctttgg | AA118062 |
| 7590 | | taactgctgaggagagaggtaa | 50194 | AA033161 | tgcattaatgcactgctgaagcct | 92798 | gtggccaacgtcgctgttgggagc | AA118062 |
| 7591 | | cctacactgacatgaagaagctgg | 50195 | AA033161 | attaatgctgctgaagctgg | 92799 | tggccaacgtcgcttttgtggagcg | AA118062 |
| 7592 | | gagacaaatactccatgctcggg | 50196 | AA117582 | aatgcactgctgaagcctgtggta | 92800 | cggagtcccagctgacattctat | W08109 |
| 7593 | | gctttcaggaattctcaggcagag | 50197 | AA117582 | ctgtcgaagcctgtggtaaggaaa | 92801 | agtccccagctgacattctatatg | W08109 |
| 7594 | | tcttcgagaagaccatggctgaca | 50198 | AA117582 | tctgaagcctgtggtaaggaaataa | 92802 | caggctcctggcactttcggtca | W08109 |
| 7595 | | gacacggcatgctgaccatggctgacca | 50199 | AA117582 | ataaccactaagcaaaatgttgccca | 92803 | gctcctgcacttcggtcatttc | W08109 |
| 7596 | | aggacacatgctgaccaggagc | 50200 | AA117582 | gaggcagccaaccaaaccatga | 92804 | cctgcacttctggtcattctta | W08109 |
| 7597 | | ccaacagccatgccgcgaatgcaa | 50201 | AA117582 | gcagccaccaaaccaacctcatgaagt | 92805 | gtgcacttctggtcattctagga | W08109 |
| 7598 | | gtggcaagaccccaattactacag | 50202 | AA117582 | gaaatgacccctaactacttaaca | 92806 | cactttctggtcatttcctagaagc | W08109 |
| 7599 | | accctgactgcctgccaaatac | 50203 | AA117582 | gacctaactactacagatga | 92807 | ctggcaatttcctaggaagccattc | W08109 |

| SEQ ID NO | sequence | DBAxnID | SEQ ID NO | sequence | DBAxnID | SEQ ID NO | sequence | DBAxnID |
|---|---|---|---|---|---|---|---|---|
| 7600 | cctggactgcctgccaaatactgag | | 50204 | cctaactacttaccagaatgacca | AA117582 | 92808 | cccattcctcgaattagccaggctg | W08109 |
| 7601 | ctggactgcctgccaaatactgaga | | 50205 | aactacttacacagaatgaccacgc | AA117582 | 92809 | atcctgaattagccaggctgaag | W08109 |
| 7602 | tggactgcctgccaaatactgagag | | 50206 | ttaacagaatgaccacgctctct | AA117582 | 92810 | cgaattagccaggctgaagaggcg | W08109 |
| 7603 | ggactgcctgccaaatactgagagt | | 50207 | cacagaatgaccacgctctctgca | AA117582 | 92811 | attagccaggctgaagaggacgacc | W08109 |
| 7604 | gactgcctgccaaatactgagagtc | | 50208 | cccggacgaggtggtgcgatcatg | W83082 | 92812 | ctccagctgacattctatatgaag | W08109 |
| 7605 | actgcctgccaaatactgagagtca | | 50209 | tgcggatcatggtcacctgtagcct | W83082 | 92813 | ccagctgacattctatatgaagatc | W08109 |
| 7606 | ctgcctgccaaatactgagagtcag | | 50210 | tgcagtccactgtggcctgtggt | W83082 | 92814 | cagtgcctgtttcctgacgtag | W08109 |
| 7607 | tctcacccagcaggatgaagctac | | 50211 | ctgtggtcctgctggcttga | W83082 | 92815 | cttgttcctgacgtagtctctc | W08109 |
| 7608 | tcatttattgggagggcttccaag | | 50212 | ttcctgctctggctgaagctct | W83082 | 92816 | gtgttcctgacgtagctcctcagg | W08109 |
| 7609 | acctcctggactgcctgccaaatac | | 50213 | gctctgggcctgaagctctgagaac | W83082 | 92817 | ttccgttgacgtagctcctcaggctc | W08109 |
| 7610 | cctggactgcctgccaaatactgag | | 50214 | ctggcctgaagctctgagaacaga | W83082 | 92818 | gtagctcctcaggctctgtgcact | W08109 |
| 7611 | ctgactgcctgccaaatactgaga | | 50215 | aagctctgagaacagagactcacgc | W83082 | 92819 | cctcaggctctgtgcactttctgg | W08109 |
| 7612 | tggactgcctgccaaatactgagag | | 50216 | ctctgagaacagactcacatgctc | W83082 | 92820 | cacacagcaaggttcattgcagaaga | AA118100 |
| 7613 | ggactgcctgccaaatactgagagt | | 50217 | tgagaccagactcacatgctcatt | W83082 | 92821 | ccacagcccgggccaagtgtgt | AA118100 |
| 7614 | gactgcctgccaaatactgagagtc | | 50218 | cagactcacatgctcattgctct | W83082 | 92822 | ggttcccactggcagttagcat | AA118100 |
| 7615 | actgcctgccaaatactgagagtcc | | 50219 | cacatgctcattgctcagag | W83082 | 92823 | tccccactgggcagttagcatcgg | AA118100 |
| 7616 | gaccactaactggagctgagtcaagtt | X14961 | 50220 | gcagtcccaagctggagcatcagaa | W83082 | 92824 | ttagcaccggattgcttcacca | AA118100 |
| 7617 | gaaactcatcctgactctcaccat | X14961 | 50221 | ctccattgctctgacaggctccca | W83082 | 92825 | tcggatttgtgttcaccagaggct | AA118100 |
| 7618 | atgctcctcatggttttccctct | X14961 | 50222 | gtccaagctgggacatcgagaactg | W83082 | 92826 | ttgctgttcaccagagctggaatt | AA118100 |
| 7619 | cctcaggttttccctctgcactt | X14961 | 50223 | gaggaaccagctgccatcgagctggtgt | W83082 | 92827 | ctgttcaccagagctggaatttg | AA118100 |
| 7620 | gattttctgagatacgggggcatc | X14961 | 50224 | cccagctgcactgtgtgagttga | W83082 | 92828 | tgattcaccactgcacagaggagcg | AA118100 |
| 7621 | gggcatcagctgaccagttcct | X14961 | 50225 | agcatcgagctgtgtgagtgacc | W83082 | 92829 | ttcaccactgcacagaggagcggt | AA118100 |
| 7622 | catcagctgaccagttcctgcact | X14961 | 50226 | tgagtgaccctgcagtgccact | W83082 | 92830 | actgcacagagagagcggcgta | AA118100 |
| 7623 | cagcctgaccagttcctgcactag | X14961 | 50227 | accctgcagtgccactgggcc | W83082 | 92831 | cagccctgcaagtgtgtcacac | AA118100 |
| 7624 | ggaccagttcctgcactatgtgtg | X14961 | 50228 | ctctgcagtcccactgtggcc | W83082 | 92832 | cagccccaagtgtgtgcgtacgg | AA118100 |
| 7625 | cccagttcctgcactatgtgtggtt | X14961 | 50229 | cggatcatgcgatcatcgcgctctg | W83082 | 92833 | cctccgggccaagtgtgtctcac | AA118100 |
| 7626 | agttcctgcactatgtgtggttat | X14961 | 50230 | gatcatgcgatcatcgcgctctgca | W83082 | 92834 | ccatcgacgccacctgcaacttgt | AA118100 |
| 7627 | gatctcaaagggtgctccaaggtca | X14961 | 50231 | tctgcagacaaggtcgtgtagaaag | W83082 | 92835 | ttgctgcacctgcaacttgtgca | AA118100 |
| 7628 | gatctcacccagccagtggtgtg | X14961 | 50232 | gtcgcgcactatgaggatggg | W83082 | 92836 | acggcacctgcaactttgtgcaag | AA118100 |
| 7629 | cacccatgcgtgtggcgagcact | X14961 | 50233 | tcgcagccactatgaggatggtccg | W83082 | 92837 | gcacctgcaactttgcacagtt | AA118100 |
| 7630 | gagcactggactatgagaagag | X14961 | 50234 | cgcagccactatgaggatggtccgg | AA138107 | 92838 | gcaacttgtgcaggttcccac | AA118100 |
| 7631 | cactggactatgagaaggaggg | X14961 | 50235 | ccactagaggatggtccggggaag | AA138107 | 92839 | ttgtgcacaggtccccactgtggc | AA118100 |
| 7632 | gtgactgagctccgtcactgac | X14961 | 50236 | cactatgaatggtccggggaaga | AA138107 | 92840 | cttcgcaaggtccaggcagctatgaa | AA118151 |
| 7633 | actggcgtctccgtcactgaccgg | X14961 | 50237 | ctatgaggatggtccgggaagaat | AA138107 | 92841 | tcgcaagtccaggcagctatgaaag | AA118151 |
| 7634 | ctcagcaccatgcgtcctcatggtt | X14961 | 50238 | ttggatctggttgcctgcacttt | AA138107 | 92842 | tatgccaggcattaacagatcaac | AA118151 |
| 7635 | agcacctagcctcatggttttc | X14961 | 50239 | tgcccgtcactttttatagtaag | AA138107 | 92843 | tgccaggcattaacagatcaacaac | AA118151 |
| 7636 | catgctcatctttgtcatctg | X03505 | 50240 | tgccgcacctttataagtaaga | AA138107 | 92844 | cagatcaacactttgtaagc | AA118151 |
| 7637 | tgccatcatctttgtcatctgatc | X03505 | 50241 | tcatgcggatctggctgctgcgac | AA138107 | 92845 | gataatgctacaacttatgtcata | AA118151 |
| 7638 | ttttctctcctgtttgcatctg | X03505 | 50242 | catgccgggatctggctgctgcgagac | AA138107 | 92846 | taatgctacaacttatgtcataaa | AA118151 |
| 7639 | ctctcctgtttgccagtcatgc | X03505 | 50243 | atgccgggatcatgcgctctgcagaca | AA138107 | 92847 | atgctacaacttatcatgcataaagg | AA118151 |
| 7640 | ttcctgtttccccagtcatcc | X03505 | 50244 | tggatcgctctgcagacaaggtcc | AA138107 | 92848 | gttacttcaacttcaggtgaagca | AA118151 |
| 7641 | atctgatcctaaacatcccaatg | X03505 | 50245 | atcatcgcgctctcgacaaggtcg | AA138107 | 92849 | acttcaactttgggaagcaagat | AA118151 |
| 7642 | tggatctctaaacatccccaaggtgc | X03505 | 50246 | atgcgctctgcagacaaggtcgtgt | AA138107 | 92850 | ttcaacttcagtgggaagcaagattt | AA118151 |
| 7643 | catccaatgtctgcataaatact | X03505 | 50247 | tgcgctctgcagacaaggtcgtgta | AA138107 | 92851 | gcttatcagcaaggctattgaaatt | AA118151 |
| 7644 | aatgcactttgtcgctcactgtt | X03505 | 50248 | gcgctctgcagacaaggtcgtgtag | AA138107 | 92852 | aagccaggcagctatgaaaggttg | AA118151 |
| 7645 | gcacttcgctgctcactgtgt | X03505 | 50249 | tctgacccatcctccagattgc | AA138107 | 92853 | gtccaggcagctatgaaaggttg | AA118151 |
| 7646 | cgctgcactgttttgacaggca | X03505 | 50250 | gggaccatcatccccagattgcat | AA033333 | 92854 | gaaatttccaagatgctgaaggc | AA118151 |
| 7647 | tgtcacgtgtttgacaggcacag | X03505 | 50251 | tcaacgtccagaacttccatatcag | AA033333 | 92855 | aatttccaagatgctgaaggcta | AA118151 |
| 7648 | catctgatccggaagtgcagccg | X03505 | 50252 | ccagaacttccatatcagctg | AA033333 | 92856 | ttccaagatgctgaaggctatg | AA118151 |
| 7649 | tgtttgacaggcacagggactcac | X03505 | 50253 | actccatatcagctgaggaccgg | AA033333 | 92857 | ctatgcactttatgccaggcatta | AA118151 |

| SEQ ID NO | sequence | DBAxnID | SEQ ID NO | sequence | DBAxnID | SEQ ID NO | sequence | DBAxnID |
|---|---|---|---|---|---|---|---|---|
| 7650 | taaagtcatcagcgatgccagagag | X03505 | 50254 | tccatatcagctgcgaaggacgggct | AA033333 | 92858 | atgcactttatgccaaggcattaac | AA118151 |
| 7651 | agtcatcagcgatgccagagaggct | X03505 | 50255 | tcaatgcactcatccacggcacag | AA033333 | 92859 | tttatgccaggcattaacagatca | AA118151 |
| 7652 | caggatgccagaggctgttcag | X03505 | 50256 | ggcacaggcctgagctgattgagta | AA033333 | 92860 | tccggcaggcatgcaccttaccaga | AA120389 |
| 7653 | gaagtcacggaacatggagagagag | X03505 | 50257 | atgatcagtcaccaacctaacaca | AA033333 | 92861 | ggcaggcatgcaccttaccagacat | AA120389 |
| 7654 | gtcacgggaacatggagagcaggac | X03505 | 50258 | atccagtcaccaacctaaacaatgc | AA033333 | 92862 | aatcaggcaccagaggattcatcaca | AA120389 |
| 7655 | ctcaagagctgaccagttgccaat | X03505 | 50259 | ccaacctaaacaatgcattgaagt | AA033333 | 92863 | acctatccgtcacgagtgtgga | AA120389 |
| 7656 | aagagctgaccagttgccaatgag | X03505 | 50260 | acctaacactgcattgaagtggc | AA033333 | 92864 | ctatacctcacgagtgtgaggac | AA120389 |
| 7657 | tgactcggcttctgtgcccagatc | X03505 | 50261 | ccatcatctcagattgccatcca | AA033333 | 92865 | agacagttctccacagttccac | AA120389 |
| 7658 | ctcggcttctgtgcccagatcact | W50708 | 50262 | tcagatttgccatccaggacalctc | AA033333 | 92866 | ctctcacagttccaaccggatcgt | AA120389 |
| 7659 | ggcatcatggtcatcgagatggttg | W50708 | 50263 | gatttgccatccaggacatctcgt | AA033333 | 92867 | cagttccaaccggatcgtcacctg | AA120389 |
| 7660 | atcatggtcatcgagatggttgaag | W50708 | 50264 | ccatccaggacatctctgtggaaga | AA033333 | 92868 | ccggattcgtcacctgagaaccal | AA120389 |
| 7661 | tacctcaacgaaaatcctcgcggg | W50708 | 50265 | aggacatctgtggaagaagactc | AA033333 | 92869 | gattcgtcacctgagaaccctata | AA120389 |
| 7662 | aacgaaaatcctcgcgggcattat | W50708 | 50266 | agacctctgctaggaaggaagactct | AA033333 | 92870 | tcacctggaaccatacagaggaga | AA120389 |
| 7663 | aatcctcgcgggcattataccga | W50708 | 50267 | aggaaggactctcctcctgtgcca | AA033333 | 92871 | cctgaaccatcacagaggaggaaga | AA120389 |
| 7664 | cctcgcgggcattataccctgatag | W50708 | 50268 | acgtcaagctccagaaccttccatat | AA033333 | 92872 | aggcatgcacctaccagacatcag | AA120389 |
| 7665 | gcatataccgtagatagctacaaatg | W50708 | 50269 | aggagctgctcacacagagtgt | AA033333 | 92873 | cgacctaccagacatcagcgagaaca | AA120389 |
| 7666 | ttataacctgatagctacaaatggaa | W50708 | 50270 | gtgactccgtcgtgatcgatcct | AA033333 | 92874 | cctaacgacatcagagagaacacac | AA120389 |
| 7667 | tacctgatagctacaaatggaactc | W50708 | 50271 | acccacctggatattcacatgga | AA033333 | 92875 | ggaaaacttctctcatagatctaac | AA120389 |
| 7668 | gctacaaatggaactcgaactc | W50708 | 50272 | atattcacatgagagctaccgtatgg | AA168903 | 92876 | aaactctctcatagatctaactta | AA120389 |
| 7669 | cggctctgtcccagatcactcct | W50708 | 50273 | acatggagctaccgtatggggacatt | AA168903 | 92877 | ctctcatagatctaacttaatcag | AA120389 |
| 7670 | ctctgtgcccagatcactctgaa | W50708 | 50274 | agatgcgcaggctcaatataccagt | AA168903 | 92878 | taacttaatccgccaagaggatt | AA120389 |
| 7671 | ctgtgcccagatcactctgaacag | W50708 | 50275 | tggcaggctcaatataccagtgcta | AA168903 | 92879 | cttaatcaggcaccagaggttcat | AA120389 |
| 7672 | tgcccagatcactctgaacacagagc | W50708 | 50276 | gcaggctcaatataccagtgctaca | AA168903 | 92880 | gcccttgccgaaagcacagctgt | AA120463 |
| 7673 | caaacgagtactatggttggaaca | W50708 | 50277 | tcaatataccagtgctacaggatga | AA168903 | 92881 | ctgccgaaagcatcagctgtgaa | AA120463 |
| 7674 | ctgatgccaccgagggtgtgacac | W50708 | 50278 | atatataccagtctacaggatgacgg | AA168903 | 92882 | caaagaatgcgctccgtctgcgcg | AA120463 |
| 7675 | tctctgggcatcgctacgaga | W50708 | 50279 | tcctttcctctgggtcacaggaag | AA168903 | 92883 | agctcaagctcggcaggattgaga | AA120463 |
| 7676 | ctgcatcatggctcatcgagaga | W50708 | 50280 | tcctctgggtcacggaagggccat | AA168903 | 92884 | atggagctctggcatacaaact | AA120463 |
| 7677 | aatactccatgctcggggaactat |  | 50281 | ctgatcgactctttccacctcagtg | AA168903 | 92885 | ttgagagctctggcatacaaactg | AA120463 |
| 7678 | atactccatgctcggggaactatg |  | 50282 | atcgactctttccacctcagtgat | AA168903 | 92886 | gctcggcatacaaactggtggictta | AA120463 |
| 7679 | caggcattcttcagcagtggacaca |  | 50283 | gttgtatccgctacctgacgtat | AA168903 | 92887 | cctggcatacaaactgggtggictta | AA120463 |
| 7680 | aggcattcttcagcagtggacaca |  | 50284 | atatccgctacctgacgtcagtat | AA168903 | 92888 | cctctcacctagcctagcacaggg | AA120463 |
| 7681 | ggcattcttcagcagtggacacaag |  | 50285 | tccgtacctgacgtcagtatctt | AA168903 | 92889 | tctcacctagcctaatgaccaggtc | AA120463 |
| 7682 | gcattcttcagcagtggacacaagg |  | 50286 | gctacctgacgtcagtatcttggg | AA168903 | 92890 | ctcacctgacctaatgaccaggtc | AA120463 |
| 7683 | cattcttcagcagtggacacaagga |  | 50287 | acgtcagtatcttgggcaaattgc | AA168903 | 92891 | cacctagctaatgaccaagtccg | AA120463 |
| 7684 | tactccatgctcggggaactatga |  | 50288 | ctgaccacctgggatattcacat | AA168903 | 92892 | tgccgaaagcatcagctgtgaag | AA120463 |
| 7685 | actctcatgctcggggaactatgat |  | 50289 | cctccaagtatgatacgtgatgg |  | 92893 | aagcatcagctgaagcggcgccg | AA120463 |
| 7686 | atgctcggggaactatgatgtgatg |  | 50290 | gaaacctcagattatatcccattg |  | 92894 | agcatcagctgaagcggcgccgc | AA120463 |
| 7687 | gggcattcaggcattcttcagcagt |  | 50291 | tactctgccttggaatggaaccca |  | 92895 | tcttgttccgcctcgctgctaa | AA120463 |
| 7688 | ggcattcaggcattcttcagcagtg |  | 50292 | ggaccaggaactgccttgccatgatg |  | 92896 | tgtgttccgcctcgctaatcc | AA120463 |
| 7689 | gcattcaggcattcttcagcagtg |  | 50293 | aggttgctcatgaaatatgaaac |  | 92897 | tgttccgcctcgctcgctaatcca | AA120463 |
| 7690 | gcattcaggcattcttcagcagttg |  | 50294 | atgaactgtctcactaaaattag |  | 92898 | tccgtaatccaagaaatgcgcct | AA120463 |
| 7691 | tcaggcattcttcagcagttggacac |  | 50295 | ctgctccactaaaattacaga |  | 92899 | ccaaagaatggcctctcctgctggc | AA120463 |
| 7692 | aatacttccatgctcggggaactat |  | 50296 | cagtacctgcgaaattaagcagag |  | 92900 | acggctcgagctggggaagaact | W08125 |
| 7693 | atacttccatgctcggggaactag |  | 50297 | aaggtgccacggatgcagtca |  | 92901 | gggaagaactgccccttcgctgct | W08125 |
| 7694 | atccatgctcggggaactag |  | 50298 | ggagcatgctctccccaaggt |  | 92902 | catctggctgatgaccctggtct | W08125 |
| 7695 | ggcattcaggcattcttcagcagt |  | 50299 | tgagtccccaaggagttctct |  | 92903 | gacaagcagcgactcttatggaa | W08125 |
| 7696 | gcattcaggcattcttcagcagtgg |  | 50300 | ttctctgagttcttcagaaggca |  | 92904 | acagaagcagcgactcttatggaa | W08125 |
| 7697 | tcaggcattcttcagcagtgggacac |  | 50301 | ctcagatatatccccattgctaata |  | 92905 | agaagcagcgactcttatggaaac | W08125 |
| 7698 | ggcattcttcagcagtgggacaca |  | 50302 | ttatatcccattgctaatagactg |  | 92906 | gaacaggcagctcttatggaaact | W08125 |
| 7699 | aggcattcttcagcagtgggacaca |  | 50303 | gtgtatccccaaagggtcaacag |  | 92907 | aagcagcgactctttatgccaacg | W08125 |

| SEQ ID NO | sequence | DBAxnID | SEQ ID NO | sequence | DBAxnID | SEQ ID NO | sequence | DBAxnID |
|---|---|---|---|---|---|---|---|---|
| 7700 | ggcattcttcagcagtggacacaag | | 50304 | atccccaaagggtcaacagtgatga | | 92908 | agcagcgactcttatggaaactgg | W08125 |
| 7701 | gcattcttcagcagtggacacaagg | | 50305 | atccatcttatgctctttcaccatg | | 92909 | aactggacaacttctatcacgggca | W08125 |
| 7702 | cattcttcagcagtggaccaagga | | 50306 | tcttatgctcttcaccatgacccac | | 92910 | actggacaacttctatcacgggcat | W08125 |
| 7703 | tacttccatgctcgggaactatga | | 50307 | ttccaactgaaaggttcagcaagg | | 92911 | ctggacaacttctatcacgggcatg | W08125 |
| 7704 | actccatgctcggggaactatgat | | 50308 | agcattgatccttagtatatcgc | | 92912 | gaagaactgccctgcgtgtcgtc | W08125 |
| 7705 | cttccatgctcggggaactatgatg | W50767 | 50309 | ggagcatgagtccctcaaggagt | | 92913 | tggacaacttctatcacgggcatga | W08125 |
| 7706 | atgctcggggaactatgatgctgcc | W50767 | 50310 | gagcatgagtccctcaaggagtt | | 92914 | agaactgccctgcgtgtcgtcg | W08125 |
| 7707 | gatcaggaggctcgggcggctga | W50767 | 50311 | catgagtccctcaaggagttctt | | 92915 | aagatgcatcttggctgatgacc | W08125 |
| 7708 | tatcaggaggctgggcggctgaa | W50767 | 50312 | atgagtccctcaaggagttcttc | | 92916 | gatgcatcttggctgatgaccct | W08125 |
| 7709 | atcaggaggctcggccggctgaag | W50767 | 50313 | tgagtctcccaaggagttcttct | | 92917 | atgtgcatcttggctgatgaccctg | W08125 |
| 7710 | tcagggaggcctggccggctgaagt | W50767 | 50314 | cttctgagttcttcagaaagcgt | | 92918 | tggcatctggcgtgatgacctgg | W08125 |
| 7711 | gtcgtcaagatcttcaagacaca | W50767 | 50315 | ttctgagtcttcagaaaggcagtg | | 92919 | gtgcattcttggatgaccctggt | W08125 |
| 7712 | tcaagatcttcaagacacaagct | W50767 | 50316 | ttttagttcatcatgagtaaaat | | 92920 | gcatcttggctgatgacccctgcc | W08125 |
| 7713 | tacaaccactctgctggcatcaaa | W50767 | 50317 | ggagcatgagtctcccaaggagt | | 92921 | tgtctctattctccctctacagc | W07927 |
| 7714 | ccactctgtggcatcaaaccactg | W50767 | 50318 | gagcatgagtctcccaaggagtt | | 92922 | ctacagtcgctcaaccactcttga | W07927 |
| 7715 | tgctggcatcaaaaccactggggttg | W50767 | 50319 | catgagtctcccaaggagttctt | | 92923 | gccagatccagatacagataagacact | W07927 |
| 7716 | catcaaaccactgaggttgggatc | W50767 | 50320 | atgagtctcccaaggagttcttc | | 92924 | attccagatcaagacactgcaca | W07927 |
| 7717 | ctcatcgtgacaatggttccag | W50767 | 50321 | tgagtctcccaaggagttctct | | 92925 | cccagactaagacactgacagtt | W07927 |
| 7718 | caatgtccaggaagcagctgga | W50767 | 50322 | ctctgagtctcagaaaggcagt | | 92926 | tgtgacagttgctgcggtccact | W07927 |
| 7719 | ttcccaggaagcagctcgaaagca | W50767 | 50323 | ttctgagtcttcagaaaggcagtg | | 92927 | ctgtcgccactgtgttttagttgc | W07927 |
| 7720 | cagcagcgccatgctgccagcgcagtt | W50767 | 50324 | atttagttcatcatgagtaaaat | | 92928 | tcggtccactgtgttttagttgcaaa | W07927 |
| 7721 | catgctcagcttggagatgctc | W50767 | 50325 | ttttagttcatcatgagtaaaat | | 92929 | ggtccactgtgttttagttgcaaaga | W07927 |
| 7722 | gatgctcttcgtctaacatccat | W50767 | 50326 | ccgcttcaccatgtagaaaaggg | | 92930 | gtccactgtgtttttagttgcaaagat | W07927 |
| 7723 | tcttcaagacacaagttctagg | W50767 | 50327 | gttcaacatgaataacaaggggtc | | 92931 | tccactgtgtttagttgcaaagat | W07927 |
| 7724 | ctttctaacatcccattcccca | W50767 | 50328 | taccacagccctgggtggactaca | | 92932 | tgttactgtcttaaggggccaca | W07927 |
| 7725 | agacacacaagttctaggaccacaa | W50767 | 50329 | actacacatcaacatcctttgc | | 92933 | ctggccctaaccactccttgagctcggg | W07927 |
| 7726 | acaagctctaggaccacatcaagt | W50767 | 50330 | acaactcaacatccttttgctga | | 92934 | tgtgctttcatagggctttccctg | W07927 |
| 7727 | ttctaggaccacacagtccagga | W50767 | 50331 | acatctccttttgctgacac | | 92935 | ttgcctaaacctgaagatgtctc | W07927 |
| 7728 | gaccacatcagaaggtccaggaa | W50767 | 50332 | tcctttttgctgacacccacatcc | | 92936 | aacctgaagatgtctcccaagct | W07927 |
| 7729 | atcaagtccaggatcgcaaggat | W50767 | 50333 | tttttgctgacaccacatcctg | | 92937 | aagatgtctcccaagcctgtggc | W07927 |
| 7730 | aggattattgcctagccaaaggt | W50767 | 50334 | ttcctgatcccccattcaaggcca | | 92938 | atgtctcctcaagcctgtgggc | W07927 |
| 7731 | caaaggctgttaagcctgctgaagaa | W50767 | 50335 | cattcaaggcccatgtggctccttg | | 92939 | ccaagcctggggcagcatgccc | W07927 |
| 7732 | gtcaagcctagccctgcgaggaaa | W50767 | 50336 | tcaaggccatgtgcttgtcttt | | 92940 | caagcctggggcagccatgccccaga | W07927 |
| 7733 | cctagccctgccgagaaacacag | W50767 | 50337 | aggccatgctgctgcttgttga | | 92941 | cacattggctctgctcaccatt | W07927 |
| 7734 | aagctcaggtgctcgggttctag | M24086 | 50338 | gcctgggcctgacagtggaaggccc | | 92942 | ttgggctctgctcaccaattctcc | U12560 |
| 7735 | ctcacatccagtgaagttgctaccg | M24086 | 50339 | atgtgctctgtgtttgatgcatc | | 92943 | tctgctttcatgaagaattgcaa | U12560 |
| 7736 | gctaccgaggtgcgtctgcctca | M24086 | 50340 | cagtggaaggccctgtgaagcaca | | 92944 | ctgctctcatgaagaatcgcaaa | U12560 |
| 7737 | atgcaccgcagccgaggtgatccag | M24086 | 50341 | aaggccctgtgaagcacagttga | | 92945 | gcgtttttgaacctgcagaaatct | U12560 |
| 7738 | ccgcagccgaggtcgatccagcaaag | M24086 | 50342 | gccctgtgaagcacagttgagtg | | 92946 | tttaacttcgtatctgctagc | U12560 |
| 7739 | tttgctgccaaaatcgaaagata | M24086 | 50343 | cctgtgaagcacagttgagtgct | | 92947 | taactttcgtattctgctagctg | U12560 |
| 7740 | agactacgcctacgatctgaaac | M24086 | 50344 | atgtacatgctcgtgtcttatgt | | 92948 | aactttgtattctgctagctga | U12560 |
| 7741 | aagcatgactcccccagaaat | M24086 | 50345 | catgctcgctctattgtacccac | | 92949 | acttcgtattctgctagctgaa | U12560 |
| 7742 | gagcattcctcccagaaataaagtc | M24086 | 50346 | ctgtcttatattgcccactgccgc | | 92950 | tttcgtattctgctagctgaata | U12560 |
| 7743 | tcctccagaaataaagttcctggg | M24086 | 50347 | caccccagctcattcctgcagtgaa | X78545 | 92951 | ttcgtatctgctagctgaatat | U12560 |
| 7744 | gtgatgcaaacagcactttgacca | M24086 | 50348 | cattcctgctgaagccatacct | X78545 | 92952 | tattctgctagctgagatcag | U12560 |
| 7745 | agcactttgaccaagacacactggtgc | M24086 | 50349 | cagaattccagtctttatgcctg | X78545 | 92953 | tggctcctgctcaccaattctca | U12560 |
| 7746 | ttgaccaagacactggtggtgtc | M24086 | 50350 | cagctttatgcctttgattcgggaa | X78545 | 92954 | atctgctagctgaaatatcgaga | U12560 |
| 7747 | aagacactggtgctgctgccccta | M24086 | 50351 | actcctgcaacacctagaaacaca | X78545 | 92955 | gggctcctgctcaccaattctccag | U12560 |
| 7748 | ggcatcaggctgctggatggaagatca | M24086 | 50352 | ctgaaccaacctgtgctggg | X78545 | 92956 | ctcgctagctgaatatgcaga | U12560 |
| 7749 | ctgccaccgccatcatccagttg | M24086 | 50353 | gaacaaaaccgtgtcggggca | X78545 | 92957 | ctcctgctcaccaattccagttg | U12560 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 7750 | tccagcaccatcatcaaggagggca | M24086 | 50354 | gccagttgccagcatccggggtat | X78545 | 92958 | tcctgctcaccaattctccaggtga | U12560 |
| 7751 | tcataccatatcaaggtgaagctca | M24086 | 50355 | agtgtccagcatccgggtatggt | X78545 | 92959 | ctgtccaccaattctccaggtgacc | U12560 |
| 7752 | ccctcaactggtcagctggactcgg | AA013831 | 50356 | cagatcctggggtatggtgtctg | X78545 | 92960 | tgtccaccaattctccaggtgacce | U12560 |
| 7753 | tccaactggcagctgactcggtc | AA013831 | 50357 | tggttgtcgagccttaataagaa | X78545 | 92961 | gtcgtcttcatgaagaatgtca | U12560 |
| 7754 | actctgaattgcctgagagggatac | AA013831 | 50358 | tgtctgagccttaataagaaatc | X78545 | 92962 | tgcactctcaaagtctgaagtgatt | AA118584 |
| 7755 | ctctgacctcactgcagtcagtacca | AA013831 | 50359 | tgaagccatactccacgagagctt | X78545 | 92963 | cactctcaaagtctgaagtgattaa | AA118584 |
| 7756 | acctcactgcagtcagtaccaaggtgaa | AA013831 | 50360 | acctcacgagctgttgacaatgaa | X78545 | 92964 | gcaaccccatccattgcatgattata | AA118584 |
| 7757 | tcactgcagtaccaaggtgaagac | AA013831 | 50361 | aacactggtcaatgacatcatgctc | X78545 | 92965 | aaccccatccattgcatgattaatg | AA118584 |
| 7758 | cttgcagtaccaaggtgaagactct | AA013831 | 50362 | catcatgctctgaagctgaacgc | X78545 | 92966 | cccatccattgcatgattaatgct | AA118584 |
| 7759 | tgaagactctgctgctaaatgctgc | AA013831 | 50363 | cattgcagttgtgccttgtgtact | X78545 | 92967 | gtattaatgctgatcctatgactgt | AA118584 |
| 7760 | agactctgctgctaaatgctgctca | AA013831 | 50364 | tccaaatttacaagctctgtggctc | X78545 | 92968 | attaatgctgatcctatgactgtag | AA118584 |
| 7761 | tgctgctaaatgctgctcagaaccac | AA013831 | 50365 | atlccacagaatttccagctttatg | X78545 | 92969 | taatgctgatcctatgactgtagtg | AA118584 |
| 7762 | ctgctcagaacaacacgcgagcatg | AA013831 | 50366 | caccagaatttcagctttatgct | X78545 | 92970 | atgctgatcctatgactgtagtgt | AA118584 |
| 7763 | agaacacacgagccatgcctgc | AA013831 | 50367 | tcaaggctgcctggagatgagat | X78545 | 92971 | tgatcctatgactgtagtgtgggct | AA118584 |
| 7764 | tcctctaaaggctgggtctgacal | AA013831 | 50368 | ttgagactacccgcggctgctgga | X78545 | 92972 | atcctatgactgtagtgtgggctta | AA118584 |
| 7765 | ttctaaaggctgggtgactatcca | AA013831 | 50369 | ttttcctgattcctctatgcaggt | X78545 | 92973 | cctatgactgtagtgtgggcttaga | AA118584 |
| 7766 | ctggtgctgacatcatgcagaagaa | AA013831 | 50370 | tggattctctatgcaggttgggtc | X78545 | 92974 | tgattaatatccacgtgtagctga | AA118584 |
| 7767 | gtgctgacatccatgcagagaatga | AA013831 | 50371 | acaatatccaatttacaagtctg | X78545 | 92975 | attaatatccacgtgtagctgcaac | AA118584 |
| 7768 | ctgacatccatgcagagaatgagga | AA013831 | 50372 | tccaatttacaagtctctgtggctc | U02880 | 92976 | taatatccacgtgtagctgcaaccc | AA118584 |
| 7769 | gcgactccgactctgaatggcctga | AA013831 | 50373 | gtcttcattgaaccccagatcacc | U02880 | 92977 | atatccacgtgtagctgcaaccat | AA118584 |
| 7770 | actccgactcgaatggcctgagag | AA013831 | 50374 | tattgaaccccagatcaccttcaac | U02880 | 92978 | acgtgtagctgcaaccatccattg | AA118584 |
| 7771 | ccgactctgaatggcctgagaggga | AA013831 | 50375 | tccactaagttttctggtcgcctg | U02880 | 92979 | gtgtagctgcaaccatccatcgca | AA118584 |
| 7772 | cagaaaactcacagacagaggtgat | AA013831 | 50376 | ttcggtcgcctgacccattttctt | U02880 | 92980 | gtagctgcaaccatccatccatg | AA118584 |
| 7773 | aactcacagaccaggtgatgcagaa | AA013831 | 50377 | tttcttttaatccccaagctttgatg | U02880 | 92981 | ctgaaccatccattgcatgatt | AA118584 |
| 7774 | acgtctgaacagctctctcacact | W50655 | 50378 | taatccacaggctttgaatggaacg | U02880 | 92982 | tagatgccaggctgaagtaagcga | AA118546 |
| 7775 | gtcttgacaacgtctctcacactcc | W50655 | 50379 | agagtcatccttttccgtcctcaa | U02880 | 92983 | gattgaagcccaagctcattgatgt | AA118546 |
| 7776 | cttgacaacgtctctcacactcctt | W50655 | 50380 | agcaccatcagtcgattcctctaa | U02880 | 92984 | cgcctgagttctaccaagtatgcca | AA118546 |
| 7777 | tctcacactctctctactacat | W50655 | 50381 | catcagttcctctaaagaacc | U02880 | 92985 | agttctaccaagtatgccacaacca | AA118546 |
| 7778 | tcacactctctactagttacataga | W50655 | 50382 | tccaagacagtcgcagagataagt | U02880 | 92986 | tatgccaaccaaaaaggattatga | AA118546 |
| 7779 | gaattaagtccctgaagcagctcca | W50655 | 50383 | catcccaggttccaggaacctgaag | U02880 | 92987 | gccaacaccaaaaaggattatgaaga | AA118546 |
| 7780 | attaatgccctgaagcagctccagg | W50655 | 50384 | acacgggctcctctgggatgcgaag | U02880 | 92988 | aaattgacctagcattgctgtca | AA118546 |
| 7781 | taatgccctgaagcagctccagttg | W50655 | 50385 | tcggaagttccagcccaggagttac | U02880 | 92989 | ttggacctagcattgctgtcacaa | AA118546 |
| 7782 | atgccctgaagcagctccaggttg | W50655 | 50386 | ttgattcagcacctgtttggggccag | U02880 | 92990 | ctagcattgctgtcacaatccagt | AA118546 |
| 7783 | tgaagcagctccaggtgatggtgag | W50655 | 50387 | tgttgtccacacaggatgacaga | U02880 | 92991 | ttgtgctcacatccagttggag | AA118546 |
| 7784 | ctcacagacccaggtgatgcagaacc | W50655 | 50388 | ttgctcccacacagagacacgaagg | Z12302 | 92992 | gtcaaatccagtgttggagtcat | AA118546 |
| 7785 | gatgcagaacccacagtgctggca | W50655 | 50389 | agaagaaataccactgccaagaacg | Z12302 | 92993 | acaatccagtgttggagtcaglc | AA118546 |
| 7786 | cagaaccccacaagtgctggcagctt | W50655 | 50390 | aatacactgcaagaacgagttga | Z12302 | 92994 | tgaagccagcctattgatgtaca | AA118546 |
| 7787 | gaaccccacaagtgctggcagttg | W50655 | 50391 | agaagagctgacctatccagaagtg | Z12302 | 92995 | agcccaagcctattgatgtacaagt | AA118546 |
| 7788 | accccacaagtgctggcagcttgca | W50655 | 50392 | agagacctgacctatccagaagtg | Z12302 | 92996 | tacaagttattacacaccatatga | AA118546 |
| 7789 | aagtgctggcagcttgcaggaag | W50655 | 50393 | gagcactgaagcacactgcatgaagga | Z12302 | 92997 | ttattacacaccatatgcagcggta | AA118546 |
| 7790 | agctttgcaggaacgcttgacaac | W50655 | 50394 | tcgtccgcaaggcacagcccccagcag | Z12302 | 92998 | accatatgcaggatgcagtctg | AA118546 |
| 7791 | gaacgttcgacaacgtctctcaca | W50655 | 50395 | gcagcccctactcatgagccgtc | Z12302 | 92999 | atgcagtctgttggaggtcaat | AA118546 |
| 7792 | gcctatacatcggacaatcaaaagt | Y00426 | 50396 | tcctgcaagactccccatctc | Z12302 | 93000 | caatgctgcttcacgccgagtt | AA118546 |
| 7793 | tatacatcggacaatcaaaagtcac | Y00426 | 50397 | cctgtgacatcagcgaggatgaaga | Z12302 | 93001 | cttccacgcgagttcctaccaagt | AA120585 |
| 7794 | atgtctgaccccaccagagacattt | Y00426 | 50398 | cacctccagaagctctgtgaat | Z12302 | 93002 | aatgtgcaaatctcctgtgaattaa | AA120585 |
| 7795 | cccacacagcatctcattttgta | Y00426 | 50399 | aaggtattccacatcagacatcat | Z12302 | 93003 | tgtgcaaatcctttgaaattac | AA120585 |
| 7796 | cacaagacattctattttgtcacg | Y00426 | 50400 | acctccagaagctctctgtcaatt | Z12302 | 93004 | atctggctcacaaggatatgtac | AA120585 |
| 7797 | acatctattttgtacagagatc | Y00426 | 50401 | cagacatcatcaccgcattgctccg | Z12302 | 93005 | ctggctcacaaggatatgtacac | AA120585 |
| 7798 | tgtacagagatccctgtcaatcc | Y00426 | 50402 | tcatcaccgcattgctcgtgacta | Z12302 | 93006 | ggctcacaaggatatgtacacat | AA120585 |
| 7799 | acagagatccctgtcaatccttaa | Y00426 | 50403 | ttgtccgactatgtatgtgatgc | Z12302 | 93007 | cacagccgaaactaccatgggca | AA120585 |

| SEQ ID NO | sequence | DBAxnID | SEQ ID NO | sequence | DBAxnID | SEQ ID NO | sequence | DBAxnID |
|---|---|---|---|---|---|---|---|---|
| 7800 | atcttacaacaaaacctcatggaca | Y00426 | 50404 | ggggctacactgccaaggagtcaa | Z12302 | 93008 | gtatactacggagcagggaaaca | AA120585 |
| 7801 | caacaaaacctcatggacatcagat | Y00426 | 50405 | acactgccaaggagctcaatgtcag | Z12302 | 93009 | atactacggagcagcaggaaacagg | AA120585 |
| 7802 | cagagttcactctatctggagctt | Y00426 | 50406 | tcaaatgcagctttatcaacgagaa | Z12302 | 93010 | gagtcttcaagatacatcttcctcac | AA120585 |
| 7803 | agttcactctatctggagctttc | Y00426 | 50407 | atgtcagcttatcaacgagaagaa | Z12302 | 93011 | gtcttcaagatcatcttcctcacca | AA120585 |
| 7804 | tcacagtccgtggatggaagaata | Y00426 | 50408 | tggctatgggctgctgtagtagg | AA032366 | 93012 | cttcaagatcatcttcctcaccatc | AA120585 |
| 7805 | ctccagtacacctatgtaccactg | Y00426 | 50409 | cggaacaaagtgctggaagacag | AA032366 | 93013 | tcaagatcatcttcctcaccatcaa | AA120585 |
| 7806 | tacacctatgtaccactgggagtc | Y00426 | 50410 | atgatgttggctacctgggattctag | AA032366 | 93014 | cataaccgcggcttctacaaggca | AA120585 |
| 7807 | ccactggagtcctcctctggcat | Y00426 | 50411 | tgttggctacctgatttctagaga | AA032366 | 93015 | taaccgcggcttctacaaaggcatg | AA120585 |
| 7808 | caccagtatagtctgcgacagga | Y00426 | 50412 | ttggctacctgatttctagaagga | AA032366 | 93016 | accgcgggcttctacaaaggcatg | AA120585 |
| 7809 | gtatagtctgcgacaggagcagga | Y00426 | 50413 | tagatgtctgctctggccatgatt | AA032366 | 93017 | cgcgggcttctacaaaggcatgaact | AA120585 |
| 7810 | tctgcgacaggagcaggataacta | Y00426 | 50414 | gatgctgctccggccatgatttta | AA032366 | 93018 | aggcatgaactcccagatacctgaa | AA120585 |
| 7811 | actatgtgtgacccacaagacat | Y00426 | 50415 | ttgctgccatgattttactgaa | AA032366 | 93019 | gcatgaactcccagatacctgaagc | AA120585 |
| 7812 | taagagttcactctggataagg | Y00426 | 50416 | tgattaacgccatgttgga | AA032366 | 93020 | gaactccagatacctgaagctgca | AA120585 |
| 7813 | aatcagtcttactgaccccagctg | M26270 | 50417 | atttaactgaaccgattgttgatg | AA032366 | 93021 | acagtccaagaaatacagatctg | AA118294 |
| 7814 | tagtaactgccatcgtggactga | M26270 | 50418 | ttaactgaaccgattgttgatgta | AA032366 | 93022 | gatcatgacggacgacatataa | AA118294 |
| 7815 | ctgcatcgtggactgacatgtg | M26270 | 50419 | taactgaaccgattgttgatgtag | AA032366 | 93023 | aatccagaagcttctagataat | AA118294 |
| 7816 | gcctatgtcccagatgacgttgtta | M26270 | 50420 | gaacacagctggtggaagacagtg | AA032366 | 93024 | ctgccaagggtgcgagttcca | AA118294 |
| 7817 | gtcccagatgacgtgttaatctac | M26270 | 50421 | aactgaaccgattgttgatgtagt | AA032366 | 93025 | tgctgagtctcagacgaggaactg | AA118294 |
| 7818 | aatctacatctctcagagtttga | M26270 | 50422 | tgtagaaccgttctctatcgagga | AA032366 | 93026 | gccttttagagccttcaccgatgtc | AA118294 |
| 7819 | tgtatactactgctataaaacat | M26270 | 50423 | tagaaccgttcctctatcgagggc | AA032366 | 93027 | ctttagaccttcaccgatgcagg | AA118294 |
| 7820 | ctcactgctatgaaaacatgcagga | M26270 | 50424 | tatcgaggagcgctaacgaacagt | AA032366 | 93028 | agcctccaccgatgtcaggaaatgg | AA118294 |
| 7821 | tgcaggactccgttcctccttg | M26270 | 50425 | agccgttactgaacagtgttgctat | AA032366 | 93029 | cttgacttgcgagggcactagtgc | AA118294 |
| 7822 | cctttattgcaactgtagta | M26270 | 50426 | ggacatgcaaccgtagatgagcatg | AA032366 | 93030 | gcacttgcgagggcactagtgctat | AA118294 |
| 7823 | attctactcatctgaggtgtgt | M26270 | 50427 | aactgaaccgctagatgagcatgat | AA032366 | 93031 | gcactgtgctatgagcgtagagtg | AA118294 |
| 7824 | ctctctgaccacagctgccaaca | M26270 | 50428 | gcatgatgttggctacctggatct | AA032366 | 93032 | agccgtgagtacaccaaactgatc | AA118294 |
| 7825 | ctgaccccagctgtcaacactgtg | M26270 | 50429 | cttacgcaaaatcgccaactgctg | AA032366 | 93033 | cctgagtacaccaaactgatctca | AA118294 |
| 7826 | taagttctccaaccatgactatagg | M26270 | 50430 | cgccaacttgctgaagccagaacaa | X60367 | 93034 | ccagagcctctagatatcag | AA118294 |
| 7827 | atttcaaacgctagcactgggcatt | M26270 | 50431 | cgaccgaagtcgatgaccacgtg | X60367 | 93035 | gagtacaccaaacgtatctcaaga | AA118294 |
| 7828 | gcactgggcattgcctaacaata | M26270 | 50432 | cactgaggctggatgtgaacagt | X60367 | 93036 | gagagccttcctagataatcaggag | AA118294 |
| 7829 | ggcatttcgcctaacaatactgga | M26270 | 50433 | tgacaaactccagtggctgcagaag | X60367 | 93037 | agccttctagattaatcaggagtag | AA118294 |
| 7830 | gggatcctcgcagggagtattta | M26270 | 50434 | actccagtgtgcagaagggagag | X60367 | 93038 | agcaacatgacgacatgctaaggat | AA118274 |
| 7831 | gtattaagtctgcacatttgt | M26270 | 50435 | tgtaggactcacctggaaatgaga | X60367 | 93039 | aacatgacgacatgctaaggatcga | AA118274 |
| 7832 | ttgtcctaccacactctttcctg | W50792 | 50436 | acttcacctgaaatgagagctgag | X60367 | 93040 | tgctaaggatcgaccaccactctca | AA118274 |
| 7833 | tgtcctaccacatccttcgt | W50792 | 50437 | agtactacctgagccgccgaacagc | X60367 | 93041 | tcgaaccactgctcaagggggttgct | AA118274 |
| 7834 | acatcctttctgctgagtccat | W50792 | 50438 | tctgcctaacatgggggacgaaacg | X60367 | 93042 | ccactgctcaagggggtctgagttt | AA118274 |
| 7835 | tcctttctgctgagtccaatgag | W50792 | 50439 | tctgccagcgaagtctcctttg | X60367 | 93043 | ttcacggcagagtccacgacaac | AA118274 |
| 7836 | cctttctgctgagtccatcgagg | W50792 | 50440 | agtgacccaataaagtgatctct | X60367 | 93044 | ccaccggagagtcacagaagacct | AA118274 |
| 7837 | ctgcatcagctgctgattaccal | W50792 | 50441 | cttgctgaagccgaacaaagagatc | X60367 | 93045 | ccaccggagtctacaagatgtggg | AA118274 |
| 7838 | gtcatcagctgctgattaccatgc | W50792 | 50442 | agagatcgtcgaggatggcgaccact | X60367 | 93046 | gacatcctccgtggaaattccgag | AA118274 |
| 7839 | tcatcagctgctgattaccatgcg | W50792 | 50443 | catgatcatccgcacgtgagacact | X60367 | 93047 | atctccctgtggaaattccgaga | AA118274 |
| 7840 | catcagctgctgattaccatgcga | W50792 | 50444 | catcgcacgtgccgagcacttttgg | X60367 | 93048 | tctccctgtggaaattccgacag | AA118274 |
| 7841 | atcagctgctgattaccatgcgag | W50792 | 50445 | cacgctgagcacttttcggaactat | X60367 | 93049 | tctccctggaaattccgaagacag | AA118274 |
| 7842 | aatataagatccgctgctcctga | W50792 | 50446 | gagcacttttcggaactatatcatg | X60367 | 93050 | gcccagtacacagagacttcatgag | AA118274 |
| 7843 | atataagatccgctgctcctgat | W50792 | 50447 | tatcatggactccagttggaag | X60367 | 93051 | cagtacacagagacttcatgagag | AA118274 |
| 7844 | gtcctaccacattcctttctctg | W50792 | 50448 | agatcggaacatagacgaccgc | X60367 | 93052 | cagtacacagagacttcatgagaga | AA118274 |
| 7845 | tataagatccgttgcctcctgatg | W50792 | 50449 | atatattgaggccccatagcaaa | X60367 | 93053 | gtacaagagacttcatgagagaca | AA118274 |
| 7846 | tcctaccacattcctttcctga | W50792 | 50450 | gttgaggccatagggacaaagtgcc | X15842 | 93054 | tacaagactttcatgagagacat | AA118274 |
| 7847 | cctaccacattcctttctgag | W50792 | 50451 | tcatgtcagtaatttccctactga | X15842 | 93055 | acggcagagtccaccgacaacctgg | AA118274 |
| 7848 | ctccactttctctctgagc | W50792 | 50452 | taattcctccactgagctgtag | X15842 | 93056 | cggcagagtccaccgacaacctggc | AA118274 |
| 7849 | taccactctctttctctgagct | W50792 | 50453 | ctgcctgaactacatacagtaagttaa | X15842 | 93057 | gcagagtccaccgacaacctggca | AA118274 |

TABLE 1-continued

| SEQ ID NO | DBAxnID | sequence | SEQ ID NO | DBAxnID | sequence | SEQ ID NO | DBAxnID |
|---|---|---|---|---|---|---|---|
| 7850 | W50792 | accacattcctttctgtgagctc | 50454 | W50837 | aagttaatacacagcttgaacagt | 93058 | AA118274 |
| 7851 | W50792 | ccacattcctttctgtgagctcc | 50455 | W50837 | agcttgaacagcttatggaaatct | 93059 | AA118274 |
| 7852 | W50792 | cacattcctttctgtgagctcca | 50456 | W50837 | aaatctgtctcagaaatagaaaag | 93060 | AA118274 |
| 7853 | W50837 | gaaggtcctcggcatactgccatg | 50457 | W50837 | ggtaaccatttgtagccctgtg | 93061 | AA118274 |
| 7854 | W50837 | cctggtactggccatgatcgac | 50458 | W50837 | ccctgtcagccctagcctatg | 93062 | AA118274 |
| 7855 | W50837 | ggacgatccagacgcagcccaattac | 50459 | W50837 | tgtgttcagccctatggaagaaa | 93063 | AA118274 |
| 7856 | W50837 | cgatccagacgcagccaattaccat | 50460 | W50837 | gtcagcccatgaagaagaacaa | 93064 | AA169951 |
| 7857 | W50837 | tccagacgcagccaattaccatgat | 50461 | W50837 | tagatgttcattcggttgatct | 93065 | AA169951 |
| 7858 | W50837 | agacgcagccaattaccatgatatt | 50462 | W50837 | atgtctcattcggttgatctcc | 93066 | AA169951 |
| 7859 | W50837 | cgagccaattaccatgatatttct | 50463 | W50837 | tcattccggttgatctcctaaagcc | 93067 | AA169951 |
| 7860 | W50837 | agccaattaccatgatatttctgat | 50464 | W50837 | ttcggttgatctcctaaagcctgt | 93068 | AA169951 |
| 7861 | W50837 | caattaccatgatatttctgatgtg | 50465 | W50837 | ggttgatctcctaaagcctgctg | 93069 | AA169951 |
| 7862 | W50837 | ttaccatgatatttctgatgtggaa | 50466 | W50837 | tcctaaagcctgctgcttcactat | 93070 | AA169951 |
| 7863 | W50837 | tatttctgatgtggaacggctgaaa | 50467 | W50837 | taaagcctgctgcttcactcatataaa | 93071 | AA169951 |
| 7864 | W50837 | gctgaaaccggctacttagaagct | 50468 | W50837 | ctgtctgcttcactcataaagaatct | 93072 | AA169951 |
| 7865 | W50837 | gggcatactgccatgatcgacgag | 50469 | W50837 | cgctcgcgagccggtaacagaccct | 93073 | AA169951 |
| 7866 | W50837 | catactgccatgatcgacgaggt | 50470 | W50837 | gctcgcgagccggtaacagaccctc | 93074 | AA169951 |
| 7867 | W50837 | actggccatgatcgacgagggtgag | 50471 | W50837 | gacccagttactggcgacacaagc | 93075 | AA169951 |
| 7868 | W50837 | ggccatgatcgacgagggtgagacc | 50472 | W50837 | ccccagttactggcgacacacccca | 93076 | AA169951 |
| 7869 | W50837 | catgatcgacgagggtgagaccgac | 50473 | W50837 | cagttactggcgacacaagcccaag | 93077 | AA169951 |
| 7870 | W50837 | ggtcatcgcattaagtggacgat | 50474 | W50837 | gttactggcgacacaagcccaagag | 93078 | AA169951 |
| 7871 | W50837 | cattgccattaagtgtggacgatca | 50475 | W50837 | ttactggcgacacaagcccaagaga | 93079 | AA169951 |
| 7872 | W50837 | tgtggacgatccagacgcagccaat | 50476 | W50837 | tactggcgacacaagcccaagagac | 93080 | AA169951 |
| 7873 | W50837 | atccaagaacaatatcgtacaa | 50477 | U01530 | tgggacacaagcccaagagacctt | 93081 | AA169951 |
| 7874 | U01530 | atgaacataaccacgagagaatcc | 50478 | U01530 | ggcgacacaagcccaagagacctg | 93082 | AA169951 |
| 7875 | U01530 | tgcctcagtctgtgtgactgcacg | 50479 | U01530 | gcgacacaagcccaagagagaccttga | 93083 | AA169951 |
| 7876 | U01530 | tgtacatagcacgccatgctgtgg | 50480 | U01530 | cgacacaagcccaagagacccttgaa | 93084 | AA118397 |
| 7877 | U01530 | tagacgccatgctctggggccaagc | 50481 | U01530 | ttttagtactggccatggacctgc | 93085 | AA118397 |
| 7878 | U01530 | cccagcactttgcctcgtgta | 50482 | U01530 | tttagtactggccatgccacctgc | 93086 | AA118397 |
| 7879 | U01530 | actttgctcagtgtcagtctat | 50483 | U01530 | ttagtactggccatgccacctgct | 93087 | AA118397 |
| 7880 | U01530 | cgtcagtctcagtgtactgtatgaatg | 50484 | U01530 | tagtactggccatgccacctgcctt | 93088 | AA118397 |
| 7881 | U01530 | attgtacagtctataggccaacac | 50485 | U01530 | gtactggccatgccaccgacctgcttac | 93089 | AA118397 |
| 7882 | U01530 | acagcctataggccaacactgcggg | 50486 | U01530 | tactggccatgccacctgacctgcttacc | 93090 | AA118397 |
| 7883 | U01530 | tataggccaacactgcggggcgtgtg | 50487 | U01530 | actggccatgccacctgacctgcttacca | 93091 | AA118397 |
| 7884 | U01530 | ccaacacgcggggtgtgactctt | 50488 | U01530 | ctggccatcggacctgcttacca | 93092 | AA118397 |
| 7885 | U01530 | ccacctcaagaataatcatgt | 50489 | U01530 | tggtccatgcaggagagccgagat | 93093 | AA118397 |
| 7886 | U01530 | caaggcaacaacagaggagagc | 50490 | U01530 | atctctggagccagaccagggattcatc | 93094 | AA118397 |
| 7887 | U01530 | ctagcgtactgggatcccagtg | 50491 | U01530 | aggccaagccagttctgcactt | 93095 | AA118397 |
| 7888 | U01530 | gtactggccatccagctgacatg | 50492 | U01530 | agccagcttctgtcacttatccac | 93096 | AA118397 |
| 7889 | U01530 | gggatcctgccagttacatgacctc | 50493 | U01530 | gtcacttatccactgcagcaacgg | 93097 | AA118397 |
| 7890 | U01530 | gacctctgccgaaggctgcctca | 50494 | U01530 | tatccactgacacgcaaggtccct | 93098 | AA118397 |
| 7891 | U01530 | ctgcgaaggctgcctcagtcgt | 50495 | U01530 | acctggtgtctctaactg | 93099 | AA118397 |
| 7892 | U01530 | aaggttgcctcagtgtctgtacat | 50496 | U01530 | gttgcaggaaccagagtgggccca | 93100 | AA118397 |
| 7893 | W50841 | gaagaaccactgccagctgacc | 50497 | W50841 | aggaaccagagtgggccagcctat | 93101 | AA118397 |
| 7894 | W50841 | aaccatcacgcaactgcaagt | 50498 | W50841 | ggcctctgaacactgcaagct | 93102 | AA118397 |
| 7895 | W50841 | tgcaacattgagctgttta | 50499 | W50841 | ctattcaagtgcctgacgcgac | 93103 | AA118397 |
| 7896 | W50841 | ttaatagctgcggttgccatgaccg | 50500 | W50841 | tgctccaggtggaatgcccag | 93104 | AA118397 |
| 7897 | W50841 | aatagctcgttgccatgacggc | 50501 | X72305 | tttcatcagcactgggcactgcca | 93105 | AA120620 |
| 7898 | W50841 | aaaccattgatcatcaggtgca | 50502 | X72305 | tgtggcactgccactggaaagcct | 93106 | AA120620 |
| 7899 | W50841 | catttgatcatcaggcgtcaacaa | 50503 | X72305 | actgcactggaagcctgcctg | 93107 | AA120620 |

| SEQ ID NO | DBAxnID | sequence | SEQ ID NO | DBAxnID | sequence | SEQ ID NO | DBAxnID |
|---|---|---|---|---|---|---|---|
| 7900 | W50841 | ttttgatcatcaggcgtcaacaaca | 50504 | W50841 | gctgcttgctgccctgcacttta | 93108 | AA120620 |
| 7901 | W50841 | ttgatcatcaggcgtcaacaacaag | 50505 | W50841 | ttgctgcctgcaccttagacatt | 93109 | AA120620 |
| 7902 | W50841 | gatcatcaggcgtcaacaacaaggt | 50506 | W50841 | accttagacatttactattctgca | 93110 | AA120620 |
| 7903 | W50841 | tcatcaggcgtcaacaacaaggtgt | 50507 | W50841 | ttactattctgcaggccaagccaagc | 93111 | AA120620 |
| 7904 | W50841 | caggcgtcaacaacaaggtgtgag | 50508 | W50841 | ttctgcaggccaagccagcttctg | 93112 | AA120620 |
| 7905 | W50841 | agcgtcaccaggtctgaacacac | 50509 | W50841 | tatcagcgtctgaacagtataa | 93113 | AA120620 |
| 7906 | W50841 | cacacactccggtgccccagaagg | 50510 | W50841 | agtataactccgtccgacagaatca | 93114 | AA120620 |
| 7907 | W50841 | cacactaggtggccccagaggat | 50511 | W50841 | catcgcctccaataagccactagaa | 93115 | AA120620 |
| 7908 | W50841 | ggccccagaaggatcctctgact | 50512 | W50841 | cgcctcaataagccactagagcatt | 93116 | AA120620 |
| 7909 | W50841 | actgggacccgctgcagaataagc | 50513 | W50841 | ctcaataagccactagagcattcac | 93117 | AA120620 |
| 7910 | W50841 | ctgagaataagctcccgaactct | 50514 | W50841 | aagccactagcattcacagaaat | 93118 | AA120620 |
| 7911 | W50841 | cctcctacaatctcaagagttgc | 50515 | W50841 | ccactagagcatttcacagaaattag | 93119 | AA120620 |
| 7912 | W50841 | gttcagcacatttgagcagttgtt | 50516 | W50841 | ctttagtcagcgcaaagagcattg | 93120 | AA120620 |
| 7913 | W50841 | gggcctcagcatgtacgacctgga | 50517 | W50841 | tagctcaggcgaaagagcattgcca | 93121 | AA120620 |
| 7914 | W50841 | tgacgacctggacgctgcaacggcta | 50518 | W50841 | aagagcatgcatgcacctcac | 93122 | AA120620 |
| 7915 | W50841 | atgaagatgccgaggatgagtcca | 50519 | W50841 | atgcatgtttacagctgtccca | 93123 | AA120620 |
| 7916 | W50841 | aagatgccgaggatgatgccacac | 50520 | W50841 | gcatgttaccagcgttcccaact | 93124 | AA120620 |
| 7917 | W50848 | cgaacgacaagatctcaggcaga | 50521 | W50848 | ataactccgtccgacagaatcacca | 93125 | AA120620 |
| 7918 | W50848 | aagatctcaggcagatggacacaa | 50522 | W50848 | actccgtccgacagaataccagtg | 93126 | AA137795 |
| 7919 | W50848 | atcttcaggcagatggacacaaaca | 50523 | W50848 | tccgacagaatccacagtgcataag | 93127 | AA137795 |
| 7920 | W50848 | gatggcaaagtctccctgaagat | 50524 | W50848 | gacagaatccacagtgcataagtat | 93128 | AA137795 |
| 7921 | W50848 | aaactgcctgaagaattcatca | 50525 | W50848 | caggctttgtcttgtatgtatctc | 93129 | AA137795 |
| 7922 | W50848 | aggtgccaagagcgaaccgtccatt | 50526 | W50848 | tgtgatgatctcatcgcctcaata | 93130 | AA137795 |
| 7923 | W50848 | tgccaagagcgaccgtccattgtc | 50527 | W50848 | tatgatctcatcgcctcaataagc | 93131 | AA137795 |
| 7924 | W50848 | cagccgtccattgccgattgctg | 50528 | W50848 | gtatctccaatagccaccgcac | 93132 | AA137795 |
| 7925 | W50848 | acgacctggacgcaacgtacact | 50529 | W50848 | aggaccaacacggtcatctctctcat | 93133 | AA137795 |
| 7926 | W50848 | gcaacgctacatcagcgcagtga | 50530 | W50848 | acacagggtcatctcatctatgagaa | 93134 | AA137795 |
| 7927 | W50848 | acggctacatacgcgcagtgaat | 50531 | W50848 | gcgtcttggacatctcaattgga | 93135 | AA137795 |
| 7928 | W50848 | acatcagccgcagtgaaatgctgga | 50532 | W50848 | ttgacatctcaatttgatgcact | 93136 | AA137795 |
| 7929 | W50848 | tcagccgcagtgaaatgctgagt | 50533 | W50848 | actgacttggcaagcagaggtgga | 93137 | AA137795 |
| 7930 | W50848 | agattgcaggccattcactacaagt | 50534 | W50848 | tgcagctgcgtcatcgatggggtgaa | 93138 | AA137795 |
| 7931 | W50848 | tccaggccatctacaagatggtgtc | 50535 | W50848 | tccacagcaaacattaactccccat | 93139 | AA137795 |
| 7932 | W50849 | tgggtgctcccccgtgatgaagatgc | 50536 | W50849 | ccaggacttctgcatatttacagt | 93140 | AA137795 |
| 7933 | W50849 | tcggtatacgttttccagtcaag | 50537 | W50849 | catatttaacagtgcccagtcactactc | 93141 | AA137795 |
| 7934 | W50849 | tacgcttttccagtcaagagttt | 50538 | W50849 | taacagtgcccagtcactactgcc | 93142 | AA137795 |
| 7935 | W50849 | gggcctgtttaccacagactggct | 50539 | W50849 | ctgcctagtaaagactccacatta | 93143 | AA137795 |
| 7936 | W50849 | ctccgttaccacagactggctgg | 50540 | W50849 | tagtaaagactccacattagtgc | 93144 | AA137795 |
| 7937 | W50849 | cagactgtggaacctcaccact | 50541 | W50849 | ttgaaagatctgccggggcctcaa | 93145 | AA137795 |
| 7938 | W50849 | actggcttgaacctcaccactca | 50542 | W50849 | agtaaagactccacattatgtgca | 93146 | AA120675 |
| 7939 | W50849 | ttggaacctcaccactcacctggc | 50543 | W50849 | gatctgccgggggcctcaaagaggt | 93147 | AA120675 |
| 7940 | W50849 | cacttcactgaacctgatalggg | 50544 | W50849 | agctgccggaagagaggctggga | 93148 | AA120675 |
| 7941 | W50849 | ttcacctgcagccccgatggtca | 50545 | W50849 | tcttgacctgcctctaacctggg | 93149 | AA120675 |
| 7942 | W50849 | acctgcagccccgatatgtcacta | 50546 | W50849 | cctgtccatctaacctgggcactgg | 93150 | AA120675 |
| 7943 | W50849 | cagccagtatgtcactattccac | 50547 | W50849 | gagccacacaaacgccactgct | 93151 | AA120675 |
| 7944 | W50849 | agtatgtcactattccacagcaga | 50548 | W50849 | aacatcaaaactgccactgctgagcaa | 93152 | AA120675 |
| 7945 | W50849 | gctttccagtcaagaggtttca | 50549 | W50849 | agatctggagaaccaggctaggca | 93153 | AA120675 |
| 7946 | W50849 | tttccagtcaagaggtttcagta | 50550 | W50849 | tctcctccaaattcatgatgtctta | 93154 | AA120675 |
| 7947 | W50849 | aaatcagactcagagctacctgaa | 50551 | X13588 | atatgcataataacctatcatctac | 93155 | AA120675 |
| 7948 | W50849 | tcgaactcagagctacctggaaact | 50552 | X13588 | gattacttcagctcttcatataagg | 93156 | AA120675 |
| 7949 | W50849 | gactcagagctacctggaaacttct | 50553 | X13588 | ctctcatataggggttcctgttg | 93157 | AA120675 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 7950 | cctggaaacttctgtctctatgcat | W50849 | 50554 | ttttctctgtccatgttgcatgtca | X13588 | 93158 | acgacatggccgatacatgtggtac | AA120675 |
| 7951 | aacttcgtctctatgcataaagat | W50849 | 50555 | ctgccatgttgcagtcaattggt | X13588 | 93159 | acatgccgatacatgtgtaccat | AA120675 |
| 7952 | tgtctctatgcataaagatgtct | W50849 | 50556 | atgttgcagtcaattggtgtcagt | X13588 | 93160 | atacatgtaccatctgccatgc | AA120675 |
| 7953 | gaacctcagtcagccgggcaaa | M91458 | 50557 | tgtcagtatgcaggtctgttggg | X13588 | 93161 | catgtgtaccacatctgccatgctgc | AA120675 |
| 7954 | tcagcttcagtcagccgggcaaa | M91458 | 50558 | tatgcaggtctgttgggcaacct | X13588 | 93162 | gtaccatcgccatgctgcagataa | AA120675 |
| 7955 | taacatggcctcccgcctgcact | M91458 | 50559 | actacactgctcagaatcagttc | X13588 | 93163 | tctgccatgctgagataagtgatt | AA120675 |
| 7956 | ctgactgctgcttgaggactgc | M91458 | 50560 | tcagaatcagtlcttttctgaata | X13588 | 93164 | ttcgatgatcctggctgaagccatt | AA120675 |
| 7957 | tgctgctttgaggactgcatctg | M91458 | 50561 | tgtacctgaacttcccccagtccatg | X13588 | 93165 | gatgatcctggctgaagccattcga | AA120675 |
| 7958 | tttgaggactgcatlctgactgtg | M91458 | 50562 | atctatcatctatlcatcagtcatc | X13588 | 93166 | tatttagctctggaatgggtaccat | AA120675 |
| 7959 | cattctgactgtgctgatgaagct | M91458 | 50563 | tccccagtccatgagtcaataaagt | X13588 | 93167 | tttagctctggaatgggtaccatct | AA120690 |
| 7960 | ttgagcactggtgtggactttctc | M91458 | 50564 | catctatlcatcagtcatccatct | X13588 | 93168 | taccaagttccatattccatglaca | AA120690 |
| 7961 | tagtgcctcacactcatccctgc | M91458 | 50565 | ttccatcagtcatccatctactgt | X13588 | 93169 | caaagttccatattccatgtacatt | AA120690 |
| 7962 | ctcacactcaattacctgcatcagt | M91458 | 50566 | agtcatccatcttactgattacatt | X13588 | 93170 | aagttccatattccatgtacattaa | AA120690 |
| 7963 | tacctgcatcagttctcactaata | M91458 | 50567 | agactgattgtcctttctcagcag | X13588 | 93171 | tccatattccatgtacattaagagt | AA120690 |
| 7964 | catcagttctcactaatagctcct | M91458 | 50568 | ctttctcagcagccacatgattacc | X13588 | 93172 | catatlccatgtacattaagagtgt | AA120690 |
| 7965 | ccctttgccaacctcaggacatcaa | M91458 | 50569 | tcagcagccacatgattacctcagc | X13588 | 93173 | tgtgacattagttgcctcagctta | AA120690 |
| 7966 | ggcaacctcaggacatcaagatgag | M91458 | 50570 | gccacatgattacctcagctctca | X13588 | 93174 | tgacacttagttgcctcagtcttata | AA120690 |
| 7967 | gatccacgtctgtctcaggggctt | M91458 | 50571 | agactaacaaggtccatggcagcccg | AA032593 | 93175 | acttagttgcctcagcttatagctg | AA120690 |
| 7968 | cgtctctgcagggcttagactg | M91458 | 50572 | ctaacaaggtccatggcagcccgct | AA032593 | 93176 | agttgcctcagcttatagctggggt | AA120690 |
| 7969 | gtcgtcagggctltagactgcacacct | M91458 | 50573 | cctggcctatgtcgtcctgccaggaa | AA032593 | 93177 | ctcagttcatagctggggtaatttg | AA120690 |
| 7970 | gttgctaattgggctggtcaat | M91458 | 50574 | ctgctatgtcgtctgccaggga | AA032593 | 93178 | tttttccattaaagctcaaccag | AA120690 |
| 7971 | aattggctgtggctcaatgtgtt | M91458 | 50575 | gtgcctatgtcgtcctcaggaacctt | AA032593 | 93179 | ttcctcattaaaggctcaaccagca | AA120690 |
| 7972 | gtcaattgtgttcccgaaggctg | M91458 | 50576 | tgcctatgtctcctcaggaaacttt | AA032593 | 93180 | attaaaggctcaaccagcacact | AA120690 |
| 7973 | ctlctttgcagacagaagcactgt | W50853 | 50577 | ctatgtctcctcaggaaacttlg | AA032593 | 93181 | attaaggctcaaccagcacgtgt | AA120690 |
| 7974 | aagcaactgtgtcaaaatagaaac | W50853 | 50578 | ctatgtcttccatggaaacttlgt | AA032593 | 93182 | ggctcaaccagcactgtggctact | AA120690 |
| 7975 | ttctgctcgaactcagattccctg | W50853 | 50579 | tatgtgtcctcaggaaacttttgtgg | AA032593 | 93183 | caaccagcactgtgggctatgac | AA120690 |
| 7976 | tgcagaactcagattcctgaaca | W50853 | 50580 | atgtgtcctcaggaaacttttgtgcc | AA032593 | 93184 | accagcactgtgggctatgtacaa | AA120690 |
| 7977 | actcagattcctgaacatagttc | W50853 | 50581 | tgtcctcaggaaacttttggcccct | AA032593 | 93185 | cagcactgtgtgggccaacaagaagt | AA120690 |
| 7978 | cagatcctgaacatagttc | W50853 | 50582 | gtcctcaggaaacttlggccctg | AA032593 | 93186 | agttctcagagcacacaattgcc | AA120690 |
| 7979 | aacatagttcttcacacagcaagaa | W50853 | 50583 | taacaaggtccatggcagcccgccgtg | AA032593 | 93187 | tcagagcacacatatlgccattgac | AA120733 |
| 7980 | atagtlcttcacacagcaagaaga | W50853 | 50584 | aaggtccatggcagcccgccgtgt | AA032593 | 93188 | aggagctgcaccctgggagggcca | AA120733 |
| 7981 | cttcacacacgaagaagacaacaagt | W50853 | 50585 | gggtgaccctggcctatgtgtc | AA032593 | 93189 | agctgcacctgggagggccaca | AA120733 |
| 7982 | tagtaacttgccagagggtgagcca | W50853 | 50586 | ggtcatgacctgccatgtgtcc | AA032593 | 93190 | acacctgggagggccacaagaatgt | AA120733 |
| 7983 | taactgccagagggtgagccaga | W50853 | 50587 | gtcatgacctgccatgtgtcct | AA032593 | 93191 | atgccatagcctcacaatcctta | AA120733 |
| 7984 | ctlgccagagggtgagccaagaaga | W50853 | 50588 | catgacctgccatgtgtcctca | AA032593 | 93192 | tagccttcaacctcaacattctacggtgtga | AA120733 |
| 7985 | tccgaatccacagttaaacaagat | W50853 | 50589 | atgacctgccatgtgtccctcag | AA032593 | 93193 | ctlttgcaagaccgtaaactctg | AA120733 |
| 7986 | gaatccacacagttaaacaagatgtg | W50853 | 50590 | tgacctgccatgtgtcctcagg | AA032593 | 93194 | acaagacctgtaaactctggggtgc | AA120733 |
| 7987 | tcccacagttaaacaagatgtgcaa | W50853 | 50591 | cagatctcagattcaaccttcagt | AA032593 | 93195 | agacctgaaactctggagtgctga | AA120733 |
| 7988 | gcaaagttacgctgctgtctgccggc | W50853 | 50592 | atctcagattcaaccttcagtgaa | AA061550 | 93196 | cctgtaaactctggagtgctgagac | AA120733 |
| 7989 | aaggactggtcgtctgccggctc | W50853 | 50593 | tgccggattccaccaagacaa | AA061550 | 93197 | accatacctcagggccacacacagc | AA120733 |
| 7990 | cctgctcagagggcgtgccaaggatat | W50853 | 50594 | accaagacaatccctgaccctg | AA061550 | 93198 | agcaccacatattgcattgaccaa | AA120733 |
| 7991 | tgaaaatcgggattctgct | W50700 | 50595 | tccctgcagcctgtcctcacgt | AA061550 | 93199 | cctcagggcccaacaacaggagat | AA120733 |
| 7992 | atcggtcggattctgctgcagaa | W50700 | 50596 | ctgcagcctgtlccttcacagtcac | AA061550 | 93200 | cacacatatgccattgaccaactg | AA120733 |
| 7993 | ccgagcccaagccaagaacgacgcgaca | W50700 | 50597 | cctgttccttcacagtcacggacg | AA061550 | 93201 | tgccattgaccaacgtggcactcaa | AA120733 |
| 7994 | acgaagacgacaggacaggagactcc | W50700 | 50598 | cagtcaccgaacgtcacatcaac | AA061550 | 93202 | caatgaccaagtgcactcaacaa | AA120733 |
| 7995 | gacggaccgcacactagatagatcat | W50700 | 50599 | tcaccgaacgtcacatcaaccag | AA061550 | 93203 | ccaactgccactcaacaagcagg | AA120733 |
| 7996 | ggccggcacactagagatcatcg | W50700 | 50600 | gtccatcaaaaccagagggccacca | AA061550 | 93204 | tggcactcaacaaagcaggcctccg | AA120733 |
| 7997 | ccggcacactagagatcatcgtac | W50700 | 50601 | cacatcaaaaccaacgagggccacatca | AA061550 | 93205 | gcttlatccacggaagctatgatcg | AA120733 |
| 7998 | cacactagagatcatctgacgaa | W50700 | 50602 | gccacatcaaacgacgaaggaccaa | AA061550 | 93206 | tcaccggaagctatgatcggacctg | AA120733 |
| 7999 | agatcatctgacgaattggccctg | W50700 | 50603 | gattcaaccttlcagtgaaggccac | AA061550 | 93207 | tctagcacgtctcagtcgaatgagc | AA146194 |

TABLE 1-continued

| SEQ ID NO | DBAxnID | sequence | SEQ ID NO | DBAxnID | sequence | SEQ ID NO | DBAxnID | sequence |
|---|---|---|---|---|---|---|---|---|
| 8000 | W50700 | tcatctgtacgaattgccctgcgt | 50604 | AA061550 | accttcagtgaaagccacatttg | 93208 | AA146194 | atgatggcttcccagacgacattgc |
| 8001 | W50700 | tctgtacgaattggccctgcgttcc | 50605 | AA061550 | ttctccagaaagctccttgccagat | 93209 | AA146194 | gtaccgactgccagagagaagtgcc |
| 8002 | W50700 | cgaattggccctgcgcgttccgaatct | 50606 | AA061550 | tccagaaagctccttgccagatagt | 93210 | AA146194 | gagaagtgccctcgcatgtggaagc |
| 8003 | W50700 | attggccctgcgtccgaatctga | 50607 | AA061550 | ctccttgccagatagtaatggctgg | 93211 | AA146194 | aagtgccctcgcatgtggaagcata |
| 8004 | W50700 | ttccgaatctggaggagaatgcatg | 50608 | AA061550 | ttcctaggtcagagtcacctgc | 93212 | AA146194 | aagcataccctcgagactgcagacg |
| 8005 | W50700 | aggagactcctcattcagaaccag | 50609 | AA061550 | aggctcaggagtcacctgcgggat | 93213 | AA146194 | catacctctgagactgcagacgctc |
| 8006 | W50700 | ccagaagctccatgcaaccatgctg | 50610 | AA061550 | aggagtcacctgcgggattccacca | 93214 | AA146194 | acctctgagactgcagacgctcct |
| 8007 | W50700 | gctccatgcaaccatgctgcacacct | 50611 | AA061550 | ccgagagcctcttgtggaaaa | 93215 | AA146194 | actgcagacgctctgctcctcggt |
| 8008 | W50700 | aaccatgctgacacctcctggaac | 50612 | AA061550 | agcctcttgtgtggaaaacgacag | 93216 | AA146194 | aagtagcaacctgatgtcaacagac |
| 8009 | W50700 | tgccactcagacattgactccgcga | 50613 | AA032596 | taacttagttccctgccatgtgc | 93217 | AA146194 | tagcaacctgatgtcaacagacgac |
| 8010 | W50700 | cacctagacattgactccgcagcgc | 50614 | AA032596 | ttagttccctgccatgtgctgtg | 93218 | AA146194 | caacctgatgtcaacagacgacgac |
| 8011 | W50700 | ctagacattgactccgcagcgcatg | 50615 | AA032596 | agttccctgccatgtgctgtgga | 93219 | AA146194 | tccagacgcattgctggctcagg |
| 8012 | W50700 | gacattgactccgcagcgcatgacg | 50616 | AA032596 | ccctgccatgtgctgtggaagcgt | 93220 | AA146194 | cagacgacattgctggctcagagc |
| 8013 | M21285 | agccactgaattgctatgtatcct | 50617 | AA032596 | ctgccatgtgctgtggaggtat | 93221 | AA146194 | ggtgacattgagctcacgggacat |
| 8014 | M21285 | gtatctgacagtctcacatctcaac | 50618 | AA032596 | ccatgtgctgtggaggtatacta | 93222 | AA146194 | gacattgagctcacgggagacatcg |
| 8015 | M21285 | gtttagtctacatgtctctcccag | 50619 | AA032596 | agcgtatactaacaactacacctt | 93223 | AA146194 | attgagctcaggggacattgtca |
| 8016 | M21285 | tctacattgtcttccagactg | 50620 | AA032596 | tatactaacaactacacctagta | 93224 | AA146194 | gggacattgctcatcaatcagaag |
| 8017 | M21285 | ttgctcttcccagactgacagat | 50621 | AA032596 | tactaacaactacacctcagtagg | 93225 | AA146194 | ttcgtcaatctagaaggtgtg |
| 8018 | M21285 | ttcccagactgacagatatgacc | 50622 | AA032596 | tacacctcctagggtcttggaga | 93226 | AA146194 | gtcatttggtaccgactgccagag |
| 8019 | M21285 | aagtccaagactactactccactgc | 50623 | AA032596 | gaagagctagactaactgacctg | 93227 | AA120701 | cccggctccacggagcagcggagga |
| 8020 | M21285 | acctaccacggccatgaaaaccat | 50624 | AA032596 | gctagcactaactgacctggcctg | 93228 | AA120701 | gctccacggcggcagcggcgaagta |
| 8021 | M21285 | ccactgcatgaaaaccattgcagg | 50625 | AA032596 | gcctggtccttagacacatgctg | 93229 | AA120701 | tcatcaacaagaataacaccaaggag |
| 8022 | M21285 | ttaatatcaactctgaagcctact | 50626 | AA032596 | ttagacaccatgctgctgctgc | 93230 | AA120701 | catcaacaagaataacaccaaggagg |
| 8023 | M21285 | tcaactctgaagcctactgtact | 50627 | AA032596 | agacaccatgctgctgctgctg | 93231 | AA120701 | gagactgccatgaacaagaataaag |
| 8024 | M21285 | cttgaagcctactgtactgattga | 50628 | AA032596 | gctgctgcagacgctgctgctg | 93232 | AA120701 | acaagaataaccgccaggaggtagct |
| 8025 | M21285 | aggtccatagcatcagctcagctgg | 50629 | AA032596 | ctgctgagcacggtcgagctg | 93233 | AA120701 | ataacgccaggagtagttcgcag |
| 8026 | M21285 | taatactgactactcactcaaggg | 50630 | AA032596 | ggagccgcagttgctaacttagttc | 93234 | AA120701 | agctagctcgcagtgtaggagata |
| 8027 | M21285 | actactcaagggcagttctgaggt | 50631 | AA032596 | ctgaaccggagttccgaaggcat | 93235 | AA120701 | ggtagttccagtgtagagagag |
| 8028 | M21285 | tccaaggcagttgcgagtgattag | 50632 | AA032596 | cgaaggcacccggagcgttgct | 93236 | AA120701 | tagcttcgcagtgtaggagatagaa |
| 8029 | M21285 | atcctccagaagggtattcataacg | 50633 | AA032596 | gctatggtagctgctggctcataac | 93237 | AA120701 | agcttcgcagtgtaggagatagaaa |
| 8030 | M21285 | ggtattcatacagactcccaagaa | 50634 | AA032596 | ctatggtagctgctggtcataact | 93238 | AA120701 | ctcacaggacagcggagcgagtag |
| 8031 | M21285 | cataacagactcccaagaactatat | 50635 | AA032596 | tgtagctgctggtcataactaggag | 93239 | AA120701 | tccacaggacagcggagcgaagtagt |
| 8032 | M21285 | tatgttctgagacgtcacgtttagt | 50636 | AA032596 | tgatactgactcatgagatagt | 93240 | AA120701 | gtgacgtcacatcgcgggcgcgca |
| 8033 | M21285 | gcaactggctcatgggggacattcg | 50637 | AA032596 | atatcggtgactcatgagatggt | 93241 | AA120701 | cgccgagtcggggtacgaagaaggt |
| 8034 | M32032 | acatctggcagttgacatctcaa | 50638 | AA032596 | tactggtgactcatgagatgttgt | 93242 | AA120701 | ccgacgccggtacgaagaaggtca |
| 8035 | M32032 | cagcactgctcacgagttctgtta | 50639 | AA032596 | agacttggagactictcgtctat | 93243 | AA120701 | tacggttcatcaacaagaataacac |
| 8036 | M32032 | actgcagttctgacatctgaactg | 50640 | AA032596 | cttggagagacttctcgtctctcaa | 93244 | AA120701 | gttcatcaacaggaataacaccaag |
| 8037 | M32032 | gttctgcatctgatctgaaggct | 50641 | AA032596 | agactictcgtctctctctcaa | 93245 | AA120701 | ttcatcaacaggaataacaccaagga |
| 8038 | M32032 | acatctggatctgaaggctgcact | 50642 | AA032596 | tcttcgtctcatcaatcgctatctc | 93246 | AA120701 | actgccctgatggtgaaggagcaa |
| 8039 | M32032 | tccatctgagccctgcctgctt | 50643 | AA032596 | aaggcatccaggagcgtgttgctgc | 93247 | AA120701 | gtccctgatggtgaaggagcaagac |
| 8040 | M32032 | ttctgagccgccctggctcacct | 50644 | AA032596 | aggcaccccaatctgcgtcaactg | 93248 | AA118715 | aggcctctgaagctctatg |
| 8041 | M32032 | caactcccaaggcactctgagac | 50645 | AA032596 | gcaaccaatctgcgtcaactgct | 93249 | AA118715 | aaggcctctgagactctatg |
| 8042 | M32032 | tccaaggcactctgagaccagcaga | 50646 | AA032596 | cacccaatctgcgtcaactgctg | 93250 | AA118715 | ctcctgagactctatgaagcc |
| 8043 | M32032 | ctgagaccagctgagatctgtagagc | 50647 | AA032596 | aatctgctcaactgctgttct | 93251 | AA118715 | ttctatggaagcccgatttcgagtg |
| 8044 | M32032 | cagcatctgtaccgttgcgtt | 50648 | AA032596 | ctgggctaactgctgtttctgtc | 93252 | AA118715 | tatggaagcccgattccgagtct |
| 8045 | M32032 | atgactctctaaccacgaagcc | 50649 | AA032596 | tggctaactgctgtttctgtca | 93253 | AA118715 | ccgattccgattctcaactaagc |
| 8046 | M32032 | tcgctggagatctcctggggg | 50650 | AA032596 | ctgtaactgctgtttctgtcatg | 93254 | AA118715 | attccgagtgtccacttaagcttc |
| 8047 | M32032 | taacctgtcagccggagccctagt | 50651 | X15592 | acttgactccagaagaattcaggac | 93255 | AA118715 | ccgagtgtcttcacttaagcttctc |
| 8048 | M32032 | gtcagccggagccctagtggtcaa | 50652 | X15592 | ctgactatctgaccacctggtcaa | 93256 | AA118715 | ctctccaaacatcaattctgtcttcc |
| 8049 | M32032 | atggcaaggctttacgccactac | 50653 | X15592 | tcaaacactgtggggacctgaactga | 93257 | AA118715 | tcaaacattcaattctgtcttcctga |

| SEQ ID NO | DBAxnID | sequence | SEQ ID NO | DBAxnID | sequence | SEQ ID NO | DBAxnID |
|---|---|---|---|---|---|---|---|
| 8050 | M32032 | agcgtcttacgccactacatcact | 50654 | M32032 | tgtgaacctgaggcacagtcatac | 93258 | AA118715 |
| 8051 | M32032 | tttacgccactacactatacag | 50655 | M32032 | gaactctgaggcacagtcatactga | 93259 | AA118715 |
| 8052 | M32032 | ttggcgcacactggctcacagagt | 50656 | M32032 | cattgccaattttagctctgaagt | 93260 | AA118715 |
| 8053 | W50888 | ctcttgattaacgtgggatgatctc | 50657 | W50888 | tgccaattttagctctgaagttcc | 93261 | AA118715 |
| 8054 | W50888 | ttaacccaaatgtgagcgggcccag | 50658 | W50888 | ttccttaaatgattctcacaaggat | 93262 | AA118715 |
| 8055 | W50888 | agtgaccttggcacttgatcccga | 50659 | W50888 | cttaaatgattctcacaaggatctt | 93263 | AA118715 |
| 8056 | W50888 | gaccttcggcacttgatcccga | 50660 | W50888 | aaatgattctcacaaggatcttag | 93264 | AA118715 |
| 8057 | W50888 | gagccttcgccacttgatcccgagt | 50661 | W50888 | atatatgccatgatgtctcaaatt | 93265 | AA118715 |
| 8058 | W50888 | gagccgtcccagctctatatggc | 50662 | W50888 | tatgccatgatgtctcaaattaa | 93266 | AA118715 |
| 8059 | W50888 | agccgtcccagctctatatggccg | 50663 | W50888 | tgacacctggaagggctcagccaga | 93267 | AA118716 |
| 8060 | W50888 | gccgtcccagctctatatggccga | 50664 | W50888 | agtgtggtcgactggtaacaata | 93268 | AA118716 |
| 8061 | W50888 | ccggtctccagtctatatggcgag | 50665 | W50888 | gagctctgtctcctggtatggga | 93269 | AA118716 |
| 8062 | W50888 | cggtctccagtctatatggcgaga | 50666 | W50888 | tctgtctcctggtatgggaagg | 93270 | AA118716 |
| 8063 | W50888 | ggtctccagtctatatggcgagat | 50667 | W50888 | gtctcctggtatgggaaggaatgat | 93271 | AA118716 |
| 8064 | W50888 | tctccagtctatatggcgagatcc | 50668 | W50888 | gaagcagccatcacacagtgtccagc | 93272 | AA118716 |
| 8065 | W50888 | taaccccaaatgtgagcgggcccagt | 50669 | W50888 | gccatcacagtgtccagcatgtgc | 93273 | AA118716 |
| 8066 | W50888 | ctccagtctatatggcgagatcct | 50670 | W50888 | gtccagcatgtctgatatgc | 93274 | AA118716 |
| 8067 | W50888 | ccaaatgtgagcgggcccagtgacc | 50671 | W50888 | tatgtatcagtgtctgccacagtg | 93275 | AA118716 |
| 8068 | W50888 | caaatgtgagcgggcccagtgacct | 50672 | W50888 | cttaggacactaatccatccaggttg | 93276 | AA118716 |
| 8069 | W50888 | aatgtgagcgggcccagtgacctc | 50673 | W50888 | aaggaaatgcctcattcctgagacc | 93277 | AA118716 |
| 8070 | W50888 | ggcccagtgacctggcacttga | 50674 | W50888 | atgcctcattcctgagacctgagg | 93278 | AA118716 |
| 8071 | W50888 | gccagtgacctcggcactttgat | 50675 | W50888 | catcctgagacagtagttgttgt | 93279 | AA118716 |
| 8072 | W50888 | cccagtgacctcggcactttgatc | 50676 | W50888 | gtactatggctcctcgaaaacacaa | 93280 | AA118716 |
| 8073 | W50888 | cagtgacctcggcacttgatcc | 50677 | W50888 | ctatggctcctcgaaaacacaaagt | 93281 | AA118716 |
| 8074 | W50888 | atagagcgtcgcagcgccggatcg | 50678 | D84372 | ttaatgccacagaagcagcagatg | 93282 | AA118716 |
| 8075 | D84372 | tccttgtggaccagacaagggtg | 50679 | D84372 | atgccacaggaagcagcagatggta | 93283 | AA118716 |
| 8076 | D84372 | ctggctgactgcctctgagaagc | 50680 | D84372 | aactcaatatttcacgaaaatgc | 93284 | AA118716 |
| 8077 | D84372 | ctgcctctgagaagcgaagttgg | 50681 | D84372 | atattttcatgaaaatgcaaccac | 93285 | AA118716 |
| 8078 | D84372 | cacggccaattggcaaccccttt | 50682 | D84372 | atgaaaatgcaaccacatgtataat | 93286 | AA118716 |
| 8079 | D84372 | gtgccctaattgcacctcctt | 50683 | D84372 | ctaatccatcaggttgactcgagg | 93287 | AA118716 |
| 8080 | D84372 | gagagactgctctcgcgttctgaca | 50684 | D84372 | atccatcaggttgactcgagtgtcc | 93288 | AA118716 |
| 8081 | D84372 | ctctcgttctgacaatgctatttt | 50685 | D84372 | catcaggttgactcgaggccgtgc | 93289 | AA118716 |
| 8082 | D84372 | tgcgttctgacaatgctattttca | 50686 | D84372 | gttgactcgaggtcctgccaacaac | 93290 | AA118716 |
| 8083 | D84372 | atttctcacattaggaggactcaaat | 50687 | D84372 | ctcgaggtcctgcaccaactggtt | 93291 | AA118716 |
| 8084 | D84372 | tttcatactcatatgggagactcaaatct | 50688 | D84372 | ctgcaccaactggtctggaaactag | 93292 | X05719 |
| 8085 | D84372 | ttatgacctaaacagatctgattt | 50689 | D84372 | tgcataaacctgatggtgatggagtg | 93293 | X05719 |
| 8086 | D84372 | agcgcccaggttctaagaacgtgg | 50690 | D84372 | ttcttcaatgatttgcaggaaacc | 93294 | X05719 |
| 8087 | D84372 | cttcctcttctggaatcag | 50691 | D84372 | agctccttcctgcagaagagaga | 93295 | X05719 |
| 8088 | D84372 | ctcatgcagcagcagcggagagttca | 50692 | D84372 | cttcctcgagaagagaagaacgctg | 93296 | X05719 |
| 8089 | D84372 | ttcagatgagccccacgggacagaa | 50693 | D84372 | ttcatgaattctctctcacaatg | 93297 | X05719 |
| 8090 | D84372 | agatgagccccacggcgacagaac | 50694 | D84372 | ttaatgcacagtttagggccaatcta | 93298 | X05719 |
| 8091 | D84372 | tgagcccacgcgacgaacagaa | 50695 | D84372 | taactgtctctgatctcctcccgt | 93299 | X05719 |
| 8092 | D84372 | tagacgagcgttccagacccgtg | 50696 | D84372 | tgattctcccgttgctcatgtgta | 93300 | X05719 |
| 8093 | D84372 | gtcagaagccggcgactggctgac | 50697 | D84372 | gtactgtgcacacatagagtgcat | 93301 | X75013 |
| 8094 | D84372 | cagaagccggcgactggctggactgc | 50698 | D84372 | agtcattactgccactttttcaa | 93302 | X75013 |
| 8095 | D84372 | cctgagcgctagacgcggactgc | 50699 | W50891 | ttactgccaccttttcaataagct | 93303 | X75013 |
| 8096 | W50891 | gcagctctgtagcactgctgctac | 50700 | W50891 | ctaaatttagactctctattgccata | 93304 | X75013 |
| 8097 | W50891 | agattgccaggatctgcttcaa | 50701 | W50891 | tagactcctttattgccatctta | 93305 | X75013 |
| 8098 | W50891 | gatttgccagatctgcttcctcaa | 50702 | W50891 | ttatttatctgatttgaaggga | 93306 | X75013 |
| 8099 | W50891 | tttgccagatctgcttcctctcaaat | 50703 | W50891 | ccatcccgtagagatgccaaaac | 93307 | U12564 |

| SEQ ID NO | sequence | DBAxnID | SEQ ID NO | sequence | DBAxnID | SEQ ID NO | sequence | DBAxnID |
|---|---|---|---|---|---|---|---|---|
| 8100 | ttgccccagatcctgctccaaatcc | W50891 | 50704 | agatggcccaaactcaccaaaatgg | X75013 | 93308 | acattgaattcctgctctccaatca | U12564 |
| 8101 | ccagatcctgctccaaatccggta | W50891 | 50705 | gtgacactctcaatccagaccag | X75013 | 93309 | tgtctccaatcatccaggtgactc | U12564 |
| 8102 | agatcctgctccaaatccggtagc | W50891 | 50706 | ctcttcaattccagaccagaccatt | X75013 | 93310 | ctctccaatcatccaggtgactcgc | U12564 |
| 8103 | gatcctgctccaaatccggtagcc | W50891 | 50707 | aattccagaccagaccattggccct | X75013 | 93311 | tctccaatcatccaggtgactcgca | U12564 |
| 8104 | atcctgctccaaatccggtagccg | W50891 | 50708 | agaccagaccattggccctcatga | X75013 | 93312 | ctccaatcatccaggtgactgcgag | U12564 |
| 8105 | ctgctccaaatccggtagccgat | W50891 | 50709 | gaccattggccctcatgaatttct | X75013 | 93313 | tccaatcatccaggtgactgcagc | U12564 |
| 8106 | tgctccaaatccggtagccggatt | W50891 | 50710 | tggccctcatgaatttctctctc | X75013 | 93314 | ggtgccaccatgccgcgatgcag | U12564 |
| 8107 | cagcctgtagcactggctgctact | W50891 | 50711 | aatagcaaactcattcatgcactgt | X75013 | 93315 | accagccgagatgccgatgtgtgc | U12564 |
| 8108 | agcctgtagcactggctgctact | W50891 | 50712 | aaaactcattcatgcactgtggtact | AA034761 | 93316 | catgccgatgcagttgatggtgcc | U12564 |
| 8109 | gcctgtagcactggctgctactc | W50891 | 50713 | tactgcaacggccagctggagtgta | AA034761 | 93317 | atgccgagatgcagttgtgccca | U12564 |
| 8110 | ggtagcactggctgctactactt | W50891 | 50714 | aacggccagctggagtgtaatccat | AA034761 | 93318 | tgcccgagatgcagttggtgccaa | U12564 |
| 8111 | gtagcactggctgctactcagctt | W50891 | 50715 | aatccataagggccatgagagaagaa | AA034761 | 93319 | cattgaattcctgctctccaatcat | U12564 |
| 8112 | tagcactggctgctactcagttc | W50891 | 50716 | taaggcacttctccaggatcagg | AA034761 | 93320 | attgaattcctgctctccaatcatc | U12564 |
| 8113 | ccagattggccagatcctgctcc | W50891 | 50717 | cactctccagatcagcctatcag | AA034761 | 93321 | tgaattcctgctctccaatcatca | U12564 |
| 8114 | cagattggccagatcctgctcca | W50891 | 50718 | tccaggatcgctatccaggaaggg | AA034761 | 93322 | aattcctgctctccaatcatccagg | U12564 |
| 8115 | gacaatggccccgatggatggagcc | W50891 | 50719 | tctctagcattgggtctcattcat | AA034761 | 93323 | attcctgctccaatcatccaggt | U12564 |
| 8116 | acaatggccccgatggatggagccg | W50891 | 50720 | tgcattggtcattcatgccaat | AA034761 | 93324 | tcctgctccaatcatccaggtga | U12564 |
| 8117 | gctacaatttgccatatccaatct | W50891 | 50721 | gggtcattcatgccaatcaggt | AA034761 | 93325 | cctgctccaatcatccaggtgac | U12564 |
| 8118 | tacaaatttgccatatccaatctgg | W50891 | 50722 | cattcatgccaatcatggtggtgac | AA034761 | 93326 | ctgctccaatcatccaggtgact | U12564 |
| 8119 | acaatttgccatatccaatctgga | W50891 | 50723 | attcatgcacgtgggtactaccagt | AA034761 | 93327 | gcagacgacactcatgcagagg | AA118701 |
| 8120 | caatttgccatatccaatctggag | W50891 | 50724 | gcactgtactaccagtgaccag | AA034761 | 93328 | cacactcatgcaggacatgt | AA118701 |
| 8121 | aatttgccatatccaatctggagg | W50891 | 50725 | tggtactaccagtgaccagttctt | AA034761 | 93329 | gactcaggtccagccaacaggcagc | AA118701 |
| 8122 | attttgccatatccaatctggaggc | W50891 | 50726 | taccagtgaccagttcttagagat | AA034761 | 93330 | ggtccagccaacaggcagcagtcag | AA118701 |
| 8123 | gccatatccaatctgaggcaaga | W50891 | 50727 | gttggccagagccaccaactgggcc | AA034761 | 93331 | cagccaacaggcagcagtcagtgg | AA118701 |
| 8124 | ccatatccaatctggaggcaagat | W50891 | 50728 | cagagccaccaactgggccaaattt | AA034761 | 93332 | gccaacaggcagcagtcagtggga | AA118701 |
| 8125 | catatccaatctgggaggcaagatt | W50891 | 50729 | caccaactgggccaaattactgca | AA034761 | 93333 | agaagaagtcaccctggactgtca | AA118701 |
| 8126 | atatccaatctggaggcaagatta | W50891 | 50730 | caaatttactgcaacggccagttg | AA034761 | 93334 | agaagctcaccctggactgttcatat | AA118701 |
| 8127 | caatggcccccgatgatggaggagccgg | W50891 | 50731 | agaacaccaatctgaggaacaatgc | AA034761 | 93335 | acccctggactgttcatatgag | AA118701 |
| 8128 | aatggccccgatgatggaggagccgga | W50891 | 50732 | cctccagctcagaaggaccgctgc | AA034761 | 93336 | cacccgactgtcatatagagaca | AA118701 |
| 8129 | agccgacgcatcgagagtaactg | W50891 | 50733 | ttctggtatttgatccagggact | AA034761 | 93337 | gtacaggcagtttttagtggggag | AA118701 |
| 8130 | ttttgaagcctgccatccagc | W50891 | 50734 | attcaggccatcatgaataccctcat | AA034761 | 93338 | ttaccaacttctttgacactcag | AA118701 |
| 8131 | aacagctacaattgccatatccaa | W50891 | 50735 | ccatcatgaataacctcatgtgtta | U05265 | 93339 | gcctcctcagagcctgctgctgtg | AA118701 |
| 8132 | acagctacaattgccatatccaat | W50891 | 50736 | atgaatacccatcatgtgtatcagaa | U05265 | 93340 | accttctttgacactcagaaccag | AA118701 |
| 8133 | cagctacaattgccatatccaatc | W50891 | 50737 | acctcatgtgtacagaagtct | U05265 | 93341 | tcctcagagcctgctgctgtg | AA118701 |
| 8134 | agctacaattgccatatccaatct | W50891 | 50738 | atcagaagttctcagaattttggg | U05265 | 93342 | tcagagcctgctctgtgtggtg | AA118701 |
| 8135 | cgacgatgctacatccagctga | U08020 | 50739 | agctctcaagatttggaatata | U05265 | 93343 | ctgggtttctggatgcaatgtg | AA118701 |
| 8136 | acgatgctacatccagctgacct | U08020 | 50740 | aaatcctctccaataaacatcat | U05265 | 93344 | ggctttctggatgccaatgtggcc | AA118701 |
| 8137 | gctacatggacccagcagagactggca | U08020 | 50741 | tcctcaataaacatcatcaatg | U05265 | 93345 | ttctctggatgccaatgtggcccag | AA118701 |
| 8138 | tacatggaccagcagagactggcaacc | U08020 | 50742 | taaccagggcacactaatcaatgaa | U05265 | 93346 | atgcaatgtgcccagagtgact | AA118701 |
| 8139 | atggaccagcagagactggcaaccca | U08020 | 50743 | atgtaaccctagcccagttgtcat | U05265 | 93347 | atgactcaggtccagcaacagc | AA118701 |
| 8140 | ctgtctccagggaccagagcctcgcatcta | U08020 | 50744 | cccagttgtgcatcaggcatggcagca | U05265 | 93348 | tgatccaggacgcccgaggacaagg | AA118789 |
| 8141 | ctcctccaggagacaacgcagatcg | U08020 | 50745 | tgtgcatcaggagacaaggaacaag | U05265 | 93349 | cgatccaggcgccgaggaacaaggc | AA118789 |
| 8142 | ctccaggatccaacgagatcgagc | U08020 | 50746 | acaacgctgaaacgcaagcaagcc | U05265 | 93350 | atcgaccgcaacttgccgaggacgg | AA118789 |
| 8143 | gacatggcccccttggctggttgt | U08020 | 50747 | gctgaaaccacgcaaagcagccaacac | U05265 | 93351 | tcgaccgcaacttgccgaggaggg | AA118789 |
| 8144 | attggccccctgctggttgtaa | U08020 | 50748 | accgccaagcagccacaacagaag | U05265 | 93352 | ctcgccgtcggagaatctggtaaaa | AA118789 |
| 8145 | ggccccttgcttgtgtgtaaactc | U08020 | 50749 | gaagaaccccagtgaaacatg | U05265 | 93353 | aaagtaccacctgaaacagatgaa | AA118789 |
| 8146 | tcctttgcattcacctttcaaactt | U08020 | 50750 | cccaattccatgaatgaaaactag | U05265 | 93354 | aagtaccacctgaaacagatgaaa | AA118789 |
| 8147 | cagctgacctctgcgcctaatgt | U08020 | 50751 | gggcctgcctggctactcgtttt | X63099 | 93355 | agtaccacctgaaacatgaatgaat | AA118789 |
| 8148 | ctgacttctgcctaatgtcca | U08020 | 50752 | gcataacgaccccagttccgagag | X63099 | 93356 | aaatcattcatggacggctatc | AA118789 |
| 8149 | ttcctgggcctaatgtcaccgagg | U08020 | 50753 | tggcttggactgagcagccagc | X63099 | 93357 | aatcattcatgaggacggctattca | AA118789 |

TABLE 1-continued

| SEQ ID NO | sequence | DBAxnID | SEQ ID NO | sequence | DBAxnID |
|---|---|---|---|---|---|
| 8150 | ctgcgcctaatgtcaccgaggcct | U08020 | 50754 | ttggcacaaccttctgaggcaaa | X63099 | 93358 | atcattcatgagacggtctattcag | AA118789 |
| 8151 | tgcaagaacagcgtagcctacatgg | U08020 | 50755 | caacttctggaggccaaagagcaa | X63099 | 93359 | tcattcatgagagacggctattcaga | AA118789 |
| 8152 | aacacggtagcctacacagaccagc | U08020 | 50756 | actgctgttgagcacaccaccacg | X63099 | 93360 | gatccatggcgccgaggacaaggcg | AA118789 |
| 8153 | agcgtagcctacatggaccagcaga | U08020 | 50757 | gcttgagcacaccaccacggtccct | X63099 | 93361 | atccatggcgccgaggacaaggcgg | AA118789 |
| 8154 | gtagctacatggaccagcagactg | U08020 | 50758 | cacccctagccaggacttgggagg | X63099 | 93362 | aagatgatcgaccgcaactgcgga | AA118789 |
| 8155 | ctgctgcaggacagctgctgaagc | M37759 | 50759 | aggacttggaggcatgcgtatcct | X63099 | 93363 | agatgatcgaccgcaactgcggag | AA118789 |
| 8156 | ctgctgcaagttctgcatgtgtg | M37759 | 50760 | tgtcatatcccgcgtatatcctt | X63099 | 93364 | ggcagaacctacatactcttccatc | AA118789 |
| 8157 | ttatctccaggtctgtatatcct | M37759 | 50761 | atccccggctatatcctgacata | X63099 | 93365 | atgatgacccgcaactgcggagaa | AA118789 |
| 8158 | ggtcctgattatcctgctgtcc | M37759 | 50762 | tgacatatccaagtctgtcctta | X63099 | 93366 | tgatcgaccgcaactgcggaggac | AA118789 |
| 8159 | tcctgattatcctgctgttccctt | M37759 | 50763 | cagaccccagctcgagagacatttt | X63099 | 93367 | gatcgaccgcaactgcgaggacg | AA118789 |
| 8160 | ttatcctgctgttccctagcact | M37759 | 50764 | cagctccgagagacattagatta | X63099 | 93368 | atcaactacagtagcctcagtatag | AA118789 |
| 8161 | tgcttcccacagctcaactcagat | M37759 | 50765 | ttttactacacagcatgcaagggtca | X63099 | 93369 | aactacagtagcctcagtatagcta | AA118692 |
| 8162 | ttccacagctcaactcagattg | M37759 | 50766 | gcttctacctactgcaggcgactcg | X63099 | 93370 | ggtcctcaggcagaacctacaatt | AA118692 |
| 8163 | cttcaactcagattggctttcgt | M37759 | 50767 | accctacgcaggggacgtccccgct | X63099 | 93371 | gcctcaggcagaacctacaattctt | AA118692 |
| 8164 | ttggtttcgtcctcaaagaag | M37759 | 50768 | tgggcaccctcagaaaagcaca | X63099 | 93372 | ggcagaacctacatacttccatc | AA118692 |
| 8165 | tcgtcctcaagagaggccatctgc | M37759 | 50769 | ccctctcagaaaaagccatgaaa | X63099 | 93373 | ctatgactctatcactctggctac | AA118692 |
| 8166 | agagccatctgtcatctactactg | M37759 | 50770 | tccatcagacatagcaacagaaca | X63099 | 93374 | ttgtatcagattcacaatatcgt | AA118692 |
| 8167 | gcaatgtccatggttgccaagg | M37759 | 50771 | ttccagatatgtcttgaaccaga | X63099 | 93375 | tatcgcagaattcacaatatcgtatc | AA118692 |
| 8168 | ctcctgtcatcatgtacctctag | M37759 | 50772 | atatgtcttgaaccagataaaac | AA034569 | 93376 | agatttcacaatatgtatctagcgt | AA118692 |
| 8169 | atgtctccatgtgttgccaaggca | M37759 | 50773 | agagcgtccaagcactgttcgccgc | AA034569 | 93377 | ttcaaatatgtatctagcgtaga | AA118692 |
| 8170 | tgaactgctcctcagctgtcgt | M37759 | 50774 | tgttcgccgcctgtgtgacagat | AA034569 | 93378 | acaatatcgtatctagcgtagatct | AA118692 |
| 8171 | actgcttcctcagctgtgggccta | M37759 | 50775 | agatcaataagtttgcccagtactg | AA034569 | 93379 | agaccattgcacttgtcgaagagaa | AA118692 |
| 8172 | gctgttgcctccagtttatctccag | M37759 | 50776 | tccataagtttgcccagtactgag | AA034569 | 93380 | tacagtagcctcagtatagctatca | AA118692 |
| 8173 | gtggcctccagttattctccaggt | M37759 | 50777 | ggattgacccatctgatgcctgg | AA034569 | 93381 | agtagctatcatcatctcatcaa | AA118692 |
| 8174 | tccagttatctccaggtcctgat | M37759 | 50778 | tcctgatcgctcaataagaaac | AA034569 | 93382 | gctatcatcatctcatcctcac | AA118692 |
| 8175 | agtttatctccaggtcctgattat | M37759 | 50779 | tgatgctctggtcaataagaaaca | AA034569 | 93383 | atcatcatctcatcctcatcccacag | AA118692 |
| 8176 | cggccagctcctggggcttgcgaa | W50919 | 50780 | gggaagccactgctgtactaaa | AA034569 | 93384 | atcatctcatcaatcctcacaggtg | AA118692 |
| 8177 | gccagctctggccaaggcaa | W50919 | 50781 | gaagccactgctgtactaaagac | AA034569 | 93385 | tcatcaatccacaggtgcctcag | AA118692 |
| 8178 | gccagctcctcagcgttcgcagt | W50919 | 50782 | actacatcagagtctgatcgacga | AA034569 | 93386 | tcaatcacagggtgcctcaggcca | AA118692 |
| 8179 | cctcctagcagacaggaacgaggag | W50919 | 50783 | tcgacgagagcgtccaagcactgt | AA034569 | 93387 | atcctacagggtgcctcaggcagga | AA118692 |
| 8180 | cagggccagtcatggccagcagagc | W50919 | 50784 | acgagcgtccacgcactgttcgc | AA034569 | 93388 | acagcagagcctaattctgttctg | AA118692 |
| 8181 | tcttagcagcaagggccagagacgc | W50919 | 50785 | ctggagatctcagcgcggagatca | AA034569 | 93389 | catcatccaggtgaagtgtgacaag | AA118692 |
| 8182 | ttagcagcaagggcagacgggcag | W50919 | 50786 | ctggagatctcagcgcggagatca | AA034569 | 93390 | catcatccaggtgaagtgtgacaag | AA118621 |
| 8183 | cagcctgctgggctgcggaagtac | W50919 | 50787 | actctgcagcgggagatcagaatgg | X63100 | 93391 | cagagctcaattctgcttgtac | AA118621 |
| 8184 | cagcctgctgggctgcggaagtagc | W50919 | 50788 | gaaacacagtgtccaaggcacatg | X63100 | 93392 | tccaaggccatcatccaggtg | AA118621 |
| 8185 | gctgggctgcggaagtacta | W50919 | 50789 | cagtgtccacaggttctcagtctcta | X63100 | 93393 | caaggccatcatccaggtgaagt | AA118621 |
| 8186 | ctgggctgcggaagtactgcgg | W50919 | 50790 | tcccagccacaggttctcagcaata | X63100 | 93394 | gccatcatcaggtgaagtgtgaca | AA118621 |
| 8187 | gaagtactgcgagctctactg | W50919 | 50791 | gcacagttctcagcaataatgcag | X63100 | 93395 | catcatccaggtgaagttgacaag | AA118621 |
| 8188 | tactgcgagctctactgcgagctg | W50919 | 50792 | gtcctcagcaataatgcagtgcag | X63100 | 93396 | tgtgacaagccttctaagccaggag | AA118621 |
| 8189 | cagcctgcgtggccgaagtac | W50919 | 50793 | gaacttcagttgtcttccaga | X63100 | 93397 | tgacagccgtgtcttaacccag | AA118621 |
| 8190 | ctgctggggctggaagtacta | W50919 | 50794 | tgtactccagatcagagaagaa | X63100 | 93398 | gccctcaccttcctccaggttgc | AA118621 |
| 8191 | gaagtactgcactgctcactcg | W50919 | 50795 | acatggcgcacagttctcag | X63100 | 93399 | tcacttcctttctcaggtgctga | AA118621 |
| 8192 | tactagctactgctcactgatgc | W50919 | 50796 | gcacagttctcagcaataatgcag | X63100 | 93400 | acttcctttccagctcctggaga | AA118621 |
| 8193 | gctcactgcagctgcgcgggcttc | W50919 | 50797 | gttctcagcaatatagcagttcag | X63100 | 93401 | ttgctgtttactctatggtgagata | AA118621 |
| 8194 | tcactgcgatgctgcgcgggcttccc | W50919 | 50798 | gaactttcaggttgtcttccaga | X63100 | 93402 | gtttttcactgcgtcgtcgatgaa | AA118621 |
| 8195 | tcgatcgcgcggggcttcccacag | W50919 | 50799 | tgtgtcctcagatccagaagaga | X63100 | 93403 | ttttcactgcgtcgtcatgtgaagg | AA118621 |
| 8196 | tcccgaaaccgagctgcgagaggaa | W50919 | 50800 | atttgtacattggactgctgtgtt | X63100 | 93404 | cactgcgtcgtcatgtgaaggaggt | AA118621 |
| 8197 | acggagctgctgcagaaccagagat | AA145547 | 50801 | tgtacattggactgctagttaca | X63100 | 93405 | ctgcgtcgtcatgtcgtgaaggt | AA118621 |
| 8198 | ggccctcaggaagtcgtagttacctt | AA145547 | 50802 | acatgtgacgtctgtagttacactt | X63100 | 93406 | ttgtgtcgtcttgcttttcc | AA118621 |
| 8199 | gaatcgtttacactgccacacagc | AA145547 | 50803 | ttggacctagcaatccacaggctacc | X63100 | 93407 | ctgctttccaaggccatccaagg | AA118621 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 8200 | tcgttacatactgccacaagcga | AA145547 | 50804 | atccaggctaccatcaccaaaaca | X63100 | 93408 | cagctgaccggcgaccagcgtttg | AA051231 |
| 8201 | acatactgccacaagccgaaagagt | AA145547 | 50805 | gtaagcagcaacttgctgaataatg | X63100 | 93409 | caccagcgttttgtgcaccggctag | AA051231 |
| 8202 | tactgccacaagccgaaagagttac | AA145547 | 50806 | gtaaacatttggctctgttactt | X63100 | 93410 | catgtgcggaaccatctgctacac | AA051231 |
| 8203 | tgccacaagccgaaagagttaccag | AA145547 | 50807 | ttatcttcaggatgctgtggctc | X63100 | 93411 | cggaaccatcgtaccacacactg | AA051231 |
| 8204 | gagttaccagctggctccatcgag | AA145547 | 50808 | ttggctcatgatccaaactcagggg | X63100 | 93412 | aaccatctgtacacacactgggg | AA051231 |
| 8205 | gcctgctccatcgagccctgatg | AA145547 | 50809 | catgatccaaactcaggggactctg | X63100 | 93413 | cctgactgctaagccttcaact | AA051231 |
| 8206 | tggctccatcgagccctgatggag | AA145547 | 50810 | ccaaactcaggggatctgaaggtg | X63100 | 93414 | gactgctctaagccttcaactcac | AA051231 |
| 8207 | catcgagccctgatggagccctg | AA145547 | 50811 | tctggaccgaccctgagacagat | X63100 | 93415 | tctaagccttttcaactcaccagcca | AA051231 |
| 8208 | aactgtgccagctctctcatagct | AA145547 | 50812 | ccgaccctggagacagattgtcac | X63100 | 93416 | gccttcacgcagagctcactctga | AA051231 |
| 8209 | gccagctctcatagctctggattc | AA145547 | 50813 | tgctgtctctgccgaggtccagc | AA034595 | 93417 | ttcacgcagagctccactctgaggc | AA051231 |
| 8210 | agctctcatagctctggattctg | AA145547 | 50814 | tctctgccgaggtccagcacagaa | AA034595 | 93418 | agcgagctccactctgaggcagc | AA051231 |
| 8211 | tagctctggattctgggctctaag | AA145547 | 50815 | tccaagcacagaatcgggctttac | AA034595 | 93419 | cagagctccactctgaggcagcatc | AA051231 |
| 8212 | ctctggattctgggctctaagcct | AA145547 | 50816 | gggctttaccatgactctcctcg | AA034595 | 93420 | cgtttgtgcaccgctagacggc | AA051231 |
| 8213 | tggattctgggctctaagcctgag | AA145547 | 50817 | acggacagtccgcagcgcagagttg | AA034595 | 93421 | agctccactctgaggcagcatcgcc | AA051231 |
| 8214 | ctggggctctaagcctgaggtccca | AA145547 | 50818 | gacagtccgcagcgcagagttgccc | AA034595 | 93422 | ttgtgcaccggctagagcggcgc | AA051231 |
| 8215 | tgaggtcccaggcccctcaggaaga | AA145547 | 50819 | cagcgcagagttgccatttagag | AA034595 | 93423 | caccggctagagcgggccataagt | AA051231 |
| 8216 | ccagtcagcgtgtgccctgtg | M37760 | 50820 | cgcagagttgccatttagagcgg | AA034595 | 93424 | cggctagagcggcgccataagtgca | AA051231 |
| 8217 | ccctgtgtctgctgccagtgtaaaatc | M37760 | 50821 | agagttgccatttagagcgcgatt | AA034595 | 93425 | ctagagcggcgccataagtgcagca | AA051231 |
| 8218 | atcctcgtttctgggctctatg | M37760 | 50822 | tttagagcgatttgccaggagctc | AA034595 | 93426 | gccataagtgcagcatttgtgca | AA051231 |
| 8219 | ttctgggctctatggtgtttcacac | M37760 | 50823 | ttgtcaccctcagatttcgacattt | AA034595 | 93427 | cataagtgcagcatttgggcaaga | AA051231 |
| 8220 | atggttttcaacacacagttcacca | M37760 | 50824 | tcacctccagattctgacatttgat | AA034595 | 93428 | aagtctcatgtcgggaaccatctgc | AA051231 |
| 8221 | ttcacacacagttcaccaaagaca | M37760 | 50825 | cctcagatttctgacatttgattcc | AA034595 | 93429 | accacatggctcctatgaccggc | AA118886 |
| 8222 | cagttcaccaaagacacctccacca | M37760 | 50826 | atttctgacatttgattcccccagag | AA034595 | 93430 | tgggctcctatggaccggcctcta | AA118886 |
| 8223 | ttcaccaaagacacctccacactg | M37760 | 50827 | tctgacatttgattcccagaggc | AA034595 | 93431 | tgcccactccggacttcagagtg | AA118886 |
| 8224 | acctccaacatgcagttcactag | M37760 | 50828 | gacatttgattcccagagggcaaa | AA034595 | 93432 | actcagagtcgagagtggggcgat | AA118886 |
| 8225 | ctctaccaaatggactccactcct | M37760 | 50829 | gttcctgcacttctagtgccagt | AA034595 | 93433 | acttcagagtgggctgatggcat | AA118886 |
| 8226 | ttaccaaatggactccactcctgcc | M37760 | 50830 | ctggcactccagtgcagtgttctg | AA034595 | 93434 | ttttcatgatcaaagctcatctgaa | AA118886 |
| 8227 | catgtcacctcctcttggtaggt | M37760 | 50831 | ttagacgtacctgatggggctga | AA034595 | 93435 | tgatcaaagctcatctgacatctt | AA118886 |
| 8228 | tgtgtgctcagtgtaaaatctga | M37760 | 50833 | gagctgacgtctcgactatgca | X66032 | 93436 | acatcttgggaacgctccaaccg | AA118886 |
| 8229 | tctggccacagatctcaggcagca | M37760 | 50834 | agcagcagatcctcgtgaatatcagc | X66032 | 93437 | tggtggaacgtccaacgaaccag | AA118886 |
| 8230 | ccacagatctcaggcagcagagctg | M37760 | 50835 | atcaagcacgatcctgcttgaact | X66032 | 93438 | aacgctccaacgaaccagagctgt | AA118886 |
| 8231 | cagatctcaggcagcagagctgatt | M37760 | 50836 | tccaaaatcaataagacctggtct | X66032 | 93439 | gtccaaccgaaccagagctgtcag | AA118886 |
| 8232 | ctttacagccctgtcattcctctgt | M37760 | 50837 | gggcagccctagcactgagctccg | X66032 | 93440 | ccaaccgaaccagagctcagcgt | AA118886 |
| 8233 | tacagcctgtctattcctctgt | M37760 | 50838 | gactcctagtgccgttcctcagat | X66032 | 93441 | tctaccaatctacgacgcttcgg | AA118886 |
| 8234 | agcctgtctattcctctgttctctgg | M37760 | 50839 | gatcctgccgttctcagatcctgta | X66032 | 93442 | gaaccagagctgcagctgcctcc | AA118886 |
| 8235 | tctatctctgttctggggctcta | M37760 | 50840 | gcgcttctcagatcctgatgtatt | X66032 | 93443 | accaatctacgacgcttctgaaca | AA118886 |
| 8236 | cctcaagctcgcgggcatggactgt | W50924 | 50841 | tcagactcatttctaattgtgtat | X66032 | 93444 | cttacgacgttctggacagtcac | AA118886 |
| 8237 | caagctcgcgggcatggactggtgac | W50924 | 50842 | acaataactctgctctgtattgaag | X66032 | 93445 | acgacgttctggacagttcacaca | AA118886 |
| 8238 | ctccaacctcgagtctgtggaga | W50924 | 50843 | actctgctctgtattgaagaaaat | X66032 | 93446 | acgttctgacagttcacacacga | AA118886 |
| 8239 | caacctcgagtctgtggaagagt | W50924 | 50844 | acgctgactacatacatgtggc | X66032 | 93447 | tttttccgtggatctgaagaacga | AA118886 |
| 8240 | ccttgagtcgggagagtggg | W50924 | 50845 | atgtgcactaccactcctcagg | X66032 | 93448 | gggtgtccgtcgagtttggagact | AA118886 |
| 8241 | agcatacactgtatctgacgccgtgc | W50924 | 50846 | tctccagttgggacgctcctgccctt | X66032 | 93449 | ttggagactgcccactctgaact | AA118886 |
| 8242 | atcactgtatctgacgcgtgcgcgat | W50924 | 50847 | tgcctgctcagaaggtgctgggc | X66032 | 93450 | gttgcttactcttcttaagccagat | AA118886 |
| 8243 | gtatctgacgcgcgtgcgatagtagt | W50924 | 50848 | tacacaggctacatggagagtgaag | X66032 | 93451 | tgccttaatctcttaagcagatg | AA118925 |
| 8244 | tctgacgccgtcgcgatagtagca | W50924 | 50849 | cacatgccaagaaacgttgtgaag | X66032 | 93452 | cagaacatccttaactcttcatgga | AA118925 |
| 8245 | cgatagtacgtcgagcgggatc | W50924 | 50850 | gacaaccgtaccaagttcactgac | X66032 | 93453 | ggacaatccttaactcttcatggagc | AA118925 |
| 8246 | tacgtgcagtcgagatcctgagg | W50924 | 50851 | aagttcactcgtcaagaacaagt | X66032 | 93454 | ccttaactctcatggagcatctta | AA118925 |
| 8247 | cagcagggatcctgagatggatgcta | W50924 | 50852 | caacttctccgagcagtcacag | AA034638 | 93455 | gtacacttgacagcagatgccaaag | AA118925 |
| 8248 | gctcagcggcatgagctgagggacag | W50924 | 50853 | ctctccggagcagtcacagtgaaga | AA034638 | 93456 | acttgacagcagatgccaaaggc | AA118925 |
| 8249 | cagctacagagcatctgtgtga | W50924 | 50854 | gacccatgctgactagtgactctgcg | AA034638 | 93457 | tatctaccacgagaaccccagaga | AA118925 |

| SEQ ID NO | sequence | DBAxnID | SEQ ID NO | sequence | DBAxnID | SEQ ID NO | sequence | DBAxnID |
|---|---|---|---|---|---|---|---|---|
| 8250 | ctacatgagcatcctgctgtgaagc | W50924 | 50854 | cccatgctagtgtactctgcgta | AA034638 | 93458 | cccagagaactcaagtggggtgt | AA118925 |
| 8251 | catgaccatcctgctgtgaagcaca | W50924 | 50855 | ccatgctagtgtactctgcgtatc | AA034638 | 93459 | agaacttcaagtgggctgtgattt | AA118925 |
| 8252 | gagcatcctgctgtgaagcacagtg | W50924 | 50856 | gctagtgtactctgcgtatcgct | AA034638 | 93460 | aacttcaagtgggctgtgttttcg | AA118925 |
| 8253 | attacgcagcgaagtcccaacctt | W50924 | 50857 | tagtgtacctctgcgtatcgcctga | AA034638 | 93461 | cttcaagtgggctgtgattttcga | AA118925 |
| 8254 | cagcgaagtcccaacctcgagtc | W50924 | 50858 | tctgcgtatcgccgagtgcacac | AA034638 | 93462 | ttgaaaaatccaactcatccagga | AA118925 |
| 8255 | agtctccaacctgagtctgcgtgg | W50924 | 50859 | gtatcgcctgagtgcacacttacag | AA034638 | 93463 | aatccaactcatccaggacatcct | AA118925 |
| 8256 | tcccaacataaccaggaatagagga | W50924 | 50860 | gcgagatcaccatacggtactt | AA034638 | 93464 | tccaactcatccaggacatctta | AA118925 |
| 8257 | ttgaacatagcaaggccccagatcta | W50926 | 50861 | ggtactttcgaggcctgtgccaga | AA034638 | 93465 | caactctatccaggacatccttaac | AA118925 |
| 8258 | gtacaacctggattgccctccg | W50926 | 50862 | tactttcgaggcctgtgccagat | AA034638 | 93466 | actctatccaggacatccttaactc | AA118925 |
| 8259 | ccttcctgggagctctgatgcg | W50926 | 50863 | ctccggagcagtcacagtgaagatc | AA034638 | 93467 | tctatccaggacatccttaactctt | AA118925 |
| 8260 | agcttcgtgatgcgatctgcagatg | W50926 | 50864 | tctcggtgctcactcggtgata | AA034638 | 93468 | tatccaggacatccttaactcttca | AA118925 |
| 8261 | tgatgccgatctgcagatgtlggtc | W50926 | 50865 | tcggtgctcactcggtgatatacg | AA034638 | 93469 | tccaggacatccttaactcttcaa | AA118925 |
| 8262 | gatgttggatctgtaccctgtatcatc | W50926 | 50866 | ggtgctcactcggtgatatacgct | AA034638 | 93470 | cacatttgagcctgctcaccaatc | AA118925 |
| 8263 | gttggtctgtaccctgatcatctc | W50926 | 50867 | tgctcactcggtgatatacgctca | AA034638 | 93471 | acatttgagcctgctcaccaatca | U12565 |
| 8264 | cttaccctgatcatctccagtctt | W50926 | 50868 | tcactcggtgatatacgctcactcc | AA034638 | 93472 | gtctgtcttcaagatgcagccgt | U12565 |
| 8265 | accctgatcatctccagtctgtc | W50926 | 50869 | ggtgatatacgctcactccaggtgt | AA034638 | 93473 | ttctgtcttcaagatgcagccgta | U12565 |
| 8266 | cagtctgtcacaggaatggcgggcc | W50926 | 50870 | tggaacccatcgctagtgtactcttg | AA034638 | 93474 | ctgctctcaagatgcagccgtagg | U12565 |
| 8267 | cacaggaatggcgggccctagaatgt | W50926 | 50871 | acctggagcaagttcaggtcac | AA034638 | 93475 | tgtctctcaagatgcagccgtagga | U12565 |
| 8268 | aacataggcaaggccccagatctacac | W50926 | 50872 | gtgttcaggtcacacagctggagc | AA034638 | 93476 | tctcttcaagatgcagccgtaggaat | U12565 |
| 8269 | aggcccagatctacacagcacctga | W50926 | 50873 | tgttcccaaggtgcaatgatatccc | AA034638 | 93477 | tcttcaagatgcagccgtaggaatg | U12565 |
| 8270 | cccagatctacacagcacctgatgt | W50926 | 50874 | gcaatgatatccccatcaaagtag | AA034638 | 93478 | ttcaagatgcagccgtaggaatggc | U12565 |
| 8271 | agatcacacagcacctgatgttg | W50926 | 50875 | atgatatccccatcaaagtagttg | AA034638 | 93479 | tcaagatgcagccgtaggaatggct | U12565 |
| 8272 | acacagcacctgatgttgacctg | W50926 | 50876 | atatccccatcaaagtagttgaagg | AA034638 | 93480 | aagatgcagccgtaggaatggctcg | U12565 |
| 8273 | cacctgatgttgacctgtggagt | W50926 | 50877 | gctatcagcaagcgcctccaaggga | AA034638 | 93481 | agatgcagccgtaggaatggctcgg | U12565 |
| 8274 | gagttccacagagtacaatcctgg | W50926 | 50878 | agcaagcgcctccaaggaggtca | AA034638 | 93482 | atttgagccctgctcaccaatcatc | U12565 |
| 8275 | ttccacagtacaatcctggatt | W50926 | 50879 | cgcctccaaggaggtcatgagcg | AA034638 | 93483 | tttgagccctgctcaccaatcatcc | U12565 |
| 8276 | gttgtatcattcctttgcatataa | X63963 | 50880 | atgcaggccattgaactgacacag | AA034646 | 93484 | gagccctgctcaccaatcatccagg | U12565 |
| 8277 | tgtatcattcctttgcatataa | X63963 | 50881 | gcaggccattgaactgacacagcaa | AA034646 | 93485 | ccctgctcaccaatcatccaggta | U12565 |
| 8278 | tcatttgttctttctttggccagca | X63963 | 50882 | aactgacgcaattgcatcaag | AA034646 | 93486 | ctgctcaccaatcatccaggtgatt | U12565 |
| 8279 | ttctttggcagcaaaagttaatgt | X63963 | 50883 | aggtcacacagctgtagcgaccac | AA034646 | 93487 | ctcaccaatcatccaggtgatccc | U12565 |
| 8280 | ttactgttcacagtccaaatcattt | X63963 | 50884 | tcacacagctggatgcgaccaccca | AA034646 | 93488 | tcaccaatcatccaggtgattccca | U12565 |
| 8281 | ttcacagtccaatcatttgcat | X63963 | 50885 | tcaaccgcctctcattgctct | AA034646 | 93489 | cccagctcaagaaactgtctt | U12565 |
| 8282 | acagtccaatcatttgtgcatcta | X63963 | 50886 | tctattgctcttgaccgagagc | AA034646 | 93490 | atcgccatgtgtgaggcctcaga | W53351 |
| 8283 | gtccaatcatttgtgcatctagaa | X63963 | 50887 | tgtcttgaccgaggagcctttat | AA034646 | 93491 | gtgcctatgtggggcctcagatc | W53351 |
| 8284 | tcatttgtcatctagaatcatt | X63963 | 50888 | ttgaccgaaggcctttatgagata | AA034646 | 93492 | gaccatgtatacctcgaaggga | W53351 |
| 8285 | tctagaatcctccataatta | X63963 | 50889 | ttatgaataccttgcctgt | AA034646 | 93493 | catcatgtatacctcgaaggatc | W53351 |
| 8286 | attcctccataattcatcaatta | X63963 | 50890 | tgagataccttgcagcctgtcc | AA034646 | 93494 | tacctcgaaggactctgtgcagc | W53351 |
| 8287 | tacattccttttcagaatttgtg | X63963 | 50891 | tctcttggttgcaacttctgt | AA034646 | 93495 | actctgctcaagatccaaatatggtga | W53351 |
| 8288 | atcattcctttgcatataatgaac | X63963 | 50892 | tcaactttcagatctgaaacccaagt | AA034646 | 93496 | ctgctcaagccaatatggtgaccc | W53351 |
| 8289 | attgaactgggacaacacaacacta | X63963 | 50893 | caatgctatattgcatctcctagt | X64713 | 93497 | ggcatgcctgtccatcaagtata | W53351 |
| 8290 | gaacctgggacaacacaccacagt | X63963 | 50894 | ctatattgcatctcctagtgtgaac | X64713 | 93498 | gcctgccatcaagtatagccag | W53351 |
| 8291 | cctggacaacacacactagatata | X63963 | 50895 | tgcatcctagtgtgaacaaactg | X64713 | 93499 | tgtccccatcaagtataggccagaag | W53351 |
| 8292 | tgtctccctagaaatcctcagaat | X63963 | 50896 | atccaagtgatctctccagtccggc | X64713 | 93500 | gcaactgtcactgcctgcgtcgta | W53351 |
| 8293 | ccctagaaatcctcagaatgattc | X63963 | 50897 | ctccacagttctttaaatgatgt | X64713 | 93501 | actgtcactgcctgcgtctg | W53351 |
| 8294 | tttataacattttcagaatcat | X63963 | 50898 | tctgctggctcaacttcagat | X64713 | 93502 | cctattggtgggctcagattcgc | W53351 |
| 8295 | atacacattttcatgcaatcattg | X63963 | 50899 | cattcaatagtcttccaggagt | X64713 | 93503 | gagcctcagatcttcctgacgagg | W53351 |
| 8296 | taccggctcgggcttgtatcacga | X63963 | 50900 | gaattcgacagcagcagatgggtg | X64713 | 93504 | cctcagattcctgcctgacgggagacc | W53351 |
| 8297 | ctcggcctgtatcacgatcctct | X63963 | 50901 | ctcctgtcttgaattgccacctgga | X64713 | 93505 | ctgccctgacggagaccatgacctca | W53351 |
| 8298 | accagtacatagacaccgacactga | M64228 | 50902 | aatgcacctgaaaagaatccttctt | X64713 | 93506 | gggaccatgtccctcaaagttgcc | W53351 |
| 8299 | acatagacacgacctgatgacga | M64228 | 50903 | ttcagatctgaaaccaagtatctt | X64713 | 93507 | ctcaaagttgccagtagttacag | W53351 |

| SEQ ID NO | sequence | DBAxnID | SEQ ID NO | sequence | DBAxnID | SEQ ID NO | sequence | DBAxnID |
|---|---|---|---|---|---|---|---|---|
| 8300 | acaccgacactgatgacgagggtca | M64228 | 50904 | ccccaagtctcactcactcaacagat | X64713 | 93508 | gtatacaagccctgatgatgaccatc | W53351 |
| 8301 | acactgatgacgaggggtcagctgct | M64228 | 50905 | tgtatctgtatatcctgtataqaa | X64713 | 93509 | aaggcctgagtgacttgaccatcatgtat | W53351 |
| 8302 | agctgtcttacagcgtggaactcag | M64228 | 50906 | catgcatatactccaaggatgatat | X64713 | 93510 | tgttgctctagacttgagcaagag | AA119014 |
| 8303 | tctacagctggactccagtctccc | M64228 | 50907 | catcaacagtattcctacagcatt | X64713 | 93511 | ttgctcagactgagcaagagat | AA119014 |
| 8304 | ccaagagtctccacgggagtaccag | M64228 | 50908 | cagtattcctatcagcattcttac | X64713 | 93512 | atacactggactatcattcaatcc | AA119014 |
| 8305 | agttcagcctggagctagaaacaga | M64228 | 50909 | tcctatcagcattcctaacaatgcc | X64713 | 93513 | acactggactatcattcaatccat | AA119014 |
| 8306 | ccgatgtgcacatgtgcctgggggg | M64228 | 50910 | cagcattcctaccaatgcctatatt | X64713 | 93514 | tggactatcattctaatccatcatg | AA119014 |
| 8307 | cacacggaggcaactcgggatcagag | M64228 | 50911 | ccaaacctgccattgcctccaaaga | X64713 | 93515 | gactatcattctaatccatcatgta | AA119014 |
| 8308 | gctgtatacagatcctcttaggaa | M64228 | 50912 | ttgcctccaaagacagtggtggtgga | X64713 | 93516 | ctatcattctaatccatcatgtagt | AA119014 |
| 8309 | atcctcttaggaacagagaggcgc | M64228 | 50913 | ttcacacagatgacacaagcttgaa | X64713 | 93517 | atcattctaatccatcatgtagtgt | AA119014 |
| 8310 | tcgccgactggagtggctcctcct | M64228 | 50914 | tgalaggctggaccagtgttgtg | X64713 | 93518 | cattctaatccatcatgtagtgtga | AA119014 |
| 8311 | tcttagacaagccgtgctgagccc | M64228 | 50915 | gctgtgaccagtgttgtgagcaaa | X64713 | 93519 | ttctaatccatcatgtagtgtgacg | AA119014 |
| 8312 | acaagccctgtctgagccctgagtc | M64228 | 50916 | gagcccaagcgtgcctaggctgc | X64713 | 93520 | ctaatccatcatgtagtgtgacgtt | AA119014 |
| 8313 | tgagccctggagctcctcatctacac | M64228 | 50917 | acagctgcctaggctgccttct | X64713 | 93521 | cacagtgctgtgtggtggtacacaa | AA119014 |
| 8314 | tctacaccagcaagtgccaggac | M64228 | 50918 | tccactgtcagccaacagcatgcc | X64713 | 93522 | gctctagactcgagcaagagatgt | AA119014 |
| 8315 | cccagaaaacacaacagcaatagc | M64228 | 50919 | glcagccaacagccatgcctcctt | X64713 | 93523 | tctagacttgagcaagagatgtgc | AA119014 |
| 8316 | atcatctactatggattaccaggag | M64228 | 50920 | catgtctgcctcatgactgcta | X64713 | 93524 | atggcggaatctcctccttcctgga | AA119014 |
| 8317 | tcatctactatggattaccaggagt | | 50921 | ctgcctcatgaactctattttg | X64713 | 93525 | tcctcctgaggagaactcatgagc | AA119014 |
| 8318 | agtgctttctgtcctctgcta | | 50922 | tcatgaactctattttgtaaggtg | X75888 | 93526 | gaactatgagctggctgaaggcaa | AA119014 |
| 8319 | gtgctttctgtcctctgcta | | 50923 | agccccctgcagatgctgtgctcat | X75888 | 93527 | gaatctgtggatacactggacta | AA119014 |
| 8320 | ttctgtcctctgctactctag | | 50924 | ggtgcatctctcaggagccgcag | X75888 | 93528 | atcctgtgtacactgggactac | AA119014 |
| 8321 | tctgtcctctgctactctagc | | 50925 | acctcagaaccaccactgcagtgctc | X75888 | 93529 | tgatacactggactatcattctaat | AA119014 |
| 8322 | ctgtcctctgctactctagcc | | 50926 | agaaccacactgcagtgctccagaag | X75888 | 93530 | agatccatgcgccgaccccggatgt | AA119014 |
| 8323 | calctactatggattaccaggagt | | 50927 | ccagtggtctccagaagctgta | X75888 | 93531 | aagttggctgactcttgccaagg | AA119035 |
| 8324 | atctactatggattaccaggagtt | | 50928 | ggtgctactgaccccactgagct | X75888 | 93532 | gctaccgcacagtgaagcagcagca | AA119035 |
| 8325 | tctactatggattaccaggagtga | | 50929 | acttgaccccactggactcttcac | X75888 | 93533 | tgaagcagcagcagcagttcat | AA119035 |
| 8326 | acaagccaacagtatttgaggaat | | 50930 | aggcttcacacagatgacacaag | X75888 | 93534 | actcctctcttgaacaacagccac | AA119035 |
| 8327 | caagccaacagtatttgaggaatt | | 50931 | acggttccaggacctgtttgcat | X75888 | 93535 | tctttgaacaacgccacgctgtt | AA119035 |
| 8328 | aacacagtctttctgtccctg | | 50932 | ggtcttccagaactgtttgctccc | X75888 | 93536 | cacgctggtgtcctactgaccatgagt | AA119035 |
| 8329 | cacagtctttctgtccctg | | 50933 | tctcaaacccacagacaagcataag | X75888 | 93537 | gctggtgtctactgaccatgagct | AA119035 |
| 8330 | acagtctttctgtccctgc | | 50934 | tcaaacccacagacaagcataagac | AA034827 | 93538 | gctggttctactgaccatgagcttgt | AA119035 |
| 8331 | calctactatggattaccaggagt | | 50935 | aaaaccacagacaagcataagaccg | AA034827 | 93539 | tgtctaccatgagctgtcttgac | AA119035 |
| 8332 | atctactatggattaccaggagtt | | 50936 | acaagcataagaccgacctcaacca | AA034827 | 93540 | tctaccatgagctgtcttgaccac | AA119035 |
| 8333 | acagtgtttctgtcctctgc | | 50937 | gcataagaccgacctcaaccacag | AA034827 | 93541 | agctgtctgaccacaaaggaatt | AA119035 |
| 8334 | aggtgctttctgtcctctgcta | | 50938 | gacctcaaccacagaccgacctcaagg | AA034827 | 93542 | gctgacttctgccaaggtgactact | AA119035 |
| 8335 | ggtgctttctgtcctctgctac | | 50939 | tcaaccacagaccgaccctcaagggttgg | AA034827 | 93543 | tgactcttgccaaggtgactact | AA119035 |
| 8336 | tgctttctgtcctctgctact | | 50940 | gacgacctggaccccaaccatgtgc | AA034827 | 93544 | tttaccactgcgaggctgactcg | AA119035 |
| 8337 | gctttctgtcctctgctactt | | 50941 | caccaaacatgtgtgagcagccgcg | AA034827 | 93545 | accaactgcgaggctgactcggag | AA119035 |
| 8338 | ctttctgtcctctgctactlc | | 50942 | cccaaacatgtgctgagcagccgcg | AA034827 | 93546 | acactgcgaggctgactcggagcgg | AA119035 |
| 8339 | ttttctgtcctctgctactct | | 50943 | tcttccaggacctgttgcatccat | AA034827 | 93547 | ggctgactcggagcggctaccgcac | AA119035 |
| 8340 | tttctgtcctctgctactcta | | 50944 | ccaggacctgtttgcatccatatc | AA034827 | 93548 | tgactcggagcggctaccgcacagt | AA119035 |
| 8341 | ttctgtcctctgctactctca | | 50945 | aggacctgttgcatccatcatcca | AA034827 | 93549 | gcggctaccgcacagtgaagcagca | AA119035 |
| 8342 | tctgtcctctgctactctagc | | 50946 | gacctgttgcatccatcatccagg | AA034827 | 93550 | tgcaggcctgtctccacaagctcc | AA119035 |
| 8343 | tctactatggattaccaggagtga | | 50947 | cctgttgcatccatcatccaggac | AA034827 | 93551 | ggccggtctccacaagctcagt | AA119035 |
| 8344 | ctgtcctctgctactctagcc | | 50948 | tttgcatccatcatccaggaccgc | AA034827 | 93552 | tcccattccaactgccagtcaggg | AA119036 |
| 8345 | taaaacaagccaacagtatttgag | | 50949 | tgcctccaaaccaacagtatttgag | AA034827 | 93553 | cccattccaagtccagttcaggt | AA119036 |
| 8346 | acaagccaacagtatttgaggaat | | 50950 | gctctcaaaaccacagacaagcata | AA034827 | 93554 | cattccaactgccagtcaggttat | AA119036 |
| 8347 | caagccaacagtatttgaggaatt | | 50951 | tgatctgctggaattaagaagaa | X01756 | 93555 | caactgccagtcaggttatgtca | AA119036 |
| 8348 | taaaacagtctttctgtgtc | | 50952 | atctctggaattaagaagaagg | X01756 | 93556 | actgccaagtcaggttatgtcaac | AA119036 |
| 8349 | aaacacagtctttctgtgtcct | | 50953 | ttaagcaacagtccagttgtata | X01756 | 93557 | aatgggcaacatgtgccttgcggaa | AA119036 |

TABLE 1-continued

| SEQ ID NO | DBAxnID | sequence | SEQ ID NO | sequence | DBAxnID | SEQ ID NO | sequence | DBAxnID |
|---|---|---|---|---|---|---|---|---|
| 8350 | | aaacacgtgctttctgttgcctc | 50954 | caacagttccagttgtatacatgct | X01756 | 93558 | tgggcacatgcgctttgggaaac | AA119036 |
| 8351 | | cacagtgctttctgttgtcctctg | 50955 | acagttccagttgtatacatgctac | X01756 | 93559 | tcaaggaattggcctccaagtagag | AA119036 |
| 8352 | W50969 | ttgaacgtccaagccaatgatgg | 50956 | agttcagttgtatacatgctacca | X01756 | 93560 | aaggaattggcctccaagtagagct | AA119036 |
| 8353 | W50969 | gtctcaaagccaatgatgggctgc | 50957 | ttgtatacatgctaccacgctctc | X01756 | 93561 | ggaattggcctccaagtagagctti | AA119036 |
| 8354 | W50969 | ccattgatggtgtcctgggatgtga | 50958 | gtatacatgctaccacggctctccc | X01756 | 93562 | gtcccacaagtcccatgccctggg | AA119036 |
| 8355 | W50969 | gtgttcctggagtgactacatcaa | 50959 | atacatgctaccacggctctccctt | X01756 | 93563 | ctccacaagtccatgtcctgggc | AA119036 |
| 8356 | W50969 | ccaactacacatgatggctacgaaa | 50960 | ggctccctttccaagataagat | X01756 | 93564 | ccacaagtccatcgtcctggggcaa | AA119036 |
| 8357 | W50969 | actacattgatggctacgaaagcc | 50961 | ctctccctttccaagataagatg | X01756 | 93565 | gctccatgtcctggggcaagtctcc | AA119036 |
| 8358 | W50969 | ttgatggctacgaaagccgaatgg | 50962 | ccctttccaagataagatggatct | X01756 | 93566 | tccatgtcctggggcaagtctccc | AA119036 |
| 8359 | W50969 | gctaccgaaagccgaatggctacat | 50963 | aatgagtaattccactgcctatt | X01756 | 93567 | catgtcctggggcaagtctcccat | AA119036 |
| 8360 | W50969 | agccgaatggctacatcggcacaca | 50964 | tgagtaattccactgccttattat | X01756 | 93568 | tgtccctggggcaagtctcccatic | AA119036 |
| 8361 | W50969 | gctacatcggcacacaggtggctgcgt | 50965 | tgtctcatggctttaatgtaccac | X01756 | 93569 | tctcccatccaactgccaagtcag | AA119036 |
| 8362 | W50969 | acatcggcacacaggtggcgctgcc | 50966 | aattcaacaccaaattcagatcat | X01756 | 93570 | gtccctgtcatccacagtcgcgccta | AA119168 |
| 8363 | W50969 | cacagggtgcgctgcctgagaccat | 50967 | ttcacacaccaaattcagatcaga | X01756 | 93571 | cctgtgcatccagagctcgcgccta | AA119168 |
| 8364 | W50969 | atgggctcaagttctcccagagta | 50968 | cacacaccaaattcagatcatgaat | X01756 | 93572 | tcgacgcgctgacaggcgcgaagc | AA119168 |
| 8365 | W50969 | tgcctgagaccatggggtgatttcg | 50969 | tttgttggacagtcgatttaagt | X01756 | 93573 | accgggtcgacaggccgaaagccag | AA119168 |
| 8366 | W50969 | ggctcaagttctcccagagtatga | 50970 | tattaagcaacagttccagttgta | X01756 | 93574 | ccgtgcagggcgaagcagcaaa | AA119168 |
| 8367 | W50969 | ctggacagcagttcacgtgggagaa | 50971 | atcatcttcacagccgcgaggaagaga | AA120740 | 93575 | gctgacagggcgaagccagcaaaa | AA119168 |
| 8368 | W50969 | agcagttcagtgggagaattccaa | 50972 | catcttcacagccgcgaggaagaaa | AA120740 | 93576 | aacgggccgaagccagcagcaaaaagca | AA119168 |
| 8369 | W50969 | agaattccaactcagaggtgaacaa | 50973 | agaccagtatatgtcgtcctcagc | AA120740 | 93577 | gaaggtgccgagtccgtgaacgat | AA119168 |
| 8370 | W50969 | attccaactcagaggtgaacaagcc | 50974 | ccagtatatgtcgtcctcagcgtgc | AA120740 | 93578 | aaggtgccgagtccgtgaacgatg | AA119168 |
| 8371 | W50969 | tcctcaactccattgatgtgttcc | 50975 | agtatatgtcgtctcagctccgt | AA120740 | 93579 | aggttgccgagtccgtgaacgattg | AA119168 |
| 8372 | W50969 | actccattgatgtgttcctgggag | 50976 | tatgtcgtctcagctgcgtcggt | AA120740 | 93580 | ggttgccgagtccgtgaacgatgc | AA119168 |
| 8373 | W50969 | ccaagcactgtctctagggcaagg | 50977 | tgtgctctcagctgccgtcgct | AA120740 | 93581 | atccagcgtcgcgctagccagt | AA119168 |
| 8374 | W50969 | actgctctagggcaagccctca | 50978 | tgctgctctcagctgccgtcgt | AA120740 | 93582 | agagctccgcagtccccagtctac | AA119168 |
| 8375 | W50969 | aacgccaaacactgccgcgagatcg | 50979 | ctgctcagctgccgtcggtgtag | AA120740 | 93583 | agaatgccatcgaccgcgctgacag | AA119168 |
| 8376 | W50969 | acgccaaacactgccgcgagatcgt | 50980 | tgtaggctgcagttgccaagcaa | AA120740 | 93584 | gaatgccatcgaccgcgctgacagg | AA119168 |
| 8377 | W50969 | tactacaatgaagctgctgcaaca | 50981 | ctgcaggtgccaagcaacacgtg | AA120740 | 93585 | ccatcgaccgcgctgacagggcg | AA119168 |
| 8378 | W50969 | tacaatgaagctgctgcaaat | 50982 | caggtgccaagcaacacgcagg | AA120740 | 93586 | ccatcgaccgcgctgacagggcga | AA119168 |
| 8379 | W50969 | cgggccatccatgggacctgggagc | 50983 | ctccgcagaattgctgctgct | AA120740 | 93587 | catcgaccgcgctgacagggccga | AA119168 |
| 8380 | W50969 | atcctagtgggacctgggagccagga | 50984 | ggttgccaagcaacacgtgcaggac | AA120740 | 93588 | atcgaccgcgctgacagggccgaag | AA119168 |
| 8381 | W50969 | gagccaggcaccatggactcagtga | 50985 | tcagaattgcgtctgtggga | AA120740 | 93589 | gcatccattatacgtccagaggc | AA119168 |
| 8382 | W50969 | agccaggcaccatggactcagtgag | 50986 | gaatttgcgtctgtggcacaga | AA120740 | 93590 | attatactcggccacgaggcgcaaat | AA119175 |
| 8383 | W50969 | ccaggcaccatggactcagtgagg | 50987 | atttgctgcgtggcacagt | AA120740 | 93591 | tgaccatcgtggccgacagcctcaa | AA119175 |
| 8384 | W50969 | caggcaccatggactcagtgaggtc | 50988 | ttgctgctgctgtggcacagagtac | AA120740 | 93592 | ccatcgtggccgacagcctcaatt | AA119175 |
| 8385 | W50969 | aggcaagagcctcacctcttcta | 50989 | gctgctgtcgtggcacagagtacct | AA120740 | 93593 | tcgtggccgacagcctcaaattccg | AA119175 |
| 8386 | W50969 | gcaagagcctcacctcttctaa | 50990 | acagagcctgtgtccctcctctgg | AA120740 | 93594 | ccgagagcctcaaattccgtggcca | AA119175 |
| 8387 | W50969 | caagagcctcacctcttctaacg | 50991 | tgcgtgcggaggagttgttact | AA120740 | 93595 | acagcctcaaattccgtggccacaa | AA119175 |
| 8388 | W50969 | caagagcctcacctcttctaagc | 50992 | aagattcctgccatggagtccta | AA120740 | 93596 | gcctcaaattccgtggccacaagt | AA119175 |
| 8389 | W50969 | agagcctcacctcttctaacgca | 50993 | atcctgcatggagtcctacga | AA034697 | 93597 | aattccgtggccacaaggtcatcct | AA119175 |
| 8390 | W50969 | tctctaacgccaacatgccgcg | 50994 | atcagttttcggttgcattgcattgcag | AA034697 | 93598 | tccgtggccacaaggtcatccgg | AA119175 |
| 8391 | W50969 | ctctaacgccaacatgccgccga | 50995 | agtttgcttggcattagcag | AA034697 | 93599 | gtggccacaaggtcatcctgccgc | AA119175 |
| 8392 | W50969 | tctaacgccaacatgccgccgaga | 50996 | tttgcgttggcattagcagttgcaga | AA034697 | 93600 | agtctctgtcgaacccagtctga | AA119175 |
| 8393 | K02296 | ttctgactctccaatatgaaaggt | 50997 | gagcctccagtgaggagatgctaggga | AA034697 | 93601 | tactggccagagccgaaatgtt | AA119175 |
| 8394 | K02296 | gaagggtctctcaattcacattcagt | 50998 | cctccagtgaggatgctaggaaac | AA034697 | 93602 | cgaaatgtctggtcacatgaacca | AA119175 |
| 8395 | K02296 | atcaaagctaccttgtaagtaatg | 50999 | aggaacctgactccctcccaca | AA034697 | 93603 | tgttcgtcacatgaaccagctccg | AA119175 |
| 8396 | K02296 | ttcaactgtacaaacccgctgc | 51000 | ccagcctccagaagaacagcaagtaca | AA034697 | 93604 | tgtcacatgaaccagctccgcgcc | AA119175 |
| 8397 | K02296 | ctctgaatgatcatcctattagat | 51001 | gccctccagaagaacagcaagtaca | AA034697 | 93605 | gtcatgaaccagctccgcgaga | AA119175 |
| 8398 | K02296 | aatgatcatccattagatttct | 51002 | aacgcaaggatccgtgtgattaa | AA034697 | 93606 | agtctgcagaggagcggtcgt | AA119175 |
| 8399 | K02296 | atctgtccattgatatggcagtgg | 51003 | agcaaggatccgtgtgattaagc | AA034697 | 93607 | aggagggtctgtgatgtgaccat | AA119175 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 8400 | atcacgcaaacgctactatactt | K02296 | 51004 | cctctgccattggagtcctacgatgt | AA034697 | 93608 | tctgtgatgaccatgtgtggcga | AA119175 |
| 8401 | tatactatactgctgtggaatga | K02296 | 51005 | ctgccattggagtcctacgatgtgat | AA034697 | 93609 | aacatgcactgtgagcggccagag | W08228 |
| 8402 | ctcttatgcgtctttcaaaaccat | K02296 | 51006 | ccatggagtcctacgatgtgatcgc | AA034697 | 93610 | acatgcacgttgagcgggccagaga | W08228 |
| 8403 | atgcgtcttcaaaaccattatcat | K02296 | 51007 | cctacgatgtgatcgccaaccagcc | AA034697 | 93611 | ccctgcagacacaaggctctcgt | W08228 |
| 8404 | tttctccaagtacaacattgactgga | K02296 | 51008 | tgatcgccaaccagcgctgtgtgat | AA034697 | 93612 | ccctgcagacacaaggctctcgt | W08228 |
| 8405 | attcacattcagtgctgtgacactc | K02296 | 51009 | ccaacagcctgtgtgatcgacaca | AA034697 | 93613 | gagcagacacaaggctctcgtgggg | W08228 |
| 8406 | attcagtgctgtgacactcttctg | K02296 | 51010 | tgatcgacacagtatcagtttg | AA034697 | 93614 | agcagacacaaggctctcgtgggga | W08228 |
| 8407 | tgctgtgacactcttctggtccta | K02296 | 51011 | gttatcagtttgcgttggcattag | AA034697 | 93615 | cagacacaaggctctcgtgggaac | W08228 |
| 8408 | gacacactcttctggtcctagtctg | K02296 | 51012 | tccgcactgatctgtgaacgcgagg | AA034706 | 93616 | agacacaaggctctcgtgggaaca | W08228 |
| 8409 | ggtcctatgtctgcagctggatca | K02296 | 51013 | gcactgatctgtgaacgcgagaac | AA034706 | 93617 | gacacaaggctctcgtgtggggaacag | W08228 |
| 8410 | atagatgtccatcaacagccacagg | K02296 | 51014 | gaagctgcacctgacaagagct | AA034706 | 93618 | cacaaggctctcgtgtggaacagct | W08228 |
| 8411 | gttcatcaacagcagcaggaaaatc | K02296 | 51015 | acctgcacagagctgtggagtct | AA034706 | 93619 | aggctctgtggggaacagctgcat | W08228 |
| 8412 | atcactgtgcaagttacagttgaaa | K02296 | 51016 | agctacgaaccctgaacacagcaacg | AA034706 | 93620 | ctttcctgtatgaatacattgca | W08228 |
| 8413 | cttttccactgagatcaacaggg | M96163 | 51017 | tacgaaccctgaacacagcacgaaa | AA034706 | 93621 | catgactgttgagcggccagagaa | W08228 |
| 8414 | gaatacaattcctctgtggctgct | M96163 | 51018 | gaacctgaacacagcacgaaatc | AA034706 | 93622 | tgcactgtgagcggccagagaagg | W08228 |
| 8415 | agagcgtctcagttggaagactg | M96163 | 51019 | tgaacacacagaaatccaccaca | AA034706 | 93623 | tggtatgtccctgcagacacaa | W08228 |
| 8416 | ttgtccctgctttaaaggcta | M96163 | 51020 | acacacagaaatccaccacaagc | AA034706 | 93624 | ggtatgtccctgcagacacaag | W08228 |
| 8417 | acaatcagaagcagtttggctgct | M96163 | 51021 | ggcccagactgacctgatgctaact | AA034706 | 93625 | gtatgtccctgcagacacaagg | W08228 |
| 8418 | agagcagtttttgctgcttaactg | M96163 | 51022 | gccagactgacctgatgctaactc | AA034706 | 93626 | atgtccctgagcagacacaaggt | W08228 |
| 8419 | gaatacactgtgttggtggaaagtg | M96163 | 51023 | cccagactgacctgatgctaactcc | AA034706 | 93627 | tgtccctgagcagacacaaggtc | W08228 |
| 8420 | attattacagccccaagcagta | M96163 | 51024 | ctgatctgaacgcgaggaactc | AA034706 | 93628 | gtccctgagcagacacaaggtct | W08228 |
| 8421 | tacagcccaagacgtatttatt | M96163 | 51025 | ccagactgacctgatgctaactcc | AA034706 | 93629 | cttgaagccagcatgctcagacgt | AA119287 |
| 8422 | gttgaccattcaaactctggcaa | M96163 | 51026 | gaggaacttccgagcatgaatgt | AA034706 | 93630 | aagcccagcatgctcagacagtgtc | AA119287 |
| 8423 | catttcaaactctggcaataaaga | M96163 | 51027 | gaacttccgagcatgaatgtgcc | AA034706 | 93631 | aggtgactctgtcattctccaaga | AA119287 |
| 8424 | aaacttggcataaagatgtatga | M96163 | 51028 | cttctccgagcatgaatgtgccag | AA034706 | 93632 | tcatttccaaagcaataacaga | AA119287 |
| 8425 | aattcctctggcctgctgactg | M96163 | 51029 | tgaatgtcgagcgagttcaca | AA034706 | 93633 | ttctccaagaagcatacacagta | AA119287 |
| 8426 | gctggaaccagacagccagcctaaggtg | M96163 | 51030 | accaagtgcgcgtggaagacgaca | AA034706 | 93634 | atgcaacgttaaaccgcttctgt | AA119287 |
| 8427 | accagacagccagcctaaggtgagt | M96163 | 51031 | aagtcagaagtgccacctgtcaa | AA034706 | 93635 | accgtctctgtgaacttccaaga | AA119287 |
| 8428 | aatcctgagtggggccgagtgca | M96163 | 51032 | tcagaagtgccacctgtacaagga | AA034706 | 93636 | tctctgaacttccagaaagcagc | AA119287 |
| 8429 | ccctgagtacctgcgtgaaaagg | M96163 | 51033 | taacctattcagtgactgactcct | AA034706 | 93637 | ctgaacttccagaaagcagctaa | AA119287 |
| 8430 | ttgactctgaagtctctctgttga | M96163 | 51034 | atctcagtactgacctcctgccaag | X67677 | 93638 | tgaacttccagaaagcagctaagtc | AA119287 |
| 8431 | ctgaagtctctctgtgagagcgt | M96163 | 51035 | tctactctgacatgagtgttta | X67677 | 93639 | aagcagtaagtccttcagcctgga | AA119287 |
| 8432 | ctgtgagagcgtcttcagtgaa | M96163 | 51036 | atggagcgctctctctataataacaa | X67677 | 96940 | ctaagcctcagcctgagatctc | AA119287 |
| 8433 | ggaccccacagtcagaaccccacag | M96163 | 51037 | cagctcctataatacaaattgtat | X67677 | 93641 | agcatgctcagacagtgtctcagc | AA119287 |
| 8434 | accagtcagaaccccacatggccagt | X04017 | 51038 | tttcaacagctttcatctgtatgt | X67677 | 93642 | ctcagcagtgtctcagcctcagaa | AA119287 |
| 8435 | cctaggcactggagggtttca | X04017 | 51039 | cagcttcatctgtagtttaacgtg | X67677 | 93643 | aatcagcaacctgactgaccta | AA119287 |
| 8436 | gcactggaggtgtttcaggaaag | X04017 | 51040 | cttcatctgtattgcttaacgtg | X67677 | 93644 | tggactgcacctagacacagtga | AA119287 |
| 8437 | ttcacatcatggctgtcataaa | X04017 | 51041 | tcatcgtattgcttaacggtgaa | X67677 | 93645 | gcacctagacaagtgatactaa | AA119287 |
| 8438 | ttccaagccaaccgaagatcgagat | X04017 | 51042 | tgttaaaagcagcctttctagcaca | X67677 | 93646 | gtgatactaattacctcttgttctg | AA119287 |
| 8439 | gtcagatctcacagctgagaaatt | X04017 | 51043 | aaagcagccttctagcacaaaacact | X67677 | 93647 | acctcttgtttcttgctacaaacaga | AA119287 |
| 8440 | tctccaggctgagaaatgttccc | X04017 | 51044 | ggacctctgagaaatgttccc | X67677 | 93648 | tcttgttcgtacaaacgcaagg | AA119287 |
| 8441 | cctccaagcattttcagaaaagct | X04017 | 51045 | cagtactgactcctgccaagg | X67677 | 93649 | agtcagaaggccttcttcttcagg | AA119287 |
| 8442 | tgctctcattaaccatgcaaactc | X04017 | 51046 | tactgactcctctgccaaggggctc | X67677 | 93650 | atggccctttctcaggaaagcaa | W33440 |
| 8443 | tcattaaccatgcaaactctcacag | X04017 | 51047 | ctctcctgccaaggggtcctga | X67677 | 93651 | tacactgatgtctatccagaaatca | W33440 |
| 8444 | accatgcaaactctcacgccgatgt | X04017 | 51048 | ctctgccaagggggtctcctgagaa | X67677 | 93652 | gtctatccagaaatcattgagcg | W33440 |
| 8445 | cagaacccacatggcaagtcttagt | X04017 | 51049 | ggtcctcgaagactgcctc | X67677 | 93653 | gaaatcattgagcgcgcatgcttg | W33440 |
| 8446 | ccacatggccagtcttagtagcta | X04017 | 51050 | cttgccctgtctactctgac | X67677 | 93654 | attgagcgcatgctttgtcctgg | W33440 |
| 8447 | tcttagtagccaaggcaaggaaag | X04017 | 51051 | acctctgtactctgtcactg | X67677 | 93655 | acctctatatctcatcagtacccg | W33440 |
| 8448 | ataatccagctgtgtgacacatg | X04017 | 51052 | atgtcactctgtgacatgatgtt | X67677 | 93656 | atctcatcagtacccgctgagtccc | W33440 |
| 8449 | ccgaacatcactcaactgcaatg | X04017 | 51053 | gatatctctgtgttccagcatcga | AA034721 | 93657 | ctcatcagtacccgctgagtcctgg | W33440 |

TABLE 1-continued

| SEQ ID NO | DBAxnID | sequence | SEQ ID NO | DBAxnID | sequence | SEQ ID NO | DBAxnID |
|---|---|---|---|---|---|---|---|
| 8450 | X04017 | catcactcaactgcaattggctt | 51054 | AA034721 | tgcttccagcatcgcaggtgctat | 93658 | W33440 |
| 8451 | X04017 | tcaactgcaattggcttcagtt | 51055 | AA034721 | accaacaaacagatcacatgtagt | 93659 | W33440 |
| 8452 | X04017 | tcttgccgggagctcaggcactgg | 51056 | AA034721 | cagatcacatgtgagtccgaggat | 93660 | W33440 |
| 8453 | M64085 | cagctcccatgcagagaaagaagc | 51057 | AA034721 | atcacatgtgagtccgaggatccct | 93661 | W33440 |
| 8454 | M64085 | tatgtcagatctctgcatgatg | 51058 | AA034721 | tccgaggatcccgtgagcgtcac | 93662 | W33440 |
| 8455 | M64085 | tgcctggtctatctgcagcatct | 51059 | AA034721 | cctgtgagcgtctactgtgtact | 93663 | W33440 |
| 8456 | M64085 | agcatctgaaatgctggtgccag | 51060 | AA034721 | gagcgtctactgtgtactgtgaca | 93664 | W33440 |
| 8457 | M64085 | gatctgctatgcctgccttctcc | 51061 | AA034721 | ctactgtgtactgtgtgcaaggctg | 93665 | W33440 |
| 8458 | M64085 | ccctgagcactcctactcagaaca | 51062 | AA034721 | tgtgacaaggctgctgtgggtgcc | 93666 | W33440 |
| 8459 | M64085 | gtctttctcaatgtctctgtgac | 51063 | AA034721 | ctgaactcctggatgctcctttct | 93667 | W33440 |
| 8460 | M64085 | tcaatgtctctgtgaccaacta | 51064 | AA034721 | aactcctgatgctcctctgcc | 93668 | W33440 |
| 8461 | M64085 | gtctctgttgaccaactagtagg | 51065 | AA034721 | ttccaggcaccgcaggtgcatgagg | 93669 | W33440 |
| 8462 | M64085 | tgtttgaccaactagtaggactggt | 51066 | AA034721 | cagactccagagacaactagtggga | 93670 | W33440 |
| 8463 | M64085 | tggacacctgcgattactcacaca | 51067 | AA034721 | cagcatgccaggtgctagaggaag | 93671 | W33440 |
| 8464 | M64085 | cctcgcattactcacacaaatga | 51068 | AA034721 | atggactgtccaagacccctgcca | 93672 | W33440 |
| 8465 | M64085 | tcaggttcctgactcaaatttgtg | 51069 | AA034721 | gaccctgccaagctcagtgcagatg | 93673 | W33440 |
| 8466 | M64085 | tcctgactgaaatttgtattc | 51070 | AA034721 | gccaagctcagtgcagatgcagatt | 93674 | W33440 |
| 8467 | M64085 | ccaaagctcgggccccagcagtgag | 51071 | AA034721 | aagctcagtgcagatgcagatgatgca | 93675 | W33440 |
| 8468 | M64085 | cagtgaggctctctccaactagg | 51072 | AA034721 | gtggattgcaaccaaacaacagatca | 93676 | L18888 |
| 8469 | M64085 | ctctaacttaggctcttagt | 51073 | AA034721 | tgcaccacaaaacacagatcacatgt | 93677 | L18888 |
| 8470 | M64085 | gctcgttagtctgcttcacca | 51074 | AA034721 | cttccaggttcaccagactctc | 93678 | L18888 |
| 8471 | M64085 | cttatgtctgcctttcatcctttg | 51075 | AA034721 | tcctgccctttcaggagagccag | 93679 | L18888 |
| 8472 | M64085 | ttcatcttcagtcatgatgggac | 51076 | X69296 | agaagctccactgatttctgtgtgg | 93680 | L18888 |
| 8473 | M64085 | cagtcgtccccagactctttg | 51077 | X69296 | gattctgtggagctccaatgtc | 93681 | L18888 |
| 8474 | M64085 | actagccccatgtccgagcctgaa | 51078 | X69296 | gagctccaatgtcgagaagagtt | 93682 | L18888 |
| 8475 | M64085 | tggtgcccagtccgcctcacctt | 51079 | X69296 | agtctctcaacctcgtcagtata | 93683 | L18888 |
| 8476 | M64085 | actcttcatttctccaggcttgc | 51080 | X69296 | tcaacctcgtcagtatagatcaa | 93684 | L18888 |
| 8477 | M64085 | ctccaggcttgcctccaggcactg | 51081 | X69296 | agatacattcctcggcactggaa | 93685 | L18888 |
| 8478 | M64085 | ctcagagatcctccacttgtcca | 51082 | X69296 | acatcctgccactggaatatcc | 93686 | L18888 |
| 8479 | M64086 | gatcctccacttgtccacatcg | 51083 | X69296 | actggaatattcccctgcttcaaag | 93687 | L18888 |
| 8480 | M64086 | ttgccacactggcacagagttag | 51084 | X69296 | ccctactaaagttactctattgag | 93688 | L18888 |
| 8481 | M64086 | gagttagccccctcacactctgcagc | 51085 | X69296 | attacaattgtcatagggctcca | 93689 | AA119538 |
| 8482 | M64086 | tcactctgcagctgcatggggtct | 51086 | X69296 | gagccaggaactgcattggaaaca | 93690 | AA119538 |
| 8483 | M64086 | tcaggagagatcttccccctggca | 51087 | X69296 | tttgccataggggtccaaatcaca | 93691 | AA119538 |
| 8484 | M64086 | cctggcactccttagaacaaag | 51088 | X69296 | tgacactgctccgcttcgaactact | 93692 | AA119538 |
| 8485 | M64086 | ccagtctcgagcctgaaattgt | 51089 | X69296 | tgctccgttcgaactactgccaga | 93693 | AA119538 |
| 8486 | M64086 | gccccatcaagtaagtcagtccca | 51090 | X69296 | gcttgaactactgctgcagactac | 93694 | AA119538 |
| 8487 | M64086 | tcaagtaagtcagtcccagttag | 51091 | X69296 | tagcccagctgctgaagtccaa | 93695 | AA119538 |
| 8488 | M64086 | aagctcagtcccagttagactctg | 51092 | X69296 | ggatctacctcactcaagaagt | 93696 | AA119538 |
| 8489 | M64086 | gtcccctagcctctgctctg | 51093 | X69296 | acctacatccaagaagctccactg | 93697 | AA119538 |
| 8490 | M64086 | ccgtgtctatccgcagcatctagga | 51094 | X69296 | atctcaagaagctccactgatttctg | 93698 | AA119538 |
| 8491 | M64086 | ctatccagcagcatctaggactact | 51095 | X69296 | agctggcagctcatatgaggctga | 93699 | AA119538 |
| 8492 | M64086 | actactggtgccagtctgcctca | 51096 | AA035834 | cagctgcatatgagcctgatactc | 93700 | AA119538 |
| 8493 | L11739 | ctctgaaccttacgagaccccaggt | 51097 | L11739 | tcgagcccattggaaaggatccta | 93701 | AA119538 |
| 8494 | L11739 | tggctgccaagctatgctgccctc | 51098 | L11739 | gatctatctagctactgctaactac | 93702 | AA119538 |
| 8495 | L11739 | atgaccagactccaggatggatgc | 51099 | L11739 | cctatctagctactgctaactactcc | 93703 | AA119538 |
| 8496 | L11739 | gggtccaactctgctctcctgaatgg | 51100 | L11739 | atctagtactgctaactactccaac | 93704 | AA119538 |
| 8497 | L11739 | gctctgaatgcgagcctgcattg | 51101 | L11739 | tactgctaactactccaacgcgt | 93705 | AA119538 |
| 8498 | L11739 | gaatgcgagcctgcattgcaccc | 51102 | L11739 | tgctaactactccaaacggctgtcaa | 93706 | AA119538 |
| 8499 | L11739 | gagcctgcattgtcacctaagcg | 51103 | L11739 | taactactccaacgcgtgcaagt | 93707 | AA119538 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 8500 | tgcattgtcacctaagcgacagg | L11739 | 51104 | gaattgctgcctgatacatgctc | AA035834 | 93708 | cctgtcatgcaccagagaactac | AA119538 |
| 8501 | ctaagcgacagggccactgataca | L11739 | 51105 | ggatacatgcctcacatgatgaagcc | AA035834 | 93709 | aaacgctacatccaagcaaacaa | AA119571 |
| 8502 | gacagggccactgatacagagtga | L11739 | 51106 | tctgaaggcccaggctacggagaa | AA035834 | 93710 | aagcgtacatccaagcaaacaact | AA119571 |
| 8503 | tcctccacaatattggctctgct | L11739 | 51107 | catatgagcctgatactcctaagac | AA035834 | 93711 | cagcgtatccaacgaaactgget | AA119571 |
| 8504 | cacaaatattggctctagtttt | L11739 | 51108 | cggagaaccctgaaagtgaagt | AA035834 | 93712 | gcgtatccaacgaaactggctc | AA119571 |
| 8505 | tgccctcaggctcagtctgccctt | L11739 | 51109 | ctgatactcctaagacatcgcatca | AA035834 | 93713 | gtatccaacggaaactggctctgc | AA119571 |
| 8506 | cacccctgcaagcagcatccatata | L11739 | 51110 | atactcctaagacatcgcatcagt | AA035834 | 93714 | atctcaacggaaactggctctg | AA119571 |
| 8507 | tgcaagcagcatccatatacgcgc | L11739 | 51111 | ctaagacatcgcatcagtcgaggt | AA035834 | 93715 | ctcaacggaaactggctctgtgcc | AA119571 |
| 8508 | cagcatccatatacggcgcalccta | L11739 | 51112 | gagatlcattcactgatgaggcaaca | AA035834 | 93716 | caacggaaactggctctgctgccag | AA119571 |
| 8509 | ccatccgcctgtlgactctatgc | L11739 | 51113 | tctacgtgaggcaaacatcgtgccca | AA035834 | 93717 | acggaaactggctctgctgccagga | AA119571 |
| 8510 | cgcctgtlgactctatgccacgc | L11739 | 51114 | tgaggcaaacatcgtgcccagagett | AA035834 | 93718 | aaactggctctgtcgcaggagacg | AA119571 |
| 8511 | ttggadctalgccagcgcggttgg | L11739 | 51115 | agaggtcgagcccatlggaaagg | AA035834 | 93719 | actgctctgctgccggagacgag | AA119571 |
| 8512 | gcatgtaaccatcatccataagaag | J04596 | 51116 | agtggccactaaggggctgtct | AA146437 | 93720 | gtgaaagcaaccaggctcaacgt | AA119571 |
| 8513 | gaagacagactgctcgatggcacc | J04596 | 51117 | tgggcatgacgcgccagccattcctc | AA146437 | 93721 | tgtccgtgcagggtgagcagatgc | AA119571 |
| 8514 | ctctgatggcaacgtctggtgaacg | J04596 | 51118 | tgtlctgtggttggctatgggact | AA146437 | 93722 | tcctgtgcagggtgagcagatgcaa | AA119571 |
| 8515 | ccactaagtgtcaacacggtctgcta | J04596 | 51119 | ttctlggttggctatgggactct | AA146437 | 93723 | agagatgcaaccaccaacaggctca | AA119571 |
| 8516 | agtgtcaaccacggtctagtagaa | J04596 | 51120 | tgggcctaactllgtlgatcaag | AA146437 | 93724 | cagatgcaaccaccaacaggctcagc | AA119571 |
| 8517 | gtcaaccacgtgtcgtagaaggg | J04596 | 51121 | ggatacattcggatggcaagaaata | AA146437 | 93725 | gatgcaaccaccaacaggctcagctc | AA119571 |
| 8518 | aagtgctcttcatatatgtatggc | J04596 | 51122 | aaatcactgcggaattgctagtlat | AA146437 | 93726 | tgcaaccacaaggctcagtctctt | AA119571 |
| 8519 | cgtgttgacgttccctggacatt | J04596 | 51123 | gctagttatlgctcttaccagaaa | AA146437 | 93727 | caaccacacaggctcagctcttc | AA119571 |
| 8520 | gttgacgctcccctgaacatttg | J04596 | 51124 | tagttatlgtcttaccagaaatc | AA146437 | 93728 | ccctcagcgtatccacgaacact | AA119571 |
| 8521 | gcttccctgacatttgtgtcta | J04596 | 51125 | agttattgtctctlaccagaaatct | AA146437 | 93729 | gtgtaagcttacacctggctcagt | AA119571 |
| 8522 | tccctlgacatttgtgtctagt | J04596 | 51126 | gttattgtcttlaccagaaatcta | AA146437 | 93730 | gcttacactggctcatgtactaccag | AA119473 |
| 8523 | cattttggtctagtlggtagccca | J04596 | 51127 | tatlgctcttaccagaaatctaa | AA146437 | 93731 | gtacctcctgacaacactcaatat | AA119473 |
| 8524 | tagcccataaggcttlacatlc | J04596 | 51128 | ttctctctacaaaagcggtatct | AA146437 | 93732 | cctgacaaccatcaatatgacatt | AA119473 |
| 8525 | cacgtctggtgaagctggcttct | J04596 | 51129 | cttctctctacaaagcgggtgtctat | AA146437 | 93733 | caacactcaatatgacattgtatc | AA119473 |
| 8526 | cgtctgtgaagctgggcttctgac | J04596 | 51130 | ttctctacaaagcgggtgtctatg | AA146437 | 93734 | tgtlatccgtgtlctgaagcagc | AA119473 |
| 8527 | ggaagctgggcttctgacaacact | J04596 | 51131 | tctctacaaagcgggtgtctatga | AA146437 | 93735 | aggcagcgtctlgttgttaaggc | AA119473 |
| 8528 | gctggcttcgcacaactacacaa | J04596 | 51132 | ttctacaaagcgggtgtctacg | AA146437 | 93736 | tgcttlaaggctggggcgccccag | AA119473 |
| 8529 | ttctgacaacactacacaattct | J04596 | 51133 | cctcctgacgggcaatgaatca | AA146437 | 93737 | gccccagaatlccatccatcata | AA119473 |
| 8530 | acatltcatcgatlggtagtlcgtl | J04596 | 51134 | ctccgtacgggcaatgaatcat | AA146437 | 93738 | gaatlccalccatlcatccaagg | AA119473 |
| 8531 | tctgcttgttcagtltaagatggl | J04596 | 51135 | tcctgcacgggcaatggaatcatg | AA146437 | 93739 | catccatccatccaaggagact | AA119473 |
| 8532 | agaccactcaagtgtcaaccactgtg | J04596 | 51136 | tcaggacgccatcaatccttacatg | X63023 | 93740 | tctcatcaaggagacctcatcca | AA119473 |
| 8533 | gctgacgtccgggttgaagctccacg | J04596 | 51137 | ggacagcatcaatccttacatgtac | X63023 | 93741 | acctggctcatgtaccagcctgc | AA119473 |
| 8534 | aagctccacgagagctcttctccgg | W51056 | 51138 | atcctgtlgaccagaaaccaaltca | X63023 | 93742 | taccagcctgctgtgtltgacat | AA119473 |
| 8535 | cctlcagagaggtlggcvtgtactt | W51056 | 51139 | accagaaaccaatlccatlcatatlgtgaa | X63023 | 93743 | ctgtgttgcacctgctlctg | AA119473 |
| 8536 | tggclgtgtactlgcagggaaga | W51056 | 51140 | tttgaactlgctcagtcctgtgaa | X63023 | 93744 | ttgacactlgctcctgctlgggca | AA119473 |
| 8537 | ctgtgtactlgcagggaagagga | W51056 | 51141 | ctlgctcagtctctgaaagttat | X63023 | 93745 | cttcctlgggaggactggtcact | AA119473 |
| 8538 | tgtactlcagggaagaatggga | W51056 | 51142 | ttatcttctgtgaacataaggggtg | X63023 | 93746 | aggactgtccactcgaagtltcg | AA119473 |
| 8539 | aglgctcagtttagccagaggac | W51056 | 51143 | tatatccaactccctggtttctgt | X63023 | 93747 | gtccactgtccctgaagtttgtacctc | AA119473 |
| 8540 | gctcagttltagccagaggacct | W51056 | 51144 | gctgcagtlcacttcattgtta | X63023 | 93748 | gttctgtacctcctgacaacact | AA119473 |
| 8541 | caagcctattctcgctgaaca | W51056 | 51145 | gtlcactlcattgtlactactat | X63023 | 93749 | aatglactlcacaggactgcetlag | AA119665 |
| 8542 | gccttatlctcgctgaacaatg | W51056 | 51146 | actactaaalaccccagattlctgat | X63023 | 93750 | tacaggacigcctlagataatltc | AA119665 |
| 8543 | ttlctgcetgaacaatggatga | W51056 | 51147 | taccccagattlctgatlgagaaacg | X63023 | 93751 | tagtgcacctgaaccgatlttccta | AA119665 |
| 8544 | ctgctgaacaatggatgatgagcc | W51056 | 51148 | caatcctacatgtacctgccclt | X63023 | 93752 | tgcacctgaaacgatlttctatga | AA119665 |
| 8545 | ctccacgagagctctcctggact | W51056 | 51149 | tcctlacatgtacctgccttlggg | X63023 | 93753 | aacgattttctatgacgccaggtg | AA119665 |
| 8546 | cacgagagctctcgactcaggcg | W51056 | 51150 | ttacatgtacctgccttlgggtt | X63023 | 93754 | gattttctatgacggcaggtggaa | AA119665 |
| 8547 | gagagctctctcggactcagcag | W51056 | 51151 | gaaagtltgctctlgtcagagtcctg | X63023 | 93755 | tttcctatgacggcagggtgaagca | AA119665 |
| 8548 | tgctccgcagtcgcggtgacctt | W51056 | 51152 | tctgcagagtcctgcagaactlc | X63023 | 93756 | agaagcgaaacatccgtggattg | AA119665 |
| 8549 | tctccgcagtcgcggtgacttcag | W51056 | 51153 | cctgcagaacttcactgtccagct | X63023 | 93757 | tgcaaacatccggtggatttcccatt | AA119665 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 8550 | ccgcagtgccggtgaccttcagaga | W51056 | 51154 | cactgtccagccttgtaaggaaact | X63023 | 93758 | tggatttccattgtgaaaatcttga | AA119665 |
| 8551 | cagtgccggtgaccttcagagagt | W51056 | 51155 | tgtcagccttgtaaggaaactgag | X63023 | 93759 | atcttgacctgtcacagtacgttat | AA119665 |
| 8552 | tgaccttcagagaggtggctgtgta | W51056 | 51156 | gtcaacttagaggcgtccggtcg | AA036584 | 93760 | tgtcaagtacgttattggtccaaa | AA119665 |
| 8553 | gggaactttgcctgtggacaaagc | W51059 | 51157 | cgtccggtcgagactccctttcgag | AA036584 | 93761 | acagattttacgcagccattgccg | AA119665 |
| 8554 | gactctgcctgtgggcaaagctg | W51059 | 51158 | ctgaagcgcggccatatgcgcctt | AA036584 | 93762 | gatttttactgcagccattgccgagc | AA119665 |
| 8555 | accctgagggggctcagctcagagtc | W51059 | 51159 | ggcccatgtgcctgtcgatgccgg | AA036584 | 93763 | tctggaaattacctcctgctgctgtt | AA119665 |
| 8556 | gggacgacctgtgctgtaggcgct | W51059 | 51160 | gtgactctggagctcagtcagactcag | AA036584 | 93764 | ggaaattacctcctgctgctagt | AA119665 |
| 8557 | gacgacgtgtgtaggcgcctgg | W51059 | 51161 | cagctcgactcagtcaagtgca | AA036584 | 93765 | aattacctcctgctgctagtgca | AA119665 |
| 8558 | cgacctgtgctgtaggcgcctgcg | W51059 | 51162 | gctccagctcagtgcaagtgcaga | AA036584 | 93766 | ctcctgctgctagtgcaactgaa | AA119665 |
| 8559 | gccaagctgcatctcctgctaggcg | W51059 | 51163 | gtcagagactcagcatggttctg | AA036584 | 93767 | ctgtgctgtagtgcaactgaaacg | AA119665 |
| 8560 | caagctgcatctcctgctaggcgg | W51059 | 51164 | agagactcagcatggttctgcaga | AA036584 | 93768 | tgctgtagtgcaactgaaacgatt | AA119665 |
| 8561 | agcctgcatctcctgctaggcggtt | W51059 | 51165 | agactcagcatggttctgcagatg | AA036584 | 93769 | atcccttaatatcagatccccaagc | AA119665 |
| 8562 | cctgcatctcctgctaggcggttgg | W51059 | 51166 | tcagccatggttctgcagatgatt | AA036584 | 93770 | ttaatatcagatccccaagcgacca | AA119665 |
| 8563 | catctcctgctaggcggttggatat | W51059 | 51167 | ccatggtctgcagatgatttca | AA036584 | 93771 | cattttctgccaggcagcaggatttgag | D21252 |
| 8564 | tctcctgctaggcggttggatattc | W51059 | 51168 | cgggtcgcagactcctcgaggcgc | AA036584 | 93772 | aactcttgactctactcgtgctta | D21252 |
| 8565 | cttctgcctgtgacaagctgg | W51059 | 51169 | gtgcagactcctcgaggcgcat | AA036584 | 93773 | ctactcgtcttaaacacatgt | D21252 |
| 8566 | ctcctgcctgtggattgatatcg | W51059 | 51170 | ggcgcatcctgcggttgacgtcg | AA036584 | 93774 | gattccagataagccttcctactag | D21252 |
| 8567 | gttagcggaactcaccatcccagac | W51059 | 51171 | tcctgtccggtgagcgtcgaacgac | AA036584 | 93775 | agataagccttcctacaggggctgg | D21252 |
| 8568 | tagcggaactcaccatcccagact | W51059 | 51172 | ctgtccggtgagcgtcgaacgactg | AA036584 | 93776 | gatagccttctccactatgggta | D21252 |
| 8569 | gcggaactcaccatcccagacctg | W51059 | 51173 | tcgaacgactgaagccggccccat | AA036584 | 93777 | aatggtcgagctgtgttgagca | D21252 |
| 8570 | cctcccgaccgatgtttgcatgg | W51059 | 51174 | acgactgaagccggccccataagt | AA036584 | 93778 | ctgagctgtgttttggcagaccaa | D21252 |
| 8571 | tccacgaccgatgtttgcatggt | W51059 | 51175 | gactgaagccgggccccatagtgcc | AA036584 | 93779 | ttgggcagcaatctctcatcagt | D21252 |
| 8572 | cacgaccgatgtttgcatggctga | W51059 | 51176 | aatgtatcacctgactgcttcg | AA036584 | 93780 | tcacagaaacaaccgttaattct | D21252 |
| 8573 | tgacctgcgagggggtcagtcagcag | W51059 | 51177 | tatcacctgactgcttcgcctgcc | AA036584 | 93781 | tcagatccccaaggcgcaccattgctc | D21252 |
| 8574 | accaacactgctaatgaggcctctg | M33975 | 51178 | gagagacaaatcttctgaagaaca | AA036584 | 93782 | cgcaccatgctcaggattatggag | D21252 |
| 8575 | actgctaatgaggcctctgggggg | M33975 | 51179 | gacaaaatcttctgaagaacaacaa | AA036584 | 93783 | ggccgctcgtgggatgagattatac | D21252 |
| 8576 | gttttgcatctctactgacttctgc | M33975 | 51180 | aaaattcttcctgaagaacaacatga | AA036584 | 93784 | gatacatcaagcctgatgtcaata | D21252 |
| 8577 | atctctactactgactttctgac | M33975 | 51181 | ttctcctgaagaacaacaacatgatct | AA036584 | 93785 | atcaagctgatgcaataagagca | D21252 |
| 8578 | tactactgacttctgcacacagac | M33975 | 51182 | gggcatccatgctgcaccttgaat | AA036584 | 93786 | tatttctcttaagcagaggagcac | D21252 |
| 8579 | tgacttctgcacacagactagaac | M33975 | 51183 | catcctaatggcaccttgaatccc | AA036584 | 93787 | tgagcactggaccattttctgcca | D21252 |
| 8580 | cacagactgacacaatcctgatttg | M33975 | 51184 | ctcaatgcccaccttgaatccagg | AA036584 | 93788 | ctggaccattttctgccaggcagc | D21252 |
| 8581 | ctagaacacctgattgatttcc | M33975 | 51185 | ccatctgcctccaggtccatcgt | AA036592 | 93789 | gaagctaacatgcttcgctactgg | AA103356 |
| 8582 | catcctgatttgatttcctccagt | M33975 | 51186 | cactctgcctgcggcgcgtccatcgt | AA036592 | 93790 | gctaacatgcttcgctactggagg | AA103356 |
| 8583 | ttatttaccctgactatctgctc | M33975 | 51187 | gccgtttcctacaagttagaacct | AA036592 | 93791 | gctgcatcggccatgtcgccgatc | AA103356 |
| 8584 | ctctctcattgctactttatcaa | M33975 | 51188 | ctttgactgctcgctgccagctct | AA036592 | 93792 | gtcatcggccatgctgccgatcata | AA103356 |
| 8585 | cattgctaacttttatcaataaat | M33975 | 51189 | gactgctgcgctgccagctctgaa | AA036592 | 93793 | ggccatgctgccgatcatatactgcc | AA103356 |
| 8586 | gatactctaatcgaccaaatgg | M33975 | 51190 | tgctcctgccagctctgcaatc | AA036592 | 93794 | tccaagcatgcccgcgtctgta | AA103356 |
| 8587 | gggtcacctccatcagaaggaag | M33975 | 51191 | ttcgcctgcagctctgcaatcaga | AA036592 | 93795 | catgcccgcgtctgtaaatacc | AA103356 |
| 8588 | acctcatcaatcagaacaatgtgaatg | M33975 | 51192 | gcctgcagctctgcaatcagagat | AA036592 | 93796 | gtcccgctgtctgtaaataccgg | AA103356 |
| 8589 | gtgaatgatacccatcagagaaac | M33975 | 51193 | tgccagctgcaatcagatttt | AA036592 | 93797 | tacctgctaacatcccatgcg | AA103356 |
| 8590 | gataatccctcaatgagaaacaagg | M33975 | 51194 | cagctgcaatcagagatttgcg | AA036592 | 93798 | gccatgtcaggcgcaggaatgg | AA103356 |
| 8591 | gataatcctcataagaaagaagaag | M33975 | 51195 | ctctcgaatcagagatttgctgg | AA036592 | 93799 | cagttcaggcgctcccaggaatgg | AA103356 |
| 8592 | acctcataagaaagaaggcaatg | M33975 | 51196 | ctcatttttcgaggtccatgag | U06948 | 93700 | ttcaggcgctcgtcaggaatgatg | AA103356 |
| 8593 | ttgaatacaattcattggtagatag | W50866 | 51197 | gtccttaatgcctgcatcatgagcc | U06948 | 93801 | tgccgctgtcttcgaaaccatcggc | AA103356 |
| 8594 | gagttctgtggctgtaggtggc | W50866 | 51198 | ctgtaccttaatgttctgagccg | U06948 | 93802 | cgctgtcttcgaaaccatcggctgg | AA103356 |
| 8595 | tgtgctgtggggcctagata | W50866 | 51199 | gtttctgtaggcgacctttgatcct | U06948 | 93803 | tgtctgaaaccatcctggcgtgcct | AA103356 |
| 8596 | aagacgctccagaatgctcctgtg | W50866 | 51200 | ttctgagccgacctttgatcctaac | U06948 | 93804 | ctgaaccatctgctggctttct | AA103356 |
| 8597 | aatgctctcgtgtgtaaatgga | W50866 | 51201 | cattctctacatagcatgcatacct | U06948 | 93805 | gaaaccatctggctgctttctgag | AA103356 |
| 8598 | aagtattttctgaagccaca | W50866 | 51202 | tctcacatagacatgcatacctcca | U06948 | 93806 | accatctggctggttctgaagtc | AA103356 |
| 8599 | ctgtgaagccacattccaactg | W50866 | 51203 | agcacatacctccagtgcaatga | U06948 | 93807 | tggcttgaaggctcttgagggtcaggcg | AA103356 |

TABLE 1-continued

| SEQ ID NO | sequence | DBAxnID | SEQ ID NO | sequence | DBAxnID | SEQ ID NO | sequence | DBAxnID |
|---|---|---|---|---|---|---|---|---|
| 8600 | agccacatttccaacatgagcctc | W50866 | 51204 | catacctccagtcgcaatgatgtctg | U06948 | 93808 | ctggctttctgaggtcaggctggt | AA103356 |
| 8601 | atttccaacatgagcctcatgaag | W50866 | 51205 | gaaacctgttacatttgatgctaga | U06948 | 93809 | gttttccatgcatgaaagaactca | AA119762 |
| 8602 | caacatgagcctcatgaagccaacg | W50866 | 51206 | acctgttacatttgatgctagatat | U06948 | 93810 | tttttcacatgcatgaagaactcat | AA119762 |
| 8603 | gagcctcatgaagccaacgaagtgt | W50866 | 51207 | atatctgaatgtttctggcaataa | U06948 | 93811 | ttgcatatgcgccatctcaaag | AA119762 |
| 8604 | ctaccctccataactcagtgtag | W50866 | 51208 | cttaatgctgcatcatgagccaga | U06948 | 93812 | gcatattgctgccatcttcaaagc | AA119762 |
| 8605 | tctcaataactcagtgtgcactt | W50866 | 51209 | gcctgcatcatgagccagatggaag | U06948 | 93813 | catattgctgccatcttcaaagca | AA119762 |
| 8606 | ctagatatccacaaaagatggtgg | W50866 | 51210 | atcatgagccagatgaaggaggcc | U06948 | 93814 | atattgctgccatcttcaaaggcat | AA119762 |
| 8607 | taactcagtgtagcacttcaagt | W50866 | 51211 | tgggtctacttactactccacgag | U06948 | 93815 | attgctgccatcttcaaaggcatga | AA119762 |
| 8608 | gtgtgactttgatcaactagtcac | W50866 | 51212 | ctacctcacagaggccgtttttgag | U06948 | 93816 | ctgccatcttcaaaggcatgaaagg | AA119762 |
| 8609 | gatcactagtcaccagcacttttg | W50866 | 51213 | cacagaggccgtttttgagacatag | U06948 | 93817 | tgccatcttcaaaggcatgaaaggt | AA119762 |
| 8610 | tagtcaccgacttttgctttct | W50866 | 51214 | agtgtcattggcaccactcttac | U06948 | 93818 | gccatcttcaaaggcatgaaaggtg | AA119762 |
| 8611 | cccagcactttgctttctctcca | W50866 | 51215 | gtctcattggcaccatctttactgt | U06948 | 93819 | catctcaaaggcatgaaaggtgtc | AA119762 |
| 8612 | gctttctccatctgaagatc | W50866 | 51216 | cacccaactctagtgtgaatccct | U06948 | 93820 | atcttcaaaggcatgaaaggtgtca | AA119762 |
| 8613 | ttctccatctgaagatcgctca | W50866 | 51217 | tactttccatagcagtgggtattgc | X55674 | 93821 | ggtaaagccttgcatattgctgcc | AA119762 |
| 8614 | ctgctcaagacgtccagcaatgctc | W50866 | 51218 | ccaagtctctctgccagtgcct | X55674 | 93822 | gtaaagccttgcatattgctgcca | AA119762 |
| 8615 | gtctcttaggctacaggcccgacta | U22465 | 51219 | tctgccagtgcctctgccttagag | X55674 | 93823 | taaagccttgcatattgctgccat | AA119762 |
| 8616 | caggcccgactactgcctgaacg | U22465 | 51220 | tctgccttagaggctgtggatg | X55674 | 93824 | aagccttgcatattgctgccatct | AA119762 |
| 8617 | ccattagtcgggtaatgtgagt | U22465 | 51221 | gctgctgataccattgggtctggcc | X55674 | 93825 | agccttgcatattgctgccatctt | AA119762 |
| 8618 | tccaaactttctgaaagagtcag | U22465 | 51222 | gataccattgggtctggccctgagt | X55674 | 93826 | gccttgcatattgctgccatcttc | AA119762 |
| 8619 | gagtcgctacacctctcatctc | U22465 | 51223 | tctgggctccaactctgtaacatca | X55674 | 93827 | ccttgcatattgctgccatcttcaa | AA119762 |
| 8620 | catctctcacaactctgtaccaa | U22465 | 51224 | ctccaactctgtaacatccaccatac | X55674 | 93828 | tttgcatattgctgccatctcaaa | AA119762 |
| 8621 | actctgtaccaacagagaggacag | U22465 | 51225 | ctctgtaacatcaccatacatgcac | X55674 | 93829 | agccacaatccctccagagcagc | AA119824 |
| 8622 | cagtcgcctctgtatacatgggc | U22465 | 51226 | catgcaaccaatcaataaaacctig | X55674 | 93830 | ccatgcaatccccagcagagcagcaa | AA119824 |
| 8623 | gccttcgtatacatgggccttact | U22465 | 51227 | caataaaacctigacaagagtcatt | X55674 | 93831 | ttgtatgtccgaagaacagccagt | AA119824 |
| 8624 | tgtatacatgggccttactctgcc | U22465 | 51228 | gtattgctatgttcccactgtat | X55674 | 93832 | agacagccagtgggtatatgctaca | AA119824 |
| 8625 | catgggcctactctgccaattct | U22465 | 51229 | ctcaagggccccaagagagactgta | X55674 | 93833 | tatatgctacagtgtgagctctaga | AA119824 |
| 8626 | caattctgctaactgtcatagaaa | U22465 | 51230 | ccgccacttctgacatacattgga | X55674 | 93834 | tatgctacagtgtgagctctagaaa | AA119824 |
| 8627 | aatgcccacagtagaagacagagc | U22465 | 51231 | cttctgacatacattggacatagc | X55674 | 93835 | agacggttccataacagctgtgtt | AA119824 |
| 8628 | tgtgcaacatgtagatgcgtgt | U22465 | 51232 | acatagccttcccacacagatg | X55674 | 93836 | actggttccataacagctgtgttcc | AA119824 |
| 8629 | catgcttgtgcaccctgggtgt | U22465 | 51233 | cccacagatgctggacagcctg | X55674 | 93837 | tggttccataacagctgtgtccc | AA119824 |
| 8630 | catattaagggccacagtggcatgg | U22465 | 51234 | ttgagcctgaccagtgttggagc | X55674 | 93838 | gttccataacagctgtgttccctt | AA119824 |
| 8631 | aagggccacagtggcatgggtctt | U22465 | 51235 | cctggaccagtgttggactgaagt | X55674 | 93839 | ggatccagtcgtggcaggctaaagat | AA119824 |
| 8632 | tgcaaaatacatgtttaggtactg | U22465 | 51236 | acaactggtgagctacacgccaa | AA036546 | 93840 | gatccagtcgtggcaggctaaagatgt | AA119824 |
| 8633 | aatacatgcttaggtactgagcctg | U22465 | 51237 | caaactggtgagctacacgccaac | AA036546 | 93841 | gcattccctgagctagcagccaacta | AA119824 |
| 8634 | gtgtgaccatttagtgcgggtaat | U22465 | 51238 | ccattgagctcctcgtggagactg | AA036546 | 93842 | attccctcagagcagccaacctagc | AA119824 |
| 8635 | tcaaccaactgtgttgaaggaactg | W51025 | 51239 | cattgagctcctcgtgggactgg | AA036546 | 93843 | cctcagcagccaacctagccaag | AA119824 |
| 8636 | ggaactgcacgtgggcatgttgt | W51025 | 51240 | attgagctcctcgtgggactgga | AA036546 | 93844 | agagcagccaacctagccaagatga | AA119824 |

SEQUENCE LISTING

The patent contains a lengthy "Sequence Listing" section. A copy of the "Sequence Listing" is available in electronic form from the USPTO web site (http://seqdata.uspto.gov/sequence.html?DocID=6821724B1). An electronic copy of the "Sequence Listing" will also be available from the USPTO upon request and payment of the fee set forth in 37 CFR 1.19(b)(3).

What is claimed is:

1. An array comprising a plurality of nucleic acid probes, wherein said plurality of nucleic acid probes comprises each of the sequences listed in SEQ ID NOS. 1–127,811, or the perfect match or antisense match thereof.

* * * * *